(12) United States Patent
Staben et al.

(10) Patent No.: US 9,034,866 B2
(45) Date of Patent: May 19, 2015

(54) TRICYCLIC COMPOUNDS AND METHODS OF USE THEREFOR

(71) Applicant: Genentech, Inc., South San Francisco, CA (US)

(72) Inventors: Steven Staben, South San Francisco, CA (US); Georgette Castanedo, South San Francisco, CA (US); Christian A. G. N. Montalbetti, Abingdon (GB); Jianwen Feng, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/768,873

(22) Filed: Feb. 15, 2013

(65) Prior Publication Data

US 2013/0217666 A1   Aug. 22, 2013

Related U.S. Application Data

(60) Provisional application No. 61/600,494, filed on Feb. 17, 2012.

(51) Int. Cl.
| | |
|---|---|
| C07D 498/04 | (2006.01) |
| C07D 498/14 | (2006.01) |
| C07D 519/00 | (2006.01) |
| C07D 513/04 | (2006.01) |
| C07D 498/00 | (2006.01) |
| C07D 498/12 | (2006.01) |

(52) U.S. Cl.
CPC ............ *C07D 513/04* (2013.01); *C07D 498/04* (2013.01); *C07D 498/00* (2013.01); *C07D 498/12* (2013.01)

(58) Field of Classification Search
CPC ... C07D 498/04; C07D 498/15; C07D 519/00
USPC ........ 540/548, 550, 551; 548/151; 514/211.1, 514/211.11, 211.12, 366
See application file for complete search history.

(56) References Cited

U.S. PATENT DOCUMENTS

| | | |
|---|---|---|
| 7,928,248 B2 | 4/2011 | Do et al. |
| 8,242,104 B2 | 8/2012 | Blaquiere et al. |
| 8,263,633 B2 | 9/2012 | Blaquiere et al. |
| 8,343,955 B2 | 1/2013 | Blaquiere et al. |
| 8,399,690 B2 | 3/2013 | Do et al. |
| 2009/0247567 A1 | 10/2009 | Do et al. |
| 2011/0076291 A1 | 3/2011 | Blaquiere et al. |
| 2011/0076292 A1 | 3/2011 | Blaquiere et al. |
| 2011/0130363 A1 | 6/2011 | Do et al. |
| 2012/0244149 A1 | 9/2012 | Blaquiere et al. |
| 2012/0245144 A1 | 9/2012 | Heffron et al. |
| 2013/0012488 A1 | 1/2013 | Blaquiere et al. |
| 2013/0079331 A1 | 3/2013 | Blaquiere et al. |
| 2013/0123263 A1 | 5/2013 | Do et al. |

FOREIGN PATENT DOCUMENTS

| | | |
|---|---|---|
| WO | 2009/123971 A1 | 10/2009 |
| WO | 2009/158011 A1 | 12/2009 |
| WO | 2011/036280 A1 | 3/2011 |
| WO | 2011/036284 A1 | 3/2011 |
| WO | 2012/126901 A1 | 9/2012 |

*Primary Examiner* — Bruck Kifle
(74) *Attorney, Agent, or Firm* — Tamara Kale; Genentech, Inc.

(57) ABSTRACT

The invention relates to novel compounds of Formula I:

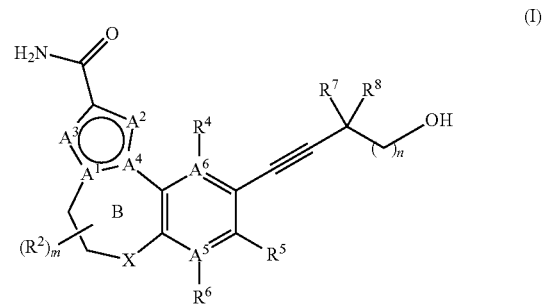

wherein $A^1$, $A^2$, $A^3$, $A^4$, $A^5$, $A^6$, $R^2$, $R^4$, $R^5$, $R^6$, $R^7$, $R^8$ and subscripts m and n each has the meaning as described herein. Compounds of Formula I and pharmaceutical compositions thereof are useful in the treatment of disease and disorders in which undesired or over-activation of NF-kB signaling is observed.

29 Claims, No Drawings

TRICYCLIC COMPOUNDS AND METHODS OF USE THEREFOR

CROSS-REFERENCE TO RELATED APPLICATION

This application claims the benefit of priority to U.S. Provisional Application No. 61/600,494, filed on Feb. 17, 2012.

FIELD OF THE INVENTION

The present invention relates to organic compounds useful for therapy and/or prophylaxis in a mammal, and in particular to inhibitors of NF-kB-inducing kinase (NIK) useful for treating cancer and inflammatory diseases and disorders, among others. NF-kB inducing kinase (NIK) is also known as MAPK kinase kinase 14 (MAP3K14) and is a serine/threonine kinase and a member of the MAPK family. It was originally identified in a two-hybrid screen as a binding partner of TNF receptor (TNFR) associated factor 2 (TRAF2) [See, Malinin, N L, et al, Nature, 1997, 385:540-4]. Overexpression of NIK leads to the activation of NF-kB and dominant negative forms of NIK lacking kinase activity were able to inhibit NF-kB activation in response to TNF and IL-1 treatment. Thus NIK has been identified as an important component of the NF-kB signaling pathway. Scientific research has shown that in blocking the NF-kB signaling pathway in cancer cells can cause such cells to stop proliferating, to die, and/or to become more sensitive to the action of other anticancer therapies. Additionally, research has shown that NF-κB controls the expression of many genes involved in inflammation and that NF-kB signaling is found to be chronically active in many inflammatory diseases, such as lupus (including systemic lupus erythematosus), rheumatoid arthritis, inflammatory bowel disease, arthritis, sepsis, gastritis, asthma, among others. Accordingly, organic compounds capable of inhibiting NIK and thereby inhibiting, weakening and/or lessening the undesired or over-activation of the NF-kB signaling pathway can have a therapeutic benefit for the treatment diseases and disorders for which such undesired or over-activation of NF-kB signaling is observed.

SUMMARY OF THE INVENTION

A compound of Formula I

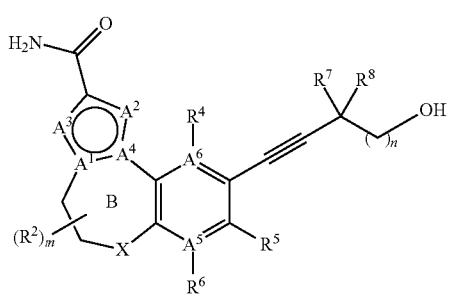

(I)

wherein
$A^1$, $A^2$, $A^3$ and $A^4$ are selected from group consisting of $A^1$, $A^2$, $A^3$ are each N and $A^4$ is C; $A^1$ and $A^2$ are each N, $A^3$ is $C(R^{43})$ and $A^4$ is C; $A^1$ is C, $A^2$ is N, $A^3$ is $N(R^{N3})$ and $A^4$ is C; $A^1$ is C, $A^2$ is $N(R^{N2})$, $A^3$ is N and $A^4$ is C, wherein $R^{N2}$ is hydrogen, $C_{1-3}$ alkyl, $C_{1-3}$ haloalkyl, $C_{1-3}$ alkyl-C(=O)— or $C_{1-3}$ haloalkyl-C(=O)—; $A^1$ is C and one of $A^2$ and $A^3$ is N and the other is S and $A^4$ is C; $A^1$ is C, $A^2$ is S, $A^3$ is $C(R^{43})$ and $A^4$ is C; $A^1$ is C, $A^2$ is N, $A^3$ and $A^4$ is N; $A^1$ is C, $A^2$ is N, $A^3$ is $C(R^{43})$ and $A^4$ is N; $A^1$ is C, $A^2$ is $C(R^{C2})$, $A^3$ is S and $A^4$ is C, wherein $R^{C2}$ is hydrogen, halogen, $C_{1-3}$ alkyl, $C_{1-3}$ haloalkyl, alkyl-C(=O)— or $C_{1-3}$ haloalkyl-C(=O)—; and $A^1$ is C, $A^2$ and $A^3$ and $A^4$ are each N; $A^5$ and $A^6$ are each independently C or N; X is O or $C(R^1)_2$; m is an integer from 0 to 4; $R^1$, $R^2$ and $R^{43}$ and $R^{N3}$ at each occurrence each is independently selected from the group consisting of hydrogen, —F, —Cl, —Br, —I, —$(X^1)_{0-1}$—CN, —$(X^1)_{0-1}$—$NO_2$, —$(X^1)_{0-1}$—$SF_5$, —$(X)_{0-1}$—OH, —$(X^1)_{0-1}$—$NH_2$, —$(X^1)_{0-1}$—N(H)($R^{1a}$), —$(X^1)_{0-1}$—N($R^1NR^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —C(=O)$(X^1)_1$—$C_{3-10}$ cycloalkyl, —C(=O)$(X^1)_1$—$C_{2-9}$ heterocycloalkyl, =O, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)$OR^{1a}$, —$(X^1)_{0-1}$—N($R^{1b}$)C(=$Y^1$)$OR^{1a}$, —$(X^1)_{0-1}$—S(O)$_{1-2}R^{1a}$, —$(X)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X)_{0-1}$—S(O)$_{0-1}$N($R^{1b}$)($R^{1a}$), —$(X)_{0-4}$—S(O)$_{0-1}NH_2$, —$(X)_{0-1}$—S(=O)(=$NR^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)($R^{1a}$), —$(X^1)_{0-1}$—NHC(=$Y^1$)$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)$NH_2$, —$(X^1)_{0-1}$—OC(=$Y^1$)$R^{1a}$, —$(X)_{0-1}$—OC(=$Y^1$)H, —$(X^1)_{0-1}$—C(=$Y^1$)$OR^{1a}$, —$(X^1)_{0-1}$—OP(=$Y^1$)($OR^{1a}$)($OR^{1b}$), —$(X^1)$—SC(=$Y^1$)$OR^{1a}$ and —$(X^1)$—SC(=$Y^1$)N($R^{1a}$)($R^{1b}$) wherein $X^1$ is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, $C_{1-4}$ alkyleneoxy, $C_{3-7}$ cycloalkylene and $C_{2-6}$ heterocycloalkylene, phenylene, 5-6 membered heteroarylene, $R^{1a}$ and $R^{1b}$ are each independently selected from the group consisting of $C_{1-6}$ alkyl, $C_{1-6}$ haloalkyl, $C_{1-6}$ heteroalkyl, $C_{3-7}$ cycloalkyl, $C_{3-7}$ cycloalkyl-$C_{1-4}$ alkyl, $C_{2-6}$ heterocycloalkyl, $C_{2-6}$ heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl, or $R^a$ and $R^{1b}$ when attached to the same nitrogen atom are optionally combined to form a 3 to 7 membered heterocyclic ring comprising 0-2 additional heteroatoms selected from N, O and S; $Y^1$ is O, $NR^{1d}$ or S wherein $R^{1d}$ is hydrogen or $C_{1-6}$ alkyl; wherein any portion of $R^1$, $R^2$ and $R^{43}$ and $R^{N3}$ substituent at each occurrence is each independently further substituted with from 0 to 4 $R^{1/2}$ substituents selected from the group consisting of —F, —Cl, —Br, —I, —CN, —$NO_2$, —$SF_5$, —OH, —$NH_2$, —N($C_{1-6}$ alkyl)$_2$, —NH($C_{1-6}$ alkyl), —$CF_3$, =O, $C_{1-6}$ alkyl, $C_{1-6}$ haloalkyl, $C_{1-6}$ hydroxyalkyl, $C_{1-6}$ heteroalkyl, $C_{1-6}$ alkoxy, $C_{1-6}$ alkylthio, $C_{3-7}$ cycloalkyl, $C_{2-6}$ heterocycloalkyl, —C(=O)N(H)($C_{1-6}$ (halo)alkyl), —C(=O)N($C_{1-6}$ (halo)alkyl)$_2$, —C(=O)$NH_2$, —C(=O)$OC_{1-6}$ (halo)alkyl, —C(=O)OH, —N(H)C(=O)($C_{1-6}$ (halo)alkyl), —N($C_{1-6}$ (halo)alkyl)C(=O)($C_{1-6}$ (halo)alkyl), —N(H)C(=O)$OC_{1-6}$ (halo)alkyl, —N($C_{1-6}$ (halo)alkyl)C(=O)$OC_{1-6}$ (halo)alkyl, —S(O)$_{1-2}C_{1-6}$ (halo)alkyl, —N(H)S(O)$_{1-2}C_{1-6}$ (halo)alkyl, —N($C_{1-6}$ (halo)alkyl)S(O)$_{1-2}C_{1-6}$ (halo)alkyl, —S(O)$_{0-1}$N(H)($C_{1-6}$ (halo)alkyl), —S(O)$_{0-1}$N($C_{1-6}$ (halo)alkyl)$_2$, —S(O)$_{0-1}NH_2$, —C(=O)$C_{1-6}$ (halo)alkyl, —C(=O)$C_{3-7}$ cycloalkyl, —C(=NOH)$C_{1-6}$ (halo)alkyl, —C(=$NOC_{1-6}$ alkyl)$C_{1-6}$ (halo)alkyl, —NHC(=O)N(H)($C_{1-6}$ (halo)alkyl), —NHC(=O)N($C_{1-6}$ (halo)alkyl)$_2$, —NHC(=O)NH$_2$, —N($C_{1-6}$ (halo)alkyl)C(=O)N(H)($C_{1-6}$ (halo)alkyl), —N($C_{1-6}$ (halo)alkyl)C(=O)NH$_2$, —OC(=O)$C_{1-6}$ (halo)alkyl, —OC(=O)O$C_{1-6}$ (halo)alkyl, —OP(=O)(O$C_{1-6}$ (halo)alkyl)$_2$, —SC(=O)O$C_{1-6}$ (halo)alkyl and —SC(=O)N($C_{1-6}$ (halo)alkyl)$_2$, wherein any two $R^2$ substituents attached to the same or different ring vertices in the B ring or a $R^1$ and $R^2$ substituents attached to different ring vertices in the B ring are optionally combined to form a 3 to 6-membered carbocyclic or heterocyclic ring comprising 1 to 2 heteroatoms selected from N, O and S, wherein said 3 to 6-membered carbocyclic or heterocyclic ring is optionally substituted with 1 to 2 $R^{1/2}$ substituents; $R^4$ and $R^6$ are each independently absent if attached to a nitrogen atom or selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$; $R^5$ is selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$; $R^7$ at each occurrence is independently selected from the group consisting of hydrogen, $C_{1-6}$ alkyl, $C_{1-6}$ haloalkyl, $C_{3-10}$ cycloalkyl, $C_{2-9}$ heterocycloalkyl, 6-10 membered aryl, 5-10 membered heteroaryl, —C(=O)$R^{7a}$, —C(=O)H, —C(=O)O$R^{7a}$ or —C(=O)N$R^{7a}R^{7b}$, wherein $R^{7a}$ and $R^{7b}$ at each occurrence is independently selected from the group consisting of hydrogen, $C_{1-6}$ alkyl, $C_{2-6}$ alkenyl, $C_{2-6}$ alkynyl, $C_{1-6}$ heteroalkyl, $C_{3-10}$ cycloalkyl, $C_{2-9}$ heterocycloalkyl, —($C_{1-6}$ alkylene)-($C_{3-10}$ cycloalkyl), —($C_{1-6}$ alkylene)-($C_{2-9}$ heterocycloalkyl), —($C_{1-6}$ alkylene)-(6-membered aryl) and —($C_{1-6}$ alkylene)-(5-6 membered heteroaryl), and wherein $R^{7a}$ and $R^{7b}$, when attached to the same nitrogen atom, are optionally combined to form a $C_{2-9}$ heterocycloalkyl further comprising 0-2 additional heteroatoms selected from N, O and S; $R^8$ at each occurrence is independently selected from the group consisting of hydrogen, $C_{1-6}$ alkyl, $C_{1-6}$ haloalkyl or —CH$_2$—OH; or alternatively $R^7$ and $R^8$ are combined to form a $C_{3-10}$ cycloalkyl, $C_{2-9}$ heterocycloalkyl, wherein optionally fused to said $C_{3-10}$ cycloalkyl and $C_{2-9}$ heterocycloalkyl is a 6 membered aryl, 5-6 membered heteroaryl ring or 3-6 membered heterocycloalkyl ring; and wherein the $R^7$ substituent, either alone or as combined with $R^8$, are optionally substituted with 1 to 5 $R^{R7/8}$ substitutents selected from the group consisting of F, Cl, Br, I, —OH, —NH$_2$, —SH, —CF$_3$, —OCF$_3$, —SF$_5$, —OCH$_3$, $C_{1-6}$ alkyl, CD$_3$, $C_{1-6}$ haloalkyl, $C_{1-6}$ heteroalkyl, $C_{1-6}$ alkoxy, $C_{1-6}$ alkylthio, $C_{3-5}$ cycloalkyl and $C_{2-5}$ heterocycloalkyl, =O, —($X^7$)$_{0-1}$—CN, —($X^7$)$_{0-1}$—NO$_2$, —($X^7$)$_{0-1}$—N$_3$, —($X^7$)$_{0-1}$—OH, —($X^7$)$_{0-1}$—H, —($X^7$)$_{0-1}$—O$R^{R7}$, —($X^7$)$_{0-1}$—N(H)$R^{R7}$, —($X^7$)$_{0-1}$—N(H)$_2$, —($X^7$)$_{0-1}$—N(e)$_2$, —($X^7$)$_{0-1}$—S$R^{R7}$, —($X^7$)$_{0-1}$—SH, ($X^7$)$_{0-1}R^7$—($X^7$)$_{0-1}$—C(O)H, —($X^7$)$_{0-1}$—S(O)$_2R^{R7}$, —($X^7$)$_{0-1}$—S(O)$R^{R7}$, —($X^7$)$_{0-1}$—N(H)S(O)$_2R^{R7}$, —($X^7$)$_{0-1}$—N($R^{R7}$)S(O)$_2R^{R7}$, —($X^7$)$_{0-1}$—OC(O)$R^{R7}$, —($X^7$)$_{0-1}$—N(H)C(O)O$R^{R7}$, —(X)$_{0-1}$—N($X^7$)C(O)O$R^{R7}$, —($X^1$)$_{0-1}$—C(=O)O$R^{R7}$, —($X^7$)$_{0-1}$—C(=O)OH, —($X^7$)$_{0-1}$—C(=O)N(H)$R^{R7}$, —($X^7$)$_{0-1}$—C(=O)N($R^{R7}$)$R^{R7}$, —($X^7$)$_{0-1}$—N(H)C(=O)$R^{R7}$, —($X^7$)$_{0-1}$—N($R^{R7}$)C(=O)$R^{R7}$, —($X^7$)$_{0-1}$—N(H)C(=O)O$R^{R7}$ and —($X^7$)$_{0-1}$—N($R^{R7}$)C(=O)O$R^{R7}$, wherein $X^7$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{2-6}$ heterocycloalkylene, and $R^{R7}$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl and $C_{2-6}$ heterocycloalkyl; and the subscript n is an integer from 0 to 1.

In one embodiment, and within aspects any of the preceding or subsequent embodiments, the present invention provides for compounds of formula I wherein in Formula I

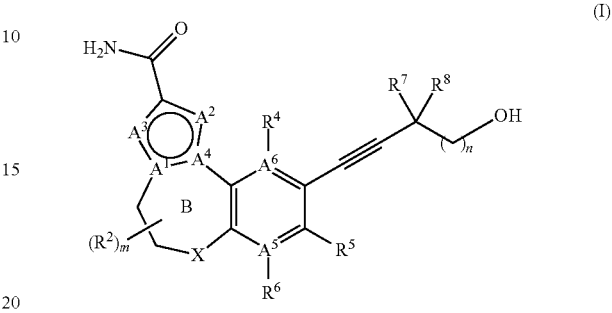

(I)

wherein $A^1$, $A^2$, $A^3$ and $A^4$ are selected from group consisting of $A^1$, $A^2$, $A^3$ are each N and $A^4$ is C; $A^1$ and $A^2$ are each N, $A^3$ is C($R^{A3}$) and $A^4$ is C; $A^1$ is C, $A^2$ is N, $A^3$ is N($R^{N3}$) and $A^4$ is C; $A^1$ is C, $A^2$ is N($R^{N2}$), $A^3$ is N and $A^4$ is C, wherein $R^{N2}$ is hydrogen, $C_{1-3}$ alkyl, $C_{1-3}$ haloalkyl, alkyl-C(=O)— or $C_{1-3}$ haloalkyl-C(=O)—; $A^1$ is C and one of $A^2$ and $A^3$ is N and the other is S and $A^4$ is C; $A^1$ is C, $A^2$ is S, $A^3$ is C($R^{A3}$) and $A^4$ is C; $A^1$ is C, $A^2$ is N, $A^3$ and $A^4$ is N; $A^1$ is C, $A^2$ is N, $A^3$ is C($R^{A3}$) and $A^4$ is N; $A^1$ is C, $A^2$ is C($R^{C2}$), $A^3$ is S and $A^4$ is C, wherein leis hydrogen, halogen, $C_{1-3}$ alkyl, $C_{1-3}$ haloalkyl, $C_{1-3}$ alkyl-C(=O)— or $C_{1-3}$ haloalkyl-C(=O)—; and $A^1$ is C, $A^2$ and $A^3$ and $A^4$ are each N. The symbols $A^5$ and $A^6$ are each independently C or N. The symbol X is O or C($R^1$)$_2$. The subscript m is an integer from 0 to 4. $R^1$, $R^2$ and $R^{A3}$ and $R^{N3}$ at each occurrence each is independently selected from the group consisting of hydrogen, —F, —Cl, —Br, —I, —($X^1$)$_{0-1}$—CN, —($X^1$)$_{0-1}$—NO$_2$, —($X^1$)$_{0-1}$—SF$_5$, 4)$_{1-0}$—OH, —($X^1$)$_{0-1}$—NH$_2$, —($X^1$)$_{0-1}$—N(H)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^1$)$_{0-1}$—$C_{3-10}$ cycloalkyl, —($X^1$)$_{0-1}$—$C_{2-9}$ heterocycloalkyl, —($X^1$)$_{0-1}$-5-10 membered heteroaryl, —($X^1$)$_{0-1}$-6-10 membered aryl, =O, —($X^1$)$_{0-1}$—C(=$Y^1$)N(H)($R^1a$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)O$R^{1a}$, —($X^1$)$_{0-1}$—C(=$Y^1$)OH, —($X^1$)$_{0-1}$—N(H)C(=$Y^1$)($R^{1a}$), —($X^1$)$_{0-1}$—N($R^{1b}$)C(=$Y^1$)($R^{1a}$), —($X^1$)$_{0-1}$—N($R^{1b}$)C(=$Y^1$)(H), —($X^1$)$_{0-1}$—N(H)C(=$Y^1$)O$R^{1a}$, —($X^1$)$_{0-1}$—N($R^{1b}$)C(=$Y^1$)O$R^{1a}$, —($X^1$)$_{0-1}$—S(O)$_{1-2}R^{1a}$, —($X^1$)$_{0-1}$—N(H)S(O)$_{1-2}R^{1a}$, —($X^1$)$_{0-1}$—N($R^{1b}$)S(O)$_{1-2}R^{1a}$, —($X^1$)$_{0-1}$—S(O)$_{0-1}$N(H)($R^{1a}$), —($X^1$)$_{0-1}$—S(O)$_{0-1}$N($R^{1b}$)($R^{1a}$), —($X^1$)$_{0-1}$—S(O)$_{0-1}$—NH$_2$, —($X^1$)$_{0-1}$—S(=O)(=N$R^{1b}$)$R^{1a}$, —($X^1$)$_{0-1}$—C(=$Y^1$)$R^{1a}$, —($X^1$)$_{0-1}$—C(=$Y^1$)H, —($X^1$)$_{0-1}$—C(=NOH)$R^{1a}$, ($X^1$)$_{0-1}$C(=NO$R^{1b}$)$R^{1a}$, —($X^1$)$_{0-1}$—NHC(=$Y^1$)N(H)($R^{1a}$), —($X^1$)$_{0-1}$—NHC(=$Y^1$)NH$_2$, —($X^1$)$_{0-1}$—NHC(=$Y^1$)N($R^{1b}$)($R^{1a}$), (C—)$_{0-1}$—N($R^{1a}$)C(=$Y^1$)N(H)($R^{1a}$), —($X^1$)$_{0-1}$—N($R^{1a}$)C(=$Y^1$)N($R^{1a}$)($R^{1a}$), —($X^1$)$_{0-1}$—N($R^{1a}$)C(=$Y^1$)NH$_2$, —($X^1$)$_{0-1}$—OC(=$Y^1$)$R^{1a}$, —($X^1$)$_{0-1}$—OC(=$Y^1$)H, —($X^1$)$_{0-1}$—C(=$Y^1$)O$R^{1a}$, —($X^1$)$_{0-1}$—OP(=$Y^1$)(O$R^{1a}$)(O$R^{1b}$), —($X^1$)—SC(=$Y^1$)O$R^{1a}$ and —($X^1$)—SC(=$Y^1$)N($R^{1a}$)($R^{1b}$) wherein $X^1$ is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, $C_{3-7}$ cycloalkylene and $C_{2-6}$ heterocycloalkylene, phenylene, 5-6 membered heteroarylene, $R^{1a}$ and $R^{1b}$ are each independently selected from the group consisting of $C_{1-6}$ alkyl, $C_{1-6}$ haloalkyl, $C_{1-6}$ heteroalkyl, $C_{3-7}$ cycloalkyl, $C_{3-7}$ cycloalkyl-$C_{1-4}$ alkyl, $C_{2-6}$ heterocycloalkyl, $C_{2-6}$ heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl, or $R^{1a}$ and $R^{1b}$ when attached to the same nitrogen atom are optionally combined to form a 3 to 7 membered heterocyclic ring comprising 0-2 additional heteroatoms selected from N, O and S; $Y^1$ is O, $NR^{1d}$ or S wherein $R^{1d}$ is hydrogen or $C_{1-6}$ alkyl; wherein any portion of $R^1$, $R^2$ and $R^{A3}$ and $R^{N3}$ substituent at each occurrence is each independently further substituted with from 0 to 4 $R^{1/2}$ substituents selected from the group consisting of —F, —Cl, —Br, —I, —CN, —NO$_2$, —SF$_5$, —OH, —NH$_2$, —CF$_3$, =O, $C_{1-6}$ alkyl, $C_{1-6}$ haloalkyl, $C_{1-6}$ heteroalkyl, $C_{1-6}$ alkoxy, $C_{1-6}$ alkylthio, $C_{3-7}$ cycloalkyl, $C_{2-6}$ heterocycloalkyl, —C(=O)N(H)($C_{1-6}$ (halo)alkyl), —C(=O)N($C_{1-6}$ (halo)alkyl)$_2$, —C(=O)NH$_2$, —C(=O)O$C_{1-6}$ (halo)alkyl, —C(=O)OH, —N(H)C(=O)($C_{1-6}$ (halo)alkyl), —N($C_{1-6}$ (halo)alkyl)C(=O)($C_{1-6}$ (halo)alkyl), —N(H)C(=O)O$C_{1-6}$ (halo)alkyl, —N($C_{1-6}$ (halo)alkyl)C(=O)O$C_{1-6}$ (halo)alkyl, —S(O)$_{1-2}$$C_{1-6}$ (halo)alkyl, —N(H)S(O)$_{1-2}$$C_{1-6}$ (halo)alkyl, —N($C_{1-6}$ (halo)alkyl)S(O)$_{1-2}$$C_{1-6}$ (halo)alkyl, —S(O)$_{0-1}$N(H)($C_{1-6}$ (halo)alkyl), —S(O)$_{0-1}$N($C_{1-6}$ (halo)alkyl)$_2$, —S(O)$_{0-1}$NH$_2$, —C(=O)$C_{1-6}$ (halo)alkyl, —C(=NOH)$C_{1-6}$ (halo)alkyl, —C(=NO$C_{1-6}$ alkyl)$C_{1-6}$ (halo)alkyl, —NHC(=O)N(H)($C_{1-6}$ (halo)alkyl), —NHC(=O)N($C_{1-6}$ (halo)alkyl)$_2$, —NHC(=O)NH$_2$, —N($C_{1-6}$ (halo)alkyl)C(=O)N(H)($C_{1-6}$ (halo)alkyl), —N($C_{1-6}$ (halo)alkyl)C(=O)NH$_2$, —OC(=O)$C_{1-6}$ (halo)alkyl, —OC(=O)O$C_{1-6}$ (halo)alkyl, —OP(=O)(O$C_{1-6}$(halo)alkyl)$_2$, —SC(=O)O$C_{1-6}$ (halo)alkyl and —SC(=O)N($C_{1-6}$ (halo)alkyl)$_2$, wherein any two $R^2$ substituents attached to the same or different ring vertices in the B ring or a $R^1$ and $R^2$ substituents attached to different ring vertices in the B ring are optionally combined to form a 3 to 6-membered carbocyclic or heterocyclic ring comprising 1 to 2 heteroatoms selected from N, O and S, wherein said 3 to 6-membered carbocyclic or heterocyclic ring is optionally substituted with 1 to 2 $R^{1/2}$ substituents. $R^4$ and $R^6$ are each independently absent if attached to a nitrogen atom or selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$. $R^5$ is selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$ $R^7$ at each occurrence is independently selected from the group consisting of hydrogen, $C_{1-6}$ alkyl, $C_{1-6}$ haloalkyl, $C_{3-10}$ cycloalkyl, $C_{2-9}$ heterocycloalkyl, 6-10 membered aryl, 5-10 membered heteroaryl, —C(=O)$R^{7a}$, —C(=O)O$R^{7a}$ or —C(=O)N$R^{7a}R^{7b}$, wherein $R^{7a}$ and $R^{7b}$ at each occurrence is independently selected from the group consisting of hydrogen, $C_{1-6}$ alkyl, $C_{2-6}$ alkenyl, $C_{2-6}$ alkynyl, $C_{1-6}$ heteroalkyl, $C_{3-10}$ cycloalkyl, $C_{2-9}$ heterocycloalkyl, —($C_{1-6}$ alkylene)-($C_{3-10}$ cycloalkyl), —($C_{1-6}$ alkylene)-($C_{2-9}$ heterocycloalkyl), —($C_{1-6}$ alkylene)-(6-membered aryl) and —($C_{1-6}$ alkylene)-(5-6 membered heteroaryl), and wherein $R^{7a}$ and $R^{7b}$, when attached to the same nitrogen atom, are optionally combined to form a $C_{2-9}$ heterocycloalkyl further comprising 0-2 additional heteroatoms selected from N, O and S. $R^8$ at each occurrence is independently selected from the group consisting of hydrogen, $C_{1-6}$ alkyl, $C_{1-6}$ haloalkyl or —CH$_2$—OH or alternatively $R^7$ and $R^8$ are combined to form a $C_{3-10}$ cycloalkyl, $C_{2-9}$ heterocycloalkyl, wherein optionally fused to said $C_{3-10}$ cycloalkyl and $C_{2-9}$ heterocycloalkyl is a 6 membered aryl or 5-6 membered heteroaryl ring; and wherein the $R^7$ substituent, either alone or as combined with $R^8$, are optionally substituted with 1 to 5 $R^{R7/8}$ substitutents selected from the group consisting of F, Cl, Br, I, —OH, —NH$_2$, —SH, —CF$_3$, —OCF$_3$, —SF$_5$, —OCH$_3$, $C_{1-6}$ alkyl, $C_{1-6}$ haloalkyl, $C_{1-6}$ heteroalkyl, $C_{1-6}$ alkoxy, $C_{1-6}$ alkylthio, $C_{3-5}$ cycloalkyl and $C_{2-5}$ heterocycloalkyl, —(X$^7$)$_{0-1}$—CN, —(X$^7$)$_{0-1}$—NO$_2$, —(X$^7$)$_{0-1}$—N$_3$, —(X$^7$)$_{0-1}$—OH, —(X$^7$)$_{0-1}$—H, —(X$^7$)$_{0-1}$—OR$^{R7}$, —(X$^7$)$_{0-1}$—N(H)R$^{R7}$, —(X$^7$)$_{0-1}$—N(H)$_2$, —(X$^7$)$_{0-1}$—N(R$^{R7}$)$_2$, —(X$^7$)$_{0-1}$—SR$^{R7}$, —(X$^7$)$_{0-1}$—SH, —(X$^7$)$_{0-1}$—C(O)R$^{R7}$, —(X$^7$)$_{0-1}$—S(O)$_2$R$^{R7}$, —(X$^7$)$_{0-1}$—S(O)R$^{R7}$, —(X$^7$)$_{0-1}$—N(H)S(O)$_2$R$^{R7}$, —(X$^7$)$_{0-1}$—N(R$^{R7}$)S(O)$_2$R$^{R7}$, —(X$^7$)$_{0-1}$—OC(O)R$^{R7}$, —(X$^7$)$_{0-1}$—N(H)C(O)OR$^{R7}$, —(X$^7$)$_{0-1}$—N(R$^{R7}$)C(O)OR$^{R7}$, —(X$^7$)$_{0-1}$—C(=O)OR$^{R7}$, —(X$^7$)$_{0-1}$—C(=O)OH, —(X$^7$)$_{0-1}$—C(=O)N(H)R$^{R7}$, —(X$^7$)$_{0-1}$—C(=O)N(R$^{R7}$)R$^{R7}$, —(X$^7$)$_{0-1}$—N(H)C(=O)R$^{R7}$, —(X$^7$)$_{0-1}$—N(R$^{R7}$)C(=O)R$^{R7}$, —(X$^7$)$_{0-1}$—N(H)C(=O)OR$^{R7}$ and —(X$^7$)$_{0-1}$—N(R$^{R7}$)C(=O)OR$^{R7}$, wherein X$^7$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{2-6}$ heterocycloalkylene, and R$^{R7}$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl and $C_{2-6}$ heterocycloalkyl; and the subscript n is an integer from 0 to 1.

In one embodiment, and within aspects of any of the preceding or subsequent embodiments, the present invention provides for compound of Formula I-A or I-B

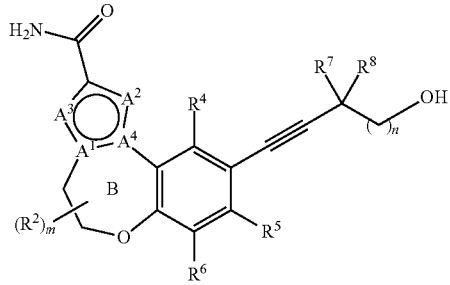
(I-A)

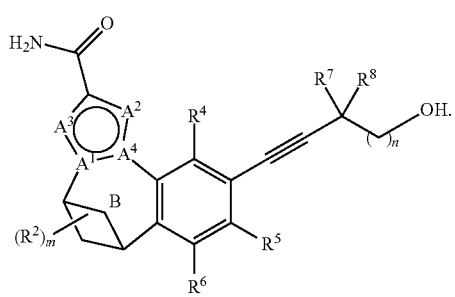
(I-B)

In one embodiment, and within aspects of any of the preceding or subsequent embodiments, the compounds are of a Formula selected from the group consisting of

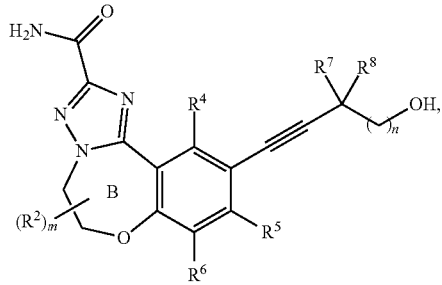
(I-A$^1$)

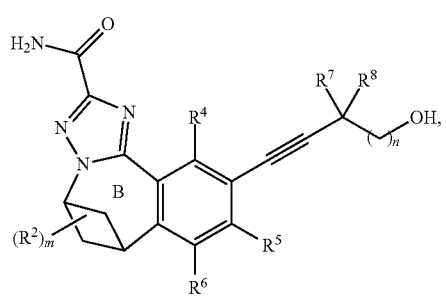
(I-B¹)
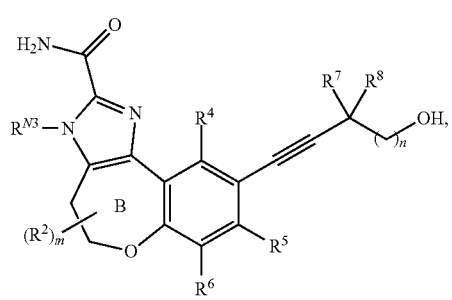
(I-A²)
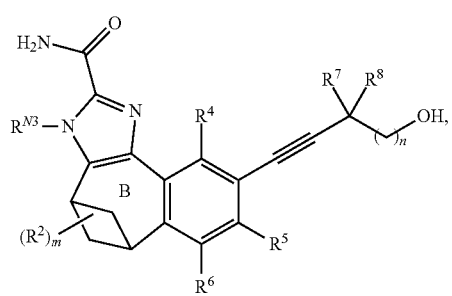
(I-B²)
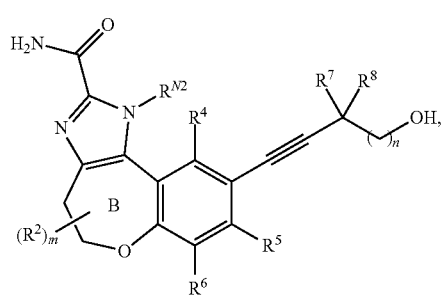
(I-A³)
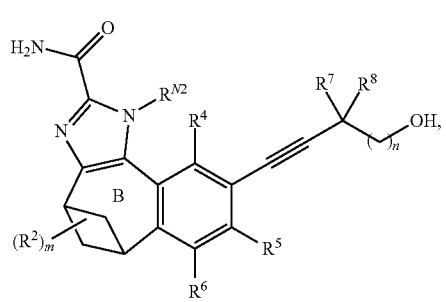
(I-B³)
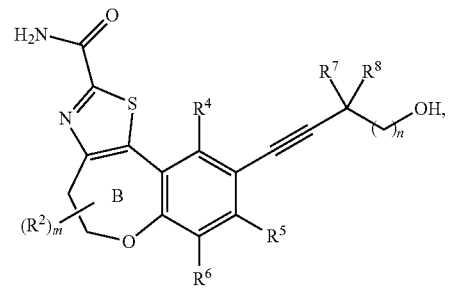
(I-A⁴)
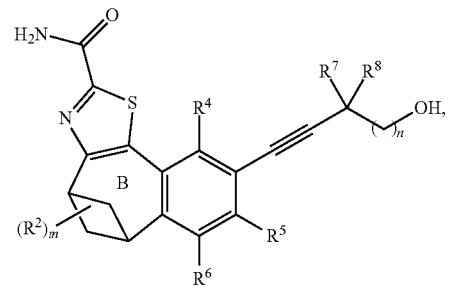
(I-B⁴)
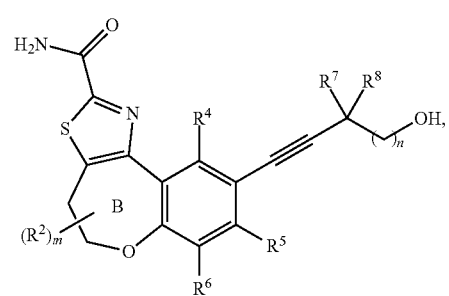
(I-A⁵)
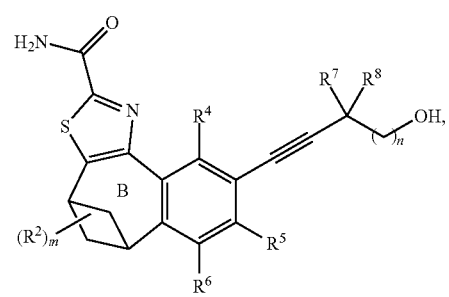
(I-B⁵)
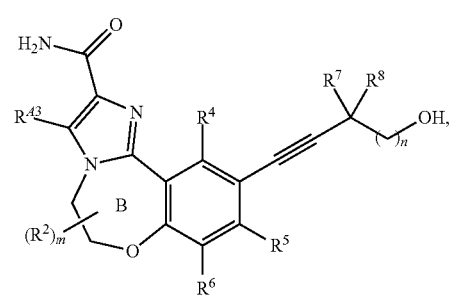
(I-A⁶)

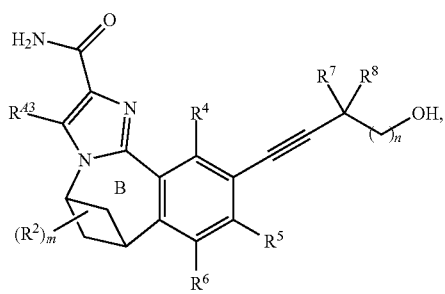
(I-B⁶)
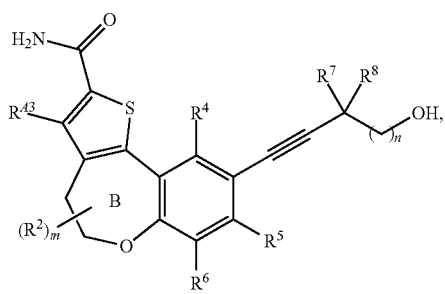
(I-A⁷)
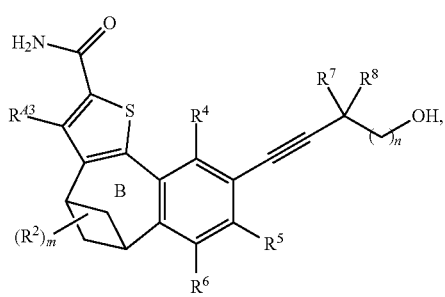
(I-B⁷)
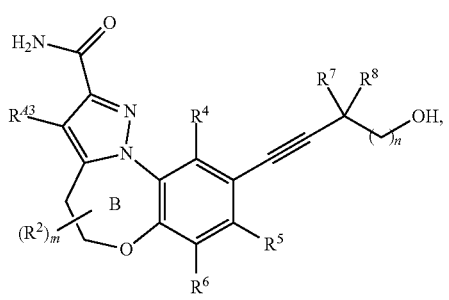
(I-A⁸)
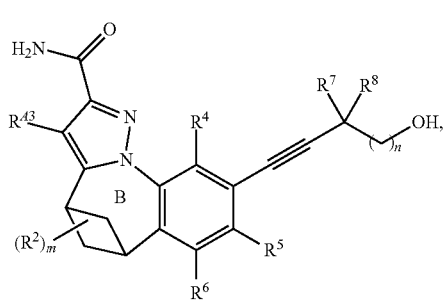
(I-B⁸)
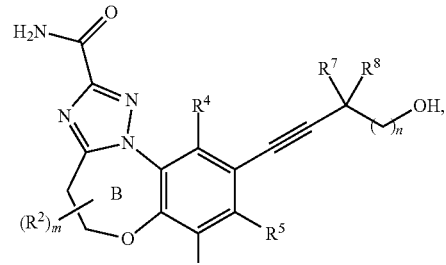
(I-A⁹)
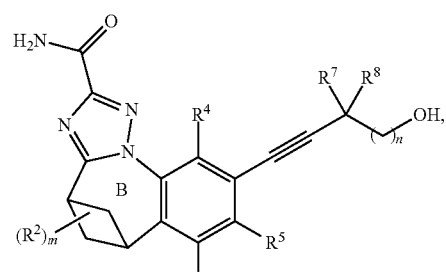
(I-B⁹)
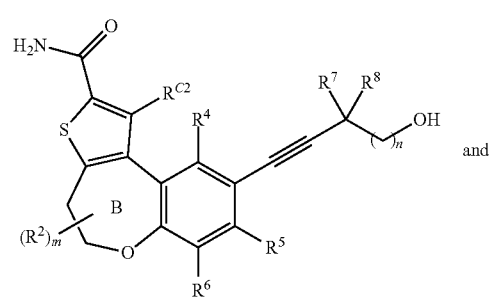
(I-A¹⁰) and
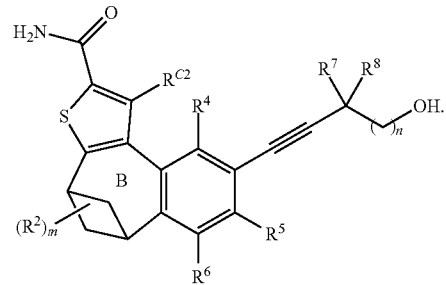
(I-B¹⁰)
In one embodiment, and within aspects of any of the preceding or subsequent embodiments, the compounds are of a Formula selected from the group consisting of
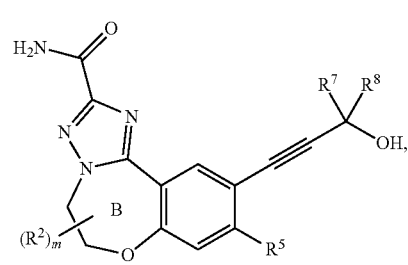
(II-A¹)

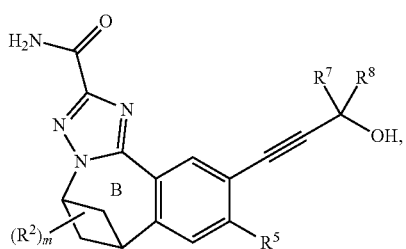 (II-B¹)
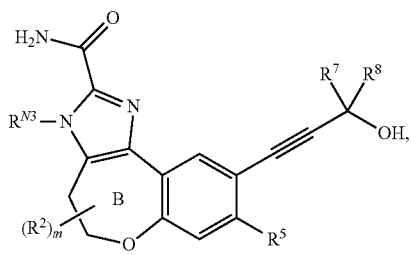 (II-A²)
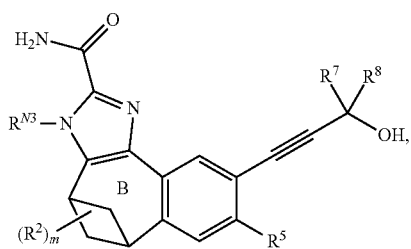 (II-B²)
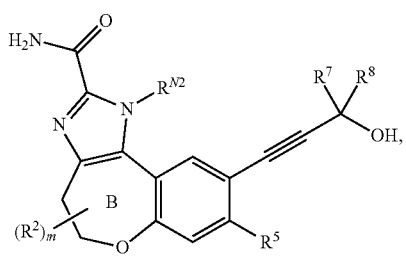 (II-A³)
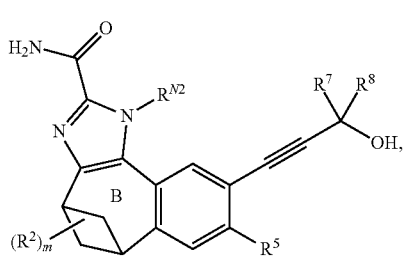 (II-B³)
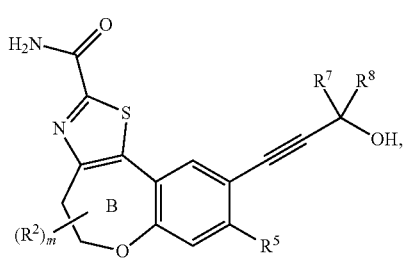 (II-A⁴)
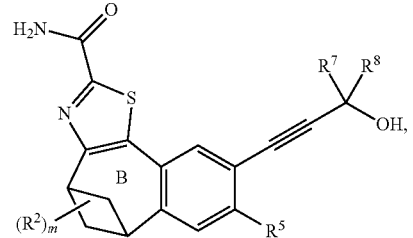 (II-B⁴)
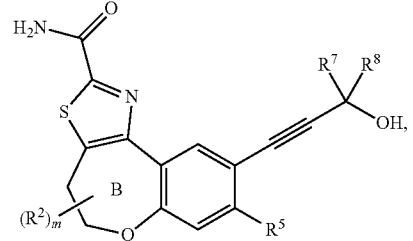 (II-A⁵)
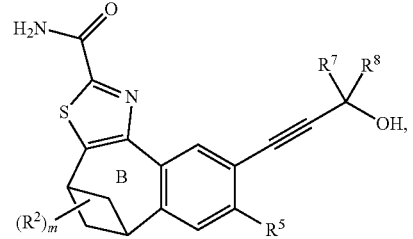 (II-B⁵)
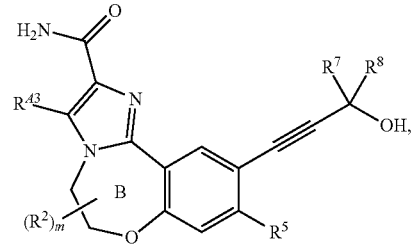 (II-A⁶)
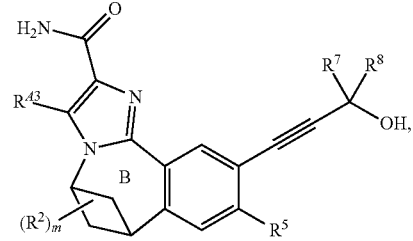 (II-B⁶)
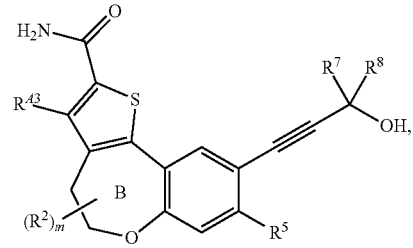 (II-A⁷)

-continued

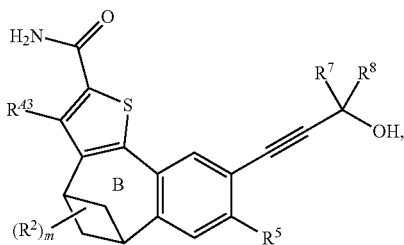
(II-B⁷)

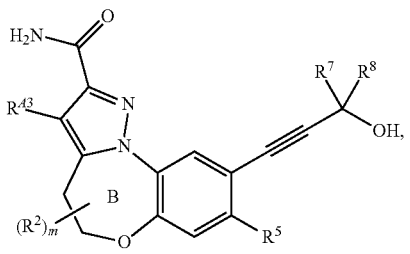
(II-A⁸)

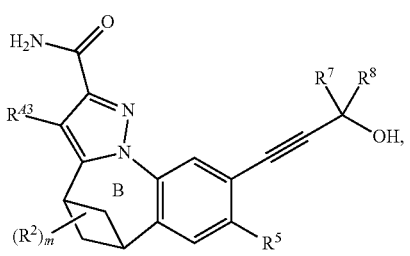
(II-B⁸)

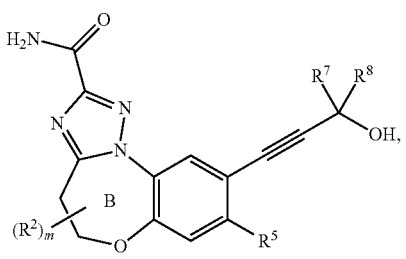
(II-A⁹)

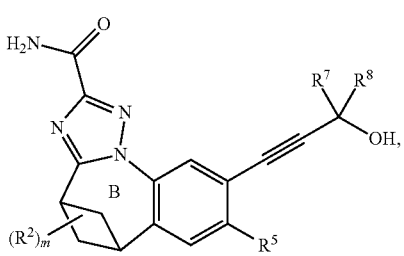
(II-B⁹)

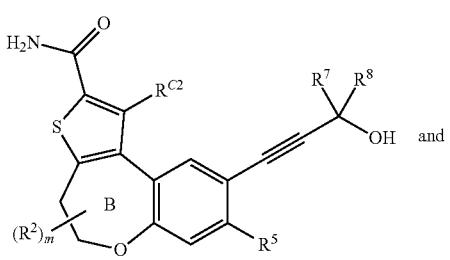
(II-A¹⁰)

-continued

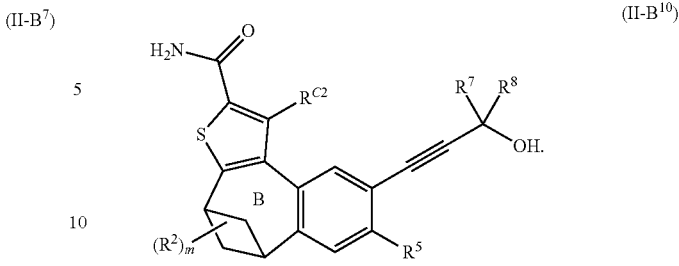
(II-B¹⁰)

In one embodiment, and within aspects of any of the preceding or subsequent embodiments, in compound of formula I of a subformula thereof, $A^1$, $A^2$ and $A^3$ are each N and $A^4$ is C, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X)_{0-1}$—NO₂, —$(X^1)_{0-1}$—SF₅, —$(X^1)_{0-1}$—OH, —$(X^1)_{0-1}$—NH₂, —$(X^1)_{0-1}$—N(H)($R^{1a}$), —$(X^1)_{0-1}$—N($R^{1b}$)($R^{1a}$), —$(X^1)_{0-1}$—CF₃, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)NH₂, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{0-2}$$R^{1a}$, —$(X^1)_{0-1}$—N(H)S(O)$_{1-2}$$R^{1a}$, —$(X^1)_{0-1}$—N($R^{1b}$)S(O)$_{1-2}$$R^{1a}$, —$(X^1)_{0-1}$—S(O)$_{0-1}$N(H)($R^{1a}$), —$(X^1)_{0-1}$—S(O)$_{0-1}$N($R^1$N$R^{1a}$), —$(X^1)_{0-1}$—S(O)O—NH₂, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=NO$R^{1b}$)$R^{1a}$, —$(X^1)_{0-1}$—NHC(=$Y^1$)N(H)($R^{1a}$), —$(X^1)_{0-1}$—NHC(=$Y^1$)NH₂, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH₂, —$(X^1)_{0-1}$—OC(=$Y^1$)$R^{1a}$, —$(X^1)_{0-1}$—OC(=$Y^1$)H, —$(X^1)_{0-1}$—C(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$); and in additional occurrences of $R^2$, $R^2$ is optionally substituted and selected from the group consisting of hydrogen, —F, —Cl, —Br, —I, —CN, —NO₂, —SF₅, —OH, —NH₂, —N(H)($R^{1a}$), —N($R^{1b}$)($R^{1a}$), —CF₃, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

In one embodiment, and within aspects of any of the preceding or subsequent embodiments, in compound of Formula I or a subformula thereof, m is 1-4.

In one embodiment, and within aspects of any of the preceding or subsequent embodiments, in compounds of Formula I or a subformula thereof, $A^1$ and $A^2$ are each N, $A^3$ is C($R^{A3}$) and $A^4$ is C, wherein $R^{A3}$ is optionally substituted and selected from the group consisting of hydrogen, —F, —Cl, —Br, —I, —$(X^1)_{0-1}$—CN, —$(X^1)_{0-1}$—NO₂, —$(X^1)_{0-1}$—SF₅, —$(X^1)_{0-1}$—NH₂, —$(X^1)_{0-1}$—N(H)($R^{1a}$), —$(X^1)_{0-1}$—N($R^{1b}$)($R^{1a}$), —$(X^1)_{0-1}$—CF₃, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N($R^{1b}$)($R^{1a}$), —$(X^1)_{0-1}$—C(=$Y^1$)NH₂, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)

C(=Y¹)(H), —(X¹)₀₋₁—N(H)C(=Y¹)OR¹ᵃ, —(X¹)₀₋₁—N(R¹ᵇ)C(=Y¹)OR¹ᵃ, —(X¹)₀₋₁—S(O)₁₋₂R¹ᵃ, —(X¹)₀₋₁—N(H)S(O)₁₋₂R¹ᵃ, —(X¹)₀₋₁—N(R¹ᵇ)S(O)₁₋₂R¹ᵃ, —(X¹)₀₋₁—S(O)₀₋₁N(H)(R¹ᵃ), —(X¹)₀₋₁—S(O)₀₋₁—N(R¹ᵇ)(R¹ᵃ), —(X¹)₀₋₁—S(O)₀₋₁NH₂, —(X¹)₀₋₁—S(=O)(=NR¹ᵇ)R¹ᵃ, —(X¹)₀₋₁—C(=Y¹)R¹ᵃ, —(X¹)₀₋₁—C(=Y¹)H, —(X¹)₀₋₁—C(=NOH)R¹ᵃ, —(X¹)₀₋₁—C(=NOR¹ᵇ)R¹ᵃ, —(X¹)₀₋₁—NHC(=Y¹)N(H)(R¹ᵃ), —(X¹)₀₋₁—NHC(=Y¹)NH₂, —(X¹)₀₋₁—NHC(=Y¹)N(R¹ᵇ)(R¹ᵃ), —(X¹)₀₋₁—N(R¹ᵃ)C(=Y¹)N(H)(R¹ᵃ), —(X¹)₀₋₁—N(R¹ᵃ)C(=Y¹)N(R¹ᵃ)(R¹ᵃ), —(X¹)₀₋₁—N(R¹ᵃ)C(=Y¹)NH₂, —(X¹)₀₋₁—OC(=Y¹)R¹ᵃ, —(X¹)₀₋₁—OC(=Y¹)H, —(X¹)₀₋₁—OC(=Y¹)OR¹ᵃ, —(X¹)₀₋₁—OP(=Y¹)(OR¹ᵃ)(OR¹ᵇ), —(X¹)—SC(=Y¹)OR¹ᵃ and —(X¹)—SC(=Y¹)N(R¹ᵃ)(R¹ᵇ); R² is optionally substituted and selected from the group consisting of hydrogen, —F, —Br, —I, —CN, —NO₂, —SF₅, —OH, —NH₂, —N(H)(R¹ᵃ), —N(R¹ᵇ)(R¹ᵃ), —CF₃, C₁₋₆ alkyl, C₁₋₆ haloalkyl, C₁₋₆ heteroalkyl, C₁₋₆ alkoxy and C₁₋₆ alkylthio; and m is 0 to 4.

In one embodiment, and within aspects of any of the preceding or subsequent embodiments, in compound of Formula I or a subformula thereof, m is 0-2 and R⁴³ is other than hydrogen.

In one embodiment, and within aspects of any of the preceding or subsequent embodiments, in compound of formula I of a subformula thereof, A¹ and A² are each N, A³ is C(R⁴³) and A⁴ is C, wherein m is 0 to 4. R² is optionally substituted and selected from the group consisting of consisting of hydrogen, —F, —Cl, —Br, —I, —(X¹)₀₋₁—CN, —(X¹)₀₋₁—NO₂, —(X¹)₀₋₁—SF₅, —(X¹)₀₋₁—NH₂, —(X¹)₀₋₁—N(H)(R¹ᵃ), —(X¹)₀₋₁—N(R¹ᵇ)(R¹ᵃ), —(X¹)₀₋₁—CF₃, C₁₋₆ alkyl, C₁₋₆ haloalkyl, C₁₋₆ heteroalkyl, C₁₋₆ alkoxy, C₁₋₆ alkylthio, —(X¹)₀₋₁—C₃₋₁₀ cycloalkyl, —(X¹)₀₋₁—C₂₋₉heterocycloalkyl, —(X¹)₀₋₁-5-10 membered heteroaryl, —(X¹)₀₋₁-6-10 membered aryl, —(X¹)₀₋₁—C(=Y¹)N(H)(R¹ᵃ), —(X¹)₀₋₁—C(=Y¹)NH₂, —(X¹)₀₋₁—C(=Y¹)N(R¹ᵃ)(R¹ᵇ), —(X)₀₋₁—C(=Y¹)OR¹ᵃ, —(X¹)₀₋₁—C(=Y¹)OH, —(X¹)₀₋₁—N(H)C(=Y)(R¹), —(X¹)₀₋₁—N(R¹ᵇ)C(=Y¹)(R¹ᵃ), —(X¹)₀₋₁—N(R¹ᵇ)C(=Y¹)(H), —(X¹)₀₋₁—N(H)C(=Y¹)OR¹ᵃ, —(X¹)₀₋₁—N(R¹ᵇ)C(=Y¹)OR¹ᵃ, —(X)₀₋₁—S(O)₁₋₂R¹ᵃ, —(X)₀₋₁—N(H)S(O)₁₋₂R¹ᵃ, —(X¹)₀₋₁—N(R¹ᵇ)S(O)₁₋₂R¹ᵃ, —(X¹)₀₋₁—S(O)₀₋₁N(H)(R¹ᵃ), —(X)₀₋₁—S(O)₀₋₁N(R¹ᵇ)(R¹ᵃ), —(X¹)₀₋₁—S(O)₀₋₁NH₂, —(X¹)₀₋₁—S(=O)(=NR¹ᵇ)R¹ᵃ, —(X¹)₀₋₁—C(=Y¹)R¹ᵃ, —(X¹)₀₋₁—C(=Y¹)H, —(X¹)₀₋₁—C(=NOH)R¹ᵃ, —(X¹)₀₋₁—C(=NOR¹ᵇ)R¹ᵃ, —(X¹)₀₋₁—NHC(=Y¹)N(H)(R¹ᵃ), —(X¹)₀₋₁—NHC(=Y¹)NH₂, —(X¹)₀₋₁—NHC(=Y¹)N(R¹ᵇ)(R¹ᵃ), —(X¹)₀₋₁—N(R¹ᵃ)C(=Y¹)N(H)(R¹ᵃ), —(X¹)₀₋₁—N(R¹ᵃ)C(=Y¹)N(R¹ᵃ)(R¹ᵃ), —(X¹)₀₋₁—N(R¹ᵃ)C(=Y¹)NH₂, —(X¹)₀₋₁—C(=Y¹)R¹ᵃ, —(X¹)₀₋₄—OC(=Y¹)H, —(X¹)₀₋₁—C(=Y¹)OR¹ᵃ, —(X¹)₀₋₁—OP(=Y¹)(OR¹ᵃ)(OR¹ᵇ), —(X¹)—SC(=Y¹)OR¹ᵃ and —(X¹)—SC(=Y¹)N(R¹ᵃ)(R¹ᵇ); and R⁴³ is optionally substituted and selected from the group consisting of hydrogen, —F, —Cl, —Br, —I, —CN, —NO₂, —SF₅, —OH, —NH₂, —N(H)(R¹ᵃ), —N(R¹ᵇ)(R¹ᵃ), —CF₃, C₁₋₆ alkyl, C₁₋₆ haloalkyl, C₁₋₆ heteroalkyl, C₁₋₆ alkoxy and C₁₋₅ alkylthio.

In one embodiment, and within aspects of any of the preceding or subsequent embodiments, in compound of formula I of a subformula thereof, m is 1-2.

In one embodiment, and within aspects of any of the preceding or subsequent embodiments, in compound of formula I of a subformula thereof, A¹ and A⁴ are each C and A² is NR^N2 are and A³ is N, wherein m is 0-4, wherein in a first occurrence of R², R² is optionally substituted and selected from the group consisting of consisting of —F, —Cl, —Br, —I, —(X¹)₀₋₁—CN, —(X¹)₀₋₁—NO₂, —(X¹)₀₋₁—SF₅, —(X¹)₀₋₁—OH, —(X¹)₀₋₁—NH₂, —(X¹)₀₋₁—N(H)(R¹ᵃ), —(X¹)₀₋₁—N(R¹ᵇ)(R¹ᵃ), —(X¹)₀₋₁—CF₃, C₁₋₆ alkyl, C₁₋₆ haloalkyl, heteroalkyl, C₁₋₆ alkoxy, C₁₋₆ alkylthio, —(X¹)₀₋₁—C₃₋₁₀ cycloalkyl, —(X¹)₀₋₁—C₂₋₉heterocycloalkyl, —(X¹)₀₋₁-5-10 membered heteroaryl, —(X¹)₀₋₁-6-10 membered aryl, —(X¹)₀₋₁—C(=Y¹)N(H)(R¹ᵃ), —(X¹)₀₋₁—C(=Y¹)NH₂, —(X¹)₀₋₁—C(=Y¹)N(R¹ᵃ)(R¹ᵇ), —(X¹)₀₋₁—C(=Y¹)OR¹ᵃ, —(X¹)₀₋₁—C(=Y¹)OH, —(X¹)₀₋₁—N(H)C(=Y¹)(R¹ᵃ), —(X¹)₀₋₁—N(R¹ᵇ)C(=Y¹)(R¹ᵃ), —(X¹)₀₋₁—N(R¹ᵇ)C(=Y¹)(H), —(X¹)₀₋₁—N(H)C(=Y¹)OR¹ᵃ, —(X¹)₀₋₁—N(R¹ᵇ)C(=Y¹)OR¹ᵃ, —(X¹)₀₋₁—S(O)₁₋₂R¹ᵃ, —(X¹)₀₋₁—N(H)S(O)₁₋₂R¹ᵃ, —(X¹)₀₋₁—N(R¹ᵇ)S(O)₁₋₂R¹ᵃ, —(X¹)₀₋₁—S(O)₀₋₁—N(H)(R¹ᵃ), —(X¹)₀₋₁—S(O)₀₋₁N(R¹ᵇ)(R¹ᵃ), —(X¹)₀₋₁—S(O)₀₋₁NH₂, —(X¹)₀₋₁—S(=O)(=NR¹ᵇ)R¹ᵃ, —(X)₀₋₁—C(=Y¹)R¹ᵃ, —(X¹)₀₋₁—C(=Y¹)H, —(X¹)₀₋₁—C(=NOH)R¹ᵃ, —(X¹)₀₋₁—C(=NOR¹ᵇ)R¹ᵃ, —(X¹)₀₋₁—NHC(=Y¹)N(H)(R¹ᵃ), —(X¹)₀₋₁—NHC(=Y¹)NH₂, —(X¹)₀₋₁—NHC(=Y¹)N(R¹NR¹ᵃ)—(X¹)₀₋₁—N(R¹ᵃ)C(=Y¹)N(H)(R¹ᵃ), —(X¹)₀₋₁—N(R¹ᵃ)C(=Y¹)N(R¹ᵃ)(R¹ᵃ), —(X¹)₀₋₁—N(R¹ᵃ)C(=Y¹)NH₂, —(X¹)₀₋₁—C(=Y¹)R¹ᵃ, —(X¹)₀₋₁—OC(=Y¹)H, —(X¹)₀₋₁—OC(=Y¹)OR¹ᵃ, —(X¹)₀₋₁—OP(=Y¹)(OR¹ᵃ)(OR¹ᵇ), —(X¹)—SC(=Y¹)OR¹ᵃ and —(X¹)—SC(=Y¹)N(R¹ᵃ)(R¹ᵇ); and in additional occurrences of R², R² is optionally substituted and selected from the group consisting of hydrogen, —F, —Cl, —Br, —I, —CN, —NO₂, —SF₅, —OH, —NH₂, —N(H)(R¹ᵃ), —N(R¹ᵇ)(R¹ᵃ), —CF₃, C₁₋₆ alkyl, C₁₋₆ haloalkyl, C₁₋₆ heteroalkyl, C₁₋₆ alkoxy, C₁₋₆ alkylthio.

In one embodiment, and within aspects of any of the preceding or subsequent embodiments, in compound of formula I of a subformula thereof, m is 1-4.

In one embodiment, and within aspects of any of the preceding or subsequent embodiments, in compound of formula I of a subformula thereof, A¹ and A⁴ are each C, A² is N and A³ is N(R^N3); wherein R^N3 is optionally substituted and selected from the group consisting of consisting of hydrogen, —(X¹)₀₋₁—CN, —(X¹)₀₋₁—NO₂, —(X¹)₀₋₁—SF₅, —(X¹)₀₋₁—OH, —(X¹)₀₋₁—NH₂, —(X¹)₀₋₁—N(H)(R¹ᵃ), —(X¹)₀₋₁—N(R¹ᵇ)(R¹ᵃ), —(X¹)₀₋₁—CF₃, C₁₋₆ alkyl, C₁₋₆ haloalkyl, C₁₋₆ heteroalkyl, C₁₋₆ alkoxy, C₁₋₆ alkylthio, —(X¹)₀₋₁—C₃₋₁₀ cycloalkyl, —(X¹)₀₋₁—C₂₋₉ heterocycloalkyl, —(X¹)₀₋₁-5-10 membered heteroaryl, —(X¹)₀₋₁-6-10 membered aryl, —(X¹)₀₋₁—C(=Y¹)N(H)(R¹ᵃ), —(X¹)₀₋₁—C(=Y¹)NH₂, —(X¹)₀₋₁—C(=Y¹)N(R¹ᵃ)(R¹ᵇ), —(X¹)₀₋₁—C(=Y¹)OR¹ᵃ, —(X¹)₀₋₁—C(=Y¹)OH, —(X¹)₀₋₁—N(H)C(=Y¹)(R¹ᵃ), —(X¹)₀₋₁—N(R¹ᵇ)C(=Y¹)(R¹ᵃ), —(X¹)₀₋₁—N(R¹ᵇ)C(=Y¹)(H), —(X¹)₀₋₁—N(H)C(=Y¹)OR¹ᵃ, —(X¹)₀₋₁—N(R¹ᵇ)C(=Y¹)OR¹ᵃ, —(X¹)₀₋₁—S(O)₁₋₂R¹ᵃ, —(X¹)₀₋₁—N(H)S(O)₁₋₂R¹ᵃ, —(X)₀₋₁—N(R¹ᵇ)S(O)₁₋₂R¹ᵃ, —(X¹)₀₋₁—S(O)₀₋₁—N(H)(R¹ᵃ), —(X¹)₀₋₁—S(O)₀₋₁N(R¹ᵇ)(R¹ᵃ), —(X¹)₀₋₁—S(O)₀₋₁NH₂, —(X¹)₀₋₁—S(=O)(=NR¹ᵇ)R¹ᵃ, —(X¹)₀₋₁—C(=Y¹)R¹ᵃ, —(X¹)₀₋₁—C(=Y¹)H, —(X¹)₀₋₁—C(=NOH)R¹ᵃ, —(X)₀₋₁—C(=NOR¹ᵇ)R¹ᵃ, —(X¹)₀₋₁—NHC(=Y¹)N(H)(R¹ᵃ), —(X¹)₀₋₁—NHC(=Y¹)NH₂, —(X¹)₀₋₁—NHC(=Y¹)N(R¹ᵇ)(R¹ᵃ), —(X¹)₀₋₁—N(R¹'')C(=Y¹)N(H)(R¹ᵃ), —(X¹)₀₋₁—N(R¹ᵃ)C(=Y¹)N(R¹ᵃ)(R¹ᵃ), —(X¹)₀₋₁—N(R¹ᵃ)C(=Y¹)NH₂, —(X¹)₀₋₁—OC(=Y¹)R¹ᵃ, —(X¹)₀₋₁—C(=Y¹)H, —(X¹)₀₋₁—C(=Y¹)OR¹ᵃ, —(X¹)₀₋₁—OP(=Y¹)(OR¹ᵃ)(OR¹ᵇ), —(X¹)—SC(=Y¹)OR¹ᵃ and —(X¹)—SC(=Y¹)N(R¹ᵃ)(R¹ᵇ). R² is optionally substituted and selected from the group consisting of hydrogen, —F, —Cl, —Br, —I, —CN, —NO₂, —SF₅, —OH, —NH₂, —N(H)(R¹ᵃ), —N(R¹ᵇ)(R¹ᵃ), —CF₃, C₁₋₆ alkyl, C₁₋₆ haloalkyl, C₁₋₆ heteroalkyl, C₁₋₆ alkoxy and C₁₋₆ alkylthio; and m is from 0 to 4.

In one embodiment, and within aspects of any of the preceding or subsequent embodiments, in compound of formula I of a subformula thereof, m is 0-2 and $R^{N3}$ is other than hydrogen.

In one embodiment, and within aspects of any of the preceding or subsequent embodiments, in compound of formula I of a subformula thereof, $A^1$ and $A^4$ are each C, $A^2$ is N and $A^3$ is $N(R^{N3})$; wherein m is from 0 to 4; $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-6}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=X^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^{1b})(R^{14})$, —$(X^1)_{0-1}$—$S(O)_{0-1}NH_2$, —$(X^1)_{0-1}$—$S(=O)(=NR^{1b})R^{1a}$, —$(X^1)_{0-1}$—$C(=Y^1)R^{1a}$, —$(X^1)_{0-1}$—$C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=Y^1)N(R^{1b})(R^{1a})$, —$(X^1)_{0-1}$—$N(R^{1a})C(=Y^1)N(H)(R^{1a})$, —$(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$C(=Y^1)R^{1a}$, —$(X^1)_{0-1}$—$OC(=Y^1)H$, —$(X^1)_{0-1}$—$OC(=Y^1)OR^{1a}$, —$(X^1)_{0-1}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})R^{N3}$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, C alkyl, $C_{1-6}$ haloalkyl, $C_{1-6}$ heteroalkyl, $C_{1-6}$ alkoxy, $C_{1-6}$ alkylthio.

In one embodiment, and within aspects of any of the preceding or subsequent embodiments, in compound of formula I of a subformula thereof, m is 1-2.

In one embodiment, and within aspects of any of the preceding or subsequent embodiments, in compound of formula I of a subformula thereof, $A^1$ and $A^4$ are each C and one of $A^2$ and $A^3$ is N and the other is S, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{14})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-6}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^{1b})(R^{1a})$, —$(X^1)_{0-1}$—$S(O)_{0-1}NH_2$, —$(X^1)_{0-1}$—$S(=O)(=NR^1)R^{1a}$, —$(X^1)_{0-1}$—$C(=Y^1)R^{1a}$, —$(X^1)_{0-1}$—$C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC$ $(=Y^1)N(R^{1b})(R^{1a})$, —$(X^1)_{0-1}$—$N(R^{1a})C(=Y^1)N(H)(R^{1a})$, $(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$OC(=Y^1)R^{1a}$, —$(X^1)_{0-1}$—$OC(=Y^1)H$, —$(X^1)_{0-1}$—$OC(=Y^1)OR^{1a}$, —$(X^1)_{0-1}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})$; and in additional occurrences of $R^2$, $R^2$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

In one embodiment, and within aspects of any of the preceding or subsequent embodiments, in compound of formula I of a subformula thereof, m is 1-4.

In one embodiment, and within aspects of any of the preceding or subsequent embodiments, in compound of formula I of a subformula thereof, $A^1$ and $A^2$ are each N, $A^3$ is $C(R^{43})$ and $A^4$ is N; wherein $R^{43}$ is optionally substituted and selected from the group consisting of consisting of hydrogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-40}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, $(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, $(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^1NR^{1a})$, —$(X^1)_{0-1}$—$S(O)_{0-1}NH_2$,—$(X^1)_{0-1}$—$S(=O)(=NR^{1b})R^{1a}$, $(X^1)_{0-1}$—$OC(=Y^1)R^{1a}$, $(X^1)_{0-1}$—$C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=Y^1)N(R^{1b})(R^{1a})$, —$(X^1)_{0-1}$—$N(R^{1a})C(=Y^1)N(H)(R^{1a})$, $(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$OC(=Y^1)R^{1a}$, —$(X^1)_{0-1}$—$OC(=Y^1)H$, —$(X^1)_{0-1}$—$C(=Y^1)OR^{1a}$, —$(X^1)_{0-1}$—$P(=Y^1)(OR^{1a})(OR^{1b})$, —$(X^1)$—$SC(=Y^1)OR^{1a}$ and —$(X^1)$—$SC(=Y^1)N(R^{1a})(R^{1b})$; $R^2$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

In one embodiment, and within aspects of any of the preceding or subsequent embodiments, in compound of formula I of a subformula thereof, m is 0-2 and $R^{N3}$ is other than hydrogen.

In one embodiment, and within aspects of any of the preceding or subsequent embodiments, in compound of formula I of a subformula thereof, $A^1$ and $A^2$ are each N, $A^3$ is $C(R^{43})$ and $A^4$ is N; wherein m is from 0 to 4; $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X)_{0-1}$—$N(R^{1b})(R^{1a})$, $(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio,—$(X^1)_{0-1}$—$C_{3-40}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N$ $(R^{1a})(R^{1b})$, —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}$NH$_2$, —$(X^1)_{0-1}$—S(=O)(=N$R^{1b}$)$R^{1a}$, $(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=NO$R^{1b}$)$R^{1a}$, —$(X^1)_{0-1}$—NHC(=$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), $(X^1)_{0-1}$—N($R^{1a}$)(=$Y^1$)N($R^{1b}$)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH$_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$). $R^{N3}$ is optionally substituted and selected from the group consisting of hydrogen, —F, —Cl, —Br, —I, —CN, —NO$_2$, —SF$_5$, —OH, —NH$_2$, —N(H)($R^{1a}$), —N($R^{1b}$)($R^{1a}$), —CF$_3$, $C_{1-6}$ alkyl, $C_{1-6}$ haloalkyl, $C_{1-6}$ heteroalkyl, $C_{1-6}$ alkoxy, $C_{1-6}$ alkylthio.

In one embodiment, and within aspects of any of the preceding or subsequent embodiments, in compound of formula I of a subformula thereof, m is 1-2.

In one embodiment, and within aspects of any of the preceding or subsequent embodiments, in compound of formula I of a subformula thereof, wherein $A^1$, $A^4$ are each C, $A^2$ is S and $A^3$ is C($R^{A3}$); wherein $R^{A3}$ is optionally substituted and selected from the group consisting of consisting of hydrogen, —$(X^1)_{0-1}$—CN, —$(X^1)_{0-1}$—NO$_2$, —$(X)_{0-1}$—SF$_5$, —$(X)_{0-1}$—NH$_2$, —$(X^1)_{0-1}$—N(H)($R^{1a}$), —$(X^1)_{0-1}$—N($R^{1b}$)($R^{1a}$), —$(X^1)_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X)_{0-1}$—C(=$Y^1$)N(H)($R^{1a}$), —$(X^1)_{0-1}$—C(=$Y^1$)NH$_2$, —$(X^1)_{0-1}$—C(=$Y^1$)N($R^{1a}$)($R^{1b}$), $(X^1)_{0-1}$—C(=$Y^1$)O$R^{1a}$, $(X^1)_{0-1}$—C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}$NH$_2$, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X)_{0-1}$—C(=NO$R^{1b}$)$R^{1a}$, —$(X^1)_{6-1}$—NHC(=$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH$_2$, —$(X^1)_{0-1}$—C(=$Y^1$)$R^{1a}$, —$(X^1)_{0-1}$—OC(=$Y^1$)H, —$(X^1)_{0-1}$—OC(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$); $R^2$ is optionally substituted and selected from the group consisting of hydrogen, —F, —Cl, —Br, —I, —CN, —NO$_2$, —SF$_5$, —OH, —NH$_2$, —N(H)($R^{1a}$), —N($R^{1b}$)($R^{1a}$), —CF$_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

In one embodiment, and within aspects of any of the preceding or subsequent embodiments, in compound of formula I of a subformula thereof, m is 0-2 and $R^{N3}$ is other than hydrogen.

In one embodiment, and within aspects of any of the preceding or subsequent embodiments, in compound of formula I of a subformula thereof, $A^1$, $A^4$ are each C, $A^2$ is S and $A^3$ is C($R^{A3}$); wherein m is from 0 to 4; $R^2$ is optionally substituted and selected from the group consisting of consisting of —F, —Cl, —Br, —I, —$(X^1)_{0-1}$—CN, —$(X^1)_{0-1}$—NO$_2$, —$(X^1)_{0-1}$—SF$_5$, —$(X^1)_{0-1}$—OH, —$(X^1)_{0-1}$—NH$_2$, —$(X^1)_{0-1}$—N(H)($R^{1a}$), —$(X^1)_{0-}$—N($R^{1b}$)($R^{1a}$), —$(X^1)_{0-1}$—CF$_3$, Cl_6 alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)NH$_2$, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-4}$—N($R^{1b}$)C(=$Y^1$)O$R^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}$NH$_2$, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=NO$R^{1b}$)$R^{1a}$, —$(X^1)_{0-1}$—NHC(=$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH$_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$). $R^{N3}$ is optionally substituted and selected from the group consisting of hydrogen, —F, —Cl, —Br, —I, —CN, —NO$_2$, —SF$_5$, —OH, —NH$_2$, —N(H)($R^{1a}$), —N($R^{1b}$)($R^{1a}$), —CF$_3$, $C_{1-6}$ alkyl, $C_{1-6}$ haloalkyl, $C_{1-6}$ heteroalkyl, $C_{1-6}$ alkoxy, $C_{1-6}$ alkylthio.

In one embodiment, and within aspects of any of the preceding or subsequent embodiments, in compound of formula I of a subformula thereof, m is 1-2.

In one embodiment, and within aspects of any of the preceding or subsequent embodiments, in compound of formula I of a subformula thereof, wherein $A^1$ is C, $A^2$ and $A^4$ are each N and $A^3$ is C($R^{A3}$); wherein $R^{A3}$ is optionally substituted and selected from the group consisting of consisting of hydrogen, —$(X^1)_{0-1}$—CN, —$(X^1)_{0-1}$—NO$_2$, —$(X^1)_{0-1}$—SF$_5$, —$(X^1)_{0-1}$—OH, —$(X^1)_{0-1}$—NH$_2$, —$(X^1)_{0-1}$—N(H)($R^{14}$), —$(X^1)_{0-1}$—N($R^{1b}$)($R^{1a}$), —$(X^1)_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)NH$_2$, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)O$R^{1a}$, —$(X^1)_{0-4}$—N($R^{1b}$)C(=$Y^1$)($R^{1a}$), —$(X^1)_{0-1}$—N($R^{1b}$)C(=Y)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)O$_{0-1}$—NH$_2$, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{4a}$, —$(X^1)_{0-1}$—C(=NO$R^{4b}$)$R^{1a}$, —$(X^1)_{0-1}$—NHC(=—$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH$_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)O$R^{1a}$, —OF(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$). $R^2$ is optionally substituted and selected from the group consisting of hydrogen, —F, —Cl, —Br, —I, —CN, —NO$_2$, —SF$_5$, —OH, —NH$_2$, —N(H)($R^{1a}$), —N($R^{1b}$)

($R^{1a}$), —$CF_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

In one embodiment, and within aspects of any of the preceding or subsequent embodiments, in compound of formula I of a subformula thereof, m is 0-2 and $R^{N3}$ is other than hydrogen.

In one embodiment, and within aspects of any of the preceding or subsequent embodiments, in compound of formula I of a subformula thereof, $A^1$ is C, $A^2$ and $A^4$ are each N and $A^3$ is C($R^{A3}$), wherein m is from 0 to 4; $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-6}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=Y)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)$OR^{1a}$, —$(X^1)_{0-1}$—N($R^{1b}$)C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)($R^{1a}$), —$(X^1)_{0-1}$—NHC(=$Y^1$)$NH_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)$NH_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)$OR^{1a}$, —$(X^1)_{0-1}$—OP(=$Y^1$)($OR^{1a}$)($OR^{1b}$), —$(X^1)$—SC(=$Y^1$)$OR^{1a}$ and —$(X^1)$—SC(=$Y^1$)N($R^{1a}$)($R^{1b}$). $R^{N3}$ is optionally substituted and selected from the group consisting of hydrogen, —F, —Cl, —Br, —I, —CN, —$NO_2$, —$SF_5$, —OH, —$NH_2$, —N(H)($R^{1a}$), —N($R^{1b}$)($R^{1a}$), —$CF_3$, $C_{1-6}$ alkyl, $C_{1-6}$ haloalkyl, $C_{1-6}$ heteroalkyl, $C_{1-6}$ alkoxy, $C_{1-6}$ alkylthio.

In one embodiment, and within aspects of any of the preceding or subsequent embodiments, in compound of formula I of a subformula thereof, m is 1-2.

In one embodiment, and within aspects of any of the preceding or subsequent embodiments, in compound of formula I of a subformula thereof, $A^1$ is C and $A^2$, $A^3$ and $A^4$ are each N, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—OH, —$(X^1)_{0-1}$—$NH_2$, —$(X^1)_{0-1}$—N(H)($R^1$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)($R^{1a}$), —$(X)_{0-1}$—N($R^1$)C(=$Y^1$)($R^{1a}$), —$(X^1)_{0-1}$—N($R^{1b}$)C(=$Y^1$)(H), —$(X^1)_{0-1}$—N(H)C(=$Y^1$)$OR^{1a}$, —$(X^1)_{0-1}$—N($R^{1b}$)C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, $(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)($R^{1a}$), —$(X^1)_{0-1}$—NHC(=$Y^1$)$NH_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)$NH_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)$OR^{1a}$, —$(X^1)_{0-1}$—OP(=$Y^1$)($OR^{1a}$)($OR^{1b}$), —$(X^1)$—SC(=$Y^1$)$OR^{1a}$ and —$(X^1)$—SC(=$Y^1$)N($R^{1a}$)($R^{1b}$); and in additional occurrences of $R^2$, $R^2$ is optionally substituted and selected from the group consisting of hydrogen, —F, —Cl, —Br, —I, —CN, —$NO_2$, —$SF_5$, —OH, —$NH_2$, —N(H)(O), —N($R^{1b}$)($R^{1a}$), —$CF_3$, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

In one embodiment, and within aspects of any of the preceding or subsequent embodiments, in compound of formula I of a subformula thereof, $A^1$ and $A^4$ are each C and $A^2$ is $CR^{A2}$ are and $A^3$ is S, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, alkoxy, $C_{1-6}$ alkylthio, —$(X^1)_{0-1}$—$C_{3-10}$cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$X^1$)N($R^{1a}$)($R^{1b}$), —$(X^1)_{0-1}$—C(=$Y^1$)$OR^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)$OR^{1a}$, —$(X^1)_{0-1}$—N($R^{1b}$)C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^{1a}$)$R^{1a}$, —$(X^1)_{0-1}$—C(=$Y^1$)H, —$(X^1)_{0-1}$—C(=NOH)$R^{1a}$, —$(X^1)_{0-1}$—C(=$NOR^{1b}$)$R^{1a}$, —$(X^1)_{0-1}$—NHC(=$Y^1$)N(H)($R^{1a}$), —$(X^1)_{0-1}$—NHC(=$Y^1$)$NH_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)$NH_2$, —$(X)_{0-1}$—OC(=$Y^1$)$R^{1a}$, —$(X^1)_{0-1}$—C(=$Y^1$)H, —$(X^1)_{0-1}$—C(=$Y^1$)$OR^{1a}$, —$(X^1)_{0-1}$—OP(=$Y^1$)($OR^{1a}$)($OR^{1b}$), —$(X^1)$—SC(=$Y^1$)$OR^{1a}$ and —$(X^1)$—SC(=$Y^1$)N($R^{1a}$)($R^{1b}$); and in additional occurrences of $R^2$, $R^2$ is optionally substituted and selected from the group consisting of hydrogen, —F, —Cl, —Br, —I, —CN, —$NO_2$, —$SF_5$, —OH, —$NH_2$, —N(H)($R^{1a}$), —N($R^{1b}$)($R^{1a}$), —$CF_3$, $C_{1-6}$ alkyl, $C_{1-6}$ haloalkyl, heteroalkyl, $C_{1-6}$ alkoxy, $C_{1-6}$ alkylthio and is optionally substituted.

In one embodiment, and within aspects of any of the preceding or subsequent embodiments, in compound of formula I of a subformula thereof, m is 1-4.

In one embodiment, and within aspects of any of the preceding or subsequent embodiments, in compound of formula I of a subformula thereof, $Y^1$ is O.

In one embodiment, and within aspects of any of the preceding or subsequent embodiments, in compound of formula I of a subformula thereof, $R^7$ at each occurrence is optionally substituted and independently selected from the group consisting of hydrogen, $C_{1-6}$ alkyl, $C_{1-6}$ haloalkyl, 3-10 membered heterocycloalkyl, 5-10 membered heteroaryl or —C(=O)$NR^{7a}R^{7b}$; and $R^8$ at each occurrence is independently selected from the group consisting of hydrogen $C_{1-6}$ alkyl, $C_{1-6}$ haloalkyl or —$CH_2$—OH.

In one embodiment, and within aspects of any of the preceding or subsequent embodiments, in compound of formula I of a subformula thereof, $R^7$ is optionally substituted and selected from the group consisting of: furan, oxazole, isoxazole, oxadiazole, pyrrole, pyrazole, imidazole, triazole, tetrazole, thiazole, thiadiazole, thiophene, pyridine, pyrimidine, pyridazine, pyrazine, indole, indazole, indole, 1H-pyrrolo[2,3-b]pyridine, 1H-pyrrolo[2,3-c]pyridine, 1H-pyrrolo[3,2-c]pyridine, 1H-pyrrolo[3,2-b]pyridine, 5H-pyrrolo[3,2-d]pyrimidine, 7H-pyrrolo[2,3-d]pyrimidine, 5H-pyrrolo[2,3-b]pyrazine, benzimidazole, benzofuran and benzothiophene.

In one embodiment, and within aspects of any of the preceding or subsequent embodiments, in compound of formula I of a subformula thereof, $R^7$ is optionally substituted and selected from the group consisting of: furan, oxazole, isoxazole, oxadiazole, pyrrole, pyrazole, imidazole, triazole, tetrazole, thiazole, thiophene, pyridine, pyrimidine, pyridazine, pyrazine, indole, indazole, indole, 1H-pyrrolo[2,3-b]pyridine, 1H-pyrrolo[2,3-c]pyridine, 1H-pyrrolo[3,2-c]pyridine, 1H-pyrrolo[3,2-b]pyridine, 5H-pyrrolo[3,2-d]pyrimidine, 7H-pyrrolo[2,3-d]pyrimidine, 5H-pyrrolo[2,3-b]pyrazine, benzimidazole, benzofuran and benzothiophene.

In one embodiment, and within aspects of any of the preceding or subsequent embodiments, in compound of formula I of a subformula thereof, $R^7$ is optionally substituted and selected from the group consisting of: oxazole, isoxazole, 1,2,4-oxadiazole, 1,2,5-oxadiazole, thiazole, thiazole, 1,3,4-thiadiazole, imidazole, pyrazole, triazole, pyrimidine, pyridazine, pyrazine, pyridine, 2H-1,2,3-triazole, 1H-1,2,4-triazole.

In one embodiment, and within aspects of any of the preceding or subsequent embodiments, in compound of formula I of a subformula thereof, $R^7$ is optionally substituted and selected from the group consisting of: oxazole, isoxazole, 1,2,4-oxadiazole, 1,2,5-oxadiazole, thiazole, thiazole, imidazole, pyrazole, triazole, pyrimidine, pyridazine, pyrazine, pyridine, 2H-1,2,3-triazole, 1H-1,2,4-triazole.

In one embodiment, and within aspects of any of the preceding or subsequent embodiments, in compound of formula I of a subformula thereof, $R^7$ is optionally substituted with from 1 to 5 substituents selected from the group consisting of F, Cl, Br, —OH, $C_{1-6}$ alkyl, $C_{1-6}$ haloalkyl, —$(X^7)_{0-1}$—CN, —$(X^7)_{0-1}$—OH, —$(X^7)_{0-1}$—H and —$(X^7)_{0-1}$—OR$^a$.

In one embodiment, and within aspects of any of the preceding or subsequent embodiments, in compound of formula I of a subformula thereof, $R^7$ is selected from the group consisting of:

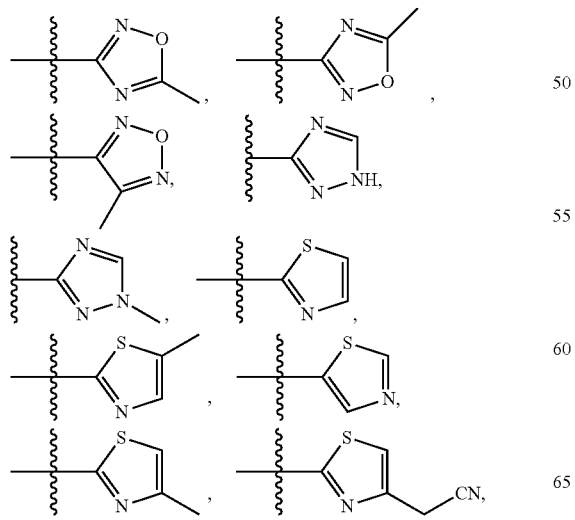

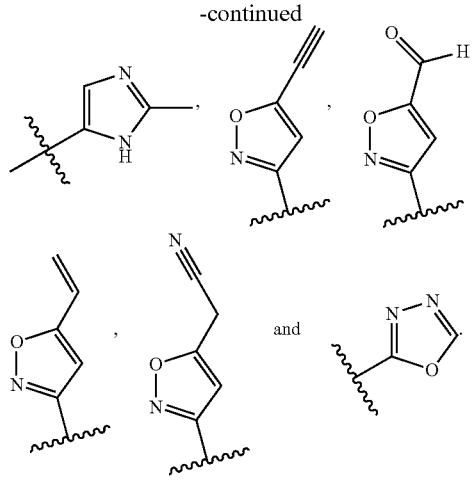

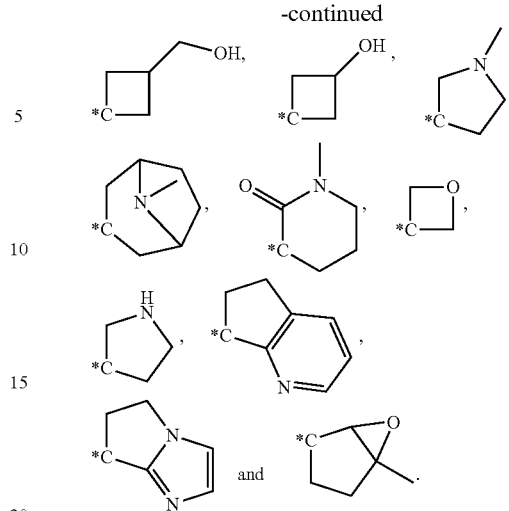

In one embodiment, and within aspects of any of the preceding or subsequent embodiments, in compound of formula I of a subformula thereof, $R^7$ is selected from the group consisting of methyl, ethyl hydroxymethyl, fluoromethyl, difluoromethyl, trifluoromethyl, methoxymethyl, cyanomethyl, cyclopropyl, 3-hydroxycyclobut-1-yl cyclopropylmethyl, isopropyl and 1-hydroxyeth-1-yl.

In one embodiment, and within aspects of any of the preceding or subsequent embodiments, in compound of formula I of a subformula thereof, $R^7$ and $R^8$ are combined with the carbon atom to each is attached to form an optionally substituted $C_{3-10}$ cycloalkyl or $C_{2-9}$ heterocycloalkyl, and wherein optionally fused to said $C_{3-10}$ cycloalkyl and $C_{2-9}$ heterocycloalkyl is a 6 membered aryl or 5-6 membered heteroaryl ring.

In one embodiment, and within aspects of any of the preceding or subsequent embodiments, in compound of formula I of a subformula thereof, $R^7$ and $R^8$ are combined with the carbon atom to each is attached to form an optionally substituted cyclopropane, cyclobutane, cyclopentane, oxetane, piperidine, pyrrolidine, pyrrolidinone, valerolactam, caprolactam, tetrahydrofuran, teterhydropyran, 6,7-dihydro-5H-cyclopenta[b]pyridine, bicyclo[2.2.1]heptane, 8-azabicyclo[3.2.1]octane and 6-oxabicyclo[3.2.1]hexane.

In one embodiment, and within aspects of any of the preceding or subsequent embodiments, in compound of formula I of a subformula thereof, $R^7$ and $R^8$ are combined with the carbon atom in Formula I (denoted as "*C" below) to which each is attached to form a ring selected from the group consisting of:

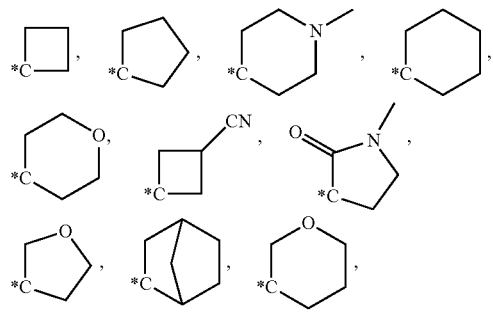

In one embodiment, and within aspects of any of the preceding or subsequent embodiments, in compound of formula I of a subformula thereof, n is 0.

In one embodiment, and within aspects of any of the preceding or subsequent embodiments, in compound of formula I of a subformula thereof, $R^4$, $R^5$ and $R^6$, if present, are each independently selected from the group consisting of hydrogen, methyl, trifluoromethyl, methoxy, OH, F, Cl, Br, I, CN and $NO_2$.

In one embodiment, and within aspects of any of the preceding or subsequent embodiments, in compound of formula I of a subformula thereof, $R^4$, $R^5$ and $R^6$ are each independently selected from the group consisting of hydrogen, F, Cl, CN and $NO_2$.

In one embodiment, and within aspects of any of the preceding or subsequent embodiments, in compound of formula I of a subformula thereof, $R^4$, $R^5$ and $R^7$ are each independently selected from the group consisting of hydrogen, methyl, trifluoromethyl, methoxy, OH, F, Cl, Br, I, CN and $NO_2$.

In one embodiment, and within aspects of any of the preceding or subsequent embodiments, in compound of formula I of a subformula thereof, m is 0 and $R^{43}$ and $R^{N3}$, if present, is hydrogen.

In one embodiment, and within aspects of any of the preceding or subsequent embodiments, in compound of formula I of a subformula thereof, $R^{43}$ and $R^{N3}$, if present, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)$C(=$Y^1$)$_{0-1}$—N($R^{1a}$)($R^{1b}$)$NH_2$, —$(X^1)_{0-1}$—C(=$Y^1$—$(X^1)_{0-1}$—C(=$Y^1$)$OR^{1a}$ and —$(X^1)_{0-1}$—C(=$Y^1$)OH.

In one embodiment, and within aspects of any of the preceding or subsequent embodiments, in compound of formula I of a subformula thereof, $R^{43}$ and $R^{N3}$, if present, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —($X^1$)$_{0-1}$-5-10 membered heteroaryl, —($X^1$)$_{0-1}$-6-10 membered aryl, —($X^1$)$_{0-1}$—C(=$Y^1$)N(H)($R^{1a}$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)OR$^{1a}$ and —($X^1$)$_{0-1}$—C(=$Y^1$)OH; and $R^2$ is optionally substituted and selected from the group consisting of hydrogen, —F, —Cl, —Br, —I, —($X^1$)$_{0-1}$—CN, —($X^1$)$_{0-1}$—OH, —($X^1$)$_{0-1}$—NH$_2$, —($X^1$)$_{0-1}$—N(H)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy and $C_{1-6}$ alkylthio; or in the alternative any two $R^2$ substituents attached to the same or different ring vertices in the B ring or a $R^1$ and $R^2$ substituent attached to different ring vertices in the B ring are optionally combined to for a 3-6 membered carbocyclic or heterocyclic ring comprising 1 to 2 heteroatoms selected from N, O and S, and wherein said 3-7 membered carbocyclic or heterocyclic ring is optionally substituted.

In one embodiment, and within aspects of any of the preceding or subsequent embodiments, in compound of formula I of a subformula thereof, m is 0 and $R^{43}$ and $R^{N3}$, if present, is selected from the group consisting of —F, —Cl, —Br, —I, —($X^1$)$_{0-1}$—CN, —($X^1$)$_{0-1}$—SF$_5$, —($X^1$)$_{0-1}$—OH, —($X^1$)$_{0-1}$—NH$_2$, —($X^1$)$_{0-1}$—N($R^{1b}$)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^1$)$_{0-1}$—$C_{3-10}$ cycloalkyl, —($X^1$)$_{0-1}$—$C_{2-9}$ heterocycloalkyl, —($X^1$)$_{0-1}$-5-10 membered heteroaryl, —($X^1$)$_{0-1}$-6-10 membered aryl, —($X^1$)$_{0-1}$—C(=$Y^1$)N(H)($R^{1a}$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)OR$^{1a}$ and —($X^1$)$_{0-1}$—C(=$Y^1$)OH.

In one embodiment, and within aspects of any of the preceding or subsequent embodiments, in compound of formula I of a subformula thereof, $R^{43}$ and $R^{N3}$, if present, is selected from the group consisting of hydrogen, —F, —Cl, —Br, —I, —($X^1$)$_{0-1}$—CN, —($X^1$)$_{0-1}$—NO$_2$, —($X^1$)$_{0-1}$—SF$_5$, —($X^1$)$_{0-1}$—OH, —($X^1$)$_{0-1}$—NH$_2$, —($X^1$)$_{0-1}$—N(H)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio; m is 1 to 2; and $R^2$ is at each occurrence, independently selected from the group consisting of —F, —Cl, —Br, —I, —($X^1$)$_{0-1}$—CN, —($X^1$)$_{0-1}$—OH, —($X^1$)$_{0-1}$—NH$_2$, —($X^1$)$_{0-1}$—N(H)($R^{1a}$), —($X^1$)$_{0-1}$—NR$^1$NR$^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^1$)$_{0-1}$—$C_{3-40}$ cycloalkyl, —($X^1$)$_{6-1}$—$C_{2-6}$ heterocycloalkyl, —($X^1$)$_{0-1}$-5-10 membered heteroaryl, —($X^1$)$_{0-1}$-6-10 membered aryl, —($X^1$)$_{0-1}$—C(=$Y^1$)N(H)($R^{1a}$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)OR$^{1a}$ and —($X^1$)$_{0-1}$—C(=$Y^1$)OH.

In one embodiment, and within aspects of any of the preceding or subsequent embodiments, in compound of formula I of a subformula thereof, $R^{43}$ and $R^{N3}$, if present, is hydrogen and m is 1 to 2 and $R^2$ is at each occurrence, independently selected from the group consisting of —F, —Cl, —Br, —I, —($X^1$)$_{0-1}$—CN, —($X^1$)$_{0-1}$—SF$_5$, —($X^1$)$_{0-1}$—OH, —($X^1$)$_{0-1}$—NH$_2$, —($X^1$)$_{0-1}$—N(H)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^1$)$_{0-1}$—$C_{3-10}$ cycloalkyl, —($X^1$)$_{0-1}$—$C_{2-9}$ heterocycloalkyl, —($X^1$)$_{0-1}$-5-10 membered heteroaryl, —($X^1$)$_{0-1}$-6-10 membered aryl, —($X^1$)$_{0-1}$—C(=$Y^1$)N(H)($R^{1a}$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)OR$^{1a}$ and —($X^1$)$_{0-1}$—C(=$Y^1$)OH.

In one embodiment, and within aspects of any of the preceding or subsequent embodiments, in compound of formula I of a subformula thereof, $R^2$, at its first occurrence, is selected from the group consisting of —F, —Cl, —Br, —I, —($X^1$)$_{0-1}$—CN, —($X^1$)$_{0-1}$—SF$_5$, —($X^1$)$_{0-1}$—OH, —($X^1$)$_{0-1}$—NH$_2$, —($X^1$)$_{0-1}$—N(H)($R^{1a}$), —($X^1$)$_{0-1}$—N($R^{1b}$)($R^{1a}$), —($X^1$)$_{0-1}$—CF$_3$, $C_{1-6}$ alkyl, $C_{1-6}$ haloalkyl, $C_{1-6}$ heteroalkyl, $C_{1-6}$ alkoxy, $C_{1-6}$ alkylthio, —($X^1$)$_{0-1}$—$C_{3-10}$ cycloalkyl, —($X^1$)$_{0-1}$—$C_{2-9}$ heterocycloalkyl, —($X^1$)$_{0-1}$-5-10 membered heteroaryl, —($X^1$)$_{0-1}$-6-10 membered aryl, —($X^1$)$_{0-1}$—C(=$Y^1$)N(H)($R^{1a}$), —($X^1$)$_{0-1}$—C(=$Y^1$)NH$_2$, —($X^1$)$_{0-1}$—C(=$Y^1$)N($R^{1a}$)($R^{1b}$), —($X^1$)$_{0-1}$—C(=$Y^1$)OR$^{1a}$ and —($X^1$)$_{0-1}$—C(=$Y^1$)OH.

In one embodiment, and within aspects of any of the preceding or subsequent embodiments, in compound of formula I of a subformula thereof, $X^1$ is absent, or $X^1$ is $C_{1-4}$ alkylene, $C_{1-4}$ alkyleneoxy, $C_{2-4}$ alkenylene, $C_{2-4}$ alkynylene, $C_{1-4}$ haloalkylene and 5-6 membered heteroarylene, and wherein $X^1$ is optionally substituted with from 1-2 $R^{1/2}$ groups.

In one embodiment, and within aspects of any of the preceding or subsequent embodiments, in compound of formula I of a subformula thereof, $X^1$ is absent, or $X^1$ is methylene, ethylene, propylene, methyleneoxy.

In one embodiment, and within aspects of any of the preceding or subsequent embodiments, in compound of formula I of a subformula thereof, $X^1$ is absent, or $X^1$ is optionally substituted and is selected from the group consisting of pyrrole, pyrazole, triazole, imidazole, tetrazole, oxazole, oxadiazole, thiazole and thiadiazole.

In one embodiment, and within aspects of any of the preceding or subsequent embodiments, in compound of formula I of a subformula thereof, $Y^1$ is O.

In one embodiment, and within aspects of any of the preceding or subsequent embodiments, in compound of Formula I, I-A, I-A$^1$-I-A$^{10}$ or II-A$^1$-II-A$^{10}$, any two $R^2$ substituents attached to the same or different ring vertices in the B ring are combined to form a 3 to 6 membered carbocyclic are heterocyclic ring and is substituted with from 1 to 2 $R^{1/2}$ substituents.

In one embodiment, and within aspects of any of the preceding or subsequent embodiments, in compound of formula I of a subformula thereof, $R^1$, $R^2$ in its first occurrence, $R^{43}$ and $R^{N3}$, each if present, is independently selected from the group consisting of:

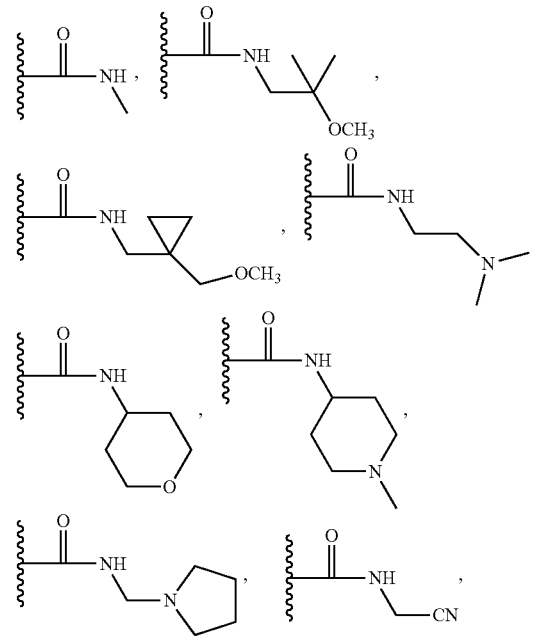

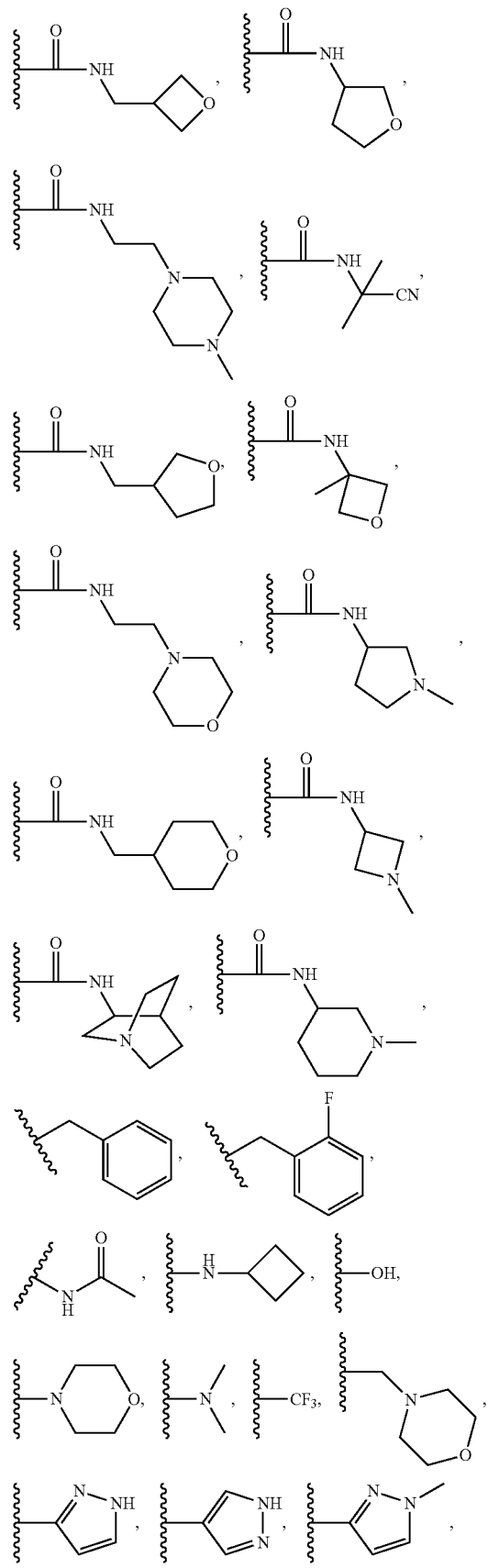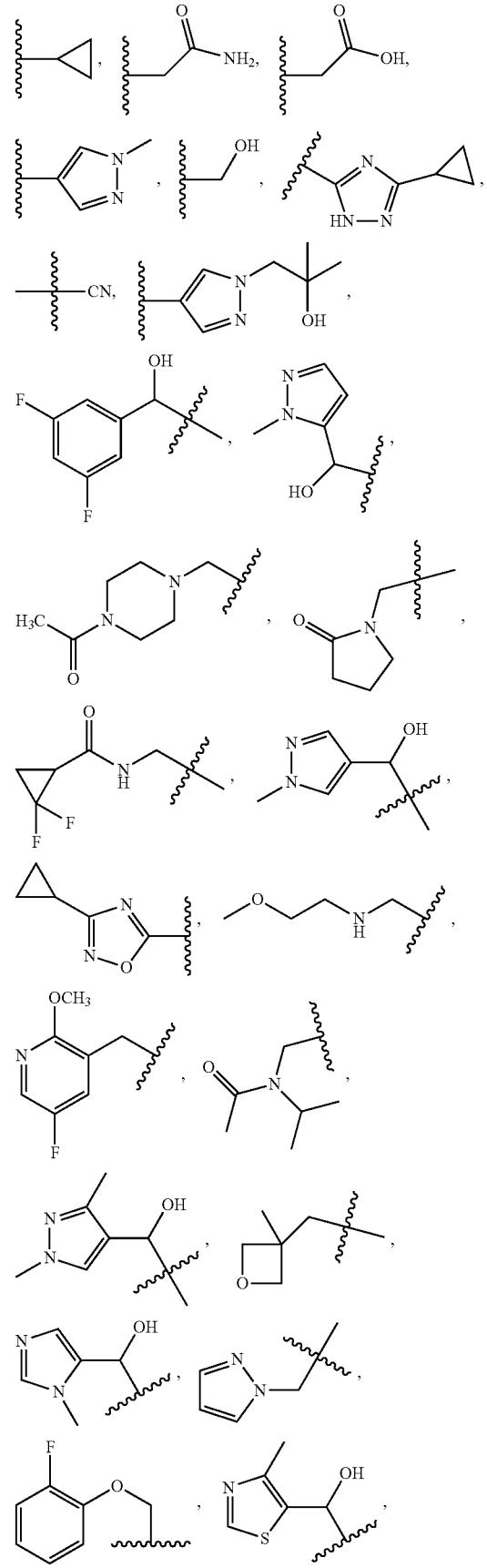

-continued

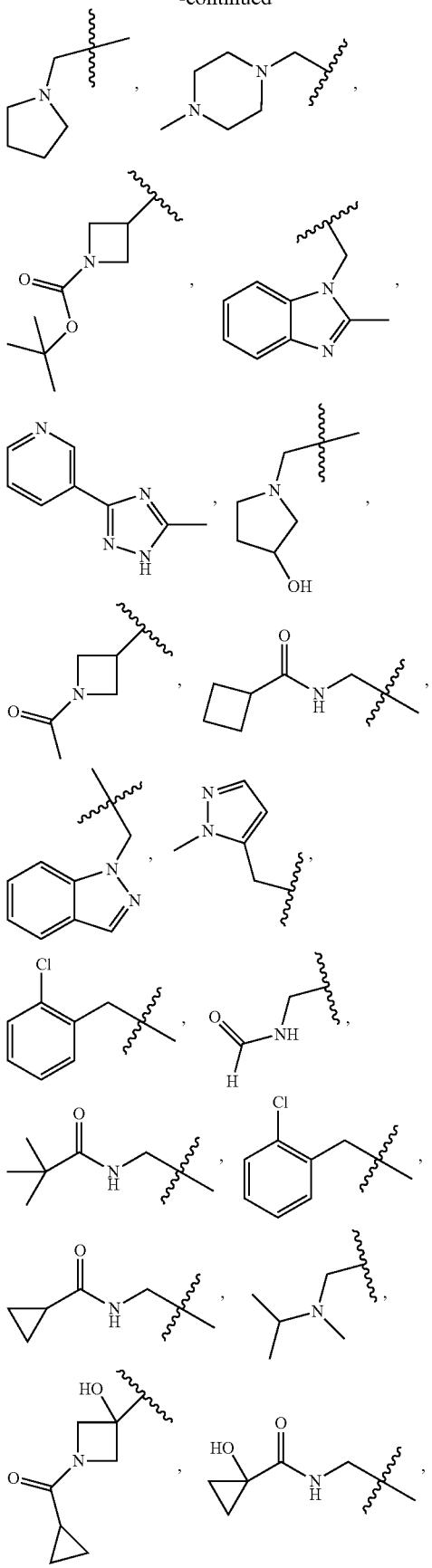

-continued

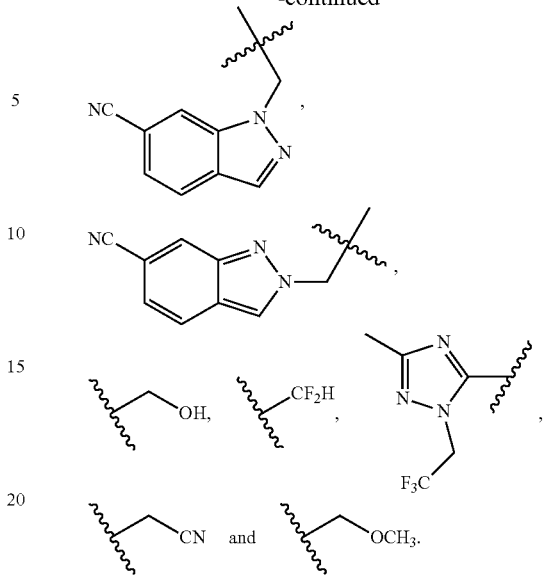

In one embodiment, and within aspects of any of the preceding or subsequent embodiments, in compound of formula I of a subformula thereof, wherein said compounds of the invention are selected from the group as set forth in Table 1 below:

In another aspect, the invention provides for compound intermediates useful in synthesis of compounds of Formula I (or stereoisomers, geometric isomers, tautomers, solvates, metabolites, isotopes, pharmaceutically acceptable salts, or prodrugs thereof).

In another aspect, the invention provides for pharmaceutical compositions comprising a compound of Formula I (or stereoisomers, geometric isomers, tautomers, solvates, metabolites, isotopes, pharmaceutically acceptable salts, or prodrugs thereof) and a therapeutically inert carrier.

In another aspect, the invention provides for a method (and/or use) of compounds of Formula I in the treatment of diseases and disorders, such as, for example, cancer, inflammatory diseases, autoimmune diseases, among others.

In another aspect, the invention provides for compounds of Formula I for the preparation of a medicament for the treatment of cancer, inflammatory diseases, autoimmune diseases, among others.

In another aspect, the inventions provides for compounds of Formula I for the treatment of diseases and disorders, including, cancer, inflammatory disease, autoimmune disease, among others.

DETAILED DESCRIPTION OF THE INVENTION

The invention provides a for compounds of Formula I, pharmaceutical compositions comprising compounds of Formula I and methods of using such compounds and compositions in treating diseases and disordered related to undesired or overactivation of NF-kB signaling pathway, such as, for example, certain cancers and inflammatory diseases and disorders.

Definitions

As used herein, the term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds. Similarly, the term "alkynyl" refers to an unsaturated alkyl radical having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl," "carbocyclic," or "carbocycle" refers to hydrocarbon ring system having 3 to 10 overall number of ring atoms (e.g., 3-10 membered cycloalkyl is a cycloalkyl with 3 to 10 ring atoms, or $C_{3-10}$ cycloalkyl is a cycloalkyl with 3-10 carbon ring atoms) and for a 3-5 membered cycloalkyl being fully saturated or having no more than one double bond between ring vertices and for a 6 membered cycloalkyl or larger being fully saturated or having no more than two double bonds between ring vertices. The monocyclic or polycyclic ring may be optionally substituted with one or more oxo groups. The terms "cycloalkyl," "carbocyclic," or "carbocycle" also include polycyclic ring systems wherein the ring radical attached to the remainder of the molecule is a saturated or partially unsaturated ring as defined above and wherein such polycyclic ring systems can also include fused aryl rings and fused heteroaryl rings as defined herein within the polycyclic ring systems. As used herein, "cycloalkyl," "carbocyclic," or "carbocycle" is also meant to refer to bicyclic, polycyclic and spirocyclic hydrocarbon ring system, such as, for example, bicyclo[2.2.1]heptane, pinane, bicyclo[2.2.2]octane, adamantane, norborene, spirocyclic $C_{5-12}$ alkane, etc. As used herein, the terms, "alkenyl," "alkynyl," "cycloalkyl,", "carbocycle," and "carbocyclic," are meant to include mono and polyhalogenated variants thereof and can be optionally substituted with for example =O. The term "cycloalkylene" by itself or as part of another substituent means a divalent radical derived from a cycloalkyl, carbocyclic or carbocycle group.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation, and also include mono- and poly-halogenated variants, or combinations thereof. Examples include —CH$_2$—CH$_2$—O—CH$_3$, —CH$_2$—CH$_2$—O—CF$_3$, —CH$_2$—CH$_2$—NH—CH$_3$, —CH$_2$—CH$_2$—N(CH$_3$)—CH$_3$, —CH$_2$—S—CH$_2$—CH$_3$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH=N(CH$_3$)—CH$_3$. Up to two heteroatoms can be consecutive, such as, for example, —CH$_2$—NH—OCH$_3$ and —CH$_2$—O—Si(CH$_3$)$_3$. The term "hydroxyalkyl" as used herein includes alkyl groups substituted with one or more hydroxyl groups.

The term "heterocycloalkyl," "heterocyclic," or "heterocycle" refers to a saturated or partially unsaturated ring system radical having the overall having from 3-10 ring atoms (e.g., 3-10 membered heterocycloalkyl is a heterocycloalkyl radical with 3-10 ring atoms, a $C_{2-9}$ heterocycloalkyl is a heterocycloalkyl having 3-10 ring atoms with between 2-9 ring atoms being carbon) that contain from one to five heteroatoms selected from N, O, and S, wherein the nitrogen and sulfur atoms are optionally oxidized, nitrogen atom(s) are optionally quaternized, as ring atoms. The terms "heterocycloalkyl," "heterocyclic," and "heterocycle" also include polycyclic ring systems wherein the ring radical attached to the remainder of the molecule is a saturated or partially unsaturated ring that contains from one to five heteroatoms selected from N, O, and S, as defined above and wherein such polycyclic ring systems can also include fused aryl rings and fused heteroaryl rings as defined herein within the polycyclic ring systems. Unless otherwise stated, a "heterocycloalkyl," "heterocyclic," or "heterocycle" ring can be a monocyclic, a bicyclic, spirocyclic or a polycylic ring system. Non limiting examples of "heterocycloalkyl," "heterocyclic," or "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like A "heterocycloalkyl," "heterocyclic," or "heterocycle" group can be attached to the remainder of the molecule through one or more ring carbons or heteroatoms. A "heterocycloalkyl," "heterocyclic," or "heterocycle" can include mono- and polyhalogenated variants thereof and can be optionally substituted with for example =O. The term "heterocycloalkylene" by itself or as part of another substituent means a divalent radical derived from a heterocycloalkyl, heterocyclic or heterocycle group.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively. "Alkylene", "alkenylene" and "alkynylene" are also meant to include mono and poly-halogenated variants.

The term "heteroalkylene" by itself or as part of another substituent means a divalent radical, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$—O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like). The term "heteroalkylene" is also meant to include mono and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively, and further include mono- and poly-halogenated variants thereof. Additionally, for dialkylamino groups, the alkyl portions can be the same or different.

The terms "halo" or "halogen," by themselves or as part of another substituent, mean, unless otherwise stated, a fluorine, chlorine, bromine, or iodine atom. The term "(halo)alkyl" is meant to include both a "alkyl" and "haloalkyl" substituent.

Additionally, the term "haloalkyl," is meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, difluoromethyl, and the like. The term "(halo)alkyl" as used herein includes optionally halogenated alkyl. Thus the term "(halo)alkyl" includes both alkyl and haloalkyl (e.g., monohaloalkyl and polyhaloalkyl).

The term "aryl" means, unless otherwise stated, a polyunsaturated, typically aromatic, hydrocarbon ring radical, which can be a single ring or multiple rings (up to three rings) which are fused together and having the stated number of aryl ring atoms. The term "heteroaryl" refers to aryl ring(s) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indoliziinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from the group of acceptable substituents described further below.

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl, cycloalkyl and heterocycloalkyl) can be a variety of groups including, but not limited to, -halogen, —OR', —NR'R", —SR', —SiR'R"R''', —OC(O)R¹, —C(O)R¹, —CO₂R', —CONR'R", —OC(O)NR'R", —NR"C(O)R¹, —NR"C(O) NR'R", —NR"C(O)₂R¹, —NHC(NH₂)=NH, —NRC(NH₂) =NH, —NHC(NH₂)=NR', —NR'''C(NR'R")=N—CN, —NR'''C(NR'R")=NOR¹, —NHC(NH₂)=NR¹, —S(O)R', —S(O)₂R¹, —S(O)₂NR'R", —NR'S(O)₂R", —NR'''S(O)₂ NR'R", —CN, —NO₂, —(CH₂)₁₋₄—OR¹, —(CH₂)₁₋₄—NR'R", —(CH₂)₁₋₄—SR', —(CH)₁₋₄—SiR'R"R''', —(CH₂)₁₋₄—OC(O)R', —(CH₂)₁₋₄—C(O)R¹, —(CH₂)₁₋₄—CO₂R¹, —(CH₂)₁₋₄CONR'R", in a number ranging from zero to (2 m'+1), where m' is the total number of carbon atoms in such radical. R¹, R" and R''' each independently refer groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR¹, =N—CN, =NH, wherein R' include substituents as described above.

Similarly, substituents for the aryl and heteroaryl groups are varied and are generally selected from the group including, but not limited to, -halogen, —OR¹, —OC(O)R¹, —NR'R", —R¹, —CN, —NO₂, —CONR'R", —C(O)R¹, —OC(O)NR'R", —NR"C(O)R¹, —NR"C(O)₂R¹, —NR'C (O)NR"R''', —NHC(NH₂)=NH, —NR'C(NH₂)=NH, —NHC(NH₂)=NR',—S(O)R¹,—S(O)₂R¹,—S(O)₂NR'R", —NR'S(O)₂R", —N₃, perfluoro-$C_{1-4}$ alkoxy, and perfluoro-$C_{1-4}$ alkyl, —(CH₂)₁₋₄—OR', —(CH₂)₁₋₄—NR'R", —(CH₂)₁₋₄—SR'(—CH₂)SiR'R"R''', —(CH₂)₁₋₄—OC(O) R¹, —(CH₂)₁₋₄—C(O)R', —(CH₂)₁₋₄—CO₂R', —(CH₂)₁₋₄ CONR'R", in a number ranging from zero to the total number of open valences on the aromatic ring system; and where R', R" and R''' are independently selected from hydrogen, $C_{1-6}$ alkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms. When a substituent for the aryl or heteroaryl group contains an alkylene linker (e.g., —(CH₂)₁₋₄—NR'R"), the alkylene linker includes halo variants as well. For example, the linker "—(CH₂)₁₋₄—" when used as part of a substituent is meant to include difluoromethylene, 1,2-difluoroethylene, etc.

As used herein, the term "heteroatom" is meant to include oxygen (O), nitrogen (N), sulfur (S) and silicon (Si).

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "~~~" that intersects a bond in a chemical structure indicate the point of attachment of the atom to which the wavy bond is connected in the chemical structure to the remainder of a molecule, or to the remainder of a fragment of a molecule.

As used herein, the representation of a group (e.g., $X^d$) in parenthesis followed by a subscript integer range (e.g., $(X^d)_{0-2}$) means that the group can have the number of occurrences as designated by the integer range. For example, $(X^d)_{0-1}$ means the group $X^d$ can be absent or can occur one time.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy) ethyl, $(C_{1-6})$alkoxycarbonyloxymethyl, N—$(C_{1-6})$alkoxycarbonylaminomethyl, succinoyl, $(C_{1-6})$alkanoyl, alpha-amino $(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the present invention can also contain unnatural proportions of atomic isotopes at one or more of the atoms that constitute such compounds. For example, the present invention also embraces isotopically-labeled variants of the present invention which are identical to those recited herein, bur the for the fact that one or more atoms are replace by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2H$ ("D"), $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically labeled compounds of the present invention (e.g., those labeled with $^3H$ or $^{14}C$) are useful in compound and/or substrate tissue distribution assays. Tritiated ($^3H$) and carbon-14 ($^{14}C$) isotopes are useful for their ease of preparation and detectability. Further substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR). In the case of immunological disease, the therapeutic effective amount is an amount sufficient to decrease or alleviate an allergic disorder, the symptoms of an autoimmune and/or inflammatory disease (e.g. psoriasis or inflammatory bowel disease), or the symptoms of an acute inflammatory reaction (e.g. asthma). In some embodiments, a therapeutically effective amount is an amount of a chemical entity described herein sufficient to significantly decrease the activity or number of B-cells.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory disease or disorder" as used herein can refer to any disease, disorder, or syndrome in which an excessive or unregulated inflammatory response leads to excessive inflammatory symptoms, host tissue damage, or loss of tissue function.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses.

The terms "cancer" and "cancerous" refer to or describe the physiological condition in mammals that is typically characterized by unregulated cell growth and/or proliferation. A "tumor" comprises one or more cancerous cells. Examples of cancer include, but are not limited to, carcinoma, lymphoma, blastoma, sarcoma, and leukemia or lymphoid malignancies.

"Autoimmune disease" as used herein refers to any group of disorders in which tissue injury is associated with humoral or cell-mediated responses to the body's own constituents Compounds In one aspect the present invention provides for novel compounds. In a first embodiment of such compounds (Embodiment 1; abbreviated as "E1") the invention provides for compounds of Formula I E1: A compound of Formula I (I)

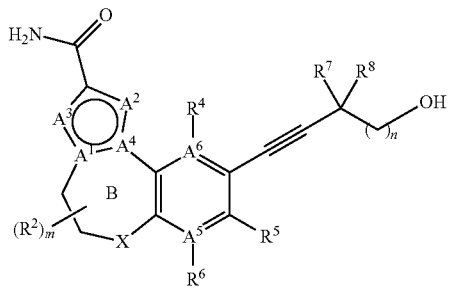

wherein
$A^1$, $A^2$, $A^3$ and $A^4$ are selected from group consisting of $A^1$, $A^2$, $A^3$ are each N and $A^4$ is C; $A^1$ and $A^2$ are each N, $A^3$ is $C(R^{A3})$ and $A^4$ is C; $A^1$ is C, $A^2$ is N, $A^3$ is $N(R^{N3})$ and $A^4$ is C; $A^1$ is C, $A^2$ is $N(R^{N2})$, $A^3$ is N and $A^4$ is C, wherein $R^{N2}$ is hydrogen, $C_{1-3}$ alkyl, $C_{1-3}$ haloalkyl, $C_{1-3}$ alkyl-C(=O)— or $C_{1-3}$ haloalkyl-C(=O)—; $A^1$ is C and one of $A^2$ and $A^3$ is N and the other is S and $A^4$ is C; $A^1$ is C, $A^2$ is S, $A^3$ is $C(R^{A3})$ and $A^4$ is C; $A^1$ is C, $A^2$ is N, $A^3$ and $A^4$ is N; $A^1$ is C, $A^2$ is N, $A^3$ is $C(R^{A3})$ and $A^4$ is N; $A^1$ is C, $A^2$ is $C(R^{C2})$, $A^3$ is S and $A^4$ is C, wherein $R^{C2}$ is hydrogen, halogen, $C_{1-3}$ alkyl, $C_{1-3}$ haloalkyl, $C_{1-3}$ alkyl-C(=O)— or $C_{1-3}$ haloalkyl-C(=O)—; and $A^1$ is C, $A^2$ and $A^3$ and $A^4$ are each N; $A^5$ and $A^6$ are each independently C or N; X is O or $C(R^1)_2$; m is an integer from 0 to 4; $R^1$, $R^2$ and $R^{A3}$ and $R^{N3}$ at each occurrence each is independently selected from the group consisting of hydrogen, —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —C(=O)($X^1$)$_{1-0}$—$C_{3-10}$ cycloalkyl, —C(=O)($X^1$), —$C_{2-9}$ heterocycloalkyl, =O, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), ($X^1)_{0-1}$—C(=$Y^1$)$OR^{1a}$, —$(X^1)_{0-1}$—C(=$Y^1$)N($X^1$)$_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)$OR^{1a}$, —$(X^1)_{0-1}$—N($R^{1b}$)C(=$Y^1$)$OR^{1a}$, —$(X^1)_{0-1}$—S(O)$_{1-2}R^{1a}$, —$(X^1)_{0-1}$—N(H)S(O)$_{1-2}R^{1a}$, —$(X^1)_{0-1}$—N($R^{1b}$)S(O)$_{1-2}R^{1a}$, —$(X^1)_{0-1}$—S(O)$_{0-1}$N(H)($R^{1a}$), —$(X^1)_{0-1}$—S(O)$_{0-1}$N($R^{1b}$)($R^{1a}$), —$(X^1)_{0-1}$—S(O)$_{0-1}NH_2$, —$(X^1)_{0-1}$—S(=O)(=$NR^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X^1)_{0-1}$—C(=NOR$^{1b}$)$R^{1a}$, —$(X^1)_{0-1}$—NHC(=$Y^1$)N(H)($R^{1a}$), —$(X^1)_{0-1}$—NHC(=$Y^1$)$NH_2$, —$(X^1)_{0-1}$—NHC(=$Y^1$)N($R^{1b}$)($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)$NH_2$, —$(X^1)_{0-1}$—OC(=$Y^1$)$R^{1a}$, —$(X^1)_{0-1}$—OC(=$Y^1$)H, —$(X^1)_{0-1}$—OC(=$Y^1$)$OR^{1a}$, —$(X^1)_{0-1}$—OP(=$Y^1$)(OR$^{1a}$)(OR$^{1b}$), —$(X^1)$—SC(=$Y^1$)$OR^{1a}$ and —$(X^1)$—SC(=$Y^1$)N($R^{1a}$)($R^{1b}$) wherein $X^1$ is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, $C_{1-4}$ alkyleneoxy, $C_{3-7}$ cycloalkylene and $C_{2-6}$ heterocycloalkylene, phenylene, 5-6 membered heteroarylene, $R^{1a}$ and $R^{1b}$ are each independently selected from the group consisting of $C_{1-6}$ alkyl, $C_{1-6}$ haloalkyl, $C_{1-6}$ heteroalkyl, $C_{3-7}$ cycloalkyl, $C_{3-7}$ cycloalkyl-$C_{1-4}$ alkyl, $C_{2-6}$ heterocycloalkyl, $C_{2-6}$ heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl, or $R^{1a}$ and $R^{1b}$ when attached to the same nitrogen atom are optionally combined to form a 3 to 7 membered heterocyclic ring comprising 0-2 additional heteroatoms selected from N, O and S; $Y^1$ is O, $NR^{1d}$ or S wherein $R^{1d}$ is hydrogen or $C_{1-6}$ alkyl; wherein any portion of $R^1$, $R^2$ and $R^{A3}$ and $R^{N3}$ substituent at each occurrence is each independently further substituted with from 0 to 4 $R^{1/2}$ substituents selected from the group consisting of —F, —Cl, —Br, —I, —CN, —$NO_2$, —$SF_5$, —OH, —$NH_2$, —N($C_{1-6}$ alkyl)$_2$, —NH($C_{1-6}$ alkyl), —$CF_3$, =O, $C_{1-6}$ alkyl, $C_{1-6}$ haloalkyl, $C_{1-6}$ hydroxyalkyl, $C_{1-6}$ heteroalkyl, $C_{1-6}$ alkoxy, $C_{1-6}$ alkylthio, $C_{3-7}$ cycloalkyl, $C_{2-6}$ heterocycloalkyl, —C(=O)N(H)($C_{1-6}$ (halo)alkyl), —C(=O)N($C_{1-6}$ (halo)alkyl)$_2$, —C(=O)$NH_2$, —C(=O)OC$_{1-6}$(halo)alkyl, —C(=O)OH, —N(H)C(=O)($C_{1-6}$ (halo)alkyl), —N($C_{1-6}$ (halo)alkyl)C(=O)($C_{1-6}$ (halo)alkyl), —N(H)C(=O)OC$_{1-6}$ (halo)alkyl, —N(C$_{1-6}$ (halo)alkyl)C(=O)OC$_{1-6}$ (halo)alkyl, —S(O)$_{1-2}$C$_{1-6}$ (halo)alkyl, —N(H)S(O)$_{1-2}$C$_{1-6}$ (halo)alkyl, —N(C$_{1-6}$ (halo)alkyl)S(O)$_{1-2}$C$_{1-6}$ (halo)alkyl, —S(O)$_{0-1}$N(H)(C$_{1-6}$ (halo)alkyl), —S(O)$_{0-1}$N(C$_{1-6}$ (halo)alkyl)$_2$, —S(O)$_{0-1}$NH$_2$, —C(=O)C$_{1-6}$ (halo)alkyl, —C(=O)C$_{3-7}$ cycloalkyl, —C(=NOH)C$_{1-6}$ (halo)alkyl, —C(=NOC$_{1-6}$ alkyl)C$_{1-6}$ (halo)alkyl, —NHC(=O)N(H)(C$_{1-6}$ (halo)alkyl), —NHC(=O)N(C$_{1-6}$ (halo)alkyl)$_2$, —NHC(=O)NH$_2$, —N(C$_{1-6}$ (halo)alkyl)C(=O)N(H)(C$_{1-6}$ (halo)alkyl), —N(C$_{1-6}$ (halo)alkyl)C(=O)NH$_2$, —OC(=O)C$_{1-6}$ (halo)alkyl, —OC(=O)OC$_{1-6}$ (halo)alkyl, —OP(=O)(OC$_{1-6}$(halo)alkyl)$_2$, —SC(=O)OC$_{1-6}$(halo)alkyl and —SC(=O)N(C$_{1-6}$ (halo)alkyl)$_2$, wherein any two R$^2$ substituents attached to the same or different ring vertices in the B ring or a R$^1$ and R$^2$ substituents attached to different ring vertices in the B ring are optionally combined to form a 3 to 6-membered carbocyclic or heterocyclic ring comprising 1 to 2 heteroatoms selected from N, O and S, wherein said 3 to 6-membered carbocyclic or heterocyclic ring is optionally substituted with 1 to 2 R$^{1/2}$ substituents; R$^4$ and R$^6$ are each independently absent if attached to a nitrogen atom or selected from the group consisting of hydrogen, C$_{1-3}$ alkyl, C$_{1-3}$ haloalkyl, C$_{1-3}$ alkyl-C(=O)— or C$_{1-3}$ haloalkyl-C(=O)—, C$_{1-3}$ alkoxy, C$_{1-3}$ alkylamino, C$_{1-3}$ dialkylamino, C$_{1-3}$ alkylthio, NH$_2$, OH, F, Cl, Br, I, CN and NO$_2$; R$^5$ is selected from the group consisting of hydrogen, C$_{1-3}$ alkyl, C$_{1-3}$ haloalkyl, C$_{1-3}$ alkyl-C(=O)— or C$_{1-3}$ haloalkyl-C(=O)—, C$_{1-3}$ alkoxy, C$_{1-3}$ alkylamino, C$_{1-3}$ dialkylamino, C$_{1-3}$ alkylthio, NH$_2$, OH, F, Cl, Br, I, CN and NO$_2$; R$^7$ at each occurrence is independently selected from the group consisting of hydrogen, C$_{1-6}$ alkyl, C$_{1-6}$ haloalkyl, C$_{3-10}$cycloalkyl, C$_{2-9}$ heterocycloalkyl, 6-10 membered aryl, 5-10 membered heteroaryl, —C(=O)R$^{7a}$, —C(=O)H, —C(=O)OR$^{7a}$ or —C(=O)NR$^{7a}$R$^{7b}$, wherein R$^{7a}$ and R$^{7b}$ at each occurrence is independently selected from the group consisting of hydrogen, C$_{1-6}$ alkyl, C$_{2-6}$ alkenyl, C$_{2-6}$ alkynyl, C$_{1-6}$ heteroalkyl, C$_{3-10}$ cycloalkyl, C$_{2-9}$ heterocycloalkyl, —(C$_{1-6}$ alkylene)-(C$_{3-40}$ cycloalkyl), —(C$_{1-6}$ alkylene)-(C$_{2-9}$ heterocycloalkyl), —(C$_{1-6}$ alkylene)-(6-membered aryl) and —(C$_{1-6}$ alkylene)-(5-6 membered heteroaryl), and wherein R$^{7a}$ and R$^{7b}$, when attached to the same nitrogen atom, are optionally combined to form a C$_{2-9}$ heterocycloalkyl further comprising 0-2 additional heteroatoms selected from N, O and S; R$^8$ at each occurrence is independently selected from the group consisting of hydrogen, C$_{1-6}$ alkyl, C$_{1-6}$ haloalkyl or —CH$_2$—OH; or alternatively R$^7$ and R$^8$ are combined to form a C$_{3-10}$ cycloalkyl, C$_{2-9}$ heterocycloalkyl, wherein optionally fused to said C$_{3-19}$ cycloalkyl and C$_{2-9}$ heterocycloalkyl is a 6 membered aryl, 5-6 membered heteroaryl ring or 3-6 membered heterocycloalkyl ring; and wherein the R$^7$ substituent, either alone or as combined with R$^8$, are optionally substituted with 1 to 5 R$^{R7/8}$ substitutents selected from the group consisting of F, Cl, Br, I, —OH, —NH$_2$, —SH, —CF$_3$, —OCF$_3$, —SF$_5$, —OCH$_3$, C$_{1-6}$ alkyl, CD$_3$, C$_{1-6}$ haloalkyl, C$_{1-6}$ heteroalkyl, C$_{1-6}$ alkoxy, C$_{1-6}$ alkylthio, C$_{3-5}$ cycloalkyl and C$_{2-5}$ heterocycloalkyl, =O, —(X$^7$)$_{0-1}$—CN, —(X$^7$)$_{0-1}$—NO$_2$, —(X$^7$)$_{0-1}$—N$_3$, —(X$^7$)$_{0-1}$—OH, —(X$^7$)$_{0-1}$—H, —(X$^7$)$_{0-1}$—OR$^{R7}$, —(X$^7$)$_{0-1}$—N(H)R$^{R7}$, —(X$^7$)$_{0-1}$—N(H)$_2$, —(X$^7$)$_{0-1}$—N(R$^{R7}$)$_2$, —(X$^7$)$_{0-1}$—S(O)R$^{R7}$, —(X$^7$)$_{0-1}$—SH, —(X$^7$)$_{0-1}$—C(O)R$^{R7}$, —(X$^7$)$_{0-1}$—C(O)H, —(X$^7$)$_{0-1}$—S(O)$_2$R$^{87}$, —(X$^7$)$_{0-1}$—S(O)R$^{R7}$, —(X$^7$)$_{0-1}$—N(H)S)$_{0-1}$—N(H)S(O)$_2$R$^{R7}$, —(X$^7$)$_{0-1}$—N(R$^{R7}$)S(O)$_2$R$^{R7}$, —(X$^7$)$_{0-1}$—OC(O)R$^{R7}$, —(X$^7$)$_{0-1}$—N(H)C(O)OR$^{R7}$, —(X$^7$)$_{0-1}$—N(R$^{R7}$)C(O)OR$^{R7}$, —(X$^7$)$_{0-1}$—N(H)C(=O)R$^{R2}$, —(X$^7$)$_{0-1}$—C(=O)OH, —(X$^7$)$_{0-1}$—C(=O)N(H)R$^{R7}$, —(X$^7$)$_{0-1}$—C(=O)N(R$^{R7}$)R$^{R7}$, —(X$^7$)$_{0-1}$—N(H)C(=O)R$^{R2}$, —(X$^7$)$_{0-1}$—N(R$^{R7}$)C(=O)R$^{R7}$, —(X)$_{0-1}$—N(H)C(=O)OR$^{R7}$ and —(X$^7$)$_{0-1}$—N(R$^{R7}$)C(=O)OR$^{R7}$, wherein X$^7$ is selected from the group consisting of C$_{1-6}$ alkylene, C$_{2-6}$ alkenylene, C$_{2-6}$ alkynylene, C$_{1-6}$ heteroalkylene, C$_{3-7}$ cycloalkylene and C$_{2-6}$ heterocycloalkylene, and R$^{R7}$ at each occurrence is independently selected from the group consisting of C$_{1-6}$ alkyl, C$_{1-6}$ haloalkyl, C$_{1-6}$ heteroalkyl, C$_{2-6}$ alkenyl, C$_{7-6}$ alkynyl, C$_{3-7}$ cycloalkyl and C$_{2-6}$ heterocycloalkyl; and the subscript n is an integer from 0 to 1.

E2: A compound of E1 wherein in Formula I

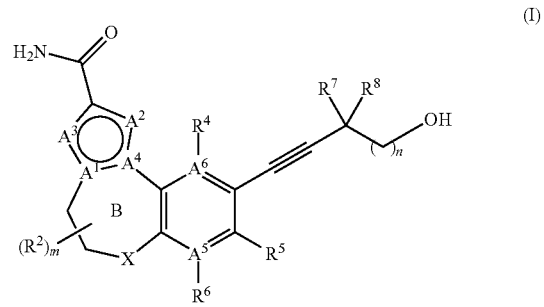

(I)

wherein A$^1$, A$^2$, A$^3$ and A$^4$ are selected from group consisting of A$^1$, A$^2$, A$^3$ are each N and A$^4$ is C; A$^1$ and A$^2$ are each N, A$^3$ is C(R$^{A3}$) and A$^4$ is C; A$^1$ is C, A$^2$ is N, A$^3$ is N(R$^{N3}$) and A$^4$ is C; A$^4$ is C, A$^2$ is N(R$^{N2}$), A$^3$ is N and A$^4$ is C, wherein R$^{N2}$ is hydrogen, C$_{1-3}$ alkyl, C$_{1-3}$ haloalkyl, C$_{1-3}$ alkyl-C(=O)— or C$_{1-3}$ haloalkyl-C(=O)—; A$^1$ is C and one of A$^2$ and A$^3$ is N and the other is S and A$^4$ is C; A$^1$ is C, A$^2$ is S, A$^3$ is C(R$^{A3}$) and A$^4$ is C; A$^1$ is C, A$^2$ is N, A$^3$ and A$^4$ is N; A$^1$ is C, A$^2$ is N, A$^3$ is C(R$^{A3}$) and A$^4$ is N; A$^1$ is C, A$^2$ is C(R$^{C2}$), A$^3$ is S and A$^4$ is C, wherein R$^{C2}$ is hydrogen, halogen, C$_{1-3}$ alkyl, C$_{1-3}$ haloalkyl, C$_{1-3}$ alkyl-C(=O)— or C$_{1-3}$ haloalkyl-C(=O)—; and A$^1$ is C, A$^2$ and A$^3$ and A$^4$ are each N. The symbols A$^5$ and A$^6$ are each independently C or N. The symbol X is O or C(R$^1$)$_2$. The subscript m is an integer from 0 to 4. R$^1$, R$^2$ and R$^{A3}$ and R$^{N3}$ at each occurrence each is independently selected from the group consisting of hydrogen, —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, Cl_6 alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, =O, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)$_{0-1}$—SC(=Y$^1$)OR$^{1a}$ and —(X$^1$)—SC(=Y$^1$)N(R$^{1a}$)(R$^{1b}$) wherein X$^1$ is selected from the group consisting of C$_{1-4}$ alkylene, C$_{1-4}$ haloalkylene, C$_{1-4}$ heteroalkylene, C$_{2-4}$ alkenylene, C$_{2-4}$ alkynylene, $C_{3-7}$ cycloalkylene and $C_{2-6}$ heterocycloalkylene, phenylene, 5-6 membered heteroarylene, $R^{1a}$ and $R^{1b}$ are each independently selected from the group consisting of $C_{1-6}$ alkyl, $C_{1-6}$ haloalkyl, $C_{1-6}$ heteroalkyl, $C_{3-7}$ cycloalkyl, $C_{3-7}$ cycloalkyl-$C_{1-4}$ alkyl, $C_{2-6}$ heterocycloalkyl, $C_{2-6}$ heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl, or $R^{1a}$ and $R^{1b}$ when attached to the same nitrogen atom are optionally combined to form a 3 to 7 membered heterocyclic ring comprising 0-2 additional heteroatoms selected from N, O and S; $Y^1$ is O, $NR^{1d}$ or S wherein $R^{1d}$ is hydrogen or $C_{1-6}$ alkyl; wherein any portion of $R^1$, $R^2$ and $R^{A3}$ and $R^{N3}$ substituent at each occurrence is each independently further substituted with from 0 to 4 $R^{1/2}$ substituents selected from the group consisting of —F, —Cl, —Br, —I, —CN, —NO$_2$, —SF$_5$, —OH, —NH$_2$, —CF$_3$, =O, $C_{1-6}$ alkyl, $C_{1-6}$ haloalkyl, $C_{1-6}$ heteroalkyl, $C_{1-6}$ alkoxy, $C_{1-6}$ alkylthio, $C_{3-7}$ cycloalkyl, $C_{2-7}$ heterocycloalkyl, —C(=O)N(H)($C_{1-6}$ (halo)alkyl), —C(=O)N($C_{1-6}$ (halo)alkyl)$_2$, —C(=O)NH$_2$, —C(=O)OC$_{1-6}$ (halo)alkyl, —C(=O)OH, —N(H)C(=O)($C_{1-6}$ (halo) alkyl), —N($C_{1-6}$ (halo)alkyl)C(=O)($C_{1-6}$ (halo)alkyl), —N(H)C(=O)OC$_{1-6}$ (halo)alkyl, —N($C_{1-6}$ (halo)alkyl)C (=O)OC$_{1-6}$ (halo)alkyl, —S(O)$_{1-2}$C$_{1-6}$ (halo)alkyl, —N(H) S(O)$_{1-2}$C$_{1-6}$ (halo)alkyl, —N($C_{1-6}$ (halo)alkyl)S(O)$_{1-2}$C$_{1-6}$ (halo)alkyl, S(O)$_{0-1}$N(H)($C_{1-6}$ (halo)alkyl), —S(O)$_{0-1}$N($C_{1-6}$ (halo)alkyl)$_2$, —S(O)$_{0-1}$NH$_2$, —C(=O)$C_{1-6}$ (halo)alkyl, —C(=NOH)$C_{1-6}$ (halo)alkyl, —C(=NOC$_{1-6}$ alkyl)$C_{1-6}$ (halo)alkyl, —NHC(=O)N(H)($C_{1-6}$ (halo)alkyl), —NHC (=O)N($C_{1-6}$ (halo)alkyl)$_2$, —NHC(=O)NH$_2$, —N($C_{1-6}$ (halo)alkyl)C(=O)N(H)($C_{1-6}$ (halo)alkyl), —N($C_{1-6}$ (halo) alkyl)C(=O)NH$_2$, —OC(=O)$C_{1-6}$ (halo)alkyl, —OC(=O) OC$_{1-6}$ (halo)alkyl, OP(=O)(OC$_{1-6}$ (halo)alkyl)$_2$, —SC(=O) OC$_{1-6}$ (halo)alkyl and —SC(=O)N($C_{1-6}$ (halo)alkyl)$_2$, wherein any two $R^2$ substituents attached to the same or different ring vertices in the B ring or a $R^1$ and $R^2$ substituents attached to different ring vertices in the B ring are optionally combined to form a 3 to 6-membered carbocyclic or heterocyclic ring comprising 1 to 2 heteroatoms selected from N, O and S, wherein said 3 to 6-membered carbocyclic or heterocyclic ring is optionally substituted with 1 to 2 $R^{1/2}$ substituents. $R^4$ and $R^6$ are each independently absent if attached to a nitrogen atom or selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$. $R^5$ is selected from the group consisting of hydrogen, $C_{1-3}$ alkyl, $C_{1-3}$ haloalkyl, $C_{1-3}$ alkyl-C(=O)— or $C_{1-3}$ haloalkyl-C(=O)—, $C_{1-3}$ alkoxy, $C_{1-3}$ alkylamino, $C_{1-3}$ dialkylamino, $C_{1-3}$ alkylthio, NH$_2$, OH, F, Cl, Br, I, CN and NO$_2$ $R^7$ at each occurrence is independently selected from the group consisting of hydrogen, $C_{1-6}$ alkyl, $C_{1-6}$ haloalkyl, $C_{3-10}$ cycloalkyl, $C_{2-9}$ heterocycloalkyl, 6-10 membered aryl, 5-10 membered heteroaryl, —C(=O)$R^{7a}$, —C(=O)OR$^{7a}$ or —C(=O)NR$^{7a}$R$^{7b}$, wherein $R^{7a}$ and $R^{7b}$ at each occurrence is independently selected from the group consisting of hydrogen, $C_{1-6}$ alkyl, $C_{2-6}$ alkenyl, $C_{2-6}$ alkynyl, $C_{1-6}$ heteroalkyl, $C_{3-10}$ cycloalkyl, $C_{2-9}$ heterocycloalkyl, —($C_{1-6}$ alkylene)-($C_{3-10}$ cycloalkyl), —($C_{1-6}$ alkylene)-($C_{2-6}$ heterocycloalkyl), —($C_{1-6}$ alkylene)-(6-membered aryl) and —($C_{1-6}$ alkylene)-(5-6 membered heteroaryl), and wherein $R^{7a}$ and $R^{7b}$, when attached to the same nitrogen atom, are optionally combined to form a $C_{2-9}$ heterocycloalkyl further comprising 0-2 additional heteroatoms selected from N, O and S. $R^8$ at each occurrence is independently selected from the group consisting of hydrogen, $C_{1-6}$ alkyl, $C_{1-6}$ haloalkyl or —CH$_2$—OH or alternatively $R^7$ and $R^8$ are combined to form a $C_{3-10}$ cycloalkyl, $C_{2-9}$ heterocycloalkyl, wherein optionally fused to said $C_{3-10}$ cycloalkyl and $C_{2-9}$ heterocycloalkyl is a 6 membered aryl or 5-6 membered heteroaryl ring; and wherein the $R^7$ substituent, either alone or as combined with $R^8$, are optionally substituted with 1 to 5 $R^{R7/8}$ substitutents selected from the group consisting of F, Cl, Br, I, —OH, —NH$_2$, —SH, —CF$_3$, —OCF$_3$, —SF$_5$, —OCH$_3$, $C_{1-6}$ alkyl, $C_{1-6}$ haloalkyl, $C_{1-6}$ heteroalkyl, $C_{1-6}$ alkoxy, $C_{1-6}$ alkylthio, $C_{3-5}$ cycloalkyl and $C_{2-5}$ heterocycloalkyl, =O, —(X$^7$)$_{0-1}$—CN, —(X$^7$)$_{0-1}$—NO$_2$, —(X$^7$)$_{0-1}$—N$_3$, —(X$^7$)$_{0-1}$—OH, —(X$^7$)$_{0-1}$—H, —(X$^7$)$_{0-1}$—OR$^{R7}$, —(X$^7$)$_{0-1}$—N(H)R$^{R7}$, —(X$^7$)$_{0-1}$—N(H)$_2$, —(X$^7$)$_{0-1}$—N(R$^{R7}$)$_2$, —(X$^7$)$_{0-1}$—SR$^{R7}$, —(X$^7$)$_{0-1}$—SH, —(X$^7$)$_{0-1}$—C(O)R$^{R7}$, —(X$^7$)$_{0-1}$—S(O)$_2$R$^{R7}$, —(X$^7$)$_{0-1}$—S(O)R$^{R7}$, —(X$^7$)$_{0-1}$—N(H)S(O)$_2$R$^{R7}$, —(X$^7$)$_{0-1}$—N(R$^{R7}$)S(O)$_2$R$^{R7}$, —(X$^7$)$_{0-1}$—OC(O)R$^{R7}$, —(X$^7$)$_{0-1}$—N(H)C(O)OR$^{R7}$, —(X$^7$)$_{0-1}$—N(R$^{R7}$)C(O)OR$^{R7}$, —(X$^7$)$_{0-1}$—C(=O)OR$^{R7}$, —(X$^7$)$_{0-1}$—C(=O)OH, —(X$^7$)$_{0-1}$—C(=O)N(H)R$^{R7}$, —(X$^7$)$_{0-1}$—C(=O)N(R$^{R7}$) R$^{R7}$, —(X$^7$)$_{0-1}$—N(H)C(=O)R$^{R7}$, —(X$^7$)$_{0-1}$—N(R$^{R7}$)C (=O)R$^{R7}$, —(X$^7$)$_{0-1}$—N(H)C(=O)OR$^{R7}$ and —(X$^7$)$_{0-1}$—N (R$^{R7}$)C(=O)OR$^{R7}$, wherein X$^7$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{2-6}$ heterocycloalkylene, and R$^{R7}$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl and $C_{2-6}$ heterocycloalkyl; and the subscript n is an integer from 0 to 1.

E3 A compound of any of E1 or E2, wherein said compound is of Formula I-A or I-B

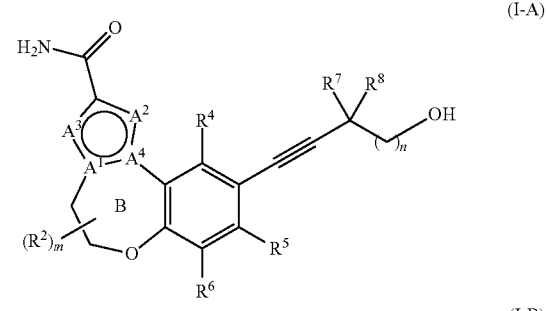

(I-A)

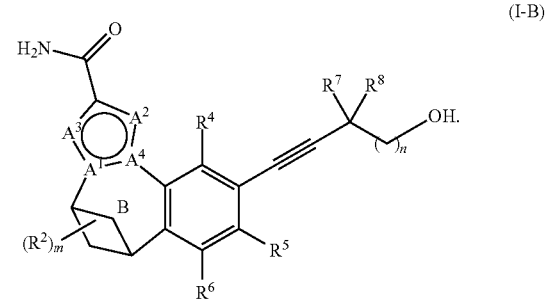

(I-B)

E4 A compound of any of E1, E2 or E3, wherein the compounds are of a Formula selected from the group consisting of

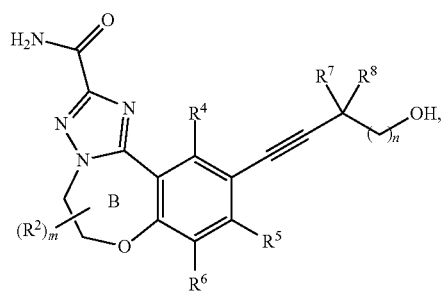
(I-A¹)
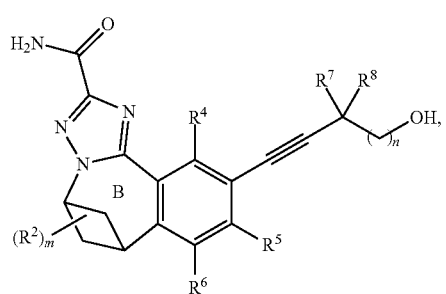
(I-B¹)

(I-A²)
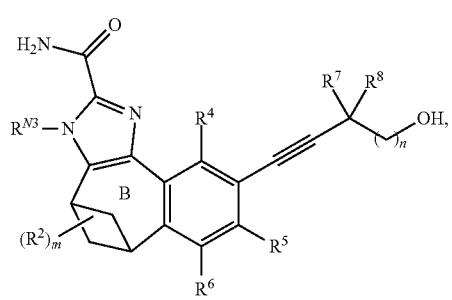
(I-B²)
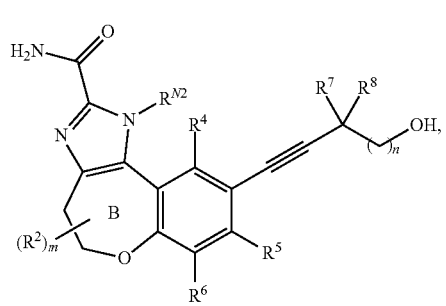
(I-A³)
-continued
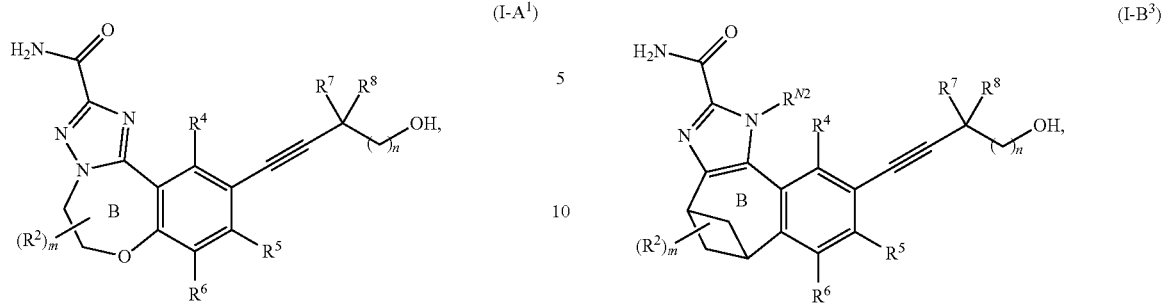
(I-B³)
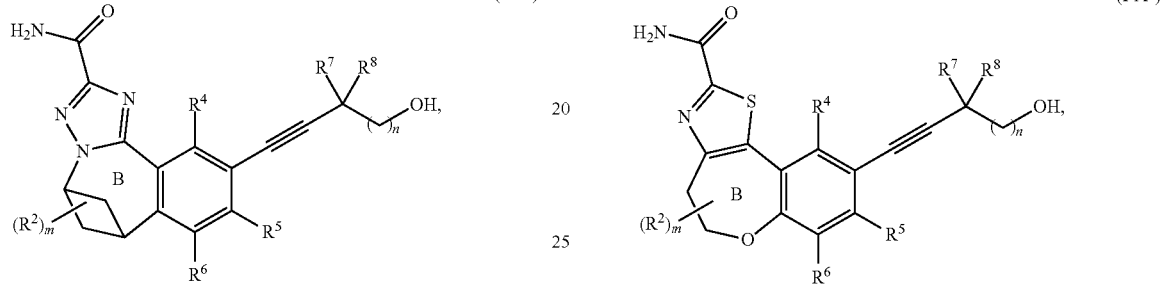
(I-A⁴)
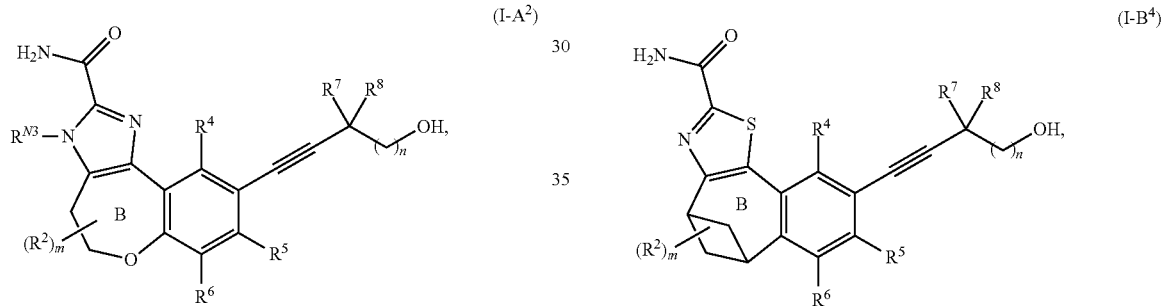
(I-B⁴)
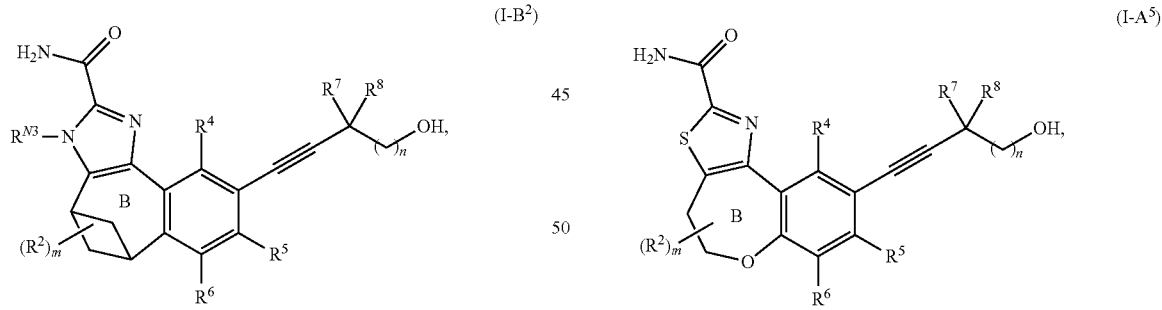
(I-A⁵)
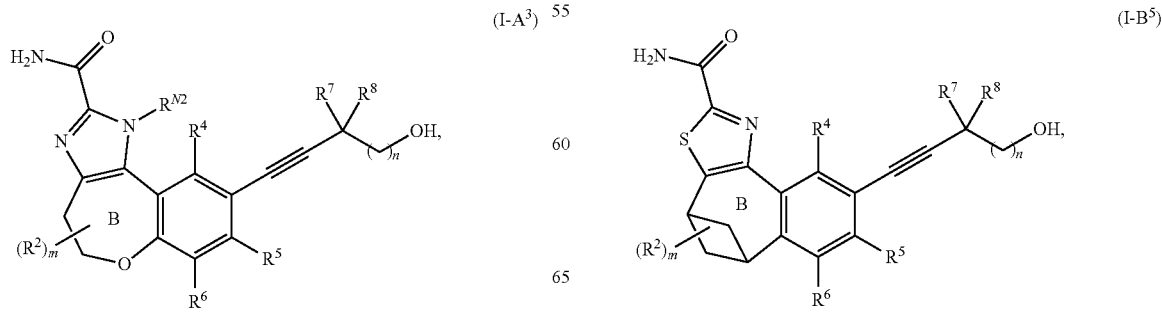
(I-B⁵)

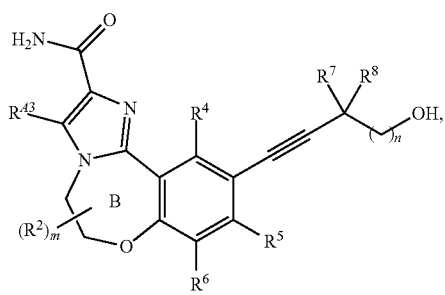
(I-A⁶)
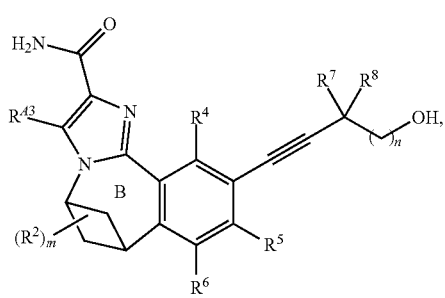
(I-B⁶)
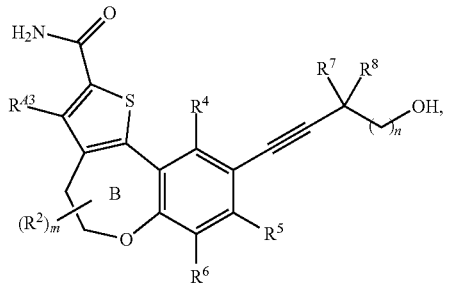
(I-A⁷)
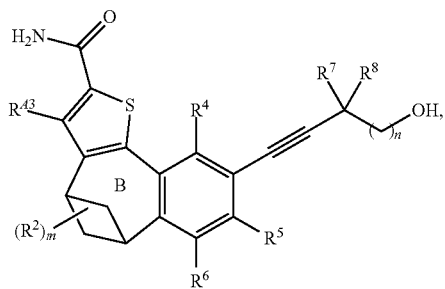
(I-B⁷)
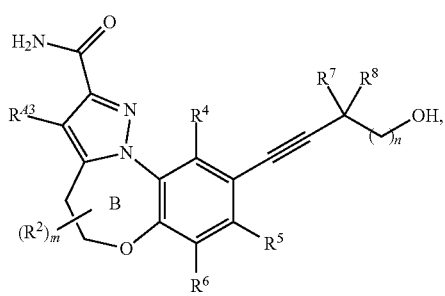
(I-A⁸)
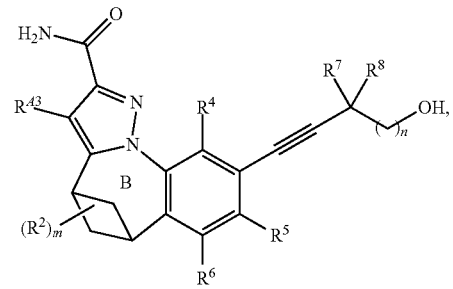
(I-B⁸)
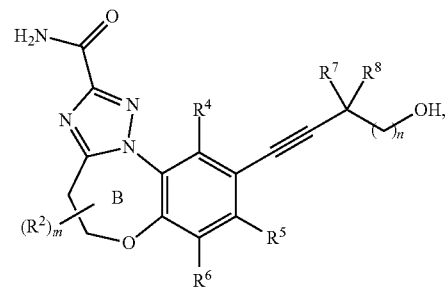
(I-A⁹)
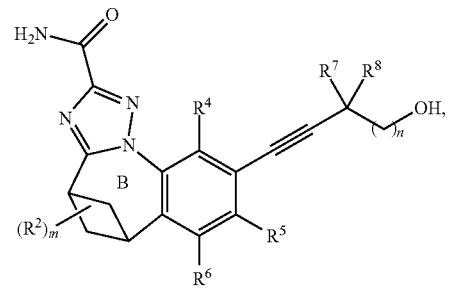
(I-B⁹)
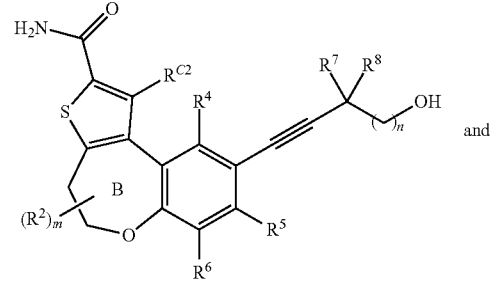
(I-A¹⁰) and
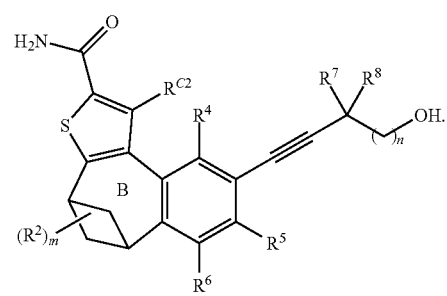
(I-B¹⁰).
E5 A compound of any of E1, E2, E3 or E4, wherein the compounds are of a Formula selected from the group consisting of

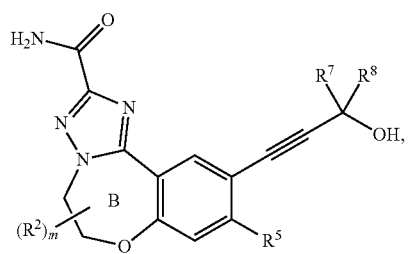 (II-A¹)
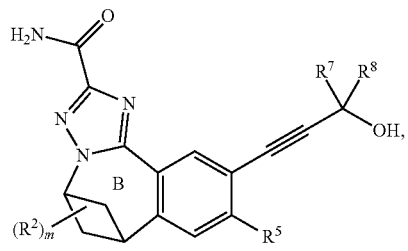 (II-B¹)
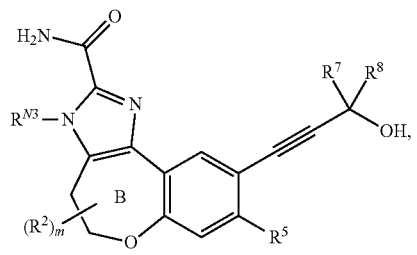 (II-A²)
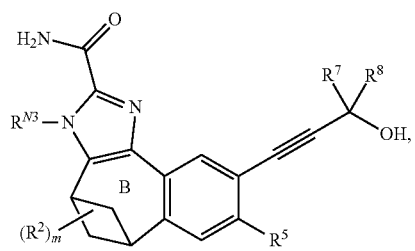 (II-B²)
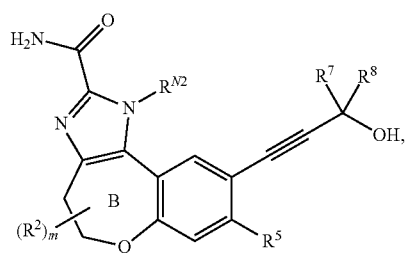 (II-A³)
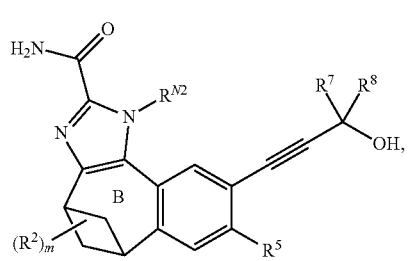 (II-B³)
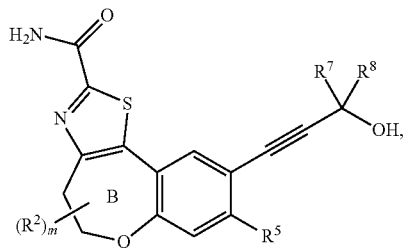 (II-A⁴)
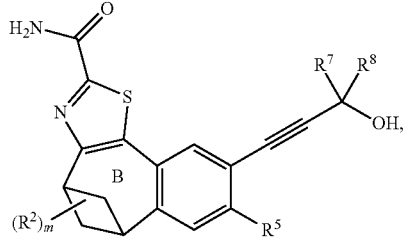 (II-B⁴)
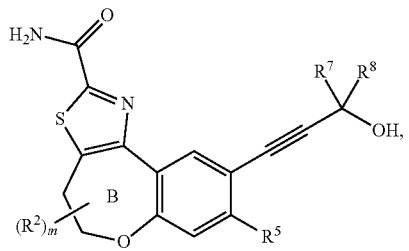 (II-A⁵)
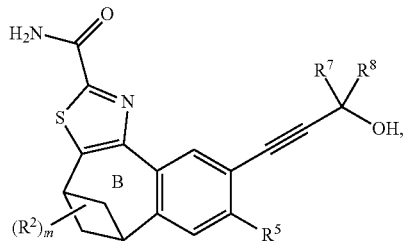 (II-B⁵)
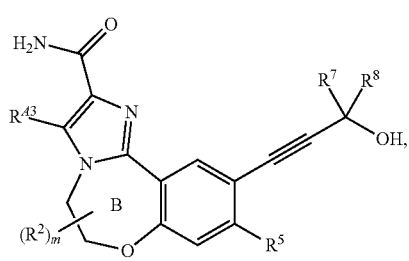 (II-A⁶)
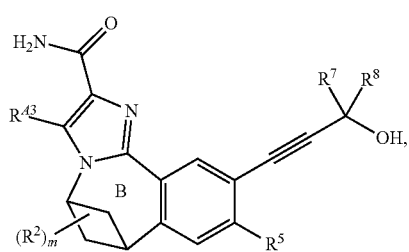 (II-B⁶)

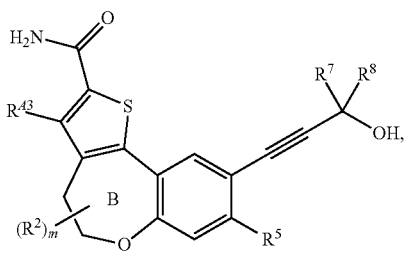
(II-A⁷)

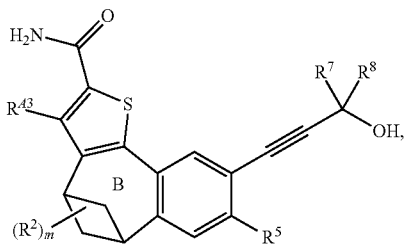
(II-B⁷)

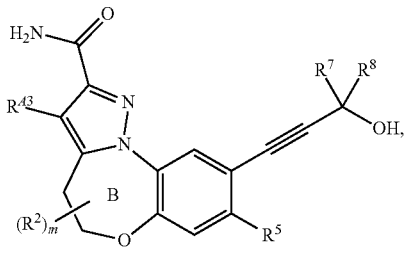
(II-A⁸)

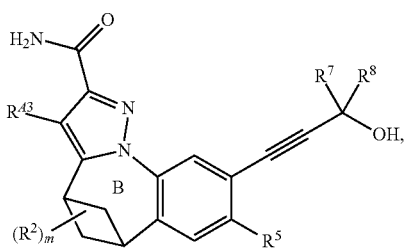
(I-B⁸)

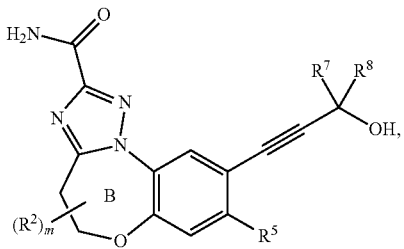
(II-A⁹)

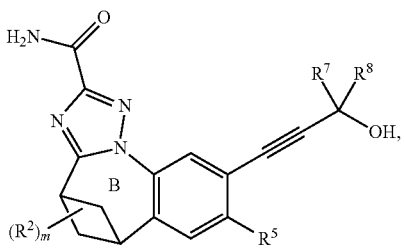
(II-B⁹)

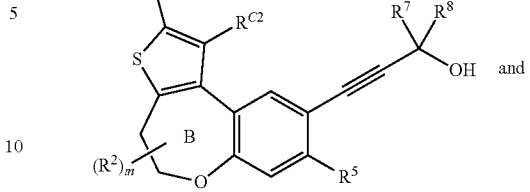
(II-A¹⁰)

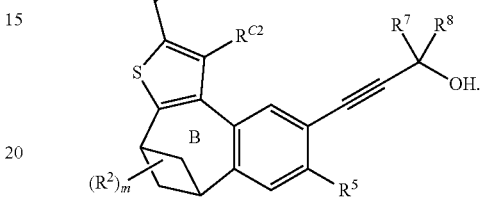
(II-B¹⁰)

E6: A compound of any one of E1, E2, or E3, wherein in compounds of Formula I or a subformula thereof, $A^1$, $A^2$ and $A^3$ are each N and $A^4$ is C, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X^1)_{0-1}$—NO$_2$, —$(X^1)_{0-1}$—SF$_5$, —$(X^1)_{0-1}$—OH, —$(X^1)_{0-1}$—NH$_2$, —$(X^1)_{0-1}$—N(H)($R^{1a}$), —$(X^1)_{0-1}$—N($R^{1b}$)($R^{1a}$), —$(X^1)_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —$(X^1)_{0-1}$—C$_{3-10}$ cycloalkyl, —$(X^1)_{0-1}$—C$_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)NH$_2$, —$(X^1)_{0-1}$—C(=$Y^1$)N($R^{1a}$)($R^{1b}$), —$(X^1)_{0-1}$—C(=$Y^1$)O$R^{1a}$, —$(X^1)_{0-1}$—C(=$Y^1$)OH, —$(X^1)_{0-1}$—N(H)C(=$Y^1$)($R^{1a}$), —$(X^1)_{0-1}$—N($R^{1b}$)C(=$Y^1$)($R^{1a}$), —$(X^1)_{0-1}$—N($R^{1b}$)C(=$Y^1$)(H), —$(X^1)_{0-1}$—N(H)C(=$Y^1$)O$R^{1a}$, —$(X^1)_{0-1}$—N($R^{1b}$)C(=$Y^1$)O$R^{1a}$, —$(X^1)_{0-1}$—S(O)$_{1-2}$$R^{1a}$, —$(X^1)_{0-1}$—N(H)S(O)$_{1-2}$$R^{1a}$, —$(X^1)_{0-1}$—N($R^{1b}$)S(O)$_{1-2}$$R^{1a}$, —$(X^1)_{0-1}$—S(O)$_{0-1}$N(H)($R^{1a}$), —$(X^1)_{0-1}$—S(O)$_{0-1}$—N($R^{1b}$)($R^{1a}$), —$(X^1)_{0-1}$—NH$_2$, —$(X^1)_{0-1}$—S(=O)(=N$R^{1b}$)$R^{1a}$, —$(X^1)_{0-1}$—C(=$Y^1$)$R^{1a}$, —$(X^1)_{0-1}$—C(=$Y^1$)H, —$(X^1)_{0-1}$—C(=NOH)$R^{1a}$, —$(X)_{0-1}$—C(=NO$R^{1b}$)$R^{1a}$, —$(X^1)_{0-1}$—NHC(=$Y^1$)N(H)($R^{1a}$), —$(X^1)_{0-1}$—NHC(=$Y^1$)NH$_2$, —$(X^1)_{0-1}$—NHC(=$Y^1$)N($R^{1b}$)($R^{1a}$), —$(X^1)_{0-1}$—N($R^{1a}$)C(=$Y^1$)N(H)($R^{1a}$), —$(X^1)_{0-1}$—N($R^{1a}$)C(=$Y^1$)N($R^{1a}$)($R^{1a}$), —$(X^1)_{0-1}$—N($R^{1a}$)C(=$Y^1$)NH$_2$, —$(X^1)_{0-1}$—C(=$Y^1$)$R^{1a}$, —$(X^1)_{0-1}$—C(=$Y^1$)H, —$(X^1)_{0-1}$—OC(=$Y^1$)O$R^{1a}$, —$(X^1)_{0-1}$—OP(=$Y^1$)(O$R^{1a}$)(O$R^{1b}$), —$(X^1)$—SC(=$Y^1$)O$R^{1a}$ and —$(X^1)$—SC(=$Y^1$)N($R^{1a}$)($R^{1b}$); and in additional occurrences of $R^2$, $R^2$ is optionally substituted and selected from the group consisting of hydrogen, —F, —Cl, —Br, —I, —CN, —NO$_2$, —SF$_5$, —OH, —NH$_2$, —N(H)($R^{1a}$), —N($R^{1b}$)($R^{1a}$), —CF$_3$, C$_{1-6}$ alkyl, C$_{1-6}$ haloalkyl, C$_{1-6}$ heteroalkyl, alkoxy, C$_{1-6}$ alkylthio and is optionally substituted.

E7 A compound of E6, wherein in compound of Formula I or a subformula thereof, m is 1-4.

E8 A compound of any one of E1, E2, or E3, wherein in compounds of Formula I or a subformula thereof, $A^1$ and $A^2$ are each N, $A^3$ is C($R^{A3}$) and $A^4$ is C, wherein $R^{A3}$ is optionally substituted and selected from the group consisting of hydrogen, —F, —Cl, —Br, —I, —$(X^1)_{0-1}$—CN, —$(X^1)_{0-1}$—NO$_2$, —$(X^1)_{0-1}$—SF$_5$, —$(X^1)_{0-1}$—OH, —$(X^1)_{0-1}$—NH$_2$, —$(X^1)_{0-1}$—N(H)($R^{1a}$), —$(X^1)_{0-1}$—N$R^1$N$R^{1a}$), —$(X^1)_{0-1}$—

CF$_3$, C$_{1-6}$ alkyl, C$_{1-6}$ haloalkyl, C$_{1-6}$ heteroalkyl, alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)(R$^{1a}$), —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X)$_{0-1}$—S(O)$_{0-1}$N(H)(R$^{1a}$), —(X$^1$)$_{0-1}$—S(O)$_{0-1}$N(R$^{1b}$)(R$^{1a}$), —(X)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and (X$^1$)—SC(=Y$^1$)N(R$^{1a}$)(R$^{1b}$); R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy and C$_{1-6}$ alkylthio; and m is 0 to 4.

E9: A compound of E8, wherein in compound of Formula I or a subformula thereof, m is 0-2 and R$^{A3}$ is other than hydrogen.

E10 A compound of any one of E1, E2, or E3, wherein in compounds of Formula I or a subformula thereof, A$^1$ and A$^2$ are each N, A$^3$ is C(R$^{A3}$) and A$^4$ is C, wherein m is 0 to 4. R$^2$ is optionally substituted and selected from the group consisting of consisting of hydrogen, —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—C(=Y$^1$)N(R$^{1a}$), —(X$^1$)$_{0-1}$—N(R$^{1b}$)C(=Y$^1$)(H), —(X$^1$)$_{0-1}$—N(H)C(=Y$^1$)(R$^{1a}$), —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$)—(X$^1$)$_{0-1}$—N(R$^{1a}$)C(=Y$^1$)N(H)(R$^{1a}$), —(X$^1$)$_{1-0}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—C(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$); and R$^{A3}$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy and C$_{1-6}$ alkylthio.

E11 A compound of E10, wherein in compound of Formula I or a subformula thereof, m is 1-2.

E12 A compound of any one of E1, E2, or E3, wherein in compounds of Formula I or a subformula thereof, A$^1$ and A$^4$ are each C and A$^2$ is NR$^{N2}$ are and A$^3$ is N, wherein m is 0-4, wherein in a first occurrence of R$^2$, R$^2$ is optionally substituted and selected from the group consisting of consisting of —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—NR$^1$NR$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(R$^{1b}$)(R$^{1a}$), —(X)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—C(=Y$^1$)R$^{1a}$, —(X$^1$)$_{0-1}$—OC(=Y$^1$)H, —(X$^1$)$_{0-1}$—OC(=Y$^1$)OR$^{1a}$, —(X)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$); and in additional occurrences of R$^2$, R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy, C$_{1-6}$ alkylthio.

E13 A compound of E10, wherein in compound of Formula I or a subformula thereof, m is 1-4.

E14 A compound of any one of E1, E2, or E3, wherein in compounds of Formula I or a subformula thereof, A$^1$ and A$^4$ are each C, A$^2$ is N and A$^3$ is N(R$^{N3}$); wherein R$^{N3}$ is optionally substituted and selected from the group consisting of consisting of hydrogen, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$)cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—C(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$).

R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

E15 A compound of E14, wherein in compound of Formula I or a subformula thereof, m is 0-2 and $R^{N3}$ is other than hydrogen.

E16 A compound of any one of E1, E2, or E3, wherein in compounds of Formula I or a subformula thereof, $A^1$ and $A^4$ are each C, $A^2$ is N and $A^3$ is $N(R^{N3})$; wherein m is from 0 to 4; $R^2$ is optionally substituted and selected from the group consisting of consisting of —F, —Cl, —Br, —I, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{13}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^1NR^{1a})$, —$(X^1)_{0-1}$—$S(O)_{0-1}NH_2$, —$(X^1)_{0-1}$—$S(=O)(=NR^{1b})R^{1a}$, —$(X^1)_{0-1}$—$C(=Y^1)R^{1a}$, —$(X^1)_{0-1}$—$C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=Y^1)N(R^{1b})(R^{1a})$, —$(X^1)_{0-1}$—$N(R^{1'''})C(=Y^1)N(H)(R^{1a})$, —$(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$OC(=Y^1)R^{1a}$, —$(X^1)_{0-1}$—$OC(=Y^1)H$, —$(X^1)_{0-1}$—$OC(=Y^1)OR^{1a}$, —$(X^1)_{0-1}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})$. $R^{N3}$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, $C_{1-6}$ alkyl, $C_{1-6}$ haloalkyl, $C_{1-6}$ heteroalkyl, $C_{1-6}$ alkoxy, $C_{1-6}$ alkylthio.

E17 A compound of E16, wherein in compound of Formula I or a subformula thereof, m is 1-2.

E18 A compound of any one of E1, E2, or E3, wherein in compounds of Formula I or a subformula thereof, $A^1$ and $A^4$ are each C and one of $A^2$ and $A^3$ is N and the other is S, wherein m is 0-4, wherein in a first occurrence of $R^2$, $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(R^{1b})(R^{1a})$, —$(X^1)_{0-1}$—$S(O)_{0-1}N(R^{1b})(R^{1a})$, —$(X^1)_{0-1}$—$S(O)_{0-1}NH_2$, —$(X^1)_{0-1}$—$S(=O)(=NR^{1b})R^{1a}$, —$(X^1)_{0-1}$—$C(=Y^1)R^{1a}$, —$(X^1)_{0-1}$—$C(=Y^1)_{1-1}$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=Y^1)N(R^{1b})(R^{1a})$—$S(=O)_{0-1}N(R^{1a})C(=Y^1)N(H)(R^{1a})$, —$(X^1)_{0-1}$—$N(R^{1a})C(=Y^1)N(R^1NR^{1a})$, —$(X^1)_{0-1}$—$N(R^{1a})C(=Y^1)N_{1-2}$, —$(X^1)_{0-1}$—$OC(=Y^1)R^{1a}$, —$(X^1)_{0-1}$—$OC(=Y^1)H$, —$(X^1)_{0-1}$—$C(=Y^1)OR^{1a}$, —$(X^1)_{0-1}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})$; and in additional occurrences of $R^2$, $R^2$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

E19 A compound of E18, wherein in compound of Formula I or a subformula thereof, m is 1-4.

E20 A compound of any one of E1, E2, or E3, wherein in compounds of Formula I or a subformula thereof, wherein $A^1$ and $A^2$ are each N, $A^3$ is $C(R^{A3})$ and $A^4$ is N; wherein $R^{A3}$ is optionally substituted and selected from the group consisting of consisting of hydrogen, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(MS (O)_{1-2}R^{1a}$, —$(X^1)_{0-1}$—$N(R^{1b})S(O)_{1-2}R^{1a}$, —$(X^1)_{0-1}$—$S(O)_{0-1}N(R^{1b})(R^{1a})$, —$(X^1)_{0-1}$—$S(O)_{0-1}N(R^{1b})(R^{1a})$, —$(X^1)_{0-1}$—$S(O)_{0-1}NH_2$, —$(X^1)_{0-1}$—$S(=O)(=N(R^{1b})R^{1a}$, —$(X^1)_{0-1}$—$C(=Y^1)R^{1a}$, —$(X^1)_{0-1}$—$C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=O)$, —$(X^1)_{0-1}$—$N(R^{1a})C(=Y^1)N(H)(R^{1a})$, —$(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$OC(=Y^1)R^{1a}$, —$(X^1)_{0-1}$—$OC(=Y^1)H$, —$(X^1)_{0-1}$—$C(=Y^1)OR^{1a}$, —$(X^1)_{1-0}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})$. $R^2$ is optionally substituted and selected from the group consisting of hydrogen, —F, —Cl, —Br, —I, —CN, —$NO_2$, —$SF_5$, —OH, —$NH_2$, —$N(H)(R^{1a})$, —$N(R^{1b})(R^{1a})$, —$CF_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

E21 A compound of E20, wherein in compound of Formula I or a subformula thereof, m is 0-2 and $R^{N3}$ is other than hydrogen.

E22 A compound of any one of E1, E2, or E3, wherein in compounds of Formula I or a subformula thereof, wherein $A^1$ and $A^2$ are each N, $A^3$ is $C(R^{A3})$ and $A^4$ is N; wherein m is from 0 to 4; $R^2$ is optionally substituted and selected from the group consisting of consisting of —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—N, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$, —$(X^1)_{0-1}$—$C(=Y^1)OH$, —$(X^1)_{0-1}$—$N(H)C(=Y^1)(R^{1a})$, —$(X^1)_{0-1}$—$N(R^{1b})C(=Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—N $(R^{1b})S(O)_{1-2}R^{1a}$, $-(X^1)_{0-1}-S(O)_{0-1}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^{1b})(R^{1a})$, $-(X^1)_{0-1}-N(R^{1a})C(=Y^1)N(H)(R^{1a})$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^{1a}$ and $-(X^1)-SC(=Y^1)N(R^{1a})(R^{1b})$. $R^{N3}$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^{1b})(R^{1a})$, $-CF_3$, $C_{1-6}$ alkyl, $C_{1-6}$ haloalkyl, $C_{1-6}$ heteroalkyl, $C_{1-6}$ alkoxy, $C_{1-6}$ alkylthio.

E23 A compound of E22, wherein in compound of Formula I or a subformula thereof, m is 1-2.

E24 A compound of any one of E1, E2, or E3, wherein in compounds of Formula I or a subformula thereof, wherein $A^1$, $A^4$ are each C, $A^2$ is S and $A^3$ is $C(R^{43})$; wherein $R^{43}$ is optionally substituted and selected from the group consisting of consisting of hydrogen, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{1-6}$alkyl, $-(X^1)_{0-1}-C_{3-10}$ cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$; $-(X^1)_{0-1}-C(=Y^1)OR^{1a}$; $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{1-2}R^{1a}$, $-(X)_{0-1}-S(O)_{0-1}N(H)(R^{1a})$, $-(X)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-H(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R)N(R^{1a})C(=Y^1)N(R^{1a})(R^{1a})$, $R^{1b})(R^{1a})$, $-(X^1)_{0-1}-N(R^{1a})C(=Y^1)N(H)(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^{1a}$ and $-(X^1)-SC(=Y^1)N(R^{1a})(R^{1b})$; $R^2$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^1NR^{1a})$, $-CF_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

E25 A compound of E24, wherein in compound of Formula I or a subformula thereof, m is 0-2 and $R^{N3}$ is other than hydrogen.

E26 A compound of any one of E1, E2, or E3, wherein in compounds of Formula I or a subformula thereof, wherein $A^1$, $A^4$ are each C, $A^2$ is S and $A^3$ is $C(R^{43})$; wherein m is from 0 to 4; $R^2$ is optionally substituted and selected from the group consisting of consisting of $-F$, $-Cl$, $-Br$, $-I$, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{3-10}$ cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{1-2}R^{1a}$, $-(X^1)_{0-1}-S(O)_{0-1}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^{1b})(R^{1a})$, $-(X^1)_{0-1}-N(R^{1a})C(=Y^1)N(H)(R^{1a})$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^1NOR^{1b})$, $-(X^1)-SC(=Y^1)OR^{1a}$ and $-(X^1)-SC(=Y^1)N(R^{1a})(R^{1b})$. $R^{N3}$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^{1b})(R^{1a})$, $-CF_3$, $C_{1-6}$ alkyl, $C_{1-6}$ haloalkyl, $C_{1-6}$ heteroalkyl, $C_{1-6}$ alkoxy, $C_{1-6}$ alkylthio.

E27 A compound of E22, wherein in compound of Formula I or a subformula thereof, m is 1-2.

E28 A compound of any one of E1, E2, or E3, wherein in compounds of Formula I or a subformula thereof, wherein $A^1$ is C, $A^2$ and $A^4$ are each N and $A^3$ is $C(R^{43})$; wherein $R^{43}$ is optionally substituted and selected from the group consisting of consisting of hydrogen, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{16})(R^{1a})$, $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{1-6}$ alkyl, $-(X^1)_{0-1}-C_{3-10}$ cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{1-2}R^{1a}$, $-(X^1)_{0-1}-S(O)_{0-1}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^{1b})(R^{1a})$, $-(X^1)_{0-1}-N(R^{1a})C(=Y^1)N(H)(R^{1a})$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^{1a}$ and $-(X^1)-SC(=Y^1)N(R^{1a})(R^{1b})$. $R^2$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^{1b})(R^{1a})$, $-CF_3$, $C_{1-6}$ alkyl, $C_{1-6}$ haloalkyl, $C_{1-6}$ heteroalkyl, $C_{1-6}$ alkoxy and $C_{1-6}$ alkylthio; and m is from 0 to 4.

E29 A compound of E28, wherein in compound of Formula I or a subformula thereof, m is 0-2 and $R^{N3}$ is other than hydrogen.

E30 A compound of any one of E1, E2, or E3, wherein in compounds of Formula I or a subformula thereof, wherein $A^1$ is C, $A^2$ and $A^4$ are each N and $A^3$ is $C(R^{43})$, wherein m is from 0 to 4; $R^2$ is optionally substituted and selected from the group consisting of consisting of $-F$, $-Cl$, $-Br$, $-I$, $-(X^1)_{0-1}-$ CN, $-(X^1)_{0-1}-NO_2$, $-(X^1)_{0-1}-SF_5$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{3-10}$cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{12}R^{1a}$, $-(X^1)_{0-1}-S(O)_{0-1}N(H)(R^{1a})$, $-(X)_{0-1}-S(O)_{0-1}N(R^{1b})(R^{1a})$, $-(X^1)_{0-1}-S(O)_{0-1}-NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^1)N(R^{1a})C(=Y^1)N(H)(R^{1a})$, $-(X^1)_{0-1}-N(R^{1a})C(=Y^1)N(R^{1a})(R^{1a})$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^{1a}$ and $-(X^1)_{0-1}-SC(=Y^1)N(R^{1a})(R^{1b})$. $R^{N3}$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^1NR^{1a})$, $-CF_3$, $C_{1-6}$ alkyl, $C_{1-6}$ haloalkyl, $C_{1-6}$ heteroalkyl, $C_{1-6}$ alkoxy, $C_{1-6}$ alkylthio, E31 A compound of E30, wherein in compound of Formula I or a subformula thereof, m is 1-2.

E32 A compound of any one of E1, E2, or E3, wherein in compounds of Formula I or a subformula thereof, $A^1$ is C and $A^2$, $A^3$ and $A^4$ are each N, wherein m is 0-4, wherein in a first occurrence of $R^2$, $R^2$ is optionally substituted and selected from the group consisting of consisting of $-F$, $-Cl$, $-Br$, $-I$, $-(X^1)_{0-1}-CN$, $-(X^1)_{0-1}-NO_2$, $-(X^1)_{0-1}-SF_5$, $-(X^1)_{0-1}-NH_2$, $-(X^1)_{0-1}-N(H)(R^{1a})$, $-(X^1)_{0-1}-N(R^{1b})(R^{1a})$, $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{3-10}$ cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-1}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{12}R^{1a}$, $-(X^1)_{0-1}-S(O)_{0-4}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^{1b})(R^{1a})$, $-(X^1)_{0-1}-N(R^{1a})C(=Y^1)N(H)(R^{1a})$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-OP(=Y^1)(OR^{1a})(OR^{1b})$, $-(X^1)-SC(=Y^1)OR^{1a}$ and $-(X^1)-SC(=Y^1)N(R^{1a})(R^{1b})$; and in additional occurrences of $R^2$, $R^2$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^{1b})(R^{1a})$, $-CF_3$, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

E33 A compound of any one of E1, E2, or E3, wherein in compounds of Formula I or a subformula thereof, $A^1$ and $A^4$ are each C and $A^2$ is $CR^{A2}$ are and $A^3$ is S, wherein m is 0-4, wherein in a first occurrence of $R^2$, $R^2$ is optionally substituted and selected from the group consisting of consisting of $-F$, $-Cl$, $-Br$, $-I$, $-(X^1)_{0-1}-CN$, $-(X^1)_{0-1}-NO_2$, $-(X^1)_{0-1}-SF_5$, $-(X^1)_{0-1}-OH$, $-(X^1)_{0-1}-NH_2$, $-(X^1)_{0-1}-N(H)(R^{1a})$, $-(X^1)_{0-1}-N(R^{1b})(R^{1a})$; $-(X^1)_{0-1}-CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}-C_{3-10}$ cycloalkyl, $-(X^1)_{0-1}-C_{2-9}$ heterocycloalkyl, $-(X^1)_{0-1}$-5-10 membered heteroaryl, $-(X^1)_{0-1}$-6-10 membered aryl, $-(X^1)_{0-1}-C(=Y^1)N(H)(R^{1a})$, $-(X^1)_{0-1}-C(=Y^1)NH_2$, $-(X^1)_{0-4}-C(=Y^1)N(R^{1a})(R^{1b})$, $-(X^1)_{0-1}-C(=Y^1)OR^{1a}$, $-(X^1)_{0-1}-C(=Y^1)OH$, $-(X^1)_{0-1}-N(H)C(=Y^1)(R^{1a})$, $-(X^1)_{0-1}-N(R^{1b})C(=Y^1)(R^{1a})$, $-(X^1)_{0-1}-N(R^{1b})C(=Y^1)(H)$, $-(X^1)_{0-1}-N(H)C(=Y^1)OR^{1a}$, $-(X^1)_{0-1}-N(R^{1b})C(=Y^1)OR^{1a}$, $-(X^1)_{0-1}-S(O)_{1-2}R^{1a}$, $-(X^1)_{0-1}-N(H)S(O)_{1-2}R^{1a}$, $-(X^1)_{0-1}-N(R^{1b})S(O)_{12}R^{1a}$, $-(X^1)_{0-1}-S(O)_{0-1}N(H)(R^{1a})$, $-(X^1)_{0-1}-S(O)_{0-1}N(R^{1b})(R^{1a})$, $-(X^1)_{0-1}-S(O)_{0-1}NH_2$, $-(X^1)_{0-1}-S(=O)(=NR^{1b})R^{1a}$, $-(X^1)_{0-1}-C(=Y^1)R^{1a}$, $-(X^1)_{0-1}-C(=Y^1)H$, $-(X^1)_{0-1}-C(=NOH)R^{1a}$, $-(X^1)_{0-1}-C(=NOR^{1b})R^{1a}$, $-(X^1)_{0-1}-NHC(=Y^1)N(H)(R^{1a})$, $-(X^1)_{0-1}-NHC(=Y^1)NH_2$, $-(X^1)_{0-1}-NHC(=Y^1)N(R^{1b})(R^{1a})$, $-(X^1)_{0-1}-N(R^{1a})C(=Y^1)N(H)(R^1)$, $-(X^1)_{0-1}-N(R^{1a})C(=Y^1)N(R^{1a})(R^{1a})$, $-(X^1)_{0-1}-N(R^{1a})C(=Y^1)NH_2$, $-(X^1)_{0-1}-OC(=Y^1)R^{1a}$, $-(X^1)_{0-1}-OC(=Y^1)H$, $-(X^1)_{0-1}-OC(=Y^1)OR^{1a}$, $-(X^1)_{0-1}-P(=Y^1)(OR^{1a})(OR^{1b})$, $-(X^1)-SC(=Y^1)OR^{1a}$ and $-(X^1)-SC(=Y^1)N(R^{1a})(R^{1b})$; and in additional occurrences of $R^2$, $R^2$ is optionally substituted and selected from the group consisting of hydrogen, $-F$, $-Cl$, $-Br$, $-I$, $-CN$, $-NO_2$, $-SF_5$, $-OH$, $-NH_2$, $-N(H)(R^{1a})$, $-N(R^{1b})(R^{1b})(R^{1a})$, $-CF_3$, $C_{1-6}$ alkyl, $C_{1-6}$ haloalkyl, $C_{1-6}$ heteroalkyl, $C_{1-6}$ alkoxy, $C_{1-6}$ alkylthio and is optionally substituted.

E34 A compound of E33, wherein in compound of Formula I or a subformula thereof, m is 1-4.

E35 A compound of any one of E1-E30, E52 or E54-E57, wherein in compound of Formula I or a subformula thereof, $Y^1$ is O.

E36 A compound of any one of E1-E35, wherein in compounds of Formula I or a subformula thereof, $R^7$ at each occurrence is optionally substituted and independently selected from the group consisting of hydrogen, $C_{1-6}$ alkyl, $C_{1-6}$ haloalkyl, 3-10 membered heterocycloalkyl, 5-10 membered heteroaryl or $-C(=O)NR^{7a}R^{7b}$; and $R^8$ at each occurrence is independently selected from the group consisting of hydrogen $C_{1-6}$ alkyl, $C_{1-6}$ haloalkyl or $-CH_2-OH$.

E37 A compound of any one of E1-E36, wherein in compound of Formula I or a subformula thereof, $R^7$ is optionally substituted and selected from the group consisting of: furan, oxazole, isoxazole, oxadiazole, pyrrole, pyrazole, imidazole, triazole, tetrazole, thiazole, thiadiazole, thiophene, pyridine, pyrimidine, pyridazine, pyrazine, indole, indazole, indole, 1H-pyrrolo[2,3-b]pyridine, 1H-pyrrolo[2,3-c]pyridine, 1H-pyrrolo[3,2-c]pyridine, 1H-pyrrolo[3,2-b]pyridine, 5H-pyrrolo[3,2-d]pyrimidine, 7H-pyrrolo[2,3-d]pyrimidine, 5H-pyrrolo[2,3-b]pyrazine, benzimidazole, benzofuran and benzothiophene.

E38 A compound of any one of E1-E37, wherein in compound of Formula I or a subformula thereof, $R^7$ is optionally substituted and selected from the group consisting of: furan, oxazole, isoxazole, oxadiazole, pyrrole, pyrazole, imidazole, triazole, tetrazole, thiazole, thiophene, pyridine, pyrimidine, pyridazine, pyrazine, indole, indazole, indole, 1H-pyrrolo[2,3-b]pyridine, 1H-pyrrolo[2,3-c]pyridine, 1H-pyrrolo[3,2-c]

pyridine, 1H-pyrrolo[3,2-b]pyridine, 5H-pyrrolo[3,2-d]pyrimidine, 7H-pyrrolo[2,3-d]pyrimidine, 5H-pyrrolo[2,3-b]pyrazine, benzimidazole, benzofuran and benzothiophene.

E39 A compound of any one of E1-E38, wherein in compound of Formula I or a subformula thereof, $R^7$ is optionally substituted and selected from the group consisting of: oxazole, isoxazole, 1,2,4-oxadiazole, 1,2,5-oxadiazole, thiazole, thiazole, 1,3,4-thiadiazole, imidazole, pyrazole, triazole, pyrimidine, pyridazine, pyrazine, pyridine, 2H-1,2,3-triazole, 1H-1,2,4-triazole E40 A compound of any one of E1-E36 or E38, wherein in compound of Formula I or a subformula thereof, $R^7$ is optionally substituted and selected from the group consisting of: oxazole, isoxazole, 1,2,4-oxadiazole, 1,2,5-oxadiazole, thiazole, thiazole, imidazole, pyrazole, triazole, pyrimidine, pyridazine, pyrazine, pyridine, 2H-1,2,3-triazole, 1H-1,2,4-triazole.

E41 A compound of any one of E36-E340, wherein in compound of Formula I or a subformula thereof, $R^7$ is optionally substituted with from 1 to 5 substituents selected from the group consisting of F, Cl, Br, —OH, $C_{1-6}$ alkyl, $C_{1-6}$ haloalkyl, —$(X^7)_{0-1}$—CN, —$(X^7)_{0-1}$—OH, —$(X^7)_{0-1}$—H and —$(X^7)_{0-1}$—$OR^a$.

E42 A compound of any one of E36-E41, wherein in compound of Formula I or a subformula thereof, $R^7$ is selected from the group consisting of:

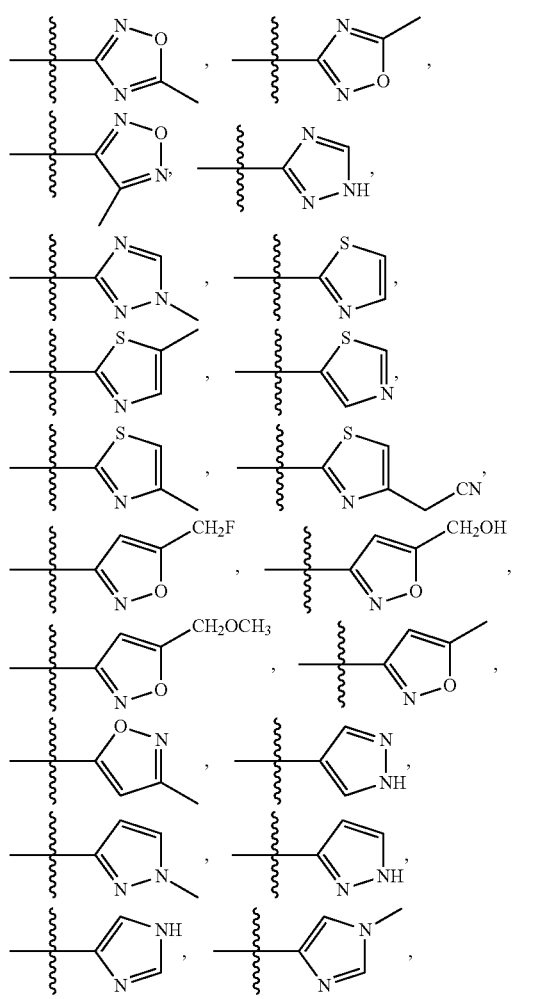

E43 A compound of any one of E1-E3 or E36, wherein in compound of Formula I or a subformula thereof, $R^7$ is selected from the group consisting of methyl, ethyl hydroxymethyl, fluoromethyl, difluoromethyl, trifluoromethyl, methoxymethyl, cyanomethyl, cyclopropyl, 3-hydroxycyclobut-1-cyclopropylmethyl, isopropyl and 1-hydroxyeth-1-yl.

E44 A compound of any one of E1-E43, wherein in compound of Formula I or a subformula thereof, $R^7$ and $R^8$ are combined with the carbon atom to each is attached to form an optionally substituted $C_{3-10}$ cycloalkyl or $C_{2-9}$ heterocycloalkyl, and wherein optionally fused to said $C_{3-10}$ cycloalkyl and $C_{2-9}$ heterocycloalkyl is a 6 membered aryl or 5-6 membered heteroaryl ring.

E45 A compound of E44, wherein in compound of Formula I or a subformula thereof, $R^7$ and $R^8$ are combined with the carbon atom to each is attached to form an optionally substituted cyclopropane, cyclobutane, cyclopentane, oxetane, piperidine, pyrrolidine, pyrrolidinone, valerolactam, caprolactam, tetrahydrofuran, teterhydropyran, 6,7-dihydro-5H-cyclopenta[b]pyridine, bicyclo[2.2.1]heptane, 8-azabicyclo[3.2.1]octane and 6-oxabicyclo[3.2.1]hexane.

E46 A compound of E44 or E45, wherein in compound of Formula I or a subformula thereof, $R^7$ and $R^8$ are combined with the carbon atom in Formula I (denoted as "*C" below) to which each is attached to form a ring selected from the group consisting of:

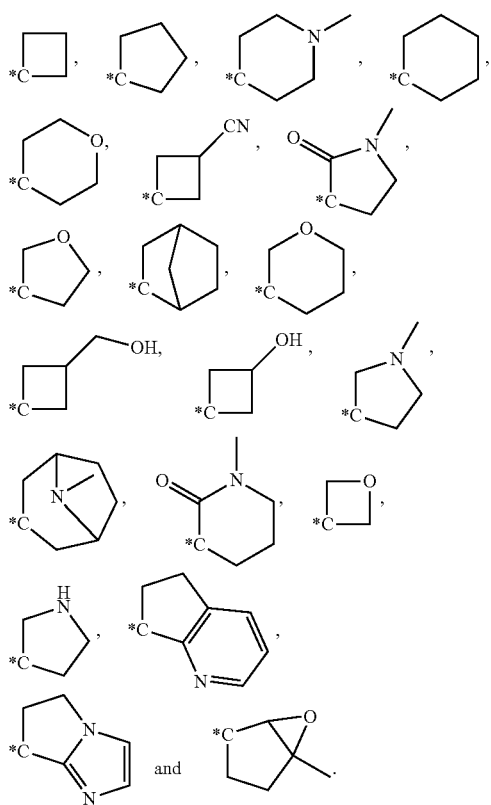

E47 A compound of any one of E1-E2, E4-E46, wherein in compound of Formula I or a subformula thereof, n is 0.

E48 A compound of any one of E1-E47, wherein in compound of Formula I or a subformula thereof, $R^4$, $R^5$ and $R^6$, if present, are each independently selected from the group consisting of hydrogen, methyl, trifluoromethyl, methoxy, OH, F, Cl, Br, I, CN and $NO_2$.

E49 A compound of E48, wherein in compound of Formula I or a subformula thereof, $R^4$, $R^5$ and $R^6$ are each independently selected from the group consisting of hydrogen, F, Cl, CN and $NO_2$.

E50 A compound of any one of E1-E49, wherein in compound of Formula I or a subformula thereof, $R^4$, $R^5$ and $R^7$ are each independently selected from the group consisting of hydrogen, methyl, trifluoromethyl, methoxy, OH, F, Cl, Br, I, CN and $NO_2$.

E51 A compound of E1-E5 or E36-E50, wherein, in compound of Formula I or a subformula thereof, m is 0 and $R^{43}$ and $R^{N3'}$, if present, is hydrogen.

E52 A compound of any one of E1-E51, wherein in compound of Formula I or a subformula thereof, $R^{43}$ and $R^{N3}$, if present, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)$_N$($R^{1a}$)($R^{1b}$), —$(X^1)_{0-1}$—C(=$Y^1$)$OR^{1a}$ and —$(X^1)_{0-1}$—C(=$Y^1$)OH.

E53 A compound of any one of E1-E5 or E36-E50, wherein in compound of Formula I or a subformula thereof, $R^{43}$ and $R^{N3}$, if present, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-6}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$ and —$(X^1)_{0-1}$—C(=$Y^1$)OH; and $R^2$ is optionally substituted and selected from the group consisting of hydrogen, —F, —Cl, —Br, —I, —$(X^1)_{0-1}$—CN, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, alkyl, $C_{1-6}$ haloalkyl, $C_{1-6}$ heteroalkyl, $C_{1-6}$ alkoxy and $C_{1-6}$ alkylthio; or in the alternative any two $R^2$ substituents attached to the same or different ring vertices in the B ring or a $R^1$ and $R^2$ substituent attached to different ring vertices in the B ring are optionally combined to for a 3-6 membered carbocyclic or heterocyclic ring comprising 1 to 2 heteroatoms selected from N, O and S, and wherein said 3-7 membered carbocyclic or heterocyclic ring is optionally substituted.

E54 A compound of any one of E1-E7, E8-E9, E15-E15, E20-E21, E24-E25, E28-E29 or E35, wherein in compound of Formula I or a subformula thereof, m is 0 and $R^{43}$ and $R^{N3}$, if present, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^1NR^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—C(=$Y^1$)N(H)($R^{1a}$)($R^{1a}$), —$(X^1)_{0-1}$—C(=$Y^1$)$NH_2$, —$(X^1)_{0-1}$—C(=$Y^1$)N($R^{1a}$)($R^{1b}$), —$(X^1)_{0-1}$—C(=$Y^1$)$OR^{1a}$ and —$(X^1)_{0-1}$—C(=$Y^1$)OH.

E55 A compound of any one of E1-E5 or E36-E50, wherein compound of Formula I or a subformula thereof, $R^{43}$ and $R^{N3'}$, if present, is selected from the group consisting of hydrogen, —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—N(H)($R^{1a}$), —$(X^1)_{0-1}$—N($R^{1b}$)($R^{1a}$), —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio; m is 1 to 2; and $R^2$ is at each occurrence, independently selected from the group consisting of —F, —Cl, —Br, —I, —$(X^1)_{0-1}$—CN, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$ and —$(X^1)_{0-1}$—$C(=Y^1)OH$.

E56 A compound of any one of E1-E5, E6-E7, E10-E11, E12-E13, E16-E17, E18-E19, E22-E23, E26-E27 or E30-E35, wherein compound of Formula I or a subformula thereof, $R^{43}$ and $R^{N3}$, if present, is hydrogen and m is 1 to 2 and $R^2$ is at each occurrence, independently selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$ and —$(X^1)_{0-1}$—$C(=Y^1)OH$.

E57 A compound of E56, wherein in compound of Formula I or a subformula thereof, $R^2$, at its first occurrence, is selected from the group consisting of —F, —Cl, —Br, —I, —$(X^1)_{0-1}$—CN, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(=Y^1)OR^{1a}$ and —$(X^1)_{0-1}$—$C(=Y^1)OH$.

E58 A compound of any one of E1-E57, wherein in compound of Formula I or a subformula thereof, $X^1$ is absent, or $X^1$ is $C_{1-4}$ alkylene, $C_{1-4}$ alkyleneoxy, $C_{2-4}$ alkenylene, $C_{2-4}$ alkynylene, $C_{1-4}$ haloalkylene and 5-6 membered heteroarylene, and wherein $X^1$ is optionally substituted with from 1-2 $R^{1/2}$ groups.

E59 A compound of E58, wherein in a compound of Formula I or a subformula thereof, $X^1$ is absent, or $X^1$ is methylene, ethylene, propylene, methyleneoxy.

E60 A compound of E58, wherein in a compound of Formula I or a subformula thereof, $X^1$ is absent, or $X^1$ is optionally substituted and is selected from the group consisting of pyrrole, pyrazole, triazole, imidazole, tetrazole, oxazole, oxadiazole, thiazole and thiadiazole.

E61 A compound of any one of E52-E59, wherein in a compound of Formula I or a subformula thereof, $Y^1$ is O.

E62 A compound of any one of E1-E5, wherein in Formula I, I-A, I-$A^1$-I-$A^{10}$ or II-$A^1$-II-$A^{10}$, any two $R^2$ substituents attached to the same or different ring vertices in the B ring are combined to form a 3 to 6 membered carbocyclic are heterocyclic ring and is substituted with from 1 to 2 $R^{1/2}$ substituents.

E63 A compound of any one of E1-E62, wherein in compound of Formula I or a subformula thereof, $R^1$, $R^2$ in its first occurrence, $R^{43}$ and $R^{N3}$, each if present, is independently selected from the group consisting of:

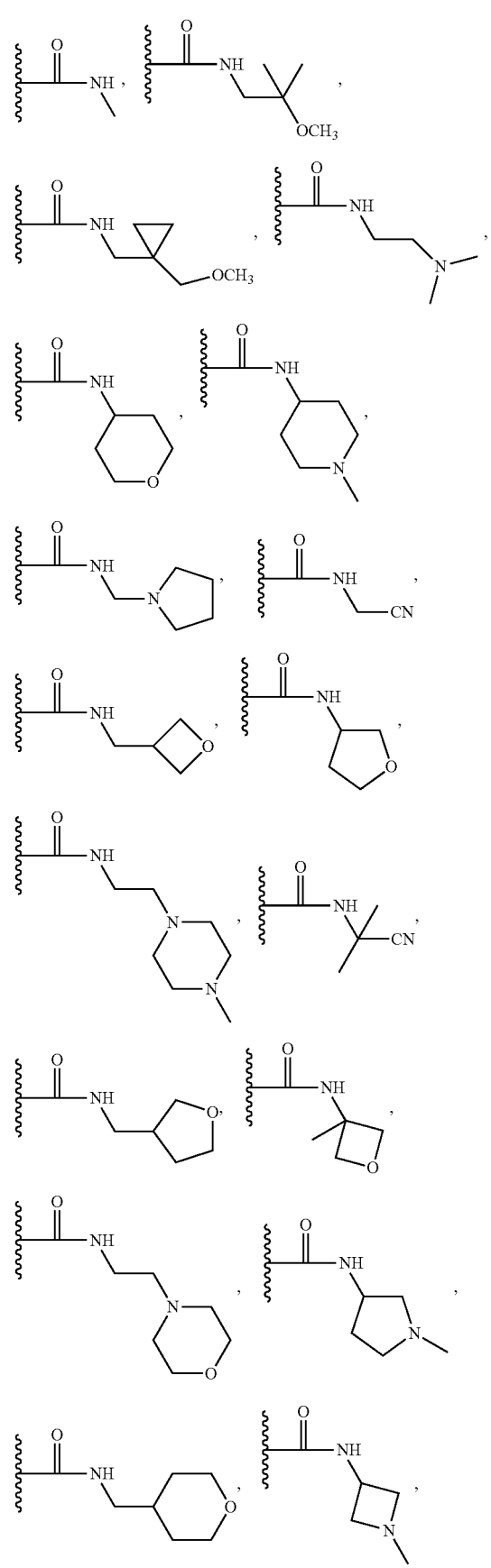

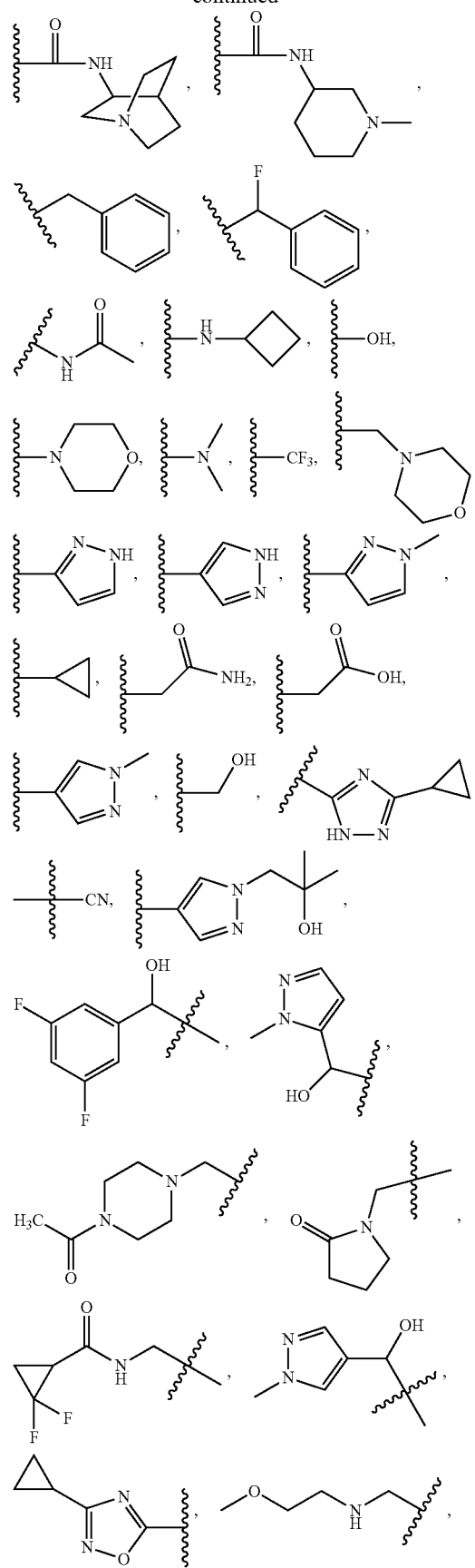
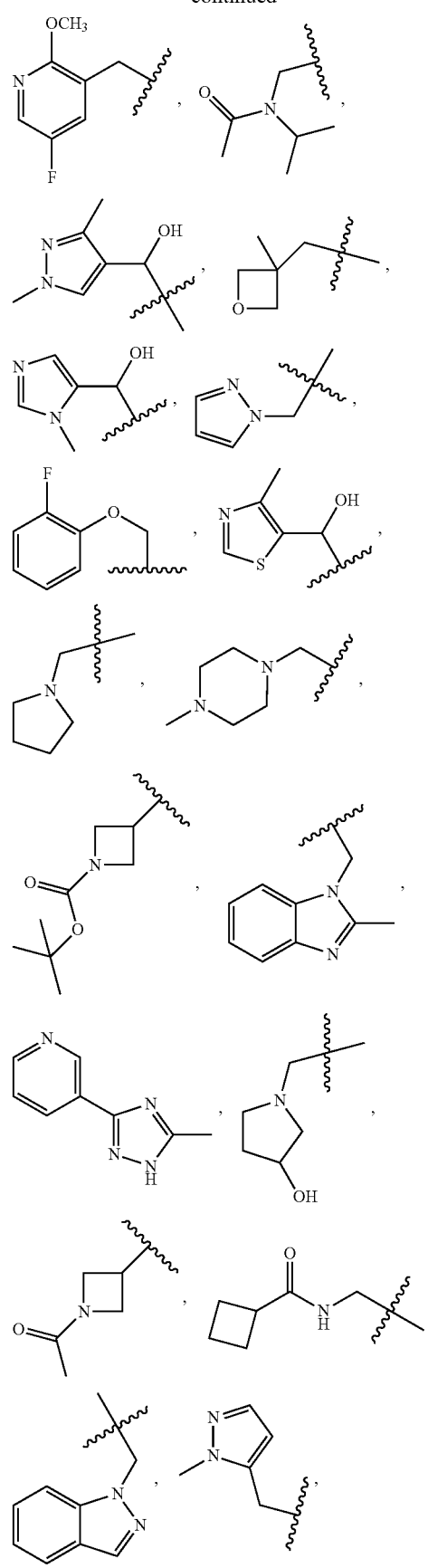

71
-continued

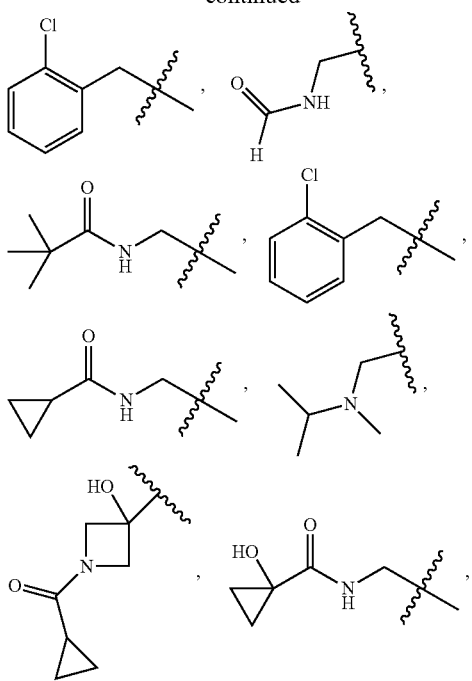

72
-continued

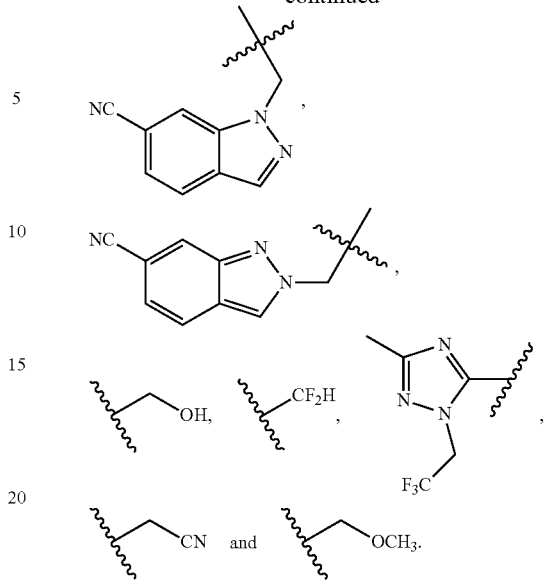

E63 A compound of E1, wherein said compounds of the invention are selected from the group as set forth in Table 1 below:

TABLE 1

| No. | Structure | Name |
|---|---|---|
| 1 | 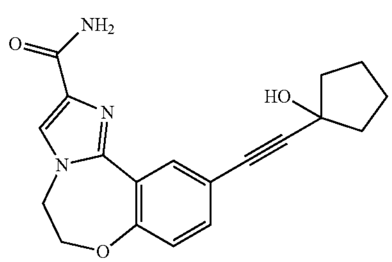 [SMILES: NC(=O)c1cn2c(n1)-c1cc(C#CC3(O)CCCC3)ccc1OCC2] | 9-(1-hydroxy-cyclopentylethynyl)-4,5-dihydro-6-oxa-1,3a-diaza-benzo[e]azulene-2-carboxylic acid amide |
| 2 | 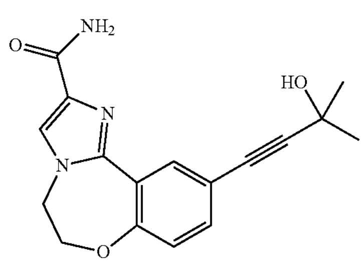 [SMILES: CC(C)(O)C#Cc1ccc2c(c1)-c1nc(C(N)=O)cn1CCO2] | 9-(3-hydroxy-3-methyl-but-1-ynyl)-4,5-dihydro-6-oxa-1,3a-diaza-benzo[e]azulene-2-carboxylic acid amide |
| 3 | 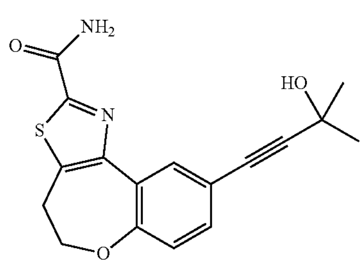 [SMILES: CC(C)(O)C#Cc1ccc2c(c1)-c1nc(C(N)=O)sc1CCO2] | 9-(3-hydroxy-3-methyl-but-1-ynyl)-4,5-dihydro-6-oxa-3-thia-1-aza-benzo[e]azulene-2-carboxylic acid amide |

TABLE 1-continued

| No. | Structure | Name |
|---|---|---|
| 4 | 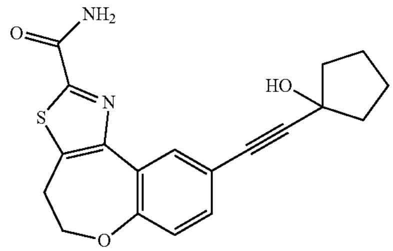 [SMILES: NC(=O)c1nc2c(s1)CCOc1ccc(C#CC3(O)CCCC3)cc1-2] | 9-(1-hydroxy-cyclopentylethynyl)-4,5-dihydro-6-oxa-3-thia-1-aza-benzo[e]azulene-2-carboxylic acid amide |
| 5 | 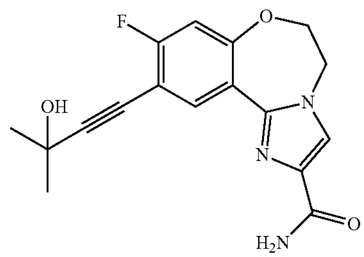 [SMILES: CC(C)(O)C#Cc1cc2c(cc1F)OCCn1cc(C(N)=O)nc1-2] | 8-fluoro-9-(3-hydroxy-3-methyl-but-1-ynyl)-4,5-dihydro-6-oxa-1,3a-diaza-benzo[e]azulene-2-carboxylic acid amide |
| 6 | 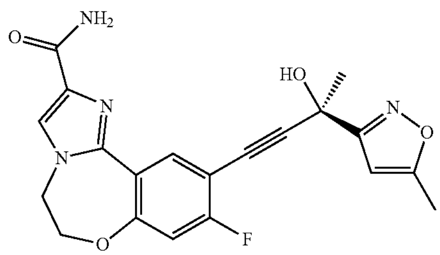 [SMILES: Cc1cc([C@](C)(O)C#Cc2cc3c(cc2F)OCCn2cc(C(N)=O)nc2-3)no1] | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 7 | 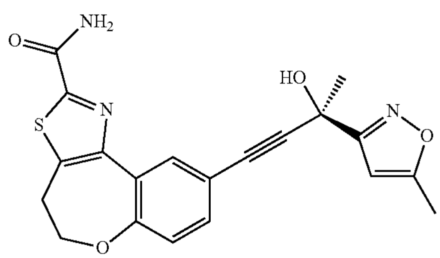 [SMILES: Cc1cc([C@](C)(O)C#Cc2ccc3c(c2)-c2nc(C(N)=O)sc2CCO3)no1] | 9-[(R)-3-hydroxy-3-(5-methyl-isoxazol-3-yl)-but-1-ynyl]-4,5-dihydro-6-oxa-3-thia-1-aza-benzo[e]azulene-2-carboxylic acid amide |
| 8 | 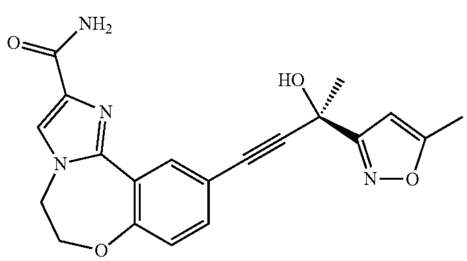 [SMILES: Cc1cc([C@](C)(O)C#Cc2ccc3c(c2)-c2nc(C(N)=O)cn2CCO3)no1] | 9-[(R)-3-Hydroxy-3-(5-methyl-isoxazol-3-yl)-but-1-ynyl]-4,5-dihydro-6-oxa-1,3a-diaza-benzo[e]azulene-2-carboxylic acid amide |
| 9 | 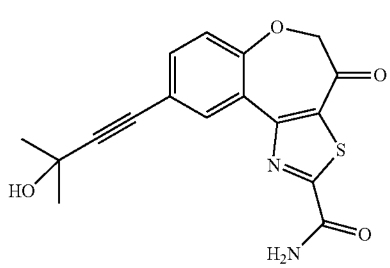 [SMILES: CC(C)(O)C#Cc1ccc2c(c1)-c1nc(C(N)=O)sc1C(=O)CO2] | 9-(3-hydroxy-3-methyl-but-1-ynyl)-4-oxo-4,5-dihydro-6-oxa-3-thia-1-aza-benzo[e]azulene-2-carboxylic acid amide |

TABLE 1-continued

| No. | Structure | Name |
|---|---|---|
| 10 | 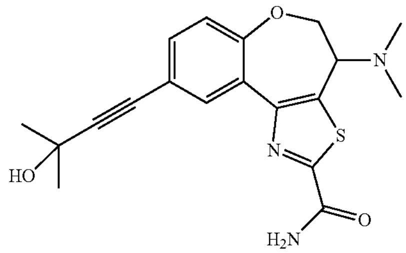 [SMILES: CN(C)C1COc2ccc(C#CC(C)(C)O)cc2-c2nc(C(N)=O)sc21] | 4-dimethylamino-9-(3-hydroxy-3-methyl-but-1-ynyl)-4,5-dihydro-6-oxa-3-thia-1-aza-benzo[e]azulene-2-carboxylic acid amide |
| 11 | 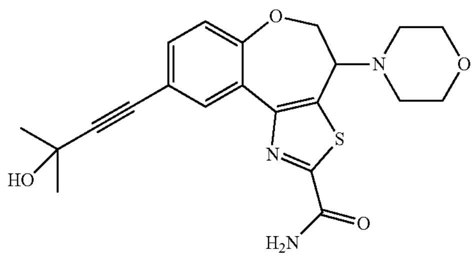 [SMILES: CC(C)(O)C#Cc1ccc2c(c1)-c1nc(C(N)=O)sc1C(N1CCOCC1)CO2] | 9-(3-hydroxy-3-methyl-but-1-ynyl)-4-morpholin-4-yl-4,5-dihydro-6-oxa-3-thia-1-aza-benzo[e]azulene-2-carboxylic acid amide |
| 12 | 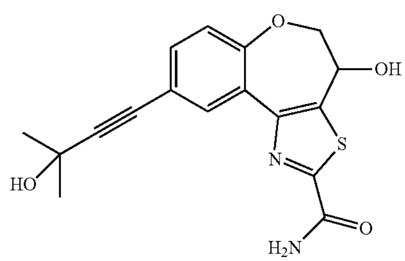 [SMILES: CC(C)(O)C#Cc1ccc2c(c1)-c1nc(C(N)=O)sc1C(O)CO2] | 4-hydroxy-9-(3-hydroxy-3-methyl-but-1-ynyl)-4,5-dihydro-6-oxa-3-thia-1-aza-benzo[e]azulene-2-carboxylic acid amide |
| 13 | 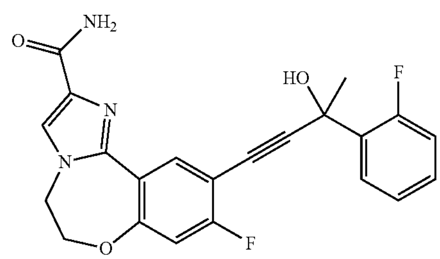 [SMILES: CC(O)(C#Cc1cc2c(cc1F)OCCn1cc(C(N)=O)nc1-2)c1ccccc1F] | 8-fluoro-9-[3-(2-fluoro-phenyl)-3-hydroxy-but-1-ynyl]-4,5-dihydro-6-oxa-1,3a-diaza-benzo[e]azulene-2-carboxylic acid amide |
| 14 | 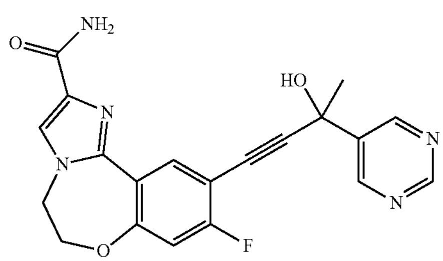 [SMILES: CC(O)(C#Cc1cc2c(cc1F)OCCn1cc(C(N)=O)nc1-2)c1cncnc1] | 8-Fluoro-9-(3-hydroxy-3-pyrimidin-5-yl-but-1-ynyl)-4,5-dihydro-6-oxa-1,3a-diaza-benzo[e]azulene-2-carboxylic acid amide |
| 15 | 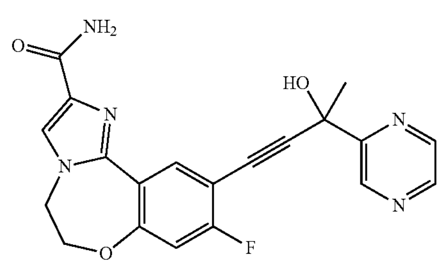 [SMILES: CC(O)(C#Cc1cc2c(cc1F)OCCn1cc(C(N)=O)nc1-2)c1cnccn1] | 8-fluoro-9-(3-hydroxy-3-pyrazin-2-yl-but-1-ynyl)-4,5-dihydro-6-oxa-1,3a-diaza-benzo[e]azulene-2-carboxylic acid amide |

TABLE 1-continued

| No. | Structure | Name |
|---|---|---|
| 16 | 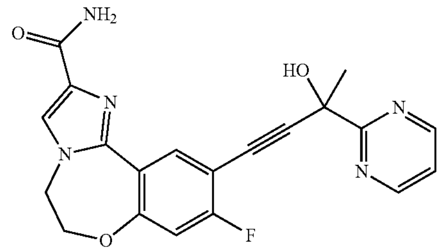 [SMILES: CC(O)(C#Cc1cc2c(cc1F)OCCn1cc(C(N)=O)nc1-2)c1ncccn1] | 8-fluoro-9-(3-hydroxy-3-pyrimidin-2-yl-but-1-ynyl)-4,5-dihydro-6-oxa-1,3a-diaza-benzo[e]azulene-2-carboxylic acid amide |
| 17 | 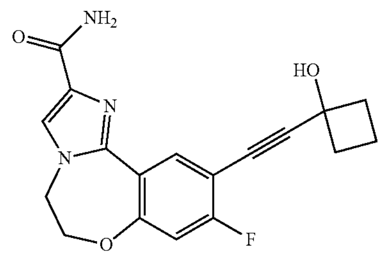 [SMILES: NC(=O)c1cn2c(n1)-c1cc(C#CC3(O)CCC3)c(F)cc1OCC2] | 8-fluoro-9-(1-hydroxy-cyclobutylethynyl)-4,5-dihydro-6-oxa-1,3a-diaza-benzo[e]azulene-2-carboxylic acid amide |
| 18 | 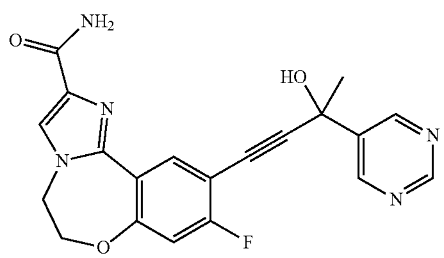 [SMILES: CC(O)(C#Cc1cc2c(cc1F)OCCn1cc(C(N)=O)nc1-2)c1cncnc1] | 8-fluoro-9-(3-hydroxy-3-pyrimidin-5-yl-but-1-ynyl)-4,5-dihydro-6-oxa-1,3a-diaza-benzo[e]azulene-2-carboxylic acid amide |
| 19 | 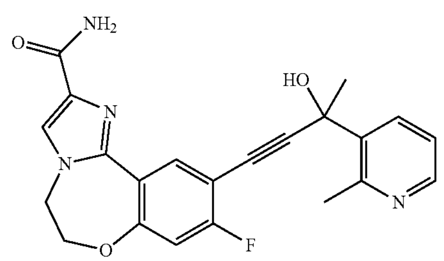 [SMILES: Cc1ncccc1C(C)(O)C#Cc1cc2c(cc1F)OCCn1cc(C(N)=O)nc1-2] | 8-fluoro-9-[3-hydroxy-3-(2-methyl-pyridin-3-yl)-but-1-ynyl]-4,5-dihydro-6-oxa-1,3a-diaza-benzo[e]azulene-2-carboxylic acid amide |
| 20 | 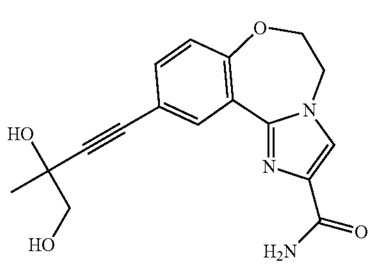 [SMILES: CC(O)(C#Cc1ccc2c(c1)-c1nc(C(N)=O)cn1CCO2)CO] | 9-(3,4-dihydroxy-3-methyl-but-1-ynyl)-4,5-dihydro-6-oxa-1,3a-diaza-benzo[e]azulene-2-carboxylic acid amide |
| 21 | 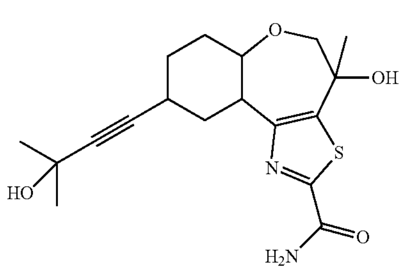 [SMILES: CC(C)(O)C#CC1CCC2OCC(C)(O)c3sc(C(N)=O)nc3C2C1] | 4-hydroxy-9-(3-hydroxy-3-methyl-but-1-ynyl)-4-methyl-4,5-dihydro-6-oxa-3-thia-1-aza-benzo[e]azulene-2-carboxylic acid amide |

TABLE 1-continued

| No. | Structure | Name |
|---|---|---|
| 22 | 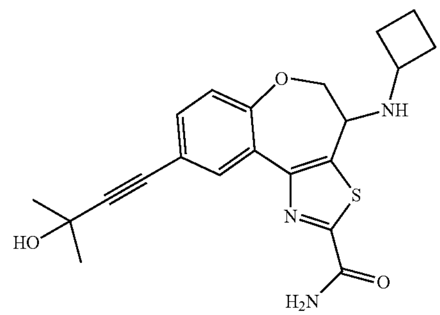 [SMILES: CC(C)(O)C#Cc1ccc2c(c1)-c1nc(C(N)=O)sc1C(NC1CCC1)CO2] | 4-cyclobutylamino-9-(3-hydroxy-3-methyl-but-1-ynyl)-4,5-dihydro-6-oxa-3-thia-1-aza-benzo[e]azulene-2-carboxylic acid amide |
| 23 | 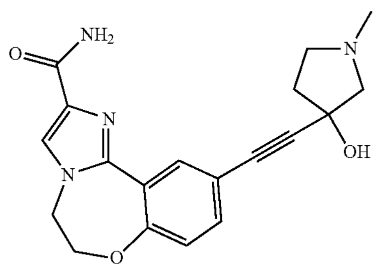 [SMILES: CN1CCC(O)(C#Cc2ccc3c(c2)-c2nc(C(N)=O)cn2CCO3)C1] | 9-(3-hydroxy-1-methyl-pyrrolidin-3-yl-ethynyl)-4,5-dihydro-6-oxa-1,3a-diaza-benzo[e]azulene-2-carboxylic acid amide |
| 24 | 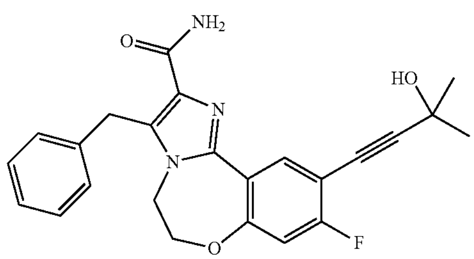 [SMILES: CC(C)(O)C#Cc1cc2c(cc1F)OCCn1c-2nc(C(N)=O)c1Cc1ccccc1] | 3-benzyl-8-fluoro-9-(3-hydroxy-3-methyl-but-1-ynyl)-4,5-dihydro-6-oxa-1,3a-diaza-benzo[e]azulene-2-carboxylic acid amide |
| 25 | 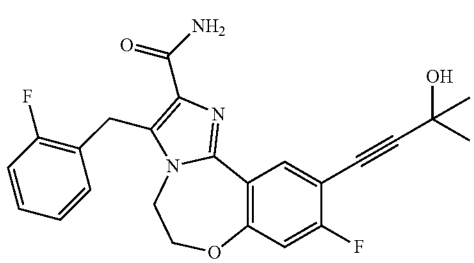 [SMILES: CC(C)(O)C#Cc1cc2c(cc1F)OCCn1c-2nc(C(N)=O)c1Cc1ccccc1F] | 8-fluoro-3-(2-fluoro-benzyl)-9-(3-hydroxy-3-methyl-but-1-ynyl)-4,5-dihydro-6-oxa-1,3a-diaza-benzol[e]azulene-2-carboxylic acid amide |
| 26 | 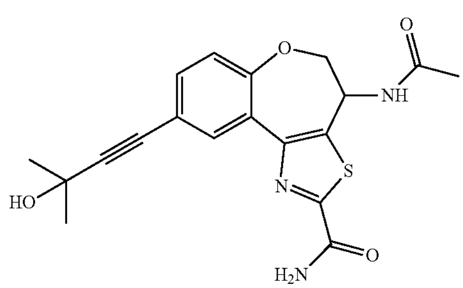 [SMILES: CC(=O)NC1COc2ccc(C#CC(C)(C)O)cc2-c2nc(C(N)=O)sc21] | 4-acetylamino-9-(3-hydroxy-3-methyl-but-1-ynyl)-4,5-dihydro-6-oxa-3-thia-1-aza-benzo[e]azulene-2-carboxylic acid amide |

TABLE 1-continued

| No. | Structure | Name |
| --- | --- | --- |
| 27 | 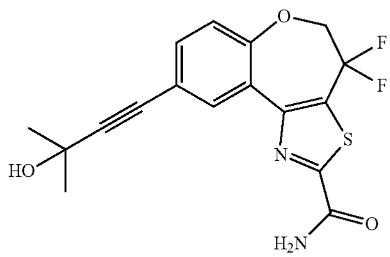 [SMILES: CC(C)(O)C#Cc1ccc2c(c1)-c1nc(C(N)=O)sc1C(F)(F)CO2] | 4,4-diriuoro-9-(3-hydroxy-3-methyl-but-1-ynyl)-4,5-dihydro-6-oxa-3-thia-1-aza-benzo[c]azulene-2-carboxylic acid amide |
| 28 | 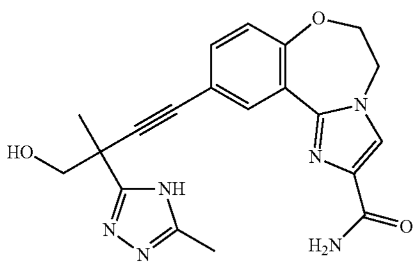 [SMILES: Cc1nnc(C(C)(C#Cc2ccc3c(c2)-c2nc(C(N)=O)cn2CCO3)CO)[nH]1] | 9-[4-hydroxy-3-methyl-3-(5-methyl-4H-[1,24]triazol-3-yl)-but-1-ynyl]-4,5-dihydro-6-oxa-1,3a-diaza-benzo[e]azulene-2-carboxylic acid amide |
| 29 | 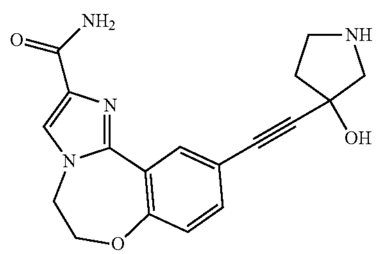 [SMILES: NC(=O)c1cn2c(n1)-c1cc(C#CC3(O)CCNC3)ccc1OCC2] | 9-(3-hydroxy-pyrrolidin-3-ylethynyl)-4,5-dihydro-6-oxa-1,3a-diaza-benzo[e]azulene-2-carboxylic acid amide |
| 30 | 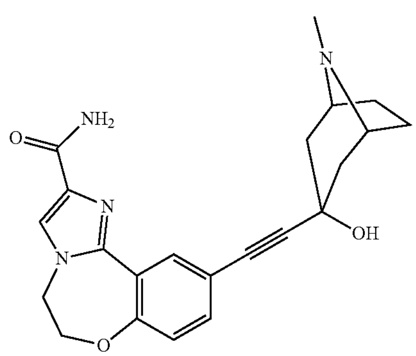 [SMILES: CN1C2CCC1CC(O)(C#Cc1ccc3c(c1)-c1nc(C(N)=O)cn1CCO3)C2] | 9-(3-hydroxy-8-methyl-8-aza-bicyclo[3.2.1]oct-3-ylethynyl)-4,5-dihydro-6-oxa-1,3a-diaza-benzo[e]azulene-2-carboxylic acid amide |
| 31 | 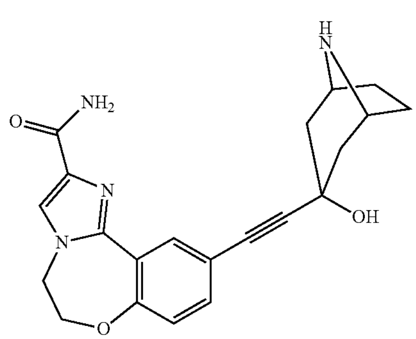 [SMILES: NC(=O)c1cn2c(n1)-c1cc(C#CC3(O)CC4CCC(C3)N4)ccc1OCC2] | 9-(3-hydroxy-8-aza-bicyclo[3.2.1]oct-3-ylethynyl)-4,5-dihydro-6-oxa-1,3a-diaza-benzo[e]azulene-2-carboxylic acid amide |

TABLE 1-continued

| No. | Structure | Name |
|---|---|---|
| 32 | 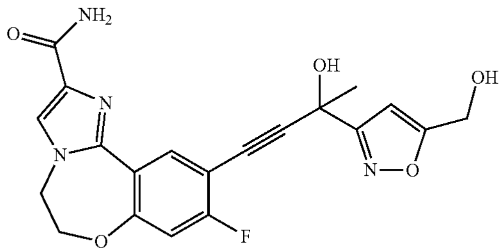 [SMILES: CC(O)(C#Cc1cc2c(cc1F)OCCn1cc(C(N)=O)nc1-2)c1cc(CO)on1] | 8-fluoro-9-[3-hydroxy-3-(5-hydroxymethyl-isoxazol-3-yl)-but-1-ynyl]-4,5-dihydro-6-oxa-1,3a-diaza-benzo[c]azulene-2-carboxylic acid amide |
| 33 | 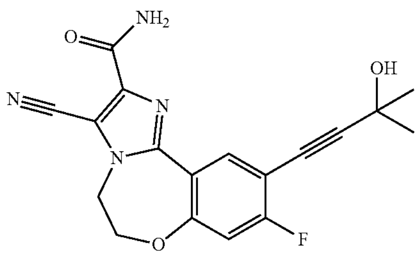 [SMILES: CC(C)(O)C#Cc1cc2c(cc1F)OCCn1c-2nc(C(N)=O)c1C#N] | 3-cyano-8-fluoro-9-(3-hydroxy-3-methyl-but-1-ynyl)-4,5-dihydro-6-oxa-1,3a-diaza-benzo[e]azulene-2-carboxylic acid amide |
| 34 | 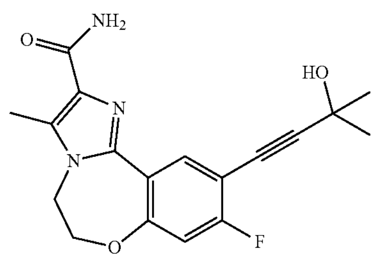 [SMILES: Cc1c(C(N)=O)nc2n1CCOc1cc(F)c(C#CC(C)(C)O)cc1-2] | 8-fluoro-9-(3-hydroxy-3-methyl-but-1-ynyl)-3-methyl-4,5-dihydro-6-oxa-1,3a-diaza-benzo[e]azulene-2-carboxylic acid amide |
| 35 | 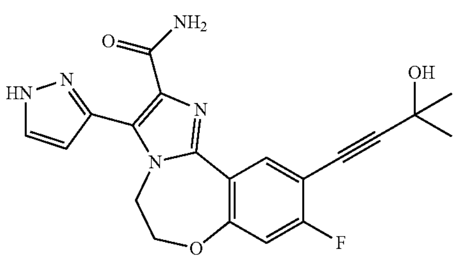 [SMILES: CC(C)(O)C#Cc1cc2c(cc1F)OCCn1c-2nc(C(N)=O)c1-c1cc[nH]n1] | 8-fluoro-9-(3-hydroxy-3-methyl-but-1-ynyl)-3-(1H-pyrazol-3-yl)-4,5-dihydro-6-oxa-1,3a-diaza-benzo[e]azulene-2-carboxylic acid amide |
| 36 | 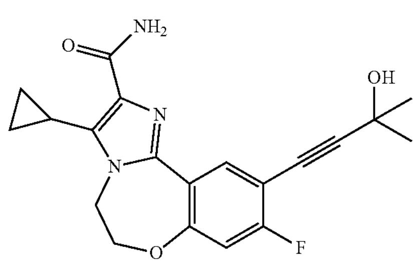 [SMILES: CC(C)(O)C#Cc1cc2c(cc1F)OCCn1c-2nc(C(N)=O)c1C1CC1] | 3-cyclopropyl-8-fluoro-9-(3-hydroxy-3-methyl-but-1-ynyl)-4,5-dihydro-6-oxa-1,3a-diaza-benzo[e]azulene-2-carboxylic acid amide |
| 37 | 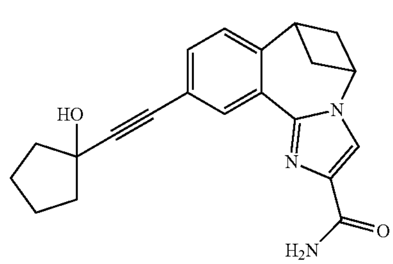 [SMILES: NC(=O)c1cn2c(n1)-c1cc(C#CC3(O)CCCC3)ccc1C1CC2C1] | 9-[2-(1-hydroxycyclopentyl)ethynyl]-2,5-diazatetracyclo[11.1.1.0$^{2,6}$,0$^{7,12}$]pentadeca-3,5,7,9,11-pentaene-4-carboxamide |

TABLE 1-continued

| No. | Structure | Name |
|---|---|---|
| 38 | 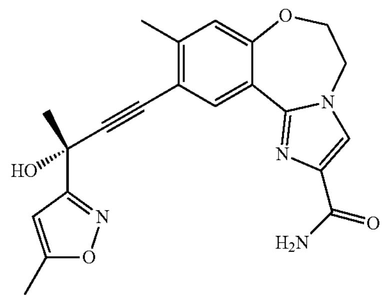 [SMILES: Cc1cc([C@](C)(O)C#Cc2cc3c(cc2C)OCCn2cc(C(N)=O)nc2-3)no1] | 9-[(R)-3-hydroxy-3-(5-methyl-isoxazol-3-yl)-but-1-ynyl]-8-methyl-4,5-dihydro-6-oxa-1,3a-diaza-benzo[e]azulene-2-carboxylic acid amide |
| 39 | 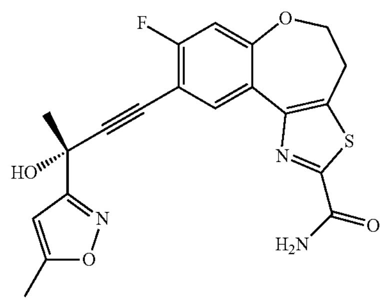 [SMILES: Cc1cc([C@](C)(O)C#Cc2cc3c(cc2F)OCCc2sc(C(N)=O)nc2-3)no1] | 8-fluoro-9-[(R)-3-hydroxy-3-(5-methyl-isoxazol-3-yl)-but-1-ynyl]-4,5-dihydro-6-oxa-3-thia-1-aza-benzo[e]azulene-2-carboxylic acid amide |
| 40 | 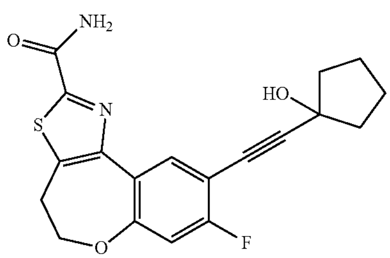 [SMILES: NC(=O)c1nc2c(s1)CCOc1cc(F)c(C#CC3(O)CCCC3)cc1-2] | 8-fluoro-9-(1-hydroxy-cyclopentyl-ethynyl)-4,5-dihydro-6-oxa-3-thia-1-aza-benzo[e]azulene-2-carboxylic acid amide |
| 41 | 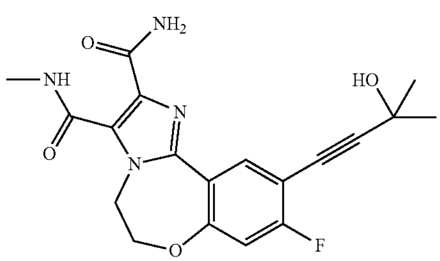 [SMILES: CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-methylamide |
| 42 | 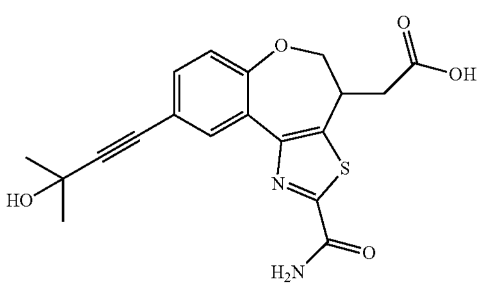 [SMILES: CC(C)(O)C#Cc1ccc2c(c1)-c1nc(C(N)=O)sc1C(CC(=O)O)CO2] | [2-carbamoyl-9-(3-hydroxy-3-methyl-but-1-ynyl)-4,5-dihydro-6-oxa-3-thia-1-aza-benzo[e]azulen-4-yl]-acetic acid |

TABLE 1-continued

| No. | Structure | Name |
|---|---|---|
| 43 | 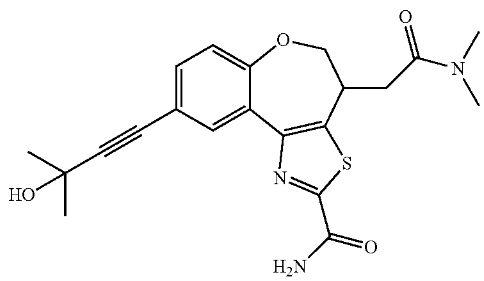 [SMILES: CN(C)C(=O)CC1COc2ccc(C#CC(C)(C)O)cc2-c2nc(C(N)=O)sc21] | 4-dimethylcarbamoylmethyl-9-(3-hydroxy-3-methyl-but-1-ynyl)-4,5-dihydro-6-oxa-3-thia-1-aza-benzo[e]azulene-2-carboxylic acid amide |
| 44 | 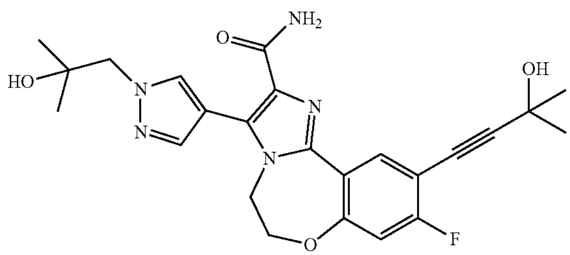 [SMILES: CC(C)(O)C#Cc1cc2c(cc1F)OCCn1c-2nc(C(N)=O)c1-c1cnn(CC(C)(C)O)c1] | 8-fluoro-9-(3-hydroxy-3-methyl-but-1-ynyl)-3-[1-(2-hydroxy-2-methyl-propyl)-1H-pyrazol-4-yl]-4,5-dihydro-6-oxa-1,3a-diaza-benzo[e]azulene-2-carboxylic acid amide |
| 45 | 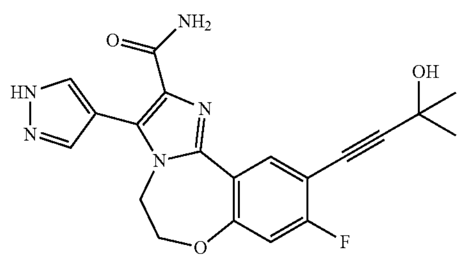 [SMILES: CC(C)(O)C#Cc1cc2c(cc1F)OCCn1c-2nc(C(N)=O)c1-c1cn[nH]c1] | 8-fluoro-9-(3-hydroxy-3-methyl-but-1-ynyl)-3-(1H-pyrazol-4-yl)-4,5-dihydro-6-oxa-1,3a-diaza-benzo[e]azulene-2-carboxylic acid amide |
| 46 | 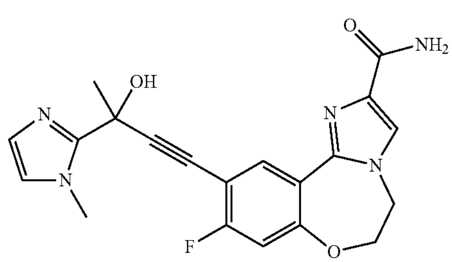 [SMILES: Cn1ccnc1C(C)(O)C#Cc1cc2c(cc1F)OCCn1cc(C(N)=O)nc1-2] | 8-fluoro-9-[3-hydroxy-3-(1-methyl-1H-imidazol-2-yl)-but-1-ynyl]-4,5-dihydro-6-oxa-1,3a-diaza-benzo[e]azulene-2-carboxylic acid amide |
| 47 | 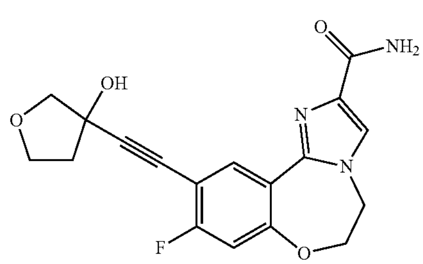 [SMILES: NC(=O)c1cn2c(n1)-c1cc(C#CC3(O)CCOC3)c(F)cc1OCC2] | 8-fluoro-9-(3-hydroxy-tetrahydro-furan-3-ylethynyl)-4,5-dihydro-6-oxa-1,3a-diaza-benzo[e]azulene-2-carboxylic acid amide |
| 48 | 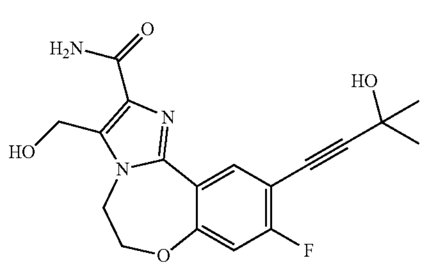 [SMILES: CC(C)(O)C#Cc1cc2c(cc1F)OCCn1c-2nc(C(N)=O)c1CO] | 8-fluoro-3-hydroxymethyl-9-(3-hydroxy-3-methyl-but-ynyl)-4,5-dihydro-6-oxa-1,3a-diaza-benzo[e]azulene-2-carboxylic acid amide |

TABLE 1-continued

| No. | Structure | Name |
|---|---|---|
| 49 | 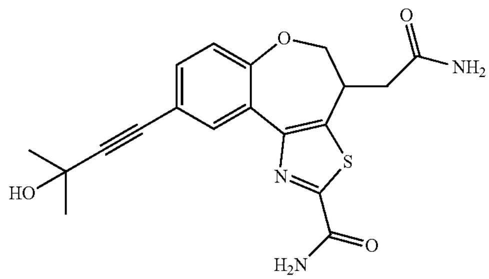 [SMILES: CC(C)(O)C#Cc1ccc2c(c1)-c1nc(C(N)=O)sc1C(CC(N)=O)CO2] | 4-carbamoylmethyl-9-(3-hydroxy-3-methyl-but-1-ynyl)-4,5-dihydro-6-oxa-3-thia-1-aza-benzo[e]azulene-2-carboxylic acid amide |
| 50 | 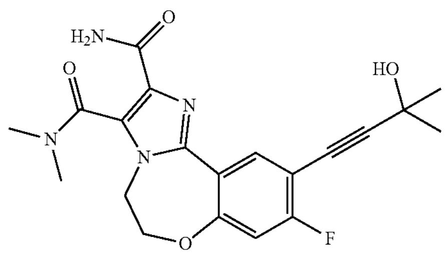 [SMILES: CN(C)C(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-dimethylamide |
| 51 | 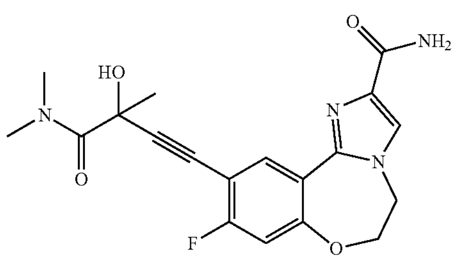 [SMILES: CN(C)C(=O)C(C)(O)C#Cc1cc2c(cc1F)OCCn1cc(C(N)=O)nc1-2] | 9-(3-dimethylcarbamoyl-3-hydroxy-but-1-ynyl)-8-fluoro-4,5-dihydro-6-oxa-1,3a-diaza-benzo[e]azulene-2-carboxylic acid amide |
| 52 | 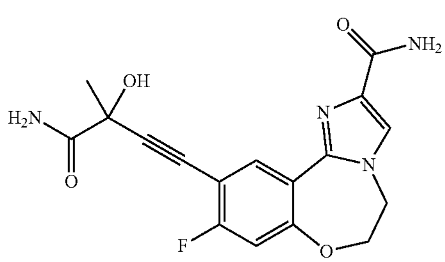 [SMILES: CC(O)(C#Cc1cc2c(cc1F)OCCn1cc(C(N)=O)nc1-2)C(N)=O] | 9-(3-carbamoyl-3-hydroxy-but-1-ynyl)-8-fluoro-4,5-dihydro-6-oxa-1,3a-diaza-benzo[e]azulene-2-carboxylic acid amide |
| 53 | 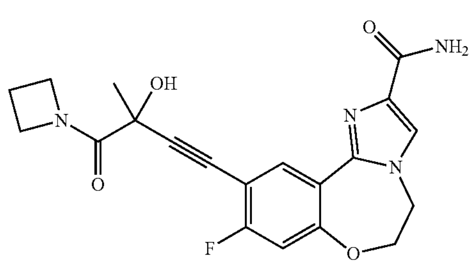 [SMILES: CC(O)(C#Cc1cc2c(cc1F)OCCn1cc(C(N)=O)nc1-2)C(=O)N1CCC1] | 9-(4-azetidin-1-yl-3-hydroxy-3-methyl-4-oxo-but-1-ynyl)-8-fluoro-4,5-dihydro-6-oxa-1,3a-diaza-benzo[e]azulene-2-carboxylic acid amide |
| 54 | 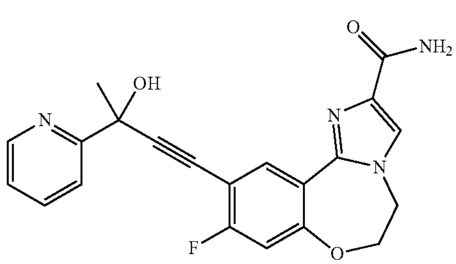 [SMILES: CC(O)(C#Cc1cc2c(cc1F)OCCn1cc(C(N)=O)nc1-2)c1ccccn1] | 8-fluoro-9-(3-hydroxy-3-pyridin-2-yl-but-1-ynyl)-4,5-dihydro-6-oxa-1,3a-diaza-benzo[e]azulene-2-carboxylic acid amide |

TABLE 1-continued

| No. | Structure | Name |
|---|---|---|
| 55 | 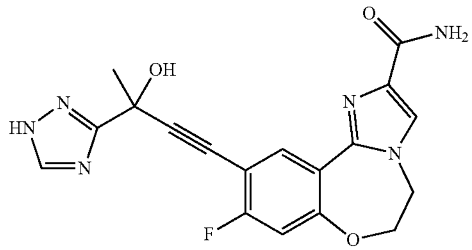 [SMILES: CC(O)(C#Cc1cc2c(cc1F)OCCn1cc(C(N)=O)nc1-2)c1nc[nH]n1] | 8-fluoro-9-[3-hydroxy-3-(1H-[1,2,4]triazol-3-yl)-but-1-ynyl]-4,5-dihydro-6-oxa-1,3a-diaza-benzo[e]azulene-2-carboxylic acid amide |
| 56 | 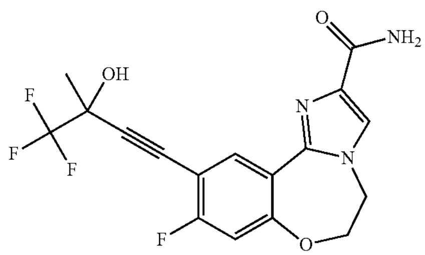 [SMILES: CC(O)(C#Cc1cc2c(cc1F)OCCn1cc(C(N)=O)nc1-2)C(F)(F)F] | 8-fluoro-9-(4,4,4-trifluoro-3-hydroxy-3-methyl-but-1-ynyl)-4,5-dihydro-6-oxa-1,3a-diaza-benzo[e]azulene-2-carboxylic acid amide |
| 57 | 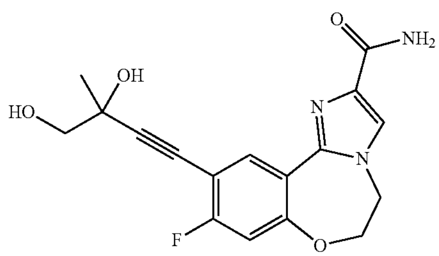 [SMILES: CC(O)(C#Cc1cc2c(cc1F)OCCn1cc(C(N)=O)nc1-2)CO] | 9-(3,4-dihydroxy-3-methyl-but-1-ynyl)-8-fluoro-4,5-dihydro-6-oxa-1,3a-diaza-benzo[e]azulene-2-carboxylic acid amide |
| 58 | 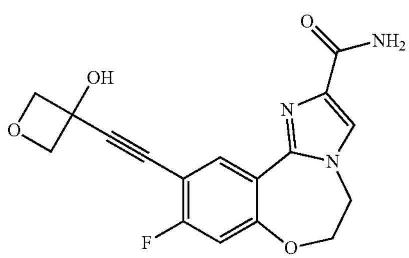 [SMILES: NC(=O)c1cn2c(n1)-c1cc(C#CC3(O)COC3)c(F)cc1OCC2] | 8-fluoro-9-(3-hydroxy-oxetan-3-ylethynyl)-4,5-dihydro-6-oxa-1,3a-diaza-benzo[e]azulene-2-carboxylic acid amide |
| 59 | 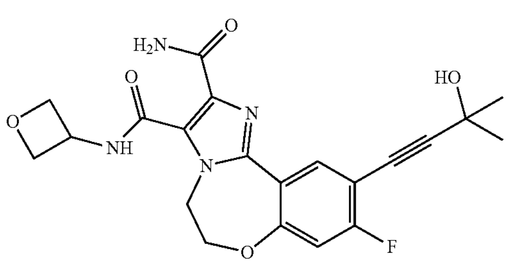 [SMILES: CC(C)(O)C#Cc1cc2c(cc1F)OCCn1c-2nc(C(N)=O)c1C(=O)NC1COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-oxetan-3-ylamide |
| 60 | 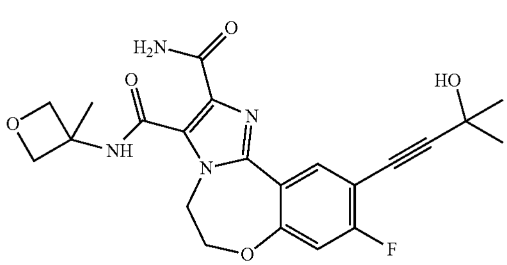 [SMILES: CC(C)(O)C#Cc1cc2c(cc1F)OCCn1c-2nc(C(N)=O)c1C(=O)NC1(C)COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(3-methyl-oxetan-3-yl)-amide] |

TABLE 1-continued

| No. | Structure | Name |
|---|---|---|
| 61 | 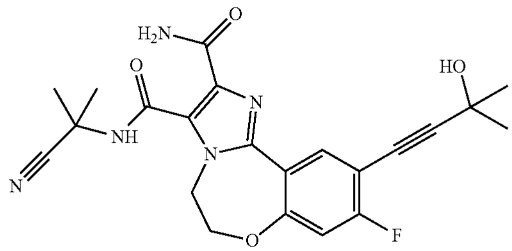 [SMILES: CC(C)(O)C#Cc1cc2c(cc1F)OCCn1c-2nc(C(N)=O)c1C(=O)NC(C)(C)C#N] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(cyano-dimethyl-methyl)-amide] |
| 62 | 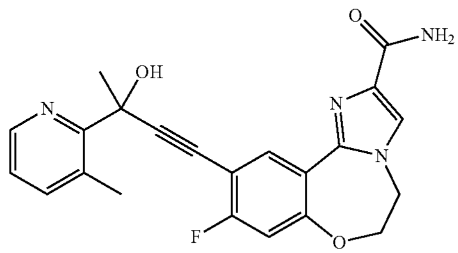 [SMILES: Cc1cccnc1C(C)(O)C#Cc1cc2c(cc1F)OCCn1cc(C(N)=O)nc1-2] | 8-fluoro-9-[3-hydroxy-3-(3-methyl-pyridin-2-yl)-but-1-ynyl]-4,5-dihydro-6-oxa-1,3a-diaza-benzo[e]azulene-2-carboxylic acid amide |
| 63 | 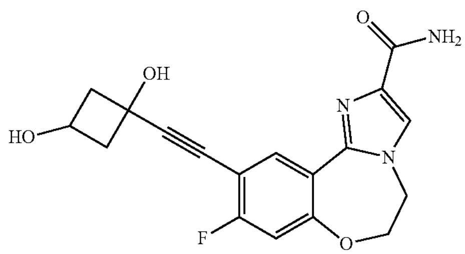 [SMILES: NC(=O)c1cn2c(n1)-c1cc(C#CC3(O)CC(O)C3)c(F)cc1OCC2] | 9-(1,3-dihydroxy-cyclobutylethynyl)-8-fluoro-4,5-dihydro-6-oxa-1,3a-diaza-benzo[e]azulene-2-carboxylic acid amide |
| 64 | 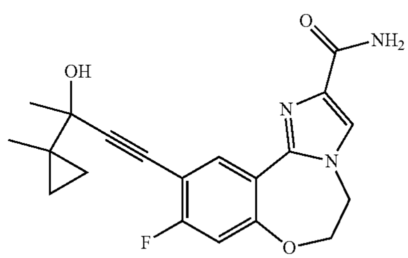 [SMILES: CC(O)(C#Cc1cc2c(cc1F)OCCn1cc(C(N)=O)nc1-2)C1(C)CC1] | 8-fluoro-9-[3-hydroxy-3-(1-methyl-cyclopropyl)-but-1-ynyl]-4,5-dihydro-6-oxa-1,3a-diaza-benzo[e]azulene-2-carboxylic acid amide |
| 65 | 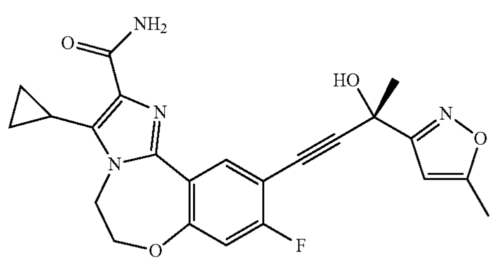 [SMILES: Cc1cc([C@@](C)(O)C#Cc2cc3c(cc2F)OCCn2c-3nc(C(N)=O)c2C2CC2)no1] | 3-cyclopropyl-8-fluoro-9-[(S)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 66 | 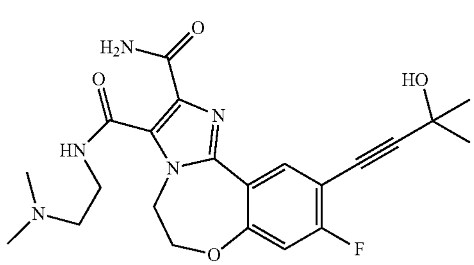 [SMILES: CN(C)CCNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-dimethylamino-ethyl)-amide] |

TABLE 1-continued

| No. | Structure | Name |
|---|---|---|
| 67 | 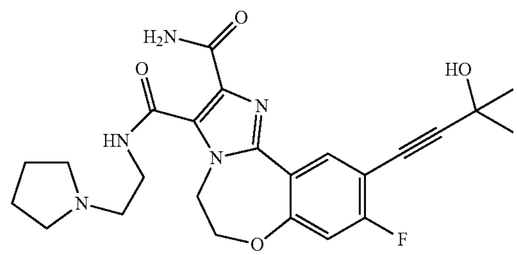 [SMILES: CC(C)(O)C#Cc1cc2c(cc1F)OCCn1c-2nc(C(N)=O)c1C(=O)NCCN1CCCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-pyrrolidin-1-yl-ethyl)-amide] |
| 68 | 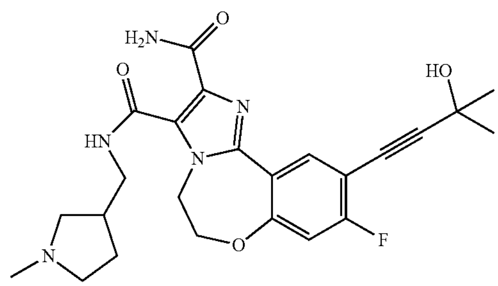 [SMILES: CN1CCC(CNC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-3-ylmethyl)-amide] |
| 69 | 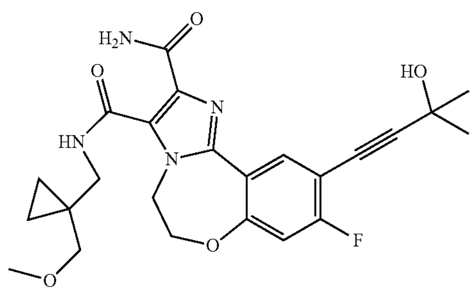 [SMILES: COCC1(CNC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methoxymethyl-cyclopropylmethyl)-amide] |
| 70 | 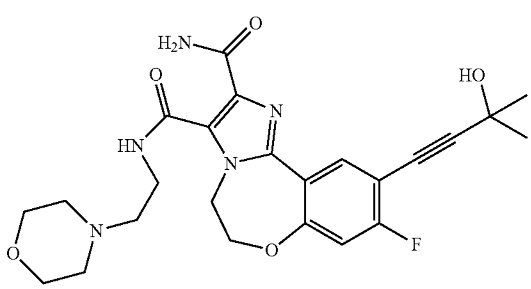 [SMILES: CC(C)(O)C#Cc1cc2c(cc1F)OCCn1c-2nc(C(N)=O)c1C(=O)NCCN1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-morpholin-4-yl-ethyl)-amide] |
| 71 | 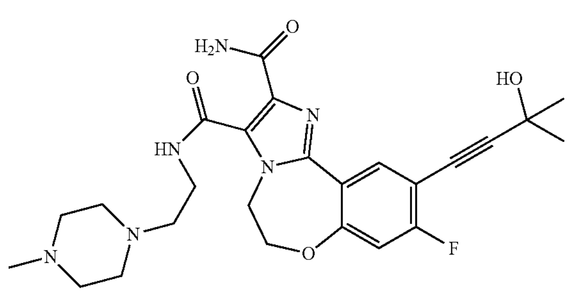 [SMILES: CN1CCN(CCNC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-{[2-(4-methyl-piperazin-1-yl)-ethyl]-amide} |

TABLE 1-continued

| No. | Structure | Name |
|---|---|---|
| 72 | 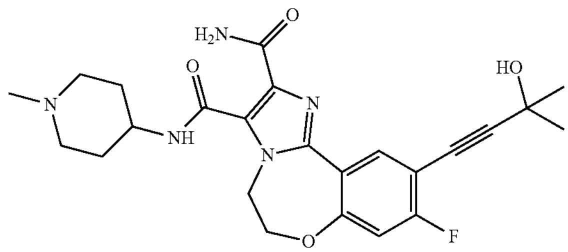 [SMILES: CN1CCC(NC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-piperidin-4-yl)-amide] |
| 73 | 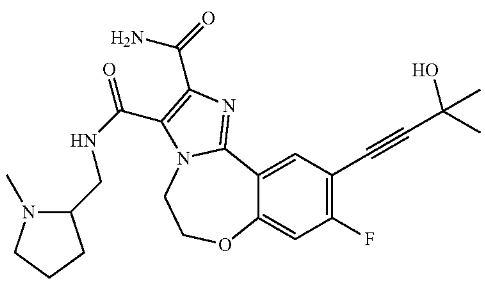 [SMILES: CN1CCCC1CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-2-ylmethyl)-amide] |
| 74 | 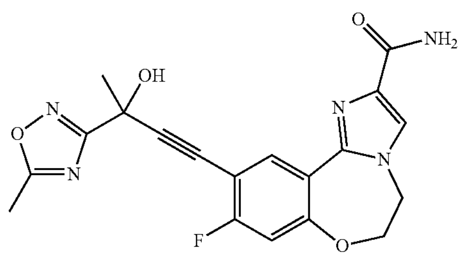 [SMILES: Cc1nc(C(C)(O)C#Cc2cc3c(cc2F)OCCn2cc(C(N)=O)nc2-3)no1] | 8-fluoro-9-[3-hydroxy-3-(5-methyl-[1,2,4]oxadiazol-3-yl)-but-1-ynyl]-4,5-dihydro-6-oxa-1,3a-diaza-benzo[e]azulene-2-carboxylic acid amide |
| 75 | 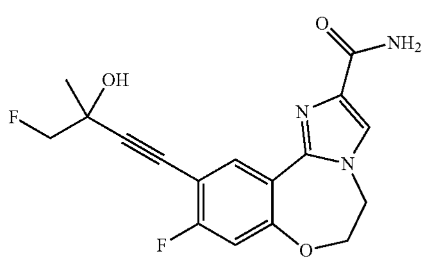 [SMILES: CC(O)(C#Cc1cc2c(cc1F)OCCn1cc(C(N)=O)nc1-2)CF] | 8-fluoro-9-(4-fluoro-3-hydroxy-3-methyl-but-1-ynyl)-4,5-dihydro-6-oxa-1,3a-diaza-benzo[e]azulene-2-carboxylic acid amide |
| 76 | 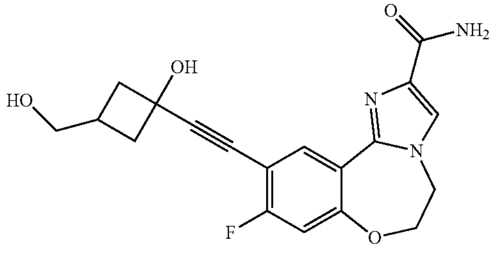 [SMILES: NC(=O)c1cn2c(n1)-c1cc(C#CC3(O)CC(CO)C3)c(F)cc1OCC2] | 8-fluoro-9-(1-hydroxy-3-hydroxymethyl-cyclobutylethynyl)-4,5-dihydro-6-oxa-1,3a-diaza-benzo[e]azulene-2-carboxylic acid amide |

TABLE 1-continued

| No. | Structure | Name |
|---|---|---|
| 77 | 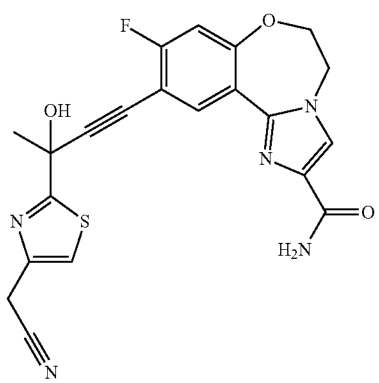 [SMILES: CC(O)(C#Cc1cc2c(cc1F)OCCn1cc(C(N)=O)nc1-2)c1nc(CC#N)cs1] | 9-[3-(4-cyanomethyl-thiazol-2-yl)-3-hydroxy-but-1-ynyl]-8-fluoro-4,5-dihydro-6-oxa-1,3a-diaza-benzo[e]azulene-2-carboxylic acid amide |
| 78 | 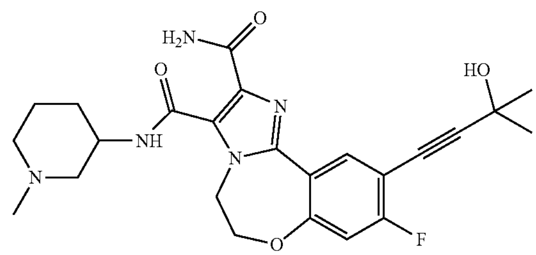 [SMILES: CN1CCCC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-piperidin-3-yl)-amide] |
| 79 | 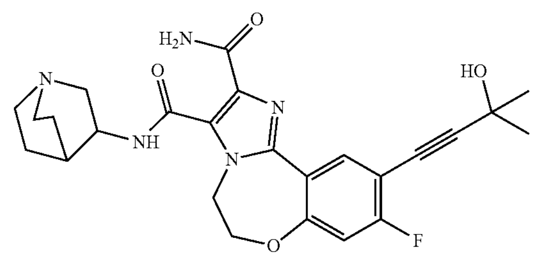 [SMILES: CC(C)(O)C#Cc1cc2c(cc1F)OCCn1c-2nc(C(N)=O)c1C(=O)NC1CN2CCC1CC2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-aza-bicyclo[2.2.2]oct-3-yl)-amide] |
| 80 | 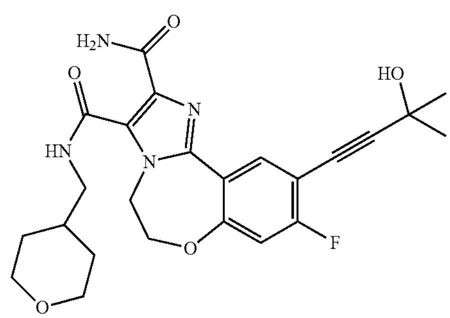 [SMILES: CC(C)(O)C#Cc1cc2c(cc1F)OCCn1c-2nc(C(N)=O)c1C(=O)NCC1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-pyran-4-ylmethyl)-amide] |
| 81 | 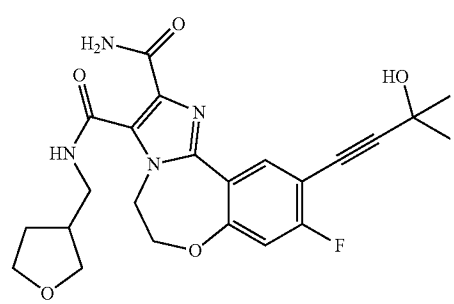 [SMILES: CC(C)(O)C#Cc1cc2c(cc1F)OCCn1c-2nc(C(N)=O)c1C(=O)NCC1CCOC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-furan-3-ylmethyl)-amide] |

TABLE 1-continued

| No. | Structure | Name |
|---|---|---|
| 82 | 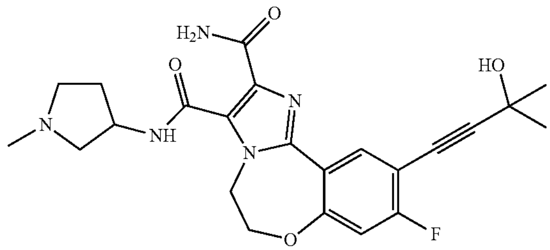 [SMILES: CN1CCC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-3-yl)-amide] |
| 83 | 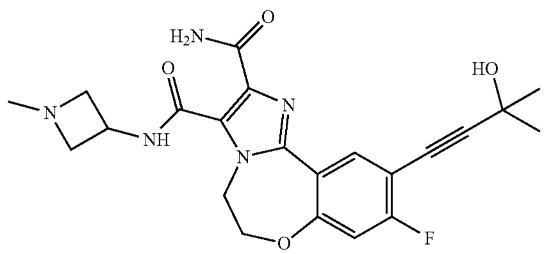 [SMILES: CN1CC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-azetidin-3-yl)-amide] |
| 84 | 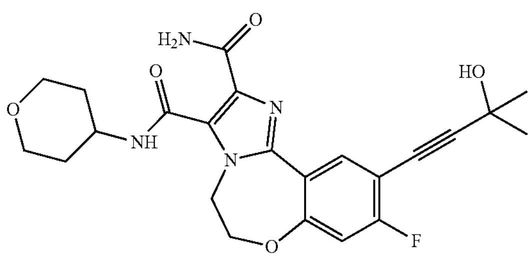 [SMILES: CC(C)(O)C#Cc1cc2c(cc1F)OCCn1c-2nc(C(N)=O)c1C(=O)NC1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-pyran-4-yl)-amide] |
| 85 | 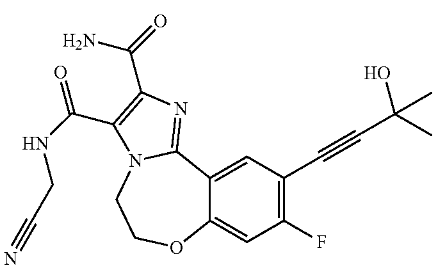 [SMILES: CC(C)(O)C#Cc1cc2c(cc1F)OCCn1c-2nc(C(N)=O)c1C(=O)NCC#N] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-cyanomethyl-amide |
| 86 | 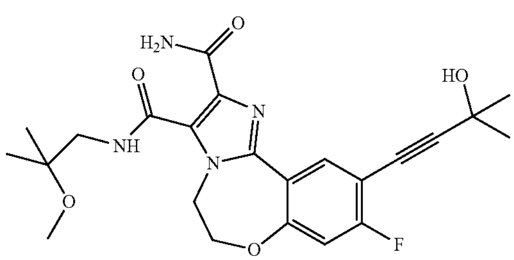 [SMILES: COC(C)(C)CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-methoxy-2-methyl-propyl)-amide] |
| 87 | 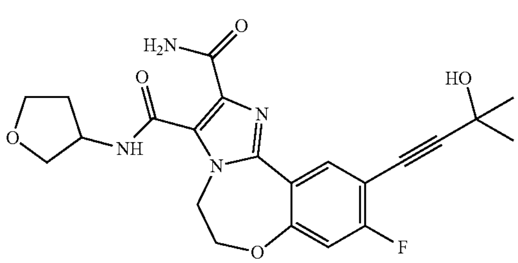 [SMILES: CC(C)(O)C#Cc1cc2c(cc1F)OCCn1c-2nc(C(N)=O)c1C(=O)NC1CCOC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-furan-3-yl)-amide] |

TABLE 1-continued

| No. | Structure | Name |
|---|---|---|
| 88 | 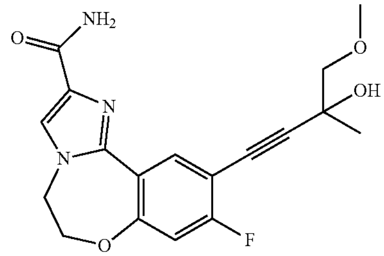 [SMILES: COCC(C)(O)C#Cc1cc2c(cc1F)OCCn1cc(C(N)=O)nc1-2] | 8-fluoro-9-(3-hydroxy-4-methoxy-3-methyl-but-1-ynyl)-4,5-dihydro-6-oxa-1,3a-diaza-benzo[e]azulene-2-carboxylic acid amide |
| 89 | 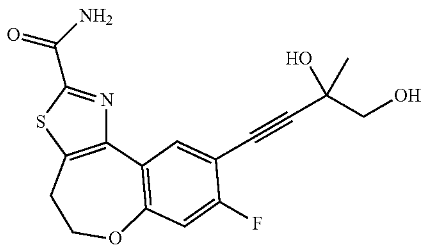 [SMILES: CC(O)(C#Cc1cc2c(cc1F)OCCc1sc(C(N)=O)nc1-2)CO] | 9-(3,4-dihydroxy-3-methyl-but-1-ynyl)-8-fluoro-4,5-dihydro-6-oxa-3-thia-1-aza-benzo[e]azulene-2-carboxylic acid amide |
| 90 | 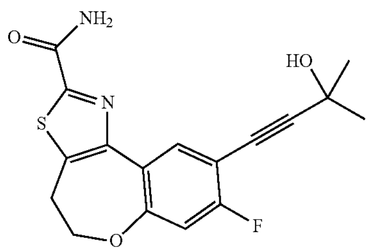 [SMILES: CC(C)(O)C#Cc1cc2c(cc1F)OCCc1sc(C(N)=O)nc1-2] | 8-fluoro-9-(3-hydroxy-3-methyl-but-1-ynyl)-4,5-dihydro-6-oxa-3-thia-1-aza-benzo[e]azulene-2-carboxylic acid amide |
| 91 | 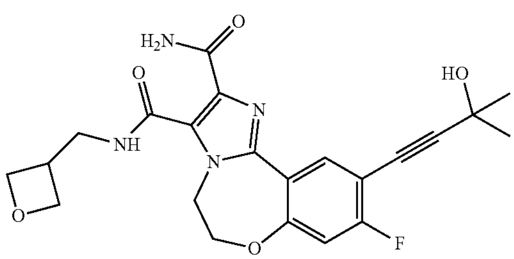 [SMILES: CC(C)(O)C#Cc1cc2c(cc1F)OCCn1c-2nc(C(N)=O)c1C(=O)NCC1COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(oxetan-3-ylmethyl)-amide] |
| 92 | 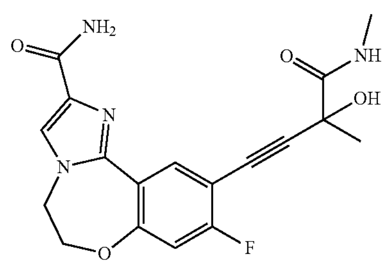 [SMILES: CNC(=O)C(C)(O)C#Cc1cc2c(cc1F)OCCn1cc(C(N)=O)nc1-2] | 8-fluoro-9-(3-hydroxy-3-methylcarbamoyl-but-1-ynyl)-4,5-dihydro-6-oxa-1,3a-diaza-benzo[e]azulene-2-carboxylic acid amide |
| 93 | 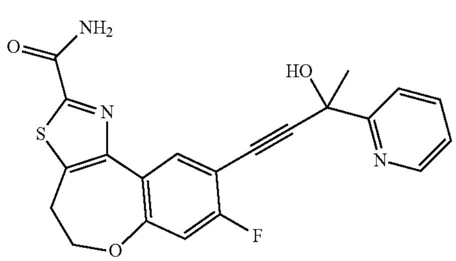 [SMILES: CC(O)(C#Cc1cc2c(cc1F)OCCc1sc(C(N)=O)nc1-2)c1ccccn1] | 8-fluoro-9-(3-hydroxy-3-pyridin-2-yl-but-1-ynyl)-4,5-dihydro-6-oxa-3-thia-1-aza-benzo[e]azulene-2-carboxylic acid amide |

TABLE 1-continued

| No. | Structure | Name |
|---|---|---|
| 94 | 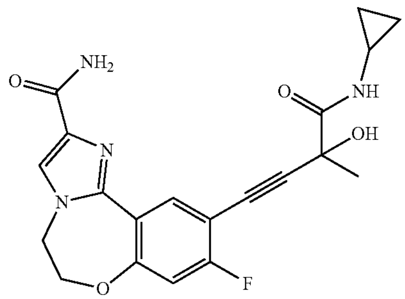 [SMILES: CC(O)(C#Cc1cc2c(cc1F)OCCn1cc(C(N)=O)nc1-2)C(=O)NC1CC1] | 9-(3-cyclopropylcarbamoyl-3-hydroxy-but-1-ynyl)-8-fluoro-4,5-dihydro-6-oxa-1,3a-diaza-benzo[e]azulene-2-carboxylic acid amide |
| 95 | 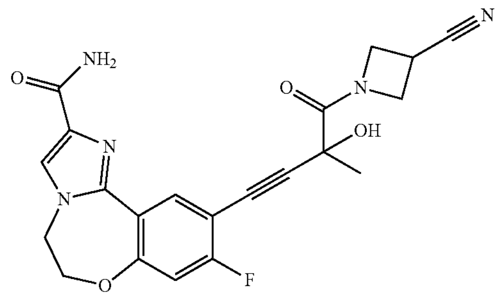 [SMILES: CC(O)(C#Cc1cc2c(cc1F)OCCn1cc(C(N)=O)nc1-2)C(=O)N1CC(C#N)C1] | 9-[4-(3-cyano-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide |
| 96 | 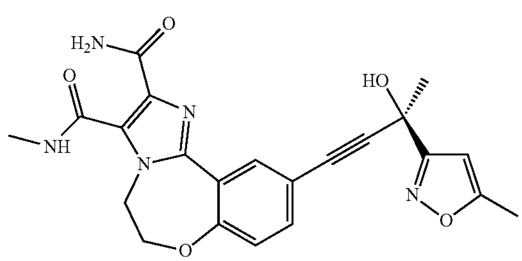 | 9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-methylamide |
| 97 | 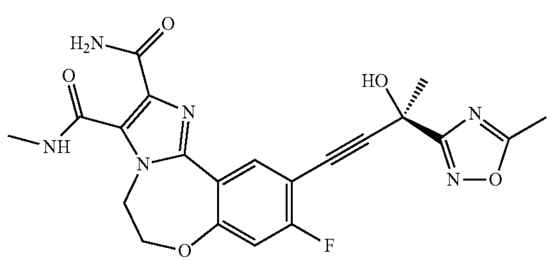 | 8-fluoro-9-[(R)-3-hydroxy-3-(5-methyl-[1,2,4]oxadiazol-3-yl)-but-1-ynyl]-4,5-dihydro-6-oxa-1,3a-diaza-benzo[e]azulene-2,3-dicarboxylic acid 2-amide 3-methylamide |
| 98 | 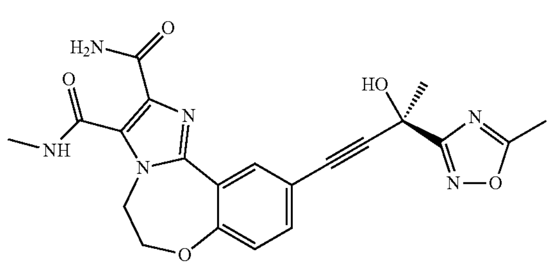 | 9-[(R)-3-hydroxy-3-(5-methyl-[1,2,4]oxadiazol-3-yl)-but-1-ynyl]-4,5-dihydro-6-oxa-1,3a-diaza-benzo[e]azulene-2,3-dicarboxylic acid 2-amide 3-methylamide |

TABLE 1-continued

| No. | Structure | Name |
|---|---|---|
| 99 | 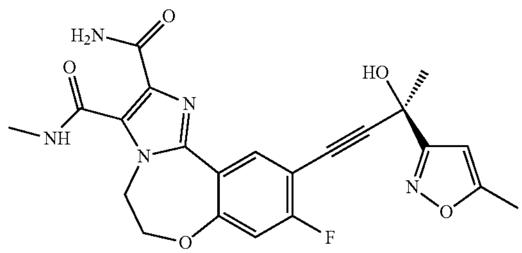 | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-methylamide |
| 100 | 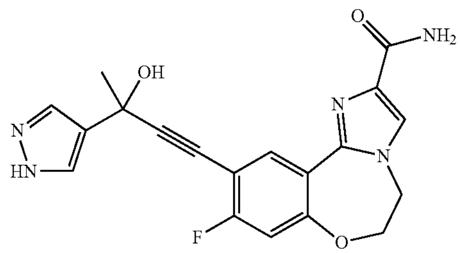 [SMILES: CC(O)(C#Cc1cc2c(cc1F)OCCn1cc(C(N)=O)nc1-2)c1cn[nH]c1] | 8-fluoro-9-[3-hydroxy-3-(1H-pyrazol-4-yl)-but-1-ynyl]-4,5-dihydro-6-oxa-1,3a-diaza-benzo[e]azulene-2-carboxylic acid amide |
| 101 | 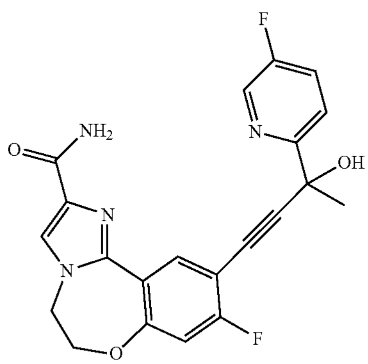 [SMILES: CC(O)(C#Cc1cc2c(cc1F)OCCn1cc(C(N)=O)nc1-2)c1ccc(F)cn1] | 8-fluoro-9-[3-(5-fluoro-pyridin-2-yl)-3-hydroxy-but-1-ynyl]-4,5-dihydro-6-oxa-1,3a-diaza-benzo[e]azulene-2-carboxylic acid amide |
| 102 | 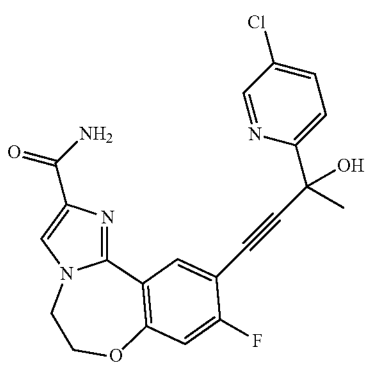 | 9-[3-(5-chloro-pyridin-2-yl)-3-hydroxy-but-1-ynyl]-8-fluoro-4,5-dihydro-6-oxa-1,3a-diaza-benzo[e]azulene-2-carboxylic acid amide |
| 103 | 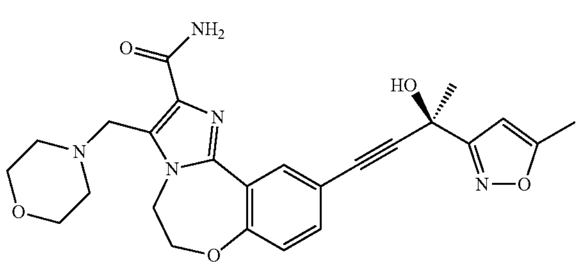 [SMILES: Cc1cc([C@](C)(O)C#Cc2ccc3c(c2)-c2nc(C(N)=O)c(CN4CCOCC4)n2CCO3)no1] | 9-[(R)-3-hydroxy-3-(5-methyl-isoxazol-3-yl)-but-1-ynyl]-3-morpholin-4-ylmethyl-4,5-dihydro-6-oxa-1,3a-diaza-benzo[e]azulene-2-carboxylic acid amide |

TABLE 1-continued

| No. | Structure | Name |
|---|---|---|
| 104 | 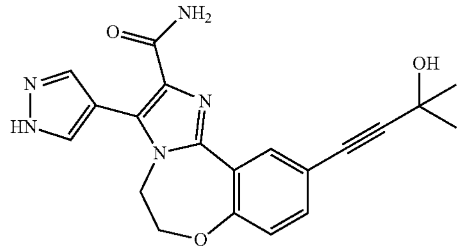 [SMILES: CC(C)(O)C#Cc1ccc2c(c1)-c1nc(C(N)=O)c(-c3cn[nH]c3)n1CCO2] | 9-(3-hydroxy-3-methyl-but-1-ynyl)-3-(1H-pyrazol-4-yl)-4,5-dihydro-6-oxa-1,3a-diaza-benzo[e]azulene-2-carboxylic acid amide |
| 105 | 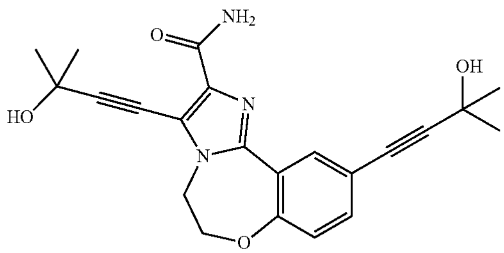 [SMILES: CC(C)(O)C#Cc1ccc2c(c1)-c1nc(C(N)=O)c(C#CC(C)(C)O)n1CCO2] | 3,9-bis-(3-hydroxy-3-methyl-but-1-ynyl)-4,5-dihydro-6-oxa-1,3a-diaza-benzo[e]azulene-2-carboxylic acid amide |
| 106 | 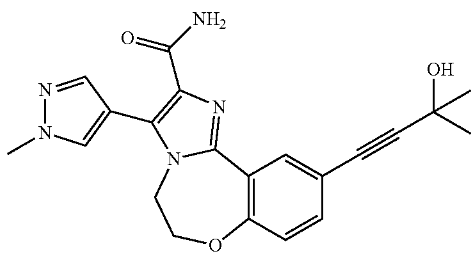 [SMILES: Cn1cc(-c2c(C(N)=O)nc3n2CCOc2ccc(C#CC(C)(C)O)cc2-3)cn1] | 9-(3-hydroxy-3-methyl-but-1-ynyl)-3-(1-methyl-1H-pyrazol-4-yl)-4,5-dihydro-6-oxa-1,3a-diaza-benzo[e]azulene-2-carboxylic acid amide |
| 107 | 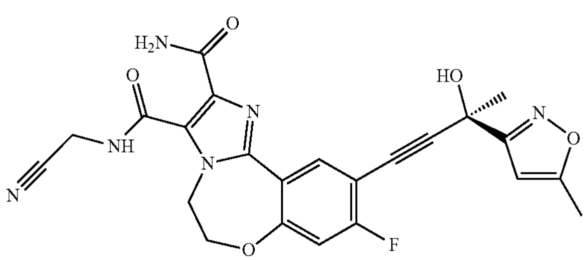 [SMILES: Cc1cc([C@](C)(O)C#Cc2cc3c(cc2F)OCCn2c-3nc(C(N)=O)c2C(=O)NCC#N)no1] | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-cyanomethyl-amide |
| 108 | 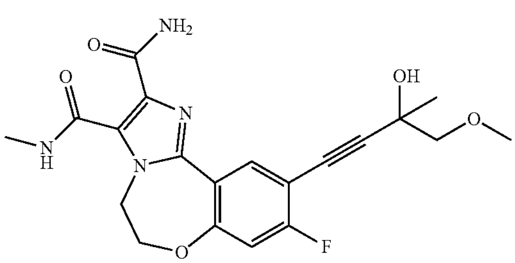 | 8-fluoro-9-(3-hydroxy-4-methoxy-3-methyl-but-1-ynyl)-4,5-dihydro-6-oxa-1,3a-diaza-benzo[e]azulene-2,3-dicarboxylic acid 2-amide 3-methylamide |
| 109 | 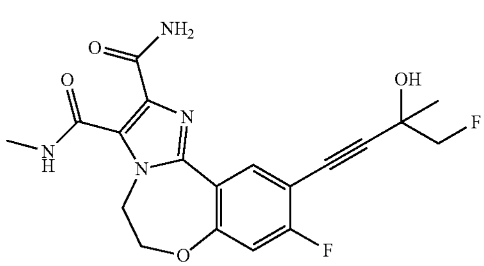 [SMILES: CNC(=O)c1c(C(N)=O)nc2n1CCOc1cc(F)c(C#CC(C)(O)CF)cc1-2] | 8-fluoro-9-(4-fluoro-3-hydroxy-3-methyl-but-1-ynyl)-4,5-dihydro-6-oxa-1,3a-diaza-benzo[e]azulene-2,3-dicarboxylic acid 2-amide 3-methylamide |

TABLE 1-continued

| No. | Structure | Name |
|---|---|---|
| 110 | 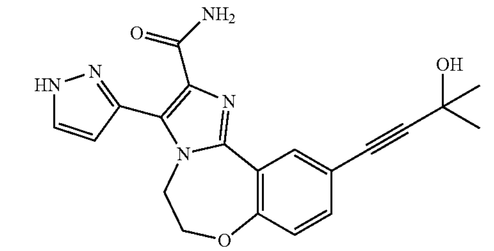 [SMILES: CC(C)(O)C#Cc1ccc2c(c1)-c1nc(C(N)=O)c(-c3cc[nH]n3)n1CCO2] | 9-(3-hydroxy-3-methyl-but-1-ynyl)-3-(1H-pyrazol-3-yl)-4,5-dihydro-6-oxa-1,3a-diaza-benzo[e]azulene-2-carboxylic acid amide |
| 111 | 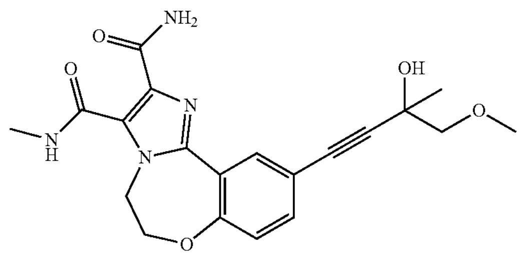 | 9-(3-hydroxy-4-methoxy-3-methyl-but-1-ynyl)-4,5-dihydro-6-oxa-1,3a-diaza-benzo[e]azulene-2,3-dicarboxylic acid 2-amide 3-methylamide |
| 112 | 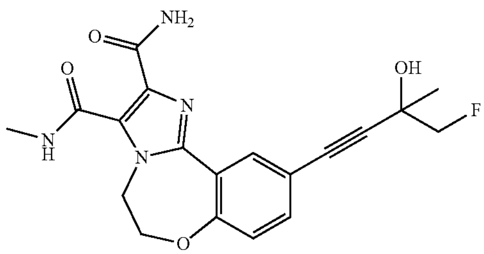 [SMILES: CNC(=O)c1c(C(N)=O)nc2n1CCOc1ccc(C#CC(C)(O)CF)cc1-2] | 9-(4-fluoro-3-hydroxy-3-methyl-but-1-ynyl)-4,5-dihydro-6-oxa-1,3a-diaza-benzo[e]azulene-2,3-dicarboxylic acid 2-amide 3-methylamide |
| 113 | 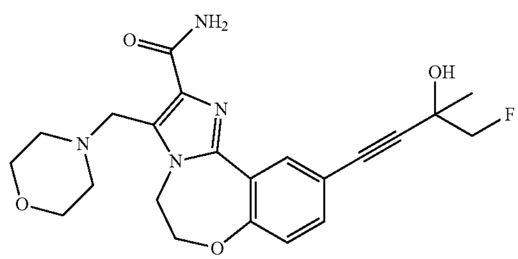 [SMILES: CC(O)(C#Cc1ccc2c(c1)-c1nc(C(N)=O)c(CN3CCOCC3)n1CCO2)CF] | 9-(4-fluoro-3-hydroxy-3-methyl-but-1-ynyl)-3-morpholin-4-ylmethyl-4,5-dihydro-6-oxa-1,3a-diaza-benzo[e]azulene-2-carboxylic acid amide |
| 114 | 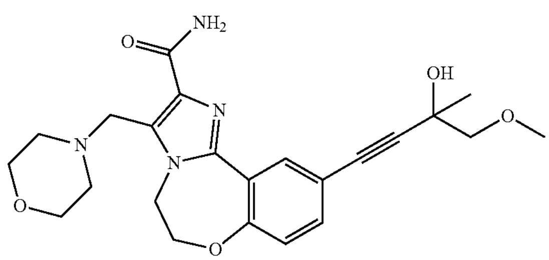 [SMILES: COCC(C)(O)C#Cc1ccc2c(c1)-c1nc(C(N)=O)c(CN3CCOCC3)n1CCO2] | 9-(3-hydroxy-4-methoxy-3-methyl-but-1-ynyl)-3-morpholin-4-ylmethyl-4,5-dihydro-6-oxa-1,3a-diaza-benzo[e]azulene-2-carboxylic acid amide |
| 115 | 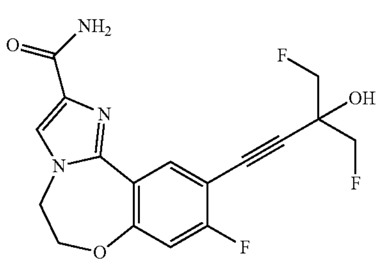 [SMILES: NC(=O)c1cn2c(n1)-c1cc(C#CC(O)(CF)CF)c(F)cc1OCC2] | 8-fluoro-9-(4-fluoro-3-fluoromethyl-3-hydroxy-but-1-ynyl)-4,5-dihydro-6-oxa-1,3a-diaza-benzo[e]azulene-2-carboxylic acid amide |

TABLE 1-continued

| No. | Structure | Name |
|---|---|---|
| 116 | 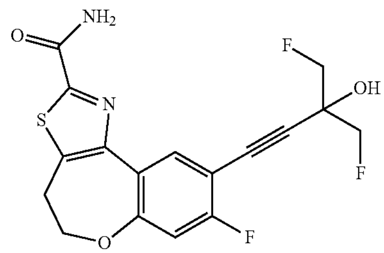 [SMILES: NC(=O)c1nc2c(s1)CCOc1cc(F)c(C#CC(O)(CF)CF)cc1-2] | 8-fluoro-9-(4-fluoro-3-fluoromethyl-3-hydroxy-but-1-ynyl)-4,5-dihydro-6-oxa-3-thia-1-aza-benzo[e]azulene-2-carboxylic acid amide |
| 117 | 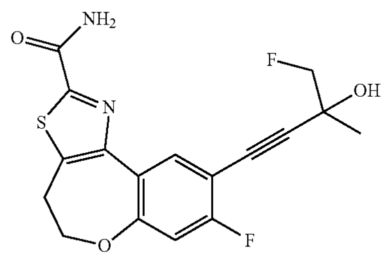 [SMILES: CC(O)(C#Cc1cc2c(cc1F)OCCc1sc(C(N)=O)nc1-2)CF] | 8-fluoro-9-(4-fluoro-3-hydroxy-3-methyl-but-1-ynyl)-4,5-dihydro-6-oxa-3-thia-1-aza-benzo[e]azulene-2-carboxylic acid amide |
| 118 | 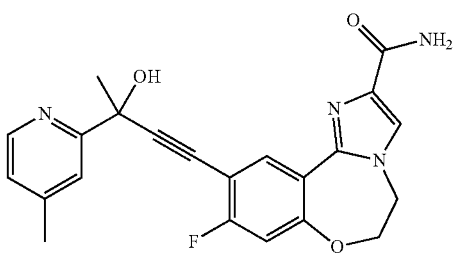 [SMILES: Cc1ccnc(C(C)(O)C#Cc2cc3c(cc2F)OCCn2cc(C(N)=O)nc2-3)c1] | 8-fluoro-9-[3-hydroxy-3-(4-methyl-pyridin-2-yl)-but-1-ynyl]-4,5-dihydro-6-oxa-1,3a-diaza-benzo[e]azulene-2-carboxylic acid amide |
| 119 | 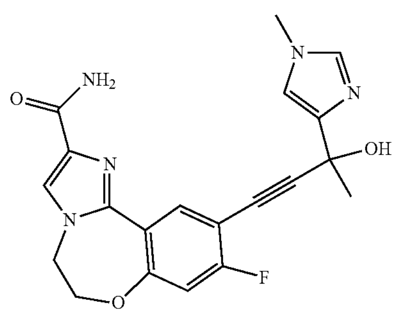 [SMILES: Cn1cnc(C(C)(O)C#Cc2cc3c(cc2F)OCCn2cc(C(N)=O)nc2-3)c1] | 8-fluoro-9-[3-hydroxy-3-(1-methyl-1H-imidazol-4-yl)-but-1-ynyl]-4,5-dihydro-6-oxa-1,3a-diaza-benzo[e]azulene-2-carboxylic acid amide |
| 120 | 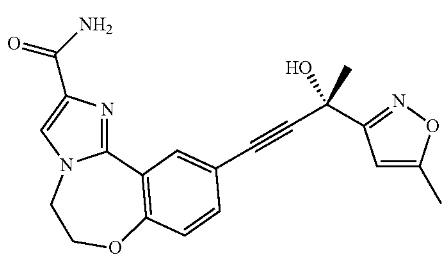 [SMILES: Cc1cc([C@@](C)(O)C#Cc2ccc3c(c2)-c2nc(C(N)=O)cn2CCO3)no1] | 9-[(S)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 121 | 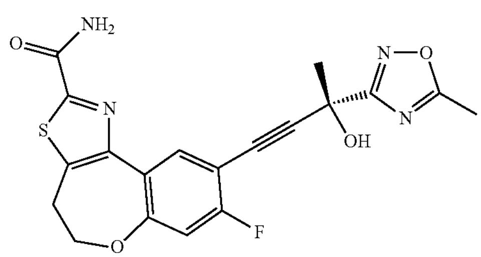 [SMILES: Cc1nc([C@](C)(O)C#Cc2cc3c(cc2F)OCCc2sc(C(N)=O)nc2-3)no1] | 8-fluoro-9-[(R)-3-hydroxy-3-(5-methyl-[1,2,4]oxadiazol-3-yl)-but-1-ynyl]-4,5-dihydro-6-oxa-3-thia-1-aza-benzo[e]azulene-2-carboxylic acid amide |

| No. | Structure | Name |
|---|---|---|
| 122 | 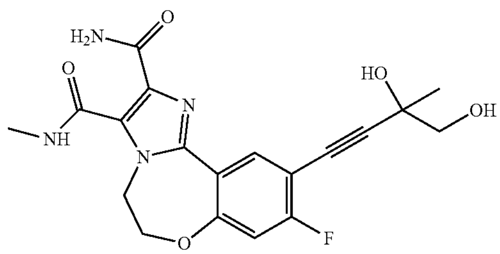 [SMILES: CNC(=O)c1c(C(N)=O)nc2n1CCOc1cc(F)c(C#CC(C)(O)CO)cc1-2] | 9-(3,4-dihydroxy-3-methyl-but-1-ynyl)-8-fluoro-4,5-dihydro-6-oxa-1,3a-diaza-benzo[e]azulene-2,3-dicarboxylic acid 2-amide 3-methylamide |
| 123 | 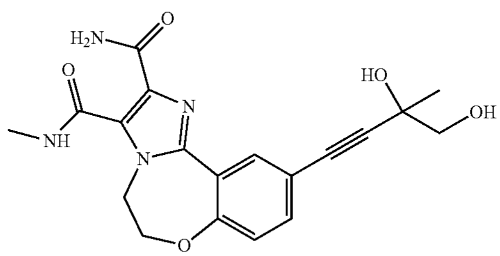 [SMILES: CNC(=O)c1c(C(N)=O)nc2n1CCOc1ccc(C#CC(C)(O)CO)cc1-2] | 9-(3,4-dihydroxy-3-methyl-but-1-ynyl)-4,5-dihydro-6-oxa-1,3a-diaza-benzo[e]azulene-2,3-dicarboxylic acid 2-amide 3-methylamide |
| 124 | 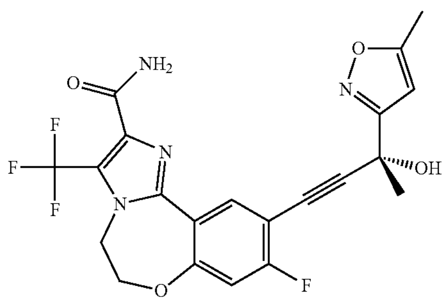 [SMILES: Cc1cc([C@](C)(O)C#Cc2cc3c(cc2F)OCCn2c-3nc(C(N)=O)c2C(F)(F)F)no1] | 8-fluoro-9-[(R)-3-hydroxy-3-(5-methyl-isoxazol-3-yl)-but-1-ynyl]-3-trifluoro-methyl-4,5-dihydro-6-oxa-1,3a-diaza-benzo[e]azulene-2-carboxylic acid amide |
| 125 | 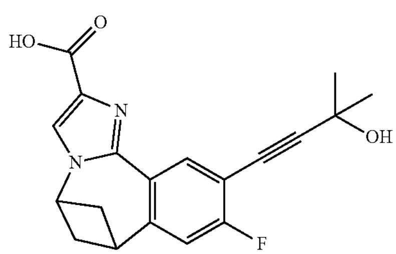 [SMILES: CC(C)(O)C#Cc1cc2c(cc1F)C1CC(C1)n1cc(C(=O)O)nc1-2] | 9-fluoro-10-(3-hydroxy-3-methylbut-1-yn-1-yl)-6,7-dihydro-5H-5,7-methano-benzo[c]imidazo[1,2-a]azepine-2-carbox-amide. |
| 126 | 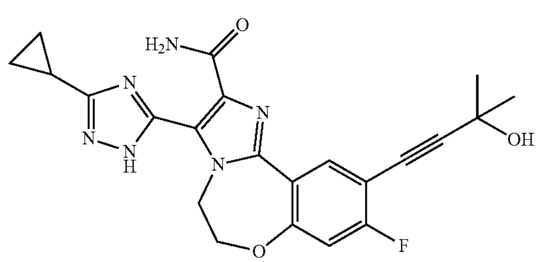 [SMILES: CC(C)(O)C#Cc1cc2c(cc1F)OCCn1c-2nc(C(N)=O)c1-c1nc(C2CC2)n[nH]1] | 3-(5-cyclopropyl-2H-[1,2,4]triazol-3-yl)-8-fluoro-9-(3-hydroxy-3-methyl-but-1-ynyl)-4,5-dihydro-6-oxa-1,3a-diaza-benzo[e]azulene-2-carboxylic acid amide |
| 127 | 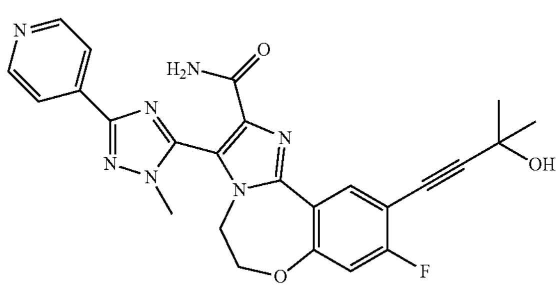 [SMILES: Cn1nc(-c2ccncc2)nc1-c1c(C(N)=O)nc2n1CCOc1cc(F)c(C#CC(C)(C)O)cc1-2] | 8-fluoro-9-(3-hydroxy-3-methyl-but-1-ynyl)-3-(2-methyl-5-pyridin-4-yl-2H-[1,2,4]triazol-3-yl)-4,5-dihydro-6-oxa-1,3a-diaza-benzo[e]azulene-2-carboxylic acid amide |

TABLE 1-continued

| No. | Structure | Name |
|---|---|---|
| 128 | 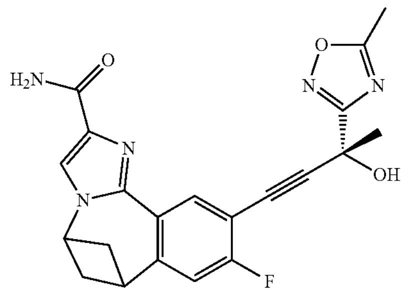 [SMILES: Cc1nc([C@](C)(O)C#Cc2cc3c(cc2F)C2CC(C2)n2cc(C(N)=O)nc2-3)no1] | 10-fluoro-9-[(3R)-3-hydroxy-3-(5-methyl-1,2,4-oxadiazol-3-yl)but-1-yn-1-yl]-2,5-diazatetracyclo[11.1.1.0$^{2,6}$.0$^{7,12}$]pentadeca-3,5,7(12),8,10-pentaene-4-carboxamide |
| 129 | 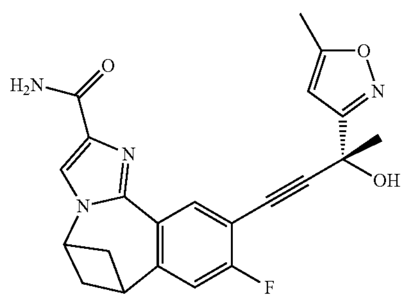 [SMILES: Cc1cc([C@](C)(O)C#Cc2cc3c(cc2F)C2CC(C2)n2cc(C(N)=O)nc2-3)no1] | 10-fluoro-9-[(3R)-3-hydroxy-3-(5-methyl-1,2,-oxazol-3-yl)but-1-yn-1-yl]-2,5-diazatetracyclo[11.1.1.0$^{2,6}$.0$^{7,12}$]pentadeca-3,5,7(12),8,10-pentaene-4-carboxamide |
| 130 | 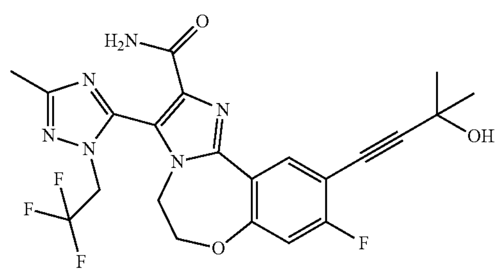 [SMILES: Cc1nc(-c2c(C(N)=O)nc3n2CCOc2cc(F)c(C#CC(C)(C)O)cc2-3)n(CC(F)(F)F)n1] | 8-fluoro-9-(3-hydroxy-3-methyl-but-1-ynyl)-3-[5-methyl-2-(2,2,2-trifluoro-ethyl)-2H-[1,2,4]triazol-3-yl]-4,5-dihydro-6-oxa-1,3a-diaza-benzo[e]azulene-2-carboxylic acid amide |
| 131 | 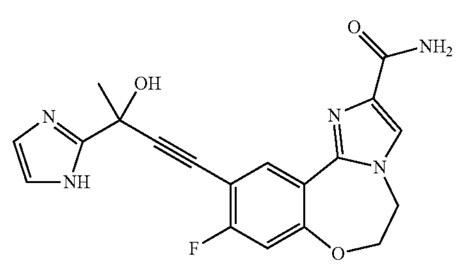 [SMILES: CC(O)(C#Cc1cc2c(cc1F)OCCn1cc(C(N)=O)nc1-2)c1ncc[nH]1] | 8-fluoro-9-[3-hydroxy-3-(1H-imidazol-2-yl)-but-1-ynyl]-4,5-dihydro-6-oxa-1,3a-diaza-benzo[e]azulene-2-carboxylic acid amide |
| 132 | 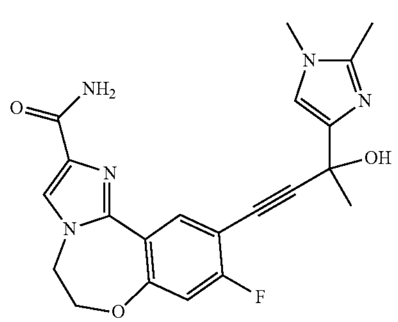 [SMILES: Cc1nc(C(C)(O)C#Cc2cc3c(cc2F)OCCn2cc(C(N)=O)nc2-3)cn1C] | 9-[3-(1,2-dimethyl-1H-imidazol-4-yl)-3-hydroxy-but-1-ynyl]-8-fluoro-4,5-dihydro-6-oxa-1,3a-diaza-benzo[e]azulene-2-carboxylic acid amide |

TABLE 1-continued

| No. | Structure | Name |
|---|---|---|
| 133 | 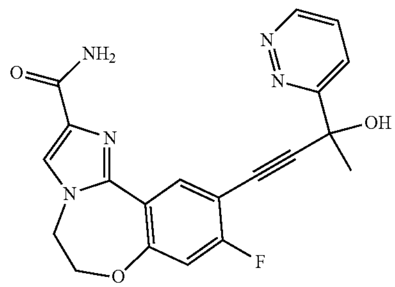 [SMILES: CC(O)(C#Cc1cc2c(cc1F)OCCn1cc(C(N)=O)nc1-2)c1cccnn1] | 8-fluoro-9-(3-hydroxy-3-pyridazin-3-yl-but-1-ynyl)-4,5-dihydro-6-oxa-1,3a-diaza-benzo[e]azulene-2-carboxylic acid amide |
| 134 | 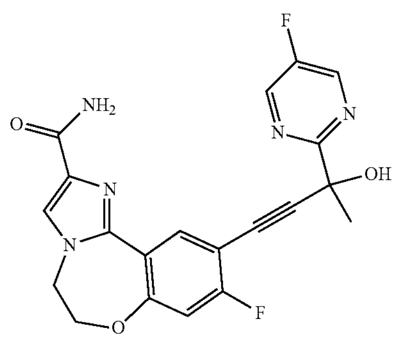 [SMILES: CC(O)(C#Cc1cc2c(cc1F)OCCn1cc(C(N)=O)nc1-2)c1ncc(F)cn1] | 8-fluoro-9-[3-(5-fluoro-pyrimidin-2-yl)-3-hydroxy-but-1-ynyl]-4,5-dihydro-6-oxa-1,3a-diaza-benzo[e]azulene-2-carboxylic acid amide |
| 135 | 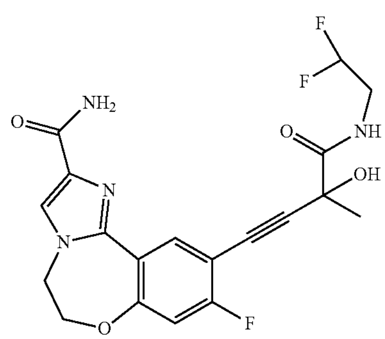 [SMILES: CC(O)(C#Cc1cc2c(cc1F)OCCn1cc(C(N)=O)nc1-2)C(=O)NCC(F)F] | 9-[3-(2,2-difluoro-ethylcarbamoyl)-3-hydroxy-but-1-ynyl]-8-fluoro-4,5-dihydro-6-oxa-1,3a-diaza-benzo[e]azulene-2-carboxylic acid amide |
| 136 | 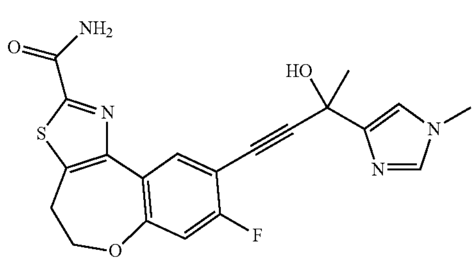 [SMILES: Cn1cnc(C(C)(O)C#Cc2cc3c(cc2F)OCCc2sc(C(N)=O)nc2-3)c1] | 8-fluoro-9-[3-hydroxy-3-(1-methyl-1H-imidazol-4-yl)-but-1-ynyl]-4,5-dihydro-6-oxa-3-thia-1-aza-benzo[e]azulene-2-carboxylic acid amide |
| 137 | 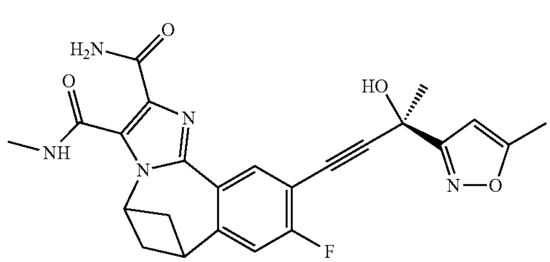 | 10-fluoro-9-[(3R)-3-hydroxy-3-(5-methyl-1,2-oxazol-3-yl)but-1-yn-1-yl]-3-N-methyl-2,5-diazatetracyclo[11.1.1.0$^{2,6}$.0$^{7,12}$]pentadeca-3,5,7,9,11-pentaene-3,4-dicarboxamide |

TABLE 1-continued

| No. | Structure | Name |
|---|---|---|
| 138 | 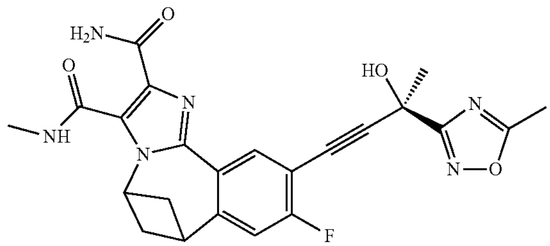 | 10-fluoro-9-[(3R)-3-hydroxy-3-(5-methyl-1,2,4-oxadiazol-3-yl)but-1-yn-1-yl]-3-N-methyl-2,5-diazatetracyclo[11.1.1.0²,⁶.0⁷,¹²]pentadeca-3,5,7,9,11-pentaene-3,4-dicarboxamide |
| 139 | 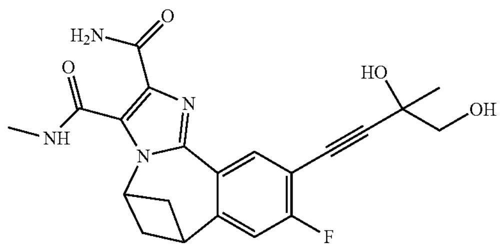 [SMILES: CNC(=O)c1c(C(N)=O)nc2n1C1CC(C1)c1cc(F)c(C#CC(C)(O)CO)cc1-2] | 9-(3,4-dihydroxy-3-methylbut-1-yn-1-yl)-10-fluoro-3-N-methyl-2,5-diazatetracyclo[11.1.1.0²,⁶.0⁷,¹²]pentadeca-3,5,7,9,11-pentaene-3,4-dicarboxamide |
| 140 | 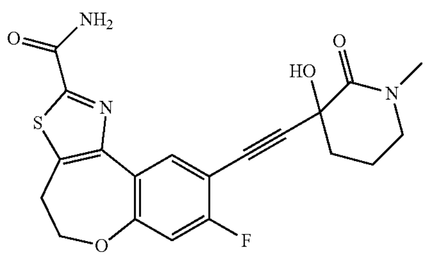 [SMILES: CN1CCCC(O)(C#Cc2cc3c(cc2F)OCCc2sc(C(N)=O)nc2-3)C1=O] | 8-fluoro-9-(3-hydroxy-1-methyl-2-oxo-piperidin-3-ylethynyl)-4,5-dihydro-6-oxa-3-thia-1-aza-benzo[e]azulene-2-carboxylic acid amide |
| 141 | 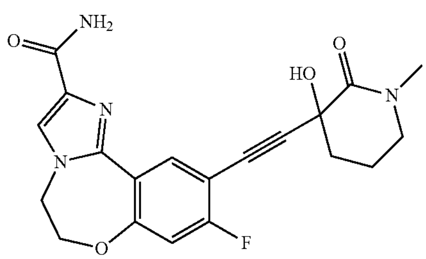 [SMILES: CN1CCCC(O)(C#Cc2cc3c(cc2F)OCCn2cc(C(N)=O)nc2-3)C1=O] | 8-fluoro-9-(3-hydroxy-1-methyl-2-oxo-piperidin-3-ylethynyl)-4,5-dihydro-6-oxa-1,3a-diaza-benzo[e]azulene-2-carboxylic acid amide |
| 142 | 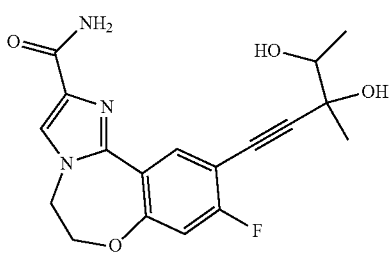 [SMILES: CC(O)C(C)(O)C#Cc1cc2c(cc1F)OCCn1cc(C(N)=O)nc1-2] | 9-(3,4-dihydroxy-3-methyl-pent-1-ynyl)-8-fluoro-4,5-dihydro-6-oxa-1,3a-diaza-benzo[e]azulene-2-carboxylic acid amide |
| 143 | 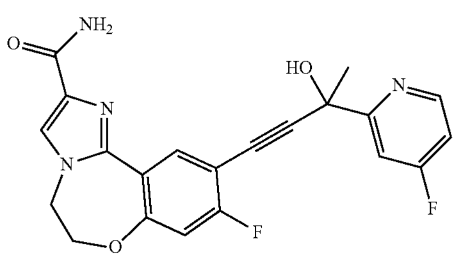 [SMILES: CC(O)(C#Cc1cc2c(cc1F)OCCn1cc(C(N)=O)nc1-2)c1cc(F)ccn1] | 8-fluoro-9-[3-(4-fluoro-pyridin-2-yl)-3-hydroxy-but-1-ynyl]-4,5-dihydro-6-oxa-1,3a-diaza-benzo[e]azulene-2-carboxylic acid amide |

TABLE 1-continued

| No. | Structure | Name |
|---|---|---|
| 144 | 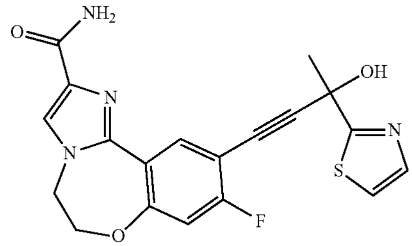 [SMILES: CC(O)(C#Cc1cc2c(cc1F)OCCn1cc(C(N)=O)nc1-2)c1nccs1] | 8-fluoro-9-(3-hydroxy-3-thiazol-2-yl-but-1-ynyl)-4,5-dihydro-6-oxa-1,3a-diaza-benzo[e]azulene-2-carboxylic acid amide |
| 145 | 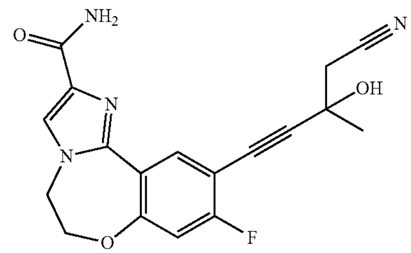 [SMILES: CC(O)(C#Cc1cc2c(cc1F)OCCn1cc(C(N)=O)nc1-2)CC#N] | 9-(4-cyano-3-hydroxy-3-methyl-but-1-ynyl)-8-fluoro-4,5-dihydro-6-oxa-1,3a-diaza-benzo[e]azulene-2-carboxylic acid amide |
| 146 | 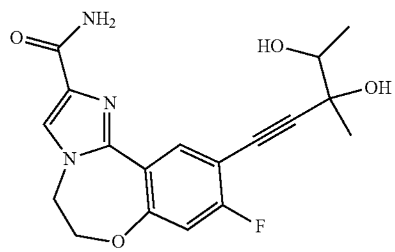 [SMILES: CC(O)C(C)(O)C#Cc1cc2c(cc1F)OCCn1cc(C(N)=O)nc1-2] | 9-(3,4-dihydroxy-3-methyl-pent-1-ynyl)-8-fluoro-4,5-dihydro-6-oxa-1,3a-diaza-benzo[e]azulene-2-carboxylic acid amide |
| 147 | 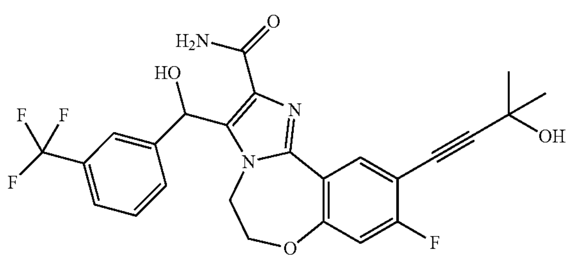 [SMILES: CC(C)(O)C#Cc1cc2c(cc1F)OCCn1c-2nc(C(N)=O)c1C(O)c1cccc(C(F)(F)F)c1] | 8-fluoro-9-(3-hydroxy-3-methyl-but-1-ynyl)-3-[hydroxy-(3-trifluoromethyl-phenyl)-methyl]-4,5-dihydro-6-oxa-1,3a-diaza-benzo[e]azulene-2-carboxylic acid amide |
| 148 | 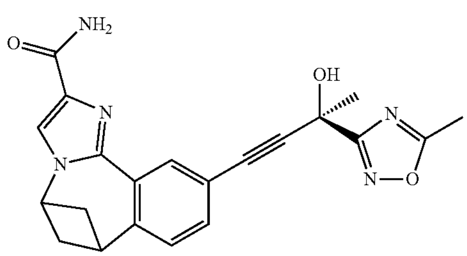 [SMILES: Cc1nc([C@](C)(O)C#Cc2ccc3c(c2)-c2nc(C(N)=O)cn2C2CC3C2)no1] | 9-[(3R)-3-hydroxy-3-(5-methyl-1,2,4-oxadiazol-3-yl)but-1-yn-1-yl]-2,5-diazatetracyclo[11.1.1.0$^{2,6}$.0$^{7,12}$]pentadeca-3,5,7(12),8,10-pentaene-4-carboxamide |
| 149 | 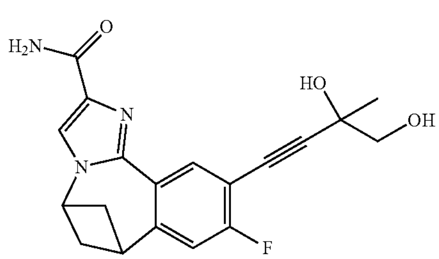 [SMILES: CC(O)(C#Cc1cc2c(cc1F)C1CC(C1)n1cc(C(N)=O)nc1-2)CO] | 9-(3,4-dihydroxy-3-methylbut-1-yn-1-yl)-10-fluoro-2,5-diazatetracyclo[11.1.1.0$^{2,6}$.0$^{7,12}$]pentadeca-3,5,7,9,11-pentaene-4-carboxamide |

TABLE 1-continued

| No. | Structure | Name |
| --- | --- | --- |
| 150 | 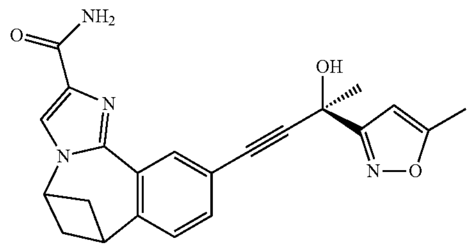 [SMILES: Cc1cc([C@](C)(O)C#Cc2ccc3c(c2)-c2nc(C(N)=O)cn2C2CC3C2)no1] | 9-[(3R)-3-hydroxy-3-(5-methyl-1,2-oxazol-3-yl)but-1-yn-1-yl]-2,5-diazatetracyclo[11.1.1.0$^{2,6}$.0$^{7,12}$]pentadeca-3,5,7(12),8,10-pentaene-4-carboxamide |
| 151 | 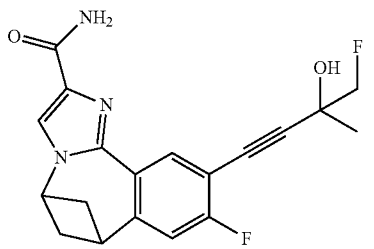 [SMILES: CC(O)(C#Cc1cc2c(cc1F)C1CC(C1)n1cc(C(N)=O)nc1-2)CF] | 10-fluoro-9-(4-fluoro-3-hydroxy-3-methylbut-1-yn-1-yl)-2,5-diazatetracyclo[11.1.1.0$^{2,6}$.0$^{7,12}$]pentadeca-3,5,7(12),8,10-pentaene-4-carboxamide |
| 152 | 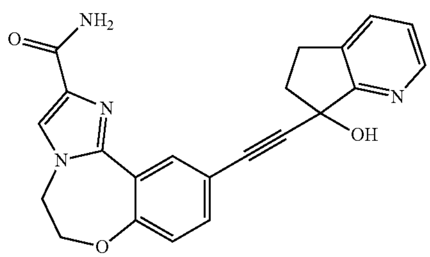 [SMILES: NC(=O)c1cn2c(n1)-c1cc(C#CC3(O)CCc4cccnc43)ccc1OCC2] | 9-(7-hydroxy-6,7-dihydro-5H-[1]pyrindin-7-ylethynyl)-4,5-dihydro-6-oxa-1,3a-diaza-benzo[e]azulene-2-carboxylic acid amide |
| 153 | 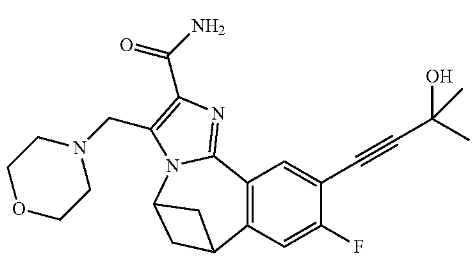 [SMILES: CC(C)(O)C#Cc1cc2c(cc1F)C1CC(C1)n1c-2nc(C(N)=O)c1CN1CCOCC1] | 10-fluoro-9-(3-hydroxy-3-methylbut-1-yn-1-yl)-3-(morpholin-4-ylmethyl)-2,5-diazatetracyclo[11.1.1.0$^{2,6}$.0$^{7,12}$]pentadeca-3,5,7(12),8,10-pentaene-4-carboxamide |
| 154 | 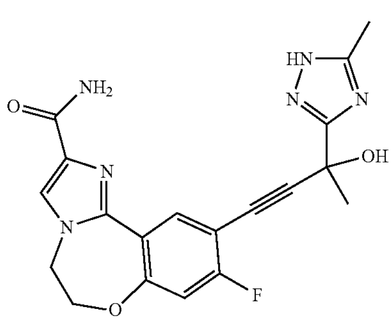 [SMILES: Cc1nc(C(C)(O)C#Cc2cc3c(cc2F)OCCn2cc(C(N)=O)nc2-3)n[nH]1] | 8-fluoro-9-[3-hydroxy-3-(5-methyl-1H-[1,2,4]triazol-3-yl)-but-1-ynyl]-4,5-dihydro-6-oxa-1,3a-diaza-benzo[e]azulene-2-carboxylic acid amide |

TABLE 1-continued

| No. | Structure | Name |
|---|---|---|
| 155 | 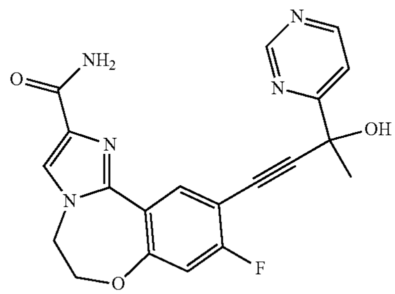 [SMILES: CC(O)(C#Cc1cc2c(cc1F)OCCn1cc(C(N)=O)nc1-2)c1ccncn1] | 8-fluoro-9-(3-hydroxy-3-pyrimidin-4-yl-but-1-ynyl)-4,5-dihydro-6-oxa-1,3a-diaza-benzo[e]azulene-2-carboxylic acid amide |
| 156 | 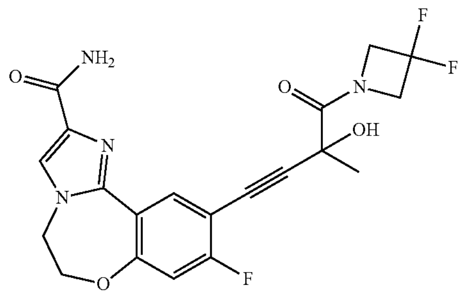 [SMILES: CC(O)(C#Cc1cc2c(cc1F)OCCn1cc(C(N)=O)nc1-2)C(=O)N1CC(F)(F)C1] | 9-[4-(3,3-difluoro-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide |
| 157 | 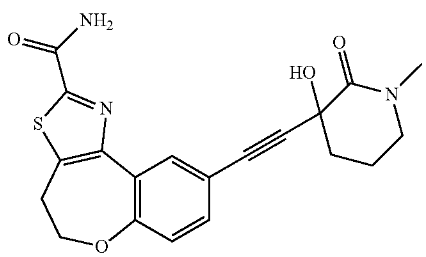 [SMILES: CN1CCCC(O)(C#Cc2ccc3c(c2)-c2nc(C(N)=O)sc2CCO3)C1=O] | 9-[2-(3-hydroxy-1-methyl-2-oxo-3-piperidyl)ethynyl]-4,5-dihydro-[1]benzoxepino[5,4-d]thiazole-2-carboxamide |
| 158 | 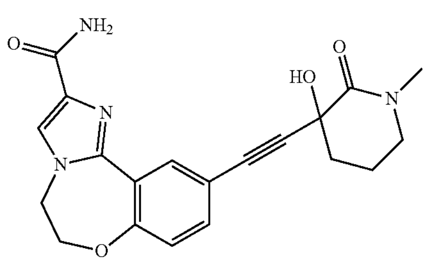 [SMILES: CN1CCCC(O)(C#Cc2ccc3c(c2)-c2nc(C(N)=O)cn2CCO3)C1=O] | 10-[2-(3-hydroxy-1-methyl-2-oxo-3-piperidyl)ethynyl]-5,6-dihydroimidazo[1,2-d][1,4]benzoxazepine-2-carboxamide |
| 159 | 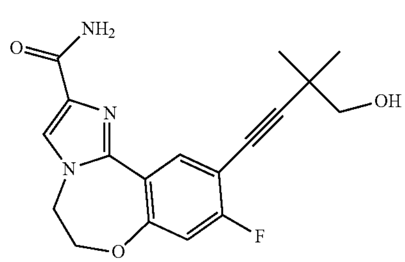 [SMILES: CC(C)(C#Cc1cc2c(cc1F)OCCn1cc(C(N)=O)nc1-2)CO] | 9-fluoro-10-(4-hydroxy-3,3-dimethyl-but-1-ynyl)-5,6-dihydroimidazo[1,2-d][1,4]benzoxazepine-2-carboxamide |

| No. | Structure | Name |
|---|---|---|
| 160 | 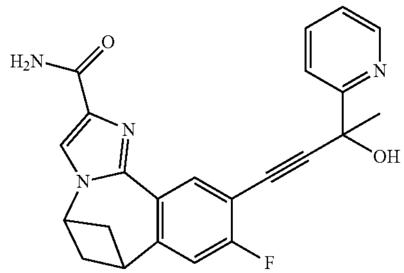 [SMILES: CC(O)(C#Cc1cc2c(cc1F)C1CC(C1)n1cc(C(N)=O)nc1-2)c1ccccn1] | 9-fluoro-10-[3-hydroxy-3-(2-pyridyl)but-1-ynyl]-5,6,7,12-tetrahydro-5,7-methanobenzo[c]imidazo[1,2-a]azepine-2-carboxamide |
| 161 | 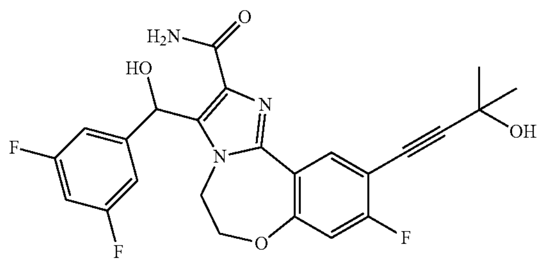 [SMILES: CC(C)(O)C#Cc1cc2c(cc1F)OCCn1c-2nc(C(N)=O)c1C(O)c1cc(F)cc(F)c1] | 3-[(3,5-difluorophenyl)-hydroxy-methyl]-9-fluoro-10-(3-hydroxy-3-methyl-but-1-ynyl)-5,6-dihydroimidazo[1,2-d][1,4]benzoxazepine-2-carboxamide |
| 162 | 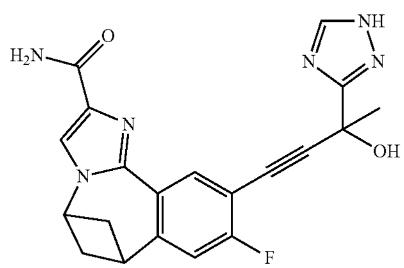 [SMILES: CC(O)(C#Cc1cc2c(cc1F)C1CC(C1)n1cc(C(N)=O)nc1-2)c1nc[nH]n1] | 9-fluoro-10-[3-hydroxy-3-(1H-1,2,4-triazol-3-yl)but-1-ynyl]-5,6,7,12-tetrahydro-5,7-methanobenzo[c]imidazo[1,2-a]azepine-2-carboxamide |
| 163 | 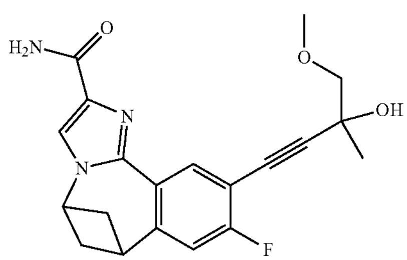 [SMILES: COCC(C)(O)C#Cc1cc2c(cc1F)C1CC(C1)n1cc(C(N)=O)nc1-2] | 9-fluoro-10-[3-hydroxy-4-methoxy-3-methyl-but-1-ynyl]-5,6,7,12-tetrahydro-5,7-methanobenzo[c]imidazo[1,2-a]azepine-2-carboxamide |
| 164 | 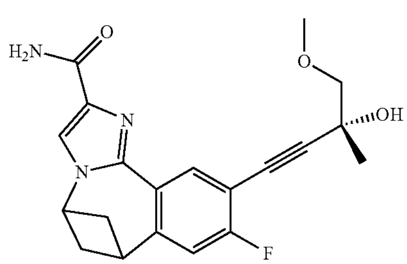 [SMILES: COC[C@](C)(O)C#Cc1cc2c(cc1F)C1CC(C1)n1cc(C(N)=O)nc1-2] | 9-fluoro-10-[(3R)-3-hydroxy-4-methoxy-3-methyl-but-1-ynyl]-5,6,7,12-tetrahydro-5,7-methanobenzo[c]imidazo[1,2-a]azepine-2-carboxamide |
| 165 | 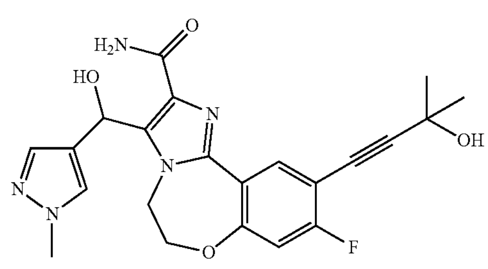 [SMILES: Cn1cc(C(O)c2c(C(N)=O)nc3n2CCOc2cc(F)c(C#CC(C)(C)O)cc2-3)cn1] | 9-fluoro-10-(3-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |

TABLE 1-continued

| No. | Structure | Name |
|---|---|---|
| 166 | 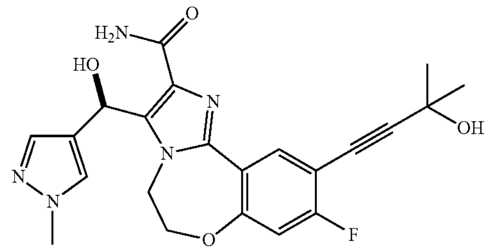 [SMILES: Cn1cc([C@@H](O)c2c(C(N)=O)nc3n2CCOc2cc(F)c(C#CC(C)(C)O)cc2-3)cn1] | 9-fluoro-10-(3-(R)-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |
| 167 | 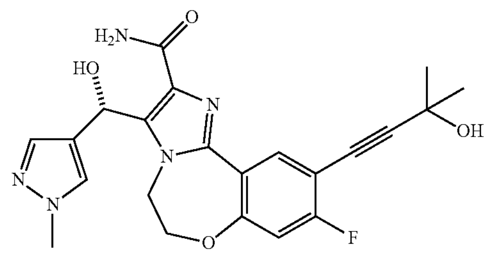 [SMILES: Cn1cc([C@H](O)c2c(C(N)=O)nc3n2CCOc2cc(F)c(C#CC(C)(C)O)cc2-3)cn1] | 9-fluoro-10-(3-(S)-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |
| 168 | 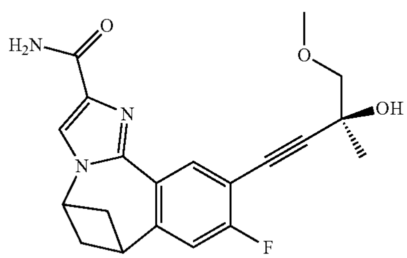 [SMILES: COC[C@@](C)(O)C#Cc1cc2c(cc1F)C1CC(C1)n1cc(C(N)=O)nc1-2] | 9-fluoro-10-[(3S)-3-hydroxy-4-methoxy-3-methyl-but-1-ynyl]-5,6,7,12-tetrahydro-5,7-methanobenzo[c]imidazo[1,2-a]azepine-2-carboxamide |
| 169 | 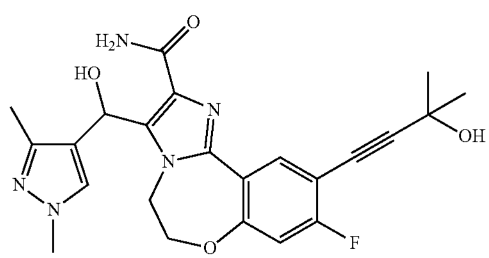 [SMILES: Cc1nn(C)cc1C(O)c1c(C(N)=O)nc2n1CCOc1cc(F)c(C#CC(C)(C)O)cc1-2] | 3-[(1,3-dimethylpyrazol-4-yl)-hydroxy-methyl]-9-fluoro-10-(3-hydroxy-3-methyl-but-1-ynyl)-5,6-dihydroimidazo[1,2-d][1,4]benzoxazepine-2-carboxamide |
| 170 | 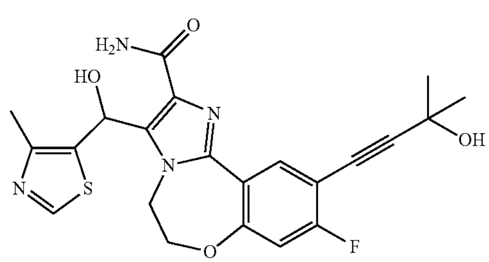 [SMILES: Cc1ncsc1C(O)c1c(C(N)=O)nc2n1CCOc1cc(F)c(C#CC(C)(C)O)cc1-2] | 9-fluoro-10-(3-hydroxy-3-methyl-but-1-ynyl)-3-[hydroxy-(4-methylthiazol-5-yl)methyl]-5,6-dihydroimidazo[1,2-d][1,4]benzoxazepine-2-carboxamide |
| 171 | 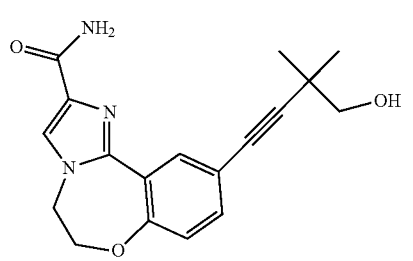 [SMILES: CC(C)(C#Cc1ccc2c(c1)-c1nc(C(N)=O)cn1CCO2)CO] | 10-(4-hydroxy-3,3-dimethyl-but-1-ynyl)-5,6-dihydroimidazo[1,2-d][1,4]benzoxazepine-2-carboxamide |

TABLE 1-continued

| No. | Structure | Name |
| --- | --- | --- |
| 172 | 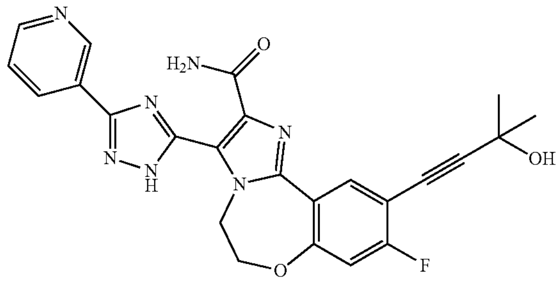 [SMILES: CC(C)(O)C#Cc1cc2c(cc1F)OCCn1c-2nc(C(N)=O)c1-c1nc(-c2cccnc2)n[nH]1] | 9-fluoro-10-(3-hydroxy-3-methyl-but-1-ynyl)-3-[3-(3-pyridyl)-1H-1,2,4-triazol-5-yl]-5,6-dihydroimidazo[1,2-d][1,4]benzoxazepine-2-carboxamide |
| 173 | 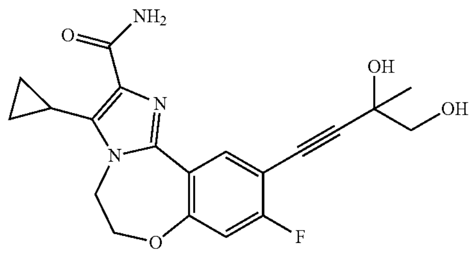 [SMILES: CC(O)(C#Cc1cc2c(cc1F)OCCn1c-2nc(C(N)=O)c1C1CC1)CO] | 3-cyclopropyl-10-(3,4-dihydroxy-3-methyl-but-1-ynyl)-9-fluoro-5,6-dihydroimidazo[1,2-d][1,4]benzoxazepine-2-carboxamide |
| 174 | 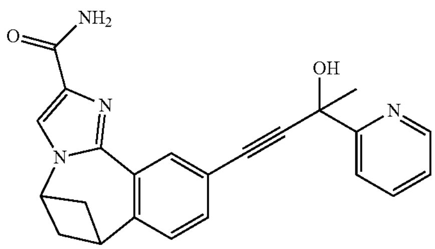 [SMILES: CC(O)(C#Cc1ccc2c(c1)-c1nc(C(N)=O)cn1C1CC2C1)c1ccccn1] | 10-[3-hydroxy-3-(2-pyridyl)but-1-ynyl]-5,6,7,12-tetrahydro-5,7-methanobenzo[c]imidazo[1,2-a]azepine-2-carboxamide |
| 175 | 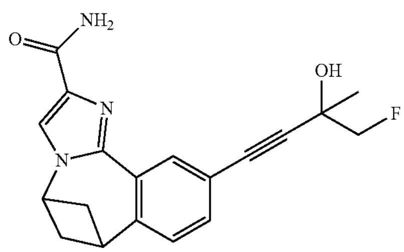 [SMILES: CC(O)(C#Cc1ccc2c(c1)-c1nc(C(N)=O)cn1C1CC2C1)CF] | 10-(4-fluoro-3-hydroxy-3-methyl-but-1-ynyl)-5,6,7,12-tetrahydro-5,7-methanobenzo[c]imidazo[1,2-a]azepine-2-carboxamide |
| 176 | 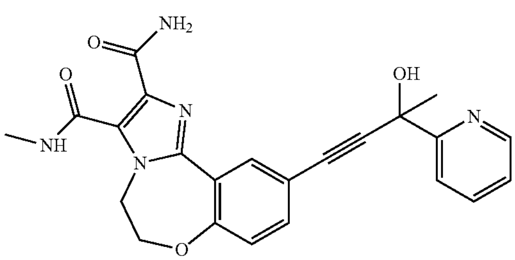 [SMILES: CNC(=O)c1c(C(N)=O)nc2n1CCOc1ccc(C#CC(C)(O)c3ccccn3)cc1-2] | 10-[3-hydroxy-3-(2-pyridyl)but-1-ynyl]-N3-methyl-5,6-dihydroimidazo[1,2-d][1,4]benzoxazepine-2,3-dicarboxamide |
| 177 | 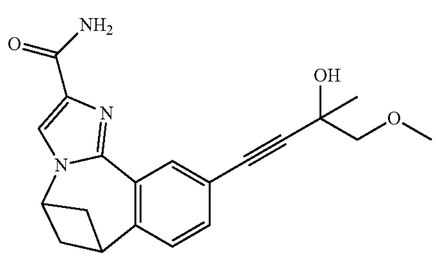 [SMILES: COCC(C)(O)C#Cc1ccc2c(c1)-c1nc(C(N)=O)cn1C1CC2C1] | 10-(3-hydroxy-4-methoxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 178 | 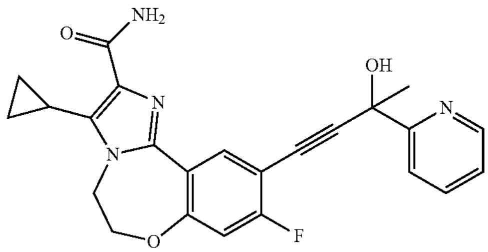 [SMILES: CC(O)(C#Cc1cc2c(cc1F)OCCn1c-2nc(C(N)=O)c1C1CC1)c1ccccn1] | 3-cyclopropyl-9-fluoro-10-[3-hydroxy-3-(2-pyridyl)but-1-ynyl]-5,6-dihydroimidazo[1,2-d][1,4]benzoxazepine-2-carboxamide |
| 179 | 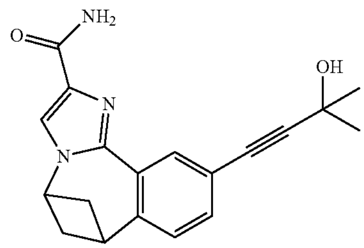 [SMILES: CC(C)(O)C#Cc1ccc2c(c1)-c1nc(C(N)=O)cn1C1CC2C1] | 10-(3-hydroxy-3-methyl-but-1-ynyl)-5,6,7,12-tetrahydro-5,7-methanobenzo[c]imidazo[1,2-a]azepine-2-carboxamide |
| 180 | 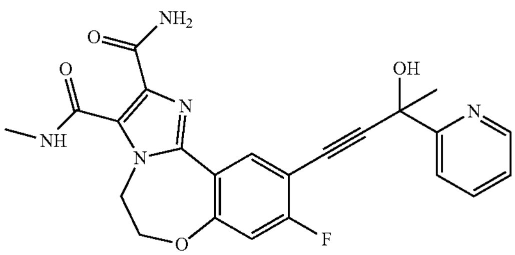 [SMILES: CNC(=O)c1c(C(N)=O)nc2n1CCOc1cc(F)c(C#CC(C)(O)c3ccccn3)cc1-2] | 9-fluoro-10-[3-hydroxy-3-(2-pyridyl)but-1-ynyl]-N3-methyl-5,6-dihydroimidazo[1,2-d][1,4]benzoxazepine-2,3-dicarboxamide |
| 181 | 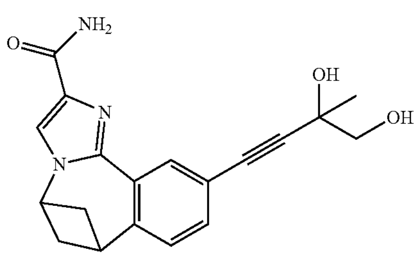 [SMILES: CC(O)(C#Cc1ccc2c(c1)-c1nc(C(N)=O)cn1C1CC2C1)CO] | 10-(3,4-dihydroxy-3-methyl-but-1-ynyl)-5,6,7,12-tetrahydro-5,7-methanobenzo[c]imidazo[1,2-a]azepine-2-carboxamide |
| 182 | 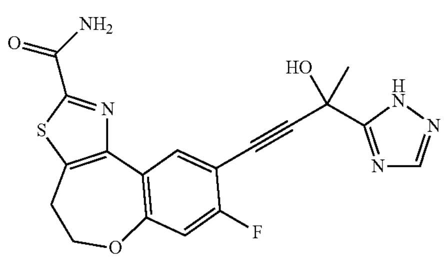 [SMILES: CC(O)(C#Cc1cc2c(cc1F)OCCc1sc(C(N)=O)nc1-2)c1ncn[nH]1] | 8-fluoro-9-[3-hydroxy-3-(1H-1,2,4-triazol-5-yl)but-1-ynyl]-4,5-dihydro-[I]benzoxepino[5,4-d]thiazole-2-carboxamide |
| 183 | 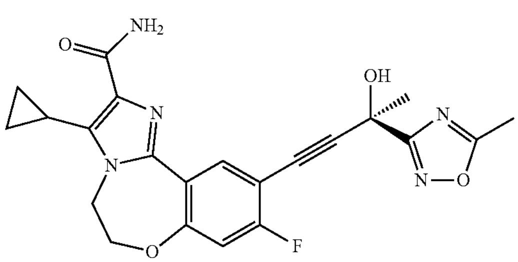 [SMILES: Cc1nc([C@](C)(O)C#Cc2cc3c(cc2F)OCCn2c-3nc(C(N)=O)c2C2CC2)no1] | 3-cyclopropyl-9-fluoro-10-[(3R)-3-hydroxy-3-(5-methyl-1,2,4-oxadiazol-3-yl)but-1-ynyl]-5,6-dihydroimidazo[1,2-d][1,4]benzoxazepine-2-carboxamide |

TABLE 1-continued

| No. | Structure | Name |
|---|---|---|
| 184 | 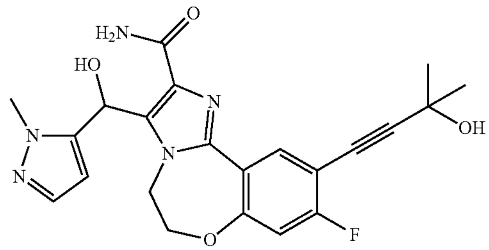 [SMILES: Cn1nccc1C(O)c1c(C(N)=O)nc2n1CCOc1cc(F)c(C#CC(C)(C)O)cc1-2] | 9-fluoro-10-(3-hydroxy-3-methyl-but-1-ynyl)-3-[hydroxy-(2-methylpyrazol-3-yl)methyl]-5,6-dihydroimidazo[1,2-d][1,4]benzoxazepine-2-carboxamide |
| 185 | 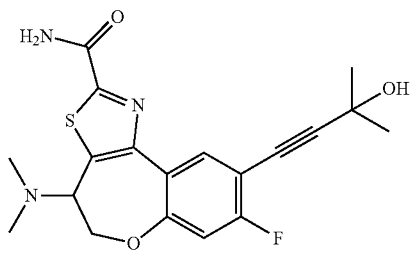 [SMILES: CN(C)C1COc2cc(F)c(C#CC(C)(C)O)cc2-c2nc(C(N)=O)sc21] | 4-(dimethylamino)-8-fluoro-9-(3-hydroxy-3-methyl-but-1-ynyl)-4,5-dihydro-[1]benzoxepino[5,4-d]thiazole-2-carboxamide |
| 186 | 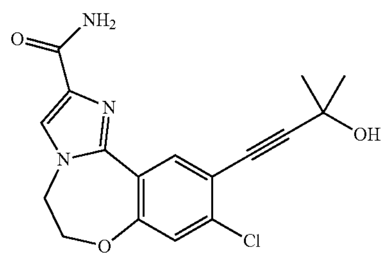 [SMILES: CC(C)(O)C#Cc1cc2c(cc1Cl)OCCn1cc(C(N)=O)nc1-2] | 9-chloro-10-(3-hydroxy-3-methyl-but-1-ynyl)-5,6-dihydroimidazo[1,2-d][1,4]benzoxazepine-2-carboxamide |
| 187 | 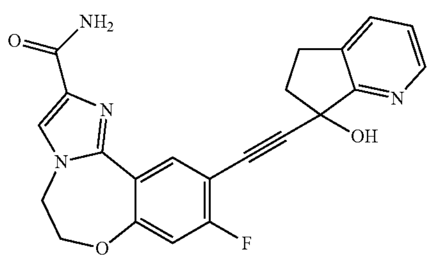 [SMILES: NC(=O)c1cn2c(n1)-c1cc(C#CC3(O)CCc4cccnc43)c(F)cc1OCC2] | 9-fluoro-10-[2-(7-hydroxy-5,6-dihydrocyclopenta[b]pyridin-7-yl)ethynyl]-5,6-dihydroimidazo[1,2-d][1,4]benzoxazepine-2-carboxamide |
| 188 | 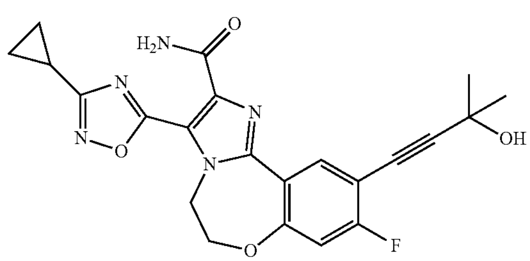 [SMILES: CC(C)(O)C#Cc1cc2c(cc1F)OCCn1c-2nc(C(N)=O)c1-c1nc(C2CC2)no1] | 3-(3-cyclopropyl-1,2,4-oxadiazol-5-yl)-9-fluoro-10-(3-hydroxy-3-methyl-but-1-ynyl)-5,6-dihydroimidazo[1,2-d][1,4]benzoxazepine-2-carboxamide |
| 189 | 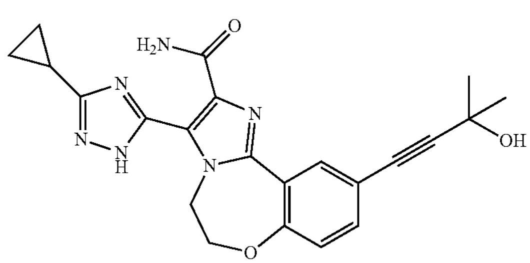 [SMILES: CC(C)(O)C#Cc1ccc2c(c1)-c1nc(C(N)=O)c(-c3nc(C4CC4)n[nH]3)n1CCO2] | 3-(3-cyclopropyl-1H-1,2,4-triazol-5-yl)-10-(3-hydroxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 190 | 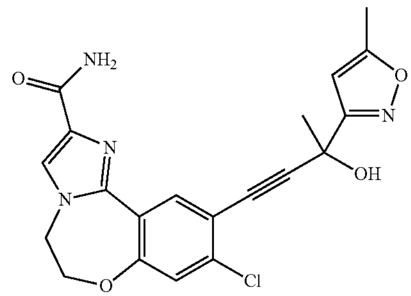 [SMILES: Cc1cc(C(C)(O)C#Cc2cc3c(cc2Cl)OCCn2cc(C(N)=O)nc2-3)no1] | 9-chloro-10-[3-hydroxy-3-(5-methyl-isoxazol-3-yl)but-1-ynyl]-5,6-dihydro-imidazo[1,2-d][1,4]benzoxazepine-2-carboxamide |
| 191 | 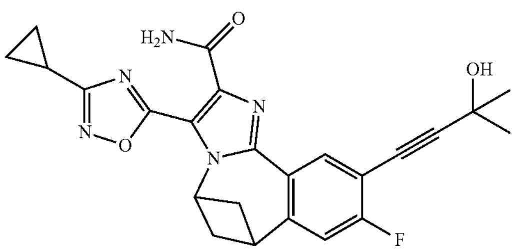 [SMILES: CC(C)(O)C#Cc1cc2c(cc1F)C1CC(C1)n1c-2nc(C(N)=O)c1-c1nc(C2CC2)no1] | 3-(3-cyclopropyl-1,2,4-oxadiazol-5-yl)-9-fluoro-10-(3-hydroxy-3-methyl-but-1-ynyl)-5,6,7,12-tetrahydro-5,7-methanobenzo[c]imidazo[1,2-a]azepine-2-carboxamide |
| 192 | 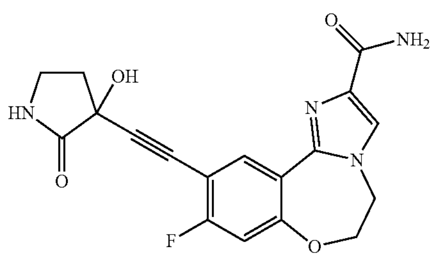 [SMILES: NC(=O)c1cn2c(n1)-c1cc(C#CC3(O)CCNC3=O)c(F)cc1OCC2] | 9-fluoro-10-[2-(3-hydroxy-2-oxo-pyrrolidin-3-yl)ethynyl]-5,6-dihydroimidazo[1,2-d][1,4]benzoxazepine-2-carboxamide |
| 193 | 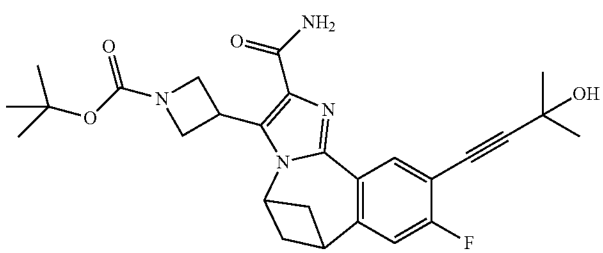 [SMILES: CC(C)(O)C#Cc1cc2c(cc1F)C1CC(C1)n1c-2nc(C(N)=O)c1C1CN(C(=O)OC(C)(C)C)C1] | tert-butyl 3-[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]azetidine-1-carboxylate |
| 194 | 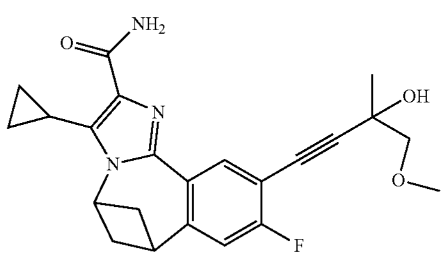 [SMILES: COCC(C)(O)C#Cc1cc2c(cc1F)C1CC(C1)n1c-2nc(C(N)=O)c1C1CC1] | 3-cyclopropyl-9-fluoro-10-(3-hydroxy-4-methoxy-3-methyl-but-1-ynyl)-5,6,7,12-tetrahydro-5,7-methanobenzo[c]imidazo[1,2-a]azepine-2-carboxamide |
| 195 | 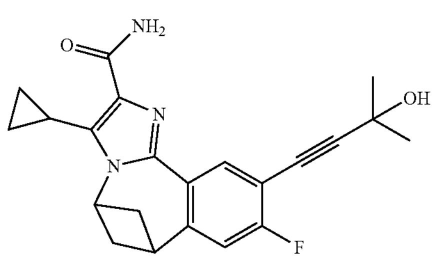 [SMILES: CC(C)(O)C#Cc1cc2c(cc1F)C1CC(C1)n1c-2nc(C(N)=O)c1C1CC1] | 3-cyclopropyl-9-fluoro-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 196 | 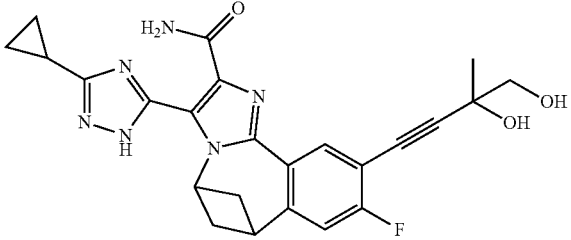 [SMILES: CC(O)(C#Cc1cc2c(cc1F)C1CC(C1)n1c-2nc(C(N)=O)c1-c1nc(C2CC2)n[nH]1)CO] | 3-(3-cyclopropyl-1H-1,2,4-triazol-5-yl)-10-(3,4-dihydroxy-3-methyl-but-1-ynyl)-9-fluoro-5,6,7,12-tetrahydro-5,7-methano-benzo[c]imidazo[1,2-a]azepine-2-carboxamide |
| 197 | 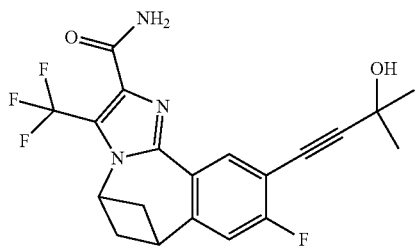 [SMILES: CC(C)(O)C#Cc1cc2c(cc1F)C1CC(C1)n1c-2nc(C(N)=O)c1C(F)(F)F] | 9-fluoro-10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide |
| 198 | 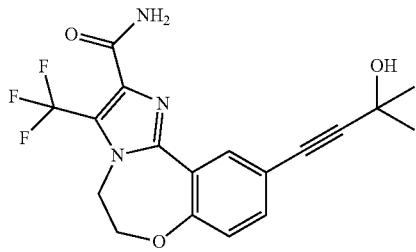 [SMILES: CC(C)(O)C#Cc1ccc2c(c1)-c1nc(C(N)=O)c(C(F)(F)F)n1CCO2] | 10-(3-hydroxy-3-methyl-but-1-ynyl])-3-(trifluoromethyl)-5,6-dihydroimidazo[1,2-d][1,4]benzoxazepine-2-carboxamide |
| 199 | 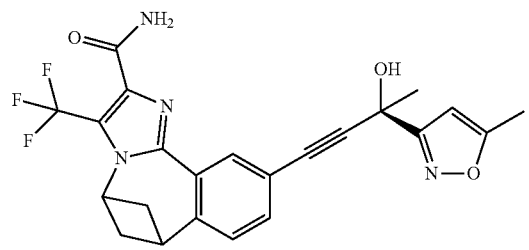 | 10-[(3R)-3-hydroxy-3-(5-methylisoxazol-3-yl)but-1-ynyl]-3-(trifluoromethyl)-5,6,7,12-tetrahydro-5,7-methanobenzo[c]imidazo[1,2-a]azepine-2-carboxamide |
| 200 | 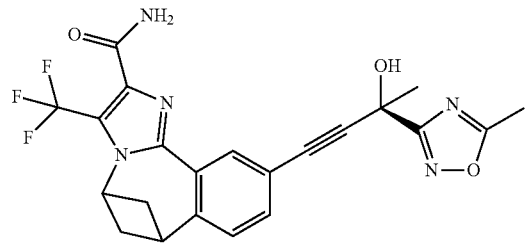 [SMILES: Cc1nc([C@](C)(O)C#Cc2ccc3c(c2)-c2nc(C(N)=O)c(C(F)(F)F)n2C2CC3C2)no1] | 10-[(3R)-3-hydroxy-3-(5-methyl-1,2,4-oxadiazol-3-yl)but-1-ynyl]-3-(trifluoromethyl)-5,6,7,12-tetrahydro-5,7-methanobenzo[c]imidazo[1,2-a]azepine-2-carboxamide |
| 201 | 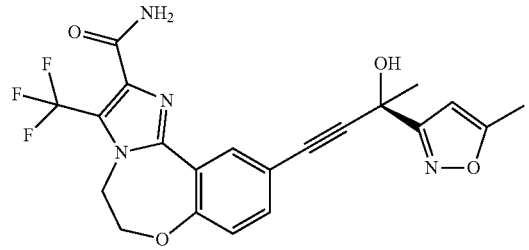 [SMILES: Cc1cc([C@](C)(O)C#Cc2ccc3c(c2)-c2nc(C(N)=O)c(C(F)(F)F)n2CCO3)no1] | 10-[(3R)-3-hydroxy-3-(5-methylisoxazol-3-yl)but-1-ynyl]-3-(trifluoromethyl)-5,6-dihydroimidazo[1,2-d][1,4]benzoxazepine-2-carboxamide |

TABLE 1-continued

| No. | Structure | Name |
|---|---|---|
| 202 | 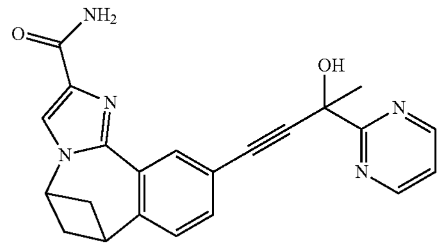 [SMILES: CC(O)(C#Cc1ccc2c(c1)-c1nc(C(N)=O)cn1C1CC2C1)c1ncccn1] | 10-(3-hydroxy-3-pyrimidin-2-yl-but-1-ynyl)-5,6,7,12-tetrahydro-5,7-methano-benzo[c]imidazo[1,2-a]azepine-2-carboxamide |
| 203 | 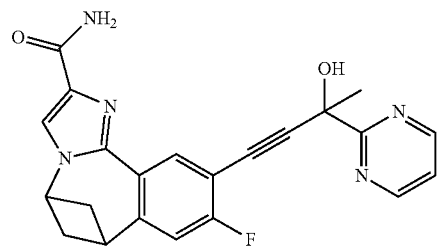 [SMILES: CC(O)(C#Cc1cc2c(cc1F)C1CC(C1)n1cc(C(N)=O)nc1-2)c1ncccn1] | 9-fluoro-10-(3-hydroxy-3-pyrimidin-2-yl-but-1-ynyl)-5,6,7,12-tetrahydro-5,7-methanobenzo[c]imidazo[1,2-a]azepine-2-carboxamide |
| 204 | 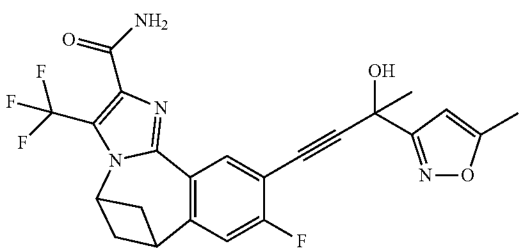 [SMILES: Cc1cc(C(C)(O)C#Cc2cc3c(cc2F)C2CC(C2)n2c-3nc(C(N)=O)c2C(F)(F)F)no1] | 9-fluoro-10-[3-hydroxy-3-(5-methyl-isoxazol-3-yl)but-1-ynyl]-3-(trifluoromethyl)-5,6,7,12-tetrahydro-5,7-methanobenzo[c]imidazo[1,2-a]azepine-2-carboxamide |
| 205 | 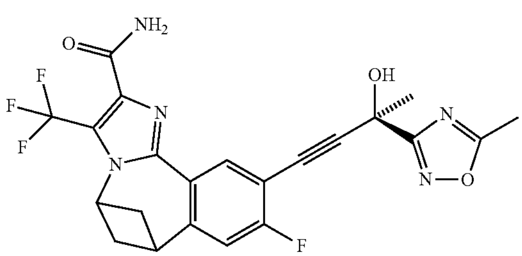 [SMILES: Cc1nc([C@](C)(O)C#Cc2cc3c(cc2F)C2CC(C2)n2c-3nc(C(N)=O)c2C(F)(F)F)no1] | 9-fluoro-10-[(3R)-3-hydroxy-3-(5-methyl-1,2,4-oxadiazol-3-yl)but-1-ynyl]-3-(trifluoromethyl)-5,6,7,12-tetrahydro-5,7-methanobenzo[c]imidazo[1,2-a]azepine-2-carboxamide |
| 206 | 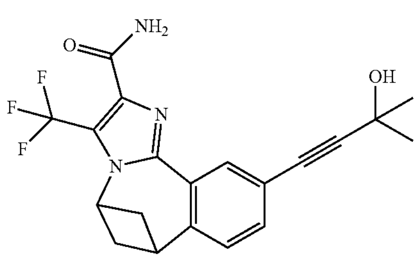 [SMILES: CC(C)(O)C#Cc1ccc2c(c1)-c1nc(C(N)=O)c(C(F)(F)F)n1C1CC2C1] | 10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide |
| 207 | 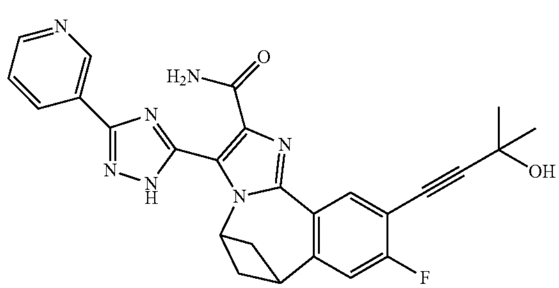 [SMILES: CC(C)(O)C#Cc1cc2c(cc1F)C1CC(C1)n1c-2nc(C(N)=O)c1-c1nc(-c2cccnc2)n[nH]1] | 9-fluoro-10-(3-hydroxy-3-methyl-but-1-ynyl)-3-[3-(3-pyridyl)-1H-1,2,4-triazol-5-yl]-5,6,7,12-tetrahydro-5,7-methano-benzo[c]imidazo[1,2-a]azepine-2-carboxamide |

TABLE 1-continued

| No. | Name |
|---|---|
| 208 | 3-(3-cyclopropyl-1H-1,2,4-triazol-5-yl)-10-(3,4-dihydroxy-3-methyl-but-1-ynyl)-9-fluoro-5,6-dihydroimidazo[1,2-d][1,4]benzoxazepine-2-carboxamide |
| 209 | 10-[(3R)-3-hydroxy-3-(5-methylisoxazol-3-yl)but-1-ynyl]-N3-methyl-5,6,7,12-tetrahydro-5,7-methanobenzo[c]imidazo[1,2-a]azepine-2,3-dicarboxamide |
| 210 | 10-[3-hydroxy-3-(1H-1,2,4-triazol-3-yl)but-1-yny]-5,6,7,12-tetrahydro-5,7-methanobenzo[c]imidazo[1,2-a]azepine-2-carboxamide |
| 211 | 10-[(3R)-3-hydroxy-3-(5-methyl-1,2,4-oxadiazol-3-yl)but-1-ynyl]-N3-methyl-5,6,7,12-tetrahydro-5,7-methanobenzo[c]imidazo[1,2-a]azepine-2,3-dicarboxamide |
| 212 | 10-[(3R)-3-hydroxy-3-(5-methylisoxazol-3-yl)but-1-ynyl]-N3,N3-dimethyl-5,6,7,12-tetrahydro-5,7-methanobenzo[c]imidazo[1,2-a]azepine-2,3-dicarboxamide |
| 213 | 3-(3-cyclopropyl-1H-1,2,4-triazol-5-yl)-9-fluoro-10-(3-hydroxy-4-methoxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 214 | 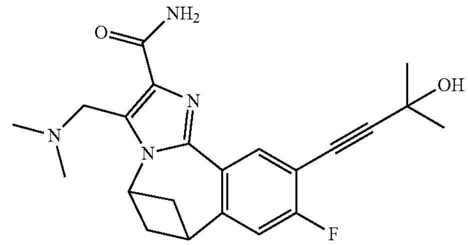 [SMILES: CN(C)Cc1c(C(N)=O)nc2n1C1CC(C1)c1cc(F)c(C#CC(C)(C)O)cc1-2] | 3-[(dimethylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |
| 215 | 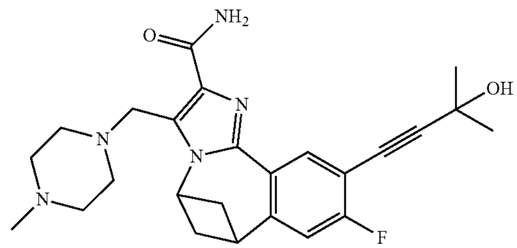 [SMILES: CN1CCN(Cc2c(C(N)=O)nc3n2C2CC(C2)c2cc(F)c(C#CC(C)(C)O)cc2-3)CC1] | 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide |
| 216 | 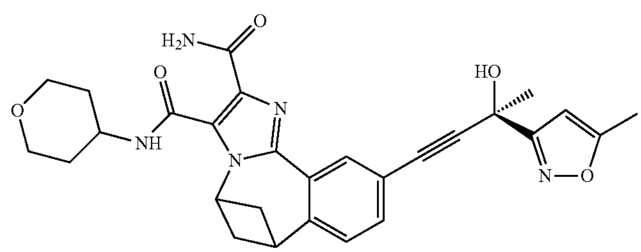 [SMILES: Cc1cc([C@](C)(O)C#Cc2ccc3c(c2)-c2nc(C(N)=O)c(C(=O)NC4CCOCC4)n2C2CC3C2)no1] | 10-[(3R)-3-hydroxy-3-(5-methylisoxazol-3-yl)but-1-ynyl]-N3-tetrahydropyran-4-yl-5,6,7,12-tetrahydro-5,7-methanobenzo[c]imidazo[1,2-a]azepine-2,3-dicarboxamide |
| 217 | 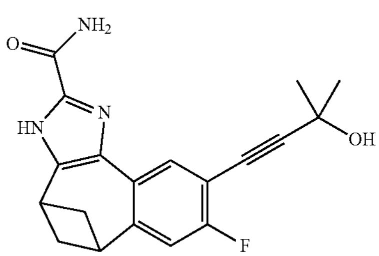 [SMILES: CC(C)(O)C#Cc1cc2c(cc1F)C1CC(C1)c1[nH]c(C(N)=O)nc1-2] | 8-fluoro-9-(3-hydroxy-3-methylbut-1-yn-1-yl)-3,4,5,6-tetrahydro-4,6-methanobenzo[3,4]cyclohepta[1,2-d]imidazole-2-carboxamide |
| 218 | 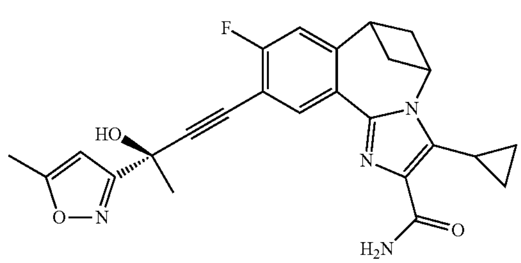 [SMILES: Cc1cc([C@](C)(O)C#Cc2cc3c(cc2F)C2CC(C2)n2c-3nc(C(N)=O)c2C2CC2)no1] | 3-cyclopropyl-9-fluoro-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide |
| 219 | 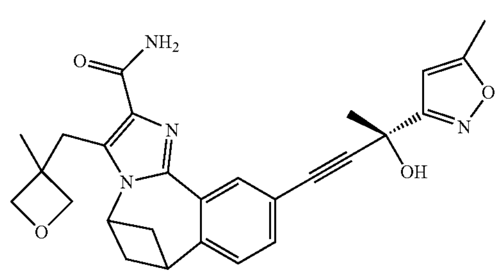 [SMILES: Cc1cc([C@](C)(O)C#Cc2ccc3c(c2)-c2nc(C(N)=O)c(CC4(C)COC4)n2C2CC3C2)no1] | 10-[(3R)-3-hydroxy-3-(5-methylisoxazol-3-yl)but-1-ynyl]-3-[(3-methyloxetan-3-yl)methyl]-5,6,7,12-tetrahydro-5,7-methanobenzo[c]imidazo[1,2-a]azepine-2-carboxamide |

TABLE 1-continued

| No. | Structure | Name |
|---|---|---|
| 220 | 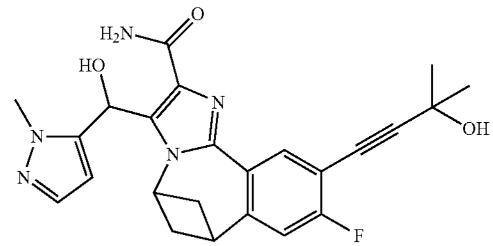 [SMILES: Cn1nccc1C(O)c1c(C(N)=O)nc2n1C1CC(C1)c1cc(F)c(C#CC(C)(C)O)cc1-2] | 9-fluoro-10-(3-hydroxy-3-methyl-but-1-ynyl)-3-[hydroxy-(2-methylpyrazol-3-yl)methyl]-5,6,7,12-tetrahydro-5,7-methanobenzo[c]imidazo[1,2-a]azepine-2-carboxamide |
| 221 | 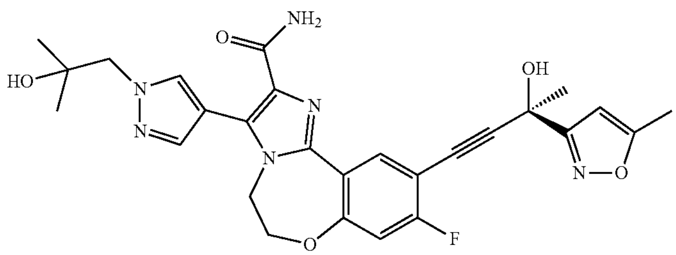 [SMILES: Cc1cc([C@](C)(O)C#Cc2cc3c(cc2F)OCCn2c-3nc(C(N)=O)c2-c2cnn(CC(C)(C)O)c2)no1] | 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6-dihydroimidazo[1,2-d][1,4]benzoxazepine-2-carboxamide |
| 222 | 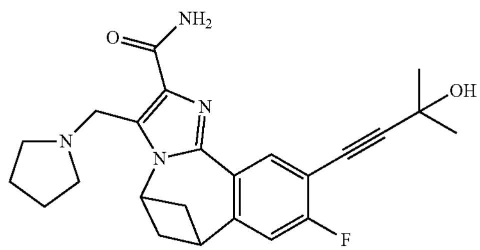 [SMILES: CC(C)(O)C#Cc1cc2c(cc1F)C1CC(C1)n1c-2nc(C(N)=O)c1CN1CCCC1] | 9-fluoro-10-(3-hydroxy-3-methyl-but-1-ynyl)-3-(pyrrolidin-1-ylmethyl)-5,6,7,12-tetrahydro-5,7-methanobenzo[c]imidazo[1,2-a]azepine-2-carboxamide |
| 223 | 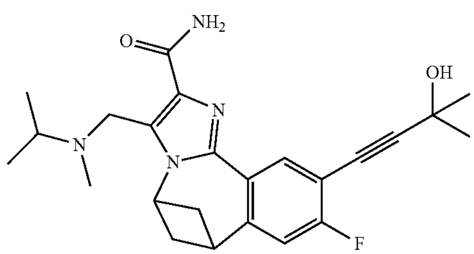 [SMILES: CC(C)N(C)Cc1c(C(N)=O)nc2n1C1CC(C1)c1cc(F)c(C#CC(C)(C)O)cc1-2] | 9-fluoro-10-(3-hydroxy-3-methyl-but-1-ynyl)-3-[[isopropyl(methyl)amino]methyl]-5,6,7,12-tetrahydro-5,7-methanobenzo[c]imidazo[1,2-a]azepine-2-carboxamide |
| 224 | 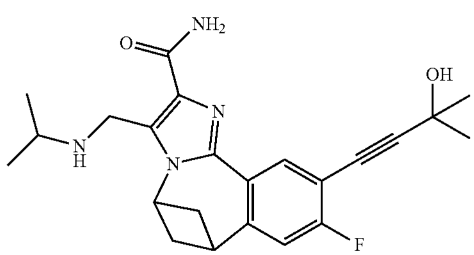 [SMILES: CC(C)NCc1c(C(N)=O)nc2n1C1CC(C1)c1cc(F)c(C#CC(C)(C)O)cc1-2] | 9-fluoro-10-(3-hydroxy-3-methyl-but-1-ynyl)-3-[(isopropylamino)methyl]-5,6,7,12-tetrahydro-5,7-methanobenzo[c]imidazo[1,2-a]azepine-2-carboxamide |
| 225 | 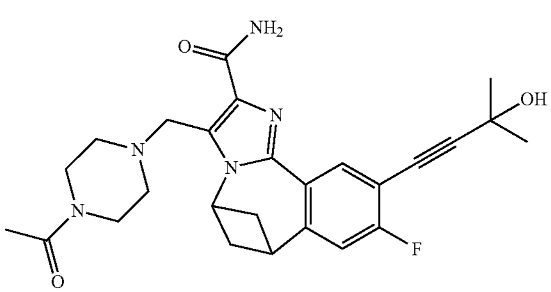 [SMILES: CC(=O)N1CCN(Cc2c(C(N)=O)nc3n2C2CC(C2)c2cc(F)c(C#CC(C)(C)O)cc2-3)CC1] | 3-[(4-acetylpiperazin-1-yl)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 226 | 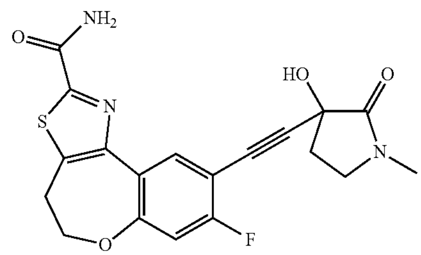 [SMILES: CN1CCC(O)(C#Cc2cc3c(cc2F)OCCc2sc(C(N)=O)nc2-3)C1=O] | 8-fluoro-9-[2-(3-hydroxy-1-methyl-2-oxo-pyrrolidin-3-yl)ethynyl]-4,5-dihydro-[1]benzoxepino[5,4-d]thiazole-2-carboxamide |
| 227 | 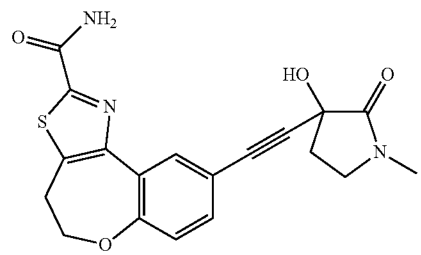 [SMILES: CN1CCC(O)(C#Cc2ccc3c(c2)-c2nc(C(N)=O)sc2CCO3)C1=O] | 9-[2-(3-hydroxy-1-methyl-2-oxo-pyrrolidin-3-yl)ethynyl]-4,5-dihydro-[1]benzoxepino[5,4-d]thiazole-2-carboxamide |
| 228 | 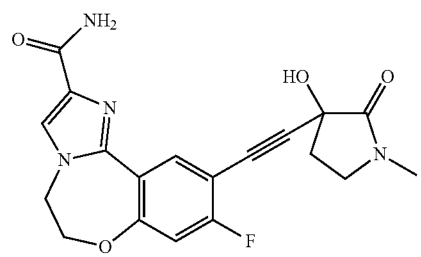 [SMILES: CN1CCC(O)(C#Cc2cc3c(cc2F)OCCn2cc(C(N)=O)nc2-3)C1=O] | 9-fluoro-10-[2-(3-hydroxy-1-methyl-2-oxo-pyrrolidin-3-yl)ethyny]-5,6-dihydro-imidazo[1,2-d][1,4]benzoxazepine-2-carboxamide |
| 229 | 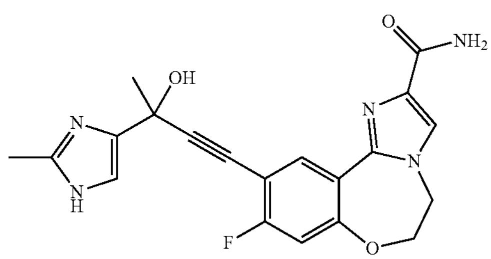 [SMILES: Cc1nc(C(C)(O)C#Cc2cc3c(cc2F)OCCn2cc(C(N)=O)nc2-3)c[nH]1] | 9-fluoro-10-[3-hydroxy-3-(2-methyl-1H-imidazol-4-yl)but-1-ynyl]-5,6-dihydro-imidazo[1,2-d][1,4]benzoxazepine-2-carboxamide |
| 230 | 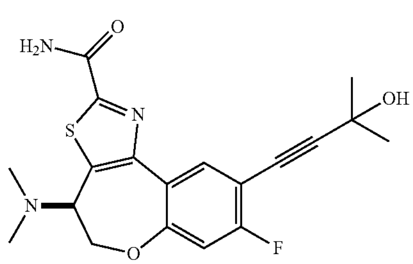 | 4-(R)-(dimethylamino)-8-fluoro-9-(3-hydroxy-3-methyl-but-1-ynyl)-4,5-dihydro-[1]benzoxepino[5,4-d]thiazole-2-carboxamide |
| 231 | 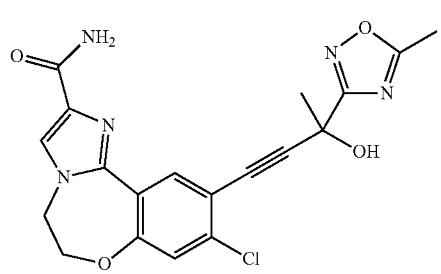 [SMILES: Cc1nc(C(C)(O)C#Cc2cc3c(cc2Cl)OCCn2cc(C(N)=O)nc2-3)no1] | 9-chloro-10-[3-hydroxy-3-(5-methyl-1,2,4-oxadiazol-3-yl)but-1-ynyl]-5,6-dihydroimidazo[1,2-d][1,4]benzoxazepine-2-carboxamide |

TABLE 1-continued

| No. | Structure | Name |
|---|---|---|
| 232 | 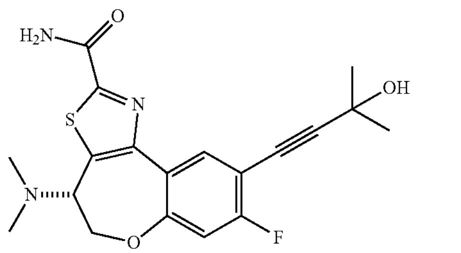 [SMILES: CN(C)[C@H]1COc2cc(F)c(C#CC(C)(C)O)cc2-c2nc(C(N)=O)sc21] | 4-(S)-(dimethylamino)-8-fluoro-9-(3-hydroxy-3-methyl-but-1-ynyl)-4,5-dihydro-[1]benzoxepino[5,4-d]thiazole-2-carboxamide |
| 233 | 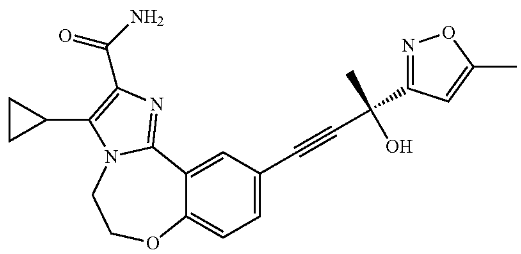 [SMILES: Cc1cc([C@](C)(O)C#Cc2ccc3c(c2)-c2nc(C(N)=O)c(C4CC4)n2CCO3)no1] | 3-cyclopropyl-10-[(3R)-3-hydroxy-3-(5-methylisoxazol-3-yl)but-1-ynyl]-5,6-dihydroimidazo[1,2-d][1,4]benzoxazepine-2-carboxamide |
| 234 | 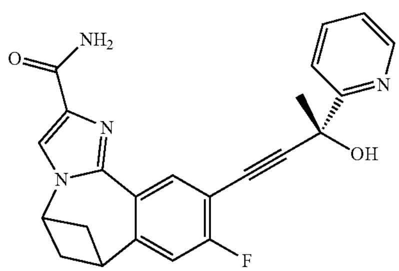 [SMILES: C[C@@](O)(C#Cc1cc2c(cc1F)C1CC(C1)n1cc(C(N)=O)nc1-2)c1ccccn1] | 9-fluoro-10-[(3R)-3-hydroxy-3-(2-pyridyl)but-1-ynyl]-5,6,7,12-tetrahydro-5,7-methanobenzo[c]imidazo[1,2-a]azepine-2-carboxamide |
| 235 | 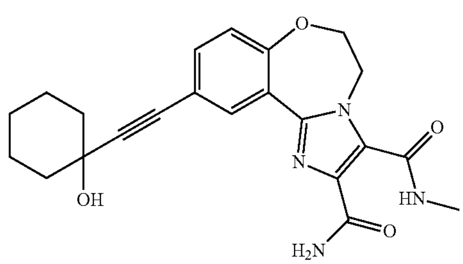 [SMILES: CNC(=O)c1c(C(N)=O)nc2n1CCOc1ccc(C#CC3(O)CCCCC3)cc1-2] | 10-[2-(1-hydroxycyclohexyl)ethynyl]-N3-methyl-5,6-dihydroimidazo[1,2-d][1,4]benzoxazepine-2,3-dicarboxamide |
| 236 | 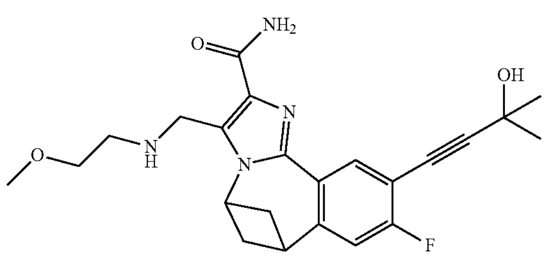 [SMILES: COCCNCc1c(C(N)=O)nc2n1C1CC(C1)c1cc(F)c(C#CC(C)(C)O)cc1-2] | 9-fluoro-10-(3-hydroxy-3-methyl-but-1-ynyl)-3-[(2-methoxyethylamino)methyl]-5,6,7,12-tetrahydro-5,7-methanobenzo[c]imidazo[1,2-a]azepine-2-carboxamide |
| 237 | 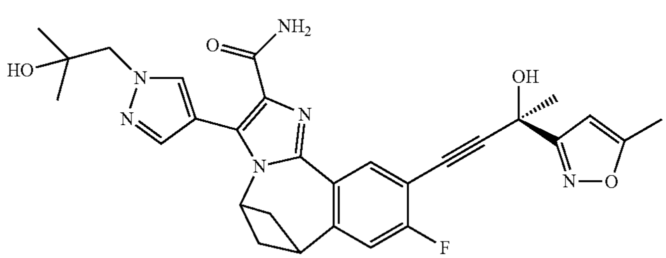 [SMILES: Cc1cc([C@](C)(O)C#Cc2cc3c(cc2F)C2CC(C2)n2c-3nc(C(N)=O)c2-c2cnn(CC(C)(C)O)c2)no1] | 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide |

TABLE 1-continued

| No. | Structure | Name |
|---|---|---|
| 238 | 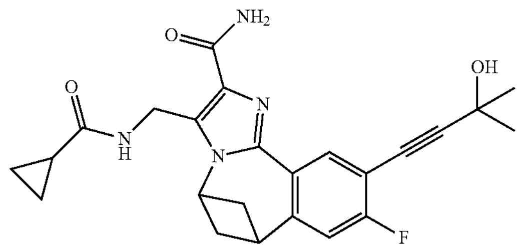 [SMILES: CC(C)(O)C#Cc1cc2c(cc1F)C1CC(C1)n1c-2nc(C(N)=O)c1CNC(=O)C1CC1] | 3-[(cyclopropanecarbonylamino)methyl]-9-fluoro-10-(3-hydroxy-3-methyl-but-1-ynyl)-5,6,7,12-tetrahydro-5,7-methano-benzo[c]imidazo[1,2-a]azepine-2-carboxamide |
| 239 | 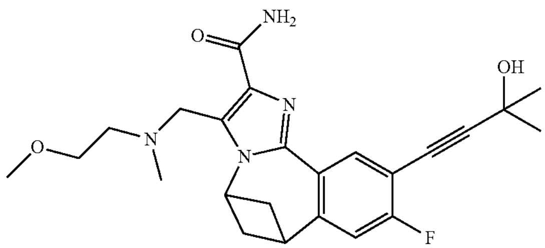 [SMILES: COCCN(C)Cc1c(C(N)=O)nc2n1C1CC(C1)c1cc(F)c(C#CC(C)(C)O)cc1-2] | 9-fluoro-10-(3-hydroxy-3-methyl-but-1-ynyl)-3-[[2-methoxyethyl(methyl)amino]methyl]-5,6,7,12-tetrahydro-5,7-methano-benzo[c]imidazo[1,2-a]azepine-2-carboxamide |
| 240 | 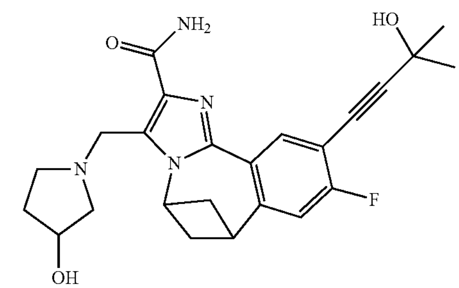 [SMILES: CC(C)(O)C#Cc1cc2c(cc1F)C1CC(C1)n1c-2nc(C(N)=O)c1CN1CCC(O)C1] | 9-fluoro-10-(3-hydroxy-3-methyl-but-1-ynyl)-3-[(3-hydroxypyrrolidin-1-yl)methyl]-5,6,7,12-tetrahydro-5,7-methano-benzo[c]imidazo[1,2-a]azepine-2-carboxamide |
| 241 | 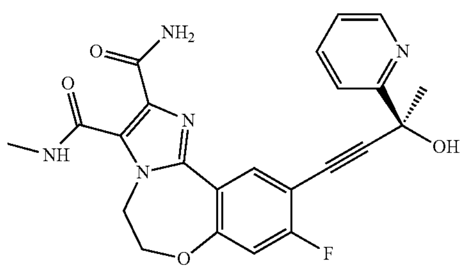 [SMILES: CNC(=O)c1c(C(N)=O)nc2n1CCOc1cc(F)c(C#C[C@](C)(O)c3ccccn3)cc1-2] | 9-fluoro-10-[(3S)-3-hydroxy-3-(2-pyridyl)but-1-ynyl]-N3-methyl-5,6-dihydro-imidazo[1,2-d][1,4]benzoxazepine-2,3-dicarboxamide |
| 242 | 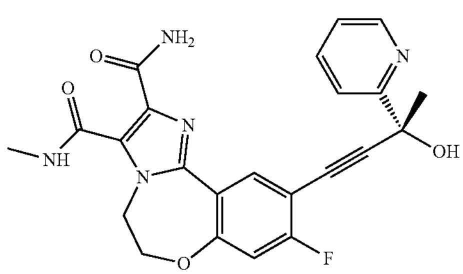 [SMILES: CNC(=O)c1c(C(N)=O)nc2n1CCOc1cc(F)c(C#C[C@@](C)(O)c3ccccn3)cc1-2] | 9-fluoro-10-[(3R)-3-hydroxy-3-(2-pyridyl)but-1-ynyl]-N3-methyl-5,6-dihydro-imidazo[1,2-d][1,4]benzoxazepine-2,3-dicarboxamide |
| 243 | 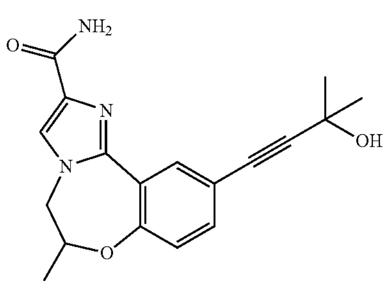 [SMILES: CC1Cn2cc(C(N)=O)nc2-c2cc(C#CC(C)(C)O)ccc2O1] | 10-(3-hydroxy-3-methyl-but-1-ynyl)-6-methyl-5,6-dihydroimidazo[1,2-d][1,4]benzoxazepine-2-carboxamide |

TABLE 1-continued

| No. | Structure | Name |
|---|---|---|
| 244 | 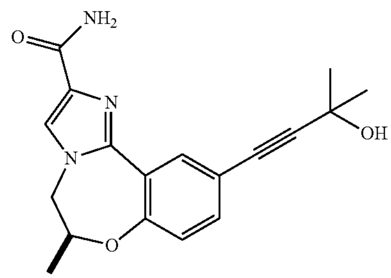 [SMILES: C[C@H]1Cn2cc(C(N)=O)nc2-c2cc(C#CC(C)(C)O)ccc2O1] | 10-(3-hydroxy-3-methyl-but-1-ynyl)-6-(S)-methyl-5,6-dihydroimidazo[1,2-d][1,4]benzoxazepine-2-carboxamide |
| 245 | 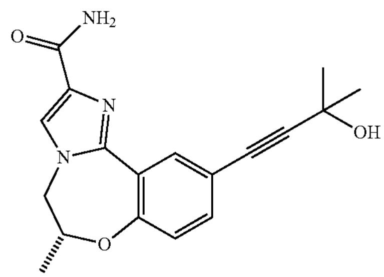 [SMILES: C[C@@H]1Cn2cc(C(N)=O)nc2-c2cc(C#CC(C)(C)O)ccc2O1] | 10-(3-hydroxy-3-methyl-but-1-ynyl)-6-(R)-methyl-5,6-dihydroimidazo[1,2-d][1,4]benzoxazepine-2-carboxamide |
| 246 | 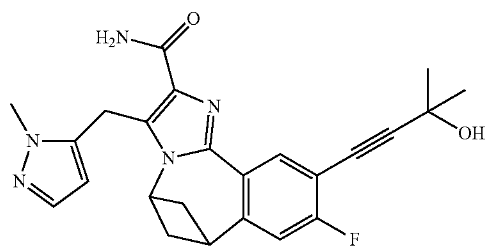 [SMILES: Cn1nccc1Cc1c(C(N)=O)nc2n1C1CC(C1)c1cc(F)c(C#CC(C)(C)O)cc1-2] | 9-fluoro-10-(3-hydroxy-3-methyl-but-1-ynyl)-3-[(2-methylpyrazol-3-yl)methyl]-5,6,7,12-tetrahydro-5,7-methano-benzo[c]imidazo[1,2-a]azepine-2-carboxamide |
| 247 | 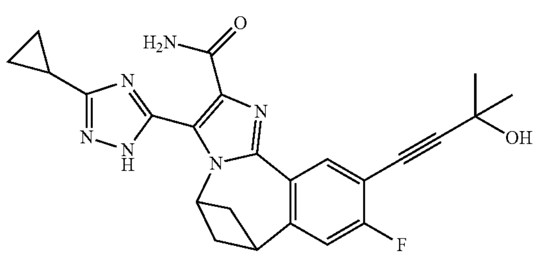 [SMILES: CC(C)(O)C#Cc1cc2c(cc1F)C1CC(C1)n1c-2nc(C(N)=O)c1-c1nc(C2CC2)n[nH]1] | 3-(3-cyclopropyl-1H-1,2,4-triazol-5-yl)-9-fluoro-10-(3-hydroxy-3-methyl-but-1-ynyl)-5,6,7,12-tetrahydro-5,7-methano-benzo[c]imidazo[1,2-a]azepine-2-carboxamide |
| 248 | 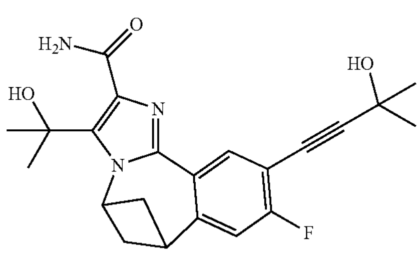 [SMILES: CC(C)(O)C#Cc1cc2c(cc1F)C1CC(C1)n1c-2nc(C(N)=O)c1C(C)(C)O] | 9-fluoro-10-(3-hydroxy-3-methyl-but-1-ynyl)-3-(1-hydroxy-1-methyl-ethyl)-5,6,7,12-tetrahydro-5,7-methanobenzo[c]imidazo[1,2-a]azepine-2-carboxamide |
| 249 | 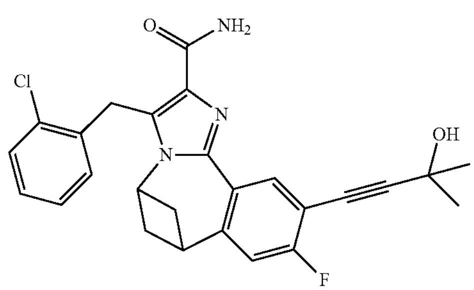 [SMILES: CC(C)(O)C#Cc1cc2c(cc1F)C1CC(C1)n1c-2nc(C(N)=O)c1Cc1ccccc1Cl] | 3-[(2-chlorophenyl)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 250 | 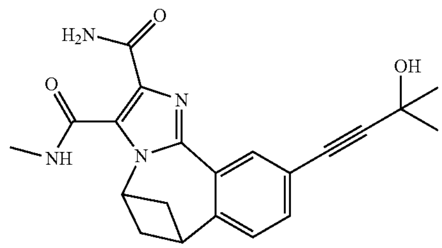 [SMILES: CNC(=O)c1c(C(N)=O)nc2n1C1CC(C1)c1ccc(C#CC(C)(C)O)cc1-2] | 10-(3-hydroxy-3-methyl-but-1-ynyl)-N3-methyl-5,6,7,12-tetrahydro-5,7-methano-benzo[c]imidazo[1,2-a]azepine-2,3-dicarboxamide |
| 251 | 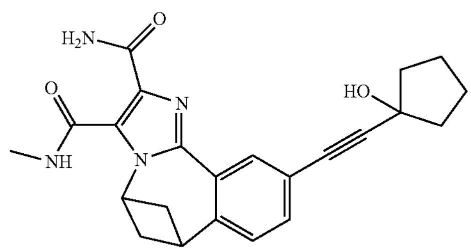 [SMILES: CNC(=O)c1c(C(N)=O)nc2n1C1CC(C1)c1ccc(C#CC3(O)CCCC3)cc1-2] | 10-[2-(1-hydroxycyclopentyl)ethynyl]-N3-methyl-5,6,7,12-tetrahydro-5,7-methano-benzo[c]imidazo[1,2-a]azepine-2,3-dicarboxamide |
| 252 | 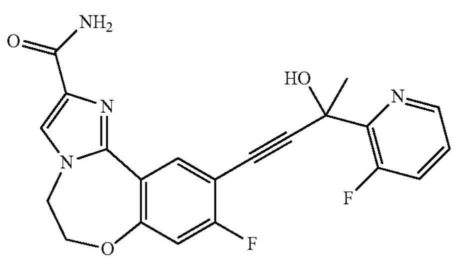 [SMILES: CC(O)(C#Cc1cc2c(cc1F)OCCn1cc(C(N)=O)nc1-2)c1ncccc1F] | 9-fluoro-10-[3-(3-fluoro-2-pyridyl)-3-hydroxy-but-1-ynyl]-5,6-dihydroimidazo[1,2-d][1,4]benzoxazepine-2-carboxamide |
| 253 | 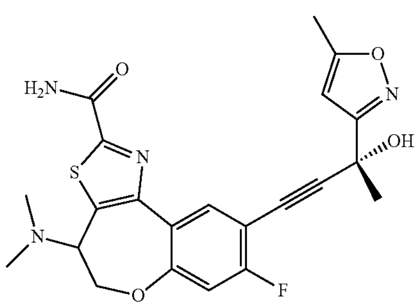 [SMILES: Cc1cc([C@](C)(O)C#Cc2cc3c(cc2F)OCC(N(C)C)c2sc(C(N)=O)nc2-3)no1] | 4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 254 | 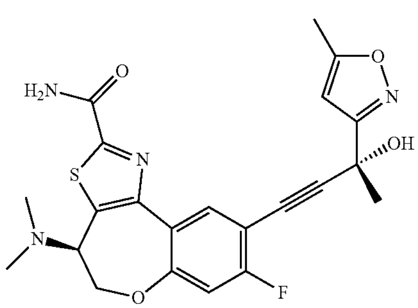 [SMILES: Cc1cc([C@](C)(O)C#Cc2cc3c(cc2F)OC[C@@H](N(C)C)c2sc(C(N)=O)nc2-3)no1] | (R)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |

TABLE 1-continued

| No. | Structure | Name |
|---|---|---|
| 255 | 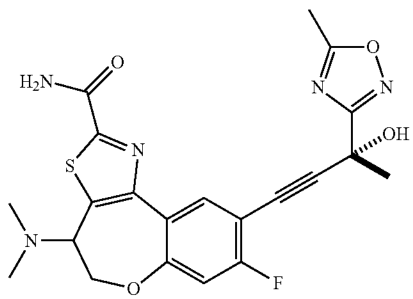 | 4-(dimethylamino)-8-fluoro-9-[(R)-3-hydroxy-3-(5-methyl-1,2,4-oxadiazol-3-yl)but-1-ynyl]-4,5-dihydro-[1]benzoxepino[5,4-d]thiazole-2-carboxamide |
| 256 | 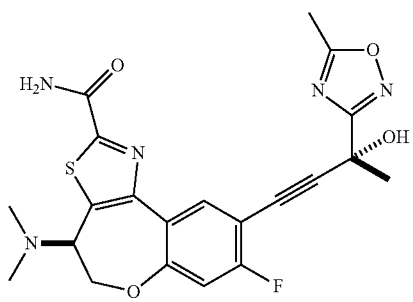 | (R)-4-(dimethylamino)-8-fluoro-9-[(R)-3-hydroxy-3-(5-methyl-1,2,4-oxadiazol-3-yl)but-1-ynyl]-4,5-dihydro-[1]benzoxepino[5,4-d]thiazole-2-carboxamide |
| 257 | 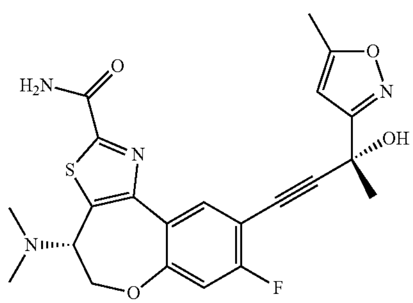 [SMILES: Cc1cc([C@](C)(O)C#Cc2cc3c(cc2F)OC[C@H](N(C)C)c2sc(C(N)=O)nc2-3)no1] | (S)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 258 | 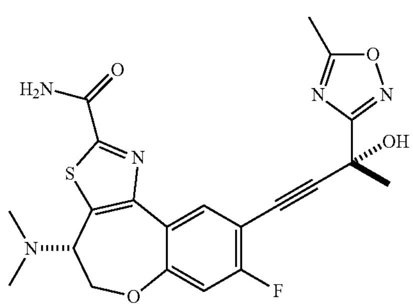 | (S)-4-(dimethylamino)-8-fluoro-9-[3-(R)-hydroxy-3-(5-methyl-1,2,4-oxadiazol-3-yl)but-1-ynyl]-4,5-dihydro-[1]benzoxepino[5,4-d]thiazole-2-carboxamide |
| 259 | 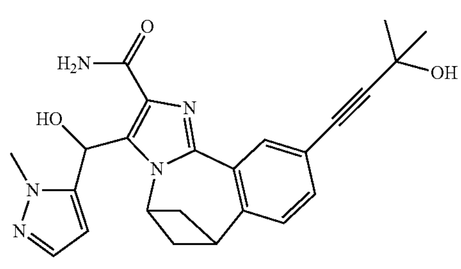 [SMILES: Cn1nccc1C(O)c1c(C(N)=O)nc2n1C1CC(C1)c1ccc(C#CC(C)(C)O)cc1-2] | 10-(3-hydroxy-3-methyl-but-1-ynyl)-3-[hydroxy-(2-methylpyrazol-3-yl)methyl]-5,6,7,12-tetrahydro-5,7-methano-benzo[c]imidazo[1,2-a]azepine-2-carboxamide |

TABLE 1-continued

| No. | Structure | Name |
|---|---|---|
| 260 | 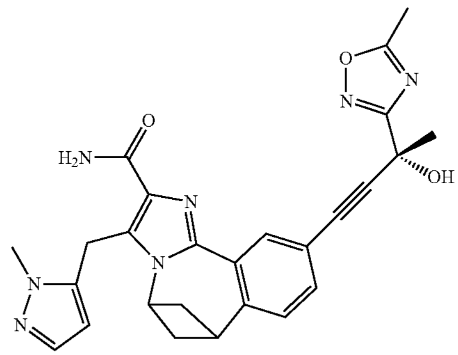 [SMILES: Cc1nc([C@](C)(O)C#Cc2ccc3c(c2)-c2nc(C(N)=O)c(Cc4ccnn4C)n2C2CC3C2)no1] | 10-[(3R)-3-hydroxy-3-(5-methyl-1,2,4-oxadiazol-3-yl)but-1-ynyl]-3-[(2-methyl-pyrazol-3-yl)methyl]-5,6,7,12-tetrahydro-5,7-methanobenzo[c]imidazo[1,2-a]azepine-2-carboxamide |
| 261 | 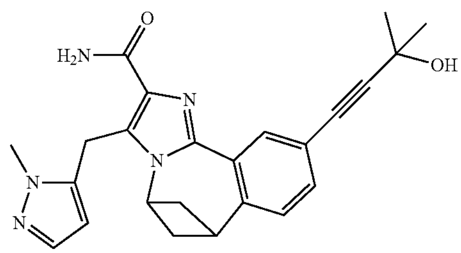 [SMILES: Cn1nccc1Cc1c(C(N)=O)nc2n1C1CC(C1)c1ccc(C#CC(C)(C)O)cc1-2] | 10-(3-hydroxy-3-methyl-but-1-ynyl)-3-[(2-methylpyrazol-3-yl)methyl]-5,6,7,12-tetrahydro-5,7-methanobenzo[c]imidazo[1,2-a]azepine-2-carboxamide |
| 262 | 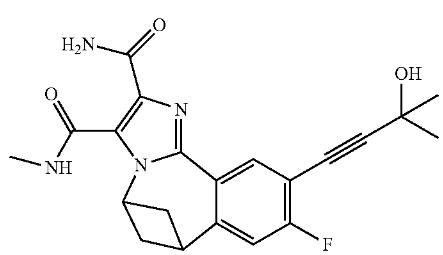 [SMILES: CNC(=O)c1c(C(N)=O)nc2n1C1CC(C1)c1cc(F)c(C#CC(C)(C)O)cc1-2] | 9-fluoro-10-(3-hydroxy-3-methyl-but-1-ynyl)-N3-methyl-5,6,7,12-tetrahydro-5,7-methanobenzo[c]imidazo[1,2-a]azepine-2,3-dicarboxamide |
| 263 | 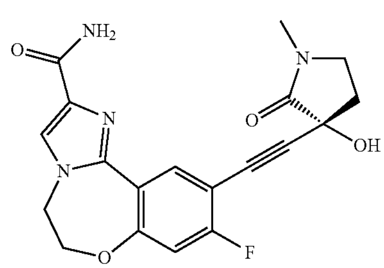 [SMILES: CN1CC[C@@](O)(C#Cc2cc3c(cc2F)OCCn2cc(C(N)=O)nc2-3)C1=O] | 9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide |
| 264 | 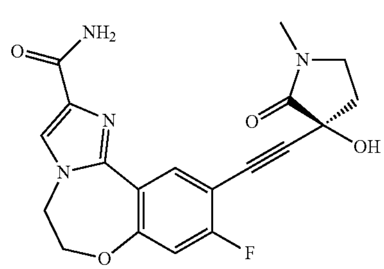 [SMILES: CN1CC[C@](O)(C#Cc2cc3c(cc2F)OCCn2cc(C(N)=O)nc2-3)C1=O] | 9-fluoro-10-[2-[(3S)-3-hydroxy-1-methyl-2-oxo-pyrrolidin-3-yl]ethynyl]-5,6-dihydroimidazo[1,2-d][1,4]benzoxazepine-2-carboxamide |

TABLE 1-continued

| No. | Structure | Name |
|---|---|---|
| 265 | 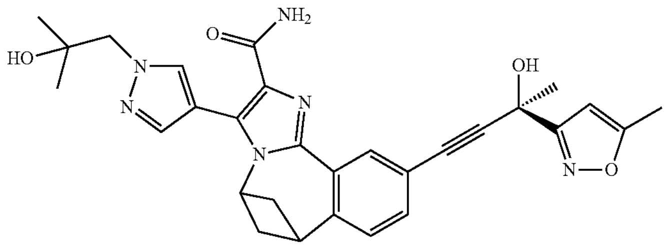 [SMILES: Cc1cc([C@](C)(O)C#Cc2ccc3c(c2)-c2nc(C(N)=O)c(-c4cnn(CC(C)(C)O)c4)n2C2CC3C2)no1] | 10-[(3R)-3-hydroxy-3-(5-methylisoxazol-3-yl)but-1-ynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide |
| 266 | 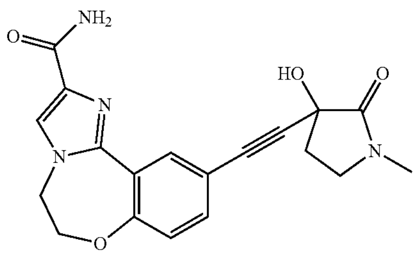 [SMILES: CN1CCC(O)(C#Cc2ccc3c(c2)-c2nc(C(N)=O)cn2CCO3)C1=O] | 10-[2-(3-hydroxy-1-methyl-2-oxo-pyrrolidin-3-yl)ethynyl]-5,6-dihydroimidazo[1,2-d][1,4]benzoxazepine-2-carboxamide |
| 267 | 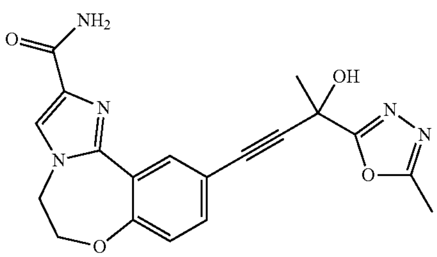 [SMILES: Cc1nnc(C(C)(O)C#Cc2ccc3c(c2)-c2nc(C(N)=O)cn2CCO3)o1] | 10-[3-hydroxy-3-(5-methyl-1,3,4-oxadiazol-2-yl)but-1-ynyl]-5,6-dihydroimidazo[1,2-d][1,4]benzoxazepine-2-carboxamide |
| 268 | 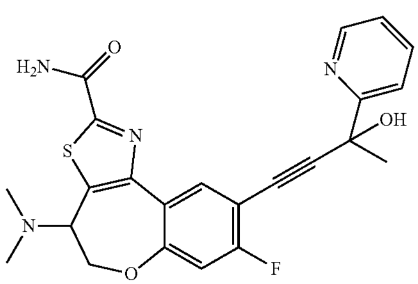 [SMILES: CN(C)C1COc2cc(F)c(C#CC(C)(O)c3ccccn3)cc2-c2nc(C(N)=O)sc21] | 4-(dimethylamino)-8-fluoro-9-[3-hydroxy-3-(2-pyridyl)but-1-ynyl]-4,5-dihydro-[1]benzoxepino[5,4-d]thiazole-2-carboxamide |
| 269 | 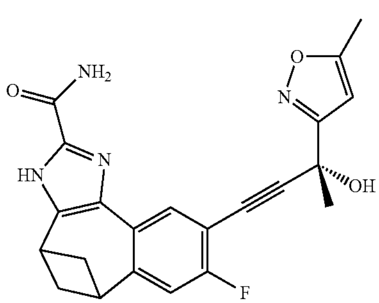 [SMILES: Cc1cc([C@](C)(O)C#Cc2cc3c(cc2F)C2CC(C2)c2[nH]c(C(N)=O)nc2-3)no1] | (R)-8-fluoro-9-(3-hydroxy-3-(5-methylisoxazol-3-yl)but-1-yn-1-yl)-3,4,5,6-tetrahydro-4,6-methanobenzo[3,4]cyclohepta[1,2-d]imidazole-2-carboxamide |
| 270 | 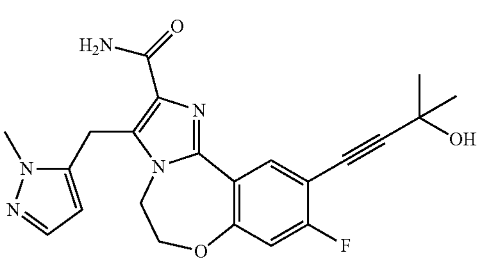 [SMILES: Cn1nccc1Cc1c(C(N)=O)nc2n1CCOc1cc(F)c(C#CC(C)(C)O)cc1-2] | 9-fluoro-10-(3-hydroxy-3-methyl-but-1-ynyl)-3-[(2-methylpyrazol-3-yl)methyl]-5,6-dihydroimidazo[1,2-d][1,4]benzoxazepine-2-carboxamide |

TABLE 1-continued

| No. | Structure | Name |
|---|---|---|
| 271 | 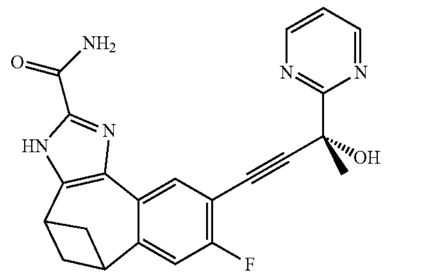 [SMILES: C[C@@](O)(C#Cc1cc2c(cc1F)C1CC(C1)c1[nH]c(C(N)=O)nc1-2)c1ncccn1] | (R)-8-fluoro-9-(3-hydroxy-3-(pyrimidin-2-yl)but-1-yn-1-yl)-3,4,5,6-tetrahydro-4,6-methanobenzo[3,4]cyclohepta[1,2-d]imidazole-2-carboxamide |
| 272 | 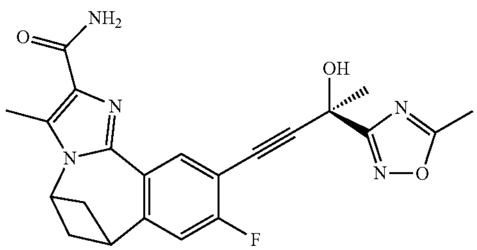 | 9-fluoro-10-1(3R)-3-hydroxy-3-(5-methyl-1,2,4-oxadiazol-3-yl)but-1-ynyl]-3-methyl-5,6,7,12-tetrahydro-5,7-methanobenzo[c]imidazo[1,2-a]azepine-2-carboxamide |
| 273 | 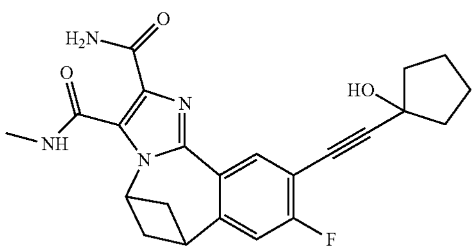 [SMILES: CNC(=O)c1c(C(N)=O)nc2n1C1CC(C1)c1cc(F)c(C#CC3(O)CCCC3)cc1-2] | 9-fluoro-10-[2-(1-hydroxycyclopentyl)ethynyl]-N3-methyl-5,6,7,12-tetrahydro-5,7-methanobenzo[c]imidazo[1,2-a]azepine-2,3-dicarboxamide |
| 274 | 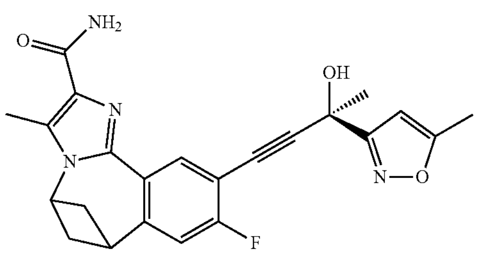 | 9-fluoro-10-[(3R)-3-hydroxy-3-(5-methylisoxazol-3-yl)but-1-ynyl]-3-methyl-5,6,7,12-tetrahydro-5,7-methanobenzo[c]imidazo[1,2-a]azepine-2-carboxamide |
| 275 | 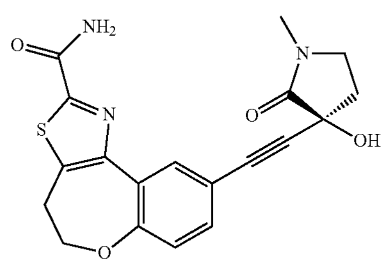 [SMILES: CN1CC[C@](O)(C#Cc2ccc3c(c2)-c2nc(C(N)=O)sc2CCO3)C1=O] | 9-[2-[(3S)-3-hydroxy-1-methyl-2-oxopyrrolidin-3-yl]ethynyl]-4,5-dihydro-[1]benzoxepino[5,4-d]thiazole-2-carboxamide |
| 276 | 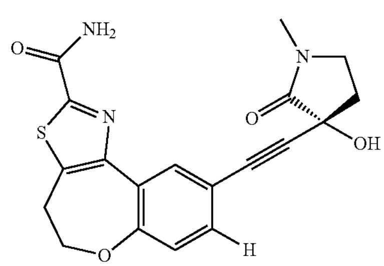 [SMILES: CN1CC[C@@](O)(C#Cc2ccc3c(c2)-c2nc(C(N)=O)sc2CCO3)C1=O] | 9-[2-[(3R)-3-hydroxy-1-methyl-2-oxopyrrolidin-3-yl]ethynyl]-4,5-dihydro-[1]benzoxepino[5,4-d]thiazole-2-carboxamide |

TABLE 1-continued

| No. | Structure | Name |
|---|---|---|
| 277 | 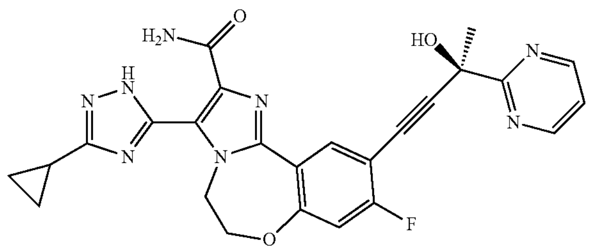 [SMILES: C[C@@](O)(C#Cc1cc2c(cc1F)OCCn1c-2nc(C(N)=O)c1-c1nc(C2CC2)n[nH]1)c1ncccn1] | 3-(3-cyclopropyl-1H-1,2,4-triazol-5-yl)-9-fluoro-10-[(3R)-3-hydroxy-3-pyrimidin-2-yl-but-1-ynyl]-5,6-dihydroimidazo[1,2-d][1,4]benzoxazepine-2-carboxamide |
| 278 | 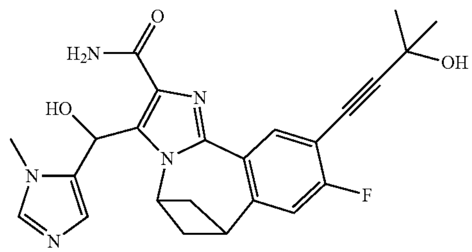 [SMILES: Cn1cncc1C(O)c1c(C(N)=O)nc2n1C1CC(C1)c1cc(F)c(C#CC(C)(C)O)cc1-2] | 9-fluoro-10-(3-hydroxy-3-methyl-but-1-ynyl)-3-[hydroxy-(3-methylimidazol-4-yl)methyl]-5,6,7,12-tetrahydro-5,7-methanobenzo[c]imidazo[1,2-a]azepine-2-carboxamide |
| 279 | 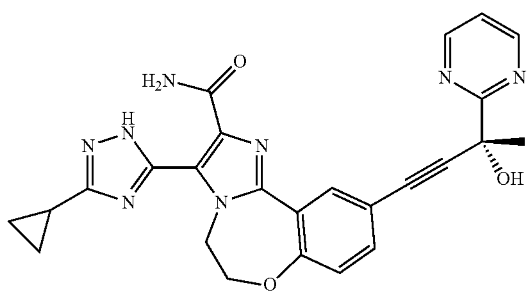 [SMILES: C[C@@](O)(C#Cc1ccc2c(c1)-c1nc(C(N)=O)c(-c3nc(C4CC4)n[nH]3)n1CCO2)c1ncccn1] | 3-(3-cyclopropyl-1H-1,2,4-triazol-5-yl)-10-[(3R)-3-hydroxy-3-pyrimidin-2-yl-but-1-ynyl]-5,6-dihydroimidazo[1,2-d][1,4]benzoxazepine-2-carboxamide |
| 280 | 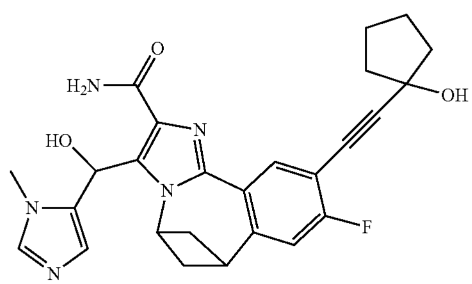 [SMILES: Cn1cncc1C(O)c1c(C(N)=O)nc2n1C1CC(C1)c1cc(F)c(C#CC3(O)CCCC3)cc1-2] | 9-fluoro-10-[2-(1-hydroxycyclopentyl)ethynyl]-3-[hydroxy-(1-methylimidazol-2-yl)methyl]-5,6,7,12-tetrahydro-5,7-methanobenzo[c]imidazo[1,2-a]azepine-2-carboxamide |
| 281 | 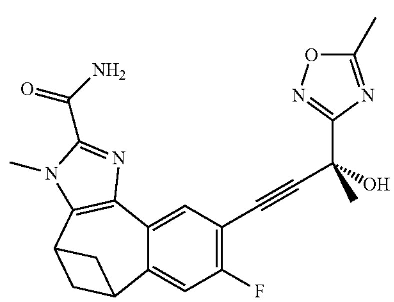 | (R)-8-fluoro-9-(3-hydroxy-3-(5-methyl-1,2,4-oxadiazol-3-yl)but-1-yn-1-yl)-3-methyl-3,4,5,6-tetrahydro-4,6-methanobenzo[3,4]cyclohepta[1,2-d]imidazole-2-carboxamide |

TABLE 1-continued

| No. | Structure | Name |
|---|---|---|
| 282 | 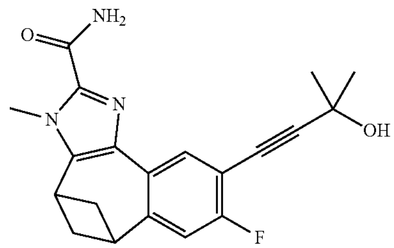 [SMILES: Cn1c(C(N)=O)nc2c1C1CC(C1)c1cc(F)c(C#CC(C)(C)O)cc1-2] | 8-fluoro-9-(3-hydroxy-3-methylbut-1-yn-1-yl)-3-methyl-3,4,5,6-tetrahydro-4,6-methanobenzo[3,4]cyclohepta[1,2-d]imidazole-2-carboxamide |
| 283 | 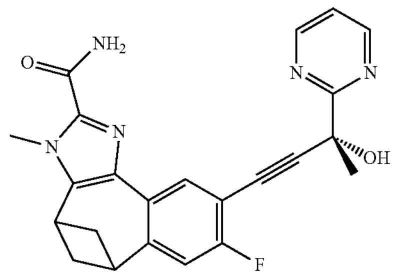 [SMILES: Cn1c(C(N)=O)nc2c1C1CC(C1)c1cc(F)c(C#C[C@@](C)(O)c3ncccn3)cc1-2] | (R)-8-fluoro-9-(3-hydroxy-3-(pyrimidin-2-yl)but-1-yn-1-yl)-3-methyl-3,4,5,6-tetrahydro-4,6-methanobenzo[3,4]cyclohepta[1,2-d]imidazole-2-carboxamide |
| 284 | 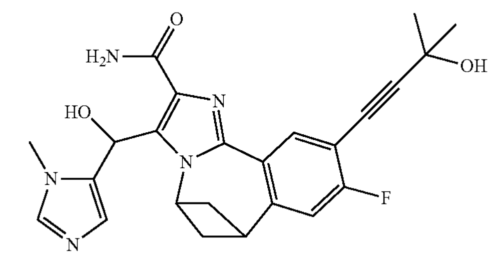 [SMILES: Cn1cncc1C(O)c1c(C(N)=O)nc2n1C1CC(C1)c1cc(F)c(C#CC(C)(C)O)cc1-2] | 9-fluoro-10-(3-hydroxy-3-methyl-but-1-ynyl)-3-[hydroxy-(1-methylimidazol-2-yl)methyl]-5,6,7,12-tetrahydro-5,7-methanobenzo[c]imidazo[1,2-a]azepine-2-carboxamide |
| 285 | 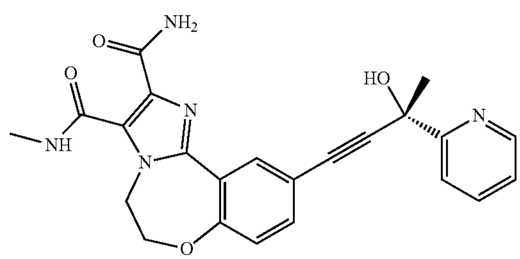 [SMILES: CNC(=O)c1c(C(N)=O)nc2n1CCOc1ccc(C#C[C@](C)(O)c3ccccn3)cc1-2] | 10-[(3S)-3-hydroxy-3-(2-pyridyl)but-1-ynyl]-N3-methyl-5,6-dihydroimidazo[1,2-d][1,4]benzoxazepine-2,3-dicarboxamide |
| 286 | 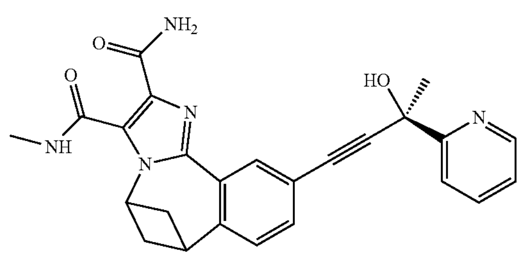 [SMILES: CNC(=O)c1c(C(N)=O)nc2n1C1CC(C1)c1ccc(C#C[C@@](C)(O)c3ccccn3)cc1-2] | 10-[(3R)-3-hydroxy-3-(2-pyridyl)but-1-ynyl]-N3-methyl-5,6,7,12-tetrahydro-5,7-methanobenzo[c]imidazo[1,2-a]azepine-2,3-dicarboxamide |
| 287 | 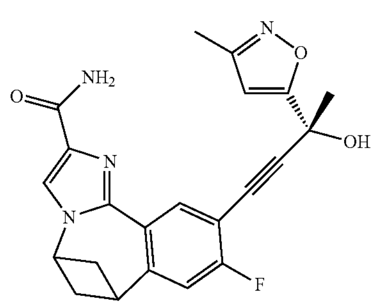 [SMILES: Cc1cc([C@](C)(O)C#Cc2cc3c(cc2F)C2CC(C2)n2cc(C(N)=O)nc2-3)on1] | 9-fluoro-10-[(3R)-3-hydroxy-3-(3-methylisoxazol-5-yl)but-1-ynyl]-5,6,7,12-tetrahydro-5,7-methanobenzo[c]imidazo[1,2-a]azepine-2-carboxamide |

TABLE 1-continued

| No. | Structure | Name |
|---|---|---|
| 288 | 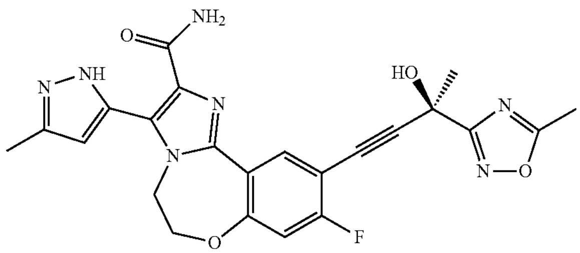 | 9-fluoro-10-[(3R)-3-hydroxy-3-(5-methyl-1,2,4-oxadiazol-3-yl)but-1-ynyl]-3-(3-methyl-1H-pyrazol-5-yl)-5,6-dihydroimidazo[1,2-d][1,4]benzoxazepine-2-carboxamide |
| 289 | 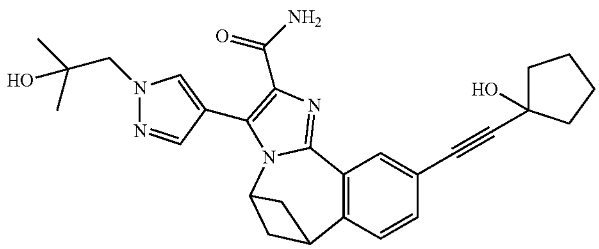 [SMILES: CC(C)(O)Cn1cc(-c2c(C(N)=O)nc3n2C2CC(C2)c2ccc(C#CC4(O)CCCC4)cc2-3)cn1] | 10-[2-(1-hydroxycyclopentyl)ethynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide |
| 290 | 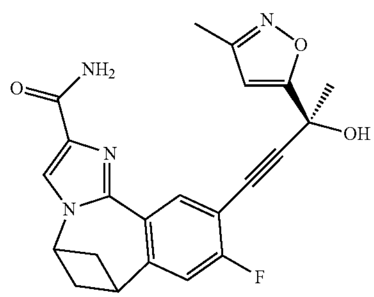 [SMILES: Cc1cc([C@@](C)(O)C#Cc2cc3c(cc2F)C2CC(C2)n2cc(C(N)=O)nc2-3)on1] | 9-fluoro-10-[(3S)-3-hydroxy-3-(3-methylisoxazol-5-yl)but-1-ynyl]-5,6,7,12-tetrahydro-5,7-methanobenzo[c]imidazo[1,2-a]azepine-2-carboxamide |
| 291 | 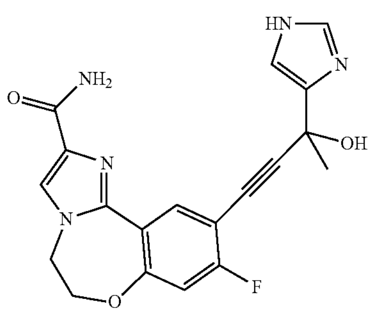 [SMILES: CC(O)(C#Cc1cc2c(cc1F)OCCn1cc(C(N)=O)nc1-2)c1c[nH]cn1] | 9-fluoro-10-[3-hydroxy-3-(1H-imidazol-4-yl)but-1-ynyl]-5,6-dihydroimidazo[1,2-d][1,4]benzoxazepine-2-carboxamide |
| 292 | 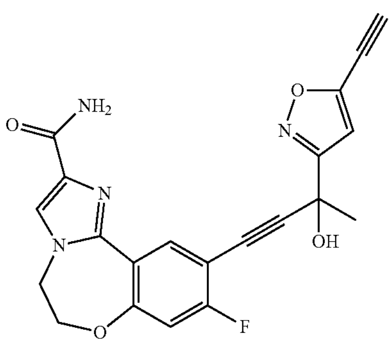 [SMILES: C#Cc1cc(C(C)(O)C#Cc2cc3c(cc2F)OCCn2cc(C(N)=O)nc2-3)no1] | 10-[3-(5-ethynylisoxazol-3-yl)-3-hydroxy-but-1-ynyl]-9-fluoro-5,6-dihydroimidazo[1,2-d][1,4]benzoxazepine-2-carboxamide |

TABLE 1-continued

| No. | Structure | Name |
|---|---|---|
| 293 | 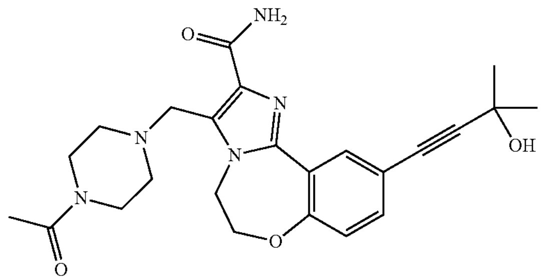 [SMILES: CC(=O)N1CCN(Cc2c(C(N)=O)nc3n2CCOc2ccc(C#CC(C)(C)O)cc2-3)CC1] | 3-[(4-acetylpiperazin-1-yl)methyl]-10-(3-hydroxy-3-methyl-but-1-ynyl)-5,6-dihydroimidazo[1,2-d][1,4]benzoxazepine-2-carboxamide |
| 294 | 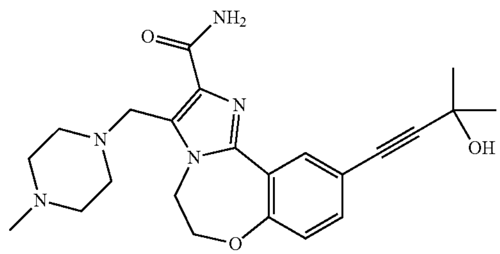 [SMILES: CN1CCN(Cc2c(C(N)=O)nc3n2CCOc2ccc(C#CC(C)(C)O)cc2-3)CC1] | 10-(3-hydroxy-3-methyl-but-1-ynyl)-3-[(4-methylpiperazin-1-yl)methyl]-5,6-dihydroimidazo[1,2-d][1,4]benzoxazepine-2-carboxamide |
| 295 | 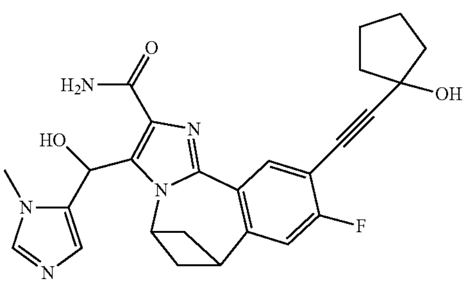 [SMILES: Cn1cncc1C(O)c1c(C(N)=O)nc2n1C1CC(C1)c1cc(F)c(C#CC3(O)CCCC3)cc1-2] | 9-fluoro-10-[2-(1-hydroxycyclopentyl)ethynyl]-3-[hydroxy-(3-methylimidazol-4-yl)methyl]-5,6,7,12-tetrahydro-5,7-methanobenzo[c]imidazo[1,2-a]azepine-2-carboxamide |
| 296 | 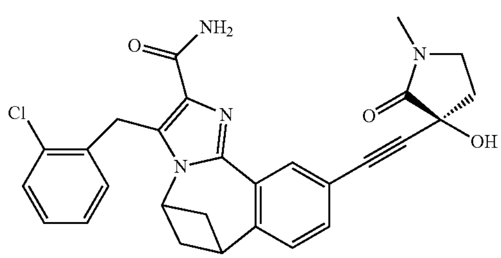 [SMILES: CN1CC[C@](O)(C#Cc2ccc3c(c2)-c2nc(C(N)=O)c(Cc4ccccc4Cl)n2C2CC3C2)C1=O] | 3-[(2-chlorophenyl)methy]-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 297 | 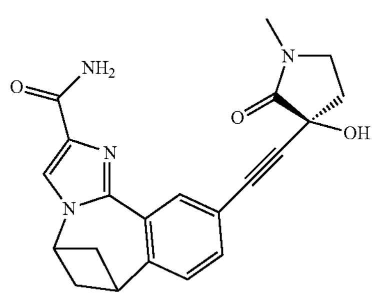 [SMILES: CN1CC[C@](O)(C#Cc2ccc3c(c2)-c2nc(C(N)=O)cn2C2CC3C2)C1=O] | 10-12-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |

TABLE 1-continued

| No. | Structure | Name |
|---|---|---|
| 298 | 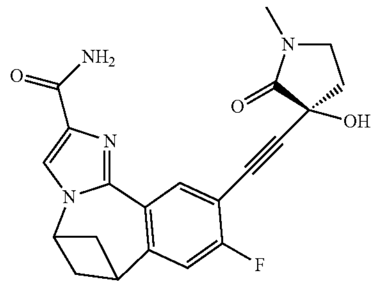 [SMILES: CN1CC[C@](O)(C#Cc2cc3c(cc2F)C2CC(C2)n2cc(C(N)=O)nc2-3)C1=O] | 9-fluoro-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 299 | 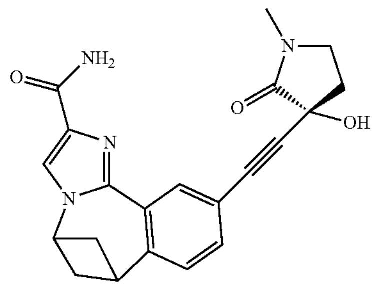 [SMILES: CN1CC[C@@](O)(C#Cc2ccc3c(c2)-c2nc(C(N)=O)cn2C2CC3C2)C1=O] | 10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 300 | 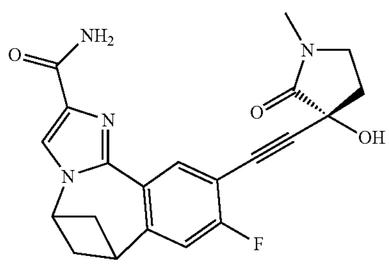 [SMILES: CN1CC[C@@](O)(C#Cc2cc3c(cc2F)C2CC(C2)n2cc(C(N)=O)nc2-3)C1=O] | 9-fluoro-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 301 | 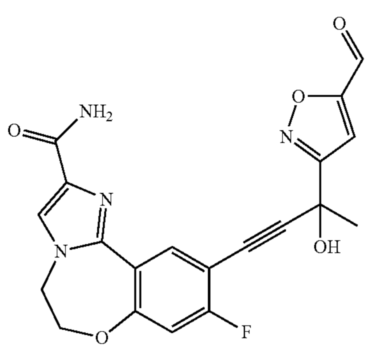 [SMILES: CC(O)(C#Cc1cc2c(cc1F)OCCn1cc(C(N)=O)nc1-2)c1cc(C=O)on1] | 9-fluoro-10-[3-(5-formylisoxazol-3-yl)-3-hydroxy-but-1-ynyl]-5,6-dihydroimidazo[1,2-d][1,4]benzoxazepine-2-carboxamide |
| 302 | 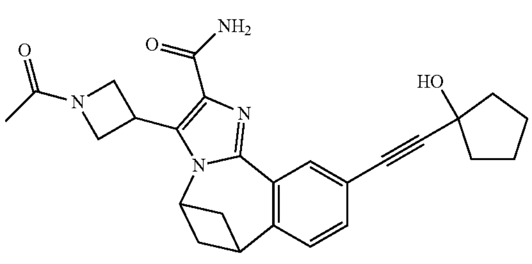 [SMILES: CC(=O)N1CC(c2c(C(N)=O)nc3n2C2CC(C2)c2ccc(C#CC4(O)CCCC4)cc2-3)C1] | 3-(1-acetylazetidin-3-yl)-10-[2-(1-hydroxycyclopentyl)ethynyl]-5,6,7,12-tetrahydro-5,7-methanobenzo[c]imidazo[1,2-a]azepine-2-carboxamide |

TABLE 1-continued

| No. | Structure | Name |
|---|---|---|
| 303 | 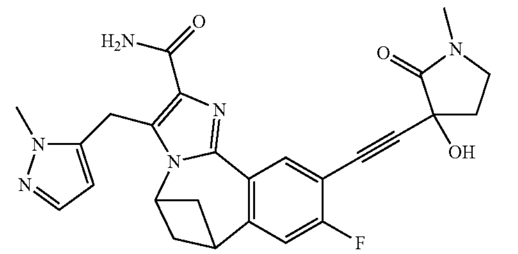 [SMILES: CN1CCC(O)(C#Cc2cc3c(cc2F)C2CC(C2)n2c-3nc(C(N)=O)c2Cc2ccnn2C)C1=O] | 9-fluoro-10-[2-(3-hydroxy-1-methyl-2-oxo-pyrrolidin-3-yl)ethynyl]-3-[(2-methylpyrazol-3-yl)methyl]-5,6,7,12-tetrahydro-5,7-methanobenzo[c]imidazo[1,2-a]azepine-2-carboxamide |
| 304 | 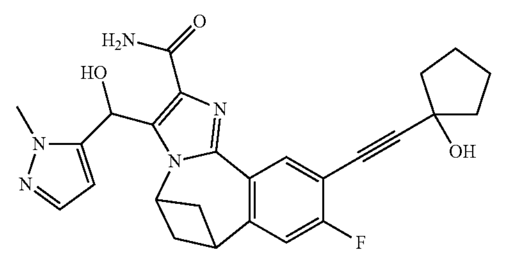 [SMILES: Cn1nccc1C(O)c1c(C(N)=O)nc2n1C1CC(C1)c1cc(F)c(C#CC3(O)CCCC3)cc1-2] | 9-fluoro-10-[2-(1-hydroxycyclopentyl)ethynyl]-3-[hydroxy-(2-methylpyrazol-3-yl)methyl]-5,6,7,12-tetrahydro-5,7-methanobenzo[c]imidazo[1,2-a]azepine-2-carboxamide |
| 305 | 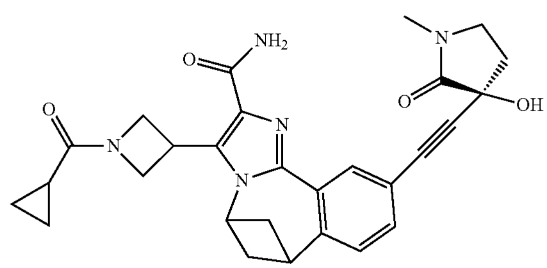 [SMILES: CN1CC[C@](O)(C#Cc2ccc3c(c2)-c2nc(C(N)=O)c(C4CN(C(=O)C5CC5)C4)n2C2CC3C2)C1=O] | 3-[1-(cyclopropanecarbonyl)azetidin-3-yl]-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 306 | 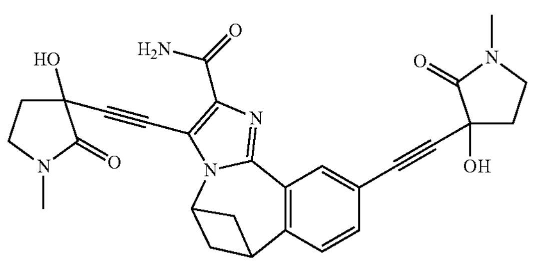 [SMILES: CN1CCC(O)(C#Cc2ccc3c(c2)-c2nc(C(N)=O)c(C#CC4(O)CCN(C)C4=O)n2C2CC3C2)C1=O] | 3,10-bis[2-(3-hydroxy-1-methyl-2-oxo-pyrrolidin-3-yl)ethynyl]-5,6,7,12-tetrahydro-5,7-methanobenzo[c]imidazo[1,2-a]azepine-2-carboxamide |
| 307 | 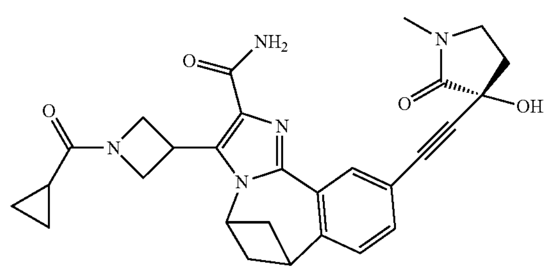 [SMILES: CN1CC[C@@](O)(C#Cc2ccc3c(c2)-c2nc(C(N)=O)c(C4CN(C(=O)C5CC5)C4)n2C2CC3C2)C1=O] | 3-[1-(cyclopropanecarbonyl)azetidin-3-yl]-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 308 | 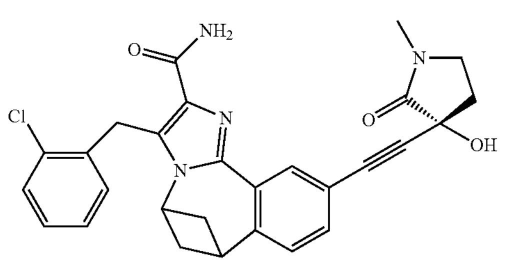 [SMILES: CN1CC[C@@](O)(C#Cc2ccc3c(c2)-c2nc(C(N)=O)c(Cc4ccccc4Cl)n2C2CC3C2)C1=O] | 3-[(2-chlorophenyl)methyl]-10-[2-[(3R)-3-hydroxy-1-methyl-2-oxo-pyrrolidin-3-yl]ethynyl]-5,6,7,12-tetrahydro-5]-methanobenzo[c]imidazo[1,2-a]azepine-2-carboxamide |

TABLE 1-continued

| No. | Structure | Name |
|---|---|---|
| 309 | 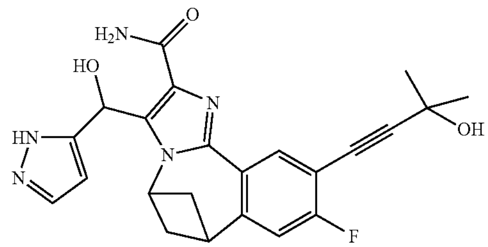 [SMILES: CC(C)(O)C#Cc1cc2c(cc1F)C1CC(C1)n1c-2nc(C(N)=O)c1C(O)c1ccn[nH]1] | 9-fluoro-10-(3-hydroxy-3-methyl-but-1-ynyl)-3-[hydroxy(1H-pyrazol-5-yl)methyl]-5,6,7,12-tetrahydro-5,7-methanobenzo[c]imidazo[1,2-a]azepine-2-carboxamide |
| 310 | 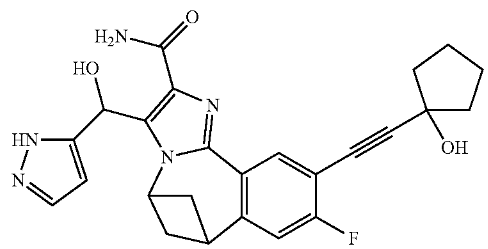 [SMILES: NC(=O)c1nc2n(c1C(O)c1ccn[nH]1)C1CC(C1)c1cc(F)c(C#CC3(O)CCCC3)cc1-2] | 9-fluoro-10-[2-(1-hydroxycyclopentyl)ethynyl]-3-[hydroxy(1H-pyrazol-5-yl)methyl]-5,6,7,12-tetrahydro-5,7-methano-benzo[c]imidazo[1,2-a]azepine-2-carboxamide |
| 311 | 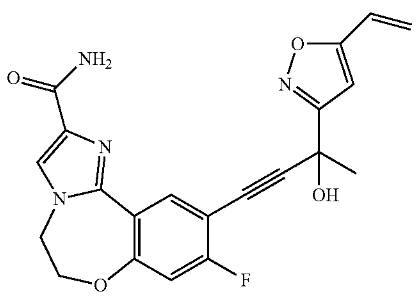 [SMILES: C=Cc1cc(C(C)(O)C#Cc2cc3c(cc2F)OCCn2cc(C(N)=O)nc2-3)no1] | 9-fluoro-10-[3-hydroxy-3-(5-vinylisoxazol-3-yl)but-1-ynyl]-5,6-dihydroimidazo[1,2-d][1,4]benzoxazepine-2-carboxamide |
| 312 | 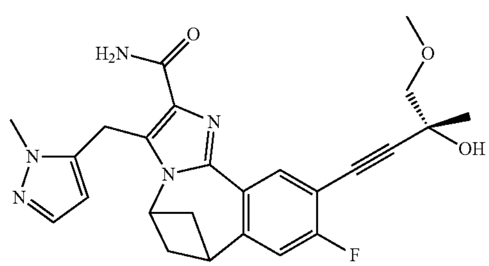 [SMILES: COC[C@](C)(O)C#Cc1cc2c(cc1F)C1CC(C1)n1c-2nc(C(N)=O)c1Cc1ccnn1C] | 9-fluoro-10-[(3R)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide |
| 313 | 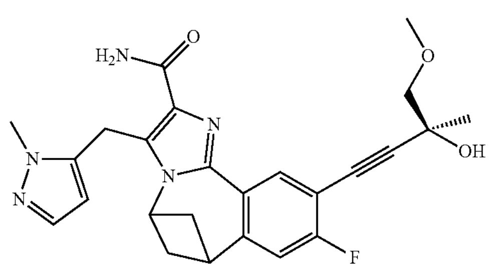 [SMILES: COC[C@@](C)(O)C#Cc1cc2c(cc1F)C1CC(C1)n1c-2nc(C(N)=O)c1Cc1ccnn1C] | 9-fluoro-10-[(3S)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide |
| 314 | 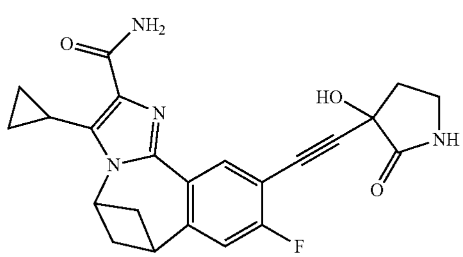 [SMILES: NC(=O)c1nc2n(c1C1CC1)C1CC(C1)c1cc(F)c(C#CC3(O)CCNC3=O)cc1-2] | 3-cyclopropyl-9-fluoro-10-[2-(3-hydroxy-2-oxo-pyrrolidin-3-yl)ethynyl]-5,6,7,12-tetrahydro-5,7-methanobenzo[c]imidazo[1,2-a]azepine-2-carboxamide |

TABLE 1-continued

| No. | Structure | Name |
|---|---|---|
| 315 | 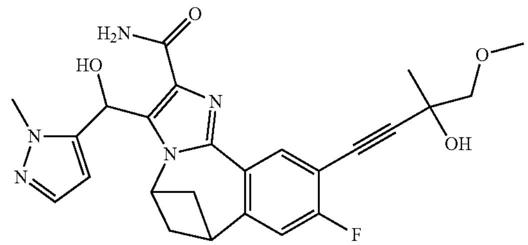 | 9-fluoro-10-(3-hydroxy-4-methoxy-3-methyl-but-1-ynyl)-3-[hydroxy-(2-methyl-pyrazol-3-yl)methyl]-5,6,7,12-tetrahydro-5,7-methanobenzo[c]imidazo[1,2-a]azepine-2-carboxamide |
| 316 | 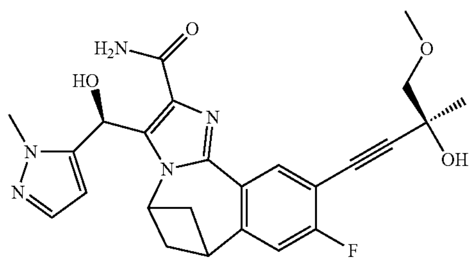 [SMILES: COC[C@@](C)(O)C#Cc1cc2c(cc1F)C1CC(C1)n1c-2nc(C(N)=O)c1[C@H](O)c1ccnn1C] | 9-fluoro-3-((S)-hydroxy(1-methyl-1H-pyrazol-5-yl)methyl)-10-((S)-3-hydroxy-4-methoxy-3-methylbut-1-yn-1-yl)-6,7-dihydro-5H-5,7-methanobenzo[c]imidazo[1,2-a]azepine-2-carboxamide |
| 317 | 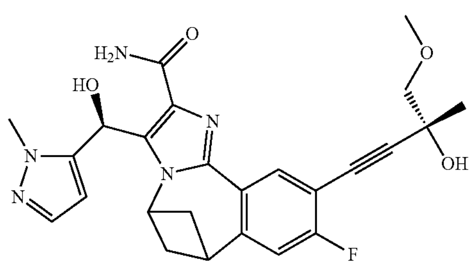 [SMILES: COC[C@](C)(O)C#Cc1cc2c(cc1F)C1CC(C1)n1c-2nc(C(N)=O)c1[C@H](O)c1ccnn1C] | 9-fluoro-3-((S)-hydroxy(1-methyl-1H-pyrazol-5-yl)methyl)-10-((R)-3-hydroxy-4-methoxy-3-methylbut-1-yn-1-yl)-6,7-dihydro-5H-5,7-methanobenzo[c]imidazo[1,2-a]azepine-2-carboxamide |
| 318 | 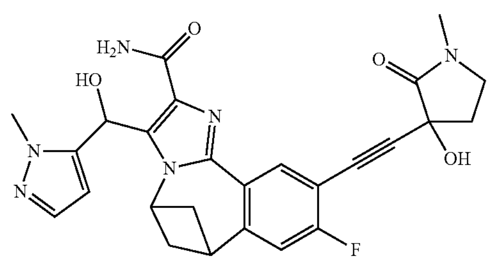 [SMILES: CN1CCC(O)(C#Cc2cc3c(cc2F)C2CC(C2)n2c-3nc(C(N)=O)c2C(O)c2ccnn2C)C1=O] | 9-fluoro-10-[2-(3-hydroxy-1-methyl-2-oxo-pyrrolidin-3-yl)ethynyl]-3-[hydroxy-(2-methylpyrazol-3-yl)methyl]-5,6,7,12-tetrahydro-5,7-methanobenzo[c]imidazo[1,2-a]azepine-2-carboxamide |
| 319 | 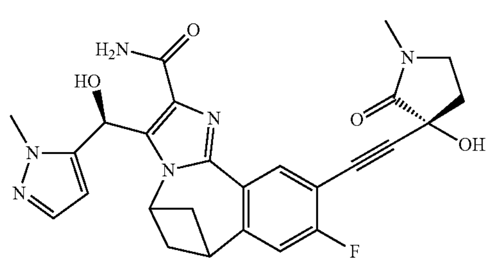 [SMILES: CN1CC[C@@](O)(C#Cc2cc3c(cc2F)C2CC(C2)n2c-3nc(C(N)=O)c2[C@H](O)c2ccnn2C)C1=O] | 9-fluoro-3-((S)-hydroxy(1-methyl-1H-pyrazol-5-yl)methyl)-10-(((R)-3-hydroxy-1-methyl-2-oxopyrrolidin-3-yl)ethynyl)-6,7-dihydro-5H-5,7-methanobenzo[c]imidazo[1,2-a]azepine-2-carboxamide |
| 320 | 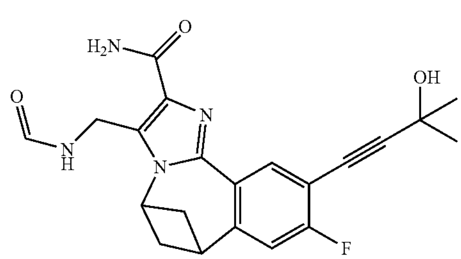 [SMILES: CC(C)(O)C#Cc1cc2c(cc1F)C1CC(C1)n1c-2nc(C(N)=O)c1CNC=O] | 9-fluoro-3-(formamidomethyl)-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 321 | 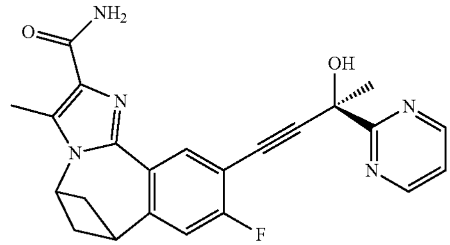 [SMILES: Cc1c(C(N)=O)nc2n1C1CC(C1)c1cc(F)c(C#C[C@@](C)(O)c3ncccn3)cc1-2] | 9-fluoro-10-[(3R)-3-hydroxy-3-pyrimidin-2-yl-but-1-ynyl]-3-methyl-5,6,7,12-tetrahydro-5,7-methanobenzo[c]imidazo[1,2-a]azepine-2-carboxamide |
| 322 | 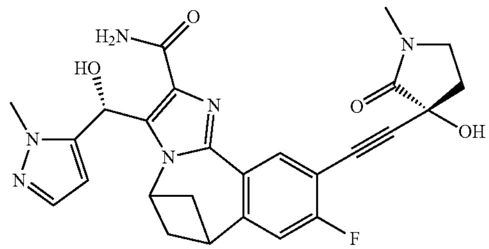 [SMILES: CN1CC[C@@](O)(C#Cc2cc3c(cc2F)C2CC(C2)n2c-3nc(C(N)=O)c2[C@@H](O)c2ccnn2C)C1=O] | 9-fluoro-3-((R)-hydroxy(1-methyl-1H-pyrazol-5-yl)methyl)-10-(((R)-3-hydroxy-1-methyl-2-oxopyrrolidin-3-yl)ethynyl)-6,7-dihydro-5H-5,7-methanobenzo[c]imidazo[1,2-a]azepine-2-carboxamide |
| 323 | 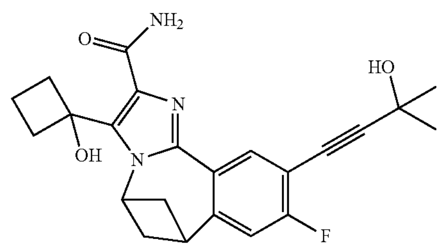 [SMILES: CC(C)(O)C#Cc1cc2c(cc1F)C1CC(C1)n1c-2nc(C(N)=O)c1C1(O)CCC1] | 9-fluoro-3-(1-hydroxycyclobutyl)-10-(3-hydroxy-3-methyl-but-1-ynyl)-5,6,7,12-tetrahydro-5,7-methanobenzo[c]imidazo[1,2-a]azepine-2-carboxamide |
| 324 | 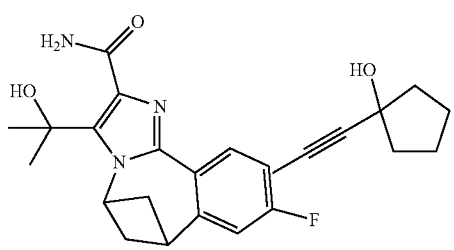 | 9-fluoro-10-[2-(1-hydroxycyclopentyl)ethynyl]-3-(1-hydroxy-1-methyl-ethyl)-5,6,7,12-tetrahydro-5,7-methanobenzo[c]imidazo[1,2-a]azepine-2-carboxamide |
| 325 | 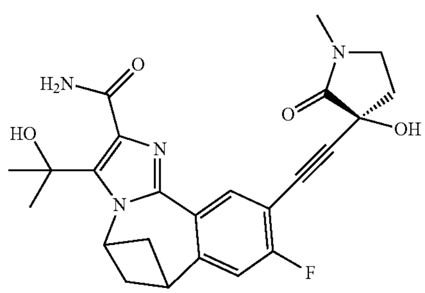 [SMILES: CN1CC[C@](O)(C#Cc2cc3c(cc2F)C2CC(C2)n2c-3nc(C(N)=O)c2C(C)(C)O)C1=O] | 9-fluoro-3-(1-hydroxy-1-methyl-ethyl)-10-[2-[(3S)-3-hydroxy-1-methyl-2-oxopyrrolidin-3-yl]ethynyl]-5,6,7,12-tetrahydro-5,7-methanobenzo[c]imidazo-[1,2-a]azepine-2-carboxamide |
| 326 | 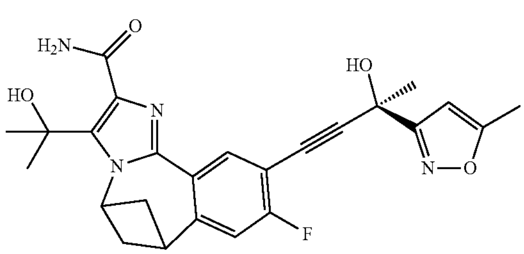 [SMILES: Cc1cc([C@](C)(O)C#Cc2cc3c(cc2F)C2CC(C2)n2c-3nc(C(N)=O)c2C(C)(C)O)no1] | 9-fluoro-3-(1-hydroxy-1-methyl-ethyl)-10-[(3R)-3-hydroxy-3-(5-methylisoxazol-3-yl)but-1-ynyl]-5,6,7,12-tetrahydro-5,7-methanobenzo[c]imidazo[1,2-azazepine-2-carboxamide |

TABLE 1-continued

| No. | Structure | Name |
|---|---|---|
| 327 | 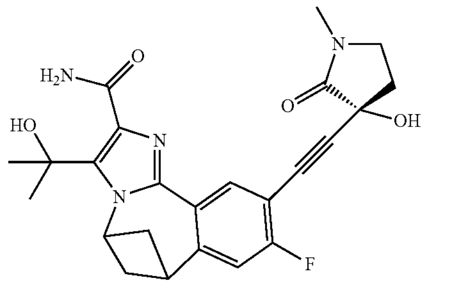 [SMILES: CN1CC[C@@](O)(C#Cc2cc3c(cc2F)C2CC(C2)n2c-3nc(C(N)=O)c2C(C)(C)O)C1=O] | 9-fluoro-3-(1-hydroxy-1-methyl-ethyl)-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 328 | 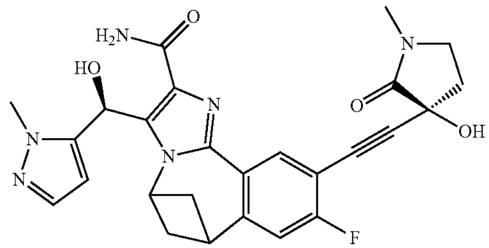 [SMILES: CN1CC[C@](O)(C#Cc2cc3c(cc2F)C2CC(C2)n2c-3nc(C(N)=O)c2[C@H](O)c2ccnn2C)C1=O] | 9-fluoro-3-((S)-hydroxy(1-methyl-1H-pyrazol-5-yl)methyl)-10-(((S)-3-hydroxy-1-methyl-2-oxopyrrolidin-3-yl)ethynyl)-6,7-dihydro-5H-5,7-methanobenzo[c]imidazo[1,2-a]azepine-2-carboxamide |
| 329 | 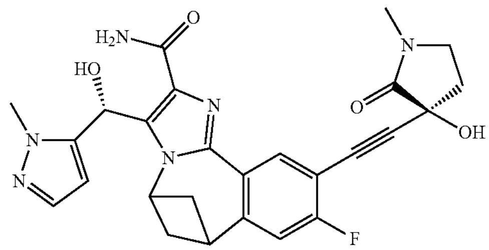 [SMILES: CN1CC[C@](O)(C#Cc2cc3c(cc2F)C2CC(C2)n2c-3nc(C(N)=O)c2[C@@H](O)c2ccnn2C)C1=O] | 9-fluoro-3-((R)-hydroxy(1-methyl-1H-pyrazol-5-yl)methyl)-10-(((S)-3-hydroxy-1-methyl-2-oxopyrrolidin-3-yl)ethynyl)-6,7-dihydro-5H-5,7-methanobenzo[c]imidazo[1,2-a]azepine-2-carboxamide |
| 330 | 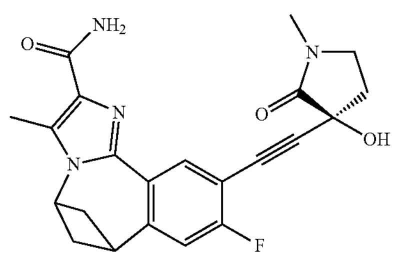 [SMILES: Cc1c(C(N)=O)nc2n1C1CC(C1)c1cc(F)c(C#C[C@@]3(O)CCN(C)C3=O)cc1-2] | 9-fluoro-10-[2-[(3S)-3-hydroxy-1-methyl-2-oxo-pyrrolidin-3-yl]ethynyl]-3-methyl-5,6,7,12-tetrahydro-5,7-methanobenzo[c]imidazo[1,2-a]azepine-2-carboxamide |
| 331 | 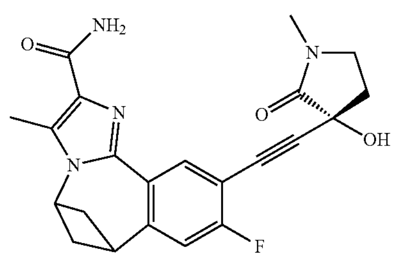 [SMILES: Cc1c(C(N)=O)nc2n1C1CC(C1)c1cc(F)c(C#C[C@]3(O)CCN(C)C3=O)cc1-2] | 9-fluoro-10-[2-[(3R)-3-hydroxy-1-methyl-2-oxo-pyrrolidin-3-yl]ethynyl]-3-methyl-5,6,7,12-tetrahydro-5,7-methanobenzo[c]imidazo[1,2-a]azepine-2-carboxamide |
| 332 | 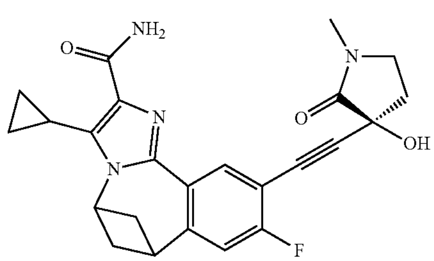 [SMILES: CN1CC[C@](O)(C#Cc2cc3c(cc2F)C2CC(C2)n2c-3nc(C(N)=O)c2C2CC2)C1=O] | 3-cyclopropyl-9-fluoro-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |

TABLE 1-continued

| No. | Structure | Name |
|---|---|---|
| 333 | 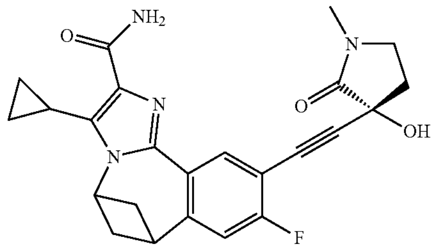 [SMILES: CN1CC[C@@](O)(C#Cc2cc3c(cc2F)C2CC(C2)n2c-3nc(C(N)=O)c2C2CC2)C1=O] | 3-cyclopropyl-9-fluoro-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 334 | 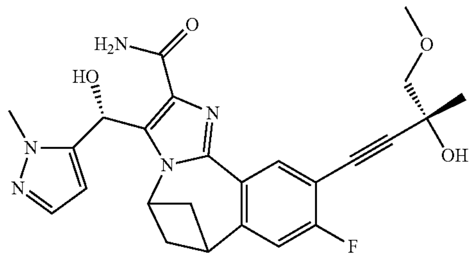 [SMILES: COC[C@](C)(O)C#Cc1cc2c(cc1F)C1CC(C1)n1c-2nc(C(N)=O)c1[C@@H](O)c1ccnn1C] | 9-fluoro-3-((R)-hydroxy(1-methyl-1H-pyrazol-5-yl)methyl)-10-((R)-3-hydroxy-4-methoxy-3-methylbut-1-yn-1-yl)-6,7-dihydro-5H-5,7-methanobenzo[c]imidazo[1,2-a]azepine-2-carboxamide |
| 335 | 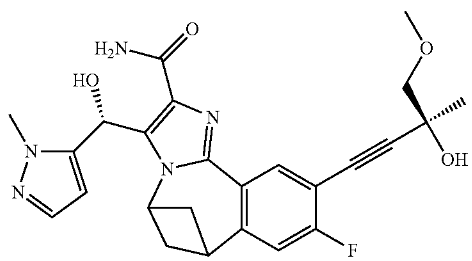 [SMILES: COC[C@@](C)(O)C#Cc1cc2c(cc1F)C1CC(C1)n1c-2nc(C(N)=O)c1[C@@H](O)c1ccnn1C] | 9-fluoro-3-((R)-hydroxy(1-methyl-1H-pyrazol-5-yl)methyl)-10-((S)-3-hydroxy-4-methoxy-3-methylbut-1-yn-1-yl)-6,7-dihydro-5H-5,7-methanobenzo[c]imidazo[1,2-a]azepine-2-carboxamide |
| 336 | 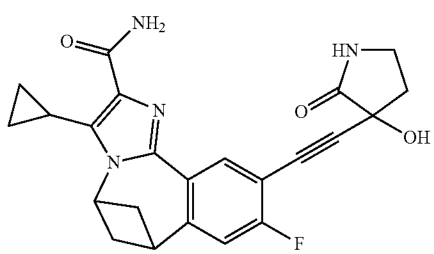 [SMILES: NC(=O)c1nc2n(c1C1CC1)C1CC(C1)c1cc(F)c(C#CC3(O)CCNC3=O)cc1-2] | 3-cyclopropyl-9-fluoro-10-[2-[(3S)-3-hydroxy-2-oxo-pyrrolidin-3-yl]ethynyl]-5,6,7,12-tetrahydro-5,7-methanobenzo[c]imidazo[1,2-a]azepine-2-carboxamide |
| 337 | 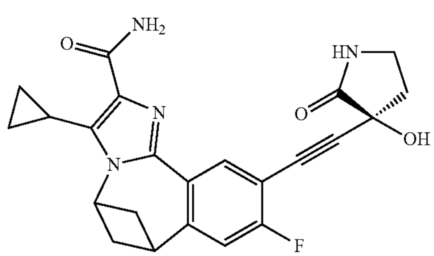 [SMILES: NC(=O)c1nc2n(c1C1CC1)C1CC(C1)c1cc(F)c(C#C[C@@]3(O)CCNC3=O)cc1-2] | 3-cyclopropyl-9-fluoro-10-[2-[(3S)-3-hydroxy-2-oxo-pyrrolidin-3-yl]ethynyl]-5,6,7,12-tetrahydro-5,7-methanobenzo[c]imidazo[1,2-a]azepine-2-carboxamide |
| 338 | 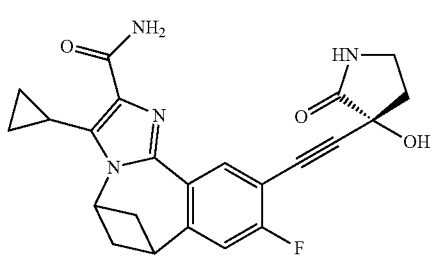 [SMILES: NC(=O)c1nc2n(c1C1CC1)C1CC(C1)c1cc(F)c(C#C[C@]3(O)CCNC3=O)cc1-2] | 3-cyclopropyl-9-fluoro-10-[2-[(3R)-3-hydroxy-2-oxo-pyrrolidin-3-yl]ethynyl]-5,6,7,12-tetrahydro-5,7-methanobenzo[c]imidazo[1,2-a]azepine-2-carboxamide |

TABLE 1-continued

| No. | Structure | Name |
|---|---|---|
| 339 | 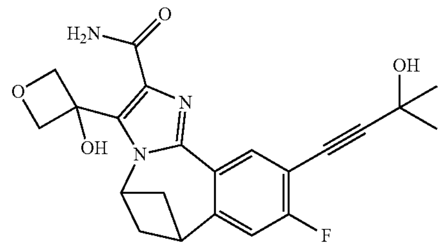 [SMILES: CC(C)(O)C#Cc1cc2c(cc1F)C1CC(C1)n1c-2nc(C(N)=O)c1C1(O)COC1] | 9-fluoro-10-(3-hydroxy-3-methyl-but-1-ynyl)-3-(3-hydroxyoxetan-3-yl)-5,6,7,12-tetrahydro-5,7-methanobenzo[c]imidazo[1,2-a]azepine-2-carboxamide |
| 340 | 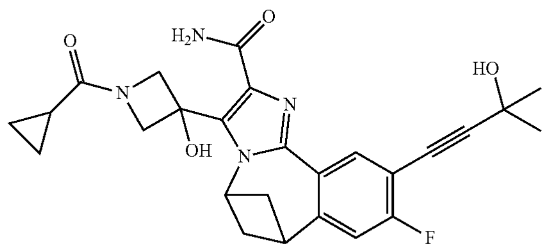 [SMILES: CC(C)(O)C#Cc1cc2c(cc1F)C1CC(C1)n1c-2nc(C(N)=O)c1C1(O)CN(C(=O)C2CC2)C1] | 3-[1-(cyclopropanecarbonyl)-3-hydroxy-azetidin-3-yl]-9-fluoro-10-(3-hydroxy-3-methyl-but-1-ynyl)-5,6,7,12-tetrahydro-5,7-methanobenzo[c]imidazo[1,2-a]azepine-2-carboxamide |
| 341 | 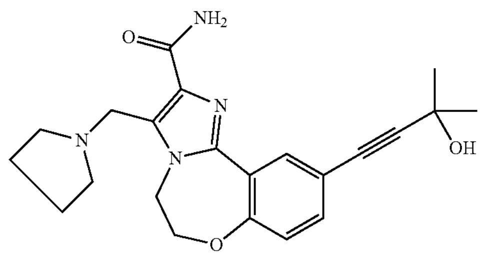 [SMILES: CC(C)(O)C#Cc1ccc2c(c1)-c1nc(C(N)=O)c(CN3CCCC3)n1CCO2] | 10-(3-hydroxy-3-methyl-but-1-ynyl)-3-(pyrrolidin-1-ylmethyl)-5,6-dihydro-imidazo[1,2-d][1,4]benzoxazepine-2-carboxamide |
| 342 | 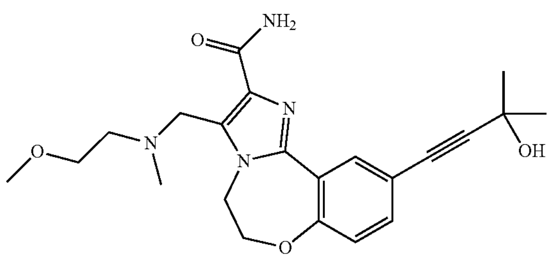 [SMILES: COCCN(C)Cc1c(C(N)=O)nc2n1CCOc1ccc(C#CC(C)(C)O)cc1-2] | 10-(3-hydroxy-3-methyl-but-1-ynyl)-3-[2-methoxyethyl(methyl)amino]methyl]-5,6-dihydroimidazo[1,2-d][1,4]benzoxazepine-2-carboxamide |
| 343 | 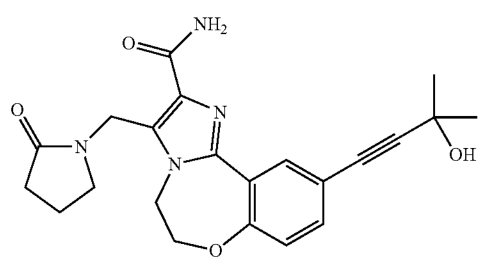 [SMILES: CC(C)(O)C#Cc1ccc2c(c1)-c1nc(C(N)=O)c(CN3CCCC3=O)n1CCO2] | 10-(3-hydroxy-3-methyl-but-1-ynyl)-3-[(2-oxopyrrolidin-1-yl)methyl]-5,6-dihydroimidazo[1,2-d][1,4]benzoxazepine-2-carboxamide |
| 344 | 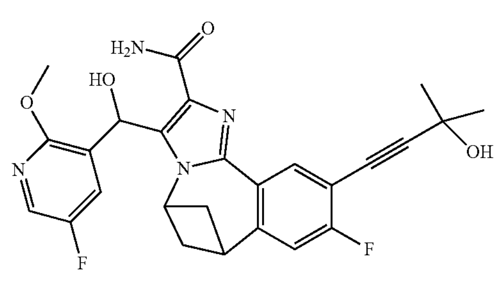 [SMILES: COc1ncc(F)cc1C(O)c1c(C(N)=O)nc2n1C1CC(C1)c1cc(F)c(C#CC(C)(C)O)cc1-2] | 9-fluoro-3-[(5-fluoro-2-methoxy-3-pyridyl)-hydroxy-methyl]-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 345 | 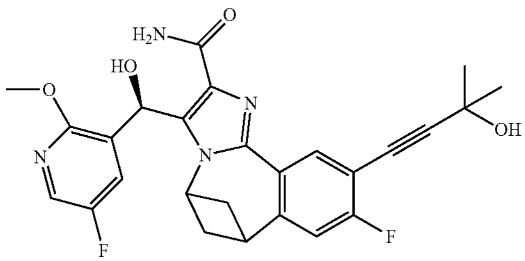 [SMILES: COc1ncc(F)cc1[C@@H](O)c1c(C(N)=O)nc2n1C1CC(C1)c1cc(F)c(C#CC(C)(C)O)cc1-2] | 9-fluoro-3-[(5-fluoro-2-methoxy-3-pyridyl)-(R)-hydroxy-methyl]-10-(3-hydroxy-3-methyl-but-1-ynyl)-5,6,7,12-tetrahydro-5,7-methanobenzo[c]imidazo[1,2-a]azepine-2-carboxamide |
| 346 | 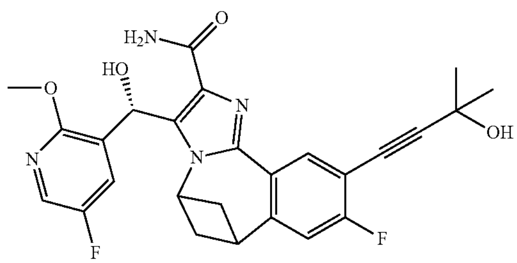 [SMILES: COc1ncc(F)cc1[C@H](O)c1c(C(N)=O)nc2n1C1CC(C1)c1cc(F)c(C#CC(C)(C)O)cc1-2] | 9-fluoro-3-[(5-fluoro-2-methoxy-3-pyridyl)-(S)-hydroxy-methyl]-10-(3-hydroxy-3-methyl-but-1-ynyl)-5,6,7,12-tetra-hydro-5,7-methanobenzo[c]imidazo[1,2-a]azepine-2-carboxamide |
| 347 | 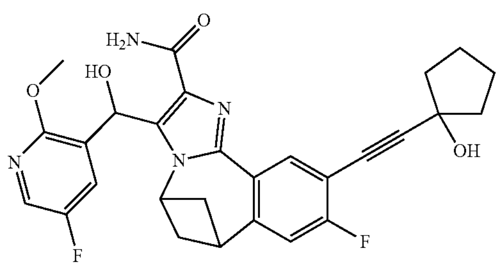 [SMILES: COc1ncc(F)cc1C(O)c1c(C(N)=O)nc2n1C1CC(C1)c1cc(F)c(C#CC3(O)CCCC3)cc1-2] | 9-fluoro-3-[(5-fluoro-2-methoxy-3-pyridyl)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide |
| 348 | 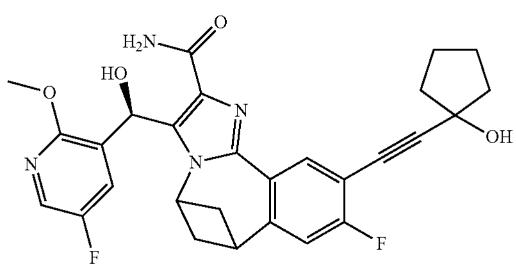 [SMILES: COc1ncc(F)cc1[C@@H](O)c1c(C(N)=O)nc2n1C1CC(C1)c1cc(F)c(C#CC3(O)CCCC3)cc1-2] | 9-fluoro-3-[(5-fluoro-2-methoxy-3-pyridyl)-(R)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide |
| 349 | 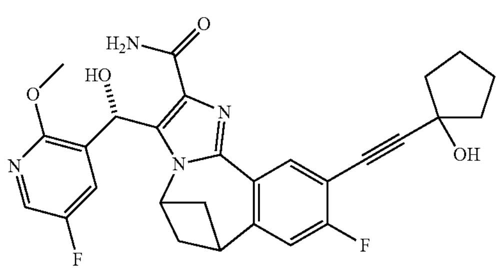 | 9-fluoro-3-[(5-fluoro-2-methoxy-3-pyridyl)-(S)-hydroxy-methyl]-10-[2-(1-hydroxycyclopentyl)ethynyl]-5,6,7,12-tetrahydro-5,7-methanobenzo[c]imidazo[1,2-alazepine-2-carboxamide |

TABLE 1-continued

| No. | Structure | Name |
|---|---|---|
| 350 | 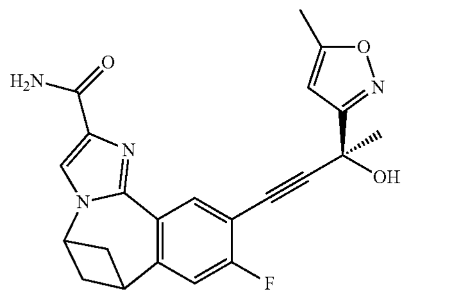 [SMILES: Cc1cc([C@@](C)(O)C#Cc2cc3c(cc2F)C2CC(C2)n2cc(C(N)=O)nc2-3)no1] | 9-fluoro-10-[(3S)-3-hydroxy-3-(5-methylisoxazol-3-yl)but-1-ynyl]-5,6,7,12-tetrahydro-5,7-methanobenzo[c]imidazo[1,2-a]azepine-2-carboxamide |
| 351 | 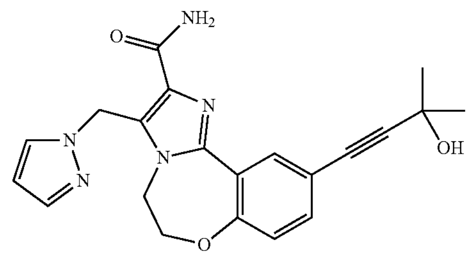 [SMILES: CC(C)(O)C#Cc1ccc2c(c1)-c1nc(C(N)=O)c(Cn3cccn3)n1CCO2] | 10-(3-hydroxy-3-methyl-but-1-ynyl)-3-(pyrazol-1-ylmethyl)-5,6-dihydroimidazo[1,2-d][1,4]benzoxazepine-2-carboxamide |
| 352 | 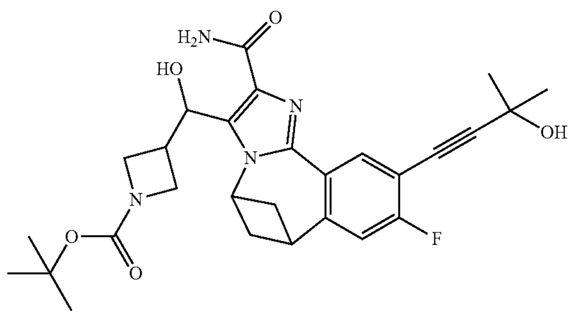 [SMILES: CC(C)(O)C#Cc1cc2c(cc1F)C1CC(C1)n1c-2nc(C(N)=O)c1C(O)C1CN(C(=O)OC(C)(C)C)C1] | tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-hydroxy-methyl]azetidine-1-carboxylate |
| 353 | 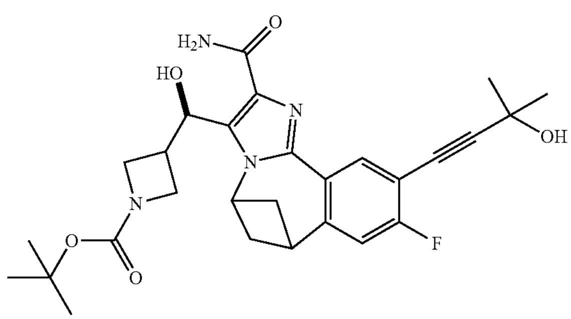 [SMILES: CC(C)(O)C#Cc1cc2c(cc1F)C1CC(C1)n1c-2nc(C(N)=O)c1[C@H](O)C1CN(C(=O)OC(C)(C)C)C1] | tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-(R)-hydroxy-methyl]azetidine-1-carboxylate |
| 354 | 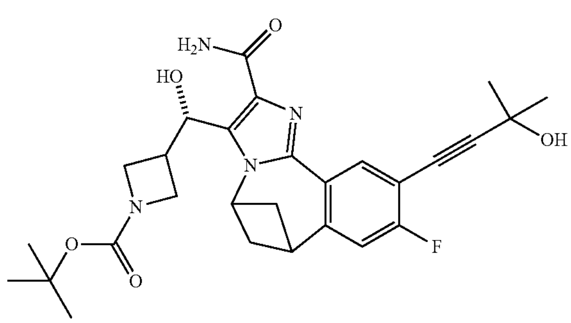 [SMILES: CC(C)(O)C#Cc1cc2c(cc1F)C1CC(C1)n1c-2nc(C(N)=O)c1[C@@H](O)C1CN(C(=O)OC(C)(C)C)C1] | tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-(S)-hydroxy-methyl]azetidine-1-carboxylate |

TABLE 1-continued

| No. | Structure | Name |
|---|---|---|
| 355 | 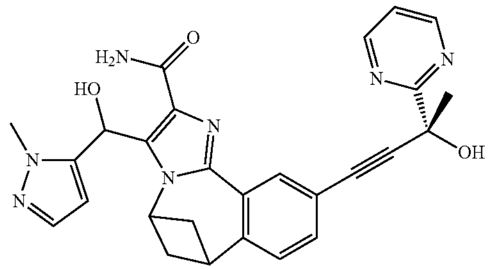 [SMILES: Cn1nccc1C(O)c1c(C(N)=O)nc2n1C1CC(C1)c1ccc(C#C[C@@](C)(O)c3ncccn3)cc1-2] | 3-[hydroxy-(2-methylpyrazol-3-yl)methyl]-10-(3-(R)-hydroxy-3-pyrimidin-2-yl-but-1-ynyl)-5,6,7,12-tetrahydro-5,7-methanobenzo[c]imidazo[1,2-a]azepine-2-carboxamide |
| 356 | 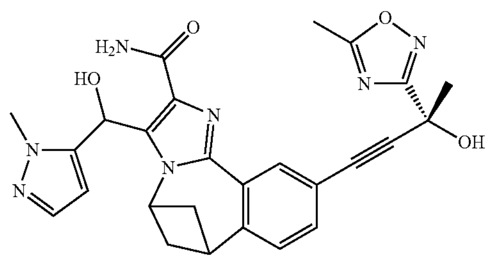 [SMILES: Cc1nc([C@](C)(O)C#Cc2ccc3c(c2)-c2nc(C(N)=O)c(C(O)c4ccnn4C)n2C2CC3C2)no1] | 10-[3-(R)-hydroxy-3-(5-methyl-1,2,4-oxadiazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide |
| 357 | 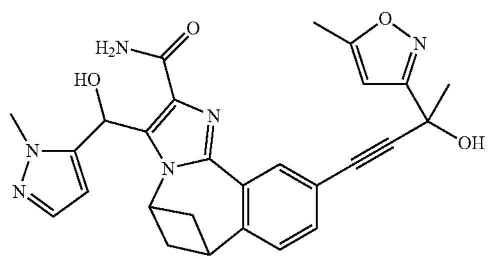 [SMILES: Cc1cc(C(C)(O)C#Cc2ccc3c(c2)-c2nc(C(N)=O)c(C(O)c4ccnn4C)n2C2CC3C2)no1] | 10-[3-hydroxy-3-(5-methylisoxazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide |
| 358 | 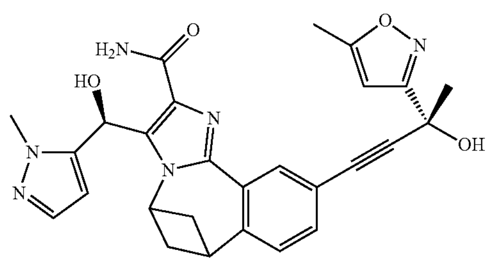 [SMILES: Cc1cc([C@](C)(O)C#Cc2ccc3c(c2)-c2nc(C(N)=O)c([C@H](O)c4ccnn4C)n2C2CC3C2)no1] | 10-[3-(R)-hydroxy-3-(5-methylisoxazol-3-yl)but-1-ynyl]-3-(S)-[hydroxy-(2-methylpyrazol-3-yl)methyl]-5,6,7,12-tetrahydro-5,7-methanobenzo[c]imidazo[1,2-a]azepine-2-carboxamide |
| 359 | 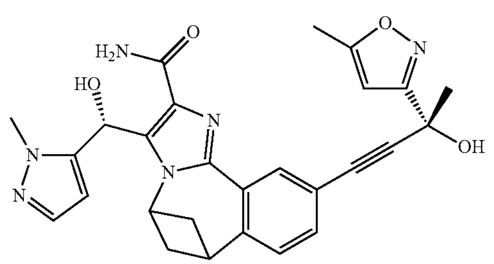 [SMILES: Cc1cc([C@](C)(O)C#Cc2ccc3c(c2)-c2nc(C(N)=O)c([C@@H](O)c4ccnn4C)n2C2CC3C2)no1] | 10-[3-(R)-hydroxy-3-(5-methylisoxazol-3-yl)but-1-ynyl]-3-(R)-[hydroxy-(2-methylpyrazol-3-yl)methyl]-5,6,7,12-tetrahydro-5,7-methanobenzo[c]imidazo[1,2-a]azepine-2-carboxamide |
| 360 | 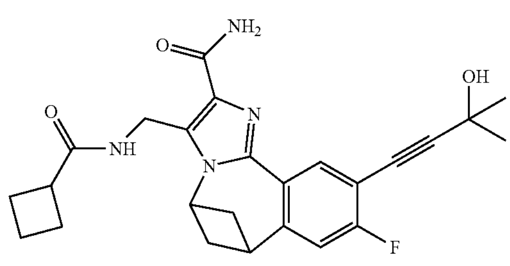 [SMILES: CC(C)(O)C#Cc1cc2c(cc1F)C1CC(C1)n1c-2nc(C(N)=O)c1CNC(=O)C1CCC1] | 3-[(cyclobutanecarbonylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 361 | 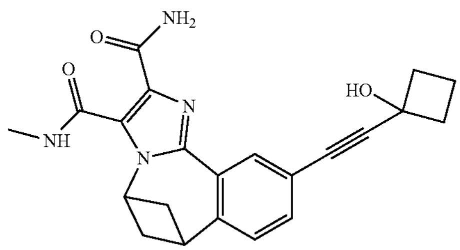 [SMILES: CNC(=O)c1c(C(N)=O)nc2n1C1CC(C1)c1ccc(C#CC3(O)CCC3)cc1-2] | 10-[2-(1-hydroxycyclobutyl)ethynyl]-N3-methyl-5,6,7,12-tetrahydro-5,7-methanobenzo[c]imidazo[1,2-a]azepine-2,3-dicarboxamide |
| 362 | 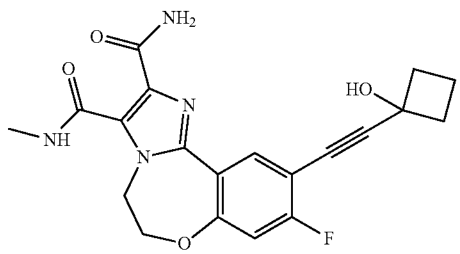 [SMILES: CNC(=O)c1c(C(N)=O)nc2n1CCOc1cc(F)c(C#CC3(O)CCC3)cc1-2] | 9-fluoro-10-[2-(1-hydroxycyclobutyl)ethynyl]-N3-methyl-5,6-dihydroimidazo[1,2-d][1,4]benzoxazepine-2,3-dicarboxamide |
| 363 | 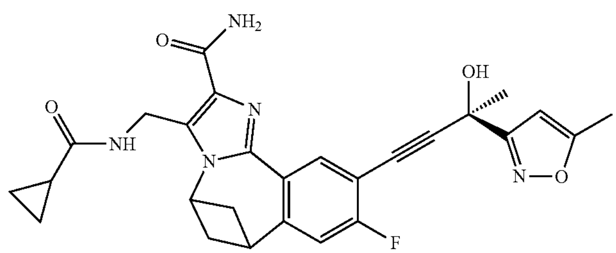 [SMILES: Cc1cc([C@](C)(O)C#Cc2cc3c(cc2F)C2CC(C2)n2c-3nc(C(N)=O)c2CNC(=O)C2CC2)no1] | 3-[(cyclopropanecarbonylamino)methyl-9-fluoro-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide |
| 364 | 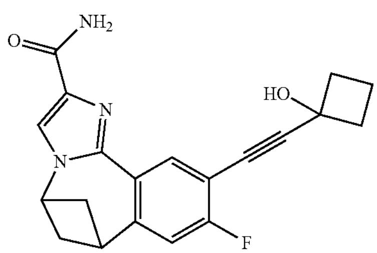 [SMILES: NC(=O)c1cn2c(n1)-c1cc(C#CC3(O)CCC3)c(F)cc1C1CC2C1] | 9-fluoro-10-[2-(1-hydroxycyclobutyl)ethynyl]-5,6,7,12-tetrahydro-5,7-methanobenzo[c]imidazo[1,2-a]azepine-2-carboxamide |
| 365 | 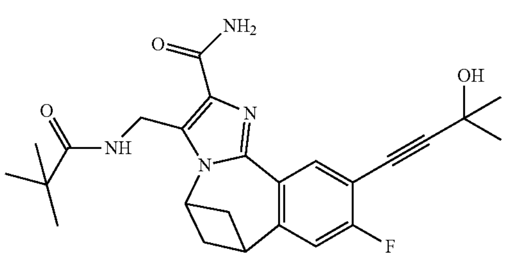 [SMILES: CC(C)(O)C#Cc1cc2c(cc1F)C1CC(C1)n1c-2nc(C(N)=O)c1CNC(=O)C(C)(C)C] | 3-[(2,2-dimethylpropanoylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |
| 366 | 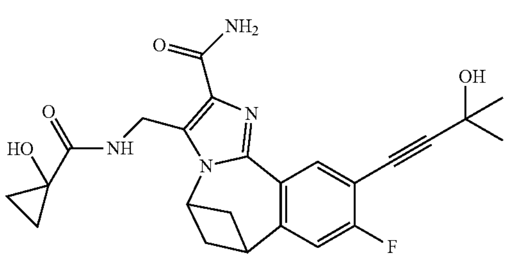 [SMILES: CC(C)(O)C#Cc1cc2c(cc1F)C1CC(C1)n1c-2nc(C(N)=O)c1CNC(=O)C1(O)CC1] | 9-fluoro-3-[[(1-hydroxycyclopropanecarbonyl)amino]methyl]-10-(3-hydroxy-3-methyl-but-1-ynyl)-5,6,7,12-tetrahydro-5,7-methanobenzo[c]imidazo[1,2-a]azepine-2-carboxamide |

TABLE 1-continued

| No. | Structure | Name |
|---|---|---|
| 367 | 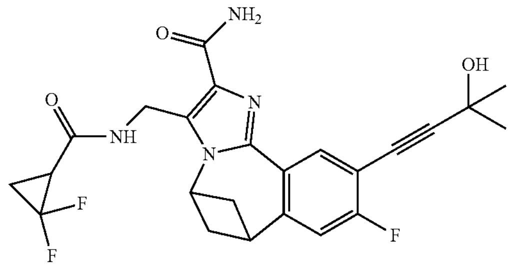 [SMILES: CC(C)(O)C#Cc1cc2c(cc1F)C1CC(C1)n1c-2nc(C(N)=O)c1CNC(=O)C1CC1(F)F] | 3-[[(2,2-difluorocyclopropanecarbonyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |
| 368 | 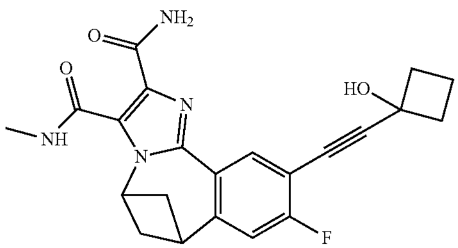 [SMILES: CNC(=O)c1c(C(N)=O)nc2n1C1CC(C1)c1cc(F)c(C#CC3(O)CCC3)cc1-2] | 9-fluoro-10-[2-(1-hydroxycyclobutyl)ethynyl]-N3-methyl-5,6,7,12-tetrahydro-5,7-methanobenzo[c]imidazo[1,2-a]azepine-2,3-dicarboxamide |
| 369 | 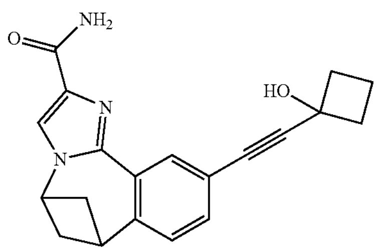 [SMILES: NC(=O)c1cn2c(n1)-c1cc(C#CC3(O)CCC3)ccc1C1CC2C1] | 10-[2-(1-hydroxycyclobutyl)ethynyl]-5,6,7,12-tetrahydro-5,7-methanobenzo[c]imidazo[1,2-a]azepine-2-carboxamide |
| 370 | 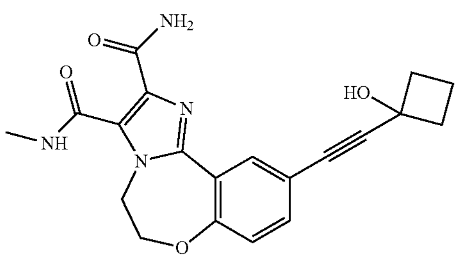 [SMILES: CNC(=O)c1c(C(N)=O)nc2n1CCOc1ccc(C#CC3(O)CCC3)cc1-2] | 10-[2-(1-hydroxycyclobutyl)ethynyl]-N3-methyl-5,6-dihydroimidazo[1,2-d][1,4]benzoxazepine-2,3-dicarboxamide |
| 371 | 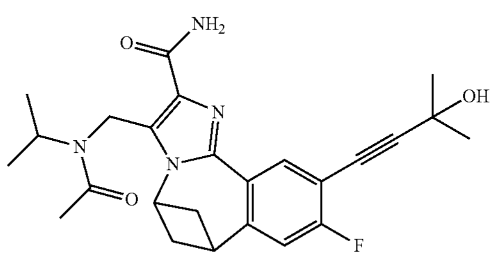 [SMILES: CC(=O)N(Cc1c(C(N)=O)nc2n1C1CC(C1)c1cc(F)c(C#CC(C)(C)O)cc1-2)C(C)C] | 3-[[acetyl(isopropyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide |
| 372 | 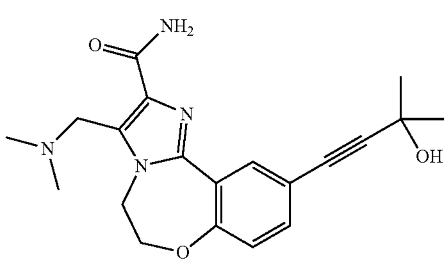 [SMILES: CN(C)Cc1c(C(N)=O)nc2n1CCOc1ccc(C#CC(C)(C)O)cc1-2] | 3-[(dimethylamino)methyl]-10-(3-hydroxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 373 | 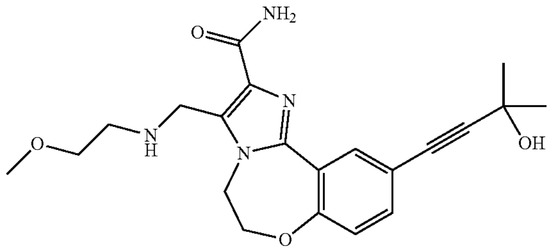 [SMILES: COCCNCc1c(C(N)=O)nc2n1CCOc1ccc(C#CC(C)(C)O)cc1-2] | 10-(3-hydroxy-3-methyl-but-1-ynyl)-3-[(2-methoxyethylamino)methyl]-5,6-dihydroimidazo[1,2-d][1,4]benzoxazepine-2-carboxamide |
| 374 | 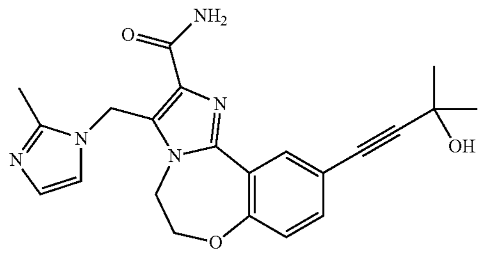 [SMILES: Cc1nccn1Cc1c(C(N)=O)nc2n1CCOc1ccc(C#CC(C)(C)O)cc1-2] | 10-(3-hydroxy-3-methyl-but-1-ynyl)-3-[(2-methylimidazol-1-yl)methyl]-5,6-dihydroimidazo[1,2-d][1,4]benzoxazepine-2-carboxamide |
| 375 | | 3-[(2-fluorophenoxy)methyl]-10-(3-hydroxy-3-methyl-but-1-ynyl)-5,6-dihydroimidazo[1,2-d][1,4]benzoxazepine-2-carboxamide |
| 376 | 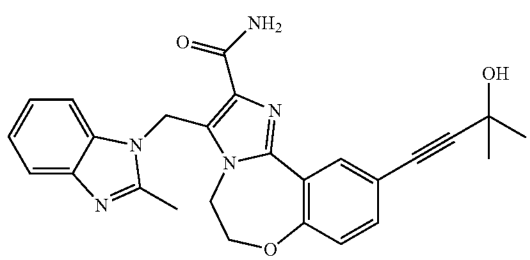 [SMILES: Cc1nc2ccccc2n1Cc1c(C(N)=O)nc2n1CCOc1ccc(C#CC(C)(C)O)cc1-2] | 10-(3-hydroxy-3-methyl-but-1-ynyl)-3-[(2-methylbenzimidazol-1-yl)methyl]-5,6-dihydroimidazo[1,2-d][1,4]benzoxazepine-2-carboxamide |
| 377 | 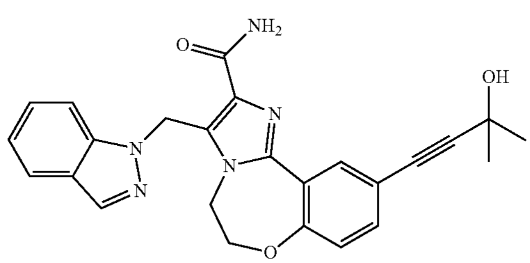 [SMILES: CC(C)(O)C#Cc1ccc2c(c1)-c1nc(C(N)=O)c(Cn3ncc4ccccc43)n1CCO2] | 10-(3-hydroxy-3-methyl-but-1-ynyl)-3-(indazol-1-ylmethyl)-5,6-dihydroimidazo[1,2-d][1,4]benzoxazepine-2-carboxamide |
| 378 | 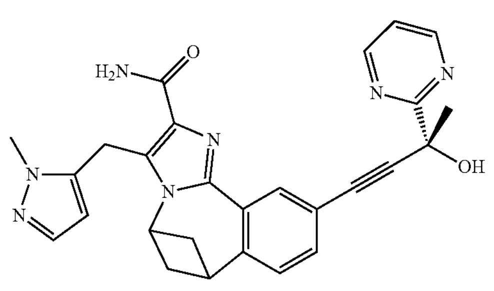 [SMILES: Cn1nccc1Cc1c(C(N)=O)nc2n1C1CC(C1)c1ccc(C#C[C@@](C)(O)c3ncccn3)cc1-2] | 10-[(3R)-3-hydroxy-3-pyrimidin-2-yl-but-1-ynyl]-3-[(2-methylpyrazol-3-yl)methyl]-5,6,7,12-tetrahydro-5,7-methanobenzo[c]imidazo[1,2-a]azepine-2-carboxamide |

TABLE 1-continued

| No. | Structure | Name |
|-----|-----------|------|
| 379 | 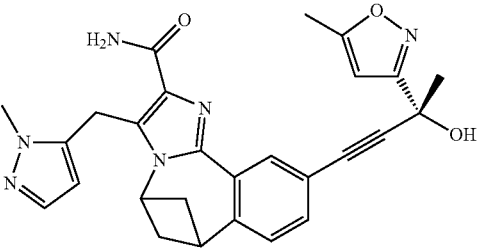 [SMILES: Cc1cc([C@](C)(O)C#Cc2ccc3c(c2)-c2nc(C(N)=O)c(Cc4ccnn4C)n2C2CC3C2)no1] | 10-[(3R)-3-hydroxy-3-(5-methylisoxazol-3-yl)but-1-ynyl]-3-[(2-methy]pyrazol-3-yl)methyl]-5,6,7,12-tetrahydro-5,7-methanobenzo[c]imidazo[1,2-a]azepine-2-carboxamide |
| 380 | 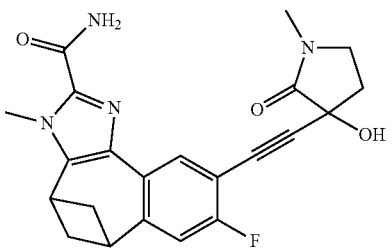 [SMILES: CN1CCC(O)(C#Cc2cc3c(cc2F)C2CC(C2)c2c-3nc(C(N)=O)n2C)C1=O] | 8-fluoro-9-((3-hydroxy-1-methyl-2-oxo-pyrrolidin-3-yl)ethynyl)-3-methyl-3,4,5,6-tetrahydro-4,6-methanobenzo[3,4]cyclo-hepta[1,2-d]imidazole-2-carboxamide |
| 381 | 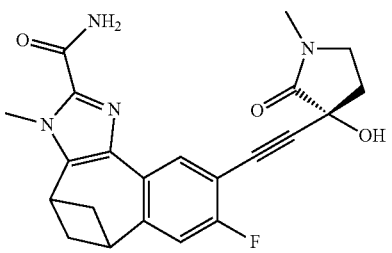 [SMILES: CN1CC[C@@](O)(C#Cc2cc3c(cc2F)C2CC(C2)c2c-3nc(C(N)=O)n2C)C1=O] | (R)-8-fluoro-9-((3-hydroxy-1-methyl-2-oxopyrrolidin-3-yl)ethynyl)-3-methyl-3,4,5,6-tetrahydro-4,6-methanoben-zo[3,4]cyclohepta[1,2-d]imidazole-2-carboxamide |
| 382 | 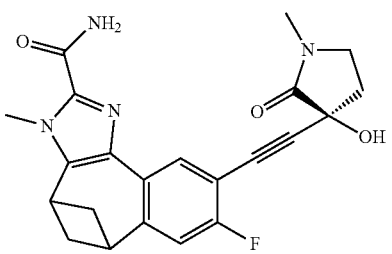 [SMILES: CN1CC[C@](O)(C#Cc2cc3c(cc2F)C2CC(C2)c2c-3nc(C(N)=O)n2C)C1=O] | (S)-8-fluoro-9-((3-hydroxy-1-methyl-2-oxopyrrolidin-3-yl)ethynyl)-3-methyl-3,4,5,6-tetrahydro-4,6-methanoben-zo[3,4]cyclohepta[1,2-d]imidazole-2-carboxamide |
| 383 | 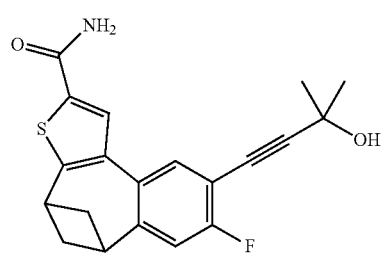 [SMILES: CC(C)(O)C#Cc1cc2c(cc1F)C1CC(C1)c1sc(C(N)=O)cc1-2] | 8-fluoro-9-(3-hydroxy-3-methylbut-1-yn-1-yl)-5,6-dihydro-4H-4,6-methano-benzo[3,4]cyclohepta[1,2-b]thiophene-2-carboxamide |
| 384 | 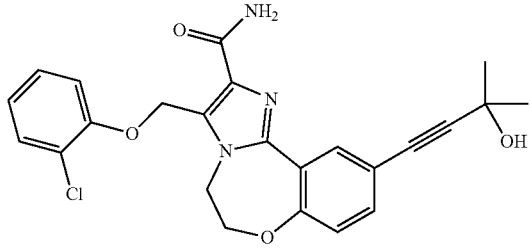 [SMILES: CC(C)(O)C#Cc1ccc2c(c1)-c1nc(C(N)=O)c(COc3ccccc3Cl)n1CCO2] | 3-[(2-chlorophenoxy)methyl]-10-(3-hy-droxy-3-methyl-but-1-ynyl)-5,6-dihydro-imidazo[1,2-d][1,4]benzoxazepine-2-carboxamide |

TABLE 1-continued

| No. | Structure | Name |
|---|---|---|
| 385 | 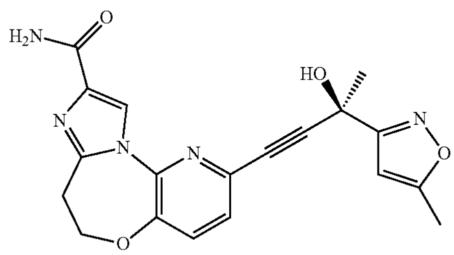 [SMILES: Cc1cc([C@](C)(O)C#Cc2ccc3c(n2)-n2cc(C(N)=O)nc2CCO3)no1] | (R)-2-(3-hydroxy-3-(5-methylisoxazol-3-yl)but-1-yn-1-yl)-6,7-dihydroimidazo[1,2-d]pyrido[3,2-b][1,4]oxazepine-9-carboxamide |
| 386 | 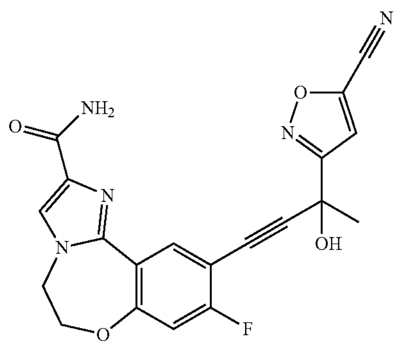 [SMILES: CC(O)(C#Cc1cc2c(cc1F)OCCn1cc(C(N)=O)nc1-2)c1cc(C#N)on1] | 10-[3-(5-cyanoisoxazol-3-yl)-3-hydroxy-but-1-ynyl]-9-fluoro-5,6-dihydroimidazo[1,2-d][1,4]benzoxazepine-2-carboxamide |
| 387 | 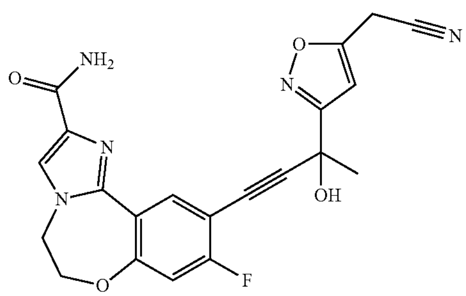 [SMILES: CC(O)(C#Cc1cc2c(cc1F)OCCn1cc(C(N)=O)nc1-2)c1cc(CC#N)on1] | 10-[3-[5-(cyanomethyl)isoxazol-3-yl]-3-hydroxy-but-1-ynyl]-9-fluoro-5,6-dihydroimidazo[1,2-d][1,4]benzoxazepine-2-carboxamide |
| 388 | 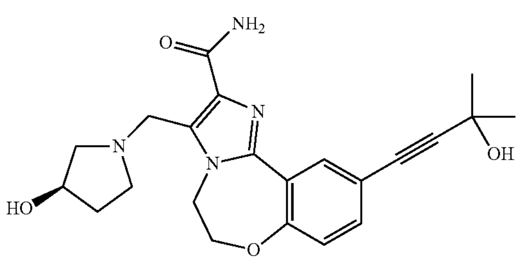 [SMILES: CC(C)(O)C#Cc1ccc2c(c1)-c1nc(C(N)=O)c(CN3CC[C@@H](O)C3)n1CCO2] | 10-(3-hydroxy-3-methyl-but-1-ynyl)-3-[[(3R)-3-hydroxypyrrolidin-1-yl]methyl]-5,6-dihydroimidazo[1,2-d][1,4]benzoxazepine-2-carboxamide |
| 389 | 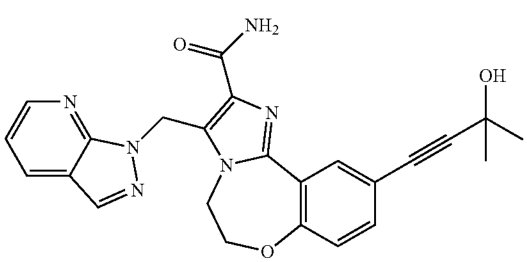 [SMILES: CC(C)(O)C#Cc1ccc2c(c1)-c1nc(C(N)=O)c(Cn3ncc4cccnc43)n1CCO2] | 10-(3-hydroxy-3-methyl-but-1-ynyl)-3-(pyrazolo[3,4-b]pyridin-1-ylmethyl)-5,6-dihydroimidazo[1,2-d][1,4]benzoxazepine-2-carboxamide |

| No. | Name |
|---|---|
| 390 | 3-(5-cyclopropyl-1,3,4-thiadiazol-2-yl)-10-(3-hydroxy-3-methyl-but-1-ynyl)-5,6,7,12-tetrahydro-5,7-methanobenzo[c]imidazo[1,2-a]azepine-2-carboxamide |
| 391 | 8-fluoro-9-(3-hydroxy-3-methylbut-1-yn-1-yl)-3-((1-methyl-1H-pyrazol-5-yl)methyl)-3,4,5,6-tetrahydro-4,6-methanonbezo[3,4]cyclohepta[1,2-d]imidazole-2-carboxamide |
| 392 | 3-(2-chlorobenzyl)-8-fluoro-9-(3-hydroxy-3-methylbut-1-yn-1-yl)-3,4,5,6-tetrahydro-4,6-methanobenzo[3,4]cyclohepta[1,2-d]imidazole-2-carboxamide |
| 393 | 2-(3-hydroxy-3-methylbut-1-yn-1-yl)-6,7-dihydroimidazo[1,2-d]pyrido[3,2-b][1,4]oxazepine-9-carboxamide |
| 394 | 3-[(6-cyanoindazol-1-yl)methyl]-10-(3-hydroxy-3-methyl-but-1-ynyl)-5,6-dihydroimidazo[1,2-d][1,4]benzoxazepine-2-carboxamide |
| 395 | 3-[(6-cyanoindazol-2-yl)methyl]-10-(3-hydroxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 396 | 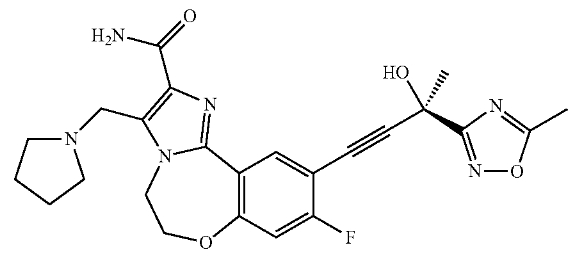 [SMILES: Cc1nc([C@](C)(O)C#Cc2cc3c(cc2F)OCCn2c-3nc(C(N)=O)c2CN2CCCC2)no1] | 9-fluoro-10-[(3R)-3-hydroxy-3-(5-methyl-1,2,4-oxadiazol-3-yl)but-1-ynyl]-3-(pyrrolidin-1-ylmethyl)-5,6-dihydroimidazo[1,2-d][1,4]benzoxazepine-2-carboxamide |
| 397 | 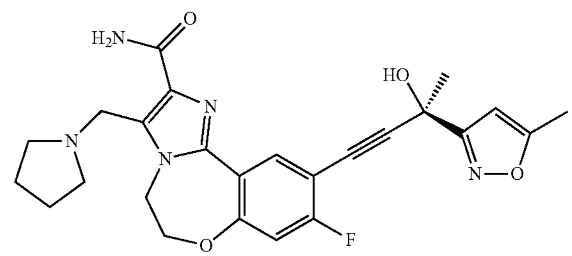 [SMILES: Cc1cc([C@](C)(O)C#Cc2cc3c(cc2F)OCCn2c-3nc(C(N)=O)c2CN2CCCC2)no1] | 9-fluoro-10-[(3R)-3-hydroxy-3-(5-methylisoxazol-3-yl)but-1-ynyl]-3-(pyrrolidin-1-ylmethyl)-5,6-dihydroimidazo[1,2-d][1,4]benzoxazepine-2-carboxamide |
| 398 | 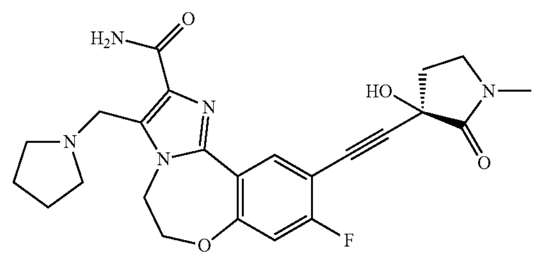 [SMILES: CN1CC[C@@](O)(C#Cc2cc3c(cc2F)OCCn2c-3nc(C(N)=O)c2CN2CCCC2)C1=O] | 9-fluoro-10-[2-[(3R)-3-hydroxy-1-methyl-2-oxo-pyrrolidin-3-yl]ethynyl]-3-(pyrrolidin-1-ylmethyl)-5,6-dihydroimidazo[1,2-d][1,4]benzoxazepine-2-carboxamide |
| 399 | 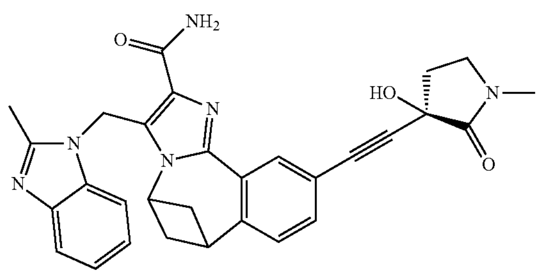 | 10-[2-[(3R)-3-hydroxy-1-methyl-2-oxo-pyrrolidin-3-yl]ethynyl]-3-[(2-methyl-benzimidazol-1-yl)methyl]-5,6,7,12-tetrayrahdro-5,7-methanobenzo[c]imidazo[1,2-a]azepine-2-carboxamide |
| 400 | 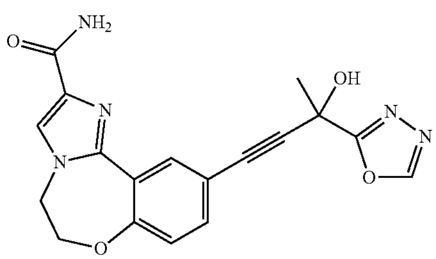 [SMILES: CC(O)(C#Cc1ccc2c(c1)-c1nc(C(N)=O)cn1CCO2)c1nnco1] | 10-[3-hydroxy-3-(1,3,4-oxadiazol-2-yl)but-1-ynyl]-5,6-dihydroimidazo[1,2-d][1,4]benzoxazepine-2-carboxamide |
| 401 | 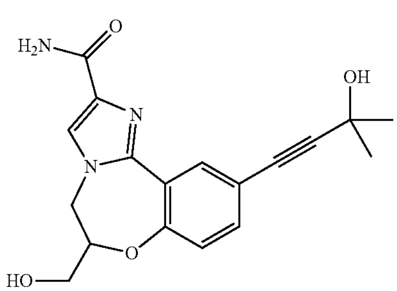 | 6-(hydroxymethyl)-10-(3-hydroxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 402 | 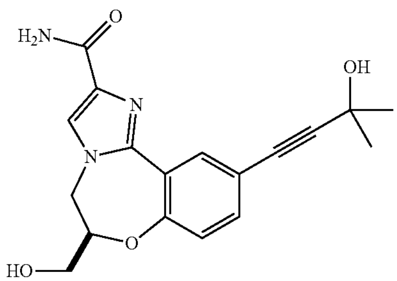 [SMILES: CC(C)(O)C#Cc1ccc2c(c1)-c1nc(C(N)=O)cn1C[C@H](CO)O2] | (R)-10-(3-hydroxy-3-methylbut-1-yn-1-yl)-6-(hydroxymethyl)-5,6-dihydro-benzo[f]imidazo[1,2-d][1,4]oxazepine-2-carboxamide |
| 403 | 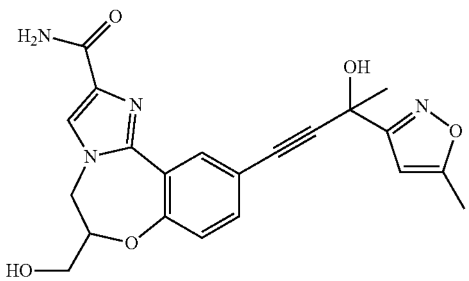 [SMILES: Cc1cc(C(C)(O)C#Cc2ccc3c(c2)-c2nc(C(N)=O)cn2CC(CO)O3)no1] | 6-(hydroxymethyl)-10-[3-hydroxy-3-(5-methylisoxazol-3-yl)but-1-ynyl]-5,6-dihydroimidazo[1,2-d][1,4]benzoxazepine-2-carboxamide |
| 404 | 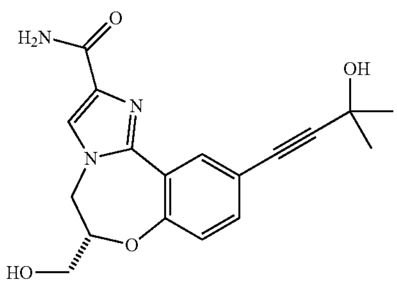 | (S)-10-(3-hydroxy-3-methylbut-1-yn-1-yl)-6-(hydroxymethyl)-5,6-dihydro-benzo[f]imidazo[1,2-d][1,4]oxazepine-2-carboxamide |
| 405 | 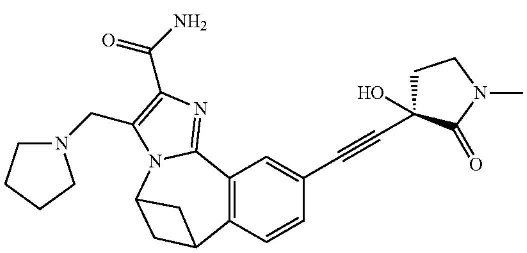 [SMILES: CN1CC[C@@](O)(C#Cc2ccc3c(c2)-c2nc(C(N)=O)c(CN4CCCC4)n2C2CC3C2)C1=O] | 10-[2-[(3R)-3-hydroxy-1-methyl-2-oxo-pyrrolidin-3-yl]ethynyl]-3-(pyrrolidin-1-ylmethyl)-5,6,7,12-tetrahydro-5,7-methanobenzo[c]imidazo[1,2-a]azepine-2-carboxamide |
| 406 | 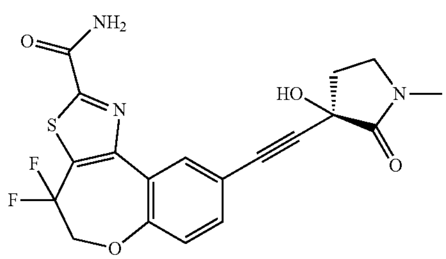 [SMILES: CN1CC[C@@](O)(C#Cc2ccc3c(c2)-c2nc(C(N)=O)sc2C(F)(F)CO3)C1=O] | 4,4-difluoro-9-[2-[(3R)-3-hydroxy-1-methyl-2-oxo-pyrrolidin-3-yl]ethynyl]-5H-[1]benzoxepino[5,4-d]thiazole-2-carboxamide |
| 407 | 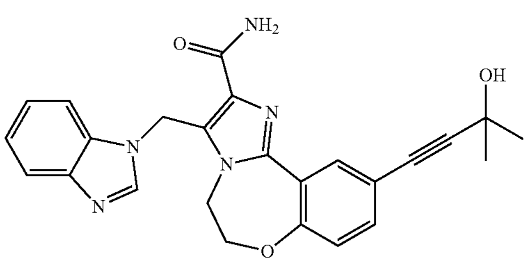 | 3-(benzimidazol-1-ylmethyl)-10-(3-hydroxy-3-methyl-but-1-ynyl)-5,6-dihydroimidazo[1,2-d][1,4]benzoxazepine-2-carboxamide |

TABLE 1-continued

| No. | Structure | Name |
|---|---|---|
| 408 | 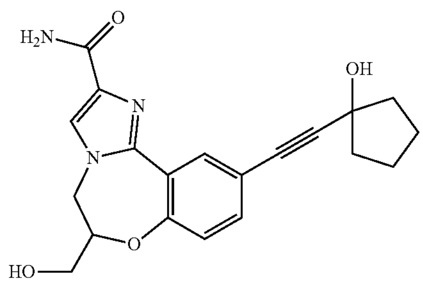 [SMILES: NC(=O)c1cn2c(n1)-c1cc(C#CC3(O)CCCC3)ccc1OC(CO)C2] | 10-[2-(1-hydroxycyclopentyl)ethynyl]-6-(hydroxymethyl)-5,6-dihydroimidazo[1,2-d][1,4]benzoxazepine-2-carboxamide |
| 409 | 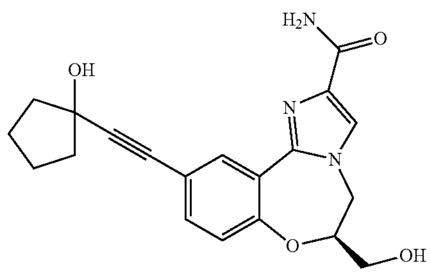 [SMILES: NC(=O)c1cn2c(n1)-c1cc(C#CC3(O)CCCC3)ccc1O[C@H](CO)C2] | (S)-10-((1-hydroxycyclopentyl)ethynyl)-6-(hydroxymethyl)-5,6-dihydro-benzo[f]imidazo[1,2-d][1,4]oxazepine-2-carboxamide |
| 410 | 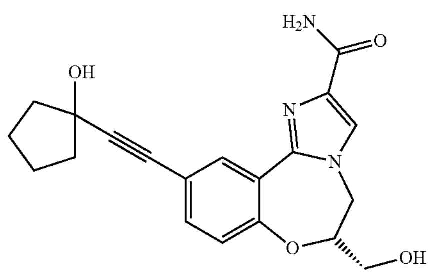 | (R)-10-((1-hydroxycyclopentyl)ethynyl)-6-(hydroxymethyl)-5,6-dihydrobenzo[f]imidazo[1,2-d][1,4]oxazepine-2-carboxamide |
| 411 | 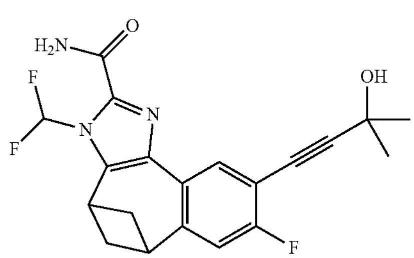 [SMILES: CC(C)(O)C#Cc1cc2c(cc1F)C1CC(C1)c1c-2nc(C(N)=O)n1C(F)F] | 3-(difluoromethyl)-8-fluoro-9-(3-hydroxy-3-methylbut-1-yn-1-yl)-3,4,5,6-tetrahydro-4,6-methanobenzo[3,4]cyclohepta[1,2-d]imidazole-2-carboxamide |
| 412 | 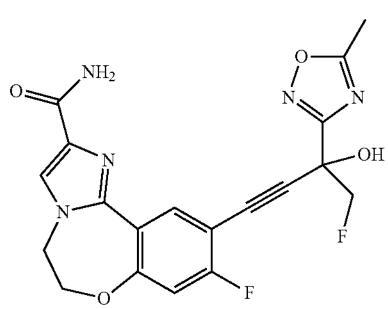 [SMILES: Cc1nc(C(O)(C#Cc2cc3c(cc2F)OCCn2cc(C(N)=O)nc2-3)CF)no1] | 9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |

TABLE 1-continued

| No. | Structure | Name |
|---|---|---|
| 413 | 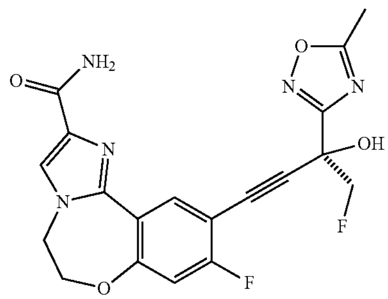 [SMILES: Cc1nc([C@@](O)(C#Cc2cc3c(cc2F)OCCn2cc(C(N)=O)nc2-3)CF)no1] | (S)-9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |
| 414 | 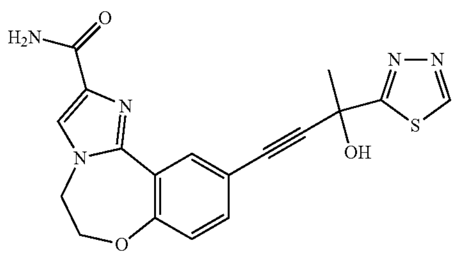 [SMILES: CC(O)(C#Cc1ccc2c(c1)-c1nc(C(N)=O)cn1CCO2)c1nncs1] | 10-[3-hydroxy-3-(1,3,4-thiadiazol-2-yl)but-1-ynyl]-5,6-dihydroimidazo[1,2-d][1,4]benzoxazepine-2-carboxamide |
| 415 | 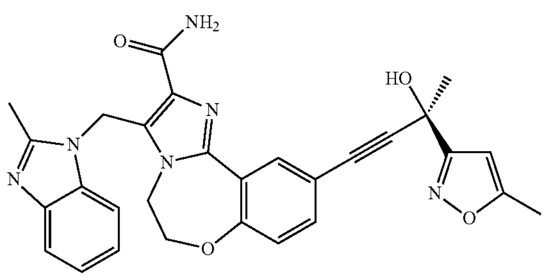 | 10-[(3R)-3-hydroxy-3-(5-methylisoxazol-3-yl)but-1-ynyl]-3-[(2-methylbenzimidazol-1-yl)methyl]-5,6-dihydraimidazo[1,2-d][1,4]benzoxazepine-2-carboxamide |
| 416 | 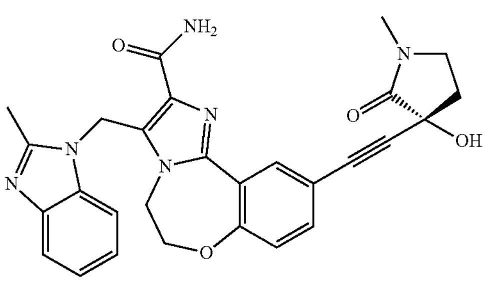 [SMILES: Cc1nc2ccccc2n1Cc1c(C(N)=O)nc2n1CCOc1ccc(C#C[C@]3(O)CCN(C)C3=O)cc1-2] | 10-[2-[(3R)-3-hydroxy-1-methyl-2-oxo-pyrrolidin-3-yl]ethynyl]-3-[(2-methyl-benzimidazol-1-yl)methyl]-5,6-dihydro-imidazo[1,2-d][1,4]benzoxazepine-2-carboxamide |
| 417 | 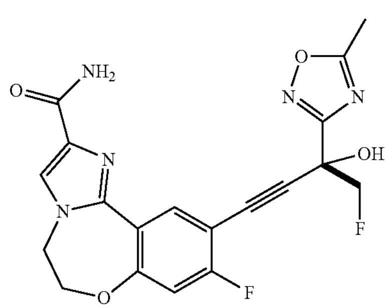 [SMILES: Cc1nc([C@](O)(C#Cc2cc3c(cc2F)OCCn2cc(C(N)=O)nc2-3)CF)no1] | (R)-9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |

TABLE 1-continued

| No. | Structure | Name |
|---|---|---|
| 418 | 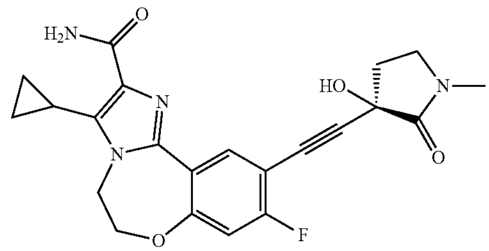 [SMILES: CN1CC[C@@](O)(C#Cc2cc3c(cc2F)OCCn2c-3nc(C(N)=O)c2C2CC2)C1=O] | 3-cyclopropyl-9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide |
| 419 | 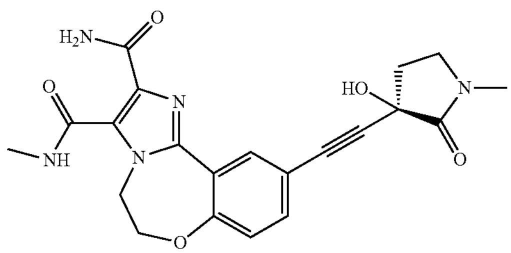 | 10-[2-[(3R)-3-hydroxy-1-methyl-2-oxo-pyrrolidin-3-yl]ethynyl]-N3-methyl-5,6-dihydroimidazo[1,2-d][1,4]benzoxazepine-2,3-dicarboxamide |
| 420 | 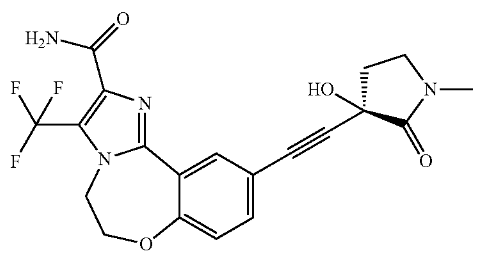 [SMILES: CN1CC[C@@](O)(C#Cc2ccc3c(c2)-c2nc(C(N)=O)c(C(F)(F)F)n2CCO3)C1=O] | 10-[2-[(3R)-3-hydroxy-1-methyl-2-oxo-pyrrolidin-3-yl]ethynyl]-3-(trifluoromethyl)-5,6-dihydroimidazo[1,2-d][1,4]benzoxazepine-2-carboxamide |
| 421 | 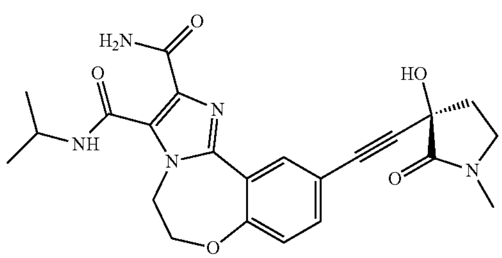 [SMILES: CC(C)NC(=O)c1c(C(N)=O)nc2n1CCOc1ccc(C#C[C@]3(O)CCN(C)C3=O)cc1-2] | 10-[2-[(3R)-3-hydroxy-1-methyl-2-oxo-pyrrolidin-3-yl]ethynyl]-N3-isopropyl-5,6-dihydroimidazo[1,2-d][1,4]benzoxazepine-2,3-dicarboxamide |
| 422 | 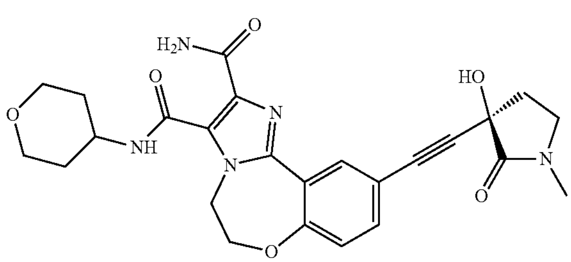 [SMILES: CN1CC[C@@](O)(C#Cc2ccc3c(c2)-c2nc(C(N)=O)c(C(=O)NC4CCOCC4)n2CCO3)C1=O] | 10-[2-[(3R)-3-hydroxy-1-methyl-2-oxo-pyrrolidin-3-yl]ethynyl]-N3-tetrahydropyran-4-yl-5,6-dihydroimidazo[1,2-d][1,4]benzoxazepine-2,3-dicarboxamide |
| 423 | 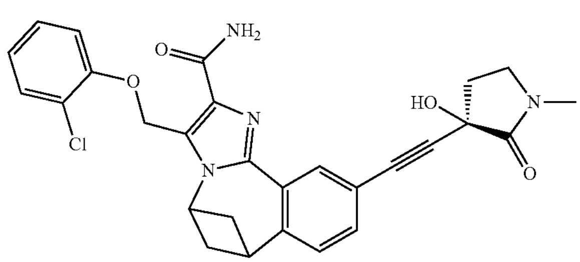 [SMILES: CN1CC[C@@](O)(C#Cc2ccc3c(c2)-c2nc(C(N)=O)c(COc4ccccc4Cl)n2C2CC3C2)C1=O] | 3-[(2-chlorophenoxy)methyl]-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |

TABLE 1-continued

| No. | Name |
|-----|------|
| 424 | 10-[(3R)-3-hydroxy-3-(5-methylisoxazol-3-yl)but-1-ynyl]-3-(pyrrolidin-1-ylmethyl)-5,6,7,12-tetrahydro-5,7-methano-benzo[c]imidazo[1,2-a]azepine-2-carboxamide |
| 425 | 9-(3-hydroxy-3-methylbut-1-yn-1-yl)-3-methyl-3,4,5,6-tetrahydro-4,6-methanobenzo[3,4]cyclohepta[1,2-d]imidazole-2-carboxamide |
| 426 | (R)-9-(3-hydroxy-3-(5-methyl-1,2,4-oxadiazol-3-yl)but-1-yn-1-yl)-3-methyl-3,4,5,6-tetrahydro-4,6-methanobenzo[3,4]cyclohepta[1,2-d]imidazole-2-carboxamide |
| 427 | (R)-9-(3-hydroxy-3-(pyrimidin-2-yl)but-1-yn-1-yl)-3-methyl-3,4,5,6-tetrahydro-4,6-methanobenzo[3,4]cyclohepta[1,2-d]imidazole-2-carboxamide |
| 428 | 10-[2-(2-hydroxy-5-methyl-6-oxabicyclo[3.1.0]hexan-2-yl)ethynyl]-5,6-dihydroimidazo[1,2-d][1,4]benzoxazepine-2-carboxamide |
| 429 | 8-fluoro-9-[(3R)-3-hydroxy-3-(5-methylisoxazol-3-yl)but-1-ynyl]-4,5-dihydrothieno[3,2-d][1]benzoxepine-2-carboxamide |

TABLE 1-continued

| No. | Structure | Name |
|---|---|---|
| 430 | 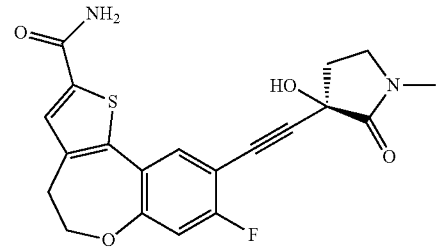 [SMILES: CN1CC[C@@](O)(C#Cc2cc3c(cc2F)OCCc2cc(C(N)=O)sc2-3)C1=O] | 8-fluoro-9-[2-[(3R)-3-hydroxy-1-methyl-2-oxo-pyrrolidin-3-yl]ethynyl]-4,5-dihydrothieno[3,2-d][1]benzoxepine-2-carboxamide |
| 431 | 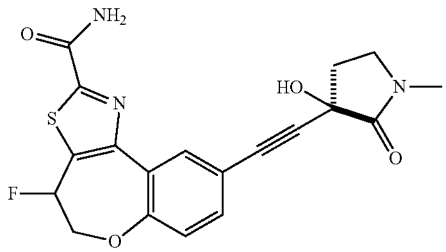 [SMILES: CN1CC[C@@](O)(C#Cc2ccc3c(c2)-c2nc(C(N)=O)sc2C(F)CO3)C1=O] | 4-fluoro-9-(((R)-3-hydroxy-1-methyl-2-oxopyrrolidin-3-yl)ethynyl)-4,5-dihydro-benzo[2,3]oxepino[4,5-d]thiazole-2-carboxamide |
| 432 | 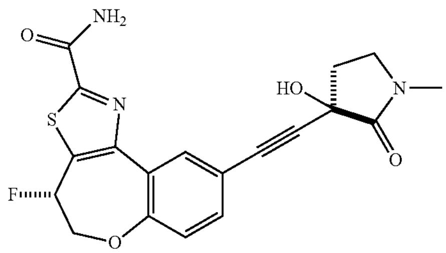 | (S)-4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 433 | 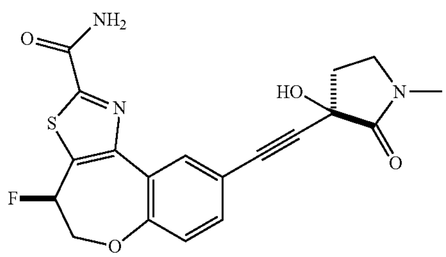 | (R)-4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 434 | 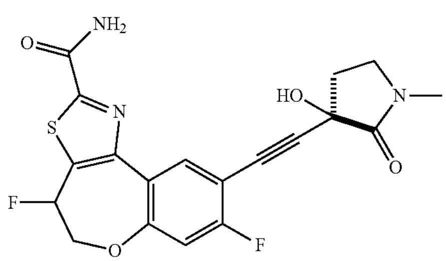 | 4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 435 | 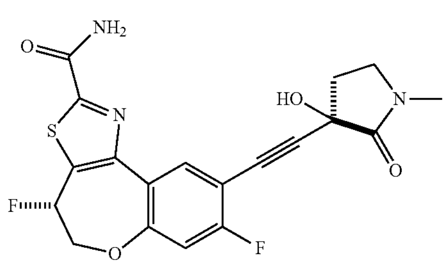 [SMILES: CN1CC[C@@](O)(C#Cc2cc3c(cc2F)OC[C@H](F)c2sc(C(N)=O)nc2-3)C1=O] | (S)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1-continued

| No. | Structure | Name |
|---|---|---|
| 436 | 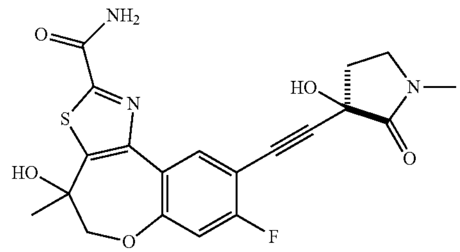 [SMILES: CN1CC[C@@](O)(C#Cc2cc3c(cc2F)OCC(C)(O)c2sc(C(N)=O)nc2-3)C1=O] | 8-fluoro-4-hydroxy-9-((3-(R)-hydroxy-1-methyl-2-oxopyrrolidin-3-yl)ethynyl)-4-methyl-4,5-dihydrobenzo[2,3]oxepino[4,5-d]thiazole-2-carboxamide |
| 437 | 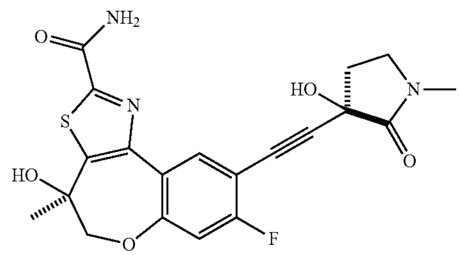 [SMILES: CN1CC[C@@](O)(C#Cc2cc3c(cc2F)OC[C@@](C)(O)c2sc(C(N)=O)nc2-3)C1=O] | (R)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 438 | 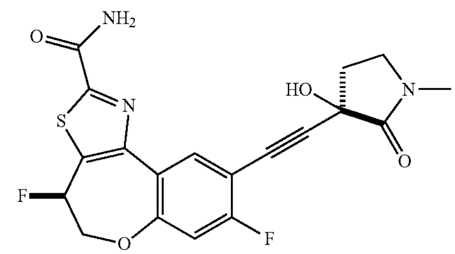 [SMILES: CN1CC[C@@](O)(C#Cc2cc3c(cc2F)OC[C@@H](F)c2sc(C(N)=O)nc2-3)C1=O] | (R)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 439 | 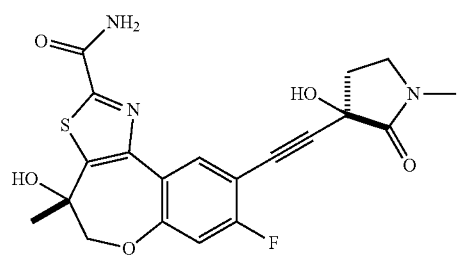 [SMILES: CN1CC[C@@](O)(C#Cc2cc3c(cc2F)OC[C@](C)(O)c2sc(C(N)=O)nc2-3)C1=O] | (S)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 440 | 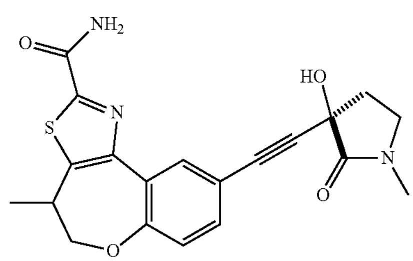 | 9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 441 | 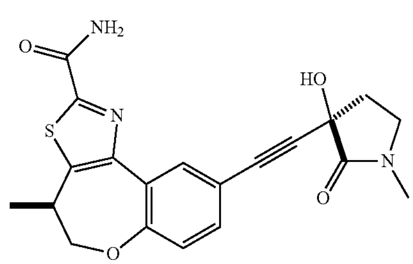 | (R)-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |

TABLE 1-continued

| No. | Structure | Name |
|---|---|---|
| 442 | 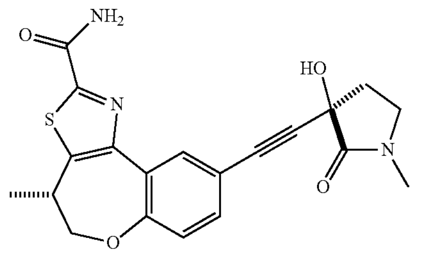 | (S)-9-(((R)-3-hydroxy-1-methyl-2-oxo-pyrrolidin-3-yl)ethynyl)-4-methyl-4,5-di-hydrobenzo[2,3]oxepino[4,5-d]thiazole-2-carboxamide |
| 443 | 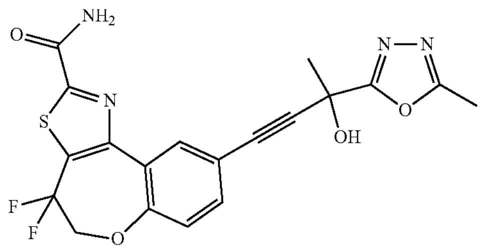 [SMILES: Cc1nnc(C(C)(O)C#Cc2ccc3c(c2)-c2nc(C(N)=O)sc2C(F)(F)CO3)o1] | 4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide |
| 444 | 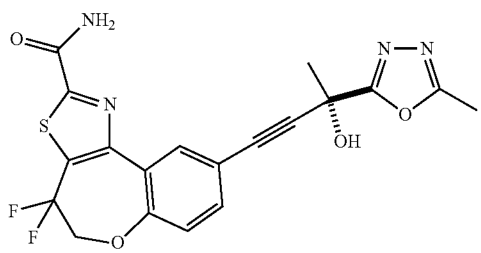 [SMILES: Cc1nnc([C@@](C)(O)C#Cc2ccc3c(c2)-c2nc(C(N)=O)sc2C(F)(F)CO3)o1] | (S)-4,4-difluoro-9-(3-hydroxy-3-(5-methyl-13,4-oxadiazol-2-yl)but-1-yn-1-yl)-4,5-dihydrobenzo[2,3]oxepino[4,5-d]thiazole-2-carboxamide |
| 445 | 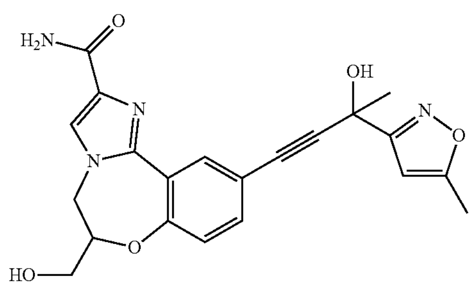 | 6-(hydroxymethyl)-10-[3-hydroxy-3-(5-methylisoxazol-3-yl)but-1-ynyl]-5,6-dihydroimidazo[1,2-d][1,4]benzoxazepine-2-carboxamide |
| 446 | 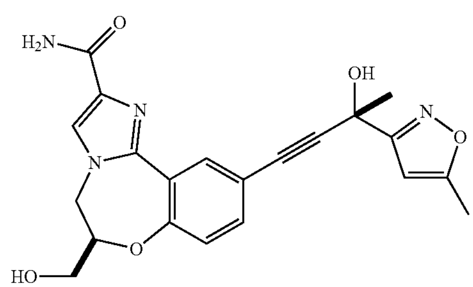 [SMILES: Cc1cc([C@@](C)(O)C#Cc2ccc3c(c2)-c2nc(C(N)=O)cn2C[C@H](CO)O3)no1] | 6-(R)-(hydroxymethyl)-10-[3-(S)-hydroxy-3-(5-methylisoxazol-3-yl)but-1-ynyl]-5,6-dihydroimidazo[1,2-d][1,4]benzoxazepine-2-carboxamide |
| 447 | 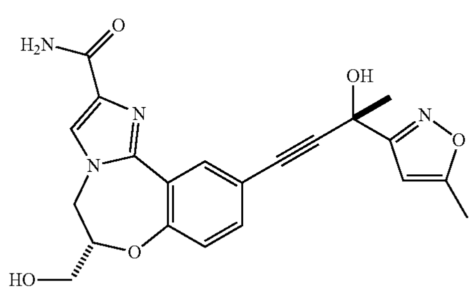 [SMILES: Cc1cc([C@@](C)(O)C#Cc2ccc3c(c2)-c2nc(C(N)=O)cn2C[C@@H](CO)O3)no1] | (S)-10-((S)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |

TABLE 1-continued

| No. | Structure | Name |
|---|---|---|
| 448 | 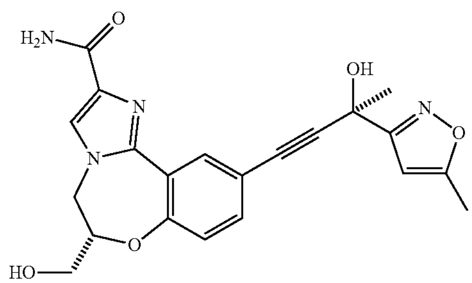 [SMILES: Cc1cc([C@](C)(O)C#Cc2ccc3c(c2)-c2nc(C(N)=O)cn2C[C@@H](CO)O3)no1] | (S)-10-((R)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |
| 449 | 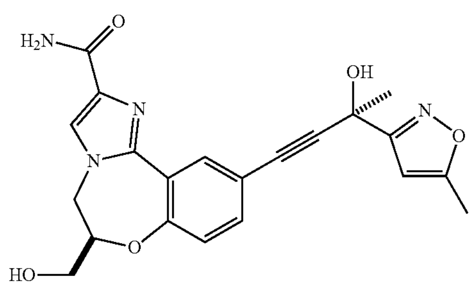 [SMILES: Cc1cc([C@](C)(O)C#Cc2ccc3c(c2)-c2nc(C(N)=O)cn2C[C@H](CO)O3)no1] | (R)-10-((R)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |
| 450 | 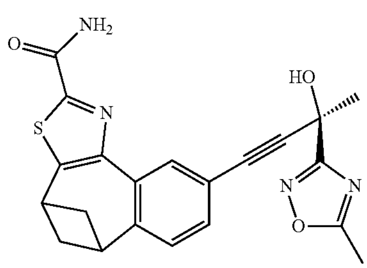 [SMILES: Cc1nc([C@](C)(O)C#Cc2ccc3c(c2)-c2nc(C(N)=O)sc2C2CC3C2)no1] | (R)-9-(3-hydroxy-3-(5-methyl-1,2,4-oxadiazol-3-yl)but-1-yn-1-yl)-5,6-dihydro-4H-4,6-methanobenzo[6,7]cyclohepta[1,2-d]thiazole-2-carboxamide |
| 451 | 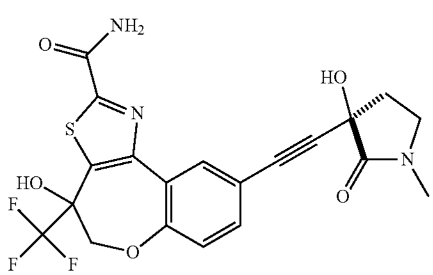 | 4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |
| 452 | 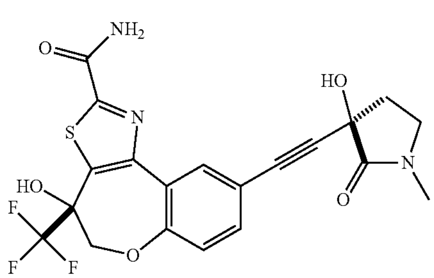 | (R)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |

TABLE 1-continued

| No. | Structure | Name |
|---|---|---|
| 453 | 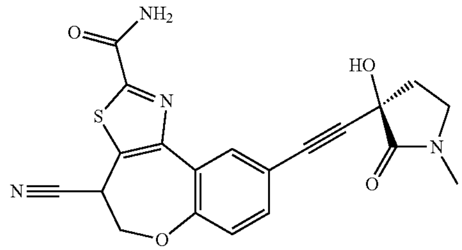 [SMILES: CN1CC[C@@](O)(C#Cc2ccc3c(c2)-c2nc(C(N)=O)sc2C(C#N)CO3)C1=O] | 4-cyano-9-(((R)-3-hydroxy-1-methyl-2-oxopyrrolidin-3-yl)ethynyl)-4,5-dihydro-benzo[2,3]oxepino[4,5-d]thiazole-2-carboxamide |
| 454 | 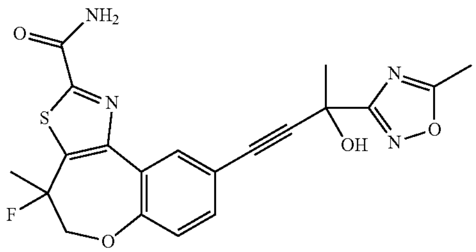 | 4-fluoro-9-[3-hydroxy-3-(5-methyl-1,2,4-oxadiazol-3-yl)but-1-ynyl]-4-methyl-5H-[1]benzoxepino[5,4-d]thiazole-2-carboxamide |
| 455 | 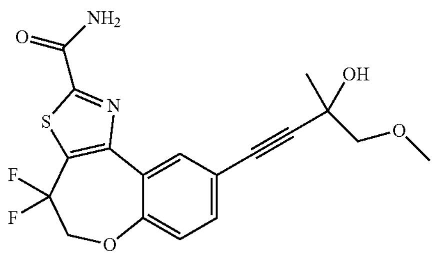 [SMILES: COCC(C)(O)C#Cc1ccc2c(c1)-c1nc(C(N)=O)sc1C(F)(F)CO2] | 4,4-difluoro-9-(3-hydroxy-4-methoxy-3-methylbut-1-yn-1-yl)-4,5-dihydrobenzo[2,3]oxepino[4,5-d]thiazole-2-carboxamide |
| 456 | 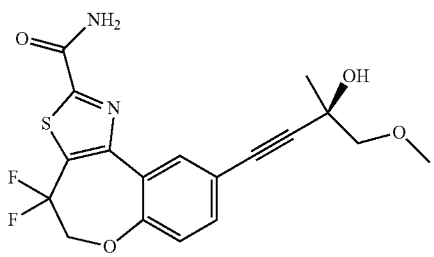 [SMILES: COC[C@](C)(O)C#Cc1ccc2c(c1)-c1nc(C(N)=O)sc1C(F)(F)CO2] | (R)-4,4-difluoro-9-(3-hydroxy-4-methoxy-3-methylbut-1-yn-1-yl)-4,5-dihydro-benzo[2,3]oxepino[4,5-d]thiazole-2-carboxamide |
| 457 | 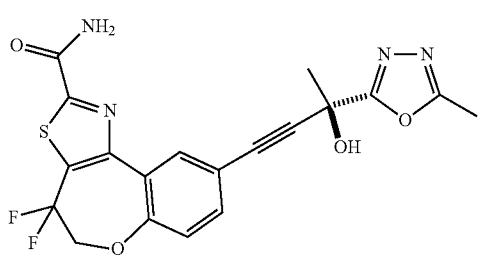 [SMILES: Cc1nnc([C@](C)(O)C#Cc2ccc3c(c2)-c2nc(C(N)=O)sc2C(F)(F)CO3)o1] | (R)-4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide |
| 458 | 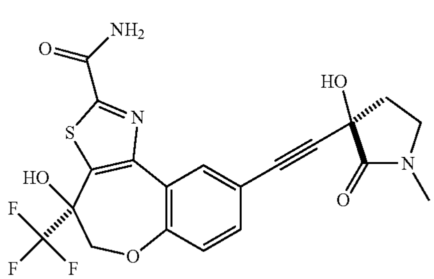 | (S)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |

TABLE 1-continued

| No. | Structure | Name |
|---|---|---|
| 459 | 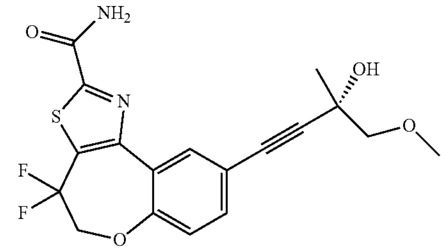 | (S)-4,4-difluoro-9-(3-hydroxy-4-methoxy-3-methylbut-1-yn-1-yl)-4,5-dihydrobenzo[2,3]oxepino[4,5-d]thiazole-2-carboxamide |
| 460 | 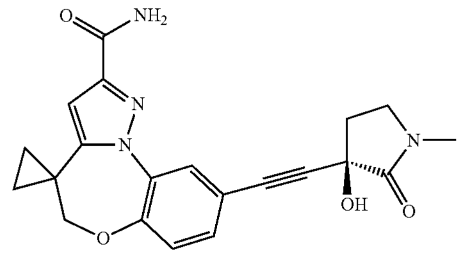 [SMILES: CN1CC[C@@](O)(C#Cc2ccc3c(c2)-n2nc(C(N)=O)cc2C2(CC2)CO3)C1=O] | 9-[2-[(3R)-3-hydroxy-1-methyl-2-oxopyrrolidin-3-yl]ethynyl]spiro[5H-pyrazolo[5,1-d][1,5]benzoxazepine-4,1'-cyclopropane]-2-carboxamide |
| 461 | 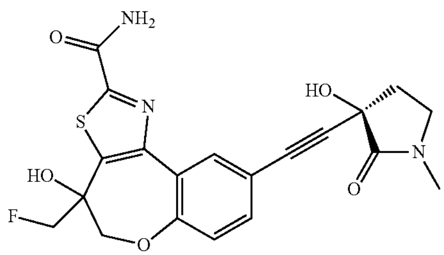 [SMILES: CN1CC[C@@](O)(C#Cc2ccc3c(c2)-c2nc(C(N)=O)sc2C(O)(CF)CO3)C1=O] | 4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 462 | 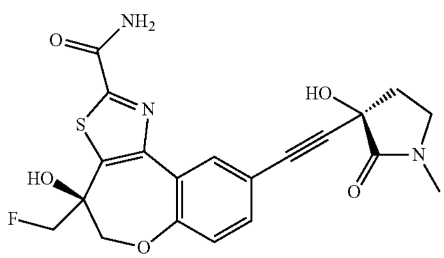 [SMILES: CN1CC[C@@](O)(C#Cc2ccc3c(c2)-c2nc(C(N)=O)sc2[C@@](O)(CF)CO3)C1=O] | (S)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 463 | 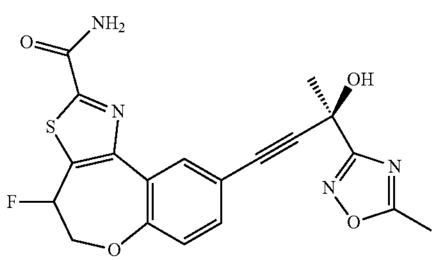 [SMILES: Cc1nc([C@](C)(O)C#Cc2ccc3c(c2)-c2nc(C(N)=O)sc2C(F)CO3)no1] | 4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 464 | 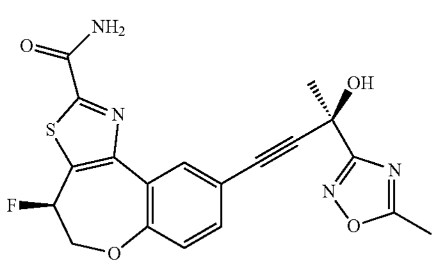 [SMILES: Cc1nc([C@](C)(O)C#Cc2ccc3c(c2)-c2nc(C(N)=O)sc2[C@H](F)CO3)no1] | (R)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |

TABLE 1-continued

| No. | Structure | Name |
|---|---|---|
| 465 | 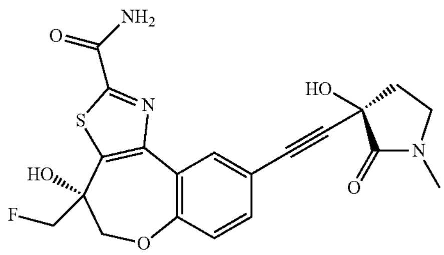 | (R)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 466 | 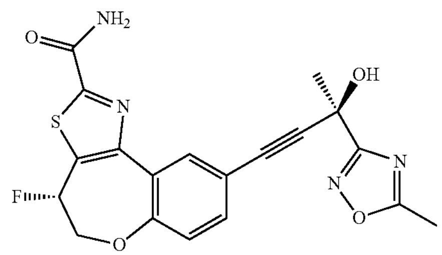 [SMILES: Cc1nc([C@](C)(O)C#Cc2ccc3c(c2)-c2nc(C(N)=O)sc2[C@@H](F)CO3)no1] | (S)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 467 | 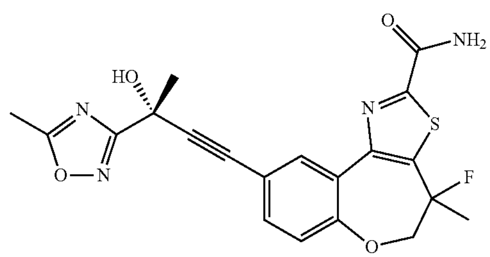 | 4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |
| 468 | 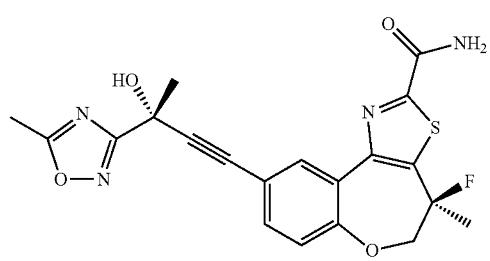 | (S)-4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |
| 469 | 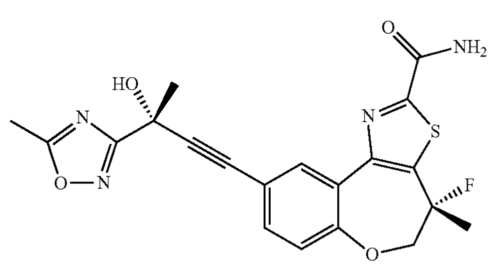 | (R)-4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |
| 470 | 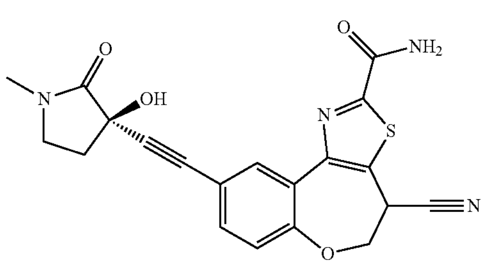 [SMILES: CN1CC[C@@](O)(C#Cc2ccc3c(c2)-c2nc(C(N)=O)sc2C(C#N)CO3)C1=O] | 4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |

TABLE 1-continued

| No. | Structure | Name |
|---|---|---|
| 471 | 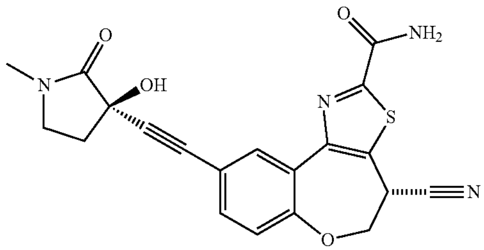 [SMILES: CN1CC[C@@](O)(C#Cc2ccc3c(c2)-c2nc(C(N)=O)sc2[C@H](C#N)CO3)C1=O] | (R)-4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |
| 472 | 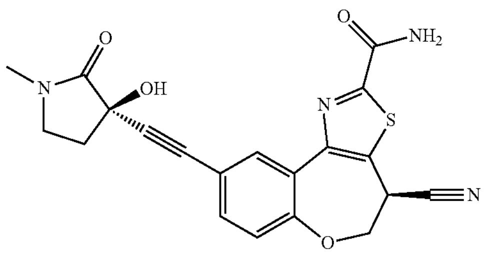 [SMILES: CN1CC[C@@](O)(C#Cc2ccc3c(c2)-c2nc(C(N)=O)sc2[C@@H](C#N)CO3)C1=O] | (S)-4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |
| 473 | 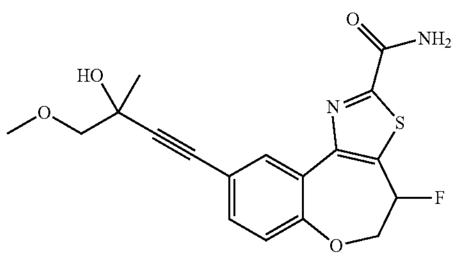 [SMILES: COCC(C)(O)C#Cc1ccc2c(c1)-c1nc(C(N)=O)sc1C(F)CO2] | (S)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 474 | 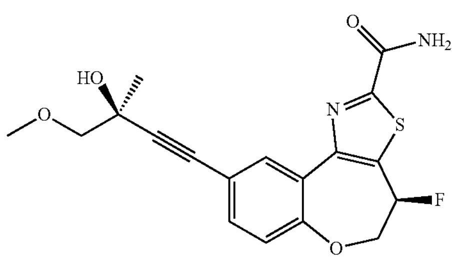 [SMILES: COC[C@@](C)(O)C#Cc1ccc2c(c1)-c1nc(C(N)=O)sc1[C@@H](F)CO2] | (S)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 475 | 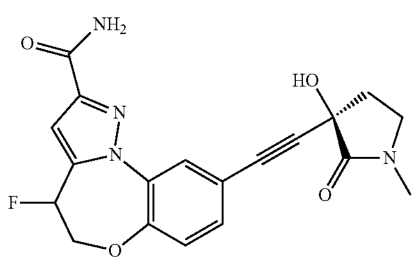 | 4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxaide |
| 476 | 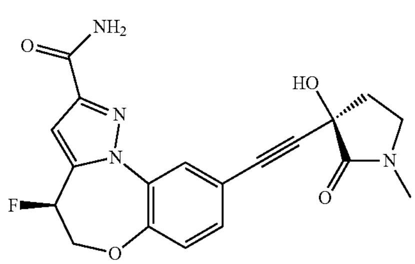 | (S)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1-continued

| No. | Structure | Name |
|---|---|---|
| 477 | 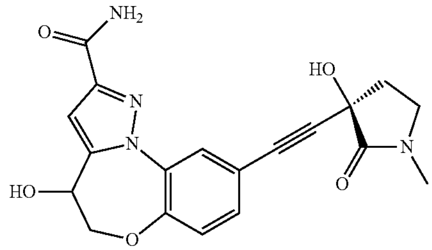 [SMILES: CN1CC[C@@](O)(C#Cc2ccc3c(c2)-n2nc(C(N)=O)cc2C(O)CO3)C1=O] | 4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 478 | 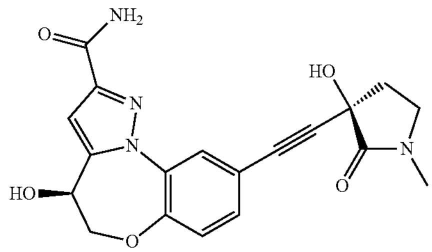 [SMILES: CN1CC[C@@](O)(C#Cc2ccc3c(c2)-n2nc(C(N)=O)cc2[C@H](O)CO3)C1=O] | (S)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 479 | 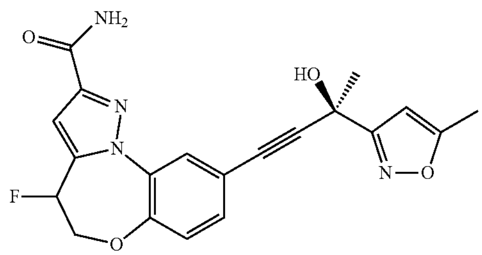 [SMILES: Cc1cc([C@](C)(O)C#Cc2ccc3c(c2)-n2nc(C(N)=O)cc2C(F)CO3)no1] | 4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 480 | 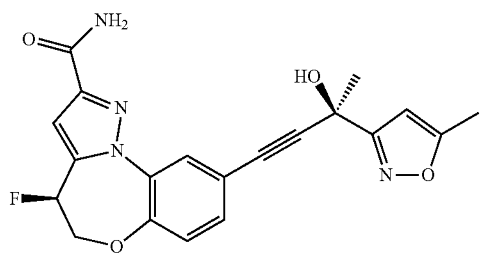 [SMILES: Cc1cc([C@](C)(O)C#Cc2ccc3c(c2)-n2nc(C(N)=O)cc2[C@H](F)CO3)no1] | (S)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 481 | 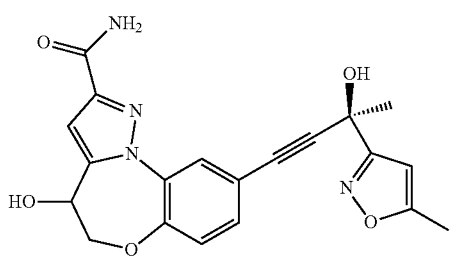 | 4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 482 | 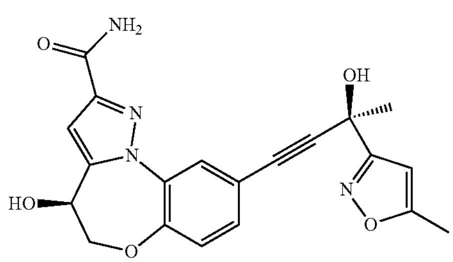 [SMILES: Cc1cc([C@](C)(O)C#Cc2ccc3c(c2)-n2nc(C(N)=O)cc2[C@H](O)CO3)no1] | (S)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |

| No. | Structure | Name |
|---|---|---|
| 483 | 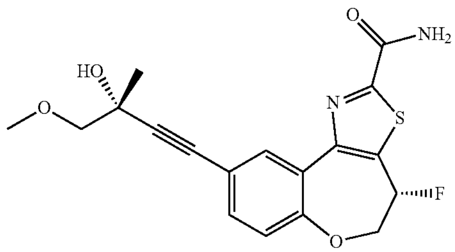 [SMILES: COC[C@](C)(O)C#Cc1ccc2c(c1)-c1nc(C(N)=O)sc1[C@H](F)CO2] | (R)-4-fluoro-9-((R)-3-hydroxy-4-methoxy-3-methylbut-1-yn-1-yl)-4,5-dihydrobenzo[2,3]oxepino[4,5-d]thiazole-2-carboxamide |
| 484 | 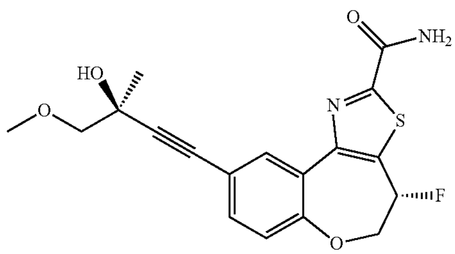 [SMILES: COC[C@@](C)(O)C#Cc1ccc2c(c1)-c1nc(C(N)=O)sc1[C@H](F)CO2] | (R)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 485 | 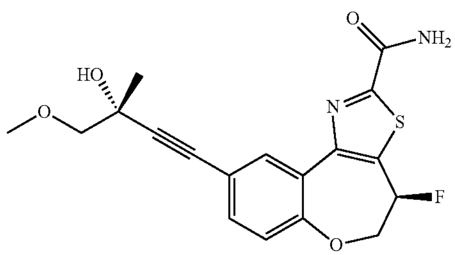 [SMILES: COC[C@](C)(O)C#Cc1ccc2c(c1)-c1nc(C(N)=O)sc1[C@@H](F)CO2] | (S)-4-fluoro-9-((R)-3-hydroxy-4-methoxy-3-methylbut-1-yn-1-yl)-4,5-dihydrobenzo[2,3]oxepino[4,5-d]thiazole-2-carboxamide |
| 486 | 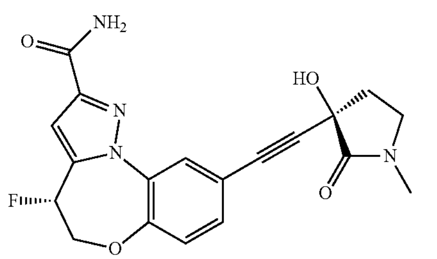 [SMILES: CN1CC[C@@](O)(C#Cc2ccc3c(c2)-n2nc(C(N)=O)cc2[C@@H](F)CO3)C1=O] | (R)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 487 | 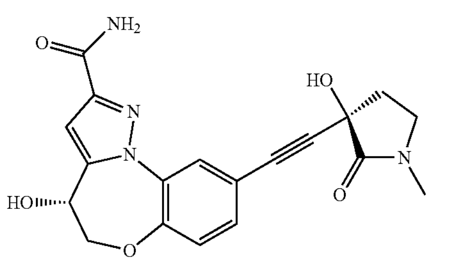 [SMILES: CN1CC[C@@](O)(C#Cc2ccc3c(c2)-n2nc(C(N)=O)cc2[C@@H](O)CO3)C1=O] | (R)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 488 | 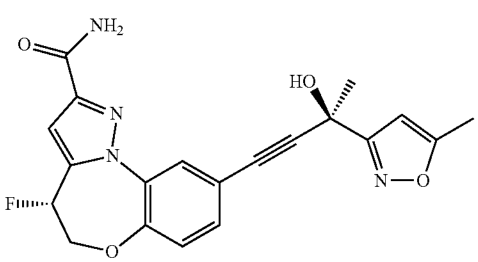 [SMILES: Cc1cc([C@](C)(O)C#Cc2ccc3c(c2)-n2nc(C(N)=O)cc2[C@@H](F)CO3)no1] | (R)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |

TABLE 1-continued

| No. | Structure | Name |
|---|---|---|
| 489 | 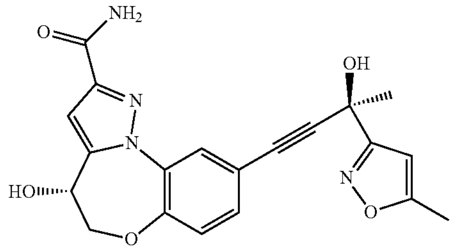 | (R)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 490 | 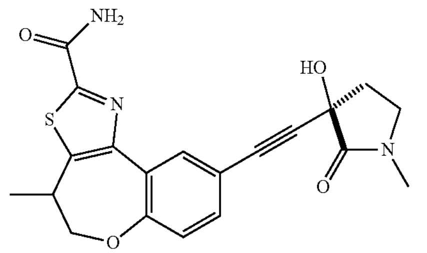 | 9-[2-((R)-3-hydroxy-1-methyl-2-oxopyrrolidin-3-yl)ethynyl]-4-methyl-4,5-dihydro-[1]benzoxepino[5,4-d]thiazole-2-carboxamide |
| 491 | 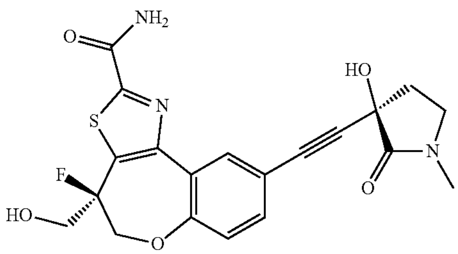 [SMILES: CN1CC[C@@](O)(C#Cc2ccc3c(c2)-c2nc(C(N)=O)sc2[C@@](F)(CO)CO3)C1=O] | (R)-4-fluoro-9-(((R)-3-hydroxy-i-methyl-2-oxopyrrolidin-3-yl)ethynyl)-4-(hydroxymethyl)-4,5-dihydrobenzo[2,3]oxepino[4,5-d]thiazole-2-carboxamide |
| 492 | 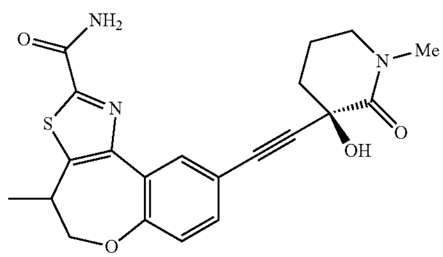 | 9-(((R)-3-hydroxy-1-methyl-2-oxopiperidin-3-yl)ethynyl)-4-methyl-4,5-dihydrobenzo[2,3]oxepino[4,5-d]thiazole-2-carboxamide |
| 493 | 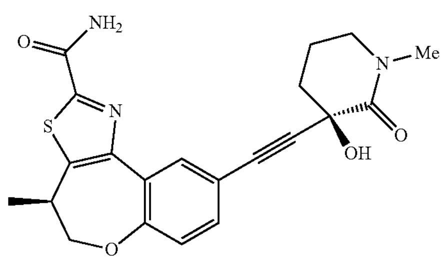 | (R)-9-(((R)-3-hydroxy-1-methyl-2-oxopiperidin-3-yl)ethynyl)-4-methyl-4,5-dihydrobenzo[2,3]oxepino[4,5-d]thiazole-2-carboxamide |
| 494 | 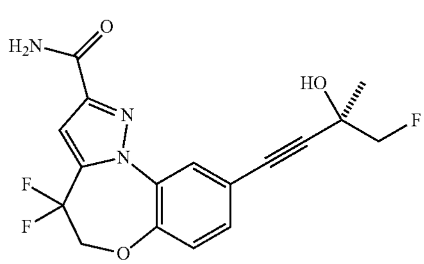 [SMILES: C[C@@](O)(C#Cc1ccc2c(c1)-n1nc(C(N)=O)cc1C(F)(F)CO2)CF] | 4,4-difluoro-9-(4-fluoro-(R)-3-hydroxy-3-methyl-but-1-ynyl)-5H-pyrazolo[5,1-d][1,5]benzoxazepine-2-carboxamide |

TABLE 1-continued

| No. | Name |
|---|---|
| 495 | 9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 496 | (S)-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 497 | 9-[3-(R)-hydroxy-3-(5-methyl-1,3,4-oxadiazol-2-yl)but-1-ynyl]-4-methyl-4,5-dihydropyrazolo[5,1-d][1,5]benzoxazepine-2-carboxamide |
| 498 | 9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |
| 499 | (R)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |

TABLE 1-continued

| No. | Structure | Name |
|---|---|---|
| 500 | 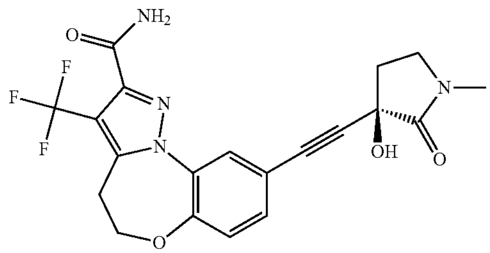 [SMILES: CN1CC[C@@](O)(C#Cc2ccc3c(c2)-n2nc(C(N)=O)c(C(F)(F)F)c2CCO3)C1=O] | 9-[2-[(3R)-3-hydroxy-1-methyl-2-oxo-pyrrolidin-3-yl]ethynyl]-3-(trifluoromethyl)-4,5-dihydropyrazolo[5,1-d][1,5]benzoxazepine-2-carboxamide |
| 501 | 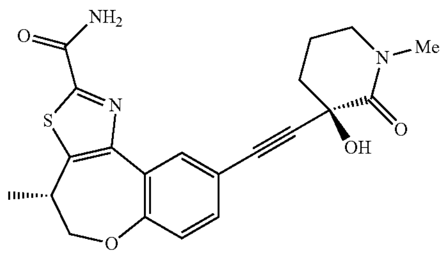 [SMILES: C[C@H]1COc2ccc(C#C[C@]3(O)CCCN(C)C3=O)cc2-c2nc(C(N)=O)sc21] | (S)-9-(((R)-3-hydroxy-1-methyl-2-oxo-piperidin-3-yl)ethynyl)-4-methyl-4,5-dihydrobenzo[2,3]oxepino[4,5-d]thiazole-2-carboxamie |
| 502 | 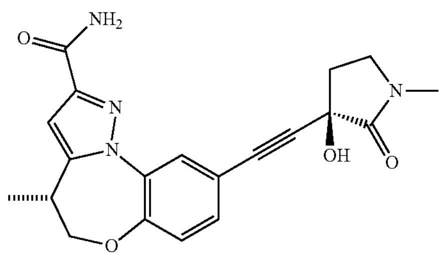 | (R)-9-(((R)-3-hydroxy-1-methyl-2-oxo-pyrrolidin-3-yl)ethynyl)-4-methyl-4,5-dihydrobenzo[b]pyrazolo[1,5-d][1,4]oxazepine-2-carboxamide |
| 503 | 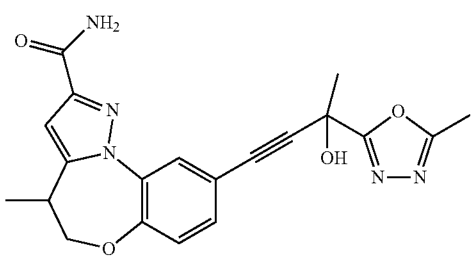 | 9-[3-hydroxy-3-(5-methyl-1,3,4-oxadiazol-2-yl)but-1-ynyl]-4-methyl-4,5-dihydropyrazolo[5,1-d][1,5]benzoxazepine-2-carboxamide |
| 504 | 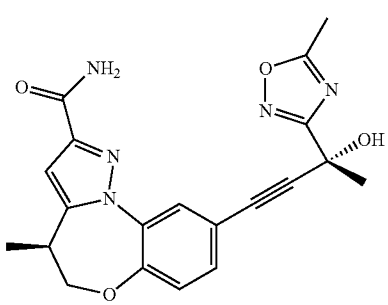 [SMILES: Cc1nc([C@](C)(O)C#Cc2ccc3c(c2)-n2nc(C(N)=O)cc2[C@H](C)CO3)no1] | (S)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |
| 505 | 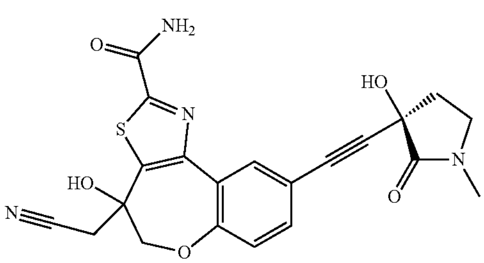 | 4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1-continued

| No. | Structure | Name |
|---|---|---|
| 506 | 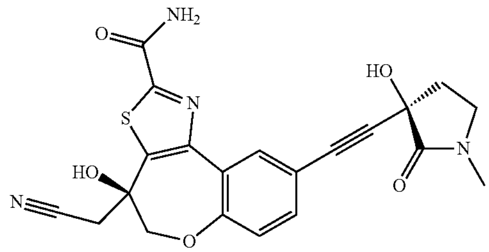 [SMILES: CN1CC[C@@](O)(C#Cc2ccc3c(c2)-c2nc(C(N)=O)sc2[C@@](O)(CC#N)CO3)C1=O] | (R)-4-(cyanomethyl)-4-hydroxy-9-(((R)-3-hydroxy-1-[methyl-2-oxopyrrolidin-3-yl]ethynyl)-4,5-dihydrobenzo[2,3]oxepino[4,5-d]thiazole-2-carboxamide |
| 507 | 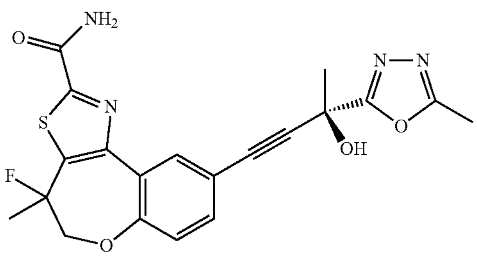 [SMILES: Cc1nnc([C@](C)(O)C#Cc2ccc3c(c2)-c2nc(C(N)=O)sc2C(C)(F)CO3)o1] | 4-fluoro-9-((R)-3-hydroxy-3-(5-methyl-1,3,4-oxadiazol-2-yl)but-1-yn-1-y)-4-methyl-4,5-dihydrobenzo[2,3]oxepino[4,5-d]thiazole-2-carboxamide |
| 508 | 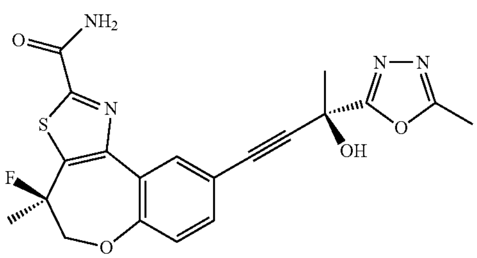 [SMILES: Cc1nnc([C@](C)(O)C#Cc2ccc3c(c2)-c2nc(C(N)=O)sc2[C@](C)(F)CO3)o1] | (R)-4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide |
| 509 | 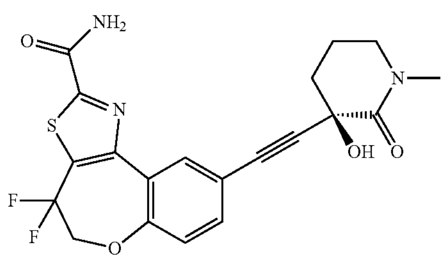 [SMILES: CN1CCC[C@@](O)(C#Cc2ccc3c(c2)-c2nc(C(N)=O)sc2C(F)(F)CO3)C1=O] | 4,4-difluoro-9-[2-[(3R)-3-hydroxy-1-methyl-2-oxo-3-piperidyl]ethynyl]-5H-[1]benzoxepino[5,4-d]thiazole-2-carboxamide |
| 510 | 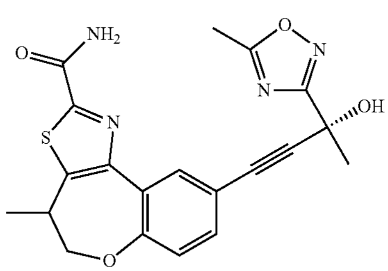 [SMILES: Cc1nc([C@](C)(O)C#Cc2ccc3c(c2)-c2nc(C(N)=O)sc2C(C)CO3)no1] | 9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 511 | 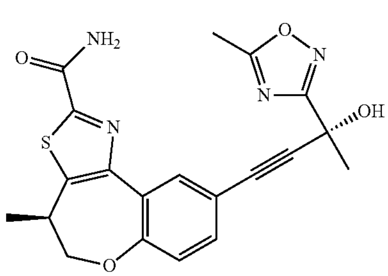 [SMILES: Cc1nc([C@](C)(O)C#Cc2ccc3c(c2)-c2nc(C(N)=O)sc2[C@H](C)CO3)no1] | (R)-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |

TABLE 1-continued

| No. | Structure | Name |
|---|---|---|
| 512 | 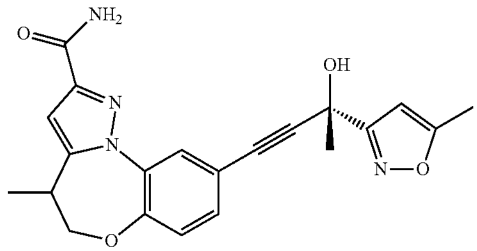 | 9-((S)-3-hydroxy-3-(5-methylisoxazol-3-yl)but-1-yn-1-yl)-4-methyl-4,5-dihydro-benzo[b]pyrazolo[1,5-d][1,4]oxazepine-2-carboxamide |
| 513 | 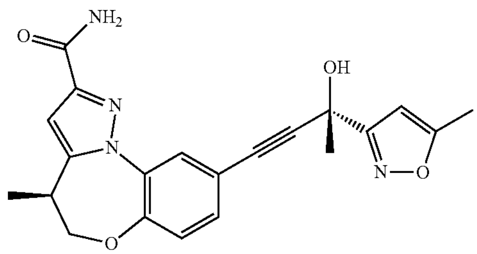 | (R)-9-((S)-3-hydroxy-3-(5-methylisoxazol-3-yl)but-1-yn-1-yl)-4-methyl-4,5-di-hydrobenzo[b]pyrazolo[1,5-d][1,4]oxa-zepine-2-carboxamide |
| 514 | 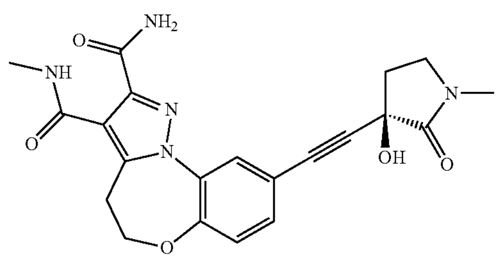 | 9-[2-[(3R)-3-hydroxy-1-methyl-2-oxo-pyrrolidin-3-yl]ethynyl]-N3-methyl-4,5-dihydropyrazolo[5,1-d][1,5]benzoxazepine-2,3-dicarboxamide |
| 515 | 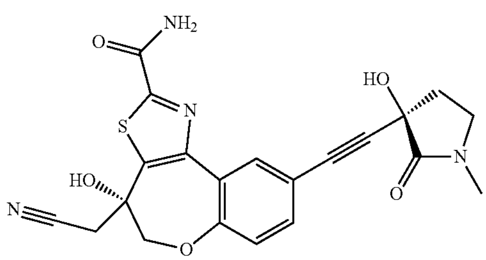 [SMILES: CN1CC[C@@](O)(C#Cc2ccc3c(c2)-c2nc(C(N)=O)sc2[C@](O)(CC#N)CO3)C1=O] | (S)-4-(cyanomethyl)-4-hydroxy-9-(((R)-3-hydroxy-1-methyl-2-oxopyrrolidin-3-yl)ethynyl)-4,5-dihydrobenzo[2,3]oxe-pino[4,5-d]thiazole-2-carboxamide |
| 516 | 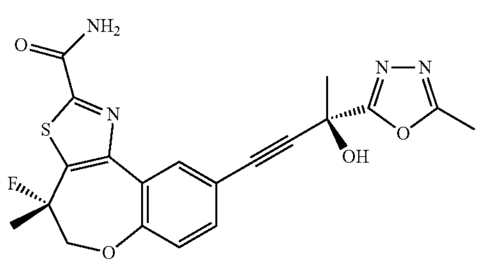 [SMILES: Cc1nnc([C@](C)(O)C#Cc2ccc3c(c2)-c2nc(C(N)=O)sc2[C@@](C)(F)CO3)o1] | (S)-4-fluoro-9-((R)-3-hydroxy-3-(5-methyl-1,3,4-oxadiazol-2-yl)but-1-yn-1-yl)-4-methyl-4,5-dihydrobenzo[2,3]oxe-pino[4,5-d]thiazole-2-carboxamide |
| 517 | 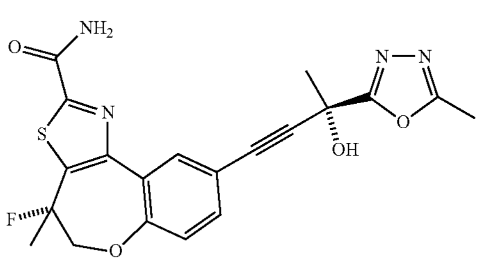 [SMILES: Cc1nnc([C@@](C)(O)C#Cc2ccc3c(c2)-c2nc(C(N)=O)sc2[C@@](C)(F)CO3)o1] | 4-(S)-fluoro-9-[3-(S)-hydroxy-3-(5-meth-yl-1,3,4-oxadiazol-2-yl)but-1-ynyl]-4-methyl-5H-[1]benzoxepino[5,4-d]thia-zole-2-carboxamide |

TABLE 1-continued

| No. | Structure | Name |
|---|---|---|
| 518 | 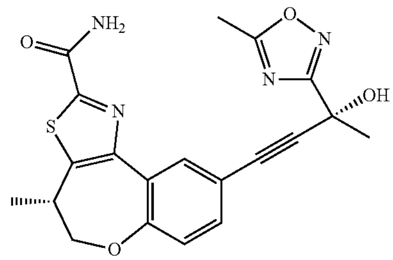 [SMILES: Cc1nc([C@](C)(O)C#Cc2ccc3c(c2)-c2nc(C(N)=O)sc2[C@@H](C)CO3)no1] | (S)-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 519 | 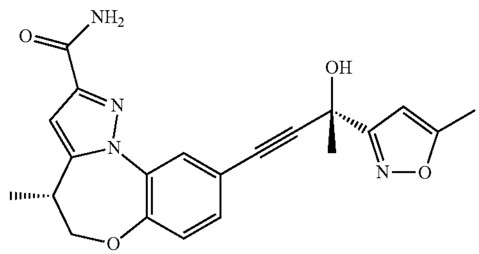 | (S)-9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 520 | 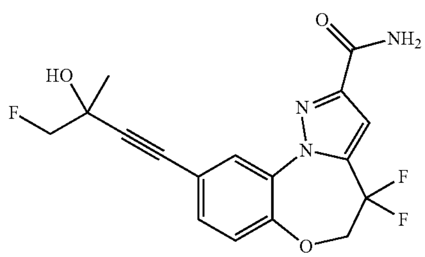 [SMILES: CC(O)(C#Cc1ccc2c(c1)-n1nc(C(N)=O)cc1C(F)(F)CO2)CF] | 4,4-difluoro-9-(4-fluoro-3-hydroxy-3-methyl-but-1-ynyl)-5H-pyrazolo[5,1-d][1,5]benzoxazepine-2-carboxamide |
| 521 | 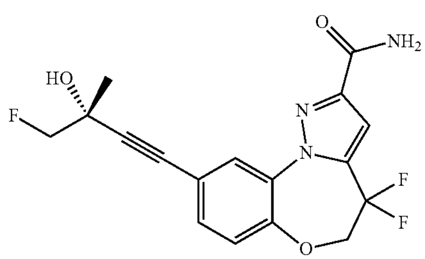 [SMILES: C[C@@](O)(C#Cc1ccc2c(c1)-n1nc(C(N)=O)cc1C(F)(F)CO2)CF] | 4,4-difluoro-9-(4-fluoro-(R)-3-hydroxy-3-methyl-but-1-ynyl)-5H-pyrazolo[5,1-d][1,5]benzoxazepine-2-carboxamide |
| 522 | 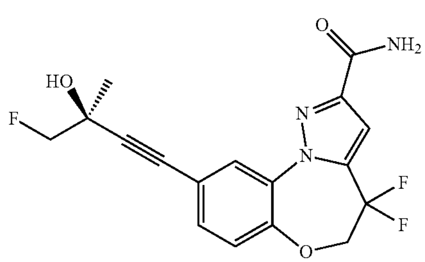 [SMILES: C[C@](O)(C#Cc1ccc2c(c1)-n1nc(C(N)=O)cc1C(F)(F)CO2)CF] | 4,4-difluoro-9-(4-fluoro-3-(S)-hydroxy-3-methyl-but-1-ynyl)-5H-pyrazolo[5,1-d1,5]benzoxazepine-2-carboxamide |
| 523 | 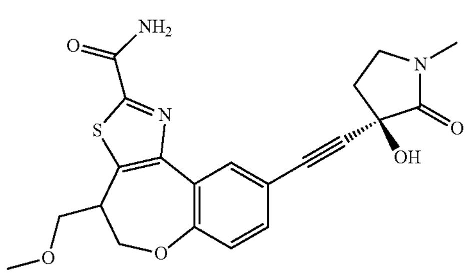 | 9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide |

TABLE 1-continued

| No. | Structure | Name |
|---|---|---|
| 524 | 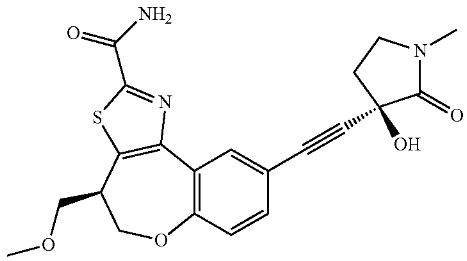 | (R)-9-(((R)-3-hydroxy-1-methyl-2-oxo-pyrrolidin-3-yl)ethynyl)-4-(methoxymethyl)-4,5-dihydrobenzo[2,3]oxepino[4,5-d]thiazole-2-carboxamide |
| 525 | 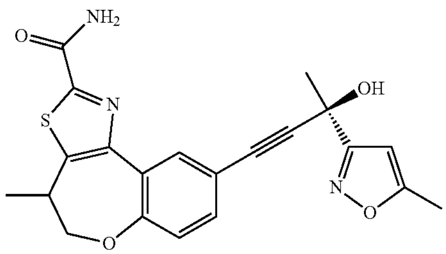 | 9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 526 | 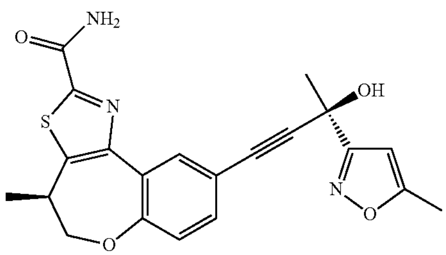 | (R)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 527 | 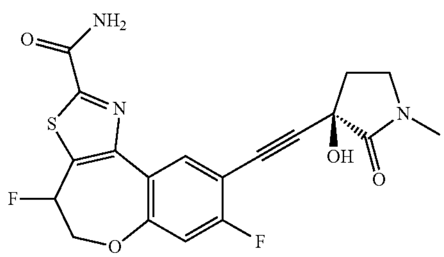 [SMILES: CN1CC[C@@](O)(C#Cc2cc3c(cc2F)OCC(F)c2sc(C(N)=O)nc2-3)C1=O] | 7,12-difluoro-13-[2-[(3R)-3-hydroxy-1-methyl-2-oxopyrrolidin-3-yl]ethynyl]-9-oxa-5-thia-3-azatricyclo[8.4.0.0[2,6]]tetradeca-1(10),2(6),3,11,13-pentaene-4-carboxamide |
| 528 | 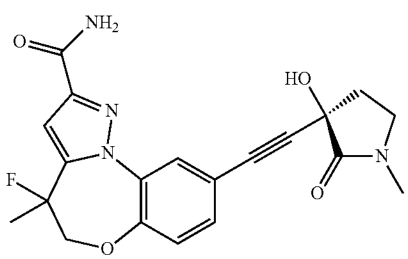 [SMILES: CN1CC[C@@](O)(C#Cc2ccc3c(c2)-n2nc(C(N)=O)cc2C(C)(F)CO3)C1=O] | 4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 529 | 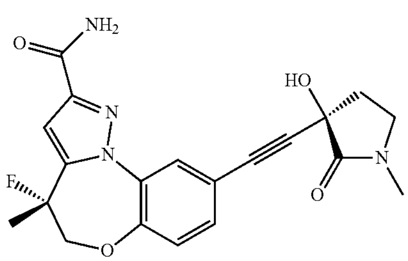 [SMILES: CN1CC[C@@](O)(C#Cc2ccc3c(c2)-n2nc(C(N)=O)cc2[C@@](C)(F)CO3)C1=O] | (R)-4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |

TABLE 1-continued

| No. | Structure | Name |
|---|---|---|
| 530 | 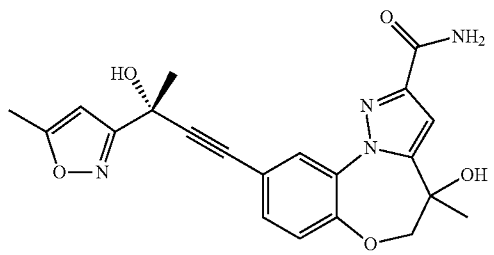 | 4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxamide |
| 531 | 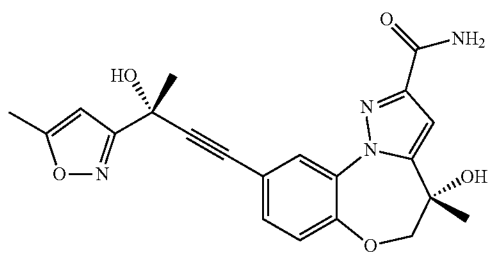 | (S)-4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxmide |
| 532 | 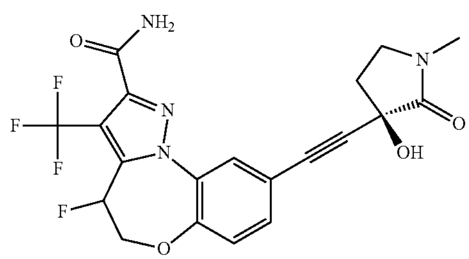 [SMILES: CN1CC[C@@](O)(C#Cc2ccc3c(c2)-n2nc(C(N)=O)c(C(F)(F)F)c2C(F)CO3)C1=O] | 4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 533 | 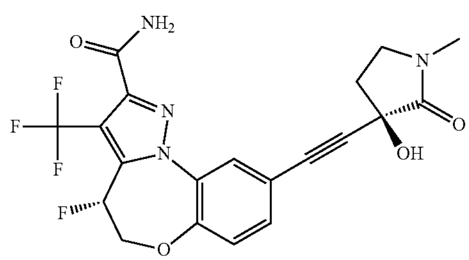 [SMILES: CN1CC[C@@](O)(C#Cc2ccc3c(c2)-n2nc(C(N)=O)c(C(F)(F)F)c2[C@@H](F)CO3)C1=O] | (R)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 534 | 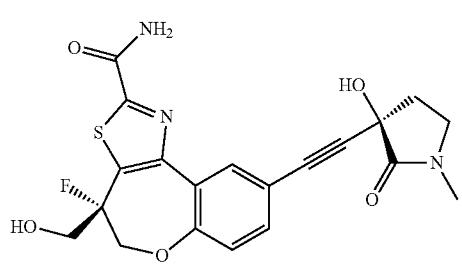 [SMILES: CN1CC[C@@](O)(C#Cc2ccc3c(c2)-c2nc(C(N)=O)sc2[C@](F)(CO)CO3)C1=O] | (S)-4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 535 | 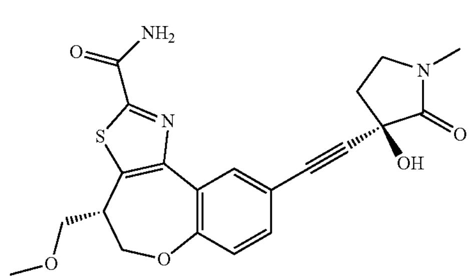 | (S)-9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide |

TABLE 1-continued

| No. | Structure | Name |
|---|---|---|
| 536 | 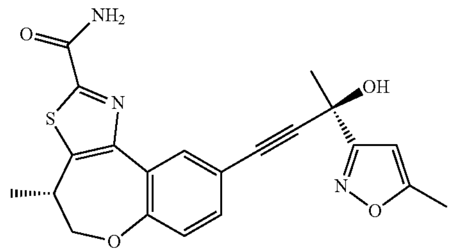 | (S)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 537 | 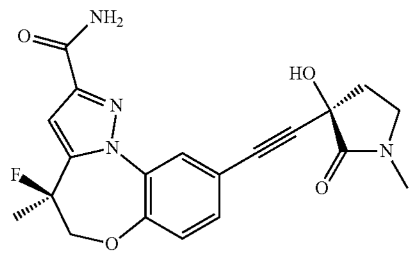 [SMILES: CN1CC[C@@](O)(C#Cc2ccc3c(c2)-n2nc(C(N)=O)cc2[C@](C)(F)CO3)C1=O] | (S)-4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 538 | 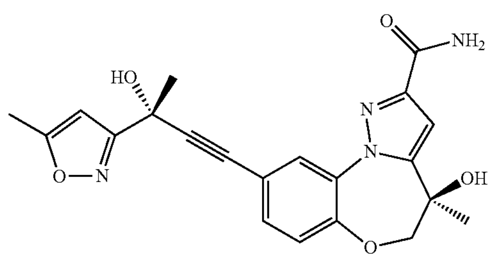 | (R)-4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxamide |
| 539 | 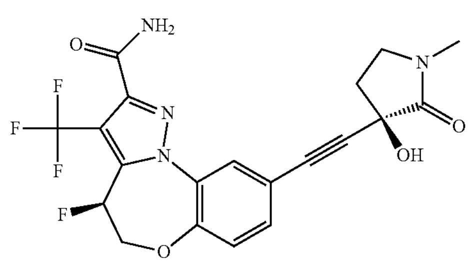 [SMILES: CN1CC[C@@](O)(C#Cc2ccc3c(c2)-n2nc(C(N)=O)c(C(F)(F)F)c2[C@H](F)CO3)C1=O] | (S)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 540 | 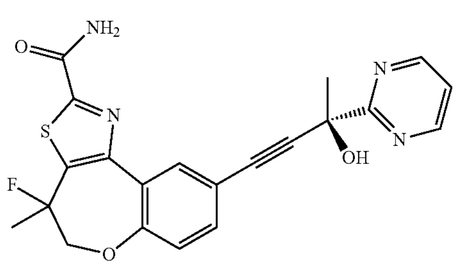 [SMILES: CC1(F)COc2ccc(C#C[C@@](C)(O)c3ncccn3)cc2-c2nc(C(N)=O)sc21] | 4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 541 | 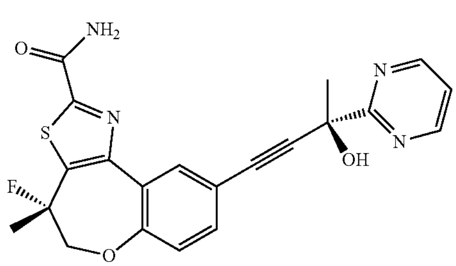 [SMILES: C[C@]1(F)COc2ccc(C#C[C@@](C)(O)c3ncccn3)cc2-c2nc(C(N)=O)sc21] | (S)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |

| No. | Structure | Name |
|---|---|---|
| 542 | 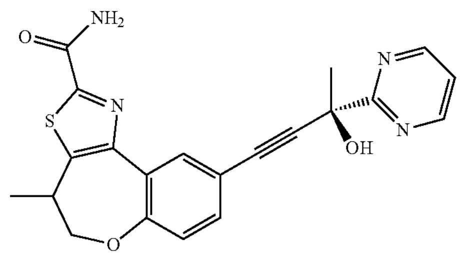 | 9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 543 | 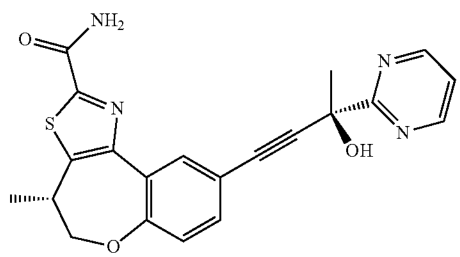 | (S)-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 544 | 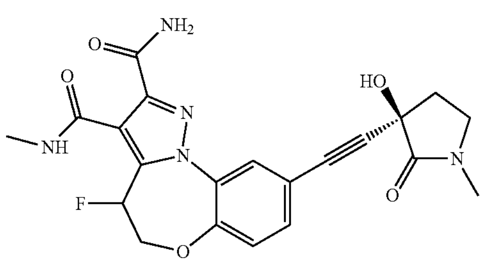 | 4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |
| 545 | 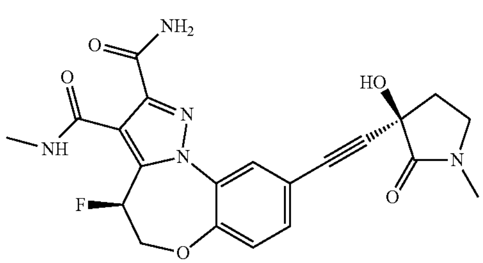 | (S)-4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |
| 546 | 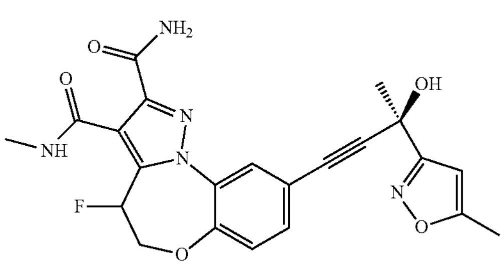 | 4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |
| 547 | 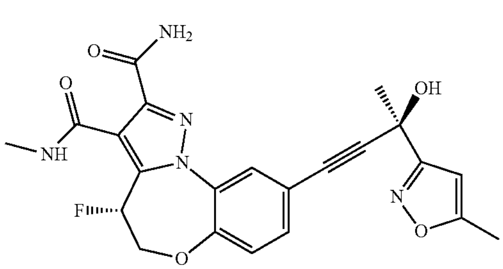 | (R)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |

TABLE 1-continued

| No. | Structure | Name |
|---|---|---|
| 548 | 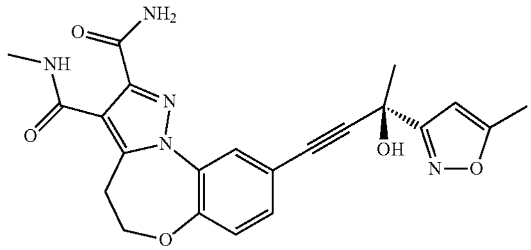 | 9-[(3R)-3-hydroxy-3-(5-methylisoxazol-3-yl)but-1-ynyl]-N3-methyl-4,5-dihydro-pyrazolo[5,1-d][1,5]benzoxazepine-2,3-dicarboxamide |
| 549 | 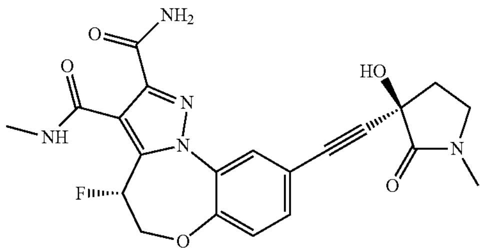 | (R)-4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |
| 550 | 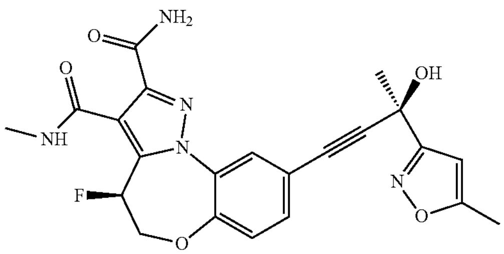 | (S)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |
| 551 | 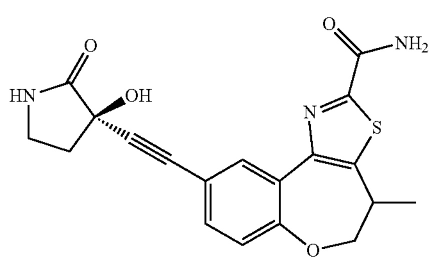 [SMILES: CC1COc2ccc(C#C[C@]3(O)CCNC3=O)cc2-c2nc(C(N)=O)sc21] | 9-[2-((R)-3-hydroxy-2-oxo-pyrrolidin-3-yl)ethynyl]-4-methyl-4,5-dihydro-[1]benzoxepino[5,4-d]thiazole-2-carboxamide |
| 552 | 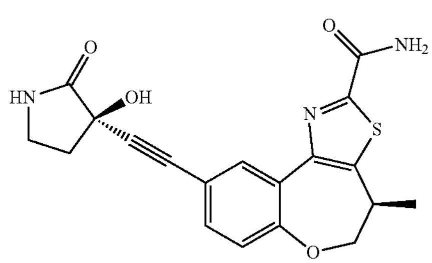 | 9-[2-((R)-3-hydroxy-2-oxo-pyn-olidin-3-yl)ethynyl]-(S)-4-methyl-4,5-dihydro-[1]benzoxepino[5,4-d]thiazole-2-carboxamide |
| 553 | 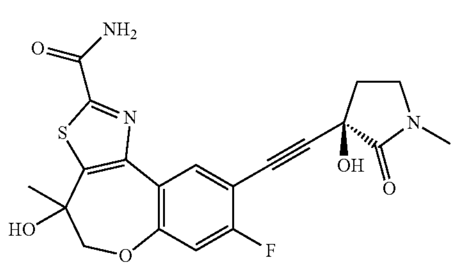 | 8-fluoro-4-hydroxy-9-[2-((R)-3-hydroxy-1-methyl-2-oxo-pyrrolidin-3-yl)ethynyl]-4-methyl-5H-[1]benzoxepino[5,4-d]thiazole-2-carboxamide |

TABLE 1-continued

| No. | Structure | Name |
|---|---|---|
| 554 | 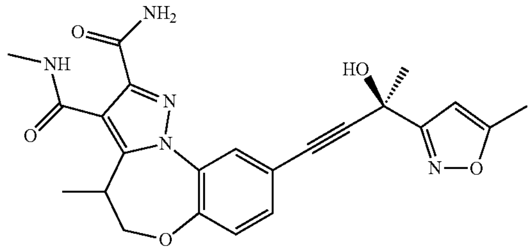 | 9-[(R)-3-hydroxy-3-(5-methylisoxazol-3-yl)but-1-ynyl]-N3,4-dimethyl-4,5-dihydropyrazolo[5,1-d][1,5]benzoxazepine-2,3-dicarboxamide |
| 555 | 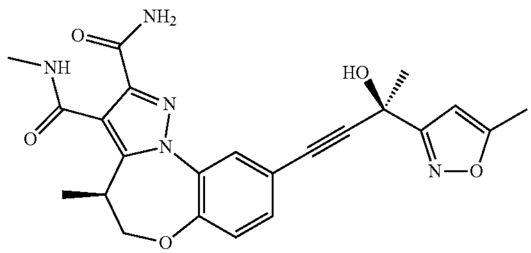 | 9-[(R)-3-hydroxy-3-(5-methylisoxazol-3-yl)but-1-ynyl]-N3,4-(S)-dimethyl-4,5-dihydropyrazolo[5,1-d][1,5]benzoxazepine-2,3-dicarboxamide |
| 556 | 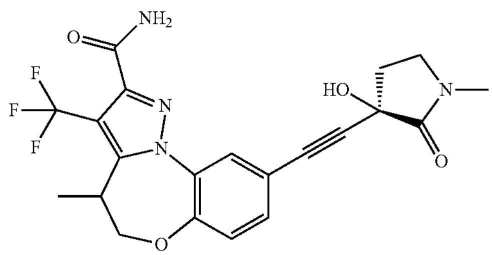 [SMILES: CC1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-methyl-3-(trifluoromethyl)-4,5-dihydropyrazolo[5,1-d][1,5]benzoxazepine-2-carboxamide |
| 557 | 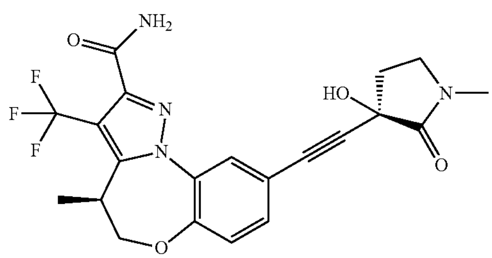 [SMILES: C[C@@H]1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-(S)-methyl-3-(trifluoromethyl)-4,5-dihydropyrazolo[5,1-d][1,5]benzoxazepine-2-carboxamide |
| 558 | 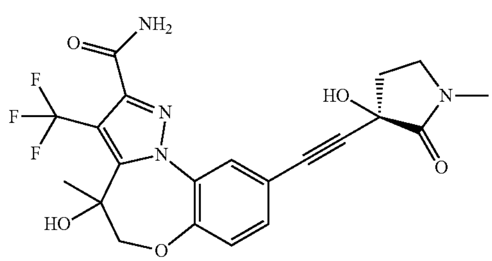 [SMILES: CN1CC[C@@](O)(C#Cc2ccc3c(c2)-n2nc(C(N)=O)c(C(F)(F)F)c2C(C)(O)CO3)C1=O] | 4-hydroxy-9-[2-((R)-3-hydroxy-1-methyl-2-oxo-pyrrolidin-3-yl)ethynyl]-4-methyl-3-(trifluoromethyl)-5H-pyrazolo[5,1-d][1,5]benzoxazepine-2-carboxamide |
| 559 | 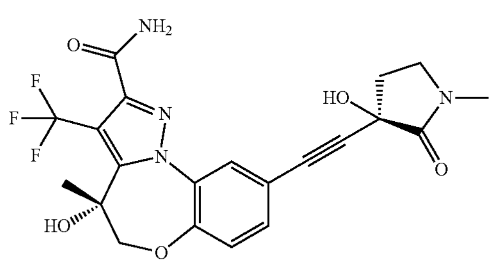 [SMILES: CN1CC[C@@](O)(C#Cc2ccc3c(c2)-n2nc(C(N)=O)c(C(F)(F)F)c2[C@@](C)(O)CO3)C1=O] | (R)-4-hydroxy-9-[2-((R)-3-hydroxy-1-methyl-2-oxo-pyrrolidin-3-yl)ethynyl]-4-methyl-3-(trifluoromethyl)-5H-pyrazolo[5,1-d][1,5]benzoxazepine-2-carboxamide |

TABLE 1-continued

| No. | Structure | Name |
|---|---|---|
| 560 | 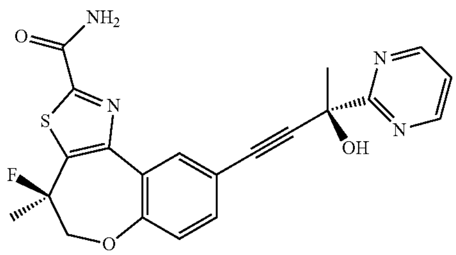 [SMILES: C[C@@](O)(C#Cc1ccc2c(c1)-c1nc(C(N)=O)sc1[C@](C)(F)CO2)c1ncccn1] | (R)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 561 | 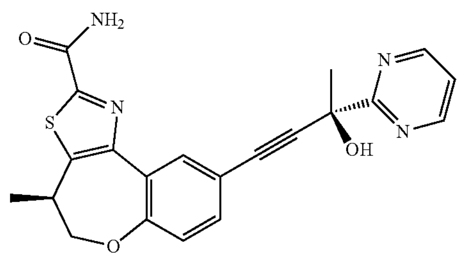 [SMILES: C[C@@H]1COc2ccc(C#C[C@@](C)(O)c3ncccn3)cc2-c2nc(C(N)=O)sc21] | (R)-9-((R)-3-hydroxy-3-(pyrimidin-2-yl)but-1-yn-1-yl)-4-methyl-4,5-dihydro-benzo[2,3]oxepino[4,5-d]thiazole-2-carboxamide |
| 562 | 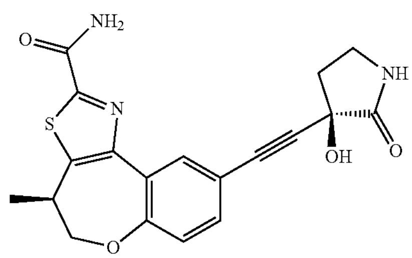 [SMILES: C[C@@H]1COc2ccc(C#C[C@]3(O)CCNC3=O)cc2-c2nc(C(N)=O)sc21] | 9-[2-((R)-3-hydroxy-2-oxo-pyrrolidin-3-yl)ethynyl]-(R)-4-methyl-4,5-dihydro-[1]benzoxepino[5,4-d]thiazole-2-carboxamide |
| 563 | 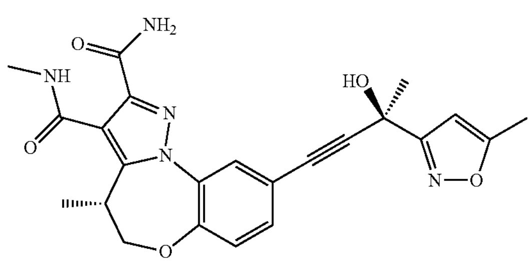 | 9-[(R)-3-hydroxy-3-(5-methylisoxazol-3-yl)but-1-ynyl]-N3,4-(R)-dimethyl-4,5-dihydropyrazolo[5,1-d][1,5]benzoxazepine-2,3-dicarboxamide |
| 564 | 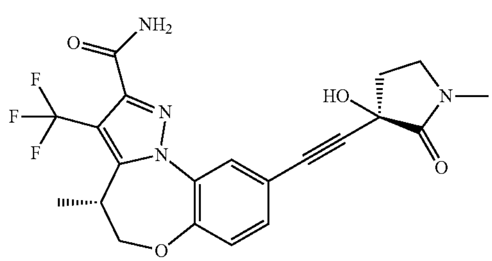 [SMILES: C[C@H]1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-(R)-methyl-3-(trifluoromethyl)-4,5-dihydropyrazolo[5,1-d][1,5]benzoxazepine-2-carboxamide |
| 565 | 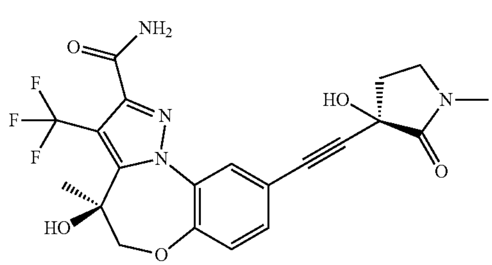 [SMILES: CN1CC[C@@](O)(C#Cc2ccc3c(c2)-n2nc(C(N)=O)c(C(F)(F)F)c2[C@](C)(O)CO3)C1=O] | (S)-4-hydroxy-9-[2-((R)-3-hydroxy-1-methyl-2-oxo-pyrrolidin-3-yl)ethynyl]-4-methyl-3-(trifluoromethyl)-5H-pyiazolo[5,1-d][1,5]benzoxazepine-2-carboxamide |

TABLE 1-continued

| No. | Structure | Name |
|---|---|---|
| 566 | 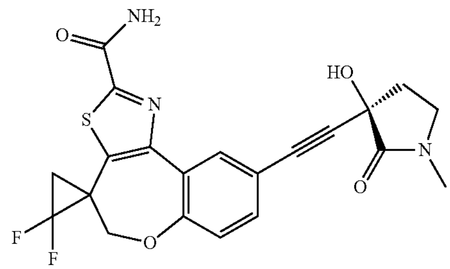 | 1',1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 567 | 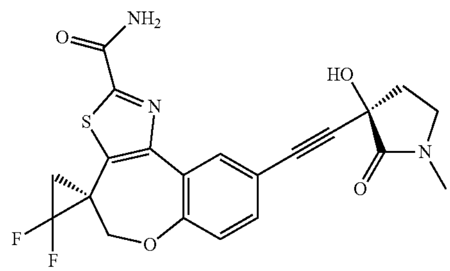 [SMILES: CN1CC[C@@](O)(C#Cc2ccc3c(c2)-c2nc(C(N)=O)sc2C2(CO3)CC2(F)F)C1=O] | (S)-1'1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 568 | 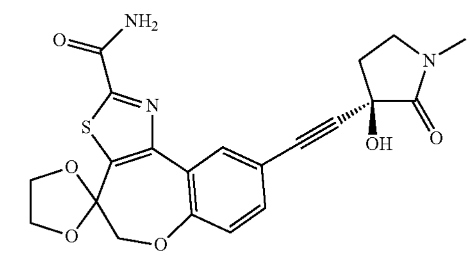 [SMILES: CN1CC[C@@](O)(C#Cc2ccc3c(c2)-c2nc(C(N)=O)sc2C2(CO3)OCCO2)C1=O] | 9'-[2-[(3R)-3-hydroxy-1-methyl-2-oxo-pyrrolidin-3-yl]ethynyl]spiro[1,3-dioxolane-2,4'-5H-[1]benzoxepino[5,4-d]thiazole]-2'-carboxamide |
| 569 | 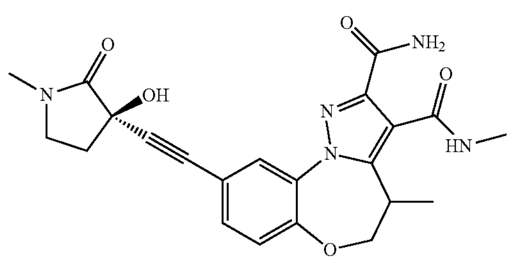 | 9-[2-((R)-3-hydroxy-1-methyl-2-oxo-pyrrolidin-3-yl)ethynyl]-N3,4-dimethyl-4,5-dihydropyrazolo[5,1-d][1,5]benzoxazepine-2,3-dicarboxamide |
| 570 | 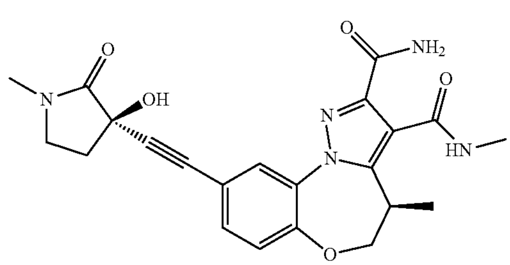 | 9-[2-((R)-3-hydroxy-1-methyl-2-oxo-pyrrolidin-3-yl)ethynyl]-N3,4-(R)-dimethyl-4,5-dihydropyrazolo[5,1-d][1,5]benzoxazepine-2,3-dicarboxamide |
| 571 | 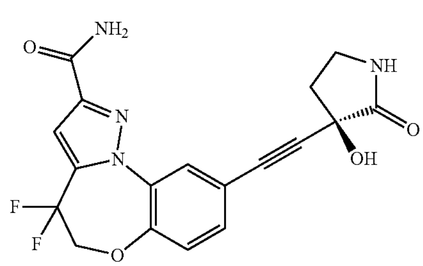 [SMILES: NC(=O)c1cc2n(n1)-c1cc(C#C[C@]3(O)CCNC3=O)ccc1OCC2(F)F] | 4,4-difluoro-9-[2-[(3R)-3-hydroxy-2-oxo-pyrrolidin-3-yl]ethynyn-5H-pyrazolo[5,1-d][1,5]benzoxazepine-2-carboxamide |

TABLE 1-continued

| No. | Structure | Name |
|---|---|---|
| 572 | 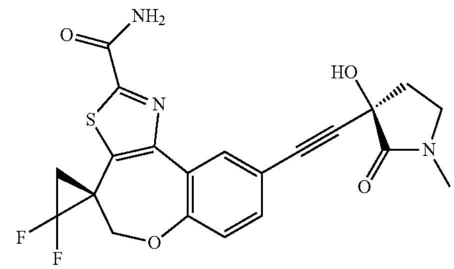 [SMILES: CN1CC[C@@](O)(C#Cc2ccc3c(c2)-c2nc(C(N)=O)sc2[C@@]2(CO3)CC2(F)F)C1=O] | (R)-1',1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 573 | 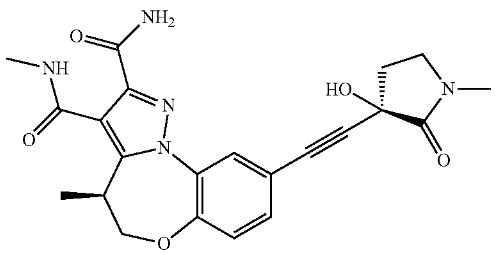 | 9-[2-((R)-3-hydroxy-1-methyl-2-oxo-pyrrolidin-3-yl)ethynyl]-N3,4-(S)-dimethyl-4,5-dihydropyrazolo[5,1-d][1,5]benzoxazepine-2,3-dicarboxamide |
| 574 | 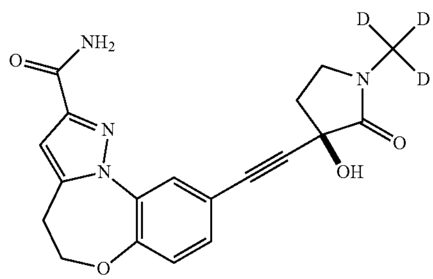 [SMILES: [2H]C([2H])([2H])N1CC[C@@](O)(C#Cc2ccc3c(c2)-n2nc(C(N)=O)cc2CCO3)C1=O] | 9-[2-[3-(R)-hydroxy-2-oxo-1-(trideuteriomethyl)pyrrolidin-3-yl]ethynyl]-4,5-dihydropyrazolo[5,1-d][1,5]benzoxazepine-2-carboxamide |
| 575 | 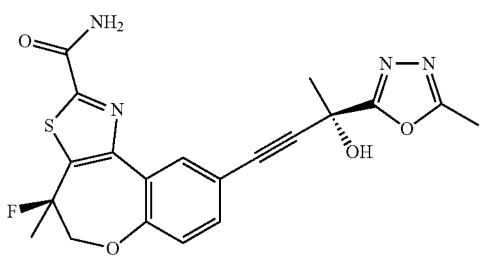 [SMILES: Cc1nnc([C@@](C)(O)C#Cc2ccc3c(c2)-c2nc(C(N)=O)sc2[C@](C)(F)CO3)o1] | 4-(R)-fluoro-9-[3-(S)-hydroxy-3-(5-methyl-1,3,4-oxadiazol-2-yl)but-1-ynyl]-4-methyl-5H-[1]benzoxepino[5,4-d]thiazole-2-carboxamide |
| 576 | 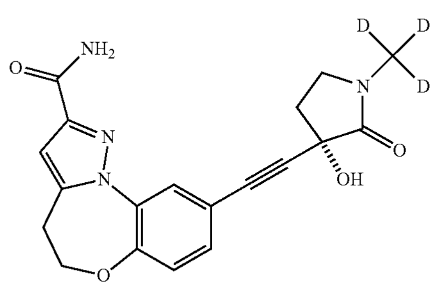 [SMILES: [2H]C([2H])([2H])N1CC[C@](O)(C#Cc2ccc3c(c2)-n2nc(C(N)=O)cc2CCO3)C1=O] | 9-[2-[3-(S)-hydroxy-2-oxo-1-(trideuteriomethyl)pyrrolidin-3-yl]ethynyl]-4,5-dihydropyrazolo[5,1-d][1,5]benzoxazepine-2-carboxamide |
| 577 | 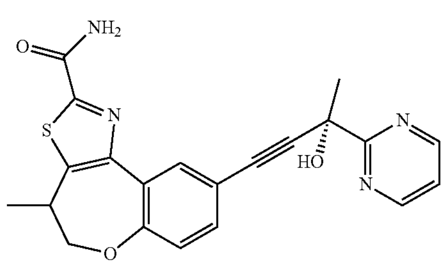 [SMILES: CC1COc2ccc(C#C[C@](C)(O)c3ncccn3)cc2-c2nc(C(N)=O)sc21] | 9-(3-hydroxy-3-pyrimidin-2-yl-but-1-ynyl)-4-methyl-4,5-dihydro-[1]benzoxepino[5,4-d]thiazole-2-carboxamide |

TABLE 1-continued

| No. | Structure | Name |
|---|---|---|
| 578 | 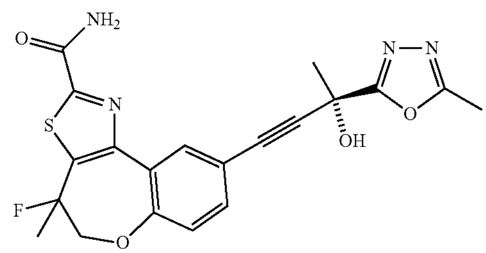 | 4-fluoro-9-[3-(S)-hydroxy-3-(5-methyl-1,3,4-oxadiazol-2-yl)but-1-ynyl]-4-methyl-5H-[1]benzoxepino[5,4-d]thiazole-2-carboxamide |
| 579 | 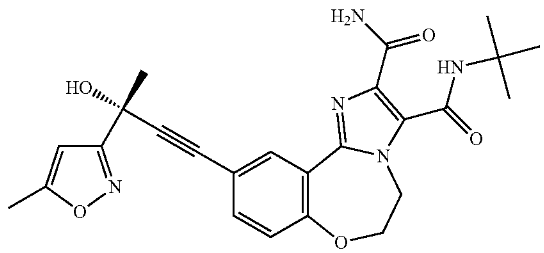 [SMILES: Cc1cc([C@](C)(O)C#Cc2ccc3c(c2)-c2nc(C(N)=O)c(C(=O)NC(C)(C)C)n2CCO3)no1] | (R)-N3-(tert-butyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 580 | 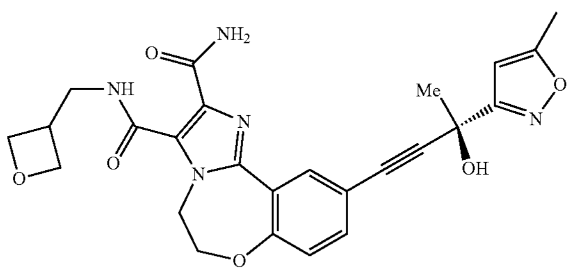 [SMILES: Cc1cc([C@](C)(O)C#Cc2ccc3c(c2)-c2nc(C(N)=O)c(C(=O)NCC4COC4)n2CCO3)no1] | (R)-10-(3-hydroxy-3-(5-methylisoxazol-3-yl)but-1-yn-1-yl)-N3-(oxetan-3-ylmethyl)-5,6-dihydrobenzo[f]imidazo[1,2-d][1,4]oxazepine-2,3-dicarboxamide |
| 581 | 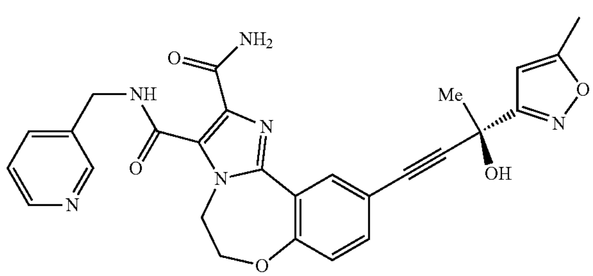 [SMILES: Cc1cc([C@](C)(O)C#Cc2ccc3c(c2)-c2nc(C(N)=O)c(C(=O)NCc4cccnc4)n2CCO3)no1] | (R)-10-(3-hydroxy-3-(5-methylisoxazol-3-yl)but-1-yn-1-yl)-N3-(pyridin-3-ylmethyl)-5,6-dihydrobenzo[f]imidazo[1,2-d][1,4]oxazepine-2,3-dicarboxamide |
| 582 | 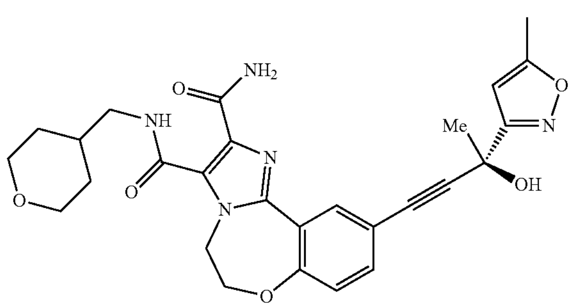 [SMILES: Cc1cc([C@](C)(O)C#Cc2ccc3c(c2)-c2nc(C(N)=O)c(C(=O)NCC4CCOCC4)n2CCO3)no1] | (R)-10-(3-hydroxy-3-(5-methylisoxazol-3-yl)but-1-yn-1-yl)-N3-((tetrahydro-2H-pyran-4-yl)methyl)-5,6-dihydrobenzo[f]imidazo[1,2-d][1,4]oxazepine-2,3-dicarboxamide |

TABLE 1-continued

| No. | Structure | Name |
|---|---|---|
| 583 | 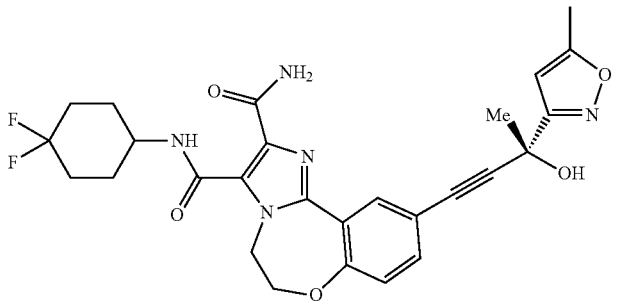 [SMILES: Cc1cc([C@](C)(O)C#Cc2ccc3c(c2)-c2nc(C(N)=O)c(C(=O)NC4CCC(F)(F)CC4)n2CCO3)no1] | (R)-N3-(4,4-difluorocyclohexyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 584 | 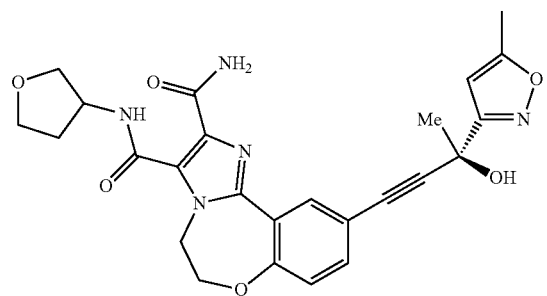 [SMILES: Cc1cc([C@](C)(O)C#Cc2ccc3c(c2)-c2nc(C(N)=O)c(C(=O)NC4CCOC4)n2CCO3)no1] | 10-((R)-3-hydroxy-3-(5-methylisoxazol-3-yl)but-1-yn-1-yl)-N3-(tetrahydrofuran-3-yl)-5,6-dihydrobenzo[f]imidazo[1,2-d][1,4]oxazepine-2,3-dicarboxamide |
| 585 | 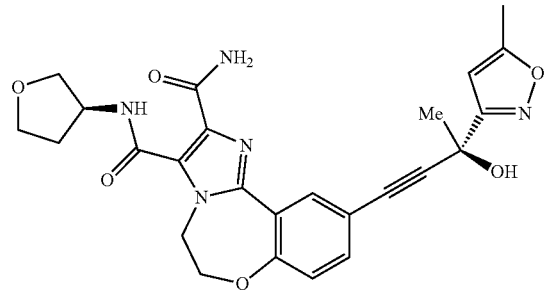 [SMILES: Cc1cc([C@](C)(O)C#Cc2ccc3c(c2)-c2nc(C(N)=O)c(C(=O)N[C@H]4CCOC4)n2CCO3)no1] | 10-((R)-3-hydroxy-3-(5-methylisoxazol-3-yl)but-1-yn-1-yl)-N3-((S)-tetrahydrofuran-3-yl)-5,6-dihydrobenzo[f]imidazo[1,2-d][1,4]oxazepine-2,3-dicarboxamide |
| 586 | 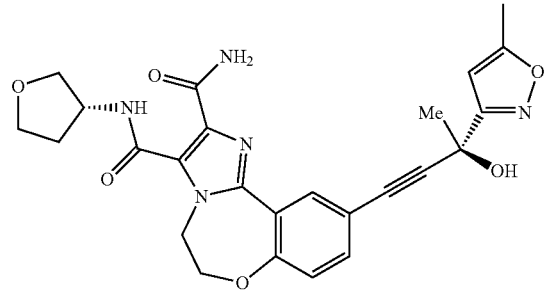 [SMILES: Cc1cc([C@](C)(O)C#Cc2ccc3c(c2)-c2nc(C(N)=O)c(C(=O)N[C@@H]4CCOC4)n2CCO3)no1] | 10-((R)-3-hydroxy-3-(5-methylisoxazol-3-yl)but-1-yn-1-yl)-N3-((R)-tetrahydrofuran-3-yl)-5,6-dihydrobenzo[f]imidazo[1,2-d][1,4]oxazepine-2,3-dicarboxamide |
| 587 | 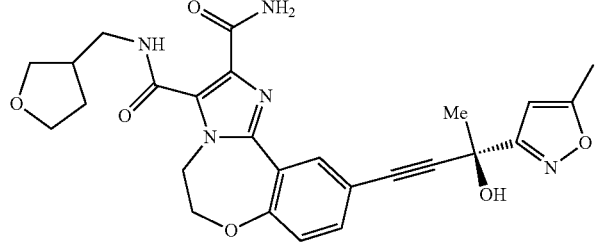 [SMILES: Cc1cc([C@](C)(O)C#Cc2ccc3c(c2)-c2nc(C(N)=O)c(C(=O)NCC4CCOC4)n2CCO3)no1] | 10-((R)-3-hydroxy-3-(5-methylisoxazol-3-yl)but-1-yn-1-yl)-N3-((tetrahydrofuran-3-yl)methyl)-5,6-dihydrobenzo[f]imidazo[1,2-d][1,4]oxazepine-2,3-dicarboxamide |

TABLE 1-continued

| No. | Structure | Name |
|---|---|---|
| 588 | 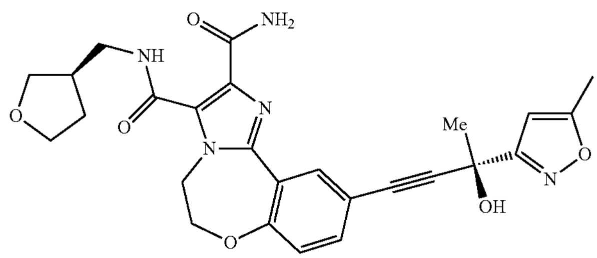 [SMILES: Cc1cc([C@](C)(O)C#Cc2ccc3c(c2)-c2nc(C(N)=O)c(C(=O)NC[C@H]4CCOC4)n2CCO3)no1] | 10-((R)-3-hydroxy-3-(5-methylisoxazol-3-yl)but-1-yn-1-yl)-N3-(((R)-tetrahydrofuran-3-yl)methyl)-5,6-dihydrobenzo[f]imidazo[1,2-d][1,4]oxazepine-2,3-dicarboxamide |
| 589 | 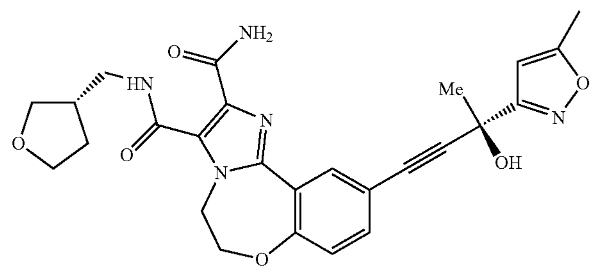 [SMILES: Cc1cc([C@](C)(O)C#Cc2ccc3c(c2)-c2nc(C(N)=O)c(C(=O)NC[C@@H]4CCOC4)n2CCO3)no1] | 10-((R)-3-hydroxy-3-(5-methylisoxazol-3-yl)but-1-yn-1-yl)-N3-(((S)-tetrahydrofuran-3-yl)methyl)-5,6-dihydrobenzo[f]imidazo[1,2-d][1,4]oxazepine-2,3-dicarboxamide |
| 590 | 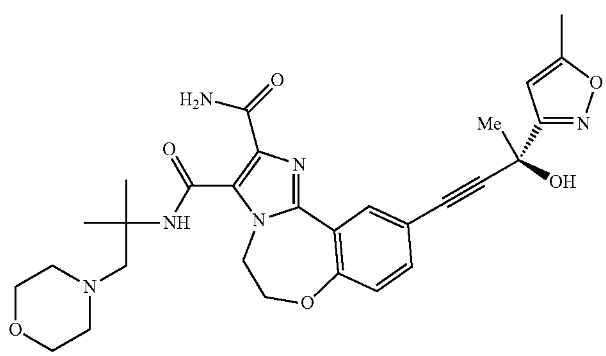 [SMILES: Cc1cc([C@](C)(O)C#Cc2ccc3c(c2)-c2nc(C(N)=O)c(C(=O)NC(C)(C)CN4CCOCC4)n2CCO3)no1] | (R)-10-(3-hydroxy-3-(5-methylisoxazol-3-yl)but-1-yn-1-yl)-N3-(2-methyl-1-morpholinopropan-2-yl)-5,6-dihydrobenzo[f]imidazo[1,2-d][1,4]oxazepine-2,3-dicarboxamide |
| 591 | 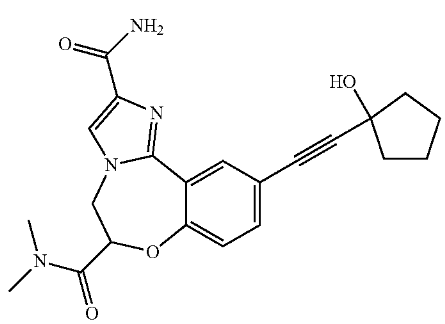 [SMILES: CN(C)C(=O)C1Cn2cc(C(N)=O)nc2-c2cc(C#CC3(O)CCCC3)ccc2O1] | 10-((1-hydroxycyclopentyl)ethynyl)-N6,N6-dimethyl-5,6-dihydrobenzo[f]imidazo[1,2-d][1,4]oxazepine-2,6-dicarboxamide |
| 592 | 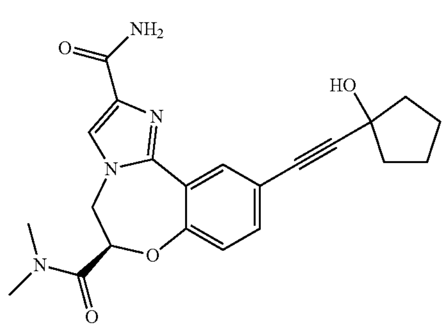 [SMILES: CN(C)C(=O)[C@H]1Cn2cc(C(N)=O)nc2-c2cc(C#CC3(O)CCCC3)ccc2O1] | (R)-10-((1-hydroxycyclopentyl)ethynyl)-N6,N6-dimethyl-5,6-dihydrobenzo[f]imidazo[1,2-d][1,4]oxazepine-2,6-dicarboxamide |

TABLE 1-continued

| No. | Structure | Name |
|---|---|---|
| 593 | 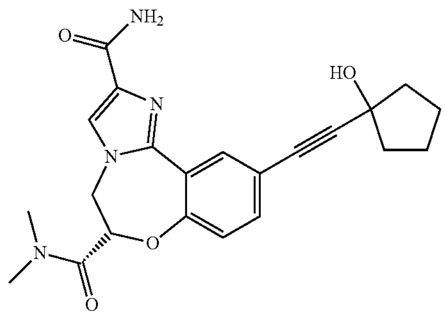 | (S)-10-((1-hydroxycyclopentyl)ethynyl)-N6,N6-dimethyl-5,6-dihydrobenzo[f]imidazo[1,2-d][1,4]oxazepine-2,6-dicarboxamide |
| 594 | 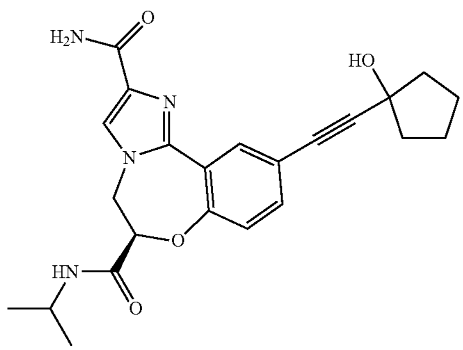 [SMILES: CC(C)NC(=O)[C@H]1Cn2cc(C(N)=O)nc2-c2cc(C#CC3(O)CCCC3)ccc2O1] | 10-((1-hydroxycyclopentyl)ethynyl)-N6-isopropyl-5,6-dihydrobenzo[f]imidazo[1,2-d][1,4]oxazepine-2,6-dicarboxamide |
| 595 | 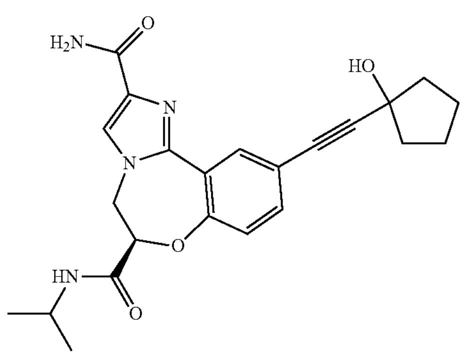 [SMILES: CC(C)NC(=O)[C@H]1Cn2cc(C(N)=O)nc2-c2cc(C#CC3(O)CCCC3)ccc2O1] | (R)-10-((1-hydroxycyclopentyl)ethynyl)-N6-isopropyl-5,6-dihydrobenzo[f]imidazo[1,2-d][1,4]oxazepine-2,6-dicarboxamide |
| 596 | 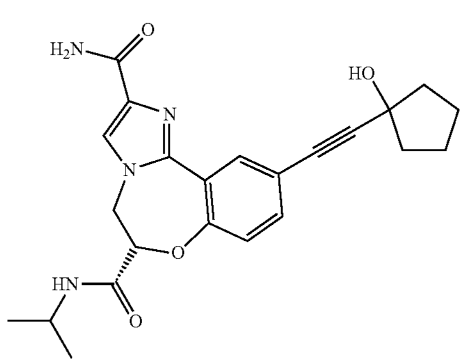 | (S)-10-((1-hydroxycyclopentyl)ethynyl)-N6-isopropyl-5,6-dihydrobenzo[f]imidazo[1,2-d][1,4]oxazepine-2,6-dicarboxamide |

TABLE 1-continued

| No. | Structure | Name |
|---|---|---|
| 597 | 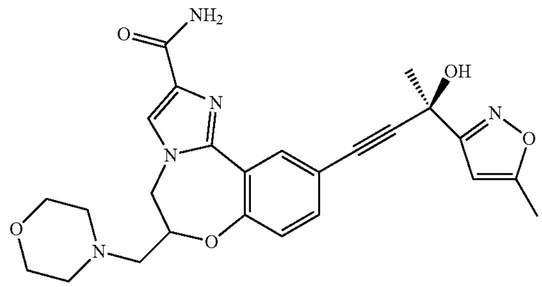 [SMILES: Cc1cc([C@](C)(O)C#Cc2ccc3c(c2)-c2nc(C(N)=O)cn2CC(CN2CCOCC2)O3)no1] | 10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide |
| 598 | 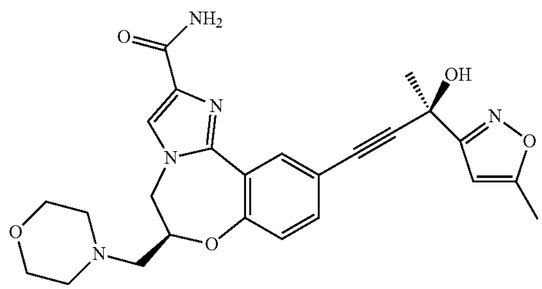 [SMILES: Cc1cc([C@](C)(O)C#Cc2ccc3c(c2)-c2nc(C(N)=O)cn2C[C@H](CN2CCOCC2)O3)no1] | (S)-10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepin-2-carboxamide |
| 599 | 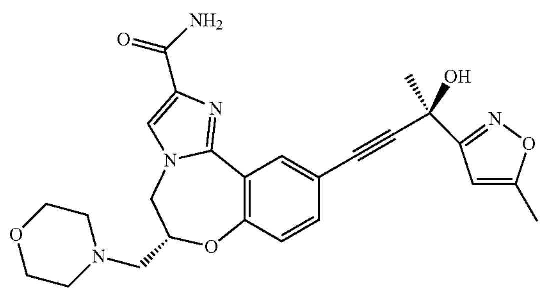 [SMILES: Cc1cc([C@](C)(O)C#Cc2ccc3c(c2)-c2nc(C(N)=O)cn2C[C@@H](CN2CCOCC2)O3)no1] | (R)-10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide |
| 600 | 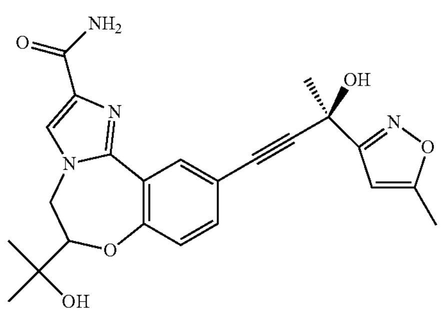 | 10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide |
| 601 | 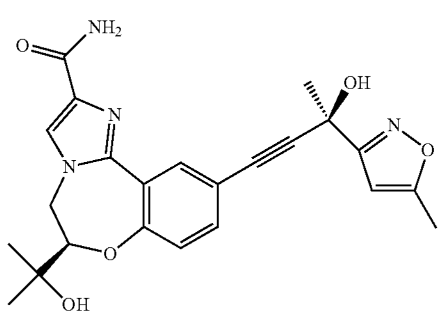 [SMILES: Cc1cc([C@](C)(O)C#Cc2ccc3c(c2)-c2nc(C(N)=O)cn2C[C@H](C(C)(C)O)O3)no1] | (R)-10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide |

TABLE 1-continued

| No. | Structure | Name |
|---|---|---|
| 602 | 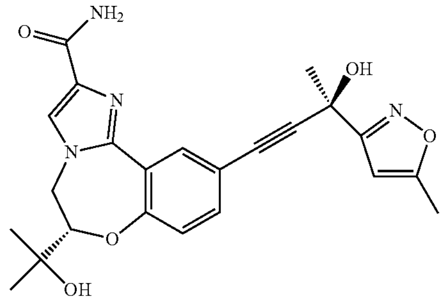 [SMILES: Cc1cc([C@](C)(O)C#Cc2ccc3c(c2)-c2nc(C(N)=O)cn2C[C@@H](C(C)(C)O)O3)no1] | (S)-10-((R)-3-hydroxy-3-(5-methyl-isoxazol-3-yl)but-1-yn-1-yl)-6-(2-hydroxy-propan-2-yl)-5,6-dihydrobenzo[f]imidazo[1,2-d][1,4]oxazepine-2-carboxamide |
| 603 | 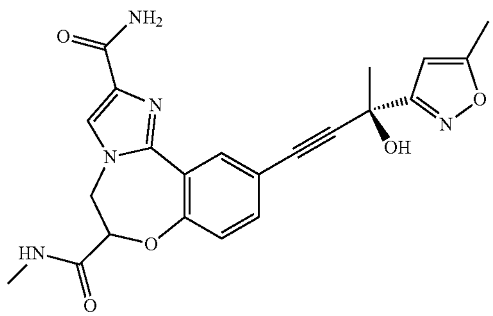 | 10-((R)-3-hydroxy-3-(5-methylisoxazol-3-yl)but-1-yn-1-yl)-N6-methyl-5,6-dihydrobenzo[f]imidazo[1,2-d][1,4]oxazepine-2,6-dicarboxamide |
| 604 | 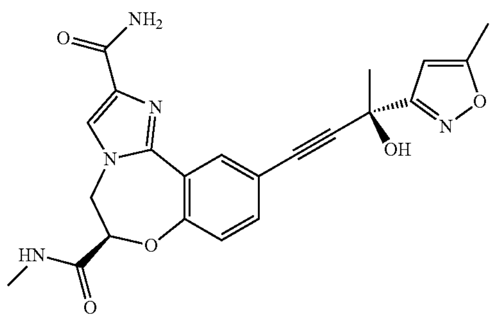 | (R)-10-((R)-3-hydroxy-3-(5-methyl-isoxazol-3-yl)but-1-yn-1-yl)-N6-methyl-5,6-dihydrobenzo[f]imidazo[1,2-d][1,4]oxazepine-2,6-dicarboxamide |
| 605 | 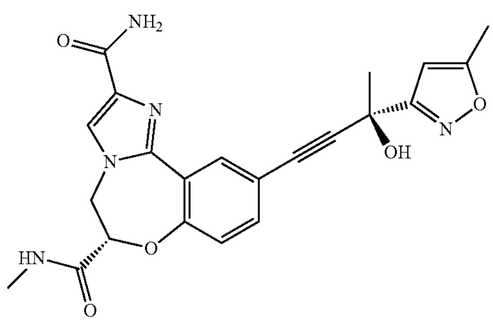 | (R)-10-((R)-3-hydroxy-3-(5-methyl-isoxazol-3-yl)but-1-yn-1-yl)-N6-methyl-5,6-dihydrobenzo[f]imidazo[1,2-d][1,4]oxazepine-2,6-dicarboxamide |
| 606 | 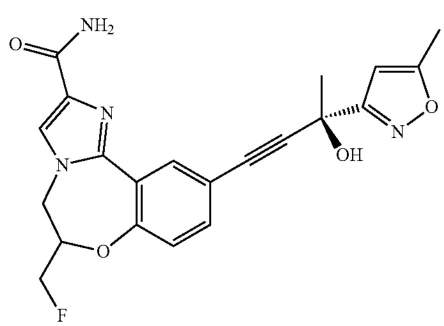 [SMILES: Cc1cc([C@](C)(O)C#Cc2ccc3c(c2)-c2nc(C(N)=O)cn2CC(CF)O3)no1] | 6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide and (S)-6-(fluoromethyl)-10-(R)-3-hydroxy-3-(5-methylisoxazol-3-yl)but-1-yn-1-yl)-5,6-dihydrobenzo[f]imidazo[1,2-d][1,4]oxazepine-2-carboxamide |

TABLE 1-continued

| No. | Structure | Name |
|---|---|---|
| 607 | 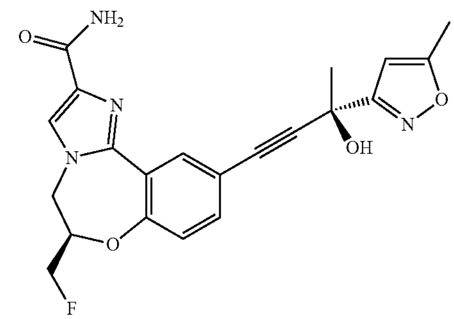 [SMILES: Cc1cc([C@](C)(O)C#Cc2ccc3c(c2)-c2nc(C(N)=O)cn2C[C@H](CF)O3)no1] | (R)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide |
| 608 | 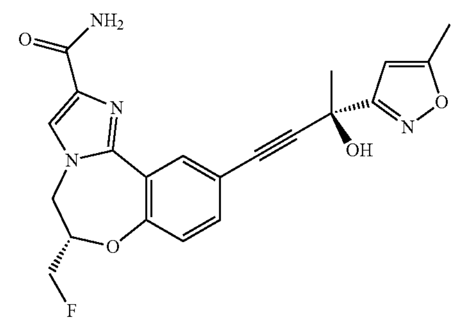 [SMILES: Cc1cc([C@](C)(O)C#Cc2ccc3c(c2)-c2nc(C(N)=O)cn2C[C@@H](CF)O3)no1] | (S)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide |
| 609 | 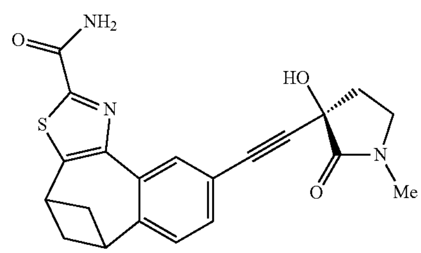 [SMILES: CN1CC[C@@](O)(C#Cc2ccc3c(c2)-c2nc(C(N)=O)sc2C2CC3C2)C1=O] | (R)-9-((3-hydroxy-1-methyl-2-oxopyrrolidin-3-yl)ethynyl)-5,6-dihydro-4H-4,6-methanobenzo[6,7]cyclohepta[1,2-d]thiazole-2-carboxamide |
| 610 | 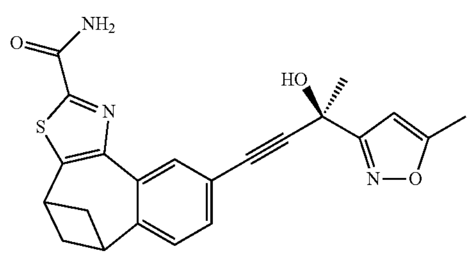 [SMILES: Cc1cc([C@](C)(O)C#Cc2ccc3c(c2)-c2nc(C(N)=O)sc2C2CC3C2)no1] | (R)-9-(3-hydroxy-3-(5-methylisoxazol-3-yl)but-1-yn-1-yl)-5,6-dihydro-4H-4,6-methanobenzo[6,7]cyclohepta[1,2-d]thiazole-2-carboxamide |
| 611 | 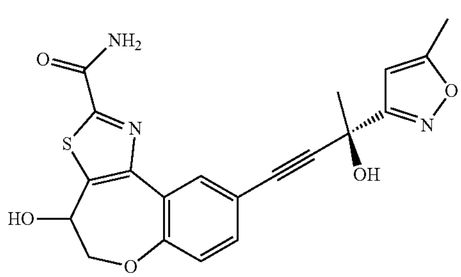 [SMILES: Cc1cc([C@](C)(O)C#Cc2ccc3c(c2)-c2nc(C(N)=O)sc2C(O)CO3)no1] | 4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |

TABLE 1-continued

| No. | Structure | Name |
|---|---|---|
| 612 | 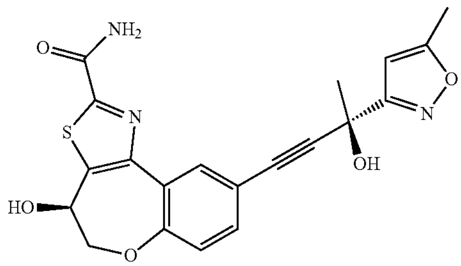 [SMILES: Cc1cc([C@](C)(O)C#Cc2ccc3c(c2)-c2nc(C(N)=O)sc2[C@H](O)CO3)no1] | (R)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 613 | 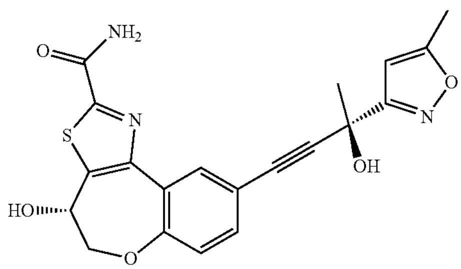 | and (S)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 614 | 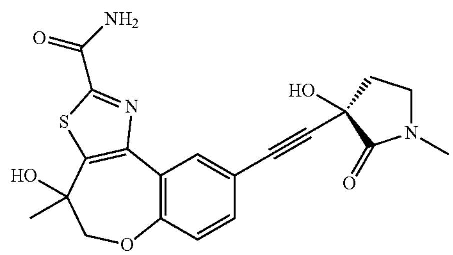 [SMILES: CN1CC[C@@](O)(C#Cc2ccc3c(c2)-c2nc(C(N)=O)sc2C(C)(O)CO3)C1=O] | 4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 615 | 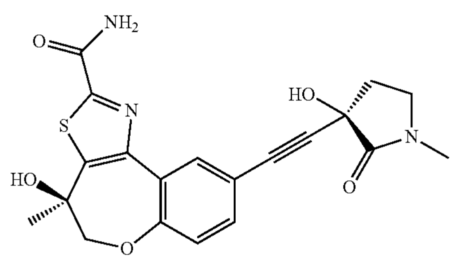 [SMILES: CN1CC[C@@](O)(C#Cc2ccc3c(c2)-c2nc(C(N)=O)sc2[C@](C)(O)CO3)C1=O] | (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 616 | 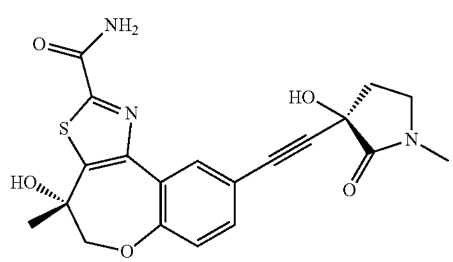 [SMILES: CN1CC[C@@](O)(C#Cc2ccc3c(c2)-c2nc(C(N)=O)sc2[C@@](C)(O)CO3)C1=O] | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 617 | 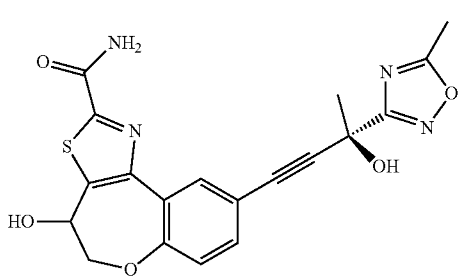 [SMILES: Cc1nc([C@](C)(O)C#Cc2ccc3c(c2)-c2nc(C(N)=O)sc2C(O)CO3)no1] | 4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |

TABLE 1-continued

| No. | Structure | Name |
|---|---|---|
| 618 | 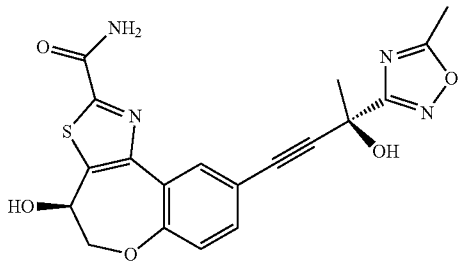 [SMILES: Cc1nc([C@](C)(O)C#Cc2ccc3c(c2)-c2nc(C(N)=O)sc2[C@H](O)CO3)no1] | (R)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 619 | 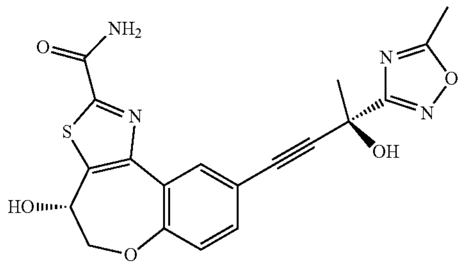 [SMILES: Cc1nc([C@](C)(O)C#Cc2ccc3c(c2)-c2nc(C(N)=O)sc2[C@@H](O)CO3)no1] | (S)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 620 | 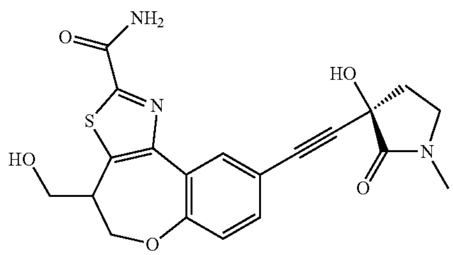 [SMILES: CN1CC[C@@](O)(C#Cc2ccc3c(c2)-c2nc(C(N)=O)sc2C(CO)CO3)C1=O] | 9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 621 | 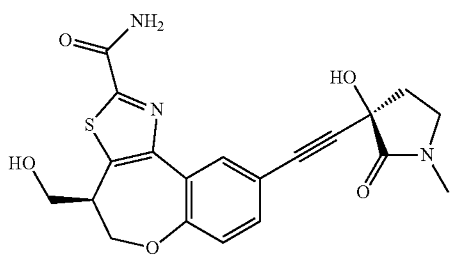 [SMILES: CN1CC[C@@](O)(C#Cc2ccc3c(c2)-c2nc(C(N)=O)sc2[C@H](CO)CO3)C1=O] | (R)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 622 | 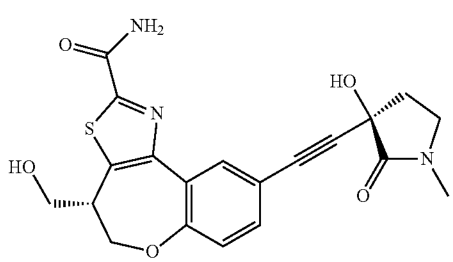 [SMILES: CN1CC[C@@](O)(C#Cc2ccc3c(c2)-c2nc(C(N)=O)sc2[C@@H](CO)CO3)C1=O] | (S)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 623 | 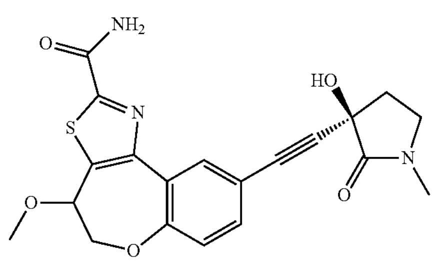 | 9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide |

TABLE 1-continued

| No. | Structure | Name |
|---|---|---|
| 624 | 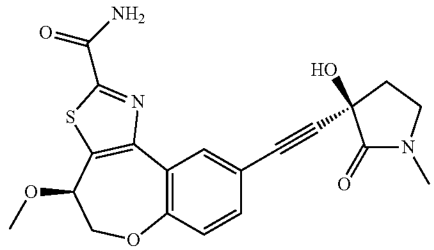 | (R)-9-(((R)-3-hydroxy-1-methyl-2-oxo-pyrrolidin-3-yl)ethynyl)-4-methoxy-4,5-dihydrobenzo[2,3]oxepino[4,5-d]thiazole-2-carboxamide |
| 625 | 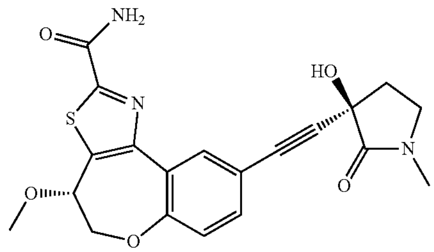 | (S)-9-(((R)-3-hydroxy-1-methyl-2-oxo-pyrrolidin-3-yl)ethynyl)-4-methoxy-4,5-dihydrobenzo[2,3]oxepino[4,5-d]thiazole-2-carboxamide |
| 626 | 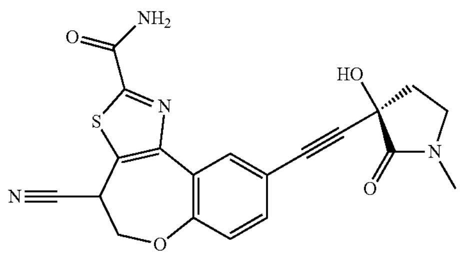 [SMILES: CN1CC[C@@](O)(C#Cc2ccc3c(c2)-c2nc(C(N)=O)sc2C(C#N)CO3)C1=O] | 4-cyano-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 627 | 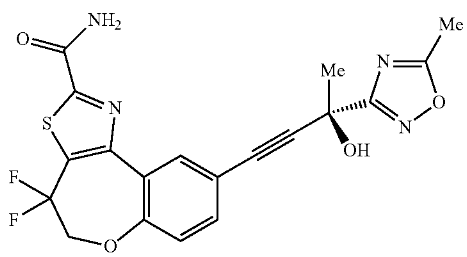 [SMILES: Cc1nc([C@](C)(O)C#Cc2ccc3c(c2)-c2nc(C(N)=O)sc2C(F)(F)CO3)no1] | (R)-4,4-difluoro-9-(3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 628 | 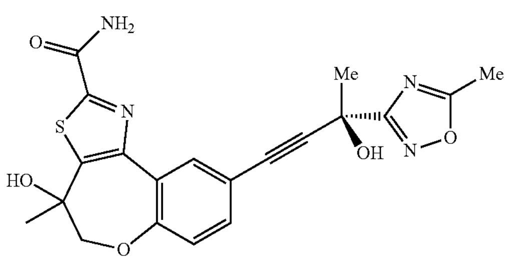 [SMILES: Cc1nc([C@](C)(O)C#Cc2ccc3c(c2)-c2nc(C(N)=O)sc2C(C)(O)CO3)no1] | 4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 629 | 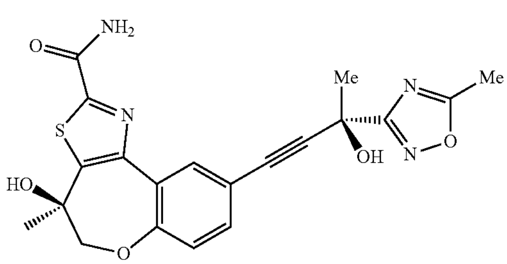 [SMILES: Cc1nc([C@](C)(O)C#Cc2ccc3c(c2)-c2nc(C(N)=O)sc2[C@](C)(O)CO3)no1] | (R)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |

TABLE 1-continued

| No. | Structure | Name |
|---|---|---|
| 630 | 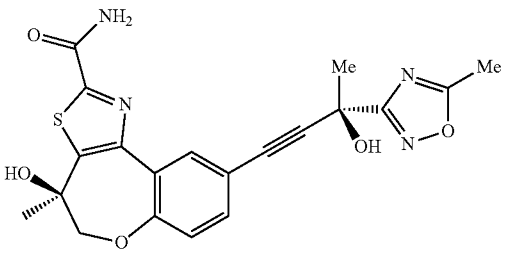 [SMILES: Cc1nc([C@](C)(O)C#Cc2ccc3c(c2)-c2nc(C(N)=O)sc2[C@](C)(O)CO3)no1] | (S)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 631 | 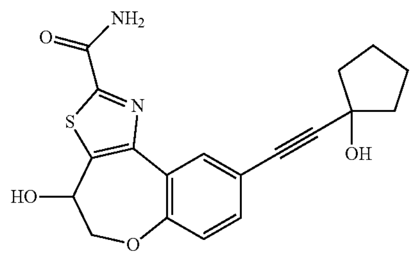 [SMILES: NC(=O)c1nc2c(s1)C(O)COc1ccc(C#CC3(O)CCCC3)cc1-2] | 4-hydroxy-9-((1-hydroxycyclopentyl)ethynyl)-4,5-dihydrobenzo[2,3]oxepino[4,5-d]thiazole-2-carboxamide |
| 632 | 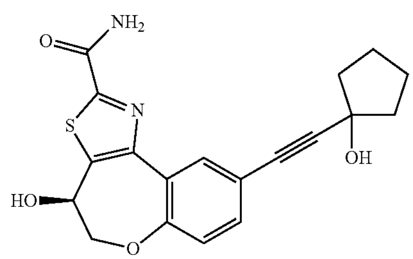 [SMILES: NC(=O)c1nc2c(s1)[C@H](O)COc1ccc(C#CC3(O)CCCC3)cc1-2] | (R)-4-hydroxy-9-((1-hydroxycyclopentlty)ethynyl)-4,5-dihydrobenzo[2,3]oxepino[4,5-d]thiazole-2-carboxamide |
| 633 | 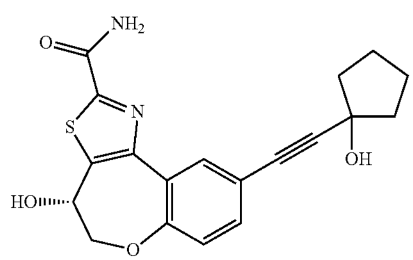 [SMILES: NC(=O)c1nc2c(s1)[C@@H](O)COc1ccc(C#CC3(O)CCCC3)cc1-2] | (S)-4-hydroxy-9-((1-hydroxycyclopentyl)ethynyl)-4,5-dihydrobenzo[2,3]oxepino[4,5-d]thiazole-2-carboxamide |
| 634 | 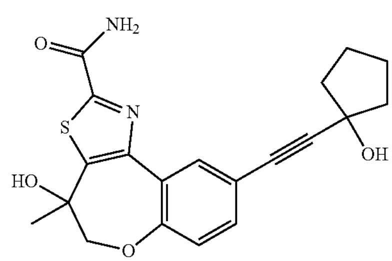 [SMILES: CC1(O)COc2ccc(C#CC3(O)CCCC3)cc2-c2nc(C(N)=O)sc21] | 4-hydroxy-9-((1-hydroxycyclopentyl)ethynyl)-4-methyl-4,5-dihydrobenzo[2,3]oxepino[4,5-d]thiazole-2-carboxamide |
| 635 | 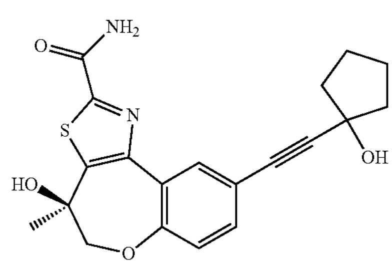 [SMILES: C[C@@]1(O)COc2ccc(C#CC3(O)CCCC3)cc2-c2nc(C(N)=O)sc21] | (R)-4-hydroxy-9-((1-hydroxycyclopentyl)ethynyl)-4-methyl-4,5-dihydrobenzo[2,3]oxepino[4,5-d]thiazole-2-carboxamide |

TABLE 1-continued

| No. | Structure | Name |
|---|---|---|
| 636 | 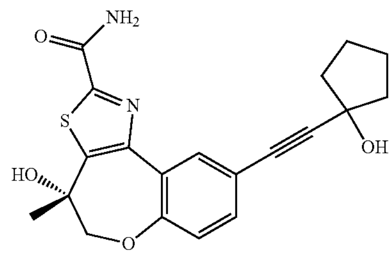 [SMILES: C[C@]1(O)COc2ccc(C#CC3(O)CCCC3)cc2-c2nc(C(N)=O)sc21] | (S)-4-hydroxy-9-((1-hydroxycyclopen-pentyl)ethynyl)-4-methyl-4,5-dihydrobenzo[2,3]oxepino[4,5-d]thiazole-2-carboxamide |
| 637 | 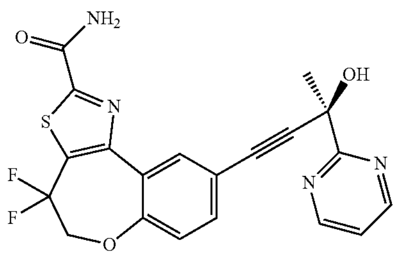 [SMILES: C[C@@](O)(C#Cc1ccc2c(c1)-c1nc(C(N)=O)sc1C(F)(F)CO2)c1ncccn1] | (R)-4,4-difluoro-9-(3-hydroxy-3-(pyrimidin-2-yl)but-1-yn-1-yl)-4,5-dihydrobenzo[2,3]oxepino[4,5-d]thiazole-2-carboxamide |
| 638 | 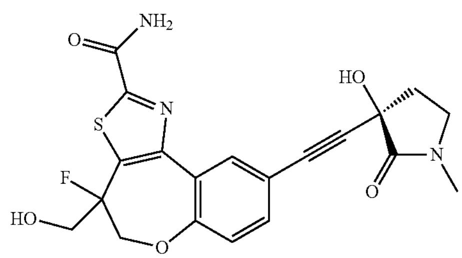 [SMILES: CN1CC[C@@](O)(C#Cc2ccc3c(c2)-c2nc(C(N)=O)sc2C(F)(CO)CO3)C1=O] | 4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 639 | 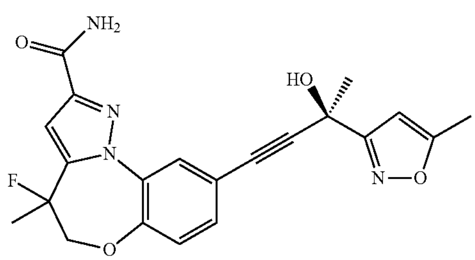 [SMILES: Cc1cc([C@](C)(O)C#Cc2ccc3c(c2)-n2nc(C(N)=O)cc2C(C)(F)CO3)no1] | 4-fluoro-9-((R)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 640 | 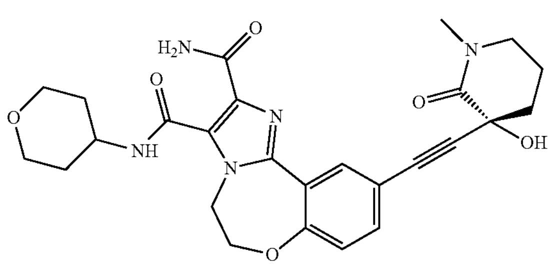 [SMILES: CN1CCC[C@@](O)(C#Cc2ccc3c(c2)-c2nc(C(N)=O)c(C(=O)NC4CCOCC4)n2CCO3)C1=O] | 10-[2-[(3R)-3-hydroxy-1-methyl-2-oxo-3-piperidyl]ethynyl]-N3-tetrahydropyran-4-yl-5,6-dihydroimidazo[1,2-d][1,4]benzoxazepine-2,3-dicarboxamide |
| 641 | 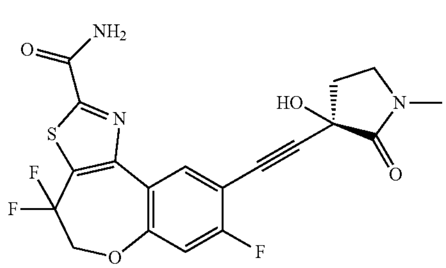 [SMILES: CN1CC[C@@](O)(C#Cc2cc3c(cc2F)OCC(F)(F)c2sc(C(N)=O)nc2-3)C1=O] | 4,4,8-trifluoro-9-[2-[(3R)-3-hydroxy-1-methyl-2-oxo-pyrrolidin-3-yl]ethynyl]-5H-[1]benzoxepino[5,4-d]thiazole-2-carboxamide |

TABLE 1-continued

| No. | Structure | Name |
|---|---|---|
| 642 | 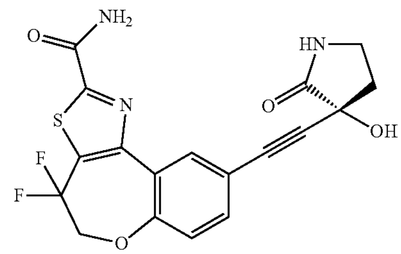 [SMILES: NC(=O)c1nc2c(s1)C(F)(F)COc1ccc(C#C[C@]3(O)CCNC3=O)cc1-2] | (R)-4,4-difluoro-9-((3-hydroxy-2-oxo-pyrrolidin-3-yl)ethynyl)-4,5-dihydrobenzo[2,3]oxepino[4,5-d]thiazole-2-carboxamide |
| 643 | 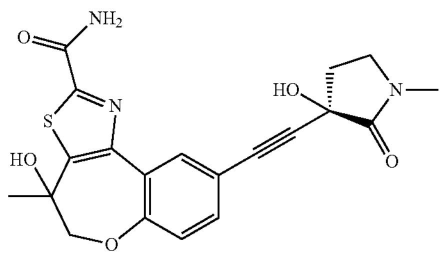 | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 644 | 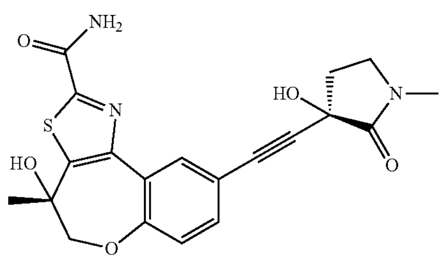 | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 645 | 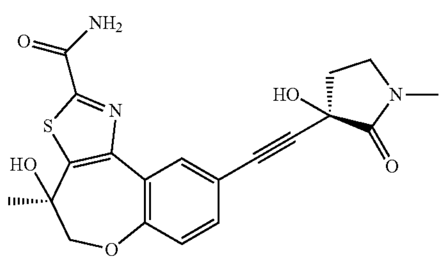 | (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 646 | 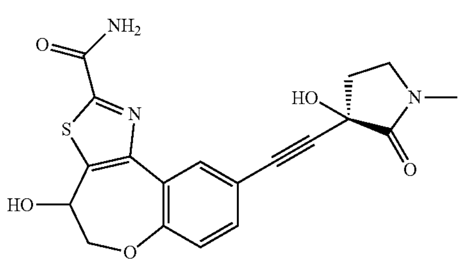 [SMILES: CN1CC[C@@](O)(C#Cc2ccc3c(c2)-c2nc(C(N)=O)sc2C(O)CO3)C1=O] | 4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 647 | 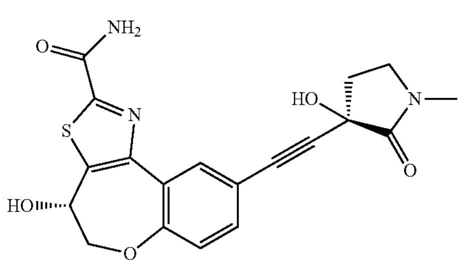 [SMILES: CN1CC[C@@](O)(C#Cc2ccc3c(c2)-c2nc(C(N)=O)sc2[C@@H](O)CO3)C1=O] | (S)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1-continued

| No. | Structure | Name |
|---|---|---|
| 648 | 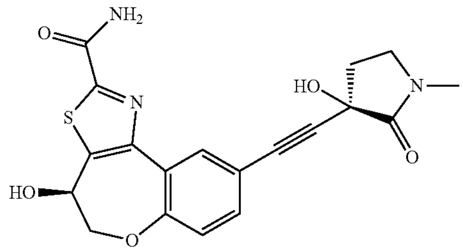 [SMILES: CN1CC[C@@](O)(C#Cc2ccc3c(c2)-c2nc(C(N)=O)sc2[C@H](O)CO3)C1=O] | (R)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 649 | 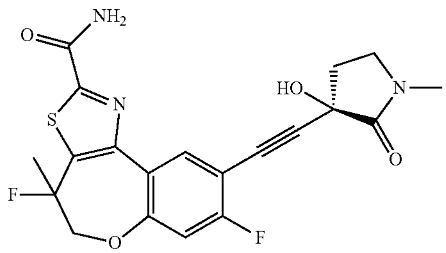 [SMILES: CN1CC[C@@](O)(C#Cc2cc3c(cc2F)OCC(C)(F)c2sc(C(N)=O)nc2-3)C1=O] | 4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 650 | 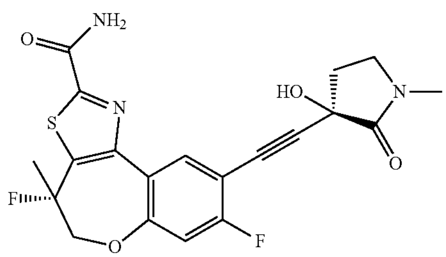 [SMILES: CN1CC[C@@](O)(C#Cc2cc3c(cc2F)OC[C@](C)(F)c2sc(C(N)=O)nc2-3)C1=O] | (S)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 651 | 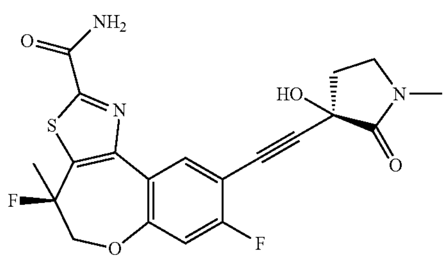 [SMILES: CN1CC[C@@](O)(C#Cc2cc3c(cc2F)OC[C@@](C)(F)c2sc(C(N)=O)nc2-3)C1=O] | (R)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 652 | 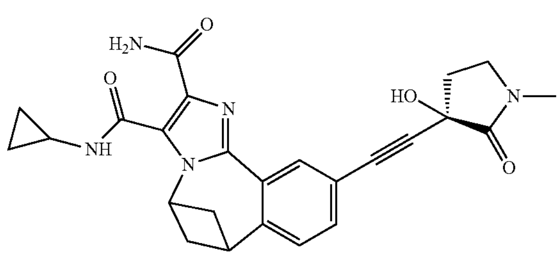 [SMILES: CN1CC[C@@](O)(C#Cc2ccc3c(c2)-c2nc(C(N)=O)c(C(=O)NC4CC4)n2C2CC3C2)C1=O] | N3-cyclopropyl-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2,3-dicarboxamide |
| 653 | 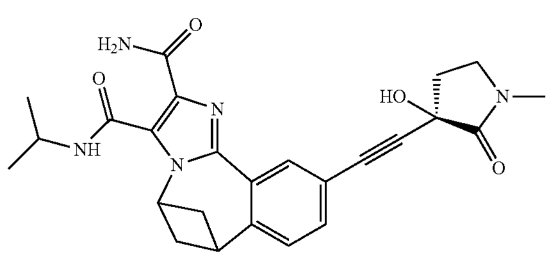 [SMILES: CC(C)NC(=O)c1c(C(N)=O)nc2n1C1CC(C1)c1ccc(C#C[C@]3(O)CCN(C)C3=O)cc1-2] | 10-[2-[(3R)-3-hydroxy-1-methyl-2-oxo-pyrrolidin-3-yl]ethynyl]-N3-isopropyl-5,6,7,12-tetrahydro-5,7-methanobenzo[c]imidazo[1,2-a]azepine-2,3-dicarboxamide |

TABLE 1-continued

| No. | Structure | Name |
|---|---|---|
| 654 | 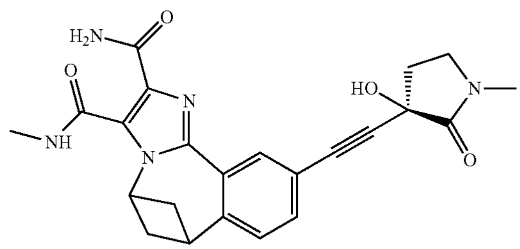 | 10-[2-[(3R)-3-hydroxy-1-methyl-2-oxo-pyrrolidin-3-yl]ethynyl]-N3-methyl-5,6,7,12-tetrahydro-5,7-methanobenzo[c]imidazo[1,2-a]azepine-2,3-dicarboxamide |
| 655 | 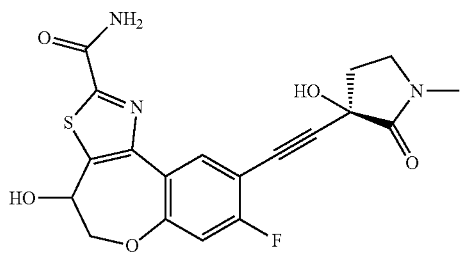 [SMILES: CN1CC[C@@](O)(C#Cc2cc3c(cc2F)OCC(O)c2sc(C(N)=O)nc2-3)C1=O] | 8-fluoro-4-hydroxy-9-(((R)-3-hydroxy-1-methyl-2-oxopyrrolidin-3-yl)ethynyl)-4,5-dihydrobenzo[2,3]oxepino-4,5-d]thiazole-2-carboxamide |
| 656 | 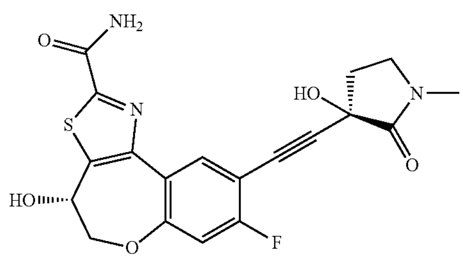 [SMILES: CN1CC[C@@](O)(C#Cc2cc3c(cc2F)OC[C@H](O)c2sc(C(N)=O)nc2-3)C1=O] | (S)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 657 | 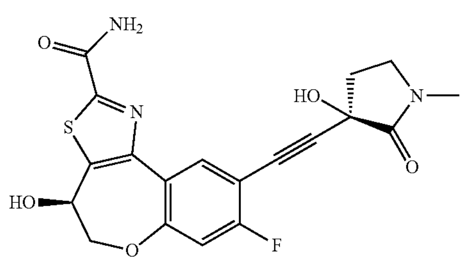 [SMILES: CN1CC[C@@](O)(C#Cc2cc3c(cc2F)OC[C@@H](O)c2sc(C(N)=O)nc2-3)C1=O] | (R)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 658 | 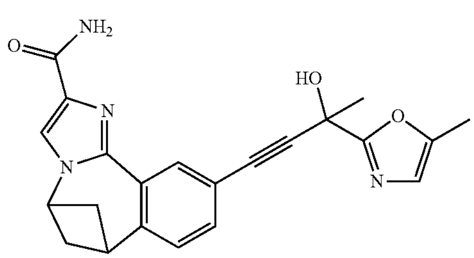 [SMILES: Cc1cnc(C(C)(O)C#Cc2ccc3c(c2)-c2nc(C(N)=O)cn2C2CC3C2)o1] | 10-[3-hydroxy-3-(5-methyloxazol-2-yl)-but-1-ynyl]-5,6,7,12-tetrahydro-5,7-methanobenzo[c]imidazo[1,2-a]azepine-2-carboxamide |
| 659 | 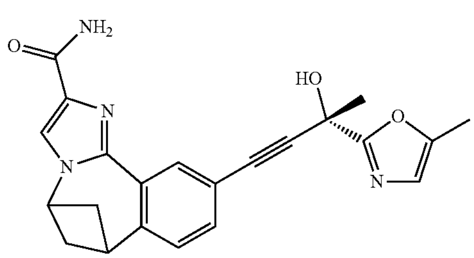 [SMILES: Cc1cnc([C@@](C)(O)C#Cc2ccc3c(c2)-c2nc(C(N)=O)cn2C2CC3C2)o1] | 10-[(3S)-hydroxy-3-(5-methyloxazol-2-yl)but-1-ynyl]-5,6,7,12-tetrahydro-5,7-methanobenzo[c]imidazo[1,2-a]azepine-2-carboxamide |

TABLE 1-continued

| No. | Structure | Name |
|---|---|---|
| 660 | 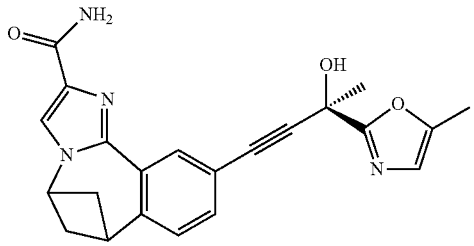 [SMILES: Cc1cnc([C@](C)(O)C#Cc2ccc3c(c2)-c2nc(C(N)=O)cn2C2CC3C2)o1] | 10-[(3R)-3-hydroxy-3-(5-methyloxazol-2-yl)but-1-ynyl]-5,6,7,12-tetrahydro-5,7-methanobenzo[c]imidazo[1,2-a]azepine-2-carboxamide |
| 661 | 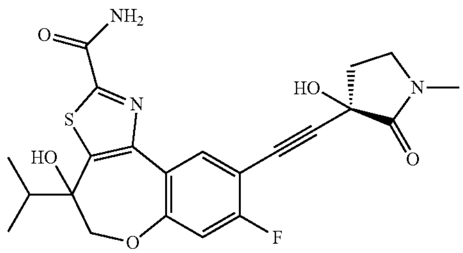 [SMILES: CC(C)C1(O)COc2cc(F)c(C#C[C@]3(O)CCN(C)C3=O)cc2-c2nc(C(N)=O)sc21] | 8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 662 | 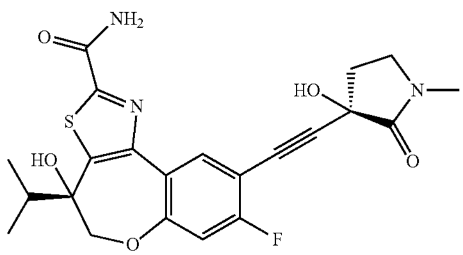 [SMILES: CC(C)[C@]1(O)COc2cc(F)c(C#C[C@]3(O)CCN(C)C3=O)cc2-c2nc(C(N)=O)sc21] | (S)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 663 | 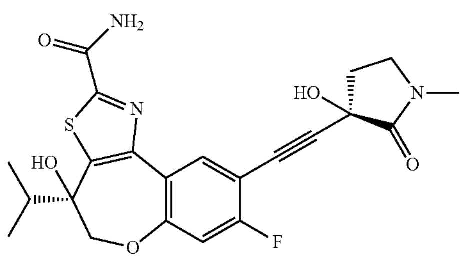 | (R)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 664 | 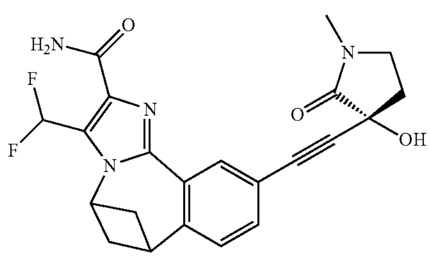 [SMILES: CN1CC[C@@](O)(C#Cc2ccc3c(c2)-c2nc(C(N)=O)c(C(F)F)n2C2CC3C2)C1=O] | 3-(difluoromethyl)-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide |
| 665 | 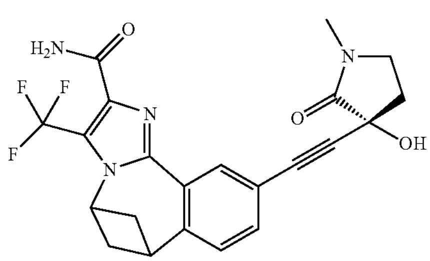 [SMILES: CN1CC[C@@](O)(C#Cc2ccc3c(c2)-c2nc(C(N)=O)c(C(F)(F)F)n2C2CC3C2)C1=O] | 10-[2-[(3R)-3-hydroxy-1-methyl-2-oxopyrrolidin-3-yl]ethynyl]-3-(trifluoromethyl)-5,6,7,12-tetrahydro-5,7-methanobenzo[c]imidazo[1,2-a]azepine-2-carboxamide |

TABLE 1-continued

| No. | Structure | Name |
|---|---|---|
| 666 | 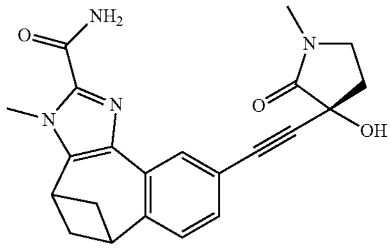 [SMILES: CN1CC[C@@](O)(C#Cc2ccc3c(c2)-c2nc(C(N)=O)n(C)c2C2CC3C2)C1=O] | 9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide |
| 667 | 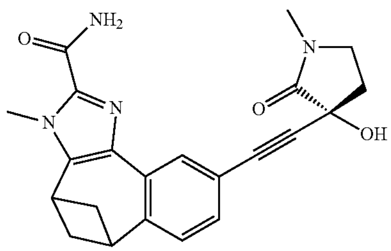 [SMILES: CN1CC[C@@](O)(C#Cc2ccc3c(c2)-c2nc(C(N)=O)n(C)c2C2CC3C2)C1=O] | (R)-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide |
| 668 | 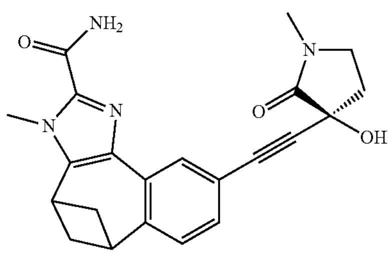 [SMILES: CN1CC[C@](O)(C#Cc2ccc3c(c2)-c2nc(C(N)=O)n(C)c2C2CC3C2)C1=O] | (S)-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide |
| 669 | 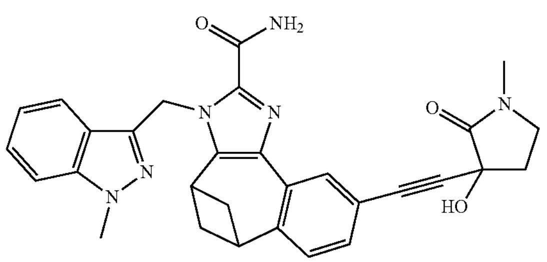 [SMILES: CN1CCC(O)(C#Cc2ccc3c(c2)-c2nc(C(N)=O)n(Cc4nn(C)c5ccccc45)c2C2CC3C2)C1=O] | 9-((3-hydroxy-1-methyl-2-oxopyrrolidin-3-yl)ethynyl)-3-((1-methyl-1H-indazol-3-yl)methyl)-3,4,5,6-tetrahydro-4,6-methanobenzo[3,4]cyclohepta[1,2-d]imidazole-2-carboxamide |
| 670 | 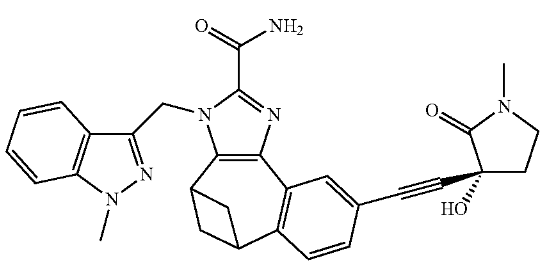 [SMILES: CN1CC[C@@](O)(C#Cc2ccc3c(c2)-c2nc(C(N)=O)n(Cc4nn(C)c5ccccc45)c2C2CC3C2)C1=O] | (R)-9-((3-hydroxy-1-methyl-2-oxopyrrolidin-3-yl)ethynyl)-3-((1-methyl-1H-indazol-3-yl)methyl)-3,4,5,6-tetrahydro-4,6-methanobenzo[3,4]cyclohepta[1,2-d]imidazole-2-carboxamide |
| 671 | 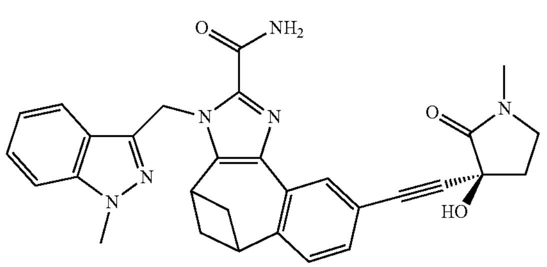 [SMILES: CN1CC[C@](O)(C#Cc2ccc3c(c2)-c2nc(C(N)=O)n(Cc4nn(C)c5ccccc45)c2C2CC3C2)C1=O] | (S)-9-((3-hydroxy-1-methyl-2-oxopyrrolidin-3-yl)ethynyl)-3-((1-methyl-1H-indazol-3-yl)methyl)-3,4,5,6-tetrahydro-4,6-methanobenzo[3,4]cyclohepla[1,2-d]imidazole-2-carboxamide |

TABLE 1-continued

| No. | Structure | Name |
|---|---|---|
| 672 | 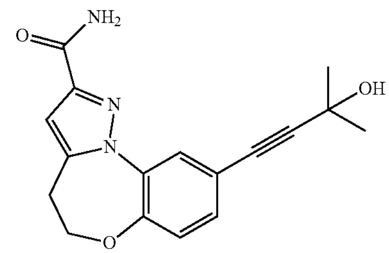 [SMILES: CC(C)(O)C#Cc1ccc2c(c1)-n1nc(C(N)=O)cc1CCO2] | 9-(3-hydroxy-3-methylbut-1-yn-1-yl)-4,5-dihydrobenzo[b]pyrazolo[1,5-d][1,4]oxazepine-2-carboxamide |
| 673 | 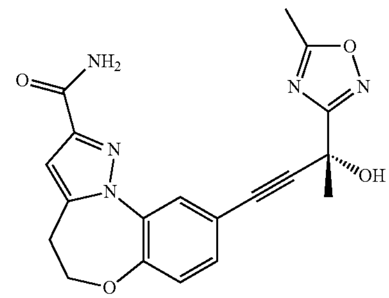 [SMILES: Cc1nc([C@](C)(O)C#Cc2ccc3c(c2)-n2nc(C(N)=O)cc2CCO3)no1] | (R)-9-(3-hydroxy-3-(5-methyl-1,2,4-oxadiazol-3-yl)but-1-yn-1-yl)-4,5-dihydrobenzo[b]pyrazolo[1,5-d][1,4]oxazepine-2-carboxamide |
| 674 | 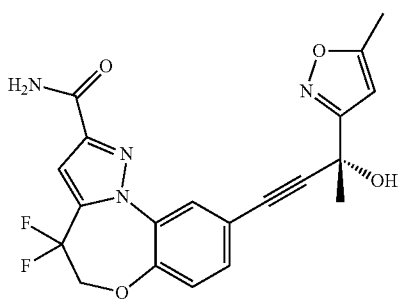 [SMILES: Cc1cc([C@](C)(O)C#Cc2ccc3c(c2)-n2nc(C(N)=O)cc2C(F)(F)CO3)no1] | (R)-4,4-difluoro-9-(3-hydroxy-3-(5-methylisoxazol-3-yl)but-1-yn-1-yl)-4,5-dihydrobenzo[b]pyrazolo[1,5-d][1,4]oxazepine-2-carboxamide |
| 675 | 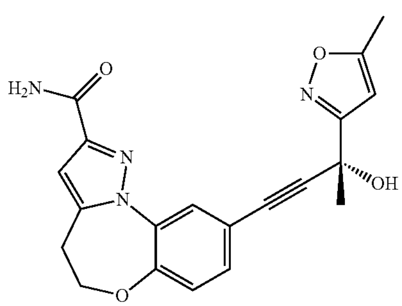 [SMILES: Cc1cc([C@](C)(O)C#Cc2ccc3c(c2)-n2nc(C(N)=O)cc2CCO3)no1] | (R)-9-(3-hydroxy-3-(5-methylisoxazol-3-yl)but-1-yn-1-yl)-4,5-dihydrobenzo[b]pyrazolo[1,5-d][1,4]oxazepine-2-carboxamide |
| 676 | 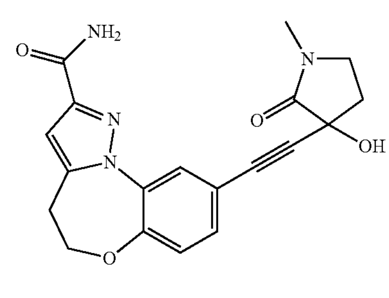 [SMILES: CN1CCC(O)(C#Cc2ccc3c(c2)-n2nc(C(N)=O)cc2CCO3)C1=O] | 9-((3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1-continued

| No. | Structure | Name |
|---|---|---|
| 677 | 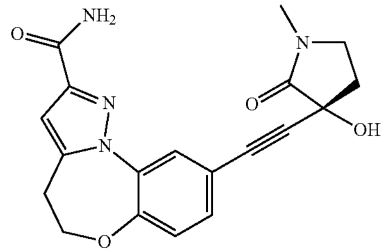 [SMILES: CN1CC[C@@](O)(C#Cc2ccc3c(c2)-n2nc(C(N)=O)cc2CCO3)C1=O] | (R)-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 678 | 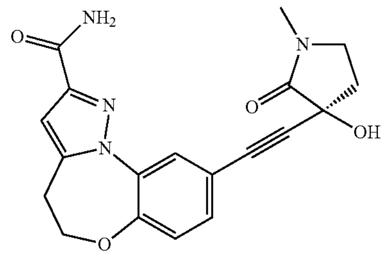 [SMILES: CN1CC[C@](O)(C#Cc2ccc3c(c2)-n2nc(C(N)=O)cc2CCO3)C1=O] | (S)-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 679 | 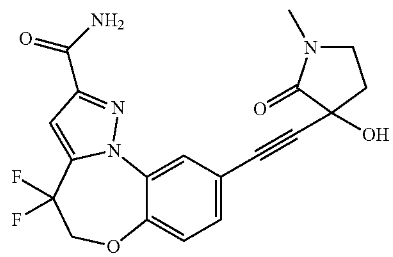 [SMILES: CN1CCC(O)(C#Cc2ccc3c(c2)-n2nc(C(N)=O)cc2C(F)(F)CO3)C1=O] | 4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 680 | 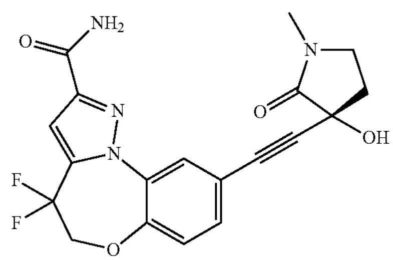 [SMILES: CN1CC[C@@](O)(C#Cc2ccc3c(c2)-n2nc(C(N)=O)cc2C(F)(F)CO3)C1=O] | (R)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 681 | 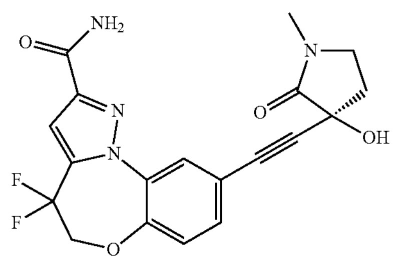 | (S)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 682 | 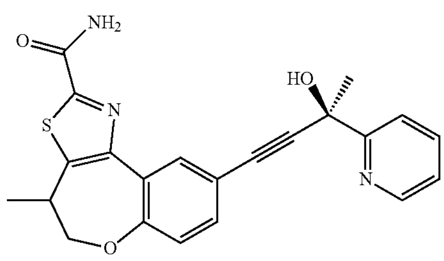 [SMILES: CC1COc2ccc(C#C[C@@](C)(O)c3ccccn3)cc2-c2nc(C(N)=O)sc21] | 9-((R)-3-hydroxy-3-(pyridin-2-yl)but-1-yn-1-yl)-4-methyl-4,5-dihydrobenzo[2,3]oxepino[4,5-d]thiazole-2-carboxamide |

TABLE 1-continued

| No. | Structure | Name |
|---|---|---|
| 683 | 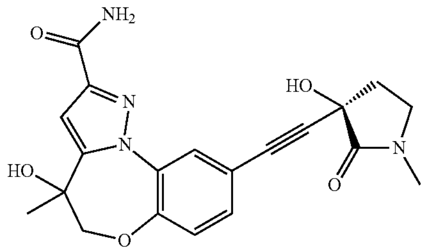 [SMILES: CN1CC[C@@](O)(C#Cc2ccc3c(c2)-n2nc(C(N)=O)cc2C(C)(O)CO3)C1=O] | 4-hydroxy-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 684 | 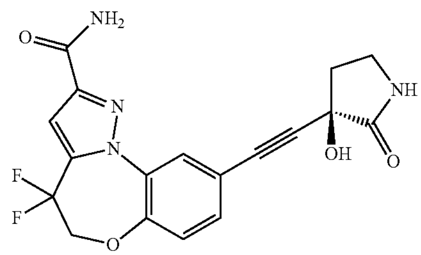 [SMILES: NC(=O)c1cc2n(n1)-c1cc(C#C[C@]3(O)CCNC3=O)ccc1OCC2(F)F] | (R)-4,4-difluoro-9-((3-hydroxy-2-oxopyrrolidin-3-yl)ethynyl)-4,5-dihydrobenzo[b]pyrazolo[1,5-d][1,4]oxazepine-2-carboxamide |
| 685 | 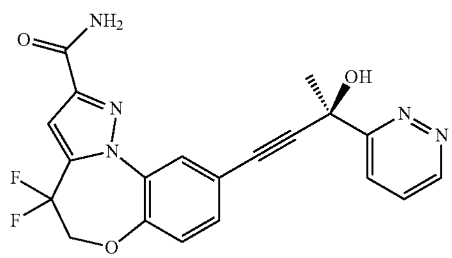 [SMILES: C[C@@](O)(C#Cc1ccc2c(c1)-n1nc(C(N)=O)cc1C(F)(F)CO2)c1cccnn1] | (R)-4,4-difluoro-9-(3-hydroxy-3-(pyridazin-3-yl)but-1-yn-1-yl)-4,5-dihydrobenzo[b]pyrazolo[1,5-d][1,4]oxazepine-2-carboxamide |
| 686 | 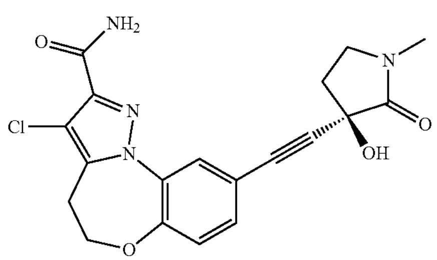 [SMILES: CN1CC[C@@](O)(C#Cc2ccc3c(c2)-n2nc(C(N)=O)c(Cl)c2CCO3)C1=O] | (R)-3-chloro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 687 | 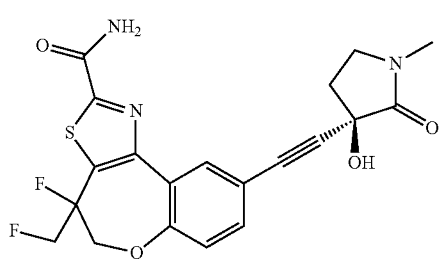 [SMILES: CN1CC[C@@](O)(C#Cc2ccc3c(c2)-c2nc(C(N)=O)sc2C(F)(CF)CO3)C1=O] | 4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 688 | 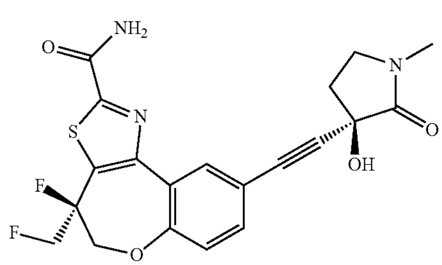 [SMILES: CN1CC[C@@](O)(C#Cc2ccc3c(c2)-c2nc(C(N)=O)sc2[C@@](F)(CF)CO3)C1=O] | (S)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1-continued

| No. | Structure | Name |
|---|---|---|
| 689 | 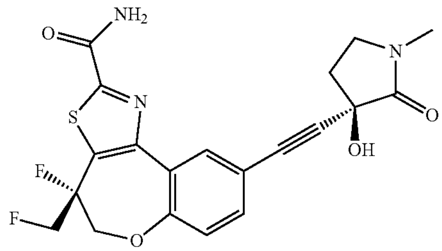 [SMILES: CN1CC[C@@](O)(C#Cc2ccc3c(c2)-c2nc(C(N)=O)sc2[C@](F)(CF)CO3)C1=O] | (R)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 690 | 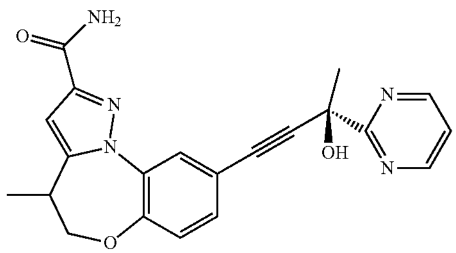 | 9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |
| 691 | 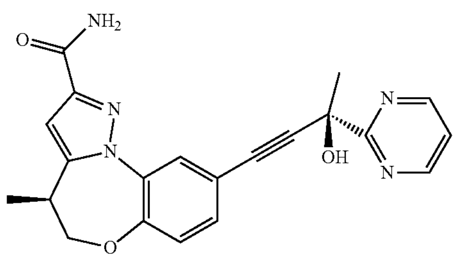 [SMILES: C[C@@H]1COc2ccc(C#C[C@@](C)(O)c3ncccn3)cc2-n2nc(C(N)=O)cc21] | (S)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |
| 692 | 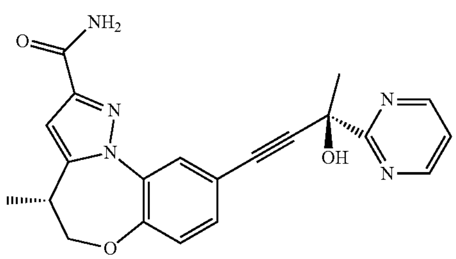 [SMILES: C[C@H]1COc2ccc(C#C[C@@](C)(O)c3ncccn3)cc2-n2nc(C(N)=O)cc21] | (R)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |
| 693 | 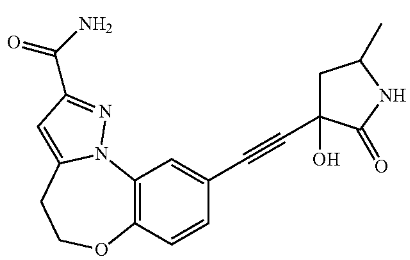 [SMILES: CC1CC(O)(C#Cc2ccc3c(c2)-n2nc(C(N)=O)cc2CCO3)C(=O)N1] | 9-((3-hydroxy-5-methyl-2-oxopyrrolidin-3-yl)ethynyl)-4,5-dihydrobenzo[b]pyrazolo[1,5-d][1,4]oxazepine-2-carboxamide |
| 694 | 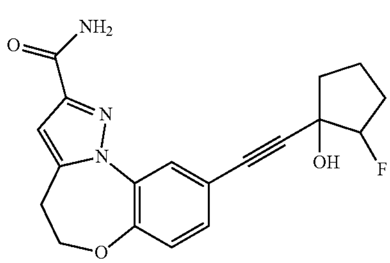 [SMILES: NC(=O)c1cc2n(n1)-c1cc(C#CC3(O)CCCC3F)ccc1OCC2] | 9-((2-fluoro-1-hydroxycyclopentyl)ethynyl)-4,5-dihydrobenzo[b]pyrazolo[1,5-d][1,4]oxazepine-2-carboxamide |

TABLE 1-continued

| No. | Structure | Name |
|---|---|---|
| 695 | 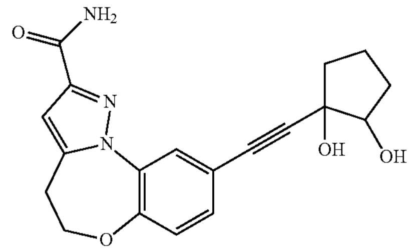 [SMILES: NC(=O)c1cc2n(n1)-c1cc(C#CC3(O)CCCC3O)ccc1OCC2] | 9-((1,2-dihydroxycyclopentyl)ethynyl)-4,5-dihydrobenzo[b]pyrazolo[1,5-d][1,4]oxazepine-2-carboxamide |
| 696 | 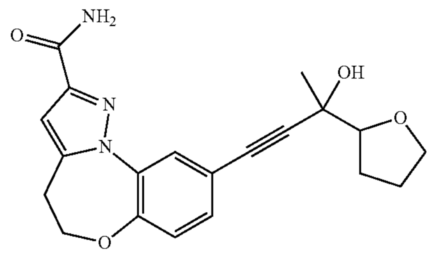 [SMILES: CC(O)(C#Cc1ccc2c(c1)-n1nc(C(N)=O)cc1CCO2)C1CCCO1] | 9-(3-hydroxy-3-(tetrahydrofuran-2-yl)but-1-yn-1-yl)-4,5-dihydrobenzo[b]pyrazolo[1,5-d][1,4]oxazepine-2-carboxamide |
| 697 | 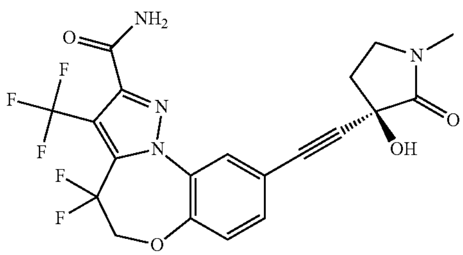 [SMILES: CN1CC[C@@](O)(C#Cc2ccc3c(c2)-n2nc(C(N)=O)c(C(F)(F)F)c2C(F)(F)CO3)C1=O] | (R)-4,4-difluoro-9-((3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 698 | 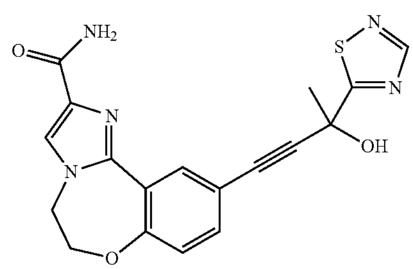 [SMILES: CC(O)(C#Cc1ccc2c(c1)-c1nc(C(N)=O)cn1CCO2)c1ncns1] | 10-(3-hydroxy-3-(1,2,4-thiadiazol-5-yl)but-1-yn-1-yl)-5,6-dihydrobenzo[f]imiadzo[1,2-d][1,4]oxazepine-2-carboxamide |
| 699 | 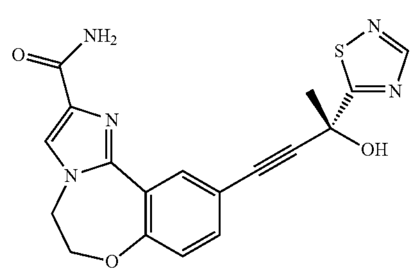 [SMILES: C[C@@](O)(C#Cc1ccc2c(c1)-c1nc(C(N)=O)cn1CCO2)c1ncns1] | (R)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide |
| 700 | 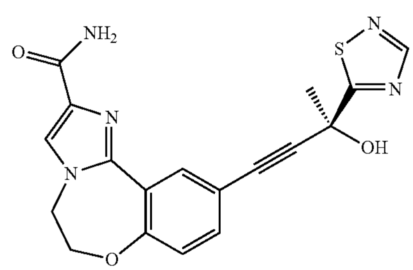 [SMILES: C[C@](O)(C#Cc1ccc2c(c1)-c1nc(C(N)=O)cn1CCO2)c1ncns1] | S)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide |

TABLE 1-continued

| No. | Structure | Name |
|---|---|---|
| 701 | 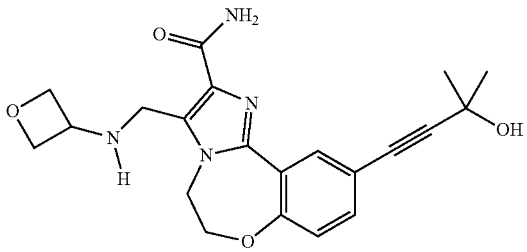 [SMILES: CC(C)(O)C#Cc1ccc2c(c1)-c1nc(C(N)=O)c(CNC3COC3)n1CCO2] | 10-(3-hydroxy-3-methylbut-1-yn-1-yl)-3-((oxetan-3-ylamino)methyl)-5,6-dihydrobenzo[f]imidazo[1,2-d][1,4]oxazepine-2-carboxamide |
| 702 | 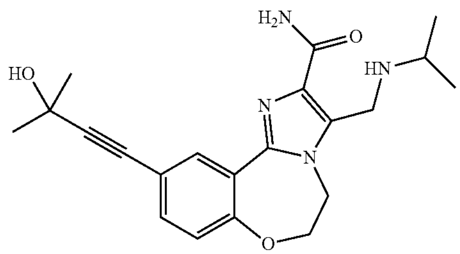 [SMILES: CC(C)NCc1c(C(N)=O)nc2n1CCOc1ccc(C#CC(C)(C)O)cc1-2] | 10-(3-hydroxy-3-methylbut-1-yn-1-yl)-3-((isopropylamino)methyl)-5,6-dihydrobenzo[f]imidazo[1,2-d][1,4]oxazepine-2-carboxamide |
| 703 | 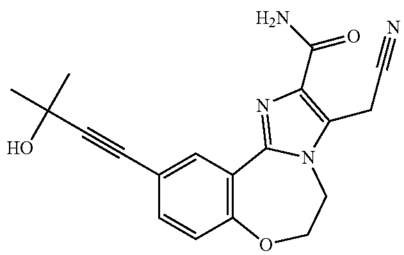 [SMILES: CC(C)(O)C#Cc1ccc2c(c1)-c1nc(C(N)=O)c(CC#N)n1CCO2] | 3-(cyanomethyl)-10-(3-hydroxy-3-methylbut-1-yn-1-yl)-5,6-dihydrobenzo[f]imidazo[1,2-d][1,4]oxazepine-2-carboxamide |
| 704 | 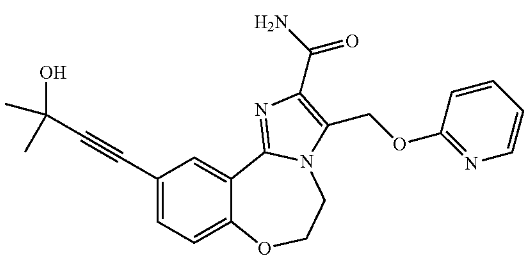 [SMILES: CC(C)(O)C#Cc1ccc2c(c1)-c1nc(C(N)=O)c(COc3ccccn3)n1CCO2] | 10-(3-hydroxy-3-methylbut-1-yn-1-yl)-3-((pyridin-2-yloxy)methyl)-5,6-dihydrobenzo[f]imidazo[1,2-d][1,4]oxazepine-2-carboxamide |
| 705 | 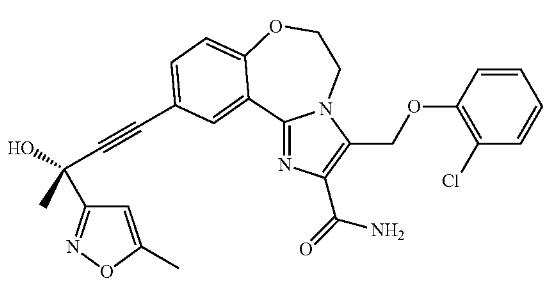 [SMILES: Cc1cc([C@](C)(O)C#Cc2ccc3c(c2)-c2nc(C(N)=O)c(COc4ccccc4Cl)n2CCO3)no1] | (R)-3-((2-chlorophenoxy)methyl)-10-(3-hydroxy-3-(5-methylisoxazol-3-yl)but-1-yn-1-yl)-5,6-dihydrobenzo[f]imidazo[1,2-d][1,4]oxazepine-2-carboxamide |
| 706 | 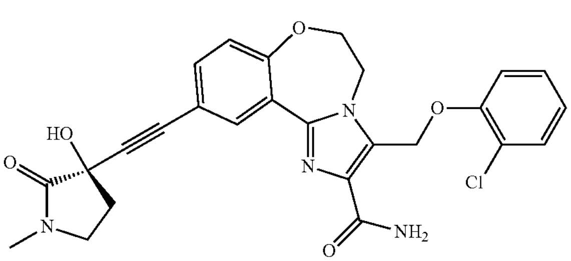 [SMILES: CN1CC[C@@](O)(C#Cc2ccc3c(c2)-c2nc(C(N)=O)c(COc4ccccc4Cl)n2CCO3)C1=O] | (R)-3-((2-chlorophenoxy)methyl)-10-((3-hydroxy-1-methyl-2-oxopyrrolidin-3-yl)ethynyl)-5,6-dihydrobenzo[f]imidazo[1,2-d][1,4]oxazepine-2-carboxamide |

TABLE 1-continued

| No. | Structure | Name |
|---|---|---|
| 707 | 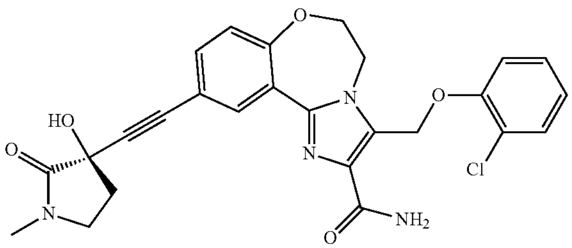 [SMILES: CN1CC[C@@](O)(C#Cc2ccc3c(c2)-c2nc(C(N)=O)c(COc4ccccc4Cl)n2CCO3)C1=O] | (R)-3-((2-chlorophenoxy)methyl)-10-((3-hydroxy-1-methyl-2-oxopyrrolidin-3-yl)ethynyl)-5,6-dihydrobenzo[f]imidazo[1,2-d][1,4]oxazepine-2-carboxamide |
| 708 | 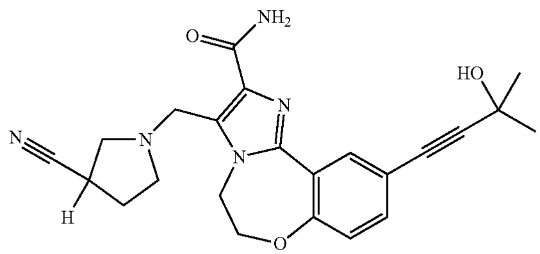 [SMILES: CC(C)(O)C#Cc1ccc2c(c1)-c1nc(C(N)=O)c(CN3CCC(C#N)C3)n1CCO2] | 3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |
| 709 | 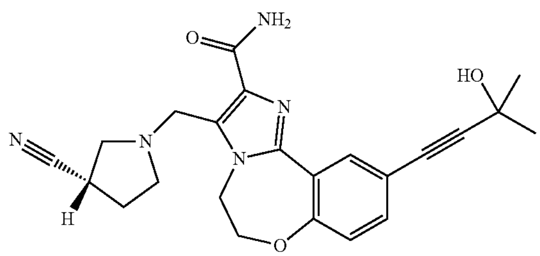 [SMILES: CC(C)(O)C#Cc1ccc2c(c1)-c1nc(C(N)=O)c(CN3CC[C@H](C#N)C3)n1CCO2] | (S)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |
| 710 | 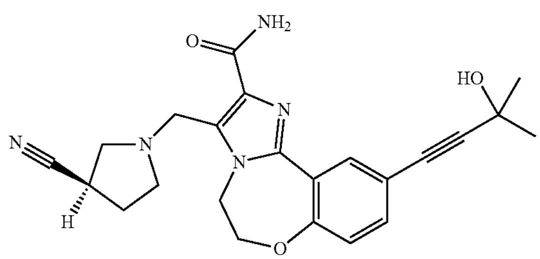 [SMILES: CC(C)(O)C#Cc1ccc2c(c1)-c1nc(C(N)=O)c(CN3CC[C@@H](C#N)C3)n1CCO2] | (R)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |
| 711 | 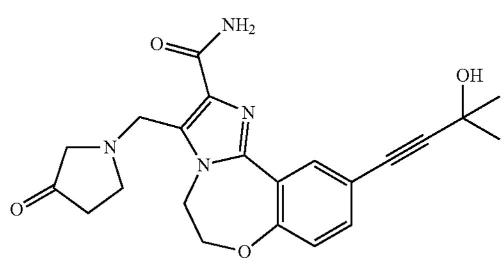 [SMILES: CC(C)(O)C#Cc1ccc2c(c1)-c1nc(C(N)=O)c(CN3CCC(=O)C3)n1CCO2] | 10-(3-hydroxy-3-methylbut-1-yn-1-yl)-3-((3-oxopyrrolidin-1-yl)methyl)-5,6-dihydrobenzo[f]imidazo[1,2-d][1,4]oxazepine-2-carboxamide |
| 712 | 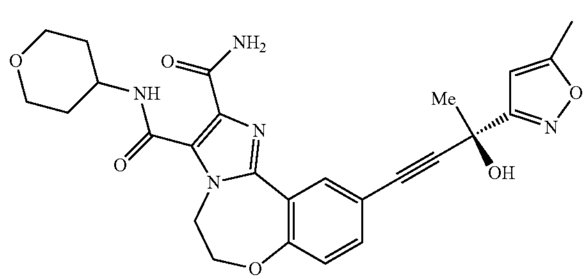 [SMILES: Cc1cc([C@](C)(O)C#Cc2ccc3c(c2)-c2nc(C(N)=O)c(C(=O)NC4CCOCC4)n2CCO3)no1] | (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide |

TABLE 1-continued

| No. | Structure | Name |
|---|---|---|
| 713 | 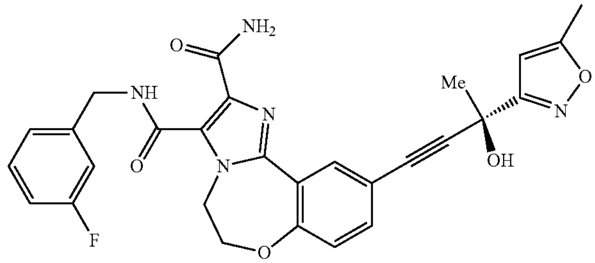 [SMILES: Cc1cc([C@](C)(O)C#Cc2ccc3c(c2)-c2nc(C(N)=O)c(C(=O)NCc4cccc(F)c4)n2CCO3)no1] | (R)-N3-(3-fluorobenzyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 714 | 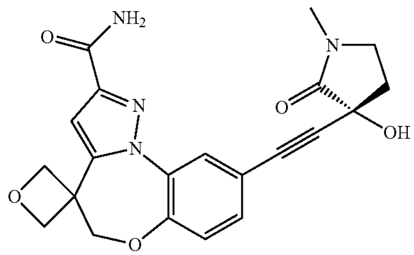 [SMILES: CN1CC[C@@](O)(C#Cc2ccc3c(c2)-n2nc(C(N)=O)cc2C2(COC2)CO3)C1=O] | (R)-9-((3-hydroxy-1-methyl-2-oxopyrrolidin-3-yl)ethynyl)-5H-spiro[benzo[b]pyrazolo[1,5-d][1,4]oxazepine-4,3'-oxetane]-2-carboxamide |
| 715 | 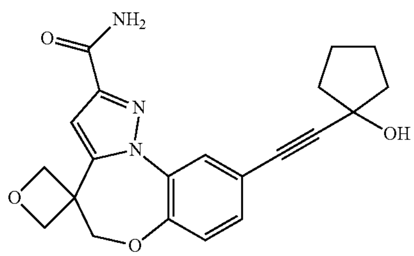 [SMILES: NC(=O)c1cc2n(n1)-c1cc(C#CC3(O)CCCC3)ccc1OCC21COC1] | 9-((1-hydroxycyclopentyl)ethynyl)-5H-spiro[benzo[b]pyrazolo[1,5-d][1,4]oxazepine-4,3'-oxetane]-2-carboxamide |
| 716 | 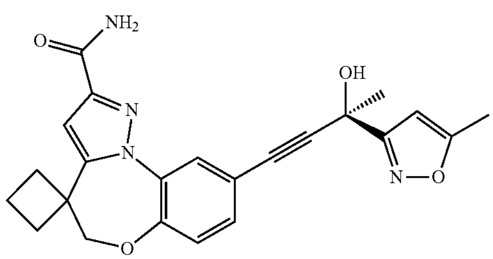 [SMILES: Cc1cc([C@](C)(O)C#Cc2ccc3c(c2)-n2nc(C(N)=O)cc2C2(CCC2)CO3)no1] | (R)-9-(3-hydroxy-3-(5-methylisoxazol-3-yl)but-1-yn-1-yl)-5H-spiro[benzo[b]pyrazolo[1,5-d][1,4]oxazepine-4,1'-cyclobutane]-2-carboxamide |
| 717 | 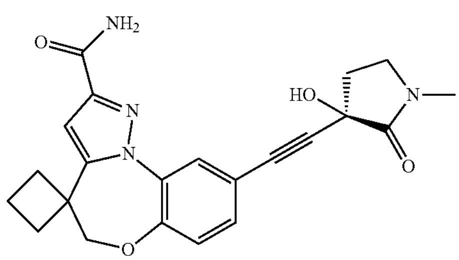 [SMILES: CN1CC[C@@](O)(C#Cc2ccc3c(c2)-n2nc(C(N)=O)cc2C2(CCC2)CO3)C1=O] | (R)-9-((3-hydroxy-1-methyl-2-oxopyrrolidin-3-yl)ethynyl)-5H-spiro[benzo[b]pyrazolo[1,5-d][1,4]oxazepine-4,1'-cyclobutane]-2-carboxamide |
| 718 | 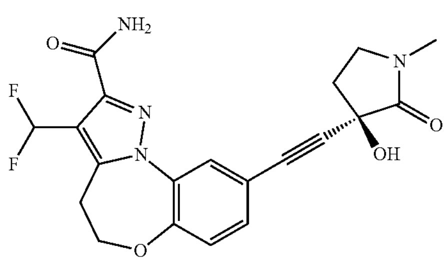 [SMILES: CN1CC[C@@](O)(C#Cc2ccc3c(c2)-n2nc(C(N)=O)c(C(F)F)c2CCO3)C1=O] | (R)-3-(difluoromethyl)-9-((3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1-continued

| No. | Structure | Name |
|---|---|---|
| 719 | 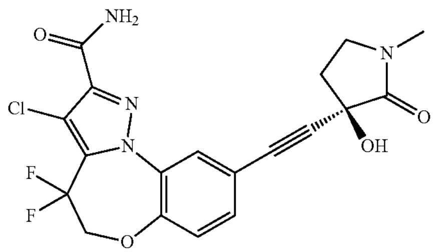 [SMILES: CN1CC[C@@](O)(C#Cc2ccc3c(c2)-n2nc(C(N)=O)c(Cl)c2C(F)(F)CO3)C1=O] | (R)-3-chloro-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 720 | 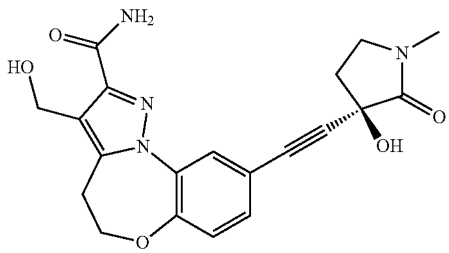 [SMILES: CN1CC[C@@](O)(C#Cc2ccc3c(c2)-n2nc(C(N)=O)c(CO)c2CCO3)C1=O] | (R)-9-((3-hydroxy-1-methyl-2-oxopyrrolidin-3-yl)ethynyl)-3-(hydroxymethyl)-4,5-dihydrobenzo[b]pyrazolo[1,5-d][1,4]oxazepine-2-carboxamide |

In another embodiment, the invention provides for intermediate compounds useful in the synthesis of compounds of Formula I.

Synthesis of Compounds

For illustrative purposes, Schemes 1-19 show general methods for preparing key intermediates and compounds of the present invention. For a more detailed description of certain individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or Beilstein's Handbuch der organishcen chemie, 4, Aufl. Ed. Springer-Verlag, Berlin including supplements also included via the Beilstein online database.

In preparing compounds of Formula I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Intermediates and compounds of the invention can be synthesized according to the Schemes presented below, in which, R, R' and R" at each occurrence independently represents generally a non-interfering substituent (unless otherwise a specific substituent is specified in the description of the scheme); the symbol A at each occurrence represents independently a nitrogen or carbon atom; the symbol X, X', X" and $X^1$, represents any halogen (unless otherwise a specific halogen is specified in the description of the scheme) and the subscript n represents and integer from 0 to 6.

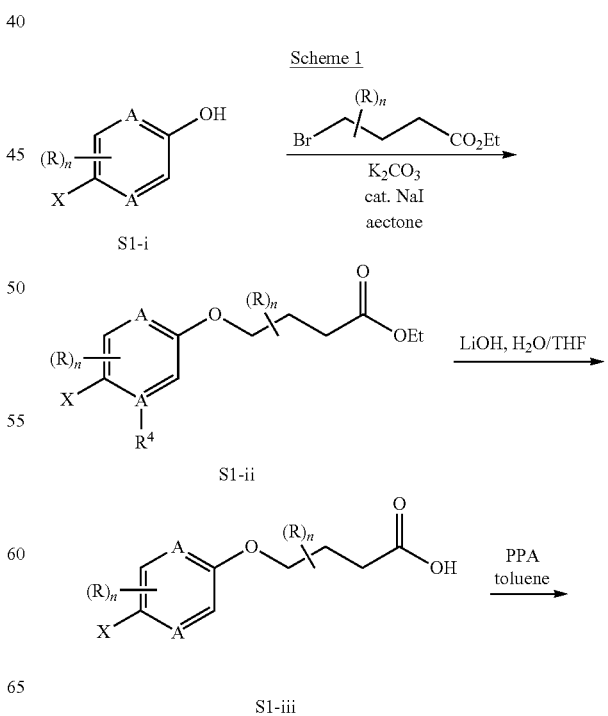

Scheme 1

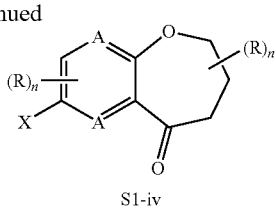

S1-iv

Scheme 1 shows a general method for preparation of intermediates S1-iv by O-alkylation of phenolic compounds S1-i with an optionally substituted ethyl 4-bromobutanoate compound to give an optionally substituted ethyl 4-phenoxybutanoate intermediates S1-ii, followed by saponification to the carboxylic acid S1-iii and intramolecular cyclization under acidic conditions.

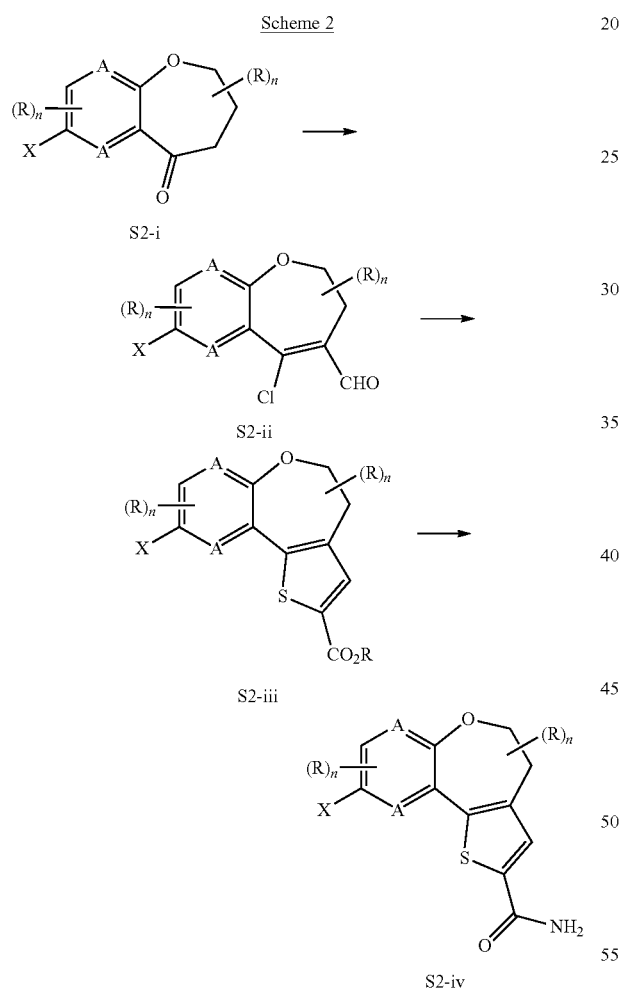

Scheme 2 shows a general method of preparation of intermediates S2-iv. Intermediates S2-i are formylated with phosphorus oxytrichloride and dimethylformamide (DMF) to give chloro aldehyde intermediates S2-ii. Cyclization of S2-ii with an optionally substituted mercapto acetate ester (HSCH$_2$CO$_2$R where R is alkyl or aryl) in potassium carbonate and DMF gives ester intermediates S2-iii. Saponification of the ester group in S2-iii with lithium hydroxide in THF and water gives corresponding acids (not shown) which is treated with thionyl chloride at reflux followed by ammonia source with a catalytic amount of DMAP (4,4-dimethylaminopyridine), triethylamine, and dichloromethane to give amide intermediates S2-iv. Alternatively, the acid is treated with oxalyl chloride and a catalytic amount of DMF to generate the acid chloride, followed by reaction with an ammonia source and potassium carbonate in acetonitrile to give amides such as S2-iv. Where X is bromo or another halogen, the bromide of S2-iv, or of another intermediate such as S2-i, S2-ii or S2-iii where X is bromide, may be displaced by Sonogashira coupling to give alkynyl (—C≡CR) or by any of the other methods described in detail in Example 3 below.

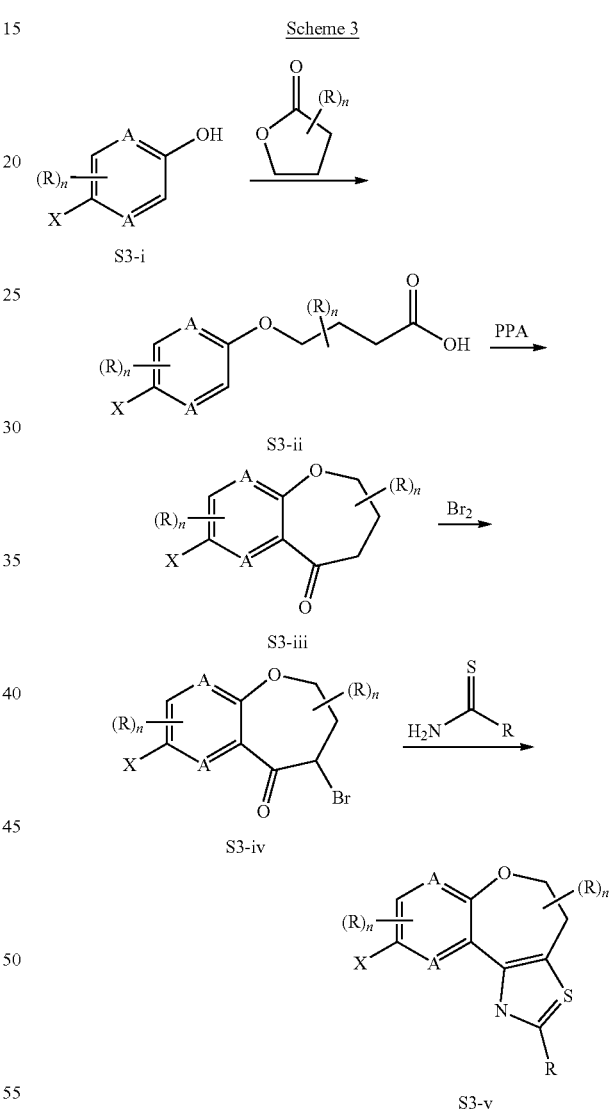

Scheme 3 shows a general method of preparation of benzoxepin thiazoles S3-v. Bromination of keto benzoxepins S3-iii forms 2-bromo keto benzoxepin intermediates S3-iv. Cyclization with thioamides in which the R in the thioamide reagent is a protected carboxy or amido group forms S3-v (see: Rueeger et al (2004) Bioorganic & Med. Chem. Letters 14:2451-2457; US 2005/0277630; WO 2001/064675; U.S. Pat. No. 6,222,040; U.S. Pat. No. 6,225,330; U.S. Pat. No. 5,314,889). Where X is bromo or another halogen, the bromide of S3-iv, or of another intermediate such as S3-1,53-H, S3-iii or S3-iv where X is bromide, may be displaced by Sonogashira coupling (Chinchilla, R.; Najera, C. (2007), "The Sonogashira Reaction: A Booming Methodology in Synthetic Organic Chemistry", Chem. Rev. 107: 874-922) to give alkynyl (—C≡CR) or by any of the other methods described in detail in Example 3 below.

reacted with oxalyl chloride and ammonium hydroxide to form primary amides S4-v. Iodination of S4-v with N-iodosuccinimide yield the iodo intermediates S4-vi. For certain other iodo-imidazole tricycles S4-iii, palladium mediated carbonylation followed by trapping with HMDS (Hexamethyldisilazane) directly provides primary amides S4-v. Iodina- Scheme 4

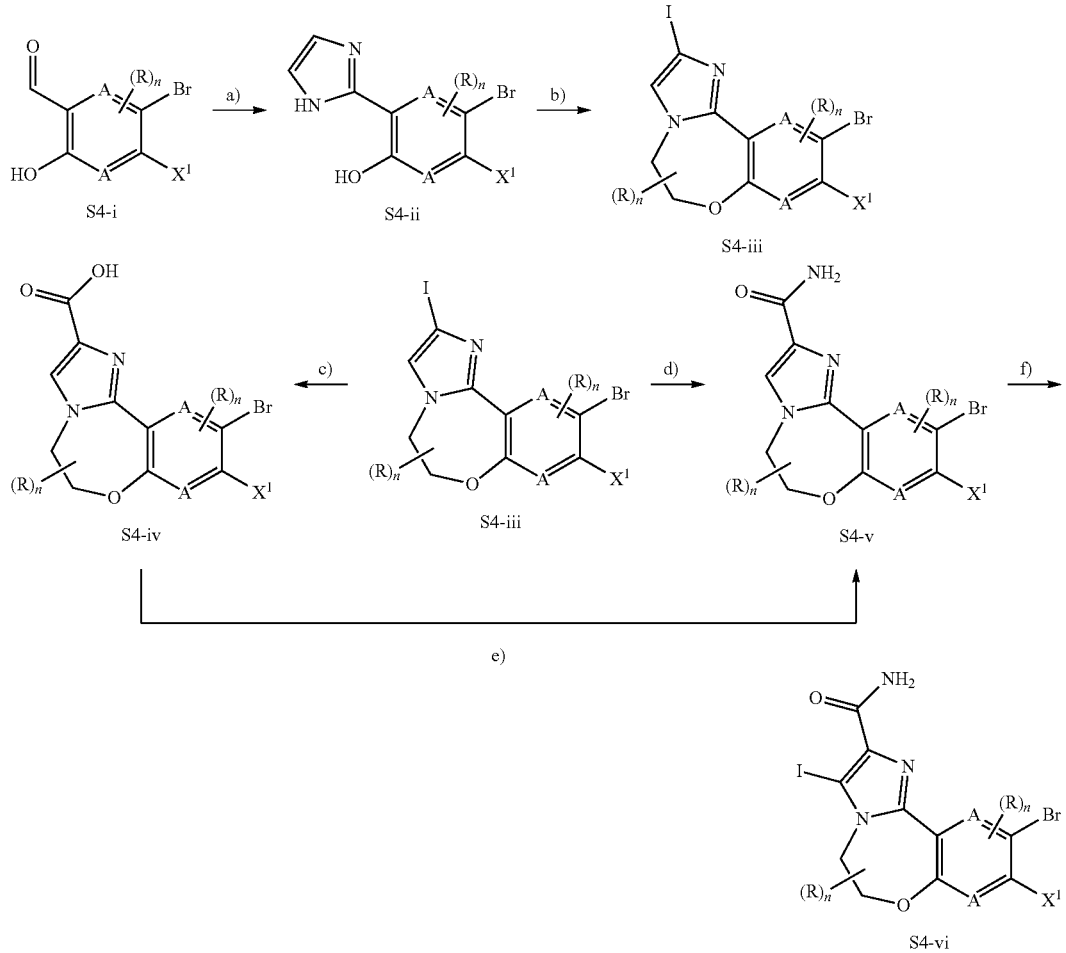

The reagents and conditions reference in a-f in Scheme 4 are as follows: in step a) glyoxal, ammonia, methanol r.t.; in step b) I. dibromoethane, $Cs_2CO_3$, $K_2CO_3$ DMF 100° C.; II. NIS (N-iodosuccinimide), DMF, 80° C.; Iii. EtMgBr, THF then $NH_4Cl$ (aq); in step c) ($X^1$=H) EtMgBr, $CO_2$, THF; in step e) $(COCl)_2$, ACN (acetonitrile) then $NH_4OH$; in step d) ($X^1$=F) $PdCl_2(PPh_3)_2$, HMDS, CO, DMF 50° C.; and in step f) ($X^1$=H) NIS, DMF, 80° C.; ($X^1$=F) NIS, DMSO, 80° C.

Scheme 4 shows a general method for preparing imidazole tricycle intermediates S4-vi. Hydroxyaldehydes S4-i are condensed with glyoxal and ammonia to form the imidazole compounds S4-ii. Cyclization of S4-ii with an optionally substituted dibromoethane followed by iodination with N-iodosuccinimide produces iodo-imidazole tricycles S4-iii. For certain iodo-imidazole tricycles S4-iii, transmetallation with ethyl magnesium bromide followed by reaction with $CO_2$ produces carboxylic acid intermediates S4-iv, which is tion of primary amides S4-v provides intermediates S4-vi. Primary amide compounds S4-v or iodo intermediates S4-vi can be further modified at the 5 membered heteroaryl ring by methods disclosed herein in Example 7 and Example 8. The bromide of S4-v, or of another intermediate such as S4-i, S4-ii, S4-iii or S4-iv, may be displaced by Sonogashira coupling to give alkynyl (—C≡CR) or by any of the other methods described in detail in Example 3 below.

Scheme 5

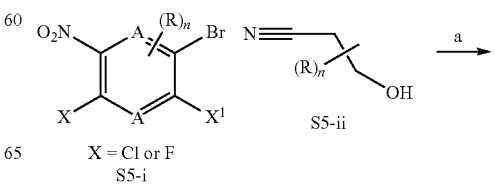

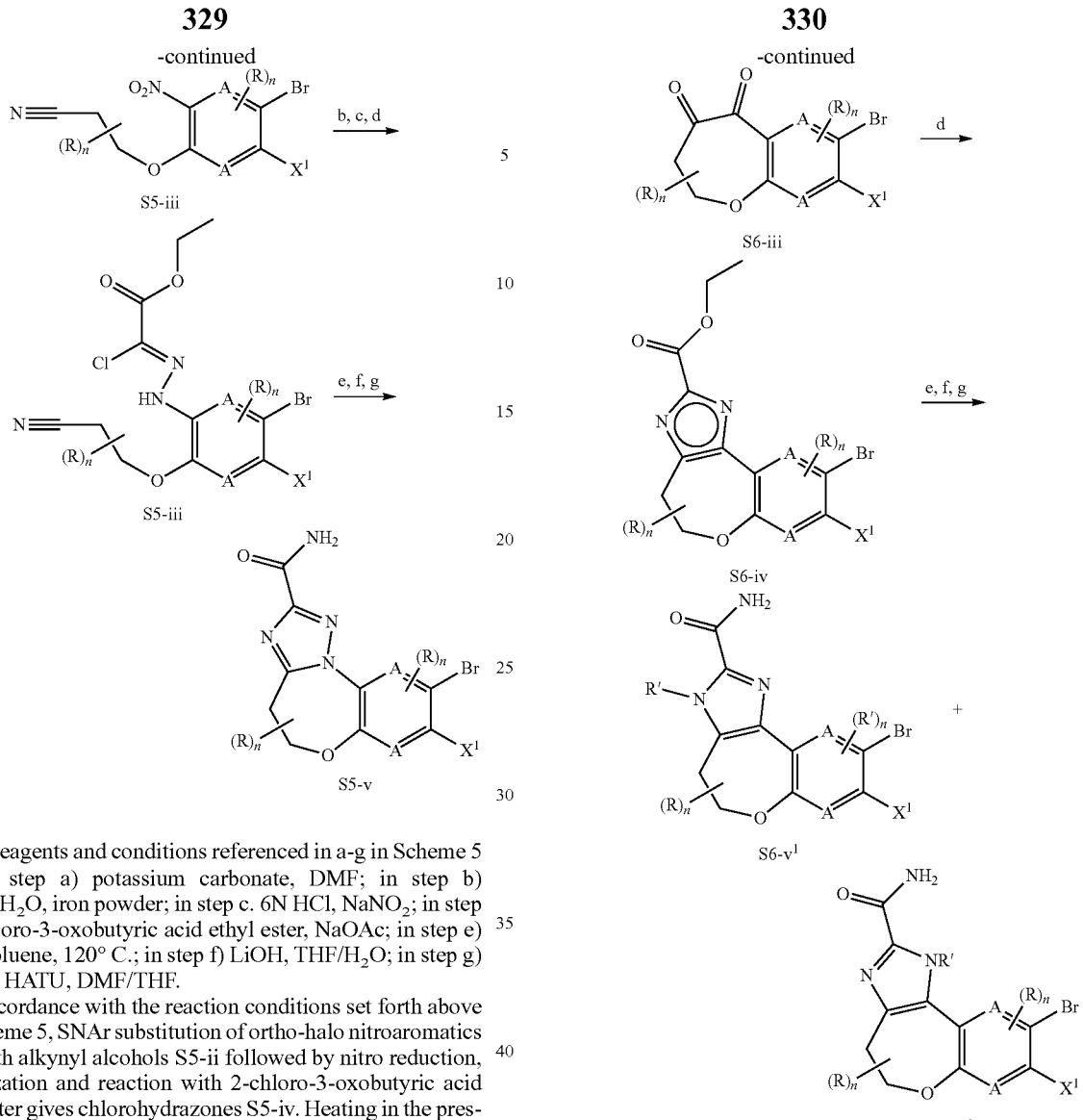

The reagents and conditions referenced in a-g in Scheme 5 are: in step a) potassium carbonate, DMF; in step b) FeCl$_3$.6H$_2$O, iron powder; in step c. 6N HCl, NaNO$_2$; in step d) 2-chloro-3-oxobutyric acid ethyl ester, NaOAc; in step e) TEA, toluene, 120° C.; in step f) LiOH, THF/H$_2$O; in step g) NH$_4$Cl, HATU, DMF/THF.

In accordance with the reaction conditions set forth above for Scheme 5, SNAr substitution of ortho-halo nitroaromatics S5-i with alkynyl alcohols S5-ii followed by nitro reduction, diazotization and reaction with 2-chloro-3-oxobutyric acid ethyl ester gives chlorohydrazones S5-iv. Heating in the presence of triethyl amine give tricyclic intermediates (for example Zecchi et al Heterocycles, 1976, 13, 1339) which can be converted to primary amides S5-v via a two step synthesis. The bromide of S5-v, may be displaced by Sonogashira coupling to give alkynyl (—C≡CR) or by any of the other methods described in detail in Example 3 below.

Scheme 6

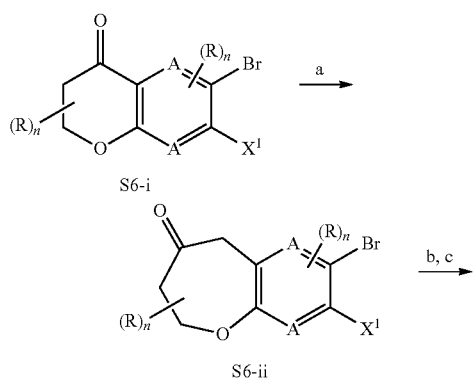

The reagents and conditions referenced in a-g in Scheme 6 are: in step a) CH$_2$N$_2$ (or TMSCHN$_2$), BF$_3$.Et$_2$O, Et$_2$O; in step b) CuBr$_2$, EtOAc, reflux; in step c) DMSO, 100° C.; in step d) ethylglyoxalate, NH$_4$OAc, THF/MeOH; in step e) for R'=alkyl: alkyl-halide, CsCO$_3$ DMF/THF, for R'=Aryl, Aryl-halide, see reference; in step f) LiOH, THF/H$_2$O; g. NH$_4$Cl, HATU, DMF/THF.

In accordance with the reaction conditions set forth above for Scheme 6, diazomethane mediated Tiffeneau-Demjanov type ring expansion reaction provides intermediates S6-ii (See: Fattori, D. et al. Tetrahedron, 1993, 49, 1649.). Treatment of S6-ii under alpha bromination and Kornblum oxidation conditions provides dione intermediates S6-iii. Treatment of S6-iii with ethylgloxylate and ammonium acetate promotes formation of 2-carboxy imidazole tricycles S6-iv, which can be further functionalized on the nitrogen atom of the imidazole ring (e.g., arylation (see Buchwald et al J. Am. Chem. Soc. 2012, 134, 700) or alkylation (R') of such nitrogen atom and even further transformed to provide the regioisomers of primary amides S6-v$^1$ and S6-v$^2$ which can be separated chromatographically. The bromides of 56-v$^1$ and 56-v², may be displaced by Sonogashira coupling to give alkynyl (—C≡CR) or by any of the other methods described in detail in Example 3 below.

Scheme 7

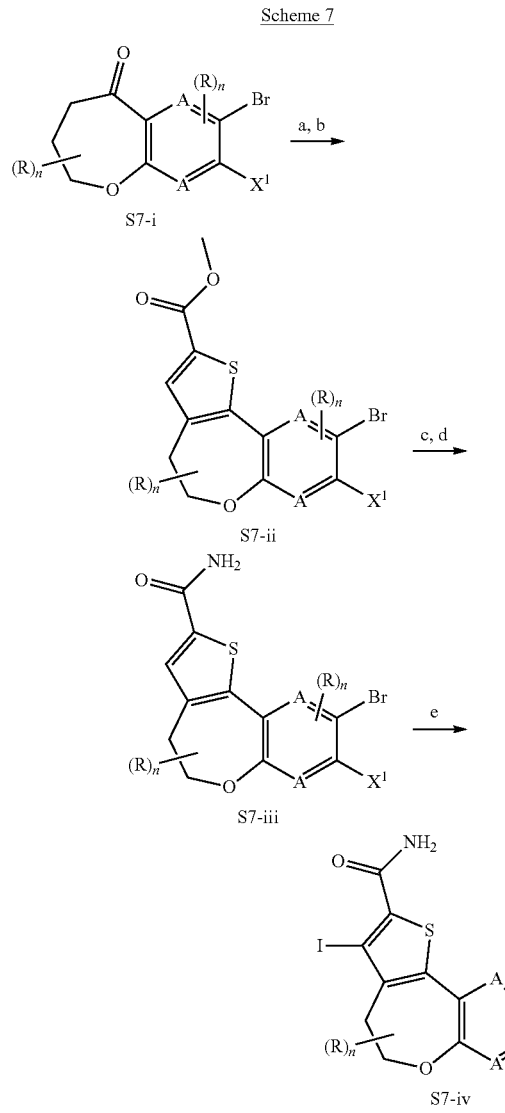

Scheme 8

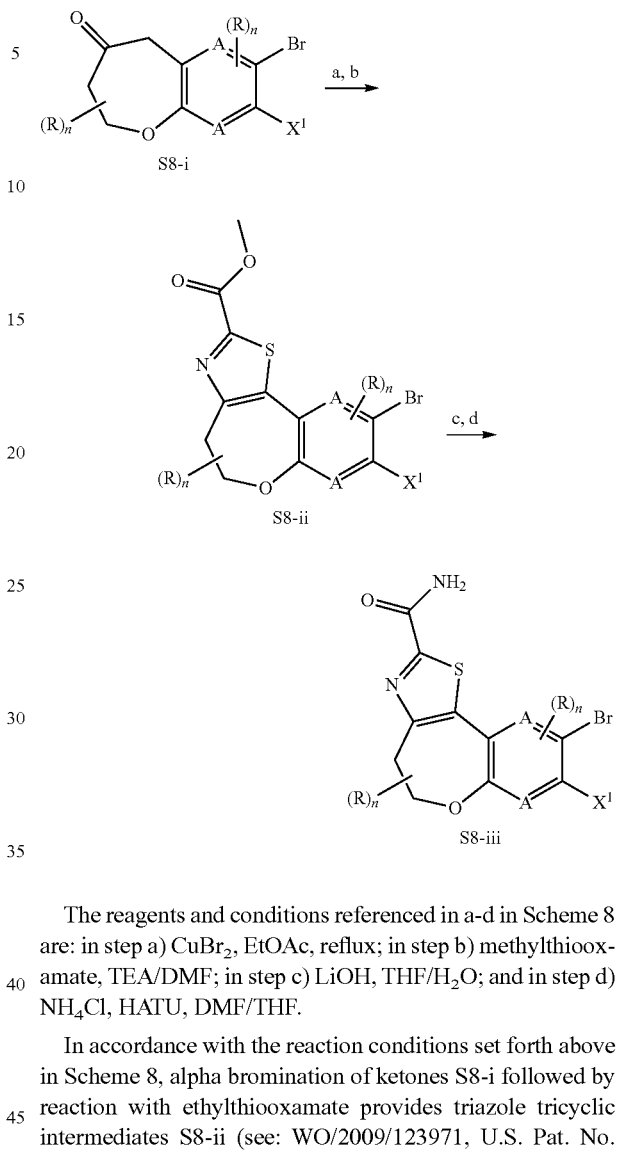

The reagents and conditions referenced in a-d in Scheme 8 are: in step a) CuBr₂, EtOAc, reflux; in step b) methylthiooxamate, TEA/DMF; in step c) LiOH, THF/H₂O; and in step d) NH₄Cl, HATU, DMF/THF.

In accordance with the reaction conditions set forth above in Scheme 8, alpha bromination of ketones S8-i followed by reaction with ethylthiooxamate provides triazole tricyclic intermediates S8-ii (see: WO/2009/123971, U.S. Pat. No. 7,928,248), which can be further converted to primary amides S8-iii. The bromides of S8-iii can be displaced by Sonogashira coupling to give alkynyl (—C≡CR) or by any of the other methods described in detail in Example 3 below.

The reagents and conditions referenced in a-e in Scheme 7 are: in step a) POCl₃, DMF; in step b) methylthioacetate, K₂CO₃, DMF; in step c) LiOH, THF/H₂O; in step d) NH₄Cl, HATU, DMF/THF; in step e) NIS, DMF.

In accordance with the reaction conditions set forth above in Scheme 7, treatment of compounds S7-i under modified Vilsmeier formylation and reaction with methylthioacetate gives tricyclic intermediates 57-ii (see, WO/2009/123971, U.S. Pat. No. 7,928,248). This compound could be transformed into the primary amide S7-iii. Iodination of the thiophene intermediates can be accomplished with NIS to form iodo intermediates S7-iv. Primary amide compounds S7-iii or iodo intermediates S7-iv can be further modified at the 5 membered heteroaryl ring by methods disclosed herein in Example 7 and Example 8. Also the bromides of S7-iii or any another intermediate, e.g., S7-ii, S7-i may be displaced by Sonogashira coupling to give alkynyl (—C≡CR) or by any of the other methods described in detail in Example 3 below.

Scheme 9

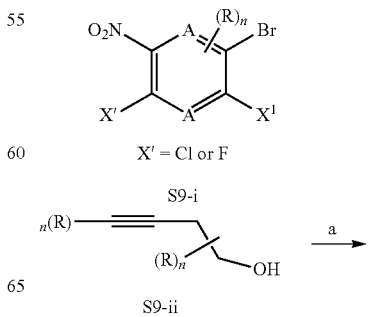

X' = Cl or F

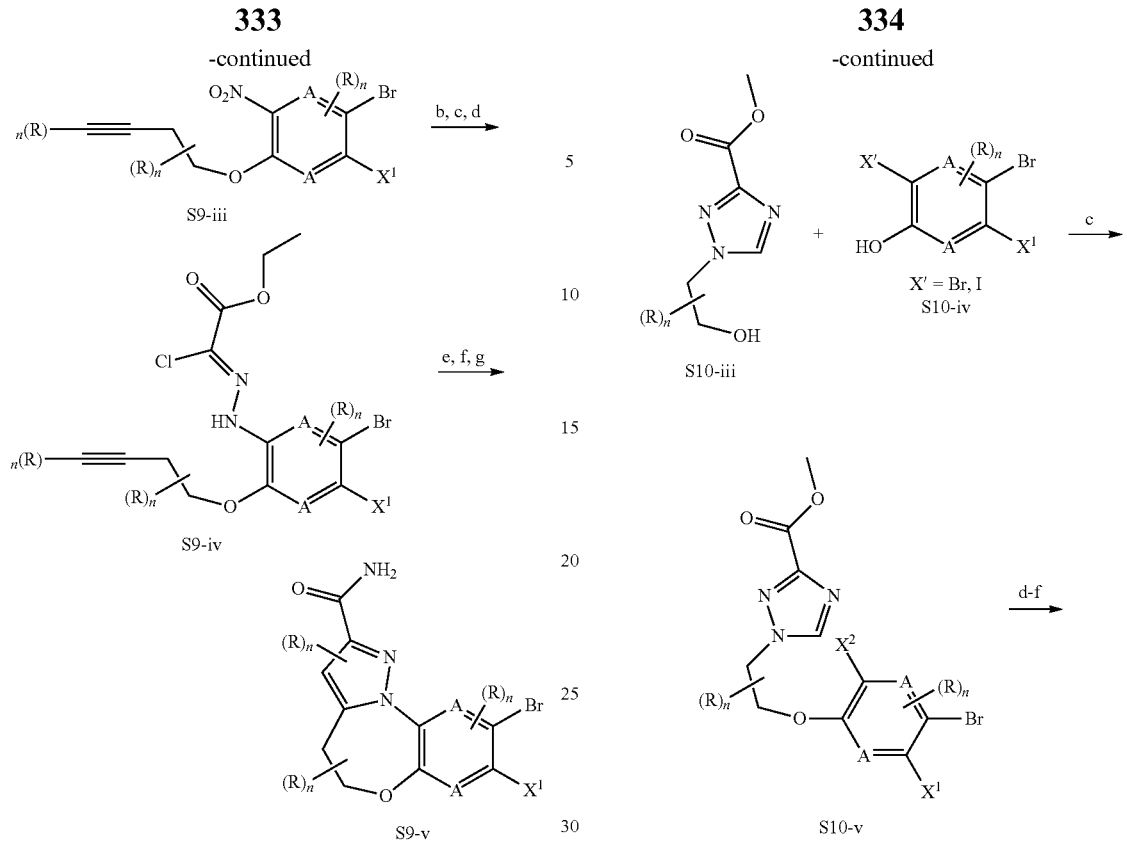

The reagents and conditions referenced in a-g in Scheme 9 are: in step a) potassium carbonate, DMF; in step b) FeCl₃·6H₂O, iron powder or 5 nCl₂, 6N HCl; in step c) 6N HCl, NaNO₂; in step d) 2-chloro-3-oxobutyric acid ethyl ester, NaOAc; in step e) TEA, toluene, 120° C.; in step f) LiOH, THF/H₂O; and in step g) NH₄Cl, HATU, DMF/THF.

In accordance with the reaction conditions set forth for Scheme 9, Nucleophillic aromatic (SNAr) substitution of ortho-halo nitroaromatics S9-i with alkynyl alcohols S9-ii followed by nitro reduction, diazotization and reaction with 2-chloro-3-oxobutyric acid ethyl ester gives chlorohydrazones S9-iv. Intramolecular 3+2 cyclization of S9-iv can be promoted under basic conditions to produce tricyclic intermediate ester compounds (see: Padwa, A. et al J. Org. Chem. 1978, 43, 1664), which can be saponified and converted to the primary amide intermediates S9-v. The bromides of S9-v or any earlier intermediates S9-i, S9-ii, S9-iii or S9-iv, may be displaced by Sonogashira coupling to give alkynyl (—C≡CR) or by any of the other methods described in detail in Example 3 below.

Scheme 10

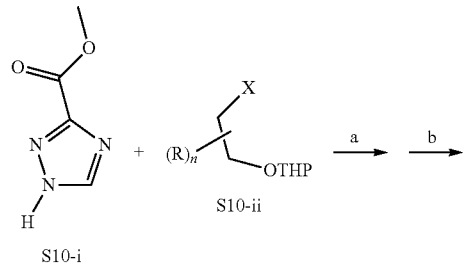

The reagents and conditions referenced in a-f in Scheme 10 are: in step a) sodium hydride, then S10-ii, THF/DMF; in step b) PPTS, MeOH, separate regioisomeric products; in step c) DIAD, PPh₃, THF; in step d) Pd(OAc)₂, PivOH, DMF—or— CuI, base DMF; in step e) LiOH, THF/H₂O; in step f) NH₄Cl, HATU, DMF/THF.

In accordance with the reaction conditions set forth above, alkylation of S10-i with a protected haloethanol S10-ii affords intermediates S10-iii in which the alcohol protecting group can be removed to provide deprotected compounds S10-iii. Mitsunobu-type etherification followed by palladium promoted intramolecular arylation (see: Gevorgyan et al Org. Lett. 2007, 9, 2333) or copper (see: Miura et al Org. Lett. 2009, 11, 3702) produces tricyclic intermediates which can be further modified to provide primary amides S10-vi. The bromides of S10-vi or earlier intermediates, e.g., S10-v, may be displaced by Sonogashira coupling to give alkynyl compounds (—C≡CR) or by any of the other methods described in detail in Example 3 below.

Scheme 11

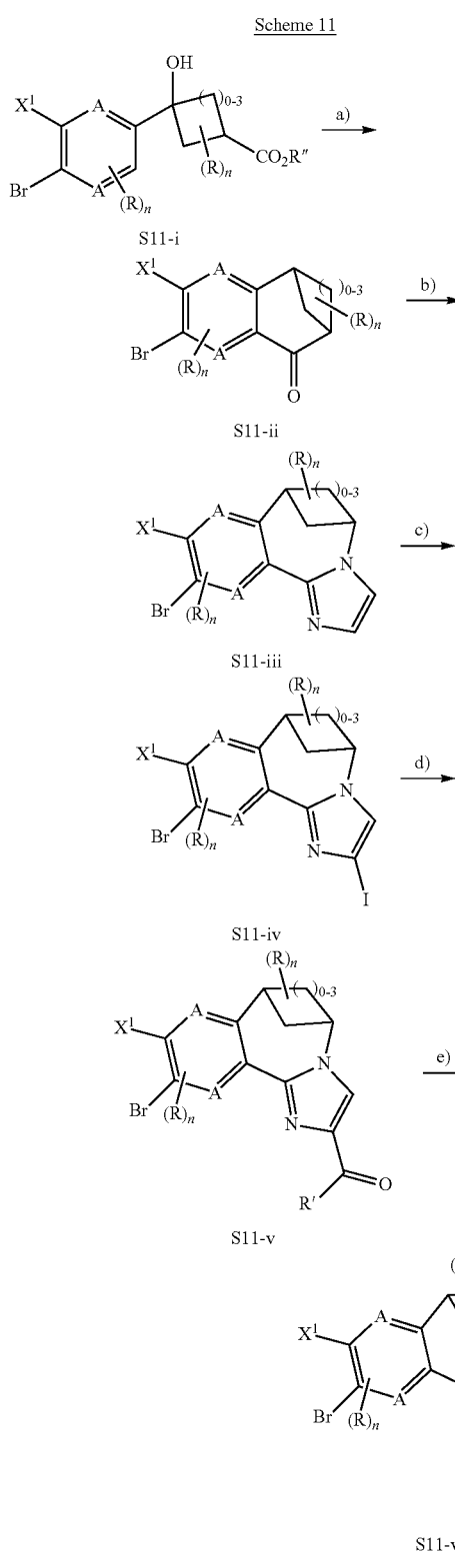

DIPEA, toluene 85° C., step IV. H$_2$NCH$_2$CH(OMe)$_2$, tBuOH 85° C., step V. 10% aqueous HCl 100° C. and (for X$^1$=F) step I. H$_2$OH—HCl, Na$_2$CO$_3$, MeOH, THF, step II. SOCl$_2$, 1,4-dioxane, reflux, step III. PCl$_5$, toluene 25° C., step IV. H$_2$NCH$_2$CH(OMe)$_2$, nBuOH 100° C.; V. 3N aqueous HCl r.t.; in step c) step I. NIS, DMF, 90° C., step II. EtMgBr then NH$_4$Cl (aq); in step d) (for X$^1$=H, R'=OMe) Pd(dppf)Cl$_2$, CO, MeOH/TEA 50° C. and (for X$^1$=H, =NH$_2$) PdCl$_2$(PPh$_3$)$_2$, HMDS, CO, DMF 60° C., and (for X$^1$=F, R'=OMe) Pd(dppf)Cl$_2$, CO, MeOH/TEA 50° C. then I. NaOH/MeOH/H$_2$O and II. HBTU, DIPEA, THF, NH$_4$OH (for X$^1$=F, =NH$_2$); in step e) NIS, DMF 85° C.

In accordance with the reaction conditions set forth in Scheme 11, intramolecular cyclization of compounds S11-i can produces the bridge bicyclic compounds S11-ii. Compounds S11-ii can be converted to imidazole intermediates Sx-iii via a Beckman-type rearrangement followed by condensation of the resultant amide product with an alpha-aminoacetal. Such imidazole intermediates S11-iii can be iodinated and the resultant iodination products S11-iv can be converted into the amide or ester products S11-v by treatment under palladium mediated carbonylation process. Such amide or ester compounds and be further halogenated by treatment with iodinating reagent to provide iodo-intermediates S11-vi. Primary amide compounds S11-v or iodo intermediates S11-vi can be further modified at the 5 membered heteroaryl ring by methods disclosed herein in Example 7 and Example 8. The bromides of S11-v, or of another intermediate such as S11-i, S11-ii, S11-iii, S11-iv or S11-vi may be displaced by Sonogashira coupling to give alkynyl (—C≡CR) or by any of the other methods described in detail in Example 3 below.

Scheme 12

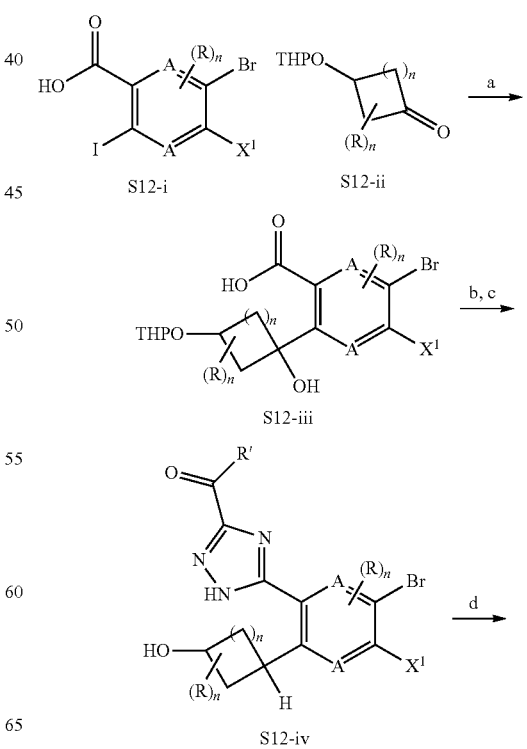

The reagents and conditions referenced in steps a-e of Scheme 11 are: in step a) (for X$^1$=H, R"=Me) step I. Et$_3$SiH, TFA, step II. NaOH, H$_2$O/MeOH, step III. PPA, 120° C. and (for X$^1$=F, R"=H) step I. Et$_3$SiH, TFA, step II. PPA, 90° C.; in step b) (for X$^1$=H) step I. NH$_2$OH—HCl, KOH, MeOH, THF, step II. SOCl$_2$, 1,4-dioxane, reflux, step III. PCl$_5$,

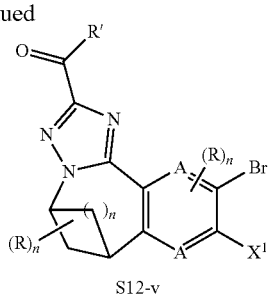

S12-v

The reagents and conditions referenced in steps a-d of Scheme 12 are: in step a) LHMDS, then iPrMgCl—LiCl followed by the cyclobutanone; in step b) TFA, TES-H; in step c) HATU, DIPEA, 2-amino-2-iminoacetamide, DMF then hydrazine, AcOH; in step d) PPh3, DIAD, THF.

In accordance with the reaction conditions set forth in Scheme 12, treatment of S12-i under deprotonation and metal halogen exchange conditions followed by addition of with a suitably protected hydroxycycloalkanone S12-ii provides addition products S12-iii. Treatment of 512-iii under TFA mediated reduction of the benzylic alcohol with TES-H followed by a two-step one-pot triazole synthesis (Staben et al J. Org. Chem. 2011, 76, 1177) 2-amino-2-iminoacetamide provides triazole intermediates S12-iv. Treatment of the unprotected alcohol S12-iv under Mitsunobu-type reaction provides cyclic compounds S12-v (R'=NH2). The bromides of S12-v, may be displaced by Sonogashira coupling to give alkynyl (—C≡CR) or by any of the other methods described in detail in Example 3 below.

Scheme 13

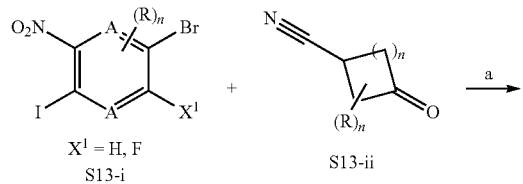

X¹ = H, F
S13-i

S13-ii

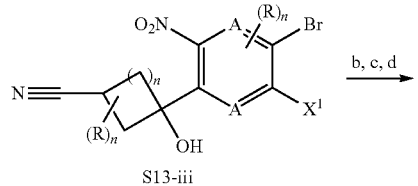

S13-iii

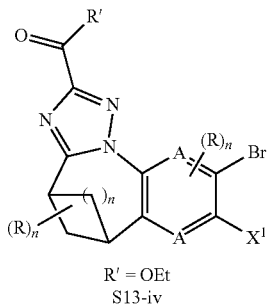

R' = OEt
S13-iv

The reagents and conditions referenced in steps a-d of Scheme 13 are: in step a) iPrMgCl—LiCl followed by the cyclobutanone; in step b) TFA, TES-H; in step c) NaNO₂, HCl then 2-chloro-3-oxobutyric acid ethyl ester, NaOAc; in step d) TEA, toluene, 120° C.

In accordance with the reaction conditions set forth in Scheme 13, treatment of S13-i compounds under metal halogen exchange conditions followed by addition of cyanocycloalkanones provides addition products S13-iii. Treatment of addition products S13-iii under TFA mediated conditions to reduce the benzylic alcohol group and with TES-H to reduce the and nitro group precedes diazotization of the resultant reduction products and subsequent reaction with 2-chloro-3-oxobutyric acid ethyl to provide chlorohydrazone intermediates, which can be heated in the presence of triethyl amine gives the tricyclic intermediates S13-iv (see: Zecchi et al Heterocycles, 1976, 13, 1339). The bromides of S13-iv, may be displaced by Sonogashira coupling to provide alkynyl compounds (—C≡CR) or by any of the other methods described in detail in Example 3 below.

Scheme 14

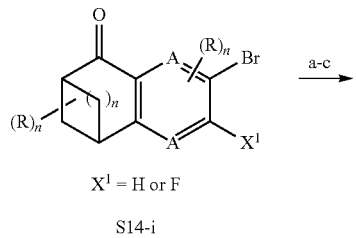

X¹ = H or F

S14-i

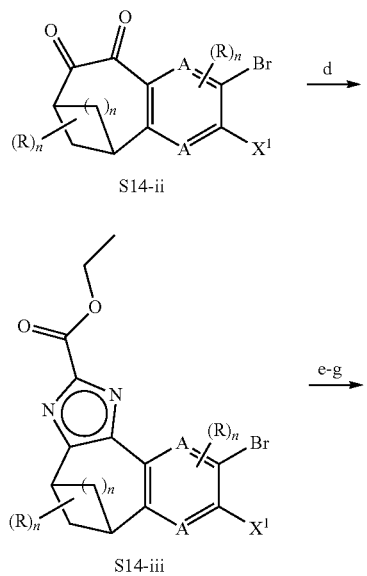

S14-ii

S14-iii

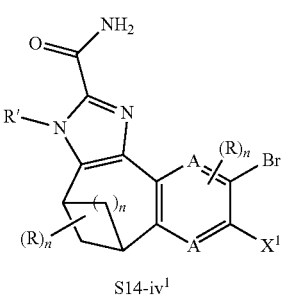

S14-iv¹

-continued

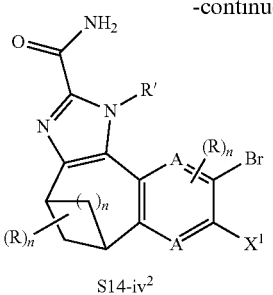

S14-iv²

The reagents and conditions referenced in steps a-g of Scheme 14 are: in step a) CH₂N₂ (or TMSCHN₂), BF₃GEt₂O; in step b) CuBr₂.EtOAc reflux; in step c) DMSO, heat; in step d) ethylglyoxalate, NH₄OAc, THF/MeOH; in step e) for R'=alkyl: alkyl-halide, CsCO₃ DMF/THF, for R'=Aryl, Aryl-halide, see reference; in step f) LiOH, THF/H₂O; in step g) NH₄Cl, HATU, DMF/THF.

In accordance with the reaction conditions set forth in Scheme 14, diazomethane mediated Tiffeneau-Demjanov type ring expansion of compounds S14-i provides intermediates (see, Fattori, D. et al. Tetrahedron, 1993, 49, 1649.) which can be further treated under conditions of alpha bromination and Kornblum oxidation to provide diones S14-ii. Treatment of diones S14-ii with ethylgloxylate and ammonium acetate promotes formation of the 2-carboxy imidazoles S14-iii. Functionalization of the nitrogen atom of imidazoles S14-iii can be accomplished with many functional groups including aryls (for arylation see Buchwald et al J. Am. Chem. Soc. 2012, 134, 700) or alkyls, via alkylation of the alkylation to install the R' group on the imidazole nitrogen atoms. The ester functional group of S14-iii can be converted to the corresponding primary amides to provide S14-iv¹ and S14-iv² which can be separated by chromatography. The bromides of S14-iv¹ and S14-iv², may be displaced by Sonogashira coupling to provide alkynyl compounds (—C≡CR) or by any of the other methods described in detail in Example 3 below.

Scheme 15

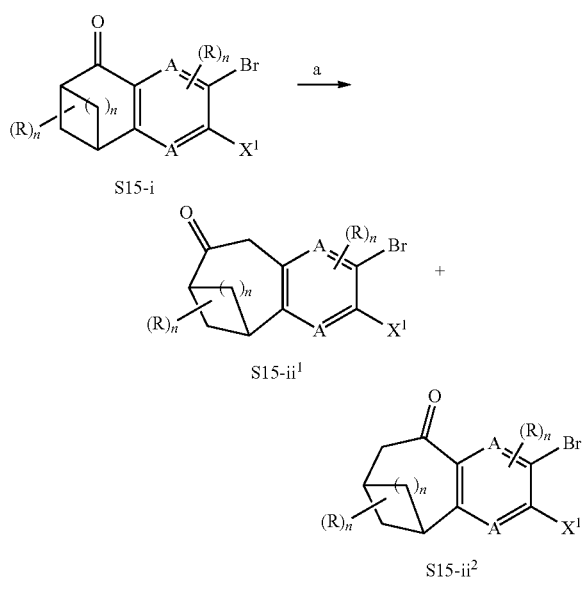

-continued

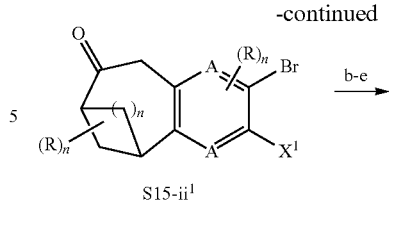

S15-ii¹

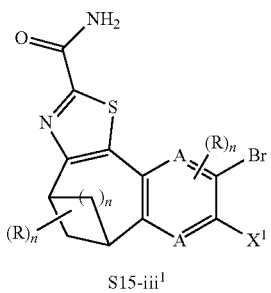

S15-iii¹

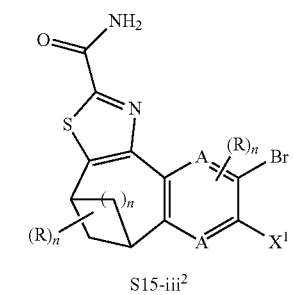

S15-iii²

The reagents and conditions referenced in steps a-e of Scheme 15 are: in step a) CH₂N₂ (or TMSCHN₂), BF₃.Et₂O; in step b) CuBr₂, EtOAc, reflux; in step c) ethylthiooxamate, TEA, heat; in step d) LiOH, THF/H₂O; in step e) NH₄Cl, HATU, DMF/THF.

In accordance with the reaction conditions set forth for Scheme 15 diazomethane mediated Tiffeneau-Demjanov type ring expansion provides a mixture of S15-ii¹ and S15-ii² (see, Fattori, D. et al. Tetrahedron, 1993, 49, 1649.) which can be separated by chromatography. Treatment of S15-ii¹ and S15-ii² under conditions for alpha bromination and reaction of the resultant bromide products with ethylthiooxamate provides tricyclic intermediates (see: WO/2009/123971, U.S. Pat. No. 7,928,248), which are converted to their corresponding tricyclic primary made intermediates via a two step synthesis to provide S15-iii¹ and S15-iii². The bromides of S15-iii¹ and S15-iii², may be displaced by Sonogashira coupling to give alkynyl (—C≡CR) or by any of the other methods described in detail in Example 3 below.

Scheme 16

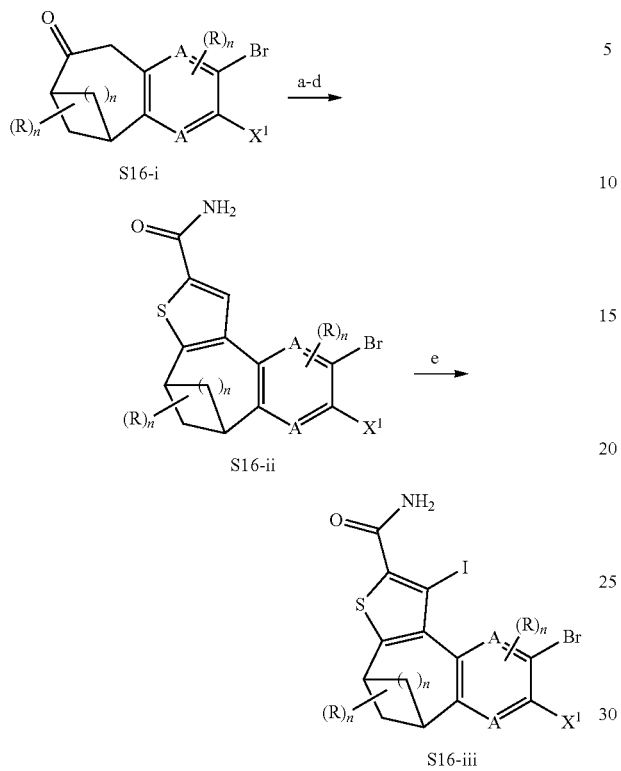

The reagents and conditions referenced in steps a-e of Scheme 16 are: in step a) POCl$_3$, DMF; in step b) methylthioacetate, K$_2$CO$_3$, DMF; in step c) LiOH, THF/H$_2$O; in step d) NH$_4$Cl, HATU, DMF/THF; in step e) NIS, DMF.

In accordance with the reaction conditions set forth for Scheme 16, treatment of ketones S16-i under modified Vilsmeier formylation conditions followed by reaction of with methylthioacetate provide thiophene tricyclic intermediates (see WO/2009/123971, U.S. Pat. No. 7,928,248). Such thiophene tricyclics S16-ii can be converted into the primary amide S16-ii via a two step synthesis. Iodination of the thiophene can be accomplished with NIS to provide intermediates S16-iii, which can be further functionalized off the carbon atom attached to the iodide atom following, e.g., procedures described Example 7 and Example 8. Bromides intermediates, e.g., S16-iii (after further functionalization of the iodo group) or other intermediates, e.g., S16-ii, may be displaced by Sonogashira coupling to give alkynyl (—C≡CR) or by any of the other methods described in detail in Example 3 below.

Scheme 17

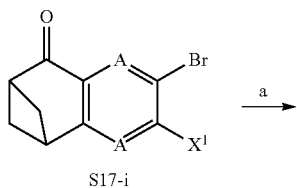

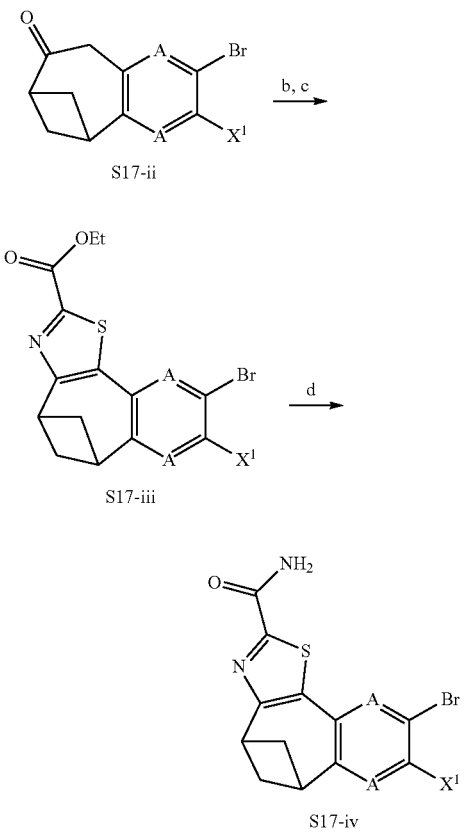

The reagents and conditions referenced in steps a-d of Scheme 17 are: in step a) trimethylsilyldiazomethane, BF$_3$.Et$_2$O; in step b) CuBr$_2$, EtOAc; in step c) ethylthioxoamate, DMF; in step d) LiOH, THF/H$_2$O, then NH$_4$Cl, HATU, DMF/THF.

In accordance with the reaction conditions set forth for Scheme 17, ring expansion aided by trimethylsilyldiazomethane and BF$_3$.Et$_2$O gives ketone S17-ii. Alpha bromination and Hansch thiazole synthesis gives ester S17-iii. Saponification and amidation gives primary amide intermediates S17-iv. The bromide of S17-iv, may be displaced by Sonogashira coupling to give alkynyl (—C≡CR).

Scheme 18

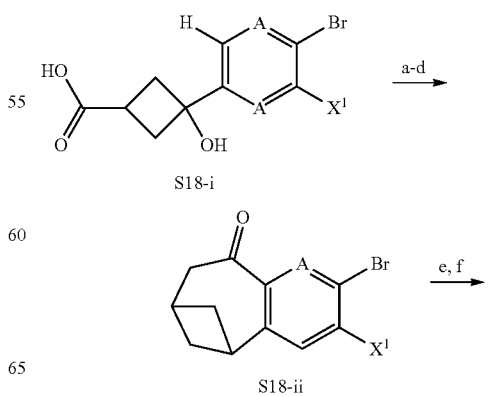

-continued

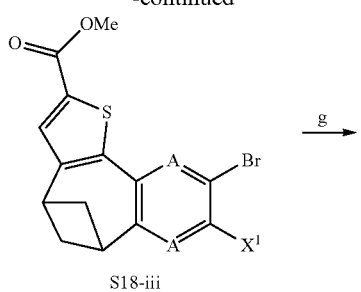
S18-iii

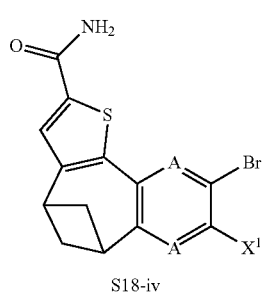
S18-iv

-continued

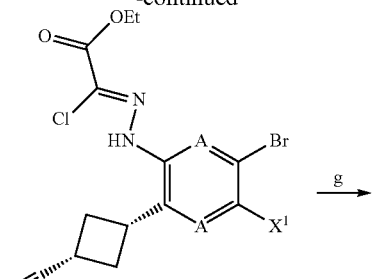
S19-iii

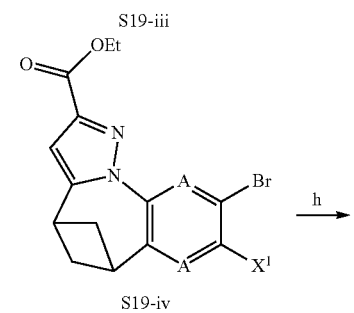
S19-iv

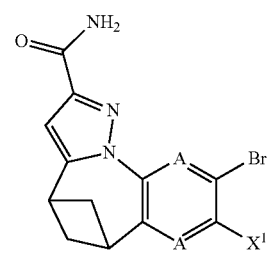
S19-v

The reagents and conditions referenced in steps a-g of Scheme 18 are: in step a) Et$_3$SiH, trifluoroacetic acid; in step b) SOCl$_2$ then diazolmethane; in step c) cat. PhCO$_2$Ag, dioxane/water; in step d) polyphosphoric acid, >100° C.; in step e) POCl$_3$, DMF; in step f) methylthioacetate, K$_2$CO$_3$, DMF; in step g) LiOH, THF/H$_2$O, then NH$_4$Cl, HATU, DMF/THF.

In accordance with the reaction conditions set forth for Scheme 18, reduction of the benzylic alcohol followed by Arndt-Eistert homologation and Friedel-Crafts cyclization gives ketone S18-ii. Modified Vilsmeyer formylation and reaction with methylthioacetate gives ester intermediate S18-iii (for example: WO/2009/123971, U.S. Pat. No. 7,928,248). Saponification and amidation gives primary amide intermediates S18-iv. The bromide of XX, may be displaced by Sonagoshira coupling to give alkynyl (—C≡CR).

Scheme 19

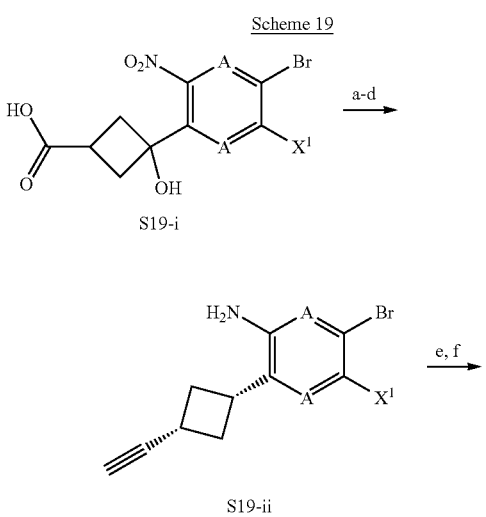

The reagents and conditions referenced in steps a-h of Scheme 19 are: in step a) Et$_3$SiH, trifluoroacetic acid; in step b) LiAlH$_4$, THF; in step c) Pyridinium chlorochromate, CH$_2$Cl$_2$; in step d) dimethyl (1-diazo-2-oxopropyl)phosphonate, K$_2$CO$_3$, MeOH; in step e) 6N HCl, NaNO$_2$; in step f) 2-chloro-3-oxobutyric acid ethyl ester, NaOAc; in step g) TEA, toluene, 120° C.; in step h) LiOH, THF/H$_2$O then NH$_4$Cl, HATU, DMF/THF.

In accordance with the reaction conditions set forth above for Scheme 19, simultaneous reduction of the nitro and benzylic alcohol and conversion of the carboxylic acid to an alkyne gives aniline S19-ii. Diazitization and reaction with 2-chloro-3-oxobutyric acid ethyl ester gives chlorohydrazones S19-iii. Intramolecular 3+2 cyclization is promoted under basic conditions to produce the tricyclic intermediate compounds (for example see: Padwa, A. et al *J. Org. Chem.* 1978, 43, 1664). Saponification and amidation gives primary amide intermediates S19-v. The bromide of S19-v, may be displaced by Sonagoshira coupling to give alkynyl (—C≡CR).

Further synthetic detail and additional synthetic procedures are described in the Examples section below.

Pharmaceutical Compositions and Administration

In addition to one or more of the compounds provided above (or stereoisomers, geometric isomers, tautomers, solvates, metabolites, isotopes, pharmaceutically acceptable salts, or prodrugs thereof), the invention also provides for compositions and medicaments comprising a compound of Formula I and at least one pharmaceutically acceptable carrier, diluent or excipient. The compositions of the invention can be used inhibiting NF-kB signaling activity in mammals (e.g., human patients), by for example, inhibiting NIK activity The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions (or medicaments) comprising a compound of Formula I (or stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of Formula I and compositions comprising compounds of Formula I to a mammal (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit NIK activity as required to prevent or treat the undesired disease or disorder, such as for example, neurodegeneration, amyloidosis, formation of neurofibrillary tangles, or undesired cell growth (e.g., cancer cell growth). For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compositions comprising compounds of Formula I are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of Formula I) can be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philadelphia, Pa. Such methods include the step of bringing into association the active ingredient with the carrier which constitutes one or more accessory ingredients.

In general the formulations are prepared by uniformly and intimately bringing into association the active ingredient with liquid carriers, diluents or excipients or finely divided solid carriers, diluents or excipients, or both, and then, if necessary, shaping the product. A typical formulation is prepared by mixing a compound of the present invention and a carrier, diluent or excipient. The formulations can be prepared using conventional dissolution and mixing procedures. For example, the bulk drug substance (i.e., compound of the present invention or stabilized form of the compound (e.g., complex, with a cyclodextrin derivative or other known complexation agent) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

In one example, compounds of Formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Formulations of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

Formulations of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment of disorders as described below.

Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Indications and Methods of Treatment

The compounds of Formula I inhibit the activity of NIK. Accordingly, in another aspect of the invention the compounds of the invention (e.g., compounds of Formula I, or stereoisomers, geometric isomers, tautomers, solvates, metabolites, isotopes, pharmaceutically acceptable salts, or prodrugs thereof) can be used for the treatment of diseases and disorders in a mammal, for example a human patient, I which the inhibition of NIK in the patient would be therapeutically effective. For example, the compounds of the invention are useful for the treatment of diseases or disorders in a mammal (e.g., human patient) associated with overactive or undesired NF-kB signaling through, for example, the overactivation of NIK. In one embodiment, the compounds of the invention (e.g., compounds of Formula I, or stereoisomers, geometric isomers, tautomers, solvates, metabolites, isotopes, pharmaceutically acceptable salts, or prodrugs thereof) are used to inhibit the activity of NIK, for example in an in vitro assay setting, by contacting said compound of Formula I with NIK. For example, compounds of Formula I can be used as a control compound in an in vitro assay setting.

In another embodiment, the compounds of the invention (e.g., compounds of Formula I, or stereoisomers, geometric isomers, tautomers, solvates, metabolites, isotopes, pharmaceutically acceptable salts, or prodrugs thereof) are used to inhibit the undesired signaling of NF-kB, e.g. in an cell proliferation assay, by introducing into a cell a compound of Formula I. In another embodiment, the present invention provides the treatment of diseases or disorders in a mammal (e.g., human patient) associated with overactive or undesired NF-kB signaling (e.g., cancer, inflammatory diseases, among others) said method comprising administering to a mammal (e.g., human patient) in need thereof a therapeutically effective amount of a compound of the invention (e.g., compounds of Formula I, or stereoisomers, geometric isomers, tautomers, solvates, metabolites, isotopes, pharmaceutically acceptable salts, or prodrugs thereof).

Diseases and disorders treatable according to the methods of this invention include, cancer, inflammatory diseases autoimmune disease and proliferation induced after medical procedures (e.g., arthritis, graft rejection, inflammatory bowel disease, cell proliferation induced after surgery angioplasty, among others). In one embodiment, a mammal (e.g., a human patient) is treated with a compound of the invention (e.g., compounds of Formula I, or stereoisomers, geometric isomers, tautomers, solvates, metabolites, isotopes, pharmaceutically acceptable salts, or prodrugs thereof) and a pharmaceutically acceptable carrier, adjuvant, or vehicle, wherein said compound of the invention (e.g., compounds of Formula I, or stereoisomers, geometric isomers, tautomers, solvates, metabolites, isotopes, pharmaceutically acceptable salts, or prodrugs thereof) is present in an amount to inhibit NF-kB signaling through, for example but not limited to, inhibition of NIK.

In one embodiment, a compound of the invention (e.g., compound of Formula I, or stereoisomers, geometric isomers, tautomers, solvates, metabolites, isotopes, pharmaceutically acceptable salts, or prodrugs thereof) can be used in the treatment of cell proliferative disorders, including cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of cancers.

In one embodiment of the invention, cancers that may be treated by the compounds of Formula I (or stereoisomer, geometric isomer, tautomer, solvate, metabolite, pharmaceutically acceptable salt, or prodrug thereof), are selected from the group consisting of Lung (brochogenic carcinoma (non-small cell lung); Gatrointestinal—rectal, colorectal and colon; Genitourinary tract—kidney (papillary renal cell carcinoma); and skin—head and neck squamous cell carcinoma.

In one embodiment, compound of Formula I (or stereoisomer, geometric isomer, tautomer, solvate, metabolite, pharmaceutically acceptable salt, or prodrug thereof), can be use for the treatment of a cancer selected from the group consisting of head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancers, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of a cancer selected from the group consisting of histiocytic lymphoma, lung adenocarcinoma, small cell lung cancer, pancreatic cancer, liver cancer, gastric cancer, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of a cancer selected from the group consisting of histiocytic lymphoma, lung adenocarcinoma, small cell lung cancers, pancreatic cancer, liver cancer gastric cancer, colon cancer, leukemias, lymphomas, multiple myeloma, glioblastomas and breast carcinoma.

In one embodiment, compound of Formula I (or stereoisomer, geometric isomer, tautomer, solvate, metabolite, pharmaceutically acceptable salt, or prodrug thereof), can be used for the treatment of cancer selected from the group consisting of lymphomas, leukemias and multiple myeloma.

In one embodiment, the invention provide for the use of a compound of Formula I (or stereoisomers, geometric isomers, tautomers, solvates, metabolites, isotopes, pharmaceutically acceptable salts, or prodrugs thereof) for the treatment of lymphoma, leukemia or multiple myeloma.

In one embodiment, the invention provides for the preparation of a medicament comprising a compound of Formula I (or stereoisomers, geometric isomers, tautomers, solvates, metabolites, isotopes, pharmaceutically acceptable salts, or prodrugs thereof) for the treatment of lymphoma, leukemia or multiple myeloma.

In one embodiment, the invention provides for the treatment of lymphoma, leukemia or multiple myeloma, which method comprises administering an effective amount of a compound of Formula I (or stereoisomers, geometric isomers, tautomers, solvates, metabolites, isotopes, pharmaceutically acceptable salts, or prodrugs thereof).

In one embodiment, compound of the invention (e.g., compounds of Formula I, or stereoisomers, geometric isomers, tautomers, solvates, metabolites, isotopes, pharmaceutically acceptable salts, or prodrugs thereof) are useful for the treatment of inflammatory diseases and conditions including, but not limited to, lupus (including systemic lupus erythematosus), asthma, COPD, rhinitis, multiple sclerosis, IBD, arthritis, gastritis, rheumatoid arthritis, dermatitis, endometriosis, transplant rejection, cardiac infarction, Alzheimer's diseases, diabetes Type II, inflammatory bowel disease, sepsis, and artherosclerosis.

In one embodiment, the invention provides for the use of a compound of Formula I (or stereoisomers, geometric isomers, tautomers, solvates, metabolites, isotopes, pharmaceutically acceptable salts, or prodrugs thereof) for the treatment of an inflammatory condition.

In one embodiment, the invention provides for the use of a compound of Formula I (or stereoisomers, geometric isomers, tautomers, solvates, metabolites, isotopes, pharmaceutically acceptable salts, or prodrugs thereof) for the preparation of a medicament for the treatment of an inflammatory condition.

In one embodiment, the invention provides for a compound of Formula I (or stereoisomers, geometric isomers, tautomers, solvates, metabolites, isotopes, pharmaceutically acceptable salts, or prodrugs thereof) for the treatment of an inflammatory condition.

In one embodiment, the invention provides for a method for the treatment of an inflammatory condition, which method comprises administering an effective amount of a compound of Formula I (or stereoisomers, geometric isomers, tautomers, solvates, metabolites, isotopes, pharmaceutically acceptable salts, or prodrugs thereof).

In one embodiment, the invention provides for the treatment of an inflammatory condition selected from the group consisting of lupus (including systemic lupus erythematosus), COPD, rhinitis, multiple sclerosis, IBD, arthritis, rheumatoid arthritis, dermatisis, endometriosis and transplant rejection, which method comprises administering an effective amount of a compound of Formula I (or stereoisomers, geometric isomers, tautomers, solvates, metabolites, isotopes, pharmaceutically acceptable salts, or prodrugs thereof).

Combinations

The compounds of Formula I (or stereoisomer, geometric isomer, tautomer, solvate, metabolite, pharmaceutically acceptable salt, or prodrug thereof) may be employed alone or in combination with other therapeutic agents for treatment. In one embodiment, compounds of this invention may be employed alone or in combination with chemotherapeutic agents. In one embodiment, compounds of this invention may be employed alone or in combination with anti-inflammatory agents. The compounds of the present invention can be used in combination with one or more additional drugs, for example an anti-inflammatory compound or anti-cancer compound that works by a different mechanism of action. The second compound of the pharmaceutical combination formulation or dosing regimen preferably has complementary activities to the compound of this invention such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

In certain embodiments, a compound of Formula I, or a subformula thereof is combined in a pharmaceutical combination formulation, or dosing regimen as combination therapy, with a second therapeutic compound that has anti-inflammatory or anti-cancer properties or that is useful for treating an inflammation, immune-response disorder, or hyperproliferative disorder (e.g., cancer). The second therapeutic agent may be a NSAID (Non-Steroidal Anti-Inflammatory Drug) or other anti-inflammatory agent. The second therapeutic agent may be a chemotherapeutic agent. In one embodiment, a pharmaceutical composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Suitable dosages for any of the above coadministered agents are those presently used and may be lowered due to the combined action (synergy) of the newly identified agent and other chemotherapeutic agents or treatments.

EXAMPLES

The invention will be more fully understood by reference to the following examples. They should not, however, be construed as limiting the scope of the invention. These examples are not intended to limit the scope of the present invention, but rather to provide guidance to a skilled artisan to prepare and use the compounds, compositions, and methods of the present invention. While particular embodiments of the present invention are described, the skilled artisan will appreciate that various changes and modifications can be made without departing from the spirit and scope of the invention.

The chemical reactions in the Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Description of General Reaction Conditions

Commercially available reagents were purchased from suppliers such as Aldrich Chemical Company, Lancaster, TCI or Maybridge, and were used without further purification unless otherwise indicated. 2-methylbut-3-yn-2-ol, 1-ethynylcyclopentan-1-ol and 3-methoxy-3-methylbut-1-yne were readily available and purchased from commercial sources. The reactions set forth below were done generally under a positive pressure of nitrogen or argon or with a drying tube (unless otherwise stated), in anhydrous solvents, and the reaction flasks were typically fitted with rubber septa for the introduction of substrates and reagents via syringe. Glassware was oven dried and/or heat dried. Column chromatography was conducted on a Biotage system (Isolera Four) having a silica gel column or, alternatively column chromatography was carried out using an Isolute® silica gel cartridge (Biotage). $^1$H NMR spectra were recorded on either on a Bruker DPX instrument operating at 250 MHz or a Bruker DRX instrument operating at 500 MHz. $^1$H NMR spectra were obtained in deuterated CDCl$_3$, d$_5$-DMSO or CH$_3$OD (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, were reported in Hertz (Hz). When possible, product formations in the reaction mixtures were monitored by LC-MS one of the following LC-MS parameters:

LC-MS Method 1

| Column | Waters Atlantis dC18 100 × 2.1 mm, 3 µm column 40° C. |
| --- | --- |
| Mobile phase | A - 0.1% Formic acid (water) B - 0.1% Formic acid (acetonitrile) |
| Flow rate | 0.6 ml/min |
| Injection volume | 3 µL |
| Detector | 215 nm and 254 nm |
| | Time (mins) %B |
| Gradient | 0 5 |
| | 5 100 |
| | 5.4 100 |
| | 5.42 5 |

LC-MS Method 2

| Column | Waters Atlantis dC18 100 × 2.1 mm, 3 µm column |
| --- | --- |
| Mobile phase | A - 0.1% Formic acid (water) B - 0.1% Formic acid (acetonitrile) |
| Flow rate | 1.0 ml/min |
| Injection volume | 3 µL |
| Detector | 215 nm (nominal) |
| | Time (mins) %B |
| Gradient | 0 5 |
| | 2.5 100 |
| | 2.7 100 |
| | 2.71 5 |
| | 3.0 5 |

Reverse phase HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 um, 30×150 mm column b) Phenomenex Gemini Axia C18 5 um, 30×100 mm column c) Waters XBridge Prep C18 5 um, 19×100 mm The definitions of abbreviations and acronyms used to describe reagents follow the general guidelines set forth for manuscripts by the Journal of Organic Chemistry: http://pubs.acs.org/paragonplus/submission/joceah/joceah auth-guide.pdfChemical, or as otherwise described herein, including: NIS=N-iodosuccinimide, NBS=N-bromosuccinimide, EA=ethylacetate, ES(I)=electrospray (ionization), APCI=atmospheric pressure chemical ionization, ACN=acetonitrile; DCM=dichloromethane, EtOAc=ethyl acetate, DMF N,N-dimethylformamide, TEA=triethylamine; THF=tetrahydrofuran, NMP=N-methylpyrrolidinone, TMEDA=N,N,N',N'-tetramethylethylenediamine, LDA=lithium diisopropylamide, TMP=2,2,6,6-tetramethylpiperidine, LiHMDS=lithium hexamethyldisilazide, NaHMDS=sodium hexamethyldisilazide, DMSO=dimethylsulfoxide, DIPEA=diisopropylethylamine, Py=pyridine, ACN=MeCN=acetonitrile, TES-H=triethylsilane; TFA trifluoroacetic acid; HATU=2-(1H-7-Azabenzotriazol-1-yl)-1,1,3,3-tetramethyl uronium hexafluorophosphate Methanaminium. DIAD=diisopropylazodicarboxylate; TBAF=tetrabutylammonium fluoride. Chemical structures were named according to: vendor designation; IUPAC convention; J Chem for Excel, Version 5.3.8.14, ChemAxon Ltd. or Autonom 2000 Name, MDL Inc. It is recognized by those skilled in the art that a compound may have more than one name, according to different conventions.

Example 1

General Routes for the Synthesis of Propargyl Alcohol Reagents

Procedure A

Ethynylmagnesium Bromide to Ketones.

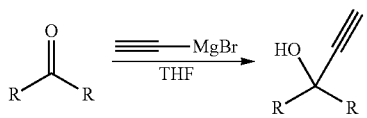

(A)

To a solution of bromo(ethynyl)magnesium (1.3 eq of 0.5 mol/L in THF solution) at 0° C. was added dropwise a solution of generic ketone in THF (1 mL/mmol). The reaction mixture was warmed to room temperature and stirred for 1 hr, then concentrated to dryness to obtain crude alkyne which was purified by flash column chromatography or used in subsequent sonagashira reactions without purification.

Procedure B

Lithium Silylacetylide Addition to Ketones and Deprotection.

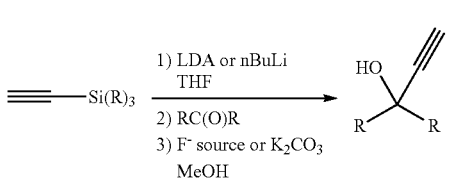

(B)

A solution of silylacetyline (1 eq) in tetrahydrofuran (10 mL/mmol) is treated with n-BuLi (1 eq) at −78° C. The solution was stirred for 0.5 h. The ketone is then added and the solution is allowed to warm up to room temperature and stirred while monitored for conversion by LCMS. The reaction mixture is quenched with ammonium chloride and extracted with organic solvent. The organics are collected, dried over sodium sulfate and concentrated to be typically used in the next step without purification.

A solution silylalkyne product from above in tetrahydrofuran (10 mL/mmol) was added in Tetrabutyl-ammonium fluoride (0.94 g, 3.6 mmol). The solution was stirred overnight at room temperature, concentrated and the residue purified by column chromatography or used in subsequent operations without purification.

Procedure C

Addition of an aryl organometallic to 4-(trimethylsilyl) but-3-yn-one.

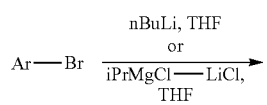

(C)

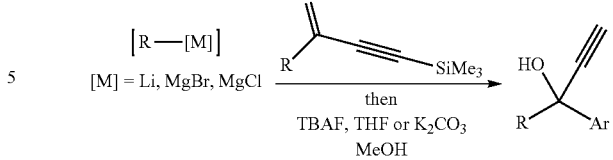

A solution of aryl halide (Ar—Br, 1.00 equiv) in tetrahydrofuran (10 mL/mmol) is treated with n-BuLi (1.20 eq) dropwise with stirring at −78° C. The resulting solution is stirred at −78° C. until complete metal halogen exchange is evident by LCMS. To this solution is added a 3-trialkylsilyl-2,3-yne-1-one (1.10 equiv) dropwise with stirring at −78° C. The resulting solution is warmed slowly to 0° C. and stirred while monitored for complete conversion by TLC or LCMS. The reaction is quenched by the addition of 10 mL, of sat. aq. ammonium chloride. Work-up as above provides the crude silyl protected propargyl alcohol. Deprotection of the alkyne is accomplished through fluoride (TBAF, KF as described above) or the crude silyl protected propargyl alcohol is dissolved in methanol (5 mL/mmol) and treated with solid $K_2CO_3$ (excess). The mixture is stirred at room temperature while monitoring for conversion. The $K_2CO_3$ is filtered and the mixture concentrated and purified by chromatography or used as is in subsequent operations without purification.

Example 2

Amide Synthesis from Heterocyclic Carboxylic Acids

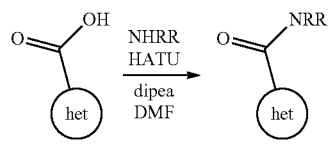

Aromatic or non-aromatic heterocyclic acid (1 eq) and HATU (1.2 eq) were weighed out and transferred to a vial to which DMF and DIPEA (3-5 eq) were subsequently added. The amine ($HNR^3R^4$) was added to the reaction mixture as a free base or HCl salt after a short period and the reaction was stirred at room temperature or at 50° C. for 2-18 hours. Reaction conversion was monitored by LCMS. Upon completion, the reaction was cooled and the crude product was triturated via addition of water and collected by filtration or extracted with sat ammonium chloride and DCM. Trituration or purification by chromatography gave the amide.

Example 3

General Procedures for Aryl-Halide (ArX) to Terminal Alkyne Cross-Coupling

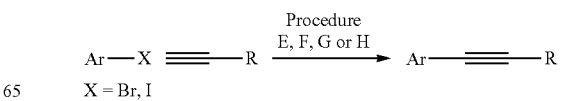

Procedure E

Aryl halide was weighed out, transferred to a sealed tube and brought up in Acetonitrile (3 mL/mmol) and Triethylamine (3 mL/mmol). The solution was degassed with nitrogen and Copper(I) Iodide (0.05 eq) and Bis(triphenylphosphine)palladium(II)chloride (0.1 eq) were added. DMF (3 mL/mmol) was then added followed by dropwise addition of alkyne (2-3 eq). The reaction mixture heated for 3-18 h at 80° C. and monitored by LCMS for consumption of starting material. Upon completion, the reaction was cooled and the crude product was either triturated via addition of water and collected by filtration or extracted with saturated ammonium chloride and DCM whereupon the organic layer was dried, filtered and concentrated to dryness. Crude products were submitted for reverse phase hplc HPLC purification.

Procedure F

Aryl halide (where X=bromide) (1 eq), Copper (I) Iodide (0.06 eq), tri-t-butylphosphonium tetrafluoroborate (0.2 eq) and dichlorobis(phenyl cyanide)palladium (0.1 eq) were weighed out and transferred to a microwave vessel. Upon addition of DMSO (3 mL/mmol), the reaction mixture was subsequently degassed whereupon a solution of alkyne (3 eq) in Diisopropylamine (3 eq) was added dropwise. The reaction mixture was capped and heated thermally at 80° C. and monitored by LCMS for consumption of starting material. Workup is the same for as in procedure E.

Procedure G

Aryl halide (wherein X=bromide) was weighed out, transferred to a sealed tube and brought up in DMSO or DMF (3 mL/mmol) and Triethylamine (3 mL/mmol). The solution was degassed with nitrogen and Bis(triphenylphosphine)palladium(II)chloride (0.2 eq) and alkyne (2-3 eq) were added ("copper-free" conditions). The reaction mixture heated for 2-18 hrs at 80° C. and monitored by LCMS for consumption of starting material. Workup is the same for as in above procedure E.

Procedure H

Aryl halide (where X=bromide) was weighed out, transferred to a sealed tube and brought up in DMSO, acetonitrile or DMF (3 mL/mmol) and $K_2CO_3$ was added (2 eq)). The solution was degassed with nitrogen and CuI (0.10 eq), Pd(OAc)$_2$ (0.2 eq), diphenylphosphinopropane (dppp) then the alkyne (1-3 eq) were added. The reaction mixture heated for 2-18 hrs at 80° C. and monitored by LCMS for consumption of starting material. Workup is the same for as in above procedure E.

Example 4

Suzuki coupling with boronic acids or boronic esters with aryl iodides.

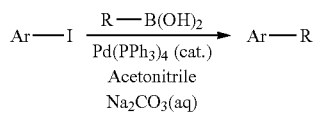

Aryl Iodide, tetrakis (triphenylphosphine)palladium or Palladium (II) bis(triphenylphosphine)dichloride (0.05 eq) and boronic acid or pinnacol ester (1.2 eq) were weighed out into a microwave vessel or sealed tube. Acetonitrile (3 mL/mmol) and a 1M aqueous solution of Sodium Carbonate (3 eq) were added. The vessel was capped and heated thermally 3-18 hrs at 100° C. Upon completion, the reaction was cooled and crude product was either triturated via addition of water and collection by filtration or extracted with sat ammonium chloride and DCM. If the crude product was an intermediate, it was taken into the next step in most cases w/o further purification or alternatively submitted for reverse phase hplc HPLC purification when it was a final product.

Example 5

Suzuki Coupling of Aryl Iodides with Potassium Trifluoroborate Salts

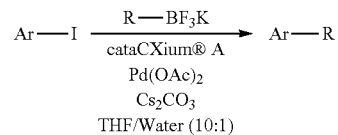

To a microwave vessel or sealed tube containing trifluoroborate salt (1.5 eq), cesium carbonate (3 eq), Palladium (II) Acetate (0.06 eq), butyldi-1-adamantylphosphine ("cataCXium® A") (0.12 eq) and generic iodide (1 eq) was added a 10:1 mixture of THF/H2O (20 mL/mmmol). The reaction was sealed and heated under a nitrogen atmosphere at 70° C. for 24 hours. The reaction was monitored by LCMS and recharged with ligand and catalyst when necessary to progress reaction to completion. Upon cooling, the reaction mixture was extracted with saturated ammonium chloride and DCM. The organic layer was dried with magnesium sulfate, filtered and concentrated to dryness. The crude material was purified by reverse phase HPLC to afford pure intermediate.

Example 6

Carbonylative Methanolysis of Aryl Iodides

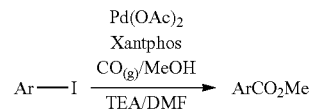

To a nitrogen-purged solution of aryl iodide in TEA (3 mL/mmol), DMF (3 mL/mmol) and MeOH (3 mL/mmol) was added Palladium (II)Acetate (0.03 eq) and Xantphos (0.06 eq). The reaction mixture was flushed with Carbon Monoxide gas for several minutes and then sealed with CO balloon attached and heated to 60° C. for 3 hours. Upon completion, the reaction was cooled to room temperature and the crude product was triturated via addition of water and collected by filtration. The crude intermediate was taken into the next step w/o further purification.

Example 7

Reductive Amination of Arylaldehydes

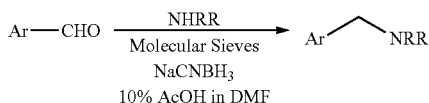

To a vial containing aryl aldehyde (1 eq) in 10% Acetic Acid in DMF (6 mL/mmol) was added molecular sieves (1 eq by wt), amine (HNR$^1$R$^2$, 4 eq) then sodium cyanoborohydride (1.2 eq). The reaction was either heated at 45° C. or stirred at room temperature. Upon completion, the reaction was extracted with DCM and saturated ammonium chloride. The organic layer was dried with magnesium sulfate, filtered and concentrated to give crude product which was taken into the next step without purification.

Example 8

Direct Lithiation and Electrophilic Trapping of an Imidazole-4-carboxylic ester

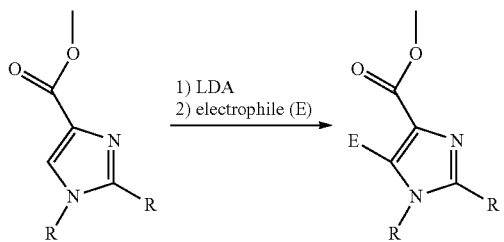

To a solution of aryl ester in THF at −78° C. was added lithium diisopropylamide (2 eq)
dropwise over 20 mins. The reaction was stirred at −78° C. for 1 hour before addition of electrophile (eg. Methyl iodide or ethyl formate). The reaction mixture was stirred −78° C. then warmed to 0° C. and quenced with a saturated ammonium chloride solution. The quenched reaction was extracted immediately with DCM. The organic layer was dried with magnesium sulfate, filtered and concentrated to dryness. The crude material was either purified by reverse phase HPLC or triturated by addition of water and collected by filtration.

Example 9

Direct Magnesiation and Electrophilic Trapping of an Imidazole-4-carboxylic ester

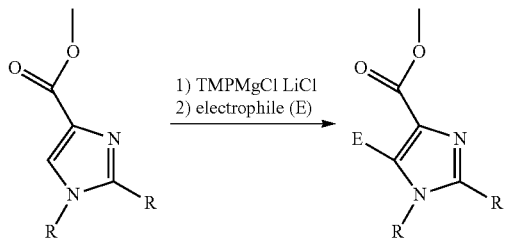

The imidazole-4-carboxylic ester (1 eq) was dissolved in THF (3 mL/mmol) and the solution was cooled to 0° C. A solution of TMPMgCl/LiCl (1M in toluene/THF, 1.6 equiv) was added down the side of the vial slowly. The mixture was allowed to stir for 30 minutes. After 30 minutes, the electrophile is added (1.0-10 eq) and the reaction continued to stirred and monitored for conversion by LCMS. The reaction was quenched with saturated NH$_4$Cl and extracted 3 times with methylene chloride. The organic layers are combined, dried with Na$_2$SO$_4$ or MgSO$_4$ and concentrated. The crude is purified by chromatography or used in subsequent operations without purification.

Example 10

Carbonylative Amidation with HMDS

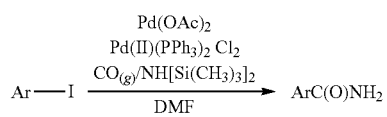

To a nitrogen-degassed solution of generic aryl iodide (Ar—I) in DMF (170 eq) was added Palladium(II)bis(triphenylphosphine)dichloride (0.05 eq) and hexamethyldisilazane (6 eq). The reaction mixture was flushed with Carbon Monoxide gas for several minutes and then sealed with CO balloon attached and heated to 70° C. for 18 hrs. Upon completion, the reaction was cooled to room temperature and the crude was triturated via addition of water and collected by filtration. The crude intermediate was taken into the next step w/o further purification.

Example 11

Synthesis of Intermediate Compounds

9-Bromo-4,5-dihydro-6-oxa-1,3a-diaza-benzo[e]azulene-2-carboxylic acid amide;
9-Bromo-8-fluoro-4,5-dihydro-6-oxa-1,3a-diaza-benzo[e]azulene-2-carboxylic acid amide;
9-Bromo-3-iodo-4,5-dihydro-6-oxa-1,3a-diaza-benzo[e]azulene-2-carboxylic acid amide and
9-Bromo-8-fluoro-3-iodo-4,5-dihydro-6-oxa-1,3a-diaza-benzo[e]azulene-2-carboxylic acid amide

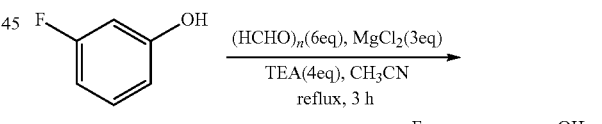

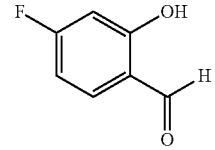

4-Fluoro-2-hydroxybenzaldehyde

Into a 20-L 4-necked round-bottom flask purged and maintained with an inert atmosphere of nitrogen was placed a solution of 3-fluorophenol (400 g, 3.57 mol, 1.00 equiv) in CH$_3$CN (5 L), followed by the addition of MgCl$_2$ (1018 g, 3.00 equiv) in several batches at 0° C. To this was added TEA (1443 g, 14.26 mol, 4.00 equiv) dropwise with stirring at 0-5° C., followed by paraformaldehyde (640 g, 6.00 equiv). The resulting solution was stirred at 80° C. for 3 h, cooled to 20° C., quenched by the addition of 5 L of 2N HCl and extracted with 3×3 L of ethyl acetate. The organic layers were combined, dried over anhydrous sodium sulfate and concentrated under vacuum to afford 545 g (crude) of 4-fluoro-2-hydroxybenzaldehyde as a yellow solid.

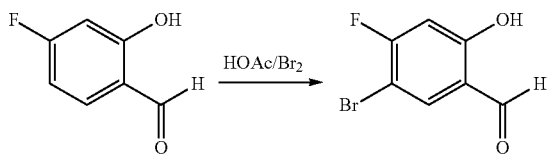 [SMILES: O=Cc1ccc(F)cc1O ; O=Cc1cc(Br)c(F)cc1O]

5-Bromo-4-fluoro-2-hydroxybenzaldehyde

Into a 20-L 4-necked round-bottom flask purged and maintained with an inert atmosphere of nitrogen was placed a solution of 4-fluoro-2-hydroxybenzaldehyde (545 g, 3.89 mol, 1.00 equiv) in AcOH (5 L), followed by the addition of $Br_2$ (623 g, 3.90 mol, 1.00 equiv) dropwise with stirring at 0-5° C. The resulting solution was stirred overnight at room temperature, quenched by the addition of 3 L of saturated aqueous $Na_2SO_3$ and diluted with 6 L of ice/water. The solids were collected by filtration, washed with 2×1.5 L of water and dried to afford 145 g (crude) of 5-bromo-4-fluoro-2-hydroxybenzaldehyde as a yellow solid.

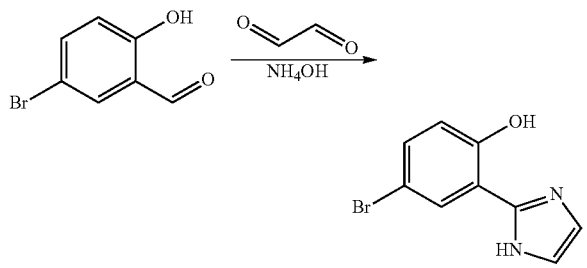

4-Bromo-2-(1H-imidazol-2-yl)phenol

Into a 50-L bucket was placed a solution of 5-bromo-2-hydroxybenzaldehyde (1500 g, 7.46 mol, 1.00 equiv) in methanol (30 L), oxaldehyde (3.42 L, 4.00 equiv), and ammonia (7.8 L, 20 equiv). The resulting solution was stirred at room temperature overnight and concentrated under vacuum. The solids were collected by filtration to afford 1350 g (crude) of 4-bromo-2-(1H-imidazol-2-yl)phenol as a gray solid.

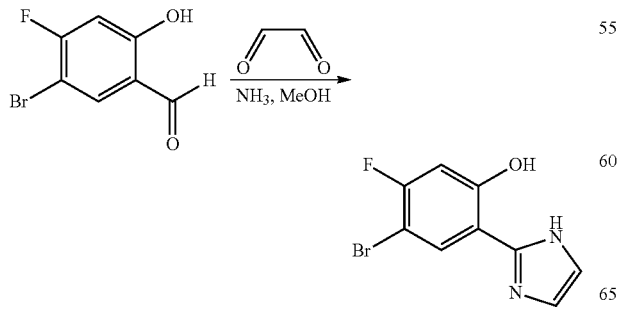

4-Bromo-5-fluoro-2-(1H-imidazol-2-yl)phenol

Into a 3-L 4-necked round-bottom flask purged and maintained with an inert atmosphere of nitrogen was placed a solution of 5-bromo-4-fluoro-2-hydroxybenzaldehyde (145 g, 662.08 mmol, 1.00 equiv) in methanol (1.5 L), glyoxal (373.4 g, 4.00 equiv, 40%), followed by the addition of ammonium hydroxide (720 g, 16.50 equiv) dropwise with stirring at 0-5° C. The resulting solution was stirred overnight at room temperature and concentrated under vacuum. The solids were collected by filtration, washed with 2×250 mL of water and dried to afford 170 g (crude) of 4-bromo-5-fluoro-2-(1H-imidazol-2-yl)phenol as a brown solid.

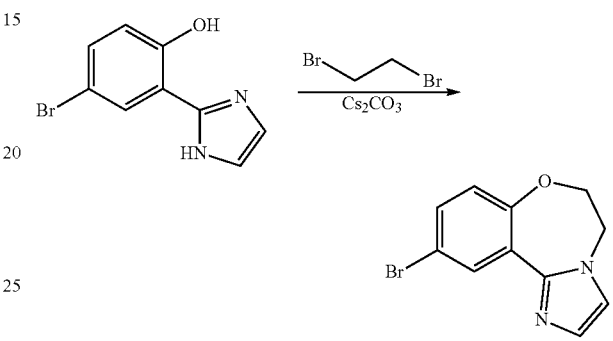

9-Bromo-4,5-dihydro-6-oxa-1,3a-diaza-benzo[e]azulene

Into a 20 L 4-necked round-bottom flask purged and maintained with an inert atmosphere of nitrogen was placed a solution of 4-bromo-2-(1H-imidazol-2-yl)phenol (835 g, 3.49 mol, 1.00 equiv) in N,N-dimethylformamide (8.5 L), 1,2-dibromoethane (2366 g, 12.59 mol, 3.60 equiv), potassium carbonate (1930 g, 4.00 equiv), and $Cs_2CO_3$ (1160 g, 1.00 equiv). The resulting solution was stirred at 100° C. overnight, quenched by the addition of 20 L of water/ice and extracted with 4×10 L of ethyl acetate. The combined organic layers were washed with 4×5 L of brine, dried over anhydrous sodium sulfate and concentrated under vacuum. The crude product was re-crystallized from EA:PE (1:2) to afford 350 g (38%) of 9-Bromo-4,5-dihydro-6-oxa-1,3a-diaza-benzo[e]azulene.

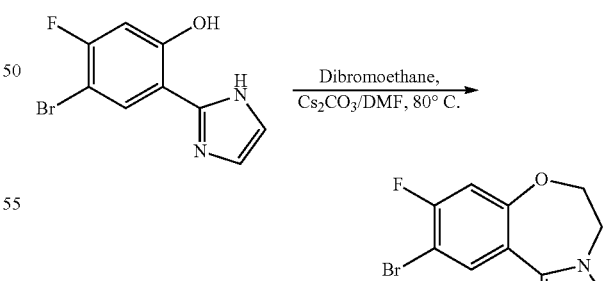

9-Bromo-8-fluoro-4,5-dihydro-6-oxa-1,3a-diaza-benzo[e]azulene

Into a 20-L 4-necked round-bottom flask purged and maintained with an inert atmosphere of nitrogen was placed a solution of 4-bromo-5-fluoro-2-(1H-imidazol-2-yl)phenol (755 g, 2.94 mol, 1.00 equiv) in N,N-dimethylformamide (7.5 L), Cs$_2$CO$_3$ (3350 g, 10.28 mol, 3.50 equiv), followed by the addition of 1,2-dibromoethane (2208 g, 11.75 mol, 4.00 equiv). The resulting solution was stirred overnight at 80° C. To this was added 1,2-dibromoethane (200 g). The resulting solution was stirred at 80° C. for 5.5 h. This reaction was repeated for 2 times. The reaction mixture was cooled to room temperature and diluted with 20 L of ice/water. The solids were collected by filtration, washed with 2×4 L of water and dried to afford 1870 g (crude) of 9-Bromo-8-fluoro-4,5-dihydro-6-oxa-1,3a-diaza-benzo[e]azulene as a gray solid.

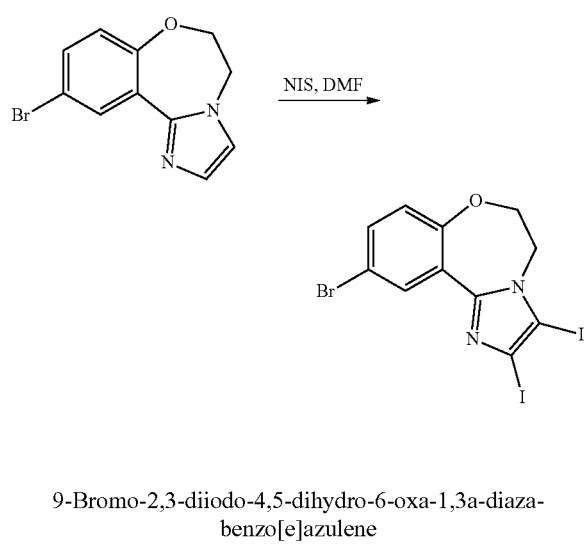

9-Bromo-2,3-diiodo-4,5-dihydro-6-oxa-1,3a-diaza-benzo[e]azulene

Into a 20 L 4-necked round-bottom flask purged and maintained with an inert atmosphere of nitrogen was placed a solution of 9-Bromo-4,5-dihydro-6-oxa-1,3a-diaza-benzo[e]azulene (1050 g, 3.96 mol, 1.00 equiv) in N,N-dimethylformamide (10.5 L) and NIS (2416 g, 2.70 equiv). The resulting solution was stirred at 80° C. overnight, quenched by the addition of 20 L of water/ice and decolorized by the addition of NaHSO$_3$. The solids were collected by filtration, washed with 5×1000 mL of water and 3×500 mL of EA, and dried in a vacuum oven to afford 1800 g (88%) of 9-Bromo-2,3-diiodo-4,5-dihydro-6-oxa-1,3a-diaza-benzo[e]azulene as a yellow solid.

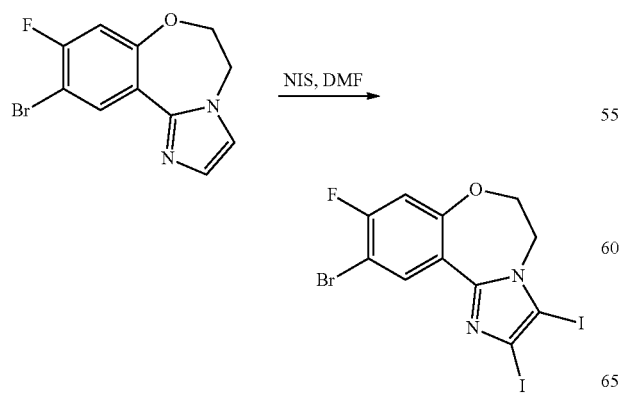

9-Bromo-8-fluoro-2,3-diiodo-4,5-dihydro-6-oxa-1, 3a-diaza-benzo[e]azulene

Into a 20-L 4-necked round-bottom flask purged and maintained with an inert atmosphere of nitrogen was placed a solution of 9-Bromo-8-fluoro-4,5-dihydro-6-oxa-1,3a-diaza-benzo[e]azulene (915 g, 3.23 mol, 1.00 equiv) in N,N-dimethylformamide (9.5 L) and NIS (1600 g, 7.11 mol, 2.20 equiv). The resulting solution was stirred overnight at 90° C., cooled to room temperature and diluted with 15 L of saturated aqueous Na$_2$CO$_3$. To the resulting solution was added 1.7 L of saturated aqueous Na$_2$SO$_3$. The mixture was stirred for 30 min. The solids were collected by filtration, washed with 2×4 L of water and dried to afford 1338 g (crude) of 9-Bromo-8-fluoro-2,3-diiodo-4,5-dihydro-6-oxa-1,3a-diaza-benzo[e]azulene.

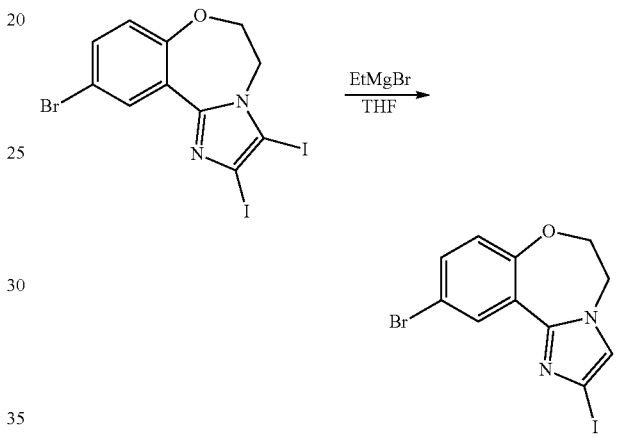

9-Bromo-2-iodo-4,5-dihydro-6-oxa-1,3a-diaza-benzolelazulene

Into a 20 L 4-necked round-bottom flask purged and maintained with an inert atmosphere of nitrogen was placed a solution of 9-Bromo-2,3-diiodo-4,5-dihydro-6-oxa-1,3a-diaza-benzo[e]azulene (900 g, 1.74 mol, 1.00 equiv) in tetrahydrofuran (9 L), followed by the addition of EtMgBr (755 mL, 1.30 equiv) dropwise with stirring at −30° C. over 60 min. The resulting solution was stirred at −30-15° C. for 10 min, quenched by the addition of 1500 mL of saturated aqueous NH$_4$Cl and extracted with 3×3000 mL of tetrahydrofuran. The combined organic layers were washed with 2×2000 mL of brine, dried over anhydrous sodium sulfate and concentrated under vacuum to afford 450 g (66%) of 9-Bromo-2-iodo-4,5-dihydro-6-oxa-1,3a-diaza-benzo[e]azulene as a yellow solid.

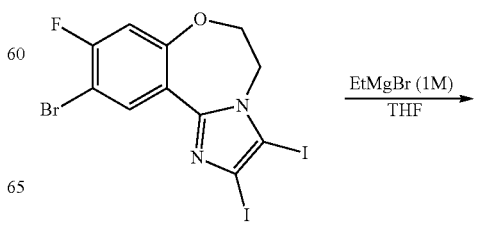

-continued

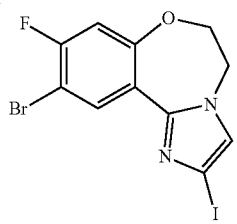

9-Bromo-8-fluoro-2-iodo-4,5-dihydro-6-oxa-1,3a-diaza-benzo[e]azulene

Into a 20-L 4-necked round-bottom flask purged and maintained with an inert atmosphere of nitrogen was placed a solution of 9-Bromo-8-fluoro-2,3-diiodo-4,5-dihydro-6-oxa-1,3a-diaza-benzo[e]azulene (886 g, 1.66 mol, 1.00 equiv) in tetrahydrofuran (7 L), followed by the addition of ethylmagnesium bromide (1987 mL, 1.20 equiv, 1 M) dropwise with stirring at −40° C. The resulting solution was stirred at room temperature for 30 min. This reaction was repeated for 2 times. The reaction was then quenched by the addition of 10 L of saturated aqueous NH$_4$Cl and diluted with 24 L of tetrahydrofuran. The resulting solution was separated and the aqueous layer was extracted with 4×3 L of tetrahydrofuran. The organic layers were combined and concentrated under vacuum. The solids were collected by filtration, washed with 1)(2 L of EA and dried to afford 2100 g (crude) of 9-Bromo-8-fluoro-2-iodo-4,5-dihydro-6-oxa-1,3a-diaza-benzo[e]azulene as a brown solid.

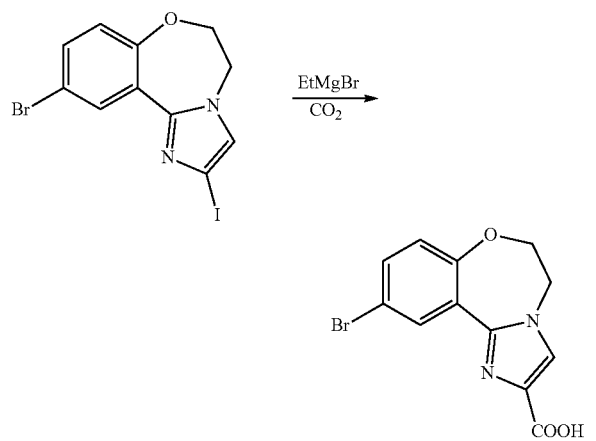

9-Bromo-4,5-dihydro-6-oxa-1,3a-diaza-benzo[e] azulene-2-carboxylic acid

Into a 20 L 4-necked round-bottom flask purged and maintained with an inert atmosphere of nitrogen was placed a solution of 9-Bromo-2-iodo-4,5-dihydro-6-oxa-1,3a-diaza-benzo[e]azulene (700 g, 1.79 mol, 1.00 equiv) in tetrahydrofuran (13 L), followed by the addition of EtMgBr (1400 mL) dropwise with stirring at −30° C. over 60 min. To the above an excess of CO$_2$ (gas) was introduced in over 3 h at −78° C. The resulting solution was warmed to room temperature naturally. The pH value of the solution was adjusted to 3 with hydrogen chloride (2 mol/L). The precipitates were collected by filtration, washed with 2×100 mL of EA and dried in a vacuum oven to afford 410 g (74%) of 9-Bromo-4,5-dihydro-6-oxa-1,3a-diaza-benzo[e]azulene-2-carboxylic acid as a white solid.

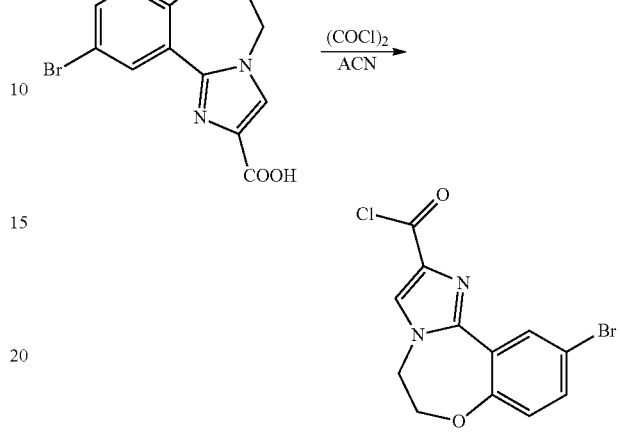

9-Bromo-4,5-dihydro-6-oxa-1,3a-diaza-benzo[e] azulene-2-carbonyl chloride

Into a 10000-mL 4-necked round-bottom flask purged and maintained with an inert atmosphere of nitrogen was placed a solution of 9-Bromo-4,5-dihydro-6-oxa-1,3a-diaza-benzo[e]azulene-2-carboxylic acid (450 g, 1.46 mol, 1.00 equiv) in ACN (4500 mL), followed by the addition of (COCl)$_2$ (450 mL) dropwise with stirring at 0° C. over 45 min. To this was added N,N-dimethylformamide (5 mL). The resulting solution was stirred at room temperature for 7 h, diluted with 2000 mL of DCM and concentrated under vacuum to afford 450 g (94%) of 9-Bromo-4,5-dihydro-6-oxa-1,3a-diaza-benzo[e]azulene-2-carbonyl chloride as a gray solid.

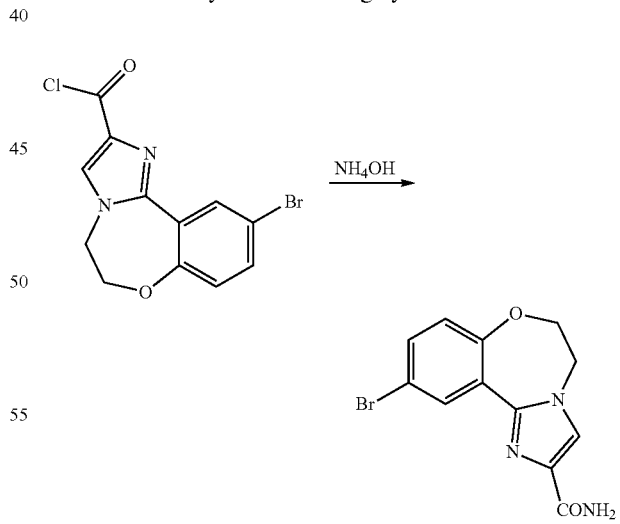

9-Bromo-4,5-dihydro-6-oxa-1,3a-diaza-benzo[e] azulene-2-carboxylic acid amide

Into a 20 L 4-necked round-bottom flask purged and maintained with an inert atmosphere of nitrogen was placed a solution of 9-Bromo-4,5-dihydro-6-oxa-1,3a-diaza-benzo[e]

azulene-2-carbonyl chloride (460 g, 1.40 mol, 1.00 equiv) in tetrahydrofuran (4.5 L), followed by the addition ammonia (0° C.) (9 L) in one portion. The resulting solution was stirred at 0=8° C. for 5 h. The reaction progress was monitored by LCMS. The precipitates were collected by filtration, washed with 5×500 mL of water and 3×500 mL of EA, and dried in a vacuum oven to afford 300 g (69%) of 9-Bromo-4,5-dihydro-6-oxa-1,3a-diaza-benzo[e]azulene-2-carboxylic acid amide as an off-white solid. LC-MS: 308 [M+H]$^+$ $^1$H-NMR (300 MHz, DMSO, ppm): δ 4.48 (4H, s), 6.99-7.02 (1H, d), 7.16 (1H, s), 7.43-7.47 (1H, m), 7.59 (1H, s), 7.80 (1H, s), 8.62-8.63 (1H, d).

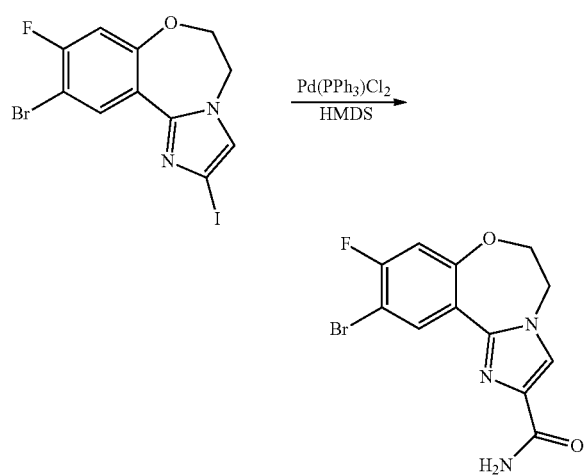

9-Bromo-8-fluoro-4,5-dihydro-6-oxa-1,3a-diaza-benzo[e]azulene-2-carboxylic acid amide Into a 5000-mL pressure tank reactor (10 atm) purged and maintained with an inert atmosphere of nitrogen was placed 9-Bromo-8-fluoro-2-iodo-4,5-dihydro-6-oxa-1,3a-diaza-benzo[e]azulene (204 g, 498.79 mmol, 1.00 equiv), HMDS (403.5 g, 2.50 mol, 5.00 equiv), Pd(PPh$_3$)Cl$_2$ (11 g, 25.02 mmol, 0.05 equiv), and N,N-dimethylformamide (3 L). To the above CO (10 atm) was introduced in. The resulting solution was stirred overnight at 80° C. and quenched by the addition of 5 L of water. The solids were collected by filtration. The crude product was re-crystallized from 800 mL of EA. The mixture was stirred at 50° C. for 3 h. The solids were collected by filtration, washed with 3×100 mL of EA and dried to afford 48.5 g (30%) of 9-Bromo-8-fluoro-4,5-dihydro-6-oxa-1,3a-diaza-benzo[e]azulene-2-carboxylic acid amide as a yellow solid. LC-MS: 326 [M+H]$^+$; $^1$H-NMR (DMSO, 300 MHz, ppm): δ 8.75 (d, J=8.4 Hz, 1H), 7.79 (s, 1H), 7.61 (s, 1H), 7.16-7.11 (m, 2H), 4.49-4.50 (m, 4H).

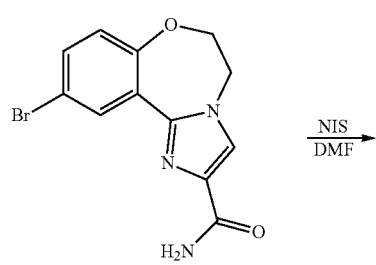

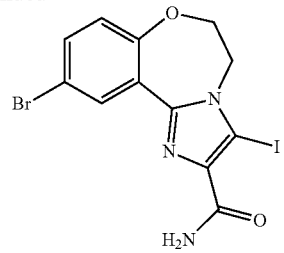

9-Bromo-3-iodo-4,5-dihydro-6-oxa-1,3a-diaza-benzo[e]azulene-2-carboxylic acid amide Into a 3000-mL 4-necked round-bottom flask purged and maintained with an inert atmosphere of nitrogen was placed a solution of 9-Bromo-4,5-dihydro-6-oxa-1,3a-diaza-benzo[e]azulene-2-carboxylic acid amide (150 g, 486.81 mmol, 1.00 equiv in N,N-dimethylformamide (2000 mL) and NIS (296 g, 2.10 equiv). The resulting solution was stirred at 80° C. overnight, cooled to 25° C., quenched by the addition of 4 L of water/ice and decolorized by the addition of 500 g of NaHSO$_3$. The solids were collected by filtration. The crude product was purified by re-crystallization from methanol and dried in a vacuum oven to afford 158 g (75%) of 9-Bromo-3-iodo-4,5-dihydro-6-oxa-1,3a-diaza-benzo[e]azulene-2-carboxylic acid amide as a pink solid. LC-MS: 434 [M+H]$^+$; $^1$H NMR (DMSO, 300 MHz, ppm): δ 4.36-4.38 (2H, m), 4.50-4.53 (2H, m), 6.99-7.02 (1H, d), 7.20 (1H, s), 7.44-7.48 (1H, dd), 7.73 (1H, s), 8.66-8.67 (1H, d).

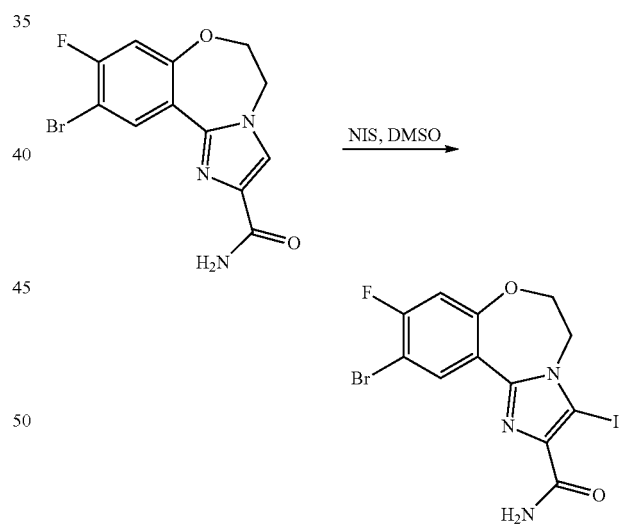

9-Bromo-8-fluoro-3-iodo-4,5-dihydro-6-oxa-1,3a-diaza-benzo[e]azulene-2-carboxylic acid amide Into a 3000-mL 4-necked round-bottom flask purged and maintained with an inert atmosphere of nitrogen was placed a solution of 9-Bromo-8-fluoro-4,5-dihydro-6-oxa-1,3a-diaza-benzo[e]azulene-2-carboxylic acid amide (150 g, 459.95 mmol, 1.00 equiv) in DMSO (1500 mL), and NIS (206.1 g, 916.08 mmol, 2.00 equiv). The resulting solution was stirred overnight at 80° C., cooled to room temperature, quenched by the addition of 6 L of water, and diluted with 600 mL of saturated aqueous Na₂SO₃ and 600 mL saturated aqueous Na₂CO₃. The solids were collected by filtration and washed with 5×300 mL of water. The crude product was purified by Flash-Prep-HPLC to afford 98 g (47%) of 9-Bromo-8-fluoro-3-iodo-4,5-dihydro-6-oxa-1,3a-diaza-benzo[e]azulene-2-carboxylic acid amide as a light brown solid. LC-MS: 452 [M+H]⁺; ¹H-NMR (DMSO, 300 MHz, ppm): δ 8.80 (d, J=8.1 Hz, 1H), 7.76 (s, 1H), 7.20 (s, 1H), 7.14 (d, J=9.6 Hz, 1H), 4.57-4.54 (m, 2H), 4.39-4.36 (m, 2H).

Example 12

Synthesis of 9-Bromo-8-fluoro-4,5-dihydro-6-oxa-3-thia-1-aza-benzo[e]azulene-2-carboxylic acid amide

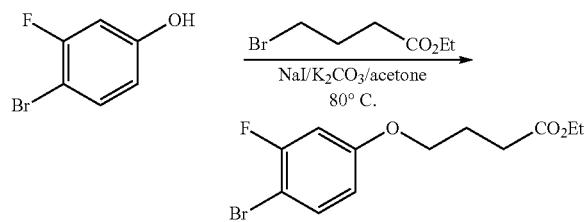

Ethyl 4-(4-bromo-3-fluorophenoxy)butanoate

Into a 2000-mL 4-necked round-bottom flask purged and maintained with an inert atmosphere of argon was placed 4-bromo-3-fluorophenol (50 g, 261.78 mmol, 1.00 equiv), acetone (500 mL), NaI (2.8 g, 0.07 equiv), potassium carbonate (54.2 g, 392.16 mmol, 1.50 equiv), and ethyl 4-bromobutanoate (61.3 g, 314.27 mmol, 1.20 equiv). The resulting solution was stirred at 56° C. overnight. The solids were filtered out and the filtrate was concentrated under vacuum. The residue was dissolved in 1000 mL of EA and the resulting mixture was washed with 2×100 mL of sodium hydroxide (1 N) and 3×100 mL, of water. The combined organic layers were dried over anhydrous sodium sulfate and concentrated under vacuum to afford 80.6 g (crude) of ethyl 4-(4-bromo-3-fluorophenoxy)butanoate as a light yellow oil.

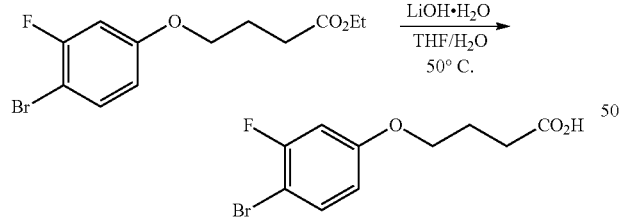

4-(4-bromo-3-fluorophenoxy)butanoic acid

Into a 2000-mL 4-necked round-bottom flask purged and maintained with an inert atmosphere of argon was placed ethyl 4-(4-bromo-3-fluorophenoxy)butanoate (80.6 g, 264.14 mmol, 1.00 equiv), LiOH (12.7 g, 530.27 mmol, 2.00 equiv), tetrahydrofuran (250 mL), and water (240 mL). The resulting solution was stirred at 50° C. overnight, cooled to 0° C. with a water/ice bath, adjusted to pH=3-4 with hydrochloric acid (2 N) and extracted with 3×100 mL of ethyl acetate. The combined organic layers were dried over anhydrous sodium sulfate and concentrated under vacuum. The residue was triturated in 30 mL of EA to afford 50 g (68%) of 4-(4-bromo-3-fluorophenoxy)butanoic acid as a white solid.

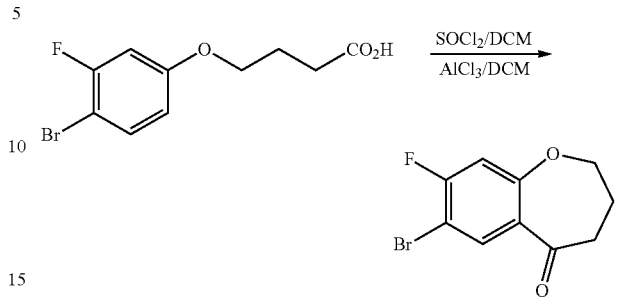

7-Bromo-8-fluoro-3,4-dihydro-2H-benzo[b]oxepin-5-one

Into a 250-mL 3-necked round-bottom flask purged and maintained with an inert atmosphere of argon was placed a solution of 4-(4-bromo-3-fluorophenoxy)butanoic acid (30 g, 108.27 mmol, 1.00 equiv) in DCM (60 mL) at 0° C., followed by the addition of thionyl chloride (14.3 g, 120.17 mmol, 1.10 equiv) dropwise at 5° C. The resulting solution was heated at 55° C. for 1.5 h and at 80° C. overnight. The resulting solution was cooled, concentrated under vacuum and dissolved in dichloromethane (150 mL) to give solution A. Into another 500-mL 3-necked round-bottom flask purged and maintained with an inert atmosphere of argon was placed a solution of AlCl₃ (21.8 g, 1.50 equiv) in dichloromethane (300 mL), followed by the addition of the solution A dropwise at 0° C. over 1 h. The resulting solution was stirred at room temperature for 3 h, quenched by the addition of 350 mL of HCl (10%) and extracted with 3×50 mL of dichloromethane. The combined organic layers were dried over anhydrous sodium sulfate and concentrated under vacuum to afford 24.6 g (88%) of 7-Bromo-8-fluoro-3,4-dihydro-2H-benzo[b]oxepin-5-one as a light yellow solid.

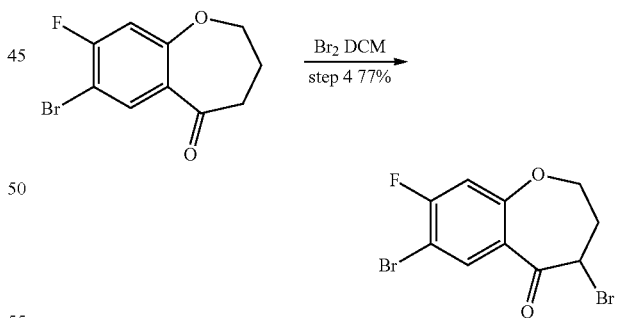

4,7-Dibromo-8-fluoro-3,4-dihydro-2H-benzo[b]oxepin-5-one

Into a 20-L 4-necked round-bottom flask purged and maintained with an inert atmosphere of argon was placed 7-Bromo-8-fluoro-3,4-dihydro-2H-benzo[b]oxepin-5-one (1168 g, 4.51 mol, 1.00 equiv) and dichloromethane (8 L), followed by the addition of Br₂ (724.3 g, 4.53 mol, 1.00 equiv) dropwise with stirring at −20° C. over 90 min. The resulting solution was stirred at −20° C. for 30 min and at room temperature for 3 h. The reaction was then quenched by the addition of 6000 mL of saturated aqueous Na₂SO₃ at 0° C.

and extracted with 4×2 L of dichloromethane. The combined organic layers were washed with 2×3000 mL of brine, dried over anhydrous sodium sulfate and concentrated under vacuum to afford 1170 g (77%) of 4,7-dibromo-8-fluoro-2,3,4,5-tetrahydro-1-benzoxepin-5-one as a yellow solid.

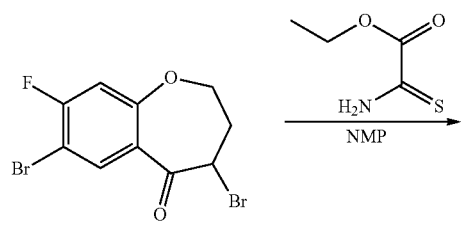

9-Bromo-8-fluoro-4,5-dihydro-6-oxa-3-thia-1-aza-benzo[e]azulene-2-carboxylic acid ethyl ester Into a 20-L 4-necked round-bottom flask purged and maintained with an inert atmosphere of nitrogen was placed 4,7-Dibromo-8-fluoro-3,4-dihydro-2H-benzo[b]oxepin-5-one (1400 g, 4.14 mol, 1.00 equiv), NMP (0 mg), and ethyl carbamothioylformate (554 g, 4.16 mol, 1.00 equiv). The resulting solution was stirred at 80° C. for 3 h, cooled to 25° C. and diluted with 6 L of ethanol. The solids were collected by filtration, washed with 3×1 L of ethanol and dried to afford 390 g (25%) of 9-Bromo-8-fluoro-4,5-dihydro-6-oxa-3-thia-1-aza-benzo[e]azulene-2-carboxylic acid ethyl ester

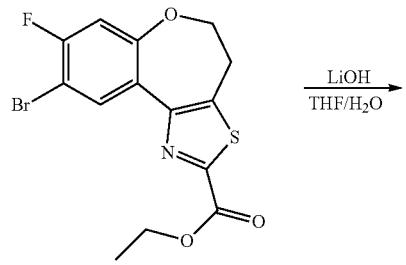

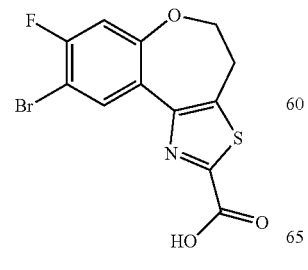

9-Bromo-8-fluoro-4,5-dihydro-6-oxa-3-thia-1-aza-benzo[e]azulene-2-carboxylic acid Into a 10-L 4-necked round-bottom flask purged and maintained with an inert atmosphere of argon was placed ethyl 9-Bromo-8-fluoro-4,5-dihydro-6-oxa-3-thia-1-aza-benzo[e]azulene-2-carboxylic acid ethyl ester (350 g, 940.33 mmol, 1.00 equiv), tetrahydrofuran (1.3 L), water (2.6 L), and LiOH (62 g, 2.59 mol, 2.73 equiv). The resulting solution was stirred at room temperature for 3 h, cooled to <10° C. and adjusted to pH=2-3 with hydrochloric acid. The precipitates were collected by filtration, washed with 4×1 L of water and dried to afford 260 g (80%) of 9-Bromo-8-fluoro-4,5-dihydro-6-oxa-3-thia-1-aza-benzo[e]azulene-2-carboxylic acid as a brown solid.

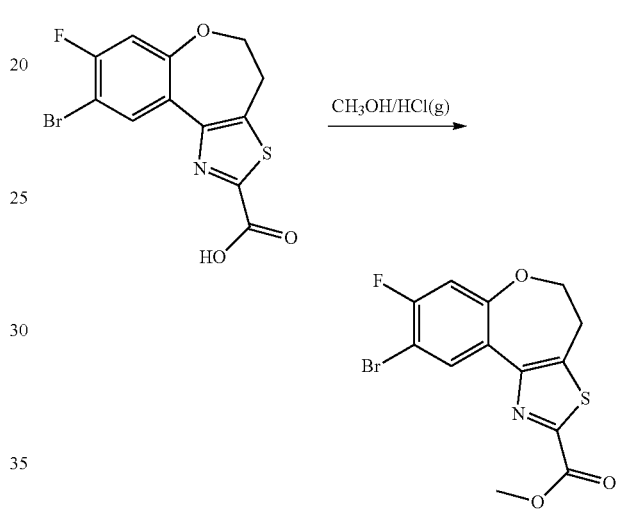

9-Bromo-8-fluoro-4,5-dihydro-6-oxa-3-thia-1-aza-benzo[e]azulene-2-carboxylic acid methyl ester Into a 2000-mL 4-necked round-bottom flask was placed methanol (1 L), followed by the addition of hydrogen chloride (gas) and then 9-Bromo-8-fluoro-4,5-dihydro-6-oxa-3-thia-1-aza-benzo[e]azulene-2-carboxylic acid (130 g, 377.74 mmol, 1.00 equiv). The resulting solution was heated to reflux at 70° C. overnight. The solids were collected by filtration, washed with 4×200 mL of methanol and 3×200 mL of EA, and dried to afford 74.8 g (55%) of methyl 9-Bromo-8-fluoro-4,5-dihydro-6-oxa-3-thia-1-aza-benzo[e]azulene-2-carboxylic acid methyl ester. LC-MS: 358 [M+H]$^{+1}$H-NMR (300HMz, CD$_3$COCD$_3$, ppm) δ 3.51-3.54 (m, 2H), 3.99 (s, 3H), 4.47-4.50 (m, 2H), 6.98-7.01 (d, 1H), 8.70-8.73 (d, 1H).

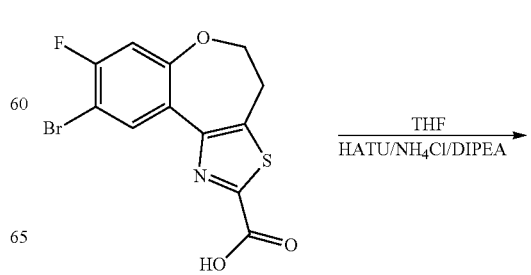

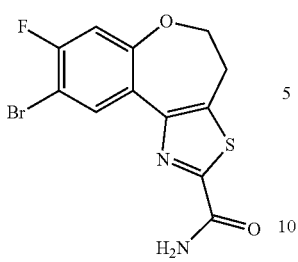

9-Bromo-8-fluoro-4,5-dihydro-6-oxa-3-thia-1-aza-benzo[e]azulene-2-carboxylic acid amide Into a 3-L 4-necked round-bottom flask purged and maintained with an inert atmosphere of argon was placed 9-Bromo-8-fluoro-4,5-dihydro-6-oxa-3-thia-1-aza-benzo[e]azulene-2-carboxylic acid (130 g, 377.74 mmol, 1.00 equiv), $NH_4Cl$ (81.95 g, 1.53 mol, 4.08 equiv), tetrahydrofuran (1 L), DIEA (97.782 g, 756.59 mmol, 2.00 equiv), and HATU (158.08 g, 415.75 mmol, 1.10 equiv). The resulting solution was stirred at room temperature overnight and diluted with 2.5 L of ice/water. The solids were collected by filtration, washed with 4×1 L of water and dried to afford 84.2 g (65%) of 9-Bromo-8-fluoro-4,5-dihydro-6-oxa-3-thia-1-aza-benzo[e]azulene-2-carboxylic acid amide as a brown solid. LC-MS: 343 [M+H]$^+$ $^1$H NMR (300 MHz, DMSO, ppm) δ 3.33-3.43 (m, 2H), 4.36-4.39 (m, 2H), 7.02-7.14 (d, 1H), 7.88 (s, 1H), 8.52 (s, 1H), 8.88-8.90 (d, 1H). $^{19}$F-NMR (300 MHz, DMSO, ppm) δ 107.91 (s, 1F).

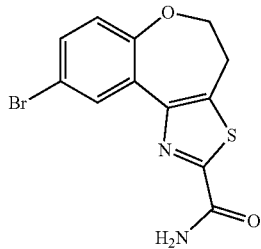 [SMILES: NC(=O)c1nc2c(s1)CCOc1ccc(Br)cc1-2]

9-Bromo-4,5-dihydro-6-oxa-3-thia-1-aza-benzo[e]azulene-2-carboxylic acid amide This material was prepared according to the protocols described in WO2011/036284.

Example 13

Synthesis of Intermediates 9-bromo-2,5-diazatetracyclo[11.1.1.0$^{[2,6]}$.0$^{[7,12]}$]pentadeca-3,5,7,9,11-pentaene-4-carboxamide; 9-bromo-10-fluoro-2,5-diazatetracyclo[11.1.1.0$^{[2,6]}$.0$^{[7,12]}$]pentadeca-3,5,7,9,11-pentaene-4-carboxamide and 10-fluoro-9-bromo-3-iodo-2,5-diazatetracyclo[11.1.1.0$^{2,6}$.0$^{7,12}$]pentadeca-3,5,7(12),8,10-pentaene-4-carboxamide

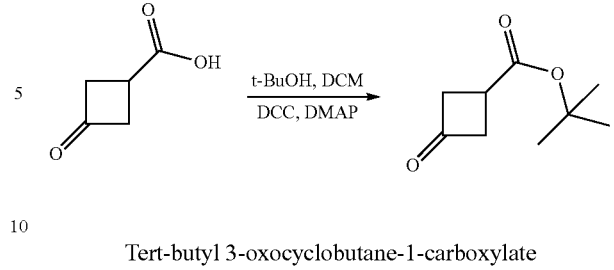

Tert-butyl 3-oxocyclobutane-1-carboxylate

Into a 2000-mL 4-necked round-bottom flask was placed a solution of 3-oxocyclobutane-1-carboxylic acid (114 g, 999.13 mmol, 1.00 equiv) in dichloromethane (400 mL), 2-methylpropan-2-ol (102 g, 1.38 mol, 1.37 equiv), N,N-dimethylpyridin-4-amine (67.2 g, 550.06 mmol, 0.55 equiv), followed by the addition of a solution of N—(N-cyclohexylcarboximidoyl)cyclohexanamine (226.6 g, 1.10 mol, 1.10 equiv) in dichloromethane (300 mL) dropwise with stirring at room temperature over 25 min. The resulting solution was stifled overnight at room temperature. The solids were filtered out and the filtrate was washed with 2×500 mL of HCl (1 M) and 1×500 mL of saturated aqueous $NaHCO_3$, and concentrated under vacuum. The residue was diluted with 500 mL of hexane. The mixture was decolorized by 50 g of active carbon and stirring for 3 minutes. The solids were filtered out and the filtrate was concentrated under vacuum to afford 102 g (60%) of tert-butyl 3-oxocyclobutane-1-carboxylate as a light yellow liquid.

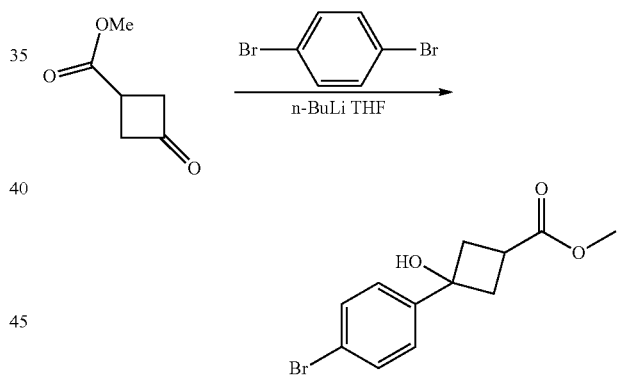

Methyl 3-(4-bromophenyl)-3-hydroxycyclobutane-1-carboxylate

Into a 20-L 4-necked round-bottom flask purged and maintained with an inert atmosphere of nitrogen was placed tetrahydrofuran (12 L), 1,4-dibromobenzene (2020 g, 8.56 mol, 1.03 equiv), followed by the addition of n-BuLi (3566 mL, 1.03 equiv, 2.4 M) dropwise with stirring at −78° C. The mixture was stirred at −78° C. for 1 h. Into another 20-L 4-necked round-bottom flask purged and maintained with an inert atmosphere of nitrogen was placed a solution of methyl 3-oxocyclobutane-1-carboxylate (1064 g, 8.30 mol, 1.00 equiv) in tetrahydrofuran (4 L). To this was added the resulting solution in the first flask dropwise with stirring at −78° C. The resulting solution was stirred overnight at 25° C. This reaction was repeated for 2 more times. The reaction was then quenched by the addition of 15 L of saturated aqueous $NH_4Cl$, concentrated under vacuum, diluted with 15 L of $H_2O$ and extracted with 2×5 L of ethyl acetate. The organic layers were combined, washed with 1×8 L of brine, dried over anhydrous sodium sulfate and concentrated under vacuum to afford 6500 g (92%) of methyl 3-(4-bromophenyl)-3-hydroxycyclobutane-1-carboxylate as a dark red oil.

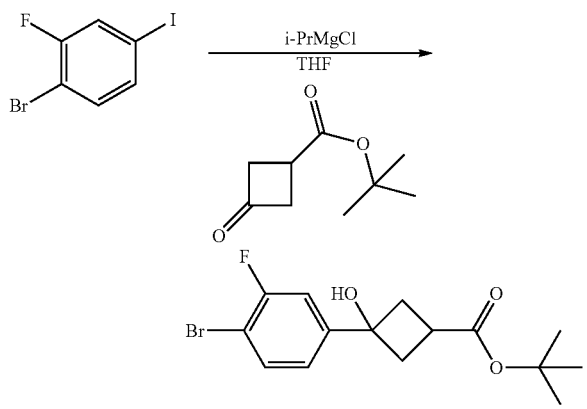

Tert-butyl 3-(4-bromo-3-fluorophenyl)-3-hydroxycyclobutane-1-carboxylate

Into a 2000-mL 4-necked round-bottom flask purged and maintained with an inert atmosphere of nitrogen was placed a solution of 1-bromo-2-fluoro-4-iodobenzene (58 g, 192.76 mmol, 1.00 equiv) in tetrahydrofuran (600 mL), followed by the addition of i-PrMgCl (96.3 mL, 1.00 equiv) dropwise with stirring at 0° C. over 30 min. The mixture was stirred at 0° C. for 3 h. To this was added tert-butyl 3-oxocyclobutane-1-carboxylate (32.7 g, 192.12 mmol, 1.00 equiv) dropwise with stirring at −78° C. over 10 min. The mixture was stirred at −78 degree C. for 1 h and overnight at room temperature. The reaction was then quenched by the addition of 200 mL of saturated aqueous NH4Cl at 0° C. and extracted with 3×500 mL of ethyl acetate. The organic layers were combined, dried over anhydrous sodium sulfate and concentrated under vacuum to afford 62 g (crude) of tert-butyl 3-(4-bromo-3-fluorophenyl)-3-hydroxycyclobutane-1-carboxylate as a yellow oil.

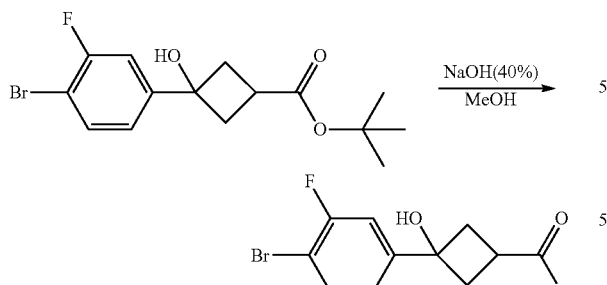

3-(4-Bromo-3-fluorophenyl)-3-hydroxycyclobutane-1-carboxylic acid

Into a 1000-mL round-bottom flask was placed a solution of tert-butyl 3-(4-bromo-3-fluorophenyl)-3-hydroxycyclobutane-1-carboxylate (62 g, 179.60 mmol, 1.00 equiv) in methanol/NaOH (40%) (300/300 mL). The resulting solution was stirred at room temperature for 3 h, concentrated under vacuum and extracted with 3×200 mL of ethyl acetate. The pH value of the aqueous layer was adjusted to 4 with hydrogen chloride (2 mol/L). The resulting solution was extracted with 3×300 mL of ethyl acetate. The organic layers were combined, washed with 1×500 mL of water and 1×500 mL of brine, dried over anhydrous sodium sulfate and concentrated under vacuum to afford 50 g (96%) of 3-(4-bromo-3-fluorophenyl)-3-hydroxycyclobutane-1-carboxylic acid as a yellow liquid.

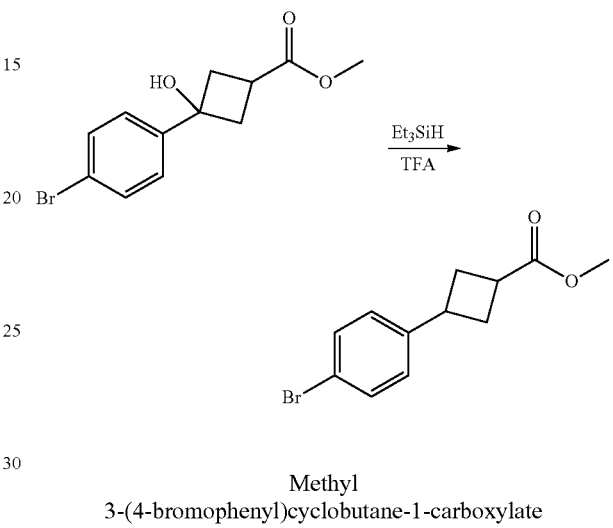

Methyl 3-(4-bromophenyl)cyclobutane-1-carboxylate

Into a 20-L 4-necked round-bottom flask was placed trifluoroacetic acid (12 L), methyl 3-(4-bromophenyl)-3-hydroxycyclobutane-1-carboxylate (2330 g, 8.17 mol, 1.00 equiv), followed by the addition of Et₃SiH (3556 g, 30.58 mol, 5.00 equiv) dropwise with stirring at 10-25° C. The resulting solution was stirred at room temperature for 0.5 h, concentrated under vacuum, diluted with 8 L of H₂O and extracted with 1×8 L of ethyl acetate. The organic layers were combined, washed with 1×3 L of saturated aqueous sodium bicarbonate and 1×2 L of brine, dried over anhydrous sodium sulfate and concentrated under vacuum to afford 2175 g (crude) of methyl 3-(4-bromophenyl)cyclobutane-1-carboxylate as an orange oil.

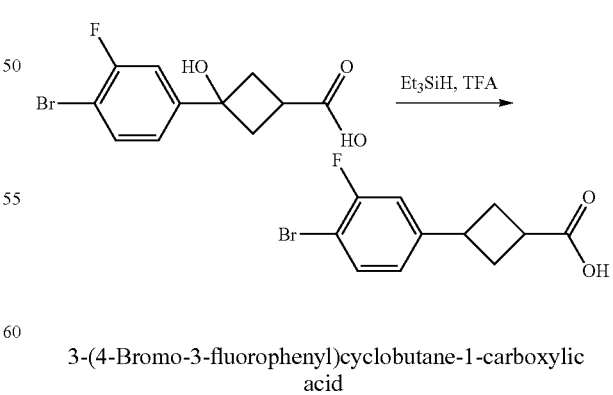

3-(4-Bromo-3-fluorophenyl)cyclobutane-1-carboxylic acid

Into a 1000-mL round-bottom flask was placed a solution of 3-(4-bromo-3-fluorophenyl)-3-hydroxycyclobutane-1-carboxylic acid (50 g, 172.95 mmol, 1.00 equiv) in trifluoroacetic acid (500 mL) and triethylsilane (40.1 g, 344.87 mmol, 2.00 equiv). The resulting solution was stirred at room temperature for 4 h and concentrated under vacuum. The resulting solution was diluted with 200 mL of EA and washed with 2×200 mL of saturated aqueous sodium carbonate. The aqueous layers were combined and extracted with 3×500 mL of EA. The pH value of the aqueous layer was adjusted to 4 with hydrogen chloride (1 mol/L). The resulting solution was extracted with 3×500 mL of ethyl acetate. The organic layers were combined, washed with 1×1000 mL of water and 1)(1000 mL of brine, dried over anhydrous sodium sulfate and concentrated under vacuum to afford 35 g (crude) of 3-(4-bromo-3-fluorophenyl)cyclobutane-1-carboxylic acid as a yellow liquid.

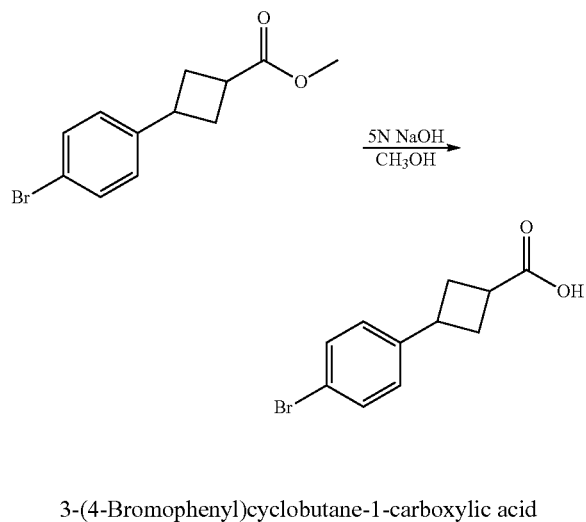

3-(4-Bromophenyl)cyclobutane-1-carboxylic acid

Into a 20-L 4-necked round-bottom flask was placed methanol (5 L), methyl 3-(4-bromophenyl)cyclobutane-1-carboxylate (2175 g, 8.08 mol, 1.00 equiv), followed by the addition of a solution of sodium hydroxide (1623 g, 40.58 mol, 5.02 equiv, 5 M) in water (5 L). The resulting solution was stirred at 80° C. for 3 h, cooled to 30° C. and concentrated under vacuum. The resulting solution was diluted with 10 L of H$_2$O and 8 L of DCM, and then extracted with 2×2 L of dichloromethane. The pH value of the combined aqueous layers was adjusted to 5-6 with hydrogen chloride (6 mol/L). The resulting solution was extracted with 3×4 L of dichloromethane. The organic layers were combined, dried over anhydrous sodium sulfate and concentrated under vacuum. The residue was triturated with 1.5 L of hexane and 300 mL of EA. The solids were collected by filtration. The filtrate was concentrated under vacuum and combined with the previous solids to afford 1312 g (crude) of 3-(4-bromophenyl)cyclobutane-1-carboxylic acid as a dark red solid.

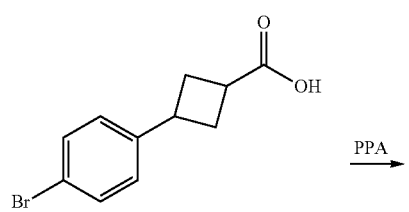

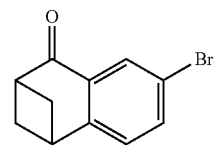

5-Bromotricyclo[7.1.1.0[2,7]]undeca-2,4,6-trien-8-one

Into a 20-L 4-necked round-bottom flask was placed PPA (13000 g), followed by the addition of 3-(4-bromophenyl)cyclobutane-1-carboxylic acid (1400 g, 5.49 mol, 1.00 equiv) in several batches with stirring at 90° C. The resulting solution was stirred at 120° C. for 3 h, cooled to 90° C. and quenched by the addition of 30 L of water/ice. The solids were collected by filtration and then dissolved in 10 L of EA. The pH value of the solution was adjusted to 7 with saturated aqueous sodium bicarbonate. The organic layer was dried over anhydrous sodium sulfate, stirred for 2 h with 500 g of active carbon and concentrated under vacuum to afford 920 g (71%) of 5-bromotricyclo[7.1.1.0[2,7]]undeca-2,4,6-trien-8-one as a brown solid.

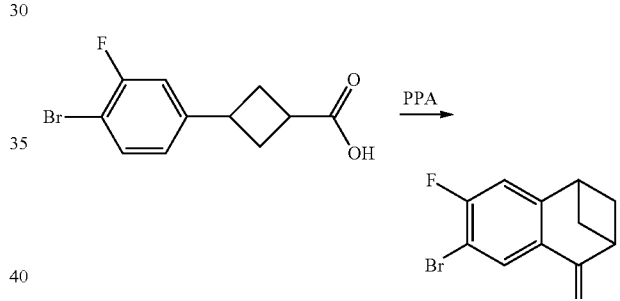

6-Bromo-7-fluoro-2,3-dihydro-1H-1,3-methano-naphthalen-4-one

Into a 500-mL round-bottom flask was placed a solution of 3-(4-bromo-3-fluorophenyl)cyclobutane-1-carboxylic acid (55.5 g, 203.22 mmol, 1.00 equiv) in PPA (300 g). The resulting solution was stirred at 90° C. for 8 h, cooled to room temperature, quenched by the addition of 1000 mL of water/ice and extracted with 3×500 mL of ethyl acetate. The organic layers were combined, washed with 1×1000 mL of water, 1×1000 mL of saturated aqueous sodium carbonate and 1×1000 mL of brine, dried over anhydrous sodium sulfate and concentrated under vacuum. The residue was purified on a silica gel column eluting with ethyl acetate: petroleum ether (1:20) to afford 27.1 g (52%) of 6-Bromo-7-fluoro-2,3-dihydro-1H-1,3-methano-naphthalen-4-one as a white solid. LC-MS: 255 [M+H]$^+$; $^1$H-NMR (300 MHz, CDCl$_3$, ppm) □ 2.31-2.37 (2H, m), 2.92-3.02 (2H, m); 3.20-3.29 (1H, m); 3.30-3.34 (1H); 7.01-7.04 (1H, d, J=8.1 Hz); 8.16-8.19 (1H, m).

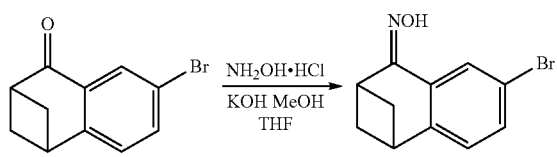

6-Bromo-2,3-dihydro-1H-1,3-methano-naphthalen-4-one oxime

Into a 20-L 4-necked round-bottom flask was placed 6-Bromo-7-fluoro-2,3-dihydro-1H-1,3-methano-naphthalen-4-one (920 g, 3.88 mol, 1.00 equiv), methanol (7.5 L), tetrahydrofuran (2.5 L), NH$_2$OH.HCl (538.2 g, 2.00 equiv), and KOH (655.2 g, 3.00 equiv, 50%). The resulting solution was stirred at 80° C. for 2.5 h and cooled to 25° C. The solids were filtered out and washed with 3×1 L of DCM. The filtrate was concentrated under vacuum and the residue was diluted with 5 L of H$_2$O and 8 L of EA. The pH value of the solution was adjusted to 7 with HCl (3 M). The organic layer was washed with 1×2 L of brine, dried over anhydrous sodium sulfate and concentrated under vacuum to afford 980 g (crude) of 6-Bromo-2,3-dihydro-1H-1,3-methano-naphthalen-4-one oxime as a dark red solid.

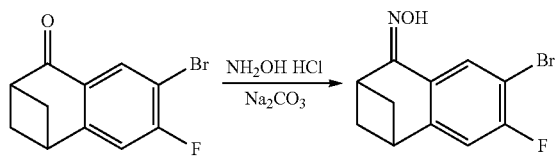

6-Bromo-7-fluoro-2,3-dihydro-1H-1,3-methano-naphthalen-4-one oxime

Into a 100-mL 3-necked round-bottom flask was placed a solution of 6-Bromo-7-fluoro-2,3-dihydro-1H-1,3-methano-naphthalen-4-one (4.5 g, 17.64 mmol, 1.00 equiv) in ethanol/H$_2$O (20/20 mL), sodium carbonate (3.8 g, 35.85 mmol, 2.00 equiv), and NH$_2$OH.HCl (2.4 g, 2.00 equiv). The resulting solution was stirred overnight at 85° C., cooled and concentrated under vacuum. The solids were collected by filtration, washed with 2×50 mL of water and dried to afford 3.5 g (73%) of 6-Bromo-7-fluoro-2,3-dihydro-1H-1,3-methano-naphthalen-4-one oxime as a white solid.

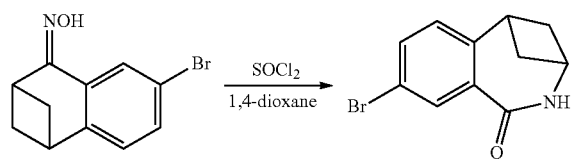

5-Bromo-9-aza-tricyclo[8.1.1.0$^{[2,7]}$]dodeca-2,4,6-trien-8-one

Into a 20-L 4-necked round-bottom flask was placed 6-Bromo-2,3-dihydro-1H-1,3-methano-naphthalen-4-one oxime (790 g, 3.13 mol, 1.00 equiv), 1,4-dioxane (7.5 L), followed by the addition of a solution of thionyl chloride (12000 g, 32.00 equiv) in 1,4-dioxane (7.5 L) dropwise with stirring at 25° C. The resulting solution was stirred at 65° C. for 6 h. This reaction was repeated for 2 more times. The resulting mixture was concentrated under vacuum, diluted with 10 L of DCM and then quenched by the addition of 8 L of water. The resulting solution was extracted with 2×10 L of dichloromethane and the organic layers were combined. The pH value of the solution was adjusted to 7 with sodium bicarbonate (sat.). The organic layer was dried over anhydrous sodium sulfated and concentrated under vacuum. The residue was diluted with 4 L of EA and stirred at reflux for 0.5 h. The solids were collected by filtration and washed with 2×500 mL, of EA. The filtrate was concentrated under vacuum. The residue was applied onto a silica gel column eluting with PE:EA (5:1-3:1). This solid was combined with the previous solids to afford 1749 g (74%) of 5-Bromo-9-azatricyclo[8.1.1.0$^{[2,7]}$]dodeca-2,4,6-trien-8-one as an off-white solid.

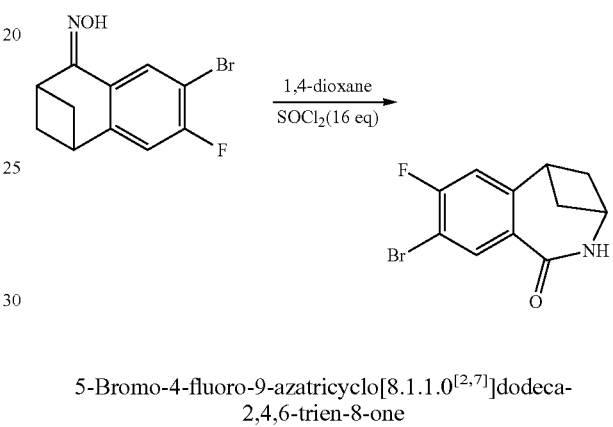

5-Bromo-4-fluoro-9-azatricyclo[8.1.1.0$^{[2,7]}$]dodeca-2,4,6-trien-8-one

Into a 100-mL round-bottom flask was placed a solution of 6-Bromo-7-fluoro-2,3-dihydro-1H-1,3-methano-naphthalen-4-one oxime (3.5 g, 12.96 mmol, 1.00 equiv) in 1,4-dioxane (30 mL) and thionyl chloride (24.7 g, 207.56 mmol, 16.00 equiv). The resulting solution was heated to reflux for 6 h, cooled, concentrated under vacuum, and quenched by the addition of 50 mL of water/ice. The solids were collected by filtration, washed with 2×50 mL of saturated aqueous NaHCO$_3$ and 2×50 mL of water to afford 3.1 g (89%) of 5-bromo-4-fluoro-9-azatricyclo[8.1.1.0$^{[2,7]}$]dodeca-2,4,6-trien-8-one as a white solid.

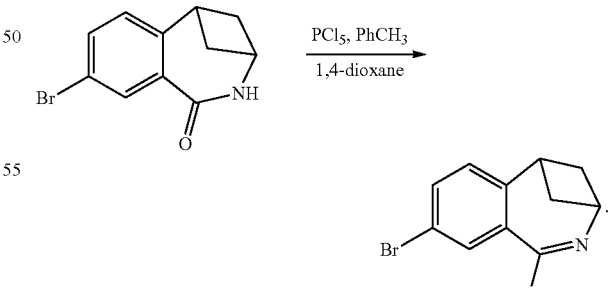

5-Bromo-8-chloro-9-azatricyclo[8.1.1.0$^{[2,7]}$]dodeca-2,4,6,8-tetraene

Into a 5000-mL 3-necked round-bottom flask was placed 5-bromo-9-azatricyclo[8.1.1.0$^{[2,7]}$]dodeca-2,4,6-trien-8-one (223 g, 884.55 mmol, 1.00 equiv), PhCH$_3$ (3500 mL), PCl$_5$ (560 g, 2.69 mol, 3.00 equiv), and DIPEA (275 g, 3.00 equiv). The resulting solution was stirred at 85° C. for 5 h and quenched by the addition of 300 g of DIPEA. The solids were filtered out and the filtrate was concentrated under vacuum to afford 260 g (crude) of 5-bromo-8-chloro-9-azatricyclo[8.1.1.0$^{[2,7]}$]dodeca-2,4,6,8-tetraene as a black oil.

5-Bromo-8-chloro-4-fluoro-9-azatricyclo[8.1.1.0$^{[2,7]}$]dodeca-2,4,6,8-tetraene Into a 20000-mL 4-necked round-bottom flask was placed a solution of 5-bromo-4-fluoro-9-azatricyclo[8.1.1.0$^{[2,7]}$]dodeca-2,4,6-trien-8-one (800 g, 2.96 mol, 1.00 equiv) in toluene (10000 mL), followed by the addition of PCl$_5$ (1540 g, 7.40 mol, 2.50 equiv) in several batches at 25° C. over 1 hour. The resulting solution was heated to reflux for 5 hr, cooled to room temperature and diluted with 5000 mL of ether. The solids were collected by filtration and dissolved in 10000 mL of ether. The resulting mixture was washed with 5000 mL of ammonia (10%), dried over anhydrous sodium sulfate and concentrated under vacuum to afford 700 g (82%) of 5-bromo-8-chloro-4-fluoro-9-azatricyclo[8.1.1.0$^{[2,7]}$]dodeca-2,4,6,8-tetraene as a white solid.

5-Bromo-N-(2,2-dimethoxyethyl)-9-azatricyclo[8.1.1.0$^{[2,7]}$]dodeca-2,4,6,8-tetraen-8-amine Into a 10-L 4-necked round-bottom flask was placed 5-bromo-8-chloro-9-azatricyclo[8.1.1.0$^{[2,7]}$]dodeca-2,4,6,8-tetraene (260 g, 960.99 mmol, 1.00 equiv), 2-methylpropan-2-ol (6000 mL), and 2,2-dimethoxyethan-1-amine (600 g, 5.71 mol, 6.00 equiv). The resulting solution was stirred at 85° C. for 5 h, cooled to room temperature and concentrated under vacuum. The residue was washed with 2×500 mL water and extracted with 3×500 mL of ethyl acetate. The organic layers were combined and concentrated under vacuum to afford 340 g (crude) of 5-bromo-N-(2,2-dimethoxyethyl)-9-azatricyclo[8.1.1.0$^{[2,7]}$]dodeca-2,4,6,8-tetraen-8-amine as a black oil.

5-Bromo-N-(2,2-dimethoxyethyl)-4-fluoro-9-azatricyclo[8.1.1.0$^{[2,7]}$]dodeca-2,4,6,8-tetraen-8-amine Into a 100-mL 3-necked round-bottom flask was placed a solution of 5-bromo-8-chloro-4-fluoro-9-azatricyclo[8.1.1.0$^{[2,7]}$]dodeca-2,4,6,8-tetraene (3.75 g, 13.00 mmol, 1.00 equiv) in n-BuOH (50 mL) and 2,2-dimethoxyethan-1-amine (1.5 g, 14.27 mmol, 1.10 equiv). The resulting solution was stirred at 100° C. for 1.5, diluted with 50 mL of water and extracted with 1×50 mL of ethyl acetate. The organic layers were combined and concentrated under vacuum to afford 5.0 g (crude) of 5-bromo-N-(2,2-dimethoxyethyl)-4-fluoro-9-azatricyclo[8.1.1.0$^{[2,7]}$]dodeca-2,4,6,8-tetraen-8-amine as a yellow oil.

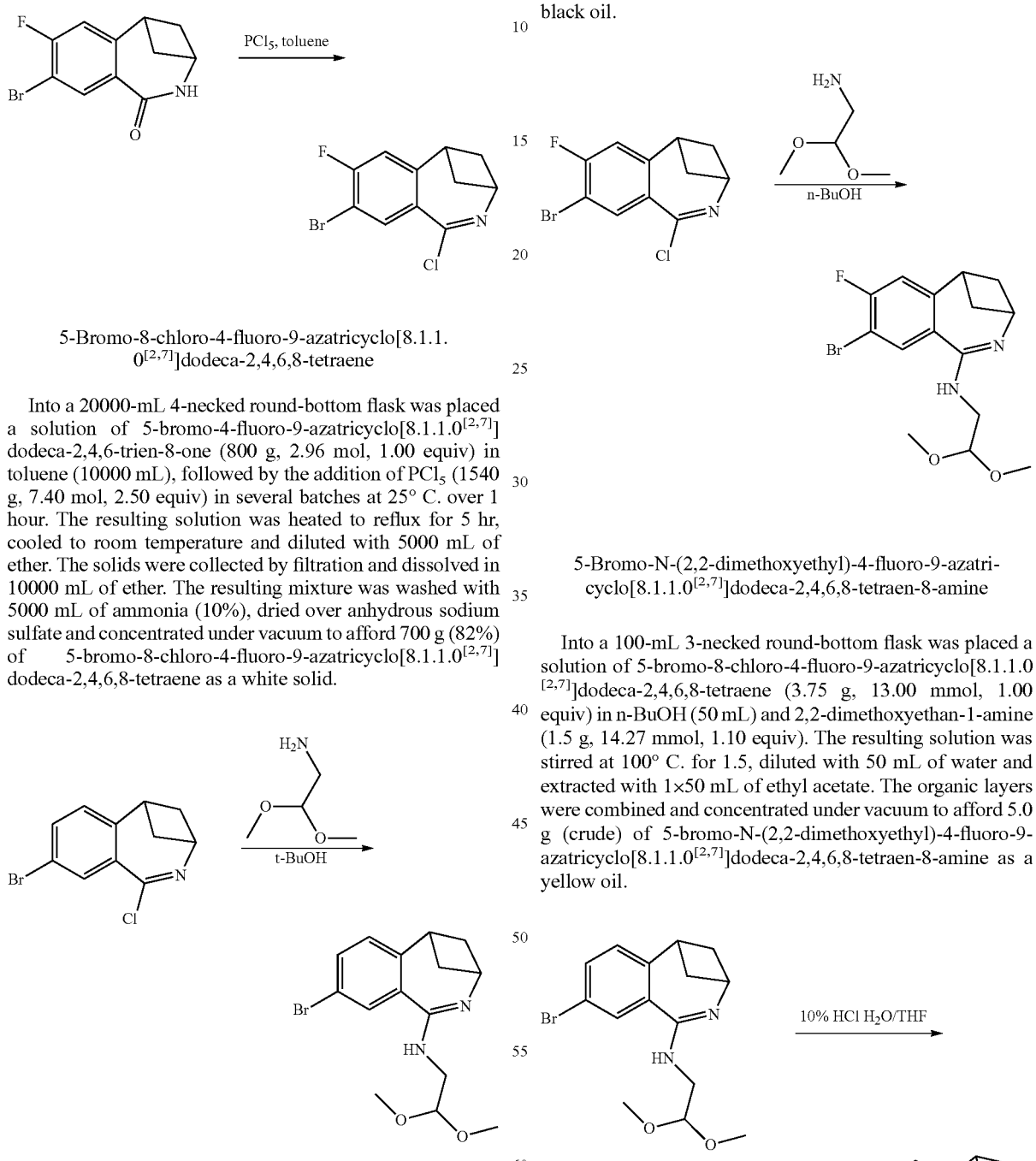

9-Bromo-2,5-diazatetracyclo[11.1.1.0[2,6].0[7,12]]pentadeca-3,5,7,9,11-pentaene Into a 1000-mL round-bottom flask was placed 5-bromo-N-(2,2-dimethoxyethyl)-9-azatricyclo[8.1.1.0[2,7]]dodeca-2,4,6,8-tetraen-8-amine (33.4 g, 98.46 mmol, 1.00 equiv), tetrahydrofuran (340 mL), and hydrogen chloride (340 mL, 10%). The resulting solution was heated to reflux for 2 h, concentrated under vacuum and extracted with 2×150 mL of ethyl acetate. The pH value of the combined aqueous layers was adjusted to 8-9 with sodium hydroxide (2 mol/L). The resulting solution was extracted with 3×300 mL of dichloromethane. The organic layers were combined, washed with 2×150 mL of water and 1×150 mL of brine, dried over anhydrous sodium sulfated and concentrated under vacuum. The crude product was decolorized by the addition of active carbon, stirring for 30 min. The solids were filtered out and the filtrate was concentrated under vacuum to afford 15 g (55%) of 9-bromo-2,5-diazatetracyclo[11.1.1.0[2,6].0[7,12]]pentadeca-3,5,7,9,11-pentaene as a white solid.

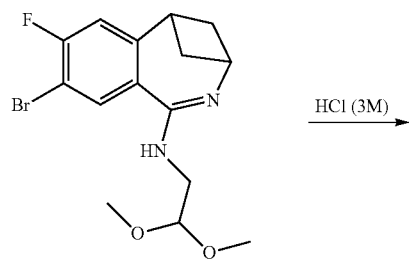

9-Bromo-10-fluoro-2,5-diazatetracyclo[11.1.1.0[2,6].0[7,12]]pentadeca-3,5,7,9,11-pentaene Into a 3000-mL 4-necked round-bottom flask was placed a solution of 5-bromo-N-(2,2-dimethoxyethyl)-4-fluoro-9-azatricyclo[8.1.1.0[2,7]]dodeca-2,4,6,8-tetraen-8-amine (350 g, 979.79 mmol, 1.00 equiv) in hydrogen chloride (3M) (1500 mL). The resulting solution was stirred at 90° C. for 90 min and extracted with 1×1000 mL of ethyl acetate. The pH value of the aqueous layer was adjusted to 10 with sodium hydroxide (3 mol/L). The resulting solution was extracted with 3×500 mL of ethyl acetate. The organic layers were combined and concentrated under vacuum. The residue was applied onto a silica gel column eluting with ethyl acetate: petroleum ether (1:2) to afford 150 g (52%) of 9-bromo-10-fluoro-2,5-diazatetracyclo[11.1.1.0[2,6].0[7,12]]pentadeca-3,5,7,9,11-pentaene as a white solid.

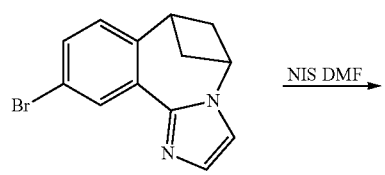

9-Bromo-3,4-diiodo-2,5-diazatetracyclo[11.1.1.0[2,6].0[7,12]]pentadeca-3,5,7,9,11-pentaene Into a 2-L 4-necked round-bottom flask purged and maintained with an inert atmosphere of nitrogen was placed 9-bromo-2,5-diazatetracyclo[11.1.1.0[2,6].0[7,12]]pentadeca-3,5,7,9,11-pentaene (43 g, 156.28 mmol, 1.00 equiv), N,N-dimethylformamide (800 mL), and NIS (105.5 g, 468.93 mmol, 3.00 equiv). The resulting solution was stirred at 90° C. for 3 h. This reaction was repeated for 2 more times. The reaction mixture was cooled to 25° C., quenched by the addition of 1 L of NaOH (1 M) and washed with 1×300 mL of sat Na$_2$SO$_3$. The solids were collected by filtration and dried to afford 262 g (crude) of 9-bromo-3,4-diiodo-2,5-diazatetracyclo[11.1.1.0[2,6].0[7,12]]pentadeca-3,5,7,9,11-pentaene as a pink solid.

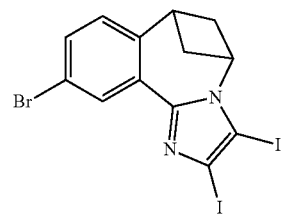

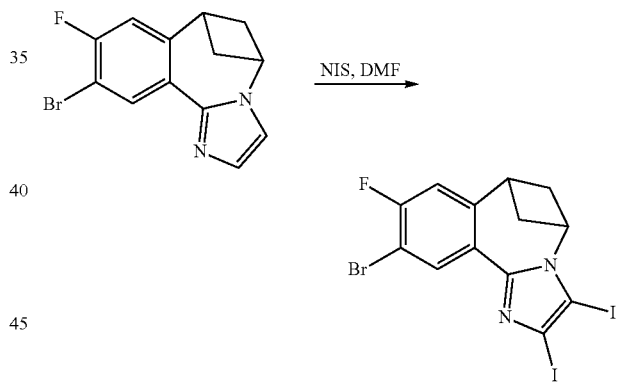

9-Bromo-10-fluoro-3,4-diiodo-2,5-diazatetracyclo[11.1.1.0[2,6].0[7,12]]pentadeca-3,5,7,9,11-pentaene Into a 5000-mL 4-necked round-bottom flask was placed a solution of 9-bromo-10-fluoro-2,5-diazatetracyclo[11.1.1.0[2,6].0[7,12]]pentadeca-3,5,7,9,11-pentaene (150 g, 511.71 mmol, 1.00 equiv) in N,N-dimethylformamide (2000 mL) and NIS (288 g, 1.28 mol, 2.50 equiv). The resulting solution was stirred at 90° C. for 6 h and diluted with 4000 mL of H$_2$O. The solids were collected by filtration, washed with 1×1000 mL of saturated aqueous Na$_2$CO$_3$, 1×1000 mL of saturated aqueous Na$_2$SO$_3$ and 2×1000 mL of water, and dried to afford 252 g (90%) of 9-bromo-10-fluoro-3,4-diiodo-2,5-diazatetracyclo[11.1.1.0[2,6].0[7,12]]pentadeca-3,5,7,9,11-pentaene as a gray solid.

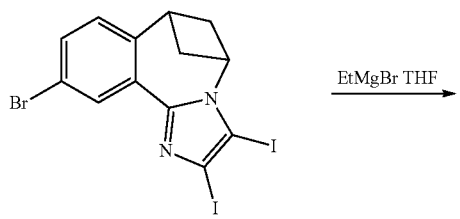

9-Bromo-4-iodo-2,5-diazatetracyclo[11.1.1.0[2,6].0[7,12]]pentadeca-3,5,7,9,11-pentaene Into a 3-L 4-necked round-bottom flask purged and maintained with an inert atmosphere of nitrogen was placed tetrahydrofuran (1200 mL), 9-bromo-3,4-diiodo-2,5-diazatetracyclo[11.1.1.0[2,6].0[7,12]]pentadeca-3,5,7,9,11-pentaene (119.3 g, 226.40 mmol, 1.00 equiv), followed by the addition of EtMgBr (90.7 mL, 1.20 equiv) dropwise with stirring at −40° C. The resulting solution was stirred at −40° C. for 1 h. This reaction was repeated for 2 more times. The reaction was then quenched by the addition of 500 mL of 5% hydrogen chloride and extracted with 3×500 mL of dichloromethane. The organic layers were combined, dried over anhydrous sodium sulfate and concentrated under vacuum to afford 259 g (97%) of 9-bromo-4-iodo-2,5-diazatetracyclo[11.1.1.0[2,6].0[7,12]]pentadeca-3,5,7,9,11-pentaene as a brown solid.

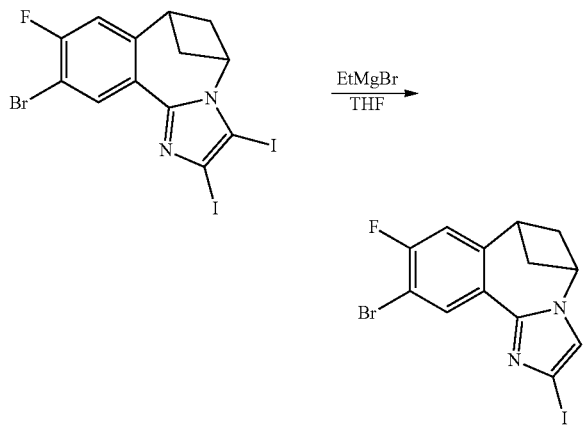

9-Bromo-10-fluoro-4-iodo-2,5-diazatetracyclo[11.1.1.0[2,6].0[7,12]]pentadeca-3,5,7,9,11-pentaene Into a 3000-mL 4-necked round-bottom flask purged and maintained with an inert atmosphere of nitrogen was placed a solution of 9-bromo-10-fluoro-3,4-diiodo-2,5-diazatetracyclo[11.1.1.0[2,6]. 0[7,12]]pentadeca-3,5,7,9,11-pentaene (252 g, 462.45 mmol, 1.00 equiv) in tetrahydrofuran (2000 mL), followed by the addition of EtMgBr (163 mL, 1.05 equiv, 3 M) dropwise with stirring at −40° C. over 30 min. The resulting solution was stirred at −40° C. for 30 min, quenched by the addition of 200 mL of NH$_4$Cl (sat) and extracted with 2×1000 mL of ethyl acetate. The organic layers were combined, washed with 1×1000 mL of water and 1×1000 mL of brine, dried over anhydrous sodium sulfate and concentrated under vacuum to afford 173 g (89%) of 9-bromo-10-fluoro-4-iodo-2,5-diazatetracyclo[11.1.1.0[2,6].0[7,12]]pentadeca-3,5,7,9,11-pentaene as a red solid.

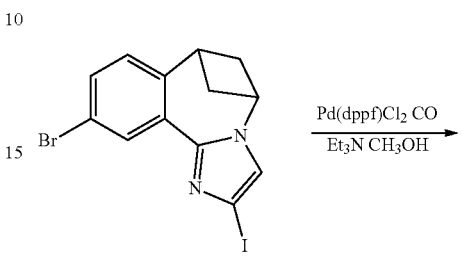

Methyl 9-bromo-2,5-diazatetracyclo[11.1.1.0[2,6].0[7,12]]pentadeca-3,5,7,9,11-pentaene-4-carboxylate Into a 5-L pressure tank reactor (20 atm) was placed methanol (2.5 L), 9-bromo-4-iodo-2,5-diazatetracyclo[11.1.1.0[2,6].0[7,12]]pentadeca-3,5,7,9,11-pentaene (180 g, 448.83 mmol, 1.00 equiv), triethylamine (136.4 g, 1.35 mol, 3.00 equiv), and Pd(dppf)Cl$_2$ (18 g, 24.60 mmol, 0.10 equiv). To the above CO (enough, amount) was introduced in. The resulting solution was stirred overnight at 50° C. To this was added Pd(dppf)Cl$_2$ (7 g). The mixture was stirred at 50° C. for 5 h, cooled to 25° C. and concentrated under vacuum. The resulting solution was diluted with 1 L of H$_2$O and extracted with 2×2 L of dichloromethane. The organic layers were combined, dried over anhydrous sodium sulfated and concentrated under vacuum. The residue was applied onto a silica gel column eluting with dichloromethane:methanol (50:1) to afford 90 g (60%) of methyl 9-bromo-2,5-diazatetracyclo[11.1.1.0[2,6].0[2,12]]pentadeca-3,5,7,9,11-pentaene-4-carboxylate as a gray solid. LC-MS: [M+1]$^+$333 $^1$H-NMR (DMSO, 300 MHz, ppm): ☐ 8.63 (s, 1H), 8.14 (s, 1H), 7.44-7.45 (dd, 1H), 7.25-7.28 (dd, 1H), 4.93-4.99 (m, 1H), 3.79 (s, 3H), 3.68-3.74 (m, 1H), 3.05-3.105 (m, 2H), 1.66-1.70 (m, 2H).

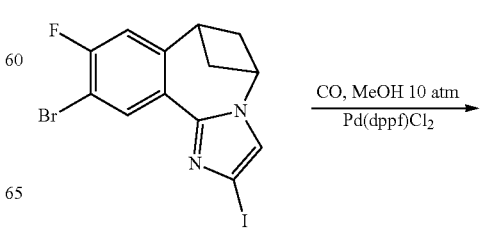

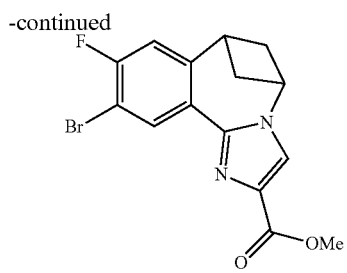

Methyl 9-bromo-10-fluoro-2,5-diazatetracyclo[11.1.1.0[2,6].0[7,12]]pentadeca-3,5,7,9,11-pentaene-4-carboxylate Into a 2000-mL pressure tank reactor (10 atm) was placed a solution of 9-bromo-10-fluoro-4-iodo-2,5-diazatetracyclo[11.1.1.0[2,6].0[7,12]]pentadeca-3,5,7,9,11-pentaene (150 g, 357.97 mmol, 1.00 equiv) in methanol (1200 mL), triethylamine (108.5 g, 1.07 mol, 3.00 equiv), followed by the addition of Pd(dppf)Cl$_2$ (13.1 g, 17.90 mmol, 0.05 equiv). To the above CO (enough, amount) was introduced in. The resulting solution was stirred at 50° C. for 5 h and concentrated under vacuum. The solids were collected by filtration and washed with 1×500 mL of water. The filter cake was dissolved in 1000 mL of hydrogen chloride (6 M) and extracted with 5×500 mL of EA. The pH value of the aqueous layer was adjusted to 10 with sodium hydroxide (3 mol/L). The resulting solution was extracted with 3×1000 mL of dichloromethane. The organic layers were combined, washed with 1×1000 mL of water and 1×1000 mL of brine, dried over anhydrous sodium sulfate and concentrated under vacuum to afford 76.2 g (61%) of methyl 9-bromo-10-fluoro-2,5-diazatetracyclo[11.1.1.0[2,6].0[7,12]]pentadeca-3,5,7,9,11-pentaene-4-carboxylate as a white solid. LC-MS: 351 [M+H]$^+$ $^1$H-NMR (DMSO, 300 MHz, ppm) □ 1.68-1.73 (2H, m), 3.06-3.15 (2H, m), 3.68-3.75 (1H, m), 3.79 (3H, s), 4.93-4.98 (1H, m), 7.39-7.42 (1H, d, J=9.6 Hz), 8.13 (1H, s), 8.69-8.71 (1H, d, J=7.5 Hz).

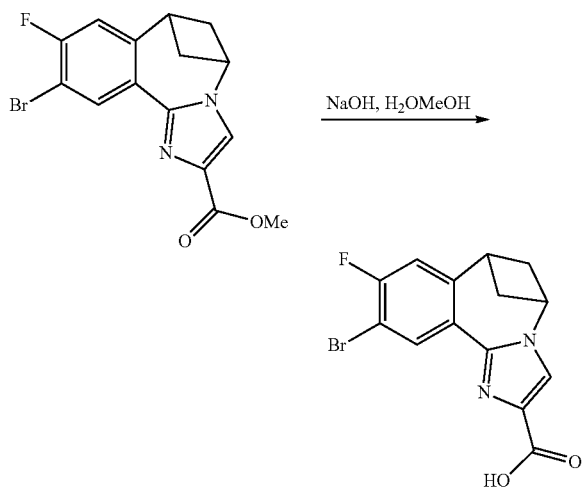

9-bromo-10-fluoro-2,5-diazatetracyclo[11.1.1.0[2,6].0[7,12]]pentadeca-3,5,7,9,11-pentaene-4-carboxylic acid Into a 5000-mL 4-necked round-bottom flask was placed a solution of methyl 9-bromo-10-fluoro-2,5-diazatetracyclo[11.1.1.0[2,6].0[7,12]]pentadeca-3,5,7,9,11-pentaene-4-carboxylate (110 g, 313.24 mmol, 1.00 equiv) in methanol/NaOH (40%) (1000 mL). The resulting solution was heated to reflux for 1.5 hours and concentrated under vacuum. Hydrogen chloride (2 mol/L) was used to adjust the pH to 4. The precipitates were collected by filtration, washed with 1×1000 mL of water and dried to afford 91 g (86%) of 9-bromo-10-fluoro-2,5-diazatetracyclo[11.1.1.0[2,6].0[7,12]]pentadeca-3,5,7,9,11-pentaene-4-carboxylic acid as a white solid.

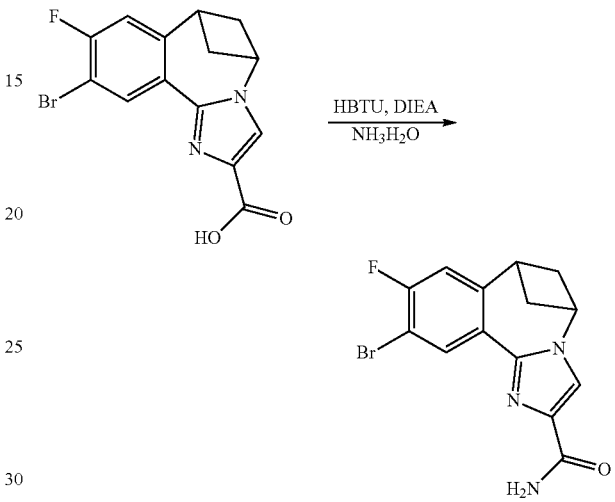

9-Bromo-10-fluoro-2,5-diazatetracyclo[11.1.1.0[2,6].0[7,12]]pentadeca-3,5,7,9,11-pentaene-4-carboxamide Into a 5000-mL 4-necked round-bottom flask was placed a solution of 9-bromo-10-fluoro-2,5-diazatetracyclo[11.1.1.0[2,6].0[7,12]]pentadeca-3,5,7,9,11-pentaene-4-carboxylic acid (280 g, 830.51 mmol, 1.00 equiv) in N,N-dimethylformamide (2500 mL), HBTU (315 g, 830.61 mmol, 1.00 equiv), and DIEA (139 g, 1.08 mol, 1.30 equiv). The resulting solution was stirred at room temperature for 1.5 h. This was followed by the addition of amine hydrate (300 mL). The resulting solution was stirred at room temperature for 0.5 h and diluted with 2000 mL of H2O. The solids were collected by filtration, washed with 3×1000 mL of water and dried to afford 150.6 g (54%) of 9-bromo-10-fluoro-2,5-diazatetracyclo[11.1.1.0[2,6].0[7,12]]pentadeca-3,5,7,9,11-pentaene-4-carboxamide as a white solid. LC-MS: [M+H]$^+$336 $^1$H-NMR (DMSO, 300 MHz, ppm) □ 1.66-1.70 (2H, m), 3.08-3.12 (2H, m), 3.70-3.71 (1H, m), 4.88-4.94 (1H, m), 7.14 (1H, s), 7.36-7.39 (1H, m), 7.60 (1H, s), 7.83 (1H, s), 8.84-8.86 (1H, m).

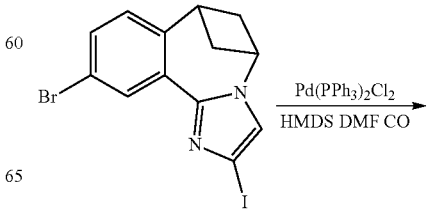

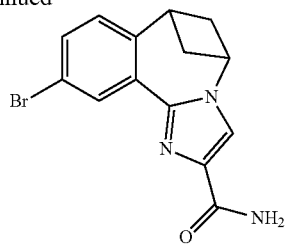

9-Bromo-2,5-diazatetracyclo[11.1.1.0[2,6].0[7,12]]pentadeca-3,5,7,9,11-pentaene-4-carboxamide Into a 2-L 4-necked round-bottom flask purged and maintained with an inert atmosphere of nitrogen was placed 9-bromo-4-iodo-2,5-diazatetracyclo[11.1.1.0[2,6].0[7,12]]pentadeca-3,5,7,9,11-pentaene (65 g, 162.08 mmol, 1.00 equiv), N,N-dimethylformamide (1.2 L), HMDS (208 g, 1.29 mol, 8.00 equiv), and Pd(PPh$_3$)$_2$Cl (9.1 g, 0.08 equiv). To the above CO (2 atm) was introduced in. The resulting solution was stirred at 60° C. for 2 h. This reaction was repeated for 3 more times. The reaction mixture was cooled to 40° C. and quenched by the addition of 1500 mL of water. The solids were collected by filtration and washed with 3×500 mL of water. The solids were diluted with 2 L of EA and stirred at room temperature for 1 h. The solids were collected by filtration. The filter cake was diluted with 2 L of EA and stirred at 50° C. for 1 h. The solids were collected by filtration and dried to afford 172 g (83%) of 9-bromo-2,5-diazatetracyclo [11.1.1.0[2,6].0[7,12]]pentadeca-3,5,7,9,11-pentaene-4-carboxamide as a brown solid. LC-MS: 318 [M+1]$^{+1}$H-NMR (DMSO, 300 MHz, ppm): ☐ 18.75 (s, 1H), 7.85 (s, 1H), 7.58 (s, 1H), 7.44-4.44 (dd, 1H), 7.23-7.25 (dd, 1H), 7.14 (s, 1H), 4.89-4.95 (m, 1H), 3.67-3.73 (m, 1H), 3.04-3.12 (m, 2H), 1.64-1.68 (m, 2H).

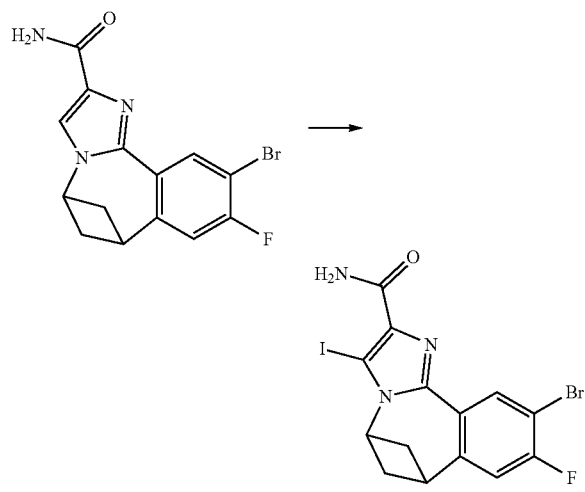

10-Fluoro-9-bromo-3-iodo-2,5-diazatetracyclo [11.1.1.0[2,6].0[7,12]]pentadeca-3,5,7(12),8,10-pentaene-4-carboxamide 9-bromo-10-fluoro-2,5-diazatetracyclo[11.1.1.0[2,6].0[7,12]]pentadeca-3,5,7,9,11-pentaene-4-carboxamide (20.00 g, 59.5 mmol) and N-iodosuccinimide (2.00 equiv., 27.60 g, 119 mmol) were dissolved in DMF (300 mL, 5 mL/mmol) and stirred at 70° C. overnight. After 24 hours, the solution was concentrated in vacuo and diluted with water, then triturated for 1 hour and filtered. The solid was redissolved in ethyl acetate, triturated for 1 hour, and filtered to afford 23.93 g (87% yield) of the titled compound as a light orange solid, $^1$H NMR (400 MHz, DMSO) δ 8.92 (d, J=7.4 Hz, 1H), 7.74 (br s, 1H), 7.37 (d, J=9.5 Hz, 1H), 7.16 (br s, 1H), 5.12 (td, J=6.7, 4.1 Hz, 1H), 3.68 (td, J=7.6, 4.1 Hz, 1H), 3.25-3.11 (m, 2H), 1.78-1.64 (m, 2H).

9-Bromo-4-oxo-4,5-dihydro-6-oxa-3-thia-1-aza-benzo[e]azulene-2-carboxylic acid methyl ester

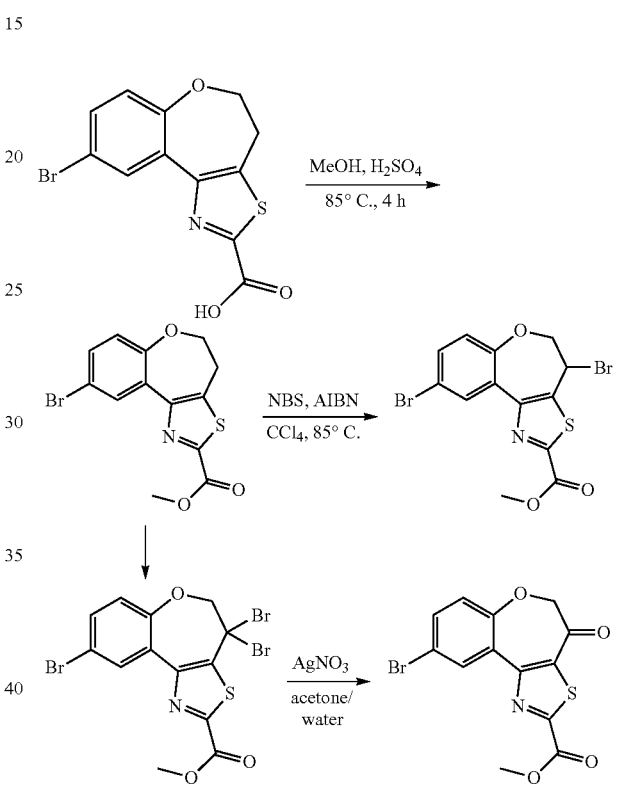

To a stirred mixture of 9-Bromo-4,5-dihydro-6-oxa-3-thia-1-aza-benzo[e]azulene-2-carboxylic acid (20.0 g, 61.3 mmol) in MeOH (280 mL), was added H$_2$SO$_4$ (45.1 g, 450 mmol) dropwise at room temperature. Then the mixture was heated to reflux (85° C.) mixture was filtered and the solid was washed with saturated aqueous NaHCO$_3$ solution, dried in vacuo to afford 9-Bromo-4,5-dihydro-6-oxa-3-thia-1-aza-benzo[e]azulene-2-carboxylic acid methyl ester (12 g, 57%) as a yellow solid which was directly used for the next step without any further purification. LC-MS: 341.8 (M+2).

To a stirred mixture of 9-Bromo-4,5-dihydro-6-oxa-3-thia-1-aza-benzo[e]azulene-2-carboxylic acid methyl ester (5 g, 14.70 mmol) in CCl$_4$ (100 mL) was added AIBN (0.24 g, 1.46 mmol) and NBS (2.88 g, 16.18 mmol). The mixture was heated to reflux overnight. Then the mixture was partitioned between EtOAc and H$_2$O. The aqueous layer was extracted with EtOAc (2×100 mL). The combined organic layers were washed with brine, dried over Na$_2$SO$_4$, filtered, concentrated in vacuo, and purified by flash column chromatography to afford 4,9-Dibromo-4,5-dihydro-6-oxa-3-thia-1-aza-benzo[e]azulene-2-carboxylic acid methyl ester (5.8 g, 94%) as a light yellow solid; LC-MS: 422.3 (M+3). $^1$H NMR (400 MHz, DMSO-d$_6$): δ 8.40 (d, J=2.4 Hz, 1H), 7.53 (dd, J$_1$=8.6 Hz, J$_2$=2.44 Hz, 1H), 7.10 (d, J=8.64 Hz, 1H), 6.34 (d, J=1.8 Hz, 1H), 4.57 (m, 2H), 3.93 (s, 3H)

To a stirred mixture of 9-Bromo-4,5-dihydro-6-oxa-3-thia-1-aza-benzo[e]azulene-2-carboxylic acid methyl ester (9.6 g 28.22 mmol) in CCl$_4$ (500 mL) was added AIBN (3.70 g, 22.53 mmol) and NBS (25.0 g, 140.4 mmol). The mixture was heated to reflux overnight. Then the mixture was partitioned between EtOAc and H$_2$O. The aqueous layer was extracted with EtOAc (2×300 mL). The combined organic layers were washed with brine, dried over Na$_2$SO$_4$, filtered, concentrated in vacuo, and purified by flash column chromatography to afford 4,4,9-Tribromo-4,5-dihydro-6-oxa-3-thia-1-aza-benzo[e]azulene-2-carboxylic acid methyl ester (9 g, 64%) as a light yellow solid. LC-MS: 500.3 (M+2). $^1$H NMR (400 MHz, CDCl$_3$): δ 8.59 (d, J=2.48 Hz, 1H), 7.45 (dd, J=8.6 Hz, J$_2$=2.48 Hz, 1H), 7.01 (d, J=8.64 Hz, 1H), 4.72 (s, 2H), 4.05 (s, 3H).

The mixture of 4,4,9-Tribromo-4,5-dihydro-6-oxa-3-thia-1-aza-benzo[e]azulene-2-carboxylic acid methyl ester (9.0 g, 18.07 mmol) in acetone (250 mL) and water (250 mL) was stirred at room temperature for 4 h. Then the mixture was partitioned between EtOAc and H$_2$O. The aqueous layer was extracted with EtOAc (2×200 mL). The combined organic layers were washed with brine, dried over Na$_2$SO$_4$, concentrated to afford the crude product which was triturated with EtOAc and hexane (EtOAc/hexane=1/5). After filtration, the solid was dried in vacuo to afford compound 9-Bromo-4-oxo-4,5-dihydro-6-oxa-3-thia-1-aza-benzo[e]azulene-2-carboxylic acid methyl ester (5.5 g, 86%) as a light yellow solid.

Example 14

Synthesis of (±)-Ethyl 3-ethynyl-3-hydroxycyclobutane-1-carboxylate

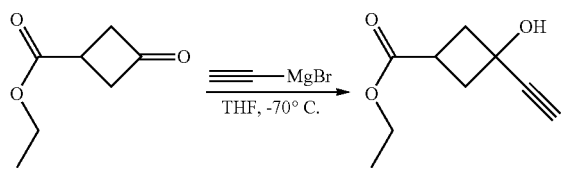

This compound was prepared according to a procedure similar to that described in Procedure A. To a 100-mL 3-necked round-bottom flask purged and maintained with an inert atmosphere of nitrogen, was placed bromo(ethynyl)magnesium (0.5M in THF, 50 mL, 1.20 equiv). This was followed by the addition of a solution of ethyl 3-oxocyclobutane-1-carboxylate (3.0 g, 21.10 mmol, 1.00 equiv) in tetrahydrofuran (3 mL) dropwise with stirring at −70° C. in 15 min. The resulting solution was stirred for 30 min at −70° C. The reaction was then quenched by the addition of 10 mL of sat. aq. ammonium chloride. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:10). This resulted in 2.6 g (66%) of ethyl 3-ethynyl-3-hydroxycyclobutane-1-carboxylate as light yellow oil (single undetermined diastereomer).

Example 15

Synthesis of 3-Ethynyl-3-hydroxy-pyrrolidine-1-carboxylic acid tert-butyl ester

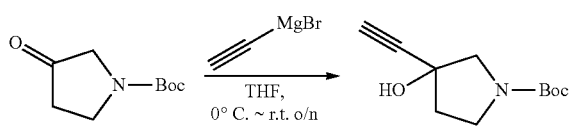

This compound was prepared according to a procedure similar to that described in Procedure A. In a solution of 3-Oxo-pyrrolidine-1-carboxylic acid tert-butyl ester (3.0 g, 16.2 mmol) in tetrahydrofuran (40 mL) was dropped in ethynyl magnesium bromide (70 mL, 35 mmol) at −78° C. Then the solution was stirred overnight at room temperature. Then the reaction mixture was quenched with saturated NH$_4$Cl and extracted with dichloromethane, dried with anhydrous sodium sulfate to afford 3-Ethynyl-3-hydroxy-pyrrolidine-1-carboxylic acid tert-butyl ester (1.5 g, 44%).

Example 16

Synthesis of (±)-2-Methylbut-3-yne-1,2-diol

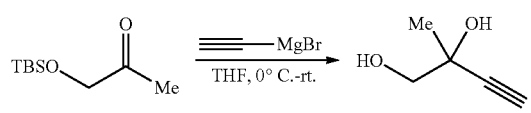

This compound was prepared according to a procedure similar to that described in Procedure A. Into a 100-mL 3-necked round-bottom flask purged and maintained with an inert atmosphere of nitrogen, was placed bromo(ethynyl)magnesium (54 mL, 1.20 equiv). This was followed by the addition of 1-[(tert-butyldiphenylsilyl)oxy]propan-2-one (7.0 g, 69.89 mmol, 1.00 equiv, 312%) dropwise with stirring at 0° C. The resulting solution was stirred for 12 h at room temperature. The reaction was then quenched by the addition of 10 mL of saturated aqueous ammonium chloride. The resulting solution was diluted with 20 mL of water. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (1:1). This resulted in 0.24 g (3%) of 2-methylbut-3-yne-1,2-diol as yellow oil.

Example 17

Synthesis of (±)-1-Fluoro-2-methylbut-3-yn-2-ol

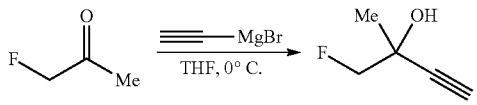

This compound was prepared according to a procedure similar to that described in Procedure A. Into a 50-mL 3-necked round-bottom flask purged and maintained with an inert atmosphere of nitrogen, was placed a solution of bromo(ethynyl)magnesium (0.5M in THF, 16 mL, 1.20 equiv). This was followed by the addition of 1-fluoropropan-2-one (500 mg, 6.24 mmol, 1.00 equiv) dropwise with stirring at 0° C. The resulting solution was stirred for 1 h at 0° C. The reaction was then quenched by the addition of 20 mL of sat. aq. NH4Cl. The resulting solution was extracted with 3×30 mL of ether and the organic layers combined and dried over anhydrous sodium sulfate and concentrated under vacuum. This resulted in 0.7 g (55%) of 1-fluoro-2-methylbut-3-yn-2-ol as light yellow oil.

Example 18

Synthesis of (±)-1,1,1-trifluoro-2-methylbut-3-yn-2-ol

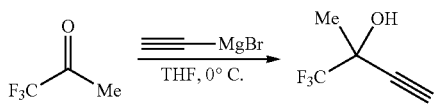

This compound was prepared according to a procedure similar to that described in Procedure A. In a 250-mL 3-necked round-bottom flask purged and maintained with an inert atmosphere of nitrogen, 1,1,1-trifluoropropan-2-one (5.6 g, 49.98 mmol, 1.00 equiv) was added into a solution of bromo(ethynyl)magnesium (0.5M in THF, 150 mL, 1.50 equiv) with stirring at 0° C. The resulting solution was stirred for 15 min at 0° C. Then the solution was warmed to room temperature and stirred for 4 h. The reaction was then quenched by the addition of 10 mL of sat. aq. NH4Cl. The resulting solution was extracted with 2×100 mL of ether and the organic layers combined and dried over anhydrous sodium sulfate and concentrated under vacuum. This resulted in 5.0 g (36%) of 1,1,1-trifluoro-2-methylbut-3-yn-2-ol as colorless oil.

Example 19

Synthesis of (±)-2-(1-Methyl-1H-imidazol-2-yl)but-3-yn-2-ol

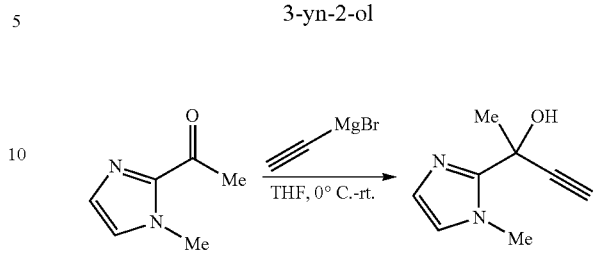

Into a 250-mL 3-necked round-bottom flask purged and maintained with an inert atmosphere of nitrogen, was placed bromo(ethynyl)magnesium (0.5M in THF, 77 mL, 1.20 equiv). This was followed by the addition of a solution of 1-(1-methyl-1H-imidazol-2-yl)ethan-1-one (4.0 g, 32.22 mmol, 1.00 equiv) in tetrahydrofuran (15 mL) dropwise with stirring at 0° C. in 20 min. The resulting solution was stirred for 20 min at 0° C. The resulting solution was allowed to react with stirring for an additional 5 h at room temperature. The reaction was then quenched by the addition of 50 mL of saturated aqueous NH4Cl. The resulting solution was extracted with 3×100 mL of ethyl acetate and the organic layers combined and dried over anhydrous sodium sulfate and concentrated under vacuum. The residue was applied onto a silica gel column with ethyl acetate/hexane (1/3) to give 2.8 g (58%) of 2-(1-methyl-1H-imidazol-2-yl)but-3-yn-2-ol as a off-white solid. $^1$H-NMR (300 MHz, CDCl$_3$, ppm) δ 7.065 (d, 1H), 6.842 (d, 1H), 3.935 (d, 3H), 3.092 (s, 3H), 1.950 (s, 3H).

Example 20

Synthesis of (±)-2-(1H-1,2,4-triazol-3-yl)but-3-yn-2-ol

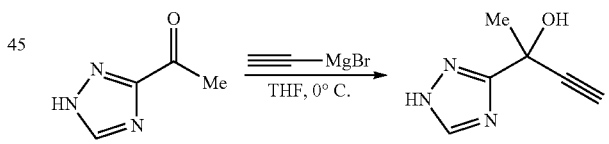

This compound was prepared according to a procedure similar to that described in Procedure A. Into a 100-mL 3-necked round-bottom flask purged and maintained with an inert atmosphere of nitrogen, was placed ethynylmagnesium bromide (45 mL, 2.50 equiv). This was followed by the addition of a solution of 1-(1H-1,2,4-triazol-3-yl)ethan-1-one (1000 mg, 9.00 mmol, 1.00 equiv) in THF (2 mL) dropwise with stirring at 0° C. The resulting solution was stirred for 10 min at 0° C. The resulting solution was allowed to react with stiffing for an additional 6 h at room temperature. The reaction was then quenched by the addition of 10 mL of sat. aq. NH4Cl. The resulting solution was extracted with 2×50 mL of ethyl acetate and the organic layers combined and dried over anhydrous sodium sulfate. The residue was applied onto a silica gel column with petroleum ether:ethyl acetate (1:1). This resulted in 0.4 g (32%) of 2-(1H-1,2,4-triazol-3-yl)but-3-yn-2-ol as a white solid.

Example 21

Synthesis of (±)-2-(Pyridin-2-yl)but-3-yn-2-ol

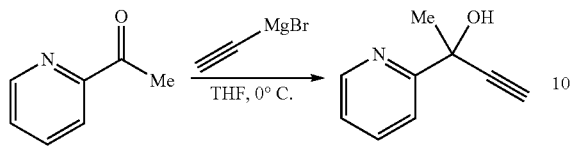

This compound was prepared according to a procedure similar to that described in Procedure A. Into a 500-mL 3-necked round-bottom flask purged and maintained with an inert atmosphere of nitrogen, was placed a solution of 1-(pyridin-2-yl)ethan-1-one (6.0 g, 49.53 mmol, 1.00 equiv) in tetrahydrofuran (20 mL). This was followed by the addition of bromo(ethynyl)magnesium (0.5 M in THF, 250 mL, 2.50 equiv) dropwise with stirring at 0° C. The resulting solution was stirred for 30 min at 0° C. The resulting solution was allowed to react, with stirring, for an additional 18 h at room temperature. The reaction was then quenched by the addition of 50 mL of saturated aqueous NH4Cl. The resulting solution was diluted with 100 mL of water. The resulting solution was extracted with 3×200 mL of ethyl acetate and the organic layers combined and dried over anhydrous sodium sulfate and concentrated under vacuum. The residue was applied onto a silica gel column with ethyl acetate/hexane (1/10). This resulted in 0.8 g (11%) of 2-(pyridin-2-yl)but-3-yn-2-ol as a off-white solid. $^1$H-NMR (300 MHz, CDCl$_3$, ppm) δ: 8.534 (d, 1H), 7.800-7.744 (t, 1H), 7.620 (d, 1H), 7.295-7.263 (m, 1H), 5.481-5.300 (br s, 1H), 2.546 (s, 1H), 1.797 (s, 3H).

Example 22

Synthesis of (±)-1-(Azetidin-1-yl)-2-hydroxy-2-methylbut-3-yn-1-one

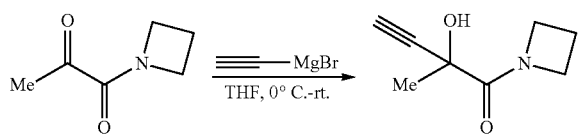

This compound was prepared according to a procedure similar to that described in Procedure A. Into a 100-mL round-bottom flask purged and maintained with an inert atmosphere of nitrogen, was placed a solution of bromo(ethynyl)magnesium (0.5M in THF, 38 mL, 1.20 equiv). This was followed by the addition of a solution of 1-(azetidin-1-yl)propane-1,2-dione (2 g, 15.73 mmol, 1.00 equiv) in tetrahydrofuran (10 mL) dropwise with stirring at 0° C. The resulting solution was warmed to room temperature and stirred for 3 h at this temperature. The reaction mixture was cooled with a water/ice bath. Then quenched by the addition of 150 mL of sat. aq. NH$_4$Cl. Extracted with 3×100 mL of ethyl acetate and the organic layers combined and dried over anhydrous sodium sulfate and concentrated under vacuum. The residue was applied onto a silica gel column with ethyl acetate/petroleum ether (1:3). This resulted in 1 g (38%) of 1-(azetidin-1-yl)-2-hydroxy-2-methylbut-3-yn-1-one as brown oil.

Example 23

Synthesis of (±)-2-Hydroxy-N,N,2-trimethylbut-3-ynamide

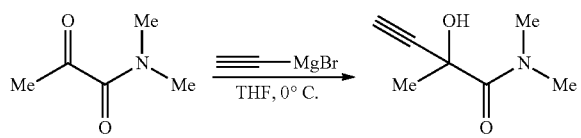

This compound was prepared according to a procedure similar to that described in Procedure A. Into a 100-mL 3-necked round-bottom flask purged and maintained with an inert atmosphere of nitrogen, was placed bromo(ethynyl)magnesium (0.5 M in THF, 41.7 mL, 1.20 equiv). This was followed by the addition of a solution of N,N-dimethyl-2-oxopropanamide (2 mg, 0.02 mmol, 1.00 equiv) in tetrahydrofuran (10 mL) dropwise with stirring at 0° C. The resulting solution was warmed to room temperature and stirred for 120 min. The reaction mixture was cooled with a water/ice bath. The reaction was then quenched by the addition of 100 mL of sat. aq. NH$_4$Cl. The resulting solution was extracted with 3×100 mL of ethyl acetate and the organic layers combined and dried over anhydrous sodium sulfate, filtered and concentrated under vacuum. The residue was applied onto a silica gel column with ethyl acetate/petroleum ether (1/5). This resulted in 1 g (37%) of 2-hydroxy-N,N,2-trimethylbut-3-ynamide as yellow oil.

$^1$H-NMR: (300 MHz, CDCl$_3$, ppm) δ 5.235 (s, 1H), 3.306 (s, 3H), 3.074 (s, 3H), 2.639 (s, 1H), 1.674 (s, 3H).

Example 24

Synthesis of (±)-2-(1-Methylcyclopropyl)but-3-yn-2-ol

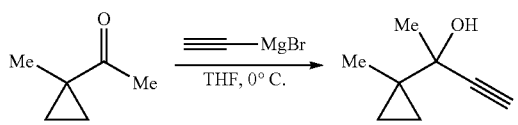

This compound was prepared according to a procedure similar to that described in Procedure A. In a 100-mL 3-necked round-bottom flask, a solution of 1-(1-methylcyclopropyl)ethan-1-one (2 g, 20.38 mmol, 1.00 equiv) in tetrahydrofuran (5 mL) was added into a solution of bromo(ethynyl)magnesium (0.5 M in THF, 53 mL, 1.30 equiv) in tetrahydrofuran (5 mL). The resulting solution was stirred for 8 h at 0° C. in an ice/salt bath. The reaction was then quenched by the addition of 50 mL of sat. aq. NH$_4$Cl. The resulting solution was extracted with 3×150 mL of ethyl acetate and the organic layers combined. The resulting mixture was washed with 3×150 mL of brine. The mixture was dried over anhy-

Example 25

Synthesis of (±)-3-Ethynyl-3-hydroxycyclobutyl benzoate

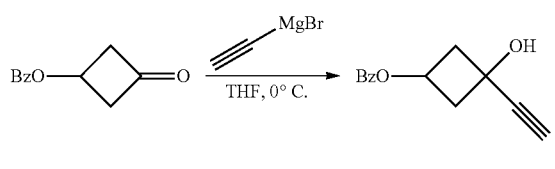

This compound was prepared according to a procedure similar to that described in Procedure A. Into a 25-mL three neck-round bottle flask, was placed a solution of 3-oxocyclobutyl benzoate (380 mg, 2.0 mmol, 1.00 equiv) in tetrahydrofuran (10 mL). Ethynylmagnesium bromide (0.5 M in tetrahydrofuran, 6 mL) was added dropwise, then resulting solution was stirred for 30 min at −76° C. When the mixture was warmed to room temperature in air, quenched by addition of saturated aqueous ammonium chloride (5 mL), the organic layer was washed by brine (10 mL), dried and concentrated under vacuum. The residue was applied onto a silica gel column with ethyl acetate/petroleum ether (1:6). This resulted in 300 mg (69%) of 3-ethynyl-3-hydroxycyclobutyl benzoate as a white solid. $^1$H-NMR: (300 MHz, CDCl$_3$, ppm) δ 8.100-8.000 (m, 1H), 7.610-7.500 (t, 1H), 7.499-7.380 (m, 2H), 5.160-5.040 (m, 1H), 3.150-3.010 (m, 2H), 2.610-2.470 (m, 3H).

Example 26

Synthesis of (±)-2-(3-Methylpyridin-2-yl)but-3-yn-2-ol

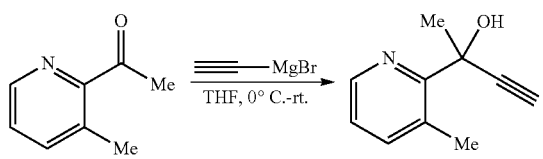

This compound was prepared according to a procedure similar to that described in Procedure A. 1-(3-Methylpyridin-2-yl)ethan-1-one. (3.2 g, 23.68 mmol, 1.00 equiv) was dissolved in 6 mL of THF under inert nitrogen atmosphere in a 100-mL 3-necked round-bottom flask. Then ethynylmagnesium bromide (2M in THF, 61 mL, 1.30 equiv) was added dropwise into the solution at 0° C. The resulting solution was stirred for 10 min and then allowed to rise to room temperature and stirred for additional 2 h. The reaction was then quenched by the addition of 20 mL of sat. aqueous NH$_4$Cl and the resulting solution was extracted with 2×25 mL of ethyl acetate. The organic layers were combined, dried over anhydrous sodium sulfate and concentrated under vacuum. This resulted in 120 mg (5%) of 2-(1-methylcyclopropyl)but-3-yn-2-ol as colorless oil.

drous sodium sulfate and concentrated under vacuum to get a residue, which was applied onto a silica gel column with ethyl acetate/petroleum ether (1:5) to obtain 3.5 g (88%) of 2-(3-methylpyridin-2-yl)but-3-yn-2-ol as a light yellow solid.

Example 27

Synthesis of tert-butyl 3-ethynyl-3-hydroxy-8-azabicyclo[3.2.1]octane-8-carboxylate

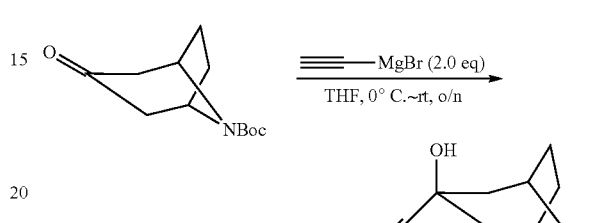

This compound was prepared according to a procedure similar to that described in Procedure A. In a solution of 3-Oxo-8-aza-bicyclo[3.2.1]octane-8-carboxylic acid tert-butyl ester (2.25 g, 10 mmol) in tetrahydrofuran (20 mL) was dropped in ethynyl magnesium bromide (60 mL, 30 mmol) at −0° C. Then the solution was stirred overnight at room temperature. Then the reaction mixture was quenched with saturated NH$_4$Cl and extracted with dichloromethane, dried with anhydrous sodium sulfate to afford 3-Ethynyl-3-hydroxy-8-aza-bicyclo[3.2.1]octane-8-carboxylic acid tert-butyl ester (0.8 g, 32%). $^1$H NMR: (DMSO-d$_6$, 400 MHz) δ 5.43 (s, 1H), 3.98 (s, 2H), 3.24 (s, 1H), 2.08-1.91 (m, 8H), 1.37 (s, 9H).

Example 28

Synthesis of 3-Ethynyl-3-hydroxy-pyrrolidine-1-carboxylic acid tert-butyl ester

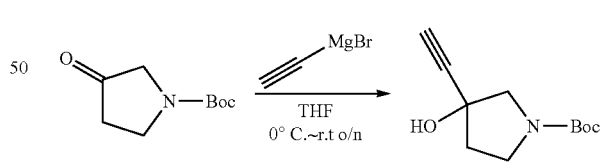

This compound was prepared according to a procedure similar to that described in Procedure A. In a solution of 3-Oxo-pyrrolidine-1-carboxylic acid tert-butyl ester (3.0 g, 16.2 mmol) in tetrahydrofuran (40 mL) was dropped in ethynyl magnesium bromide (70 mL, 35 mmol) at −78° C. Then the solution was stirred overnight at room temperature. Then the reaction mixture was quenched with saturated NH4Cl and extracted with dichloromethane, dried with anhydrous sodium sulfate to afford 3-Ethynyl-3-hydroxy-pyrrolidine-1-carboxylic acid tert-butyl ester (1.5 g, 44%).

Example 29

Synthesis of tert-butyl 3-ethynyl-3-hydroxy-8-azabicyclo[3.2.1]octane-8-carboxylate

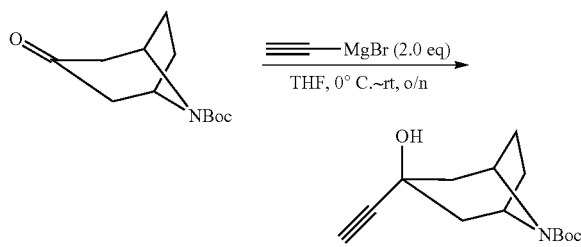

This compound was prepared according to a procedure similar to that described in Procedure A. I In a solution of 3-Oxo-8-aza-bicyclo[3.2.1]octane-8-carboxylic acid tert-butyl ester (2.25 g, 10 mmol) in tetrahydrofuran (20 mL) was dropped in ethynyl magnesium bromide (60 mL, 30 mmol) at ~0° C. Then the solution was stirred overnight at room temperature. Then the reaction mixture was quenched with saturated NH$_4$Cl and extracted with dichloromethane, dried with anhydrous sodium sulfate to afford 3-Ethynyl-3-hydroxy-8-aza-bicyclo[3.2.1]octane-8-carboxylic acid tert-butyl ester (0.8 g, 32%). $^1$H NMR: (DMSO-d$_6$, 400 MHz) δ 5.43 (s, 1H), 3.98 (s, 2H), 3.24 (s, 1H), 2.08-1.91 (m, 8H), 1.37 (s, 9H).

Example 30

Synthesis of 7-ethynyl-6,7-dihydro-5H-cyclopenta[b]pyridin-7-ol

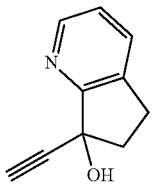

This compound was prepared according to a procedure similar to that described in Procedure B. To a solution of 2.5 M n-butyllithium in hexanes (3.91 ml) in THF (3 ml) at -78° C. was added dropwise ethynyl(trimethyl)silane (1.28 ml, 9.01 mmol). The reaction was stirred at -78° C. for 10 min before addition of a solution of 5,6-dihydro-7H-cyclopenta[b]pyridin-7-one (1 g, 7.51 mmol) in THF (7 ml). The reaction mixture was stirred and allowed to warm up to RT for 3 hr. The mixture was then diluted with water and the volatiles removed. The product was extracted with CHCl$_3$:IPA (2:1 ratio, 2×25 ml). The organic phase was washed with water (20 mL) followed by brine (20 mL); dried over (Na$_2$SO$_4$), and the solvent removed in vacuo. Purification by column chromatography (25 g Isolute column, 100% DCM to 5% MeOH in DCM) followed by the second column chromatography (30% EtOAc-heptane) gave the title compound: $^1$H NMR (500 MHz, CDCl$_3$) δ 2.49 (1H, ddd, J=13.44, 8.24, 6.07 Hz), 2.63-2.76 (2H, m), 2.90-3.02 (1H, m), 3.03-3.13 (1H, m), 3.42 (1H, s), 7.22 (1H, dd, J=7.57, 4.89 Hz), 7.62 (1H, d, J=7.57 Hz), 8.51 (1H, d, J=4.73 Hz); LC-MS: 459.95 (M+H)$^+$.

Example 31

Synthesis of fluoro-2-methyl-4-triethylsilyl-but-3-yn-2-ol

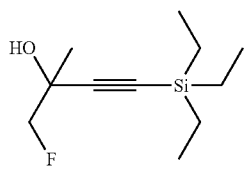

This compound was prepared according to a procedure similar to that described in Procedure B. A stirred solution of triethyl(ethynyl)silane (1.05 eq, 5.4 mL) in THF. at -78° C. was treated with n-BuLi (2.5 mol/L in hexanes, 1.1 eq) dropwise. The reaction was stirred for 15 minutes before addition of 1-fluoropropan-2-one (2.1 mL) then stirred for another hour at -78° C. whereupon it was slowly warmed to room temperature. The reaction was quenched with a saturated ammonium chloride solution then extracted with ethyl acetate. The organic layer was dried with magnesium sulfate, filtered and concentrated to give a clear oil. This crude intermediate was purified by ISCO with ELSD option (0-100% Heptane: Ethyl acetate over 25 minutes) to afford 1-fluoro-2-methyl-4-triethylsilyl-but-3-yn-2-ol. $^1$H NMR (400 MHz, MeOD) δ 4.81 (s, 1H), 4.36-4.27 (m, 1H), 4.24-4.14 (m, 1H), 1.45 (d, J=1.8 Hz, 3H), 1.06-0.97 (m, 9H), 0.65-0.55 (m, 6H).

Example 32

Synthesis of 3-ethynyl-1-methylpyrrolidin-3-ol

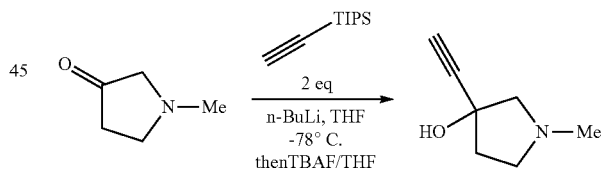

This compound was prepared according to a procedure similar to that described in Procedure B. Into a solution of Ethynyl-triisopropyl-silane (1.1 g, 6 mmol) in tetrahydrofuran (10 mL) was dropped in n-BuLi (2.4 mL, 6 mmol) at -78° C. The solution was stirred for 0.5 h. Then 1-Methyl-pyrrolidin-3-one (0.5 g, 5 mmol) was added. The solution was allowed to warm up to room temperature and stirred for 3 h. Then the reaction mixture was added in 50 mL EtOAc and washed with water three times. The solvent was removed under vacuum to afford 1-Methyl-3-[(triisopropylsilanyl)-ethynyl]-pyrrolidin-3-ol (0.55 g, 39%). $^1$H NMR (DMSO-d$_6$, 400 MHz): δ 5.53 (s, 1H), 2.74-2.63 (m, 2H), 2.46-2.44 (m, 1H), 2.23 (s, 3H), 2.13-1.96 (m, 2H), 1.07-0.97 (m, 21H). A solution of 1-Methyl-3-[(triisopropylsilanyl)-ethynyl]-pyrrolidin-3-ol (1.0 g, 3.6 mmol) in tetrahydrofuran (10 mL) was treated with Tetrabutyl-ammonium fluoride (0.94 g, 3.6 mmol). The solution was stirred overnight at room temperature. Then the reaction mixture was purified by column (eluent: $CH_2Cl_2$: MeOH=10:1) to afford 3-Ethynyl-1-methyl-pyrrolidin-3-ol (0.26 g, 58%). $^1H$ NMR (DMSO-$d_6$, 400 MHz): δ 5.55 (s, 1H), 3.31 (s, 1H), 2.74-2.56 (m, 3H), 2.49-2.46 (m, 1H), 2.22 (s, 3H), 2.11-1.91 (m, 2H).

Example 33

Synthesis of (±)-2-(4-methylpyridin-2-yl)but-3-yn-2-ol

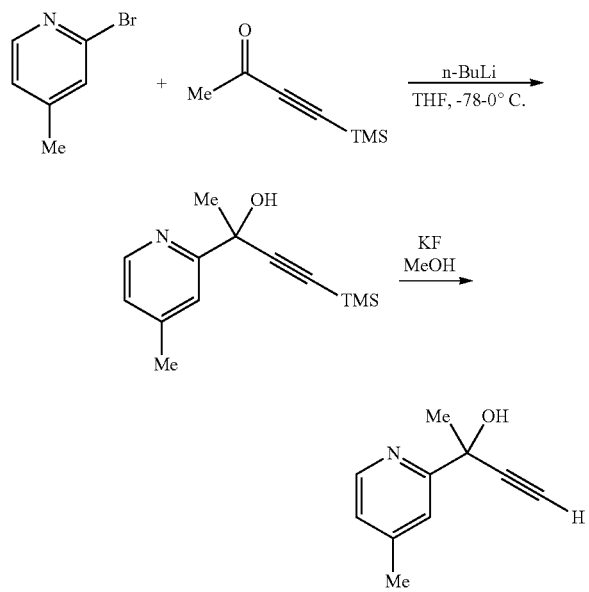

This compound was prepared according to a procedure similar to that described in Procedure C. Into a 250-mL 3-necked round-bottom flask purged and maintained with an inert atmosphere of nitrogen, was placed a solution of 2-bromo-4-methylpyridine (8.5 g, 49.41 mmol, 1.00 equiv) in tetrahydrofuran (110 mL). This was followed by the addition of n-BuLi (22 mL, 1.20 equiv) dropwise with stirring at −78° C. The resulting solution was stirred for 30 min at −78° C. To this was added 4-(trimethylsilyl)but-3-yn-2-one (7.6 g, 54.19 mmol, 1.10 equiv) dropwise with stirring at −78° C. The resulting solution was warmed slowly to 0° C. and stirred for 10 min at this temperature. The reaction was then quenched by the addition of 10 mL of sat. aq. ammonium chloride. The resulting solution was extracted with 2×40 mL of ethyl acetate and the organic layers combined and dried over sodium sulfate and concentrated under vacuum. The residue was applied onto a silica gel column with petroleum ether: ethyl acetate (5:1). This resulted in 6.5 g (56%) of 2-(4-methylpyridin-2-yl)-4-(trimethylsilyl)but-3-yn-2-ol as colourless oil. Into a 250-mL round-bottom flask, was placed a suspension of 2-(4-methylpyridin-2-yl)-4-(trimethylsilyl)but-3-yn-2-ol (6.5 g, 27.85 mmol, 1.00 equiv) and potassium fluoride dihydrate (6.6 g, 2.50 equiv) in methanol (50 mL). The resulting solution was stirred for 4 h at 50° C. The resulting mixture was concentrated under vacuum. The resulting solution was diluted with 100 mL of ethyl acetate. The resulting mixture was washed with 2×50 mL of brine. The mixture was dried over anhydrous sodium sulfate and concentrated under vacuum. The residue was applied onto a silica gel column with ethyl acetate/petroleum ether (1:5). This resulted in 3.5 g (78%) of 2-(4-methylpyridin-2-yl)but-3-yn-2-ol as a pink solid.

Example 34

Synthesis of (±)-2-(5-chloropyridin-2-yl)but-3-yn-2-ol

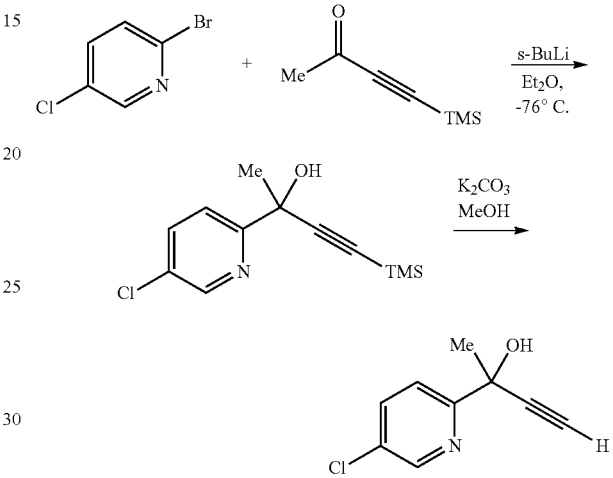

This compound was prepared according to a procedure similar to that described in Procedure C. to a 100-mL 3-necked round-bottom flask, s-BuLi (1.3M in hexane, 10 mL) was added into a solution of 2-bromo-5-chloropyridine (1.92 g, 9.98 mmol, 1.00 equiv) in ethyl ether (20 mL) under −76° C., Stirred for 1 h at this temp., 4-(trimethylsilyl)but-3-yn-2-one (1.54 g, 10.98 mmol, 1.10 equiv) was added. The resulting solution was stirred for 2 h at −76° C. The reaction was then quenched by the addition of 10 mL of ammonium chloride (sat., aq.). The resulting solution was extracted with 3×20 mL of ethyl acetate and the organic layers combined. The resulting mixture was washed with 1×20 mL of brine. The solid was dried in an oven under reduced pressure. This resulted in 2.5 g (crude) of 1-(5-chloropyridin-2-yl)-3-(trimethylsilyl)prop-2-yn-1-one as brown oil. In a 50-mL round-bottom flask, potassium carbonate (2.8 g, 20.29 mmol, 2.06 equiv) was added batchwise into a solution of 2-(5-chloropyridin-2-yl)-4-(trimethylsilyl)but-3-yn-2-ol (2.5 g, 9.85 mmol, 1.00 equiv) in methanol (25 mL). The resulting solution was stirred for 2 h at room temperature. TLC indicated the reaction completed, the solvent was concentrated under vacuum. The residue was diluted with 20 mL of water. The resulting solution was extracted with 3×20 mL of ethyl acetate and the organic layers combined. The resulting mixture was washed with 1×20 mL of brine. The solids were filtered out. The mixture was dried over anhydrous sodium sulfate and concentrated under vacuum, the residue was applied onto a silica gel column with ethyl acetate/petroleum ether (1:10). This resulted in 800 mg (45%) of 2-(5-chloropyridin-2-yl)but-3-yn-2-ol as brown oil.

Example 35

Synthesis of (±)-2-(5-fluoropyridin-2-yl)but-3-yn-2-ol

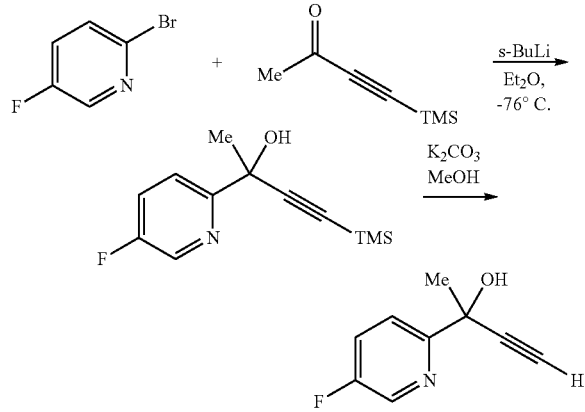

This compound was prepared according to a procedure similar to that described in Procedure C. In a 100-mL 3-necked round-bottom flask, s-BuLi (1.3M in hexane 10 mL) was added dropwise into a solution of 2-bromo-5-fluoropyridine (1.76 g, 10.00 mmol, 1.00 equiv) in ethyl ether (20 mL) under −76° C. The resulting solution was stirred for 1 h, then 4-(trimethylsilyl)but-3-yn-2-one (1.54 g, 10.98 mmol, 1.10 equiv) was added. The resulting solution was stirred for 2 h at −76° C. The reaction was then quenched by the addition of 10 mL of $NH_4Cl$ (sat., aq.). The resulting solution was extracted with 3×20 mL of ethyl acetate and the organic layers combined. The resulting mixture was washed with 1×20 mL of brine. The mixture was dried over anhydrous sodium sulfate and concentrated under vacuum. This resulted in 2.2 g (crude) of 2-(5-fluoropyridin-2-yl)-4-(trimethylsilyl)but-3-yn-2-ol as brown oil. In a 50-mL round-bottom flask, potassium carbonate (2.8 g, 20.29 mmol, 2.19 equiv) was added batchwise into a solution of 2-(5-fluoropyridin-2-yl)-4-(trimethylsilyl)but-3-yn-2-ol (2.2 g, 9.27 mmol, 1.00 equiv) in methanol (25 mL). The resulting solution was stirred for 2 h at room temperature. When completed monitored by TLC and LCMS, solvent was concentrated under vacuum. The residue was diluted with 20 mL of water. The resulting solution was extracted with 3×20 mL of ethyl acetate and the organic layers combined. The resulting mixture was washed with 1×20 mL of brine. The solids were filtered out. The resulting solution was dried over anhydrous sodium sulfate and concentrated under vacuum, the residue was applied onto a silica gel column with ethyl acetate/petroleum ether (1:10). This resulted in 700 mg (46%) of 2-(5-fluoropyridin-2-yl)but-3-yn-2-ol as a light brown solid.

Example 36

Synthesis of (±)-2-(1-Methyl-1H-imidazol-4-yl)but-3-yn-2-ol

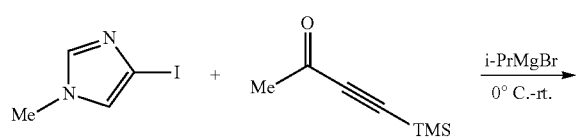

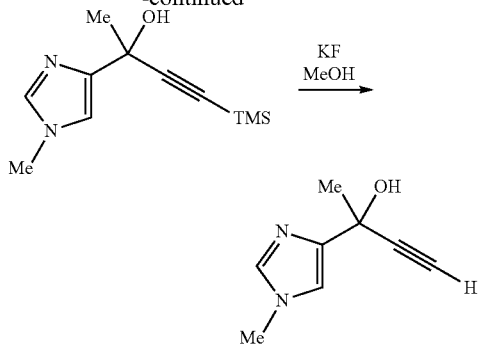

This compound was prepared according to a procedure similar to that described in Procedure C. In a 50-mL 3-necked round-bottom flask, isopropylmagnesium bromide (1M in tetrahydrofuran, 6 mL) was added dropwise into a solution of 4-iodo-1-methyl-1H-imidazole (1.04 g, 5.00 mmol, 1.00 equiv) in dichloromethane (20 mL) under 0° C. After stirred for 30 min at 0° C., 4-(trimethylsilyl)but-3-yn-2-one (840 mg, 5.99 mmol, 1.20 equiv) was added into the resultant solution at 0° C. The resulting solution was warmed to room temperature and stirred for 24 h. The reaction was then quenched by the addition of 10 mL of sat. aq. ammonium chloride. The resulting solution was extracted with 3×10 mL of ethyl acetate and the organic layers combined. The resulting mixture was washed with 1×10 mL of brine. The mixture was dried over anhydrous sodium sulfate and concentrated under vacuum. The residue was applied onto a silica gel column with dichloromethane/methanol (20:1). This resulted in 890 mg (80%) of 2-(1-methyl-1H-imidazol-4-yl)-4-(trimethylsilyl)but-3-yn-2-ol as a brown solid.

Into a 15-mL Schlenk tube, was placed a suspension of potassium fluoride dihydrate (940 mg, 10.00 mmol, 2.50 equiv) and 2-(1-methyl-1H-imidazol-4-yl)-4-(trimethylsilyl)but-3-yn-2-ol (888 mg, 3.99 mmol, 1.00 equiv) in methanol (10 mL). The resulting solution was stirred for 2 h at 50° C. Then most of solvent was concentrated under vacuum and the resulting mixture was diluted with 30 mL of ethyl acetate. The resulting mixture was washed with 2×10 mL of water and 1×10 mL of brine. The mixture was dried over anhydrous sodium sulfate, filtered and concentrated under vacuum. This resulted in 255 mg (43%) of 2-(1-methyl-1H-imidazol-4-yl)but-3-yn-2-ol as a gray solid.

Example 37

Synthesis of (±)-2-(1H-pyrazol-4-yl)but-3-yn-2-ol

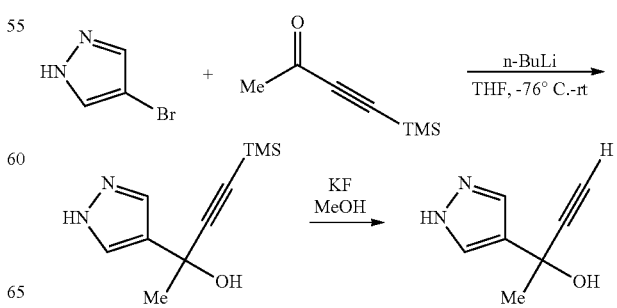

This compound was prepared according to a procedure similar to that described in Procedure C. Into a 250-mL 3-necked round-bottom flask purged and maintained with an inert atmosphere of nitrogen, was placed a solution of 4-bromo-1H-pyrazole (3 g, 20.41 mmol, 1.00 equiv) in tetrahydrofuran (40 mL). This was followed by the addition of n-BuLi (19.5 mL, 2.40 equiv) dropwise with stirring at −78° C. Then warmed slowly to room temperature and stirred for 1.5 h at this temperature. Cooled to −70° C., to this was added 4-(trimethylsilyl)but-3-yn-2-one (2.9 g, 20.68 mmol, 1.00 equiv) in tetrahydrofuran (40 mL) dropwise with stirring. After addition the resulting solution was warmed to room temperature and stirred for an additional 3.5 h. The reaction was then quenched by the addition of 20 mL of sat. aq. ammonium chloride. The resulting solution was diluted with 150 mL, of water. The resulting solution was extracted with 2×150 mL of ethyl acetate and the organic layers combined and dried over anhydrous sodium sulfate and concentrated under vacuum. The residue was applied onto a silica gel column with ethyl acetate/hexane. This resulted in 1.2 g (28%) of 2-(1H-pyrazol-4-yl)-4-(trimethylsilyl)but-3-yn-2-ol as a yellow solid.

In a 20-mL sealed tube, a suspension of 2-(1H-pyrazol-4-yl)-4-(trimethylsilyl)but-3-yn-2-ol (1.4 g, 6.72 mmol, 1.00 equiv) and potassium fluoride dihydrate (2.0 g) in methanol (10 mL) was stirred for 1.5 h at 50° C. The resulting mixture was concentrated under vacuum. The resulting solution was diluted with 20 mL of water. The resulting solution was extracted with 3×20 mL of tetrahydrofuran/ethyl acetate (2/1) and the organic layers combined and dried over anhydrous sodium sulfate and concentrated under vacuum. This resulted in 1 g (98%) of 2-(1H-pyrazol-4-yl)but-3-yn-2-ol as a solid.

Example 38

Synthesis of 9-[4-(tert-Butyl-dimethyl-silanyloxy)-3-hydroxy-3-methyl-but-1-ynyl]-4,5-dihydro-6-oxa-1,3a-diaza-benzo[e]azulene-2-carboxylic acid amide

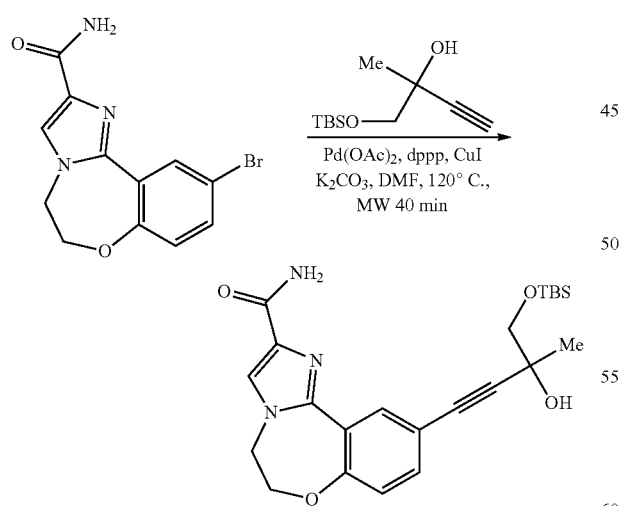

This compound was prepared according to a procedure similar to that described in Procedure H. A mixture of bromide (100 mg×3, 1.0 mmol), propargyl alcohol (140 mg×3, 2.0 mmol) in DMF (2 mL×3) was added K₂CO₃ (90 mg×3, 2.0 mmol), Pd(OAc)₂ (10 mg×3), dppp (20 mg×3) at room temperature. Then the mixture was bubbled with N₂ and heated at 120° C. under microwave for 40 min. LC-MS showed 50% of the desired MS. Then filtrated and concentrated, the residue was used directly for the next step.

Example 39

Synthesis of 9-(3,4-Dihydroxy-3-methyl-but-1-ynyl)-4,5-dihydro-6-oxa-1,3a-diaza-benzo[e]azulene-2-carboxylic acid amide

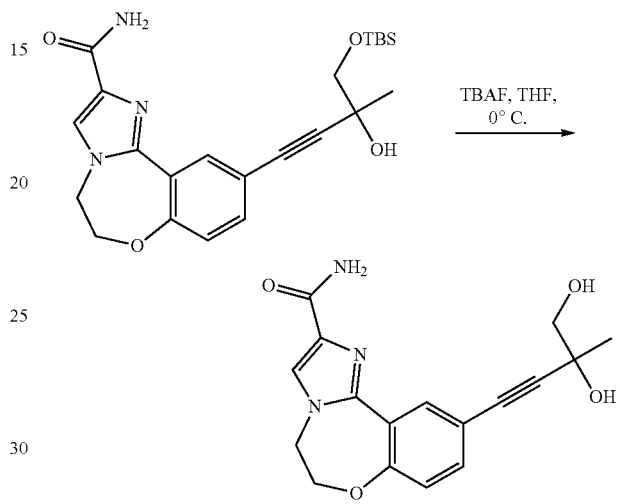

To a solution of compound 9-[4-(tert-Butyl-dimethyl-silanyloxy)-3-hydroxy-3-methyl-but-1-ynyl]-4,5-dihydro-6-oxa-1,3a-diaza-benzo[e]azulene-2-carboxylic acid amide (300 mg, 0.66 mmol) in THF (20 mL) was added TBAF (340 mg, 1.3 mmol) at 0° C. for about 1 h. After washed with water and extracted with EtOAc, the crude product was purified by Pre-HPLC to get the titled compound (100.0 mg, yield 46.5%). LCMS=328.1 [M+H]⁺; ¹H NMR (DMSO-d₆, 400 MHz) δ 8.50 (d, J=2.0 Hz, 1H), 7.84 (s, 1H), 7.64 (s, 1H), 7.34 (d, J=8.4 Hz, 1H), 7.26 (s, 1H), 7.04 (d, J=8.4 Hz, 1H), 4.50 (s, 4H), 3.45-3.37 (q, J=10.4 Hz, 2H), 1.39 (s, 3H).

Example 40

Synthesis of tert-butyl 3-((2-carbamoyl-5,6-dihydrobenzo[f]imidazo[1,2-d][1,4]oxazepin-10-yl)ethynyl)-3-hydroxypyrrolidine-1-carboxylate

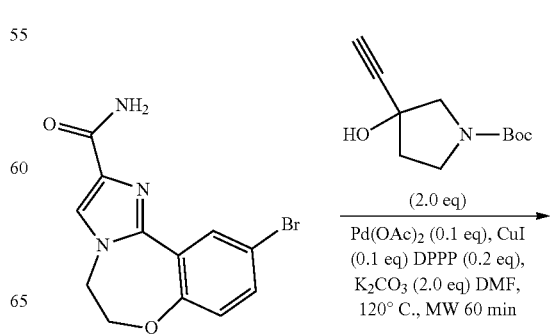

409

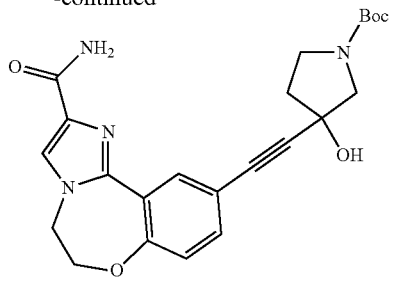

This compound was prepared according to a procedure similar to that described in Procedure H. In a solution of 9-Bromo-4,5-dihydro-6-oxa-1,3a-diaza-benzo[e]azulene-2-carboxylic acid amide (100 mg, 0.32 mmol) in N,N-Dimethyl-formamide (3 mL) were added 1,3-bis(diphenylphosphino)-propane (26 mg, 0.064 mmol), Pd(OAc)$_2$ (7.2 mg, 0.032 mmol), K$_2$CO$_3$ (110 mg, 0.8 mmol), 3-Ethynyl-3-hydroxy-pyrrolidine-1-carboxylic acid tert-butyl ester (136 mg, 0.64 mmol) and CuI (12 mg, 0.064 mmol). Then the solution was bubbled N$_2$ for 5 min and microwaved for 1 h at 120° C. under nitrogen. The reaction mixture was filtrated and the filtrate was purified by column to afford crude titled compound (40 mg, 28%). LCMS=383.0 [M-56]$^+$.

Example 41

Synthesis of 10-((3-hydroxypyrrolidin-3-yl)ethynyl)-5,6-dihydrobenzo[f]imidazo[1,2-d][1,4]oxazepine-2-carboxamide

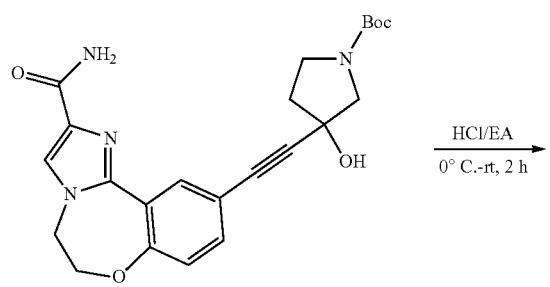

In a solution of 3-(2-Carbamoyl-4,5-dihydro-6-oxa-1,3a-diaza-benzo[e]azulen-9-ylethynyl)-3-hydroxy-pyrrolidine-1-carboxylic acid tert-butyl ester (40 mg, 0.1 mmol) in methanol (20 ml) was added HCl/EA (20 ml). The solution was stirred for 3 h at room temperature. The reaction mixture was purified by column to afford the titled compound (3.5 mg, 10%). $^1$HNMR (Methanol-d$_4$, 400 MHz): δ 8.62 (d, J=2.0 Hz, 1H), 7.78 (s, 1H), 7.41 (dd, J=2.0, 8.8 Hz, 1H), 7.08 (d, J=8.4 Hz, 1H), 4.52 (s, 4H), 3.54-3.40 (m, 4H), 2.43 (t, J=5.4 Hz, 2H), LCMS: 339.1 [M+H]$^+$.

Example 42

Synthesis of 9-(3-Hydroxy-1-methyl-pyrrolidin-3-ylethynyl)-4,5-dihydro-6-oxa-1,3a-diaza-benzo[e]azulene-2-carboxylic acid amide

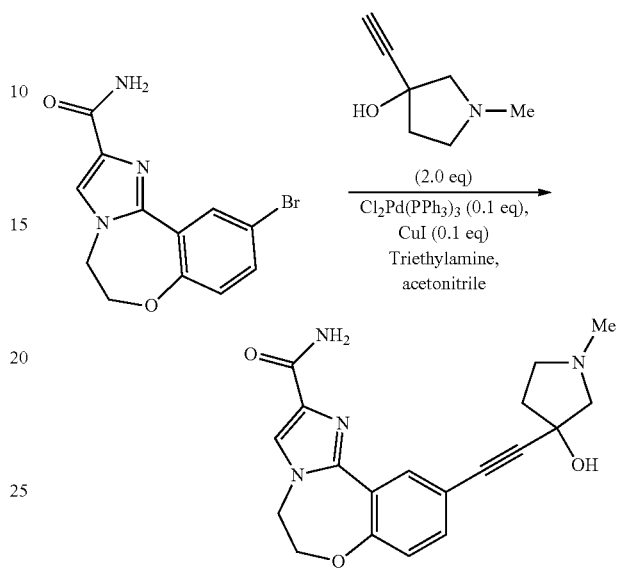

This compound was prepared according to a procedure similar to that described in Procedure E. In a solution of 9-Bromo-4,5-dihydro-6-oxa-1,3a-diaza-benzo[e]azulene-2-carboxylic acid amide (200 mg, 0.64 mmol) in acetonitrile (3 mL) and triethylamine (3 mL) were added, Pd(PPh$_3$)$_2$Cl$_2$ (44 mg, 0.06 mmol), 3-Ethynyl-1-methyl-pyrrolidin-3-ol (160 mg, 1.3 mmol) and CuI (12 mg, 0.06 mmol). Then the solution was bubbled N$_2$ for 5 min and heated by microwave for 1 h at 100° C. under nitrogen. The reaction mixture was filtered and the filtrate was purified by column to afford crude product. The crude product was purified by Prep HPLC to afford the titled compound (22.3 mg, 10%). $^1$H NMR (DMSO-d$_6$, 400 MHz): δ 8.52 (d, J=2.0 Hz, 1H), 8.18 (s, 1H), 7.79 (s, 1H), 7.56 (s, 1H), 7.32 (d, J=8.8 Hz, 1H), 7.15 (s, 1H), 7.03 (d, J=8.4 Hz, 1H), 4.48 (s, 4H), 2.95 (m, 1H), 2.77 (m, 2H), 2.67 (m, 1H), 2.31 (s, 3H), 2.28 (m, 1H), 2.08 (m, 1H). LCMS=353.1 [M+H]$^+$.

Example 44

Synthesis of tert-butyl 3-((2-carbamoyl-5,6-dihydrobenzo[f]imidazo[1,2-d][1,4]oxazepin-10-yl)ethynyl)-3-hydroxy-8-azabicyclo[3.2.1]octane-8-carboxylate

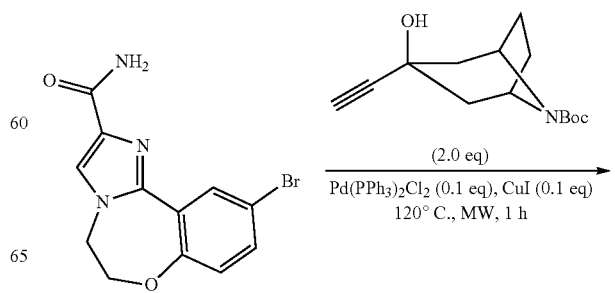

411

-continued

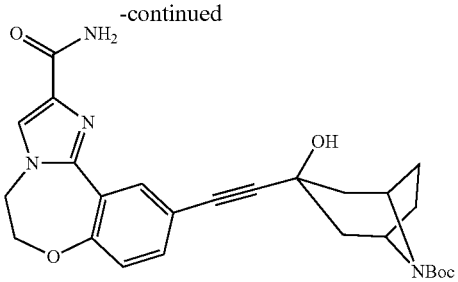

This compound was prepared according to a procedure similar to that described in Procedure E. In a solution of 9-Bromo-4,5-dihydro-6-oxa-1,3a-diaza-benzo[e]azulene-2-carboxylic acid amide (300 mg, 1.0 mmol) in acetonitrile (6 mL) and triethylamine (3 mL) were added Pd(PPh3)$_2$Cl$_2$ (70 mg, 0.1 mmol), 3-Ethynyl-3-hydroxy-8-aza-bicyclo[3.2.1]octane-8-carboxylic acid tert-butyl ester (0.5 g, 2 mmol) and CuI (19 mg, 0.1 mmol). Then the solution was bubbled N$_2$ for 5 min and microwaved for 2 h at 120° C. under nitrogen. The reaction mixture was filtered and the filtrate was purified by column (EtOAc/hexanes 2:1) to afford crude product (0.5 g, 99%). LCMS=479.2 [M+H]$^+$.

Example 45

Synthesis of 10-(((1R,5S)-3-hydroxy-8-azabicyclo[3.2.1]octan-3-yl)ethynyl)-5,6-dihydrobenzo[f]imidazo[1,2-d][1,4]oxazepine-2-carboxamide

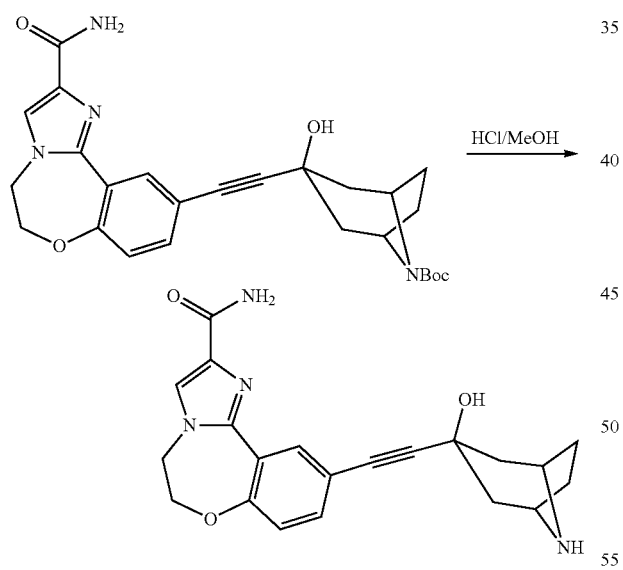

In a solution of 3-(2-Carbamoyl-4,5-dihydro-6-oxa-1,3a-diaza-benzo[e]azulen-9-ylethynyl)-3-hydroxy-8-aza-bicyclo[3.2.1]octane-8-carboxylic acid tert-butyl ester (0.5 g, 1.1 mmol) in methanol (20 mL) was added HCl/EtOAc (4 M, 20 mL) at 0° C. The solution was stirred for 3 h at room temperature. The reaction mixture was filtered and washed with EtOAc to afford desired product as HCl salt (400 mg, 96%). $^1$H NMR: (DMSO-d$_6$, 400 MHz): δ 9.44 (s, 1H), 9.10 (s, 1H), 8.52 (s, 1H), 8.02 (s, 1H), 7.46 (s, 1H), 7.38 (d, J=8.8 Hz, 1H), 7.08 (d, J=8.4 Hz, 1H), 4.55 (s, 4H), 3.96 (s, 2H), 2.45-2.17 (m, 6H), 1.91-1.88 (m, 2H). LCMS [M+H]$^+$=379.0.

412

Example 46

Synthesis of 9-(3-Hydroxy-8-methyl-8-aza-bicyclo[3.2.1]oct-3-ylethynyl)-4,5-dihydro-6-oxa-1,3a-diaza-benzo[e]azulene-2-carboxylic acid amide

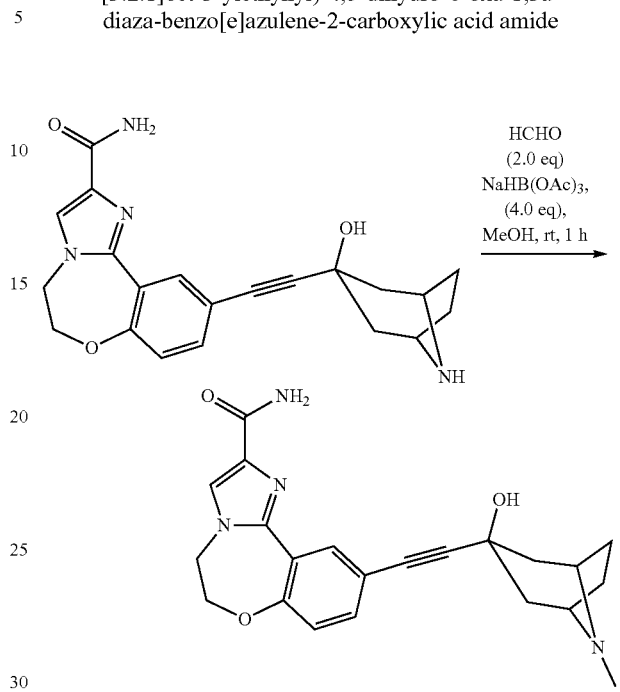

In a solution of 10-(((1R,5S)-3-hydroxy-8-azabicyclo[3.2.1]octan-3-yl)ethynyl)-5,6-dihydrobenzo[f]imidazo[1,2-d][1,4]oxazepine-2-carboxamide (0.15 g, 0.4 mmol) in methanol (20 ml) was added (HCHO)n (144 mg, 4.8 mmol) and NaBH(OAc)$_3$ (260 mg, 1.2 mmol). The solution was stirred for 1 h at room temperature. The reaction mixture was quenched with water and purified by Prep HPLC to afford 9-(3-Hydroxy-8-methyl-8-aza-bicyclo[3.2.1]oct-3-ylethynyl)-4,5-dihydro-6-oxa-1,3a-diaza-benzo[e]azulene-2-carboxylic acid amide (13.5 mg, 8.5%). $^1$H NMR (Methanol-d4, 400 MHz): δ 8.30 (m, 1H), 8.10 (s, 1H), 7.56 (d, J=8.4 Hz, 1H), 7.19 (d, J=8.4 Hz, 1H), 4.67 (s, 4H), 3.94 (s, 2H), 2.81 (s, 3H), 2.65-2.20 (m, 8H). LCMS [M+H]$^+$=393.0.

Example 47

Synthesis of 10-(4-(tert-butyldimethylsilyloxy)-3-methyl-3-(5-methyl-4H-1,2,4-triazol-3-yl)but-1-ynyl)-5,6-dihydrobenzo[f]imidazo[1,2-d][1,4]oxazepine-2-carboxamide

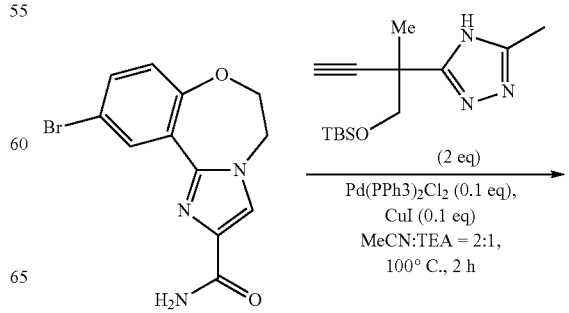

-continued

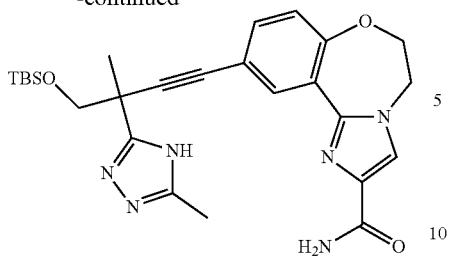

This compound was prepared according to a procedure similar to that described in Procedure E. Aryl bromide (200 mg, 0.64 mmol), 9 (568 mg, 1.92 mmol), Pd(PPh$_3$)$_2$Cl$_2$ (87.2 mg, 0.065 mmol), CuI (47.2 mg, 0.065 mmol) were combined in a tube, MeCN:H$_2$O (2:1, 10 mL) was added, the mixture was stirred at 100° C. for 2 h. The mixture was concentrated, purified via chromatography on silica gel to afford the desired product (120 mg, 37.1%).

LCMS (Method 0-60AB, ESI): RT=1.459 min/2 min, M+H$^+$=507.2.

Example 48

Synthesis of 9-[4-hydroxy-3-methyl-3-(5-methyl-4H-[1,2,4]triazol-3-yl)-but-1-ynyl]-4,5-dihydro-6-oxa-1,3a-diaza-benzo[e]azulene-2-carboxylic acid amide

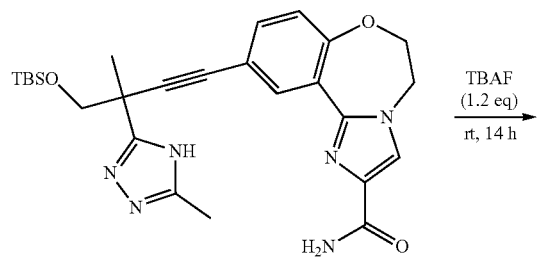

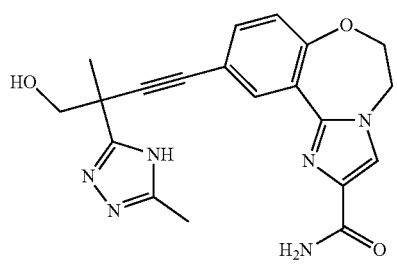

9-[4-(tert-Butyl-dimethyl-silanyloxy)-3-methyl-3-(5-methyl-4H-[1,2,4]triazol-3-yl)-but-1-ynyl]-4,5-dihydro-6-oxa-1,3a-diaza-benzo[e]azulene-2-carboxylic acid amide (120 mg, 0.2 mmol) was dissolved in THF (10 mL), TBAF (62.9 mg, 0.24 mmol) was added. The mixture was stirred at room temperature for 14 h. The mixture was purified via HPLC separation (0.1% HCOOH) to afford the titled compound (17.6 mg, 23.0%). $^1$H-NMR (DMSO-d$_6$, 400 MHz): δ 114 (s, 1H), 8.45 (s, 1H), 7.77 (s, 1H), 7.51 (s, 1H), 7.29 (s, 1H), 7.11 (s, 1H), 6.98 (d, J=8.4 Hz, 1H), 5.05 (s, 1H), 4.45 (s, 4H), 3.77 (s, 2H), 2.29 (s, 3H), 1.21 (s, 3H). LCMS: [M+H]$^+$=393.0.

Example 49

Synthesis of (±)-8-Fluoro-9-[3-hydroxy-3-(5-methyl-[1,2,4]oxadiazol-3-yl)-but-1-ynyl]-4,5-dihydro-6-oxa-1,3a-diaza-benzo[e]azulene-2-carboxylic acid amide

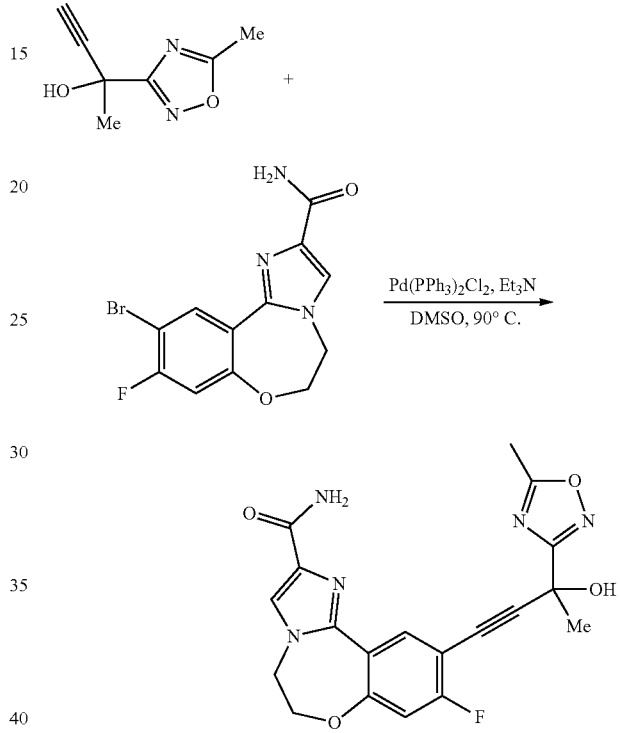

This compound was prepared according to a procedure similar to that described in Procedure G. Into a 10-mL sealed tube purged and maintained with an inert atmosphere of nitrogen, was placed a suspension of 2-(5-methyl-1,2,4-oxadiazol-3-yl)but-3-yn-2-ol (150 mg, 0.99 mmol, 3.50 equiv), 9-Bromo-4,5-dihydro-6-oxa-1,3a-diaza-benzo[e]azulene-2-carboxylic acid amide (91.92 mg, 0.28 mmol, 1.00 equiv) and Pd(PPh$_3$)$_2$Cl$_2$ (98.97 mg, 0.14 mmol, 0.50 equiv) in DMSO (1 mL) and triethylamine (1 mL). The resulting solution was stirred for 12 h at 90° C. in an oil bath. The resulting mixture was diluted with 10 mL of H$_2$O and extracted with 3×50 mL of dichloromethane, the organic layer combined and dried over anhydrous sodium sulfate. Concentrated and the residue was applied onto a silica gel column with dichloromethane/methanol (10:1). This resulted in 5.3 mg (5%) of 8-Fluoro-9-[3-hydroxy-3-(5-methyl-[1,2,4]oxadiazol-3-yl)-but-1-ynyl]-4,5-dihydro-6-oxa-1,3a-diaza-benzo[e]azulene-2-carboxylic acid amide as a brown solid. LC-MS: 398 [M+H]$^+$, $^1$H-NMR (300 MHz, DMSO-d6, ppm) δ 8.571 (d, 1H), 7.776 (s, 1H), 7.562 (br s, 1H), 7.117 (br s, 1H), 7.026 (d, 1H), 6.775 (s, 1H), 4.560-4.410 (m, 4H), 2.612 (s, 3H), 1.841 (s, 3H).

Example 50

Synthesis of (±)-8-Fluoro-9-[3-hydroxy-3-(3-methyl-pyridin-2-yl)-but-1-ynyl]-4,5-dihydro-6-oxa-1,3a-diaza-benzo[e]azulene-2-carboxylic acid amide

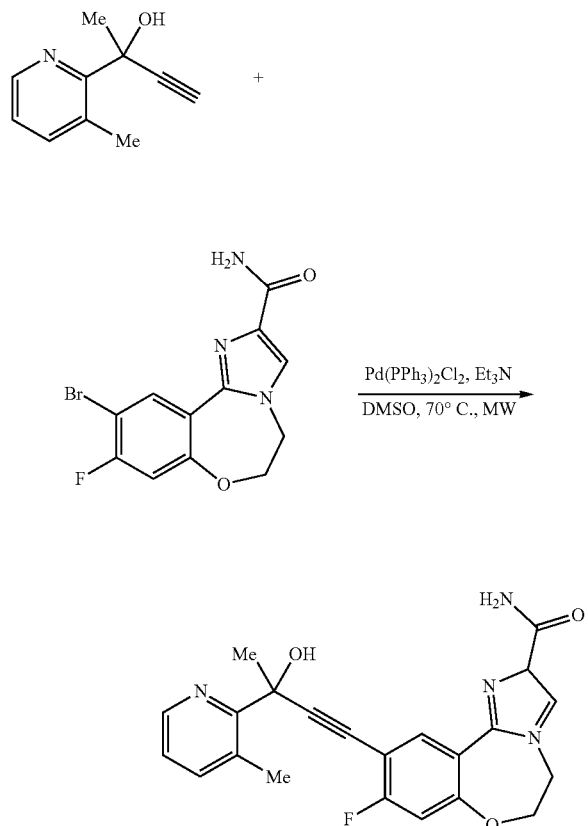

This compound was prepared according to a procedure similar to that described in Procedure G. Into a 10-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (170 mg, 0.52 mmol, 1.00 equiv), 2-(3-methylpyridin-2-yl)but-3-yn-2-ol (269 mg, 1.67 mmol, 3.50 equiv) and Pd(PPh$_3$)Cl$_2$ (141 mg, 0.40 equiv) in DMSO (1 mL) and triethylamine (1 mL) and the reaction mixture was irradiated under microwave for 2 h at 70° C. Then the resulting solution was diluted with 50 mL of dichloromethane, washed with 2×20 mL of water, dried over anhydrous sodium sulfate and concentrated under vacuum to get a residue, which was purified by silica gel column with dichloromethane/methanol (10:1) to afford 15.0 mg (7%) of 8-Fluoro-9-[3-hydroxy-3-(3-methyl-pyridin-2-yl)-but-1-ynyl]-4,5-dihydro-6-oxa-1,3a-diaza-benzo[e]azulene-2-carboxylic acid amide as a light yellow solid. LC-MS: 407[M+H]$^+$, $^1$H-NMR (300 MHz, DMSO-d6, ppm) δ 9.000 (d, 1H), 8.648 (br s, 1H), 7.789 (br s, 1H), 7.210 (s, 2H), 7.021 (d, 1H), 6.670 (d, 1H), 6.745 (d, 1H), 5.677 (s, 1H), 5.481 (t, 1H), 4.472 (s, 4H), 1.988 (s, 3H), 1.414 (s, 3H).

Example 51

Synthesis of (±)-8-Fluoro-9-[3-hydroxy-3-(1H-pyrazol-4-yl)-but-1-ynyl]-4,5-dihydro-6-oxa-1,3a-diaza-benzo[e]azulene-2-carboxylic acid amide

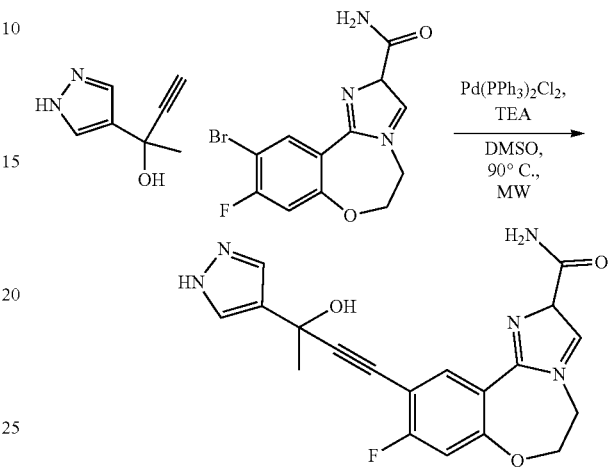

This compound was prepared according to a procedure similar to that described in Procedure G. Into a 10-mL sealed vial purged and maintained with an inert atmosphere of nitrogen, was placed a suspension of 9-Bromo-4,5-dihydro-6-oxa-1,3a-diaza-benzo[e]azulene-2-carboxylic acid amide (200 mg, 0.61 mmol, 1.00 equiv), 2-(1H-pyrazol-4-yl)but-3-yn-2-ol (300 mg, 2.20 mmol, 3.50 equiv) and Pd(PPh$_3$)Cl$_2$ (200 mg, 0.50 equiv) in DMSO (1.5 mL) and triethylamine (1.5 mL). The final reaction mixture was irradiated with microwave radiation for 2 h at 90° C. The resulting solution was diluted with 20 mL of water. The resulting solution was extracted with 3×30 mL of ethyl acetate and the organic layers combined and dried over anhydrous sodium sulfate and concentrated under vacuum. The residue was applied onto a silica gel column with DCM:MeOH (10:1). This resulted in 46.3 mg (19%) of 8-Fluoro-9-[3-hydroxy-3-(1H-pyrazol-4-yl)-but-1-ynyl]-4,5-dihydro-6-oxa-1,3a-diaza-benzo[e]azulene-2-carboxylic acid amide as a off-white solid. LC-MS: 382 [M+H]$^+$;

$^1$H-NMR (400 MHz, DMSO-d6, ppm) δ 12.660 (br s, 1H), 8.581 (d, 1H), 7.779 (s, 1H), 7.586 (s, 3H), 7.128 (s, 1H), 7.021 (d, 1H), 5.955 (s, 1H), 4.531-4.410 (m, 4H), 1.764 (s, 3H).

Example 52

Synthesis of 3-((2-carbamoyl-9-fluoro-5,6-dihydrobenzo[f]imidazo[1,2-d][1,4]oxazepin-10-yl)ethynyl)-3-hydroxycyclobutyl benzoate

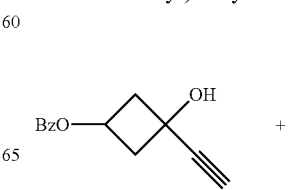

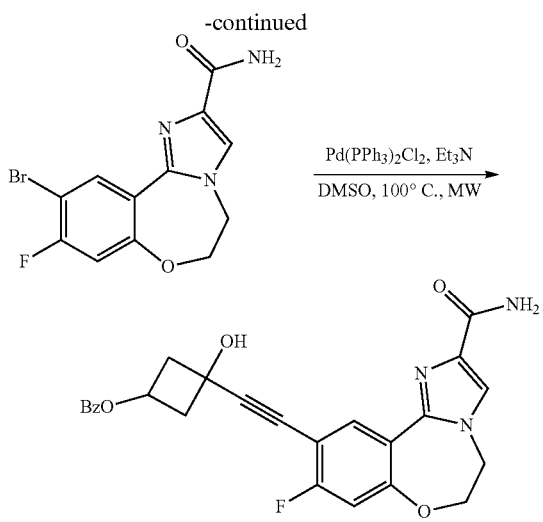

This compound was prepared according to a procedure similar to that described in Procedure G. In a 5-mL sealed tube, a suspension of 9-Bromo-4,5-dihydro-6-oxa-1,3a-diaza-benzo[e]azulene-2-carboxylic acid amide (163 mg, 0.50 mmol, 1.00 equiv), 3-ethynyl-3-hydroxycyclobutyl benzoate (216 mg, 1.00 mmol, 2.00 equiv) and Pd(PPh₃)₂Cl₂ (70 mg, 0.10 mmol, 0.20 equiv) in triethylamine (1 mL) and DMSO (1 mL) was degassed with N₂. Then the reaction mixture was irradiated with microwave radiation for 30 min at 100° C. After cooling to room temperature, the resulting solution was diluted with 40 mL of ethyl acetate. The resulting mixture was washed with 2×10 mL of water and 1×10 mL, of brine. The mixture was dried over anhydrous sodium sulfate, filtered and concentrated under vacuum to give 190 mg crude titled product.

Example 53

Synthesis of 9-(1,3-Dihydroxy-cyclobutylethynyl)-8-fluoro-4,5-dihydro-6-oxa-1,3a-diaza-benzo[e]azulene-2-carboxylic acid amide

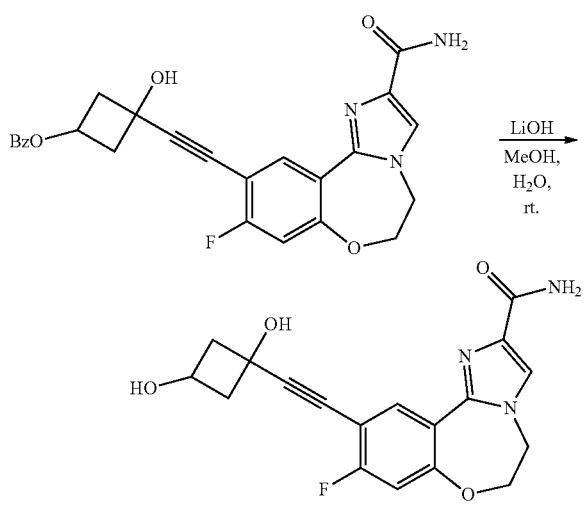

In a 25-mL round-bottom flask, a suspension of 9-(1-hydroxy-3-benzoyloxy-cyclobutylethynyl)-8-fluoro-4,5-dihy-dro-6-oxa-1,3a-diaza-benzo[e]azulene-2-carboxylic acid amide (190 mg, ~0.4 mmol), lithiumol (96 mg, 4.01 mmol) in methanol (0.5 mL) and water (1 mL) was stirred at room temperature overnight. The resulting solution was diluted with 20 mL of dichloromethane and 10 mL water. The organic layer was washed with 10 mL of brine. The mixture was dried over anhydrous sodium sulfate and concentrated under vacuum. The residue was applied onto a silica gel column with dichloromethane/methanol (1:10). This resulted in 7 mg of 9-(1,3-Dihydroxy-cyclobutylethynyl)-8-fluoro-4,5-dihydro-6-oxa-1,3a-diaza-benzo[e]azulene-2-carboxylic acid amide as a light yellow solid (single undetermined diastereomer). LC-MS (ES, m/z):358[M+H]⁺; ¹H-NMR (400 MHz, DMSO-d6, ppm) δ: 8.570 (d, 1H), 7.783 (s, 1H), 7.591 (br s, 1H), 7.139 (br s, 1H), 7.015 (d, 1H), 5.982 (s, 1H), 5.200 (d, 1H), 4.520-4.496 (m, 4H), 4.000-3.949 (m, 1H), 2.760-2.716 (m, 2H), 2.164-2.115 (m, 2H).

Example 54

Synthesis of (±)-8-Fluoro-9-[3-hydroxy-3-(1-methyl-cyclopropyl)-but-1-ynyl]-4,5-dihydro-6-oxa-1,3a-diaza-benzo[e]azulene-2-carboxylic acid amide

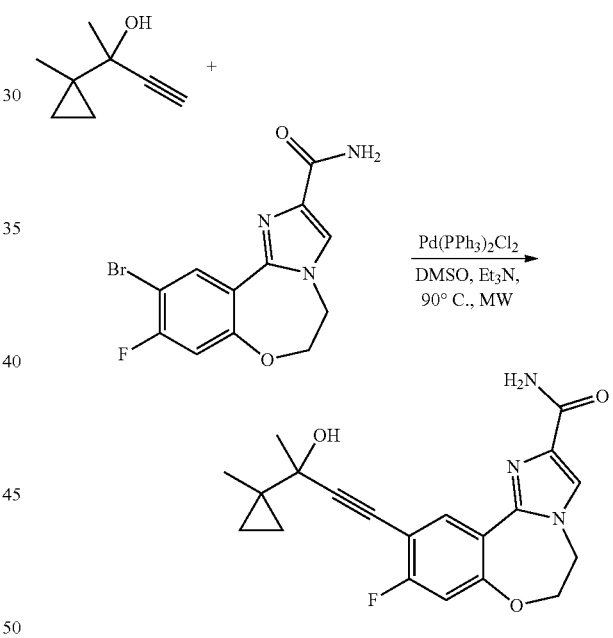

This compound was prepared according to a procedure similar to that described in Procedure G. In a 10-mL sealed tube, was placed a solution of 2-(1-methylcyclopropyl)but-3-yn-2-ol (120 mg, 0.97 mmol, 3.50 equiv), 9-Bromo-4,5-dihydro-6-oxa-1,3a-diaza-benzo[e]azulene-2-carboxylic acid amide (90 mg, 0.28 mmol, 1.00 equiv) and Pd(PPh₃)₂Cl₂ (19.5 mg, 0.03 mmol, 0.1 equiv) in DMSO (1 mL) and triethylamine (1 mL). The resulting solution was irradiated with microwave radiation for 2 h at 90° C. Then resulting mixture was diluted by ethyl acetate (50 mL), washed with 2×5 mL of brine. The organic layers was dried over anhydrous sodium sulfate and concentrated under vacuum. This resulted in 7.8 mg (8%) of 8-Fluoro-9-[3-hydroxy-3-(1-methyl-cyclopropyl)-but-1-ynyl]-4,5-dihydro-6-oxa-1,3a-diaza-benzo[e]azulene-2-carboxylic acid amide as a white solid. LC-MS:

(ES, m/z): 370[M+H]+; 1H-NMR: (300 MHz, DMSO-d6, ppm) δ 8.525 (d, 1H), 7.782 (s, 1H), 7.556 (s, 1H), 7.155 (d, 1H), 7.099 (d, 1H), 5.323 (s, 1H), 4.500-4.400 (m, 4H), 1.477 (s, 3H), 1.169 (s, 3H), 0.780 (t, 2H), 0.222 (t, 2H).

Example 55

Synthesis of 8-Fluoro-9-(3-hydroxy-3-methyl-but-1-ynyl)-4,5-dihydro-6-oxa-1,3a-diaza-benzo[e]azulene-2-carboxylic acid amide

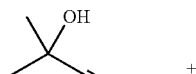

+

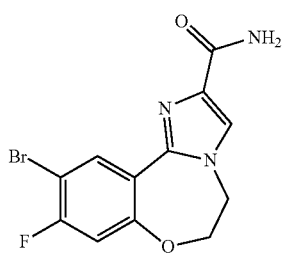

Pd(PPh₃)₂Cl₂
DMSO, Et₃N,
70° C., MW

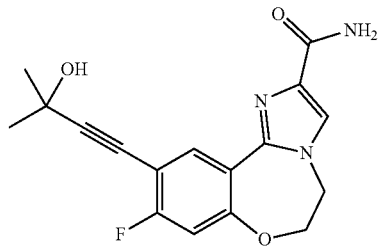

This compound was prepared according to a procedure similar to that described in Procedure G. Into a 8-mL vial purged and maintained with an inert atmosphere of nitrogen, was placed a suspension of 2-methylbut-3-yn-2-ol (300 mg, 3.57 mmol, 1.00 equiv), 9-Bromo-4,5-dihydro-6-oxa-1,3a-diaza-benzo[e]azulene-2-carboxylic acid amide (270 mg, 0.83 mmol, 3.50 equiv) and Pd(PPh₃)₂Cl₂ (70 mg, 0.10 mmol, 0.10 equiv) in DMSO (1 mL) and triethylamine (1 mL). The resulting solution was stirred for 12 h at 70° C. The resulting solution was diluted with 20 mL of H2O. The resulting solution was extracted with 3×50 mL of dichloromethane and the organic layers combined and dried over anhydrous sodium sulfate and concentrated under vacuum. The residue was applied onto a silica gel column with dichloromethane/methanol (10:1). This resulted in 0.173 g (14%) of 8-Fluoro-9-(3-hydroxy-3-methyl-but-1-ynyl)-4,5-dihydro-6-oxa-1,3a-diaza-benzo[e]azulene-2-carboxylic acid amide as a light brown solid. LC-MS: (ES, m/z): 330[M+11]+; 1H-NMR: (400 MHz, DMSO-d6, ppm) δ 8.553 (d, 1H), 7.782 (s, 1H), 7.567 (br s, 1H), 7.136 (br s, 1H), 7.006 (d, 1H), 5.534 (s, 1H), 4.516-4.400 (m, 4H), 1.891 (s, 6H).

Example 56

Synthesis of methyl 4-(2-carbamoyl-9-fluoro-5,6-dihydrobenzo[f]imidazo[1,2-d][1,4]oxazepin-10-yl)-2-hydroxy-2-methylbut-3-ynoate

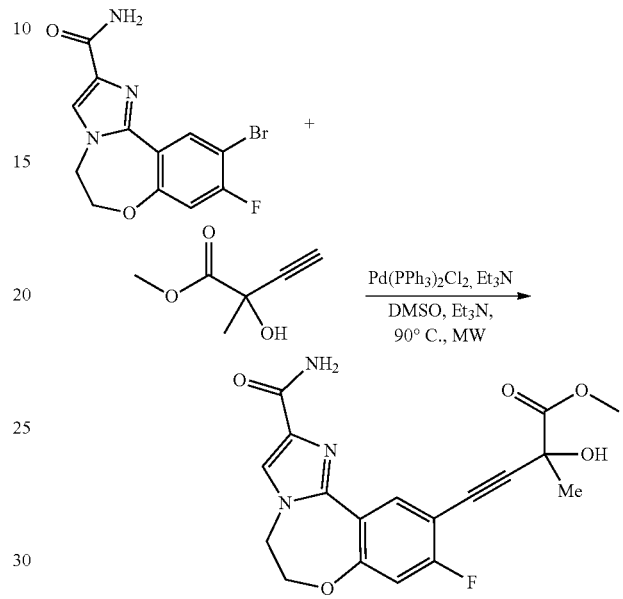

This compound was prepared according to a procedure similar to that described in Procedure G. Into a 8-mL vial, was placed a suspension of 9-Bromo-4,5-dihydro-6-oxa-1,3a-diaza-benzo[e]azulene-2-carboxylic acid amide (200 mg, 0.61 mmol, 1.00 equiv), methyl 2-hydroxy-2-methylbut-3-ynoate (236 mg, 1.84 mmol, 3.00 equiv), Pd(PPh₃)₂Cl₂ (43 mg, 0.06 mmol, 0.10 equiv) in DMSO (0.5 mL) and triethylamine (0.5 mL). The final reaction mixture was irradiated with microwave radiation for 2 h at 90° C. The resulting solution was diluted with 20 mL of ethyl acetate. The resulting mixture was washed with 2×10 mL, of brine. The mixture was dried over anhydrous sodium sulfate and concentrated under vacuum. This resulted in 300 mg (crude) of the titled compound as a brown solid.

Example 57

Synthesis of (±)-9-[4-(3-Cyano-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide

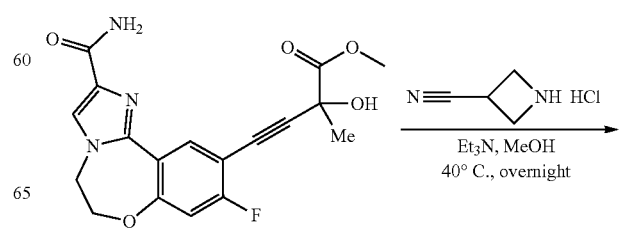

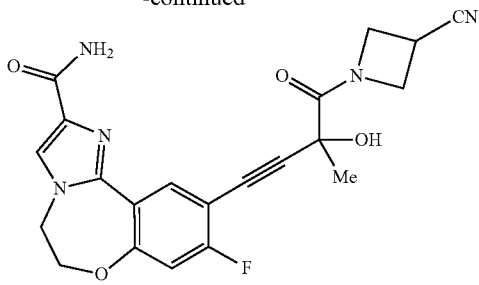

Into a 10-mL sealed tube, was placed a solution of methyl 4-[4-carbamoyl-12-fluoro-9-oxa-3,6-diazatricyclo[8.4.0.0[2,6]]tetradeca-1(10),2,4,11,13-pentaen-13-yl]-2-hydroxy-2-methylbut-3-ynoate (150 mg, 0.40 mmol, 1.00 equiv), azetidine-3-carbonitrile hydrochloride (237 mg, 2.00 mmol, 5.00 equiv), triethylamine (203 mg, 2.01 mmol, 5.00 equiv) in methanol (5 mL). The resulting solution was stirred for 12 h at 40° C. in an oil bath. The resulting mixture was concentrated under vacuum. The residue was applied onto a silica gel column with dichloromethane/methanol (30:1). This resulted in 8.8 mg (5%) of 9-[4-(3-Cyano-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide as a off-white solid. LC-MS: (ES, m/z): 424 [M+H]+ 1H-NMR: (300 MHz, DMSO-d6, ppm): δ 8.594 (d, 1H), 7.785 (s, 1H), 7.562 (d, 1H), 7.145 (s, 1H), 7.062 (d, 1H), 6.438 (d, 1H), 4.748 (t, 1H), 4.600-4.410 (m, 5H), 4.300-4.190 (m, 1H), 4.180-4.000 (m, 1H), 3.900-3.710 (m, 1H), 1.610 (s, 3H).

Example 58

Synthesis of (±)-8-Fluoro-9-(3-hydroxy-3-methylcarbamoyl-but-1-ynyl)-4,5-dihydro-6-oxa-1,3a-diaza-benzo[e]azulene-2-carboxylic acid amide

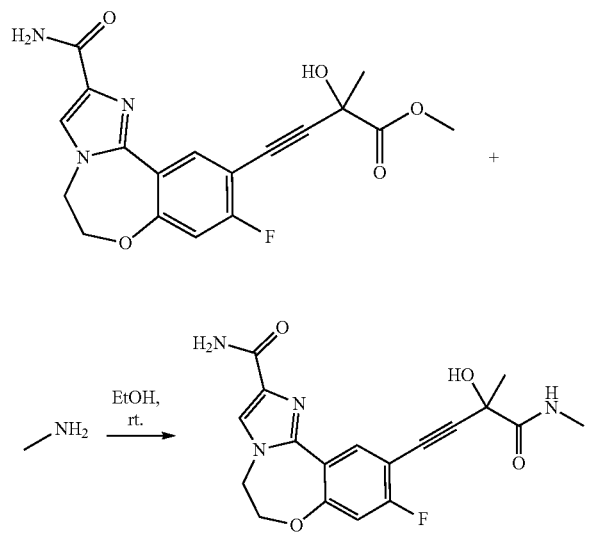

In a 20-mL sealed tube, methyl 4-[4-carbamoyl-12-fluoro-9-oxa-3,6-diazatricyclo[8.4.0.0[2,6]]tetradeca-1(14),2,4,10,12-pentaen-13-yl]-2-hydroxy-2-methylbut-3-ynoate (120 mg, 0.32 mmol, 1.00 equiv) was added into a solution of methanamine (30% w/w in ethanol, 5 mL). The resulting solution was stirred for 8 h at room temperature. The resulting mixture was concentrated under vacuum. The residue was applied onto a silica gel column with ethyl acetate/petroleum ether (1:5). This resulted in 35 mg (29%) of 8-Fluoro-9-(3-hydroxy-3-methylcarbamoyl-but-1-ynyl)-4,5-dihydro-6-oxa-1,3a-diaza-benzo[e]azulene-2-carboxylic acid amide as a yellow solid. LC-MS: (ES, m/z): 373 [M+H]; 1H-NMR: (300 MHz, DMSO-d6, ppm): δ 8.548 (d, 1H), 8.000-7.800 (m, 1H), 7.773 (s, 1H), 7.564 (br s, 1H), 7.108 (br s, 1H), 7.012 (d, 1H), 6.551 (s, 1H), 4.551-4.481 (m, 4H), 2.624 (d, 3H), 1.603 (s, 3H).

Example 59

Synthesis of (±)-9-(3-Cyclopropylcarbamoyl-3-hydroxy-but-1-ynyl)-8-fluoro-4,5-dihydro-6-oxa-1,3a-diaza-benzo[e]azulene-2-carboxylic acid amide

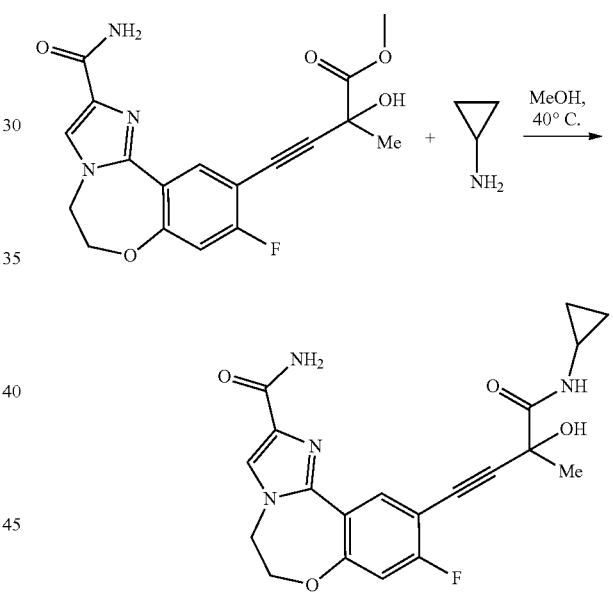

Into a 8-mL vial, was placed a solution of methyl 4-[4-carbamoyl-12-fluoro-9-oxa-3,6-diazatricyclo[8.4.0.0[2,6]] tetradeca-1(14),2,4,10,12-pentaen-13-yl]-2-hydroxy-2-methylbut-3-ynoate (120 mg, 0.32 mmol, 1.00 equiv) and cyclopropanamine (1.83 g, 32.05 mmol, 99.72 equiv) in methanol (2 mL). The resulting solution was stirred for 12 h at 40° C. in an oil bath and concentrated under vacuum. The residue was applied onto a silica gel column with dichloromethane/methanol (30:1). This resulted in 23 mg (18%) of 9-(3-Cyclopropylcarbamoyl-3-hydroxy-but-1-ynyl)-8-fluoro-4,5-dihydro-6-oxa-1,3a-diaza-benzo[e]azulene-2-carboxylic acid amide as a yellow solid. LC-MS: (ES, m/z): 399 [M+H]+; 1H-NMR: (300 MHz, DMSO-d6, ppm): δ 8.558 (d, 1H), 7.892 (d, 1H), 7.782 (s, 1H), 7.575 (br s, 1H), 7.126 (br s, 1H), 7.023 (d, 1H), 6.510 (s, 1H), 4.600-4.400 (m, 4H), 2.800-2.600 (m, 1H), 1.600 (s, 3H), 0.633-0565 (m, 4H).

Example 60

Synthesis of 8-Fluoro-9-(4-fluoro-3-fluoromethyl-3-hydroxy-but-1-ynyl)-4,5-dihydro-6-oxa-3-thia-1-aza-benzo[e]azulene-2-carboxylic acid amide

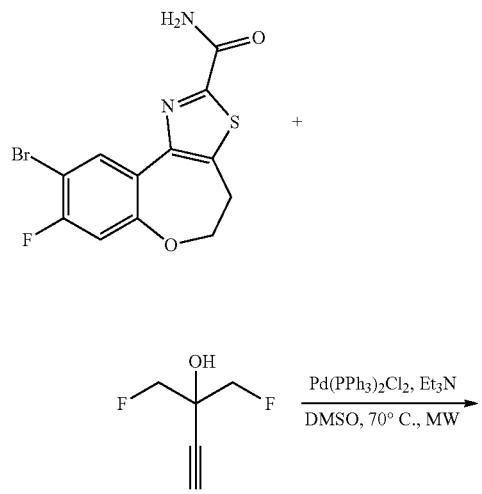

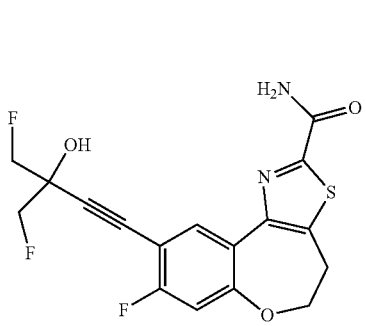

The title compound was prepared according to a procedure similar to that described in Procedure G. Into a 10-mL sealed tube purged and maintained with an inert atmosphere of nitrogen, was placed a suspension of 9-Bromo-8-fluoro-4,5-dihydro-6-oxa-3-thia-1-aza-benzo[e]azulene-2-carboxylic acid amide (200 mg, 0.58 mmol, 1.00 equiv), 1-fluoro-2-(fluoromethyl)but-3-yn-2-ol (280 mg, 1.75 mmol, 3.00 equiv) and Pd(PPh$_3$)Cl$_2$ (82 mg, 0.20 equiv) in DMSO (0.7 mL) and triethylamine (0.7 mL). The final reaction mixture was irradiated with microwave radiation for 1 h at 70° C. The resulting solution was diluted with 15 mL of water. The resulting solution was extracted with 3×15 mL of dichloromethane and the organic layers combined and dried over anhydrous sodium sulfate and concentrated under vacuum. The residue was applied onto a silica gel column with DCM:MeOH (10: 1). This resulted in 72.9 mg (32%) of 8-Fluoro-9-(4-fluoro-3-fluoromethyl-3-hydroxy-but-1-ynyl)-4,5-dihydro-6-oxa-3-thia-1-aza-benzo[e]azulene-2-carboxylic acid amide as a off-white solid. LC-MS: (ES, m/z): 383[M+H]$^+$; $^1$H-NMR: (400 MHz, CD$_3$OD, ppm) δ 8.735 (d, 1H), 6.875 (d, 1H), 4.559 (d, 4H), 4.400 (t, 2H), 3.450 (t, 2H).

Example 61

Synthesis of (±)-8-Fluoro-9-(4-fluoro-3-hydroxy-3-methyl-but-1-ynyl)-4,5-dihydro-6-oxa-3-thia-1-aza-benzo[e]azulene-2-carboxylic acid amide

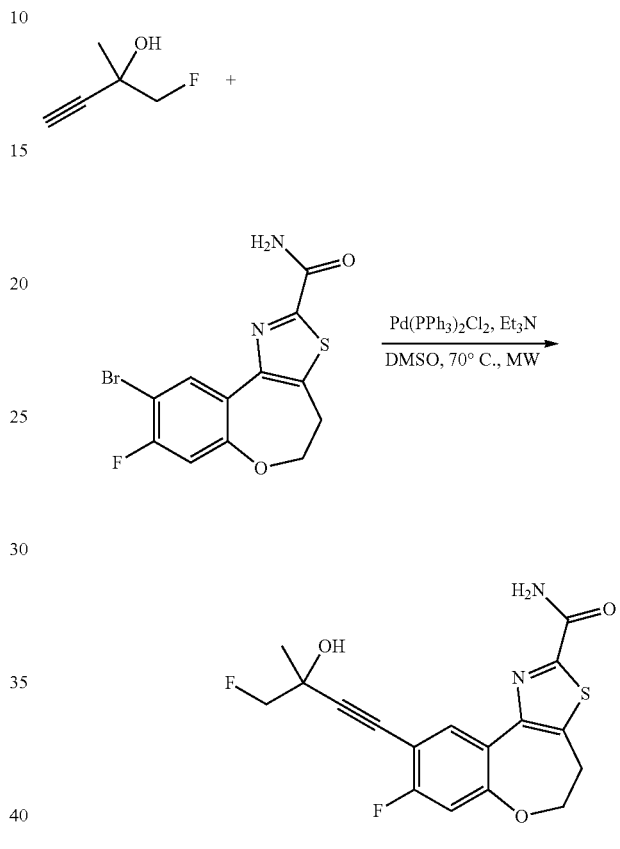

The title compound was prepared according to a procedure similar to that described in Procedure G. Into a 10-mL sealed tube purged and maintained with an inert atmosphere of nitrogen, was placed a suspension of 13-bromo-12-fluoro-9-oxa-5-thia-3-azatricyclo[8.4.0.0$^{[2,6]}$]tetradeca-1(14),2(6),3,10,12-pentaene-4-carboxamide (200 mg, 0.58 mmol, 1.00 equiv), 1-fluoro-2-methylbut-3-yn-2-ol (360 mg, 1.76 mmol, 3.00 equiv) and Pd(PPh$_3$)Cl$_2$ (82 mg, 0.20 equiv) in DMSO (0.5 mL) and triethylamine (0.5 mL). The final reaction mixture was irradiated with microwave radiation for 1 h at 70° C. The resulting solution was diluted with 10 mL of water. The resulting solution was extracted with 3×15 mL of dichloromethane and the organic layers combined and dried over anhydrous sodium sulfate and concentrated under vacuum. The residue was applied onto a silica gel column with DCM: MeOH (10:1). This resulted in 0.06 g (28%) of 8-Fluoro-9-(4-fluoro-3-hydroxy-3-methyl-but-1-ynyl)-4,5-dihydro-6-oxa-3-thia-1-aza-benzo[e]azulene-2-carboxylic acid amide. LC-MS: (ES, m/z): 365[M+H]$^+$; $^1$H-NMR: (400 MHz, CD$_3$OD, ppm) δ 8.708 (d, 1H), 6.857 (d, 1H), 4.427 (t, 2H), 4.410 (d, 2H), 3.442 (t, 2H), 1.601 (s, 3H).

Example 62

Synthesis of (±)-9-(3-Dimethylcarbamoyl-3-hydroxy-but-1-ynyl)-8-fluoro-4,5-dihydro-6-oxa-1,3a-diaza-benzo[e]azulene-2-carboxylic acid amide

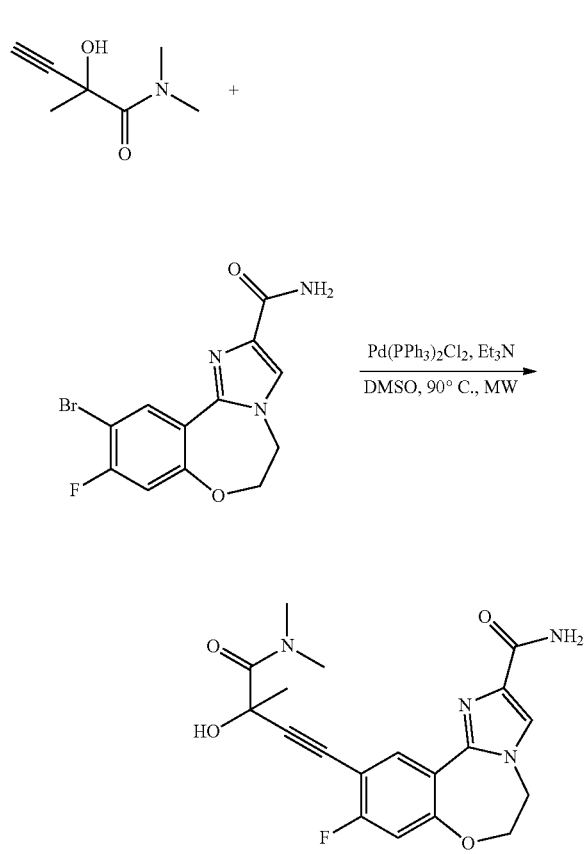

The title compound was prepared according to a procedure similar to that described in Procedure G. Into a 10-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (150 mg, 0.46 mmol, 1.00 equiv), 2-hydroxy-N,N,2-trimethylbut-3-ynamide (194 mg, 1.37 mmol, 3.00 equiv) and Pd(PPh$_3$)$_2$Cl$_2$ (32 mg, 0.05 mmol, 0.10 equiv) in DMSO/Et$_3$N (0.5/0.5 mL). The final reaction mixture was irradiated with microwave radiation for 2 h at 90° C. The resulting solution was diluted with 30 mL of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1/1). This resulted in 24.2 mg (13%) of 9-(3-Dimethylcarbamoyl-3-hydroxy-but-1-ynyl)-8-fluoro-4,5-dihydro-6-oxa-1,3a-diaza-benzo[e]azulene-2-carboxylic acid amide as a brown solid. LC-MS: (ES, m/z): 387[M+H]$^+$; $^1$H-NMR: (300 MHz, DMSO-d6, ppm) δ 8.569 (d, 1H), 7.786 (s, 1H), 7.589 (br s, 1H), 7.138 (br s, 1H), 7.038 (d, 1H), 6.235 (s, 1H), 4.580-4.450 (m, 4H), 3.340 (s, 3H), 2.901 (s, 3H), 1.661 (s, 3H).

Example 63

Synthesis of (±)-9-(3-Carbamoyl-3-hydroxy-but-1-ynyl)-8-fluoro-4,5-dihydro-6-oxa-1,3a-diaza-benzo[e]azulene-2-carboxylic acid amide

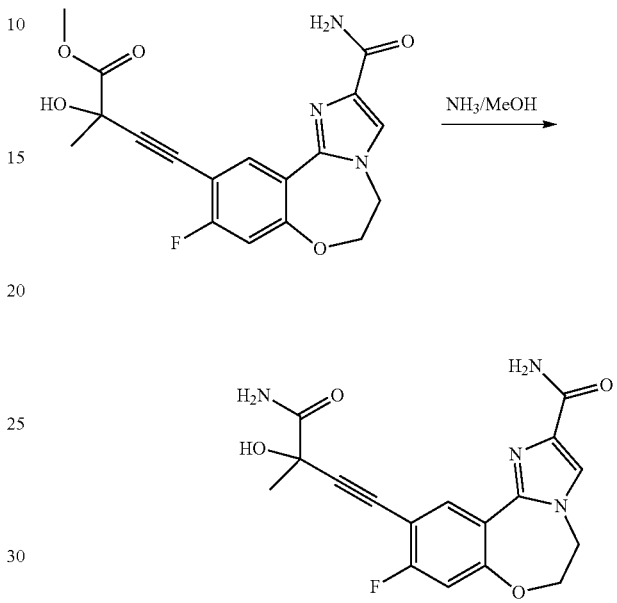

Into a 100-mL round-bottom flask, was placed a solution of methyl 4-[4-carbamoyl-12-fluoro-9-oxa-3,6-diazatricyclo[8.4.0.0$^{[2,6]}$]tetradeca-1(14),2,4,10,12-pentaen-13-yl]-2-hydroxy-2-methylbut-3-ynoate (300 mg, 0.80 mmol, 1.00 equiv) in NH$_3$/MeOH (30 w/w %, 40 mL). The resulting solution was stirred for 12 h at 25° C. The resulting mixture was concentrated under vacuum. The resulting mixture was washed with 3×10 mL of methanol and 2×5 mL of CH$_3$CN. The trace solvents were removed under reduced pressure. This resulted in 43 mg (15%) of 9-(3-Carbamoyl-3-hydroxy-but-1-ynyl)-8-fluoro-4,5-dihydro-6-oxa-1,3a-diaza-benzo[e]azulene-2-carboxylic acid amide as a brown solid. LC-MS: (ES, m/z): 359[M+H]$^+$; $^1$H-NMR: (400 MHz, DMSO-d6, ppm): δ 8.579 (d, 1H), 7.786 (s, 1H), 7.589 (br s, 1H), 7.378 (br s, 2H), 7.128 (br s, 1H), 7.029 (d, 1H), 6.423 (s, 1H), 4.600-4.410 (m, 4H), 1.612 (s, 3H).

Example 64

Synthesis of (±)-9-(4-Azetidin-1-yl-3-hydroxy-3-methyl-4-oxo-but-1-ynyl)-8-fluoro-4,5-dihydro-6-oxa-1,3a-diaza-benzo[e]azulene-2-carboxylic acid amide

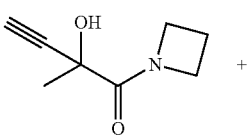

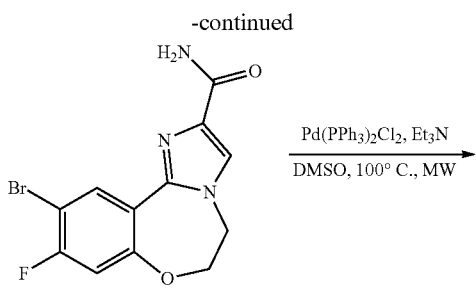

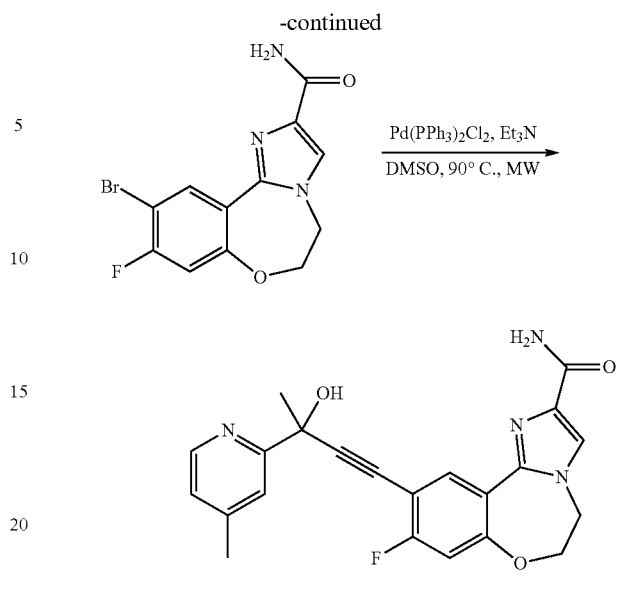

The title compound was prepared according to a procedure similar to that described in Procedure G. Into a 10-mL sealed tube purged and maintained with an inert atmosphere of nitrogen, was placed a solution of 1-(azetidin-1-yl)-2-hydroxy-2-methylbut-3-yn-1-one (211 mg, 1.38 mmol, 3.00 equiv), 9-Bromo-4,5-dihydro-6-oxa-1,3a-diaza-benzo[e]azulene-2-carboxylic acid amide (150 mg, 0.46 mmol, 1.00 equiv) and Pd(PPh$_3$)$_2$Cl$_2$ (32 mg, 0.05 mmol, 0.10 equiv) in DMSO/Et$_3$N (0.5/0.5 mL). The final reaction mixture was irradiated with microwave radiation for 2 h at 100° C. The resulting solution was diluted with 20 ml of H$_2$O. The resulting solution was extracted with 3×100 ml of ethyl acetate and the organic layers combined, dried over anhydrous sodium sulfate, filtered and concentrated under vacuum. The residue was applied onto a silica gel column with petroleum ether/ethyl acetate (1/1). This resulted in 40 mg (22%) of 9-(4-Azetidin-1-yl-3-hydroxy-3-methyl-4-oxo-but-1-ynyl)-8-fluoro-4,5-dihydro-6-oxa-1,3a-diaza-benz[e]azulene-2-carboxylic acid amide as a yellow solid. LC-MS: (ES, m/z): 399[M+H]$^{+1}$H-NMR: (300 MHz, DMSO-d6, ppm): δ8.576 (d, 1H), 7.784 (s, 1H) 7.590 (br s, 1H), 7.134 (br s, 1H), 7.036 (d, 1H), 6.138 (s, 1H), 4.523-4.446 (m, 6H), 3.932 (t, 2H), 2.282-2.182 (m, 2H), 1.589 (s, 3H).

Example 65

Synthesis of (±)-8-Fluoro-9-[3-hydroxy-3-(4-methyl-pyridin-2-yl)-but-1-ynyl]-4,5-dihydro-6-oxa-1,3a-diaza-benzo[e]azulene-2-carboxylic acid amide

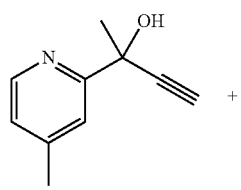 +

The title compound was prepared according to a procedure similar to that described in Procedure G. Into a 10-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (300 mg, 0.92 mmol, 1.00 equiv), 2-(4-methylpyridin-2-yl)but-3-yn-2-ol (520 mg, 3.23 mmol, 3.50 equiv) and Pd(PPh$_3$)$_2$Cl$_2$ (130 mg, 0.19 mmol, 0.20 equiv) in DMSO/TEA (1/1 mL). The final reaction mixture was irradiated with microwave radiation for 2 h at 90° C. The resulting solution was diluted with 20 mL of water. The resulting solution was extracted with 4×50 mL of dichloromethane and the organic layers combined and dried over anhydrous sodium sulfate and concentrated under vacuum. The residue was purified by Prep-HPLC with the following conditions 1#-Pre-HPLC-016(Waters)): Column, Xbridge Prep C18, 5 um, 19*50 mm; mobile phase, water with 0.5% NH$_4$HCO$_3$ and CH$_3$CN (35% CH$_3$CN up to 55% in 17 min); Detector, uv 254/220 nm. This resulted in 39 mg (10%) of 8-Fluoro-9-[3-hydroxy-3-(4-methyl-pyridin-2-yl)-but-1-ynyl]-4,5-dihydro-6-oxa-1,3a-diaza-benzo[e]azulene-2-carboxylic acid amide as a brown solid. LC-MS: (ES, m/z): 407[M+H]$^+$; $^1$H-NMR: (400 MHz, DMSO-d6, ppm) δ 8.539 (d, 1H), 8.419 (d, 1H), 7.780 (s, 1H), 7.596 (s, 1H), 7.576 (br s, 1H), 7.164 (d, 1H), 7.127 (br s, 1H), 7.010 (d, 1H), 6.378 (s, 1H), 4.530-4.450 (m, 4H), 2.370 (s, 3H), 1.809 (s, 3H).

Example 66

Synthesis of (±)-8-Fluoro-9-(3-hydroxy-3-pyridin-2-yl-but-1-ynyl)-4,5-dihydro-6-oxa-1,3a-diaza-benzo[e]azulene-2-carboxylic acid amide

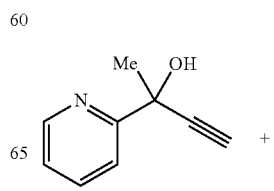 +

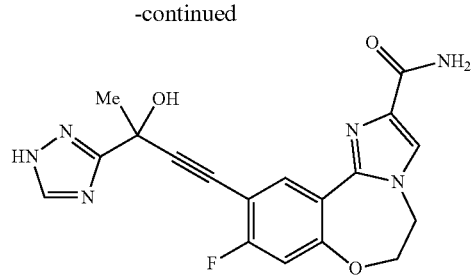

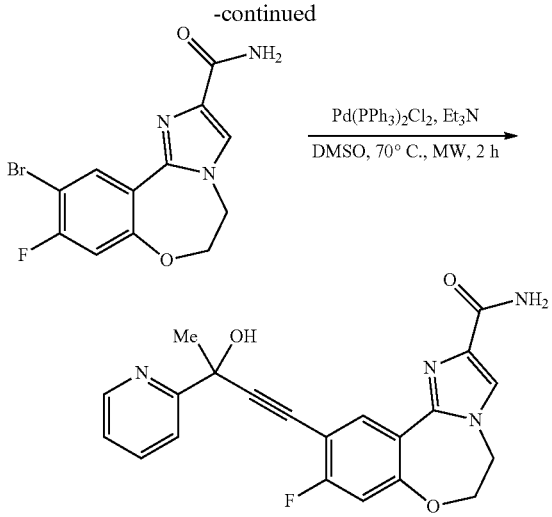

The title compound was prepared according to a procedure similar to that described in Procedure G. In a 5-mL sealed tube, was placed a suspension of 9-Bromo-4,5-dihydro-6-oxa-1,3a-diaza-benzo[e]azulene-2-carboxylic acid amide (220 mg, 0.67 mmol, 1.00 equiv), 2-(pyridin-2-yl)but-3-yn-2-ol (294 mg, 2.00 mmol, 2.96 equiv) and Pd(PPh3)2Cl2 (49 mg) in triethylamine (2 mL) and DMSO (2 mL). The final reaction mixture was degassed with N2, then sealed and irradiated with microwave radiation for 2 h at 70° C. After cooling to room temperature, the resultant mixture was diluted by EtOAc (20 mL), then washed by water (10×2 mL) and brine (10 mL), dried over anhydrous sodium sulfate, filtered and concentrated under vacuum. The residue was further purified by FC(Silica, Ethyl acetate:Petroleum ether 2:1) to give 80 mg (30%) of 8-Fluoro-9-(3-hydroxy-3-pyridin-2-yl-but-1-ynyl)-4,5-dihydro-6-oxa-1,3a-diaza-benzo[e]azulene-2-carboxylic acid amide as a gray solid. LC-MS: (ES, m/z): 393 [M+H]+ H-NMR: (300 MHz, DMSO-d6, ppm) δ: 8.568-8.520 (m, 2H), 7.883-7.826 (m, 1H), 7.768-7.744 (m, 2H), 7.556 (br s, 1H), 7.347-7.303 (m, 1H), 7.103 (br s, 1H), 6.997 (d, 1H), 6.404 (s, 1H), 4.522-4.464 (m, 4H), 1.816 (s, 3H).

Example 67

Synthesis of (±)-8-Fluoro-9-[3-hydroxy-3-(1H-[1,2,4]triazol-3-yl)-but-1-ynyl]-4,5-dihydro-6-oxa-1,3a-diaza-benzo[e]azulene-2-carboxylic acid amide

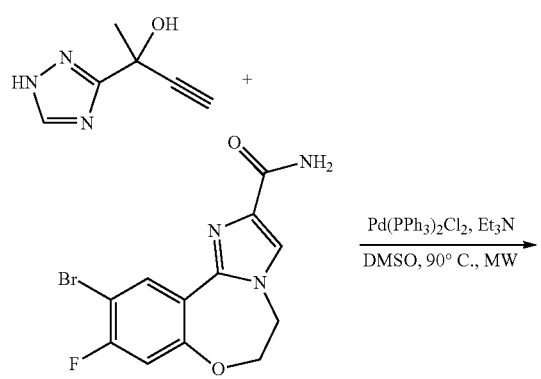

The title compound was prepared according to a procedure similar to that described in Procedure G. Into a 10-mL pressure tank reactor purged and maintained with an inert atmosphere of nitrogen, was placed a suspension of 9-bromo-4,5-dihydro-6-oxa-1,3a-diaza-benzo[e]azulene-2-carboxylic acid amide (170 mg, 0.52 mmol, 1.00 equiv), 2-(1H-1,2,4-triazol-3-yl)but-3-yn-2-ol (250 mg, 1.82 mmol, 3.50 equiv) and Pd(PPh3)Cl2 (146 mg, 0.50 equiv) in DMSO (1 mL) and triethylamine (1 mL). The final reaction mixture was irradiated with microwave radiation for 2 h at 90° C. Cooled to room temperature and diluted with 40 mL of ethyl acetate and washed with 10 mL of brine, dried over anhydrous sodium sulfate, filtered and concentrated under vacuum. The residue (200 mg) was purified by Prep-HPLC with the following conditions (1#-Pre-HPLC-006(Waters)): Column, 1#-PrepC-010(XBridge $C_{is}$ 19*100 18600297801471381 83113 09), n; mobile phase, water with 50 mmol NH4HCO3 and CH3CN (5% CH3CN up to 40% in 10 min, up to 100% in 1.5 min, down to 5% in 2 min); Detector, UV 220/254 nm. 40 mg product was obtained. This resulted in 40 mg (19.8%) of 8-Fluoro-9-[3-hydroxy-3-(1H-[1,2,4]triazol-3-yl)-but-1-ynyl]-4,5-dihydro-6-oxa-1,3a-diaza-benzo[e]azulene-2-carboxylic acid amide as a off-white solid. LC-MS: (ES, m/z): 383[M+H]+; 1H-NMR: (400 MHz, DMSO-d6, ppm) δ 8.547 (d, 1H), 8.488 (br s, 1H), 7.892 (hr s, 1H), 7.761 (s, 1H), 7.004 (d, 1H), 4.560-4.410 (m, 4H), 1.853 (s, 3H).

Example 68

Synthesis of (±)-8-Fluoro-9-[3-hydroxy-3-(1-methyl-1H-imidazol-2-yl)-but-1-ynyl]-4,5-dihydro-6-oxa-1,3a-diaza-benzo[e]azulene-2-carboxylic acid amide

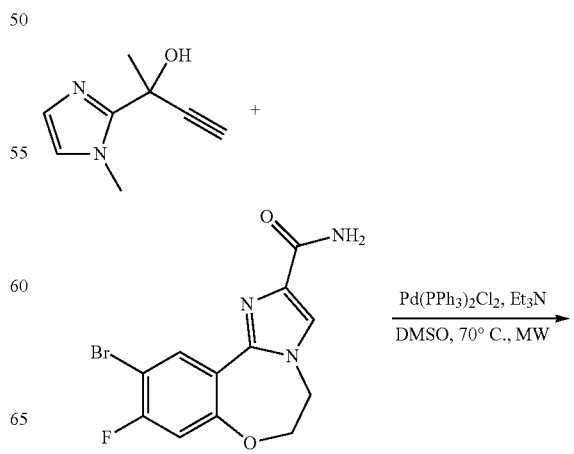

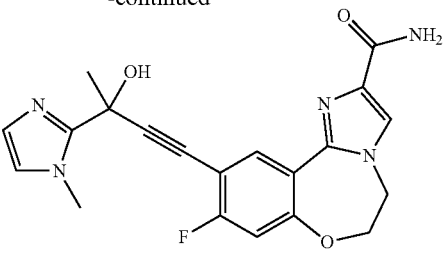

The title compound was prepared according to a procedure similar to that described in Procedure G. In a 5-mL sealed tube, was placed a suspension of 2-(1-methyl-1H-imidazol-2-yl)but-3-yn-2-ol (150 mg, 1.00 mmol, 2.96 equiv), 9-Bromo-4,5-dihydro-6-oxa-1,3a-diaza-benzo[e]azulene-2-carboxylic acid amide (110 mg, 0.34 mmol, 1.00 equiv) and Pd(PPh$_3$)$_2$Cl$_2$ (21 mg, 0.03 mmol, 0.09 equiv) in triethylamine (1 mL) and DMSO (1 mL). The final reaction mixture was degassed with N$_2$, and then irradiated with microwave radiation for 2 h at 70° C. After cooling to room temperature, the resultant mixture was diluted by ethyl acetate (20 mL), then washed by water (10×2 mL) and brine (10 mL), dried over anhydrous sodium sulfate, filtered and concentrated under vacuum. The residue was further purified by FC(Silica, Ethyl acetate:Petroleum ether 2:1) to give 22 mg (16%) of 8-Fluoro-9-[3-hydroxy-3-(1-methyl-1H-imidazol-2-yl)-but-1-ynyl]-4,5-dihydro-6-oxa-1,3a-diaza-benzo[e]azulene-2-carboxylic acid amide as a white solid. LC-MS: (ES, m/z): 396[M+H]$^+$; $^1$H-NMR: (400 MHz, DMSO-d6, ppm) δ 8.560 (d, 1H), 7.781 (s, 1H), 7.578 (br s, 1H), 7.160 (s, 1H), 7.130 (br s, 1H), 7.030 (d, 1H), 6.788 (s, 1H), 6.359 (s, 1H), 4.534-4.494 (m, 4H), 3.892 (s, 3H), 1.971 (s, 3H).

Example 69

Synthesis of (±)-8-Fluoro-9-(4,4,4-trifluoro-3-hydroxy-3-methyl-but-1-ynyl)-4,5-dihydro-6-oxa-1,3a-diaza-benzo[e]azulene-2-carboxylic acid amide

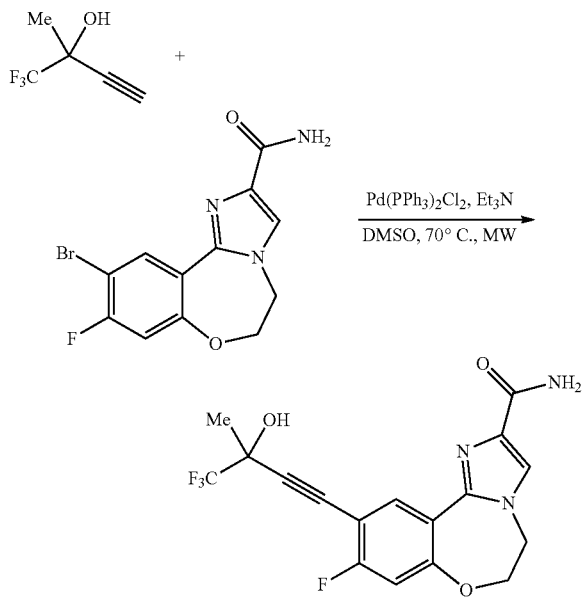

The title compound was prepared according to a procedure similar to that described in Procedure G. Into a 10-mL pressure tank reactor purged and maintained with an inert atmosphere of nitrogen, was placed a suspension of 9-Bromo-4,5-dihydro-6-oxa-1,3a-diaza-benzo[e]azulene-2-carboxylic acid amide (170 mg, 0.52 mmol, 1.00 equiv), 1,1,1-trifluoro-2-methylbut-3-yn-2-ol (509 mg, 1.84 mmol, 3.50 equiv) and Pd(PPh$_3$)Cl$_2$ (183 mg, 0.50 equiv) in DMSO (1 mL) and triethylamine (1 mL). The final reaction mixture was irradiated with microwave radiation for 2 h at 70° C. The resulting solution was diluted with 150 mL of dichloromethane. The resulting mixture was washed with 2×30 mL of water. Dried over sodium sulfate and concentrated under vacuum. The crude product (200 mg) was purified by Prep-HPLC with the following conditions (1#-Pre-HPLC-006(Waters)): Column, 1#-PrepC-014(Atlantis T3 19*150 186003698 012139334114 02), N; mobile phase, Water with 50 mmol NH$_4$HCO$_3$ and CH$_3$CN (20% CH$_3$CN up to 50% in 13 min, hold 50% in 1.5 min, up to 95% in 1.5 min, down to 20% in 2 min); Detector, UV 220/254 nm. 80 mg product was obtained. This resulted in 80 mg (40%) of 8-Fluoro-9-(4,4,4-trifluoro-3-hydroxy-3-methyl-but-1-ynyl)-4,5-dihydro-6-oxa-1,3a-diaza-benzo[e]azulene-2-carboxylic acid amide as a white solid. LC-MS: (ES, m/z): 384[M+H]$^+$; $^1$H-NMR: (300 MHz, DMSO-d6, ppm) δ 8.614 (d, 1H), 7.790 (s, 1H), 7.569 (br s, 1H), 7.194 (s, 1H), 7.140 (br s, 1H), 7.059 (d, 1H), 4.550-4.430 (m, 4H), 1.651 (s, 3H).

Example 70

Synthesis of (±)-8-Fluoro-9-(4-fluoro-3-hydroxy-3-methyl-but-1-ynyl)-4,5-dihydro-6-oxa-1,3a-diaza-benzo[e]azulene-2-carboxylic acid amide

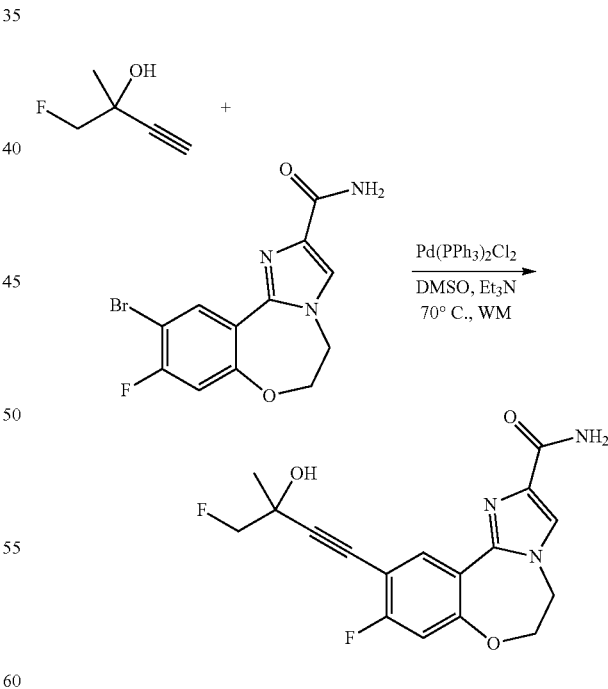

The title compound was prepared according to a procedure similar to that described in Procedure G. Into a 10-mL sealed tube purged and maintained with an inert atmosphere of nitrogen, was placed 9-Bromo-4,5-dihydro-6-oxa-1,3a-diaza-benzo[e]azulene-2-carboxylic acid amide (200 mg, 0.61 mmol, 1.00 equiv), 1-fluoro-2-methylbut-3-yn-2-ol (400 mg, 3.92 mmol, 3.50 equiv), Pd(PPh$_3$)Cl$_2$ (86 mg, 0.20 equiv), DMSO (1 mL), triethylamine (1 mL). The final reaction mixture was irradiated with microwave radiation for 2 h at 70° C. The resulting solution was diluted with 10 mL of H₂O. The solids were collected by filtration and washed with ethyl acetate (20 mL). This resulted in 70 mg (33%) of 8-Fluoro-9-(4-fluoro-3-hydroxy-3-methyl-but-1-ynyl)-4,5-dihydro-6-oxa-1,3a-diaza-benzo[e]azulene-2-carboxylic acid amide as a off-white solid. LC-MS: (ES, m/z): 348[M+H]$^+$; $^1$H-NMR: (400 MHz, DMSO-d6, ppm) δ 8.579 (d, 1H), 7.788 (s, 1H), 7.564 (s, 1H), 7.147 (s, 1H), 7.043 (d, 1H), 6.000 (s, 1H), 4.526-4.420 (m, 4H), 4.363 (d, 2H), 1.488 (s, 3H).

Example 71

Synthesis of (±)-9-(3,4-Dihydroxy-3-methyl-but-1-ynyl)-8-fluoro-4,5-dihydro-6-oxa-1,3a-diaza-benzo[e]azulene-2-carboxylic acid amide

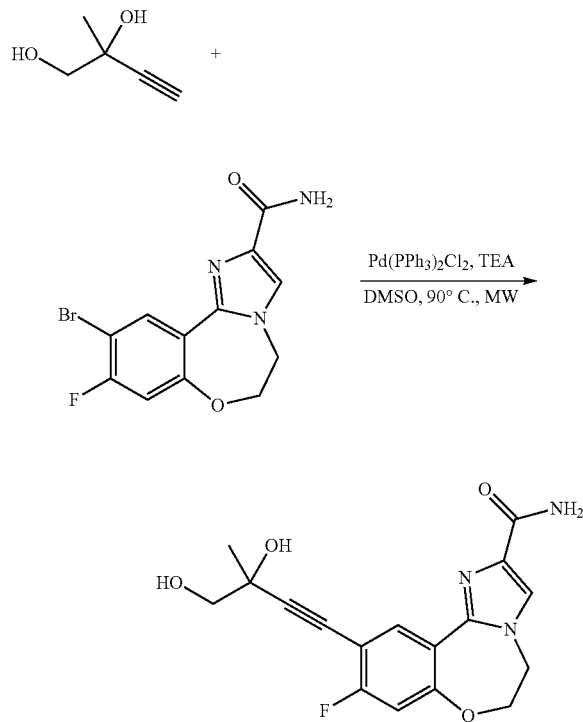

The title compound was prepared according to a procedure similar to that described in Procedure G. Into a 8-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (200 mg, 0.61 mmol, 1.00 equiv), 2-methylbut-3-yne-1,2-diol (395 mg, 1.84 mmol, 3.00 equiv) and Pd(PPh₃)₂Cl₂ (43 mg, 0.06 mmol, 0.10 equiv) in DMSO/Et₃N (1.0 mL, 1:1). The final reaction mixture was irradiated with microwave radiation for 1 h at 90° C. The resulting solution was diluted with 40 mL of ethyl acetate. The resulting mixture was washed with 2×20 mL of brine. The mixture was dried over anhydrous sodium sulfate and concentrated under vacuum. The residue was washed with 3×10 mL of methanol and 2×5 mL of acetonitrile, dried under vacuum. This resulted in 30.8 mg (15%) of 9-(3,4-Dihydroxy-3-methyl-but-1-ynyl)-8-fluoro-4,5-dihydro-6-oxa-1,3a-diaza-benzo[e]azulene-2-carboxylic acid amide as a yellow solid. LC-MS: (ES, m/z): 346 [M+H]$^+$; $^1$H-NMR: (400 MHz, DMSO-d6, ppm) δ 8.607 (d, 1H), 7.785 (s, 1H), 7.541 (br s, 1H), 7.139 (br s, 1H), 7.005 (d, 1H), 4.518-4.483 (m, 4H), 3.444-3.330 (m, 2H), 1.419 (s, 3H).

Example 72

Synthesis of (±)-8-Fluoro-9-(3-hydroxy-tetrahydro-furan-3-ylethynyl)-4,5-dihydro-6-oxa-1,3a-diaza-benzo[e]azulene-2-carboxylic acid amide

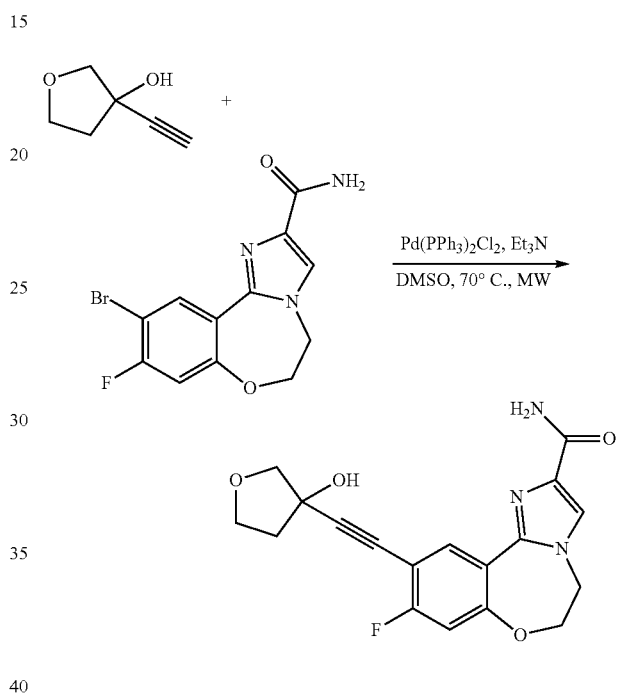

The title compound was prepared according to a procedure similar to that described in Procedure G. Into a 10-mL pressure tank reactor purged and maintained with an inert atmosphere of nitrogen, was placed a suspension of 9-Bromo-4,5-dihydro-6-oxa-1,3a-diaza-benzo[e]azulene-2-carboxylic acid amide (200 mg, 0.61 mmol, 1.00 equiv), 3-ethynyloxolan-3-ol (241 mg, 2.15 mmol, 3.50 equiv) and Pd(PPh₃)Cl₂ (43 mg, 0.06 mmol, 0.10 equiv) in DMSO (1 mL) and triethylamine (1 mL). The final reaction mixture was irradiated with microwave radiation for 2 h at 70° C. The crude product (200 mg) was purified by Prep-HPLC with the following conditions (1#-Pre-HPLC-006(Waters)): Column, 1#-PrepC-014 (Atlantis T3 19*150 186003698 012139334114 02), N; mobile phase, Water with 50 mmol NH₄HCO₃ and CH₃CN (10% CH₃CN up to 40% in 8 min, hold 40% in 1.5 min, up to 95% in 1 min, down to 10% in 2 min); Detector, UV 254/220 nm. 41 mg product was obtained. This resulted in 41 mg (19%) of 8-Fluoro-9-(3-hydroxy-tetrahydro-furan-3-ylethynyl)-4,5-dihydro-6-oxa-1,3a-diaza-benzo[e]azulene-2-carboxylic acid amide as a light brown solid. LC-MS: (ES, m/z): 358[M+H]$^+$; $^1$H-NMR: (400 MHz, DMSO-d6, ppm) δ 8.574 (d, 1H), 7.765 (s, 1H), 7.548 (br s, 1H), 7.121 (br s, 1H), 7.008 (d, 1H), 5.916 (s, 1H), 4.518-4.465 (m, 4H), 3.902 (t, 2H), 3.819 (s, 2H), 2.236 (m, 2H).

Example 73

Synthesis of ethyl 3-(2-[4-carbamoyl-12-fluoro-9-oxa-3,6-diazatricyclo[8.4.0.0[2,6]]tetradeca-1(14),2,4,10,12-pentaen-13-yl]ethynyl)-3-hydroxycyclobutane-1-carboxylate

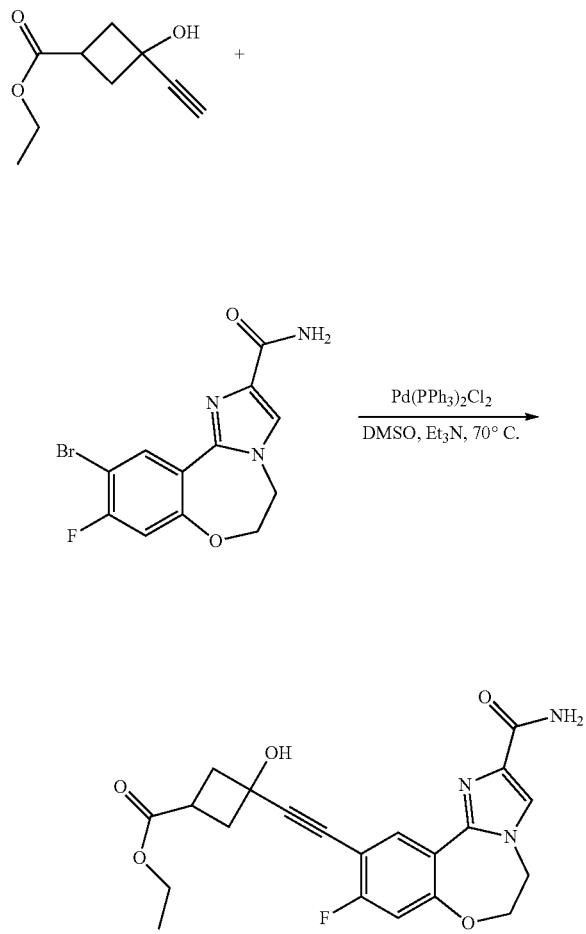

The title compound was prepared according to a procedure similar to that described in Procedure G. Into a 8-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (300 mg, 0.92 mmol, 1.00 equiv), ethyl 3-ethynyl-3-hydroxycyclobutane-1-carboxylate (600 mg, 3.57 mmol, 3.50 equiv) and Pd(PPh$_3$)Cl$_2$ (120 mg, 0.17 mmol, 0.20 equiv) in DMSO (1 mL) and triethylamine (1 mL). The resulting solution was stirred for 12 h at 70° C. The resulting solution was diluted with 20 mL, of water. The solids were collected by filtration. This resulted in 0.2 g (53%) of ethyl 3-(2-[4-carbamoyl-12-fluoro-9-oxa-3,6-diazatricyclo[8.4.0.0[2,6]]tetradeca-1(14),2,4,10,12-pentaen-13-yl]ethynyl)-3-hydroxycyclobutane-1-carboxylate as a white solid.

Example 74

Synthesis of 8-Fluoro-9-(1-hydroxy-3-hydroxymethyl-cyclobutylethynyl)-4,5-dihydro-6-oxa-1,3a-diaza-benzo[e]azulene-2-carboxylic acid amide

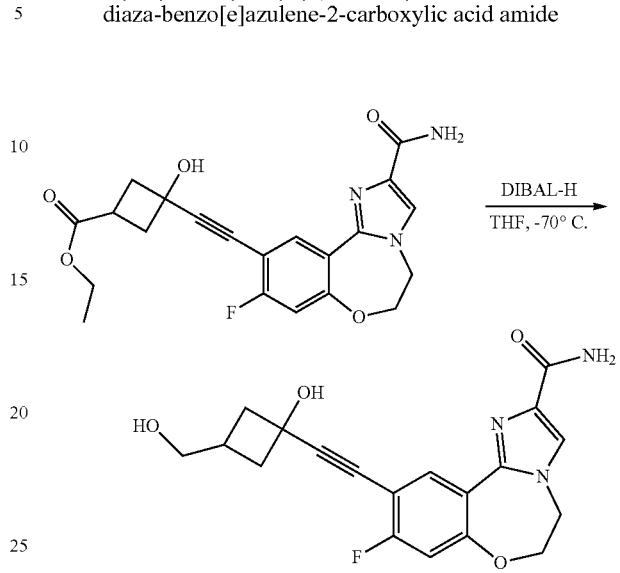

Into a 8-mL sealed tube, was placed a solution of ethyl 3-(2-[4-carbamoyl-12-fluoro-9-oxa-3,6-diazatricyclo [8.4.0.0[2,6]]tetradeca-1(14),2,4,10,12-pentaen-13-yl]ethynyl)-3-hydroxycyclobutane-1-carboxylate (140 mg, 0.34 mmol, 1.00 equiv) in tetrahydrofuran (5 mL). Then added DIBAL-H (1.0M in THF, 7 mL, 2.00 equiv) dropwise with stirring at −70° C. The resulting solution was stirred for 4 h at −70° C. The reaction was then quenched by the addition of 2 mL of 10% sodium potassium tartrate. The solids were filtered out. The mixture was diluted with 40 mL of ethyl acetate, and washed with 20 mL of brine, dried over sodium sulfate. Filtered and concentrated, the residue was purified by Prep-HPLC with the following conditions (1#-Pre-HPLC-016(Waters)): Column, Xbridge Prep C18, 5 um, 19*150 mm; mobile phase, water with 0.03% NH$_4$CO$_3$ and CH$_3$CN (10% CH$_3$CN up to 29% in 13 min); Detector, uv 254/220 nm. This resulted in 25 mg (20%) of 8-Fluoro-9-(1-hydroxy-3-hydroxymethyl-cyclobutylethynyl)-4,5-dihydro-6-oxa-1,3a-diaza-benzo[e]azulene-2-carboxylic acid amide as a white solid. (single undetermined diastereomer). LC-MS: (ES, m/z):372[M+H]$^+$ $^1$H-NMR: (400 MHz, DMSO-d6, ppm) δ 8.602 (d, 1H), 7.785 (s, 1H), 7.596 (s, 1H), 7.142 (s, 1H), 7.033 (d, 1H), 5.907 (s, 1H), 4.559-4.410 (m, 4H), 3.422 (t, 2H), 2.449 (t, 2H), 2.238-2.100 (m, 1H), 2.029 (t, 2H).

Example 75

Synthesis of (±)-8-Fluoro-9-[3-hydroxy-3-(1-methyl-1H-imidazol-4-yl)-but-1-ynyl]-4,5-dihydro-6-oxa-1,3a-diaza-benzo[e]azulene-2-carboxylic acid amide

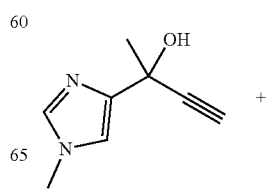

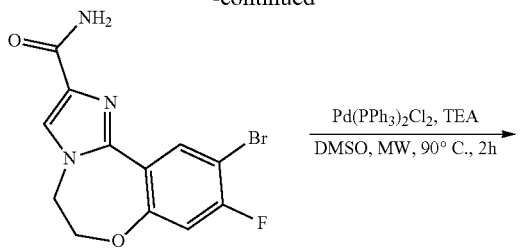

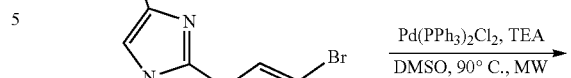

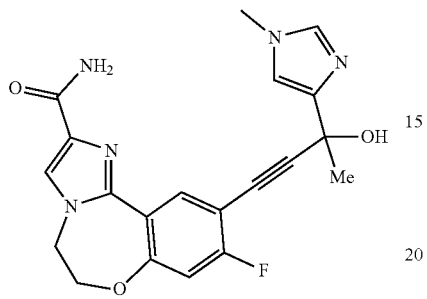

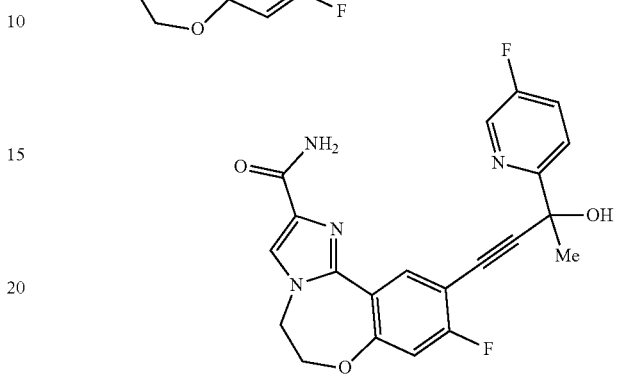

The title compound was prepared according to a procedure similar to that described in Procedure G. Into a 5-mL sealed tube, was placed a suspension of 2-(1-methyl-1H-imidazol-4-yl)but-3-yn-2-ol (150 mg, 1.00 mmol, 2.99 equiv), 9-Bromo-4,5-dihydro-6-oxa-1,3a-diaza-benzo[e]azulene-2-carboxylic acid amide (109 mg, 0.33 mmol, 1.00 equiv) and Pd(PPh$_3$)$_2$Cl$_2$ (70 mg, 0.10 mmol, 0.30 equiv) in TEA (1 mL) and DMSO (1 mL) under nitrogen atmosphere. The final reaction mixture was irradiated with microwave radiation for 2 h at 90° C. The resulting solution was diluted with 50 mL of ethyl acetate. The resulting mixture was washed with 2×10 mL of water and 1×10 mL of brine. The resulting mixture was concentrated under vacuum. The crude product was purified by Prep-HPLC with the following conditions (1#-Pre-HPLC-001(SHIMADZU)): Column, SunFire Prep C18, 19*150 mm 5 um; mobile phase, WATER WITH 0.03% NH$_3$H$_2$O and CH$_3$CN (5.0% CH$_3$CN up to 42.0% in 11 min, up to 95.0% in 2 min, down to 5.0% in 1 min); Detector, uv 254/220 nm. This resulted in 15 mg (11%) of 8-Fluoro-9-[3-hydroxy-3-(1-methyl-1H-imidazol-4-yl)-but-1-ynyl]-4,5-dihydro-6-oxa-1,3a-diaza-benzo[e]azulene-2-carboxylic acid amide as a white solid. LC-MS: (ES, m/z): 396[M+H]$^+$; $^1$H-NMR: (400 MHz, DMSO-d6, ppm): δ: 8.576 (s, 1H), 7.786 (s, 1H), 7.635 (br s, 1H), 7.585 (br s, 1H), 7.149 (br s, 1H), 7.039 (d, 1H), 6.956 (d, 1H), 6.269 (d, 1H), 4.560-4.410 (m, 4H), 3.857 (s, 3H), 1.905 (s, 3H).

The title compound was prepared according to a procedure similar to that described in Procedure G. In a 5-mL sealed tube, was placed a solution of 2-(5-fluoropyridin-2-yl)but-3-yn-2-ol (248 mg, 1.50 mmol, 3.00 equiv), 9-Bromo-4,5-dihydro-6-oxa-1,3a-diaza-benzo[e]azulene-2-carboxylic acid amide (163 mg, 0.50 mmol, 1.00 equiv) and Pd(PPh3)$_2$Cl2 (35 mg, 0.05 mmol, 0.10 equiv) in triethylamine (1 mL) and DMSO (1 mL). The final reaction mixture was irradiated with microwave radiation for 1 h at 90° C. The resulting solution was diluted with 50 mL of ethyl acetate. The resulting mixture was washed with 2×15 mL of water and 1×15 mL of brine. The mixture was dried over anhydrous sodium sulfate and concentrated under vacuum. The crude product was purified by Prep-HPLC with the following conditions (1#-Pre-HPLC-006(Waters)): Column, SunFire Prep C18, 19*150 mm 5 um; mobile phase, Water with 50 mmolNH$_4$HCO$_3$ and CH$_3$CN (20.0% CH$_3$CN up to 54.0% in 10 min, up to 95.0% in 2 min, down to 20.0% in 1 min); Detector, uv 254/220 nm. This resulted in 55 mg (27%) of 8-Fluoro-9-[3-(5-fluoro-pyridin-2-yl)-3-hydroxy-but-1-ynyl]-4,5-dihydro-6-oxa-1,3a-diaza-benzo[e]azulene-2-carboxylic acid amide as a gray solid. LC-MS: (ES, m/z): 411[M+H]$^+$; $^1$H-NMR: (300 MHz, DMSO-d6, ppm): δ: 8.555 (s, 1H), 8.546 (d, 1H), 7.844-7.748 (m, 3H), 7.739 (br s, 1H), 7.125 (br s, 1H), 7.018 (d, 1H), 6.523 (s, 1H), 4.528-4.471 (m, 1H), 1.819 (s, 1H).

Example 76

Synthesis of (±)-8-Fluoro-9-[3-(5-fluoro-pyridin-2-yl)-3-hydroxy-but-1-ynyl]-4,5-dihydro-6-oxa-1,3a-diaza-benzo[e]azulene-7-carboxylic acid amide Example 77

Synthesis of (±)-9-[3-(5-Chloro-pyridin-2-yl)-3-hydroxy-but-1-ynyl]-8-fluoro-4,5-dihydro-6-oxa-1,3a-diaza-benzo[e]azulene-2-carboxylic acid amide

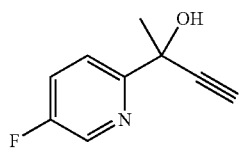 +

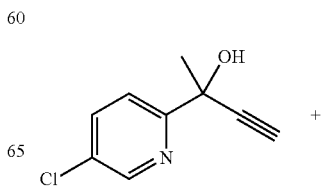 +

-continued

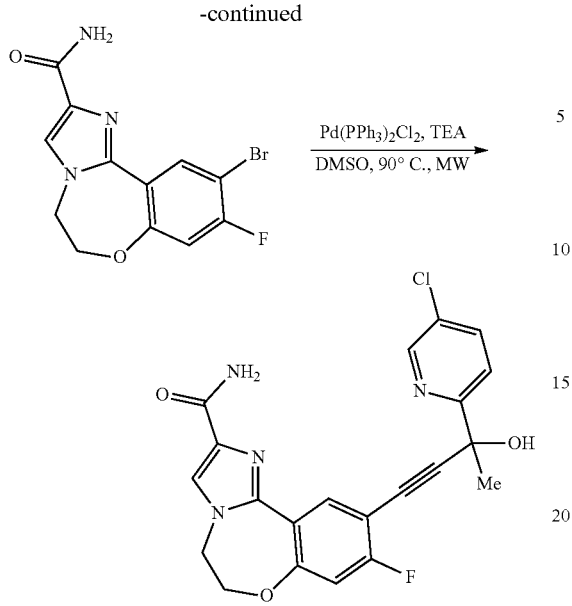

The title compound was prepared according to a procedure similar to that described in Procedure G. In a 5-mL sealed tube, was placed a solution of 2-(5-chloropyridin-2-yl)but-3-yn-2-ol (273 mg, 1.50 mmol, 3.01 equiv), 9-Bromo-4,5-dihydro-6-oxa-1,3a-diaza-benzo[e]azulene-2-carboxylic acid amide (163 mg, 0.50 mmol, 1.00 equiv), Pd(PPh₃)₂Cl₂ (35 mg, 0.05 mmol, 0.10 equiv) in DMSO (1 mL) and triethylamine (1 mL). The final reaction mixture was irradiated with microwave radiation for 1 h at 90° C. The reaction mixture was cooled to room temperature in air. The resulting solution was diluted with 50 mL of ethyl acetate. The resulting mixture was washed with 2×15 mL of water and 1×15 mL of brine. The mixture was dried over anhydrous sodium sulfate, filtered and concentrated under vacuum. The crude product (200 mg) was purified by Prep-HPLC with the following conditions (1#-Pre-HPLC-016(Waters)): Column, Xbridge Prep C18, 5 um, 19*50 mm; mobile phase, water with 0.03% NH₃H₂O and CH₃CN (39.0% CH₃CN up to 69.0% in 11 min, hold 95.0% in 2 min, hold 39.0% in 1 min); Detector, uv 254/220 nm. This resulted in 60 mg (28%) of 9-[3-(5-Chloro-pyridin-2-yl)-3-hydroxy-but-1-ynyl]-8-fluoro-4,5-dihydro-6-oxa-1,3a-diaza-benzo[e]azulene-2-carboxylic acid amide as a gray solid. LC-MS: (ES, m/z): 427[M+H]⁺; ¹H-NMR: (300 MHz, DMSO-d6, ppm): δ: 8.626 (d, 1H), 8.541 (d, 1H), 8.005 (AB, 1H), 7.977 (AB, 1H), 7.973 (s, 1H), 7.561 (br s, 1H), 7.128 (br s, 1H), 7.056 (d, 1H), 6.572 (s, 1H), 4.529-4.471 (m, 1H), 1.815 (s, 1H).

Example 78

Synthesis of 8-Fluoro-9-(4-fluoro-3-fluoromethyl-3-hydroxy-but-1-ynyl)-4,5-dihydro-6-oxa-1,3a-diaza-benzo[e]azulene-2-carboxylic acid amide

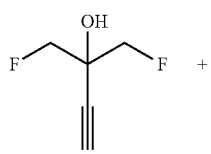

-continued

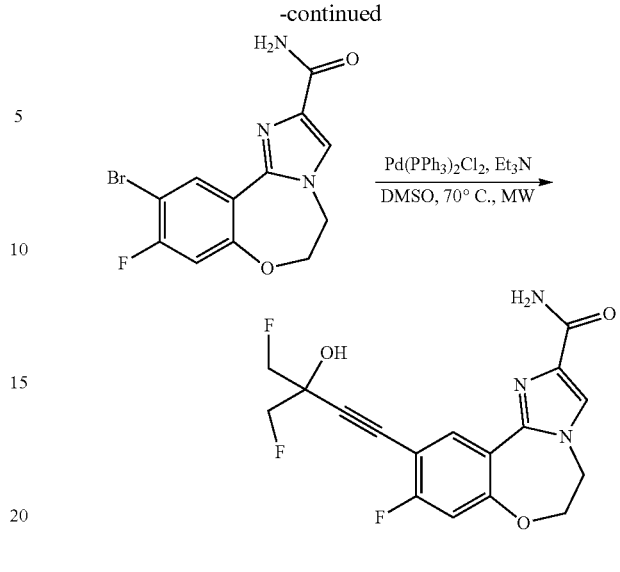

The title compound was prepared according to a procedure similar to that described in Procedure G. Into a 10-mL sealed tube purged and maintained with an inert atmosphere of nitrogen, was placed a suspension of 9-Bromo-4,5-dihydro-6-oxa-1,3a-diaza-benzo[e]azulene-2-carboxylic acid amide (200 mg, 0.61 mmol, 1.00 equiv), 1-fluoro-2-(fluoromethyl)but-3-yn-2-ol (300 mg, 2.50 mmol, 3.00 equiv) and Pd(PPh₃)Cl₂ (0.86 g, 0.20 equiv) in DMSO (0.7 mL) and triethylamine (0.7 mL). The final reaction mixture was irradiated with microwave radiation for 1 h at 70° C. The resulting solution was diluted with 10 mL of water. The solids were collected by filtration. The crude product was re-crystallized from methanol:water in the ratio of 3:1. This resulted in 42 mg (18%) of 8-Fluoro-9-(4-fluoro-3-fluoromethyl-3-hydroxy-but-1-ynyl)-4,5-dihydro-6-oxa-1,3a-diaza-benzo[e]azulene-2-carboxylic acid amide as a off-white solid. LC-MS (ES, m/z): 366[M+H]⁺; ¹H-NMR (300 MHz, DMSO-d6, ppm) δ 8.600 (d, 1H), 7.787 s, 1H), 7.541 (br s, 1H), 7.143 (br s, 1H), 7.047 (d, 1H), 6.546 (s, 1H), 4.527 (m, 4H), 4.508 (d, 4H).

Example 79

Synthesis of (±)-8-Fluoro-9-(3-hydroxy-4-methoxy-3-methyl-but-1-ynyl)-4,5-dihydro-6-oxa-1,3a-diaza-benzo[e]azulene-2-carboxylic acid amide

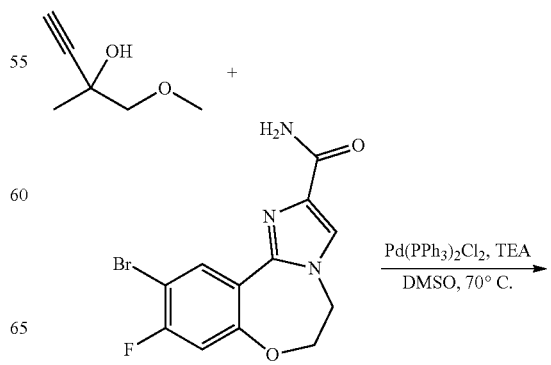

-continued

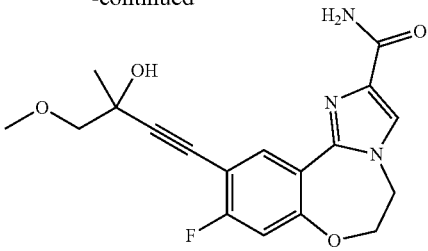

The title compound was prepared according to a procedure similar to that described in Procedure G. Into a 20-mL sealed tube purged and maintained with an inert atmosphere of nitrogen, was placed a suspension of 1-methoxy-2-methylbut-3-yn-2-ol (300 mg, 2.63 mmol, 3.00 equiv), 9-Bromo-4,5-dihydro-6-oxa-1,3a-diaza-benzo[e]azulene-2-carboxylic acid amide (285.6 mg, 0.88 mmol, 1.00 equiv) and Pd(PPh$_3$)$_2$Cl$_2$ (184.5 mg, 0.26 mmol, 0.30 equiv) in DMSO (1 mL) and triethylamine (1 mL) and stirred for 12 h at 70° C. in an oil bath. The resulting solution was diluted with 10 mL of water. Then filtered and the filter cake was washed with 10 mL of acetonitrile and 10 mL hexane to give 59.1 mg (19%) of 8-Fluoro-9-(3-hydroxy-4-methoxy-3-methyl-but-1-ynyl)-4,5-dihydro-6-oxa-1,3a-diaza-benzo[e]azulene-2-carboxylic acid amide as a gray solid. LC-MSO: (ES, m/z): 360[M+H]$^+$; $^1$H-NMR (300 MHz, CD$_3$OD, ppm) δ: 8.613 (d, 1H), 7.735 (s, 1H), 7.461 (br s, 1H), 6.856 (d, 1H), 4.600-4.410 (m, 4H), 3.521 (s, 2H), 3.494 (s, 3H), 1.554 (s, 3H).

Example 80

Synthesis of 9-[(S)-3-Hydroxy-3-(5-methyl-isoxazol-3-yl)-but-1-ynyl]-4,5-dihydro-6-oxa-1,3a-diaza-benzo[e]azulene-2-carboxylic acid amide

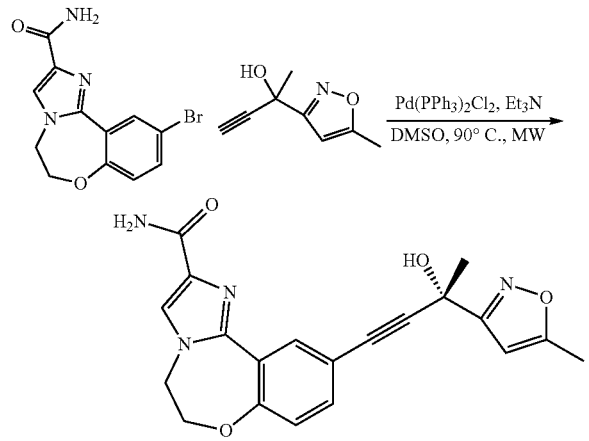

9-[(S)-3-Hydroxy-3-(5-methyl-isoxazol-3-yl)-but-1-ynyl]-4,5-dihydro-6-oxa-1,3a-diaza-benzo[e]azulene-2-carboxylic acid amide. The title compound was prepared according to a procedure similar to that described in Procedure G Into a 8-mL sealed tube purged and maintained with an inert atmosphere of nitrogen, was placed 2-(5-methylisoxazol-3-yl)but-3-yn-2-ol (515 mg, 3.41 mmol, 3.50 equiv), 13-bromo-9-oxa-3,6-diazatricyclo[8.4.0.0$^{2,6}$]tetradeca-1(14),2,4,10,12-pentaene-4-carboxamide (300 mg, 0.97 mmol, 1 equiv) and Pd(PPh$_3$)$_2$Cl$_2$ (205 mg, 0.29 mmol, 0.3 equiv) in DMSO (2 mL) and triethylamine (2 mL). The final reaction mixture was irradiated with microwave radiation for 2 h at 70° C. The resulting mixture was washed with 1×100 mL of water and 2×100 mL of CH$_3$CN. The solids were collected by filtration. The residue was further purified by Chiral-Prep-HPLC with the following conditions (2#-Gilson Gx 281(HPLC-09): Column, Chiralpak IA2*25 cm, 5 um Chiral-P(IA)004IA00CJ-MB003; Phase A:MTBE Phase B:EtOH (0.2% DEA)-HPLC (10.0% EtOH for 60 min, then down to 0%); Detector, uv 254/220 nm. This resulted in 34.2 mg (9%) of 9-[(S)-3-Hydroxy-3-(5-methyl-isoxazol-3-yl)-but-1-ynyl]-4,5-dihydro-6-oxa-1,3a-diaza-benzo[e]azulene-2-carboxylic acid amide as a off-white solid LC-MS (ES, m/z): 379[M+H]$^+$; $^1$H-NMR (400 MHz, DMSO-d6, ppm): δ 8.536 (s, 1H), 7.802 (s, 1H), 7.558 (br s, 1H), 7.340-7.300 (m, 1H), 7.143 (br s, 1H), 7.040 (d, 1H), 6.504 (s, 1H), 6.360 (s, 1H), 4.492 (s, 4H), 2.365 (s, 3H), 1.920 (s, 3H).

Example 81

Synthesis of (±)-9-(3,4-Dihydroxy-3-methyl-but-1-ynyl)-8-fluoro-4,5-dihydro-6-oxa-3-thia-1-aza-benzo azulene-2-carboxylic acid amide

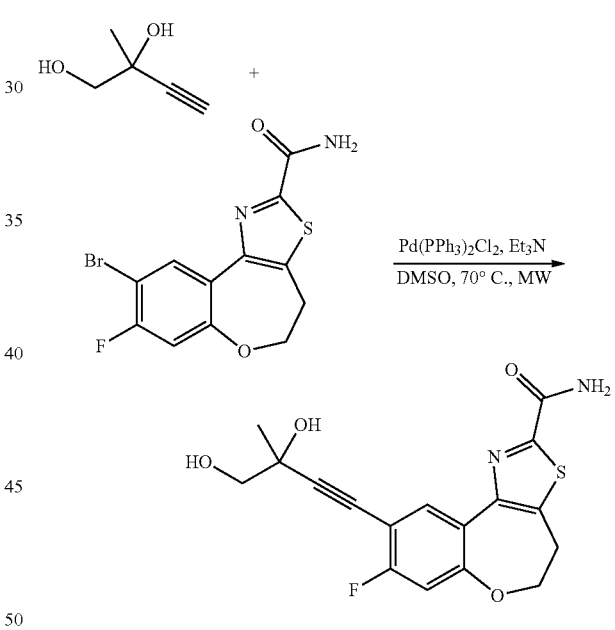

The title compound was prepared according to a procedure similar to that described in Procedure G. Into a 8-mL sealed tube purged and maintained with an inert atmosphere of nitrogen, was placed a suspension of 9-Bromo-8-fluoro-4,5-dihydro-6-oxa-3-thia-1-aza-benzo[e]azulene-2-carboxylic acid amide (200 mg, 0.58 mmol, 1.00 equiv), 2-methylbut-3-yne-1,2-diol (200 mg, 2.00 mmol, 3.50 equiv) and Pd(PPh$_3$)$_2$Cl$_2$ (40 mg, 0.06 mmol, 0.10 equiv) in DMSO (1 mL) and triethylamine (1 mL). The final reaction mixture was irradiated with microwave radiation for 1 h at 70° C. The resulting solution was diluted with 20 mL, of water. The solids were collected by filtration and washed by acetonitrile (10 mL). This resulted in 30 mg (14%) of 9-(3,4-Dihydroxy-3-methyl-but-1-ynyl)-8-fluoro-4,5-dihydro-6-oxa-3-thia-1-aza-benzo[e]azulene-2-carboxylic acid amide as a light brown solid. LC-MS (ES, m/z): 363[M+H]$^+$; $^1$H-NMR (300 MHz, DMSO-d6, ppm) δ

8.64 (d, 1H), 8.438 (br s, 1H), 7.873 (br s, 1H), 6.997 (d, 1H), 5.397 (s, 1H), 4.971 (t, 1H), 4.383 (t, 2H), 3.510-3.380 (m, 4H), 1.426 (s, 3H).

Example 82

Synthesis of (±)-8-Fluoro-9-(3-hydroxy-3-pyridin-2-yl-but-1-ynyl)-4,5-dihydro-6-oxa-3-thia-1-aza-benzo[e]azulene-2-carboxylic acid amide

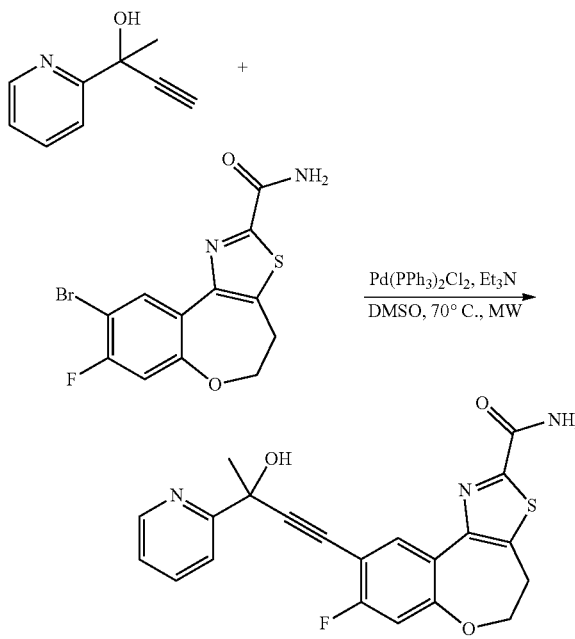

The title compound was prepared according to a procedure similar to that described in Procedure G. Into a 8-mL sealed tube purged and maintained with an inert atmosphere of nitrogen, was placed a suspension 9-Bromo-8-fluoro-4,5-dihydro-6-oxa-3-thia-1-aza-benzo[e]azulene-2-carboxylic acid amide (200 mg, 0.58 mmol, 1.00 equiv), 2-(pyridin-2-yl)but-3-yn-2-ol (300 mg, 2.04 mmol, 3.50 equiv) and Pd(PPh$_3$)$_2$Cl$_2$ (200 mg, 0.28 mmol, 0.50 equiv) in DMSO (0.5 mL) and triethylamine (0.5 mL). The final reaction mixture was irradiated with microwave radiation for 3 h at 70° C. The resulting solution was diluted with 50 mL of ethyl acetate. The resulting mixture was washed with 3×25 mL of water. The mixture was dried over sodium sulfate and concentrated under vacuum. The residue was purified by Prep-HPLC with the following conditions (1#-Pre-HPLC-016(Waters)): Column, XSelect Prep C18; mobile phase, water with 0.05% NH$_3$H$_2$O and CH$_3$CN (23% CH$_3$CN up to 63% in 10 min, hold 3 min); Detector, uv 254/220 nm. This resulted in 18 mg (7%) of 8-Fluoro-9-(3-hydroxy-3-pyridin-2-yl-but-1-ynyl)-4,5-dihydro-6-oxa-3-thia-1-aza-benzo[e]azulene-2-carboxylic acid amide as a light yellow solid. LC-MS (ES, m/z): 410[M+H]$^+$; $^1$H-NMR (400 MHz, DMSO-d6, ppm) δ 8.657 (d, 1H), 8.574 (d, 1H), 8.482 (s, 1H), 7.884 (m, 2H), 7.792 (d, 1H), 7.352 (m, 1H), 7.020 (d, 1H), 6.383 (s, 1H), 4.386 (t, 2H), 3.408 (t, 2H), 1.841 (s, 3H).

Example 83

Synthesis of 8-Fluoro-9-(3-hydroxy-3-methyl-but-1-ynyl)-4,5-dihydro-6-oxa-3-thia-1-aza-benzo[e]azulene-2-carboxylic acid amide

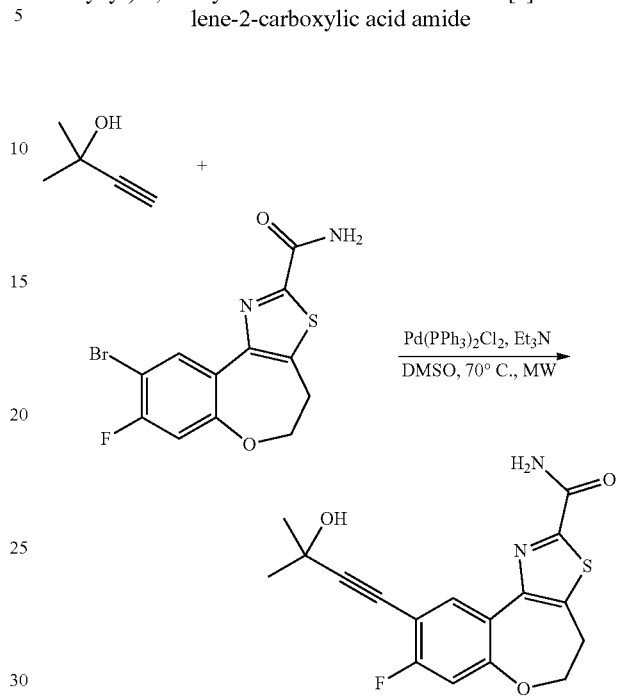

The title compound was prepared according to a procedure similar to that described in Procedure G. Into a 8-mL sealed tube purged and maintained with an inert atmosphere of nitrogen, was placed a suspension of 9-Bromo-8-fluoro-4,5-dihydro-6-oxa-3-thia-1-aza-benzo[e]azulene-2-carboxylic acid amide (300 mg, 0.87 mmol, 1.00 equiv), 2-methylbut-3-yn-2-ol (260 mg, 3.09 mmol, 3.50 equiv) and Pd(PPh$_3$)$_2$Cl$_2$ (60 mg, 0.09 mmol, 0.10 equiv) in DMSO (1 mL) and triethylamine (1 mL). The final reaction mixture was irradiated with microwave radiation for 1 h at 70° C. The resulting solution was diluted with 20 mL of water. The solids were collected by filtration and washed with 20 mL of ethyl acetate. This resulted in 0.24 g (79%) of 8-Fluoro-9-(3-hydroxy-3-methyl-but-1-ynyl)-4,5-dihydro-6-oxa-3-thia-1-aza-benzo[e]azulene-2-carboxylic acid amide as a off-white solid. LC-MS (ES, m/z): 347[M+H]$^+$; $^1$H-NMR: (300 MHz, DMSO-d6, ppm) δ 8.652 (d, 1H), 8.460 (s, 1H), 7.860 (s, 1H), 7.007 (d, 1H), 5.497 (s, 1H), 4.391 (t, 2H), 3.414 (t, 2H), 1.491 (s, 6H).

Example 84

Synthesis of 8-Fluoro-9-[(R)-3-hydroxy-3-(5-methyl-[1,2,4]oxadiazol-3-yl)-but-1-ynyl]-4,5-dihydro-6-oxa-3-thia-1-aza-benzo[e]azulene-2-carboxylic acid amide

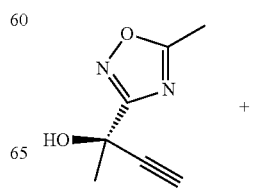

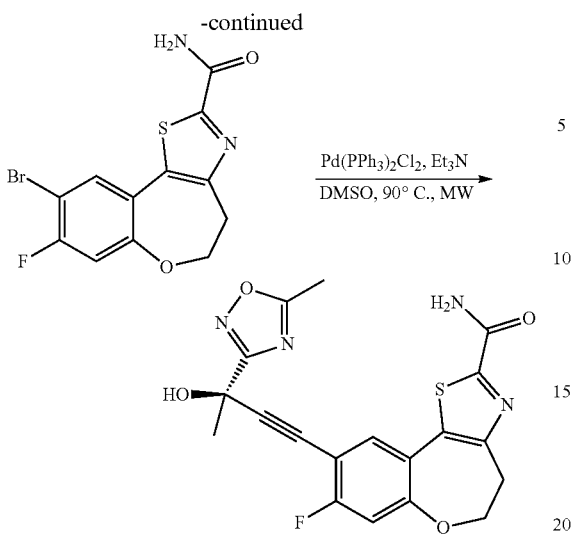

The title compound was prepared according to a procedure similar to that described in Procedure G. Into a 8-mL vial purged and maintained with an inert atmosphere of nitrogen, was placed a suspension of (2R)-2-(5-methyl-1,2,4-oxadiazol-3-e)but-3-yn-2-ol (304 mg, 2.00 mmol, 4.00 equiv), 9-Bromo-8-fluoro-4,5-dihydro-6-oxa-3-thia-1-aza-benzo[e]azulene-2-carboxylic acid amide (171 mg, 0.50 mmol, 1.00 equiv) and Pd(PPh$_3$)$_2$Cl$_2$ (140.4 mg, 0.20 mmol, 0.40 equiv) in DMSO (1.5 mL) and triethylamine (1.5 mL). The final reaction mixture was irradiated with microwave radiation for 2 h at 90° C. The resulting solution was diluted with 25 mL of water. The resulting solution was extracted with 3×50 mL of dichloromethane and the organic layers combined. The resulting mixture was washed with 2×20 mL of brine. The mixture was dried over anhydrous sodium sulfate and concentrated under vacuum. The residue was purified by Prep-HPLC with the following conditions (1#-Pre-HPLC-016 (Waters)): Column, Xbridge Prep C18, 5 um, 19*150 mm; mobile phase, water with 0.5% NH$_4$HCO$_3$ and CH$_3$CN (8% CH$_3$CN up to 56% in 12 min); Detector, uv 254/220 nm. This resulted in 11.5 mg (6%) of 8-Fluoro-9-[(R)-3-hydroxy-3-(5-methyl-[1,2,4]oxadiazol-3-yl)-but-1-ynyl]-4,5-dihydro-6-oxa-3-thia-1-aza-benzo[e]azulene-2-carboxylic acid amide as a off-white solid. LC-MS (ES, m/z): 398[M-17]$^+$; $^1$H-NMR (400 MHz, DMSO-d6, ppm): δ 8.683 (d, 1H), 8.484 (br s, 1H), 7.875 (br s, 1H), 7.037 (d, 1H), 6.765 (s, 1H), 4.399 (t, 2H), 3.400 (t, 2H), 2,624 (s, 3H), 1.868 (s, 3H).

Example 85

Synthesis of 9-[(R)-3-Hydroxy-3-(5-methyl-isoxazol-3-yl)-but-1-ynyl]-3-morpholin-4-ylmethyl-4,5-dihydro-6-oxa-1,3a-diaza-benzo[e]azulene-2-carboxylic acid amide

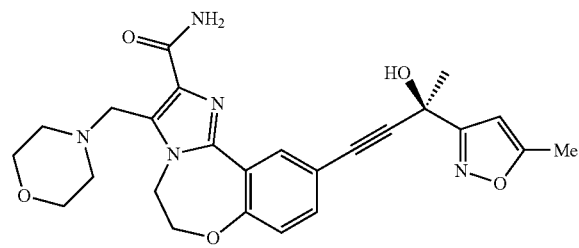 [SMILES: Cc1cc([C@](C)(O)C#Cc2ccc3c(c2)-c2nc(C(N)=O)c(CN4CCOCC4)n2CCO3)no1]

Following Procedure F, 10-bromo-3-(morpholinomethyl)-5,6-dihydrobenzo[f]imidazo[1,2-d][1,4]oxazepine-2-carboxamide was reacted with (2R)-2-(5-methylisoxazol-3-yl)but-3-yn-2-ol to give the titled compound as a colorless solid after purification by SFC. LC MS: 478.2 [M+H]$^+$; $^1$H NMR (400 MHz, DMSO) δ 8.52 (d, J=1.9 Hz, 1H), 7.57 (s, 1H), 7.33 (dd, J=8.5, 2.0 Hz, 1H), 7.09 (s, 1H), 7.03 (d, J=8.5 Hz, 1H), 6.50 (s, 1H), 6.46 (s, 1H), 6.35 (s, 1H), 4.50 (br m, 4H), 3.97 (br s, 2H), 3.52 (br m, 4H), 2.40 (s, 3H), 2.39 (m, 2H), 1.80 (s, 3H).

Example 86

Synthesis of 8-Fluoro-9-[(R)-3-hydroxy-3-(5-methyl-isoxazol-3-yl)-but-1-ynyl]-4,5-dihydro-6-oxa-3-thia-1-aza-benzo[e]azulene-2-carboxylic acid amide

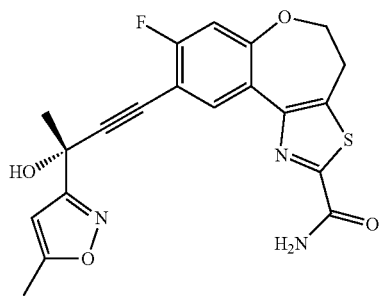

Following Procedure F, 9-Bromo-8-fluoro-4,5-dihydro-6-oxa-3-thia-1-aza-benzo[e]azulene-2-carboxylic acid amide was reacted with (2R)-2-(5-methylisoxazol-3-yl)but-3-yn-2-ol to give the titled compound as a colorless solid after purification by reverse-phase HPLC. LCMS: 396.1 [M+H]$^+$; $^1$H NMR (400 MHz, DMSO) δ 8.66 (d, J=8.5 Hz, 1H), 8.45 (s, 1H), 7.84 (s, 1H), 7.02 (d, J=10.4 Hz, 1H), 6.52 (s, 1H), 6.35 (s, 1H), 4.39 (t, J=4.8 Hz, 2H), 3.39 (m, 3H), 2.41 (s, 3H), 1.83 (s, 3H).

Example 87

Synthesis of 9-[(R)-3-Hydroxy-3-(5-methyl-isoxazol-3-yl)-but-1-ynyl]-8-methyl-4,5-dihydro-6-oxa-1,3a-diaza-benzo[e]azulene-2-carboxylic acid amide

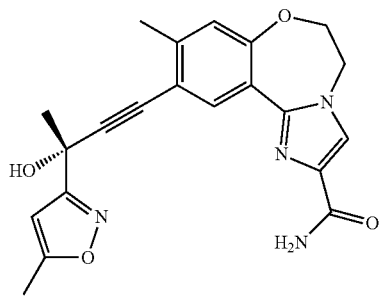

Following Procedure F, 10-bromo-9-methyl-5,6-dihydrobenzo[f]imidazo[1,2-d][1,4]oxazepine-2-carboxamide was reacted with (2R)-2-(5-methylisoxazol-3-yl)but-3-yn-2-ol to give the titled compound as a colorless solid after purification by reverse-phase HPLC. LCMS: 393.1 [M+H]$^+$; $^1$H NMR (400 MHz, DMSO) δ 8.46 (s, 1H), 7.76 (s, 1H), 7.49 (s, 1H), 7.08 (s, 1H), 7.03 (s, 1H), 6.95 (s, 1H), 6.45 (s, 1H), 6.35 (s, 1H), 4.46 (s, 4H), 2.41 (s, 3H), 2.34 (s, 3H), 1.81 (s, 3H).

Example 88

Synthesis of 9-fluoro-10-[(3R)-3-hydroxy-3-(5-methylisoxazol-3-yl)but-1-yn-1-yl]-3-(trifluoromethyl)-5,6-dihydroimidazo[1,2-d][1,4]benzoxazepine-2-carboxamide

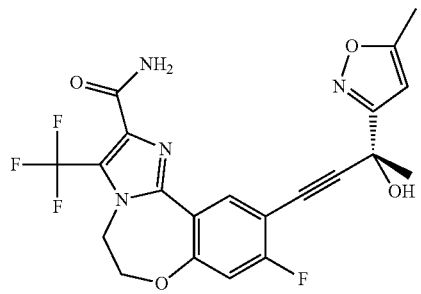 [SMILES: Cc1cc([C@](C)(O)C#Cc2cc3c(cc2F)OCCn2c-3nc(C(N)=O)c2C(F)(F)F)no1]

The title compound was prepared similarly according to Procedure E. To a solution of 10-bromo-9-fluoro-3-(trifluoromethyl)-5,6-dihydroimidazo[1,2-d][1,4]benzoxazepine-2-carboxamide (73 mg, 0.12 mmol) in a mixture of anhydrous DMF (0.5 mL) and acetonitrile (0.7 mL) were introduced (2R)-2-(5-methylisoxazol-3-yl)but-3-yn-2-ol (168 mg, 1.10 mmol), copper(I) iodide (4 mg, 0.02 mmol) and triethylamine (700 mg, 6.92 mmol). The solution was de-oxygenated by bubbling with nitrogen for 5 min, then bis(triphenylphosphine)palladium(II) chloride was added and bubbling continued for a further 5 min. The reaction mixture was warmed to 90° C. for 48 hr under an atmosphere of nitrogen, then allowed to stand at room temperature for a further 24 hr. Following evaporation of the reaction mixture in vacuo, the residue was re-dissolved in ethyl acetate (20 mL) and washed with saturated aqueous sodium bicarbonate solution (15 mL). The organic extract was dried over sodium sulfate, filtered and evaporated in vacuo. Purification by silica gel flash column chromatography (heptane/ethyl acetate gradient) furnished a tan solid which was suspended in acetonitrile (0.3 mL), sonicated for 30 seconds, and the solid isolated by suction filtration. Drying on the filter gave the title compound as an off-white solid: $^1$H NMR (500 MHz, DMSO) δ 1.81 (3H, s), 2.41 (3H, s), 4.50-4.55 (2H, m), 4.58-4.63 (2H, m), 6.35 (1H, d, J=0.63 Hz), 6.60 (1H, s), 7.10 (1H, d, J=10.40 Hz), 7.53 (1H, br. s.), 7.99 (1H, s), 8.63 (1H, d, J=8.20 Hz); $^{19}$F NMR (235 MHz, DMSO) δ −54.3, −108.0; LC-MS: m/z 465.05 (M+H)$^+$.

Example 89

Synthesis of 10-[(7-hydroxy-6,7-dihydro-5H-cyclopenta[b]pyridin-7-yl)ethynyl]-5,6-dihydroimidazo[1,2-d][1,4]benzoxazepine-2-carboxamide

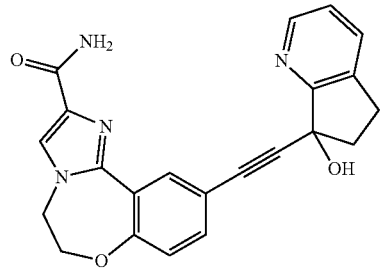 [SMILES: NC(=O)c1cn2c(n1)-c1cc(C#CC3(O)CCc4cccnc43)ccc1OCC2]

The title compound was prepared similarly according to Procedure E by reacting 10-bromo-5,6-dihydroimidazo[1,2-d][1,4]benzoxazepine-2-carboxamide with 7-ethynyl-6,7-dihydro-5H-cyclopenta[b]pyridin-7-ol. $^1$H NMR (500 MHz, DMSO) δ 2.30-2.43 (1H, m), 2.54-2.61 (1H, m), 2.83-2.95 (1H, m), 2.96-3.07 (1H, m), 4.49 (4H, s), 6.21 (1H, br. s.), 7.03 (1H, d, J=8.51 Hz), 7.14 (1H, br. s.), 7.24-7.36 (2H, m), 7.57 (1H, br. s.), 7.73 (1H, d, J=7.41 Hz), 7.80 (1H, s), 8.46 (1H, d, J=4.26 Hz), 8.53 (1H, d, J=2.05 Hz); LC-MS: m/z=387.10 (M+H)$^+$.

Example 90

Synthesis of 9-fluoro-10-(3-hydroxy-3-methylbut-1-ynyl)-3-(3-methyl-1-(2,2,2-trifluoroethyl)-1H-1,2,4-triazol-5-yl)-5,6-dihydrobenzo[f]imidazo[1,2-d][1,4]oxazepine-2-carboxamide

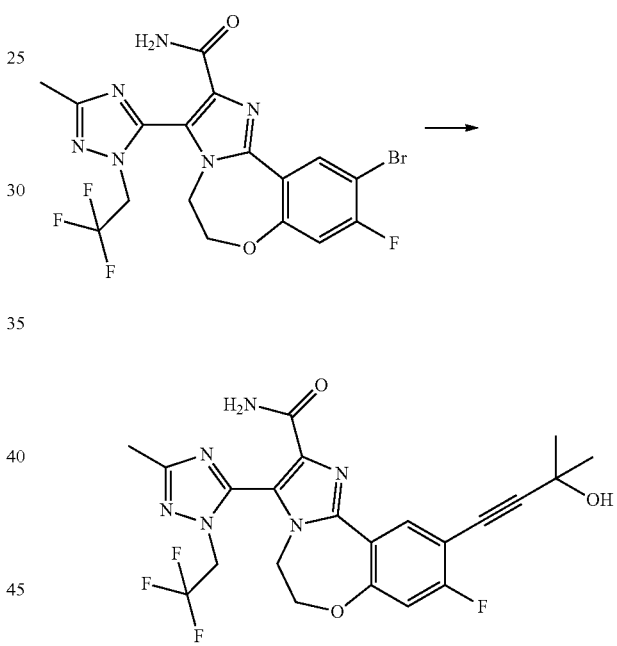

The title compound was prepared similarly according to Procedure E. To a solution of 10-bromo-9-fluoro-3-[5-methyl-2-(2,2,2-trifluoroethyl)-1,2,4-triazol-3-yl]-5,6-dihydroimidazo[1,2-d][1,4]benzoxazepine-2-carboxamide (200 mg, 0.41 mmol), PdCl2(PPh3)$_2$ (0.05 equiv., 14.5 mg, 0.02 mmol) and copper (I) iodide (0.05 equiv., 4.0 mg, 0.02 mmol) in diisopropylamine (1.1 mL, 2.6 mL/mmol) and DMF (0.53 mL, 1.3 mL/mmol) was added 2-methyl-3-butyn-2-ol (2.0 equiv., 0.08 mL, 0.82 mmol). The reaction was heated to 85° C. for 30 minutes. The reaction mixture was cooled to room temperature, diluted with methylene chloride and filtered over celite. The crude was purified by reverse-phase HPLC to afford 73 mg (36.3% yield) of a fluffy white solid. $^1$H NMR (400 MHz, DMSO) δ 8.66 (d, J=8.5 Hz, 1H), 7.99 (br s, 1H), 7.48 (br s, 1H), 7.05 (d, J=10.5 Hz, 1H), 5.53 (s, 1H), 5.12-4.96 (m, 2H), 4.56-4.47 (m, 2H), 4.30-3.98 (m, 2H), 2.37 (s, 3H), 1.50 (s, 6H). M+H=493.2.

Example 91

Synthesis of 9-fluoro-10-(3-hydroxy-3-methylbut-1-ynyl)-3-(1-methyl-3-(pyridin-4-yl)-1H-1,2,4-triazol-5-yl)-5,6-dihydrobenzo[f]imidazo[1,2-d][1,4]oxazepine-2-carboxamide

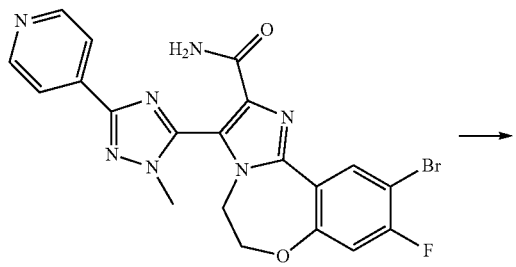

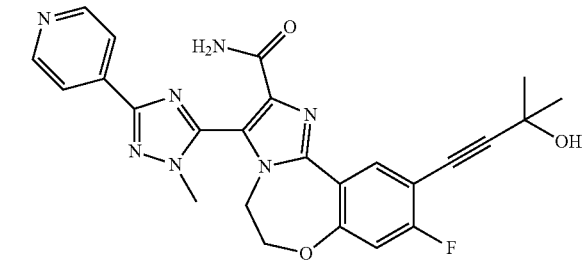

The title compound was prepared similarly according to Procedure E. 10-bromo-9-fluoro-3-(1-methyl-3-(pyridin-4-yl)-1H-1,2,4-triazol-5-yl)-5,6-dihydrobenzo[f]imidazo[1,2-d][1,4]oxazepine-2-carboxamide was reacted with 2-methyl-3-butyn-2-ol to afford 35.3% yield of the titled product. $^1$H NMR (400 MHz, DMSO) δ 8.73-8.67 (m, 3H), 7.99 (br s, 1H), 7.97-7.93 (m, 2H), 7.47 (br s, 1H), 7.06 (d, J=10.5 Hz, 1H), 5.53 (s, 1H), 4.58-4.52 (m, 2H), 4.38-4.28 (m, 2H), 3.83 (s, 3H), 1.51 (s, 6H). M+H=488.2

Example 92

Synthesis of 3-(3-cyclopropyl-1H-1,2,4-triazol-5-yl)-9-fluoro-10-(3-hydroxy-3-methylbut-1-ynyl)-5,6-dihydrobenzo[f]imidazo[1,2-d][1,4]oxazepine-2-carboxamide

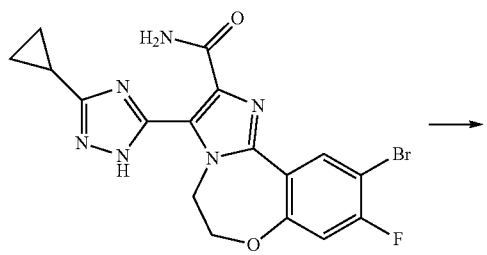

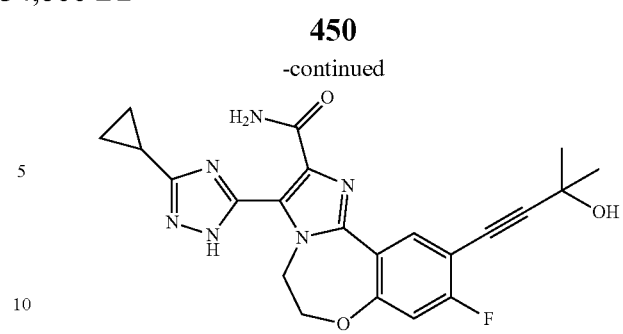

The title compound was prepared similarly according to Procedure E. 10-bromo-3-(3-cyclopropyl-1H-1,2,4-triazol-5-yl)-9-fluoro-5,6-dihydrobenzo[f]imidazo[1,2-d][1,4]oxazepine-2-carboxamide was reacted with 2-methyl-3-butyn-1-ol to afford 35.3% yield of the titled product. $^1$H NMR (400 MHz, DMSO) δ 14.85 (br s, 1H), 8.65 (d, J=8.5 Hz, 1H), 8.43 (br s, 1H), 7.75 (br s, 1H), 7.03 (d, J=10.5 Hz, 1H), 5.52 (s, 1H), 4.98-4.82 (m, 2H), 4.62-4.54 (m, 2H), 2.15-2.00 (m, 1H), 1.50 (s, 7H), 1.02-0.95 (m, 2H), 0.95-0.83 (m, 2H). M+H=437.1.

Example 93

Synthesis of 10-fluoro-9-[(3R)-3-hydroxy-3-(5-methyl-1,2-oxazol-3-yl)but-1-yn-1-yl]-2,5-diazatetracyclo[11.1.1.0$^{2,6}$.0$^{7,12}$]pentadeca-3,5,7(12),8,10-pentaene-4-carboxamide

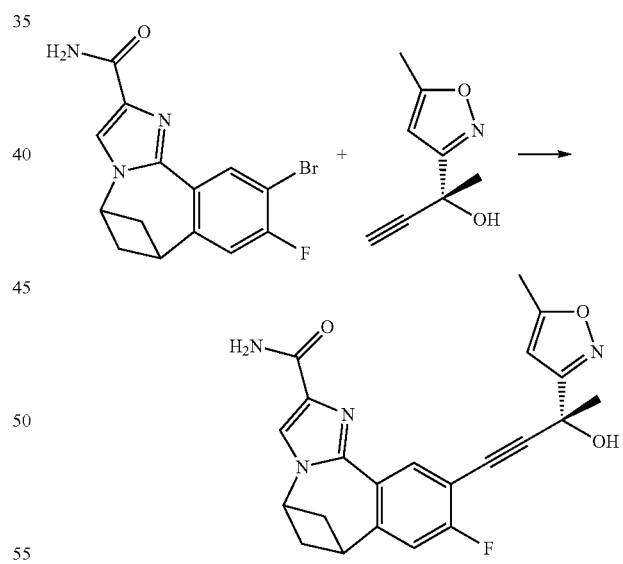

The title compound was prepared similarly according to Procedure E. 9-Bromo-4,5-dihydro-6-oxa-1,3a-diaza-benzo[e]azulene-2-carboxylic acid amide was reacted with (2R)-2-(5-methylisoxazol-3-yl)but-3-yn-2-ol to afford 92.4 mg (76.4% yield) of the titled compound. $^1$H NMR (400 MHz, DMSO) δ 8.67 (d, J=7.6 Hz, 1H), 7.82 (s, 1H), 7.55 (br s, 1H), 7.30 (d, J=10.2 Hz, 1H), 7.09 (br s, 1H), 6.59 (s, 1H), 6.36 (s, 1H), 4.95-4.88 (m, 1H), 3.76-3.69 (m, 1H), 3.17-2.99 (m, 2H), 2.42 (s, 3H), 1.82 (s, 3H), 1.72-1.65 (m, 3H). M+H=407.1.

Example 94

Synthesis of 10-fluoro-9-(3-hydroxy-3-methylbut-1-yn-1-yl)-2,5-diazatetracyclo[11.1.1.0²,⁶.0⁷,¹²]pentadeca-3,5,7(12),8,10-pentaene-4-carboxamide

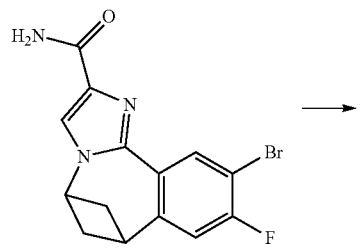

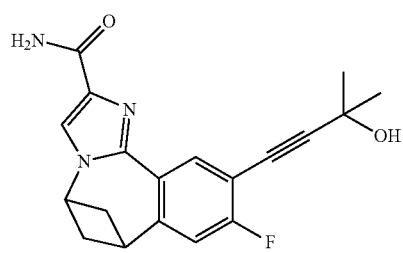

The title compound was prepared similarly according to Procedure E. 9-Bromo-4,5-dihydro-6-oxa-1,3a-diaza-benzo[e]azulene-2-carboxylic acid amide was reacted with 2-methyl-3-butyn-1-ol to afford 70.9 mg (70.2% yield) of the titled compound. ¹H NMR (400 MHz, DMSO) δ 8.65 (d, J=7.6 Hz, 1H), 7.82 (s, 1H), 7.53 (br s, 1H), 7.27 (d, J=10.3 Hz, 1H), 7.10 (br s, 1H), 5.55 (s, 1H), 4.94-4.88 (m, 1H), 3.75-3.67 (m, 1H), 3.14-3.03 (m, 2H), 1.68 (d, J=12.2 Hz, 2H), 1.50 (s, 6H). M+H=340.1.

Example 95

Synthesis of 10-fluoro-9-[(3R)-3-hydroxy-3-(5-methyl-1,2,4-oxadiazol-3-yl)but-1-yn-1-yl]-2,5-diazatetracyclo[11.1.1.0²,⁶.0⁷,¹²]pentadeca-3,5,7(12),8,10-pentaene-4-carboxamide

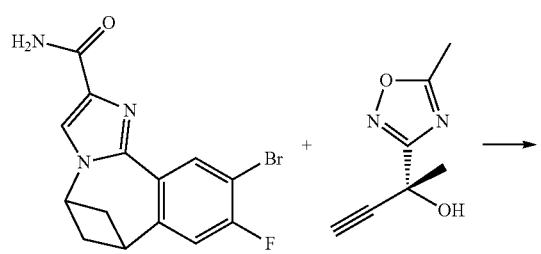

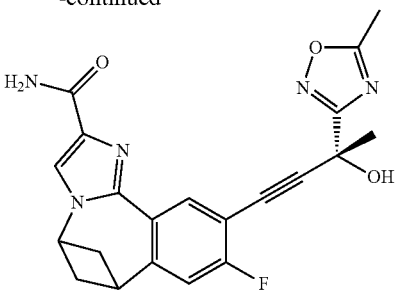

The title compound was prepared similarly according to Procedure E. 9-Bromo-4,5-dihydro-6-oxa-1,3a-diaza-benzo[e]azulene-2-carboxylic acid amide was reacted with (2R)-2-(5-methylisoxazol-3-yl)but-3-yn-2-ol to afford 26.1 mg (21.5% yield) of product. ¹H NMR (400 MHz, DMSO) δ 8.68 (d, J=7.6 Hz, 1H), 7.82 (s, 1H), 7.54 (br s, 1H), 7.31 (d, J=10.3 Hz, 1H), 7.09 (br s, 1H), 6.80 (s, 1H), 4.95-4.88 (m, 1H), 3.76-3.69 (m, 1H), 3.15-3.03 (m, 2H), 2.62 (s, 3H), 1.86 (s, 3H), 1.73-1.64 (m, 2H). M+H=408.1.

Example 96

Synthesis of 9-fluoro-3-(hydroxy(3-(trifluoromethyl)phenyl)methyl)-10-(3-hydroxy-3-methylbut-1-ynyl)-5,6-dihydrobenzo[f]imidazo[1,2-d][1,4]oxazepine-2-carboxamide

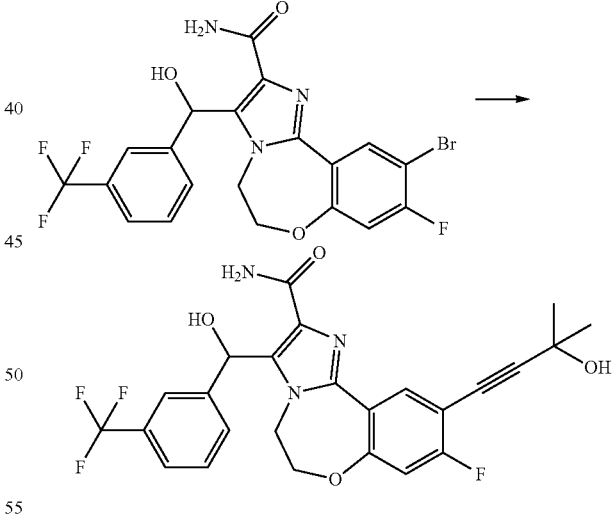

The title compound was prepared similarly according to Procedure E. 10-bromo-9-fluoro-3-(hydroxy(3-(trifluoromethyl)phenyl)methyl)-5,6-dihydrobenzo[f]imidazo[1,2-d][1,4]oxazepine-2-carboxamide was reacted with 2-methyl-3-butyn-1-ol to afford 36.9 mg (56.4% yield) of product. ¹H NMR (400 MHz, DMSO) δ 8.56 (d, J=8.4 Hz, 1H), 7.91 (br s, 1H), 7.76 (br s, 1H), 7.66-7.54 (m, 3H), 7.45 (be s, 1H), 7.12 (d, J=5.4 Hz, 1H), 6.99-6.91 (m, 2H), 5.50 (s, 1H), 4.61-4.47 (m, 1H), 4.45-4.34 (m, 2H), 4.07-3.92 (m, 1H), 1.49 (s, 6H). M+H=504.1.

Example 97

Synthesis of 10-bromo-9-fluoro-3-(3-methyl-1-(2,2,2-trifluoroethyl)-1H-1,2,4-triazol-5-yl)-5,6-dihydrobenzo[f]imidazo[1,2-d][1,4]oxazepine-2-carboxamide

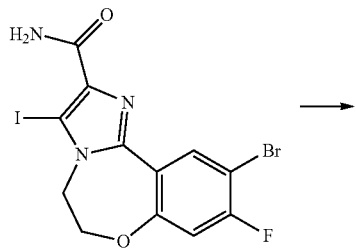

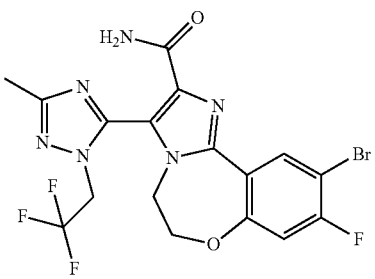

Title compound was prepared following the carbonylative triazole synthesis procedure (referred herein as Procedure I as described in: Staben, S. T.; Blaquiere, N Angew. Chem. Int. Ed. 2010, 49, p. 325. To a solution of 10-bromo-9-fluoro-3-iodo-5,6-dihydroimidazo[1,2-d][1,4]benzoxazepine-2-carboxamide (300 mg, 0.66 mmol) and acetamidine hydrochloride (1.50 equiv., 99.1 mg, 0.99 mmol) in DMF (3.3 mL, 0.2M) was added triethylamine (0.66 mL, 1.0 mL/mmol). The solution was purged with nitrogen gas. Palladium (II) acetate (0.05 equiv., 7.4 mg) and xantphos (0.05 equiv., 19.8 mg) were added and the flask was purged with a carbon monoxide balloon. The reaction was heated to 80° C. for 2 hours. The CO balloon was removed and the reaction mixture was cooled to room temperature. 2,2,2-trifluoroethylhydrazine (70% in $H_2O$, 3.0 equiv., 0.25 mL) and acetic acid (2.6 mL, 4 mL/mmol) were added and the mixture was heated to 80° C. for 1 hour. The reaction was cooled to room temperature, diluted with methylene chloride and filtered over celite. 1N NaOH was added and the solution was extracted with methylene chloride 3×. The organic layers were combined, dried with $Na_2SO_4$ and concentrated. The crude residue was purified by flash column chromatography (10-100% ethyl acetate in hexanes) to give a yellow solid (282 mg).

Example 98

Synthesis of 10-bromo-9-fluoro-3-(1-methyl-3-(pyridin-4-yl)-1H-1,2,4-triazol-5-yl)-5,6-dihydrobenzo[f]imidazo[1,2-d][1,4]oxazepine-2-carboxamide The title compound was prepared similarly according to Procedure I. Pyridine-4-carboximidamide hydrochloride was reacted with 10-bromo-9-fluoro-3-iodo-5,6-dihydroimidazo[1,2-d][1,4]benzoxazepine-2-carboxamide then methyl hydrazine to give the titled compound.

Example 99

Synthesis of 10-bromo-3-(3-cyclopropyl-1H-1,2,4-triazol-5-yl)-9-fluoro-5,6-dihydrobenzo[f]imidazo[1,2-d][1,4]oxazepine-2-carboxamide The title compound was prepared similarly according to Procedure I. Cyclopropylcarboxamidine hydrochloride was reacted with 10-bromo-9-fluoro-3-iodo-5,6-dihydroimidazo[1,2-d][1,4]benzoxazepine-2-carboxamide then hydrazine monohydrate to give the titled compound.

Example 100

Synthesis of 10-bromo-9-fluoro-3-(trifluoromethyl)-5,6-dihydroimidazo[1,2-d][1,4]benzoxazepine-2-carboxamide

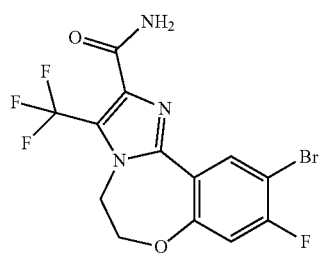 [SMILES: NC(=O)c1nc2n(c1C(F)(F)F)CCOc1cc(F)c(Br)cc1-2]

To a solution of 10-bromo-9-fluoro-3-iodo-5,6-dihydroimidazo[1,2-d][1,4]benzoxazepine-2-carboxamide (113 mg, 0.25 mmol) in anhydrous DMF (1.0 mL) was introduced trifluoromethyl(1,10-phenanthroline)copper (117 mg, 0.37 mmol). The reaction mixture was warmed to 50° C. for 20 hr under an atmosphere of nitrogen. After standing at room temperature for 36 hr, the reaction mixture was concentrated in vacuo and the residue slurried in dichloromethane (2 mL). The slurry was filtered under vacuum and the filter cake washed with dichloromethane (2 mL). Evaporation of the combined filtrates in vacuo furnished the crude title compound as a yellow-green waxy solid: $^1$H NMR (500 MHz, CDCl$_3$) δ 4.49-4.57 (4H, m), 5.55 (1H, br. s), 6.87 (1H, d, J=9.2 Hz), 7.17 (1H, br. s), 8.69 (1H, d, J=7.9 Hz); $^{19}$F NMR (235 MHz, CDCl$_3$) δ −55.1, −102.6; LC-MS: m/z+393.85/+395.70 (M+H)$^+$, (purity=68%). This intermediate was used in the next step without further purification.

Example 101

Synthesis of methyl 10-bromo-9-fluoro-3-(hydroxy(3-(trifluoromethyl)phenyl)methyl)-5,6-dihydrobenzo[f]imidazo[1,2-d][1,4]oxazepine-2-carboxylate

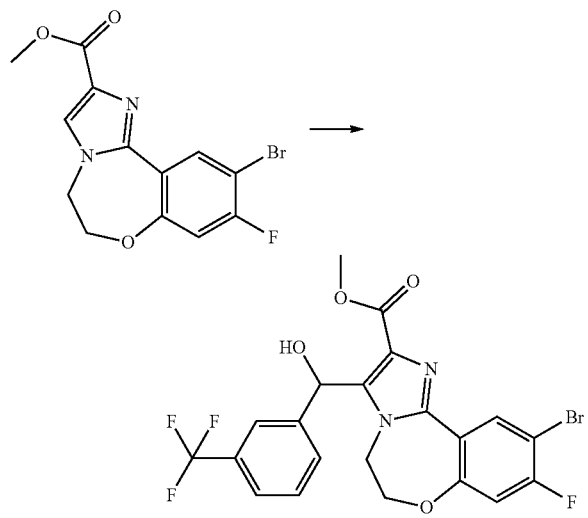

The title compound was prepared similarly according to the procedure in Example 9. Methyl 10-bromo-9-fluoro-5,6-dihydroimidazo[1,2-d][1,4]benzoxazepine-2-carboxylate (150 mg, 0.44 mmol) was dissolved in THF (1.3 mL, 3 mL/mmol) and the solution was cooled to 0° C. A solution of TMPMgCl/LiCl (1 M in toluene/THF, 1.6 equiv., 0.704 mL, 0.70 mmol) was added down the side of the vial slowly. The mixture was allowed to stir for 30 minutes. After 30 minutes, 3-(trifluoromethyl)benzaldehyde (1.0 equiv., 0.06 mL, 0.44 mmol) was added and the reaction continued to stir for 30 minutes. The reaction was quenched with saturated NH$_4$Cl and extracted 3 times with methylene chloride. The organic layers were combined, dried with Na$_2$SO$_4$ and concentrated. The crude was purified by flash chromatography to afford 73 mg (32.2% yield) of a white solid.

Example 102

Synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid

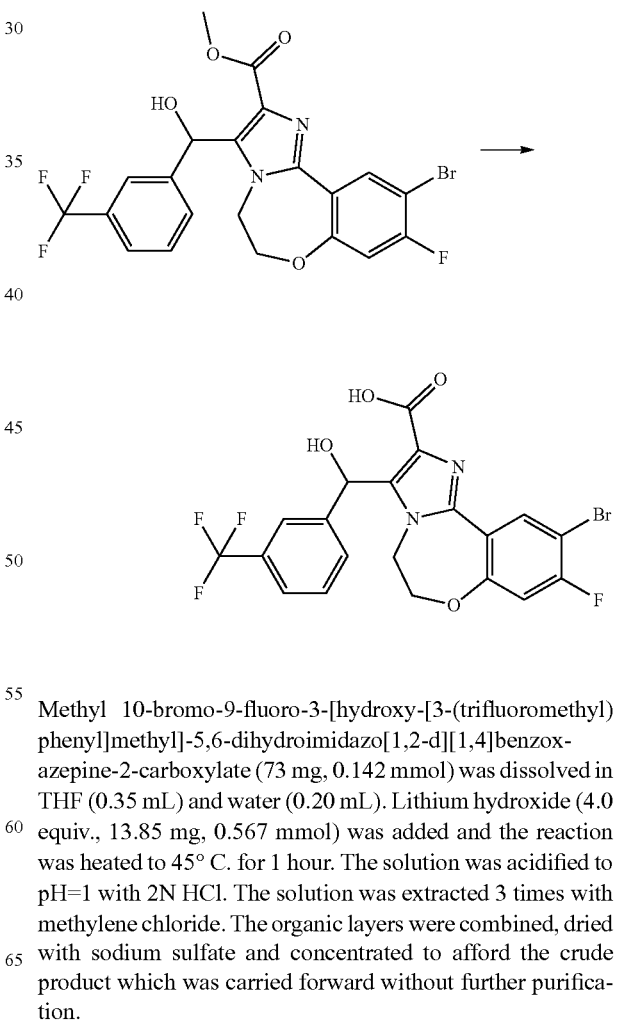

Methyl 10-bromo-9-fluoro-3-[hydroxy-[3-(trifluoromethyl)phenyl]methyl]-5,6-dihydroimidazo[1,2-d][1,4]benzoxazepine-2-carboxylate (73 mg, 0.142 mmol) was dissolved in THF (0.35 mL) and water (0.20 mL). Lithium hydroxide (4.0 equiv., 13.85 mg, 0.567 mmol) was added and the reaction was heated to 45° C. for 1 hour. The solution was acidified to pH=1 with 2N HCl. The solution was extracted 3 times with methylene chloride. The organic layers were combined, dried with sodium sulfate and concentrated to afford the crude product which was carried forward without further purification.

Example 103

Synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxamide

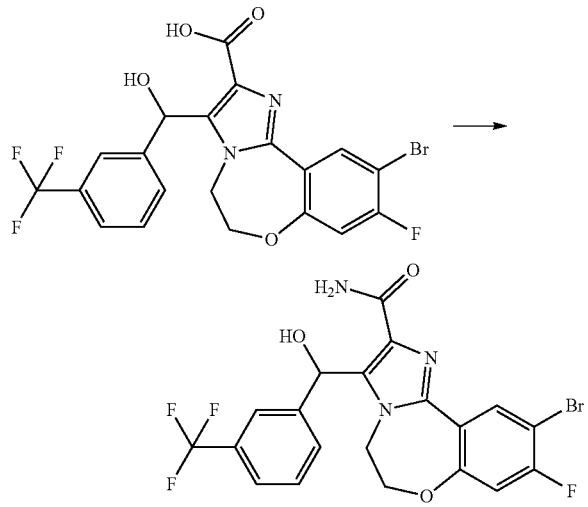

The title compound was prepared similarly according to the procedure described in Example 2. 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid was reacted with ammonium chloride to give the titled compound which was used in subsequent steps without purification.

Example 104

Synthesis of 9-(3-hydroxy-3-methyl-but-1-ynyl)-4-morpholin-4-yl-4,5-dihydro-6-oxa-3-thia-1-aza-benzo[e]azulene-2-carboxylic acid amide

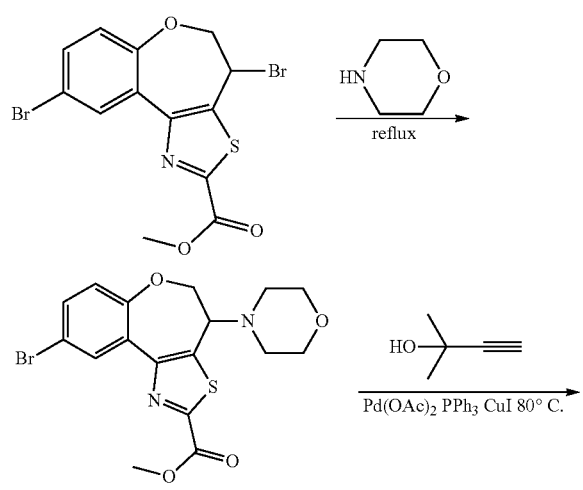

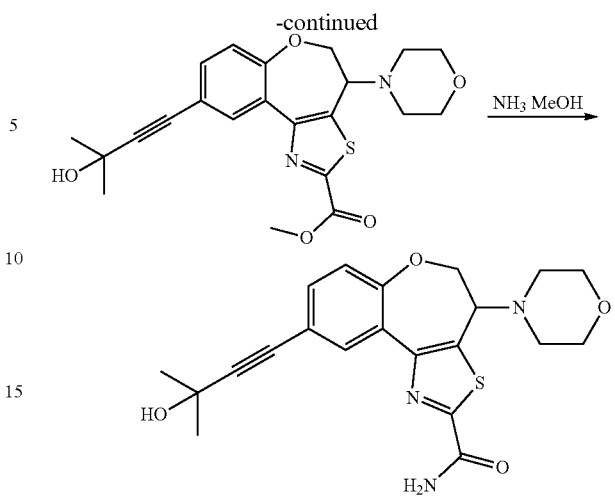

To a solution of 4,9-Dibromo-4,5-dihydro-6-oxa-3-thia-1-aza-benzo[e]azulene-2-carboxylic acid methyl ester (400 mg, 0.954 mmol) in THF (6 mL) was added morpholine (416 mg, 4.775 mmol). The reaction mixture was stirred at 60° C. for 5 h. Then the mixture was cooled to room temperature and partitioned between EtOAc and $H_2O$, and the aqueous layer was extracted with EtOAc (2×20 mL). The combined organic layers were washed with brine, dried over $Na_2SO_4$, filtered and concentrated in vacuo to afford crude product as yellow oil. The oily product was stirred in n-Hexane (6 mL) at room temperature for 0.5 h and then filtered to afford compound 9-Bromo-4-morpholin-4-yl-4,5-dihydro-6-oxa-3-thia-1-aza-benzo[e]azulene-2-carboxylic acid methyl ester (300 mg, 75%) as a light yellow solid. $^1$H NMR (400 MHz, DMSO-$d_6$): δ 8.39 (d, J=2.6 Hz, 1H), 7.48 (dd, $J_1$=8.6 Hz, $J_2$=2.6 Hz, 1H), 7.13 (d, $J_1$=8.64 Hz, 1H), 4.55 (dd, $J_1$=12.08 Hz, $J_2$=3.32 Hz, 1H), 4.40 (dd, $J_1$=6.6 Hz, $J_2$=3.2 Hz, 1H), 4.31 (m, 1H); 3.94 (s, 31-1) 3.56 (m, 4H); 2.68 (m, 4H); LC-MS (ESI & APCI): 427.2 (M+2).

To a stirred mixture of 9-Bromo-4-morpholin-4-yl-4,5-dihydro-6-oxa-3-thia-1-aza-benzo[e]azulene-2-carboxylic acid methyl ester (270 mg, 0.635 mmol) in TEA (5 mL) and DMF (1 mL) were added Pd(OAc)$_2$ (14.22 mg), PPh$_3$ (49.9 mg 0.190 mmol), CuI (24.1 mg, 0.127 mmol), 2-methylbut-3-yn-2-ol (266.6 mg, 3.174 mmol). The reaction mixture was degassed with $N_2$ and heated to 80° C. for 6 h. Then the mixture was cooled to room temperature, and EtOAc was added. The mixture was filtered though Celite, and the filtrate was washed with saturated brine, dried over $Na_2SO_4$, filtered, concentrated in vacuo, and purified by flash column chromatography (silica gel, EtOAc in hexane from 10% to 20%) to afford 9-(3-Hydroxy-3-methyl-but-1-ynyl)-4-morpholin-4-yl-4,5-dihydro-6-oxa-3-thia-1-aza-benzo[e]azulene-2-carboxylic acid methyl ester (180 mg, 66%) as a light yellow solid. LC-MS (ESI & APCI): 429.0 (M+1).

A solution of 9-(3-Hydroxy-3-methyl-but-1-ynyl)-4-morpholin-4-yl-4,5-dihydro-6-oxa-3-thia-1-aza-benzo[e]azulene-2-carboxylic acid methyl ester (130 mg, 0.30 mmol) in methanol-ammonia (5 mL) was stirred at room temperature for 0.5 h. Then the reaction mixture was concentrated to afford crude compound which was triturated with EtOAc to afford compound 9-(3-Hydroxy-3-methyl-but-1-ynyl)-4-morpholin-4-yl-4,5-dihydro-6-oxa-3-thia-1-aza-benzo[e]azulene-2-carboxylic acid amide (80 mg, 64%) as a light yellow solid. $^1$H NMR (400 MHz, DMSO-$d_6$): δ 8.51 (d, J=1.88 Hz, 1H), 8.41 (s, 1H), 7.86 (s, 1H), 7.27 (dd, $J_1$=8.4

Hz, J$_2$=1.92 Hz, 1H), 7.02 (d, J=8.32 Hz, 1H), 5.43 (s, 1H), 4.40 (m, 3H), 3.54 (m, 4H), 2.65 (m, 4H), 1.46 (s, 6H); LC-MS (ESI & APCI): 414.6 (M+1).

Example 105

Synthesis of 4-dimethylamino-9-(3-hydroxy-3-methyl-but-1-ynyl)-4,5-dihydro-6-oxa-3-thia-1-aza-benzo[e]azulene-2-carboxylic acid amide

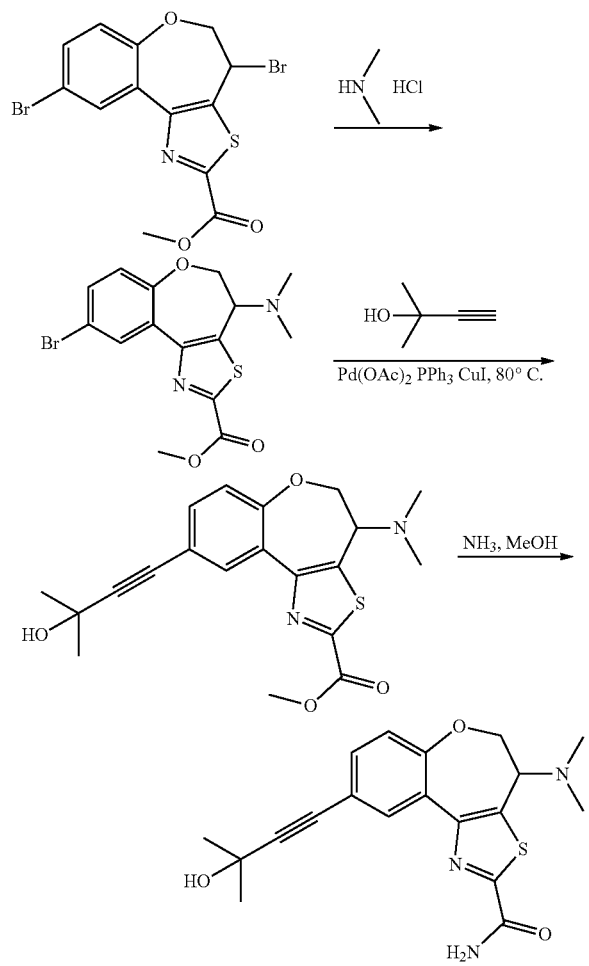

To a solution of 4,9-Dibromo-4,5-dihydro-6-oxa-3-thia-1-aza-benzo[e]azulene-2-carboxylic acid methyl ester (200 mg, 0.477 mmol) in THF (6 mL) were added Dimethylamine Hydrochloride (77.8 mg, 0.954 mmol), DIPEA (308 mg, 2.38 mmol). The reaction mixture was stirred in autoclave at 60° C. overnight. Then the mixture was cooled to room temperature and partitioned between EtOAc and H$_2$O, and the aqueous layer was extracted with EtOAc (2×20 mL). The combined organic layers were washed with brine, dried over Na$_2$SO$_4$, filtered and concentrated in vacuo and purified by flash column chromatography (silica gel, EtOAc in hexane from 10% to 20%) to afford 9-Bromo-4-dimethylamino-4,5-dihydro-6-oxa-3-thia-1-aza-benzo[e]azulene-2-carboxylic acid methyl ester (120 mg, 65%).

To a stirred mixture of 9-Bromo-4-dimethylamino-4,5-dihydro-6-oxa-3-thia-1-aza-benzo[e]azulene-2-carboxylic acid methyl ester (120 mg, 0.31 mmol) in TEA (5 mL) and DMF (1 mL) were added Pd(OAc)$_2$ (7.0 mg, 0.03 mmol), PPh$_3$ (24.6 mg, 0.09 mmol), CuI (11.9 mg, 0.06 mmol), 2-methylbut-3-yn-2-ol (131.5 mg, 1.56 mmol). The reaction mixture was degassed with N$_2$ and heated in autoclave at 80° C. overnight. Then the mixture was cooled to room temperature, and EtOAc was added. The mixture was filtered though Celite, and the filtrate was washed with saturated brine, dried over Na$_2$SO$_4$, filtered, concentrated in vacuo, and purified by flash column chromatography (silica gel, EtOAc in hexane from 10% to 20%) to afford 4-Dimethylamino-9-(3-hydroxy-3-methyl-but-1-ynyl)-4,5-dihydro-6-oxa-3-thia-1-aza-benzo[e]azulene-2-carboxylic acid methyl ester (50 mg, 41%) as a light yellow solid. LC-MS (ESI & APCI): 387.5 (M+1).

A solution of 4-Dimethylamino-9-(3-hydroxy-3-methyl-but-1-ynyl)-4,5-dihydro-6-oxa-3-thia-1-aza-benzo[e]azulene-2-carboxylic acid methyl ester (50 mg, 0.130 mmol), in methanol-ammonia (5 mL) was stirred at room temperature for 0.5 h. Then the mixture was filtered to afford compound 4-Dimethylamino-9-(3-hydroxy-3-methyl-but-1-ynyl)-4,5-dihydro-6-oxa-3-thia-1-aza-benzo[e]azulene-2-carboxylic acid amide (42 mg, 87%) as a white solid. LC-MS (ESI & APCI): 372.4 (M+1). $^1$H NMR (400 MHz, DMSO-d$_6$): δ 8.54 (d, J=1.9 Hz, 1H), 8.43 (s, 1H), 7.88 (s, 1H), 7.30 (dd, H$_1$=8.4 Hz, J$_2$=1.9 Hz, 1H), 7.05 (d, J=8.3 Hz, 1H), 5.46 (s, 1H), 4.40 (m, 3H), 2.36 (s, 6H), 1.49 (s, 6H).

Example 106

Synthesis of 4-cyclobutylamino-9-(3-hydroxy-3-methyl-but-1-ynyl)-4,5-dihydro-6-oxa-3-thia-1-aza-benzo[e]azulene-2-carboxylic acid amide

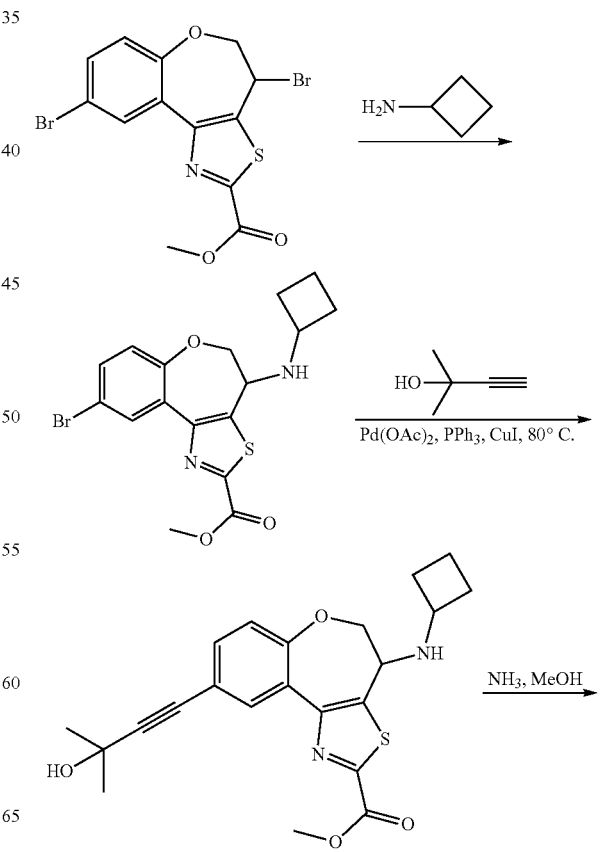

-continued

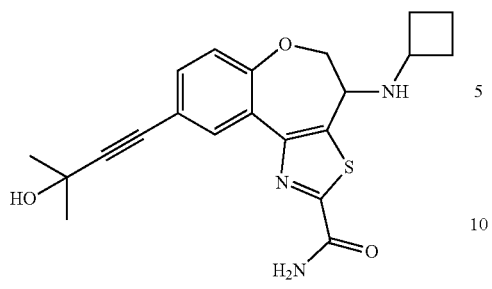

To a solution of 4,9-Dibromo-4,5-dihydro-6-oxa-3-thia-1-aza-benzo[e]azulene-2-carboxylic acid methyl ester (400 mg, 0.95 mmol) in DMF (9 mL) were added cyclobutanamine (81.5 mg, 1.15 mmol), DIPEA (370 mg, 2.86 mmol). The reaction mixture was stirred in autoclave at 90° C. overnight. Then the mixture was cooled to room temperature and partitioned between EtOAc and H$_2$O, and the aqueous layer was extracted with EtOAc (2×20 mL). The combined organic layers were washed with brine, dried over Na$_2$SO$_4$, filtered, concentrated in vacuo and purified by flash column chromatography (silica gel, EtOAc in hexane from 10% to 20%) to afford 9-Bromo-4-cyclobutylamino-4,5-dihydro-6-oxa-3-thia-1-aza-benzo[e]azulene-2-carboxylic acid methyl ester (110 mg, 28%). NMR (400 MHz, DMSO-d$_6$): δ 8.44 (d, J=2.5 Hz, 1H), 7.47 (dd, J$_1$=8.6 Hz, J$_2$=2.5 Hz, 1H), 7.05 (d, J=8.6 Hz, 1H), 4.42 (m, 2H), 3.96 (m, 1H), 3.14 (m, 1H), 2.15 (m, 1H), 1.74 (m, 2H), 1.55 (m, 2H).

To a stirred mixture of 9-Bromo-4-cyclobutylamino-4,5-dihydro-6-oxa-3-thia-1-aza-benzo[e]azulene-2-carboxylic acid methyl ester (110 mg, 0.27 mmol) in TEA (5 mL) and DMF (1 mL) were added Pd(OAc)$_2$ (6.0 mg, 0.027 mmol), PPh$_3$ (21.1 mg, 0.081 mmol), CuI (10.2 mg, 0.054 mmol) and 2-methylbut-3-yn-2-ol (113 mg, 1.34 mmol). The reaction mixture was degassed with N$_2$ and heated in autoclave at 80° C. overnight. Then the mixture was cooled to room temperature, and EtOAc was added. The mixture was filtered though Celite, and the filtrate was washed with saturated brine, dried over Na$_2$SO$_4$, filtered, concentrated in vacuo, and purified by flash column chromatography (silica gel, EtOAc in hexane from 10% to 20%) to afford 4-Cyclobutylamino-9-(3-hydroxy-3-methyl-but-1-ynyl)-4,5-dihydro-6-oxa-3-thia-1-aza-benzo[e]azulene-2-carboxylic acid methyl ester (80 mg, 72%) as a light yellow solid. $^1$H NMR (400 MHz, DMSO-d$_6$): δ 8.39 (d, J=2.1 Hz, 1H), 7.29 (d, J=2.2 Hz, 1H), 7.06 (d, J=8.4 Hz, 1H), 5.51 (s, 1H), 4.44 (m, 1H), 4.3 (m, 1H), 3.95 (m, 1H), 3.22 (m, 1H), 2.14 (m, 2H), 1.7 (m, 2H), 1.52 (m, 2H), 1.48 (s, 6H); LC-MS (ESI & APCI): 413.7 (M+1).

A solution of 4-Cyclobutylamino-9-(3-hydroxy-3-methyl-but-1-ynyl)-4,5-dihydro-6-oxa-3-thia-1-aza-benzo[e]azulene-2-carboxylic acid methyl ester (80 mg, 0.19 mmol), in methanol-ammonia (5 mL) was stirred at room temperature for 0.5 h. Then the mixture was filtered to afford 4 Cyclobutylamino-9-(3-hydroxy-3-methyl-but-1-ynyl)-4,5-dihydro-6-oxa-3-thia-1-aza-benzo[e]azulene-2-carboxylic acid amide (42 mg, 54%) as a white solid.

$^1$H NMR (400 MHz, DMSO-d$_6$): δ 8.57 (d, J=2.1 Hz, 1H), 8.42 (s, 1H), 7.85 (s, 1H), 7.28 (d, J=8.36 Hz, 1H), 7.03 (d, J=8.32 Hz, 1H), 5.45 (s, 1H), 4.36 (m, 1H), 4.28 (m, 1H), 3.97 (m, 1H), 3.01 (m, 2H), 2.13 (m, 2H), 1.76 (m, 2H), 1.70 (m, 2H), 1.48 (s, 6H); LC-MS (ESI & APCI): 398.3 (M+1).

Example 107

Synthesis of 4-Acetylamino-9-(3-hydroxy-3-methyl-but-1-ynyl)-4,5-dihydro-6-oxa-3-thia-1-aza-benzo[e]azulene-2-carboxylic acid amide

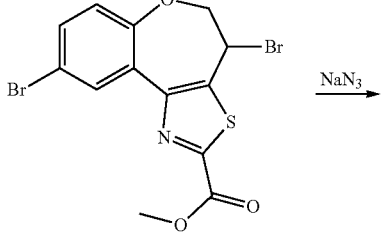

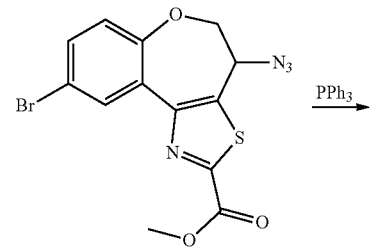

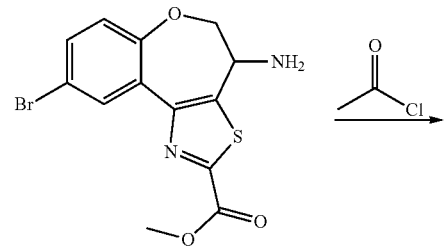

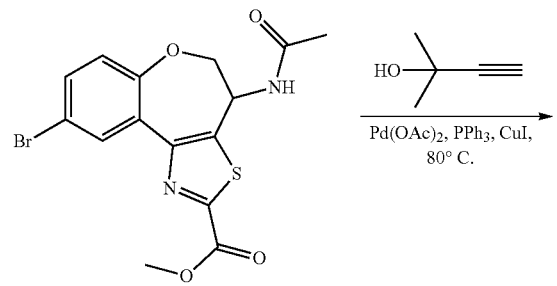

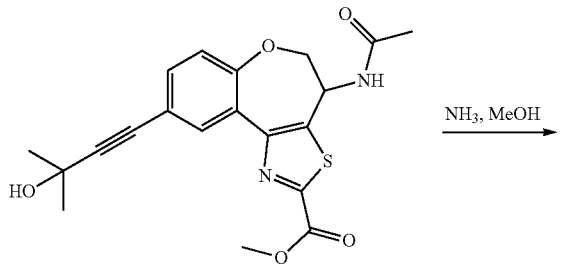

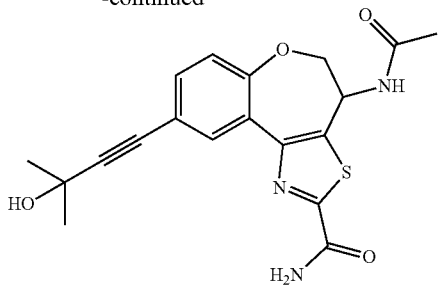

To a stirred mixture of 4,9-Dibromo-4,5-dihydro-6-oxa-3-thia-1-aza-benzo[e]azulene-2-carboxylic acid methyl ester (400 mg, 0.95 mmol) in MeOH (20 mL) was added a solution of $NaN_3$ (93.1 mg, 1.43 mmol) in water (2 mL) dropwise at room temperature. The mixture was heated to 60° C. overnight. The mixture was cooled to room temperature, and then 20 mL of water was added. The mixture was stirred for 0.5 h and then filtered to afford 4-Azido-9-bromo-4,5-dihydro-6-oxa-3-thia-1-aza-benzo[e]azulene-2-carboxylic acid methyl ester (400 mg, 28%). $^1$H NMR (400 MHz, DMSO-$d_6$): δ 8.50 (d, J=2.5 Hz, 1H), 7.56 (dd, J=8.7 Hz, $J_2$=2.6 Hz, 1H), 7.16 (d, J=8.6 Hz, 1H), 5.35 (m, 1H), 4.75 (m, 1H), 4.33 (m, 1H), 3.98 (s, 3H).

To a solution of 4-Azido-9-bromo-4,5-dihydro-6-oxa-3-thia-1-aza-benzo[e]azulene-2-carboxylic acid methyl ester (280 mg, 0.735 mmol) in THF/water (15 mL/3 mL) was added $PPh_3$ (192.5 mg, 0.735 mmol). The reaction mixture was heated to 65° C. overnight. The mixture was cooled to −5° C., and TEA (222 mg, 2.200 mmol) was added followed by acetyl chloride (86.5 mg, 1.101 mmol). Then the mixture was stirred at room temperature for 1 h. The mixture was partitioned between EtOAc and $H_2O$, and the aqueous layer was extracted with EtOAc (2×20 mL). The combined organic layers were washed with brine, dried over $Na_2SO_4$, filtered and concentrated to afford crude product which was triturated with EtOAc and hexane (1:1) and then filtered to afford 4-Acetylamino-9-bromo-4,5-dihydro-6-oxa-3-thia-1-aza-benzo[e]azulene-2-carboxylic acid methyl ester (160 mg, 51%). $^1$H NMR (400 MHz, DMSO-$d_6$): δ 8.80 (d, J=2.5 Hz, 1H), 8.48 (s, 1H), 7.53 (dd, $J_1$=8.7 Hz, $J_2$=2.6 MHz, 1H), 7.13 (d, J=8.6 Hz, 2H), 5.51 (m, 1H), 4.41 (m, 1H), 4.23 (m, 1H), 3.96 (s, 3H), 1.90 (s, 3H); LC-MS (ESI & APCI): 399.1 (M+2).

To a stirred mixture of 4-Acetylamino-9-bromo-4,5-dihydro-6-oxa-3-thia-1-aza-benzo[e]azulene-2-carboxylic acid methyl ester (180 mg, 0.453 mmol) in TEA (5 mL) and DMF (1 mL) were added $Pd(OAc)_2$ (20.3 mg, 0.091 mmol), $PPh_3$ (35.6 mg, 0.136 mmol), CuI (17.26 mg, 0.091 mmol) and 2-methylbut-3-yn-2-ol (190.6 mg, 2.266 mmol). The reaction mixture was degassed with $N_2$ and heated in a microwave reactor at 80° C. for 2 h. Then the mixture was cooled to room temperature, and EtOAc was added. The mixture was filtered though Celite, and the filtrate was washed with saturated brine, dried over $Na_2SO_4$, filtered, concentrated in vacuo, and purified by flash column chromatography (silica gel, EtOAc in hexane from 10% to 20%) to afford 4-Acetylamino-9-(3-hydroxy-3-methyl-but-1-ynyl)-4,5-dihydro-6-oxa-3-thia-1-aza-benzo[e]azulene-2-carboxylic acid methyl ester (81 mg, 45%) as a light yellow solid. LC-MS (ESI & APCI): 399.1 (M−1).

A solution of 4-Acetylamino-9-(3-hydroxy-3-methyl-but-1-ynyl)-4,5-dihydro-6-oxa-3-thia-1-aza-benzo[e]azulene-2-carboxylic acid methyl ester (81 mg, 0.202 mmol), in methanol-ammonia (5 mL) was stirred at room temperature for 0.5 h. The reaction mixture was concentrated to afford crude product, which was triturated with EtOAc and hexane (1:1) and then filtered to afford compound 4-Acetylamino-9-(3-hydroxy-3-methyl-but-1-ynyl)-4,5-dihydro-6-oxa-3-thia-1-aza-benzo[e]azulene-2-carboxylic acid amide (36 mg, 47%) as a white solid. $^1$H NMR (400 MHz, DMSO-$d_6$): δ 8.74 (d, J=8.5 Hz, 1H), 8.6 (d, J=2.2 Hz, 1H), 8.49 (s, 1H), 7.92 (s, 1H), 7.34 (dd, $J_1$=8.3 Hz, $J_2$=2.2 Hz, 1H), 7.10 (d, J=8.4 Hz, 2H), 5.53 (m, 1H), 5.45 (s, 1H), 4.37 (m, 1H), 4.18 (m, 1H), 1.89 (s, 3H), 1.49 (s, 6H); LC-MS (ESI & APCI): 386.5 (M+1).

Example 108

Synthesis of 4,4-difluoro-9-(3-hydroxy-3-methyl-but-1-ynyl)-4,5-dihydro-6-oxa-3-thia-1-aza-benzo[e]azulene-2-carboxylic acid amide

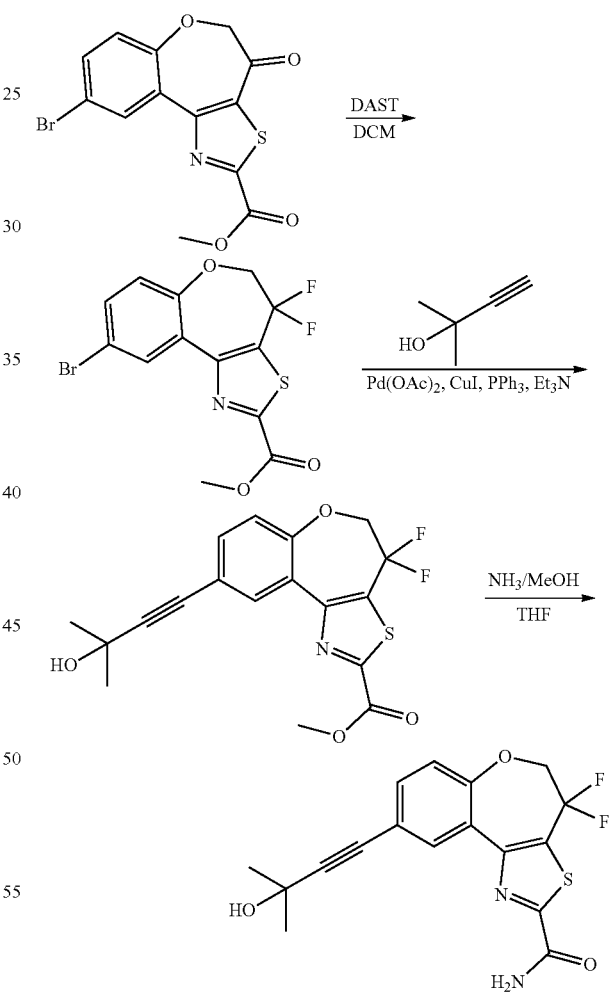

To a solution of 9-Bromo-4-oxo-4,5-dihydro-6-oxa-3-thia-1-aza-benzo[e]azulene-2-carboxylic acid methyl ester (500 mg, 1.41 mmol) in DCM at 0° C., DAST (454 mg, 2.82 mmol) was added dropwise. The mixture was stirred at room temperature overnight. The mixture was quenched with saturated aqueous $NaHCO_3$ solution, extracted with DCM (20 mL×2). The combined organic layers were washed with brine, dried over Na$_2$SO$_4$, concentrated and purified by flash column chromatography (silica gel, EtOAc in hexane from 0 to 20%) to give 9-Bromo-4,4-difluoro-4,5-dihydro-6-oxa-3-thia-1-aza-benzo[e]azulene-2-carboxylic acid methyl ester as a yellow solid (166.5 mg, 31%). LC-MS (ESI & APCI): 376.1 (M+1).

A mixture of 9-Bromo-4,4-difluoro-4,5-dihydro-6-oxa-3-thia-1-aza-benzo[e]azulene-2-carboxylic acid methyl ester as a yellow solid (166.5 mg, 0.443 mmol), 2-methyl-3-butyn-2-ol (298 mg, 3.544 mmol), Pd(OAc)$_2$ (10 mg, 0.0443 mmol), CuI (17 mg, 0.0886 mmol) and PPh$_3$ (35 mg, 0.1329 mmol) in Et$_3$N (20 mL) was degassed with N$_2$, and the mixture was stirred at 80° C. overnight. The reaction mixture was cooled to room temperature, concentrated and purified by flash column chromatography (silica gel, EtOAc in hexane from 0 to 40%) to give 4,4-Difluoro-9-(3-hydroxy-3-methyl-but-1-ynyl)-4,5-dihydro-6-oxa-3-thia-1-aza-benzo[e]azulene-2-carboxylic acid methyl ester as a yellow solid (86 mg, 51%). LC-MS (ESI & APCI): 380.4 (M+1).

To a solution of 4,4-Difluoro-9-(3-hydroxy-3-methyl-but-1-ynyl)-4,5-dihydro-6-oxa-3-thia-1-aza-benzo[e]azulene-2-carboxylic acid methyl ester (86 mg, 0.227 mmol) in THF (5 mL) at room temperature, NH$_3$/CH$_3$OH (self-made, 5 mL) was added. The mixture was stirred at room temperature for 3 h, then concentrated to give a residue which was purified by flash column chromatography (silica gel, EtOAc in hexane from 0 to 50%) to give 4,4-Difluoro-9-(3-hydroxy-3-methyl-but-1-ynyl)-4,5-dihydro-6-oxa-3-thia-1-aza-benzo[e]azulene-2-carboxylic acid amide as an off-white solid (25 mg, 30%). $^1$H NMR (400 MHz, DMSO-d$_6$): δ 8.76 (s, 1H), 8.60 (d, J=2.1 Hz, 1H), 8.18 (s, 1H), 7.46 (dd, J$_1$=8.4 Hz, J$_2$=2.2 Hz, 1H), 7.22 (d, J=8.4 Hz, 1H), 5.49 (s, 1H), 4.75 (t, J=10.7 Hz, 2H), 1.49 (s, 6H); LC-MS (ESI & APCI): 365.4 (M+1).

Example 109

Synthesis of 9-(3-hydroxy-3-methyl-but-1-ynyl)-4-oxo-4,5-dihydro-6-oxa-3-thia-1-aza-benzo[e]azulene-2-carboxylic acid amide and 4-hydroxy-9-(3-hydroxy-3-methyl-but-1-ynyl)-4,5-dihydro-6-oxa-3-thia-1-aza-benzo[e]azulene-2-carboxylic acid amide

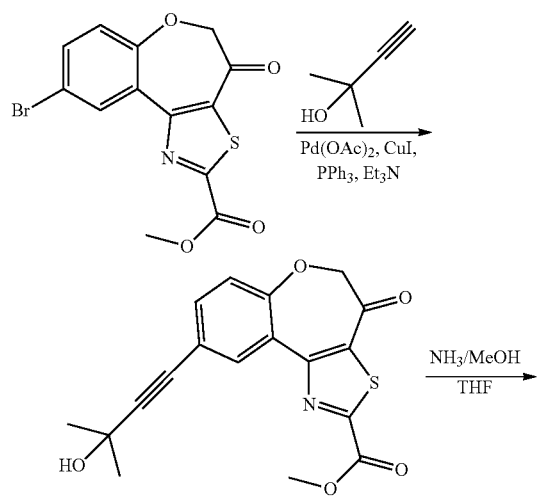

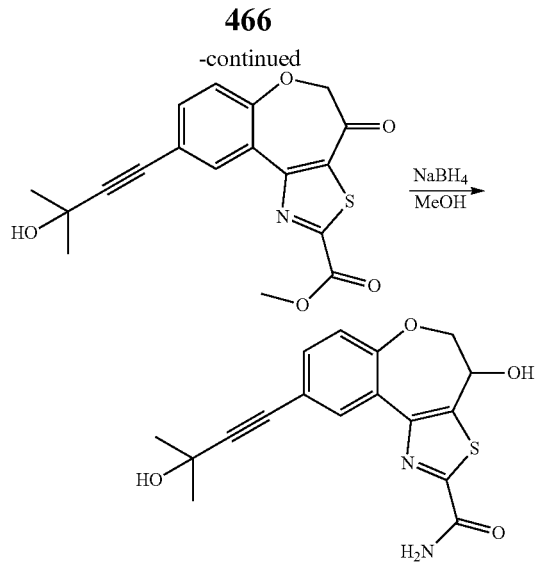

A mixture of 9-Bromo-4-oxo-4,5-dihydro-6-oxa-3-thia-1-aza-benzo[e]azulene-2-carboxylic acid methyl ester (200 mg, 0.565 mmol), 2-methyl-3-butyn-2-ol (237 mg, 2.825 mmol), Pd(OAc)$_2$ (13 mg, 0.0565 mmol), CuI (21 mg, 0.113 mmol) and PPh$_3$ (45 mg, 0.17 mmol) in Et$_3$N (10 mL) was degassed with N$_2$, and the mixture was stirred at 80° C. overnight. The reaction was cooled to room temperature, concentrated and purified by flash column chromatography (silica gel, EtOAc in hexane from 0 to 30%) to give 9-(3-Hydroxy-3-methyl-but-1-ynyl)-4-oxo-4,5-dihydro-6-oxa-3-thia-1-aza-benzo[e]azulene-2-carboxylic acid methyl ester as an off-white solid (81 mg, 40%). LC-MS (ESI & APCI): 358.2 (M+1).

To a solution of 9-(3-Hydroxy-3-methyl-but-1-ynyl)-4-oxo-4,5-dihydro-6-oxa-3-thia-1-aza-benzo[e]azulene-2-carboxylic acid methyl ester (81 mg, 0.23 mmol) in THF (4 mL) at room temperature, NH$_3$/CH$_3$OH (self-made, 4 mL) was added. The mixture was stirred at room temperature for 3 h, then concentrated to give 9-(3-Hydroxy-3-methyl-but-1-ynyl)-4-oxo-4,5-dihydro-6-oxa-3-thia-1-aza-benzo[e]azulene-2-carboxylic acid amide as a yellow oil, which was used in the next step without any further purification (crude, 80 mg). $^1$H NMR (400 MHz, DMSO-d$_6$): δ 830 (s, 1H), 8.43 (d, J=2.1 Hz, 1H), 8.18 (s, 1H), 7.50 (dd, J$_1$=8.4 Hz, J$_2$=2.2 Hz, 1H), 7.26 (d, J=8.4 Hz, 1H), 5.48 (s, 1H), 4.87 (s, 2H), 1.47 (s, 6H); LC-MS (ESI & APCI): 343.2 (M+1).

To a solution of 9-(3-Hydroxy-3-methyl-but-1-ynyl)-4-oxo-4,5-dihydro-6-oxa-3-thia-1-aza-benzo[e]azulene-2-carboxylic acid amide (80 mg, 0.23 mmol) in MeOH (5 mL) at 0° C., NaBH$_4$ (9 mg, 0.23 mmol) was added. The mixture was allowed to warm to room temperature, and stirred for 2 h, then water (2 mL) was added. The mixture was extracted with EtOAc (10 mL×3) and the combined organic layers were washed with brine, dried over Na$_2$SO$_4$, concentrated and purified by flash column chromatography (silica gel, EtOAc in hexane from 0 to 50%) to give 4-Hydroxy-9-(3-hydroxy-3-methyl-but-1-ynyl)-4,5-dihydro-6-oxa-3-thia-1-aza-benzo[e]azulene-2-carboxylic acid amide as a white solid (29 mg, 36%). $^1$H NMR (400 MHz, DMSO-d$_6$): 8.57 (d, J=2.1 Hz, 1H), 8.48 (s, 1H), 7.91 (s, 1H), 7.31 (dd, J$_1$=8.3 Hz, J$_2$=2.2 Hz, 1H), 7.07 (d, J=8.4 Hz, 1H), 6.38 (d, J=7.2 Hz, 1H), 5.45 (s, 1H), 5.09-5.14 (m, 1H), 4.08-4.35 (m, 2H), 1.49 (s, 6H); LC-MS (ESI & APCI): 345.3 (M+1).

Example 110

Synthesis of 4-hydroxy-9-(3-hydroxy-3-methyl-but-1-ynyl)-4-methyl-4,5-dihydro-6-oxa-3-thia-1-aza-benzo[e]azulene-2-carboxylic acid amide

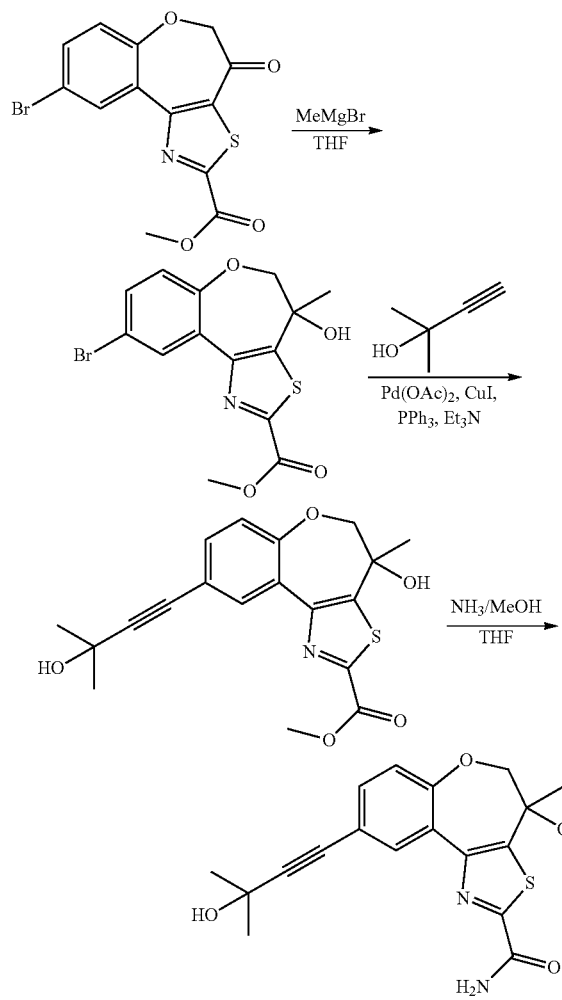

To a stirred solution of 9-Bromo-4-oxo-4,5-dihydro-6-oxa-3-thia-1-aza-benzo[e]azulene-2-carboxylic acid methyl ester (500 mg, 1.41 mmol) in THF (20 mL) at −70° C., was added MeMgBr (1.8 M in THF, 1.57 mL, 2.82 mmol) dropwise. The reaction was stirred at −70° C. for 3 h, and then warmed to −30° C. for 1 h. The reaction mixture was quenched with saturated aqueous NH$_4$Cl solution at −30° C. and extracted with EtOAc (20 mL×2). The combined organic layers were washed with brine, dried over Na$_2$SO$_4$, concentrated and purified by flash column chromatography (silica gel, EtOAc in hexane from 0 to 30%) to give 9-Bromo-4-hydroxy-4-methyl-4,5-dihydro-6-oxa-3-thia-1-aza-benzo[e]azulene-2-carboxylic acid methyl ester as a yellow solid (387 mg, 74%) LC-MS (ESI & APCI): 372.2 (M+2).

A mixture of 9-Bromo-4-hydroxy-4-methyl-4,5-dihydro-6-oxa-3-thia-1-aza-benzo[e]azulene-2-carboxylic acid methyl ester (387 mg, 1.04 mmol), 2-methyl-3-butyn-2-ol (699 mg, 8.32 mmol), Pd(OAc)$_2$ (23 mg, 0.104 mmol), CuI (39 mg, 0.208 mmol) and PPh$_3$ (82 mg, 0.312 mmol) in Et$_3$N (15 mL) was degassed with N$_2$, and the mixture was stirred at 80° C. overnight. The reaction mixture was cooled to room temperature, concentrated and purified by flash column chromatography (silica gel, EtOAc in hexane from 0 to 50%) to give 4-Hydroxy-9-(3-hydroxy-3-methyl-but-1-ynyl)-4-methyl-4,5-dihydro-6-oxa-3-thia-1-aza-benzo[e]azulene-2-carboxylic acid methyl ester as a yellow solid (312 mg, 80%). LC-MS (ESI & APCI): 374.3 (M+1).

To a solution of 4-Hydroxy-9-(3-hydroxy-3-methyl-but-1-ynyl)-4-methyl-4,5-dihydro-6-oxa-3-thia-1-aza-benzo[e]azulene-2-carboxylic acid methyl ester (312 mg, 0.84 mmol) in THF (8 mL) at room temperature, NH$_3$/CH$_3$OH (self-made, 8 mL) was added. The mixture was stirred at room temperature for 3 h, and then concentrated to give a residue which was purified by flash column chromatography (silica gel, EtOAc in hexane from 0 to 50%) to give 4-Hydroxy-9-(3-hydroxy-3-methyl-but-1-ynyl)-4-methyl-4,5-dihydro-6-oxa-3-thia-1-aza-benzo[e]azulene-2-carboxylic acid amide as an off-white solid (212 mg, 71%). $^1$H NMR (400 MHz, DMSO-d$_6$): δ 8.57 (d, J=2.0 Hz, 1H), 8.47 (s, 1H), 7.90 (s, 1H), 7.31 (dd, J$_1$=8.3 Hz, J$_2$=2.1 Hz, 1H), 7.07 (d, J=8.4 Hz, 1H), 6.26 (s, 1H), 5.46 (s, 1H), 4.21 (d, J=11.7 Hz, 1H), 4.01 (d, J=11.8 Hz, 1H), 1.57 (s, 3H), 1.49 (s, 6H); LC-MS (ESI & APCI): 359.2 (M+1).

Example 110.1

Synthesis of 4-carbamoylmethyl-9-(3-hydroxy-3-methyl-but-1-ynyl)-4,5-dihydro-6-oxa-3-thia-1-aza-benzo[e]azulene-2-carboxylic acid amide

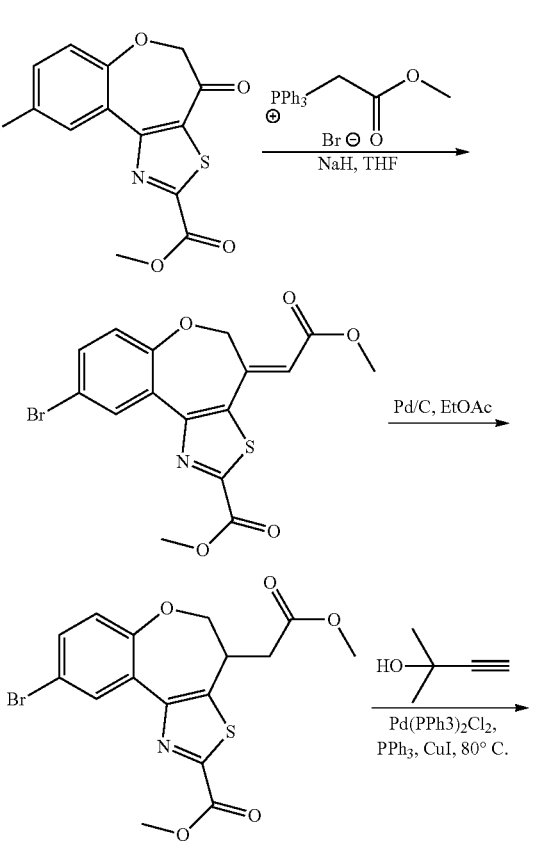

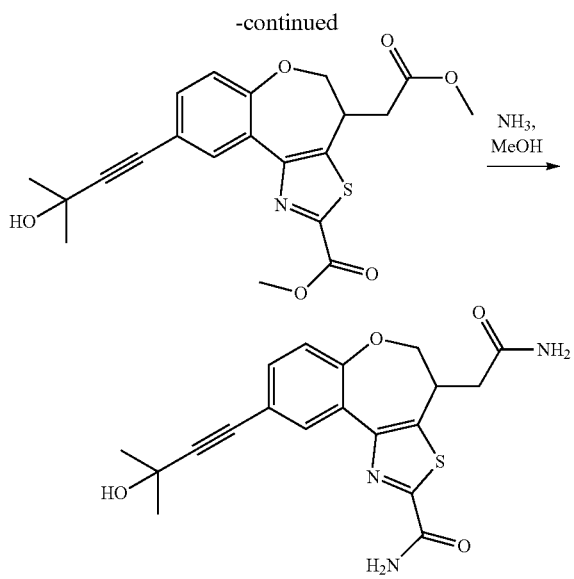

To a stirred solution of 9-Bromo-4-oxo-4,5-dihydro-6-oxa-3-thia-1-aza-benzo[e]azulene-2-carboxylic acid methyl ester (100 mg, 0.28 mmol) in THF (7 mL), was added Methoxycarbonylmethyl(triphenyl)phosphonium Bromide (120 mg, 0.28 mmol), NaH (6.8 mg, 0.28 mmol). The reaction mixture was heated to 70° C. overnight. The mixture was cooled to room temperature and partitioned between EtOAc and H$_2$O. The aqueous layer was extracted with EtOAc (2×10 mL). The combined organic layers were washed with brine, dried over Na$_2$SO$_4$, filtered, concentrated in vacuo, and purified by flash column chromatography to afford 9-Bromo-4-[1-methoxycarbonyl-meth-(E)-ylidene]-4,5-dihydro-6-oxa-3-thia-1-aza-benzo[e]azulene-2-carboxylic acid methyl ester (50 mg, 43%) as a light yellow solid. LC-MS (ESI & APCI): 412.3 (M+2).

To a stirred solution of 9-Bromo-4-[1-methoxycarbonyl-meth-(E)-ylidene]-4,5-dihydro-6-oxa-3-thia-1-aza-benzo[e]azulene-2-carboxylic acid methyl ester (70 mg, 0.17 mmol) in EtOAc (15 mL), 10% Pd/C (1% H$_2$O) (30 mg) was added. The reaction mixture was degassed with H$_2$. The mixture was stirred at 50° C. under 50 Psi of H$_2$ overnight. Then the mixture was filtered thought Celite, and the filtrate was concentrated in vacuo, and purified by flash column chromatography to afford 9-Bromo-4-methoxycarbonylmethyl-4,5-dihydro-6-oxa-3-thia-1-aza-benzo[e]azulene-2-carboxylic acid methyl ester (60 mg, 85%) as a light yellow solid. $^1$H NMR (400 MHz, CDCl$_3$): δ 8.75 (d, J=2.5 Hz, 1H), 7.38 (dd, J$_1$=8.6 Hz, J$_2$=2.5 Hz, 1H), 6.98 (d, J=8.6 Hz, 1H), 4.62 (dd, J$_1$=12.2 Hz, J$_2$=3.7 Hz, 1H), 4.07 (m, 1H), 4.04 (s, 3H), 3.98 (m, 1H), 2.79 (s, 3H), 2.88 (m, 1H); LC-MS (ESI & APCI): 414.4 (M+2).

To a stirred mixture of 9-Bromo-4-methoxycarbonylmethyl-4,5-dihydro-6-oxa-3-thia-1-aza-benzo[e]azulene-2-carboxylic acid methyl ester (90 mg, 0.22 mmol) in TEA (5 mL) and DMF (1 mL) were added Pd(PPh$_3$)$_2$Cl$_2$ (15 mg, 0.021 mmol), PPh$_3$ (17.2 mg, 0.065 mmol), CuI (8.3 mg, 0.043 mmol) and 2-methylbut-3-yn-2-ol (92 mg, 1.09 mmol). The reaction mixture was degassed with N$_2$ and heated to 80° C. in a microwave reactor for 1.5 h. Then the mixture was cooled to room temperature, EtOAc was added. The filtrate was filtered through Celite. The filtrate was washed with saturated brine, dried over Na$_2$SO$_4$, filtered, concentrated in vacuo, and purified by flash column chromatography (silica gel, EtOAc in hexane from 10% to 20%) to afford 9-(3-Hydroxy-3-methyl-but-1-ynyl)-4-methoxycarbonylmethyl-4,5-dihydro-6-oxa-3-thia-1-aza-benzo[e]azulene-2-carboxylic acid methyl ester (70 mg, 77%) as a light yellow solid. LC-MS (ESI & APCI): 416.7 (M+1).

A solution of 9-(3-Hydroxy-3-methyl-but-1-ynyl)-4-methoxycarbonylmethyl-4,5-dihydro-6-oxa-3-thia-1-aza-benzo[e]azulene-2-carboxylic acid methyl ester (60 mg, 0.144 mmol) in methanol-ammonia (40 mL) was stirred at 50° C. in autoclave overnight. Then the mixture was cooled to room temperature filtered and concentrated to afford crude compound which was triturated with EtOAc to afford 4-Carbamoylmethyl-9-(3-hydroxy-3-methyl-but-1-ynyl)-4,5-dihydro-6-oxa-3-thia-1-aza-benzo[e]azulene-2-carboxylic acid amide (30 mg, 50%) as a light yellow solid. $^1$H NMR (400 MHz, DMSO-d$_6$): δ 8.63 (d, J=2.2 Hz, 1H), 8.46 (s, 1H), 7.88 (s, 1H), 7.29 (s, 1H), 7.27 (dd, J=10.8 Hz, J$_2$=2.2 Hz, 1H), 7.05 (d, J=8.36 Hz, 2H), 5.46 (s, 1H), 4.49 (m, 1H), 4.09 (m, 1H), 3.87 (m, 1H), 2.60 (m, 1H), 1.48 (s, 6H); LC-MS (ESI & APCI): 386.4 (M+1).

Example 111

Synthesis of [2-carbamoyl-9-(3-hydroxy-3-methyl-but-1-ynyl)-4,5-dihydro-6-oxa-3-thia-1-aza-benzo[e]azulen-4-yl]-acetic acid and 4-dimethylcarbamoylmethyl-9-(3-hydroxy-3-methyl-but-1-ynyl)-4,5-dihydro-6-oxa-3-thia-1-aza-benzo[e]azulene-2-carboxylic acid amide

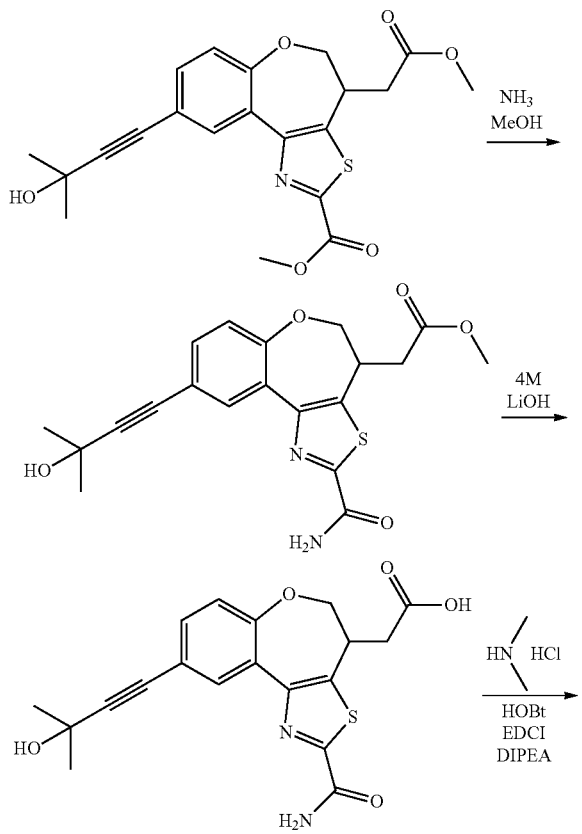

-continued

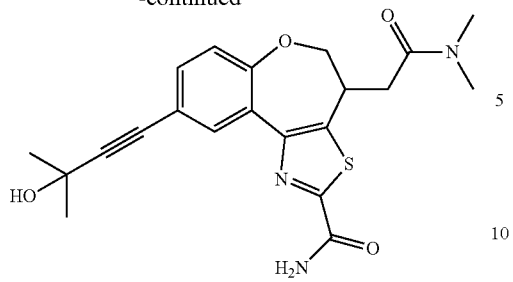

A solution of 9-(3-Hydroxy-3-methyl-but-1-ynyl)-4-methoxycarbonylmethyl-4,5-dihydro-6-oxa-3-thia-1-aza-benzo[e]azulene-2-carboxylic acid methyl ester (70 mg, 0.117 mmol) in methanol-ammonia (40 mL) was stirred at room temperature for 2 h. Then the mixture was concentrated to afford crude compound which was purified by flash column chromatography (silica gel, EtOAc in hexane from 10% to 20%) to afford [2-Carbamoyl-9-(3-hydroxy-3-methyl-but-1-ynyl)-4,5-dihydro-6-oxa-3-thia-1-aza-benzo[e]azulen-4-yl]-acetic acid methyl ester as light yellow oil. LC-MS (ESI & APCI): 401.4 (M+1).

To a solution of [2-Carbamoyl-9-(3-hydroxy-3-methyl-but-1-ynyl)-4,5-dihydro-6-oxa-3-thia-1-aza-benzo[e]azulen-4-yl]-acetic acid methyl ester in MeOH (5 mL) was added 4 mol/L aqueous solution of LiOH (0.2 mL) and the reaction mixture was stirred at room temperature for 2 h. Then the mixture was partitioned between EtOAc and H$_2$O, and the aqueous layer was extracted with EtOAc (2×20 mL). The combined organic layers were washed with brine, dried over Na$_2$SO$_4$, filtered, concentrated in vacuo, and triturated with EtOAc and hexane (1:1) to afford [2-Carbamoyl-9-(3-hydroxy-3-methyl-but-1-ynyl)-4,5-dihydro-6-oxa-3-thia-1-aza-benzo[e]azulen-4-yl]-acetic acid (20 mg) as a light yellow solid. $^1$H NMR (400 MHz, DMSO-d$_6$): δ 12.66 (br, 1H), 8.61 (d, J=2.2 Hz, 1H), 8.46 (s, 1H), 7.88 (s, 1H), 7.28 (dd, J$_1$=8.36 Hz, J$_2$=2.2 Hz, 1H), 7.04 (d, J=8.4 Hz, 1H), 5.45 (s, 1H), 4.5 (m, 1H), 4.16 (m, 1H), 2.72 (m, 1H), 2.62 (m, 1H), 1.48 (s, 6H); LC-MS (ESI & APCI): 387.6 (M+1).

To a mixture of [2-Carbamoyl-9-(3-hydroxy-3-methyl-but-1-ynyl)-4,5-dihydro-6-oxa-3-thia-1-aza-benzo[e]azulen-4-yl]-acetic acid (60 mg, 0.155 mmol) in DCM (20 mL) were added Dimethylamine Hydrochloride (31.7 mg, 0.388 mmol), HOBt (31.5 mg, 0.233 mmol), EDCI (44.7 mg, 0.233 mmol) and DIPEA (60.3 mg, 0.466 mmol). The mixture stirred in autoclave at 60° C. overnight. Then the mixture was cooled to room temperature and partitioned between EtOAc and H$_2$O, and the aqueous layer was extracted with EtOAc (2×20 mL). The combined organic layers were washed with brine, dried over Na$_2$SO$_4$, filtered and concentrated in vacuo. The residue was triturated with EtOAc and hexane (1:1) to afford 4-Dimethylcarbamoylmethyl-9-(3-hydroxy-3-methyl-but-1-ynyl)-4,5-dihydro-6-oxa-3-thia-1-aza-benzo[e]azulene-2-carboxylic acid amide (30 mg, 46%). $^1$H NMR (400 MHz, DMSO-d$_6$): δ 8.61 (d, J=1.8 Hz, 1H), 8.42 (s, 1H), 7.85 (s, 1H), 7.27 (d, J=8.4 Hz, 1H), 7.04 (d, J=8.3 Hz, 1H), 5.45 (s, 1H), 4.5 (m, 1H), 4.10 (m, 1H), 3.93 (m, 1H), 2.90 (d, J=16 Hz, 6H), 2.82 (m, 1H), 2.69 (m, 1H), 1.47 (s, 6H); LC-MS (ESI & APCI): 414.5 (M+1).

Example 112

Synthesis of (±) 10-(4-fluoro-3-hydroxy-3-methyl-but-1-ynyl)-3-(morpholinomethyl)-5,6-dihydroimidazo[1,2-d][1,4]benzoxazepine-2-carboxamide and (±) 10-(3-hydroxy-4-methoxy-3-methyl-but-1-ynyl)-3-(morpholinomethyl)-5,6-dihydroimidazo[1,2-d][1,4]benzoxazepine-2-carboxamide

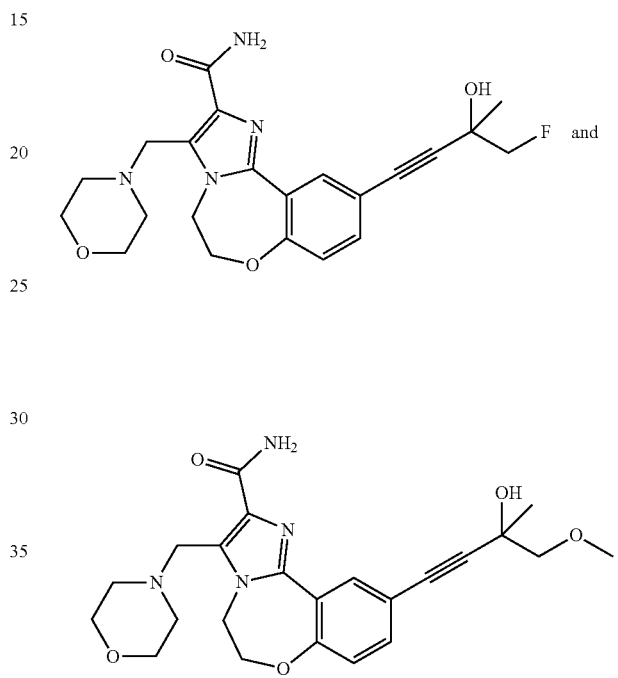

Fluoro-2-methyl-4-triethylsilyl-but-3-yn-2-ol (80 mg) was stirred for 24 hrs at room temperature with potassium carbonate (3 eq) in Methanol (1 mL) after which the carbonate was filtered and the resulting methanol was dried down to a viscous oil. This intermediate 1-fluoro-2-methyl-but-3-yn-2-ol was reacted (in accordance with a procedure described in Procedure E) with 10-bromo-3-(morpholinomethyl)-5,6-dihydroimidazo[1,2-d][1,4]benzoxazepine-2-carboxamide (30 mg) to afford 1.9 mg of (±) 10-(4-fluoro-3-hydroxy-3-methyl-but-1-ynyl)-3-(morpholinomethyl)-5,6-dihydroimidazo[1,2-d][1,4]benzoxazepine-2-carboxamide [MS (Q1) 429 (M)+] and 6.4 mg of (±) 10-(3-hydroxy-4-methoxy-3-methyl-but-1-ynyl)-3-(morpholinomethyl)-5,6-dihydroimidazo[1,2-d][1,4]benzoxazepine-2-carboxamide [MS (Q1) 441 (M)+]. $^1$H NMR (400 MHz, DMSO) δ 8.49 (d, J=2.1 Hz, 1H), 7.56 (s, 1H), 7.29 (dd, J=8.5, 2.2 Hz, 1H), 7.10 (s, 1H), 7.02 (d, J=8.5 Hz, 1H), 5.53 (s, 1H), 4.54-4.42 (m, 5H), 3.98 (s, 2H), 3.57-3.48 (m, 6H), 3.37 (s, 4H), 2.41-2.37 (m, 4H), 1.43 (s, 4H)] following reverse phase purification.

Example 113

Synthesis of (±) 10-(4-fluoro-3-hydroxy-3-methyl-but-1-ynyl)-N-3-methyl-5,6-dihydroimidazo[1,2-d][1,4]benzoxazepine-2,3-dicarboxamide and (±) 10-(3-hydroxy-4-methoxy-3-methyl-but-1-ynyl)-N-3-methyl-5,6-dihydroimidazo[1,2-d][1,4]benzoxazepine-2,3-dicarboxamide

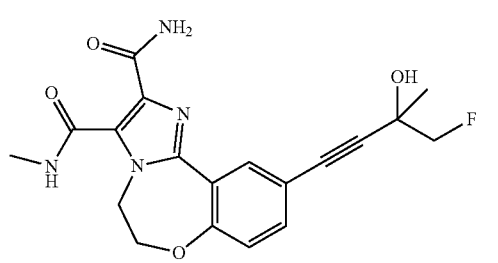

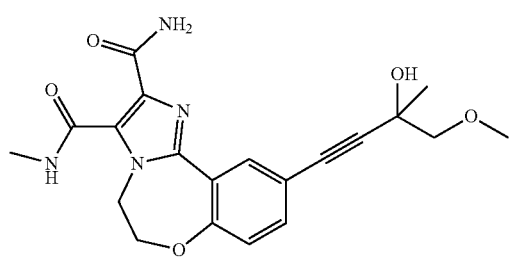

Fluoro-2-methyl-4-triethylsilyl-but-3-yn-2-ol (125 mg) was stirred for 24 hrs at room temperature with potassium carbonate (3 eq) in Methanol (1 mL) after which the carbonate was filtered and the resulting methanol was dried down to a viscous oil. This intermediate 1-fluoro-2-methyl-but-3-yn-2-ol was reacted (in accordance with a procedure described in Procedure G) with 10-bromo-N-3-methyl-5,6-dihydroimidazo[1,2-d][1,4]benzoxazepine-2,3-dicarboxamide (66 mg) to afford 12.7 mg of (±) 10-(4-fluoro-3-hydroxy-3-methyl-but-1-ynyl)-N-3-methyl-5,6-dihydroimidazo[1,2-d][1,4]benzoxazepine-2,3-dicarboxamide [MS (Q1) 387.1 (M)+. $^{1}$H NMR (400 MHz, DMSO) δ 11.06 (q, J=4.6 Hz, 1H), 8.56 (d, J=2.1 Hz, 1H), 8.32 (s, 1H), 7.89 (s, 1H), 7.39 (dd, J=8.5, 2.1 Hz, 1H), 7.06 (d, J=8.5 Hz, 1H), 5.89 (s, 1H), 5.02-4.94 (m, 2H), 4.54-4.47 (m, 2H), 4.43-4.36 (m, 1H), 4.31-4.25 (m, 1H), 2.81 (d, J=4.5 Hz, 3H), 1.48 (d, J=1.6 Hz, 3H)] and 7.1 mg of (±) 10-(3-hydroxy-4-methoxy-3-methyl-but-1-ynyl)-N-3-methyl-5,6-dihydroimidazo[1,2-d][1,4]benzoxazepine-2,3-dicarboxamide [MS (Q1) 399 (M)+. $^{1}$H NMR (400 MHz, DMSO) δ 11.06 (q, J=4.5 Hz, 1H), 8.52 (d, J=2.0 Hz, 1H), 8.32 (s, 1H), 7.88 (s, 1H), 7.36 (dd, J=8.5, 2.1 Hz, 1H), 7.05 (d, J=8.5 Hz, 1H), 5.53 (s, 1H), 4.99-4.94 (m, 2H), 4.53-4.47 (m, 2H), 3.37 (s, 3H), 2.81 (d, J=4.5 Hz, 3H), 1.43 (s, 3H), 1.30 (d, J=11.5 Hz, 2H)] following reverse phase purification.

Example 114

Synthesis of (±) 9-fluoro-10-(4-fluoro-3-hydroxy-3-methyl-but-1-ynyl)-N-3-methyl-5,6-dihydroimidazo[1,2-d][1,4]benzoxazepine-2,3-dicarboxamide and (±) 9-fluoro-10-(3-hydroxy-4-methoxy-3-methyl-but-1-ynyl)-N-3-methyl-5,6-dihydroimidazo[1,2-d][1,4]benzoxazepine-2,3-dicarboxamide

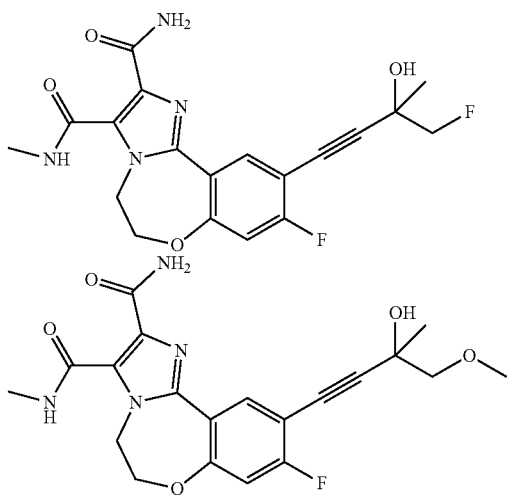

Fluoro-2-methyl-4-triethylsilyl-but-3-yn-2-ol (0.25 g) was stirred for 24 hrs at room temperature with potassium carbonate (3 eq) in Methanol (1 mL) after which the carbonate was filtered and the resulting methanol was dried down to a viscous oil. This intermediate 1-fluoro-2-methyl-but-3-yn-2-ol was reacted similar to as described in General Procedure E with 10-bromo-9-fluoro-N-3-methyl-5,6-dihydroimidazo[1,2-d][1,4]benzoxazepine-2,3-dicarboxamide (0.12 g) to afford 2.8 mg of (±) 9-fluoro-10-(4-fluoro-3-hydroxy-3-methyl-but-1-ynyl)-N-3-methyl-5,6-dihydroimidazo[1,2-d][,4]benzoxazepine-2,3-dicarboxamide [MS (Q1) 405 (M)+] and 3.2 mg of (±) 9-fluoro-10-(3-hydroxy-4-methoxy-3-methyl-but-1-ynyl)-N-3-methyl-5,6-dihydroimidazo[1,2-d][1,4]benzoxazepine-2,3-dicarboxamide [MS (Q1) 417 (M)+] following reverse phase purification.

Example 115

Synthesis of (±) 10-(3,4-dihydroxy-3-methyl-but-1-ynyl)-9-fluoro-N-3-methyl-5,6-dihydroimidazo[1,2-d][1,4]benzoxazepine-2,3-dicarboxamide

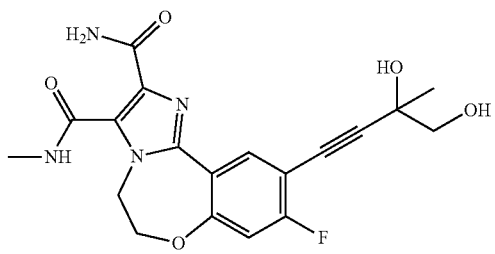 [SMILES: CNC(=O)c1c(C(N)=O)nc2n1CCOc1cc(F)c(C#CC(C)(O)CO)cc1-2]

10-Bromo-9-fluoro-N-3-methyl-5,6-dihydroimidazo[1,2-d][1,4]benzoxazepine-2,3-dicarboxamide (0.08 g) was reacted with 2-methylbut-3-yne-1,2-diol similar to as described in General Procedure E to afford 2.7 mg of (±) 10-(3,4-dihydroxy-3-methyl-but-1-ynyl)-9-fluoro-N-3-methyl-5,6-dihydroimidazo[1,2-d][1,4]benzoxazepine-2,3-dicarboxamide following reverse phase hplc purification. MS (Q1) 403 (M)+.

Example 116

Synthesis of (±) 10-(3,4-dihydroxy-3-methyl-but-1-ynyl)-N-3-methyl-5,6-dihydroimidazo[1,2-d][1,4]benzoxazepine-2,3-dicarboxamide

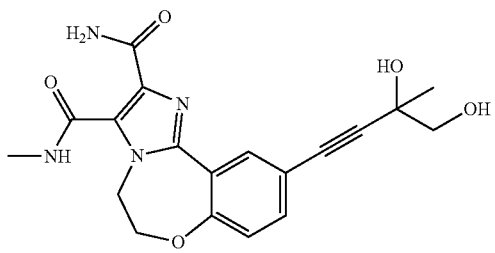 [SMILES: CNC(=O)c1c(C(N)=O)nc2n1CCOc1ccc(C#CC(C)(O)CO)cc1-2]

10-Bromo-N-3-methyl-5,6-dihydroimidazo[1,2-d][1,4]benzoxazepine-2,3-dicarboxamide (0.08 g) was reacted with 2-methylbut-3-yne-1,2-diol similar to as described in General Procedure E to afford 6.8 mg of (±) 10-(3,4-dihydroxy-3-methyl-but-1-ynyl)-N-3-methyl-5,6-dihydroimidazo[1,2-d][1,4]benzoxazepine-2,3-dicarboxamide following reverse phase purification. MS (Q1) 385 (M)+. $^1$H NMR (400 MHz, DMSO) δ 11.06 (q, J=3.9 Hz, 1H), 8.52 (d, J=2.0 Hz, 1H), 8.30 (s, 1H), 7.89 (s, 1H), 7.38 (dd, J=8.5, 2.1 Hz, 1H), 7.04 (d, J=8.5 Hz, 1H), 5.32 (s, 1H), 4.98-4.92 (m, 3H), 4.56-4.45 (m, 2H), 3.48-3.36 (m, 2H), 2.81 (d, J=4.5 Hz, 3H), 1.40 (s, 3H).

Example 117

Synthesis of 9-bromo-10-fluoro-2,5-diazatetracyclo[11.1.1.0$^{2,6}$.0$^{7,12}$]pentadeca-3,5,7,9,11-pentaene-4-carboxamide AND 9-bromo-10-fluoro-3-N-methyl-2,5-diazatetracyclo[11.1.1.0$^{2,6}$.0$^{7,12}$]pentadeca-3,5,7,9,11-pentaene-3,4-dicarboxamide

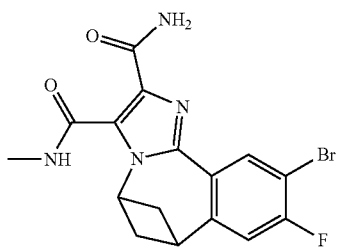 [SMILES: CNC(=O)c1c(C(N)=O)nc2n1C1CC(C1)c1cc(F)c(Br)cc1-2]

Methyl 9-bromo-10-fluoro-2,5-diazatetracyclo[11.1.1.0$^{2,6}$.0$^{7,12}$]pentadeca-3,5,7,9,11-pentaene-4-carboxylate (1.5 g) was reacted with methyl isocyanate similar to as described in Example 8 or Example 9 to give (0.86 g) of a crude mixture of 9-bromo-10-fluoro-2,5-diazatetracyclo[11.1.1.0$^{2,6}$.0$^{7,12}$]pentadeca-3,5,7,9,11-pentaene-4-carboxylic acid and 9-bromo-10-fluoro-3-(methylcarbamoyl)-2,5-diazatetracyclo[11.1.1.0$^{2,6}$.0$^{7,12}$]pentadeca-3,5,7,9,11-pentaene-4-carboxylic acid. This mixture was reacted with ammonium chloride similar to as described in Example 2 to give 0.48 g of a mixture of 9-bromo-10-fluoro-2,5-diazatetracyclo[11.1.1.0$^{2,6}$.0$^{7,12}$]pentadeca-3,5,7,9,11-pentaene-4-carboxamide and 9-bromo-10-fluoro-3-N-methyl-2,5-diazatetracyclo[11.1.1.0$^{2,6}$.0$^{7,12}$]pentadeca-3,5,7,9,11-pentaene-3,4-dicarboxamide.

Example 118

Synthesis of (±) 9-(3,4-dihydroxy-3-methylbut-1-yn-1-yl)-10-fluoro-3-N-methyl-2,5-diazatetracyclo[11.1.1.0$^{2,6}$.0$^{7,12}$]pentadeca-3,5,7,9,11-pentaene-3,4-dicarboxamide and (±) 9-(3,4-dihydroxy-3-methylbut-1-yn-1-yl)-10-fluoro-2,5 diazatetracyclo[11.1.1.0$^{2,6}$.0$^{7,12}$]pentadeca-3,5,7,9,11-pentaene-4-carboxamide

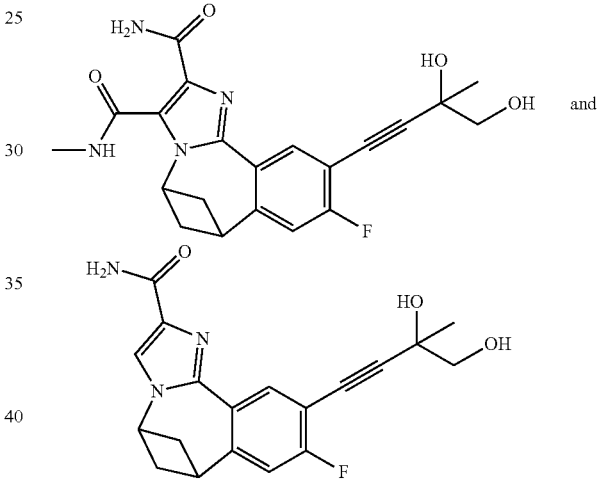

A mixture of 9-bromo-10-fluoro-2,5-diazatetracyclo[11.1.1.0$^{2,6}$.0$^{7,12}$]pentadeca-3,5,7,9,11-pentaene-4-carboxamide and 9-bromo-10-fluoro-3-N-methyl-2,5-diazatetracyclo[11.1.1.0$^{2,6}$.0$^{7,12}$]pentadeca-3,5,7,9,11-pentaene-3,4-dicarboxamide (125 mg) was reacted with 2-methylbut-3-yne-1,2-diol similar to as described in Procedure E to afford 25.2 mg of (±) 9-(3,4-dihydroxy-3-methylbut-1-yn-1-yl)-10-fluoro-3-N-methyl-2,5-diazatetracyclo[11.1.1.0$^{2,6}$.0$^{7,12}$]pentadeca-3,5,7,9,11-pentaene-3,4-dicarboxamide [MS (Q1) 413 (M)+, $^1$H NMR (400 MHz, DMSO) δ 10.56 (q, J=4.6 Hz, 1H), 8.83 (d, J=7.5 Hz, 1H), 8.24 (s, 1H), 7.75 (s, 1H), 7.29 (d, J=10.0 Hz, 1H), 6.16-6.02 (m, 1H), 5.43 (s, 1H), 4.99 (t, J=6.1 Hz, 1H), 3.74-3.60 (m, 1H), 3.54-3.37 (m, 2H), 3.20-3.02 (m, 2H), 2.78 (d, J=4.5 Hz, 3H), 1.76-1.62 (m, 2H), 1.44 (s, 3H)] and 14.3 mg of (±) 9-(3,4-dihydroxy-3-methylbut-1-yn-1-yl)-10-fluoro-2,5 diazatetracyclo[11.1.1.0$^{2,6}$.0$^{7,12}$]pentadeca-3,5,7,9,11-pentaene-4-carboxamide [MS (Q1) 356 (M)+. $^1$H NMR (400 MHz, DMSO) δ 8.65 (d, J=7.6 Hz, 1H), 7.82 (s, 1H), 7.51 (s, 1H), 7.27 (d, J=10.2 Hz, 1H), 7.09 (s, 1H), 5.45 (s, 1H), 5.01 (s, 1H), 4.91 (q, J=10.6, 1H), 3.75-3.67 (m, 1H), 3.44 (q, J=10.6 Hz, 2H), 3.14-3.03 (m, 2H), 1.68 (d, J=12.2 Hz, 2H), 1.43 (s, 3H).] following reverse phase hplc purification.

Example 119

Synthesis of 10-fluoro-9-[(3R)-3-hydroxy-3-(5-methyl-1,2-oxazol-3-yl)but-1-yn-1-yl]-3-N-methyl-2,5-diazatetracyclo[11.1.1.0²,⁶.0⁷,¹²]pentadeca-3,5,7,9,11-pentaene-3,4-dicarboxamide

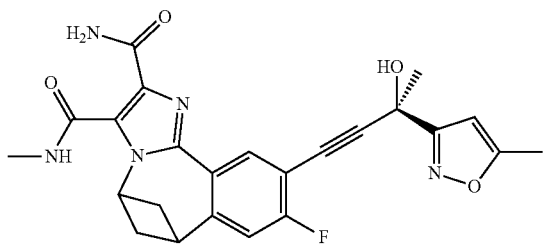

9-Bromo-10-fluoro-3-N-methyl-2,5-diazatetracyclo[11.1.1.0[2,6].0[7,12]]pentadeca-3,5,7,9,11-pentaene-3,4-dicarboxamide (125 mg) was reacted with (2R)-2-(5-methylisoxazol-3-yl)but-3-yn-2-ol similar to as described in Procedure E to afford 19.5 mg of 10-fluoro-9-[(3R)-3-hydroxy-3-(5-methyl-1,2-oxazol-3-yl)but-1-yn-1-yl]-3-N-methyl-2,5-diazatetracyclo[11.1.1.0[2,6].0[7,12]]pentadeca-3,5,7,9,11-pentaene-3,4-dicarboxamide following reverse phase hplc purification. MS (Q1) 464 (M)+. ¹H NMR (400 MHz, DMSO) δ 10.59 (q, J=4.6 Hz, 1H), 8.85 (d, J=7.5 Hz, 1H), 8.28 (s, 1H), 7.74 (s, 1H), 7.32 (d, J=10.1 Hz, 1H), 6.58 (s, 1H), 6.36 (s, 1H), 6.19-6.03 (m, 1H), 3.73-3.61 (m, 1H), 3.18-3.05 (m, 2H), 2.78 (d, J=4.5 Hz, 3H), 2.41 (s, 4H), 1.68 (d, J=12.0 Hz, 3H).

Example 120

Synthesis of 10-fluoro-9-[(3R)-3-hydroxy-3-(5-methyl-1,2,4-oxadiazol-3-yl)but-1-yn-1-yl]-3-N-methyl-2,5-diazatetracyclo[11.1.1.0[2,6].0[7,12]]pentadeca-3,5,7,9,11-pentaene-3,4-dicarboxamide

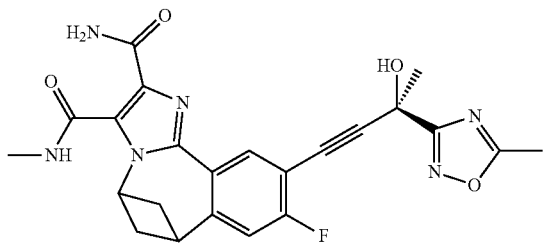

9-Bromo-10-fluoro-3-N-methyl-2,5-diazatetracyclo[11.1.1.0[2,6].0[7,12]]pentadeca-3,5,7,9,11-pentaene-3,4-dicarboxamide (125 mg) was reacted with (2R)-2-(5-methyl-1,2,4-oxadiazol-3-yl)but-3-yn-2-ol similar to as described in General Procedure G to afford 14.5 mg of 10-fluoro-9-[(3R)-3-hydroxy-3-(5-methyl-1,2,4-oxadiazol-3-yl)but-1-yn-1-yl]-3-N-methyl-2,5-diazatetracyclo[11.1.1.0[2,6].0[7,12]]pentadeca-3,5,7,9,11-pentaene-3,4-dicarboxamide following reverse phase hplc purification. MS (Q1) 465 (M)⁺. ¹H NMR (400 MHz, DMSO) δ 10.58 (q, J=4.1 Hz, 1H), 8.86 (d, J=7.5 Hz, 1H), 8.28 (s, 1H), 7.74 (s, 1H), 7.33 (d, J=10.0 Hz, 1H), 6.79 (s, 1H), 6.13-6.05 (m, 1H), 3.74-3.63 (m, 1H), 3.18-3.05 (m, 2H), 2.78 (d, J=4.6 Hz, 2H), 2.62 (s, 3H), 1.87 (s, 3H), 1.68 (d, J=12.3 Hz, 2H).

Example 121

Synthesis of 9-[2-(1-hydroxycyclopentyl)ethynyl]-2,5-diazatetracyclo[11.1.1.0²,⁶.0⁷,¹²]pentadeca-3,5,7,9,11-pentaene-4-carboxamide

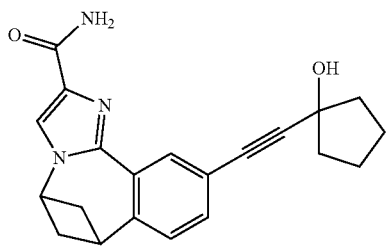 [SMILES: NC(=O)c1cn2c(n1)-c1cc(C#CC3(O)CCCC3)ccc1C1CC2C1]

9-Bromo-2,5-diazatetracyclo[11.1.1.0[2,6].0[7,12]]pentadeca-3,5,7(12),8,10-pentaene-4-carboxamide (30 mg) was reacted with 1-ethynylcyclopentanol similar to as described in Procedure E to afford 8.9 mg of 9-[2-(1-hydroxycyclopentyl)ethynyl]-2,5-diazatetracyclo[11.1.1.0[2,6].0[7,12]]pentadeca-3,5,7,9,11-pentaene-4-carboxamide following reverse phase hplc purification. MS (Q1) 348 (M)⁺. ¹H NMR (400 MHz, DMSO) δ 8.61 (d, J=11.1 Hz, 1H), 7.82 (s, 1H), 7.52 (s, 1H), 7.26 (s, 2H), 7.09 (s, 1H), 5.33 (s, 1H), 4.92 (q, J=4.5 Hz, 1H), 3.75-3.66 (m, 1H), 3.12-3.03 (m, 2H), 1.96-1.88 (m, 4H), 1.81-1.62 (m, 7H).

Example 121.1

Synthesis of 10-fluoro-9-[(3R)-3-hydroxy-3-(5-methyl-1,2-oxazol-3-yl)but-1-yn-1-yl]-3-N-methyl-2,5-diazatetracyclo[11.1.1.0²,⁶.0⁷,¹²]pentadeca-3,5,7,9,11-pentaene-3,4-dicarboxamide

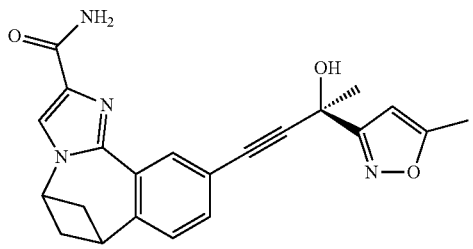 [SMILES: Cc1cc([C@](C)(O)C#Cc2ccc3c(c2)-c2nc(C(N)=O)cn2C2CC3C2)no1]

9-Bromo-2,5-diazatetracyclo[11.1.1.0[2,6].0[7,12]]pentadeca-3,5,7(12),8,10-pentaene-4-carboxamide (0.3 g) was reacted with (2R)-2-(5-methylisoxazol-3-yl)but-3-yn-2-ol similar to as described in Procedure G to afford 224 mg of 10-fluoro-9-[(3R)-3-hydroxy-3-(5-methyl-1,2-oxazol-3-yl)but-1-yn-1-yl]-3-N-methyl-2,5-diazatetracyclo[11.1.1.0[2,6].0[7,12]]pentadeca-3,5,7,9,11-pentaene-3,4-dicarboxamide following reverse phase hplc purification. MS (Q1) 389 (M)⁺. ¹H NMR (400 MHz, DMSO) δ 8.64 (s, 1H), 7.83 (s, 1H), 7.52 (s, 1H), 7.29 (s, 2H), 7.09 (s, 1H), 6.51 (s, 1H), 6.36 (s, 1H), 4.97-4.85 (m, 1H), 3.78-3.67 (m, 1H), 3.15-3.01 (m, 2H), 2.41 (s, 3H), 1.81 (s, 3H), 1.66 (d, J=11.9 Hz, 2H).

Example 121.2

Synthesis of 9-[(3R)-3-hydroxy-3-(5-methyl-1,2,4-oxadiazol-3-yl)but-1-yn-1-yl]-2,5-diazatetracyclo[11.1.1.0[2,6].0[7,12]]pentadeca-3,5,7(12),8,10-pentaene-4-carboxamide

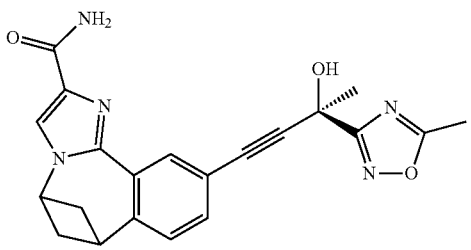 [SMILES: Cc1nc([C@](C)(O)C#Cc2ccc3c(c2)-c2nc(C(N)=O)cn2C2CC3C2)no1]

9-Bromo-2,5-diazatetracyclo[11.1.1.0[2,6].0[7,12]]pentadeca-3,5,7(12),8,10-pentaene-4-carboxamide (0.15 g) was reacted with (2R)-2-(5-methyl-1,2,4-oxadiazol-3-yl)but-3-yn-2-ol similar to as described in Procedure G to afford 24.2 mg of 9-[(3R)-3-hydroxy-3-(5-methyl-1,2,4-oxadiazol-3-yl)but-1-yn-1-yl]-2,5-diazatetracyclo[11.1.1.0[2,6].0[7,12]]pentadeca-3,5,7(12),8,10-pentaene-4-carboxamide following reverse phase hplc purification. MS (Q1) 390.1 (M)+. 1H NMR (400 MHz, DMSO) δ 8.65 (s, 1H), 7.84 (s, 1H), 7.52 (s, 1H), 7.30 (s, 2H), 7.09 (s, 1H), 6.72 (s, 1H), 4.98-4.88 (m, 1H), 3.78-3.68 (m, 1H), 3.15-3.02 (m, 2H), 2.62 (s, 3H), 1.85 (s, 3H), 1.66 (d, J=11.9 Hz, 2H).

Example 121.3

Synthesis of methyl 9-bromo-10-fluoro-3-formyl-2,5-diazatetracyclo[11.1.1.0[2,6].0[7,12]]pentadeca-3,5,7(12),8,10-pentaene-4-carboxylate

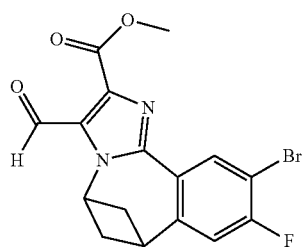 [SMILES: COC(=O)c1nc2n(c1C=O)C1CC(C1)c1cc(F)c(Br)cc1-2]

Methyl 9-bromo-10-fluoro-2,5-diazatetracyclo[11.1.1.0[2,6].0[7,12]]pentadeca-3,5,7,9,11-pentaene-4-carboxylate (4 g) was reacted with ethyl formate similar to as described in Example 8 or Example 9 to give (2.3 g) of methyl 9-bromo-10-fluoro-3-formyl-2,5-diazatetracyclo[11.1.1.0[2,6].0[7,12]]pentadeca-3,5,7(12),8,10-pentaene-4-carboxylate following trituration from water.

Example 121.4

Synthesis of 9-bromo-10-fluoro-3-formyl-2,5-diazatetracyclo[11.1.1.0[2,6].0[7,12]]pentadeca-3,5,7(12),8,10-pentaene-4-carboxylic acid

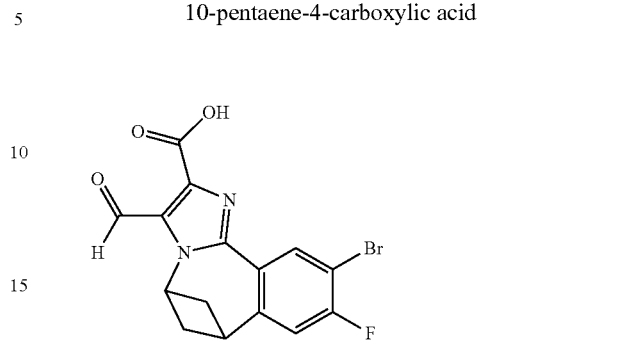

Methyl 9-bromo-10-fluoro-3-formyl-2,5-diazatetracyclo[11.1.1.0[2,6].0[7,12]]pentadeca-3,5,7(12),8,10-pentaene-4-carboxylate (125 mg) was saponified with LiOH in H2O/MeOH to give 90 mg of 9-bromo-10-fluoro-3-formyl-2,5-diazatetracyclo[11.1.1.0[2,6].0[7,12]]pentadeca-3,5,7(12),8,10-pentaene-4-carboxylic acid.

Example 121.5

Synthesis of 9-bromo-10-fluoro-3-formyl-2,5-diazatetracyclo[11.1.1.0[2,6].0[7,12]]pentadeca-3,5,7(12),8,10-pentaene-4-carboxamide

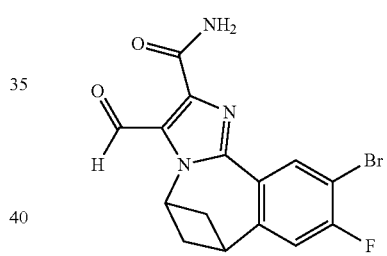

9-bromo-10-fluoro-3-formyl-2,5-diazatetracyclo[11.1.1.0[2,6].0[7,12]]pentadeca-3,5,7(12),8,10-pentaene-4-carboxylic acid (0.09 g) was reacted with ammonium chloride similar to as described in Example 2 to give 60 mg of 9-bromo-10-fluoro-3-formyl-2,5-diazatetracyclo[11.1.1.0[2,6].0[7,12]]pentadeca-3,5,7(12),8,10-pentaene-4-carboxamide.

Example 121.6

Synthesis of 9-bromo-10-fluoro-3-(morpholin-4-ylmethyl)-2,5-diazatetracyclo[11.1.1.0[2,6].0[7,12]]pentadeca-3,5,7(12),8,10-pentaene-4-carboxamide

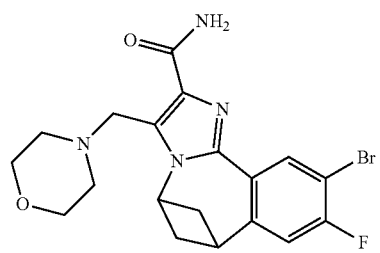 [SMILES: NC(=O)c1nc2n(c1CN1CCOCC1)C1CC(C1)c1cc(F)c(Br)cc1-2]

9-Bromo-10-fluoro-3-formyl-2,5-diazatetracyclo[11.1.1.0[2,6].0[7,12]]pentadeca-3,5,7(12),8,10-pentaene-4-carboxamide (0.06 g) was reacted with morpholine similar to as described in Example 7 to afford 72 mg of crude 9-bromo-10-fluoro-3-(morpholin-4-ylmethyl)-2,5-diazatetracyclo[11.1.1.0[2,6].0[7,12]]pentadeca-3,5,7(12),8,10-pentaene-4-carboxamide.

Example 121.7

Synthesis of 10-fluoro-9-(3-hydroxy-3-methylbut-1-yn-1-yl)-3-(morpholin-4-ylmethyl)-2,5-diazatetracyclo[11.1.1.0[2,6].0[7,12]]pentadeca-3,5,7(12),8,10-pentaene-4-carboxamide

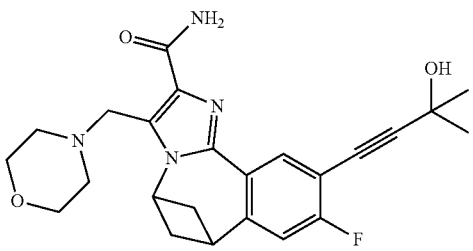 [SMILES: CC(C)(O)C#Cc1cc2c(cc1F)C1CC(C1)n1c-2nc(C(N)=O)c1CN1CCOCC1]

9-Bromo-10-fluoro-3-(morpholin-4-ylmethyl)-2,5-diazatetracyclo[11.1.1.0[2,6].0[7,12]]pentadeca-3,5,7(12),8,10-pentaene-4-carboxamide (72 mg) was reacted with 2-Methyl-3-butyne-ol similar to as described in Procedure G to afford 2.8 mg of 10-fluoro-9-(3-hydroxy-3-methylbut-1-yn-1-yl)-3-(morpholin-4-ylmethyl)-2,5-diazatetracyclo[11.1.1.0[2,6].0[7,12]]pentadeca-3,5,7(12),8,10-pentaene-4-carboxamide following reverse phase hplc purification. MS (Q1) 441.2 (M)+.

Example 121.8

Synthesis of (±) 10-fluoro-9-(4-fluoro-3-hydroxy-3-methylbut-1-yn-1-yl)-2,5-diazatetracyclo[11.1.1.0[2,6].0[7,12]]pentadeca-3,5,7(12),8,10-pentaene-4-carboxamide

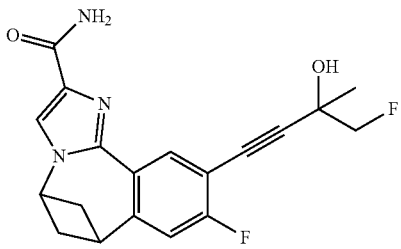 [SMILES: CC(O)(C#Cc1cc2c(cc1F)C1CC(C1)n1cc(C(N)=O)nc1-2)CF]

To a vial containing 9-bromo-10-fluoro-2,5-diazatetracyclo[11.1.1.0[2,6].0[7,12]]pentadeca-3,5,7,9,11-pentaene-4-carboxamide (0.1 g), palladium acetate (0.05 eq), sodium acetate (4 eq) and tetrabutylammonium chloride (1 eq) was added DMF (15 mL/mmol) and 1-fluoro-2-methyl-4-triethylsilyl-but-3-yn-2-ol (2 eq) dropwise. The reaction was sealed and heated to 100° C. for 15 minutes in a biotage microwave. The reaction mixture was extracted with DCM and saturated ammonium chloride. The organic layer was dried with magnesium sulfate, filtered, concentrated to dryness and purified by reverse phase hplc to afford (±) 10-fluoro-9-(4-fluoro-3-hydroxy-3-methylbut-1-yn-1-yl)-2,5-diazatetracyclo[11.1.1.0[2,6].0[7,12]]pentadeca-3,5,7(12),8,10-pentaene-4-carboxamide. MS (Q1) 358 (M)+. $^1$H NMR (400 MHz, DMSO) δ 8.67 (d, J=7.6 Hz, 1H), 7.82 (s, 1H), 7.53 (s, 1H), 7.30 (d, J=10.2 Hz, 1H), 7.10 (s, 1H), 6.01 (s, 1H), 4.91 (q, J=10.6, 6.2 Hz, 1H), 4.48-4.37 (m, 1H), 4.37-4.27 (m, 1H), 3.78-3.64 (m, 1H), 3.15-2.99 (m, 2H), 1.68 (d, J=12.2 Hz, 2H), 1.50 (s, 3H).

Example 121.9

Synthesis of 10-[(3R)-3-hydroxy-3-(5-methylisoxazol-3-yl)but-1-ynyl]-5,6-dihydroimidazo[1,2-d][1,4]benzoxazepine-2-carboxamide

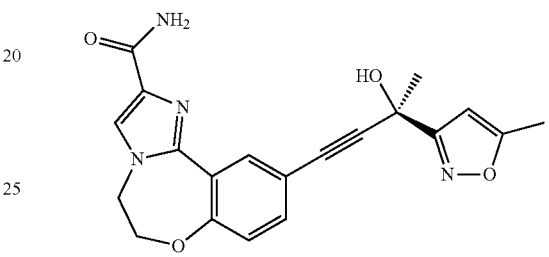

10-Bromo-5,6-dihydroimidazo[1,2-d][1,4]benzoxazepine-2-carboxamide (50 mg) was reacted with (2R)-2-(5-methylisoxazol-3-yl)but-3-yn-2-ol similar to as described in Procedure G to afford 5.7 mg of 10-[(3R)-3-hydroxy-3-(5-methylisoxazol-3-yl)but-1-ynyl]-5,6-dihydroimidazo[1,2-d][1,4]benzoxazepine-2-carboxamide following reverse phase hplc purification. MS (Q1) 379 (M)+. $^1$H NMR (400 MHz, DMSO) δ 8.53 (d, J=2.2 Hz, 1H), 7.79 (s, 1H), 7.53 (s, 1H), 7.33 (dd, J=8.5, 2.2 Hz, 1H), 7.12 (s, 1H), 7.03 (d, J=8.5 Hz, 1H), 6.50 (d, J=18.3 Hz, 1H), 6.35 (s, 1H), 4.49 (s, 4H), 2.39 (d, J=11.3 Hz, 3H), 1.80 (s, 3H).

Example 122

Synthesis of (±) 9-fluoro-10-(3-hydroxy-3-pyrazin-2-yl-but-1-ynyl)-5,6-dihydroimidazo[1,2-d][1,4]benzoxazepine-2-carboxamide

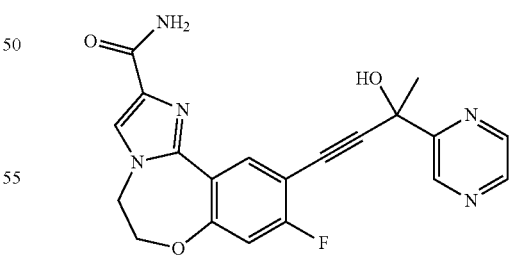

Pyrazin-2-ylethanone (0.2 g) was subjected to similar to as described in Procedure A to form crude 2-pyrazin-2-ylbut-3-yn-2-ol which was reacted with 10-bromo-9-fluoro-5,6-dihydroimidazo[1,2-d][1,4]benzoxazepine-2-carboxamide (0.1 g) similar to as described in Procedure E to afford 23 mg of (±) 9-fluoro-10-(3-hydroxy-3-pyrazin-2-yl-but-1-ynyl)-5,6-dihydroimidazo[1,2-d][1,4]benzoxazepine-2-carboxamide following reverse phase hplc purification. MS (Q1) 394 (M)+.

¹H NMR (400 MHz, DMSO) δ 9.01 (s, 1H), 8.67-8.61 (m, 2H), 8.56 (d, J=8.5 Hz, 1H), 7.77 (s, 1H), 7.56 (s, 1H), 7.11 (s, 1H), 7.01 (d, J=10.6 Hz, 1H), 6.71 (s, 1H), 4.50 (d, J=10.5 Hz, 4H), 1.86 (s, 3H).

Example 123

Synthesis of (±) 9-fluoro-10-(3-hydroxy-3-pyrimidin-2-yl-but-1-ynyl)-5,6-dihydroimidazo[1,2-d][1,4]benzoxazepine-2-carboxamide

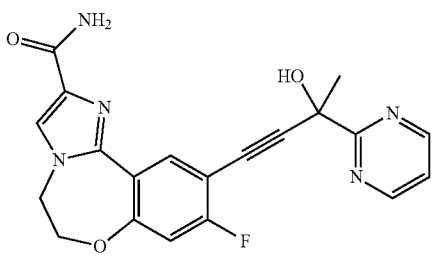

Pyrimidin-2-ylethanone (0.2 g) was subjected to similar to as described in Procedure A to form crude 2-pyrimidin-2-ylbut-3-yn-2-ol which was reacted with 10-bromo-9-fluoro-5,6-dihydroimidazo[1,2-d][1,4]benzoxazepine-2-carboxamide (0.1 g) via similar to as described in Procedure E to afford 7 mg of (±) 9-fluoro-10-(3-hydroxy-3-pyrimidin-2-yl-but-1-ynyl)-5,6-dihydroimidazo[1,2-d][1,4]benzoxazepine-2-carboxamide following reverse phase hplc purification. MS (Q1) 394 (M)+. ¹H NMR (400 MHz, DMSO) δ 8.89 (d, J=4.8 Hz, 2H), 8.54 (d, J=8.5 Hz, 1H), 7.77 (s, 1H), 7.56 (s, 1H), 7.50 (t, J=4.9 Hz, 1H), 7.11 (s, 1H), 7.00 (d, J=10.6 Hz, 1H), 4.50 (d, J=9.6 Hz, 4H), 1.88 (s, 3H).

Example 124

Synthesis of 9-fluoro-10-[(3R)-3-hydroxy-3-pyrimidin-5-yl-but-1-ynyl]-5,6-dihydroimidazo[1,2-d][1,4]benzoxazepine-2-carboxamide and 9-fluoro-10-[(3S)-3-hydroxy-3-pyrimidin-5-yl-but-1-ynyl]-5,6-dihydroimidazo[1,2-d][1,4]benzoxazepine-2-carboxamide

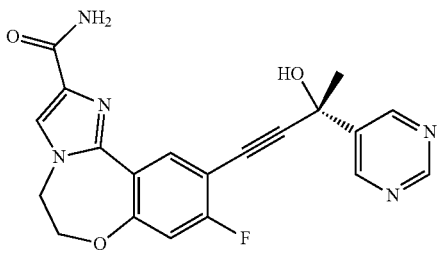

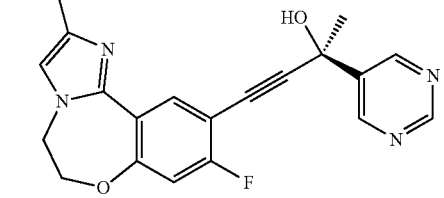

Pyrimidin-5-ylethanone (0.2 g) was subjected to similar to as described in Procedure A to form crude 2-pyrimidin-5-ylbut-3-yn-2-ol which was reacted with 10-bromo-9-fluoro-5,6-dihydroimidazo[1,2-d][1,4]benzoxazepine-2-carboxamide (0.1 g) similar to as described in Procedure E. The enantiomers were separated by chiral SFC to afford 9.3 mg of 9-fluoro-10-[(3R)-3-hydroxy-3-pyrimidin-5-yl-but-1-ynyl]-5,6-dihydroimidazo[1,2-d][1,4]benzoxazepine-2-carboxamide and 9.6 mg of 9-fluoro-10-[(3S)-3-hydroxy-3-pyrimidin-5-yl-but-1-ynyl]-5,6-dihydroimidazo[1,2-d][1,4]benzoxazepine-2-carboxamide. MS (Q1) 394 (M)+. ¹H NMR (400 MHz, DMSO) δ 9.17 (s, 1H), 9.03 (s, 2H), 8.63 (d, J=8.4 Hz, 1H), 7.78 (s, 1H), 7.56 (s, 1H), 7.13 (s, 1H), 7.05 (d, J=10.6 Hz, 1H), 6.62 (brs, 1H), 4.51 (dd, J=17.0, 5.1 Hz, 4H), 1.84 (s, 3H).

Example 125

Synthesis of (±) 9-fluoro-10-[3-(2-fluorophenyl)-3-hydroxy-but-1-ynyl]-5,6-dihydroimidazo[1,2-d][1,4]benzoxazepine-2-carboxamide

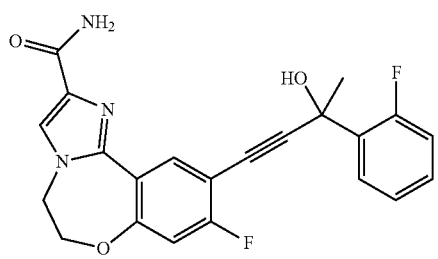

1-(2-Fluorophenyl)ethanone (0.2 g) was subjected to similar to as described in Procedure A to form crude 2-(2-fluorophenyl)but-3-yn-2-ol which was reacted with 10-bromo-9-fluoro-5,6-dihydroimidazo[1,2-d][1,4]benzoxazepine-2-carboxamide (0.1 g) similar to as described in Procedure E to afford 11 mg of (±) 9-fluoro-10-[3-(2-fluorophenyl)-3-hydroxy-but-1-ynyl]-5,6-dihydroimidazo[1,2-d][1,4]benzoxazepine-2-carboxamide following reverse phase hplc purification. MS (Q1) 410 (M)⁺. NMR (400 MHz, DMSO) δ 8.55 (d, J=8.5 Hz, 1H), 7.78 (s, 1H), 7.72 (dd, J=12.9, 6.4 Hz, 1H), 7.54 (s, 1H), 7.37 (dd, J=13.0, 5.7 Hz, 1H), 7.26-7.16 (m, 2H), 7.11 (s, 1H), 7.01 (d, J=10.5 Hz, 1H), 6.47 (s, 1H), 4.50 (dd, J=15.1, 5.3 Hz, 4H), 1.82 (s, 3H).

Example 126

Synthesis of 9-fluoro-104(1-hydroxycyclobutyl)ethynyl)-5,6-dihydrobenzo[f]imidazo[1,2-d][1,4]oxazepine-2-carboxamide

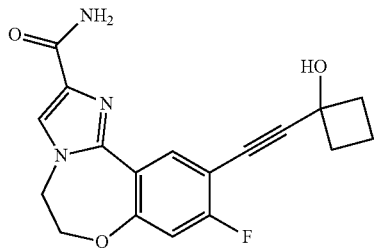 [SMILES: NC(=O)c1cn2c(n1)-c1cc(C#CC3(O)CCC3)c(F)cc1OCC2]

Cyclobutanone (0.2 g) was subjected to similar to as described in Procedure A to form crude 1-ethynylcyclobutanol which was reacted with 10-bromo-9-fluoro-5,6-dihydroimidazo[1,2-d][1,4]benzoxazepine-2-carboxamide (0.1 g) via similar to as described in Procedure E to afford 33.8 mg of 9-fluoro-10-((1-hydroxycyclobutyl)ethynyl)-5,6-dihydrobenzo[f]imidazo[1,2-d][1,4]oxazepine-2-carboxamide after triteration from methanol and activated charcoal treatment. The mother liquor was concentrated and purified by reverse phase hplc to afford and additional 8.9 mg of product. MS (Q1) 342 (M)+. $^1$H NMR (400 MHz, DMSO) δ 8.59 (d, J=8.5 Hz, 1H), 7.78 (s, 1H), 7.57 (s, 1H), 7.12 (s, 1H), 7.01 (d, J=10.6 Hz, 1H), 5.94 (s, 1H), 4.50 (dd, J=14.9, 5.3 Hz, 4H), 2.44-2.36 (m, 2H), 2.23 (m, 3H), 1.89-1.70 (m, 2H).

Example 127

Synthesis of (±) 9-fluoro-10-[3-hydroxy-3-(2-methyl-3-pyridyl)but-1-ynyl]-5,6-dihydroimidazo[1,2-d][1,4]benzoxazepine-2-carboxamide

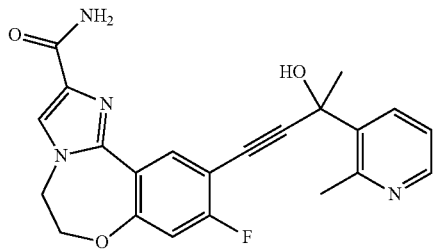 [SMILES: Cc1ncccc1C(C)(O)C#Cc1cc2c(cc1F)OCCn1cc(C(N)=O)nc1-2]

1-(2-Methyl-3-pyridyl)ethanone (0.2 g) was subjected to similar to as described in Procedure A to form crude 2-(2-methyl-3-pyridyl)but-3-yn-2-ol which was reacted with 10-bromo-9-fluoro-5,6-dihydroimidazo[1,2-d][1,4]benzoxazepine-2-carboxamide (0.1 g) similar to as described in Procedure E to afford 3.1 mg of (±) 9-fluoro-10-[3-hydroxy-3-(2-methyl-3-pyridyl)but-1-ynyl]-5,6-dihydroimidazo[1,2-d][1,4]benzoxazepine-2-carboxamide following reverse phase hplc purification. MS (Q1) 407 (M)+.

Example 128

Synthesis of 3-benzyl-9-fluoro-10-(3-hydroxy-3-methyl-but-1-ynyl)-5,6-dihydroimidazo[1,2-d][1,4]benzoxazepine-2-carboxamide

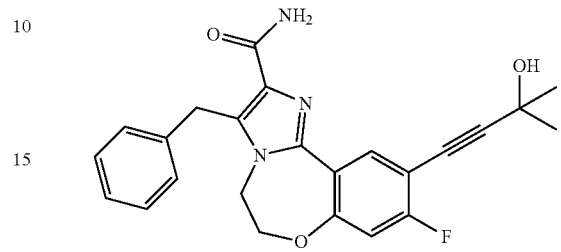

10-Bromo-9-fluoro-3-iodo-5,6-dihydroimidazo[1,2-d][1,4]benzoxazepine-2-carboxamide (70 mg) was reacted with potassium benzyltrifluoroborate similar to as described in Example 5 and purified by reverse phase hplc to give 3-benzyl-10-bromo-9-fluoro-5,6-dihydroimidazo[1,2-d][1,4]benzoxazepine-2-carboxamide. This intermediate was reacted with 2-Methyl-3-butyne-ol similar to as described in Procedure E to afford 4.9 mg of 3-benzyl-9-fluoro-10-(3-hydroxy-3-methyl-but-1-ynyl)-5,6-dihydroimidazo[1,2-d][1,4]benzoxazepine-2-carboxamide following reverse phase hplc purification. MS (Q1) 420 (M)+. $^1$H NMR (400 MHz, CDCl$_3$) δ 8.56 (d, J=8.2 Hz, 1H), 7.28 (d, J=7.1 Hz, 1H), 7.22-7.15 (m, 3H), 6.69 (d, J=9.9 Hz, 1H), 5.46 (s, 1H), 4.59 (s, 2H), 4.31 (dd, J=5.2, 3.1 Hz, 2H), 4.04 (dd, J=5.1, 3.1 Hz, 2H), 1.65 (s, 6H).

Example 129

Synthesis of 9-fluoro-3-[(2-fluorophenyl)methyl]-10-(3-hydroxy-3-methyl-but-1-ynyl)-5,6-dihydroimidazo[1,2-d][1,4]benzoxazepine-2-carboxamide

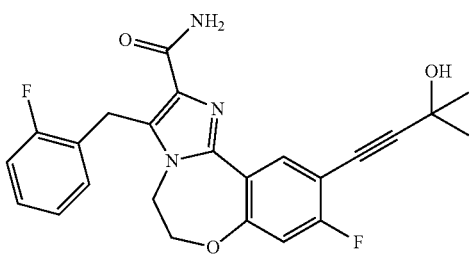 [SMILES: CC(C)(O)C#Cc1cc2c(cc1F)OCCn1c-2nc(C(N)=O)c1Cc1ccccc1F]

10-Bromo-9-fluoro-3-iodo-5,6-dihydroimidazo[1,2-d][1,4]benzoxazepine-2-carboxamide (70 mg) was reacted with 2-(2-fluorobenzyl)-4,4,5,5-tetramethyl-1,3,2-dioxaboralane similar to as described in Example 4 and purified by reverse phase hplc to give 35 mg of 10-bromo-9-fluoro-3-[(2-fluorophenyl)methyl]-5,6-dihydroimidazo[1,2-d][1,4]benzoxazepine-2-carboxamide. This intermediate was reacted with 2-Methyl-3-butyne-ol similar to as described in Procedure E to afford 14.9 mg of 9-fluoro-3-[(2-fluorophenyl)methyl]-10-(3-hydroxy-3-methyl-but-1-ynyl)-5,6-dihydroimidazo[1,2-d][1,4]benzoxazepine-2-carboxamide following reverse phase hplc purification. MS (Q1) 438 (M)+. ¹H NMR (400 MHz, CDCl₃) δ 8.55 (d, J=8.2 Hz, 1H), 7.23-7.15 (m, 2H), 7.08-7.00 (m, 2H), 6.74 (dd, J=29.1, 9.5 Hz, 1H), 5.40 (s, 1H), 4.59 (s, 2H), 4.37 (dd, J=5.0, 3.1 Hz, 2H), 4.09 (dd, J=5.1, 3.1 Hz, 2H), 1.65 (s, 6H).

Example 130

Synthesis of 3-cyano-9-fluoro-10-(3-hydroxy-3-methyl-but-1-ynyl)-5,6-dihydroimidazo[1,2-d][1,4]benzoxazepine-2-carboxamide

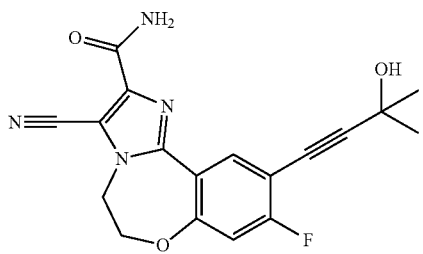 [SMILES: CC(C)(O)C#Cc1cc2c(cc1F)OCCn1c-2nc(C(N)=O)c1C#N]

Potassium Cyanide (0.8 eq) and Copper (I) Iodide (0.2 eq) were added to solution of 10-bromo-9-fluoro-3-iodo-5,6-dihydroimidazo[1,2-d][1,4]benzoxazepine-2-carboxamide (0.05 g) in DMF (3 ml/mmol). The reaction was heated overnight at 150° C., filtered and purified by reverse phase hplc to give 10-bromo-3-cyano-9-fluoro-5,6-dihydroimidazo[1,2-d][1,4]benzoxazepine-2-carboxamide. This intermediate was reacted with 2-Methyl-3-butyne-ol similar to as described in Procedure E to afford 12 mg of 3-cyano-9-fluoro-10-(3-hydroxy-3-methyl-but-1-ynyl)-5,6-dihydroimidazo[1,2-d][1,4]benzoxazepine-2-carboxamide following reverse phase hplc purification. MS (Q1) 355 (M)+. ¹H NMR (400 MHz, DMSO) δ 8.69-8.56 (m, 1H), 8.04 (s, 1H), 7.64 (s, 1H), 7.14-7.00 (m, 1H), 5.51 (d, J=10.2 Hz, 1H), 4.63-4.57 (m, 2H), 4.56-4.49 (m, 2H), 1.49 (s, 6H).

Example 131

Synthesis of (±) 9-fluoro-10-[3-hydroxy-3-[5-(hydroxymethyl)isoxazol-3-yl]but-1-ynyl]-5,6-dihydroimidazo[1,2-d][1,4]benzoxazepine-2-carboxamide

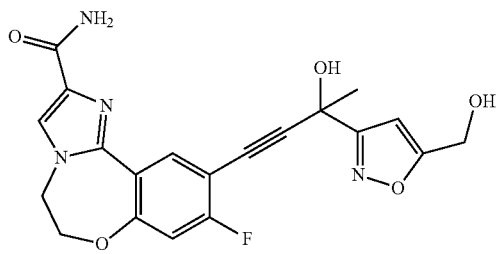 [SMILES: CC(O)(C#Cc1cc2c(cc1F)OCCn1cc(C(N)=O)nc1-2)c1cc(CO)on1]

A mixture of 2-prop-2-ynoxytetrahydropyran (3 mL) and ferric nitrate (1 eq) in acetone (60 mL) was stirred at 55° C. for 15 hrs. The reaction mixture was cooled, filtered thru celite, concentrated and purified by ISCO flash column chromatography (0-90% Ethyl Acetate:heptane over 25 mins) to give 2.16 g of 1-[5-(hydroxymethyl)isoxazol-3-yl]ethanone as a yellow oil. 1-[5-(hydroxymethyl)isoxazol-3-yl]ethanone (0.3 g) was subjected similar to as described in Procedure A to form crude 2-[5-(hydroxymethyl)isoxazol-3-yl]but-3-yn-2-ol which was reacted with 10-bromo-9-fluoro-5,6-dihydroimidazo[1,2-d][1,4]benzoxazepine-2-carboxamide (0.15 g) similar to as described in Procedure E to afford 20.7 mg of (±) 9-fluoro-10-[3-hydroxy-3-[5-(hydroxymethyl)isoxazol-3-yl]but-1-ynyl]-5,6-dihydroimidazo[1,2-d][1,4]benzoxazepine-2-carboxamide following reverse phase hplc purification. MS (Q1) 413 (M)+. ¹H NMR (400 MHz, DMSO) δ 8.57 (d, J=8.4 Hz, 1H), 7.77 (d, J=7.6 Hz, 1H), 7.54 (s, 1H), 7.10 (s, 1H), 7.02 (d, J=10.6 Hz, 1H), 6.61 (s, 1H), 6.50 (d, J=12.9 Hz, 1H), 5.63 (t, J=6.1 Hz, 1H), 4.56 (d, J=6.0 Hz, 2H), 4.55-4.45 (m, 4H), 1.83 (s, 3H).

Example 132

Synthesis of 9-fluoro-3-[(2-fluorophenyl)methyl]-10-(3-hydroxy-3-methyl-but-1-ynyl)-5,6-dihydroimidazo[1,2-d][1,4]benzoxazepine-2-carboxamide

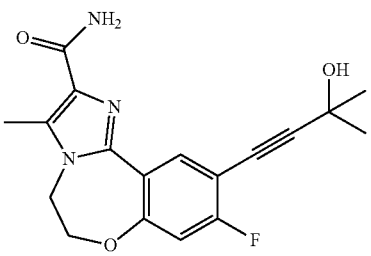 [SMILES: Cc1c(C(N)=O)nc2n1CCOc1cc(F)c(C#CC(C)(C)O)cc1-2]

10-Bromo-9-fluoro-3-iodo-5,6-dihydroimidazo[1,2-d][1,4]benzoxazepine-2-carboxamide (0.2 g) was reacted with potassium methyltrifluoroborate similar to as described in Example 5 to give 20 mg of 10-bromo-9-fluoro-3-methyl-5,6-dihydroimidazo[1,2-d][1,4]benzoxazepine-2-carboxamide after reverse phase hplc purification. This intermediate was reacted with 2-Methyl-3-butyne-ol similar to as described in Procedure E to afford 17.4 mg of 9-fluoro-3-[(2-fluorophenyl)methyl]-10-(3-hydroxy-3-methyl-but-1-ynyl)-5,6-dihydroimidazo[1,2-d][1,4]benzoxazepine-2-carboxamide following reverse phase hplc purification. MS (Q1) 344 (M)+. ¹H NMR (400 MHz, DMSO) δ 8.55 (dd, J=8.5, 3.5 Hz, 1H), 7.48 (s, 1H), 6.98 (d, J=10.5 Hz, 2H), 5.49 (s, 1H), 4.63-4.36 (m, 2H), 4.35-4.24 (m, 2H), 1.49 (s, 6H).

Example 133

Synthesis of 9-fluoro-10-(3-hydroxy-3-methyl-but-1-ynyl)-3-(1H-pyrazol-3-yl)-5,6-dihydroimidazo[1,2-d][1,4]benzoxazepine-2-carboxamide

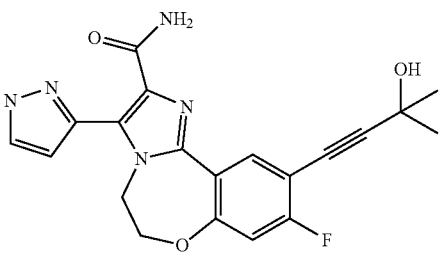 [SMILES: CC(C)(O)C#Cc1cc2c(cc1F)OCCn1c-2nc(C(N)=O)c1-c1cc[nH]n1]

10-Bromo-9-fluoro-3-iodo-5,6-dihydroimidazo[1,2-d][1,4]benzoxazepine-2-carboxamide (0.2 g) was reacted with 3-(4,4,5,5-tetramethyl-1,3,2-dioxaborolan-2-yl)-1H-pyrazole similar to as described in Example 4 and triturated from water followed by methanol to give 107 mg of 10-bromo-9-fluoro-3-(1H-pyrazol-3-yl)-5,6-dihydroimidazo[1,2-d][1,4]benzoxazepine-2-carboxamide. This intermediate was reacted with 2-Methyl-3-butyne-ol similar to as described in Procedure E to afford 3.3 mg of 9-fluoro-10-(3-hydroxy-3-methyl-but-1-ynyl)-3-(1H-pyrazol-3-yl)-5,6-dihydroimidazo[1,2-d][1,4]benzoxazepine-2-carboxamide following reverse phase hplc purification. MS (Q1) 396 (M)+.

Example 134

Synthesis of 3-cyclopropyl-9-fluoro-10-(3-hydroxy-3-methyl-but-1-ynyl)-5,6-dihydroimidazo[1,2-d][1,4]benzoxazepine-2-carboxamide

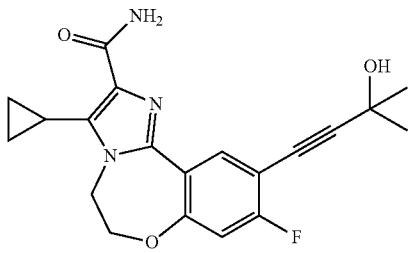 [SMILES: CC(C)(O)C#Cc1cc2c(cc1F)OCCn1c-2nc(C(N)=O)c1C1CC1]

10-Bromo-9-fluoro-3-iodo-5,6-dihydroimidazo[1,2-d][1,4]benzoxazepine-2-carboxamide (0.2 g) was reacted with potassium cyclopropyltrifluoroborate via similar to as described in Example 5 to give 48 mg of 10-bromo-3-cyclopropyl-9-fluoro-5,6-dihydroimidazo[1,2-d][1,4]benzoxazepine-2-carboxamide after reverse phase hplc purification. This intermediate was reacted with 2-Methyl-3-butyne-ol similar to as described in Procedure E to afford 26.3 mg of 3-cyclopropyl-9-fluoro-10-(3-hydroxy-3-methyl-but-1-ynyl)-5,6-dihydroimidazo[1,2-d][1,4]benzoxazepine-2-carboxamide following reverse phase hplc purification. MS (Q1) 370 (M)+. $^1$H NMR (400 MHz, DMSO) δ 8.54 (d, J=8.5 Hz, 1H), 7.45 (s, 1H), 6.97 (d, J=10.5 Hz, 1H), 6.94 (s, 1H), 5.50 (s, 1H), 4.47 (dd, J=54.2, 27.1 Hz, 4H), 1.85-1.69 (m, 1H), 1.48 (s, 6H), 1.02-0.93 (m, 2H), 0.82 (d, J=5.0 Hz, 2H).

Example 135

Synthesis of 8-fluoro-9-[2-(1-hydroxycyclopentyl)ethynyl]-4,5-dihydro-[1]benzoxepino[5,4-d]thiazole-2-carboxamide

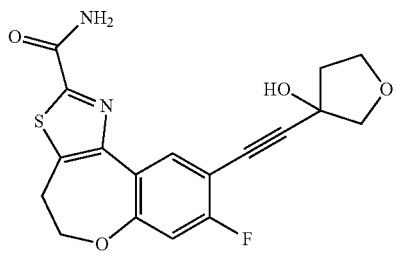 [SMILES: NC(=O)c1nc2c(s1)CCOc1cc(F)c(C#CC3(O)CCOC3)cc1-2]

9-Bromo-8-fluoro-4,5-dihydro-[1]benzoxepino[5,4-d]thiazole-2-carboxamide (0.25 g) was reacted with 1-ethynylcyclopentanol similar to as described in Procedure E to afford 157 mg of 8-fluoro-9-[2-(1-hydroxycyclopentyl)ethynyl]-4,5-dihydro-[1]benzoxepino[5,4-d]thiazole-2-carboxamide following reverse phase hplc purification. MS (Q1) 338 (M)+. $^1$H NMR (400 MHz, DMSO) δ 8.65 (d, J=8.6 Hz, 1H), 8.45 (s, 1H), 7.84 (s, 1H), 7.03 (t, J=25.1 Hz, 1H), 5.29 (d, J=38.1 Hz, 1H), 4.38 (t, J=4.8 Hz, 2H), 3.40 (t, J=4.8 Hz, 2H), 2.02-1.86 (m, 4H), 1.85-1.57 (m, 5H).

Example 136

Synthesis of 9-fluoro-10-(3-hydroxy-3-methyl-but-1-ynyl)-N3-methyl-5,6-dihydroimidazo[1,2-d][1,4]benzoxazepine-2,3-dicarboxamide

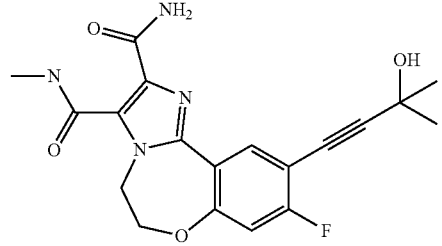 [SMILES: CNC(=O)c1c(C(N)=O)nc2n1CCOc1cc(F)c(C#CC(C)(C)O)cc1-2]

10-Bromo-9-fluoro-3-iodo-5,6-dihydroimidazo[1,2-d][1,4]benzoxazepine-2-carboxamide (2 g) was subjected similar to as described in Example 6 to yield 1.22 g of methyl 10-bromo-2-carbamoyl-9-fluoro-5,6-dihydroimidazo[1,2-d][1,4]benzoxazepine-3-carboxylate. 75 mg of methyl 10-bromo-2-carbamoyl-9-fluoro-5,6-dihydroimidazo[1,2-d][1,4]benzoxazepine-3-carboxylate was treated with LiOH in water/THF to afford 59 mg 10-bromo-2-carbamoyl-9-fluoro-5,6-dihydroimidazo[1,2-d][1,4]benzoxazepine-3-carboxylic acid. This intermediate was reacted with N-Methylamine Hydrochloride similar to as described in Example 2 to produce crude 10-bromo-9-fluoro-N3-methyl-5,6-dihydroimidazo[1,2-d][1,4]benzoxazepine-2,3-dicarboxamide which was then reacted with 2-Methyl-3-butyne-ol similar to as described in Procedure E to afford 8.6 mg of 9-fluoro-10-(3-hydroxy-3-methyl-but-1-ynyl)-N3-methyl-5,6-dihydroimidazo[1,2-d][1,4]benzoxazepine-2,3-dicarboxamide following reverse phase hplc purification. MS (Q1) 387 (M)+. $^1$H NMR (400 MHz, DMSO) δ 11.09 (q, J=4.6 Hz, 1H), 8.61 (d, J=8.5 Hz, 1H), 8.38 (s, 1H), 7.88 (s, 1H), 7.02 (d, J=10.6 Hz, 1H), 5.50 (s, 1H), 5.05-4.94 (m, 2H), 4.58-4.47 (m, 2H), 2.80 (d, J=4.6 Hz, 3H), 1.49 (s, 6H).

Example 137

Synthesis of 9-fluoro-3-(hydroxymethyl)-10-(3-hydroxy-3-methyl-but-1-ynyl)-5,6-dihydroimidazo[1,2-d][1,4]benzoxazepine-2-carboxamide

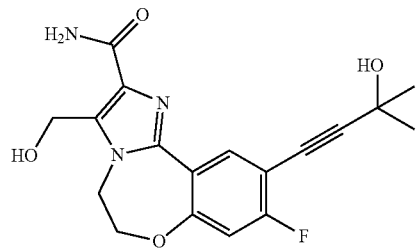 [SMILES: CC(C)(O)C#Cc1cc2c(cc1F)OCCn1c-2nc(C(N)=O)c1CO]

To methyl 10-bromo-2-carbamoyl-9-fluoro-5,6-dihydroimidazo[1,2-d][1,4]benzoxazepine-3-carboxylate (0.3 g) was added lithium borohydride (2 mol/L in THF, 1.2 eq) and the reaction was stirred for 1 hour. The reaction was quenched with water and extracted with DCM. The organic layer was dried with magnesium sulfate, filtered and concentrated to dryness. 10-bromo-9-fluoro-3-(hydroxymethyl)-5,6-dihydroimidazo[1,2-d][1,4]benzoxazepine-2-carboxamide (0.15 g) was reacted with 2-Methyl-3-butyne-ol similar to as described in Procedure E to afford 17.1 mg of 9-fluoro-3-(hydroxymethyl)-10-(3-hydroxy-3-methyl-but-1-ynyl)-5,6-dihydroimidazo[1,2-d][1,4]benzoxazepine-2-carboxamide following reverse phase hplc purification. MS (Q1) 360 (M)+. $^1$H NMR (400 MHz, DMSO) δ 8.57 (d, J=8.5 Hz, 1H), 7.65 (s, 1H), 7.19 (s, 1H), 7.00 (d, J=10.5 Hz, 1H), 5.49 (s, 1H), 5.38 (t, J=5.3 Hz, 1H), 4.90 (d, J=5.3 Hz, 2H), 4.57-4.40 (m, 4H), 1.49 (s, 6H).

Example 138

Synthesis of 9-fluoro-10-(3-hydroxy-3-methyl-but-1-ynyl)-N3,N3-dimethyl-5,6-dihydroimidazo[1,2-d][1,4]benz oxazepine-2,3-dicarboxamide

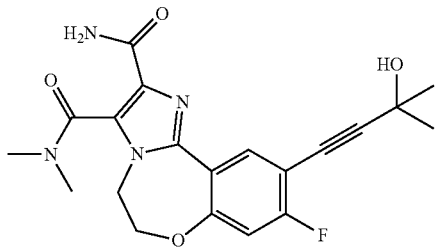 [SMILES: CN(C)C(=O)c1c(C(N)=O)nc2n1CCOc1cc(F)c(C#CC(C)(C)O)cc1-2]

10-Bromo-2-carbamoyl-9-fluoro-5,6-dihydroimidazo[1,2-d][1,4]benzoxazepine-3-carboxylic acid (60 mg) was reacted with dimethylamine Hydrochloride similar to as described in Example 2 to produce crude 10-bromo-9-fluoro-N3,N3-dimethyl-5,6-dihydroimidazo[1,2-d][1,4]benzoxazepine-2,3-dicarboxamide which was then reacted with 2-Methyl-3-butyne-ol similar to as described in Procedure E to afford 41.3 mg of 9-fluoro-10-(3-hydroxy-3-methyl-but-1-ynyl)-N3,N3-dimethyl-5,6-dihydroimidazo[1,2-d][1,4]benz oxazepine-2,3-dicarboxamide following reverse phase hplc purification. MS (Q1) 401 (M)+. $^1$H NMR (400 MHz, DMSO) δ 8.58 (d, J=8.5 Hz, 1H), 7.68 (s, 1H), 7.24 (s, 1H), 7.02 (d, J=10.5 Hz, 1H), 6.58 (s, 1H), 5.51 (s, 1H), 4.61-4.48 (m, 2H), 4.39-4.12 (m, 2H), 3.01 (s, 3H), 2.88 (s, 3H), 1.49 (s, 6H).

Example 139

Synthesis of 9-fluoro-10-(3-hydroxy-3-methyl-but-1-ynyl)-3-(1H-pyrazol-4-yl)-5,6-dihydroimidazo[1,2-d][1,4]benzoxazepine-2-carboxamide

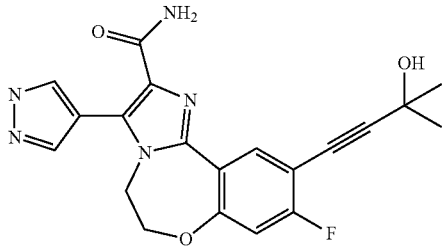 [SMILES: CC(C)(O)C#Cc1cc2c(cc1F)OCCn1c-2nc(C(N)=O)c1-c1cn[nH]c1]

10-Bromo-9-fluoro-3-iodo-5,6-dihydroimidazo[1,2-d][1,4]benzoxazepine-2-carboxamide (0.14 g) was reacted with 1-Boc-4-pyrazoleboronic acid pinacol ester similar to as described in Example 4 and triturated from water followed by methanol to give 100 mg of 10-bromo-9-fluoro-3-(1H-pyrazol-4-yl)-5,6-dihydroimidazo[1,2-d][1,4]benzoxazepine-2-carboxamide. This intermediate was reacted with 2-Methyl-3-butyne-ol via similar to as described in Procedure E to afford 47.5 mg of 9-fluoro-10-(3-hydroxy-3-methyl-but-1-ynyl)-3-(1H-pyrazol-4-yl)-5,6-dihydroimidazo[1,2-d][1,4]benzoxazepine-2-carboxamide following reverse phase hplc purification. MS (Q1) 396 (M)+. $^1$H NMR (400 MHz, DMSO) δ 13.10 (s, 1H), 8.62 (s, 1H), 8.10 (s, 1H), 7.81 (s, 1H), 7.57 (s, 1H), 7.01 (s, 1H), 6.99 (s, 1H), 5.50 (s, 1H), 4.54-4.41 (m, 2H), 4.38-4.20 (m, 2H), 2.07 (s, 1H), 1.51 (s, 6H).

Example 140

Synthesis of 9-fluoro-10-(3-hydroxy-3-methyl-but-1-ynyl)-3-[1-(2-hydroxy-2-methyl-propyl)pyrazol-4-yl]-5,6-dihydroimidazo[1,2-d][1,4]benzoxazepine-2-carboxamide

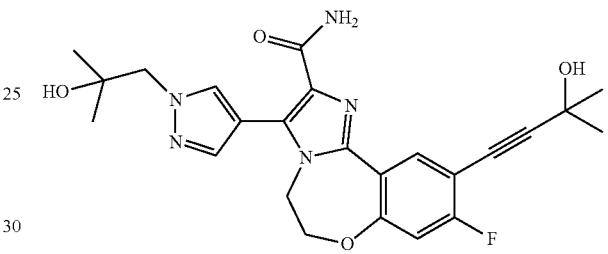

10-Bromo-9-fluoro-3-iodo-5,6-dihydroimidazo[1,2-d][1,4]benzoxazepine-2-carboxamide (0.1 g) was reacted with 2-methyl-1-[4-(4,4,5,5-tetramethyl-1,3,2-dioxaborolan-2-yl)pyrazol-1-yl]propan-2-ol similar to as described in Example 5 and triturated from water followed by methanol to give 100 mg of 10-bromo-9-fluoro-3-[1-(2-hydroxy-2-methyl-propyl)pyrazol-4-yl]-5,6-dihydroimidazo[1,2-d][1,4]benzoxazepine-2-carboxamide. This intermediate was reacted with 2-Methyl-3-butyne-ol via similar to as described in Procedure E to afford 18.1 mg of 9-fluoro-10-(3-hydroxy-3-methyl-but-1-ynyl)-3-[1-(2-hydroxy-2-methyl-propyl)pyrazol-4-yl]-5,6-dihydroimidazo[1,2-d][1,4]benzoxazepine-2-carboxamide following reverse phase hplc purification. MS (Q1) 468 (M)+. $^1$H NMR (400 MHz, DMSO) δ 8.62 (d, J=8.5 Hz, 1H), 8.08 (s, 1H), 7.75 (s, 1H), 7.57 (s, 1H), 7.08-6.91 (m, 2H), 5.50 (s, 1H), 4.68 (s, 1H), 4.54-4.45 (m, 2H), 4.41-4.29 (m, 2H), 4.07 (s, 2H), 1.50 (s, 6H), 1.10 (s, 6H).

Example 141

Synthesis of 3-cyclopropyl-9-fluoro-10-[(3R)-3-hydroxy-3-(5-methylisoxazol-3-yl)but-1-ynyl]-5,6-dihydroimidazo[1,2-d][1,4]benzoxazepine-2-carboxamide

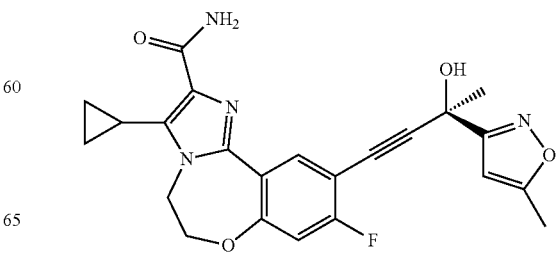

10-Bromo-3-cyclopropyl-9-fluoro-5,6-dihydroimidazo[1,2-d][1,4]benzoxazepine-2-carboxamide (62 mg) was reacted with (2R)-2-(5-methylisoxazol-3-yl)but-3-yn-2-ol similar to as described in Procedure E to afford 39.2 mg of 3-cyclopropyl-9-fluoro-10-[(3R)-3-hydroxy-3-(5-methylisoxazol-3-yl)but-1-ynyl]-5,6-dihydroimidazo[1,2-d][1,4]benzoxazepine-2-carboxamide following reverse phase hplc purification. MS (Q1) 437 (M)+. $^1$H NMR (400 MHz, DMSO) δ 8.53 (d, J=18.5 Hz, 1H), 7.44 (s, 1H), 6.99 (d, J=10.5 Hz, 1H), 6.92 (s, 1H), 6.51 (s, 1H), 6.34 (s, 1H), 4.64-4.37 (m, 4H), 2.40 (s, 3H), 1.81 (s, 2H), 1.79-1.71 (m, 1H), 1.03-0.93 (m, 2H), 0.86-0.77 (m, 2H).

Example 142

Synthesis of 2-carbamoyl-9-fluoro-10-(3-hydroxy-3-methyl-but-1-ynyl)-5,6-dihydroimidazo[1,2-d][1,4]benzoxazepine-3-carboxylic acid

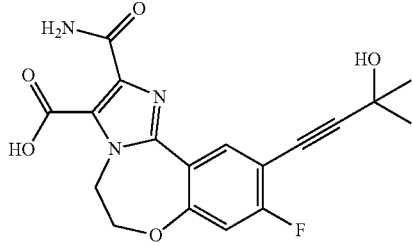 [SMILES: CC(C)(O)C#Cc1cc2c(cc1F)OCCn1c-2nc(C(N)=O)c1C(=O)O]

Methyl 10-bromo-2-carbamoyl-9-fluoro-5,6-dihydroimidazo[1,2-d][1,4]benzoxazepine-3-carboxylate (2 g) was reacted with 2-Methyl-3-butyne-ol similar to as described in Procedure E to afford 2 g of methyl 2-carbamoyl-9-fluoro-10-(3-hydroxy-3-methyl-but-1-ynyl)-5,6-dihydroimidazo[1,2-d][1,4]benzoxazepine-3-carboxylate following triteration from water. MS (Q1) 388 (M)+. Methyl 2-carbamoyl-9-fluoro-10-(3-hydroxy-3-methyl-but-1-ynyl)-5,6-dihydroimidazo[1,2-d][1,4]benzoxazepine-3-carboxylate (1.5 g) was saponified with LiOH in water/THF to afford quantitative yield of 2-carbamoyl-9-fluoro-10-(3-hydroxy-3-methyl-but-1-ynyl)-5,6-dihydroimidazo[1,2-d][1,4]benzoxazepine-3-carboxylic acid. MS (Q1) 383 (M)+.

Example 143

Synthesis of 9-fluoro-3-(hydroxymethyl)-10-(3-hydroxy-3-methyl-but-1-ynyl)-5,6-dihydroimidazo[1,2-d][1,4]benzoxazepine-2-carboxamide

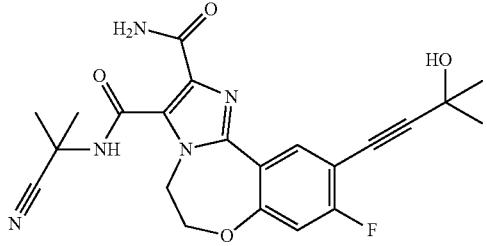 [SMILES: CC(C)(O)C#Cc1cc2c(cc1F)OCCn1c-2nc(C(N)=O)c1C(=O)NC(C)(C)C#N]

2-Carbamoyl-9-fluoro-10-(3-hydroxy-3-methyl-but-1-ynyl)-5,6-dihydroimidazo[1,2-d][1,4]benzoxazepine-3-carboxylic acid (0.09 g) was reacted with 2-amino-2-methylpropionitrile similar to as described in Example 2 to afford 20.8 mg of 9-fluoro-3-(hydroxymethyl)-10-(3-hydroxy-3-methyl-but-1-ynyl)-5,6-dihydroimidazo[1,2-d][1,4]benzoxazepine-2-carboxamide following reverse phase hplc purification. MS (Q1) 440 (M)+. $^1$H NMR (400 MHz, DMSO) δ 12.25 (s, 1H), 8.65 (d, J=8.4 Hz, 1H), 8.58 (s, 1H), 8.07 (s, 1H), 7.03 (d, J=10.5 Hz, 1H), 5.50 (s, 1H), 5.10-4.93 (m, 2H), 4.64-4.46 (m, 2H), 1.70 (s, 6H), 1.49 (s, 6H).

Example 144

Synthesis of 9-fluoro-3-(hydroxymethyl)-10-(3-hydroxy-3-methyl-but-1-ynyl)-5,6-dihydroimidazo[1,2-d][1,4]benzoxazepine-2-carboxamide

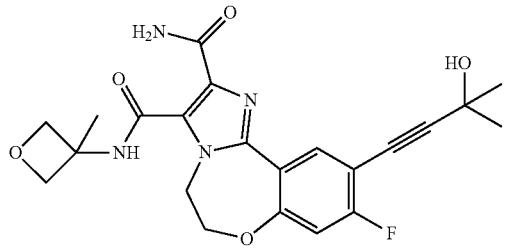 [SMILES: CC(C)(O)C#Cc1cc2c(cc1F)OCCn1c-2nc(C(N)=O)c1C(=O)NC1(C)COC1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.09 g) was reacted with 3-oxetanamine, 3-methyl similar to as described in Example 2 to afford 17.9 mg of 9-fluoro-3-(hydroxymethyl)-10-(3-hydroxy-3-methyl-but-1-ynyl)-5,6-dihydroimidazo[1,2-d][1,4]benzoxazepine-2-carboxamide following reverse phase hplc purification. MS (Q1) 443 (M)+. $^1$H NMR (400 MHz, DMSO) δ 11.84 (s, 1H), 8.62 (d, J=8.4 Hz, 1H), 8.44 (s, 1H), 7.93 (s, 1H), 7.02 (d, J=10.5 Hz, 1H), 5.49 (s, 1H), 5.07-4.92 (m, 2H), 4.69 (d, J=6.1 Hz, 2H), 4.66-4.49 (m, 2H), 4.42 (d, J=6.1 Hz, 2H), 1.63 (s, 3H), 1.49 (s, 6H).

Example 145

Synthesis of 9-fluoro-3-(hydroxymethyl)-10-(3-hydroxy-3-methyl-but-1-ynyl)-5,6-dihydroimidazo[1,2-d][1,4]benzoxazepine-2-carboxamide

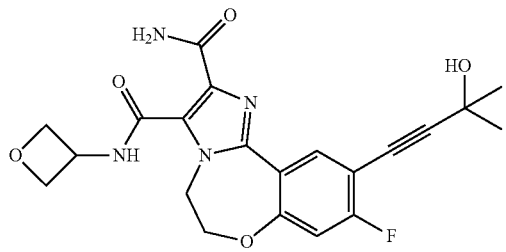 [SMILES: CC(C)(O)C#Cc1cc2c(cc1F)OCCn1c-2nc(C(N)=O)c1C(=O)NC1COC1]

2-carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 3-oxetanamine similar to as described in Example 2 g to afford 3 mg of 9-fluoro-3-(hydroxymethyl)-10-(3-hydroxy-3-methyl-but-1-ynyl)-5,6- dihydroimidazo[1,2-d][1,4]benzoxazepine-2-carboxamide following reverse phase hplc purification. MS (Q1) 429 (M)+.

Example 146

Synthesis of N3-(2-dimethylaminoethyl)-9-fluoro-10-(3-hydroxy-3-methyl-but-1-ynyl)-5,6-dihydroimidazo[1,2-d][1,4]benzoxazepine-2,3-dicarboxamide

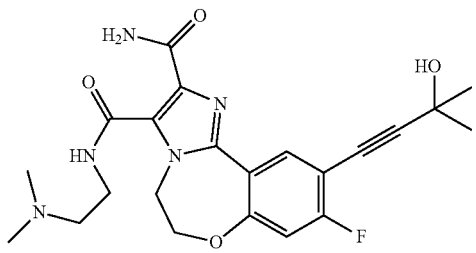 [SMILES: CN(C)CCNC(=O)c1c(C(N)=O)nc2n1CCOc1cc(F)c(C#CC(C)(C)O)cc1-2]

2-carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with N,N-dimethylethylenediame similar to as described in Example 2 to afford 19.1 mg of N3-(2-dimethylaminoethyl)-9-fluoro-10-(3-hydroxy-3-methyl-but-1-ynyl)-5,6-dihydroimidazo[1,2-d][1,4]benzoxazepine-2,3-dicarboxamide following reverse phase hplc purification. MS (Q1) 444 (M)+. $^1$H NMR (400 MHz, DMSO) δ 11.21 (t, J=5.3 Hz, 1H), 8.61 (d, J=8.4 Hz, 1H), 8.37 (s, 1H), 7.87 (s, 1H), 7.02 (d, J=10.5 Hz, 1H), 5.47 (s, 1H), 5.04-4.87 (m, 2H), 4.65-4.46 (m, 2H), 3.45 (dd, J=11.9, 6.1 Hz, 2H), 2.77-2.61 (m, 2H), 2.38 (s, 5H), 1.49 (s, 6H).

Example 147

Synthesis of 9-fluoro-10-(3-hydroxy-3-methyl-but-1-ynyl)-N3-(2-pyrrolidin-1-ylethyl)-5,6-dihydroimidazo[1,2-d][1,4]benzoxazepine-2,3-dicarboxamide

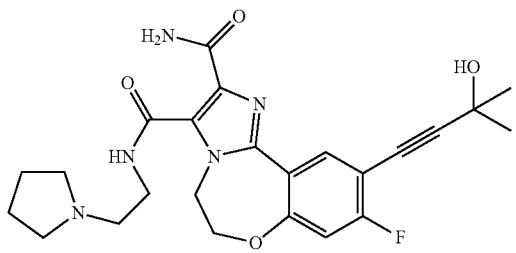 [SMILES: CC(C)(O)C#Cc1cc2c(cc1F)OCCn1c-2nc(C(N)=O)c1C(=O)NCCN1CCCC1]

2-carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 1-pyrrolidineethylamine similar to as described in Example 2 to afford 21.1 mg of 9-fluoro-10-(3-hydroxy-3-methyl-but-1-ynyl)-N3-(2-pyrrolidin-1-ylethyl)-5,6-dihydroimidazo[1,2-d][1,4]benzoxazepine-2,3-dicarboxamide following reverse phase hplc purification. MS (Q1) 470 (M)+. $^1$H NMR (400 MHz, DMSO) δ 11.20 (t, J=5.5 Hz, 1H), 8.61 (d, J=8.4 Hz, 1H), 8.42 (s, 1H), 7.90 (s, 1H), 7.03 (d, J=10.5 Hz, 1H), 5.47 (s, 1H), 5.02-4.84 (m, 2H), 4.64-4.43 (m, 2H), 3.65-3.49 (m, 2H), 3.16-2.81 (m, 6H), 1.95-1.79 (m, 4H), 1.49 (s, 6H).

Example 148

Synthesis of 9-fluoro-10-(3-hydroxy-3-methyl-but-1-ynyl)-N3-(2-morpholinoethyl)-5,6-dihydroimidazo[1,2-d][1,4]benzoxazepine-2,3-dicarboxamide

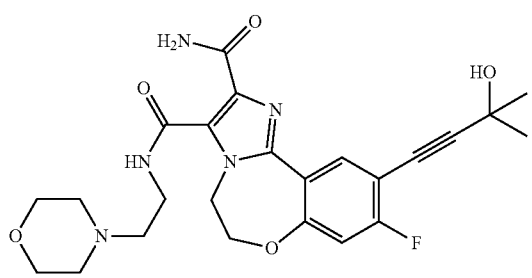 [SMILES: CC(C)(O)C#Cc1cc2c(cc1F)OCCn1c-2nc(C(N)=O)c1C(=O)NCCN1CCOCC1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 4-(2-aminoethyl)morpholine similar to as described in Example 2 to afford 13.3 mg of 9-fluoro-10-(3-hydroxy-3-methyl-but-1-ynyl)-N3-(2-morpholinoethyl)-5,6-dihydroimidazo[1,2-d][1,4]benzoxazepine-2,3-dicarboxamide following reverse phase hplc purification. MS (Q1) 486 (M)+. $^1$H NMR (400 MHz, DMSO) δ 11.06 (s, 1H), 8.61 (d, J=8.4 Hz, 1H), 8.32 (s, 1H), 7.86 (s, 1H), 7.02 (d, J=10.5 Hz, 1H), 5.47 (s, 1H), 5.08-4.77 (m, 2H), 4.61-4.48 (m, 2H), 3.70-3.51 (m, 3H), 3.51-3.35 (m, 1H), 2.49-2.30 (m, 3H), 1.49 (s, 6H).

Example 149

Synthesis of 9-fluoro-10-(3-hydroxy-3-methyl-but-1-ynyl)-N3-[2-(4-methylpiperazin-1-yl)ethyl]-5,6-dihydroimidazo[1,2-d][1,4]benzoxazepine-2,3-dicarboxamide

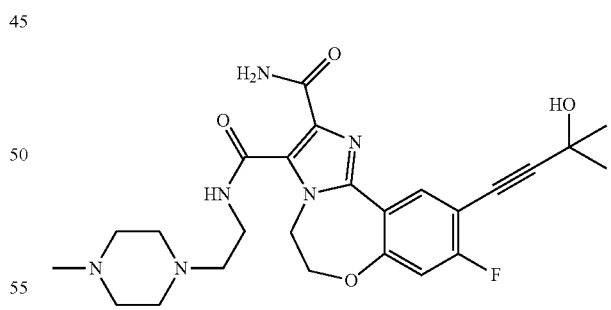

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 3-oxetanamine similar to as described in Example 2 to afford 16 mg of 9-fluoro-10-(3-hydroxy-3-methyl-but-1-ynyl)-N3-[2-(4-methylpiperazin-1-yl)ethyl]-5,6-dihydroimidazo[1,2-d][1,4]benzoxazepine-2,3-dicarboxamide following reverse phase hplc purification. MS (Q1) 499 (M)+. $^1$H NMR (400 MHz, DMSO) δ 11.24-11.05 (m, 1H), 8.60 (d, J=8.5 Hz, 1H), 8.29 (d, J=37.2 Hz, 1H), 7.83 (s, 1H), 7.02 (d, J=10.5 Hz, 1H), 5.48

(d, J=8.8 Hz, 1H), 5.06-4.90 (m, 2H), 4.52 (dd, J=16.4, 12.2 Hz, 2H), 3.39 (dd, J=12.2, 6.5 Hz, 3H), 2.54 (s, 3H), 2.33 (s, 3H), 1.49 (s, 6H).

Example 150

Synthesis of 9-fluoro-10-(3-hydroxy-3-methyl-but-1-ynyl)-N3-(1-methyl-4-piperidyl)-5,6-dihydroimidazo[1,2-d][1,4]benzoxazepine-2,3-dicarboxamide

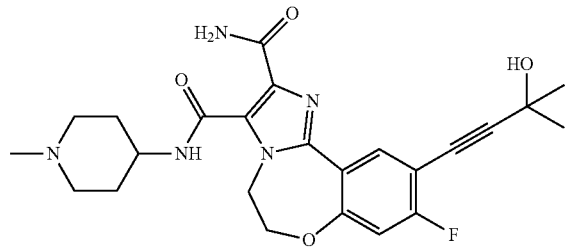 [SMILES: CN1CCC(NC(=O)c2c(C(N)=O)nc3n2CCOc2cc(F)c(C#CC(C)(C)O)cc2-3)CC1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 4-amino-1-methylpiperidine similar to as described in Example 2 to afford 17.8 mg of 9-fluoro-10-(3-hydroxy-3-methyl-but-1-ynyl)-N3-(1-methyl-4-piperidyl)-5,6-dihydroimidazo[1,2-d][1,4]benzoxazepine-2,3-dicarboxamide following reverse phase hplc purification. MS (Q1) 470 (M)+. $^1$H NMR (400 MHz, DMSO) δ 11.37 (d, J=7.0 Hz, 1H), 8.60 (d, J=8.5 Hz, 1H), 8.39 (s, 1H), 7.88 (s, 1H), 7.02 (d, J=10.6 Hz, 1H), 6.45 (s, 1H), 5.47 (s, 1H), 5.07-4.93 (m, 2H), 4.63-4.46 (m, 2H), 2.98-2.81 (m, 2H), 2.48-2.39 (m, 1H), 2.36 (s, 3H), 1.98-1.87 (m, 2H), 1.65-1.52 (m, 2H), 1.49 (s, 6H).

Example 151

Synthesis of (±) 9-fluoro-10-(3-hydroxy-3-methyl-but-1-ynyl)-N3-[(1-methylpyrrolidin-2-yl)methyl]-5,6-dihydroimidazo[1,2-d][1,4]benzoxazepine-2,3-dicarboxamide

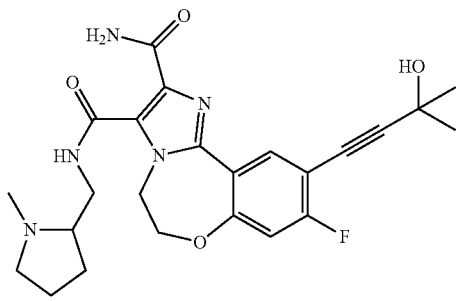 [SMILES: CN1CCCC1CNC(=O)c1c(C(N)=O)nc2n1CCOc1cc(F)c(C#CC(C)(C)O)cc1-2]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with (1-methylpyrrolidin-2-yl)methylamine similar to as described in Example 2 to afford 7.6 mg of (±) 9-fluoro-10-(3-hydroxy-3-methyl-but-1-ynyl)-N3-[(1-methylpyrrolidin-2-yl)methyl]-5,6-dihydroimidazo[1,2-d][1,4]benzoxazepine-2,3-dicarboxamide following reverse phase hplc purification. MS (Q1) 470 (M)+. $^1$H NMR (400 MHz, DMSO) δ 8.58 (d, J=8.5 Hz, 1H), 7.74 (s, 1H), 7.27 (s, 1H), 7.01 (d, J=10.4, 4.6 Hz, 1H), 4.67-4.44 (m, 2H), 4.44-4.14 (m, 2H), 2.96 (s, 2H), 2.36 (s, 1H), 2.02-1.86 (m, 2H), 1.83 (s, 1H), 1.78-1.62 (m, 1H), 1.49 (s, 6H).

Example 152

Synthesis of (±) 9-fluoro-10-(3-hydroxy-3-methyl-but-1-ynyl)-N3-[(1-methylpyrrolidin-3-yl)methyl]-5,6-dihydroimidazo[1,2-d][1,4]benzoxazepine-2,3-dicarboxamide

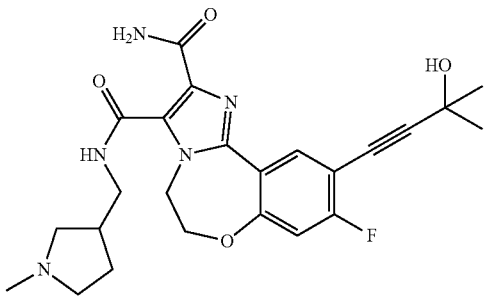 [SMILES: CN1CCC(CNC(=O)c2c(C(N)=O)nc3n2CCOc2cc(F)c(C#CC(C)(C)O)cc2-3)C1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with c-(1-methyl-pyrrolidin-3-yl)-methylamine similar to as described in Example 2 to afford 15.7 mg of (±) 9-fluoro-10-(3-hydroxy-3-methyl-but-1-ynyl)-N3-[(1-methylpyrrolidin-3-yl)methyl]-5,6-dihydroimidazo[1,2-d][1,4]benzoxazepine-2,3-dicarboxamide following reverse phase hplc purification. MS (Q1) 470 (M)+. $^1$H NMR (400 MHz, DMSO) δ 11.37 (d, J=7.0 Hz, 1H), 8.60 (d, J=8.5 Hz, 1H), 8.39 (s, 1H), 7.88 (s, 1H), 7.02 (d, J=10.6 Hz, 1H), 5.47 (s, 1H), 5.04-4.91 (m, 2H), 4.66-4.47 (m, 2H), 2.89 (s, 1H), 2.47-2.31 (m, 5H), 2.00-1.86 (m, 2H), 1.66-1.51 (m, 2H), 1.49 (s, 6H).

Example 153

Synthesis of 9-fluoro-10-(3-hydroxy-3-methyl-but-1-ynyl)-N3-(2-methoxy-2-methyl-propyl)-5,6-dihydroimidazo[1,2-d][1,4]benzoxazepine-2,3-dicarboxamide

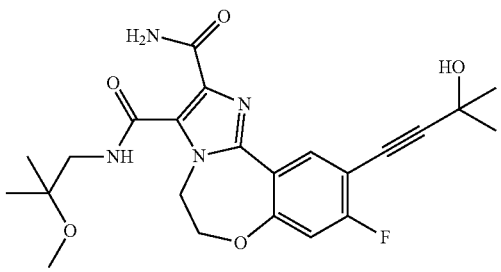 [SMILES: COC(C)(C)CNC(=O)c1c(C(N)=O)nc2n1CCOc1cc(F)c(C#CC(C)(C)O)cc1-2]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with (2-methoxy-2-methylpropyl)amine similar to as described in Example 2 to afford 14.8 mg of 9-fluoro-10-(3-hydroxy-3-methyl-but-1-ynyl)-N3-(2-methoxy-2-methyl-propyl)-5,6-dihydroimidazo[1,2-d][1,4]benzoxazepine-2,3-dicarboxamide following reverse phase hplc purification. MS (Q1) 459 (M)+. ¹H NMR (400 MHz, DMSO) δ 11.24 (t, 1H), 8.60 (d, J=8.5 Hz, 1H), 8.35 (s, 1H), 7.87 (s, 1H), 7.02 (d, J=10.6 Hz, 1H), 5.48 (s, 1H), 5.10-4.90 (m, 2H), 4.63-4.45 (m, 2H), 3.34 (d, J=5.6 Hz, 2H), 3.14 (s, 3H), 1.49 (s, 7H), 1.15 (s, 6H).

Example 154

Synthesis of 9-fluoro-10-(3-hydroxy-3-methyl-but-1-ynyl)-N3-[[1-(methoxymethyl)cyclopropyl]methyl]-5,6-dihydroimidazo[1,2-d][1,4]benzoxazepine-2,3-dicarboxamide

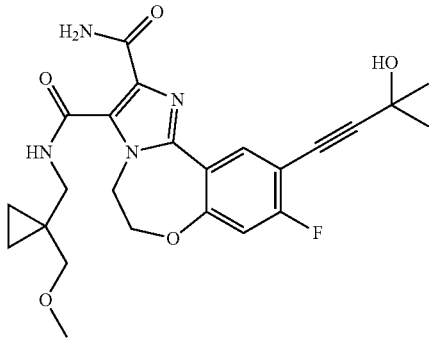 [SMILES: COCC1(CNC(=O)c2c(C(N)=O)nc3n2CCOc2cc(F)c(C#CC(C)(C)O)cc2-3)CC1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 1-[1-(methoxymethyl)cyclopropyl]methanamine monohydrochloride similar to as described in Example 2 to afford 11 mg of 9-fluoro-10-(3-hydroxy-3-methyl-but-1-ynyl)-N3-[[1-(methoxymethyl)cyclopropyl]methyl]-5,6-dihydroimidazo[1,2-d][1,4]benzoxazepine-2,3-dicarboxamide following reverse phase hplc purification. MS (Q1) 471 (M)+. ¹H NMR (400 MHz, DMSO) δ 11.34 (t, J=5.3 Hz, 1H), 8.60 (d, J=8.4 Hz, 1H), 8.38 (s, 1H), 7.90 (s, 1H), 7.01 (d, J=10.6 Hz, 1H), 5.48 (s, 1H), 5.09-4.88 (m, 2H), 4.67-4.44 (m, 2H), 3.25 (s, 4H), 1.49 (s, 5H), 0.63-0.30 (m, 4H).

Example 155

Synthesis of N3-(cyanomethyl)-9-fluoro-10-(3-hydroxy-3-methyl-but-1-ynyl)-5,6-dihydroimidazo[1,2-d][1,4]benzoxazepine-2,3-dicarboxamide

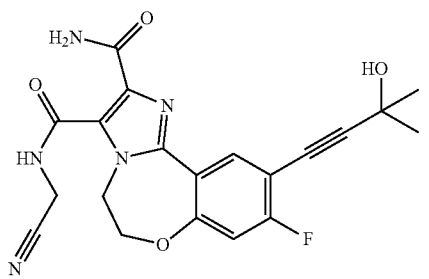 [SMILES: CC(C)(O)C#Cc1cc2c(cc1F)OCCn1c-2nc(C(N)=O)c1C(=O)NCC#N]

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with aminoacetonitrile hydrochloride similar to as described in Example 2 to afford 9 mg of N3-(cyanomethyl)-9-fluoro-10-(3-hydroxy-3-methyl-but-1-ynyl)-5,6-dihydroimidazo[1,2-d][1,4]benzoxazepine-2,3-dicarboxamide following reverse phase hplc purification. MS (Q1) 412 (M)+. ¹H NMR (400 MHz, DMSO) δ 12.03 (t, J=5.3 Hz, 1H), 8.65 (d, J=8.4 Hz, 1H), 8.53 (s, 1H), 8.04 (s, 1H), 7.03 (d, J=10.5 Hz, 1H), 5.47 (s, 1H), 5.07-4.90 (m, 2H), 4.66-4.53 (m, 2H), 4.39 (d, J=5.3 Hz, 2H), 1.50 (s, 6H).

Example 156

Synthesis of (±) 9-fluoro-10-(3-hydroxy-3-methyl-but-1-ynyl)-N3-(tetrahydrofuran-3-ylmethyl)-5,6-dihydroimidazo[1,2-d][1,4]benzoxazepine-2,3-dicarboxamide

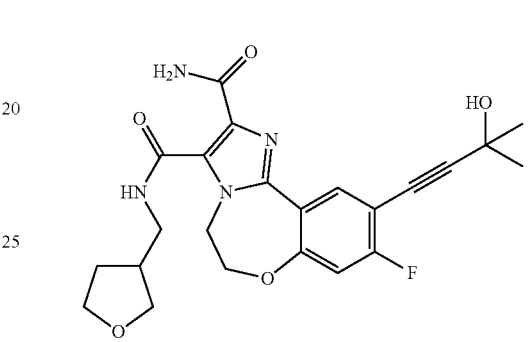

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with (tetrahydrofuran-3-yl)methanamine similar to as described in Example 2 to afford 6.2 mg of (±) 9-fluoro-10-(3-hydroxy-3-methyl-but-1-ynyl)-N3-(tetrahydrofuran-3-ylmethyl)-5,6-dihydroimidazo[1,2-d][1,4]benzoxazepine-2,3-dicarboxamide following reverse phase hplc purification. MS (Q1) 457 (M)+. ¹H NMR (400 MHz, DMSO) δ 11.33 (t, J=5.4 Hz, 1H), 8.61 (d, J=8.5 Hz, 1H), 8.38 (s, 1H), 7.89 (s, 1H), 7.01 (d, J=10.6 Hz, 1H), 5.47 (s, 1H), 5.06-4.94 (m, 2H), 4.60-4.44 (m, 2H), 3.81-3.71 (m, 2H), 3.63 (dd, J=15.2, 7.7 Hz, 1H), 3.44 (dd, J=8.6, 5.9 Hz, 1H), 2.48-2.37 (m, 1H), 2.04-1.92 (m, 1H), 1.68-1.54 (m, 1H), 1.49 (s, 6H).

Example 157

Synthesis of 9-fluoro-10-(3-hydroxy-3-methyl-but-1-ynyl)-N3-(tetrahydropyran-4-ylmethyl)-5,6-dihydroimidazo[1,2-d][1,4]benzoxazepine-2,3-dicarboxamide

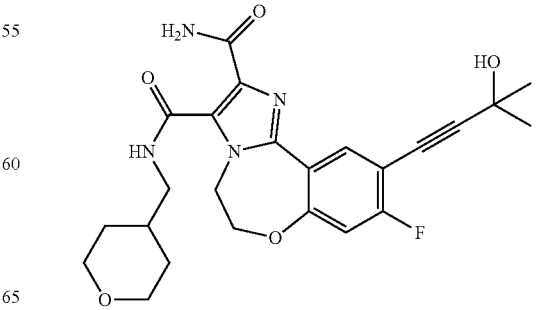

2-Carbamoyl-9-fluoro-10-(3-hydroxy-3-methyl-but-1-ynyl)-5,6-dihydroimidazo[1,2-d][1,4]benzoxazepine-3-carboxylic acid (0.05 g) was reacted with 1-tetrahydro-2H-pyran-4-ylmethanamine similar to as described in Example 2 to afford 6 mg of 9-fluoro-10-(3-hydroxy-3-methyl-but-1-ynyl)-N3-(tetrahydropyran-4-ylmethyl)-5,6-dihydroimidazo[1,2-d][1,4]benzoxazepine-2,3-dicarboxamide following reverse phase hplc purification. MS (Q1) 471 (M)+. NMR (400 MHz, DMSO) δ 11.30 (t, J=5.4 Hz, 1H), 8.60 (d, J=8.4 Hz, 1H), 8.38 (s, 1H), 7.89 (s, 1H), 7.01 (d, J=10.6 Hz, 1H), 5.47 (s, 1H), 5.05-4.97 (m, 2H), 4.59-4.51 (m, 2H), 3.91-3.74 (m, 3H), 3.19 (t, J=6.0 Hz, 2H), 1.82-1.67 (m, 1H), 1.67-1.58 (m, 2H), 1.49 (s, 6H), 1.32-1.18 (m, 3H).

Example 158

Synthesis of 9-fluoro-10-(3-hydroxy-3-methyl-but-1-ynyl)-N3-(1-methylazetidin-3-yl)-5,6-dihydroimidazo[1,2-d][1,4]benzoxazepine-2,3-dicarboxamide

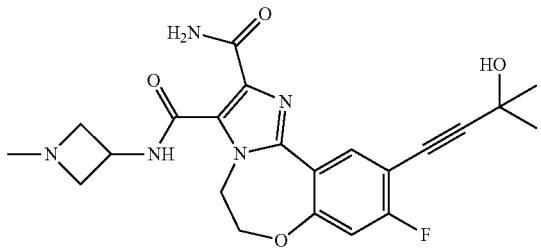 [SMILES: CN1CC(NC(=O)c2c(C(N)=O)nc3n2CCOc2cc(F)c(C#CC(C)(C)O)cc2-3)C1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.06 g) was reacted with 1-methylazetidin-3-amine hydrochloride similar to as described in Example 2 to afford 13.4 mg of 9-fluoro-10-(3-hydroxy-3-methyl-but-1-ynyl)-N3-(1-methylazetidin-3-yl)-5,6-dihydroimidazo[1,2-d][1,4]benzoxazepine-2,3-dicarboxamide following reverse phase hplc purification. MS (Q1) 442 (M)+. $^1$H NMR (400 MHz, DMSO) δ 11.76 (d, J=6.7 Hz, 1H), 8.61 (d, J=8.4 Hz, 1H), 8.41 (s, 1H), 7.90 (s, 1H), 7.01 (d, J=10.5 Hz, 1H), 5.48 (s, 1H), 5.01-4.93 (m, 2H), 4.55-4.49 (m, 2H), 4.37 (dd, J=13.4, 6.7 Hz, 1H), 3.58 (t, J=7.2 Hz, 2H), 2.84 (t, J=7.1 Hz, 2H), 2.24 (s, 3H), 1.49 (s, 6H).

Example 159

Synthesis of (±) 9-fluoro-10-(3-hydroxy-3-methyl-but-1-ynyl)-N3-(1-methylpyrrolidin-3-yl)-5,6-dihydroimidazo[1,2-d][1,4]benzoxazepine-2,3-dicarboxamide

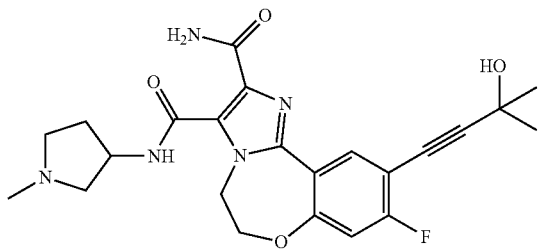 [SMILES: CN1CCC(NC(=O)c2c(C(N)=O)nc3n2CCOc2cc(F)c(C#CC(C)(C)O)cc2-3)C1]

2-Carbamoyl-9-fluoro-10-(3-hydroxy-3-methyl-but-1-ynyl)-5,6-dihydroimidazo[1,2-d][1,4]benzoxazepine-3-carboxylic acid (0.06 g) was reacted with 1-methylpyrrolidin-3-amine similar to as described in Example 2 to afford 15.9 mg of (±)9-fluoro-10-(3-hydroxy-3-methyl-but-1-ynyl)-N3-(1-methylpyrrolidin-3-yl)-5,6-dihydroimidazo[1,2-d][1,4]benzoxazepine-2,3-dicarboxamide following reverse phase hplc purification. MS (Q1) 456 (M)+. $^1$H NMR (400 MHz, DMSO) δ 11.49 (d, J=6.5 Hz, 1H), 8.59 (d, J=8.5 Hz, 1H), 8.35 (s, 1H), 7.84 (s, 1H), 7.01 (d, J=10.6 Hz, 1H), 5.48 (s, 1H), 5.07-4.91 (m, 2H), 4.62-4.45 (m, 2H), 4.42-4.24 (m, 1H), 2.75-2.67 (m, 1H), 2.64-2.55 (m, 1H), 2.43-2.34 (m, 2H), 2.24-2.14 (m, 1H), 1.68-1.56 (m, 1H), 1.50 (s, 6H).

Example 160

Synthesis of (±) 9-fluoro-10-(3-hydroxy-3-methyl-but-1-ynyl)-N3-(1-methyl-3-piperidyl)-5,6-dihydroimidazo[1,2-d][1,4]benzoxazepine-2,3-dicarboxamide

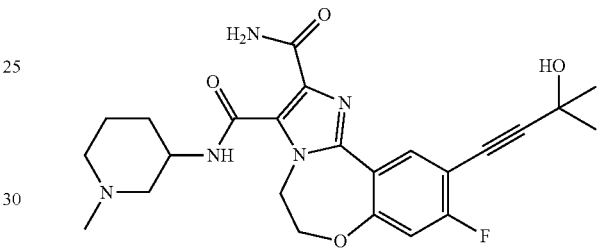

2-Carbamoyl-9-fluoro-10-(3-hydroxy-3-methyl-but-1-ynyl)-5,6-dihydroimidazo[1,2-d][1,4]benzoxazepine-3-carboxylic acid (0.06 g) was reacted with 1-methylpiperidin-3-amine dihydrochloride similar to as described in Example 2 to afford 22.3 mg of (±) 9-fluoro-10-(3-hydroxy-3-methyl-but-1-ynyl)-N3-(1-methyl-3-piperidyl)-5,6-dihydroimidazo[1,2-d][1,4]benzoxazepine-2,3-dicarboxamide following reverse phase hplc purification. MS (Q1) 470 (M)+. $^1$H NMR (400 MHz, DMSO) δ 11.28 (d, J=7.4 Hz, 1H), 8.59 (d, J=8.4 Hz, 1H), 8.34 (s, 1H), 7.83 (s, 1H), 7.01 (d, J=10.6 Hz, 1H), 5.48 (s, 1H), 5.08-4.88 (m, 2H), 4.63-4.46 (m, 2H), 3.99-3.83 (m, 1H), 2.74-2.64 (m, 1H), 2.48-2.42 (m, 1H), 2.06 (t, J=8.0 Hz, 1H), 1.97 (t, J=10.6 Hz, 1H), 1.75 (m, J=13.8 Hz, 2H), 1.59-1.51 (m, 1H), 1.49 (s, 6H), 1.36-1.19 (m, 1H).

Example 161

Synthesis of (±) 9-fluoro-10-(3-hydroxy-3-methyl-but-1-ynyl)-N3-quinuclidin-3-yl-5,6-dihydroimidazo[1,2-d][1,4]benzoxazepine-2,3-dicarboxamide

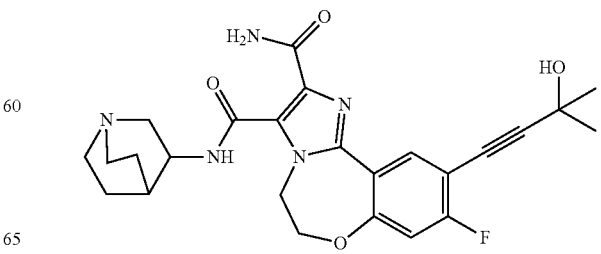

2-Carbamoyl-9-fluoro-10-(3-hydroxy-3-methyl-but-1-ynyl)-5,6-dihydroimidazo[1,2-d][1,4]benzoxazepine-3-carboxylic acid (0.06 g) was reacted with 1,3-diazabicyclo[2.2.2]octane dihydrochloride similar to as described in Example 2 to afford 20.5 mg of (±) 9-fluoro-10-(3-hydroxy-3-methyl-but-1-ynyl)-N3-quinuclidin-3-yl-5,6-dihydroimidazo[1,2-d][1,4]benzoxazepine-2,3-dicarboxamide following reverse phase hplc purification. MS (Q1) 482 (M)+. $^1$H NMR (400 MHz, DMSO) δ 11.62 (d, J=6.7 Hz, 1H), 8.60 (d, J=8.4 Hz, 1H), 8.41 (s, 1H), 7.93 (s, 1H), 7.01 (d, J=10.5 Hz, 1H), 5.48 (s, 1H), 5.03-4.99 (m, 2H), 4.56-4.51 (m, 2H), 2.89-2.59 (m, 5H), 1.88-1.79 (m, 2H), 1.68-1.52 (m, 3H), 1.49 (s, 6H), 1.44-1.30 (m, 1H).

Example 162

Synthesis of (±) 9-fluoro-10-(3-hydroxy-3-methyl-but-1-ynyl)-N3-tetrahydrofuran-3-yl-5,6-dihydroimidazo[1,2-d][1,4]benzoxazepine-2,3-dicarboxamide

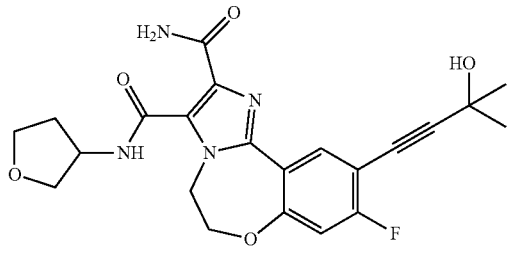 [SMILES: CC(C)(O)C#Cc1cc2c(cc1F)OCCn1c-2nc(C(N)=O)c1C(=O)NC1CCOC1]

10-Bromo-2-carbamoyl-9-fluoro-5,6-dihydroimidazo[1,2-d][1,4]benzoxazepine-3-carboxylic acid (55 mg) was reacted with tetrahydro-furan-3-ylamine similar to as described in Example 2 to produce crude 10-bromo-9-fluoro-N3-tetrahydrofuran-3-yl-5,6-dihydroimidazo[1,2-d][1,4]benzoxazepine-2,3-dicarboxamide which was then reacted with 2-Methyl-3-butyne-ol similar to as described in Procedure E to afford 26.1 mg of (±) 9-fluoro-10-(3-hydroxy-3-methyl-but-1-ynyl)-N3-tetrahydrofuran-3-yl-5,6-dihydroimidazo[1,2-d][1,4]benzoxazepine-2,3-dicarboxamide following reverse phase hplc purification. MS (Q1) 443 (M)+. $^1$H NMR (400 MHz, DMSO) δ 11.60 (d, J=6.1 Hz, 1H), 8.60 (d, J=8.4 Hz, 1H), 8.39 (s, 1H), 7.88 (s, 1H), 7.02 (d, J=10.5 Hz, 1H), 5.48 (s, 1H), 5.06-4.92 (m, 2H), 4.60-4.48 (m, 2H), 4.47-4.33 (m, 1H), 3.89-3.80 (m, 2H), 3.79-3.71 (m, 1H), 3.57 (dd, J=9.0, 3.4 Hz, 1H), 2.25-2.14 (m, 1H), 1.87-1.76 (m, 1H), 1.49 (s, 6H).

Example 163

Synthesis of 9-fluoro-10-(3-hydroxy-3-methyl-but-1-ynyl)-N3-tetrahydropyran-4-yl-5,6-dihydroimidazo[1,2-d][1,4]benzoxazepine-2,3-dicarboxamide

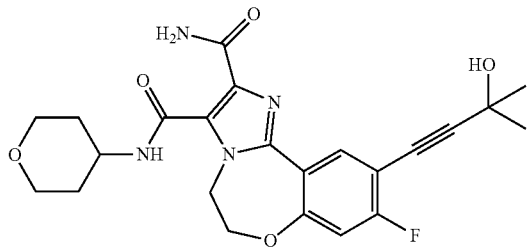 [SMILES: CC(C)(O)C#Cc1cc2c(cc1F)OCCn1c-2nc(C(N)=O)c1C(=O)NC1CCOCC1]

10-Bromo-2-carbamoyl-9-fluoro-5,6-dihydroimidazo[1,2-d][1,4]benzoxazepine-3-carboxylic acid (55 mg) was reacted with 4-aminotetrahydropyran similar to as described in Example 2 to produce crude 10-bromo-9-fluoro-N3-tetrahydropyran-4-yl-5,6-dihydroimidazo[1,2-d][1,4]benzoxazepine-2,3-dicarboxamide which was then reacted with 2-Methyl-3-butyne-ol similar to as described in Procedure E to afford 12.5 mg of 9-fluoro-10-(3-hydroxy-3-methyl-but-1-ynyl)-N3-tetrahydropyran-4-yl-5,6-dihydroimidazo[1,2-d][1,4]benzoxazepine-2,3-dicarboxamide following reverse phase hplc purification. MS (Q1) 457 (M)+. $^1$H NMR (400 MHz, DMSO) δ 11.42 (d, J=11.5 Hz, 1H), 8.60 (d, J=8.4 Hz, 1H), 8.38 (s, 1H), 7.88 (s, 1H), 7.01 (d, J=10.6 Hz, 1H), 5.47 (s, 1H), 5.08-4.94 (m, 2H), 4.60-4.49 (m, 2H), 4.10-3.92 (m, 1H), 3.91-3.79 (m, 2H), 3.54-3.43 (m, 2H), 1.93-1.80 (m, 2H), 1.49 (s, 6H), 1.48-1.42 (m, 1H).

Example 164

Synthesis of 9-fluoro-10-(3-hydroxy-3-methyl-but-1-ynyl)-N3-(oxetan-3-ylmethyl)-5,6-dihydroimidazo[1,2-d][1,4]benzoxazepine-2,3-dicarboxamide

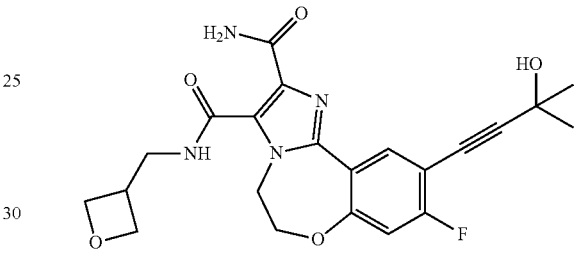

10-Bromo-2-carbamoyl-9-fluoro-5,6-dihydroimidazo[1,2-d][1,4]benzoxazepine-3-carboxylic acid (55 mg) was reacted with oxetan-3-ylmethanamine similar to as described in Example 2 to produce crude 10-bromo-9-fluoro-N3-(oxetan-3-ylmethyl)-5,6-dihydroimidazo[1,2-d][1,4]benzoxazepine-2,3-dicarboxamide which was then reacted with 2-Methyl-3-butyne-ol similar to as described in Procedure E to afford 13 mg of 9-fluoro-10-(3-hydroxy-3-methyl-but-1-ynyl)-N3-(oxetan-3-ylmethyl)-5,6-dihydroimidazo[1,2-d][1,4]benzoxazepine-2,3-dicarboxamide following reverse phase hplc purification. MS (Q1) 443 (M)+. $^1$H NMR (400 MHz, DMSO) δ 11.37 (t, 1H), 8.61 (d, J=8.4 Hz, 1H), 8.39 (s, 1H), 7.89 (s, 1H), 7.01 (d, J=10.5 Hz, 1H), 5.48 (s, 1H), 5.05-4.93 (m, 2H), 4.68-4.61 (m, 2H), 4.58-4.50 (m, 2H), 4.35 (t, J=6.0 Hz, 2H), 3.56 (t, J=6.1 Hz, 2H), 3.21-3.13 (m, 1H), 1.49 (s, 6H).

Example 165

Synthesis of 9-fluoro-10-[(3R)-3-hydroxy-3-(5-methylisoxazol-3-yl)but-1-ynyl]-N3-methyl-5,6-dihydroimidazo[1,2-d][1,4]benzoxazepine-2,3-dicarboxamide

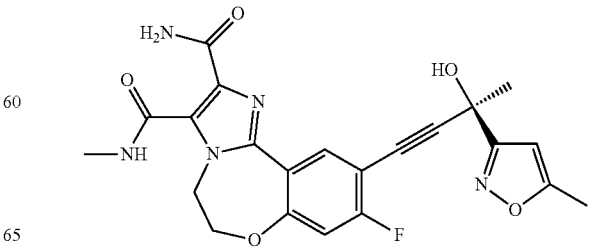

10-Bromo-9-fluoro-N3-methyl-5,6-dihydroimidazo[1,2-d][1,4]benzoxazepine-2,3-dicarboxamide (0.1 g) was reacted with (2R)-2-(5-methylisoxazol-3-yl)but-3-yn-2-ol similar to as described in Procedure E to afford 32.6 mg of 9-fluoro-10-[(3R)-3-hydroxy-3-(5-methylisoxazol-3-yl)but-1-ynyl]-N3-methyl-5,6-dihydroimidazo[1,2-d][1,4]benzoxazepine-2,3-dicarboxamide following reverse phase hplc purification. MS (Q1) 454 (M)+. ¹H NMR (400 MHz, DMSO) δ 11.08 (q, J=4.2 Hz, 1H), 8.64 (d, J=8.4 Hz, 1H), 8.39 (s, 1H), 7.88 (s, 1H), 7.05 (d, J=10.5 Hz, 1H), 6.56 (s, 1H), 6.35 (s, 1H), 5.04-4.95 (m, 2H), 4.59-4.51 (m, 2H), 2.80 (d, J=4.5 Hz, 3H), 2.41 (s, 3H), 1.82 (s, 3H).

Example 166

Synthesis of 9-fluoro-10-[(3R)-3-hydroxy-3-(5-methyl-1,2,4-oxadiazol-3-yl)but-1-ynyl]-N3-methyl-5,6-dihydroimidazo[1,2-d][1,4]benzoxazepine-2,3-dicarboxamide

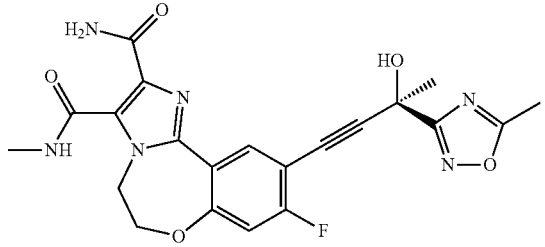

10-Bromo-9-fluoro-N3-methyl-5,6-dihydroimidazo[1,2-d][1,4]benzoxazepine-2,3-dicarboxamide (0.08 g) was reacted with (2R)-2-(5-methyl-1,2,4-oxadiazol-3-yl)but-3-yn-2-ol similar to as described in Procedure E to afford 8.6 mg of 9-fluoro-10-[(3R)-3-hydroxy-3-(5-methyl-1,2,4-oxadiazol-3-yl)but-1-ynyl]-N3-methyl-5,6-dihydroimidazo[1,2-d][1,4]benzoxazepine-2,3-dicarboxamide following reverse phase hplc purification. MS (Q1) 455 (M)+. ¹H NMR (400 MHz, DMSO) δ 11.09 (q, J=4.4 Hz, 1H), 8.65 (d, J=8.3 Hz, 1H), 8.38 (s, 1H), 7.86 (s, 1H), 7.06 (d, J=10.5 Hz, 1H), 6.76 (s, 1H), 6.59 (s, 1H), 5.08-4.94 (m, 2H), 4.63-4.41 (m, 2H), 2.80 (d, J=4.5 Hz, 3H), 2.62 (s, 3H), 1.86 (s, 3H).

Example 167

Synthesis of 10-[(3R)-3-hydroxy-3-(5-methylisoxazol-3-yl)but-1-ynyl]-N3-methyl-5,6-dihydroimidazo[1,2-d][1,4]benzoxazepine-2,3-dicarboxamide

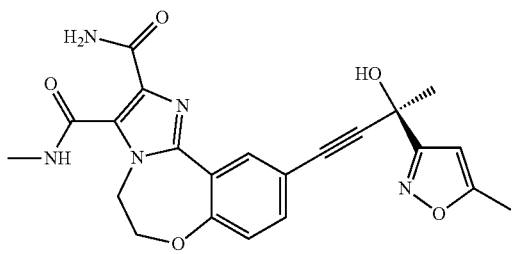

10-Bromo-3-iodo-5,6-dihydroimidazo[1,2-d][1,4]benzoxazepine-2-carboxamide (5 g) was subjected similar to as described in Example 6 to yield 4.2 g of methyl 10-bromo-2-carbamoyl-5,6-dihydroimidazo[1,2-d][1,4]benzoxazepine-3-carboxylate. Methyl 10-bromo-2-carbamoyl-5,6-dihydroimidazo[1,2-d][1,4]benzoxazepine-3-carboxylate (0.52 g) was subjected to lithium hydroxide water/THF to give 0.44 g of 10-bromo-2-carbamoyl-5,6-dihydroimidazo[1,2-d][1,4]benzoxazepine-3-carboxylic acid. 10-bromo-2-carbamoyl-5,6-dihydroimidazo[1,2-d][1,4]benzoxazepine-3-carboxylic acid (0.44 g) was reacted with Methylamine hydrochloride similar to as described in Example 2 to afford 314 mg 10-bromo-N3-methyl-5,6-dihydroimidazo[1,2-d][1,4]benzoxazepine-2,3-dicarboxamide following trituration from water. 10-bromo-9-fluoro-N3-methyl-5,6-dihydroimidazo[1,2-d][1,4]benzoxazepine-2,3-dicarboxamide (0.1 g) was then reacted with (2R)-2-(5-methylisoxazol-3-yl)but-3-yn-2-ol similar to as described in Procedure G to afford 43.9 mg of 10-[(3R)-3-hydroxy-3-(5-methylisoxazol-3-yl)but-1-ynyl]-N3-methyl-5,6-dihydroimidazo[1,2-d][1,4]benzoxazepine-2,3-dicarboxamide following reverse phase hplc purification. MS (Q1) 436 (M)+. ¹H NMR (400 MHz, DMSO) δ 11.06 (q, J=4.3 Hz, 1H), 8.55 (d, J=2.0 Hz, 1H), 8.33 (s, 1H), 7.88 (s, 1H), 7.40 (dd, J=8.5, 2.0 Hz, 1H), 7.06 (d, J=8.5 Hz, 1H), 6.47 (s, 1H), 6.36 (s, 1H), 5.04-4.91 (m, 2H), 4.57-4.44 (m, 2H), 2.81 (d, J=4.5 Hz, 3H), 2.41 (s, 3H), 1.81 (s, 3H).

Example 168

Synthesis of 10-[(3R)-3-hydroxy-3-(5-methyl-1,2,4-oxadiazol-3-yl)but-1-ynyl]-N3-methyl-5,6-dihydroimidazo[1,2-d][1,4]benzoxazepine-2,3-dicarboxamide

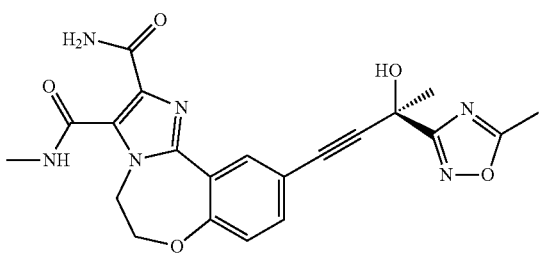

10-Bromo-9-fluoro-N3-methyl-5,6-dihydroimidazo[1,2-d][1,4]benzoxazepine-2,3-dicarboxamide (0.05 g) was reacted with (2R)-2-(5-methyl-1,2,4-oxadiazol-3-yl)but-3-yn-2-ol similar to as described in Procedure F to afford 8.4 mg of 10-[(3R)-3-hydroxy-3-(5-methyl-1,2,4-oxadiazol-3-yl)but-1-ynyl]-N3-methyl-5,6-dihydroimidazo[1,2-d][1,4]benzoxazepine-2,3-dicarboxamide following reverse phase hplc purification. MS (Q1) 437 (M)+. ¹H NMR (400 MHz, DMSO) δ 11.05 (q, J=4.1 Hz, 1H), 8.56 (d, J=2.0 Hz, 1H), 8.33 (s, 1H), 7.88 (s, 1H), 7.40 (dd, J=8.5, 2.1 Hz, 1H), 7.07 (d, J=8.5 Hz, 1H), 6.68 (s, 1H), 5.02-4.93 (m, 2H), 4.58-4.45 (m, 2H), 2.81 (d, J=4.5 Hz, 3H), 2.61 (s, 3H), 1.84 (s, 3H).

Example 169

Synthesis of 10-(3-hydroxy-3-methyl-but-1-ynyl)-3-(1-methylpyrazol-4-yl)-5,6-dihydroimidazo[1,2-d][1,4]benz oxazepine-2-carboxamide

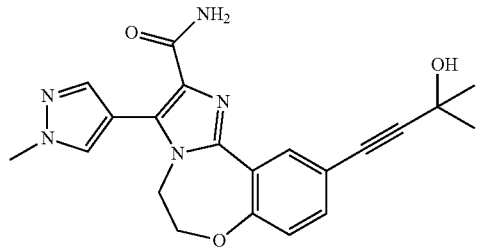 [SMILES: Cn1cc(-c2c(C(N)=O)nc3n2CCOc2ccc(C#CC(C)(C)O)cc2-3)cn1]

10-Bromo-3-iodo-5,6-dihydroimidazo[1,2-d][1,4]benzoxazepine-2-carboxamide (0.1 g) was reacted with 1-methyl-4-(4,4,5,5-tetramethyl-1,3,2-dioxaborolan-2-yl)pyrazole similar to as described in Example 4 and triturated from water to give 90 mg of 10-bromo-3-(1-methylpyrazol-4-yl)-5,6-dihydroimidazo[1,2-d][1,4]benzoxazepine-2-carboxamide. This intermediate was reacted with 2-Methyl-3-butyne-ol similar to as described in Procedure E to afford 13.2 mg of 10-(3-hydroxy-3-methyl-but-1-ynyl)-3-(1-methylpyrazol-4-yl)-5,6-dihydroimidazo[1,2-d][1,4]benz oxazepine-2-carboxamide following reverse phase hplc purification. MS (Q1) 392 (M)+. $^1$H NMR (400 MHz, DMSO) δ 8.56 (d, J=2.0 Hz, 1H), 8.07 (s, 1H), 7.74 (s, 1H), 7.54 (s, 1H), 7.29 (dd, J=8.5, 2.1 Hz, 1H), 7.05-7.00 (m, 2H), 5.43 (s, 1H), 4.46-4.40 (m, 2H), 4.31 (d, J=4.0 Hz, 2H), 3.90 (s, 3H), 1.48 (s, 6H).

Example 170

Synthesis of 10-(3-hydroxy-3-methyl-but-1-ynyl)-3-(1-methylpyrazol-4-yl)-5,6-dihydroimidazo[1,2-d][1,4]benz oxazepine-2-carboxamide and 3,10-bis(3-hydroxy-3-methyl-but-1-ynyl)-5,6-dihydroimidazo[1,2-d][1,4]benzoxazepine-2-carboxamide

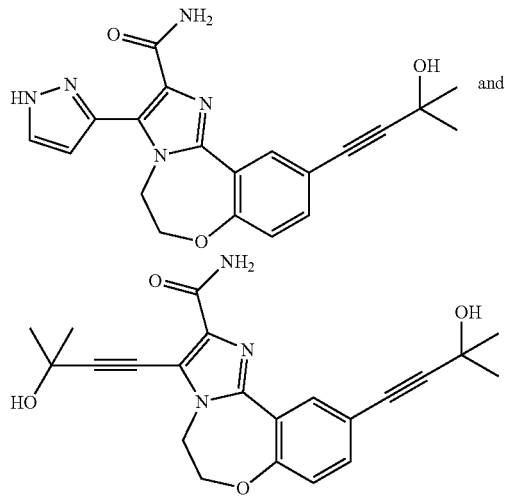

and

10-Bromo-3-iodo-5,6-dihydroimidazo[1,2-d][1,4]benzoxazepine-2-carboxamide (0.1 g) was reacted with 3-(4,4,5,5-tetramethyl-1,3,2-dioxaborolan-2-yl)-1H-pyrazole similar to as described in Example 4 and triturated from water to give 86 mg of a mixture of starting material and 10-bromo-3-(1H-pyrazol-3-yl)-5,6-dihydroimidazo[1,2-d][1,4]benzoxazepine-2-carboxamide. This mixture was reacted with 2-Methyl-3-butyne-ol similar to as described in Procedure E to afford 5 mg of 10-(3-hydroxy-3-methyl-but-1-ynyl)-3-(1-methylpyrazol-4-yl)-5,6-dihydroimidazo[1,2-d][1,4]benzoxazepine-2-carboxamide [MS (Q1) 378 (M)+] and 28.6 mg of 3,10-bis(3-hydroxy-3-methyl-but-1-ynyl)-5,6-dihydroimidazo[1,2-d][1,4]benzoxazepine-2-carboxamide [MS (Q1) 394 (M)+]. $^1$H NMR (400 MHz, DMSO) δ 8.52 (d, J=2.0 Hz, 1H), 7.52 (s, 1H), 7.32 (dd, J=8.4, 2.1 Hz, 1H), 7.20 (s, 1H), 7.03 (d, J=8.5 Hz, 1H), 5.59 (s, 1H), 5.44 (s, 1H), 4.57-4.49 (m, 2H), 4.44-4.37 (m, 2H), 1.49 (d, J=10.9 Hz, 12H)] following reverse phase hplc purification.

Example 171

Synthesis of 10-(3-hydroxy-3-methyl-but-1-ynyl)-3-(1H-pyrazol-4-yl)-5,6-dihydroimidazo[1,2-d][1,4]benzoxazepine-2-carboxamide

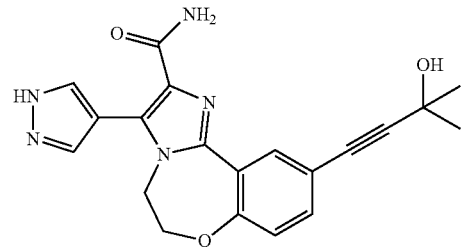 [SMILES: CC(C)(O)C#Cc1ccc2c(c1)-c1nc(C(N)=O)c(-c3cn[nH]c3)n1CCO2]

10-Bromo-3-iodo-5,6-dihydroimidazo[1,2-d][1,4]benzoxazepine-2-carboxamide (0.1 g) was reacted with tert-butyl 4-(4,4,5,5-tetramethyl-1,3,2-dioxaborolan-2-yl)pyrazole-1-carboxylate similar to as described in Example 4 and triturated from water to give 86 mg of 10-bromo-3-(1H-pyrazol-4-yl)-5,6-dihydroimidazo[1,2-d][1,4]benzoxazepine-2-carboxamide. This intermediate was reacted with 2-Methyl-3-butyne-ol similar to as described in Procedure E to afford 5.5 mg of 10-(3-hydroxy-3-methyl-but-1-ynyl)-3-(1H-pyrazol-4-yl)-5,6-dihydroimidazo[1,2-d][1,4]benzoxazepine-2-carboxamide following reverse phase hplc purification. MS (Q1) 378 (M)+. NMR (400 MHz, DMSO) δ 13.10 (s, 1H), 8.57 (d, J=2.1 Hz, 1H), 8.11 (s, 1H), 7.81 (s, 1H), 7.54 (s, 1H), 7.29 (dd, J=8.4, 2.1 Hz, 1H), 7.10-6.95 (m, 2H), 5.43 (s, 1H), 4.49-4.40 (m, 2H), 4.35-4.25 (m, 2H), 1.49 (s, 6H).

Example 172

Synthesis of N3-(cyanomethyl)-9-fluoro-10-[(3R)-3-hydroxy-3-(5-methylisoxazol-3-yl)but-1-ynyl]-5,6-dihydroimidazo[1,2-d][1,4]benzoxazepine-2,3-dicarboxamide

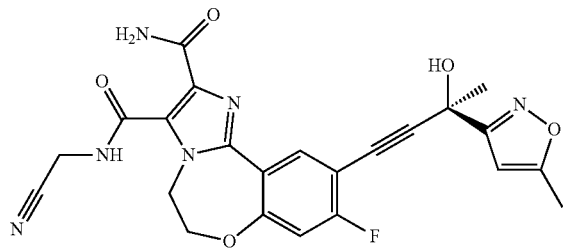 [SMILES: Cc1cc([C@](C)(O)C#Cc2cc3c(cc2F)OCCn2c-3nc(C(N)=O)c2C(=O)NCC#N)no1]

10-Bromo-2-carbamoyl-9-fluoro-5,6-dihydroimidazo[1,2-d][1,4]benzoxazepine-3-carboxylic acid (85 mg) was reacted with aminoacetonitrile hydrochloride similar to as described in Example 2 to produce 75 mg crude 10-bromo-N3-(cyanomethyl)-9-fluoro-5,6-dihydroimidazo[1,2-d][1,4]benzoxazepine-2,3-dicarboxamide which was then reacted with (2R)-2-(5-methylisoxazol-3-yl)but-3-yn-2-ol similar to as described in Procedure E to afford 26.1 mg of N3-(cyanomethyl)-9-fluoro-10-[(3R)-3-hydroxy-3-(5-methylisoxazol-3-yl)but-1-ynyl]-5,6-dihydroimidazo[1,2-d][1,4]benzoxazepine-2,3-dicarboxamide following reverse phase hplc purification. MS (Q1) 479 (M)+. $^1$H NMR (400 MHz, DMSO) δ 12.05 (t, J=5.3 Hz, 1H), 8.68 (d, J=8.4 Hz, 1H), 8.57 (s, 1H), 8.06 (s, 1H), 7.06 (d, J=10.5 Hz, 1H), 6.55 (s, 1H), 6.35 (s, 1H), 5.05-4.95 (m, 2H), 4.61-4.54 (m, 2H), 4.40 (d, J=5.3 Hz, 2H), 2.41 (s, 3H), 1.82 (s, 3H).

Example 173

Synthesis of 9-[2-(1-hydroxycyclopentyl)ethynyl]-4,5-dihydro-[1]benzoxepino[5,4-d]thiazole-2-carboxamide

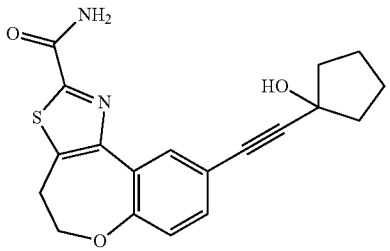 [SMILES: NC(=O)c1nc2c(s1)CCOc1ccc(C#CC3(O)CCCC3)cc1-2]

9-Bromo-4,5-dihydro-[1]benzoxepino[5,4-d]thiazole-2-carboxamide (0.15 g) was reacted with 1-ethynylcyclopentanol similar to as described in Procedure E to afford 46.2 mg of 9-[2-(1-hydroxycyclopentyl)ethynyl]-4,5-dihydro-[1]benzoxepino[5,4-d]thiazole-2-carboxamide following reverse phase hplc purification. MS (Q1) 355 (M)+. $^1$H NMR (400 MHz, DMSO) δ 8.58 (d, J=2.1 Hz, 1H), 8.40 (s, 1H), 7.84 (s, 1H), 7.27 (dd, J=8.3, 2.1 Hz, 1H), 7.01 (t, J=7.6 Hz, 1H), 5.26 (s, 1H), 4.34 (t, J=4.9 Hz, 2H), 3.41 (t, J=4.9 Hz, 2H), 2.00-1.82 (m, 4H), 1.82-1.59 (m, 5H).

Example 174

Synthesis of 9-(3-hydroxy-3-methyl-but-1-ynyl)-4,5-dihydro-[1]benzoxepino[5,4-d]thiazole-2-carboxamide

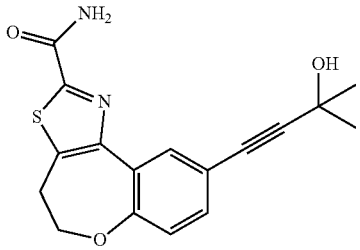 [SMILES: CC(C)(O)C#Cc1ccc2c(c1)-c1nc(C(N)=O)sc1CCO2]

9-Bromo-4,5-dihydro-[1]benzoxepino[5,4-d]thiazole-2-carboxamide (0.15 g) was reacted with dimethyl ethynyl carbinol similar to as described in Procedure E to afford 56.9 mg of 9-(3-hydroxy-3-methyl-but-1-ynyl)-4,5-dihydro-[1]benzoxepino[5,4-d]thiazole-2-carboxamide following reverse phase hplc purification. MS (Q1) 329 (M)+. $^1$H NMR (400 MHz, DMSO) δ 8.57 (d, J=2.1 Hz, 1H), 8.39 (s, 1H), 7.84 (s, 1H), 7.27 (dd, J=8.3, 2.1 Hz, 1H), 7.01 (d, J=8.3 Hz, 1H), 5.40 (s, 1H), 4.34 (t, J=4.9 Hz, 2H), 3.41 (t, J=4.9 Hz, 2H), 1.49 (s, 6H).

Example 175

Synthesis of 10-(3-hydroxy-3-methyl-but-1-ynyl)-5,6-dihydroimidazo[1,2-d][1,4]benzoxazepine-2-carboxamide

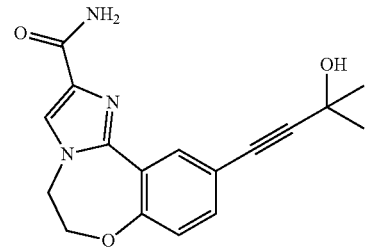 [SMILES: CC(C)(O)C#Cc1ccc2c(c1)-c1nc(C(N)=O)cn1CCO2]

10-Bromo-5,6-dihydroimidazo[1,2-d][1,4]benzoxazepine-2-carboxamide (0.1 g) was reacted with dimethyl ethynyl carbinol similar to as described in Procedure E to afford 52.2 mg of 10-(3-hydroxy-3-methyl-but-1-ynyl)-5,6-dihydroimidazo[1,2-d][1,4]benzoxazepine-2-carboxamide following reverse phase hplc purification. MS (Q1) 338 (M)+. $^1$H NMR (400 MHz, DMSO) δ 8.50 (d, J=2.1 Hz, 1H), 7.79 (s, 1H), 7.51 (s, 1H), 7.29 (dd, J=8.5, 2.2 Hz, 1H), 7.11 (s, 1H), 7.01 (d, J=8.5 Hz, 1H), 5.42 (s, 1H), 4.48 (s, 4H), 1.48 (s, 7H).

Example 176

Synthesis of 10-[2-(1-hydroxycyclopentyl)ethynyl]-5,6-dihydroimidazo[1,2-d][1,4]benzoxazepine-2-carboxamide

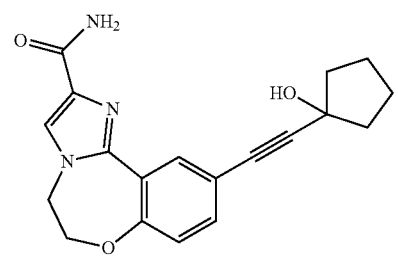 [SMILES: NC(=O)c1cn2c(n1)-c1cc(C#CC3(O)CCCC3)ccc1OCC2]

10-Bromo-5,6-dihydroimidazo[1,2-d][1,4]benzoxazepine-2-carboxamide (0.1 g) was reacted with 1-ethynylcyclopentanol similar to as described in Procedure E to afford 22.4 mg of 10-[2-(1-hydroxycyclopentyl)ethynyl]-5,6-dihydroimidazo[1,2-d][1,4]benzoxazepine-2-carboxamide following reverse phase hplc purification. MS (Q1) 338 (M)+. $^1$H NMR (400 MHz, DMSO) δ 8.50 (d, J=2.1 Hz, 1H), 7.84-7.71 (m, 1H), 7.54 (d, J=23.6 Hz, 1H), 7.29 (dd, J=8.5, 2.1 Hz, 1H), 7.10 (s, 1H), 7.01 (d, J=8.5 Hz, 1H), 5.28 (s, 1H), 4.49 (d, J=12.6 Hz, 4H), 1.94-1.84 (m, 4H), 1.82-1.62 (m, 5H).

Example 177

Synthesis of 9-fluoro-10-[(3R)-3-hydroxy-3-(5-methylisoxazol-3-yl)but-1-ynyl]-5,6-dihydroimidazo[1,2-d][1,4]benzoxazepine-2-carboxamide

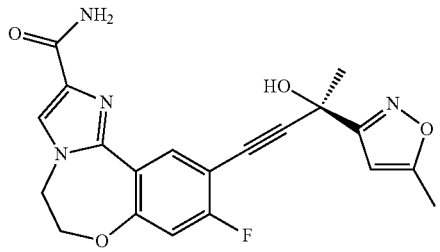 [SMILES: Cc1cc([C@](C)(O)C#Cc2cc3c(cc2F)OCCn2cc(C(N)=O)nc2-3)no1]

10-bromo-5,6-dihydroimidazo[1,2-d][1,4]benzoxazepine-2-carboxamide (0.1 g) was reacted with (2R)-2-(5-methylisoxazol-3-yl)but-3-yn-2-ol similar to as described in Procedure E to afford 66.5 mg of 9-fluoro-10-[(3R)-3-hydroxy-3-(5-methylisoxazol-3-yl)but-1-ynyl]-5,6-dihydroimidazo[1,2-d][1,4]benzoxazepine-2-carboxamide following reverse phase hplc purification. MS (Q1) 397 (M)+. $^1$H NMR (400 MHz, DMSO) δ 8.57 (d, J=8.5 Hz, 1H), 7.78 (s, 1H), 7.56 (s, 1H), 7.12 (s, 1H), 7.02 (d, J=10.6 Hz, 1H), 6.53 (d, J=23.4 Hz, 1H), 6.34 (d, J=7.8 Hz, 1H), 4.57-4.45 (m, 4H), 2.39 (s, 4H), 1.81 (s, 3H).

Example 178

Synthesis of 9-[(3R)-3-hydroxy-3-(5-methylisoxazol-3-yl)but-1-ynyl]-4,5-dihydro-[1]benzoxepino[5,4-d]thiazole-2-carboxamide

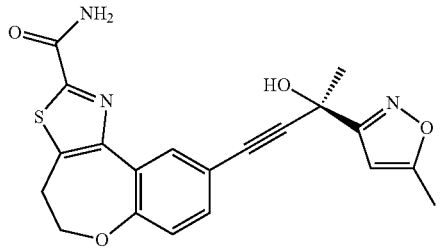 [SMILES: Cc1cc([C@](C)(O)C#Cc2ccc3c(c2)-c2nc(C(N)=O)sc2CCO3)no1]

Methyl 9-bromo-4,5-dihydro-[1]benzoxepino[5,4-d]thiazole-2-carboxylate (0.2 g) was reacted with (2R)-2-(5-methylisoxazol-3-yl)but-3-yn-2-ol similar to as described in Procedure F but substituting CuI for ZnBr and Dioxane as the solvent to afford 70 mg of methyl 9-[(3R)-3-hydroxy-3-(5-methylisoxazol-3-yl)but-1-ynyl]-4,5-dihydro-[1]benzoxepino[5,4-d]thiazole-2-carboxylate following reverse phase hplc purification. MS (Q1) 411.2 (M)+. Methyl 9-[(3R)-3-hydroxy-3-(5-methylisoxazol-3-yl)but-1-ynyl]-4,5-dihydro-[1]benzoxepino[5,4-d]thiazole-2-carboxylate (70 mg) was saponified with LiOH in THF/water followed by similar to as described in Example 2 to afford 39.7 mg of 9-[(3R)-3-hydroxy-3-(5-methylisoxazol-3-yl)but-1-ynyl]-4,5-dihydro-[1]benzoxepino[5,4-d]thiazole-2-carboxamide following reverse phase hplc purification. MS (Q1) 396 (M)+. $^1$H NMR (400 MHz, DMSO) δ 8.60 (d, J=2.1 Hz, 1H), 8.42 (s, 1H), 7.85 (s, 1H), 7.31 (dd, J=8.3, 2.2 Hz, 1H), 7.04 (d, J=8.3 Hz, 1H), 6.46 (s, 1H), 6.36 (s, 1H), 4.35 (t, J=4.9 Hz, 2H), 3.41 (t, J=4.9 Hz, 2H), 2.41 (s, 3H), 1.81 (s, 3H).

Example 179

General Procedures for Heterocycle Functionalization

General Procedure J: General Procedure Trifluoromethylation:

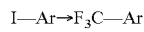

To a solution of aryl iodide in anhydrous N,N-Dimethylformamide (5 mL/mmol, 48.4 mmol) was introduced Trifluoromethyl(1,10-phenanthroline)Copper (1.5 equiv., 1.136 mmol). The reaction mixture was warmed to 50° C. for 48 hours whereupon it was concentrated to dryness. The resultant crude solid was brought up in dichloromethane and rinsed several times. The combined organic extracts were collected by filtration and concentrated to yield a gummy solid which was then brought up in water, sonicated, filtered, collected and dried under vacuum to afford a fluffy light green solid. The solid was used in subsequent reactions without further purification.

General Procedure K: General Procedure for CH Halogenation:

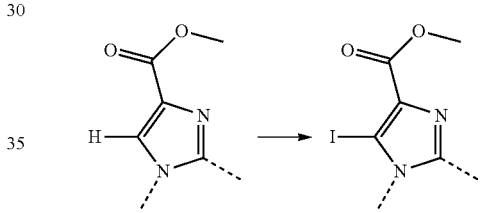

Sanford's conditions (Organic Letters, 2006, Vol. 8, No. 12, pg 2523-26) were used with minimal modifications. To the imidazole in anhydrous Acetonitrile (6 mL/mmol, 1720 mmol) was added Palladium(II) Acetate (5 mol %) and N-iodosuccinimide (1.5 eq). The reaction was heated at 100° C. under a reflux condenser for 12 hours. The reaction mixture was cooled to room temperature whereupon the crude product was triturated via addition of water. The solid was collected by filtration, rinsed 3 times with water, then 3 times with ether to afford a yellow solid which was dried under vacuum overnight. The solid was used in subsequent reactions without further purification.

Example 180

General Procedures for Carboxylate Derivative Conversion

General Procedure L: Ester to Amide Conversion with Sodium Methoxide/Formamide:

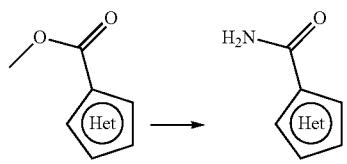

To a solution of Heterocyclic ester in N,N-Dimethylformamide was added formamide (10 eq) followed by dropwise addition of sodium methoxide (3 eq). The mixture was either stirred at room temperature or heated to 40° C. and monitored by LC-MS for completion. The crude reaction mixture was triturated via addition of saturated ammonium chloride or extracted with Dichloromethane in cases where the product did not crash out. In situations where this was an intermediate, the crude material was used directly in subsequent reactions.

General Procedure M: Amide Conversion with Ammonium Hydroxide in Dioxane:

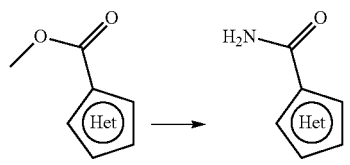

To a solution of Heterocyclic ester in Dioxane (10 mL/mmol) was added ammonium hydroxide (25% mass) in water (50 eq., 14 mmol). The reaction mixture was stirred at 40° C. and monitored by LC-MS for completion. The crude reaction mixture was concentrated to dryness and purified by reverse phase hplc to afford product.

General Procedure N: Saponification:

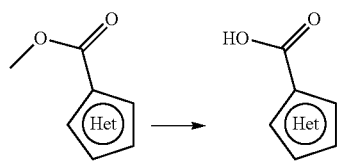

To a solution of heterocyclic ester in 1:1 Tetrahydrofuran/Water was added lithium hydroxide monohydrate (3-10 eq). The reaction was either stirred at room temperature or heated to 50° C. and monitored by LC-MS for completion. The tetrahydrofuran was then evaporated and the pH of the aqueous crude reaction mixture was adjusted to 3 whereupon the product either crashed out and was isolated, or the aqueous layer was extracted with Dichloromethane or ethyl acetate in cases where the product did not crash out. In situations where this was an intermediate, the crude material was used directly in subsequent reactions.

General Procedure O: Ketone/Aldehyde Reduction:

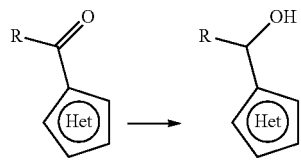

To a solution of heterocylic ketone/aldehyde in Methanol was added sodium borohydride (1-3 eq). The reaction was stirred at 0° C. or room temperature until bubbling subsided and monitored by LC-MS for completion. The reaction mixture was extracted with dichloromethane and saturated ammonium chloride whereupon the organic layer was dried, filtered and concentrated to afford crude heterocyclic alcohol intermediate and was used directly in subsequent reactions.

Example 181

General Procedure for Halogenation

General Procedure P: Fluorination:

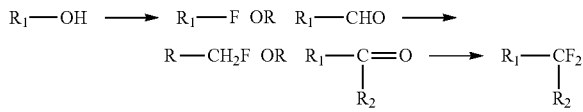

To a solution of alcohol, aldehyde or ketone in Dichloromethane or Dichloroethane was added 4 equivalents of Diethylaminosulfur trifluoride (DAST) or Bis(2-methoxyethyl)aminosulfur trifluoride (Deoxo-Fluor). The reaction was either stirred at room temperature or heated to 45° C. and monitored by LC-MS for completion. The reaction mixture was concentrated to dryness and the crude intermediate was triturated via addition of water which was used in subsequent reactions without further purification.

Example 182

Alternative synthesis of 10-bromo-9-fluoro-5,6-dihydrobenzo[f]imidazo[1,2-d][1,4]oxazepine-2-carboxamide

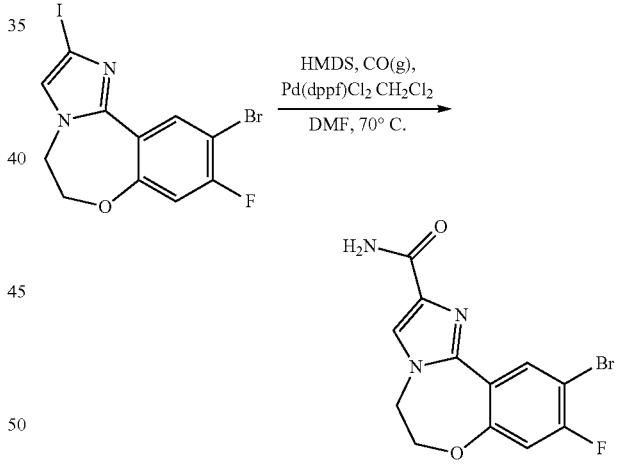

Similar to as described in Example 10, A suspension of 10-bromo-9-fluoro-2-iodo-5,6-dihydrobenzo[f]imidazo[1,2-d][1,4]oxazepine (16.0 g, 39.12 mmol, 1.00 equiv) (US2012/245144A1), HMDS (19.3 g, 119.88 mmol, 3.06 equiv) and Pd(dppf)Cl$_2$ CH$_2$Cl$_2$ (1.6 g, 1.95 mmol, 0.05 equiv) in N,N-dimethylformamide (240 mL) was stirred for 2 h at 70° C. under a carbon monoxide atmosphere (1 atm). After cooling to room temperature the reaction was quenched by addition of methanol (5 mL), diluted by ethyl acetate (1 L), washed with water (200×4 mL) and brine (200 mL), dried over sodium sulfate, and concentrated under vacuum. The residue was further purified by FC(Silica and ethyl acetate/petroether 2:1) to give 7.0 g (55%) of the titled compound as a grey solid.

Example 183

Synthesis of (±)-methyl 4-(2-carbamoyl-9-fluoro-5,6-dihydrobenzo[f]imidazo[1,2-d][1,4]oxazepin-10-yl)-2-hydroxy-2-methylbut-3-ynoate

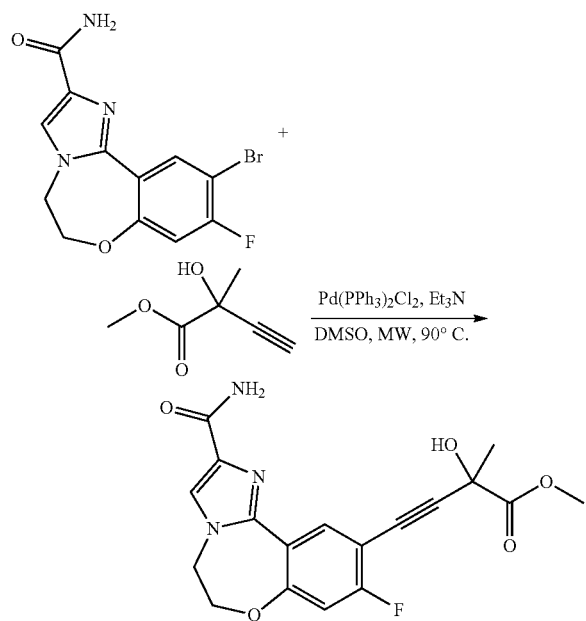

Similar to as described in General Procedure G, 10-bromo-9-fluoro-5,6-dihydrobenzo[f]imidazo[1,2-d][1,4]oxazepine-2-carboxamide was reacted with methyl 2-hydroxy-2-methylbut-3-ynoate to give the titled compound as a brown oil. M+1=374

Example 184

Synthesis of (±)-10-(4-(dimethylamino)-3-hydroxy-3-methyl-4-oxobut-1-yn-1-yl)-9-fluoro-5,6-dihydrobenzo[f]imidazo[1,2-d][1,4]oxazepine-2-carboxamide

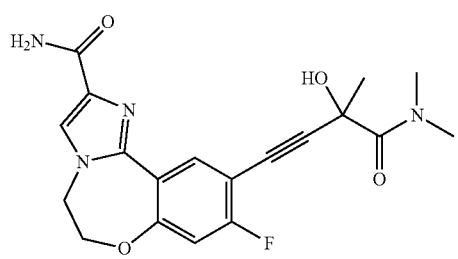 [SMILES: CN(C)C(=O)C(C)(O)C#Cc1cc2c(cc1F)OCCn1cc(C(N)=O)nc1-2]

Similar to as described in General Procedure G, 10-bromo-9-fluoro-5,6-dihydrobenzo[f]imidazo[1,2-d][1,4]oxazepine-2-carboxamide was reacted with 2-hydroxy-N,N,2-trimethylbut-3-ynamide to give 24.2 mg of the titled compound (13%), M+1=387; $^1$H NMR (300 MHz, DMSO-d6) δ: 8.57 (d, J=8.4 Hz, 1H), 7.79 (s, 1H), 7.59 (br s, 1H), 7.14 (br s, 1H), 7.04 (d, J=10.8 Hz, 1H), 6.24 (s, 1H), 4.58-4.45 (m, 4H), 3.34 (s, 3H), 2.90 (s, 3H), 1.66 (s, 3H)

Example 185

Synthesis of (±)-10-(4-amino-3-hydroxy-3-methyl-4-oxobut-1-yn-1-yl)-9-fluoro-5,6-dihydrobenzo[f]imidazo[1,2-d][1,4]oxazepine-2-carboxamide

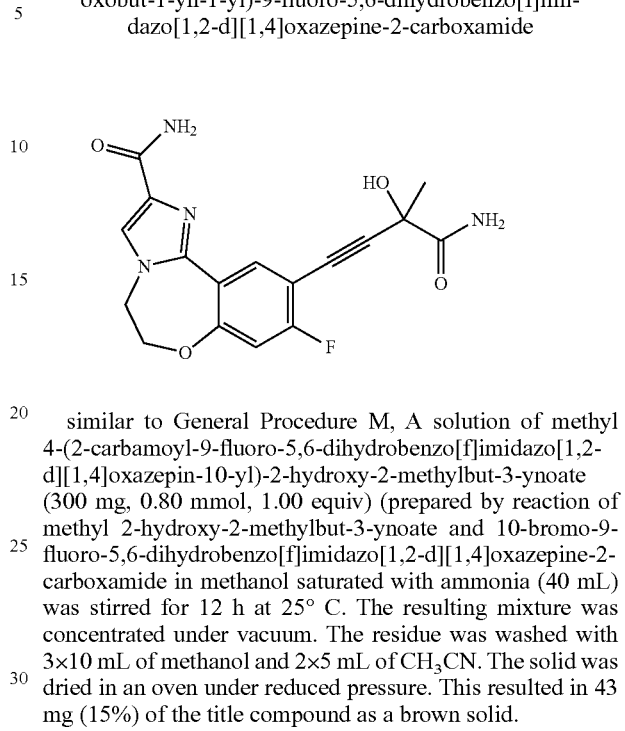

similar to General Procedure M, A solution of methyl 4-(2-carbamoyl-9-fluoro-5,6-dihydrobenzo[f]imidazo[1,2-d][1,4]oxazepin-10-yl)-2-hydroxy-2-methylbut-3-ynoate (300 mg, 0.80 mmol, 1.00 equiv) (prepared by reaction of methyl 2-hydroxy-2-methylbut-3-ynoate and 10-bromo-9-fluoro-5,6-dihydrobenzo[f]imidazo[1,2-d][1,4]oxazepine-2-carboxamide in methanol saturated with ammonia (40 mL) was stirred for 12 h at 25° C. The resulting mixture was concentrated under vacuum. The residue was washed with 3×10 mL of methanol and 2×5 mL of CH$_3$CN. The solid was dried in an oven under reduced pressure. This resulted in 43 mg (15%) of the title compound as a brown solid.

M+1=359, $^1$H NMR (400 MHz, DMSO-d6) δ 8.58 (d, J=8.4 Hz, 1H), 7.79 (s, 1H), 7.59 (br s, 1H), 7.38 (br s, 2H), 7.13 (br s, 1H), 7.028 (d, J=10.4 Hz, 1H), 6.42 (s, 1H), 4.54-4.45 (m, 4H), 1.61 (s, 3H).

Example 186

Synthesis of (±)-10-(4-(azetidin-1-yl)-3-hydroxy-3-methyl-4-oxobut-1-yn-1-yl)-9-fluoro-5,6-dihydrobenzo[f]imidazo[1,2-d][1,4]oxazepine-2-carboxamide

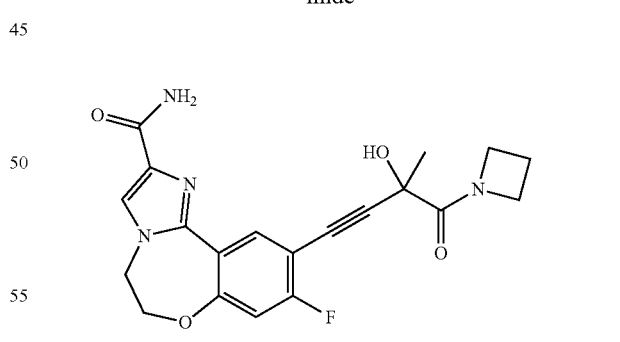

Similar to as described in General Procedure G, 10-bromo-9-fluoro-5,6-dihydrobenzo[f]imidazo[1,2-d][1,4]oxazepine-2-carboxamide was reacted with 1-(azetidin-1-yl)-2-hydroxy-2-methylbut-3-yn-1-one to give the titled compound as a yellow solid (40 mg, 22%).

M+1=399, $^1$H NMR (300 MHz, DMSO-d6) δ 8.57 (d, J=5.1 Hz, 1H), 7.78 (s, 1H) 7.59 (br s, 1H), 7.13 (br s, 1H), 7.03 (d, J=10.5 Hz, 1H), 6.14 (s, 1H), 4.52-4.44 (m, 6H), 3.95-3.90 (m, 2H), 2.28-2.18 (m, 2H), 1.59 (s, 3H).

Example 187

Synthesis of (±)-8-fluoro-9-((3-hydroxy-1-methyl-2-oxopyrrolidin-3-yl)ethynyl)-4,5-dihydrobenzo[2,3]oxepino[4,5-d]thiazole-2-carboxamide

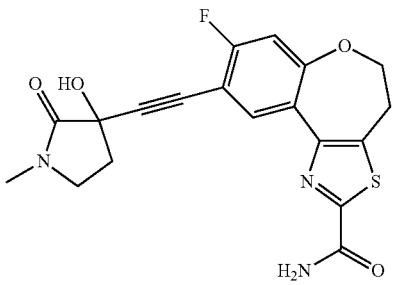 [SMILES: CN1CCC(O)(C#Cc2cc3c(cc2F)OCCc2sc(C(N)=O)nc2-3)C1=O]

Similar to as described in General Procedure G, 9-bromo-8-fluoro-4,5-dihydrobenzo[2,3]oxepino[4,5-d]thiazole-2-carboxamide was reacted with 3-ethynyl-3-hydroxy-1-methylpyrrolidin-2-one (WO2009/158011A 1) to give the titled compound (34.8 mg, 30%).

M+1=402, $^1$H NMR (300 MHz, CD$_3$OD-d4) 8.70 (d, J=8.1 Hz, 1H), 6.80 (d, J=10.2 Hz, 1H), 4.38 (t, J=4.8 Hz, 2H), 3.51-3.37 (m, 4H), 2.95 (s, 3H), 2.63-2.57 (m, 1H), 2.45-2.33 (m, 1H).

Example 188

Synthesis of (±)-9-((3-hydroxy-1-methyl-2-oxopyrrolidin-3-yl)ethynyl)-4,5-dihydrobenzo[2,3]oxepino[4,5-d]thiazole-2-carboxamide

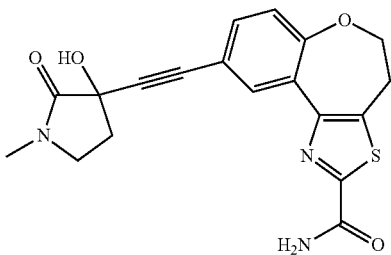 [SMILES: CN1CCC(O)(C#Cc2ccc3c(c2)-c2nc(C(N)=O)sc2CCO3)C1=O]

Similar to as described in General Procedure G, 9-bromo-4,5-dihydrobenzo[2,3]oxepino[4,5-d]thiazole-2-carboxamide) was reacted with 3-ethynyl-3-hydroxy-1-methylpyrrolidin-2-one (WO2009/158011 A1) to give the titled compound as a brown solid (56.1 mg, 48%).

M+1=406; $^1$H NMR (300 MHz, CD$_3$OD-d4) 8.65 (s, 1H), 7.31-7.27 (m, 1H), 6.97 (d, J=8.4 Hz, 1H), 4.35 (t, J=4.8 Hz, 2H), 3.51-3.38 (m, 4H), 2.93 (s, 3H), 2.63-2.51 (m, 1H), 2.32-2.22 (m, 1H).

Example 189

Synthesis of (±)-8-fluoro-9-((3-hydroxy-1-methyl-2-oxopiperidin-3-yl)ethynyl)-4,5-dihydrobenzo[2,3]oxepino[4,5-d]thiazole-2-carboxamide

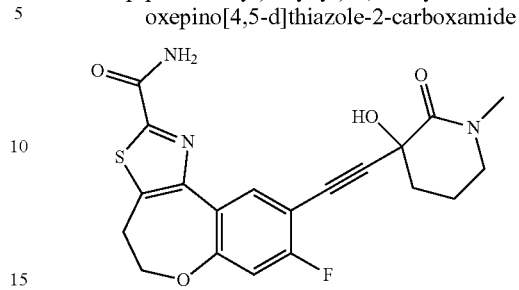

Similar to as described in General Procedure G, 9-bromo-8-fluoro-4,5-dihydrobenzo[2,3]oxepino[4,5-d]thiazole-2-carboxamide was reacted with 3-ethynyl-3-hydroxy-1-methylpiperidin-2-one (US2012/214762A1) to give the titled compound as a white solid (20 mg, 16%).

M+1=416; $^1$H NMR (400 MHz, DMSO-d6) δ: 8.65 (d, J=8.4 Hz, 1H), 8.49 (s, 1H), 7.87 (s, 1H), 7.02 (d, J=10.4 Hz, 1H), 6.09 (s, 1H), 4.39 (t, J=4.8 Hz, 2H), 3.46-3.41 (m, 4H), 2.87 (s, 3H), 2.21-2.18 (m, 1H), 2.07-1.91 (m, 3H).

Example 190

Synthesis of (±)-9-((3-hydroxy-1-methyl-2-oxopiperidin-3-yl)ethynyl)-4,5-dihydrobenzo[2,3]oxepino[4,5-d]thiazole-2-carboxamide

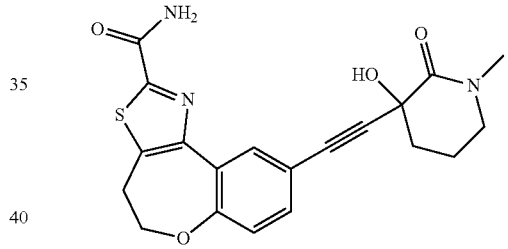

Similar to as described in General Procedure G, 9-bromo-4,5-dihydrobenzo[2,3]oxepino[4,5-d]thiazole-2-carboxamide was reacted with 3-ethynyl-3-hydroxy-1-methylpiperidin-2-one to give the titled compound as a white solid (10 mg, 8%).

M+1=398; $^1$H-NMR (400 MHz, CD$_3$OD) δ 8.69 (s, 1H), 7.35-7.32 (m, 1H), 7.02 (d, J=8.4 Hz, 1H), 4.39 (t, J=4.8 Hz, 2H), 3.55-3.44 (m, 4H), 3.01 (s, 3H), 2.37-2.03 (m, 4H).

Example 191

Synthesis of (±)-9-fluoro-104(3-hydroxy-1-methyl-2-oxopyrrolidin-3-yl)ethynyl)-5,6-dihydrobenzo[f]imidazo[1,2-d][1,4]oxazepine-2-carboxamide

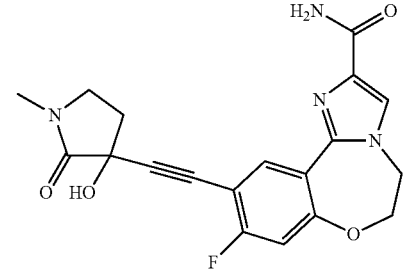 [SMILES: CN1CCC(O)(C#Cc2cc3c(cc2F)OCCn2cc(C(N)=O)nc2-3)C1=O]

Similar to as described in General Procedure G, 10-bromo-9-fluoro-5,6-dihydrobenzo[f]imidazo[1,2-d][1,4]oxazepine-2-carboxamide was reacted with 3-ethynyl-3-hydroxy-1-methylpyrrolidin-2-one (WO2009/158011A1) to give the titled compound as a brown solid (37 mg, 31%).

M+1=385; $^1$H NMR (300 MHz, CD$_3$OD) δ 8.64 (d, J=8.1 Hz, 1H), 7.72 (s, 1H), 6.85 (d, J=10.2 Hz, 1H), 4.55-4.49 (m, 4H), 3.57-3.46 (m, 2H), 2.93 (s, 3H), 2.63-2.59 (m, 1H), 2.37-2.27 (m, 1H).

Example 192

Synthesis of (±)-10-((3-hydroxy-1-methyl-2-oxopyrrolidin-3-yl)ethynyl)-5,6-dihydrobenzo[f]imidazo[1,2-d][1,4]oxazepine-2-carboxamide

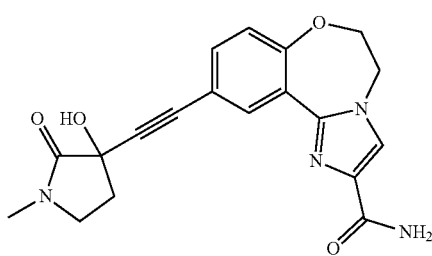 [SMILES: CN1CCC(O)(C#Cc2ccc3c(c2)-c2nc(C(N)=O)cn2CCO3)C1=O]

Similar to as described in General Procedure G, 10-bromo-5,6-dihydrobenzo[f]imidazo[1,2-d][1,4]oxazepine-2-carboxamide was reacted with 3-ethynyl-3-hydroxy-1-methylpyrrolidin-2-one (WO2009/158011A1) to give the titled compound as a light yellow solid (17 mg, 7%).

M+1=367; $^1$H NMR (300 MHz, CD$_3$OD) δ 8.57 (d, J=2.1 Hz, 1H), 7.70 (s, 1H), 7.36-7.32 (m, 1H), 3.99 (d, J=8.4 Hz, 1H), 4.47 (s, 4H), 3.51-3.40 (m, 2H), 2.90 (s, 3H), 2.59-2.51 (m, 1H), 2.32-2.22 (m, 1H).

Example 193

Synthesis of (±)-9-fluoro-10-((3-hydroxy-1-methyl-2-oxopiperidin-3-yl)ethynyl)-5,6-dihydrobenzo[f]imidazo[1,2-d][1,4]oxazepine-2-carboxamide

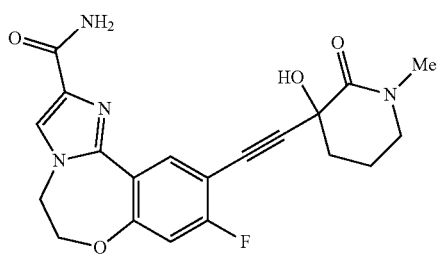 [SMILES: CN1CCCC(O)(C#Cc2cc3c(cc2F)OCCn2cc(C(N)=O)nc2-3)C1=O]

Similar to as described in General Procedure G, 10-bromo-9-fluoro-5,6-dihydrobenzo[f]imidazo[1,2-d][1,4]oxazepine-2-carboxamide was reacted with 3-ethynyl-3-hydroxy-1-methylpiperidin-2-one (US2012/214762A 1) to give the titled compound as a white solid (20 mg, 16%).

M+1=399; $^1$H NMR (400 MHz, DMSO-d$_6$) δ 8.56 (d, J=8.4 Hz, 1H), 7.79 (s, 1H), 7.58 (s, 1H), 7.13 (s, 1H), 7.03 (d, J=10.8 Hz, 1H), 6.16 (s, 1H), 4.54-4.50 (m, 4H), 3.36-3.32 (m, 2H), 2.87 (s, 3H), 2.19-2.17 (m, 1H), 2.01-1.93 (m, 3H).

Example 194

Synthesis of (±)-10-((3-hydroxy-1-methyl-2-oxopiperidin-3-yl)ethynyl)-5,6-dihydrobenzo[f]imidazo[1,2-d][1,4]oxazepine-2-carboxamide

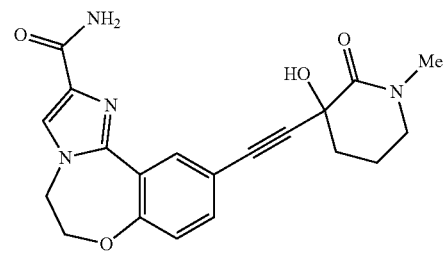 [SMILES: CN1CCCC(O)(C#Cc2ccc3c(c2)-c2nc(C(N)=O)cn2CCO3)C1=O]

Similar to as described in General Procedure G, 10-bromo-5,6-dihydrobenzo[f]imidazo[1,2-d][1,4]oxazepine-2-carboxamide was reacted with 3-ethynyl-3-hydroxy-1-methylpiperidin-2-one (US2012/214762A1) to give the titled compound as a white solid (20 mg, 17%).

M+1=381; $^1$H NMR (400 MHz, DMSO-d$_6$) δ 8.52 (d, J=2Hz, 1H), 7.80 (s, 1H), 7.55 (s, 1H), 7.33-7.31 (m, 1H), 7.14 (s, 1H), 7.04 (d, J=8.4 Hz, 1H), 6.08 (s, 1H), 4.49 (s, 4H), 3.35-3.33 (m, 2H), 2.86 (s, 3H), 2.19-2.16 (m, 1H), 2.00-1.94 (m, 3H).

Example 195

Synthesis of methyl 2-chloro-6,7-dihydroimidazo[1,2-d]pyrido[3,2-b][1,4]oxazepine-9-carboxylate Scheme for the synthesis of methyl 2-chloro-6,7-dihydroimidazo[1,2-d]pyrido[3,2-b][1,4]oxazepine-9 carboxylate

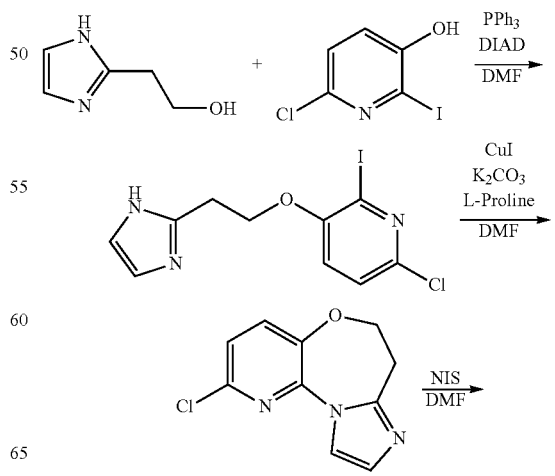

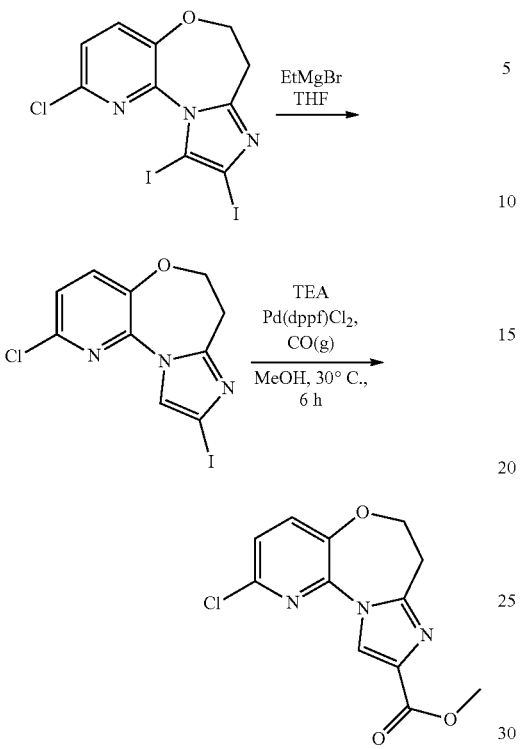

DIAD (24 g, 113.74 mmol, 2.00 equiv) was added dropwise to a stirred solution of 6-chloro-2-iodopyridin-3-ol (15 g, 58.72 mmol, 1.00 equiv), 2-(1H-imidazol-2-yl)ethan-1-ol (13.1 g, 116.83 mmol, 2.00 equiv), and PPh₃ (31 g, 118.19 mmol, 2.00 equiv) in N,N-dimethylformamide (550 mL) at 0° C. The resulting solution was stirred overnight at room temperature and concentrated under vacuum. The residue was applied onto a silica gel column with dichloromethane/methanol (100:1-2:1). This resulted in 13.6 g (66%) of 6-chloro-3-[2-(1H-imidazol-2-yl)ethoxy]-2-iodopyridine as a yellow solid. A mixture of this intermediate (10.2 g, 29.18 mmol, 1.00 equiv), L-Proline (0.67 g, 0.20 equiv), potassium carbonate (6 g, 43.41 mmol, 1.50 equiv), and copper(I) iodide (553 mg, 2.90 mmol, 0.10 equiv) in N,N-dimethylformamide (150 mL) was stirred for 24 h at 50° C. The reaction mixture was cooled to room temperature, diluted with water, extracted with ethyl acetate, dried over anhydrous sodium sulfate, and concentrated under vacuum. The residue was applied onto a silica gel column with ethyl acetate/petroleum ether (1/10-1/1). This resulted in 3.9 g (60%) of 2-chloro-6,7-dihydroimidazo[1,2-d]pyrido[3,2-b][1,4]oxazepine as a white solid. NIS (1.218 g, 5.41 mmol, 10.00 equiv) was added in portions to a stirred solution of this intermediate (120 mg, 0.54 mmol, 1.00 equiv) in N,N-dimethylformamide (30 mL) at room temperature. After being stirred for 12 h at 80° C. the resulting solution was diluted with ethyl acetate, washed with 5% of Na₂S₂O₃ and brine, dried over anhydrous sodium sulfate, and concentrated under vacuum. The residue was applied onto a silica gel column with ethyl acetate/petroleum ether (1/2). This resulted in 210 mg (crude) of 2-chloro-9,10-diiodo-6,7-dihydroimidazo[1,2-d]pyrido[3,2-b][1,4]oxazepine as a brown solid. Ethylmagnesium bromide (1 M, 8 mL, 1.00 equiv) was added dropwise to a stirred solution of this intermediate (3.8 g, 8.03 mmol, 1.00 equiv) in tetrahydrofuran (100 mL) at −5° C. The resulting solution was stirred for 15 min at −5° C. and quenched with water, extracted with ethyl acetate, dried over anhydrous sodium sulfate, and concentrated under vacuum. The residue was applied onto a silica gel column with ethyl acetate/petroleum ether (1/10-1/4). This resulted in 2 g (72%) of 2-chloro-9-iodo-6,7-dihydroimidazo[1,2-d]pyrido[3,2-b][1,4]oxazepine as a white solid. Into a 20-mL sealed tube purged and maintained with an inert atmosphere of CO(g) was placed a solution of this intermediate (600 mg, 1.73 mmol, 1.00 equiv), TEA (696 mg, 6.88 mmol, 4.00 equiv), Pd(dppf)Cl₂ (138 mg, 0.19 mmol, 0.10 equiv) in methanol (4 mL). The resulting solution was stirred for 6 h at 30° C., diluted with 20 mL of H₂O, extracted with 3×50 mL of ethyl acetate, dried over anhydrous sodium sulfate, and concentrated under vacuum. The residue was applied onto a silica gel column with ethyl acetate/petroleum ether (5:1). This resulted in 450 mg (93%) of the titled compound as a yellow solid. M+1=280.

Example 196

Synthesis of 2-(3-hydroxy-3-methylbut-1-yn-1-yl)-6,7-dihydroimidazo[1,2-d]pyrido[3,2-b][1,4]oxazepine-9-carboxamide

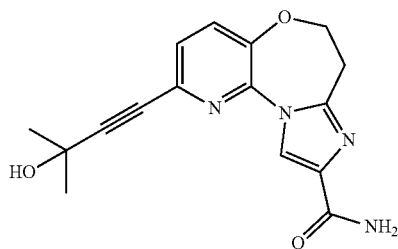 [SMILES: CC(C)(O)C#Cc1ccc2c(n1)-n1cc(C(N)=O)nc1CCO2]

Into a 20-mL sealed tube was placed a solution of methyl 2-(3-hydroxy-3-methylbut-1-yn-1-yl)-6,7-dihydroimidazo[1,2-d]pyrido[3,2-b][1,4]oxazepine-9-carboxylate (100 mg, 0.31 mmol, 1.00 equiv, prepared by reaction of methyl 2-chloro-6,7-dihydroimidazo[1,2-d]pyrido[3,2-b][1,4]oxazepine-9-carboxylate with 2-methylbut-3-yn-ol similar to as described in General Procedure G. The crude mixture was reacted with NH₃.H₂O (2 mL, 37%) in 1,4-dioxane (4 mL) similar to as described in General Procedure M. The resulting solution was stirred overnight at 100° C., diluted with 10 mL of H₂O, extracted with 3×50 mL of ethyl acetate, dried over anhydrous sodium sulfate, and concentrated under vacuum. The crude product was purified by Flash-Prep-HPLC with the following conditions (CombiFlash-1): Column, silica gel; mobile phase, DCM/MeOH (100:1-10:1); Detector, UV 254 um. This resulted in 423 mg (44%) of the titled compound as a light yellow solid.

M+1=313; ¹H NMR (300 MHz, CD₃OD) δ: 8.61 (s, 1H), 7.58 (d, J=8.1 Hz, 1H), 7.42 (d, J=8.4 Hz, 1H), 4.53 (t, J=10.2 Hz, 2H), 3.42 (t, J=10.5 Hz, 2H), 1.60 (s, 6H).

Example 197

Synthesis of (R)-2-(3-hydroxy-3-(5-methylisoxazol-3-yl)but-1-yn-1-yl)-6,7-dihydroimidazo[1,2-d]pyrido[3,2-b][1,4]oxazepine-9-carboxamide

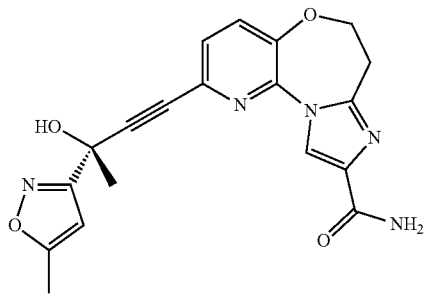 [SMILES: Cc1cc([C@](C)(O)C#Cc2ccc3c(n2)-n2cc(C(N)=O)nc2CCO3)no1]

Similar to as described in General Procedure G with the exception of replacing PdCl$_2$(PPh3)$_2$ with Pd (PPh3)$_4$, 2-chloro-6,7-dihydroimidazo[1,2-d]pyrido[3,2-b][1,4]oxazepine-9-carboxamide was reacted with (R)-2-(5-methylisoxazol-3-yl)but-3-yn-2-ol (US2012/214762A1) to give the titled compound as a white solid (36 mg, 21%).

M+1=380; $^1$H NMR (400 MHz, CD$_3$OD) δ 8.63 (s, 1H), 7.66 (d, J=9.2 Hz, 1H), 7.52 (d, J=12.4 Hz, 1H), 6.34 (s, 1H), 4.54 (t, J=10.4 Hz, 2H), 3.43 (t, J=10.4 Hz, 2H), 2.46 (s, 3H), 1.91 (s, 3H).

Example 198

Synthesis of (±)-9-fluoro-10-(3-hydroxy-3-(4-methylpyridin-2-yl)but-1-yn-1-yl)-5,6-dihydrobenzo[f]imidazo[1,2-d][1,4]oxazepine-2-carboxamide

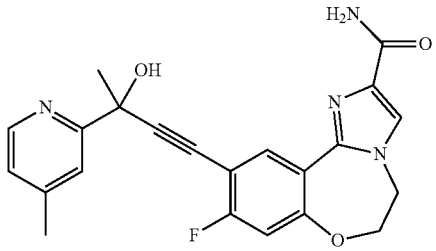 [SMILES: Cc1ccnc(C(C)(O)C#Cc2cc3c(cc2F)OCCn2cc(C(N)=O)nc2-3)c1]

Similar to as described in General Procedure G, 10-bromo-9-fluoro-5,6-dihydrobenzo[f]imidazo[1,2-d][1,4]oxazepine-2-carboxamide was reacted with 2-(4-methylpyridin-2-yl)but-3-yn-2-ol (WO2009/158011A1) to give the titled compound as a white solid (39 mg, 10%).

M+1=407; $^1$H NMR (400 MHz, DMSO-d6) δ 8.539 (d, 1H), 8.419 (d, 1H), 7.780 (s, 1H), 7.596 (s, 1H), 7.576 (br s, 1H), 7.164 (d, 1H), 7.127 (br s, 1H), 7.010 (d, 1H), 6.378 (s, 1H), 4.530-4.450 (m, 4H), 2.370 (s, 3H), 1.809 (s, 3H)

Example 199

Synthesis of 9-fluoro-10-(3-hydroxy-3-(3-methylpyridin-2-yl)but-1-yn-1-yl)-5,6-dihydrobenzo[f]imidazo[1,2-d][1,4]oxazepine-2-carboxamide

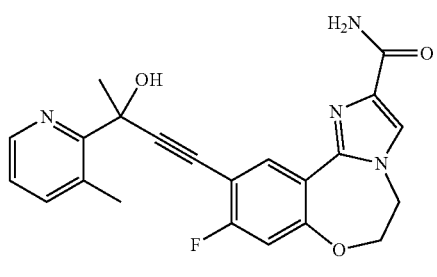 [SMILES: Cc1cccnc1C(C)(O)C#Cc1cc2c(cc1F)OCCn1cc(C(N)=O)nc1-2]

Similar to as described in General Procedure G, 10-bromo-9-fluoro-5,6-dihydrobenzo[f]imidazo[1,2-d][1,4]oxazepine-2-carboxamide was reacted with 2-(3-methylpyridin-2-yl)but-3-yn-2-ol to give the titled compound as a yellow solid (15.0 mg, 7%).

M+1=407; $^1$H NMR (300 MHz, DMSO-d6) δ 9.00 (d, 1H), 8.65 (br s, 1H), 7.79 (br s, 1H), 7.21 (s, 2H), 7.02 (d, 1H), 6.67 (d, 1H), 6.75 (d, 1H), 5.68 (s, 1H), 5.48 (t, 1H), 4.47 (s, 4H), 1.99 (s, 3H), 1.41 (s, 3H).

Example 200

Synthesis of (±)-9-fluoro-10-(3-hydroxy-3-(pyridin-2-yl)but-1-yn-1-yl)-5,6-dihydrobenzo[f]imidazo[1,2-d][1,4]oxazepine-2-carboxamide

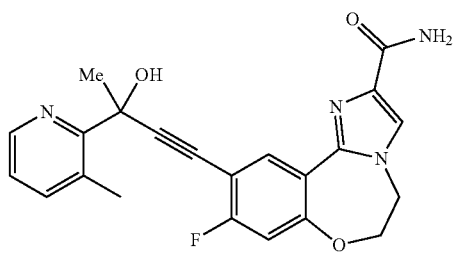 [SMILES: Cc1cccnc1C(C)(O)C#Cc1cc2c(cc1F)OCCn1cc(C(N)=O)nc1-2]

Similar to as described in General Procedure G 10-bromo-9-fluoro-5,6-dihydrobenzo[f]imidazo[1,2-d][1,4]oxazepine-2-carboxamide was reacted with 2-(pyridin-2-yl)but-3-yn-2-ol to give the titled compound (80 mg, 30%).

M+1=393; $^1$H NMR (300 MHz, DMSO-d6) δ 8.57-8.52 (m, 2H), 7.88-7.83 (m, 1H), 7.77-7.74 (m, 2H), 7.56 (br s,

M+1=313; $^1$H NMR (300 MHz, CD$_3$OD) δ: 8.61 (s, 1H), 7.58 (d, J=8.1 Hz, 1H), 7.42 (d, J=8.4 Hz, 1H), 4.53 (t, J=10.2 Hz, 2H), 3.42 (t, J=10.5 Hz, 2H), 1.60 (s, 6H). 1H), 7.35-7.30 (m, 1H), 7.10 (br s, 1H), 7.00 (d, 1H), 6.40 (s, 1H), 4.52-4.46 (m, 4H), 1.816 (s, 3H).

Example 201

Synthesis of (±)-9-fluoro-10-(3-hydroxy-3-(5-methyl-1,2,4-oxadiazol-3-yl)but-1-yn-1-yl)-5,6-dihydrobenzo[f]imidazo[1,2-d][1,4]oxazepine-2-carboxamide

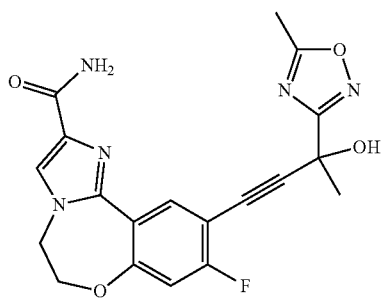 [SMILES: Cc1nc(C(C)(O)C#Cc2cc3c(cc2F)OCCn2cc(C(N)=O)nc2-3)no1]

Similar to as described in General Procedure G, 10-bromo-9-fluoro-5,6-dihydrobenzo[f]imidazo[1,2-d][1,4]oxazepine-2-carboxamide was reacted with 2-(5-methyl-1,2,4-oxadiazol-3-yl)but-3-yn-2-ol to give the titled compound as a brown solid (5.3 mg, 5%).

M+1=398; $^1$H NMR (300 MHz, DMSO-d6) δ 8.57 (d, 1H), 7.78 (s, 1H), 7.56 (s, 1H), 7.12 (s, 1H), 7.03 (d, 1H), 6.78 (s, 1H), 4.50 (d, 4H), 2.61 (s, 3H), 1.84 (s, 3H).

Example 202

Synthesis of (±)-9-fluoro-10-(3-hydroxy-3-(1H-1,2,4-triazol-3-yl)but-1-yn-1-yl)-5,6-dihydrobenzo[f]imidazo[1,2-d][1,4]oxazepine-2-carboxamide

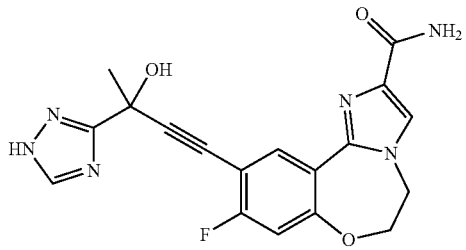 [SMILES: CC(O)(C#Cc1cc2c(cc1F)OCCn1cc(C(N)=O)nc1-2)c1nc[nH]n1]

Similar to as described in General Procedure G, 10-bromo-9-fluoro-5,6-dihydrobenzo[f]imidazo[1,2-d][1,4]oxazepine-2-carboxamide was reacted with 2-(1H-1,2,4-triazol-3-yl)but-3-yn-2-ol to give the titled compound as an off-white solid (40 mg, 20%).

M+1=383; $^1$H NMR (400 MHz, DMSO-d6) δ 8.56 (d, 1H), 8.49 (s, 1H), 7.89 (s, 1H), 7.76 (s, 1H), 7.02 (d, 1H), 4.50 (s, 2H), 4.47 (s, 2H), 1.85 (s, 3H).

Example 203

Synthesis of (±)-9-fluoro-10-(3-hydroxy-3-(1-methyl-1H-imidazol-2-yl)but-1-yn-1-yl)-5,6-dihydrobenzo[f]imidazo[1,2-d][1,4]oxazepine-2-carboxamide

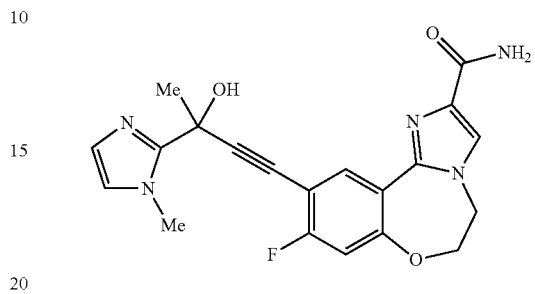

Similar to as described in General Procedure G 10-bromo-9-fluoro-5,6-dihydrobenzo[f]imidazo[1,2-d][1,4]oxazepine-2-carboxamide was reacted with 2-(1-methyl-1H-imidazol-2-yl)but-3-yn-2-ol to give the titled compound as an off-white solid (22 mg, 16%).

M+1=396; $^1$H NMR (300 MHz, DMSO-d6) δ 8.56 (d, 1H), 7.78 (s, 1H), 7.58 (br s, 1H), 7.16 (s, 1H), 7.13 (br s, 1H), 7.03 (d, 1H), 6.79 (s, 1H), 6.36 (s, 1H), 4.53-4.49 (m, 4H), 3.89 (s, 3H), 1.971 (s, 3H).

Example 204

Synthesis of (±)-9-fluoro-10-(3-hydroxy-3-(1H-imidazol-2-yl)but-1-yn-1-yl)-5,6-dihydrobenzo[f]imidazo[1,2-d][1,4]oxazepine-2-carboxamide

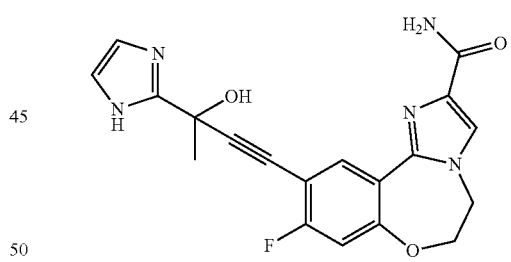

A solution of 9-fluoro-10-(3-hydroxy-3-(1-((2-(trimethylsilyl)ethoxy)methyl)-1H-imidazol-2-yl)but-1-yn-1-yl)-5,6-dihydrobenzo[f]imidazo[1,2-d][1,4]oxazepine-2-carboxamide (200 mg, 0.39 mmol, 1.00 equiv) and TFA (1.5 mL) in dichloromethane (4.5 mL) was stirred for 5 h at room temperature. The resulting solution was diluted with 50 mL of dichloromethane. The pH value of the solution was adjusted to 9 with saturated potassium carbonate. The resulting mixture was washed with water, dried over sodium sulfate, and concentrated under vacuum. The residue was applied onto a silica gel column with DCM/MeOH (10/1) to give the titled compound as an off-white solid.

M+1=382; $^1$H NMR (400 MHz, CD$_3$OD) δ 8.68 (d, J=8.0 Hz, 1H), 7.73 (s, 1H), 7.02 (s, 2H), 6.86 (d, J=10.4 Hz, 1H), 4.53 (m, 4H), 1.95 (s, 3H).

Example 204

Synthesis of (±)-9-fluoro-10-(3-hydroxy-3-(2-methyl-1H-imidazol-4-yl)but-1-yn-1-yl)-5,6-dihydrobenzo[f]imidazo[1,2-d][1,4]oxazepine-2-carboxamide

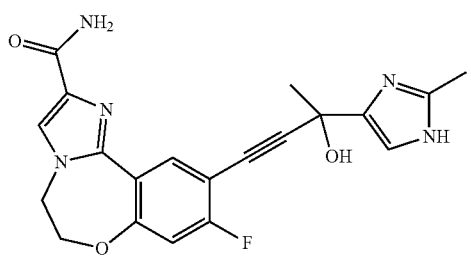 [SMILES: Cc1nc(C(C)(O)C#Cc2cc3c(cc2F)OCCn2cc(C(N)=O)nc2-3)c[nH]1]

Similar to as described in General Procedure G, 10-bromo-9-fluoro-5,6-dihydrobenzo[f]imidazo[1,2-d][1,4]oxazepine-2-carboxamide was reacted with 2-(2-methyl-1-((2-(trimethylsilyl)ethoxy)methyl)-1H-imidazol-4-yl)but-3-yn-2-ol to give the titled compound after removal of the SEM protecting group (n-Bu$_4$NF, THF). White solid (9 mg, 6%).

M+1=396; $^1$H NMR (400 MHz, DMSO-d6) δ 8.56 (d, J=8.4 Hz, 1H), 7.78 (s, 1H), 7.58 (s, 1H), 7.12 (s, 1H), 7.01 (d, J=10.4 Hz, 1H), 5.84 (br s, 1H), 4.50-4.52 (m, 4H), 2.26 (s, 3H), 1.75 (s, 3H).

Example 205

Synthesis of (±)-9-fluoro-10-(3-hydroxy-3-(1H-pyrazol-4-yl)but-1-yn-1-yl)-5,6-dihydrobenzo[f]imidazo[1,2-d][1,4]oxazepine-2-carboxamide

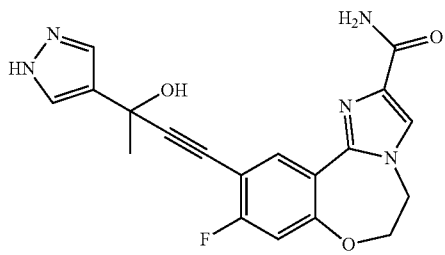 [SMILES: CC(O)(C#Cc1cc2c(cc1F)OCCn1cc(C(N)=O)nc1-2)c1cn[nH]c1]

Similar to as described in General Procedure G, 10-bromo-9-fluoro-5,6-dihydrobenzo[f]imidazo[1,2-d][1,4]oxazepine-2-carboxamide was reacted with 2-(1H-pyrazol-4-yl)but-3-yn-2-ol to give the titled compound as an off-white solid (46.3 mg, 19%).

M+1=382; $^1$H NMR (400 MHz, DMSO-d$_6$) δ 12.66 (br s, 1H), 8.58 (d, 1H), 7.78 (s, 1H), 7.59 (s, 3H), 7.13 (s, 1H), 7.02 (d, 1H), 5.96 (s, 1H), 4.53-4.41 (m, 4H), 1.764 (s, 3H).

Example 206

Synthesis of (±)-9-fluoro-10-(4,4,4-trifluoro-3-hydroxy-3-methylbut-1-yn-1-yl)-5,6-dihydrobenzo[f]imidazo[1,2-d][1,4]oxazepine-2-carboxamide

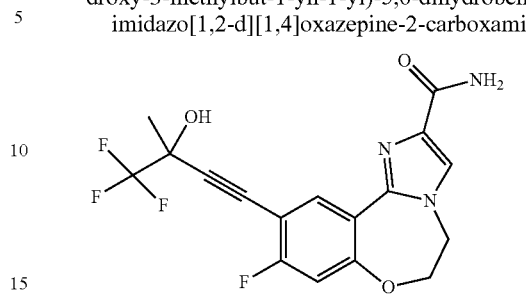

Similar to as described in General Procedure G, 10-bromo-9-fluoro-5,6-dihydrobenzo[f]imidazo[1,2-d][1,4]oxazepine-2-carboxamide was reacted with 1,1,1-trifluoro-2-methylbut-3-yn-2-ol (US2005/250741 A1) to give the titled compound as a white solid (80 mg, 40%).

M+1=384; $^1$H NMR (300 MHz, DMSO-d$_6$) δ 8.63 (d, 1H), 7.79 (s, 1H), 7.57 (s, 1H), 7.19 (s, 1H), 7.14 (s, 1H), 7.08 (d, 1H), 4.53 (m, 4H), 1.65 (s, 3H).

Example 207

Synthesis of (±)-9-fluoro-10-(4-fluoro-3-hydroxy-3-methylbut-1-yn-1-yl)-5,6-dihydrobenzo[f]imidazo[1,2-d][1,4]oxazepine-2-carboxamide

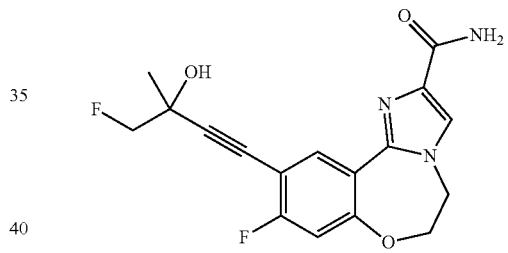

Similar to as described in General Procedure G, 10-bromo-9-fluoro-5,6-dihydrobenzo[f]imidazo[1,2-d][1,4]oxazepine-2-carboxamide was reacted with 1-fluoro-2-methylbut-3-yn-2-ol to give the titled compound as an off-white solid (70 mg, 33%).

M+1=348; $^1$H NMR (400 MHz, DMSO-d$_6$) δ 8.59 (d, 1H), 7.79 (s, 1H), 7.56 (s, 1H), 7.15 (s, 1H), 7.04 (d, 1H), 6.00 (s, 1H), 4.53 (d, 4H), 4.42 (s, 1H), 4.30 (s, 1H), 1.49 (s, 3H).

Example 208

Synthesis of (±)-10-(3,4-dihydroxy-3-methylbut-1-yn-1-yl)-9-fluoro-5,6-dihydrobenzo[f]imidazo[1,2-d][1,4]oxazepine-2-carboxamide

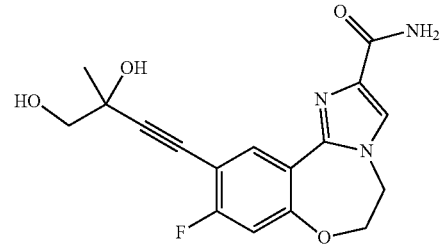 [SMILES: CC(O)(C#Cc1cc2c(cc1F)OCCn1cc(C(N)=O)nc1-2)CO]

Similar to as described in General Procedure G, 10-bromo-9-fluoro-5,6-dihydrobenzo[f]imidazo[1,2-d][1,4]oxazepine-2-carboxamide was reacted with 2-methylbut-3-yne-1,2-diol to give the titled compound as an off-white solid (30.8 mg, 15%).

M+1=346; ¹H NMR (400 MHz, DMSO-$d_6$) δ 8.61 (d, 1H), 7.79 (s, 1H), 7.54 (br s, 1H), 7.14 (br s, 1H), 7.01 (d, 1H), 4.52-4.48 (m, 4H), 3.44-3.33 (m, 2H), 1.419 (s, 3H).

Example 209

Synthesis of (±)-9-fluoro-10-((3-hydroxytetrahydrofuran-3-yl)ethynyl)-5,6-dihydrobenzo[f]imidazo[1,2-d][1,4]oxazepine-2-carboxamide

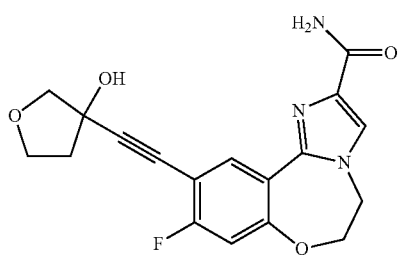 [SMILES: NC(=O)c1cn2c(n1)-c1cc(C#CC3(O)CCOC3)c(F)cc1OCC2]

Similar to as described in General Procedure G, 10-bromo-9-fluoro-5,6-dihydrobenzo[f]imidazo[1,2-d][1,4]oxazepine-2-carboxamide was reacted with 3-ethynyloxolan-3-ol (US2010/144757 A1, 2010) to give the titled compound as a light brown solid (41 mg, 19%).

M+1=358; ¹H NMR (400 MHz, DMSO-$d_6$) δ 8.59 (d, 1H), 7.77 (s, 1H), 7.55 (s, 1H), 7.12 (s, 1H), 7.02 (d, 1H), 5.92 (d, 1H), 4.50 (s, 2H), 4.47 (s, 2H), 3.90 (t, 2H), 3.82 (s, 2H), 2.24 (m, 2H).

Example 210

Synthesis of 10-((1,3-dihydroxycyclobutyl)ethynyl)-9-fluoro-5,6-dihydrobenzo[f]imidazo[1,2-d][1,4]oxazepine-2-carboxamide

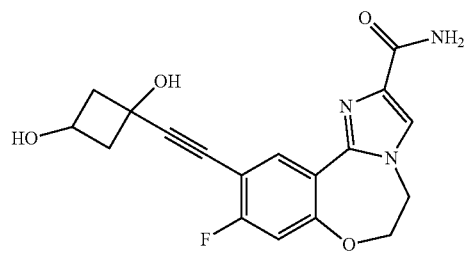 [SMILES: NC(=O)c1cn2c(n1)-c1cc(C#CC3(O)CC(O)C3)c(F)cc1OCC2]

A suspension of 3-((2-carbamoyl-9-fluoro-5,6-dihydrobenzo[f]imidazo[1,2-d][1,4]oxazepin-10-yl)ethynyl)-3-hydroxycyclobutyl benzoate (190 mg, crude product), lithium hydroxide (96 mg, 4.01 mmol) in methanol (0.5 mL) and water (1 mL) was stirred at room temperature overnight. The resulting solution was diluted with 20 mL of dichloromethane and 10 mL water. The organic layer was washed with 10 mL of brine. The organic was dried over anhydrous sodium sulfate and concentrated under vacuum. The residue was applied onto a silica gel column with dichloromethane/methanol (1:10). This resulted in 7 mg of the titled compound as a light yellow solid. This compound was isolated as a single unassigned diastereomer.

M+1=358; ¹H NMR (400 MHz, DMSO-$d_6$) δ 8.57 (d, 1H), 7.78 (s, 1H), 7.59 (br s, 1H), 7.14 (br s, 1H), 7.02 (d, 1H), 5.98 (s, 1H), 5.20 (d, 1H), 4.52-4.50 (m, 2H), 4.00-3.95 (m, 1H), 2.76-2.72 (m, 2H), 2.16-2.12 (m, 2H).

Example 211

Synthesis of 9-fluoro-10-((1-hydroxy-3-(hydroxymethyl)cyclobutyl)ethynyl)-5,6-dihydrobenzo[f]imidazo[1,2-d][1,4]oxazepine-2-carboxamide

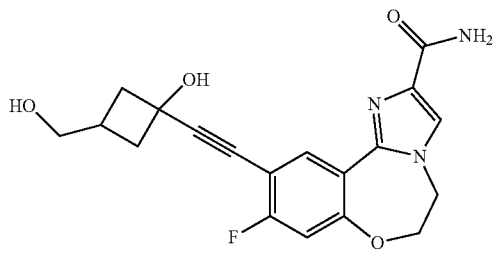 [SMILES: NC(=O)c1cn2c(n1)-c1cc(C#CC3(O)CC(CO)C3)c(F)cc1OCC2]

DIBAL (7 mL, 2.00 equiv) was added to a solution of ethyl 34(2-carbamoyl-9-fluoro-5,6-dihydrobenzo[f]imidazo[1,2-d][1,4]oxazepin-10-yl)ethynyl)-3-hydroxycyclobutanecarboxylate (140 mg, 0.34 mmol, 1.00 equiv) in tetrahydrofuran (5 mL) under nitrogen at −70° C. After 4 h at −70° C. the reaction was quenched by 2 mL of 10% sodium potassium tartrate. The solids were filtered out and the filtrate was dried over sodium sulfate. The residue was applied onto a silica gel column with DCM/MeOH (10/1) to give the titled compound as a white solid. This compound was isolated as a single unassigned diastereomer.

M+1=372; ¹H NMR (400 MHz, DMSO-$d_6$) δ 8.60 (d, 1H), 7.79 (s, 1H), 7.60 (s, 1H), 7.14 (s, 1H), 7.03 (d, 1H), 5.91 (s, 1H), 4.56 (m, 4H), 3.42 (t, 2H), 2.45 (t, 2H), 2.24 (m, 1H), 2.03 (t, 2H).

Example 211.1

Synthesis of 9-fluoro-10-((3-hydroxyoxetan-3-yl)ethynyl)-5,6-dihydrobenzo[f]imidazo[1,2-d][1,4]oxazepine-2-carboxamide

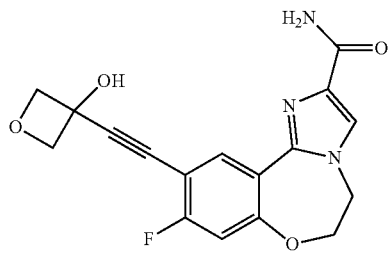 [SMILES: NC(=O)c1cn2c(n1)-c1cc(C#CC3(O)COC3)c(F)cc1OCC2]

Similar to as described in General Procedure G, 10-bromo-9-fluoro-5,6-dihydrobenzo[f]imidazo[1,2-d][1,4]oxazepine-2-carboxamide was reacted with 3-ethynyloxetan-3-ol to give the titled compound as a light brown solid (140 mg, 83%).

M+1=344; ¹H NMR (300 MHz, DMSO-d₆) δ 8.65 (d, 1H), 7.78 (s, 1H), 7.56 (s, 1H), 7.13 (s, 1H), 7.06 (d, 1H), 6.69 (s, 1H), 4.78 (d, 2H), 4.63 (d, 2H), 4.54 (br s, 4H).

Example 212

Synthesis of (±)-9-fluoro-10-(3-hydroxy-3-(1-methylcyclopropyl)but-1-yn-1-yl)-5,6-dihydrobenzo[f]imidazo[1,2-d][1,4]oxazepine-2-carboxamide

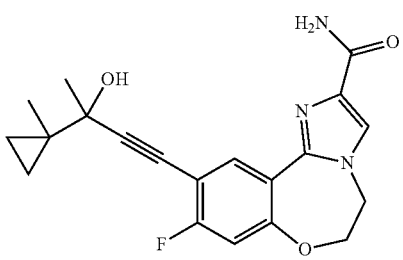 [SMILES: CC(O)(C#Cc1cc2c(cc1F)OCCn1cc(C(N)=O)nc1-2)C1(C)CC1]

Similar to as described in General Procedure G, 10-bromo-9-fluoro-5,6-dihydrobenzo[f]imidazo[1,2-d][1,4]oxazepine-2-carboxamide was reacted with 2-(1-methylcyclopropyl)but-3-yn-2-ol to give the titled compound as a light brown solid (7.8 mg, 8%).

M+1=370; ¹H NMR (300 MHz, DMSO-d₆) δ 8.53 (d, 1H), 7.78 (s, 1H), 7.56 (s, 1H), 7.16 (d, 1H), 7.10 (d, 1H), 5.32 (s, 1H), 4.50 (m, 4H), 1.48 (s, 3H), 1.17 (s, 3H), 0.78 (s, 4H), 0.22 (s, 4H).

Example 213

Synthesis of 9-fluoro-10-(3-hydroxy-3-methylbut-1-yn-1-yl)-5,6-dihydrobenzo[f]imidazo[1,2-d][1,4]oxazepine-2-carboxamide

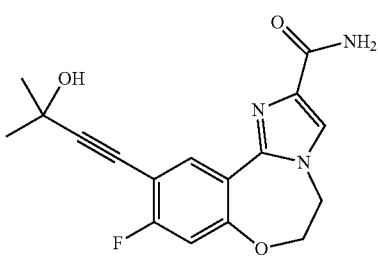 [SMILES: CC(C)(O)C#Cc1cc2c(cc1F)OCCn1cc(C(N)=O)nc1-2]

Similar to as described in General Procedure G, 10-bromo-9-fluoro-5,6-dihydrobenzo[f]imidazo[1,2-d][1,4]oxazepine-2-carboxamide was reacted with 2-methylbut-3-yn-2-ol to give the titled compound as a brown solid (140 mg, 83%).

M+1=330; ¹H NMR (400 MHz, DMSO-d₆) δ 8.56 (d, 1H), 7.78 (s, 1H), 7.57 (s, 1H), 7.14 (s, 1H), 7.02 (d, 1H), 5.53 (s, 1H), 4.52 (d, 4H), 1.89 (s, 6H).

Example 214

Synthesis of (±)-9-fluoro-10-(3-hydroxy-3-(1H-imidazol-4-yl)but-1-yn-1-yl)-5,6-dihydrobenzo[f]imidazo[1,2-d][1,4]oxazepine-2-carboxamide

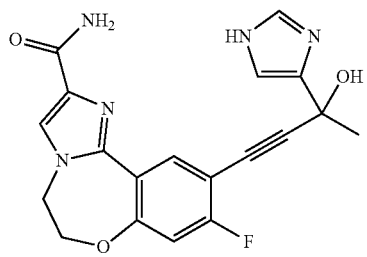 [SMILES: CC(O)(C#Cc1cc2c(cc1F)OCCn1cc(C(N)=O)nc1-2)c1c[nH]cn1]

Similar to as described in General Procedure G, 10-bromo-9-fluoro-5,6-dihydrobenzo[f]imidazo[1,2-d][1,4]oxazepine-2-carboxamide was reacted with 2-(1-((2-(trimethylsilyl)ethoxy)methyl)-1H-imidazol-4-yl)but-3-yn-2-ol and following removal of the SEM protecting group (nBu₄F, THF) gave the titled compound as an off-white solid. (1.5 mg, 3%).

M+1=382; ¹H NMR (300 MHz, CD₃OD) δ 8.69 (t, 1H), 7.98 (s, 1H), 7.75 (d, J=4.5 Hz, 1H), 7.28 (s, 1H), 6.86 (d, J=4.8 Hz 1H), 4.52 (s, 4H), 1.92 (s, 3H).

Example 215

Synthesis of (±)-9-fluoro-10-(3-hydroxy-3-(1-methyl-1H-imidazol-4-yl)but-1-yn-1-yl)-5,6-dihydrobenzo[f]imidazo[1,2-d][1,4]oxazepine-2-carboxamide

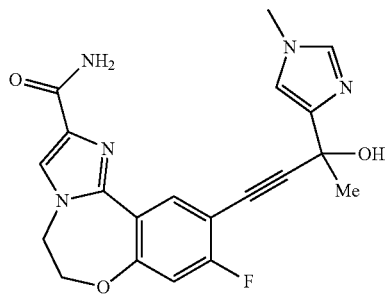 [SMILES: Cn1cnc(C(C)(O)C#Cc2cc3c(cc2F)OCCn2cc(C(N)=O)nc2-3)c1]

Similar to as described in General Procedure G, 10-bromo-9-fluoro-5,6-dihydrobenzo[f]imidazo[1,2-d][1,4]oxazepine-2-carboxamide was reacted with 2-(1-methyl-1H-imidazol-4-yl)but-3-yn-2-ol to give the titled compound as a colorless solid (15 mg, 11%).

M+1=396; ¹H NMR (400 MHz, DMSO-d₆) δ 8.58 (s, 1H), 7.79 (s, 1H), 7.66 (br s, 1H), 7.59 (br s, 1H), 7.149 (br s, 1H), 7.039 (d, 1H), 6.956 (d, 1H), 6.269 (d, 1H), 4.560-4.410 (m, 4H), 3.86 (s, 3H), 1.905 (s, 3H).

Example 216

Synthesis of (±)-9-fluoro-10-(3-hydroxy-3-(3-methyl-1H-1,2,4-triazol-5-yl)but-1-yn-1-yl)-5,6-dihydrobenzo[f]imidazo[1,2-d][1,4]oxazepine-2-carboxamide

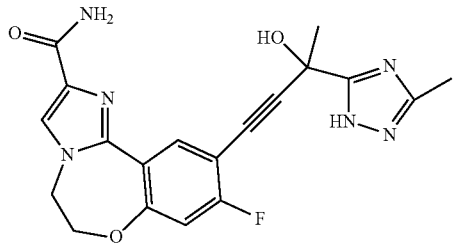 [SMILES: Cc1n[nH]c(C(C)(O)C#Cc2cc3c(cc2F)OCCn2cc(C(N)=O)nc2-3)n1]

Similar to as described in General Procedure G, 10-bromo-9-fluoro-5,6-dihydrobenzo[f]imidazo[1,2-d][1,4]oxazepine-2-carboxamide was reacted with 2-(5-methyl-1H-1,2,4-triazol-3-yl)but-3-yn-2-ol 1 to provide the titled compound as a colorless solid (7 mg, 5%).

M+1=397; $^1$H NMR (400 MHz, CD$_3$OD) δ 8.67 (d, J=8.4 Hz, 1H), 7.72 (s, 1H), 6.85 (d, J=10.4 Hz, 1H), 4.58-4.45 (m, 4H), 2.43 (s, 3H), 1.94 (s, 3H).

Example 217

Synthesis of (±)-10-(3-(1,2-dimethyl-1H-imidazol-4-yl)-3-hydroxybut-1-yn-1-yl)-9-fluoro-5,6-dihydrobenzo[f]imidazo[1,2-d][1,4]oxazepine-2-carboxamide

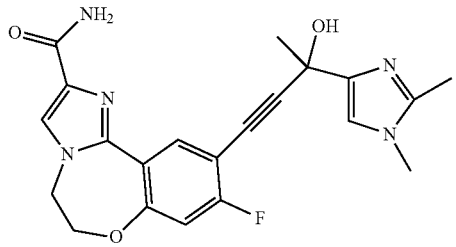 [SMILES: Cc1nc(C(C)(O)C#Cc2cc3c(cc2F)OCCn2cc(C(N)=O)nc2-3)cn1C]

Similar to as described in General Procedure G, 10-bromo-9-fluoro-5,6-dihydrobenzo[f]imidazo[1,2-d][1,4]oxazepine-2-carboxamide was reacted with 2-(1,2-dimethyl-1H-imidazol-4-yl)but-3-yn-2-ol to give the titled compound as a colorless solid (5 mg, 4%).

M+1=410; $^1$H NMR (400 MHz, CD$_3$OD) δ 8.66 (d, J=8.4 Hz, 1H), 7.74 (s, 1H), 7.05 (s, 1H), 7.05 (d, J=10.4 Hz, 1H), 4.58-4.49 (m, 4H), 3.62 (s, 3H), 2.68 (s, 3H), 1.86 (s, 3H).

Example 218

Synthesis of (±)-9-fluoro-10-(3-hydroxy-3-(pyridazin-3-yl)but-1-yn-1-yl)-5,6-dihydrobenzo[f]imidazo[1,2-d][1,4]oxazepine-2-carboxamide

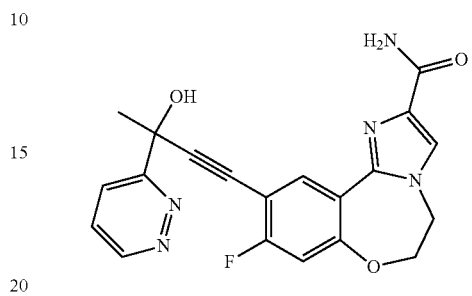

Similar to as described in General Procedure G, 10-bromo-9-fluoro-5,6-dihydrobenzo[f]imidazo[1,2-d][1,4]oxazepine-2-carboxamide was reacted with 2-(pyridazin-3-yl)but-3-yn-2-ol to give the titled compound as a brown solid (26 mg, 9%).

M+1=394; $^1$H NMR (400 MHz, DMSO-d6) δ 9.21 (d, J=1.6 Hz, 1H), 8.57 (d, J=8.4 Hz, 1H), 8.01 (d, J=1.2 Hz, 1H), 7.99 (d, J=1.6 Hz, 2H), 7.58 (s, 1H), 7.18 (s, 1H), 7.02 (d, J=10.4 Hz, 1H), 4.51 (dd, J=10.4 Hz, 4H), 1.94 (s, 3H).

Example 219

Synthesis of (±)-9-fluoro-10-(3-(5-fluoropyridin-2-yl)-3-hydroxybut-1-yn-1-yl)-5,6-dihydrobenzo[f]imidazo[1,2-d][1,4]oxazepine-2-carboxamide

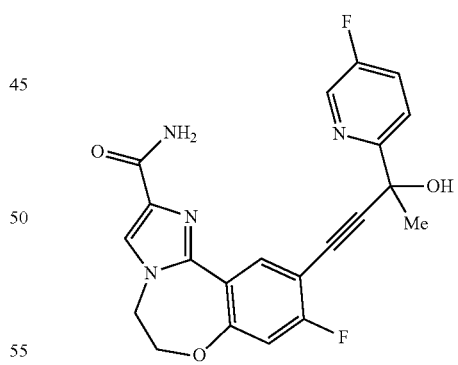

Similar to as described in General Procedure G, 10-bromo-9-fluoro-5,6-dihydrobenzo[f]imidazo[1,2-d][1,4]oxazepine-2-carboxamide was reacted with 2-(5-fluoropyridin-2-yl)but-3-yn-2-ol (US2012/214762A1) to give the titled compound as a grey solid (55 mg, 27%).

M+1=411; $^1$H NMR (300 MHz, DMSO-d$_6$) δ 8.56 (s, 1H), 8.55 (d, 1H), 7.84-7.75 (m, 3H), 7.74 (br s, 1H), 7.13 (br s, 1H), 7.02 (d, 1H), 6.52 (s, 1H), 4.53-4.47 (m, 1H), 1.82 (s, 1H).

Example 220

Synthesis of (±)-10-(3-(5-chloropyridin-2-yl)-3-hydroxybut-1-yn-1-yl)-9-fluoro-5,6-dihydrobenzo[f]imidazo[1,2-d][1,4]oxazepine-2-carboxamide

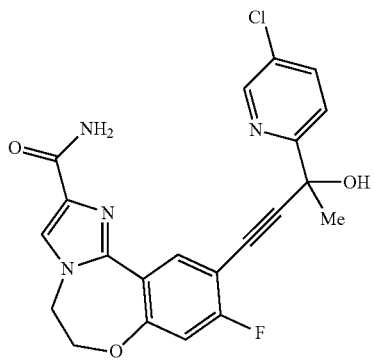 [SMILES: CC(O)(C#Cc1cc2c(cc1F)OCCn1cc(C(N)=O)nc1-2)c1ccc(Cl)cn1]

Similar to as described in General Procedure G, 10-bromo-9-fluoro-5,6-dihydrobenzo[f]imidazo[1,2-d][1,4]oxazepine-2-carboxamide was reacted with 2-(5-chloropyridin-2-yl)but-3-yn-2-ol to give the titled compound as a grey solid (60 mg, 28%).

M+1=427; $^1$H NMR (300 MHz, DMSO-$d_6$) δ 8.63 (d, 1H), 8.54 (d, 1H), 8.01 (AB, 1H), 7.977 (AB, 1H), 7.97 (s, 1H), 7.56 (br s, 1H), 7.13 (br s, 1H), 7.06 (d, 1H), 6.57 (s, 1H), 4.53-4.47 (m, 1H), 1.82 (s, 1H).

Example 221

Synthesis of (±)-9-fluoro-10-(3-(5-fluoropyrimidin-2-yl)-3-hydroxybut-1-yn-1-yl)-5,6-dihydrobenzo[f]imidazo[1,2-d][1,4]oxazepine-2-carboxamide

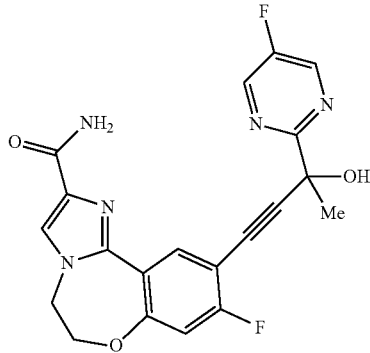 [SMILES: CC(O)(C#Cc1cc2c(cc1F)OCCn1cc(C(N)=O)nc1-2)c1ncc(F)cn1]

Similar to as described in General Procedure G, 10-bromo-9-fluoro-5,6-dihydrobenzo[f]imidazo[1,2-d][1,4]oxazepine-2-carboxamide was reacted with 2-(5-fluoropyrimidin-2-yl)but-3-yn-2-ol to give the titled compound as a brown solid (3.5 mg, 1%).

M+1=412; $^1$H NMR (400 MHz, DMSO-$d_6$) δ 8.91 (s, 2H), 8.51 (d, J=8.4 Hz, 1H), 7.76 (s, 1H), 6.99 (d, J=10.4 Hz, 1H), 4.50-4.40 (m, 4H), 1.87 (s, 3H).

Example 222

Synthesis of (±)-9-fluoro-10-(3-hydroxy-3-(pyrimidin-4-yl)but-1-yn-1-yl)-5,6-dihydrobenzo[f]imidazo[1,2-d][1,4]oxazepine-2-carboxamide

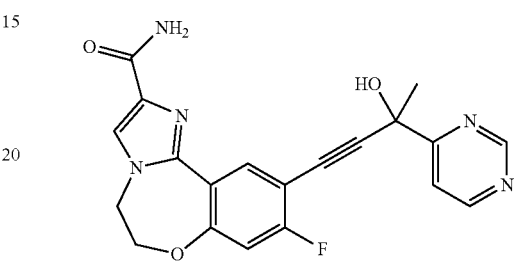

Similar to as described in General Procedure G, 10-bromo-9-fluoro-5,6-dihydrobenzo[f]imidazo[1,2-d][1,4]oxazepine-2-carboxamide was reacted with 2-(pyrimidin-4-yl)but-3-yn-2-ol to give the titled compound as a brown solid (60 mg, 33%).

M+1=394; $^1$H NMR (300 MHz, DMSO-$d_6$) δ 9.20 (d, J=1.2 Hz, 1H), 8.87 (d, J=5.4 Hz, 1H), 8.55 (d, J=8.4 Hz, 1H), 7.83-7.80 (m, 2H), 7.77 (s, 1H), 7.56 (br s, 1H), 7.12 (br s, 3H), 7.01 (d, J=10.0 Hz, 1H), 6.72 (s, 1H), 4.52-4.47 (m, 4H), 1.81 (s, 3H).

Example 223

Synthesis of 9-fluoro-10-(4-fluoro-3-(fluoromethyl)-3-hydroxybut-1-yn-1-yl)-5,6-dihydrobenzo[f]imidazo[1,2-d][1,4]oxazepine-2-carboxamide

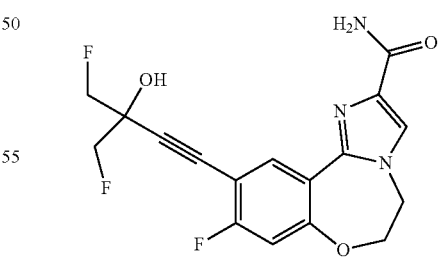

Similar to as described in General Procedure G, 10-bromo-9-fluoro-5,6-dihydrobenzo[f]imidazo[1,2-d][1,4]oxazepine-2-carboxamide was reacted with 1-fluoro-2-(fluoromethyl)but-3-yn-2-ol to give the titled compound as a brown solid (42 mg, 18%).

M+1=366; ¹H NMR (300 MHz, DMSO-d₆) δ8.60 (d, 1H), 7.79 (s, 1H), 7.54 (br s, 1H), 7.14 (br s, 1H), 7.05 (d, 1H), 6.55 (s, 1H), 4.53 (m, 4H), 4.51 (d, 4H).

Example 224

Synthesis of (±)-9-fluoro-10-(3-(4-fluoropyridin-2-yl)-3-hydroxybut-1-yn-1-yl)-5,6-dihydrobenzo[f]imidazo[1,2-d][1,4]oxazepine-2-carboxamide

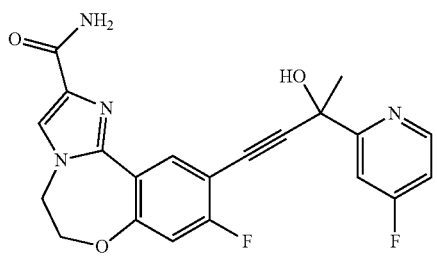 [SMILES: CC(O)(C#Cc1cc2c(cc1F)OCCn1cc(C(N)=O)nc1-2)c1cc(F)ccn1]

Similar to as described in General Procedure G, 10-bromo-9-fluoro-5,6-dihydrobenzo[f]imidazo[1,2-d][1,4]oxazepine-2-carboxamide was reacted with 2-(4-fluoropyridin-2-yl)but-3-yn-2-ol to give the titled compound as a brown solid (16 mg, 12%).

M+1=411; ¹H NMR (300 MHz, CDCl₃) δ 8.64-8.55 (m, 1H), 8.53 (d, J=8.4 Hz, 1H), 7.56-7.51 (m, 2H), 7.30-7.25 (m, 1H), 7.12 (s, 1H), 7.01 (d, J=10.8 Hz, 1H), 6.61 (s, 1H), 4.52-4.48 (m, 1H), 1.82 (s, 3H).

Example 225

Synthesis of (±)-9-fluoro-10-(3-(3-fluoropyridin-2-yl)-3-hydroxybut-1-yn-1-yl)-5,6-dihydrobenzo[f]imidazo[1,2-d][1,4]oxazepine-2-carboxamide

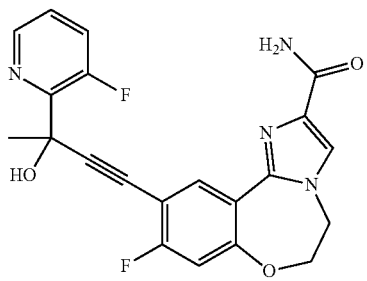 [SMILES: CC(O)(C#Cc1cc2c(cc1F)OCCn1cc(C(N)=O)nc1-2)c1ncccc1F]

Similar to as described in General Procedure G, 10-bromo-9-fluoro-5,6-dihydrobenzo[f]imidazo[1,2-d][1,4]oxazepine-2-carboxamide was reacted with 2-(3-fluoropyridin-2-yl)but-3-yn-2-ol to give the titled compound as an off-white solid (27 mg, 18%).

M+1=411; ¹H NMR (400 MHz, DMSO-d₆) δ 8.54 (d, J=8.8 Hz, 1H), 8.41 (d, J=4.8 Hz, 1H), 7.78 (t, J=10.8 Hz, 2H), 7.53 (m, J=4.4 Hz, 2H), 7.12 (s, 1H), 7.00 (d, J=10.4 Hz, 1H), 6.30 (s, 1H) 4.50 (d, J=9.6 Hz, 4H), 1.90 (s, 3H).

Example 226

Synthesis of 9-fluoro-10-(4-hydroxy-3,3-dimethylbut-1-yn-1-yl)-5,6-dihydrobenzo[f]imidazo[1,2-d][1,4]oxazepine-2-carboxamide

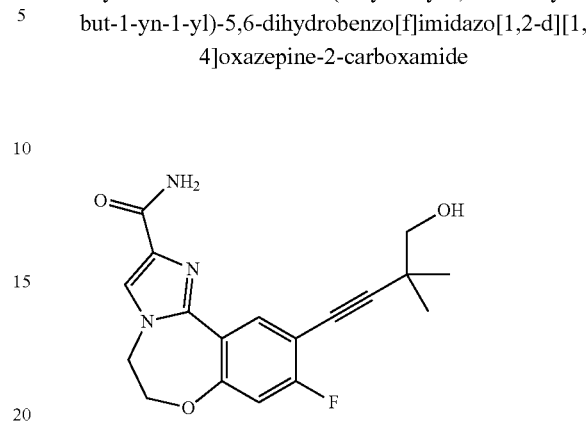

Similar to as described in General Procedure G, 10-bromo-9-fluoro-5,6-dihydrobenzo[f]imidazo[1,2-d][1,4]oxazepine-2-carboxamide was reacted with tert-butyl[(2,2-dimethylbut-3-yn-1-yl)oxy]dimethylsilane to give the titled compound after deprotection of the tert-butyldimethylsilyl ether (treatment with HF) as an off-white solid (72 mg, 60%).

M+1=344; ¹H NMR (400 MHz, DMSO-d₆) δ 8.49 (d, J=8.4 Hz, 1H), 7.77 (s, 1H), 7.54 (s, 1H), 7.14 (s, 1H), 7.96 (d, J=10.5 Hz, 1H), 5.05-5.01 (m, 1H), 4.49-4.48 (m, 4H), 3.37 (d, J=5.4 Hz, 2H), 1.22 (s, 6H).

Example 227

Synthesis of (±)-9-fluoro-10-(3-hydroxy-3-(thiazol-2-yl)but-1-yn-1-yl)-5,6-dihydrobenzo[f]imidazo[1,2-d][1,4]oxazepine-2-carboxamide

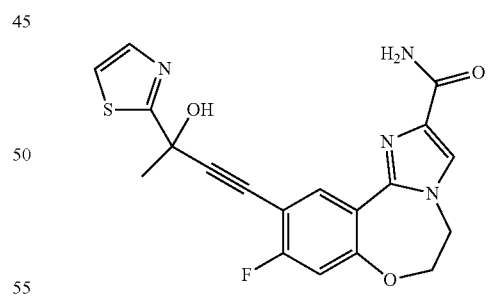

Similar to as described in General Procedure G, 10-bromo-9-fluoro-5,6-dihydrobenzo[f]imidazo[1,2-d][1,4]oxazepine-2-carboxamide was reacted with 2-(1,3-thiazol-2-yl)but-3-yn-2-ol (WO2009/158011A1) to give the titled compound as a brown solid (41 mg, 30%).

M+1=399; ¹H NMR (400 MHz, DMSO-d₆) δ 8.57 (d, J=8.4 Hz, 1H), 7.79 (t, J=3.2 Hz, 1H), 7.70 (t, J=3.2 Hz, 1H), 7.58 (br s, 1H), 7.12 (br s, 1H), 7.11 (s, 1H), 7.03 (d, J=10.4 Hz, 1H), 4.55-4.45 (m, 4H), 1.90 (d, 3H).

Example 228

Synthesis of (±)-10-(3-(5-cyanoisoxazol-3-yl)-3-hydroxybut-1-yn-1-yl)-9-fluoro-5,6-dihydrobenzo[f]imidazo[1,2-d][1,4]oxazepine-2-carboxamide

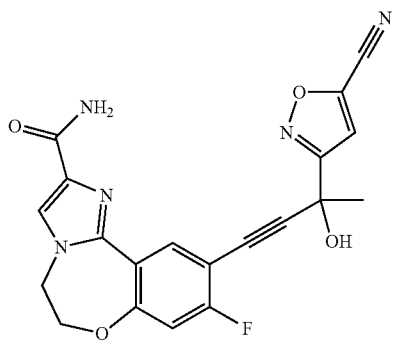 [SMILES: CC(O)(C#Cc1cc2c(cc1F)OCCn1cc(C(N)=O)nc1-2)c1cc(C#N)on1]

A solution of 9-fluoro-10-(3-(5-formylisoxazol-3-yl)-3-hydroxybut-1-yn-1-yl)-5,6-dihydrobenzo[f]imidazo[1,2-d][1,4]oxazepine-2-carboxamide (90 mg, 0.22 mmol, 1.00 equiv), hydroxylamine hydrochloride (15 mg, 0.22 mmol, 1.00 equiv) in N,N-dimethylformamide (3 mL) was heated at 140° C. for 1 h. To this was added triethylamine (90 mg, 0.89 mmol, 4.00 equiv) at 0° C. To the mixture was added TEAA (70 mg, 1.50 equiv) dropwise with stirring at 0° C. The resulting solution was stirred for 12 h at 120° C. The reaction solution was diluted with DCM and washed with water. The crude product was purified by Prep-HPLC with the following conditions (1#-Pre-HPLC-005(Waters)): Column, XBridge Shield RP18 OBD Column, 5 um, 19*150 mm; mobile phase, Water with 10 mmolNH4HCO3 and CH3CN (15% CH3CN up to 70% in 10 min, up to 95% in 1 min, hold 95% in 1 min, down to 15% in 2 min); Detector, UV 254/220 nm. This gave the titled compound (5.4 mg, 6%).

M+1=408; $^1$H NMR (400 MHz, DMSO-$d_6$) δ 8.60 (d, J=8.4 Hz, 1H), 7.78 (s, 1H), 7.80 (s, 1H), 7.05 (t, 3H), 4.52 (d, J=12.4 Hz, 4H), 1.89 (s, 3H).

Example 229

Synthesis of (±)-9-fluoro-10-(3-hydroxy-3-(5-vinylisoxazol-3-yl)but-1-yn-1-yl)-5,6-dihydrobenzo[f]imidazo[1,2-d][1,4]oxazepine-2-carboxamide

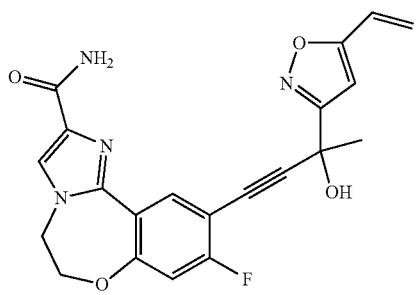 [SMILES: C=Cc1cc(C(C)(O)C#Cc2cc3c(cc2F)OCCn2cc(C(N)=O)nc2-3)no1]

A solution of KHMDS (0.9 mL, 3.20 equiv) in toluene (0.5M) was added dropwise to a stirred solution of Ph3PCH3I (180 mg, 3.02 equiv) in tetrahydrofuran (3 mL) at 0° C. and the resulting mixture was stirred at 0° C. for 30 min. To this was added a solution of 9-fluoro-10-(3-(5-formylisoxazole-3-yl)-3-hydroxybut-1-yn-1-yl)-5,6-dihydrobenzo[f]imidazo[1,2-d][1,4]oxazepine-2-carboxamide (60 mg, 0.15 mmol, 1.00 equiv) in tetrahydrofuran (0.2 mL) dropwise at 0° C. The resulting solution was stirred for 3 h at room temperature. The crude product was purified by Prep-HPLC with the following conditions (1#-Pre-HPLC-006(Waters)): Column, SunFire Prep C18 OBD Column, 5 um, 19*150 mm; mobile phase, Water with 10 mmol NH4HCO3 and CH3CN (25% CH3CN up to 40% in 10 min, up to 95% in 2 min, down to 25% in 2 min); Detector, UV 254/220 nm giving the titled compound (10%) as a light yellow solid.

M+1=409; $^1$H NMR (300 MHz, CD$_3$OD) δ 8.54 (d, J=8.1 Hz, 2H), 7.62 (s, 1H), 6.78-6.49 (m, 2H), 6.49 (s, 1H), 5.95 (d, J=16.8 Hz, 1H), 5.52 (d, J=10.5 Hz, 1H), 4.44-4.39 (m, 4H), 1.82 (s, 3H).

Example 229.1

Synthesis of (±)-10-(3-(5-ethynylisoxazol-3-yl)-3-hydroxybut-1-yn-1-yl)-9-fluoro-5,6-dihydrobenzo[f]imidazo[1,2-d][1,4]oxazepine-2-carboxamide

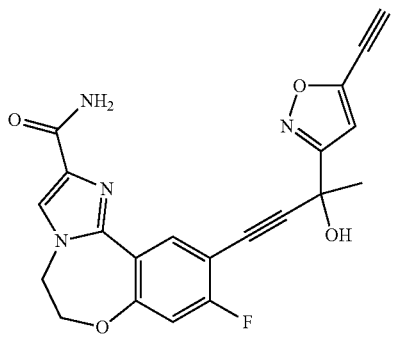 [SMILES: C#Cc1cc(C(C)(O)C#Cc2cc3c(cc2F)OCCn2cc(C(N)=O)nc2-3)no1]

Dimethyl [1-(methylidyneimino)-2-oxopropyl]phosphonate (27.9 mg, 0.15 mmol, 1.00 equiv) in methanol (0.2 mL) was added dropwise to a stirred mixture of 9-fluoro-10-(3-(5-formylisoxazol-3-yl)-3-hydroxybut-1-yn-1-yl)-5,6-dihydrobenzo[f]imidazo[1,2-d][1,4]oxazepine-2-carboxamide (60 mg, 0.15 mmol, 1.00 equiv) and potassium carbonate (39 mg, 0.28 mmol, 2.00 equiv) in methanol (1.5 mL) at room temperature. The resulting mixture was stirred for 12 h at room temperature and the solids were filtered out. The crude product (50 mg) was purified by Prep-HPLC with the following conditions (1#-Pre-HPLC-006(Waters)): Column, SunFire Prep C18 OBD Column, 5 um, 19*150 mm, mobile phase, Water with 10 mmolNH4HCO3 and CH3CN (22% CH3CN up to 43% in 15 min, up to 95% in 2 min, down to 22% in 2 min); Detector, UV 254/220 nm to give 12.7 mg of the titled compound (21%) as a colorless solid.

M+1=407; $^1$H NMR (400 MHz, DMSO) δ 8.59 (d, J=8.4 Hz, 1H), 7.79 (s, 1H), 7.58 (s, 1H), 7.147 (s, 1H), 7.03-7.07 (m, 2H), 6.79 (s, 1H), 5.26 (s, 1H), 4.49-4.55 (m, 4H), 1.851 (s, 3H).

Example 230

Synthesis of (±)-9-fluoro-10-(3-(5-formylisoxazol-3-yl)-3-hydroxybut-1-yn-1-yl)-5,6-dihydrobenzo[f]imidazo[1,2-d][1,4]oxazepine-2-carboxamide

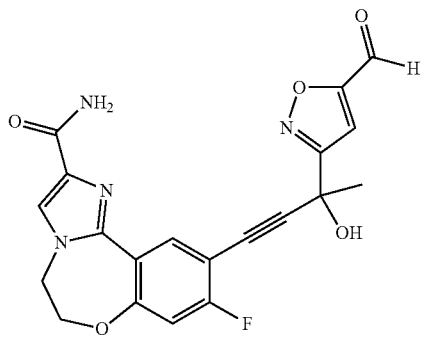 [SMILES: CC(O)(C#Cc1cc2c(cc1F)OCCn1cc(C(N)=O)nc1-2)c1cc(C=O)on1]

Similar to as described in General Procedure G, 10-bromo-9-fluoro-5,6-dihydrobenzo[f]imidazo[1,2-d][1,4]oxazepine-2-carboxamide was reacted with 3-(2-hydroxybut-3-yn-2-yl)-1,2-oxazole-5-carbaldehyde to give the titled compound as a light yellow solid (14 mg, 10%).

M+1=411; $^1$H NMR (400 MHz, DMSO-$d_6$) δ 8.65 (d, J=8.4 Hz, 1H), 7.74 (s, 1H), 6.88 (d, J=8.0 Hz, 1H), 4.51-4.53 (m, 4H), 1.937 (s, 3H).

Example 231

Synthesis of (±)-10-(3-(5-(cyanomethyl)isoxazol-3-yl)-3-hydroxybut-1-yn-1-yl)-9-fluoro-5,6-dihydrobenzo[f]imidazo[1,2-d][1,4]oxazepine-2-carboxamide

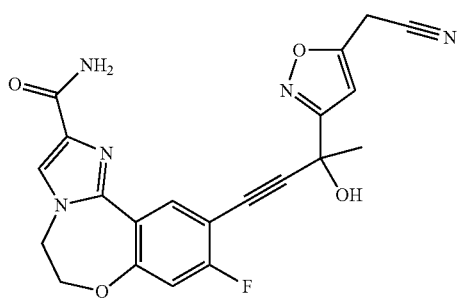 [SMILES: CC(O)(C#Cc1cc2c(cc1F)OCCn1cc(C(N)=O)nc1-2)c1cc(CC#N)on1]

Similar to as described in General Procedure G, 10-bromo-9-fluoro-5,6-dihydrobenzo[f]imidazo[1,2-d][1,4]oxazepine-2-carboxamide was reacted with 2-[3-(2-hydroxybut-3-yn-2-yl)-1,2-oxazol-5-yl] to give the titled compound as a light yellow solid (59 mg, 30%).

M+1=408; $^1$H NMR (300 MHz, DMSO-$d_6$) δ 8.58 (d, J=8.4 Hz, 1H), 7.78 (s, 1H), 7.55 (s, 1H), 7.14 (s, 1H), 7.04 (d, J=10.5 Hz, 1H), 6.73 (s, 1H), 6.64 (s, 1H), 4.52-4.46 (m, 6H), 1.84 (s, 3H).

Example 232

Synthesis of (R)—N$^3$-(tert-butyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide

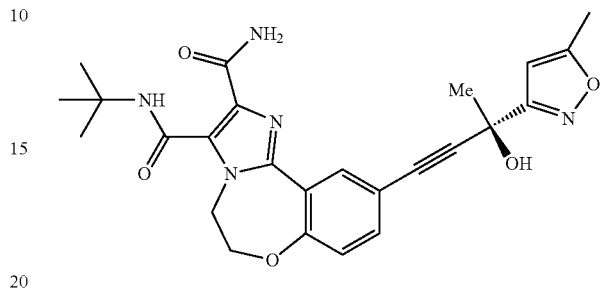

Similar to as described in Example 10 (carbonylative amidation), 10-bromo-3-iodo-5,6-dihydrobenzo[f]imidazo[1,2-d][1,4]oxazepine-2-carboxamide (500 mg, 1.15 mmol, 1.00 equiv), DMSO (5 mL), TEA (348 mg, 3.44 mmol, 3.00 equiv), Pd(dppf)Cl$_2$ (84 mg, 0.11 mmol, 0.10 equiv) and 2-methylpropan-2-amine (168 mg, 2.30 mmol, 2.00 equiv) was stirred overnight at 40° C. under a CO atmosphere. The reaction was then quenched by the addition of 100 mL of ice/water. The solids were collected to give 520 mg (crude) of 10-bromo-N$^3$-(tert-butyl)-5,6-dihydrobenzo[f]imidazo[1,2-d][1,4]oxazepine-2,3-dicarboxamide as a light yellow solid. Similar to as described in General Procedure G, the above crude solid was reacted with (2R)-2-(5-methyl-1,2-oxazol-3-yl)but-3-yn-2-ol to give the titled compound as an off-white solid (58.7 mg, 25%).

M+1=482; $^1$H NMR (300 MHz, CDCl$_3$) δ 10.94 (s, 1H), 8.45 (d, J=2.1 Hz, 1H), 7.78 (d, J=3Hz, 1H), 7.39-7.43 (m, 1H), 7.00 (d, J=8.4 Hz, 1H), 6.18 (s, 1H), 5.68 (d, J=2.1 Hz, 1H), 5.13-5.16 (m, 2H), 4.50-4.53 (m, 2H), 2.46 (s, 3H), 1.97 (s, 3H), 1.48 (s, 9H).

Example 233

Synthesis of (R)-10-(3-hydroxy-3-(5-methylisoxazol-3-yl)but-1-yn-1-yl)-N$^3$-(oxetan-3-ylmethyl)-5,6-dihydrobenzo[f]imidazo[1,2-d][1,4]oxazepine-2,3-dicarboxamide

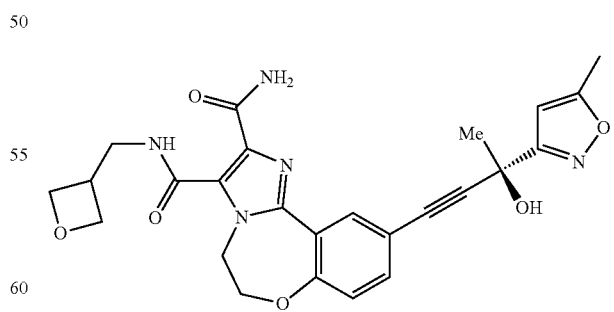

Similar to as described in General Procedure G, 10-bromo-N$^3$-(oxetan-3-ylmethyl)-5,6-dihydrobenzo[f]imidazo[1,2-d][1,4]oxazepine-2,3-dicarboxamide (prepared as described in the synthesis of (R)—N3-(tert-butyl)-10-(3-hydroxy-3-(5-methylisoxazol-3-yl)but-1-yn-1-yl)-5,6-dihydrobenzo[f]

imidazo[1,2-d][1,4]oxazepine-2,3-dicarboxamide replacing tert-butyl amine with 3-methylaminooxetane) was reacted with (2R)-2-(5-methyl-1,2-oxazol-3-yl)but-3-yn-2-ol to give the titled compound as an off-white solid (6.7 mg, 2%).

M+1=392; $^1$H NMR (300 MHz, CDOD$_3$) δ 8.59 (d, J=1.8 Hz, 1H), 7.42-7.46 (m, 1H), 7.05 (d, J=8.7 Hz, 1H), 6.32 (s, 1H), 5.00-5.02 (m, 2H), 4.82-99(m, 2H), 4.51-4.55 (m, 4H), 3.67-3.69 (m, 2H), 3.22-3.29 (m, 1H), 2.42 (s, 3H), 1.89 (s, 3H).

Example 234

Synthesis of (±)-10-(4-(3,3-difluoroazetidin-1-yl)-3-hydroxy-3-methyl-4-oxobut-1-yn-1-yl)-9-fluoro-5,6-dihydro benzo[f]imidazo[1,2-d][1,4]oxazepine-2-carboxamide

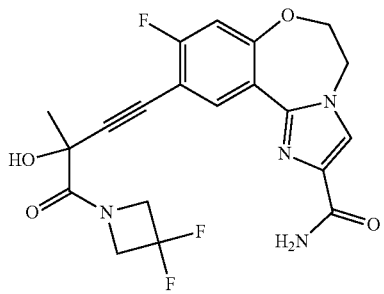 [SMILES: CC(O)(C#Cc1cc2c(cc1F)OCCn1cc(C(N)=O)nc1-2)C(=O)N1CC(F)(F)C1]

Similar to as described in General Procedure G, 10-bromo-9-fluoro-5,6-dihydrobenzo[f]imidazo[1,2-d][1,4]oxazepine-2-carboxamide was reacted with 1-(3,3-difluoroazetidin-1-yl)-2-hydroxy-2-methylbut-3-yn-1-one to give the titled compound as an off-white solid (14 mg, 5%).

M+1=435; $^1$H NMR (400 MHz, CD$_3$OD) δ 8.64 (d, J=8.4 Hz, 1H), 7.74 (s, 1H), 6.88 (d, J=10.4 Hz, 1H), 4.93 (t, 2H), 4.53 (d, J=7.2 Hz, 4H), 4.43 (t, 2H), 1.75 (s, 3H).

Example 235

Synthesis of 10-(4-(3-cyanoazetidin-1-yl)-3-hydroxy-3-methyl-4-oxobut-1-yn-1-yl)-9-fluoro-5,6-dihydrobenzo[f]imidazo[1,2-d][1,4]oxazepine-2-carboxamide

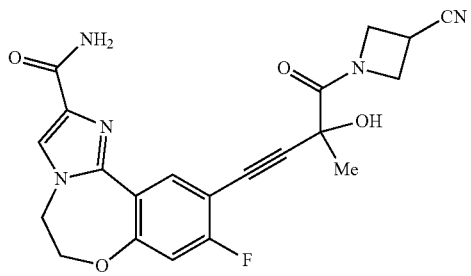 [SMILES: CC(O)(C#Cc1cc2c(cc1F)OCCn1cc(C(N)=O)nc1-2)C(=O)N1CC(C#N)C1]

A solution methyl 4-(2-carbamoyl-9-fluoro-5,6-dihydrobenzo[f]imidazo[1,2-d][1,4]oxazepin-10-yl)-2-hydroxy-2-methylbut-3-ynoate (150 mg, 0.40 mmol, 1.00 equiv), azetidine-3-carbonitrile hydrochloride (237 mg, 2.00 mmol, 5.00 equiv), triethylamine (203 mg, 2.01 mmol, 5.00 equiv) in methanol (5 mL) was stirred for 12 h at 40° C. The resulting mixture was concentrated under vacuum and the residue was applied onto a silica gel column with dichloromethane/methanol (30:1) to give 8.8 mg (5%) the titled compound as an off-white solid.

M+1=424; $^1$H NMR (300 MHz, DMSO-d6) δ8.59 (d, 1H), 7.79 (s, 1H), 7.56 (d, 1H), 7.15 (s, 1H), 7.06 (d, 1H), 6.49 (d, 1H), 4.75 (t, 1H), 4.60-4.41 (m, 5H), 4.30-4.19 (m, 1H), 4.18-4.00 (m, 1H), 3.90-3.71 (m, 1H), 1.610 (s, 3H).

Example 236

Synthesis of (±)-9-fluoro-10-(3-hydroxy-4-methoxy-3-methylbut-1-yn-1-yl)-5,6-dihydrobenzo[f]imidazo[1,2-d][1,4]oxazepine-2-carboxamide

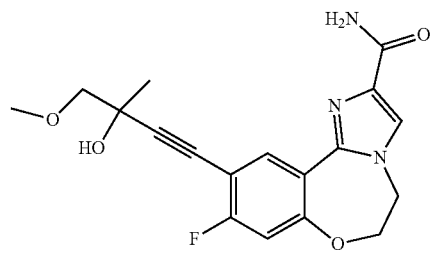 [SMILES: COCC(C)(O)C#Cc1cc2c(cc1F)OCCn1cc(C(N)=O)nc1-2]

Similar to as described in General Procedure G, 10-bromo-9-fluoro-5,6-dihydrobenzo[f]imidazo[1,2-d][1,4]oxazepine-2-carboxamide was reacted with 1-methoxy-2-methylbut-3-yn-2-ol to give the titled compound as a grey solid (59 mg, 19%).

M+1=360; $^1$H NMR (300 MHz, CD$_3$OD) δ 8.61 (d, 1H), 7.74 (s, 1H), 7.46 (s, 2H), 6.86 (d, 1H), 4.52 (d, 4H), 3.52-3.32 (m, 5H), 1.55 (s, 3H).

Example 237

Synthesis of (±)-9-fluoro-10-(3-hydroxy-3-methyl-4-(methylamino)-4-oxobut-1-yn-1-yl)-5,6-dihydrobenzo[f]imidazo[1,2-d][1,4]oxazepine-2-carboxamide

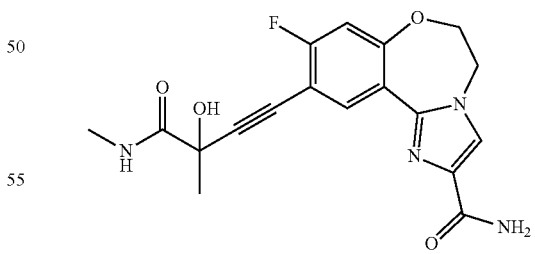

A solution of methyl 4-(2-carbamoyl-9-fluoro-5,6-dihydrobenzo[f]imidazo[1,2-d][1,4]oxazepin-10-yl)-2-hydroxy-2-methylbut-3-ynoate (120 mg, 0.32 mmol, 1.00 equiv) and methylmine (30% w/w in ethanol, 5 mL) was stirred for 8 h at room temperature. The resulting mixture was concentrated and the residue was applied onto a silica gel column with ethyl acetate/petroleum ether (1:5) to give 35 mg (29%) of the titled compound as a yellow solid.

M+1=373; ¹H NMR (300 MHz, DMSO-d6) δ 8.55 (d, 1H), 8.00-7.80 (m, 1H), 7.77 (s, 1H), 7.56 (br s, 1H), 7.11 (br s, 1H), 7.01 (d, 1H), 6.55 (s, 1H), 4.55-4.48 (m, 4H), 2.62 (d, 3H), 1.60 (s, 3H).

Example 238

Synthesis of (±)-10-(4-cyano-3-hydroxy-3-methyl-but-1-yn-1-yl)-9-fluoro-5,6-dihydrobenzo[f]imidazo[1,2-d][1,4]oxazepine-2-carboxamide

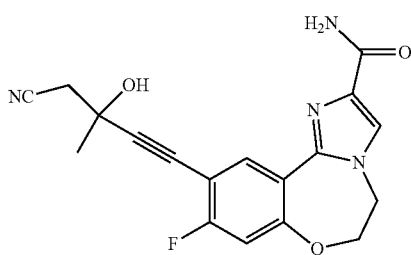 [SMILES: CC(O)(C#Cc1cc2c(cc1F)OCCn1cc(C(N)=O)nc1-2)CC#N]

Similar to as described in General Procedure G, 10-bromo-9-fluoro-5,6-dihydrobenzo[f]imidazo[1,2-d][1,4]oxazepine-2-carboxamide was reacted with 3-hydroxy-3-methylpent-4-ynenitrile to give the titled compound as a brown solid (70 mg, 30%).

M+1=355; ¹H NMR (400 MHz, DMSO-d₆) δ 8.58 (d, 1H), 7.79 (s, 1H), 7.52 (s, 1H), 7.16 (s, 1H), 7.04 (d, 1H), 6.32 (s, 1H), 4.52 (d, 4H), 3.02 (s, 2H), 1.60 (s, 3H).

Example 239

Synthesis of (±)-10-(4-(cyclopropylamino)-3-hydroxy-3-methyl-4-oxobut-1-yn-1-yl)-9-fluoro-5,6-dihydrobenzo[f]imidazo[1,2-d][1,4]oxazepine-2-carboxamide

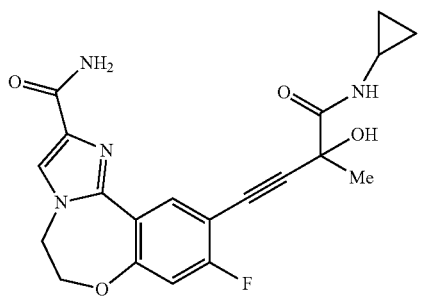 [SMILES: CC(O)(C#Cc1cc2c(cc1F)OCCn1cc(C(N)=O)nc1-2)C(=O)NC1CC1]

A solution of methyl 4-(2-carbamoyl-9-fluoro-5,6-dihydrobenzo[f]imidazo[1,2-d][1,4]oxazepin-10-yl)-2-hydroxy-2-methylbut-3-ynoate (120 mg, 0.32 mmol, 1.00 equiv) and cyclopropanamine (1.83 g, 32.05 mmol, 99.72 equiv) in methanol (2 mL) was stirred for 12 h at 40° C. The resulting mixture was concentrated under vacuum and the residue was applied onto a silica gel column with dichloromethane/methanol (30:1) to give the titled compound, 23 mg (18%), as a yellow solid.

M+1=399; ¹H NMR (300 MHz, DMSO-d₆) δ 8.56 (d, 1H), 7.89 (d, 1H), 7.78 (s, 1H), 7.58 (br s, 1H), 7.13 (br s, 1H), 7.02 (d, 1H), 6.51 (s, 1H), 4.60-4.40 (m, 4H), 2.80-2.60 (m, 1H), 1.60 (s, 3H), 0.63-057 (m, 4H).

Example 240

Synthesis of (±)-10-(44(2,2-difluoroethyl)amino)-3-hydroxy-3-methyl-4-oxobut-1-yn-1-yl)-9-fluoro-5,6-dihydrobenzo[f]imidazo[1,2-d][1,4]oxazepine-2-carboxamide

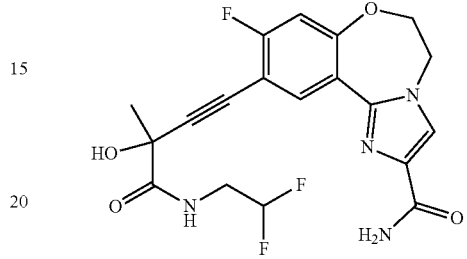

Similar to as described in General Procedure G, 10-bromo-9-fluoro-5,6-dihydrobenzo[f]imidazo[1,2-d][1,4]oxazepine-2-carboxamide was reacted with N-(2,2-difluoroethyl)-2-hydroxy-2-methylbut-3-ynamide to give the titled compound as an off-white solid (60 mg, 31%).

M+1=423; ¹H NMR (300 MHz, CD₃OD) δ 8.59 (d, J=8.1 Hz, 1H), 7.68 (s, 1H), 6.81 (d, J=10.2 Hz, 1H), 6.10-5.73 (m, 1H), 4.47 (t, 4H), 3.67-3.54 (m, 2H), 1.70 (s, 3H).

Example 241

Synthesis of (R)-9-fluoro-10-(4-fluoro-3-hydroxy-3-(5-methyl-1,2,4-oxadiazol-3-yl)but-1-yn-1-yl)-5,6-dihydrobenzo[f]imidazo[1,2-d][1,4]oxazepine-2-carboxamide and (S)-9-fluoro-10-(4-fluoro-3-hydroxy-3-(5-methyl-1,2,4-oxadiazol-3-yl)but-1-yn-1-yl)-5,6-dihydrobenzo[f]imidazo[1,2-d][1,4]oxazepine-2-carboxamide

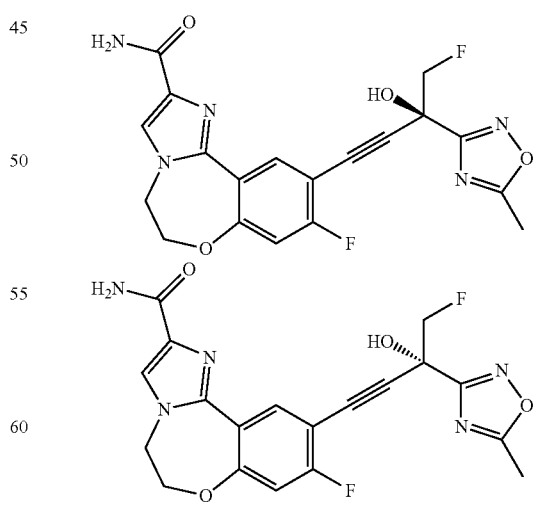

Similar to as described in General Procedure G, 10-bromo-9-fluoro-5,6-dihydrobenzo[f]imidazo[1,2-d][1,4]oxazepine-2-carboxamide was reacted with racemic 1-fluoro-2-(5-methyl-1,2,4-oxadiazol-3-yl)but-3-yn-2-ol to give a mixture of the titled compounds. The enantiomers were separated by chiral-Prep-HPLC with the following conditions (2#-Gilson Gx 281(HPLC-09)): Column, Chiralpak IC, 2*25 cm, Sum; mobile phase, Hex (0.1% TEA) and ethanol (0.2% TEA) (hold 50.0% ethanol (0.2% TEA) in 28 min); Detector, uv 220/254 nm to give 17.7 mg (5%) of Compound 116.0 mg (4%) of Compound 2. The stereochemistry of both enantiomers is arbitrarily assigned.

Compound 1: chiral HPLC retention time 11.600 min.; off-white solid; LC-MS 416[M+H]$^+$; $^1$H NMR (300 MHz, CD$_3$OD) δ 8.64 (d, J=8.1 Hz, 1H), 7.69 (s, 1H), 6.84 (d, J=10.5 Hz, 1H), 4.69 (s, 1H), 4.56-4.46 (m, 5H), 2.62 (s, 3H);

Compound 2: chiral HPLC retention time 15.728 min.; off-white solid; LC-MS 416[M+H]$^+$; $^1$H NMR (300 MHz, CD$_3$OD) δ 8.64 (d, J=8.1 Hz, 1H), 7.69 (s, 1H), 6.84 (d, J=10.5 Hz, 1H), 4.69 (s, 1H), 4.561-4.461 (m, 5H), 2.616 (s, 3H).

Example 242

Synthesis of (S)-10-(3-hydroxy-3-(5-methylisoxazol-3-yl)but-1-yn-1-yl)-5,6-dihydrobenzo[f]imidazo[1,2-d][1,4]oxazepine-2-carboxamide

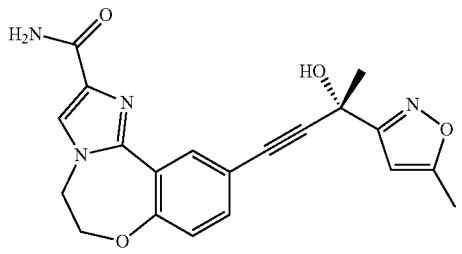 [SMILES: Cc1cc([C@@](C)(O)C#Cc2ccc3c(c2)-c2nc(C(N)=O)cn2CCO3)no1]

Similar to as described in General Procedure G, 10-bromo-5,6-dihydrobenzo[f]imidazo[1,2-d][1,4]oxazepine-2-carboxamide was reacted with (2S)-2-(5-methyl-1,2-oxazol-3-yl)but-3-yn-2-ol to give the titled compound as an off-white solid (34 mg, 9%).

M+H=379; $^1$H NMR (400 MHz, DMSO-d$_6$) δ 8.54 (s, 1H), 7.80 (s, 1H), 7.56 (br s, 1H), 7.34-7.30 (m, 1H), 7.14 (br s, 1H), 7.04 (d, 1H), 6.50 (s, 1H), 6.36 (s, 1H), 4.49 (s, 4H), 2.37 (s, 3H), 1.92 (s, 3H).

Example 243

Synthesis of (R)-10-(3-hydroxy-3-(5-methylisoxazol-3-yl)but-1-yn-1-yl)-5,6-dihydrobenzo[f]imidazo[1,2-d][1,4]oxazepine-2-carboxamide

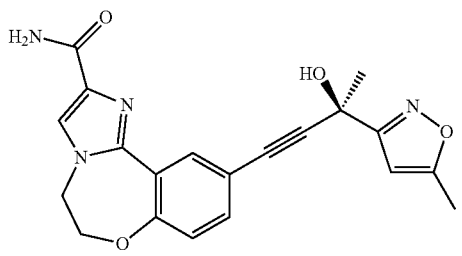 [SMILES: Cc1cc([C@](C)(O)C#Cc2ccc3c(c2)-c2nc(C(N)=O)cn2CCO3)no1]

Similar to as described in General Procedure G, 10-bromo-5,6-dihydrobenzo[f]imidazo[1,2-d][1,4]oxazepine-2-carboxamide was reacted with (2R)-2-(5-methyl-1,2-oxazol-3-yl)but-3-yn-2-ol to give the titled compound as an off-white solid (35 mg, 28%)

M+1=379; $^1$H NMR (400 MHz, DMSO-d$_6$) δ 8.54 (s, 1H), 7.80 (s, 1H), 7.56 (br s, 1H), 7.34-7.30 (m, 1H), 7.14 (br s, 1H), 7.04 (d, 1H), 6.50 (s, 1H), 6.36 (s, 1H), 4.49 (s, 4H), 2.37 (s, 3H), 1.92 (s, 3H).

Example 244

Synthesis of 10-(4-hydroxy-3,3-dimethylbut-1-yn-1-yl)-5,6-dihydrobenzo[f]imidazo[1,2-d][1,4]oxazepine-2-carboxamide

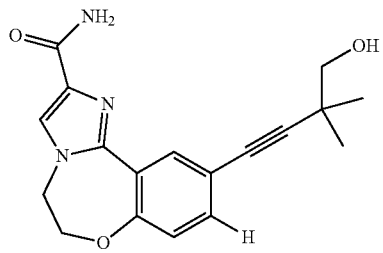 [SMILES: CC(C)(C#Cc1ccc2c(c1)-c1nc(C(N)=O)cn1CCO2)CO]

Similar to as described in General Procedure G, 10-bromo-5,6-dihydrobenzo[f]imidazo[1,2-d][1,4]oxazepine-2-carboxamide was reacted with tert-butyl[(2,2-dimethylbut-3-yn-1-yl)oxy]dimethylsilane to give the titled compound as a off-white solid (35 mg, 28%) after deprotection of the tert-butyldimethylsilyl ether (HF/MeCN).

M+1=326; $^1$H NMR (300 MHz, DMSO-d$_6$) δ 8.49 (d, J=2.1 Hz, 1H), 7.79 (s, 1H), 7.53 (s, 1H), 7.27 (dd, J$_1$=8.4 Hz, J$_2$=2.1 Hz, 1H), 7.15 (s, 1H), 6.98 (d, J=8.4 Hz, 1H), 4.99 (t, J=5.8 Hz, 1H), 4.47 (s, 4H), 3.36 (d, J=5.7 Hz, 2H), 1.21 (s, 6H).

Example 245

Synthesis of (±)-10-(3-hydroxy-3-(5-methyl-1,3,4-oxadiazol-2-yl)but-1-yn-1-yl)-5,6-dihydrobenzo[f]imidazo[1,2-d][1,4]oxazepine-2-carboxamide

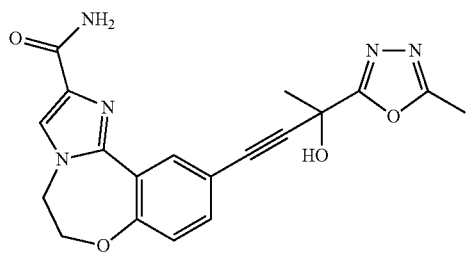 [SMILES: Cc1nnc(C(C)(O)C#Cc2ccc3c(c2)-c2nc(C(N)=O)cn2CCO3)o1]

Similar to as described in General Procedure G, 10-bromo-5,6-dihydrobenzo[f]imidazo[1,2-d][1,4]oxazepine-2-carboxamide was reacted with 2-(5-methyl-1,3,4-oxadiazol-2-yl)but-3-yn-2-ol to give the titled compound as an off-white solid (14 mg, 10%).

M+1=380; ¹H NMR (300 MHz, DMSO-d₆) δ 8.57 (d, J=2.1 Hz, 1H), 7.80 (s, 1H), 7.55 (s, 1H), 7.37 (d, J=8.4 Hz, 1H), 7.15 (s, 1H), 7.05 (d, J=8.4 Hz, 1H), 4.49 (s, 4H), 2.55 (s, 3H), 1.90 (s, 3H).

Example 246

Synthesis of 10-(3-hydroxy-3-(1,3,4-oxadiazol-2-yl)but-1-yn-1-yl)-5,6-dihydrobenzo[f]imidazo[1,2-d][1,4]oxazepine-2-carboxamide

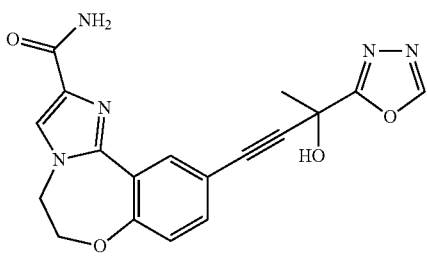 [SMILES: CC(O)(C#Cc1ccc2c(c1)-c1nc(C(N)=O)cn1CCO2)c1nnco1]

Similar to as described in General Procedure G, 10-bromo-5,6-dihydrobenzo[f]imidazo[1,2-d][1,4]oxazepine-2-carboxamide was reacted with 2-(1,3,4-oxadiazol-2-yl)but-3-yn-2-ol to give the titled compound as an off-white solid (3.1 mg, 3%).

M+1=366; ¹H NMR (300 MHz, DMSO-d₆) δ 9.29 (s, 1H), 8.57 (d, J=2.1 Hz, 1H), 7.8 (s, 1H), 7.55 (s, 1H), 7.35 (d, J=2.1 Hz, 1H), 7.07 (s, 1H), 7.06 (s, 1H), 7.03 (s, 1H), 4.49 (s, 4H), 1.94 (s, 3H).

Example 247

Synthesis of 10-(3-hydroxy-3-(1,3,4-thiadiazol-2-yl)but-1-yn-1-yl)-5,6-dihydrobenzo[f]imidazo[1,2-d][1,4]oxazepine-2-carboxamide

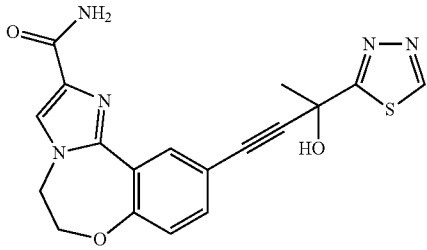

Similar to as described in General Procedure G, 10-bromo-5,6-dihydrobenzo[f]imidazo[1,2-d][1,4]oxazepine-2-carboxamide was reacted with 2-(1,3,4-thiadiazol-2-yl)but-3-yn-2-ol to give the titled compound as an off-white solid (1.7 mg, 2%).

M+1=382; ¹H NMR (300 MHz, DMSO-d₆) δ 9.58 (s, 1H), 8.54 (d, J=1.8 Hz, 1H), 7.79 (s, 1H), 7.55 (s, 1H), 7.36 (s, 1H), 7.33 (d, J=1.8 Hz, 1H), 7.05 (s, 1H), 7.02 (s, 1H), 4.49 (s, 4H), 1.97 (s, 3H).

Example 248

Synthesis of (R)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide and (S)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide

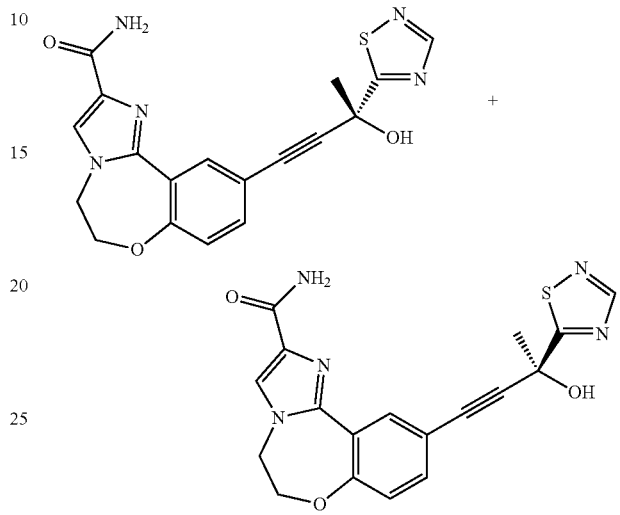

Similar to as described in General Procedure G, 10-bromo-5,6-dihydrobenzo[f]imidazo[1,2-d][1,4]oxazepine-2-carboxamide was reacted with 2-(1,2,4-thiadiazol-5-yl)but-3-yn-2-ol to give the racemic mixture of the titled compounds. The two enantiomers were separated by Chiral-Prep-HPLC with the following conditions (Prep-HPLC-032): Column, Chiralpak IC(SFC), 2*25 cm, 5 um; mobile phase, dichloromethane and IPA (hold 7.0% IPA in 26 min); Detector, uv 220/254 nm to give Compound 1 53.8 mg (34%) and then Compound 2 57.6 mg (37%). The stereochemistry of these compounds are arbitrarily assigned.

Compound 1: white solid; CHIRALPAK IC, 25° C., 254 nm, 93:7 DCM:IPA, 1.0 mL/min; $t_R$=12.4 min; LC-MS 382 [M+H]⁺; ¹H NMR (400 MHz, CD₃OD) δ 8.73 (s, 1H), 8.61 (d, J=2.0 Hz, 1H), 7.75 (s, 1H), 7.38 (dd, J=2.0, 8.4 Hz, 1H), 7.05 (d, J=8.4 Hz, 2H), 4.51 (s, 4H), 1.99 (s, 3H).

Compound 2: white solid; CHIRALPAK IC, 25° C., 254 nm, 93:7 DCM:IPA, 1.0 mL/min; $t_R$=20.7 min.; LC-MS 382 [M+H]⁺; ¹H NMR (400 MHz, CD₃OD) δ 8.73 (s, 1H), 8.61 (d, J=2.0 Hz, 1H), 7.75 (s, 1H), 7.38 (dd, J=2.0, 8.4 Hz, 1H), 7.05 (d, J=8.4 Hz, 2H), 4.51 (s, 4H), 1.99 (s, 3H).

Example 249

Synthesis of (±)-9-(3,4-dihydroxy-3-methylbut-1-yn-1-yl)-8-fluoro-4,5-dihydrobenzo[2,3]oxepino[4,5-d]thiazole-2-carboxamide

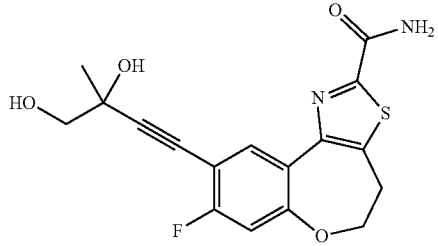 [SMILES: CC(O)(C#Cc1cc2c(cc1F)OCCc1sc(C(N)=O)nc1-2)CO]

Similar to as described in General Procedure G, 9-bromo-8-fluoro-4,5-dihydrobenzo[2,3]oxepino[4,5-d]thiazole-2-carboxamide was reacted with 2-methylbut-3-yne-1,2-diol (US2010/144757 A1) to give the titled compound as a brown solid (30 mg, 14%).

M+1=363; $^1$H NMR (300 MHz, CD$_3$OD) 6$^1$H NMR (300 MHz, DMSO-d6) δ 8.66 (d, 1H), 8.44 (s, 1H), 7.873 (s, 1H), 7.01 (s, 1H), 5.40 (s, 1H), 4.99 (t, 1H), 4.40t, 2H), 3.47 (m, 4H), 1.43 (s, 3H).

Example 250

Synthesis of (±)-8-fluoro-9-(3-hydroxy-3-(1-methyl-1H-imidazol-4-yl)but-1-yn-1-yl)-4,5-dihydrobenzo[2,3]oxepino[4,5-d]thiazole-2-carboxamide

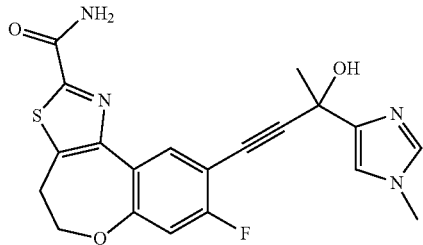 [SMILES: Cn1cnc(C(C)(O)C#Cc2cc3c(cc2F)OCCc2sc(C(N)=O)nc2-3)c1]

Similar to as described in General Procedure G, 9-bromo-8-fluoro-4,5-dihydrobenzo[2,3]oxepino[4,5-d]thiazole-2-carboxamide was reacted with 2-(1-methyl-1H-imidazol-4-yl)but-3-yn-2-ol (WO2009/158011 A1) to give the titled compound as colorless solid (19 mg, 9%).

M+1=413; $^1$H NMR (300 MHz, DMSO-d6) δ 8.67 (d, J=8.7 Hz, 1H), 8.48 (br s, 1H), 7.86 (br s, 1H), 7.58 (s, 1H), 7.02 (d, J=10.5 Hz, 1H), 6.92 (s, 1H), 6.21 (s, 1H), 4.42-4.30 (m, 2H), 3.84 (s, 3H), 3.40-3.30 (m, 2H), 1.23 (s, 3H).

Example 251

Synthesis of (±)-8-fluoro-9-(3-hydroxy-3-(pyridin-2-yl)but-1-yn-1-yl)-4,5-dihydrobenzo[2,3]oxepino[4,5-d]thiazole-2-carboxamide

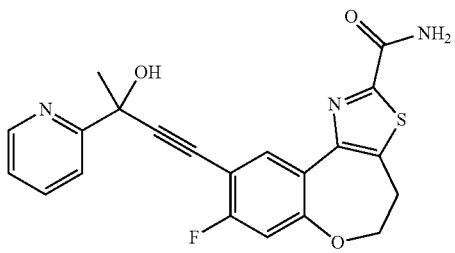 [SMILES: CC(O)(C#Cc1cc2c(cc1F)OCCc1sc(C(N)=O)nc1-2)c1ccccn1]

Similar to as described in General Procedure G, 9-bromo-8-fluoro-4,5-dihydrobenzo[2,3]oxepino[4,5-d]thiazole-2-carboxamide was reacted with 2-(pyridin-2-yl)but-3-yn-2-ol to give the titled compound as a white solid (18 mg, 7%).

M+1=410; $^1$H NMR (400 MHz, DMSO-d$_6$) δ 8.66 (d, 1H), 8.57 (d, 1H), 8.48 (s, 1H), 7.88 (m, 2H), 7.79 (d, 1H), 7.35 (m, 1H), 7.02 (d, 1H), 6.38 (s, 1H), 4.40 (t, 2H), 3.42 (t, 2H), 1.84 (s, 3H).

Example 252

Synthesis of 8-fluoro-9-(3-hydroxy-3-methylbut-1-yn-1-yl)-4,5-dihydrobenzo[2,3]oxepino[4,5-d]thiazole-2-carboxamide

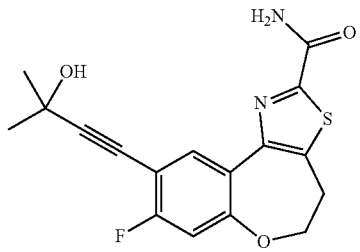 [SMILES: CC(C)(O)C#Cc1cc2c(cc1F)OCCc1sc(C(N)=O)nc1-2]

Similar to as described in General Procedure G, 9-bromo-8-fluoro-4,5-dihydrobenzo[2,3]oxepino[4,5-d]thiazole-2-carboxamide
2-methylbut-3-yn-2-ol to give an off-white solid (249 mg, 79%).

M+1=347; $^1$H NMR (300 MHz, DMSO-d$_6$) δ8.65 (d, 1H), 8.46 (s, 1H), 7.86 (s, 1H), 7.01 (d, 1H), 5.50 (s, 1H), 4.39 (t, 2H), 3.41 (t, 2H), 1.49 (s, 6H).

Example 253

Synthesis of (±)-8-fluoro-9-(3-hydroxy-3-(1H-1,2,4-triazol-5-yl)but-1-yn-1-yl)-4,5-dihydrobenzo[2,3]oxepino[4,5-d]thiazole-2-carboxamide

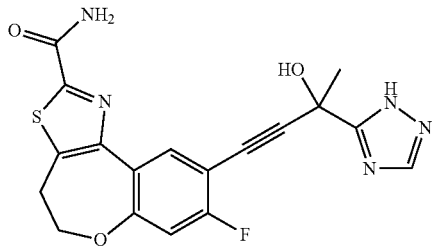 [SMILES: CC(O)(C#Cc1cc2c(cc1F)OCCc1sc(C(N)=O)nc1-2)c1ncn[nH]1]

Similar to as described in General Procedure G, 9-bromo-8-fluoro-4,5-dihydrobenzo[2,3]oxepino[4,5-d]thiazole-2-carboxamide was reacted with and 2-(1-[[2-(trimethylsilyl)ethoxy]methyl]-1H-1,2,4-triazol-3-yl)but-3-yn-2-ol to give 8-fluoro-9-(3-hydroxy-3-(1((2-(trimethylsilyl)ethoxy)methyl)-1H-1,2,4-triazol-5-yl)but-1-yn-1-yl)-4,5-dihydrobenzo[2,3]oxepino[4,5-d]thiazole-2-carboxamide. A solution of crude give 8-fluoro-9-(3-hydroxy-3-(1-((2-(trimethylsilyl)ethoxy)methyl)-1H-1,2,4-triazol-5-yl)but-1-yn-1-yl)-4,5-dihydrobenzo[2,3]oxepino[4,5-d]thiazole-2-carboxamide (150 mg, 0.28 mmol, 1.00 equiv) and hydrofluoric acid (2 mL) in CH$_3$CN (4 mL) was stirred for 3 h at room temperature. The pH value of the solution was adjusted to 10 with saturated NaHCO$_3$ (10 mL). The resulting solution was extracted with dichloromethane, dried over anhydrous sodium sulfate and concentrated under vacuum. The crude product (50 mg) was purified by Prep-HPLC with the following conditions (1#pre-HPLC-006(waters)): Column, sunfire prep C18 19*150 mm 5 um; mobile phase, Water with 0.5% CF$_3$COOH and CH$_3$CN (10% CH$_3$CN up to 45% in 12 min, up to 100% in 3 min, down to 10% in 2 min); Detector, UV 220/254 nm. 10 mg of product was obtained. This was treated by strong anion exchange resin (cleanert SAX-SPE). This resulted in 7.2 mg (6%) of the titled compound as an off-white solid.

M+1=400; $^1$H NMR (300 MHz, CD$_3$OD) δ 8.76 (d, J=8.4 Hz, 1H), 8.29 (s, 1H), 6.85 (d, J=10.2 Hz, 1H), 4.42 (t, J=4.8 Hz, 2H), 3.43 (t, J=5.1 Hz, 2H), 1.98 (s, 3H).

Example 254

Synthesis of (R)-8-fluoro-9-(3-hydroxy-3-(5-methyl-1,2,4-oxadiazol-3-yl)but-1-yn-1-yl)-4,5-dihydrobenzo[6,7]oxepino[4,5-d]thiazole-2-carboxamide

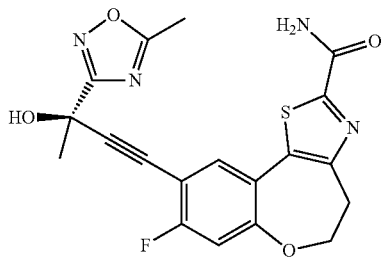 [SMILES: Cc1nc([C@](C)(O)C#Cc2cc3c(cc2F)OCCc2nc(C(N)=O)sc2-3)no1]

Similar to as described in General Procedure G, 9-bromo-8-fluoro-4,5-dihydrobenzo[2,3]oxepino[4,5-d]thiazole-2-carboxamide was reacted with (2R)-2-(5-methyl-1,2,4-oxadiazol-3-e)but-3-yn-2-to give the titled compound as an off-white solid (12 mg, 6%).

M+1=398; $^1$H NMR (400 MHz, DMSO-d$_6$) 8.68 (d, 1H), 8.48 (br s, 1H), 7.88 (br s, 1H), 7.04 (d, 1H), 6.77 (s, 1H), 4.40 (t, 2H), 3.40 (t, 2H), 2.62 (s, 3H), 1.87 (s, 3H).

Example 255

Synthesis of 8-fluoro-9-(4-fluoro-3-(fluoromethyl)-3-hydroxybut-1-yn-1-yl)-4,5-dihydrobenzo[2,3]oxepino[4,5-d]thiazole-2-carboxamide

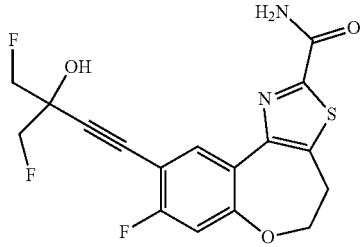 [SMILES: NC(=O)c1nc2c(s1)CCOc1cc(F)c(C#CC(O)(CF)CF)cc1-2]

Similar to as described in General Procedure G, 9-bromo-8-fluoro-4,5-dihydrobenzo[2,3]oxepino[4,5-d]thiazole-2-carboxamide was reacted with 1-fluoro-2-(fluoromethyl)but-3-yn-2-ol to give the titled compound as an off-white solid (73 mg, 32%).

M+1=383; $^1$H NMR (400 MHz, CD$_3$OD) δ 8.735 (d, 1H), 6.875 (d, 1H), 4.559 (d, 4H), 4.400 (t, 2H), 3.450 (t, 2H).

Example 256

Synthesis of (±)-8-fluoro-9-(4-fluoro-3-hydroxy-3-methylbut-1-yn-1-yl)-4,5-dihydrobenzo[2,3]oxepino[4,5-d]thiazole-2-carboxamide

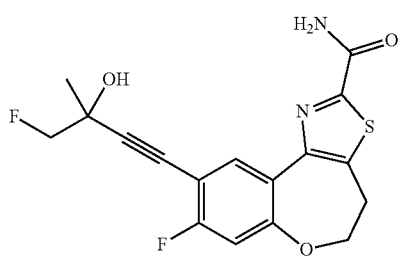 [SMILES: CC(O)(C#Cc1cc2c(cc1F)OCCc1sc(C(N)=O)nc1-2)CF]

Similar to as described in General Procedure G, 9-bromo-8-fluoro-4,5-dihydrobenzo[2,3]oxepino[4,5-d]thiazole-2-carboxamide was reacted with 1-fluoro-2-methylbut-3-yn-2-ol to give the titled compound as an off-white solid (6 mg, 28%).

M+1=365; $^1$H NMR (400 MHz, CD$_3$OD) δ 8.71 (d, 1H), 6.86 (d, 1H), 4.43 (t, 2H), 4.41 (d, 2H), 3.44 (t, 2H), 1.60 (s, 3H).

Example 257

Synthesis of (R)-4-(dimethylamino)-8-fluoro-9-(3-hydroxy-3-methylbut-1-yn-1-yl)-4,5-dihydrobenzo[2,3]oxepino[4,5-d]thiazole-2-carboxamide and (S)-4-(dimethylamino)-8-fluoro-9-(3-hydroxy-3-methylbut-1-yn-1-yl)-4,5-dihydrobenzo[2,3]oxepino[4,5-d]thiazole-2-carboxamide

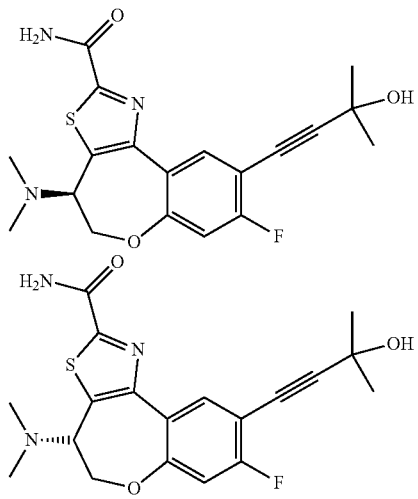

Similar to as described in General Procedure G, racemic 9-bromo-4-(dimethylamino)-8-fluoro-4,5-dihydrobenzo[2,3]oxepino[4,5-d]thiazole-2-carboxamide was reacted with 2-methylbut-3-yn-2-ol to give a racemic mixture of the titled compounds. The mixture (100 mg) was separated by Chiral- Prep-HPLC with the following conditions (2#-Gilson Gx 281(HPLC-09)): Column, Venusil Chiral OD-H, 21.1*25 cm, 5 um; mobile phase, Hex (0.2% TEA) and ethanol (0.2% TEA) (hold 10.0% ethanol (0.2% TEA) in 30 min); Detector, UV 220/254 nm. This resulted in 21.8 mg (11%) Compound 1 and 24.8 mg (12%) of Compound 2. The stereochemistry of both isomers was arbitrarily assigned.

Compound 1 chiral HPLC retention time 22.982 min.; off-white solid; M+1=390; $^1$H NMR (400 MHz, CD$_3$OD) δ 8.65 (d, J=8.7 Hz, 1H), 6.86 (d, J=10.2 Hz, 1H), 4.45-4.53 (m, 2H), 4.30-4.33 (m, 1H), 2.44 (s, 6H), 1.59 (s, 6H).

Compound 2 chiral HPLC retention time 29.276 min.; off-white solid; M+1=390; $^1$H NMR (400 MHz, CD$_3$OD) δ 8.61 (d, J=8.1 Hz, 1H), 6.82 (d, J=9.9 Hz, 1H), 4.43-4.45 (m, 2H), 4.26-4.28 (m, 1H), 2.41 (s, 6H), 1.56 (s, 6H).

Example 258

Synthesis of (S)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide and (R)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide

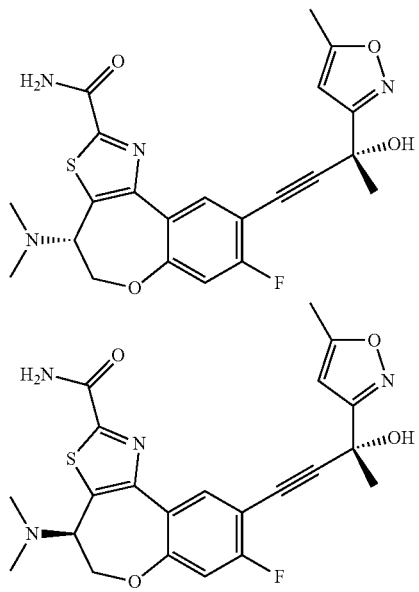

Similar to as described in General Procedure G, racemic 9-bromo-4-(dimethylamino)-8-fluoro-4,5-dihydrobenzo[2,3]oxepino[4,5-d]thiazole-2-carboxamide was reacted with (2R)-2-(5-methyl-1,2-oxazol-3-yl)but-3-yn-2-ol to give a mixture of the titled compounds. The mixture (100 mg) was separated by Chiral-Prep-HPLC with the following conditions (2#-Gilson Gx 281(HPLC-09)): Column, Chiralpak AD-H, 2*25 cm; mobile phase, Hex (0.2% TEA) and ethanol (0.2% TEA) (hold 40.0% ethanol (0.2% TEA) in 40 min); Detector, UV 220/254 nm. This resulted in 33.5 mg (19%) of Compound 1 and 18.2 mg (10%) of Compound 2. The stereochemistry at the 4-dimethylamino stereocenter for both isomers was arbitrarily assigned.

Compound 1: chiral HPLC retention time 21.482 min.; off-white solid; LC-MS (ES, m/z) 479[M+Na]$^+$; $^1$H NMR (400 MHz, CD$_3$OD) δ 8.72 (d, J=8.4 Hz, 1H), 6.88 (d, J=10.2 Hz, 1H), 6.32 (s, 1H), 4.42-4.54 (m, 2H), 4.30-4.33 (m, 1H), 2.25 (s, 9H), 1.90 (s, 3H);

Compound 2: chiral HPLC retention time 25.976 min.; off-white solid; LC-MS (ES, m/z) 479[M+Na]$^+$; $^1$H NMR (400 MHz, CD$_3$OD) δ 8.65 (d, J=8.4 Hz, 1H), 6.81 (d, J=10.2 Hz, 1H), 6.26 (s, 1H), 4.40-4.43 (m, 2H), 4.23-4.26 (m, 1H), 2.38 (s, 9H), 1.83 (s, 3H).

Example 259

Synthesis of (R)-4-(dimethylamino)-8-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide and (S)-4-(dimethylamino)-8-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide

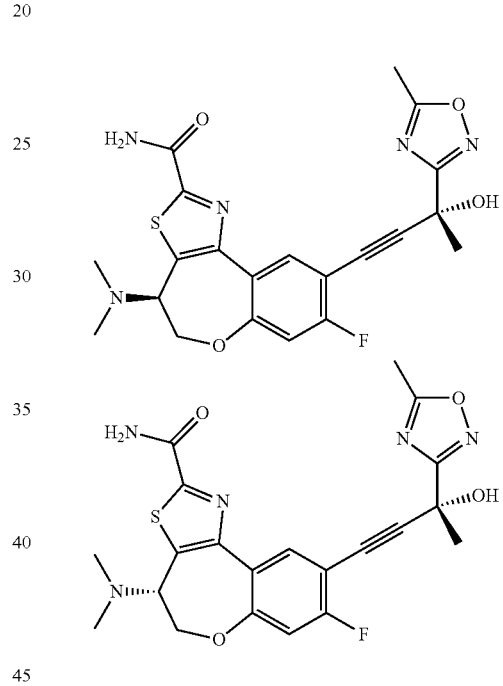

Similar to as described in General Procedure G, racemic 9-bromo-4-(dimethylamino)-8-fluoro-4,5-dihydrobenzo[2,3]oxepino[4,5-d]thiazole-2-carboxamide was reacted with (2R)-2-(5-methyl-1,2,4-oxadiazol-3-yl)but-3-yn-2-ol to give a mixture of the titled compounds (80 mg) that was separated by Chiral-Prep-HPLC with the following conditions (2#-Gilson Gx 281(HPLC-09)): Column, Venusil Chiral OD-H, 21.1*25 cm, 5 um; mobile phase, Hex (0.2% TEA) and IPA (hold 5.0% IPA in 27 min); Detector, UV 220/254 nm. This resulted in 11.9 mg (7%) of Compound 18.1 mg (4%) of Compound 2. The stereochemistry at the 4-dimethylamino stereocenter was arbitrarily assigned.

Compound 1: chiral HPLC retention time 28.497 min.; off-white solid; LC-MS (ES, m/z) 458[M+H]$^+$; $^1$H NMR (400 MHz, CD$_3$OD) δ 8.76 (d, J=8.4 Hz, 1H), 6.92 (d, J=9.9 Hz, 1H), 4.50-4.54 (m, 2H), 4.35-4.37 (m, 1H), 2.67 (s, 3H), 2.48 (s, 6H) 1.98 (s, 3H);

Compound 2: chiral HPLC retention time 34.736 min.; off-white solid; LC-MS (ES, m/z) 480[M+Na]$^+$; $^1$H NMR (400 MHz, CD$_3$OD) δ v8.69 (d, J=8.4 Hz, 1H), 6.85 (d, J=9.9 (d, J=2.0 Hz, 1H), 7.75 (s, 1H), 7.38 (dd, J=2.0, 8.4 Hz, 1H), 7.05 (d, J=8.4 Hz, 2H), 4.51 (s, 4H), 1.99 (s, 3H).

Example 260

Synthesis of 4-(dimethylamino)-8-fluoro-9-(3-hydroxy-3-(pyridin-2-yl)but-1-yn-1-yl)-4,5-dihydrobenzo[2,3]oxepino[4,5-d]thiazole-2-carboxamide

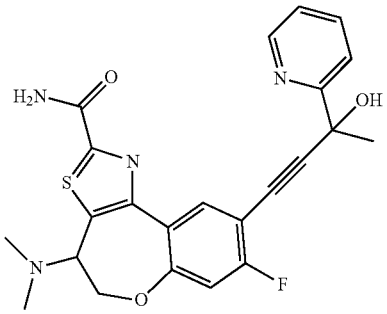

Similar to as described in General Procedure G, racemic 9-bromo-4-(dimethylamino)-8-fluoro-4,5-dihydrobenzo[2,3]oxepino[4,5-d]thiazole-2-carboxamide was reacted with racemic 2-(pyridin-2-yl)but-3-yn-2-ol to give an isomeric mixture of the titled compound. The mixture (80 mg) was separated by Chiral-Prep-HPLC with the following conditions (2#-Gilson Gx 281(HPLC-09)): Column, CHIRALPAK AD-H SFC, 5*25 cm, 5 um; mobile phase, Hex (0.2% TEA) and ethanol (0.2% TEA) (hold 30.0% ethanol (0.2% TEA) in 30 min); Detector, UV 220/254 nm to give 1$^{st}$ 3.7 mg (2%) of Compound 1, then 10.2 mg (4%) of Compounds 2 and 18.6 mg (8%) Compound 3. The stereochemistry of these compounds has not been assigned.

Compound 1: chiral HPLC retention time 10.630; LC-MS 453[M+H]$^+$; $^1$H NMR (400 MHz, CD$_3$OD) δ 8.73 (d, J=8 Hz, 1H), 8.57 (d, J=4.8 Hz, 1H), 7.90-7.93 (m, 2H), 7.36-7.40 (m, 1H), 6.89 (d, J=10.0 Hz, 1H), 4.44-4.57 (m, 2H), 4.32-4.38 (m, 2H), 2.46 (s, 6H), 1.91 (s, 3H);

Compounds 2 (racemic mixture about a single stereocenter): chiral HPLC retention time 12.480 and 13.467 min. (two peaks); LC-MS 453[M+H]$^+$; $^1$H NMR (300 MHz, CD$_3$OD) δ 8.72 (d, J=8.1 Hz, 1H), 8.56 (d, J=5.1 Hz, 1H), 7.88-7.90 (m, 2H), 7.35-7.39 (m, 1H), 6.83 (d, J=9.9 Hz, 1H), 4.46-4.54 (m, 2H), 4.30-4.33 (m, 1H), 2.44 (s, 6H), 1.93 (s, 3H);

Compound 3: chiral HPLC retention time 17.827; LC-MS 453[M+H]$^+$; $^1$H NMR (300 MHz, CD$_3$OD) δ 8.68 (d, J=8.4 Hz, 1H), 8.51 (d, J=5.1 Hz, 1H), 7.83-7.89 (m, 2H), 7.31-7.35 (m, 1H), 6.83 (d, J=9.9 Hz, 1H), 4.38-4.50 (m, 2H), 4.26-4.29 (m, 1H), 2.41 (s, 6H), 1.86 (s, 3H).

Example 261

Synthesis of 9-chloro-10-(2-hydroxy-4-(5-methylisoxazol-3-yl)but-3-yn-2-yl)-5,6-dihydrobenzo[f]imidazo[1,2-d][1,4]oxazepine-2-carboxamide

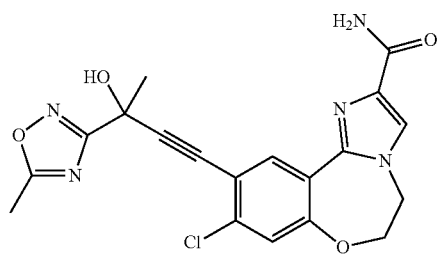 [SMILES: Cc1nc(C(C)(O)C#Cc2cc3c(cc2Cl)OCCn2cc(C(N)=O)nc2-3)no1]

Similar to as described in General Procedure G, 10-bromo-9-chloro-5,6-dihydrobenzo[f]imidazo[1,2-d][1,4]oxazepine-2-carboxamide was reacted with and 2-(5-methyl-1,2,4-oxadiazol-3-yl)but-3-yn-2-ol to give the titled compound as an off-white solid (10 mg, 8%).

M+1=414; $^1$H NMR (400 MHz, DMSO-d$_6$) δ 8.51 (s, 1H), 7.83 (s, 1H), 7.44 (s, 1H), 4.52 (d, J=5.2 Hz, 4H), 2.68 (s, 3H), 1.83 (s, 3H).

Example 262

Synthesis of (±)-9-chloro-10-(3-hydroxy-3-(5-methylisoxazol-3-yl)but-1-yn-1-yl)-5,6-dihydrobenzo[f]imidazo[1,2-d][1,4]oxazepine-2-carboxamide

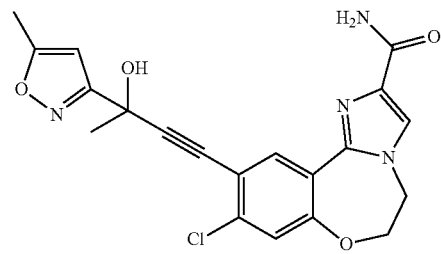 [SMILES: Cc1cc(C(C)(O)C#Cc2cc3c(cc2Cl)OCCn2cc(C(N)=O)nc2-3)no1]

Similar to as describe in General Procedure G, 10-bromo-9-chloro-5,6-dihydrobenzo[f]imidazo[1,2-d][1,4]oxazepine-2-carboxamide was reacted with racemic 2-(5-methyl-1,2-oxazol-3-yl)but-3-yn-2-ol to give the titled compound as a yellow solid (40 mg, 32%).

M+1=413; $^1$H NMR (400 MHz, DMSO-d$_6$) δ 8.52 (d, J=2.8 Hz, 1H), 7.85 (s, 1H), 7.62 (s, 1H), 7.45 (d, J=2.8 Hz, 1H), 7.18 (s, 1H), 6.53 (s, 1H), 6.37 (s, 1H), 4.54 (d, J=7.2 Hz, 4H), 2.42 (s, 3H), 1.80 (s, 3H).

Example 263

Synthesis of 9-chloro-10-(3-hydroxy-3-methylbut-1-yn-1-yl)-5,6-dihydrobenzo[f]imidazo[1,2-d][1,4]oxazepine-2-carboxamide

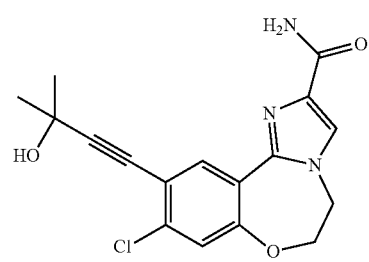 [SMILES: CC(C)(O)C#Cc1cc2c(cc1Cl)OCCn1cc(C(N)=O)nc1-2]

Similar to as described in General Procedure G, 10-bromo-9-chloro-5,6-dihydrobenzo[f]imidazo[1,2-d][1,4]oxazepine-2-carboxamide was reacted with 2-methylbut-3-yn-2-to give the titled compound as a grey solid (40 mg, 32%).

M+1=346 [M+H]$^+$; $^1$H NMR (300 MHz, DMSO-d$_6$) δ 8.47 (d, J=2.7 Hz, 1H), 7.83 (s, 1H), 7.57 (d, J=12 Hz, 1H), 7.38 (d, J=2.7 Hz, 1H), 7.158 (s, 1H), 5.49 (s, 1H), 4.52 (d, J=3.6 Hz, 4H), 1.46 (s, 6H).

Example 264

Synthesis of 10-(3-hydroxy-3-methylbut-1-yn-1-yl)-3-(pyrrolidin-1-ylmethyl)-5,6-dihydrobenzo[f]imidazo[1,2-d][1,4]oxazepine-2-carboxamide

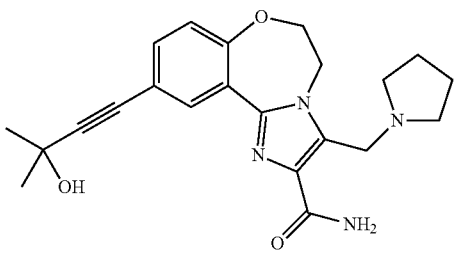 [SMILES: CC(C)(O)C#Cc1ccc2c(c1)-c1nc(C(N)=O)c(CN3CCCC3)n1CCO2]

Scheme for the synthesis of 10-(3-hydroxy-3-methylbut-1-yn-1-yl)-3-(pyrrolidin-1-ylmethyl)-5,6-dihydrobenzo[f]imidazo[1,2-d][1,4]oxazepine-2-carboxamide:

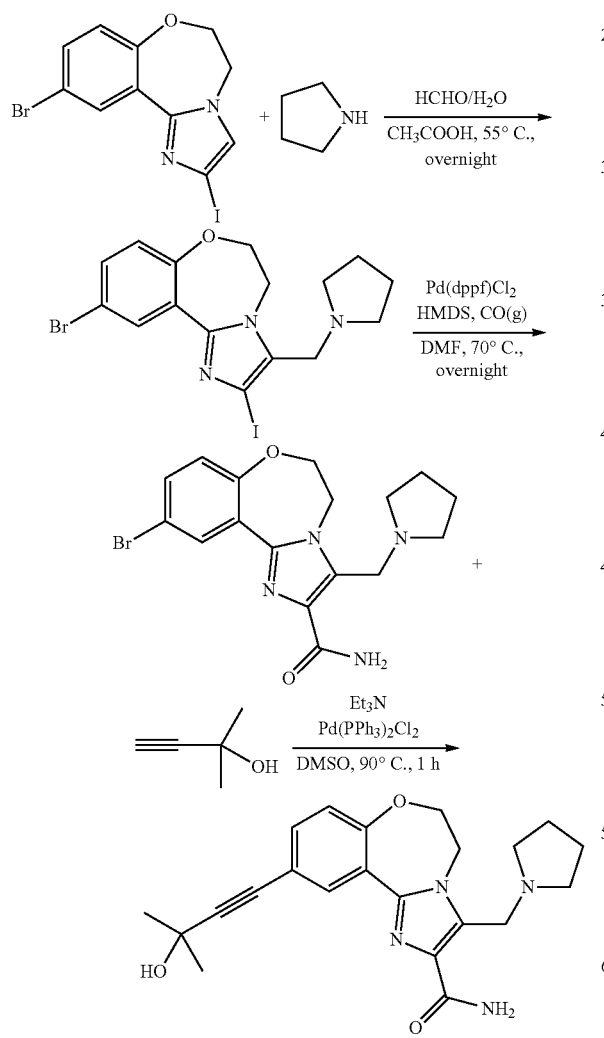

10-bromo-2-iodo-5,6-dihydrobenzo[f]imidazo[1,2-d][1,4]oxazepine (300 mg, 0.77 mmol, 1.00 equiv), HCHO/H₂O (312 mg, 4.00 equiv), pyrrolidine (332 mg, 4.67 mmol, 6.00 equiv) in acetic acid (4 mL) was stirred overnight at 55° C. The resulting solution was diluted with dichloromethane, washed with saturated aqueous NaHCO₃ solution, dried over anhydrous sodium sulfate and concentrated under vacuum. The residue was applied onto a silica gel column with dichloromethane/MeOH (10/1). This resulted in 200 mg of 10-bromo-2-iodo-3-(pyrrolidin-1-ylmethyl)-5,6-dihydrobenzo[f]imidazo[1,2-d][1,4]oxazepineas yellow oil that was used without further purification or characterization. Similar to as described in Example 10 (carbonylative amidation), a solution of this intermediate (200 mg, 0.42 mmol, 1.00 equiv), HMDS (135 mg, 0.84 mmol, 2.00 equiv), Pd(dppf)Cl₂(34 mg, 0.05 mmol, 0.10 equiv) in N,N-dimethylformamide (2 mL) was stirred overnight at 70° C. under an atmosphere of CO (g). The resulting solution was diluted with dichloromethane, washed with brine, dried over anhydrous sodium sulfate, and concentrated under vacuum. The residue was applied onto a silica gel column with dichloromethane/methanol (1:10). This resulted in 80 mg (48%) of 10-bromo-3-(pyrrolidin-1-ylmethyl)-5,6-dihydrobenzo[f]imidazo[1,2-d][1,4]oxazepine-2-carboxamide as a yellow solid. Similar to as described in General Procedure G, 10-bromo-3-(pyrrolidin-1-ylmethyl)-5,6-dihydrobenzo[f]imidazo[1,2-d][1,4]oxazepine-2-carboxamide was reacted with 2-methylbut-3-yn-2-ol to give the titled compound as a yellow solid (14 mg, 18%).

M+1=395; ¹H NMR (400 MHz, CD₃OD) δ 8.55 (s, 1H), 7.33 (q, J=2.4 Hz, 1H), 7.02 (d, J=8.4 Hz, 1H), 4.53 (q, J=6.4 Hz, 4H), 4.19 (s, 2H), 2.69 (s, 4H), 1.83 (s, 4H), 1.59 (s, 6H).

Example 265

Synthesis of 3-((dimethylamino)methyl)-10-(3-hydroxy-3-methylbut-1-yn-1-yl)-5,6-dihydrobenzo[f]imidazo[1,2-d][1,4]oxazepine-2-carboxamide

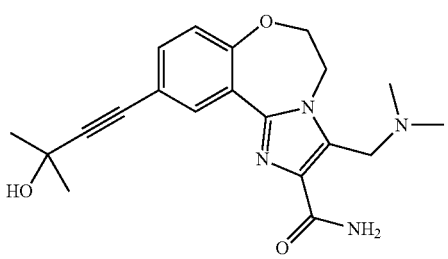 [SMILES: CN(C)Cc1c(C(N)=O)nc2n1CCOc1ccc(C#CC(C)(C)O)cc1-2]

Similar to as described in General Procedure G, 10-bromo-3-((dimethylamino)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with dimethylamine) was reacted with 2-methylbut-3-yn-2-ol to give the titled compound as a grey solid (41 mg, 34%).

M+1=369; ¹H NMR (400 MHz, CD₃OD) δ 8.55 (s, 1H), 7.33 (d, J=8.4 Hz, 1H), 7.02 (d, J=8.4 Hz, 1H), 4.51 (s, 4H), 3.97 (s, 2H), 2.31 (s, 6H), 1.59 (s, 6H).

Example 266

Synthesis of 10-(3-hydroxy-3-methylbut-1-yn-1-yl)-3-((oxetan-3-ylamino)methyl)-5,6-dihydrobenzo[f]imidazo[1,2-d][1,4]oxazepine-2-carboxamide

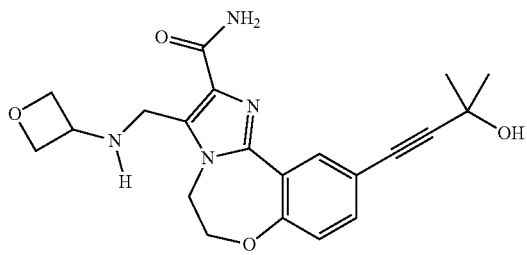 [SMILES: CC(C)(O)C#Cc1ccc2c(c1)-c1nc(C(N)=O)c(CNC3COC3)n1CCO2]

Similar to as described in General Procedure G, 10-bromo-3-((oxetan-3-ylamino)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with 3-aminooxetane) was reacted with 2-methylbut-3-yn-2-ol to give the titled compound as a brown solid (17 mg, 17%).

M+1=397; $^1$H NMR (400 MHz, CD$_3$OD) δ 8.52 (d, J=2.1 Hz, 1H), 7.61 (s, 1H), 7.29 (d, J=6.3 Hz, 1H), 7.18 (s, 1H), 7.02 (d, J=8.4 Hz, 1H), 5.46 (s, 1H), 4.57-4.45 (m, 6H), 4.23 (t, J=5.7 Hz, 2H), 4.08 (s, 2H), 3.89 (s, 1H), 1.48 (s, 6H).

Example 267

Synthesis of 10-(3-hydroxy-3-methylbut-1-yn-1-yl)-3-((isopropylamino)methyl)-5,6-dihydrobenzo[f]imidazo[1,2-d][1,4]oxazepine-2-carboxamide

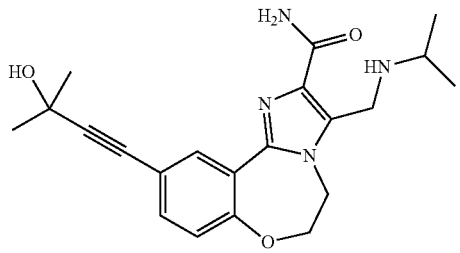 [SMILES: CC(C)NCc1c(C(N)=O)nc2n1CCOc1ccc(C#CC(C)(C)O)cc1-2]

Similar to as described in General Procedure G, 10-bromo-3-((isopropylamino)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with isopropylamine) was reacted with 2-methylbut-3-yn-2-ol to give the titled compound as a brown solid (16 mg, 39%).

M+1=383; $^1$H NMR (300 MHz, DMSO-d$_6$) δ 8.52 (s, 1H), 7.9 (br s, 1H), 7.7-7.4 (br s, 1H), 7.33-7.30 (m, 1H), 7.03 (d, J=8.4 Hz, 1H), 5.43 (s, 1H), 4.48 (t, J=4.8 Hz, 4H), 4.30 (s, 2H), 1.470 (s, 6H).

Example 268

Synthesis of (R)-10-(3-hydroxy-3-methylbut-1-yn-1-yl)-3-((3-hydroxypyrrolidin-1-yl)methyl)-5,6-dihydrobenzo[f]imidazo[1,2-d][1,4]oxazepine-2-carboxamide

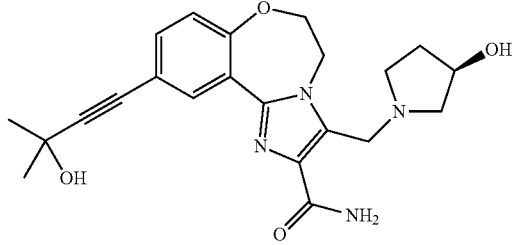 [SMILES: CC(C)(O)C#Cc1ccc2c(c1)-c1nc(C(N)=O)c(CN3CC[C@@H](O)C3)n1CCO2]

Similar to as described in General Procedure G, (R)-10-bromo-3((3-hydroxypyrrolidin-1-yl)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with (R)-3-hydroxypyrrolidine) was reacted with 2-methylbut-3-yn-2-ol to give the titled compound as a white solid (11 mg, 14%).

M+1=411; $^1$H NMR (400 MHz, CD$_3$OD) δ 8.54 (s, 1H), 7.33 (q, J=2.0 Hz, 1H), 7.02 (d, J=8.8 Hz, 1H), 4.60-4.51 (m, 4H), 4.34 (s, 1H), 4.17 (s, 2H), 2.87 (d, J=6.4 Hz, 1H), 2.80-2.77 (m, 1H), 2.68-2.62 (m, 1H), 2.55 (s, 1H), 2.21-2.15 (m, 1H), 1.75-1.71 (m, 1H), 1.59 (s, 6H).

Example 269

Synthesis of 10-(3-hydroxy-3-methylbut-1-yn-1-yl)-3-(((2-methoxyethyl)(methyl)amino)methyl)-5,6-dihydrobenzo[f]imidazo[1,2-d][1,4]oxazepine-2-carboxamide

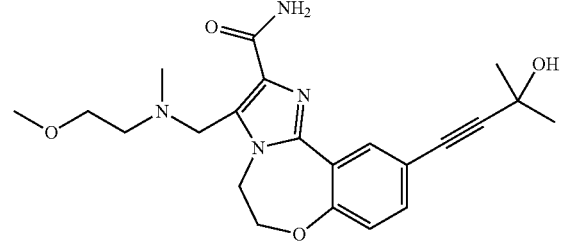 [SMILES: COCCN(C)Cc1c(C(N)=O)nc2n1CCOc1ccc(C#CC(C)(C)O)cc1-2]

Similar to as described in General Procedure G, 10-bromo-3-(((2-methoxyethyl)(methyl)amino)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with 2-methoxy-N-methylethanamine) was reacted with 2-methylbut-3-yn-2-ol to give the titled compound as a colorless solid (20 mg, 20%).

M+1=413; $^1$H NMR (400 MHz, DMSO-d$_6$) δ 8.53 (d, J=1.8 Hz, 1H), 7.30 (dd, J=1.8, 5.4 Hz, 1H), 6.99 (d, J=1.8 Hz, 1H), 4.51-4.43 (m, 4H), 3.98 (s, 2H), 3.43 (t, J=5.4 Hz, 2H), 3.23 (s, 3H), 2.57 (t, J=5.4 Hz, 3H), 2.22 (s, 3H), 1.53 (s, 6H).

Example 270

Synthesis of 10-(3-hydroxy-3-methylbut-1-yn-1-yl)-3-(((2-methoxyethyl)amino)methyl)-5,6-dihydrobenzo[f]imidazo[1,2-d][1,4]oxazepine-2-carboxamide

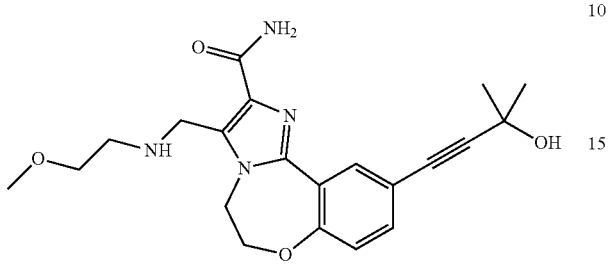

Similar to as described in General Procedure G, 10-bromo-3-(((2-methoxyethyl)amino)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with 2-methoxyethanamine) was reacted with 2-methylbut-3-yn-2-ol to give the titled compound as a colorless solid (25 mg, 20%).

M+1=399; $^1$H NMR (300 MHz, CD$_3$OD) δ 8.55 (s, 1H), 7.33 (d, J=9.0 Hz, 1H), 7.02 (d, J=8.4 Hz, 1H), 4.54-4.46 (m, 4H), 4.16 (s, 2H), 3.52 (t, J=5.1 Hz, 2H), 3.53 (s, 3H), 2.83 (t, J=5.4 Hz, 2H), 1.58 (s, 6H).

Example 271

Synthesis of 3-((4-acetylpiperazin-1-yl)methyl)-10-(3-hydroxy-3-methylbut-1-yn-1-yl)-5,6-dihydrobenzo[f]imidazo[1,2-d][1,4]oxazepine-2-carboxamide

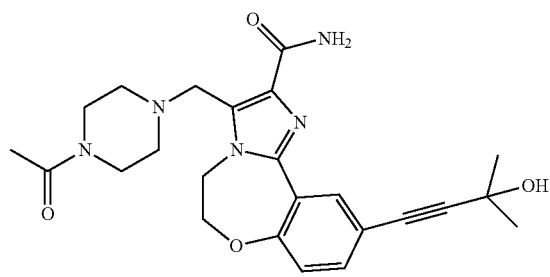 [SMILES: CC(=O)N1CCN(Cc2c(C(N)=O)nc3n2CCOc2ccc(C#CC(C)(C)O)cc2-3)CC1]

Similar to as described in General Procedure G, 3-((4-acetylpiperazin-1-yl)methyl)-10-bromo-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with 1-(piperazin-1-yl)ethanone) was reacted with 2-methylbut-3-yn-2-ol to give the titled compound as a colorless solid (34 mg, 42%).

M+1=452; $^1$H NMR (300 MHz, CD$_3$OD) δ 8.53 (d, J=4.5 Hz, 1H), 7.31-7.34 (m, 1H), 7.01 (d, J=8.7 Hz, 1H), 4.53 (s, 4H), 4.06 (s, 2H), 3.53 (d, J=18.3 Hz, 4H), 2.52 (s, 4H), 2.08 (s, 3H), 1.53 (s, 3H).

Example 272

Synthesis of 10-(3-hydroxy-3-methylbut-1-yn-1-yl)-3-((4-methylpiperazin-1-yl)methyl)-5,6-dihydrobenzo[f]imidazo[1,2-d][1,4]oxazepine-2-carboxamide

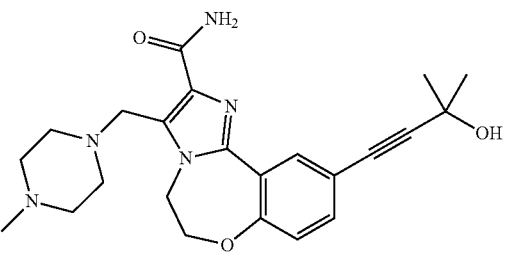 [SMILES: CN1CCN(Cc2c(C(N)=O)nc3n2CCOc2ccc(C#CC(C)(C)O)cc2-3)CC1]

Similar to as described in General Procedure G, 10-bromo-3-((4-methylpiperazin-1-yl)methyl)-5,6-dihydrobenzo[f]imidazo[1,2-d][1,4]oxazepine-2-carboxamide (prepared similarly as described in the synthesis of 10-bromo-3-(pyrrolidin-1-ylmethyl)-5,6-dihydrobenzo[f]imidazo[1,2-d][1,4]oxazepine-2-carboxamide replacing pyrrolidine with N-methylpiperazine) was reacted with 2-methylbut-3-yn-2-ol to give the titled compound as a colorless solid (12 mg, 23%).

M+1=424; $^1$H NMR (400 MHz, CDCl$_3$) δ 8.56 (d, J=2.4 Hz, 1H), 7.33 (dd, J=8.0 Hz, 2.4 Hz, 1H), 6.99 (d, J=8.0 Hz, 1H), 5.35 (s, 1H), 4.50 (s, 4H), 4.11 (s, 2H), 2.73-2.57 (m, 6H), 2.44 (s, 2H), 1.68 (s, 6H).

Example 273

Synthesis of 10-(3-hydroxy-3-methylbut-1-yn-1-yl)-3-((2-methyl-1H-imidazol-1-yl)methyl)-5,6-dihydrobenzo[f]imidazo[1,2-d][1,4]oxazepine-2-carboxamide

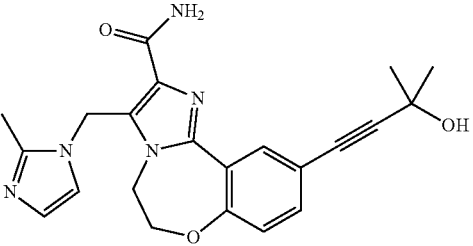 [SMILES: Cc1nccn1Cc1c(C(N)=O)nc2n1CCOc1ccc(C#CC(C)(C)O)cc1-2]

Scheme for the synthesis of 10-(3-hydroxy-3-methylbut-1-yn-1-yl)-3-((2-methyl-1H-imidazol-1-yl)methyl)-5,6-dihydrobenzo[f]imidazo[1,2-d][1,4]oxazepine-2-carboxamide:

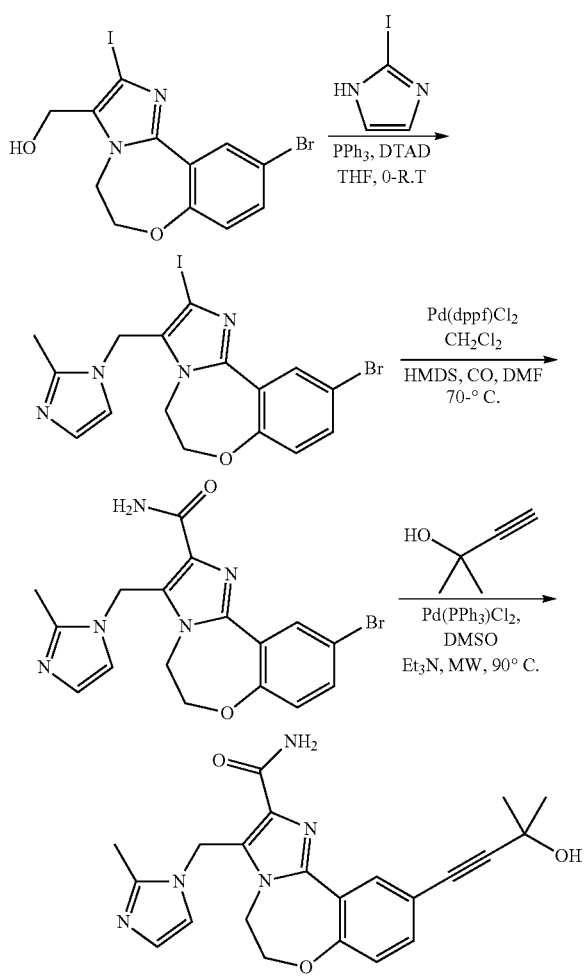

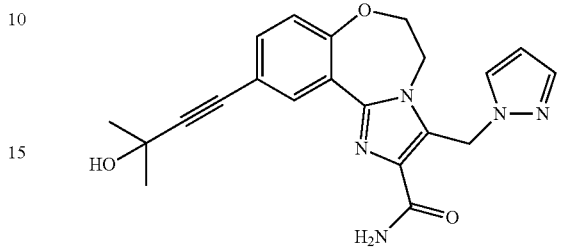

Example 274

Synthesis of 3-((1H-pyrazol-1-yl)methyl)-10-(3-hydroxy-3-methylbut-1-yn-1-yl)-5,6-dihydrobenzo[f]imidazo[1,2-d][1,4]oxazepine-2-carboxamide Similar to as described in General Procedure G, 3((1H-pyrazol-1-yl)methyl)-10-bromo-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with pyrazole) was reacted with 2-methylbut-3-yn-2-ol to give the titled compound as a colorless solid (14 mg, 14%).

M+1=392; $^1$H NMR (300 MHz, CD$_3$OD) δ 8.53 (s, 1H), 7.74 (d, J=2.1 Hz, 1H), 7.47 (s, 1H), 7.35-7.30 (m, 1H), 7.00 (d, J=8.4 Hz, 1H), 6.28 (s, 1H), 5.87 (s, 2H), 4.50-4.47 (m, 4H), 1.57 (s, 6H).

Di-tert-butyl azodicarboxylate (470 mg, 1.79 mmol, 1.50 equiv) in tetrahydrofuran (2 mL) was added dropwise to a stirred solution of (10-bromo-2-iodo-5,6-dihydrobenzo[f]imidazo[1,2-d][1,4]oxazepin-3-yl)methanol (500 mg, 1.19 mmol, 1.00 equiv)), 2-methyl-1H-imidazole (200 mg, 2.44 mmol, 2.00 equiv), and triphenylphosphine (400 mg, 1.74 mmol, 1.50 equiv) in tetrahydrofuran (3 mL) at 0° C. under nitrogen. The resulting solution was stirred for 3 h at room temperature and concentrated under vacuum. The residue was applied onto a silica gel column with dichloromethane/methanol (10:1). This resulted in 260 mg (45%) of 10-bromo-2-iodo-3-((2-methyl-1H-imidazol-1-yl)methyl)-5,6-dihydrobenzo[f]imidazo[1,2-d][1,4]oxazepineas as a colorless solid. This intermediate was converted to 10-bromo-3-((2-methyl-1H-imidazol-1-yl)methyl)-5,6-dihydrobenzo[f]imidazo[1,2-d][1,4]oxazepine-2-carboxamide similar to as described in Example 10 (carbonylative amidation). Similar to as described in General Procedure G, 10-bromo-3-((2-methyl-1H-imidazol-1-yl)methyl)-5,6-dihydrobenzo[f]imidazo[1,2-d][1,4]oxazepine-2-carboxamide was reacted with 2-methylbut-3-yn-2-ol to give the titled compound as a colorless solid (2 mg, 2%).

M+1=406$^+$; $^1$H NMR (300 MHz, CD$_3$OD) δ 8.60 (s, 1H), 7.35 (d, J=6.3 Hz, 1H), 7.01 (d, J=8.7 Hz, 1H), 6.91 (s, 1H), 6.85 (s, 1H), 5.72 (s, 2H), 4.47-4.44 (m, 2H), 4.21-4.19 (m, 2H), 2.46 (s, 3H), 1.59 (s, 6H).

Example 275

Synthesis of 10-(3-hydroxy-3-methylbut-1-yn-1-yl)-3-((2-oxopyrrolidin-1-yl)methyl)-5,6-dihydrobenzo[f]imidazo[1,2-d][1,4]oxazepine-2-carboxamide

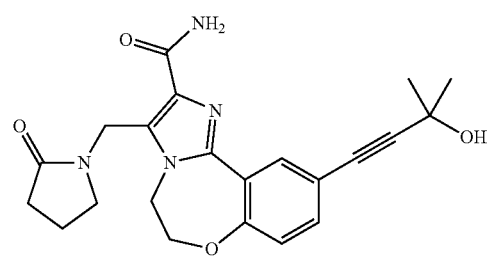 [SMILES: CC(C)(O)C#Cc1ccc2c(c1)-c1nc(C(N)=O)c(CN3CCCC3=O)n1CCO2]

Similar to as described in General Procedure G, 10-bromo-3-((2-oxopyrrolidin-1-yl)methyl)-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 2-pyrrolidinone) was reacted with 2-methylbut-3-yn-2-ol to give the titled compound as a colorless solid (64 mg, 63%).

M+1=409; $^1$H NMR (400 MHz, CD$_3$OD) δ 8.54 (d, J=2.4 Hz, 1H), 7.35 (dd, J=8.4, 2.0 Hz, 1H), 7.02 (d, J=8.4 Hz, 1H), 5.03 (s, 1H), 4.50 (t, J=4 Hz, 2H), 3.51 (t, J=4 Hz, 2H), 2.43 (t, J=8.0 Hz, 2H), 2.05-1.99 (m, 2H), 1.20 (t, J=7.2 Hz, 6H).

Example 276

Synthesis of 3-(cyanomethyl)-10-(3-hydroxy-3-methylbut-1-yn-1-yl)-5,6-dihydrobenzo[f]imidazo[1,2-d][1,4]oxazepine-2-carboxamide

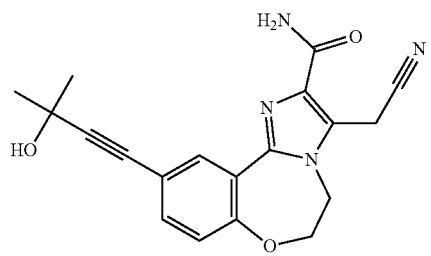 [SMILES: CC(C)(O)C#Cc1ccc2c(c1)-c1nc(C(N)=O)c(CC#N)n1CCO2]

Scheme for the synthesis of 3-(cyanomethyl)-10-(3-hydroxy-3-methylbut-1-yn-1-yl)-5,6-dihydrobenzo[f]imidazo[1,2-d][1,4]oxazepine-2-carboxamide:

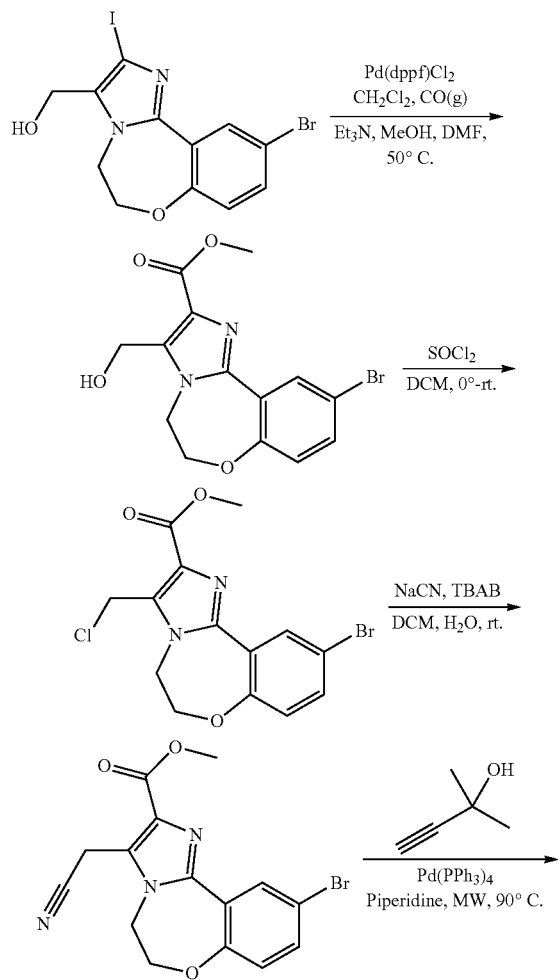

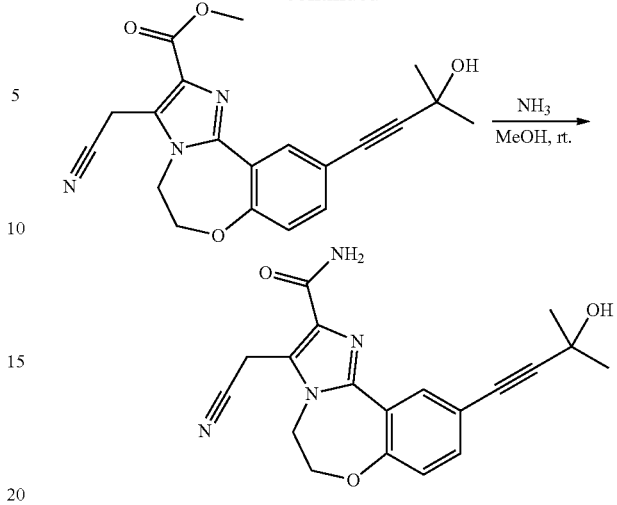

Similarly to as described in Example 6 (carbonylative methyanolysis) a suspension of (10-bromo-2-iodo-5,6-dihydrobenzo[f]imidazo[1,2-d][1,4]oxazepin-3-yl)methanol (1.5 g, 3.56 mmol, 1.00 equiv), triethylamine (1.44 g, 14.23 mmol, 4.00 equiv) and Pd(dppf)Cl$_2$CH$_2$Cl$_2$ (300 mg, 0.37 mmol, 0.10 equiv) in methanol (40 mL)/DMF (20 mL) was stirred for 14 h at 50° C. under a carbon monoxide atmosphere (1 atm). Most of methanol was removed under vacuum and the residue was diluted with 60 mL of water. The solids were collected to give 1.6 g (crude) of methyl 10-bromo-3-(hydroxymethyl)-5,6-dihydrobenzo[f]imidazo[1,2-d][1,4]oxazepine-2-carboxylate as an off-white solid. M+1=353/355. Thionyl chloride (12 mL) was added into a solution of the above intermediate (400 mg, 1.13 mmol, 1.00 equiv) in dichloromethane (20 mL) at 0° C. The resulting solution was stirred for 30 min at room temperature. The resulting mixture was concentrated to give 450 mg (crude) methyl 10-bromo-3-(chloromethyl)-5,6-dihydrobenzo[f]imidazo[1,2-d][1,4]oxazepine-2-carboxylate as a yellow solid; M+1=371/373. A mixture of sodium cyanide (296 mg, 6.04 mmol, 5.00 equiv), the above intermediate (450 mg, 1.21 mmol, 1.00 equiv), tetrabutylammonium chloride (50 mg, 0.16 mmol, 0.13 equiv) in dichloromethane (20 mL)/water (10 mL) was stirred for 14 h at room temperature. The resulting solution was diluted with 60 mL of dichloromethane, washed with brine, dried over anhydrous sodium sulfate, and concentrated under vacuum. The residue was purified on a silica gel column with ethyl acetate/petroleum ether (1:2) to give 270 mg (62%) methyl 10-bromo-3-(cyanomethyl)-5,6-dihydrobenzo[f]imidazo[1,2-d][1,4]oxazepine-2-carboxylate; M+1=362/364. Similar to as described in General Procedure E with the exception to use Pd(PPh$_3$)$_4$ and piperidine, methyl 10-bromo-3-(cyanomethyl)-5,6-dihydrobenzo[f]imidazo[1,2-d][1,4]oxazepine-2-carboxylate was reacted with 2-methylbut-3-yn-2-ol to give methyl 3-(cyanomethyl)-10-(3-hydroxy-3-methylbut-1-yn-1-yl)-5,6-dihydrobenzo[f]imidazo[1,2-d][1,4]oxazepine-2-carboxylate as a yellow solid (40 mg, 30%); M+1=366. A solution of this compound (40 mg, 0.11 mmol, 1.00 equiv) in methanol (saturated with ammonia, 40 mL) was stirred for 6 days at room temperature. The resulting mixture was concentrated under vacuum and the residue was purified by Prep-HPLC with the following conditions (Prep-HPLC-005): Column, SunFire Prep C18 OBD Column, 5 um, 19*150 mm; mobile phase, Water with 10 mmol NH$_4$HCO$_3$ and MeCN (20.0% MeCN up to 50.0% in 15 min, up to 95.0% in 2 min, down to 20.0% in 2 min); Detector, UV 254/220 nm; colorless solid (1.3 mg, 3%).

M+1=351; $^1$H NMR (300 MHz, CD$_3$OD) 8.46 (d, J=2.1 Hz, 1H), 7.24 (d, J=2.1, 8.7 Hz, 1H), 6.93 (d, J=8.7 Hz, 1H), 4.54-4.45 (m, 2H), 4.37-4.34 (m, 2H), 1.47 (s, 6H).

Example 277

Synthesis of 3-((2-chlorophenoxy)methyl)-10-(3-hydroxy-3-methylbut-1-yn-1-yl)-5,6-dihydrobenzo[f]imidazo[1,2-d][1,4]oxazepine-2-carboxamide

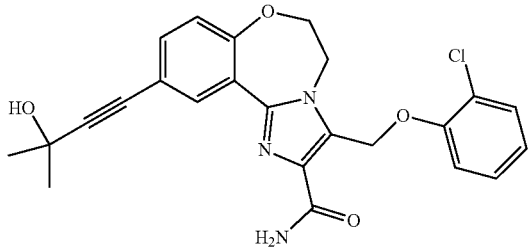 [SMILES: CC(C)(O)C#Cc1ccc2c(c1)-c1nc(C(N)=O)c(COc3ccccc3Cl)n1CCO2]

Prepared similarly to as described in the synthesis of 3-(cyanomethyl)-10-(3-hydroxy-3-methylbut-1-yn-1-yl)-5,6-dihydrobenzo[f]imidazo[1,2-d][1,4]oxazepine-2-carboxamide starting from 10-bromo-3-(chloromethyl)-5,6-dihydrobenzo[f]imidazo[1,2-d][1,4]oxazepine-2-carboxylate replacing sodium cyanide with 2-chlorophenol to give the titled compound as an off-white solid (7 mg, 6%).

M+1=452; $^1$H NMR (300 MHz, CD$_3$OD) δ 8.55 (d, J=2.1 Hz, 1H), 7.42-7.22 (m, 4H), 7.02 (d, J=8.4 Hz, 1H), 6.94 (t, J=6.6 Hz, 1H), 5.78 (s, 2H), 4.61-4.58 (m, 2H), 4.54-5.51 (m, 2H), 1.57 (s, 6H).

Example 278

Synthesis of 3((2-fluorophenoxy)methyl)-10-(3-hydroxy-3-methylbut-1-yn-1-yl)-5,6-dihydrobenzo[f]imidazo[1,2-d][1,4]oxazepine-2-carboxamide

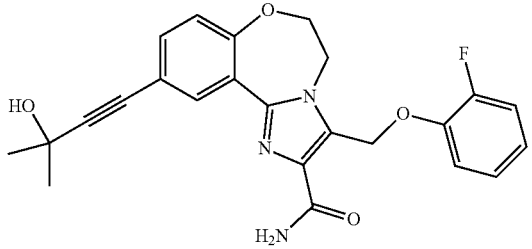

Similar to as described in General Procedure G, 10-bromo-3((2-fluorophenoxy)methyl)-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 2-fluorophenol) was reacted with 2-methylbut-3-yn-2-ol to give the titled compound as an off-white solid (7 mg, 6%).

M+1=436; $^1$H NMR (300 MHz, CD$_3$OD) δ 8.55 (d, J=2.1 Hz, 1H), 7.40-7.28 (m, 2H), 7.11-6.90 (m, 4H), 5.79 (s, 2H), 4.58-4.54 (m, 4H), 1.57 (s, 6H).

Example 279

Synthesis of 10-(3-hydroxy-3-methylbut-1-yn-1-yl)-3-((pyridin-2-yloxy)methyl)-5,6-dihydrobenzo[f]imidazo[1,2-d][1,4]oxazepine-2-carboxamide

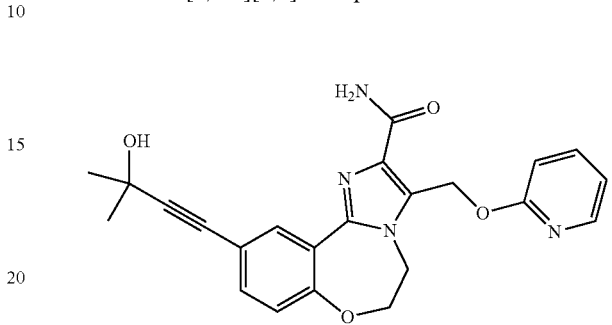

Similar to as described in General Procedure G, 10-bromo-3-((pyridin-2-yloxy)methyl)-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 2-pyridone) was reacted with 2-methylbut-3-yn-2-ol to give the titled compound as an off-white solid (5 mg, 5%).

M+1=419; $^1$H NMR (300 MHz, DMSO-d$_6$) δ 8.50 (d, J=2.4 Hz, 1H), 7.91 (d, J=6.9 Hz, 1H), 7.82 (s, 1H), 7.55-7.29 (m, 3H), 7.01 (d, J=8.4 Hz, 1H), 6.41 (d, J=8.4 Hz, 1H), 6.23 (t, J=6.3 Hz, 1H), 5.47 (d, J=10.8 Hz, 3H), 4.49 (d, J=3.0 Hz, 1H), 1.57 (s, 6H).

Example 280

Synthesis of 3-((1H-benzo[d]imidazol-1-yl)methyl)-10-(3-hydroxy-3-methylbut-1-yn-1-yl)-5,6-dihydrobenzo[f]imidazo[1,2-d][1,4]oxazepine-2-carboxamide

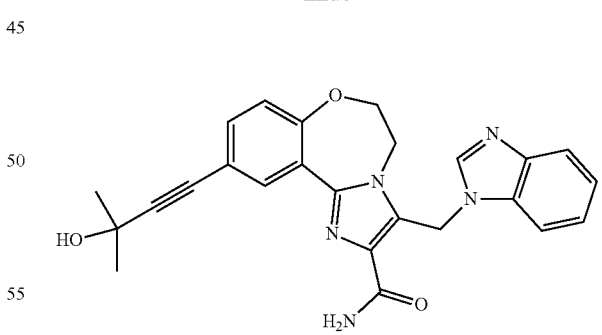

Similar to as described in General Procedure G, 3-((1H-benzo[d]imidazol-1-yl)methyl)-10-bromo-5,6-dihydrobenzo[f]imidazo[1,2-d][1,4]oxazepine-2-carboxamide (prepared similarly as described in the synthesis of 10-bromo-3((2-methyl-1H-imidazol-1-yl)methyl)-5,6-dihydrobenzo[f]imidazo[1,2-d][1,4]oxazepine-2-carboxamide replacing 2-methylimidazole with benzimidazole) was reacted with 2-methylbut-3-yn-2-ol to give the titled compound as an off-white solid (28 mg, 35%).

M+1=442; ¹H NMR (300 MHz, CD₃OD) δ 8.58 (d, J=2.1 Hz, 1H), 8.28 (s, 1H), 7.70-7.65 (m, 2H), 7.33-7.26 (m, 3H), 6.96 (d, J=8.7 Hz, 1H), 6.07 (s, 2H), 4.40 (t, J=3.9 Hz, 2H), 4.23 (t, J=3.9 Hz, 2H), 1.57 (s, 6H).

Example 281

Synthesis of 10-(3-hydroxy-3-methylbut-1-yn-1-yl)-3-((2-methyl-1H-benzo[d]imidazol-1-yl)methyl)-5,6-dihydrobenzo[f]imidazo[1,2-d][1,4]oxazepine-2-carboxamide

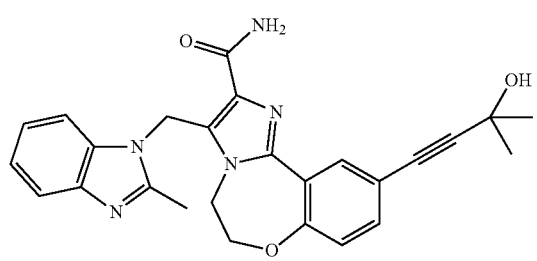 [SMILES: Cc1nc2ccccc2n1Cc1c(C(N)=O)nc2n1CCOc1ccc(C#CC(C)(C)O)cc1-2]

Similar to as described in General Procedure G, 10-bromo-3-((2-methyl-1H-benzo[d]imidazol-1-yl)methyl)-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 2-methylbenzimidazole) was reacted with 2-methylbut-3-yn-2-ol to give the titled compound as a colorless solid (26 mg, 24%).

M+1=456; ¹H NMR (300 MHz, CD₃OD) δ 8.59 (d, J=1.5 Hz, 1H), 7.59-7.56 (m, 1H), 7.40-7.21 (m, 4H), 6.94 (d, J=8.4 Hz, 1H), 6.10 (s, 2H), 4.28-4.26 (m, 2H), 3.95-3.94 (m, 2H), 2.62 (s, 3H), 1.57 (s, 6H).

Example 282

Synthesis of 3-((1H-indazol-1-yl)methyl)-10-(3-hydroxy-3-methylbut-1-yn-1-yl)-5,6-dihydrobenzo[f]imidazo[1,2-d][1,4]oxazepine-2-carboxamide

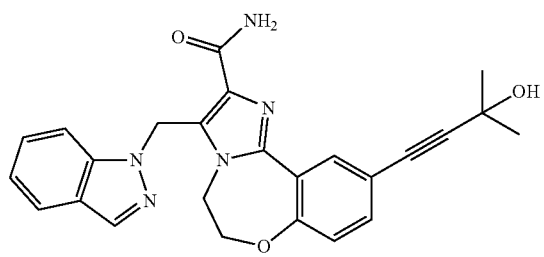 [SMILES: CC(C)(O)C#Cc1ccc2c(c1)-c1nc(C(N)=O)c(Cn3ncc4ccccc43)n1CCO2]

Similar to as described in General Procedure G, 3-((1H-indazol-1-yl)methyl)-10-bromo-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with indazole) was reacted with 2-methylbut-3-yn-2-ol to give the titled compound as a colorless solid (11 mg, 19%).

M+1=442; ¹H NMR (300 MHz, CD₃OD) δ 8.55 (s, 1H), 8.33 (s, 1H), 7.66 (d, J=8.4 Hz, 2H), 7.58 (d, J=8.7 Hz, 2H), 7.34-7.24 (m, 2H), 7.08-6.98 (m, 2H), 6.17 (s, 2H), 4.59-4.49 (m, 4H), 1.57 (s, 6H).

Example 283

Synthesis of 3-((6-cyano-1H-indazol-1-yl)methyl)-10-(3-hydroxy-3-methylbut-1-yn-1-yl)-5,6-dihydrobenzo[f]imidazo[1,2-d][1,4]oxazepine-2-carboxamide and 3-((6-cyano-2H-indazol-2-yl)methyl)-10-(3-hydroxy-3-methylbut-1-yn-1-yl)-5,6-dihydrobenzo[f]imidazo[1,2-d][1,4]oxazepine-2-carboxamide

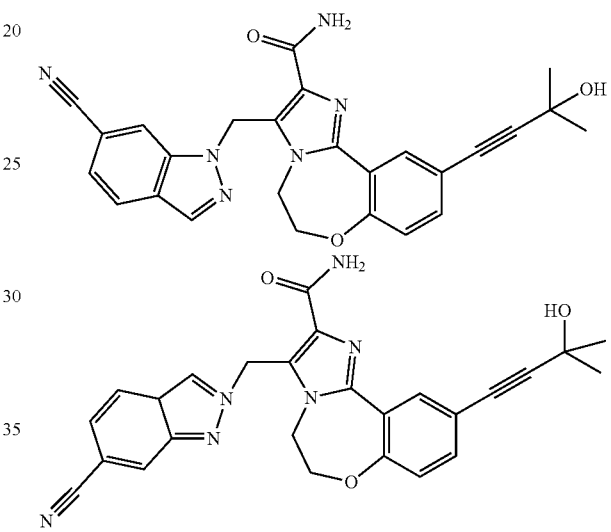

Similar to as described in General Procedure G, a mixture of 10-bromo-3-((6-cyano-1H-indazol-1-yl)methyl)-5,6-dihydrobenzo[f]imidazo[1,2-d][1,4]oxazepine-2-carboxamide and 10-bromo-3-((6-cyano-2H-indazol-2-yl)methyl)-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 6-cyanoindazole) was reacted with 2-methylbut-3-yn-2-ol to give two compounds (indazole 1- and 2-alkylation). The regio-chemistry of the two isomers was not determined.

Compound 1: white solid (13.7 mg, 27%); LC-MS (ES, m/z) 467[M+H]⁺; ¹H NMR (300 MHz, CD₃OD) δ 8.50 (d, J=2.1 Hz, 1H), 8.25 (s, 1H), 8.19 (s, 1H), 8.13 (s, 1H), 8.10 (s, 1H), 7.64 (d, J=7.2 Hz, 1H), 7.32 (d, J=6.3 Hz, 1H), 7.00 (d, J=8.7 Hz, 1H), 6.25 (s, 2H), 4.67-4.65 (m, 2H), 4.59 (s, 1H), 4.50-4.48 (m, 2H), 1.56 (s, 6H);

Compound 2: white solid (17.9 mg, 35%); LC-MS (ES, m/z) 511[M+HCOOH-1]⁺; ¹H NMR (300 MHz, DMSO-d₆) δ8.71 (s, 1H), 8.52 (s, 1H), 8.43 (s, 1H), 7.83 (s, 1H), 7.75 (d, J=9.0 Hz, 1H), 7.48 (s, 1H), 7.45 (s, 1H), 7.41 (s, 1H), 7.33-7.30 (m, 1H), 7.02 (d, J=8.4 Hz, 1H), 6.19 (s, 2H), 5.45 (s, 1H), 4.56 (d, J=7.8 Hz, 1H), 1.47 (s, 6H);

Example 284

Synthesis of 3-((1H-pyrazolo[3,4-b]pyridin-1-yl)methyl)-10-(3-hydroxy-3-methylbut-1-yn-1-yl)-5,6-dihydrobenzo[f]imidazo[1,2-d][1,4]oxazepine-2-carboxamide

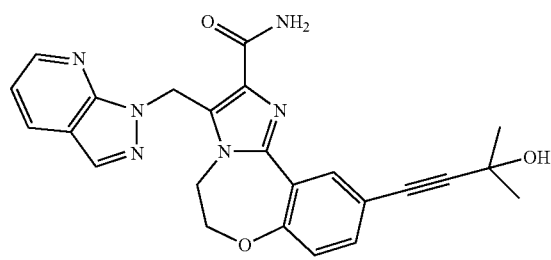 [SMILES: CC(C)(O)C#Cc1ccc2c(c1)-c1nc(C(N)=O)c(Cn3ncc4cccnc43)n1CCO2]

Similar to as described in General Procedure G, 3-((1H-pyrazolo[3,4-b]pyridin-1-yl)methyl)-10-bromo-5,6-dihydrobenzo[f]imidazo[1,2-d][1,4]oxazepine-2-carboxamide (prepared similarly as described in the synthesis of 10-bromo-3-((2-methyl-1H-imidazol-1-yl)methyl)-5,6-dihydrobenzo[f]imidazo[1,2-d][1,4]oxazepine-2-carboxamide replacing 2-methylimidazole with 6-azaindazole) was reacted with 2-methylbut-3-yn-2-ol to give the titled compound as a colorless solid (21 mg, 40%).

M+1=443; $^1$H NMR (300 MHz, CD$_3$OD) δ 8.61 (d, J=3.3 Hz, 1H), 8.58 (s, J=2.1 Hz, 1H), 8.24 (d, J=6.6 Hz, 2H), 8.08 (s, 1H), 7.34-7.25 (m, 2H), 6.99 (d, J=8.4 Hz, 1H), 6.255 (s, 2H), 4.43-4.41 (m, 2H), 4.35-4.32 (m, 2H), 1.58 (s, 6H).

Example 285

Synthesis of (R)-10-(3-hydroxy-3-(5-methylisoxazol-3-yl)but-1-yn-1-yl)-3-((2-methyl-1H-benzo[d]imidazol-1-yl)methyl)-5,6-dihydrobenzo[f]imidazo[1,2-d][1,4]oxazepine-2-carboxamide

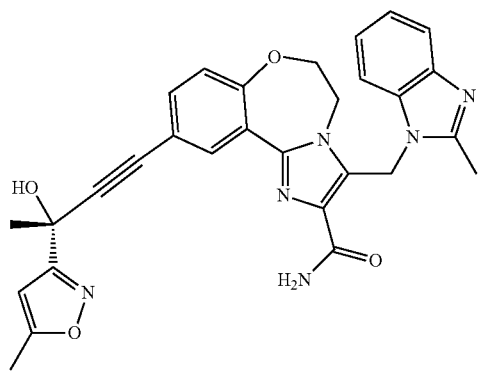 [SMILES: Cc1cc([C@](C)(O)C#Cc2ccc3c(c2)-c2nc(C(N)=O)c(Cn4c(C)nc5ccccc54)n2CCO3)no1]

Scheme for the synthesis of (R)-10-(3-hydroxy-3-(5-methylisoxazol-3-yl)but-1-yn-1-yl)-3-((2-methyl-1H-benzo[d]imidazol-1-yl)methyl)-5,6-dihydrobenzo[f]imidazo[1,2-d][1,4]oxazepine-2-carboxamide:

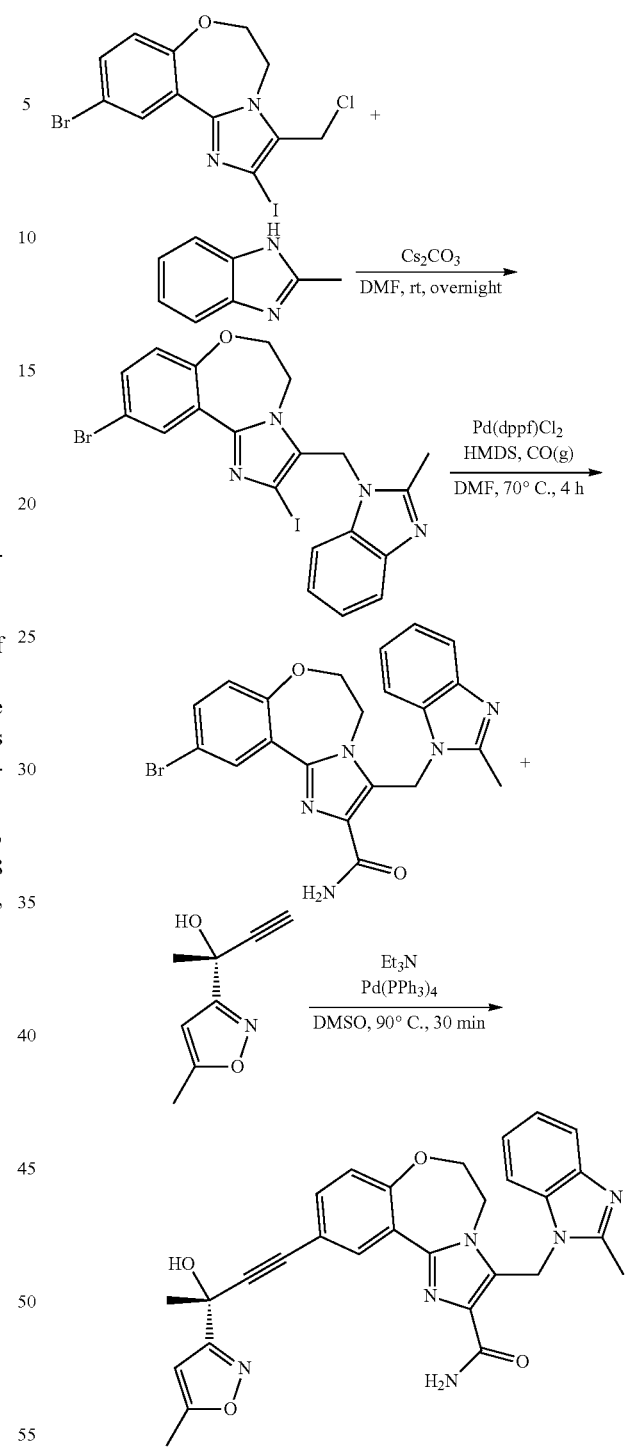

A mixture of 10-bromo-3-(chloromethyl)-2-iodo-5,6-dihydrobenzo[f]imidazo[1,2-d][1,4]oxazepine (200 mg, 0.46 mmol, 1.00 equiv), 2-methyl-1H-1,3-benzodiazole (304 mg, 2.30 mmol, 5.00 equiv), Cs$_2$CO$_3$ (450 mg, 1.38 mmol, 3.00 equiv) in N,N-dimethylformamide (2 mL) was stirred overnight at room temperature. The reaction mixture was diluted with water, extracted with ethyl acetate, dried over anhydrous sodium sulfate, and concentrated under vacuum. The residue was applied onto a silica gel column with dichloromethane/methanol (10:1). This resulted in 140 mg (57%) of 10-bromo- 2-iodo-3-((2-methyl-1H-benzo[d]imidazol-1-yl)methyl)-5,6-dihydrobenzo[f]imidazo[1,2-d][1,4]oxazepine as a colorless solid. Similar to Example 10 (carbonylative amidation) a 20-mL sealed tube purged and maintained with an inert atmosphere of CO(g), was placed a solution of 10-bromo-2-iodo-3-((2-methyl-1H-benzo[d]imidazol-1-yl)methyl)-5,6-dihydrobenzo[f]imidazo[1,2-d][1,4]oxazepine (140 mg, 0.26 mmol, 1.00 equiv), HMDS (105 mg, 0.65 mmol, 2.50 equiv), Pd(dppf)Cl$_2$ (21 mg, 0.10 equiv), and N,N-dimethylformamide (2 mL). The resulting solution was heated to 70° C. for 4 h and diluted with water. Then the resulting solution was extracted with ethyl acetate, dried over anhydrous sodium sulfate, and concentrated under vacuum. The residue was applied onto a silica gel column with dichloromethane/methanol (10:1). This resulted in 90 mg (76%) of 10-bromo-3-((2-methyl-1H-benzo[d]imidazol-1-yl)methyl)-5,6-dihydrobenzo[f]imidazo[1,2-d][1,4]oxazepine-2-carboxamide as a yellow solid. Similar to as described in General Procedure E with the exceptions of using Pd(PPh$_3$)$_4$ in DMSO, 10-bromo-3-((2-methyl-1H-benzo[d]imidazol-1-yl)methyl)-5,6-dihydrobenzo[f]imidazo[1,2-d][1,4]oxazepine-2-carboxamide was reacted with (R)-2-(5-methylisoxazol-3-yl)but-3-yn-2-ol to give the titled compound as a yellow solid (29 mg, 31%).

M+1=523; $^1$H NMR (400 MHz, CD$_3$OD) δ 8.66 (d, J=2.0 Hz, 1H), 7.59 (q, J=2.4 Hz, 1H), 7.43-7.31 (m, 2H), 7.26-7.20 (m, 2H), 6.97 (d, J=8.4 Hz, 1H), 6.32 (s, 1H), 6.11 (s, 1H), 4.30 (t, J=8 Hz, 2H), 3.96 (t, J=8 Hz, 2H), 2.63 (s, 3H), 1.90 (s, 3H).

Example 286

Synthesis of (R)-10-((3-hydroxy-1-methyl-2-oxopyrrolidin-3-yl)ethynyl)-3-((2-methyl-1H-benzo[d]imidazol-1-yl)methyl)-5,6-dihydrobenzo[f]imidazo[1,2-d][1,4]oxazepine-2-carboxamide

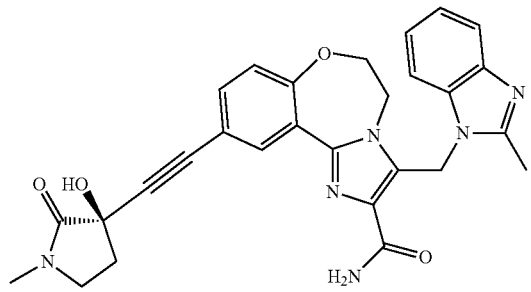

Similar to as described in General Procedure E with the exceptions of using Pd(PPh$_3$)$_4$ in DMSO, 10-bromo-3-((2-methyl-1H-benzo[d]imidazol-1-yl)methyl)-5,6-dihydrobenzo[f]imidazo[1,2-d][1,4]oxazepine-2-carboxamide was reacted with (R)-3-ethynyl-3-hydroxy-1-methylpyrrolidin-2-one to yield the titled compound as a yellow solid (21 mg, 19%).

M+1=511; $^1$H NMR (400 MHz, CD$_3$OD) δ 8.68 (d, J=2.0 Hz, 1H), 7.60-7.58 (m, 1H), 7.41-7.36 (m, 2H), 7.26-7.22 (m, 2H), 6.97 (d, J=8.4 Hz, 1H), 6.11 (s, 2H), 4.96-4.29 (m, 2H), 3.97-3.94 (m, 2H), 3.51-3.47 (m, 2H), 2.95 (s, 3H), 2.63 (s, 3H), 2.62-2.57 (m, 1H), 2.36-2.31 (m, 1H), 1.31 (s, 1H).

Example 287

Synthesis of (R)-3-((2-chlorophenoxy)methyl)-10-(3-hydroxy-3-(5-methylisoxazol-3-yl)but-1-yn-1-yl)-5,6-dihydrobenzo[f]imidazo[1,2-d][1,4]oxazepine-2-carboxamide

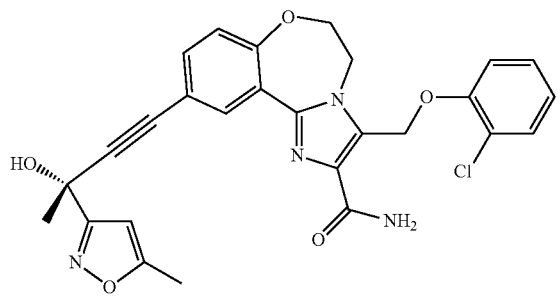 [SMILES: Cc1cc([C@](C)(O)C#Cc2ccc3c(c2)-c2nc(C(N)=O)c(COc4ccccc4Cl)n2CCO3)no1]

Similar to as in General Procedure E with the exceptions of using Pd(PPh$_3$)$_4$ in DMSO, 10-bromo-3-((2-chlorophenoxy)methyl)-5,6-dihydrobenzo[f]imidazo[1,2-d][1,4]oxazepine-2-carboxamide (prepared similarly to 10-bromo-3-((2-methyl-1H-benzo[d]imidazol-1-yl)methyl)-5,6-dihydrobenzo[f]imidazo[1,2-d][1,4]oxazepine-2-carboxamide replacing 2-methylbenzimidazole with 2-chlorophenol) was reacted with (R)-2-(5-methylisoxazol-3-yl)but-3-yn-2-ol to give the titled compound as a colorless solid (39 mg, 28%).

M+1=519; $^1$H NMR (300 MHz, CD$_3$OD) δ 8.62 (d, J=2.1 Hz, 1H), 7.43-7.35 (m, 3H), 7.29-7.23 (m, 1H), 7.04 (d, J=8.7 Hz, 2H), 6.98-6.92 (m, 1H), 6.32 (s, 1H), 5.79 (s, 2H), 4.62-4.53 (m, 4H), 2.45 (s, 3H), 1.89 (s, 3H).

Example 288

Synthesis of (R)-3-((2-chlorophenoxy)methyl)-10-((3-hydroxy-1-methyl-2-oxopyrrolidin-3-yl)ethynyl)-5,6-dihydrobenzo[f]imidazo[1,2-d][1,4]oxazepine-2-carboxamide

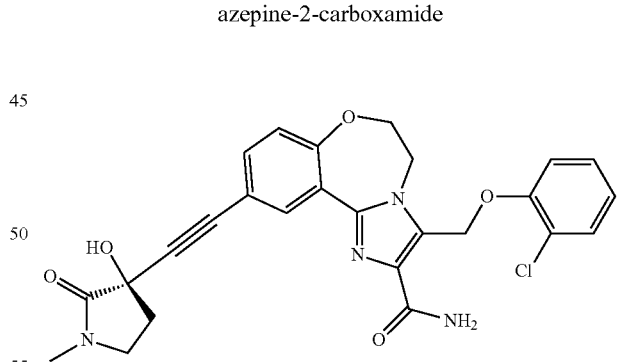

Similar to as described in General Procedure E with the exceptions of using Pd(PPh$_3$)$_4$ in DMSO, 10-bromo-3-((2-chlorophenoxy)methyl)-5,6-dihydrobenzo[f]imidazo[1,2-d][1,4]oxazepine-2-carboxamide was reacted with (R)-3-ethynyl-3-hydroxy-1-methylpyrrolidin-2-one to give the titled compound as a colorless solid (12 mg, 23%).

M+1=507; $^1$H NMR (300 MHz, CD$_3$OD) δ 8.63 (s, 1H), 7.48-7.35 (m, 3H), 7.26 (t, J=15.9 Hz 1H), 7.05 (d, J=8.7 Hz, 1H), 6.95 (t, J=15 Hz, 1H), 5.79 (s, 2H), 4.58 (d, J=12.6 Hz, 4H), 3.55-3.47 (m, 2H), 2.94 (s, 3H), 2.61-2.57 (m, 1H), 2.36-2.27 (m, 1H).

Example 289

Synthesis of (R)-3-(cyanomethyl)-104(3-hydroxy-1-methyl-2-oxopyrrolidin-3-yl)ethynyl)-5,6-dihydrobenzo[t]imidazo[1,2-d][1,4]oxazepine-2-carboxamide

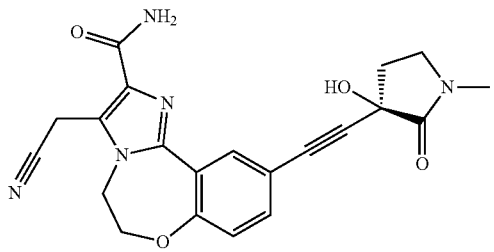 [SMILES: CN1CC[C@@](O)(C#Cc2ccc3c(c2)-c2nc(C(N)=O)c(CC#N)n2CCO3)C1=O]

Similar to as described in General Procedure G, (R)-methyl 3-(cyanomethyl)-104(3-hydroxy-1-methyl-2-oxopyrrolidin-3-yl)ethynyl)-5,6-dihydrobenzo[f]imidazo[1,2-d][1,4]oxazepine-2-carboxylate was reacted with (R)-3-ethynyl-3-hydroxy-1-methylpyrrolidin-2-one to give the titled compound after treatment of the methyl ester with ammonia.

M+1=406; $^1$H NMR (300 MHz, CD$_3$OD) 8.53 (s, 1H), 7.29 (dd, J=2.1, 8.4 Hz, 1H), 6.94 (d, J=8.7 Hz, 1H), 4.76-4.45 (m, 2H), 4.43-4.34 (m, 2H), 3.40-3.31 (m, 2H), 2.83 (s, 3H), 2.52-2.44 (m, 1H), 2.25-2.16 (m, 1H).

Example 290

Synthesis of (S)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide and (R)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide

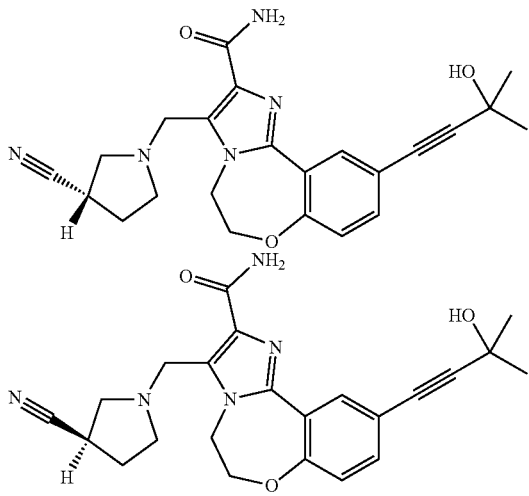

Similar to as described in General Procedure E with the exceptions of using Pd(PPh$_3$)$_4$ in DMSO, 10-bromo-3-((3-cyanopyrrolidin-1-yl)methyl)-5,6-dihydrobenzo[f]imidazo[1,2-d][1,4]oxazepine-2-carboxamide (prepared similarly to 10-bromo-3-((2-methyl-1H-benzo[d]imidazol-1-yl)methyl)-5,6-dihydrobenzo[f]imidazo[1,2-d][1,4]oxazepine-2-carboxamide replacing 2-methylbenzimidazole with racemic 3-cyanopyrrolidine) was reacted with 2-methylbut-3-yn-2-ol to give a mixture of the titled compounds. The racemic mixture (25 mg) was separated by Chiral-Prep-HPLC with the following conditions (Prep-HPLC-004): Column, Phenomenex Lux 5u Cellulose-4, 2.12*25, 5 um; mobile phase, Hex and ethanol (hold 18.0% ethanol in 37 min); Detector, uv 254/220 nm. This gave 9.7 mg (40%) of Compound 1 and 7.8 mg (32%) of Compound 2. The stereochemistry of both isomers was arbitrarily assigned.

Compound 1: colorless; $t_R$ 22.3 min (Lux cellulose-4, 25° C., UV-254 nm Hex (0.1% TEA):EtOH=80:20, 1.0 ml/min); LC-MS 420[M+H]$^+$; $^1$H NMR (400 MHz, CD$_3$OD) δ 8.54 (s, 1H), 7.34 (dd, J=0.8, 7.2 Hz 1H), 7.03 (d, J=8.4 Hz, 1H), 4.61-4.52 (m, 4H), 4.21 (dd, J=13.6, 18.8 Hz 2H), 3.19-3.02 (m, 2.90-2.84 (m, 2H), 2.66-2.60 (m, 1H), 2.24-2.10 (m, 1H), 1.89-2.00 (m, 1H), 1.49 (s, 6H).

Compound 2: colorless solid; $t_R$ 26.4 min (Lux cellulose-4, 25° C., UV-254 nm Hex (0.1% TEA):EtOH=80:20, 1.0 ml/min); LC-MS 420[M+H]$^+$; NMR (400 MHz, CD$_3$OD) δ 8.54 (s, 1H), 7.34 (d, J=8.8 Hz 1H), 7.03 (d, J=8.8 Hz, 1H), 4.61-4.52 (m, 4H), 4.21 (dd, J=13.6, 19.2 Hz, 2H), 3.21-3.15 (m, 1H), 2.90-2.84 (m, 2H), 2.66-2.60 (m, 1H), 2.35-2.10 (m, 1H), 2.09-2.05 (m, 1H), 1.49 (s, 6H).

Example 291

Synthesis of 10-(3-hydroxy-3-methylbut-1-yn-1-yl)-3-((3-oxopyrrolidin-1-yl)methyl)-5,6-dihydrobenzo[f]imidazo[1,2-d][1,4]oxazepine-2-carboxamide

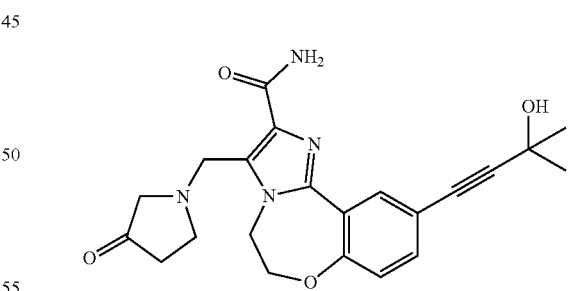

Similar to as described in General Procedure G, 10-bromo-3-((3-oxopyrrolidin-1-yl)methyl)-5,6-dihydrobenzo[f]imidazo[1,2-d][1,4]oxazepine-2-carboxamide was reacted with 2-methylbut-3-yn-2-ol to give the titled compound as a yellow solid (34.0 mg, 31%).

M+1=409; $^1$H-NMR (300 MHz, CD$_3$OD) δ 8.55 (d, J=2.1 Hz, 1H), 7.33 (dd, J=2.1, 8.4 Hz 1H), 7.01 (d, J=8.4 Hz, 1H), 4.55-4.49 (m, 4H), 4.26 (s, 2H), 3.04-3.00 (m, 4H), 2.38 (t, J=6.9 Hz, 1H), 1.58 (s, 6H).

Example 292

Synthesis of (R)-3((3-fluoropyrrolidin-1-yl)methyl)-10-(3-hydroxy-3-methylbut-1-yn-1-yl)-5,6-dihydrobenzo[f]imidazo[1,2-d][1,4]oxazepine-2-carboxamide and (S)-3-((3-fluoropyrrolidin-1-yl)methyl)-10-(3-hydroxy-3-methylbut-1-yn-1-yl)-5,6-dihydrobenzo[f]imidazo[1,2-d][1,4]oxazepine-2-carboxamide

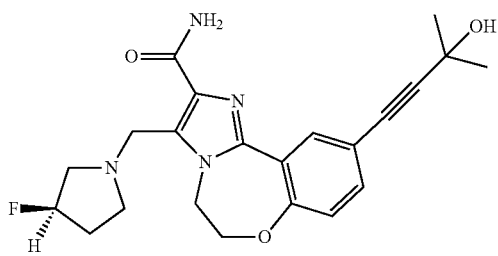

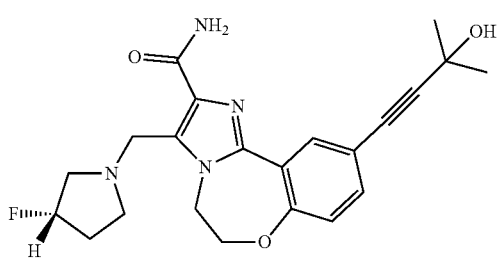

Similar to as described in General Procedure G, 10-bromo-3-((3-fluoropyrrolidin-1-yl)methyl)-5,6-dihydrobenzo[f]imidazo[1,2-d][1,4]oxazepine-2-carboxamide was reacted with 2-methylbut-3-yn-2-ol to give a mixture of the titled compounds. The racemic mixture was separated by chiral-prep-HPLC with the following conditions (2#-Gilson Gx 281 (HPLC-04)):Column, Phenomenex Lux 5u Cellulose-4, 2.12*25, 5 um; mobile phase, Hex and ethanol (hold 30.0% ethanol in 21 min); Detector, uv 254/220 nm. This resulted in 42.5 mg (41%) of Compound 1 and 33.4 mg (33%) of Compound 2. The stereochemistry of both isomers is arbitrarily assigned.

Compound 1: chiral HPLC retention time 7.550 min.; light yellow solid; LC-MS 413[M+H]$^+$; $^1$H NMR (300 MHz, CD$_3$OD) δ 8.53 (d, J=1.8 Hz, 1H), 7.33 (d, J=8.4 Hz 1H), 7.01 (d, J=8.7 Hz, 1H), 5.13 (d, J=25.2 Hz, 1H), 4.55-4.50 (m, 4H), 4.18 (s, 2H), 2.98-2.67 (m, 3H), 2.54-2.47 (m, 1H), 2.24-1.78 (m, 2H), 1.57 (s, 6H).

Compound 2: chiral HPLC retention time 9.165 min.; light yellow solid; LC-MS 413[M+H]$^+$; $^1$H NMR (300 MHz, CD$_3$OD) δ 8.53 (d, J=1.8 Hz, 1H), 7.33 (d, J=8.4 Hz 1H), 7.01 (d, J=8.7 Hz, 1H), 5.13 (d, J=25.2 Hz, 1H), 4.55-4.50 (m, 4H), 4.18 (s, 2H), 2.98-2.67 (m, 3H), 2.54-2.47 (m, 1H), 2.24-1.78 (m, 2H), 1.57 (s, 6H).

Example 293

Synthesis of (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide

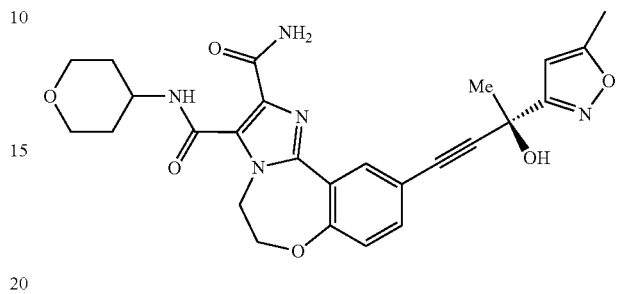

Similar to as described in Example 10 (carbonylative amidation) a mixture of 10-bromo-3-iodo-5,6-dihydrobenzo[f]imidazo[1,2-d][1,4]oxazepine-2-carboxamide (200 mg, 0.46 mmol, 1.00 equiv), 4-aminotetrahydropyran hydrochloride (126 mg, 0.92 mmol, 2.00 equiv), Pd(dppf)Cl$_2$ (34 mg, 0.05 mmol, 0.10 equiv), TEA (202 mg, 2.00 mmol, 4.00 equiv), and DMSO (5 mL) was stirred at 40° C. under an atmosphere of CO(g) overnight. The reaction was quenched with water and the solids were collected. This resulted in 250 mg (crude) of 10-bromo-N3-(tetrahydro-2H-pyran-4-yl)-5,6-dihydrobenzo[f]imidazo[1,2-d][1,4]oxazepine-2,3-dicarboxamide as a brown solid. Similar to as described General Procedure F, 10-bromo-N3-(tetrahydro-2H-pyran-4-yl)-5,6-dihydrobenzo[f]imidazo[1,2-d][1,4]oxazepine-2,3-dicarboxamide was reacted with (2R)-2-(5-methyl-1,2-oxazol-3-yl)but-3-yn-2-ol to give the titled compound as an off-white solid (38.6 mg, 6.6%).

M+1=506; $^1$H NMR (300 MHz, CD$_3$OD) δ 8.60 (d, J=1.8 Hz, 1H), 7.42-7.46 (m, 1H), 7.05 (d, J=8.4 Hz, 1H), 6.32 (s, 1H), 5.01-5.03 (m, 2H), 4.52-4.55 (m, 2H), 3.96-4.08 (m, 3H), 3.54-3.61 (m, 2H), 2.46 (s, 3H), 1.96-2.00 (m, 2H), 1.89 (s, 3H), 1.59-1.7 (m, 2H).

Example 294

Synthesis of (R)—N3-(3-fluorobenzyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide

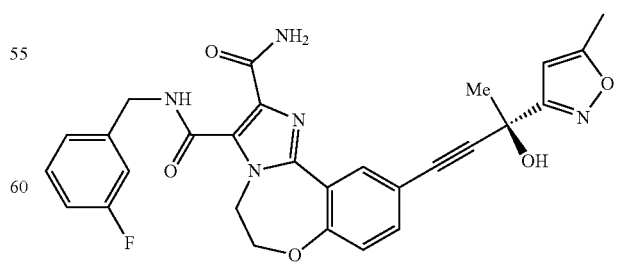

Prepared as described for (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3- dicarboxamide replacing oxan-4-amine hydrochloride with 3-fluorobenzylamine. off-white solid (45.4 mg, 5%).

M+1=530; ¹H NMR (300 MHz, CDCl₃) δ 11.72-11.76 (m, 1H), 8.44 (s, 1H), 7.75 (d, J=3.6 Hz, 1H), 7.33-7.41 (m, 1H), 7.28-7.31 (m, 1H), 7.10-7.16 (m, 2H), 6.92-7.07 (m, 2H), 6.16 (s, 1H), 5.72 (d, J=2.7 Hz, 1H), 5.15 (d, J=8.4 Hz, 2H), 4.58 (d, J=5.7 MHz, 2H), 4.47-4.49 (m, 2H), 3.17 (s, 1H), 2.44 (s, 3H), 1.96 (s, 3H).

Example 295

Synthesis of (R)—N3-(tert-butyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide

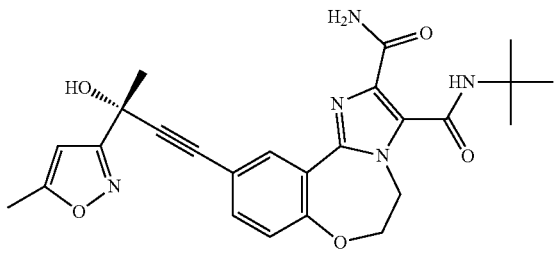 [SMILES: Cc1cc([C@](C)(O)C#Cc2ccc3c(c2)-c2nc(C(N)=O)c(C(=O)NC(C)(C)C)n2CCO3)no1]

Prepared as described for (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing oxan-4-amine hydrochloride with tert-butylamine hydrochloride. off-white solid (58.7 mg, 25%).

M+1=482; ¹H NMR (300 MHz, CDCl₃) δ 10.94 (s, 1H), 8.45-8.46 (d, J=2.1 Hz, 1H), 7.78-7.79 (d, J=3Hz, 1H), 7.39-7.43 (m, 1H), 6.99-7.02 (d, J=8.4 Hz, 1H), 6.18 (s, 1H), 5.68-5.69 (d, J=2.1 Hz, 1H), 5.13-5.16 (m, 2H), 4.50-4.53 (m, 2H), 2.46 (s, 3H), 1.97 (s, 3H), 1.48 (s, 9H).

Example 296

Synthesis of (R)-10-(3-hydroxy-3-(5-methylisoxazol-3-yl)but-1-yn-1-yl)-N3-(oxetan-3-ylmethyl)-5,6-dihydrobenzo[f]imidazo[1,2-d][1,4]oxazepine-2,3-dicarboxamide

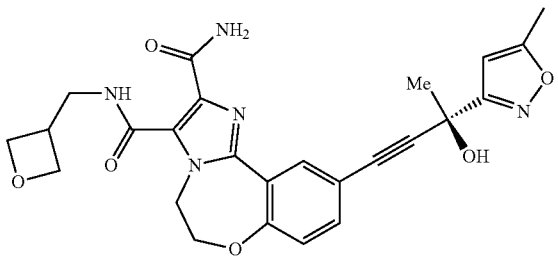 [SMILES: Cc1cc([C@](C)(O)C#Cc2ccc3c(c2)-c2nc(C(N)=O)c(C(=O)NCC4COC4)n2CCO3)no1]

Prepared as described for (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing oxan-4-amine hydrochloride with 3-methylaminooxetane hydrochloride. off-white solid (6.7 mg, 2%).

M+1=392; ¹H NMR (300 MHz, CD₃OD) δ 8.59 (d, J=1.8 Hz, 1H), 7.42-46 (m, 1H), 7.05 (d, J=8.7 Hz, 1H), 6.32 (s, 1H), 5.00-5.02 (m, 2H), 4.82-99(m, 2H), 4.51-4.55 (m, 4H), 3.67-3.69 (m, 2H), 3.22-3.29 (m, 1H), 2.42 (s, 3H), 1.89 (s, 3H).

Example 297

Synthesis of (R)-10-(3-hydroxy-3-(5-methylisoxazol-3-yl)but-1-yn-1-yl)-N3-(pyridin-3-ylmethyl)-5,6-dihydrobenzo[f]imidazo[1,2-d][1,4]oxazepine-2,3-dicarboxamide

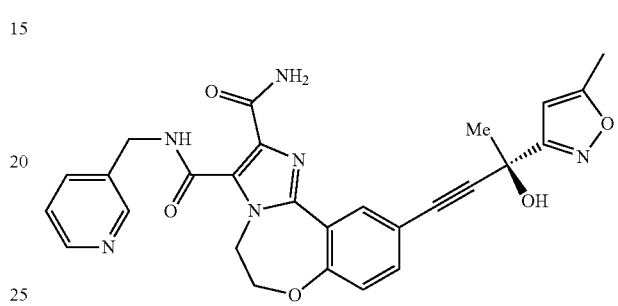

Prepared as described for (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing oxan-4-amine hydrochloride with 3-(methylamino)pyridine. off-white solid (26.4 mg, 9%).

M+1=513; ¹H NMR (300 MHz, CDCl₃) δ 8.68 (s, 1H), 8.55 (d, J=4.2 Hz, 1H), 8.47 (s, 1H), 7.90 (d, J=7.5 Hz, 1H), 7.78 (s, 1H), 7.32-7.42 (m, 2H), 7.00 (d, J=8.4 Hz, 1H), 6.17 (s, 1H), 5.71 (s, 1H), 5.12-5.15 (m, 2H), 4.65 (d, J=5.4 Hz, 2H), 4.49-4.51 (m, 2H), 2.45 (s, 3H), 1.96 (s, 3H).

Example 298

Synthesis of (R)-10-(3-hydroxy-3-(5-methylisoxazol-3-yl)but-1-yn-1-yl)-N3-((tetrahydro-2H-pyran-4-yl)methyl)-5,6-dihydrobenzo[f]imidazo[1,2-d][1,4]oxazepine-2,3-dicarboxamide

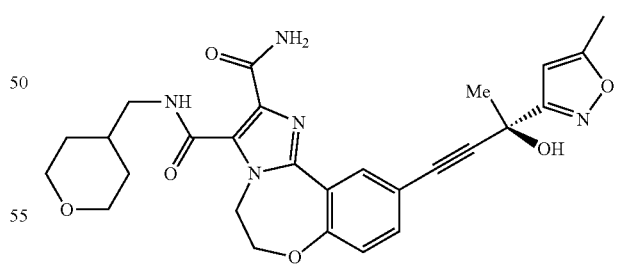

Prepared as described for (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with 4-(methylamino)tetrahydropyran. Off-white solid (19.4 mg, 7%).

M+1=520; ¹H NMR (300 MHz, CD₃OD) δ 8.59 (d, J=1.8 Hz, 1H), 7.43-7.46 (m, 1H), 7.07 (d, J=8.4 Hz, 1H), 6.32 (s, 1H), 5.01-5.03 (m, 2H), 4.52-4.62 (m, 2H), 3.95-4.00 (m,

2H), 3.32-3.36 (m, 2H), 3.09-3.29 (m, 2H), 2.46 (s, 3H), 1.89 (s, 4H), 1.75 (d, J=12.9 Hz, 2H), 1.31-1.1.45 (m, 2H).

Example 299

Synthesis of (R)—N3-(4,4-difluorocyclohexyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide

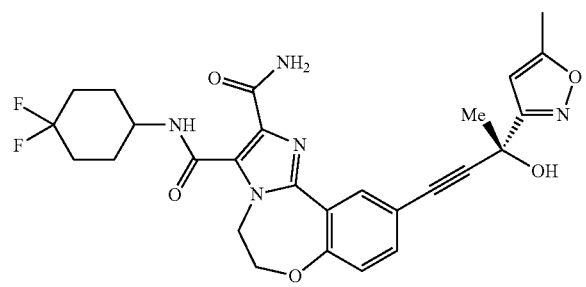 [SMILES: Cc1cc([C@](C)(O)C#Cc2ccc3c(c2)-c2nc(C(N)=O)c(C(=O)NC4CCC(F)(F)CC4)n2CCO3)no1]

Prepared as described for (R)-10-(3-hydroxy-3-(5-methyl-isoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with 4-amino-1,1-difluorocyclohexane hydrochloride. Off-white solid 40.2 mg, 12%).

M+23=562.1 (M+Na); $^1$H NMR (300 MHz, CD$_3$OD) δ 11.39 (d, J=6.3 Hz, 1H), 8.45 (s, 1H), 7.77 (s, 1H), 7.41 (d, J=8.4 Hz, 1H), 7.01 (d, J=8.4 Hz, 1H), 6.17 (s, 1H), 5.69 (s, 1H), 5.15 (s, 2H), 4.51 (s, 2H), 4.07 (s, 1H), 2.46 (s, 3H), 2.10-2.17 (m, 2H), 1.89-2.07 (m, 7H), 1.80-1.86 (m, 2H).

Example 300

Synthesis of 104(R)-3-hydroxy-3-(5-methylisoxazol-3-yl)but-1-yn-1-yl)-N3-((S)-tetrahydrofuran-3-yl)-5,6-dihydrobenzo[f]imidazo[1,2-d][1,4]oxazepine-2,3-dicarboxamide

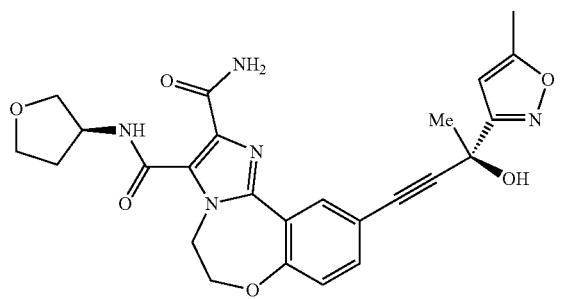 [SMILES: Cc1cc([C@](C)(O)C#Cc2ccc3c(c2)-c2nc(C(N)=O)c(C(=O)N[C@H]4CCOC4)n2CCO3)no1]

Prepared as described for (R)-10-(3-hydroxy-3-(5-methyl-isoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with (S)-3-aminotetrahydrofuran. Off-white solid 11.7 mg, 3%).

M+1=492; $^1$H NMR (300 MHz, CD$_3$OD) δ 8.65 (s, 1H), 7.43-7.46 (m, 1H), 7.06 (d, J=8.7 Hz, 1H), 6.32 (s, 1H), 5.00-5.03 (m, 2H), 4.52-4.90 (m, 3H), 3.75-4.02 (m, 4H), 2.46 (s, 3H), 2.25-2.35 (m, 1H), 1.95-2.05 (m, 1H), 1.89 (s, 3H).

Example 301

Synthesis of 104(R)-3-hydroxy-3-(5-methylisoxazol-3-yl)but-1-yn-1-yl)-N3-((R)-tetrahydrofuran-3-yl)-5,6-dihydrobenzo[f]imidazo[1,2-d][1,4]oxazepine-2,3-dicarboxamide

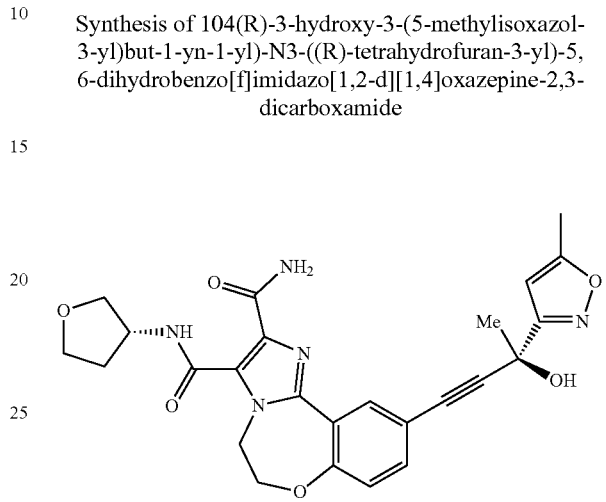

Prepared as described for (R)-10-(3-hydroxy-3-(5-methyl-isoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with (R)-3-aminotetrahydrofuran. Off-white solid 48.3 mg, 13%).

M+1=492; $^1$H NMR (300 MHz, CD$_3$OD) δ 8.60 (d, J=1.2 Hz, 1H), 7.43-7.46 (m, 1H), 7.06 (d, J=6.3 Hz, 1H), 6.33 (s, 1H), 5.01-5.03 (m, 2H), 4.52-4.90 (m, 3H), 3.75-4.03 (m, 4H), 2.46 (s, 3H), 2.26-2.36 (m, 1H), 2.00-2.02 (m, 1H), 1.99 (s, 3H).

Example 302

Synthesis of 10-((R)-3-hydroxy-3-(5-methylisoxazol-3-yl)but-1-yn-1-yl)-N3-(((R)-tetrahydrofuran-3-yl)methyl)-5,6-dihydrobenzo imidazo[1,2-d][1,4]oxazepine-2,3-dicarboxamide and 10-((R)-3-hydroxy-3-(5-methylisoxazol-3-yl)but-1-yn-1-yl)-N3-(((S)-tetrahydrofuran-3-yl)methyl)-5,6-dihydrobenzo[f]imidazo[1,2-d][1,4]oxazepine-2,3-dicarboxamide

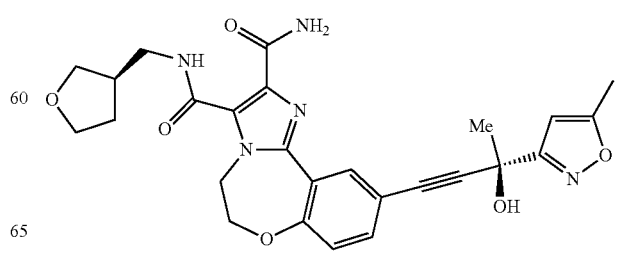

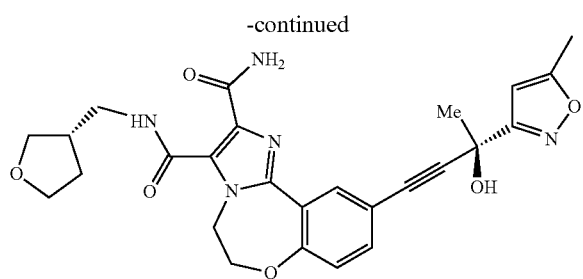

Prepared as described for (R)-10-(3-hydroxy-3-(5-methyl-isoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with racemic 3-methylaminotetrahydrofuran. The diasteromeric mixture was separated by Chiral Prep-HPLC with the following conditions (Prep-HPLC-009) Column, Chiralpak IC, 0.46*25 cm, 5 um; mobile phase, DCM:IPA=90:10; Detector, uv 254/220 nm. This resulted in 38.7 mg (14%) of Compound 1 and 37.2 mg (13%) of Compound 2. The stereochemistry at the tetrahydrofuran stereocenter for each isomer was not determined.

Compound 1: off-white solid; $t_R$=8.696 min (Lux cellulose-4, 25° C., UV-254 nm DCM:IPA=90:10, 1.0 ml/min; LC-MS (ES, m/z) 506.25 [M+H]$^+$; NMR (300 MHz, CD$_3$OD) δ 8.60 (d, J=1.5 Hz, 1H), 7.43-7.45 (m, 1H), 7.06 (d, J=6.3 Hz, 1H), 6.33 (s, 1H), 5.00-5.02 (m, 2H), 4.52-4.54 (m, 2H), 3.90-3.93 (m, 2H), 3.74-3.88 (m, 1H), 3.58-3.62 (m, 1H), 3.29-3.46 (m, 2H), 2.55-2.62 (m, 1H), 2.46 (s, 3H), 2.11-2.18 (m, 1H), 1.89 (s, 3H), 1.69-1.78 (m, 1H).

Compound 2: off-white solid; $t_R$=11.955 min (CHIRLPAK IA-3, 25° C., UV-254 nm Hex:EtOH=75:25, 1.0 ml/min); LC-MS (ES, m/z) 506.25 [M+H]$^+$; $^1$H NMR (300 MHz, CD$_3$OD) δ 8.60 (d, J=1.5 Hz, 1H), 7.43-7.45 (m, 1H), 7.06 (d, J=6.3 Hz, 1H), 6.33 (s, 1H), 5.00-5.02 (m, 2H), 4.52-4.54 (m, 2H), 3.90-3.93 (m, 2H), 3.74-3.88 (m, 1H), 3.58-3.62 (m, 1H), 3.29-3.46 (m, 2H), 2.55-2.62 (m, 1H), 2.46 (s, 3H), 2.11-2.18 (m, 1H), 1.89 (s, 3H), 1.69-1.78 (m, 1H).

Example 303

Synthesis of (R)-10-(3-hydroxy-3-(5-methylisoxazol-3-yl)but-1-yn-1-yl)-N3-(2-methyl-1-morpholinopropan-2-yl)-5,6-dihydrobenzo[f]imidazo[1,2-d][1,4]oxazepine-2,3-dicarboxamide

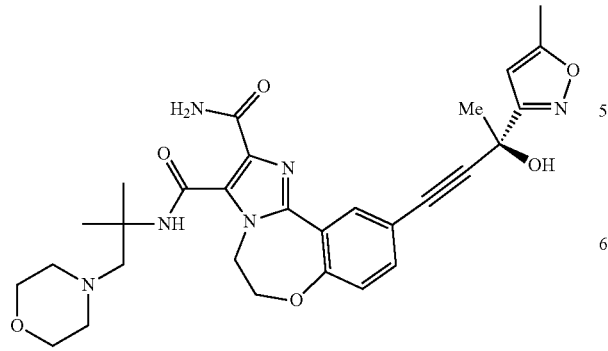

Prepared as described for (R)-10-(3-hydroxy-3-(5-methyl-isoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide replacing 4-aminotetrahydropyran with 2-methyl-1-morpholinopropan-2-amine. Off-white solid 20 mg, 12%).

M+1=503; $^1$H NMR (300 MHz, CD$_3$OD) δ 11.82 (s, 1H), 9.34 (d, J=1.8 Hz, 1H), 9.13 (s, 1H), 8.68 (s, 1H), 8.19-8.23 (m, 1H), 7.86 (d, J=8.4 Hz, 1H), 7.31 (s, 1H), 7.17 (s, 1H), 5.72 (d, J=5.1 Hz, 2H), 5.32 (d, J=5.1 Hz, 2H), 4.32-4.35 (m, 4H), 3.42 (s, 2H), 3.28-3.31 (m, 4H), 3.22 (s, 3H), 2.61 (s, 3H), 2.15 (s, 6H).

Example 303.1

Synthesis of 10-bromo-6-(hydroxymethyl)-5,6-dihydrobenzo[f]imidazo[1,2-d][1,4]oxazepine-2-carboxamide

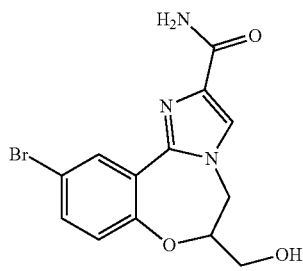 [SMILES: NC(=O)c1cn2c(n1)-c1cc(Br)ccc1OC(CO)C2]

The synthetic scheme for making 10-bromo-6-(hydroxymethyl)-5,6-dihydrobenzo[f]imidazo[1,2-d][1,4]oxazepine-2-carboxamide is:

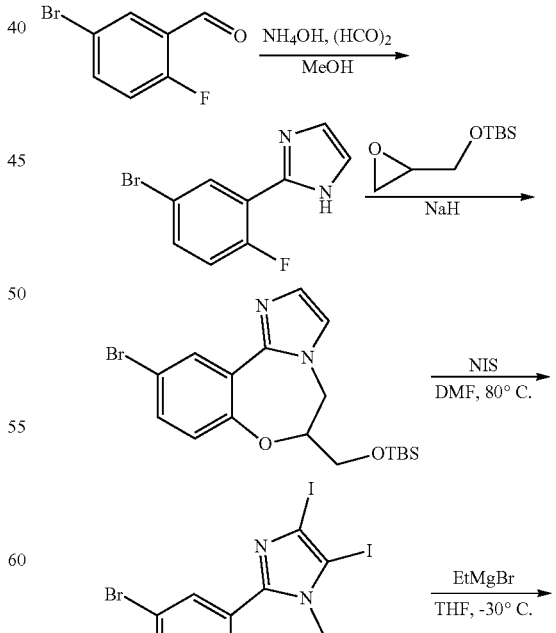

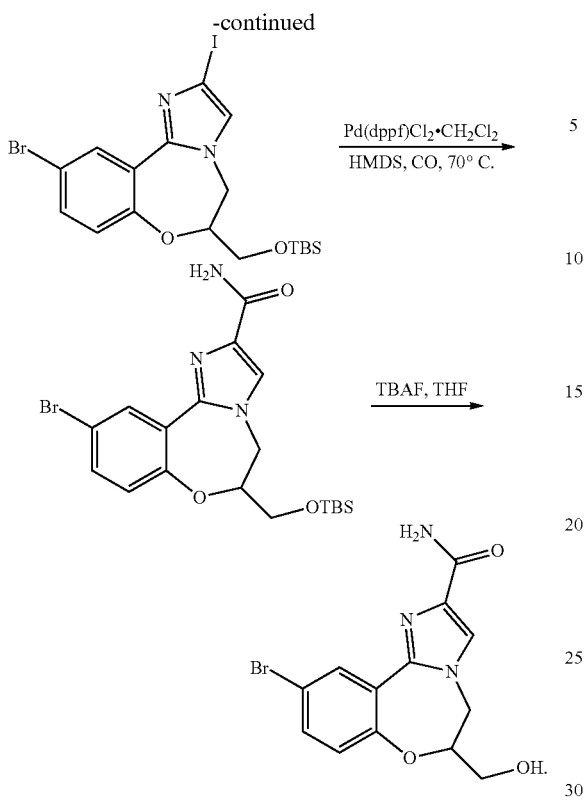

NH$_4$OH (580 g, 34.12 mol, 20.00 equiv) and C$_2$H$_2$O$_2$ (288 g, 4.97 mol, 4.00 equiv) was added sequentially in batches to a stirred solution of 5-bromo-2-fluorobenzaldehyde (100 g, 492.59 mmol, 1.00 equiv) in methanol (500 mL) at 0° C. The resulting solution was stirred overnight at room temperature and concentrated under vacuum. The residue was mixed with DCM, washed with brine, dried over anhydrous sodium sulfate, and concentrated under vacuum. The residue was applied onto a silica gel column with ethyl acetate/petroleum ether (1:4). This resulted in 50 g of 2-(5-bromo-2-fluorophenyl)-1H-imidazole as a yellow solid.

Sodium hydride (1.33 g, 55.42 mmol, 1.10 equiv) was added in batches to a stirred solution of 2-(5-bromo-2-fluorophenyl)-1H-imidazole (12.2 g, 50.61 mmol, 1.00 equiv) in N,N-dimethylformamide (148 g, 2.02 mol, 40.00 equiv) at 0° C. t-butyldimethyl(oxiran-2-ylmethoxy)silane (11.4 g, 60.53 mmol, 1.20 equiv) was added dropwise to the solution at 0° C. The resulting mixture was heated to 95° C. for 6 h and 90° C. for 2 days. The reaction was then quenched with aqueous NH$_4$Cl, extracted with ethyl acetate, dried over anhydrous sodium sulfate and concentrated under vacuum. The residue was applied onto a silica gel column with ethyl acetate/petroleum ether (1:3). This resulted in 6.8 g (33%) of 10-bromo-6-(((tert-butyldimethylsilyl)oxy)methyl)-5,6-dihydrobenzo[f]imidazo[1,2-d][1,4]oxazepine as a yellow solid.

10-bromo-6-(((tert-butyldimethylsilyl)oxy)methyl)-5,6-dihydrobenzo[f]imidazo[1,2-d][1,4]oxazepine-2-carboxamide was prepared from 10-bromo-6-(((tert-butyldimethylsilyl)oxy)methyl)-5,6-dihydrobenzo[f]imidazo[1,2-d][1,4]oxazepine using the same procedures as outlined for the synthesis of methyl 2-chloro-6,7-dihydroimidazo[1,2-d]pyrido[3,2-b][1,4]oxazepine-9 carboxylate. TBAF (1.7 g, 6.50 mmol, 2.00 equiv) was added in several batches to a stirred solution of this intermediate (1.6 g, 3.54 mmol, 1.00 equiv) in tetrahydrofuran (7 mL) at room temperature. After 1 h the resulting solution was diluted with ethyl acetate, washed with water and brine, dried over anhydrous sodium sulfate and concentrated under vacuum.

10-bromo-6-(hydroxymethyl)-5,6-dihydrobenzo[f]imidazo[1,2-d][1,4]oxazepine-2-carboxamide as a gray solid.

Example 304

Synthesis of (R)-10-(3-hydroxy-3-methylbut-1-yn-1-yl)-6-(hydroxymethyl)-5,6-dihydrobenzo[f]imidazo[1,2-d][1,4]oxazepine-2-carboxamide and (S)-10-(3-hydroxy-3-methylbut-1-yn-1-yl)-6-(hydroxymethyl)-5,6-dihydrobenzo[f]imidazo[1,2-d][1,4]oxazepine-2-carboxamide

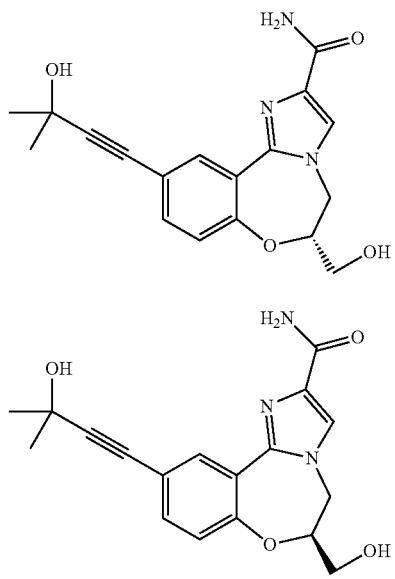 [SMILES: CC(C)(O)C#Cc1ccc2c(c1)-c1nc(C(N)=O)cn1C[C@H](CO)O2 ; CC(C)(O)C#Cc1ccc2c(c1)-c1nc(C(N)=O)cn1C[C@@H](CO)O2]

Similar to as described in General Procedure G, racemic 10-bromo-6-(hydroxymethyl)-5,6-dihydrobenzo[f]imidazo[1,2-d][1,4]oxazepine-2-carboxamide was reacted with 2-methylbut-3-yn-2-ol to give a mixture of the titled compounds. The racemate was separated by chiral Prep-HPLC. The absolute stereochemistry of each isomer was not determined.

Compound 1: chiral HPLC retention time 13.264 min.; off-white solid (17.6 mg, 9%); M+1=342; $^1$H NMR (300 MHz, DMSO-d6) δ 8.41 (d, J=2.1 Hz, 1H), 7.81 (s, 1H), 7.53 (s, 1H), 7.31 (q, J=6.6 Hz, 1H), 7.14 (s, 1H), 7.04 (d, J=8.7 Hz, 1H), 4.63 (d, J=12.9 Hz, 1H), 4.30-4.21 (m, 2H), 3.78-3.72 (dd, 1H), 3.67-3.62 (dd, 1H), 1.47 (s, 6H).

Compound 2: chiral HPLC retention time 19.880 min.; off-white solid (16 mg, 9%); M+1=342; $^1$H NMR (300 MHz, DMSO-d6) δ (8.41 (d, J=2.1 Hz, 1H), 7.81 (s, 1H), 7.53 (s, 1H), 7.31 (q, J=6.3 Hz, 1H), 7.14 (s, 1H), 7.04 (d, J=8.4 Hz, 1H), 5.46 (s, 1H), 5.22 (t, J=5.7 Hz, 1H), 4.62 (d, J=13.2 Hz, 1H), 4.30-4.21 (m, 2H), 3.77-3.63 (m, 2H), 1.48 (s, 6H).

Example 305

Synthesis of (±)-10-(3-hydroxy-3-(5-methylisoxazol-3-yl)but-1-yn-1-yl)-6-(hydroxymethyl)-5,6-dihydrobenzo[f]imidazo[1,2-d][1,4]oxazepine-2-carboxamide

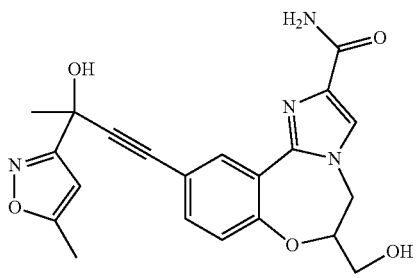 [SMILES: Cc1cc(C(C)(O)C#Cc2ccc3c(c2)-c2nc(C(N)=O)cn2CC(CO)O3)no1]

Similar to as described in General Procedure G, racemic 10-bromo-6-(hydroxymethyl)-5,6-dihydrobenzo[f]imidazo[1,2-d][1,4]oxazepine-2-carboxamide was reacted with racemic 2-(5-methyl-1,2-oxazol-3-yl)but-3-yn-2-ol to give the titled compound as a yellow solid (mixture of diasteromers, 98 mg, 40%).

M+1=409; $^1$H NMR (300 MHz, DMSO-d6) δ 8.44 (d, J=2.4 Hz, 1H), 7.81 (s, 1H), 7.55 (s, 1H), 7.36 (d, J=2.1 Hz, 1H), 7.14 (s, 1H), 7.06 (d, J=0.6 Hz, 1H), 6.50 (s, 1H), 6.36 (s, 1H), 5.22 (t, J=0.6 Hz, 1H), 4.63 (d, J=13.5 Hz, 1H), 4.34-4.22 (m, 2H), 3.79-3.61 (m, 2H), 2.41 (s, 3H), 1.80 (s, 3H).

Example 306

Synthesis of ((S)-10-((1-hydroxycyclopentyl)ethynyl)-6-(hydroxymethyl)-5,6-dihydrobenzo[f]imidazo[1,2-d][1,4]oxazepine-2-carboxamide and (R)-10-((1-hydroxycyclopentyl)ethynyl)-6-(hydroxymethyl)-5,6-dihydrobenzo[f]imidazo[1,2-d][1,4]oxazepine-2-carboxamide

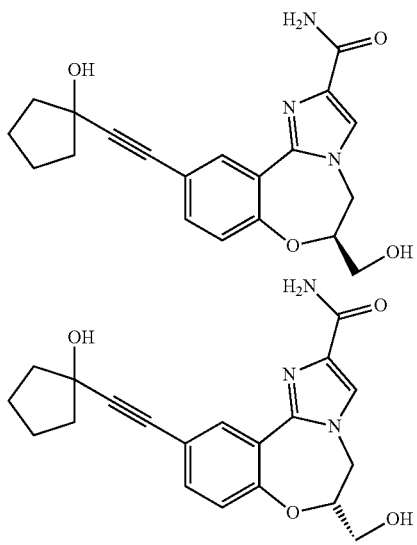

Similar to as described in General Procedure G, racemic 10-bromo-6-(hydroxymethyl)-5,6-dihydrobenzo[f]imidazo[1,2-d][1,4]oxazepine-2-carboxamide was reacted with 1-ethynylcyclopentanol to give a racemic mixture of the titled compounds. The racemate was separated by chiral Prep-HPLC. The absolute stereochemistry of each isomer was not determined.

Compound 1: chiral HPLC retention time 16.727 min.; off-white solid (4 mg, 2%); M+1=368; $^1$H NMR (300 MHz, DMSO-d$_6$) δ 8.42 (d, J=2.1 Hz, 1H), 7.81 (s, 1H), 7.53 (s, 1H), 7.30 (d, 1H), 7.25 (s, 1H), 7.05 (d, 1H), 5.31 (s, 1H), 5.21 (m, 1H), 4.66 (d, 1H), 4.29 (m, 2H), 3.80-3.60 (m, 2H), 1.90 (m, 4H), 1.744 (m, 4H).

Compound 1: chiral HPLC retention time 23.153 min.; off-white solid (3 mg, 1%); M+1=368; $^1$H NMR (300 MHz, DMSO-d$_6$) δ 8.42 (d, J=2.1 Hz, 1H), 7.81 (s, 1H), 7.53 (s, 1H), 7.30 (d, 1H), 7.25 (s, 1H), 7.05 (d, 1H), 5.31 (s, 1H), 5.21 (m, 1H), 4.66 (d, 1H), 4.29 (m, 2H), 3.80-3.60 (m, 2H), 1.90 (m, 4H), 1.74 (m, 4H).

Example 307

Synthesis of (±)-10-bromo-2-carbamoyl-5,6-dihydrobenzo[f]imidazo[1,2-d][1,4]oxazepine-6-carboxylic acid

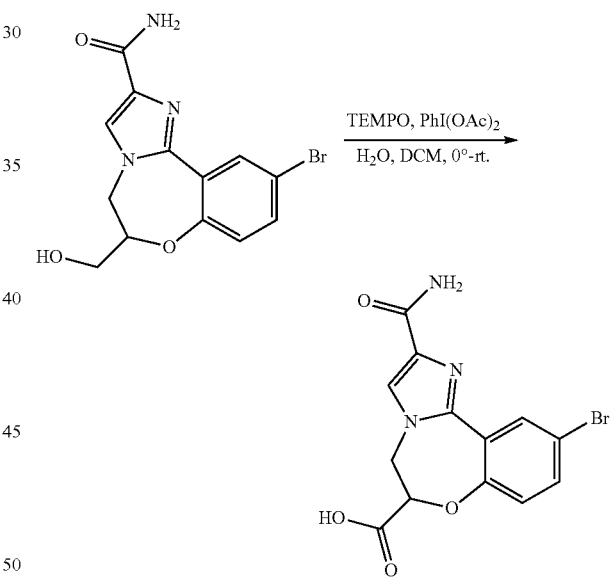

TEMPO (17 mg, 0.11 mmol, 0.33 equiv) and PhI(OAc)2 (255 mg, 0.79 mmol, 2.37 equiv) were added to a stirred suspension of 10-bromo-6-(hydroxymethyl)-5,6-dihydrobenzo[f]imidazo[1,2-d][1,4]oxazepine-2-carboxamide (113 mg, 0.33 mmol, 1.00 equiv) in dichloromethane (4 mL) and water (0.8 mL) at 0° C. After 30 min the resulting mixture was warmed to room temperature and stirred overnight. The reaction was then quenched by the addition sodium bicarbonate and washed with dichloromethane. The pH value of the aqueous solution was adjusted to 2 by 2N hydrogen chloride. The aqueous layer was extracted with ethyl acetate, dried over anhydrous sodium sulfate, and concentrated under vacuum. This resulted in to 85 mg (crude) of 10-bromo-2-carbamoyl-5,6-dihydrobenzo[f]imidazo[1,2-d][1,4]oxazepine-6-carboxylic acid as a white solid.

Example 308

Synthesis of (R)-10-((1-hydroxycyclopentyl)ethynyl)-N6,N6-dimethyl-5,6-dihydrobenzo[f]imidazo[1,2-d][1,4]oxazepine-2,6-dicarboxamide and (S)-10-((1-hydroxycyclopentyl)ethynyl)-N6,N6-dimethyl-5,6-dihydrobenzo[f]imidazo[1,2-d][1,4]oxazepine-2,6-dicarboxamide

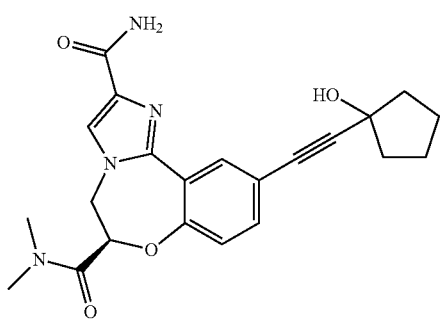

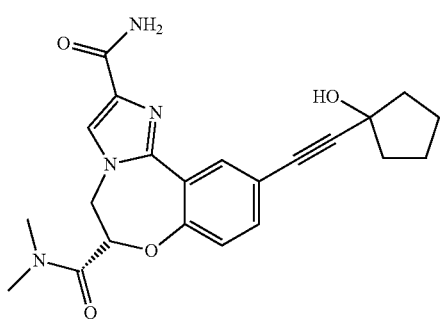

Similar to as described in General Procedure G, racemic 10-bromo-N6,N6-dimethyl-5,6-dihydrobenzo[f]imidazo[1,2-d][1,4]oxazepine-2,6-dicarboxamide was reacted with 1-ethynylcyclopentanol to give a racemic mixture of the titled compounds. The racemate was separated by chiral Prep-HPLC. The absolute stereochemistry of each isomer was not determined.

Compound 1 chiral HPLC retention time 12.658 min.; off-white solid (5 mg, 6%); M+1=409; $^1$H NMR (300 MHz, CDCl$_3$) δ 8.54 (d, J=1.8 Hz, 1H), 7.70 (s, 1H), 7.42-7.31 (m, 2H), 7.03 (d, J=8.4 Hz, 1H), 5.49 (br s, 1H), 5.00 (d, J=8.1 Hz, 1H), 4.71-4.58 (m, 2H), 3.11 (s, 3H), 3.06 (s, 3H), 2.14-1.74 (m, 8H).

Compound 1 chiral HPLC retention time 16.973 min.; off-white solid (5 mg, 6%); M+1=409; $^1$H NMR (300 MHz, CDCl$_3$) δ 8.54 (d, J=1.8 Hz, 1H), 7.70 (s, 1H), 7.42-7.31 (m, 2H), 7.03 (d, J=8.4 Hz, 1H), 5.49 (br s, 1H), 5.00 (d, J=8.1 Hz, 1H), 4.71-4.58 (m, 2H), 3.11 (s, 3H), 3.06 (s, 3H), 2.14-1.74 (m, 8H).

Example 309

Synthesis of (R)-10-((1-hydroxycyclopentyl)ethynyl)-N6-isopropyl-5,6-dihydrobenzo[f]imidazo[1,2-d][1,4]oxazepine-2,6-dicarboxamide and (S)-10-((1-hydroxycyclopentyl)ethynyl)-N6-isopropyl-5,6-dihydrobenzo[f]imidazo[1,2-d][1,4]oxazepine-2,6-dicarboxamide

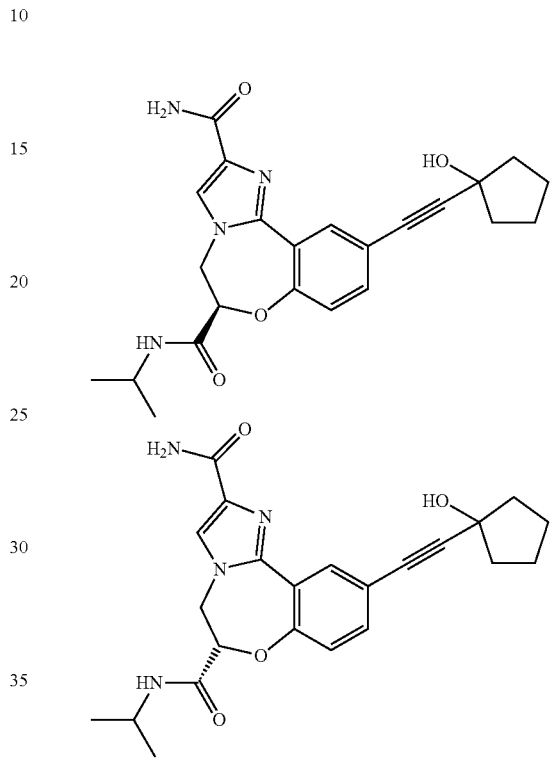

Similar to as described in General Procedure G, racemic methyl 10-bromo-6-(isopropylcarbamoyl)-5,6-dihydrobenzo[f]imidazo[1,2-d][1,4]oxazepine-2-carboxylat was reacted with 1-ethynylcyclopentanol to give a racemic mixture of methyl 104(1-hydroxycyclopentyl)ethynyl)-6-(isopropylcarbamoyl)-5,6-dihydrobenzo[f]imidazo[1,2-d][1,4]oxazepine-2-carboxylate. A solution of methyl 104(1-hydroxycyclopentyl)ethynyl)-6-(isopropylcarbamoyl)-5,6-dihydrobenzo[f]imidazo[1,2-d][1,4]oxazepine-2-carboxylate (60 mg, 0.14 mmol, 1.00 equiv) in NH$_3$/MeOH (60 mL) was stirred for 7 days at room temperature. The resulting mixture was concentrated under vacuum. The crude product was purified by Chiral-Prep-HPLC with the following conditions (2#-Gilson Gx 281(HPLC-09)); Column, Chiralpak IC, 2*25 cm, 5 um; mobile phase, Hex and ethanol (hold 40.0% ethanol in 18 min); Detector, uv 254/220 nm. This resulted in 14.3 mg (25%) of Compound 1 and 21.3 mg (37%)

Compound 2. The absolute stereochemistry of each isomer was not determined.

Compound 1: 13.542 min.; off-white solid; M+1=423; $^1$H NMR (300 MHz, CD$_3$OD) δ 8.33 (s, 1H), 7.80 (s, 1H), 7.44 (d, J=15.7 Hz, 1H), 7.30 (d, J=18.6 Hz, 1H), 5.02 (d, J=7.2 Hz, 1H), 4.89-4.78 (m, 1H), 4.57-4.49 (m, 1H), 4.14-4.03 (m, 1H), 2.04-2.01 (m, 4H), 1.89-1.75 (m, 4H), 1.38-1.31 (m, 6H);

Compound 2: 16.142 min.; off-white solid; M+1=423; ¹H NMR (300 MHz, CD₃OD) δ 8.32 (s, 1H), 7.79 (s, 1H), 7.44 (d, J=7.8 Hz, 1H), 7.28 (d, J=8.4 Hz, 1H), 4.98-4.95 (m, 1H), 4.78-4.72 (m, 1H), 4.11-4.02 (m, 1H), 2.03-1.89 (m, 4H), 1.88-1.80 (m, 4H), 1.21-1.14 (m, 6H).

Example 310

Synthesis of methyl (±)-10-bromo-6-(morpholinomethyl)-5,6-dihydrobenzo[1]imidazo[1,2-d][1,4]oxazepine-2-carboxylate

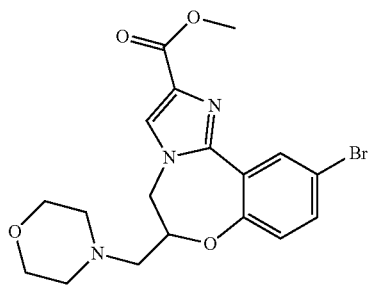 [SMILES: COC(=O)c1cn2c(n1)-c1cc(Br)ccc1OC(CN1CCOCC1)C2]

MsCl (400 mg, 3.49 mmol, 1.10 equiv) was added to a stirred solution of methyl methyl 10-bromo-6-(hydroxymethyl)-5,6-dihydrobenzo[f]imidazo[1,2-d][1,4]oxazepine-2-carboxylate (1 g, 2.83 mmol, 1.00 equiv), 4-dimethylaminopyridine (30 mg, 0.25 mmol, 0.10 equiv) and triethylamine (900 mg, 8.89 mmol, 3.00 equiv) in dichloromethane (20 mL) at 0° C. After being stirred for 2.5 h at room temperature the reaction was quenched by water, extracted with dichloromethane, dried over anhydrous sodium sulfate, and concentrated under vacuum. The residue was purified on a silica gel column with ethyl acetate/petroleum ether (3:2) to give 1.0 g (82%) methyl 10-bromo-6-(((methylsulfonyl)oxy)methyl)-5,6-dihydrobenzo[f]imidazo[1,2-d][1,4]oxazepine-2-carboxylate. M+1=431/433. A solution of this intermediate (400 mg, 0.92 mmol, 1.00 equiv) and morpholine (810 mg, 9.30 mmol, 10.00 equiv) in N,N-dimethylformamide (4 mL) was stirred overnight at 60° C. The resulting solution was diluted with DCM, washed with water, washed and brine, dried over anhydrous sodium sulfate, and concentrated under vacuum. The residue was purified on a silica gel column with ethyl acetate/petroleum ether (1:9) to give 345 mg (88%) of methyl methyl 10-bromo-6-(morpholinomethyl)-5,6-dihydrobenzo[f]imidazo[1,2-d][1,4]oxazepine-2-carboxylate as pink solid.

Example 311

Synthesis of (S)-10-((R)-3-hydroxy-3-(5-methylisoxazol-3-yl)but-1-yn-1-yl)-6-(morpholinomethyl)-5,6-dihydro benzo[f]imidazo[1,2-d][1,4]oxazepine-2-carboxamide and (R)-10-((R)-3-hydroxy-3-(5-methylisoxazol-3-yl)but-1-yn-1-yl)-6-(morpholinomethyl)-5,6-dihydro benzo[f]imidazo[1,2-d][1,4]oxazepine-2-carboxamide

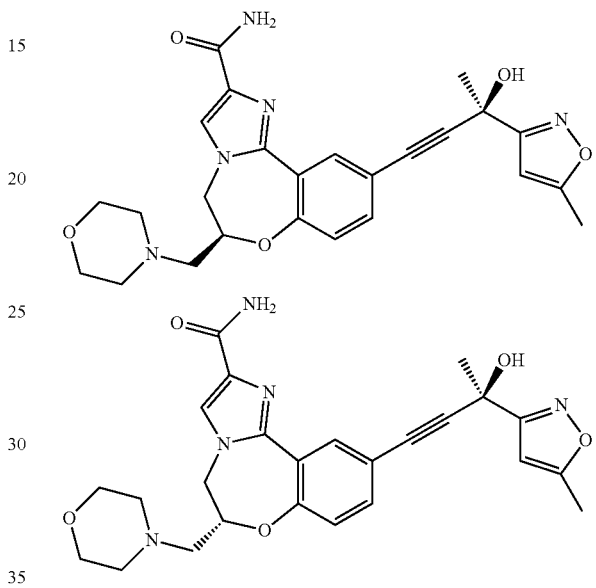

Similar to as described in General Procedure G, racemic methyl 10-bromo-6-(morpholinomethyl)-5,6-dihydrobenzo[f]imidazo[1,2-d][1,4]oxazepine-2-carboxylate was reacted with (2R)-2-(5-methyl-1,2-oxazol-3-yl)but-3-yn-2-ol to produce methyl 10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxylate as a diasteromeric mixture. A suspension of methyl 10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxylate (220 mg, 0.45 mmol, 1.00 equiv) in aqueous ammonia (40 mL) was stirred overnight at 60° C. The resulting mixture was concentrated under vacuum and the residue was purified on a silica gel column with dichloromethane/methanol (20:1). This resulted in 43 mg (20%) of 10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide as a colorless solid. The two diasteromers were separated by Chiral-Prep-HPLC with the following conditions: Column, CHIRALPAK IC-3; mobile phase, Hex (0.1% TEA):EtOH=50/50; Detector, 254 nm. This resulted in 12.2 mg (30%) of Compound 1 and 15.3 mg (38%) Compound 2.

Compound 1 chiral HPLC retention time: 6.308 min.; colorless solid; M+1=478; ¹H NMR (300 MHz, CD₃OD) δ 8.49 (d, J=2.1 Hz, 1H), 7.78 (s, 1H), 7.43 (dd, J=2.1, 8.4 Hz, 1H), 7.09 (d, J=8.4 Hz, 1H), 6.32 (s, 1H), 4.70-4.50 (m, 2H), 4.38-4.30 (m, 1H), 3.71 (t, J=4.8 Hz, 4H), 2.84-2.51 (m, 6H), 2.46 (s, 3H), 1.89 (s, 3H).

Compound 2 chiral HPLC retention time: 11.580 min.; colorless solid; M+1=478; ¹H NMR (300 MHz, CD₃OD) δ 8.49 (d, J=2.1 Hz, 1H), 7.78 (s, 1H), 7.43 (dd, J=2.1, 8.4 Hz, 1H), 7.09 (d, J=8.4 Hz, 1H), 6.32 (s, 1H), 4.70-4.50 (m, 2H), 4.38-4.30 (m, 1H), 3.71 (t, J=4.8 Hz, 4H), 2.84-2.51 (m, 6H), 2.46 (s, 3H), 1.89 (s, 3H).

Example 312

Synthesis of ((R)-10-((R)-3-hydroxy-3-(5-methyl-isoxazol-3-yl)but-1-yn-1-yl)-6-(2-hydroxypropan-2-yl)-5,6-dihydrobenzo[f]imidazo[1,2-d][1,4]oxazepine-2-carboxamide and (S)-10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide

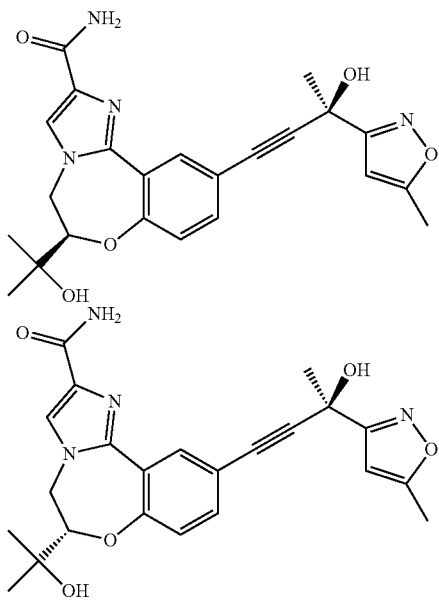

Similar to as described in General Procedure G, racemic methyl 10-bromo-6-(2-hydroxypropan-2-yl)-5,6-dihydrobenzo[f]imidazo[1,2-d][1,4]oxazepine-2-carboxylate was reacted with (2R)-2-(5-methyl-1,2-oxazol-3-yl)but-3-yn-2-ol to give methyl 10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxylate. M+1=452. A solution of the above compound (100 mg, 0.22 mmol, 1.00 equiv) in methanol (Saturated with ammonia, 20 mL) was stirred for 3 days at 60° C. The resulting mixture was concentrated under vacuum. The residue was purified on a silica gel column with dichloromethane/methanol (19:1) to give a mixture of diastereoisomers. The two diasteromers were separated by Chiral-Prep-HPLC with the following conditions (Prep-HPLC-004): Column, Chiralpak IC, 2*25 cm, 5 um; mobile phase, Hex and ethanol (hold 40.0% ethanol in 25 min); Detector, UV 254/220 nm to give 12.2 mg (13%) Compound 1 as a off-white solid, Chiralpak IC-3, 25° C., 254 nm, 60:40 Hex (0.1% TEA):EtOH, 1 mL/min, t_R=2,7 min; and 11.5 mg (12%) of Compound 2 as an off-white solid, Chiralpak IC-3, 25° C., 254 nm, 60:40 Hex (0.1% TEA):EtOH, 1 mL/min, t_R=5.0 min.

Compound 1 M+1=437; ¹H NMR (300 MHz, CD₃OD) δ 8.50 (d, J=2.4 Hz, 1H), 7.74 (s, 1H), 7.37 (dd, J=2.4, 8.4 Hz, 1H), 7.07 (d, J=8.4 Hz, 1H), 6.27 (s, 1H), 4.80-4.75 (m, 1H), 4.32-4.23 (m, 1H), 3.94 (d, J=7.8 Hz, 1H), 2.41 (s, 3H), 1.85 (s, 3H), 1.41 (s, 3H), 1.37 (s, 3H)

Compound 1 M+1=437; ¹H NMR (300 MHz, CD₃OD) δ 8.50 (d, J=2.4 Hz, 1H), 7.74 (s, 1H), 7.37 (dd, J=2.4, 8.4 Hz, 1H), 7.07 (d, J=8.4 Hz, 1H), 6.27 (s, 1H), 4.80-4.75 (m, 1H), 4.32-4.23 (m, 1H), 3.94 (d, J=7.8 Hz, 1H), 2.41 (s, 3H), 1.85 (s, 3H), 1.41 (s, 3H), 1.37 (s, 3H).

Example 313

Synthesis of (R)-10-((R)-3-hydroxy-3-(5-methyl-isoxazol-3-yl)but-1-yn-1-yl)-N6-methyl-5,6-dihydrobenzo[f]imidazo[1,2-d][1,4]oxazepine-2,6-dicarboxamide and (S)-10-((R)-3-hydroxy-3-(5-methylisoxazol-3-yl)but-1-yn-1-yl)-N6-methyl-5,6-dihydrobenzo[f]imidazo[1,2-d][1,4]oxazepine-2,6-dicarboxamide

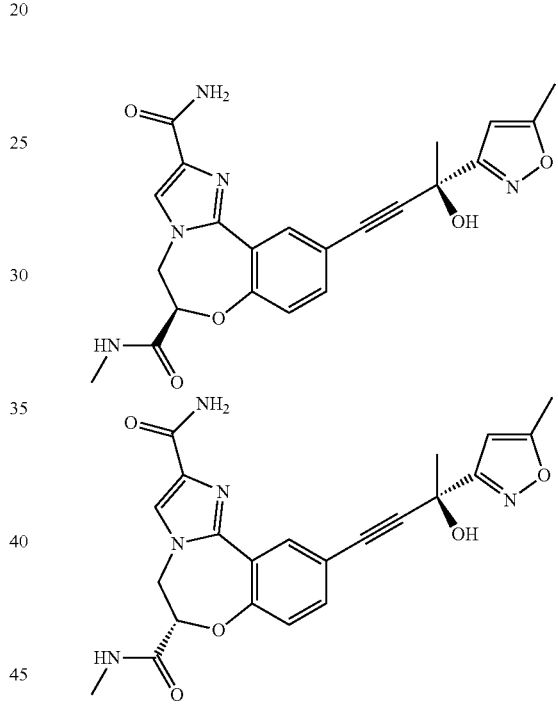

Similar to as described in General Procedure G, racemic 10-bromo-N6-methyl-5,6-dihydrobenzo[f]imidazo[1,2-d][1,4]oxazepine-2,6-dicarboxamide was reacted with (2R)-2-(5-methyl-1,2-oxazol-3-yl)but-3-yn-2-ol to give a mixture of the titled compounds that were separated by chiral prep-HPLC.

Compound 1: 4.5 mg (6%); off-white solid; Chiralpak IC-3, 25° C., 254 nm, 50:50 Hex (0.1% TEA): EtOH, 1.2 mL/min, t_R=4.4 min; M+1=436; ¹H NMR (400 MHz, CD₃OD) δ 8.47 (d, J=2.0 Hz, 1H), 7.81 (s, 1H), 7.48 (dd, J=2.0, 8.4 Hz, 1H), 7.32 (d, J=8.4 Hz, 1H), 6.32 (s, 1H), 5.05-4.82 (m, 2H), 4.55-4.48 (m, 1H), 2.84 (s, 3H), 2.46 (s, 3H), 1.89 (s, 3H);

Compound 2: 2.7 mg (3%); off-white solid, Chiralpak IC-3, 25° C., 254 nm, 50:50 Hex (0.1% TEA): EtOH, 1.2 mL/min, t_R=6.8 min. M+1=436; NMR (300 MHz, CD₃OD) δ 8.33 (d, J=2.0 Hz, 1H), 7.69 (s, 1H), 7.36 (dd, J=2.0, 8.4 Hz, 1H), 7.19 (d, J=8.4 Hz, 1H), 6.32 (s, 1H), 5.05-4.82 (m, 2H), 4.55-4.48 (m, 1H), 2.84 (s, 3H), 2.46 (s, 3H), 1.89 (s, 3H).

Example 314

Synthesis of 10-bromo-6-(fluoromethyl)-5,6-dihydrobenzo[f]imidazo[1,2-d][1,4]oxazepine-2-carboxamide Scheme for the synthesis of 10-bromo-6-(fluoromethyl)-5,6-dihydrobenzo[f]imidazo[1,2-d][1,4]oxazepine-2-carboxamide:

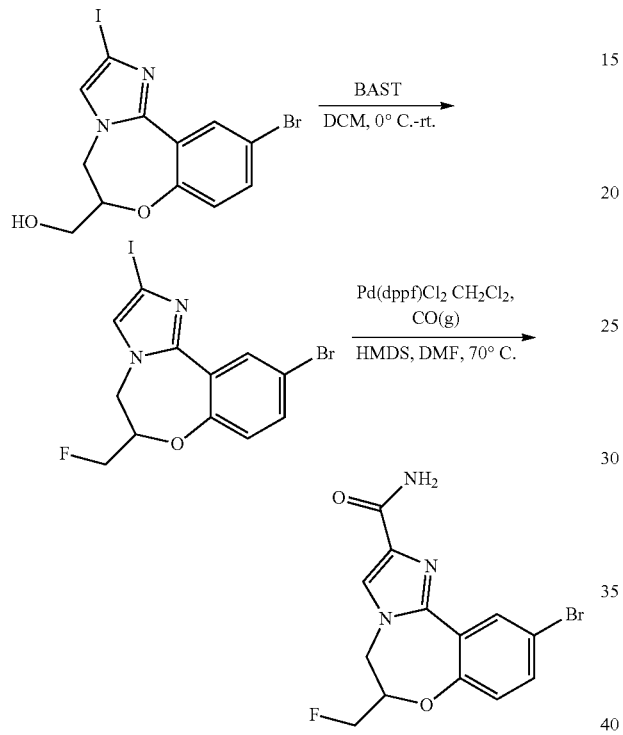

Bis(2-methoxyethyl)(trifluoro-^4-sulfanyl)amine (525 mg, 2.37 mmol, 2.00 equiv) was added dropwise into a solution of (10-bromo-2-iodo-5,6-dihydrobenzo[f]imidazo[1,2-d][1,4]oxazepin-6-yl)methanol (500 mg, 1.19 mmol, 1.00 equiv) in dichloromethane (60 mL) at 0° C. After being stirred for 4 h at room temperature the reaction solution was washed with brine, dried over anhydrous sodium sulfate and concentrated under vacuum. The residue was purified on a silica gel column with ethyl acetate/petroleum ether (1:4). This resulted in 320 mg (64%) of 10-bromo-6-(fluoromethyl)-2-iodo-5,6-dihydrobenzo[f]imidazo[1,2-d][1,4]oxazepine as a off-white solid. A suspension of this intermediate (100 mg, 0.24 mmol, 1.00 equiv), Pd(dppf)Cl$_2$ (39 mg, 0.05 mmol, 0.10 equiv) and HMDS (96 mg, 0.59 mmol, 2.50 equiv) in N,N-dimethylformamide (3 mL) was stirred for 2 h at 70° C. under a carbon monoxide atmosphere (1 atm). The reaction was then quenched by the addition of 2 mL of methanol and then it was allowed to be stirred for 30 min at room temperature. The resulting solution was diluted with 50 mL of dichloromethane, washed with 3×15 mL of brine, dried over anhydrous sodium sulfate and concentrated under vacuum. This resulted in 180 mg (crude) of the titled compound as a brown oil.

Example 315

Synthesis of (R)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide and ((S)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide

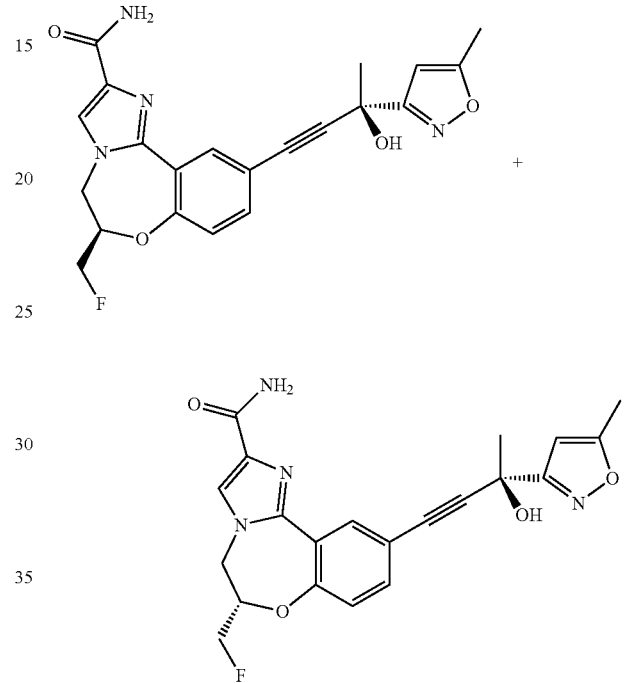

Similar to as described in General Procedure G, racemic 10-bromo-6-(fluoromethyl)-5,6-dihydrobenzo[f]imidazo[1,2-d][1,4]oxazepine-2-carboxamide was reacted with (2R)-2-(5-methyl-1,2-oxazol-3-yl)but-3-yn-2-ol to give a mixture of the titled compounds. The mixture was purified by Chiral-Prep-HPLC with the following conditions (2#-Gilson Gx 281(HPLC-09)): Column, Phenomenex Lux 5u Cellulose-3, 5*25 cm, 5 um; mobile phase, Hex; Detector, uv 220/254 nm to give 7.0 mg (6%) of Compound 1 as a off-white solid, Cellulose-4, 25° C., 254 nm, 50:50 Hex (0.1TEA): EtOH, 1 mL/min, 8.4 min; and 17.0 mg (14%) of Compound 2 as a off-white solid, Cellulose-4, 25° C., 254 nm, 50:50 Hex (0.1TEA) EtOH, 1 mL/min, 13.1 min.

Compound 1: M+1=411; $^1$H NMR (300 MHz, CD$_3$OD) δ 8.48 (d, J=2.1 Hz, 1H), 7.77 (s, 1H), 7.43 (dd, J=2.1, 8.7 Hz, 1H), 7.11 (d, J=8.7 Hz, 1H), 6.31 (s, 1H), 4.83 (d, J=5.2 Hz, 1H), 4.69-4.62 (m, 3H), 4.42-4.34 (m, 1H), 2.45 (s, 3H), 1.88 (s, 3H);

Compound 2: M+1=411; $^1$H NMR (300 MHz, CD$_3$OD) δ 8.48 (d, J=2.1 Hz, 1H), 7.77 (s, 1H), 7.43 (dd, J=2.1, 8.7 Hz, 1H), 7.11 (d, J=8.7 Hz, 1H), 6.31 (s, 1H), 4.83 (d, J=5.2 Hz, 1H), 4.69-4.62 (m, 3H), 4.42-4.34 (m, 1H), 2.45 (s, 3H), 1.88 (s, 3H).

Example 316

Synthesis of 9-bromo-5,6-dihydro-4H-4,6-methanobenzo[6,7]cyclohepta[1,2-d]thiazole-2-carboxamide Scheme for the synthesis of 9-bromo-5,6-dihydro-4H-4,6-methanobenzo[6,7]cyclohepta[1,2-d]thiazole-2-carboxamide:

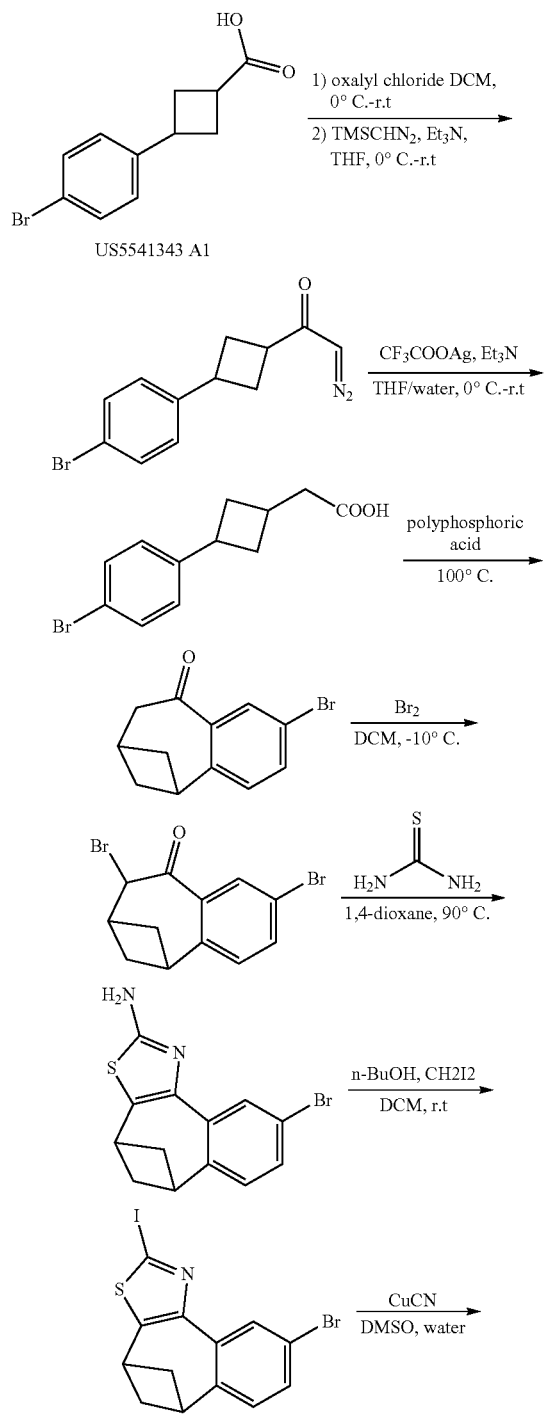

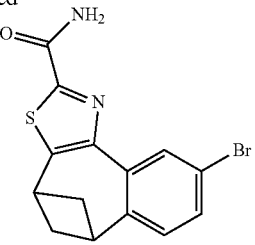

Oxalyl chloride (20.7 g, 164.29 mmol, 1.20 equiv) and two drops of DMF were added into a solution of 3-(4-bromophenyl)cyclobutane-1-carboxylic acid (38 g, 148.96 mmol, 1.00 equiv) (U.S. Pat. No. 5,541,343 A1) in dichloromethane (200 mL) at 0° C. After being stirred for 1 h at 25° C. the solvent was removed and the residue was dissolved in tetrahydrofuran (300 mL). To this was added triethylamine (16 g, 158.12 mmol, 1.07 equiv) dropwise with stirring at 0° C. The solution was stirred for 10 min at 0° C. and a solution of TMSCHN$_2$ (2.0 M in hexane, 145 mL, 1.95 equiv) was added dropwise at 0° C. The resulting solution was stirred for 3 h at room temperature, quenched with sodium bicarbonate, extracted with ethyl acetate, dried over anhydrous sodium sulfate, and concentrated under vacuum. The residue was purified on a silica gel column with ethyl acetate/petroleum ether (1:3). This resulted in 28.0 g (67%) of 2-[3-(4-bromophenyl)cyclobutyl]-2-oxoethane-1-diazonium as a yellow solid. LC-MS 279, 281 [M+H]$^+$; A solution of silver trifluoroacetate (2.7 g, 12.27 mmol, 0.10 equiv) in triethylamine (48 mL) was added into a solution of the above diazonium (35 g, 125.39 mmol, 1.00 equiv) in tetrahydrofuran (350 mL)/water (35 mL) at −30° C. under a nitrogen atmosphere (1 atm) in darkness. The reaction solution was stirred for 4 h at room temperature and the pH value of the solution was adjusted to 2 with 2N hydrogen chloride. The resulting solution was extracted with dichloromethane, dried over anhydrous sodium sulfate, and concentrated under vacuum. The residue was purified on a silica gel column with ethyl acetate/petroleum ether (1:3) to give 22 g (65%) of 2-[3-(4-bromophenyl)cyclobutyl]acetic acid as a yellow solid. LC-MS 267, 269 [M−H]$^+$. A suspension of 2-[3-(4-bromophenyl)cyclobutyl]acetic acid (6 g, 22.29 mmol, 1.00 equiv) in polyphosphoric acid (100 mL) was stirred for 12 h at 100° C. The resulting solution was diluted with water, extracted with ethyl acetate, dried over anhydrous sodium sulfate, and concentrated under vacuum. The residue was purified on a silica gel column with ethyl acetate/petroleum ether (1:10). This resulted in 1.0 g (18%) 2-bromo-7,8-dihydro-5H-5,7-methanobenzo[7]annulen-9(6H)-one as yellow oil. Bromine (100 uL, 1.00 equiv) was added into a solution of this intermediate (500 mg, 1.99 mmol, 1.00 equiv) in dichloromethane (3 mL) with stirring at −10° C. After being stirred for 2 h at −10° C. the reaction was quenched by sodium bicarbonate, diluted with 50 mL of DCM, washed with water, dried over anhydrous sodium sulfate, and concentrated under vacuum. This resulted in 600 mg (91%) of 2,8-dibromo-7,8-dihydro-5H-5,7-methanobenzo[7]annulen-9(6H)-one as yellow oil; LC-MS 329, 331 [M+H]$^+$. A solution of this intermediate (650 mg, 1.97 mmol, 1.00 equiv) and thiourea (0.6 mg, 0.01 mmol, 4.00 equiv) in 1,4-dioxane (10 mL) was stirred for 12 h at 90° C. The resulting solution was diluted with 100 mL of DCM, washed with 50 mL of saturated sodium bicarbonate and 50 mL of brine, dried over anhydrous sodium sulfate and concentrated under vacuum. The residue was purified on a silica gel column with ethyl acetate/petroleum ether (1:5). This resulted in 350 mg (58%) of 9-bromo-5,6-dihydro-4H-4,6-methanobenzo[6,7]cyclohepta[1,2-d]thiazol-2-amine as light brown oil. LC-MS 307, 309 [M+H]⁺. A solution of this intermediate (350 g, 1.14 mol, 1.00 equiv), n-BuONO (0.65 g, 5.50 equiv), $CH_2I_2$ (0.5 mL) in dichloromethane (5 mL) was stirred for 6 h at room temperature. The resulting mixture was concentrated under vacuum and the residue was purified on a silica gel column with petroleum ether. This resulted in 200 mg (42%) of 9-bromo-2-iodo-5,6-dihydro-4H-4,6-methanobenzo[6,7]cyclohepta[1,2-d]thiazole LC-MS 418, 420 [M+H]⁺. A suspension of this intermediate (200 mg, 0.48 mmol, 1.00 equiv) and cuprous cyanide (169 mg, 1.90 mmol, 4.00 equiv) in DMSO (2 mL) and water (0.2 mL) was stirred for 12 h at 90° C. The resulting solution was diluted with 100 mL of DCM and washed with water. The mixture was dried over anhydrous sodium sulfate and concentrated under vacuum. The residue was purified on a silica gel column with ethyl acetate/petroleum ether (1:4) to give 30 mg (19%) of the titled compound.

Example 317

Synthesis of (R)-9-((3-hydroxy-1-methyl-2-oxopyrrolidin-3-yl)ethynyl)-5,6-dihydro-4H-4,6-methanobenzo[6,7]cyclohepta[1,2-d]thiazole-2-carboxamide

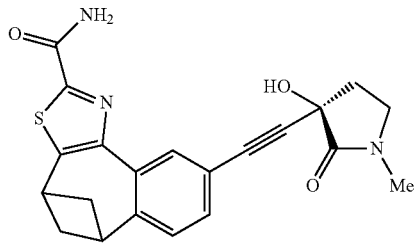 [SMILES: CN1CC[C@@](O)(C#Cc2ccc3c(c2)-c2nc(C(N)=O)sc2C2CC3C2)C1=O]

Similar to as described in General Procedure G, 9-bromo-5,6-dihydro-4H-4,6-methanobenzo[6,7]cyclohepta[1,2-d]thiazole-2-carboxamide was reacted with (3R)-3-ethynyl-3-hydroxy-1-methylpyrrolidin-2-one to give the titled compound as an off-white solid (14.4 mg, 59%).
M+1=394; ¹H NMR (400 MHz, $CD_3OD$) δ 8.80 (d, J=1.6 Hz, 1H), 7.29 (dd, J=1.6, 7.2 Hz, 1H), 7.19 (d, J=7.2 Hz, 1H), 3.80-3.74 (m, 2H), 3.55-3.46 (m, 2H), 3.08-3.02 (m, 2H), 2.96 (s, 3H), 2.65-2.59 (m, 1H), 2.37-2.34 (m, 1H), 1.68 (m, 2H).

Example 318

Synthesis of (R)-9-(3-hydroxy-3-(5-methylisoxazol-3-yl)but-1-yn-1-yl)-5,6-dihydro-4H-4,6-methanobenzo[6,7]cyclohepta[1,2-d]thiazole-2-carboxamide

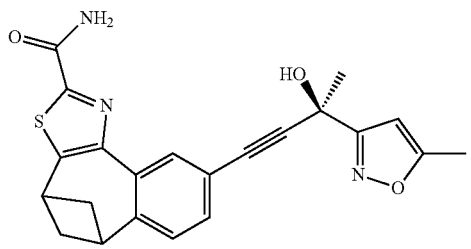 [SMILES: Cc1cc([C@](C)(O)C#Cc2ccc3c(c2)-c2nc(C(N)=O)sc2C2CC3C2)no1]

Similar to as described in General Procedure G, 9-bromo-5,6-dihydro-4H-4,6-methanobenzo[6,7]cyclohepta[1,2-d]thiazole-2-carboxamide was reacted with (2R)-2-(5-methyl-1,2-oxazol-3-yl)but-3-yn-2-ol to give the titled compound as a colorless solid (14.3 mg, 58%).
M+1=406; ¹H NMR (400 MHz, $CD_3OD$) δ 8.80 (s, 1H), 7.29 (d, J=8.0 Hz, 1H), 7.19 (d, J=8.0 Hz, 1H), 6.34 (s, 1H), 3.79-3.74 (m, 2H), 3.08-3.02 (m, 2H), 2.47 (s, 3H), 1.91 (s, 3H), 2.37-2.34 (m, 1H), 1.70-1.65 (m, 2H).

Example 319

Synthesis of (R)-9-(3-hydroxy-3-(5-methyl-1,2,4-oxadiazol-3-yl)but-1-yn-1-yl)-5,6-dihydro-4H-4,6-methanobenzo[6,7]cyclohepta[1,2-d]thiazole-2-carboxamide

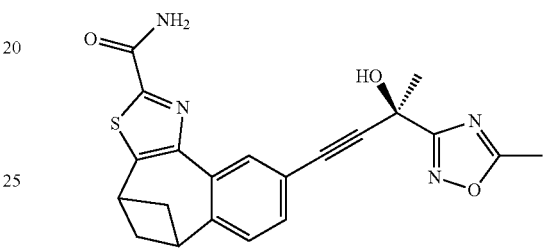

Similar to as described in General Procedure G, 9-bromo-5,6-dihydro-4H-4,6-methanobenzo[6,7]cyclohepta[1,2-d]thiazole-2-carboxamide was reacted with (2R)-2-(5-methyl-1,2,4-oxadiazol-3-yl)but-3-yn-2-ol to give the titled compound as a colorless solid (5.2 mg, 14%).
M+23=429; ¹H NMR (300 MHz, $CD_3OD$) δ 8.82 (d, J=1.8 Hz, 1H), 7.30 (d, J=1.8, 7.8 Hz, 1H), 7.20 (d, J=7.8 Hz, 1H), 3.81-3.74 (m, 2H), 3.10-3.01 (m, 2H), 2.66 (s, 3H), 2.00 (s, 3H), 1.70-1.65 (m, 2H).

Example 320

Synthesis of ethyl 9-bromo-4,4-difluoro-4,5-dihydrobenzo[2,3]oxepino[4,5-d]thiazole-2-carboxylate

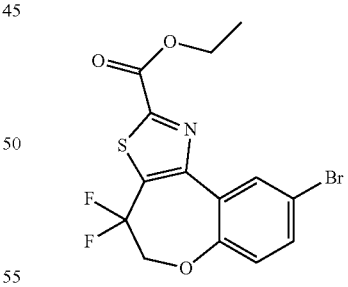

A suspension of ethyl ethyl 9-bromo-4-oxo-4,5-dihydrobenzo[2,3]oxepino[4,5-d]thiazole-2-carboxylate (700 mg, 1.90 mmol, 1.00 equiv) and diethylaminosulfur trifluoride (10 mL) in dichloromethane (2 mL) was stirred for 2 days at 30° C. The reaction was quenched with 30 mL of water, extracted with dichloromethane, dried over anhydrous sodium sulfate, and concentrated under vacuum. The residue was purified by a silica gel column with ethyl acetate/petroleum ether (1:32) to give 438 mg (49%) of the titled compound as a light yellow solid; LC-MS (ES, m/z) 390, 392 [M+H]⁺.

Example 321

Synthesis of ethyl 9-bromo-4-hydroxy-4-methyl-4,5-dihydrobenzo[2,3]oxepino[4,5-d]thiazole-2-carboxylate

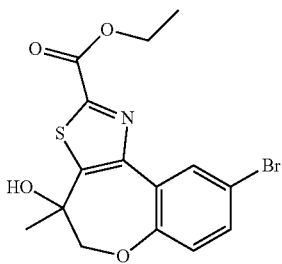 [SMILES: CCOC(=O)c1nc2c(s1)C(C)(O)COc1ccc(Br)cc1-2]

Methyl magnesium bromide (3M in tetrahydrofuran, 0.22 mL, 1.00 equiv) was added dropwise to a stirred suspension of ethyl ethyl 9-bromo-4-oxo-4,5-dihydrobenzo[2,3]oxepino[4,5-d]thiazole-2-carboxylate (200 mg, 0.54 mmol, 1.00 equiv) in tetrahydrofuran (3 mL) at −70° C. under nitrogen. The resulting solution was stirred for 1 h at −70° C., quenched with 3 mL of saturated aqueous NH$_4$Cl, extracted with ethyl acetate, dried over anhydrous sodium sulfate, and concentrated under vacuum. The residue was purified by a silica gel column with ethyl acetate/petroleum ether (1:5) to give 200 mg (96%) of the titled compound as a yellow solid; LC-MS 384,386 [M+H]$^+$.

Example 322

Synthesis of ethyl 9-bromo-4-fluoro-4-methyl-4,5-dihydrobenzo[2,3]oxepino[4,5-d]thiazole-2-carboxylate

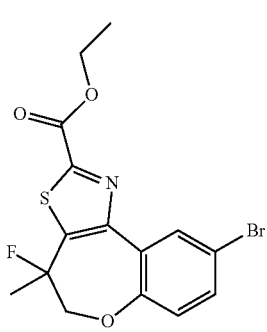 [SMILES: CCOC(=O)c1nc2c(s1)C(C)(F)COc1ccc(Br)cc1-2]

The title compound was prepared from ethyl 9-bromo-4-hydroxy-4-methyl-4,5-dihydrobenzo[2,3]oxepino[4,5-d]thiazole-2-carboxylate and DAST as described in the synthesis of ethyl 9-bromo-4,4-difluoro-4,5-dihydrobenzo[2,3]oxepino[4,5-d]thiazole-2-carboxylate.

Example 323

Synthesis of ethyl 9-bromo-4-hydroxy-4-(trifluoromethyl)-4,5-dihydrobenzo[2,3]oxepino[4,5-d]thiazole-2-carboxylate

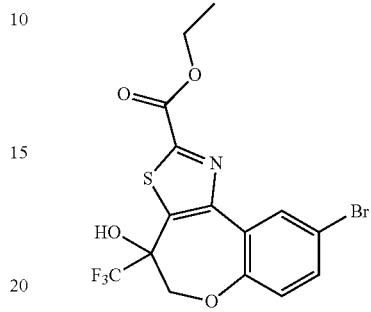

A suspension of ethyl ethyl 9-bromo-4-oxo-4,5-dihydrobenzo[2,3]oxepino[4,5-d]thiazole-2-carboxylate (300 mg, 0.81 mmol, 1.00 equiv), TMS-CF$_3$ (347.3 mg, 3.00 equiv) and TBAF (25.7 mg, 0.10 mmol, 0.10 equiv) in N,N-dimethylformamide (3 mL) was stirred for 2 h at 100° C. HCl (1M, 3 mL) was added at room temperature and the resulting solution was stirred at room temperature overnight. The reaction was quenched with Na$_2$CO$_3$, extracted with ethyl acetate, dried over anhydrous sodium sulfate, and concentrated under vacuum. The residue was purified by a silica gel column with ethyl acetate/petroleum ether (1:10) to give 120 mg (34%) of the titled compound as a yellow solid; LC-MS (ES, m/z) 438, 440[M+H]$^+$.

Example 324

Synthesis of ethyl 9-bromo-4-methoxy-4,5-dihydrobenzo[2,3]oxepino[4,5-d]thiazole-2-carboxylate

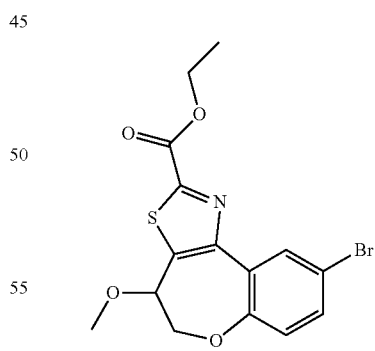

A suspension of ethyl 9-bromo-4-hydroxy-4,5-dihydrobenzo[2,3]oxepino[4,5-d]thiazole-2-carboxylate (500 mg, 1.35 mmol, 1.00 equiv), Ag$_2$O (1.247 g, 4.00 equiv), and iodomethane (763 mg, 5.38 mmol, 4.00 equiv) in dichloromethane (5 mL) was stirred for 3 h at 50. The reaction was quenched with 10 mL of brine, extracted with ethyl acetate, dried over anhydrous sodium sulfate, and concentrated under vacuum. The residue was purified by a silica gel column with ethyl acetate/petroleum ether (1:20) to give 150 mg (29%) of the titled compound as a white solid; LC-MS (ES, m/z) 384, 386[M+H]⁺.

Example 325

Synthesis of ethyl 9-bromo-4-cyano-4,5-dihydrobenzo[2,3]oxepino[4,5-d]thiazole-2-carboxylate

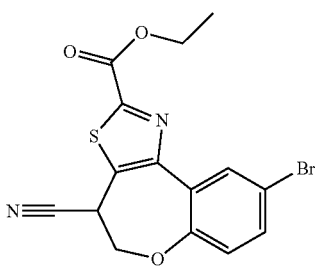 [SMILES: CCOC(=O)c1nc2c(s1)C(C#N)COc1ccc(Br)cc1-2]

Thionyl chloride (3 mL) was added dropwise to a stirred solution of ethyl 9-bromo-4-hydroxy-4,5-dihydrobenzo[2,3]oxepino[4,5-d]thiazole-2-carboxylate (600 mg, 1.61 mmol, 1.00 equiv) in dichloromethane (10 mL) at 0° C. After being stirred for 4 h at room temperature the resulting mixture was concentrated under vacuum. This resulted in 600 mg (95%) ethyl 9-bromo-4-chloro-4,5-dihydrobenzo[2,3]oxepino[4,5-d]thiazole-2-carboxylate as a yellow solid; LC-MS (ES, m/z) 388, 390 [M+H]⁺. A suspension this intermediate (600 mg, 1.54 mmol, 1.00 equiv), 18-crown-6 (320 mg, 1.21 mmol, 0.50 equiv) and KCN (524 mg, 8.05 mmol, 5.00 equiv) in CH₃CN (10 mL) was stirred overnight at room temperature. The reaction solution was diluted with of 10 mL of water, extracted with ethyl acetate, dried over anhydrous sodium sulfate, and concentrated under vacuum. The residue was purified by a silica gel column with ethyl acetate/petroleum ether (1:6) to give 206 mg (35%) of the titled compound as a yellow solid; LC-MS (ES, m/z) 379, 381 [M+H]⁺

Example 326

Synthesis of ethyl 9-bromo-5H-spiro[benzo[2,3]oxepino[4,5-d]thiazole-4,2'-oxirane]-2-carboxylate

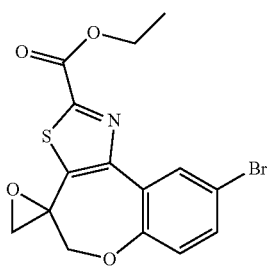 [SMILES: CCOC(=O)c1nc2c(s1)C1(COc3ccc(Br)cc3-2)CO1]

Into a 100-mL 3-necked round-bottom flask purged and maintained with an inert atmosphere of nitrogen was placed a solution of S,S-dimethylmethanesulfinyl iodide (1.15 g, 5.23 mmol, 1.60 equiv), t-BuOK (4 mL, 1.20 equiv) in dichloromethane (5 mL) at room temperature After 30 minutes a solution of ethyl 9-bromo-4-oxo-4,5-dihydrobenzo[2,3]oxepino[4,5-d]thiazole-2-carboxylate (1.2 g, 3.26 mmol, 1.00 equiv) in dichloromethane (10 mL) was added slowly. The resulting solution was stirred for 5 h at room temperature, quenched with water, extracted with dichloromethane, dried over anhydrous sodium sulfate, and concentrated under vacuum. The residue was purified by a silica gel column with ethyl acetate/petroleum ether (1:19) to give 600 mg (48%) of the titled compound as a off-white solid; LC-MS 382,384[M+H]⁺.

Example 327

Synthesis of ethyl 9-bromo-4-(hydroxymethyl)-4,5-dihydrobenzo[2,3]oxepino[4,5-d]thiazole-2-carboxylate

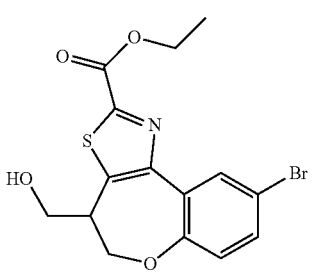 [SMILES: CCOC(=O)c1nc2c(s1)C(CO)COc1ccc(Br)cc1-2]

Boron trifluoride diethleherate (0.16 mL, 1.00 equiv) was added dropwise to a stirred solution of ethyl 9-bromo-5H-spiro[benzo[2,3]oxepino[4,5-d]thiazole-4,2'-oxirane]-2-carboxylate (500 mg, 1.31 mmol, 1.00 equiv) and Et₃SiH (227.5 mg, 1.96 mmol, 1.50 equiv) in dichloromethane (25 mL) at 0° C. After being stirred for 15 min at room temperature the reaction solution was diluted with 50 mL of aqueous NaHCO₃, extracted with dichloromethane, dried over anhydrous sodium sulfate, and concentrated under vacuum. The residue was purified by a silica gel column with ethyl acetate/petroleum ether (1:3) to give 340 mg (68%) of the titled compound as a off-white solid; LC-MS (ES, m/z) 384,386 [M+H]⁺.

Example 328

Synthesis of ethyl 9-bromo-4-(methoxymethyl)-4,5-dihydrobenzo[2,3]oxepino[4,5-d]thiazole-2-carboxylate

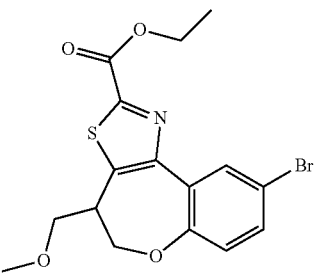 [SMILES: CCOC(=O)c1nc2c(s1)C(COC)COc1ccc(Br)cc1-2]

A suspension of ethyl 9-bromo-4-(hydroxymethyl)-4,5-dihydrobenzo[2,3]oxepino[4,5-d]thiazole-2-carboxylate (200 mg, 0.52 mmol, 1.00 equiv), MeI (750 mg, 5.28 mmol, 10.00 equiv) and silver oxide (480 mg, 2.07 mmol, 4.00 equiv) in dichloromethane (15 mL) was stirred for 6 h at 50°

C. The solids were filtered out and the filtrate was concentrated under vacuum. The residue was purified by a silica gel column with ethyl acetate/petroleum ether (1:10) to give 110 mg (53%) of the titled compound as an off-white solid; LC-MS (ES, m/z) 398,400 [M+H]$^+$.

Example 329

Synthesis of ethyl 9-bromo-4-(fluoromethyl)-4-hydroxy-4,5-dihydrobenzo[2,3]oxepino[4,5-d]thiazole-2-carboxylate

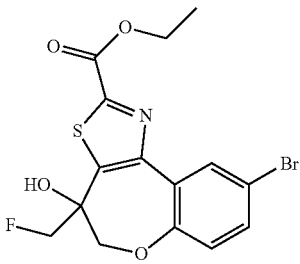 [SMILES: CCOC(=O)c1nc2c(s1)C(O)(CF)COc1ccc(Br)cc1-2]

A suspension of ethyl 9-bromo-5H-spiro[benzo[2,3]oxepino[4,5-d]thiazole-4,2'-oxirane]-2-carboxylate (421 mg, 1.10 mmol, 1.00 equiv), KHF$_2$ (258 mg, 3.00 equiv), Bu$_4$NF$_3$ (99.5 mg, 0.30 equiv) in chlorobenzene (2 mL) was stirred for 2 h at 130° C. The reaction was then quenched with 3 ml of water, extracted with 3×5 ml of ethyl acetate, dried over sodium sulfate, and concentrated under vacuum. The residue was purified by a silica gel column with EA:PE (1:5) to give 200 mg (45%) of the titled compound as a yellow solid; LC-MS (ES, m/z) 402,404[M+H]$^+$.

Example 330

Synthesis of ethyl 9-bromo-4-fluoro-4-(hydroxymethyl)-4,5-dihydrobenzo[2,3]oxepino[4,5-d]thiazole-2-carboxylate

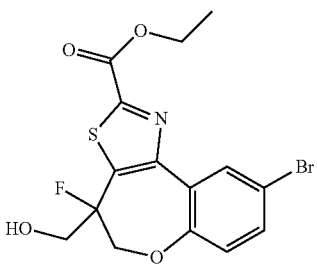 [SMILES: CCOC(=O)c1nc2c(s1)C(F)(CO)COc1ccc(Br)cc1-2]

HF-pyridine (70%) (2 mL) was added dropwise to a stirred solution of ethyl 9-bromo-5H-spiro[benzo[2,3]oxepino[4,5-d]thiazole-4,2'-oxirane]-2-carboxylate (600 mg, 1.57 mmol, 1.00 equiv) in dichloromethane (10 mL) at 0° C. After being stirred for 1 h at 0° C. the reaction was quenched with brine, extracted with dichloromethane, dried over anhydrous sodium sulfate, and concentrated under vacuum. The residue was purified by a silica gel column with ethyl acetate/petroleum ether (1:10) to give 270 mg (43%) of the titled compound as a off-white solid; LC-MS (ES, m/z) 402, 404 [M+H]$^+$.

Example 331

Synthesis of ethyl 9-bromo-4-methyl-4,5-dihydrobenzo[2,3]oxepino[4,5-d]thiazole-2-carboxylate

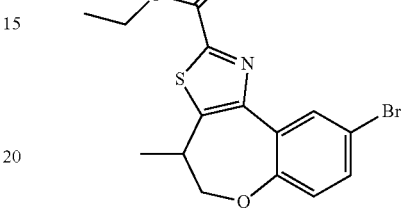

TFA (891 mg, 7.88 mmol, 30.00 equiv) was added dropwise to a stirred solution of ethyl 9-bromo-4-hydroxy-4-methyl-4,5-dihydrobenzo[2,3]oxepino[4,5-d]thiazole-2-carboxylate (100 mg, 0.26 mmol, 1.00 equiv) and Et$_3$SiH (454 mg, 3.90 mmol, 15.00 equiv) in dichloromethane (5 mL) at 0° C. After being stirred at room temperature overnight the reaction was quenched with 10 mL of saturated NaHCO$_3$, extracted with 5×20 mL of ethyl acetate, dried over anhydrous sodium sulfate, and concentrated under vacuum. The residue was purified by a silica gel column with ethyl acetate/petroleum ether (1:15) to give 70 mg (73%) of the titled compound as a light yellow solid; LC-MS (ES, m/z) 368, 369 [M+11]$^+$.

Example 332

Synthesis of ethyl 4-hydroxy-9-iodo-4,5-dihydrobenzo[b]pyrazolo[1,5-d][1,4]oxazepine-2-carboxylate

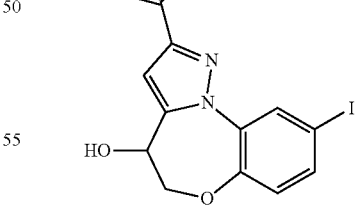

Silver nitrate (0.3 g, 2.00 equiv) was added to a stirred solution of ethyl 4-bromo-9-iodo-4,5-dihydrobenzo[b]pyrazolo[1,5-d][1,4]oxazepine-2-carboxylate (400 mg, 0.86 mmol, 1.00 equiv) in acetone (20 mL)/water (20 mL) was added. The resulting mixture was stirred for 12 hours at room temperature, diluted with water, extracted with ethyl acetate, dried over anhydrous sodium sulfate, and concentrated under vacuum. The residue was purified by a silica gel column with ethyl acetate/petroleum ether (1:3) to give 0.12 g (35%) of the titled compound as a white solid. LC-MS (ES, m/z) 401[M+H]$^+$.

Example 333

Synthesis of ethyl 4-hydroxy-9-iodo-4-methyl-4,5-dihydrobenzo[b]pyrazolo[1,5-d][1,4]oxazepine-2-carboxylate

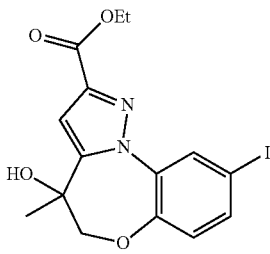 [SMILES: CCOC(=O)c1cc2n(n1)-c1cc(I)ccc1OCC2(C)O]

To a solution ethyl 9-iodo-4-oxo-4,5-dihydrobenzo[b]pyrazolo[1,5-d][1,4]oxazepine-2-carboxylate (3 g, 7.53 mmol, 1.00 equiv) in dichloromethane (50 mL) was added trimethylalumane (2.0M in toluene) (4.5 mL, 1.20 equiv) at −10° C. After being stirred for 2 hours at −10° C. the resulting solution was diluted with 20 mL of dichloromethane, washed with saturated ammonia chloride, extracted with dichloromethane, dried over anhydrous sodium sulfate, and concentrated under vacuum. The residue was purified by a silica gel column with ethyl acetate/petroleum ether (1:2) to give 2.4 g (77%) of the titled compound as a light yellow solid; LC-MS (ES, m/z): 415 [M+H]$^+$.

Example 334

Synthesis of ethyl 9-iodo-4-methyl-4,5-dihydrobenzo[b]pyrazolo[1,5-d][1,4]oxazepine-2-carboxylate

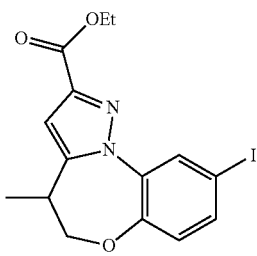 [SMILES: CCOC(=O)c1cc2n(n1)-c1cc(I)ccc1OCC2C]

To a solution of ethyl 4-hydroxy-9-iodo-4-methyl-4,5-dihydrobenzo[b]pyrazolo[1,5-d][1,4]oxazepine-2-carboxylate (2.3 g, 5.55 mmol, 1.00 equiv) in dichloromethane (50 mL) was added triethylsilane (9.7 g, 83.42 mmol, 15.00 equiv) and boron trifluoride diethyletherate (7.8 g, 10.00 equiv) at room temperature. After 1 h at room temperature the resulting mixture was diluted with 30 mL of dichloromethane, washed with saturated sodium bicarbonate solution, extracted with dichloromethane, dried over anhydrous sodium sulfate, and concentrated under vacuum. The residue was purified by a silica gel column with ethyl acetate/petroleum ether (1:9) to give 370 mg (17%) of the titled compound as a light yellow solid; LC-MS (ES, m/z) 399 [M+H]$^+$.

Example 335

Synthesis of ethyl 4-fluoro-9-iodo-4-methyl-4,5-dihydrobenzo[b]pyrazolo[1,5-d][1,4]oxazepine-2-carboxylate

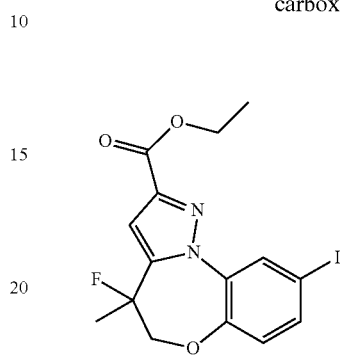

To a solution of ethyl 4-hydroxy-9-iodo-4-methyl-4,5-dihydrobenzo[b]pyrazolo[1,5-d][1,4]oxazepine-2-carboxylate (350 mg, 0.85 mmol, 1.00 equiv) in dichloromethane (5 mL) was added diethylaminosulfur trifluoride (271 mg, 1.68 mmol, 2.00 equiv) at 0° C. After being stirred overnight at room temperature the resulting mixture was washed with water, extracted with dichloromethane, dried over anhydrous sodium sulfate, and concentrated under vacuum. The residue was purified by a silica gel column with ethyl acetate/petroleum ether (1:20) to give 200 mg (57%) of the titled compound as a white solid; LC-MS (ES, m/z) 417 [M+H]$^+$.

Example 336

Synthesis of ethyl 4-fluoro-9-iodo-4,5-dihydrobenzo[b]pyrazolo[1,5-d][1,4]oxazepine-2-carboxylate

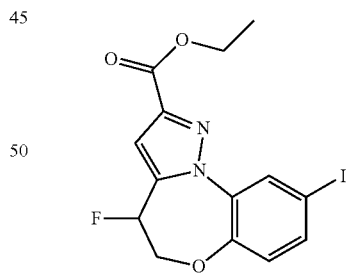

Ethyl 4-hydroxy-9-iodo-4,5-dihydrobenzo[b]pyrazolo[1,5-d][1,4]oxazepine-2-carboxylate (400 mg, 1.00 mmol, 1.00 equiv) in dichloromethane (25 mL) was added [bis(2-methoxyethyl)amino]sulfur trifluoride (442 mg, 2.00 mmol, 2.00 equiv) at 0° C. After 4 h at room temperature the resulting mixture was washed with brine, extracted with dichloromethane, dried over anhydrous sodium sulfate, and concentrated under vacuum. The residue was purified by a silica gel column with ethyl acetate/petroleum ether (1:10). It resulted in 330 mg (82%) of the titled compound as a yellow solid. LC-MS (ES, m/z) 403 [M+H]$^+$.

Example 337

Synthesis of (S)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide and (R)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide

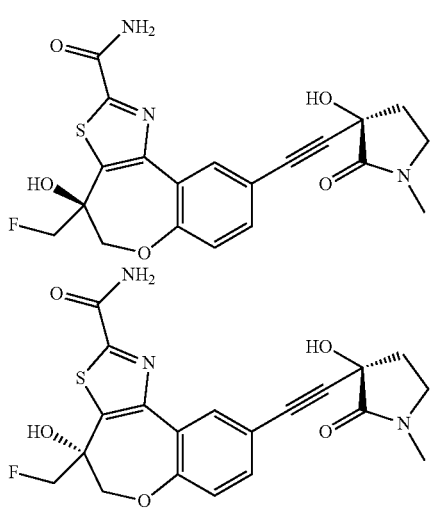

Similar to as described in General Procedure G, racemic ethyl 9-bromo-4-(fluoromethyl)-4-hydroxy-4,5-dihydrobenzo[2,3]oxepino[4,5-d]thiazole-2-carboxylate was reacted with (3R)-3-ethynyl-3-hydroxy-1-methylpyrrolidin-2-one to give a diasteromeric mixture of ethyl 4-(fluoromethyl)-4-hydroxy-9-(((R)-3-hydroxy-1-methyl-2-oxopyrrolidin-3-yl)ethynyl)-4,5-dihydro benzo[2,3]oxepino[4,5-d]thiazole-2-carboxylate. Following aminolysis of the ethyl ester (similar to as described in General Procedure M) a mixture of the titled compounds was obtained and separated by chiral Prep HPLC. The absolute stereochemistry at the 4-fluoromethyl position for each isomer was not determined.

Compound 1 colorless solid (16.9 mg, 9%); $t_R$=18.1 min (Lux cellulose-4, 25° C., UV-254 nm Hex:EtOH=50:50, 1.0 ml/min); M+1=432; $^1$H NMR (300 MHz, CD$_3$OD) δ 8.74 (d, J=1.8 Hz, 1H), 7.40 (dd, J=2.1 Hz, J=8.1 Hz, 1H), 7.08 (d, J=8.1 Hz, 1H), 4.87-4.46 (m, 3H), 4.02 (dd, J=3.0 Hz, J=12.0 Hz, 1H), 3.54-3.44 (m, 2H), 2.94 (s, 3H), 2.66-2.55 (m, 1H), 2.36-2.31 (m, 1H).

Compound 1 white solid (32 mg, 17%); $t_R$=22.5 min (Lux cellulose-4, 25° C., UV-254 nm Hex:EtOH=50:50, 1.0 ml/min); M+1=432; $^1$H NMR (300 MHz, CD$_3$OD) δ 8.76 (d, J=2.1 Hz, 1H), 7.42 (dd, J=1.8 Hz, J=8.1 Hz, 1H), 7.11 (d, J=7.8 Hz, 1H), 4.89-4.48 (m, 3H), 4.04 (dd, J=2.7 Hz, J=12.3 Hz, 1H), 3.53-3.48 (m, 2H), 2.94 (s, 3H), 2.61-2.59 (m, 1H), 2.36-2.32 (m, 1H).

Example 338

Synthesis of (R)-4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide and (S)-4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide

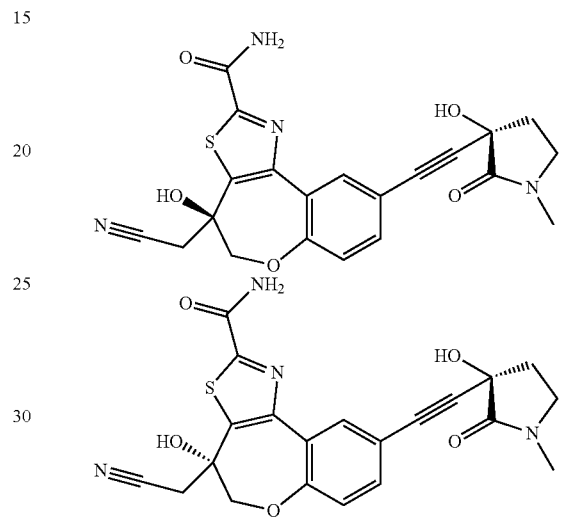

Similar to as described in General Procedure G, racemic 9-bromo-4-(cyanomethyl)-4-hydroxy-4,5-dihydrobenzo[2,3]oxepino[4,5-d]thiazole-2-carboxamide was reacted with (3R)-3-ethynyl-3-hydroxy-1-methylpyrrolidin-2-one to give a mixture of the titled compounds that were separated by Chiral-Prep-HPLC with the following conditions (Prep-HPLC-009): Column, Chiralpak IC, 2*25 cm, 5 um; mobile phase, ethanol and Hex (hold 60.0% Hex in 30 min); Detector, UV 254/220 nm. This resulted in 4.4 mg (5%) of Compound 15.2 mg (6%) of Compound 2. The absolute stereochemistry at the 4-cyanomethyl position of each isomer was not determined.

Compound 1 colorless solid (16.9 mg, 9%); $t_R$=28.1 min (CHIRALPAK IC, 25° C., 254 nm, Hex:EtOH=60:40, 1.0 mL/min); M+1=439; $^1$H NMR (300 MHz, CD$_3$OD) δ 8.75 (d, J=2.1 Hz, 1H), 7.41 (dd, J=2.1 Hz, J=8.4 Hz, 1H), 7.11 (d, J=8.4 Hz, 1H), 4.54 (d, J=11.7 Hz, 1H), 4.11 (d, J=12.0 Hz, 1H), 3.54-3.46 (m, 2H), 3.16 (s, 2H), 2.94 (s, 3H), 2.64-2.58 (m, 1H), 236-2.27 (m, 1H).

Compound 2 colorless solid (32 mg, 17%); $t_R$=32.8 min (CHIRALPAK IC, 25° C., 254 nm, Hex:EtOH=60:40, 1.0 mL/min); M+1=439; $^1$H NMR (300 MHz, CD$_3$OD) δ 8.78 (d, J=2.1 Hz, 1H), 7.43 (dd, J=2.4 Hz, J=8.4 Hz, 1H), 7.13 (d, J=8.7 Hz, 1H), 4.56 (d, J=12.0 Hz, 1H), 4.13 (d, J=12.0 Hz, 1H), 3.53-3.48 (m, 2H), 3.18 (s, 2H), 2.96 (s, 3H), 2.65-2.58 (m, 1H), 2.38-2.29 (m, 1H).

Example 339

Synthesis of (R)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide and (S)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide

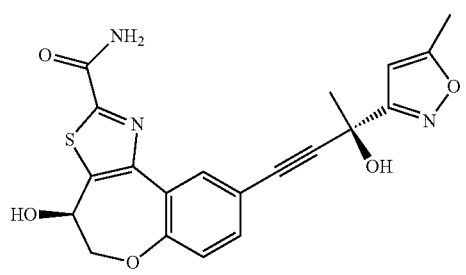

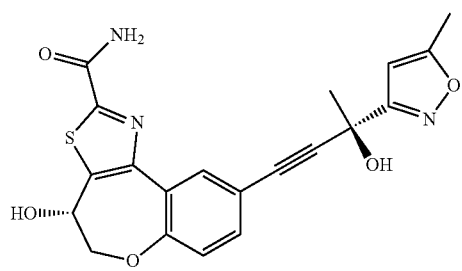

Similar to as described in General Procedure G, ethyl 9-bromo-4-hydroxy-4,5-dihydrobenzo[2,3]oxepino[4,5-d]thiazole-2-carboxylate was reacted with (2R)-2-(5-methyl-1,2-oxazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry at the 4-hydroxy position for each isomer was not determined.

Compound 1 colorless solid (14.4 mg, 15%); $t_R$=2.8 min (Chiralpak AD-H, 25° C., 254 nm, MeOH (0.1% DEA), 4.0 mL/min);); M+23=434; $^1$H NMR (300 MHz, CD$_3$OD) δ 8.68 (d, J=2.1 Hz, 1H), 7.38 (dd, J=2.1 Hz, J=8.4 Hz, 1H), 7.07 (d, J=8.4 Hz, 1H), 6.32 (s, 1H), 5.19-5.16 (q, J=3.0 Hz, 1H), 4.36-4.23 (m, 2H), 2.45 (s, 3H), 1.89 (s, 3H).

Compound 1 colorless solid (15.2 mg, 16%); $t_R$=3.5 min (Chiralpak AD-H, 25° C., 254 nm, MeOH (0.1% DEA), 4.0 mL/min); M+23=434; $^1$H NMR (300 MHz, CD$_3$OD) δ 8.68 (d, J=2.1 Hz, 1H), 7.38 (dd, J=2.1 Hz, J=8.4 Hz, 1H), 7.08 (d, J=8.4 Hz, 1H), 6.32 (s, 1H), 5.19-5.16 (q, J=3.0 Hz, 1H), 4.36-4.23 (m, 2H), 2.45 (s, 3H), 1.89 (s, 3H).

Example 340

Synthesis of (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

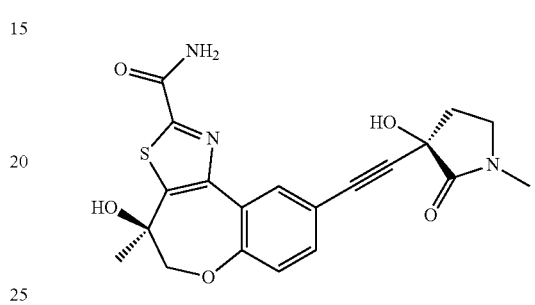

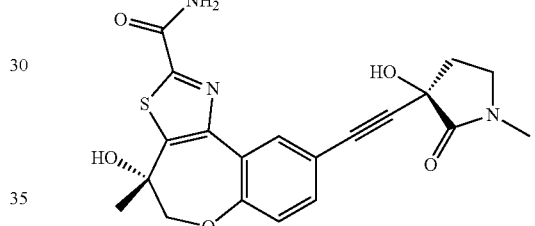

Similar to as described in General Procedure G, ethyl 9-bromo-4-hydroxy-4-methyl-4,5-dihydrobenzo[2,3]oxepino[4,5-d]thiazole-2-carboxylate was reacted with (3R)-3-ethynyl-3-hydroxy-1-methylpyrrolidin-2-one to give the diastereomeric ethyl esters which were converted to a mixture of the titled compounds via aminolysis (similar to as described in General Procedure M). The diasteromeric mixture was purified by chiral HPLC. The absolute stereochemistry at the 4-hydroxy position for each isomer was not determined.

Compound 1 colorless solid (22.7 mg, 8%); $t_R$=13.7 min (Lux Cellulose-4, 25° C., 254 nm, Hex:EtOH=65:35, 1.0 mL/min), 4.0 mL/min); M+1=414; $^1$H NMR (300 MHz, CD$_3$OD) δ 8.69 (d, J=2.1 Hz, 1H), 7.40-7.36 (dd, J=2.1 Hz, J=8.4 Hz, 1H), 7.07 (d, J=8.4 Hz, 1H), 4.22 (d, J=11.7 Hz, 1H), 4.11 (d, J=12 Hz, 1H), 3.55-3.44 (m, 2H), 2.94 (s, 3H), 2.64-2.56 (m, 1H), 2.36-2.27 (m, 1H), 1.67 (s, 3H).

Compound 2 colorless solid (23.3 mg, 8%); $t_R$=16.5 min (Lux Cellulose-4, 25° C., 254 nm, Hex:EtOH=65:35, 1.0 mL/min); M+1=414; $^1$H NMR (300 MHz, CD$_3$OD) δ 8.69 (d, J=2.1 Hz, 1H), 7.40-7.36 (dd, J=2.1 Hz, J=8.4 Hz, 1H), 7.07 (d, J=8.4 Hz, 1H), 4.22 (d, J=11.7 Hz, 1H), 4.11 (d, J=12 Hz, 1H), 3.55-3.44 (m, 2H), 2.94 (s, 3H), 2.64-2.56 (m, 1H), 2.36-2.27 (m, 1H), 1.67 (s, 3H).

Example 341

Synthesis of (R)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide and (S)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide

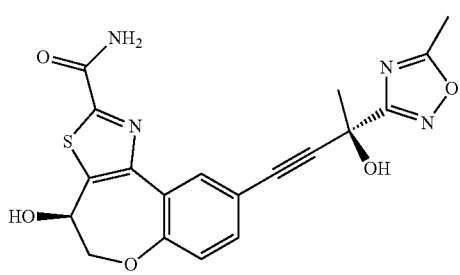

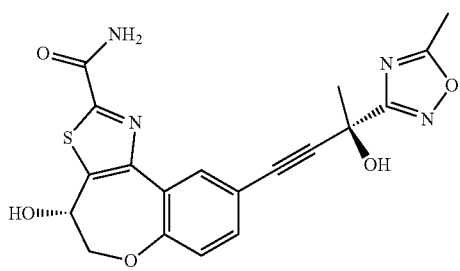

Similar to as described in General Procedure G, ethyl 9-bromo-4-hydroxy-4,5-dihydrobenzo[2,3]oxepino[4,5-d]thiazole-2-carboxylate was reacted with (R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry at the 4-hydroxy position for each isomer was not determined.

Compound 2 colorless solid (12.6 mg, 13%); $t_R$=14.7 min (Chiralpak IC, 25° C., 254 nm, Hex (0.1% TEA):IPA=55:45, 1.0 mL/min); M+23=435; NMR (300 MHz, CD$_3$OD) δ 8.70 (d, J=2.1 Hz, 1H), 7.40-7.37 (dd, J=2.1 Hz, J=8.4 Hz, 1H), 7.08 (d, J=8.1 Hz, 1H), 5.19-5.17 (q, J=3.0 Hz, 1H), 4.36-4.23 (m, 2H), 2.64 (s, 3H), 1.94 (s, 3H).

Compound 2 colorless solid (11.3 mg, 12%); $t_R$=22.7 min (Chiralpak IC, 25° C., 254 nm, Hex (0.1% TEA):IPA=55:45, 1.0 mL/min); M+23=435; $^1$H NMR (300 MHz, CD$_3$OD) δ 8.58 (d, J=2.1 Hz, 1H), 7.29-7.25 (dd, J=2.1 Hz, J=8.4 Hz, 1H), 6.97 (d, J=8.4 Hz, 1H), 5.08-5.05 (m, 1H), 4.24-4.13 (m, 2H), 2.52 (s, 3H), 1.82 (s, 3H).

Example 342

Synthesis of (R)-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (S)-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

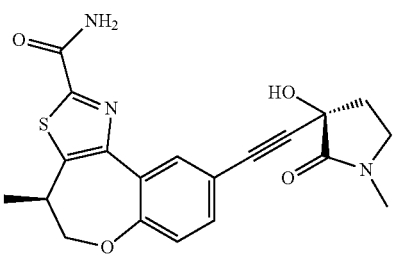

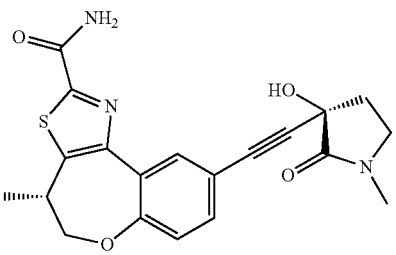

Similar to as described in General Procedure G, racemic ethyl 9-bromo-4-methyl-4,5-dihydrobenzo[2,3]oxepino[4,5-d]thiazole-2-carboxylate was reacted with (3R)-3-ethynyl-3-hydroxy-1-methylpyrrolidin-2-one to give the diastereomeric ethyl esters which were converted to a mixture of the titled compounds via aminolysis (similar to as described in General Procedure M). The diasteromeric mixture was purified by chiral HPLC. The absolute stereochemistry at the 4-methyl position for each isomer was not determined.

Compound 1 colorless solid (9.4 mg, 20%); $t_R$=2.0 min (Chiralpak IA-3, 25° C., 254 nm, Hex (0.1% TEA):EtOH=50:50, 1.0 mL/min); M+1=398; $^1$H NMR (300 MHz, CD$_3$OD) δ 8.67 (d, J=2.1 Hz, 1H), 7.32 (dd, J=2.4 Hz, J=8.4 Hz, 1H), 7.01 (d, J=8.4 Hz, 1H), 4.60 (s, 1H), 4.23 (d, J=4.2 Hz, 2H), 3.65-3.55 (m, 1H), 3.52-3.42 (m, 1H), 2.92 (s, 3H), 2.62-2.54 (m, 1H), 2.34-2.25 (m, 1H), 1.45 (d, J=6.9 Hz, 3H).

Compound 1 colorless solid (6.5 mg, 14%); $t_R$=4.6 min (Chiralpak IA-3, 25° C., 254 nm, Hex (0.1% TEA):EtOH=50:50, 1.0 mL/min); M+1=398; $^1$H NMR (300 MHz, CD$_3$OD) δ 8.67 (d, J=2.1 Hz, 1H), 7.31 (dd, J=2.1 Hz, J=8.4 Hz, 1H), 7.00 (d, J=8.4 Hz, 1H), 4.59 (s, 1H), 4.22 (d, J=4.2 Hz, 2H), 3.65-3.55 (m, 1H), 3.52-3.42 (m, 1H), 2.91 (s, 3H), 2.61-2.53 (m, 1H), 2.33-2.24 (m, 1H), 1.44 (d, J=7.2 Hz, 3H).

Example 343

Synthesis of (R)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide and (S)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide

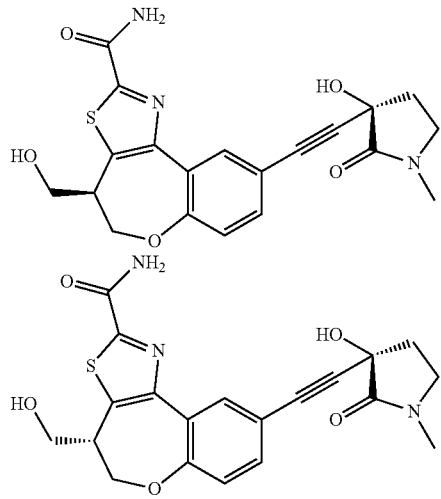

Similar to as described in General Procedure G, racemic ethyl 9-bromo-4-(hydroxymethyl)-4,5-dihydrobenzo[2,3]oxepino[4,5-d]thiazole-2-carboxylate was reacted with (3R)-3-ethynyl-3-hydroxy-1-methylpyrrolidin-2-one to give the diastereomeric ethyl esters which were converted to a mixture of the titled compounds via aminolysis (similar to as described in General Procedure M). The diasteromeric mixture was purified by chiral HPLC. The absolute stereochemistry at the 4-hydroxymethyl position for each isomer was not determined.

Compound 1 off-white solid (8.9 mg, 12%); $t_R$=16.4 min (Lux Cellulose-4, 25° C., 254 nm, Hex (0.1% TEA): EtOH=60:40, 1.0 mL):EtOH=50:50, 1.0 mL/min); M+1=414; $^1$H NMR (400 MHz, CD$_3$OD) δ 8.75 (d, J=2.4 Hz, 1H), 7.37-7.35 (dd, J=2.0 Hz, J=8.4 Hz, 1H), 7.05 (d, J=8.4 Hz, 1H), 4.72-4.68 (dd, J=4.0 Hz, J=12.4 Hz, 1H), 4.18-4.14 (dd, J=2.0 Hz, J=12.4 Hz, 1H), 3.93-3.88 (m, 1H), 3.82-3.78 (m, 1H), 3.54-3.48 (m, 3H), 2.95 (s, 3H), 2.63-2.58 (m, 1H), 2.36-2.31 (m, 1H).

Compound 1 off-white solid (15.7 mg, 21%); $t_R$=21.1 min (Lux Cellulose-4, 25° C., 254 nm, Hex (0.1% TEA): EtOH=60:40, 1.0 mL); M+23=436; NMR (300 MHz, CD$_3$OD) δ 8.73 (d, J=2.1 Hz, 1H), 7.36-7.33 (dd, J=2.1 Hz, J=8.4 Hz, 1H), 7.04 (d, J=8.4 Hz, 1H), 4.71-4.66 (dd, J=3.9 Hz, J=12.3 Hz, 1H), 4.16-4.12 (dd, J=2.1 Hz, J=12.0 Hz, 1H), 3.93-3.81 (m, 1H), 3.80-3.75 (m, 1H), 3.54-3.42 (m, 3H), 2.94 (s, 3H), 2.64-2.55 (m, 1H), 2.36-2.31 (m, 1H).

Example 344

Synthesis of (R)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide and (S)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide

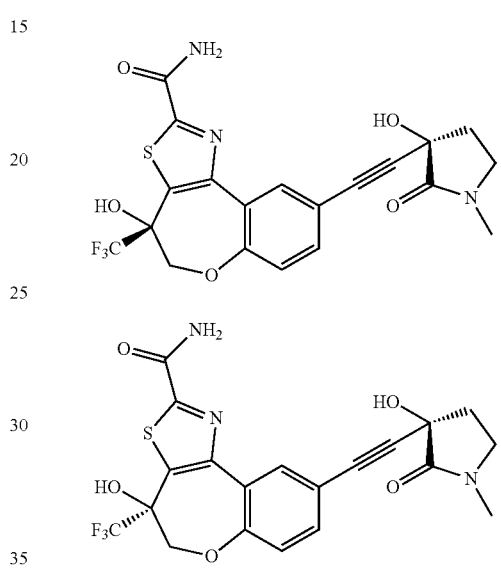

Similar to as described in General Procedure G, racemic ethyl 9-bromo-4-hydroxy-4-(trifluoromethyl)-4,5-dihydrobenzo[2,3]oxepino[4,5-d]thiazole-2-carboxylate was reacted with (3R)-3-ethynyl-3-hydroxy-1-methylpyrrolidin-2-one to give the diastereomeric ethyl esters which were converted to a mixture of the titled compounds via aminolysis (similar to as described in General Procedure M). The diasteromeric mixture was purified by chiral HPLC. The absolute stereochemistry at the 4-hydroxyl position for each isomer was not determined.

Compound 1 colorless solid (8.9 mg, 12%); $t_R$=14.3 min (Lux Cellulose-4, 25° C., 254 nm, Hex (0.1% TEA): EtOH=80:20, 1.0 mL/min); M+1=468; $^1$H NMR (400 MHz, CD$_3$OD) δ 8.82 (d, J=2.1 Hz, 1H), 7.45-7.41 (dd, J=2.1 Hz, J=8.4 Hz, 1H), 7.10 (d, J=8.4 Hz, 1H), 4.76 (d, J=12.6 Hz, 1H), 4.15-4.10 (dd, J=1.8 Hz, J=14.4 Hz, 1H), 3.55-3.45 (m, 2H), 2.94 (s, 3H), 2.63-2.56 (m, 1H), 2.32-2.27 (m, 1H).

Compound 1 colorless solid (15.7 mg, 21%); $t_R$=17.7 min (Lux Cellulose-4, 25° C., 254 nm, Hex (0.1% TEA): EtOH=80:20, 1.0 mL/min); M+1=468; $^1$H NMR (300 MHz, CD$_3$OD) δ 8.82 (d, J=2.1 Hz, 1H), 7.45-7.41 (dd, J=2.1 Hz, J=8.4 Hz, 1H), 7.10 (d, J=8.4 Hz, 1H), 4.75 (d, J=12.3 Hz, 1H), 4.15-4.10 (dd, J=1.8 Hz, J=12.6 Hz, 1H), 3.55-3.45 (m, 2H), 2.94 (s, 3H), 2.63-2.56 (m, 1H), 2.32-2.27 (m, 1H).

Example 345

Synthesis of (R)-9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide and (S)-9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide

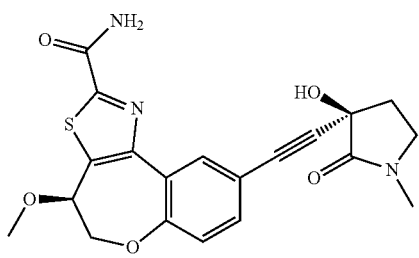

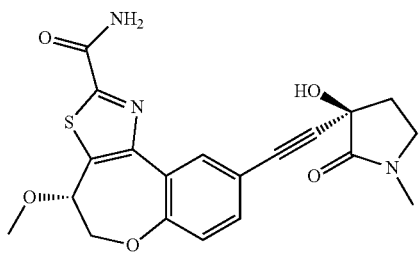

Similar to as described in General Procedure G, racemic ethyl 9-bromo-4-methoxy-4,5-dihydrobenzo[2,3]oxepino[4,5-d]thiazole-2-carboxylate with (3R)-3-ethynyl-3-hydroxy-1-methylpyrrolidin-2-one to give the diastereomeric ethyl esters which were converted to a mixture of the titled compounds via aminolysis (similar to as described in General Procedure M). The diasteromeric mixture was purified by chiral HPLC. The absolute stereochemistry at the 4-methoxy position for each isomer was not determined.

Compound 1 colorless solid (133 mg, 11%); $t_R$=9.1 min (Chiralpak IA, 25° C., 254 nm, MTBE:EtOH=80:20, 1.0 mL/min); M+1=414; $^1$H NMR (400 MHz, CD$_3$OD) δ 8.71 (d, J=2.1 Hz, 1H), 7.42-7.38 (dd, J=2.1 Hz, J=8.4 Hz, 1H), 7.09 (d, J=8.4 Hz, 1H), 4.92-4.91 (m, 1H), 4.52-4.46 (m, 1H), 4.37-4.32 (dd, J=2.7 Hz, J=12.6 Hz, 1H), 3.62 (s, 3H), 3.52-3.47 (m, 2H), 2.95 (s, 3H), 2.59 (s, 1H), 2.62-2.53 (m, 1H), 2.34-2.30 (m, 1H).

Compound 1 white solid (12.7 mg, 1%); $t_R$=11.1 min (Chiralpak IA, 25° C., 254 nm, MTBE:EtOH=80:20, 1.0 mL/min); M+1=414; $^1$H NMR (300 MHz, CD$_3$OD) δ 8.70 (d, J=2.1 Hz, 1H), 7.41-7.37 (dd, J=2.1 Hz, J=8.1 Hz, 1H), 7.08 (d, J=8.4 Hz, 1H), 4.46 (d, J=5.4 Hz, 1H), 4.37 (d, J=2.4 Hz, 1H), 3.61 (s, 3H), 3.49-3.46 (m, 2H), 2.94 (s, 3H), 2.68-2.52 (m, 1H), 2.34-2.25 (m, 1H).

Example 346

Synthesis of 4-cyano-9-(((R)-3-hydroxy-1-methyl-2-oxopyrrolidin-3-yl)ethynyl)-4,5-dihydrobenzo[2,3]oxepino[4,5-d]thiazole-2-carboxamide

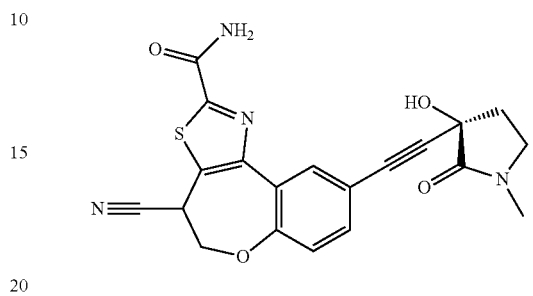

Similar to as described in General Procedure G, racemic ethyl 9-bromo-4-cyano-4,5-dihydrobenzo[2,3]oxepino[4,5-d]thiazole-2-carboxylate was reacted with (3R)-3-ethynyl-3-hydroxy-1-methylpyrrolidin-2-one to give the ethyl ester which was converted to the titled compounds via aminolysis (similar to as described in General Procedure M). Yellow solid (7.6 mg, 14%).

M+1=407; $^1$H NMR (CD$_3$OD, 300 MHz) δ 7.90 (d, J=2.1 Hz, 1H), 7.34-7.28 (m, 1H), 6.94-6.85 (m, 1H), 6.04-5.98 (m, 1H), 3.44-3.35 (m, 2H), 3.22-3.11 (m, 2H), 2.83 (s, 3H), 2.56-2.43 (m, 1H), 2.23-2.16 (m, 1H).

Example 347

Synthesis of (R)-4,4-difluoro-9-(3-hydroxy-3-(5-methyl-1,2,4-oxadiazol-3-yl)but-1-yn-1-yl)-4,5-dihydrobenzo[2,3]oxepino[4,5-d]thiazole-2-carboxamide

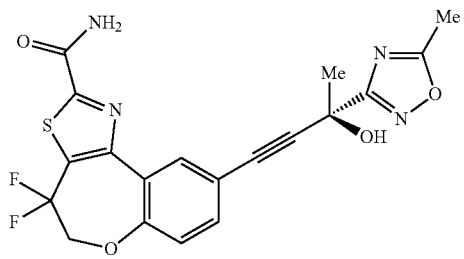 [SMILES: Cc1nc([C@](C)(O)C#Cc2ccc3c(c2)-c2nc(C(N)=O)sc2C(F)(F)CO3)no1]

Similar to as described in General Procedure G, ethyl 9-bromo-4,4-difluoro-4,5-dihydrobenzo[2,3]oxepino[4,5-d]thiazole-2-carboxylate was reacted (2R)-2-(5-methyl-1,2,4-oxadiazol-3-yl)but-3-yn-2-ol to give the ethyl ester which was converted to the titled compound via aminolysis (similar to as described in General Procedure M). Colorless solid (71.4 mg, 54%).

M+1=450; $^1$H NMR (400 MHz, CD$_3$OD) δ 8.73 (s, 1H), 7.52 (dd, J=1.2 Hz, J=6.3 Hz, 1H), 7.22 (d, J=8.4 Hz, 1H), 4.62 (t, J=10.4 Hz, 2H), 2.65 (s, 3H), 1.95 (s, 3H).

Example 348

Synthesis of (R)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide and (S)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide

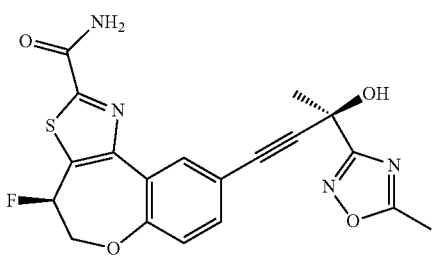

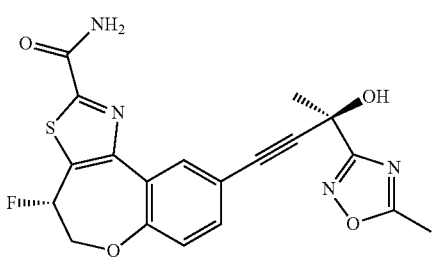

Similar to as described in General Procedure G, racemic ethyl 9-bromo-4-fluoro-4,5-dihydrobenzo[2,3]oxepino[4,5-d]thiazole-2-carboxylate was reacted with (2R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-fluorine substitution position for each isomer was not determined.

Compound 1 colorless solid (11.9 mg, 11%); $t_R$=12.6 min (Chiralpak IA, 25° C., 254 nm, MTBE:IPA=95:5, 1.0 mL/min); M+1=415; $^1$H NMR (300 MHz, CD$_3$OD) δ 8.65 (d, J=2.1 Hz, 1H), 7.41 (dd, J=2.1 Hz, J=8.4 Hz, 1H), 7.11 (d, J=8.4 Hz, 1H), 6.11-5.93 (m, 1H), 4.78-4.72 (m, 1H), 4.23-4.08 (m, 1H), 2.60 (s, 3H), 1.90 (s, 1H).

Compound 2 white solid (9.3 mg, 9%); $t_R$=15.2 min (Chiralpak IA, 25° C., 254 nm, MTBE:IPA=95:5, 1.0 mL/min); M+1=415; $^1$H NMR (300 MHz, CD$_3$OD) δ 8.68 (d, J=2.1 Hz, 1H), 7.45 (dd, J=2.1 Hz, J=8.4 Hz, 1H), 7.15 (d, J=8.1 Hz, 1H), 6.14-5.97 (m, 1H), 4.82-4.76 (m, 1H), 4.26-4.12 (m, 1H), 2.64 (s, 3H), 1.94 (s, 1H).

Example 349

Synthesis of (R)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide and (S)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide

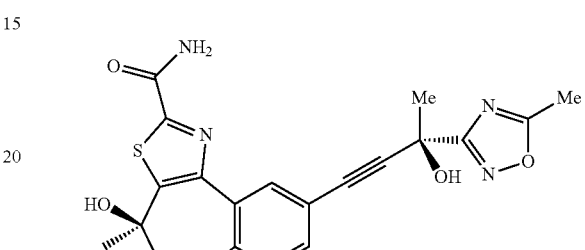

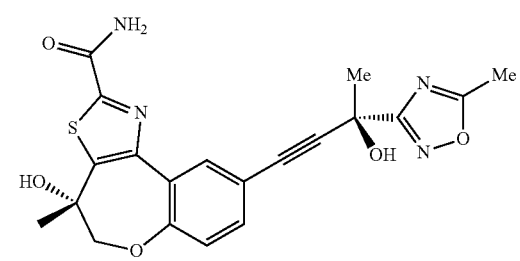

Similar to as described in General Procedure G, racemic ethyl 9-bromo-4-hydroxy-4-methyl-4,5-dihydrobenzo[2,3]oxepino[4,5-d]thiazole-2-carboxylate was reacted with (2R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-hydroxyl substitution position for each isomer was not determined.

Compound 1 colorless solid (4.3 mg, 10%); $t_R$=3.4 min (CHIRALPAK OJ-H, 25° C., 254 nm, IPA (0.2% DEA) (20%), 4.0 mL/min); M+1=427; $^1$H NMR (400 MHz, CD$_3$OD) δ 8.70 (d, J=2.0 Hz, 1H), 7.40 (dd, J=2.0, 8.4 Hz, 1H), 7.09 (d, J=8.4 Hz, 1H), 4.23 (AB, J=12.0 Hz, 1H), 4.12 (AB, J=12.0 Hz, 1H), 2.65 (s, 3H), 1.95 (s, 3H), 1.68 (s, 3H).

Compound 2 colorless solid (14.3 mg, 32%); $t_R$=4.3 min (CHIRALPAK OJ-H, 25° C., 254 nm, IPA (0.2% DEA) (20%), 4.0 mL/min); M+1=427; $^1$H NMR (400 MHz, CD$_3$OD) δ 8.70 (d, J=2.0 Hz, 1H), 7.40 (dd, J=2.0, 8.4 Hz, 1H), 7.09 (d, J=8.4 Hz, 1H), 4.23 (AB, J=12.0 Hz, 1H), 4.12 (AB, J=12.0 Hz, 1H), 2.65 (s, 3H), 1.95 (s, 3H), 1.68 (s, 3H).

Example 350

Synthesis of (4S)-4-fluoro-9-(3-hydroxy-4-methoxy-3-methylbut-1-yn-1-yl)-4,5-dihydrobenzo[2,3]oxepino[4,5-d]thiazole-2-carboxamide, (4R)-4-fluoro-9-(3-hydroxy-4-methoxy-3-methylbut-1-yn-1-yl)-4,5-dihydrobenzo[2,3]oxepino[4,5-d]thiazole-2-carboxamide, (R)-4-fluoro-9-((S)-3-hydroxy-4-methoxy-3-methylbut-1-yn-1-yl)-4,5-dihydrobenzo[2,3]oxepino[4,5-d]thiazole-2-carboxamide and (S)-4-fluoro-9-((S)-3-hydroxy-4-methoxy-3-methylbut-1-yn-1-yl)-4,5-dihydrobenzo[2,3]oxepino[4,5-d]thiazole-2-carboxamide

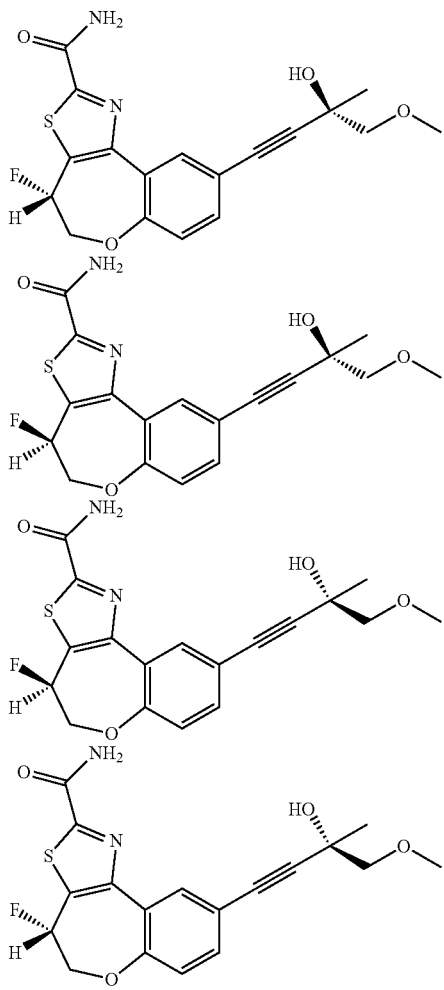

Similar to as described in General Procedure G, racemic ethyl 9-bromo-4-fluoro-4,5-dihydrobenzo[2,3]oxepino[4,5-d]thiazole-2-carboxylate was reacted with racemic 1-methoxy-2-methylbut-3-yn-2-ol to give the diastereomeric ethyl esters which were converted to a mixture of the titled compounds via aminolysis (similar to as described in General Procedure M). The diasteromeric mixture was purified by chiral HPLC. The absolute and relative stereochemistry of the 4-fluorine and propargyl alcohol substitution positions for each isomer was not determined.

Compound 1: colorless solid (16 mg, 4%); $t_R$=20.0 min (Chiralpak IC-3, 25° C., 254 nm, Hex:EtOH=85:15, 1.0 mL/min); M+23=399; $^1$H NMR (400 MHz, CD$_3$OD) δ 8.65 (d, J=2.0 Hz, 1H), 7.43-7.41 (dd, J=2.0 Hz, J=8.4 Hz, 1H), 7.15 (d, J=8.4 Hz, 1H), 6.06 (d, J=48.4 Hz, 1H), 4.85-4.78 (m, 1H), 4.25-4.14 (m, 1H), 3.52 (s, 2H), 3.50 (s, 3H), 1.56 (s, 3H);

Compound 2: colorless solid (17.3 mg, 5%); $t_R$=22.9 min (Chiralpak IC-3, 25° C., 254 nm, Hex:EtOH=85:15, 1.0 mL/min); M+23=399; $^1$H NMR (300 MHz, CD$_3$OD) δ 8.63 (d, J=2.1 Hz, 1H), 7.43-7.39 (dd, J=2.1 Hz, J=8.4 Hz, 1H), 7.13 (d, J=8.4 Hz, 1H), 6.06 (d, J=48.3 Hz, 1H), 4.85-4.76 (m, 1H), 4.25-4.14 (m, 1H), 3.51 (s, 2H), 3.48 (s, 3H), 1.55 (s, 3H);

Compound 3: colorless solid (23.1 mg, 6%); $t_R$=25.0 min (Chiralcel OJ-3, 25° C., 254 nm, Hex:EtOH=80:20, 1.0 mL/min); M+23=399; $^1$H NMR (300 MHz, CD$_3$OD) δ 8.63 (d, J=2.1 Hz, 1H), 7.43-7.39 (dd, J=2.1 Hz, J=8.4 Hz, 1H), 7.13 (d, J=8.4 Hz, 1H), 6.06 (d, J=48.3 Hz, 1H), 4.85-4.76 (m, 1H), 4.25-4.14 (m, 1H), 3.51 (s, 2H), 3.48 (s, 3H), 1.55 (s, 3H)

Compound 4: colorless solid (7.1 mg, 2%); $t_R$=29.4 min (Chiralcel OJ-3, 25° C., 254 nm, Hex:EtOH=80:20, 1.0 mL/min); M+23=399; $^1$H NMR (300 MHz, CD$_3$OD) δ 8.63 (d, J=2.1 Hz, 1H), 7.43-7.39 (dd, J=2.1 Hz, J=8.4 Hz, 1H), 7.13 (d, J=8.4 Hz, 1H), 6.06 (d, J=48.3 Hz, 1H), 4.85-4.76 (m, 1H), 4.25-4.14 (m, 1H), 3.51 (s, 2H), 3.48 (s, 3H), 1.55 (s, 3H)/

Example 351

Synthesis of (R)-4-hydroxy-9-((1-hydroxycyclopentyl)ethynyl)-4,5-dihydrobenzo[2,3]oxepino[4,5-d]thiazole-2-carboxamide and (S)-4-hydroxy-9-((1-hydroxycyclopentyl)ethynyl)-4,5-dihydrobenzo[2,3]oxepino[4,5-d]thiazole-2-carboxamide

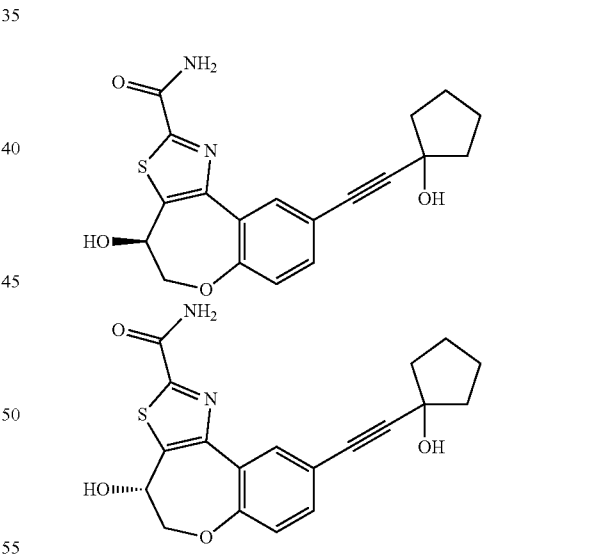

Similar to as described in General Procedure G, racemic ethyl 9-bromo-4-hydroxy-4,5-dihydrobenzo[2,3]oxepino[4,5-d]thiazole-2-carboxylate was reacted 1-ethynylcyclopentanol to give the racemic ethyl ester which was converted to a mixture of the titled compounds via aminolysis (similar to as described in General Procedure M). The racemic mixture was purified by chiral HPLC. The absolute stereochemistry of the 4-hydroxyl substitution position for each isomer was not determined.

Compound 1: colorless solid (22.8 mg, 33%); $t_R$=5.3 min (Lux Cellulose-4, 25° C., 254 nm, Hex (0.1% TEA):

EtOH=70:30, 1.0 mL/min); M+1=371; $^1$H NMR (400 MHz, CD$_3$OD) δ 8.63 (d, J=1.2 Hz, 1H), 7.34 (dd, J=1.2, 8.0 Hz, 1H), 7.07 (d, J=8.4 Hz, 1H), 5.21-5.17 (m, 1H), 4.35-4.25 (m, 2H), 2.08-2.03 (m, 4H), 1.90-1.78 (m, 4H)

Compound 2: colorless solid (23.6 mg, 34%); $t_R$=7.8 min (Lux Cellulose-4, 25° C., 254 nm, Hex (0.1% TEA): EtOH=70:30, 1.0 mL/min); M+1=371; $^1$H NMR (400 MHz, CD$_3$OD) δ 8.63 (d, J=1.2 Hz, 1H), 7.34 (dd, J=1.2, 8.0 Hz, 1H), 7.07 (d, J=8.4 Hz, 1H), 5.21-5.17 (m, 1H), 4.35-4.25 (m, 2H), 108-2.03 (m, 4H), 1.90-1.78 (m, 4H).

Example 352

Synthesis of (R)-4-hydroxy-9-((1-hydroxycyclopentyl)ethynyl)-4-methyl-4,5-dihydrobenzo[2,3]oxepino[4,5-d]thiazole-2-carboxamide and (S)-4-hydroxy-9-((1-hydroxycyclopentyl)ethynyl)-4-methyl-4,5-dihydrobenzo[2,3]oxepino[4,5-d]thiazole-2-carboxamide

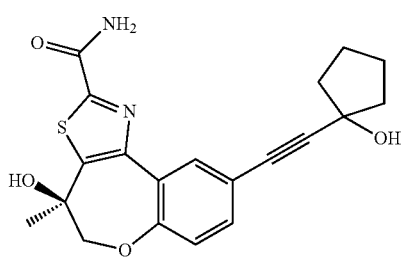

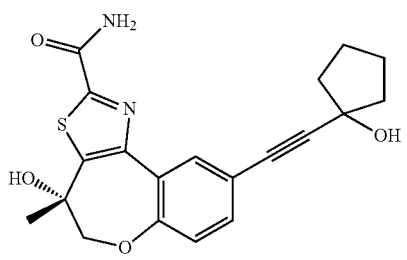

Similar to as described in General Procedure G, racemic ethyl 9-bromo-4-hydroxy-4-methyl-4,5-dihydrobenzo[2,3]oxepino[4,5-d]thiazole-2-carboxylate was reacted 1-ethynylcyclopentanol to give the racemic ethyl ester which was converted to a mixture of the titled compounds via aminolysis (similar to as described in General Procedure M). The racemic mixture was purified by chiral HPLC. The absolute stereochemistry of the 4-hydroxyl substitution position for each isomer was not determined.

Compound 1 colorless solid (16.2 mg, 30%); $t_R$=7.2 min (Lux Cellulose-4, 25° C., 254 nm, Hex:EtOH=80:20, 1.0 mL/min); M+1=385; $^1$H NMR (400 MHz, CD$_3$OD) δ 8.62 (d, J=2.0 Hz, 1H), 7.35-7.32 (dd, J=2.0 Hz, J=8.4 Hz, 1H), 7.06 (d, J=8.4 Hz, 1H), 4.22 (d, J=12.0 Hz, 1H), 4.12 (d, J=11.6 Hz, 1H), 2.08-2.02 (m, 4H), 1.91-1.82 (m, 4H), 1.68 (s, 3H);

Compound 2 colorless solid (14.7 mg, 27%); $t_R$=8.8 min (Lux Cellulose-4, 25° C., 254 nm, Hex:EtOH=80:20, 1.0 mL/min); M+1=385; $^1$H NMR (400 MHz, CD$_3$OD) δ8.62 (d, J=2.0 Hz, 1H), 7.35-7.32 (dd, J=2.0 Hz, J=8.4 Hz, 1H), 7.06 (d, J=8.4 Hz, 1H), 4.22 (d, J=12.0 Hz, 1H), 4.12 (d, J=11.6 Hz, 1H), 2.08-2.02 (m, 4H), 1.91-1.82 (m, 4H), 1.68 (s, 3H).

Example 353

Synthesis of (R)-4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide and (S)-4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide

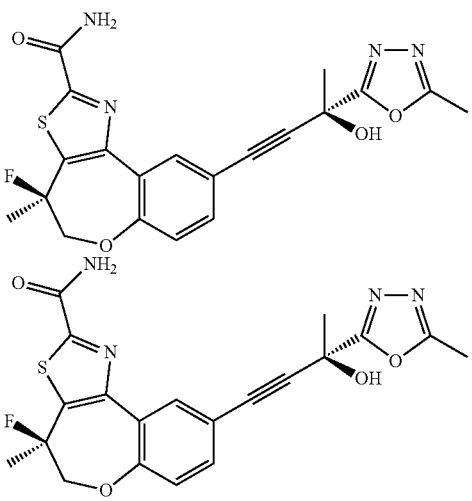

Similar to as described in General Procedure G, racemic ethyl 9-bromo-4-fluoro-4-methyl-4,5-dihydrobenzo[2,3]oxepino[4,5-d]thiazole-2-carboxylate was reacted with (2R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-fluorine substitution position for each isomer was not determined.

Compound 1 colorless solid (4.3 mg); $t_R$=21.4 min (Chiralpak IA, 25° C., 254 nm, Hex:EtOH=85:15, 1.0 mL/min); M+1=429; $^1$H NMR (400 MHz, CD$_3$OD) δ 8.70 (d, J=2.4 Hz, 1H), 7.49-7.47 (dd, J=2.4 Hz, J=8.4 Hz, 1H), 7.15 (d, J=8.4 Hz, 1H), 4.56-4.50 (m, 1H), 4.35-4.27 (m, 1H), 2.61 (s, 1H), 2.01 (s, 3H), 1.85 (d, J=20.4 Hz, 3H);

Compound 2 colorless solid (3.4 mg); $t_R$=23.9 min (Chiralpak IA, 25° C., 254 nm, Hex:EtOH=85:15, 1.0 mL/min); M+1=429; $^1$H NMR (400 MHz, CD$_3$OD) δ 8.70 (d, J=2.4 Hz, 1H), 7.49-7.47 (dd, J=2.0 Hz, J=8.4 Hz, 1H), 7.15 (d, J=8.4 Hz, 1H), 4.55-4.50 (m, 1H), 4.35-4.27 (m, 1H), 2.61 (s, 1H), 2.01 (s, 3H), 1.88-1.83 (d, J=20.4 Hz, 3H).

Example 354

Synthesis of (R)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide and (S)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide

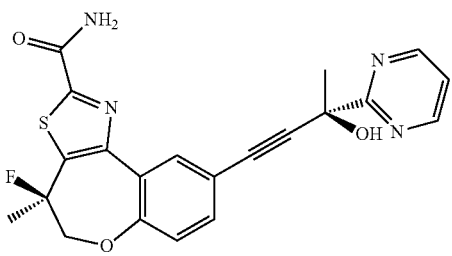

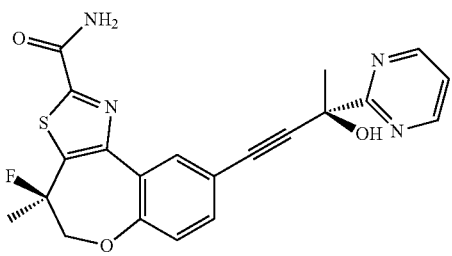

Similar to as described in General Procedure G, racemic ethyl 9-bromo-4-fluoro-4-methyl-4,5-dihydrobenzo[2,3]oxepino[4,5-d]thiazole-2-carboxylate was reacted with (R)-2-(pyrimidin-2-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-fluorine substitution position for each isomer was not determined.

Compound 1 yellow solid (8.8 mg, 11%); $t_R$=13.9 min (CHIRALPAK OJ-H, 25° C., 254 nm, Hex:EtOH=70:30, 1.0 mL/min); M+23=425; $^1$H NMR (300 MHz, CD$_3$OD) δ 8.89 (d, J=4.8 Hz, 2H), 8.66 (d, J=2.1 Hz, 1H), 7.50-7.42 (m, 2H), 7.13 (d, J=8.4 Hz, 1H), 4.56-4.49 (dd, J=8.4 Hz, J=12.9 Hz, 1H), 4.36-4.25 (dd, J=12.6 Hz, J=19.8 Hz, 1H), 1.99 (s, 3H), 1.86 (d, J=20.4 Hz, 3H).

Compound 2 yellow solid (9.3 mg, 12%); $t_R$=19.8 min (CHIRALPAK OJ-H, 25° C., 254 nm, Hex:EtOH=70:30, 1.0 mL/min); M+23=425; $^1$H NMR (300 MHz, CD$_3$OD) δ 8.88 (d, J=5.1 Hz, 2H), 8.66 (d, J=2.1 Hz, 1H), 7.50-7.42 (m, 2H), 7.13 (d, J=8.4 Hz, 1H), 4.56-4.47 (m, 1H), 4.35-4.25 (m, 1H), 1.98 (s, 3H), 1.86 (d, J=20.1 Hz, 3H).

Example 355

Synthesis of (R)-4,4-difluoro-9-(3-hydroxy-4-methoxy-3-methylbut-1-yn-1-yl)-4,5-dihydrobenzo[2,3]oxepino[4,5-d]thiazole-2-carboxamide and (S)-4,4-difluoro-9-(3-hydroxy-4-methoxy-3-methylbut-1-yn-1-yl)-4,5-dihydrobenzo[2,3]oxepino[4,5-d]thiazole-2-carboxamide

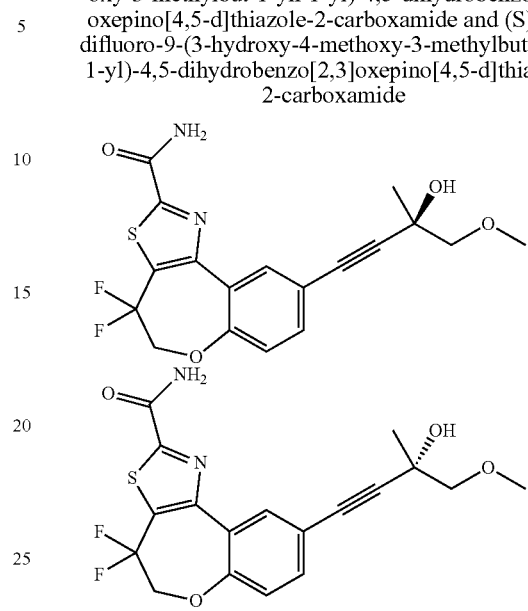

Similar to as described in General Procedure G, ethyl 9-bromo-4,4-difluoro-4,5-dihydrobenzo[2,3]oxepino[4,5-d]thiazole-2-carboxylate was reacted with racemic 1-methoxy-2-methylbut-3-yn-2-ol to give the diastereomeric ethyl esters which were converted to a mixture of the titled compounds via aminolysis (similar to as described in General Procedure M). The enantiomeric mixture was purified by chiral HPLC. The absolute stereochemistry of propargyl alcohol substitution position for each isomer was not determined.

Compound 1 colorless solid (16.2 mg, 12%); $t_R$=4.4 min (Chiralpak IC-3, 25° C., 254 nm, Hex:EtOH=90:10, 1.0 mL/min); M+23=417; $^1$H NMR (400 MHz, CD$_3$OD) δ 8.67 (d, J=2.0 Hz, 1H), 7.49-7.47 (dd, J=2.0 Hz, J=8.4 Hz, 1H), 7.20 (d, J=8.4 Hz, 1H), 4.61 (t, J=10.4 Hz, 2H), 3.52 (s, 2H), 3.50 (s, 3H), 1.56 (s, 3H).

Compound 2 colorless solid (14.2 mg, 11%); $t_R$=5.7 min (Chiralpak IC-3, 25° C., 254 nm, Hex:EtOH=90:10, 1.0 mL/min); M+23=417; $^1$H NMR (400 MHz, CD$_3$OD) δ 8.67 (d, J=2.0 Hz, 1H), 7.49-7.47 (dd, J=2.0 Hz, J=8.4 Hz, 1H), 7.20 (d, J=8.4 Hz, 1H), 4.61 (t, J=10.4 Hz, 2H), 3.52 (s, 2H), 3.50 (s, 3H), 1.56 (s, 3H).

Example 356

Synthesis of (R)-4,4-difluoro-9-(3-hydroxy-3-(pyrimidin-2-yl)but-1-yn-1-yl)-4,5-dihydrobenzo[2,3]oxepino[4,5-d]thiazole-2-carboxamide

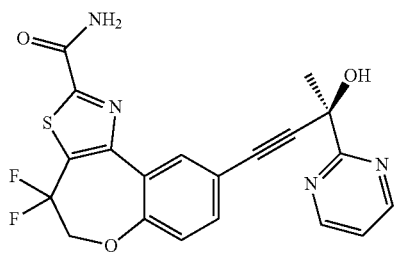 [SMILES: C[C@@](O)(C#Cc1ccc2c(c1)-c1nc(C(N)=O)sc1C(F)(F)CO2)c1ncccn1]

Similar to as described in General Procedure G, ethyl 9-bromo-4,4-difluoro-4,5-dihydrobenzo[2,3]oxepino[4,5-d]thiazole-2-carboxylate was reacted with (R)-2-(pyrimidin-2-yl)but-3-yn-2-ol to give the ethyl ester which were converted to the titled compound via aminolysis (similar to as described in General Procedure M). Colorless solid (47.7 mg, 64%).

M+H=429; $^1$H NMR (400 MHz, CD$_3$OD) δ 8.88 (d, J=5.2 Hz, 2H), 8.69 (d, J=2.0 Hz, 1H), 7.50-7.46 (m, 2H), 7.19 (d, J=8.4 Hz, 1H), 4.60 (t, J=10.4 Hz, 1H), 1.98 (s, 3H).

Example 357

Synthesis of (R)-4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide and (S)-4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide

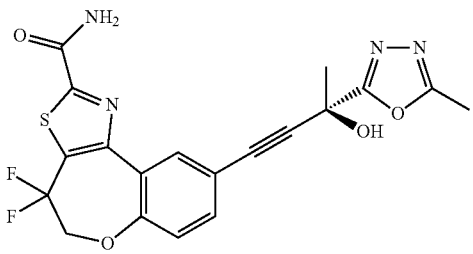

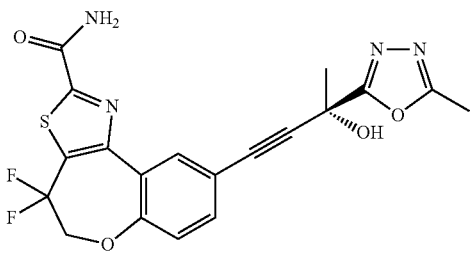

Similar to as described in General Procedure G, ethyl 9-bromo-4,4-difluoro-4,5-dihydrobenzo[2,3]oxepino[4,5-d]thiazole-2-carboxylate was reacted with racemic 2-(5-methyl-1,3,4-oxadiazol-2-yl)but-3-yn-2-ol to give the racemic ethyl esters which were converted to the titled compounds via aminolysis (similar to as described in General Procedure M). The enantiomers were separated by chiral prep HPLC. The absolute stereochemistry of propargyl alcohol substitution position for each isomer was not determined.

Compound 1 colorless solid (99.5 mg, 59%); M+1=417; $^1$H NMR (300 MHz, CD$_3$OD) δ 8.74 (d, J=2.1 Hz 1H), 7.56-7.52 (dd, J=2.1 Hz, J=8.4 Hz, 1H), 7.22 (d, J=8.4 Hz, 1H), 4.61 (t, J=10.2 Hz, 2H), 2.59 (s, 3H), 2.00 (s, 3H).

Compound 2 colorless solid (55.8 mg, 43%); M+1=417; $^1$H NMR (300 MHz, CD$_3$OD) δ 8.74 (d, J=2.1 Hz 1H), 7.56-7.52 (dd, J=2.1 Hz, J=8.4 Hz, 1H), 7.22 (d, J=8.4 Hz, 1H), 4.61 (t, J=10.2 Hz, 2H), 2.59 (s, 3H), 2.00 (s, 3H).

Example 358

Synthesis of (R)-4,4-difluoro-9-((3-hydroxy-1-methyl-2-oxopiperidin-3-yl)ethynyl)-4,5-dihydrobenzo[2,3]oxepino[4,5-d]thiazole-2-carboxamide

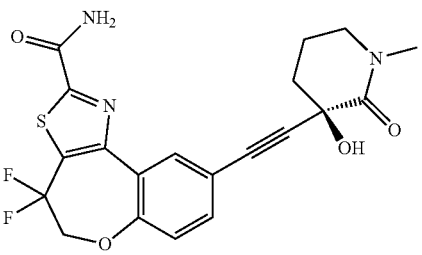 [SMILES: CN1CCC[C@@](O)(C#Cc2ccc3c(c2)-c2nc(C(N)=O)sc2C(F)(F)CO3)C1=O]

Similar to as described in General Procedure G, ethyl 9-bromo-4,4-difluoro-4,5-dihydrobenzo[2,3]oxepino[4,5-d]thiazole-2-carboxylate was reacted with (R)-3-ethynyl-3-hydroxy-1-methylpiperidin-2-one to give the ethyl ester which was converted to the titled compound via aminolysis (similar to as described in General Procedure M). Colorless solid (6.4 mg, 7%).

M+1=434; $^1$H NMR (300 MHz, CD$_3$OD) δ 8.69 (d, J=1.8 Hz 1H), 7.52-7.48 (dd, J=2.1 Hz, J=8.4 Hz, 1H), 7.20 (d, J=8.4 Hz, 1H), 4.60 (t, J=10.5 Hz, 2H), 3.51-3.42 (m, 2H), 2.99 (s, 3H), 2.35-2.22 (m, 2H), 2.19-2.07 (m, 2H).

Example 359

Synthesis of (R)-4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide and (S)-4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide

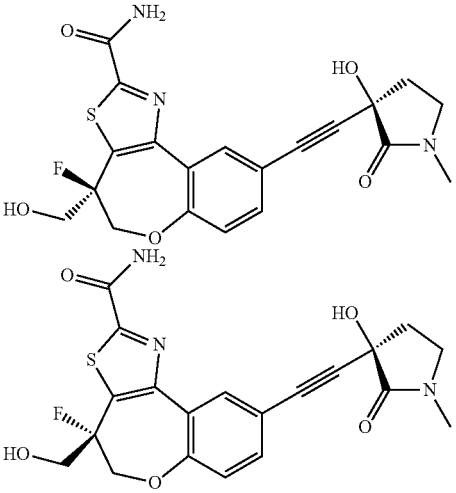

Similar to as described in General Procedure G, racemic ethyl 9-bromo-4-fluoro-4-(hydroxymethyl)-4,5-dihydrobenzo[2,3]oxepino[4,5-d]thiazole-2-carboxylate was reacted with (R)-3-ethynyl-3-hydroxy-1-methylpyrrolidin- 2-one to give the diastereomeric ethyl esters which were converted to a mixture of the titled compounds via aminolysis (similar to as described in General Procedure M). The diasteromeric mixture was purified by chiral HPLC. The absolute stereochemistry of the 4-fluorine substitution position for each isomer was not determined.

Compound 1 off-white solid (2.1 mg, 1%); $t_R$=6.7 min (Chiralcel OJ-3, 25° C., 254 nm, Hex:EtOH=60:40, 1.0 mL/min); M+1=432; $^1$H NMR (400 MHz, CD$_3$OD) δ 8.59 (d, J=2.4 Hz, 1H), 7.34-7.32 (dd, J=2.0 Hz, J=8.4 Hz, 1H), 7.02 (d, J=8.4 Hz, 1H), 4.54-4.47 (dd, J=12.4 Hz, J=15.6 Hz, 1H);

Compound 2 off-white solid (6.8 mg, 5%); $t_R$=12.5 min (Chiralcel OJ-3, 25° C., 254 nm, Hex:EtOH=60:40, 1.0 mL/min); M+1=432; $^1$H NMR (300 MHz, CD$_3$OD) δ 8.72 (d, J=2.1 Hz, 1H), 7.48-7.44 (dd, J=2.1 Hz, J=8.4 Hz, 1H), 7.15 (d, J=8.4 Hz, 1H), 4.68-4.58 (dd, J=12.6 Hz, J=15.6 Hz, 1H), 4.47-4.41 (dd, J=7.2 Hz, J=12.6 Hz, 1H), 4.01-3.95 (m, 2H), 3.53-3.48 (m, 2H), 2.96 (s, 3H), 2.64-2.59 (m, 1H), 2.38-2.31 (m, 1H).

Example 360

Synthesis of (R)-9-4(R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide and (S)-9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide

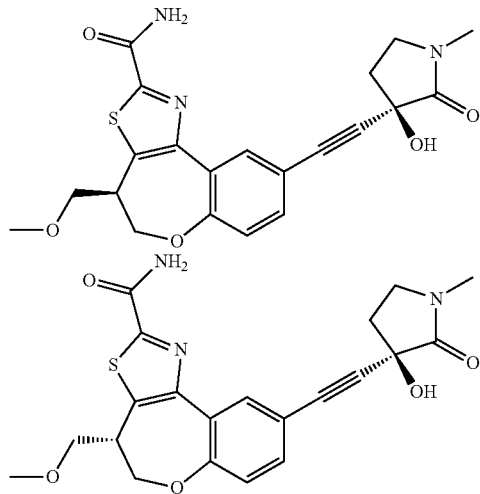

Similar to as described in General Procedure G, racemic ethyl 9-bromo-4-(methoxymethyl)-4,5-dihydrobenzo[2,3]oxepino[4,5-d]thiazole-2-carboxylate was reacted with (R)-3-ethynyl-3-hydroxy-1-methylpyrrolidin-2-one to give the diastereomeric ethyl esters which were converted to a mixture of the titled compounds via aminolysis (similar to as described in General Procedure M). The diastereomeric mixture was purified by chiral HPLC. The absolute stereochemistry of the 4-methoxymethyl substitution position for each isomer was not determined.

Compound 1 off-white solid (2.1 mg, 4%); $t_R$=8.1 min (Chiralpak IA, 25° C., 254 nm, MTBE:EtOH=80:20, 1.0 mL/min); M+18=445 [M+H+NH$_3$]$^+$; $^1$H NMR (300 MHz, CD$_3$OD) δ 8.75 (d, J=2.1 Hz, 1H), 7.37 (dd, J=2.1 Hz, J=8.4 Hz, 1H), 7.05 (d, J=8.4 Hz, 1H), 4.19 (d, J=10.2 Hz, 1H), 3.78-3.48 (m, 5H), 3.44 (s, 3H), 2.96 (s, 3H), 2.65-2.55 (m, 1H), 2.40-2.25 (m, 1H);

Compound 2 off-white solid (2.0 mg, 4%); $t_R$=12.8 min (Chiralpak IA, 25° C., 254 nm, MTBE:EtOH=80:20, 1.0 mL/min); M+18=445 [M+H+NH$_3$]$^+$; $^1$H NMR (300 MHz, CD$_3$OD) δ 8.75 (d, J=2.1 Hz, 1H), 7.37 (dd, J=2.1 Hz, J=8.4 Hz, 1H), 7.05 (d, J=8.4 Hz, 1H), 4.60 (d, J=8.1 Hz, 1H), 4.19 (d, J=10.2 Hz, 1H), 3.78-3.48 (m, 5H), 3.44 (s, 3H), 2.96 (s, 3H), 2.65-2.55 (m, 1H), 2.40-2.25 (m, 1H).

Example 361

Synthesis of (R)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide and (S)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide

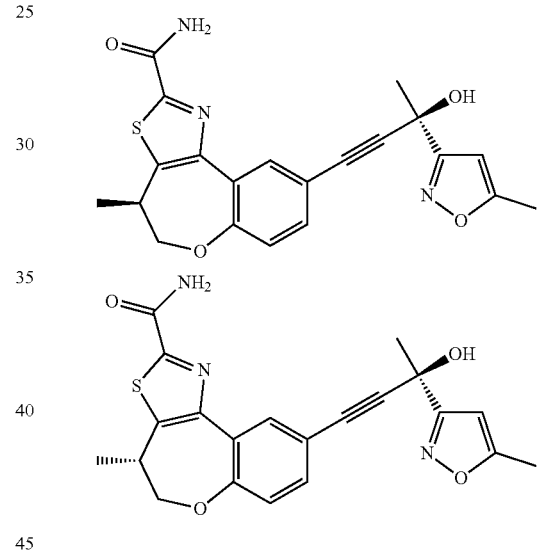

Similar to as described in General Procedure G, racemic ethyl 9-bromo-4-methyl-4,5-dihydrobenzo[2,3]oxepino[4,5-d]thiazole-2-carboxylate was reacted with (R)-2-(5-methylisoxazol-3-yl)but-3-yn-2-ol to give the diastereomeric ethyl esters which were converted to a mixture of the titled compounds via aminolysis (similar to as described in General Procedure M). The diastereomeric mixture was purified by chiral HPLC. The absolute stereochemistry of the 4-methyl substitution position for each isomer was not determined.

Compound 1 colorless solid (16.6 mg, 18%); $t_R$=8.3 min (CHIRALCEL OJ-3, 25° C., 254 nm, Hex:EtOH=70:50, 1.0 mL/min); M+1=410; $^1$H NMR (400 MHz, CD$_3$OD) δ 8.58 (d, J=2.4 Hz, 1H), 7.25-7.22 (dd, J=2.0 Hz, J=8.4 Hz, 1H), 6.92 (d, J=8.4 Hz, 1H), 6.21 (d, J=0.8 Hz, 1H), 4.17-4.11 (m, 2H), 3.55-3.49 (m, 1H), 2.34 (s, 3H), 1.78 (s, 3H), 1.36 (d, J=6.8 Hz, 3H);

Compound 2 colorless solid (15.6 mg, 17%); $t_R$=12.1 min (CHIRALCEL OJ-3, 25° C., 254 nm, Hex:EtOH=70:50, 1.0 mL/min); M+1=410; $^1$H NMR (400 MHz, CD$_3$OD) δ 8.58 (d, J=2.8 Hz, 1H), 7.25-7.22 (dd, J=2.0 Hz, J=8.4 Hz, 1H), 6.92

(d, J=8.4 Hz, 1H), 6.21 (d, J=0.8 Hz, 1H), 4.17-4.11 (m, 2H), 3.56-3.49 (m, 1H), 2.34 (s, 3H), 1.78 (s, 3H), 1.36 (d, J=7.2 Hz, 3H).

Example 362

Synthesis of (R)-9-((R)-3-hydroxy-3-(5-methyl-1,2, 4-oxadiazol-3-yl)but-1-yn-1-yl)-4-methyl-4,5-dihydrobenzo[2,3]oxepino[4,5-d]thiazole-2-carboxamide and (S)-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide

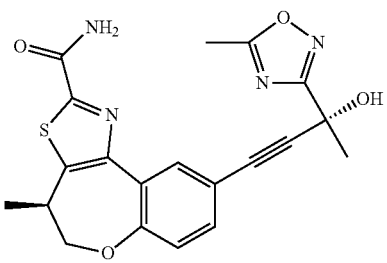

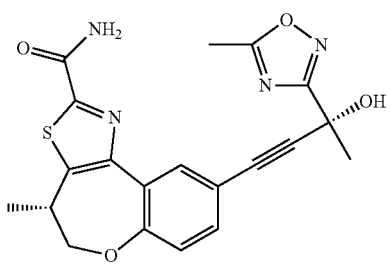

Similar to as described in General Procedure G, racemic ethyl 9-bromo-4-methyl-4,5-dihydrobenzo[2,3]oxepino[4,5-d]thiazole-2-carboxylate was reacted with (R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-methyl substitution position for each isomer was not determined.

Compound 1: off-white solid (16.6 mg, 18%); $t_R$=11.0 min (Chiralpak AD-3, 25° C., 254 nm, Hex:EtOH=75:25, 1.0 mL/min); LC-MS (ES, m/z) 433 [M+Na]$^+$; $^1$H NMR (400 MHz, CD$_3$OD) δ 8.70 (d, J=3.0 Hz, 1H), 7.34 (dd, J=2.1 Hz, J=8.4 Hz, 1H), 7.03 (d, J=8.4 Hz, 1H), 4.26 (d, J=3.9 Hz, 2H), 3.66-3.58 (m, 1H), 2.64 (s, 3H), 1.94 (s, 3H), 1.47 (d, J=7.2 Hz, 3H);

Compound 2: off-white solid (15.6 mg, 17%); $t_R$=16.4 min (Chiralpak AD-3, 25° C., 254 nm, Hex:EtOH=75:25, 1.0 mL/min); LC-MS (ES, m/z) 433 [M+Na]$^+$; $^1$H NMR (400 MHz, CD$_3$OD) δ 8.70 (d, J=3.0 Hz, 1H), 7.34 (dd, J=2.4 Hz, J=8.4 Hz, 1H), 7.03 (d, J=8.4 Hz, 1H), 4.26 (d, J=3.9 Hz, 2H), 3.66-3.58 (m, 1H), 2.64 (s, 3H), 1.94 (s, 3H), 1.47 (d, J=7.2 Hz, 3H).

Example 363

Synthesis of (S)-9-((R)-3-hydroxy-3-(pyrimidin-2-yl)but-1-yn-1-yl)-4-methyl-4,5-dihydrobenzo[2,3]oxepino[4,5-d]thiazole-2-carboxamide and (R)-9-((R)-3-hydroxy-3-(pyrimidin-2-yl)but-1-yn-1-yl)-4-methyl-4,5-dihydrobenzo[2,3]oxepino[4,5-d]thiazole-2-carboxamide

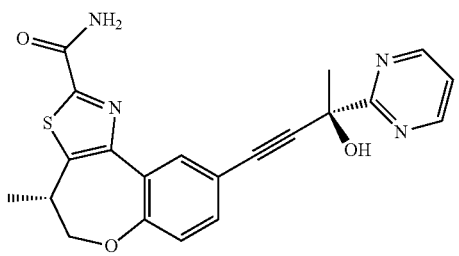

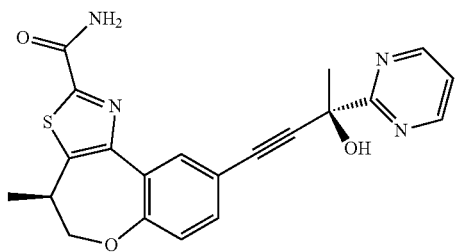

Similar to as described in General Procedure G, racemic ethyl 9-bromo-4-methyl-4,5-dihydrobenzo[2,3]oxepino[4,5-d]thiazole-2-carboxylate was reacted with (R)-2-(pyrimidin-2-yl)but-3-yn-2-ol to give the diastereomeric ethyl esters which were converted to a mixture of the titled compounds via aminolysis (similar to as described in General Procedure M). The diasteromeric mixture was purified by chiral HPLC. The absolute stereochemistry of the 4-methyl substitution position for each isomer was not determined.

Compound 1 yellow solid (13.2 mg, 15%); $t_R$=7.7 min (Chiralpak IA, 25° C., 254 nm, MTBE:IPA=90:10, 1.0 mL/min); LC-MS (ES, m/z) 407 [M+H]$^+$; $^1$H NMR (400 MHz, CD$_3$OD) δ 8.76 (d, J=4.8 Hz, 2H), 8.56 (d, J=2.0 Hz, 1H), 7.35 (t, J=4.8 Hz, 1H), 7.22-7.19 (dd, J=2.0 Hz, J=8.4 Hz, 1H), 6.90 (d, J=8.4 Hz, 1H), 4.16-4.10 (m, 2H), 3.55-3.48 (m, 1H), 1.85 (s, 3H), 1.36 (d, J=7.2 Hz, 3H);

Compound 2 colorless solid (5.8 mg, 7%); $t_R$=11.7 min (Chiralpak IA, 25° C., 254 nm, MTBE:IPA=90:10, 1.0 mL/min); M+1=407; $^1$H NMR (300 MHz, CD$_3$OD) δ 8.89 (d, J=4.8 Hz, 2H), 8.69 (d, J=2.1 Hz, 1H), 7.49 (t, J=4.8 Hz, 1H), 7.35-7.32 (dd, J=2.1 Hz, J=8.4 Hz, 1H), 7.04 (d, J=8.4 Hz, 1H), 4.28-4.26 (m, 2H), 3.67-3.62 (m, 1H), 1.99 (s, 3H), 1.49 (d, J=7.2 Hz, 3H).

Example 364

Synthesis of (R)-9-(((R)-3-hydroxy-1-methyl-2-oxopiperidin-3-yl)ethynyl)-4-methyl-4,5-dihydrobenzo[2,3]oxepino[4,5-d]thiazole-2-carboxamide and (S)-9-(((R)-3-hydroxy-1-methyl-2-oxopiperidin-3-yl)ethynyl)-4-methyl-4,5-dihydrobenzo[2,3]oxepino[4,5-d]thiazole-2-carboxamide

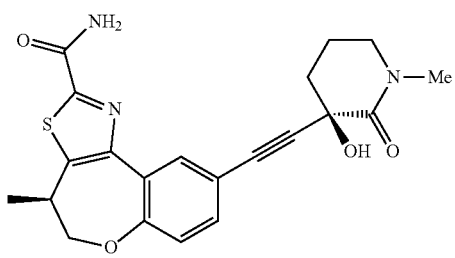

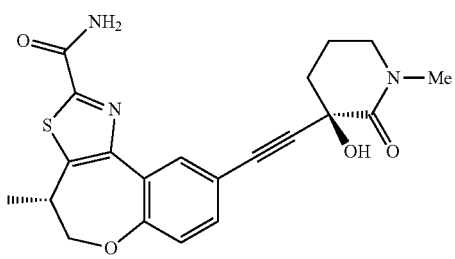

Similar to as described in General Procedure G, racemic ethyl 9-bromo-4-methyl-4,5-dihydrobenzo[2,3]oxepino[4,5-d]thiazole-2-carboxylate was reacted with (R)-3-ethynyl-3-hydroxy-1-methylpiperidin-2-one to give the diastereomeric ethyl esters which were converted to a mixture of the titled compounds via aminolysis (similar to as described in General Procedure M). The diasteromeric mixture was purified by chiral HPLC. The absolute stereochemistry of the 4-methyl substitution position for each isomer was not determined.

Compound 1 colorless solid (8.0 mg, 12%); $t_R$=2.7 min (Chiralpak IA-3, 25° C., 254 nm, Hex:EtOH=50:50, 1.0 mL/min); M+1=412; $^1$H NMR (400 MHz, CD$_3$OD) δ 8.57 (s, 1H), 7.24-7.21 (dd, J=2.0 Hz, J=8.0 Hz 1H), 6.92 (d, J=8.0 Hz, 1H), 4.15 (d, J=4.0 Hz, 2H), 3.55-3.50 (m, 1H), 3.35-3.33 (m, 2H), 2.89 (s, 3H), 2.25-2.08 (m, 2H), 2.01-1.91 (m, 2H), 1.36 (d, J=7.2 Hz, 3H);

Compound 2 colorless solid (8.1 mg, 12%); $t_R$=4.7 min (Chiralpak IA-3, 25° C., 254 nm, Hex:EtOH=50:50, 1.0 mL/min); M+1=412; $^1$H NMR (400 MHz, CD$_3$OD) δ 8.69 (s, 1H), 7.36-7.33 (dd, J=2.4 Hz, J=8.4 Hz, 1H), 7.04 (d, J=8.0 Hz, 1H), 4.26 (t, J=3.2 Hz, 2H), 3.66-3.62 (m, 1H), 3.47-3.40 (m, 2H), 3.00 (s, 3H), 2.37-2.20 (m, 2H), 2.13-0.03 (m, 2H), 1.48 (d, J=6.8 Hz, 3H).

Example 365

Synthesis of (S)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide and (R)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide

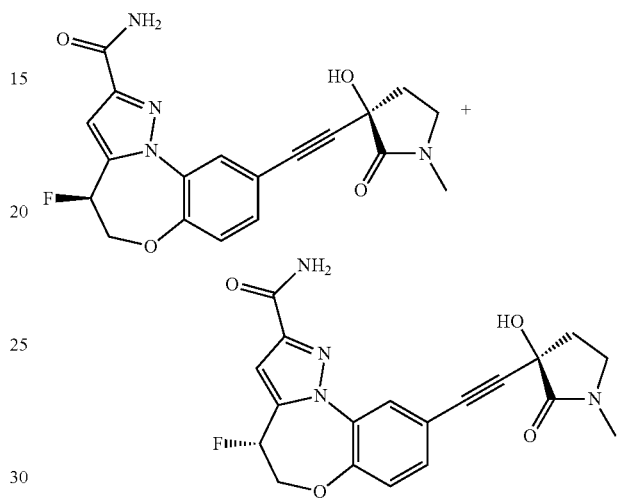

Similar to as described in General Procedure G, racemic ethyl 4-fluoro-9-iodo-4,5-dihydrobenzo[b]pyrazolo[1,5-d][1,4]oxazepine-2-carboxylate was reacted with (R)-3-ethynyl-3-hydroxy-1-methylpiperidin-2-one. The diasteromeric mixture of ethyl 4-fluoro-9-iodo-4,5-dihydrobenzo[b]pyrazolo[1,5-d][1,4]oxazepine-2-carboxylate (220 mg, 0.53 mmol, 1.00 equiv) in methanol saturated with ammonia (20 mL) was stirred for overnight at 40° C. The resulting mixture was concentrated under vacuum. The crude product was purified by Prep-HPLC with the following conditions (Prep-HPLC-005): Column, XBridge Prep Phenyl OBD Column, 5 um, 19*150 mm, mobile phase, water with 0.03% NH$_3$H$_2$O and MeCN (15.0% MeCN up to 27.0% in 15 min); Detector, UV 254/220 nm. Then it was purified by Chiral-Prep-HPLC with the following conditions (Prep-HPLC-032): Column, Phenomenex Lux 5u Cellulose-4, 2.12*25, 5 um; mobile phase, Hex and ethanol (hold 50.0% ethanol in 17 min); Detector, uv 220/254 nm. This gave 29.5 mg (29%) of Compound 1 and 46.2 mg (45%) of Compound 2.

Compound 1: colorless solid; $t_R$=12 min (Lux cellulose-4, 25° C., UV-254 nm Hex:EtOH=50:50, 1.0 ml/min); $^1$H NMR (400 MHz, CD$_3$OD) δ 8.22 (s, 1H), 7.45 (dd, J=1.6, 8.0 Hz, 1H), 7.26 (d, J=8.4 Hz, 1H), 7.15 (s, 1H), 6.00 (d, J=46.8 Hz, 1H), 4.78 (t, J=13.6 Hz 1H), 4.59 (dd, J=2.813.6 Hz 1H), 3.51-3.46 (m, 2H), 2.95 (s, 3H), 2.62-2.57 (m, 1H), 2.36-2.29 (m, 1H).

Compound 2: colorless solid; $t_R$=15.1 min (Lux cellulose-4, 25° C., UV-254 nm Hex:EtOH=50:50, 1.0 ml/min); $^1$H NMR (400 MHz, CD$_3$OD) δ 8.22 (s, 1H), 7.45 (dd, J=1.68.4 Hz, 1H), 7.26 (d, J=8.4 Hz, 1H), 7.15 (d, J=2.8 Hz 1H), 6.00 (d, J=47.2 Hz, 1H), 4.78 (dd, J=2.8, 14 Hz 1H), 4.59 (dd, J=2.8, 14 Hz 1H), 3.51-3.46 (m, 2H), 2.95 (s, 3H), 2.63-2.57 (m, 1H), 2.36-2.29 (m, 1H).

Example 366

Synthesis of (S)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide and (R)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide

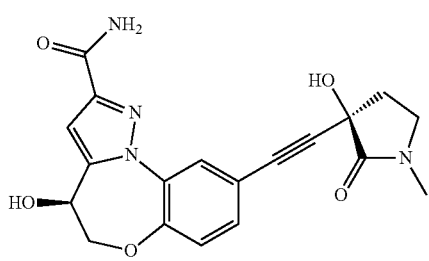

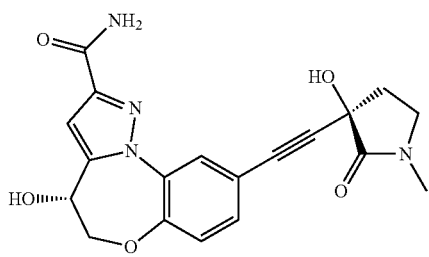

Similar to as described in General Procedure G, racemic ethyl 4-hydroxy-9-iodo-4,5-dihydrobenzo[b]pyrazolo[1,5-d][1,4]oxazepine-2-carboxylate was reacted with (R)-3-ethynyl-3-hydroxy-1-methylpiperidin-2-one to give the diastereomeric ethyl esters which were converted to a mixture of the titled compounds via aminolysis (similar to as described in General Procedure M). The diasteromeric mixture was purified by chiral HPLC. The absolute stereochemistry of the 4-hydroxyl substitution position for each isomer was not determined.

Compound 1 green solid (65.1 mg, 27%); $t_R$=12.7 min (CHIRALPAK IA, 25° C., UV-254 nm MTBE:EtOH=85:15, 1.0 ml/min); M+1=383; $^1$H NMR (400 MHz, CD$_3$OD) δ 8.26 (d, J=1.6 Hz, 1H), 7.39 (dd, J=2.0, 7.6 Hz 1H), 7.20 (d, J=8.4 Hz, 1H), 6.98 (s, 1H), 5.12 (t, J=4.4 Hz 1H), 4.55-4.40 (m, 2H), 3.53-3.46 (m, 1H), 2.95 (s, 3H), 2.63-2.57 (m, 1H), 2.36-2.29 (m, 1H);

Compound 2 green solid (59.2 mg, 25%); $t_R$=19.5 min (CHIRALPAK IA, 25° C., UV-254 nm MTBE:EtOH=85:15, 1.0 ml/min); M+1=383; $^1$H NMR (400 MHz, CD$_3$OD) δ8.27 (d, J=2Hz, 1H), 7.39 (dd, J=2.0, 8.4 Hz 1H), 7.20 (d, J=8.4, 1H), 6.98 (s, 1H), 5.13-5.10 (m, 1H), 4.55-4.40 (m, 2H), 3.53-3.46 (m, 1H), 2.95 (s, 3H), 2.63-2.57 (m, 1H), 2.36-2.29 (m, 1H).

Example 367

Synthesis of (R)-4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide and (S)-4-fluoro-9-4(R)-3-hydroxy-1-methyl-2-oxopyrrolidin-3-yl)ethynyl)-4-methyl-4,5-dihydrobenzo [b]pyrazolo[1,5-d][1,4]oxazepine-2-carboxamide

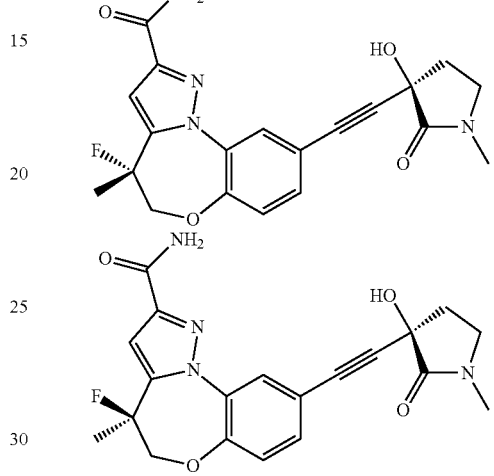

Similar to as described in General Procedure G, racemic ethyl 9-bromo-4-fluoro-4-methyl-4,5-dihydrobenzo[b]pyrazolo[1,5-d][1,4]oxazepine-2-carboxylate was reacted with (R)-3-ethynyl-3-hydroxy-1-methylpiperidin-2-one to give the diastereomeric ethyl esters which were converted to a mixture of the titled compounds via aminolysis (similar to as described in General Procedure M). The crude product was purified by Prep-HPLC with the following conditions (Prep-HPLC-025): Column, XBridge Shield RP18 OBD Column, 5 um, 19*150 mm, mobile phase, water with 10 mmol NH$_4$HCO$_3$ and MeCN (35.0% MeCN up to 45.0% in 10 min); Detector, UV 254/220 nm. Then it was purified by Chiral-Prep-HPLC with the following conditions (Prep-HPLC-032): Column, Chiralpak AD-H, 2*25 cm; mobile phase, Hex and ethanol (hold 25.0% ethanol in 26 min); Detector, UV 254/220 nm. This gave 22.2 mg (48%) of Compound 1 and 22.1 mg (47%) of Compound 2. The absolute stereochemistry of the 4-fluorine substitution position for each isomer was not determined.

Compound 1 colorless solid. $t_R$=17.2 min (CHIRLPAK AD-H, 25° C., UV-254 nm Hex:EtOH=75:25, 1.0 ml/min); M+18=416 [M+H$_2$O]$^+$; $^1$H NMR (400 MHz, CD$_3$OD) δ: 8.04 (s, 1H), 7.33 (dd, J=2.0, 8.4 Hz, 1H), 7.12 (d, J=8.0 Hz, 1H), 7.05 (s, 1H), 4.57-4.36 (m, 2H), 3.39-3.34 (m, 2H), 2.83 (s, 3H), 2.51-2.45 (m, 1H), 2.24-2.19 (m, 1H), 1.70 (d, J=16.0 Hz, 3H).

Compound 2 colorless solid. $t_R$=23.2 min (CHIRLPAK AD-H, 25° C., UV-254 nm Hex:EtOH=75:25, 1.0 ml/min); M+18=416 [M+H$_2$O]$^+$; $^1$H NMR (400 MHz, CD$_3$OD) δ 8.04 (s, 1H), 7.33 (dd, J=2.0, 8.4 Hz, 1H), 7.12 (d, J=8.4 Hz, 1H), 7.05 (s, 1H), 4.57-4.36 (m, 2H), 3.39-3.34 (m, 2H), 2.83 (s, 3H), 2.51-2.45 (m, 1H), 2.24-2.19 (m, 1H), 1.70 (d, J=16.0 Hz, 3H).

Example 368

Synthesis of (S)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide and (R)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide

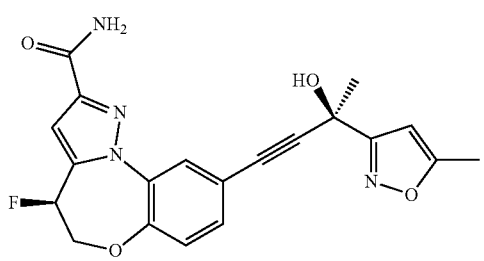

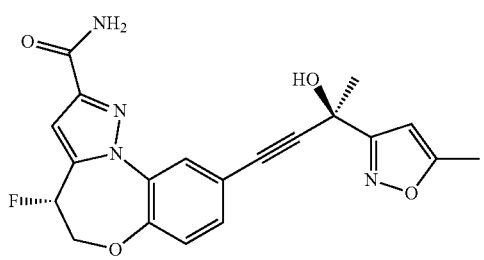

Similar to as described in General Procedure G, racemic ethyl 9-bromo-4-fluoro-4,5-dihydrobenzo[b]pyrazolo[1,5-d][1,4]oxazepine-2-carboxylate was reacted with (R)-3-ethynyl-3-hydroxy-1-methylpiperidin-2-one to give the diastereomeric ethyl esters which were converted to a mixture of the titled compounds via aminolysis (similar to as described in General Procedure M). The absolute stereochemistry of the 4-fluorine substitution position for each isomer was not determined.

Compound 1: 42.4 mg (37%); colorless solid; $t_R$=13.7 min (CHIRLPAK AD-3, 25° C., UV-254 nm Hex:EtOH=75:25, 1.5 ml/min); M−17=379 [M-OH]$^+$; $^1$H NMR (400 MHz, CD$_3$OD) δ 8.21 (s, 1H), 7.45 (d, J=8.4 Hz, 1H), 7.26 (d, J=8.4 Hz, 1H), 7.15 (d, J=2.4 Hz, 1H), 6.33 (s, 1H), 6.01 (d, J=47.2 Hz, 1H), 4.87-4.76 (m, 1H), 4.69-4.56 (m, 1H), 2.46 (s, 3H), 1.90 (s, 3H).

Compound 2: 39.9 mg (35%); colorless solid; $t_R$=20.7 min (CHIRLPAK AD-3, 25° C., UV-254 nm Hex:EtOH=75:25, 1.5 ml/min); M−17=379 [M-OH]$^+$; $^1$H NMR (400 MHz, CD$_3$OD) δ 8.09 (s, 1H), 7.33 (d, J=8.0 Hz, 1H), 7.14 (d, J=8.4 Hz, 1H), 7.03 (d, J=2.4 Hz 1H), 6.21 (s, 1H), 5.89 (d, J=47.2 Hz, 1H), 4.75-4.64 (m, 1H), 4.57-4.44 (m, 1H), 2.34 (s, 3H), 1.78 (s, 3H).

Example 369

Synthesis of (S)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide and (R)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide

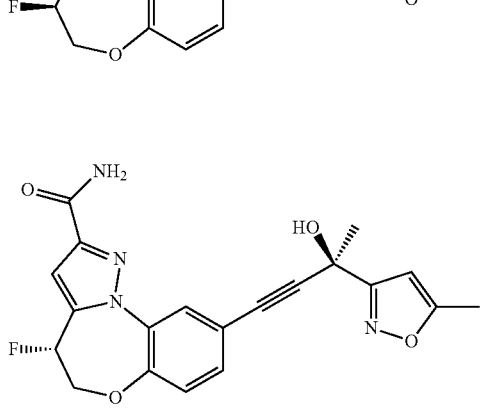

Similar to as described in General Procedure G, racemic ethyl 9-bromo-4-hydroxy-4,5-dihydrobenzo[b]pyrazolo[1,5-d][1,4]oxazepine-2-carboxylate was reacted with (R)-2-(5-methylisoxazol-3-yl)but-3-yn-2-ol to give the diastereomeric ethyl esters which were converted to a mixture of the titled compounds via aminolysis (similar to as described in General Procedure M). The absolute stereochemistry of the 4-hydroxyl substitution position for each isomer was not determined.

Compound 1: 33.5 mg (21%); colorless solid; $t_R$=4.8 min (CHIRLPAK IC-3, 25° C., UV-254 nm Hex:EtOH=75:25, 1.0 ml/min); M+1=395; $^1$H NMR (400 MHz, CD$_3$OD) δ 8.14 (d, J=1.6 Hz, 1H) 7.28 (dd, J=1.6, 8.4 Hz 1H), 7.08 (d, J=8.4 Hz, 1H), 6.87 (s, 1H), 6.20 (s, 1H), 5.01-4.98 (m, 1H), 4.43-4.27 (m, 2H), 2.34 (s, 3H), 1.77 (s, 1H).

Compound 2: 31.3 mg (20%); colorless solid; $t_R$=6.6 min (CHIRLPAK IC-3, 25° C., UV-254 nm Hex:EtOH=75:25, 1.0 ml/min); M+1=395; $^1$H NMR (400 MHz, CD$_3$OD) δ 8.14 (d, J=2.0 Hz, 1H) 7.28 (dd, J=2.0, 8.4 Hz 1H), 7.08 (d, J=8.4 Hz, 1H), 6.87 (s, 1H), 6.20 (s, 1H), 5.01-4.98 (m, 1H), 4.43-4.27 (m, 2H), 2.34 (s, 3H), 1.77 (s, 1H).

Example 370

Synthesis of 4-fluoro-9-((R)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide

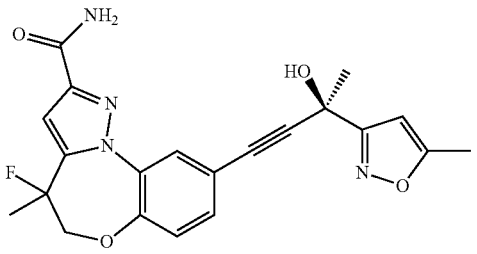

Similar to as described in General Procedure G, racemic ethyl 9-bromo-4-fluoro-4-methyl-4,5-dihydrobenzo[b]pyrazolo[1,5-d][1,4]oxazepine-2-carboxylate was reacted with (R)-2-(5-methylisoxazol-3-yl)but-3-yn-2-ol to give the titled compound as a colorless solid (19 mg, 23%).

M−17=393; $^1$H-NMR (300 MHz, CD$_3$OD) δ 8.16 (d, J=2.1 Hz, 1H), 7.46 (dd, J=0.1, 8.4 Hz, 1H), 7.26 (d, J=8.4 Hz, 1H), 7.18 (d, J=2.4 Hz, 1H), 6.34 (s, 1H), 4.72-4.47 (m, 2H), 2.47 (s, 3H), 1.91 (s, 3H), 1.81 (d, J=20.4 Hz, 3H).

Example 371

Synthesis of (S)-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide and (R)-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide

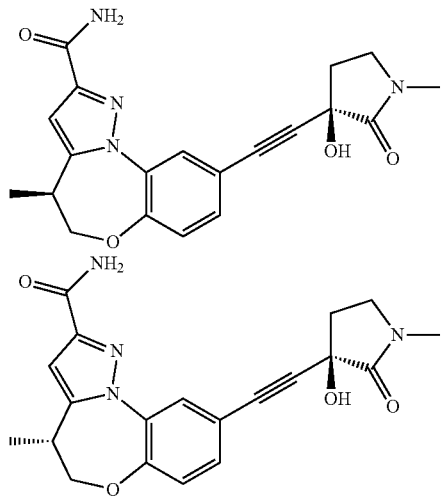

Similar to as described in General Procedure G, racemic ethyl 9-bromo-4-methyl-4,5-dihydrobenzo[b]pyrazolo[1,5-d][1,4]oxazepine-2-carboxylate was reacted with (R)-3-ethynyl-3-hydroxy-1-methylpyrrolidin-2-one to give the diastereomeric ethyl esters which were converted to a mixture of the titled compounds via aminolysis (similar to as described in General Procedure M). The crude product was purified by Chiral-Prep-HPLC with the following conditions (Prep-HPLC-032): Column, CHIRALPAK OJ-H, 2*25 cm; mobile phase, Hex and ethanol (hold 25.0% ethanol in 22 min); Detector, UV 254/220 nm. This gave 23.1 mg (42%) of Compound 1 and 21.6 mg (39%) of Compound 2. The absolute stereochemistry of the 4-methyl substitution position for each isomer was not determined.

Compound 1: colorless solid; t$_R$=23.8 min (C CHIRLCEL OJ-3, 25° C., UV-254 nm Hex:EtOH=80:20, 1.0 ml/min); M+1=381; $^1$H NMR (300 MHz, CDCl$_3$) δ 8 7.96 (s, 1H), 7.36 (d, J=4.4 Hz, 1H), 7.10 (d, J=9.6 Hz, 1H), 6.90 (s, 1H), 6.81 (s, 1H), 5.61 (s, 1H), 4.46 (q, J=5.2 Hz, 1H), 4.20 (t, J=10.4, 1H), 3.52-3.50 (m, 1H), 3.49-3.44 (m, 1H), 3.19-3.17 (m, 1H), 2.67 (s, 1H), 2.66-2.62 (m, 1H), 2.44-2.10 (m, 1H), 1.35 (d, J=6.8 Hz, 1H).

Compound 2: 25 mg (28%); colorless solid; t$_R$=30.5 min (CHIRLCEL OJ-3, 25° C., UV-254 nm Hex:EtOH=80:20, 1.0 ml/min); M+1=381; $^1$H NMR (300 MHz, CDCl$_3$) δ 7.96 (s, 1H), 7.36 (d, J=4.4 Hz, 1H), 7.10 (d, J=9.6 Hz, 1H), 6.90 (s, 1H), 6.81 (s, 1H), 5.61 (s, 1H), 4.46 (q, J=5.2 Hz, 1H), 4.20 (t, J=10.4, 1H), 3.52-3.50 (m, 1H), 3.49-3.44 (m, 1H), 3.19-3.17 (m, 1H), 2.67 (s, 1H), 2.66-2.62 (m, 1H), 2.44-2.10 (m, 1H), 1.35 (d, J=6.8 Hz, 1H).

Example 372

Synthesis of (R)-9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide and (S)-9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide dihydrobenzo[b]pyrazolo[1,5-d][1,4]oxazepine-2-carboxamide

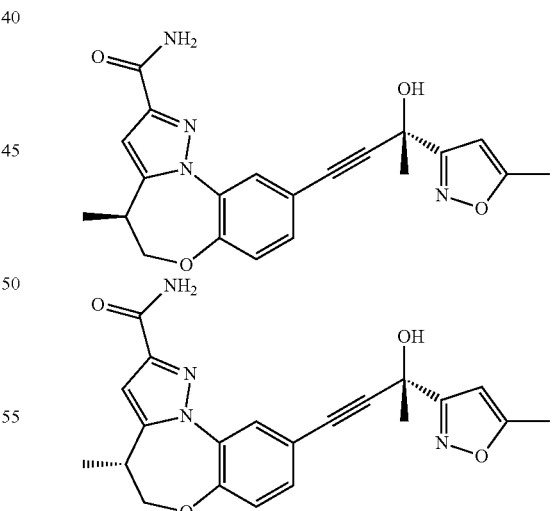

Similar to as described in General Procedure G, racemic ethyl 9-bromo-4-methyl-4,5-dihydrobenzo[b]pyrazolo[1,5-d][1,4]oxazepine-2-carboxylate was reacted with (R)-2-(5-methylisoxazol-3-yl)but-3-yn-2-ol to give the diastereomeric ethyl esters which were converted to a mixture of the titled compounds via aminolysis (similar to as described in General Procedure M). The diasteromeric mixture was separated by chiral prep HPLC. The absolute stereochemistry of the 4-methyl substitution position for each isomer was not determined.

Compound 1: 9.3 mg (22%); colorless solid; $t_R$=20.2 min (CHIRLPAK IA-3, 25° C., UV-254 nm Hex (0.1% TEA): IPA=85:15, 1.0 ml/min); M+1=393; $^1$H NMR (300 MHz, CDCl$_3$) δ 7.99 (d, J=1.8 Hz, 1H), 7.40 (dd, J=2.1, 8.4 Hz, 1H), 7.15 (d, J=8.1 Hz, 1H), 6.85 (brs, 1H), 6.84 (s, 1H), 6.18 (s, 1H), 5.60 (brs, 1H), 4.49 (dd, J=5.4. 10.5 Hz), 4.24 (t, J=10.5 Hz, 1H), 3.25 (brs, 1H), 2.48 (s, 3H), 1.98 (s, 3H), 1.39 (d, J=7.2 Hz, 3H).

Compound 2: 25 mg (28%); colorless solid; $t_R$=27.7 min (CHIRLPAK IA-3, 25° C., UV-254 nm Hex (0.1% TEA): IPA=85:15, 1.0 ml/min); M+1=393; $^1$H NMR (300 MHz, CDCl$_3$) δ 7.99 (d, J=1.8 Hz, 1H), 7.40 (dd, J=2.1, 8.4 Hz, 1H), 7.15 (d, J=8.1 Hz, 1H), 6.85 (brs, 1H), 6.84 (s, 1H), 6.18 (s, 1H), 5.60 (brs, 1H), 4.49 (dd, J=5.4. 10.5 Hz), 4.24 (t, J=10.5 Hz, 1H), 3.25 (brs, 1H), 2.48 (s, 3H), 1.98 (s, 3H), 1.39 (d, J=7.2 Hz, 3H).

Example 373

Synthesis of (R)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide and (S)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide

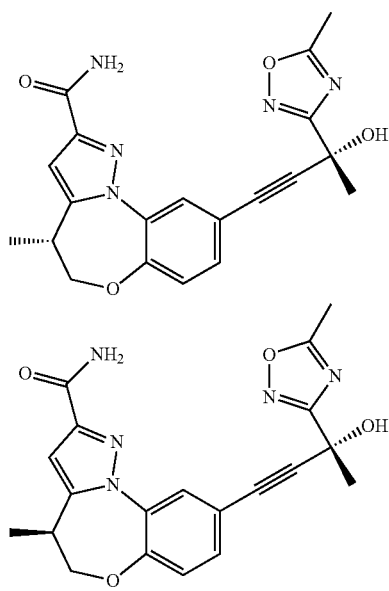

Similar to as described in General Procedure G, racemic ethyl 9-bromo-4-methyl-4,5-dihydrobenzo[b]pyrazolo[1,5-d][1,4]oxazepine-2-carboxylate was reacted with (R)-2-(5-methyl-1,2,4-oxadiazol-3-yl)but-3-yn-2-ol to give the diastereomeric ethyl esters which were converted to a mixture of the titled compounds via aminolysis (similar to as described in General Procedure M). The diasteromeric mixture was separated by chiral prep HPLC. The absolute stereochemistry of the 4-methyl substitution position for each isomer was not determined.

Compound 1: 18.8 mg; colorless solid; $t_R$=8.5 min (CHIRLPAK IC-3, 25° C., UV-254 nm Hex:EtOH=75:25, 1.0 ml/min); M+1=394; $^1$H NMR (300 MHz, CD$_3$OD) δ 8.07 (d, J=2.1 Hz, 1H), 7.43 (dd, J=2.1, 8.4 Hz 1H), 7.20 (d, J=8.1 Hz, 1H), 6.80 (s, 1H), 4.54-4.49 (m, 1H), 4.23 (t, J=10.2 Hz, 1H), 3.32-3.32 (m, 1H), 2.64 (s, 3H), 1.93 (s, 3H), 1.37 (d, J=6.9 Hz, 3H).

Compound 2: 32.8 mg; colorless solid; $t_R$=10.2 min (CHIRLPAK IC-3, 25° C., UV-254 nm Hex:EtOH=75:25, 1.0 ml/min); M+1=394; $^1$H NMR (300 MHz, CD$_3$OD) δ 8.06 (d, J=1.8 Hz, 1H), 7.49-7.41 (m, 1H), 7.20 (d, J=8.4 Hz, 1H), 6.80 (s, 1H), 4.54-4.48 (m, 1H), 4.23 (t, J=10.5 Hz, 1H), 3.32-3.24 (m, 1H), 2.63 (s, 3H), 1.92 (s, 3H), 1.39 (d, J=6.9 Hz, 3H).

Example 374

Synthesis of (R)-4-fluoro-9-4(R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide and (S)-4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide

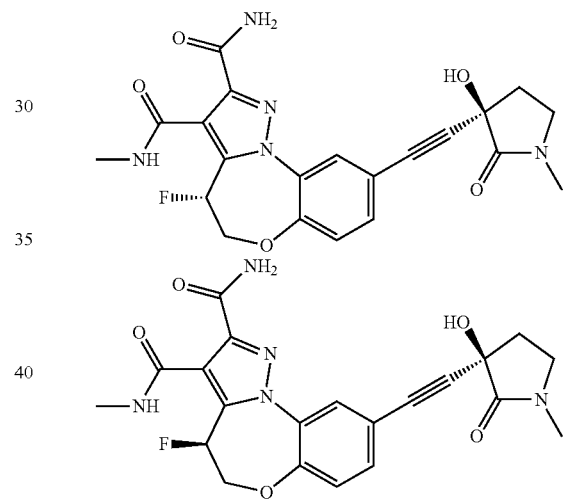

Similar to as described in General Procedure G, racemic 9-bromo-4-fluoro-N3-methyl-4,5-dihydrobenzo[b]pyrazolo[1,5-d][1,4]oxazepine-2,3-dicarboxamide was reacted with (R)-3-ethynyl-3-hydroxy-1-methylpyrrolidin-2-one to give a mixture of the titled compounds. The diasteromeric mixture was separated by chiral prep HPLC. The absolute stereochemistry of the 4-fluorine substitution position for each isomer was not determined.

Compound 1: 34 mg (39%); colorless solid; $t_R$=8.2 min (Lux cellulose-4, 25° C., UV-254 nm Hex:EtOH=50:50, 1.5 ml/min); M+1=442; NMR (300 MHz, DMSO-d$_6$) δ 10.46 (d, J=4.5 Hz, 1H), 8.58 (s, 1H), 8.14 (d, J=2.1 Hz 1H), 8.10 (s, 1H), 7.47 (dd, J=2.1, 8.1 Hz 1H), 7.33 (d, J=8.1 Hz, 1H), 6.99 (d, J=44.7 Hz, 1H), 6.49 (s, 1H), 4.86-4.69 (m, 2H), 3.37-3.33 (m, 2H), 2.82-2.80 (m, 6H), 2.47-2.41 (m, 1H), 2.23-2.14 (m, 1H).

Compound 2: 27.3 mg (32%); colorless solid; $t_R$=13.0 min (CHIRLPAK IC-3, 25° C., UV-254 nm Hex:EtOH=75:25, 1.0 ml/min); M+1=442; $^1$H NMR (300 MHz, DMSO-d$_6$) δ 10.46 (d, J=3.9 Hz, 1H), 8.58 (s, 1H), 8.14 (d, J=2.1 Hz 1H), 8.10 (s, 1H), 7.47 (dd, J=2.1, 8.4 Hz 1H), 7.33 (d, J=8.4 Hz, 1H), 6.99

(d, J=44.4 Hz, 1H), 6.49 (s, 1H), 4.86-4.69 (m, 2H), 3.37-3.35 (m, 2H), 2.82-2.81 (m, 6H), 2.46-2.40 (m, 1H), 2.23-2.14 (m, 1H).

Example 375

Synthesis of (R)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide and (S)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide

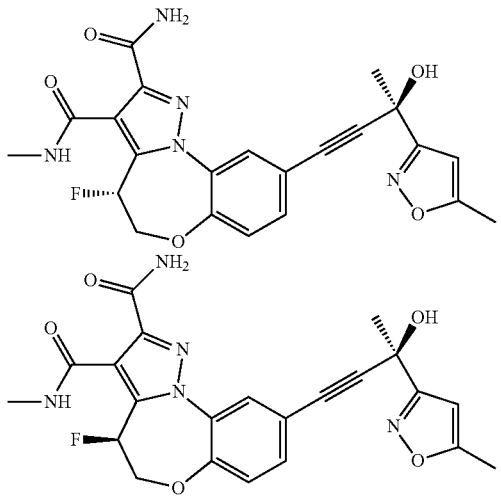

Similar to as described in General Procedure G, racemic 9-bromo-4-fluoro-N3-methyl-4,5-dihydrobenzo[b]pyrazolo[1,5-d][1,4]oxazepine-2,3-dicarboxamide was reacted with (R)-2-(5-methylisoxazol-3-yl)but-3-yn-2-ol to give a mixture of the titled compounds. The diasteromeric mixture was separated by chiral prep HPLC. The absolute stereochemistry of the 4-fluorine substitution position for each isomer was not determined.

Compound 1: 36.9 mg (42%); colorless solid; $t_R$=8.3 min (CHIRLPAK IA-3, 25° C., UV-254 nm Hex:EtOH=75:25, 1.0 ml/min); M+1=454; $^1$H NMR (300 MHz, DMSO-$d_6$) δ 10.46 (d, J=4.5 Hz, 1H), 8.58 (s, 1H), 8.13 (d, J=4.5 Hz, 1H), 8.10 (s, 1H), 7.47 (dd, J=2.1, 8.4 Hz, 1H), 7.33 (d, J=8.4 Hz, 1H), 6.99 (d, J=44.7 Hz, 1H), 6.54 (s, 1H), 6.37 (s, 1H), 4.86-4.69 (m, 2H), 2.82 (d, J=4.5 Hz, 3H), 2.41 (s, 3H), 1.80 (s, 3H).

Compound 2: 39.1 mg (44%); colorless solid; $t_R$=10.0 min (CHIRLPAK IA-3, 25° C., UV-254 nm Hex:EtOH=75:25, 1.0 ml/min); M+1=454; $^1$H NMR (300 MHz, DMSO-$d_6$) δ 10.46 (d, J=4.8 Hz, 1H), 8.58 (s, 1H), 8.13 (d, J=4.5 Hz, 1H), 8.10 (s, 1H), 7.58 (dd, J=1.8, 8.4 Hz 1H), 7.33 (d, J=8.4 Hz, 1H), 6.73 (d, J=44.4 Hz, 1H), 6.55 (s, 1H), 6.36 (s, 1H), 4.86-4.69 (m, 2H), 2.82 (d, J=4.5 Hz, 3H), 2.41 (s, 1H), 1.80 (s, 3H).

Example 376

Synthesis of (S)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide and (R)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide

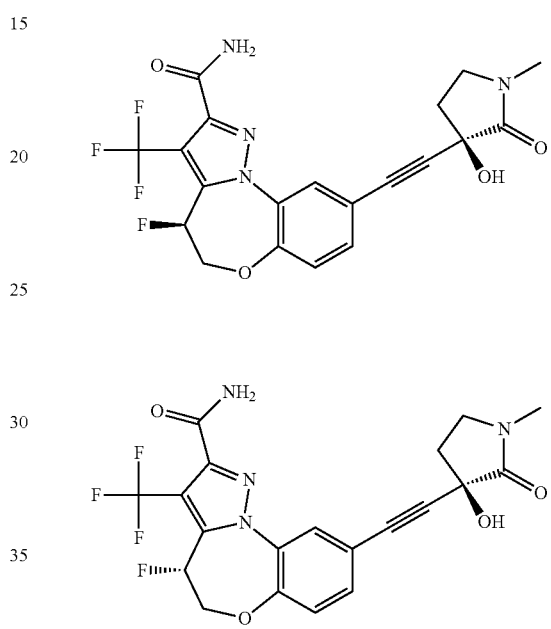

Similar to as described in General Procedure G, racemic 9-bromo-4-fluoro-3-(trifluoromethyl)-4,5-dihydrobenzo[b]pyrazolo[1,5-d][1,4]oxazepine-2-carboxamide was reacted with (R)-3-ethynyl-3-hydroxy-1-methylpyrrolidin-2-one to give a mixture of the titled compounds. The diasteromeric mixture was separated by chiral prep HPLC. The absolute stereochemistry of the 4-fluorine substitution position for each isomer was not determined.

Compound 1: 42.6 mg (89%); colorless solid; $t_R$=8.8 min (Lux cellulose-4, 25° C., UV-254 nm Hex:EtOH=60:50, 1.0 ml/min; M+23=475; $^1$H NMR (300 MHz, CD$_3$OD) δ 8.25 (d, J=2.1 Hz, 1H), 7.52 (dd, J=2.1, 8.4 Hz, 1H), 7.30 (d, J=8.4 Hz, 1H), 6.20 (d, J=45.3 Hz, 1H), 4.94-4.90 (m, 1H), 4.87-4.83 (m, 1H), 4.73-4.56 (m, 1H), 3.52-3.47 (m, 2H), 2.95 (m, 3H), 2.65-2.57 (m, 1H), 2.38-2.31 (m, 1H).

Compound 2: 39.1 mg (44%); colorless solid; $t_R$=11.0 min (CHIRLPAK IA-3, 25° C., UV-254 nm Hex:EtOH=75:25, 1.0 ml/min); M+23=475; $^1$H NMR (300 MHz, CD$_3$OD) δ8.24 (d, J=2.1 Hz, 1H), 7.52 (d, J=8.4 Hz, 1H), 7.30 (dd, J=2.1, 8.4 Hz, 1H), 6.18 (d, J=45.9 Hz, 1H), 4.94-4.90 (m, 1H), 4.87-4.83 (m, 1H), 4.73-4.56 (m, 1H), 3.50-3.46 (m, 2H), 2.93 (m, 3H), 2.63-2.55 (m, 1H), 2.36-2.27 (m, 1H).

Example 377

Synthesis of (R)-9-((3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide

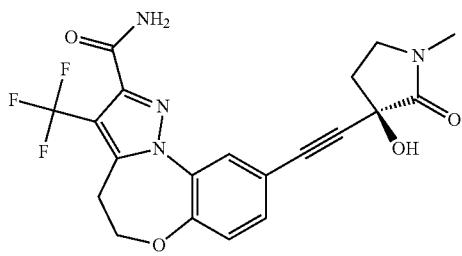 [SMILES: CN1CC[C@@](O)(C#Cc2ccc3c(c2)-n2nc(C(N)=O)c(C(F)(F)F)c2CCO3)C1=O]

Similar to as described in General Procedure G, racemic 9-bromo-4-fluoro-3-(trifluoromethyl)-4,5-dihydrobenzo[b]pyrazolo[1,5-d][1,4]oxazepine-2-carboxamide was reacted with (R)-3-ethynyl-3-hydroxy-1-methylpyrrolidin-2-one to give the titled compound as a white solid 8.9 mg (59%).

M+18=452; $^1$H NMR (300 MHz, CD$_3$OD) δ 8.03 (d, J=2.1 Hz, 1H), 7.51 (dd, J=2.1, 8.4 Hz, 1H), 7.24 (d, J=8.7 Hz, 1H), 4.60 (t, J=6.0 Hz, 1H), 3.50-3.45 (m, 2H), 3.29-3.27 (m, 2H), 2.93 (s, 3H), 2.62-2.54 (m, 1H), 2.36-2.27 (m, 1H).

Example 378

Synthesis of (R)-9-((3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide

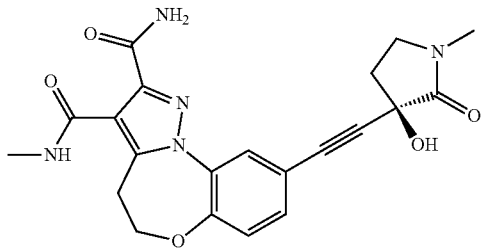 [SMILES: CNC(=O)c1c(C(N)=O)nn2c1CCOc1ccc(C#C[C@]3(O)CCN(C)C3=O)cc1-2]

Similar to as described in General Procedure G, 9-bromo-N3-methyl-4,5-dihydrobenzo[b]pyrazolo[1,5-d][1,4]oxazepine-2,3-dicarboxamide was reacted with (R)-3-ethynyl-3-hydroxy-1-methylpyrrolidin-2-one to give the titled compound as a brown solid (32 mg, 25%).

M+1=424; $^1$H NMR (300 MHz, CD$_3$OD) δ 8.05 (d, J=1.6 Hz, 1H), 7.51 (d, J=2.0 Hz, 1H), 7.24 (d, J=8.4 Hz, 1H), 4.64-4.61 (m, 2H), 3.69-3.66 (m, 2H), 3.50-3.47 (m, 2H), 2.98-2.86 (m, 6H), 2.61-2.56 (m, 1H), 2.36-2.29 (m, 1H).

Example 379

Synthesis of (R)-9-(3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide

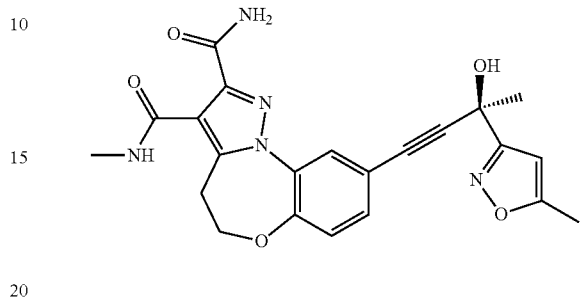

Similar to as described in General Procedure G, 9-bromo-N3-methyl-4,5-dihydrobenzo[b]pyrazolo[1,5-d][1,4]oxazepine-2,3-dicarboxamide was reacted with (R)-2-(5-methylisoxazol-3-yl)but-3-yn-2-ol to give the titled compound as an off-white solid (37 mg, 26%).

M+1=436; $^1$H NMR (300 MHz, CD$_3$OD) δ 8.02 (d, J=2.1 Hz, 1H), 7.49 (dd, J=2.1, 8.4 Hz 1H), 7.23 (d, J=8.4 Hz, 1H), 6.31 (d, J=0.9 Hz, 1H), 4.62 (t, J=6.0 Hz 2H), 3.68-3.64 (m, 2H), 2.92 (s, 3H), 2.44 (d, J=0.9 Hz, 3H), 1.88 (s, 3H).

Example 380

Synthesis of (±)-3-cyclopropyl-10-(3,4-dihydroxy-3-methyl-but-1-ynyl)-9-fluoro-5,6-dihydroimidazo[1,2-d][1,4]benzoxazepine-2-carboxamide

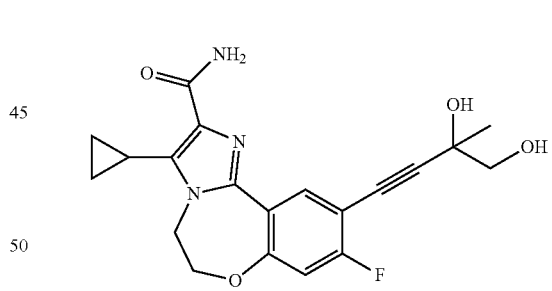

10-bromo-3-cyclopropyl-9-fluoro-5,6-dihydrobenzo[f]imidazo[1,2-d][1,4]oxazepine-2-carboxamide was reacted with 2-methylbut-3-yne-1,2-diol via General Procedure E to yield 21 mg (50%) of (±)-3-cyclopropyl-10-(3,4-dihydroxy-3-methyl-but-1-ynyl)-9-fluoro-5,6-dihydroimidazo[1,2-d][1,4]benzoxazepine-2-carboxamide.

M+1=386; $^1$H NMR (500 MHz, DMSO) δ 8.56 (d, J=8.5 Hz, 1H), 7.46 (d, J=1.9 Hz, 1H), 7.04-6.93 (m, 2H), 5.44 (s, 1H), 5.02 (t, J=6.2 Hz, 1H), 4.59-4.43 (m, 4H), 3.49-3.37 (m, 2H), 1.80-1.70 (m, 1H), 1.41 (s, 3H), 1.04-0.92 (m, 2H), 0.87-0.73 (m, 2H).

Example 381

Synthesis of (±)-10-[3-hydroxy-3-(2-pyridyl)but-1-ynyl]-5,6,7,12-tetrahydro-5,7 methanobenzo[c]imidazo[1,2-a]azepine-2-carboxamide

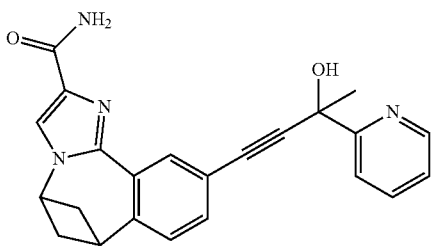 [SMILES: CC(O)(C#Cc1ccc2c(c1)-c1nc(C(N)=O)cn1C1CC2C1)c1ccccn1]

10-bromo-6,7-dihydro-5H-5,7-methanobenzo[c]imidazo[1,2-a]azepine-2-carboxamide was reacted with 2-(pyridin-2-yl)but-3-yn-2-ol via General Procedure E to yield 20 mg (11%) of (±)-10-[3-hydroxy-3-(2-pyridyl)but-1-ynyl]-5,6,7,12-tetrahydro-5,7 methanobenzo[c]imidazo[1,2-a]azepine-2-carboxamide.

M+1=385; $^1$H NMR (400 MHz, DMSO) δ 8.62 (s, 1H), 8.57 (d, J=4.7 Hz, 1H), 7.90-7.82 (m, 2H), 7.77 (d, J=7.9 Hz, 1H), 7.55 (s, 1H), 7.36-7.30 (m, 1H), 7.30-7.23 (m, 2H), 7.11 (s, 1H), 6.39 (s, 1H), 4.98-4.87 (m, 1H), 3.76-3.66 (m, 1H), 3.13-3.02 (m, 2H), 1.82 (s, 3H), 1.69-1.62 (m, 2H).

Example 382

Synthesis of (±)-10-(4-fluoro-3-hydroxy-3-methyl-but-1-ynyl)-5,6,7,12-tetrahydro-5,7-methanobenzo[c]imidazo[1,2-a]azepine-2-carboxamide

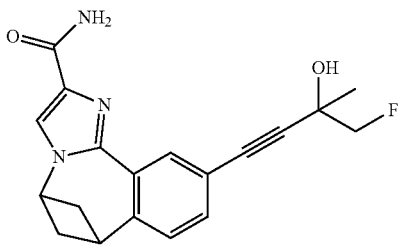 [SMILES: CC(O)(C#Cc1ccc2c(c1)-c1nc(C(N)=O)cn1C1CC2C1)CF]

To a vial containing 10-bromo-6,7-dihydro-5H-5,7-methanobenzo[c]imidazo[1,2-a]azepine-2-carboxamide (0.2 g), palladium acetate (0.05 eq), sodium acetate (4 eq) and tetrabutylammonium chloride (1 eq) was added N,N-Dimethylformamide (15 mL/mmol) and 1-fluoro-2-methyl-4-triethylsilyl-but-3-yn-2-ol (2 eq) dropwise. The reaction was sealed and heated to 100° C. for 15 minutes in a biotage microwave. The reaction mixture was extracted with dichloromethane and saturated ammonium chloride. The organic layer was dried with magnesium sulfate, filtered, concentrated to dryness and purified by reverse phase hplc to afford 9.8 mg of 10-(4-fluoro-3-hydroxy-3-methyl-but-1-ynyl)-5,6,7,12-tetrahydro-5,7-methanobenzo[c]imidazo[1,2-a]azepine-2-carboxamide.

M+1=340; $^1$H NMR (400 MHz, DMSO) δ 8.65 (s, 1H), 7.84 (s, 1H), 7.54 (s, 1H), 7.32-7.25 (m, 2H), 7.14 (s, 1H), 5.97 (s, 1H), 5.01-4.86 (m, 1H), 4.46-4.37 (m, 1H), 4.36-4.23 (m, 1H), 3.76-3.67 (m, 1H), 3.14-3.01 (m, 2H), 1.73-1.60 (m, 2H), 1.48 (s, 3H).

Example 383

Synthesis of (±)-10-[3-hydroxy-3-(2-pyridyl)but-1-ynyl]-N3-methyl-5,6-dihydroimidazo[1,2-d][1,4]benzoxazepine-2,3-dicarboxamide

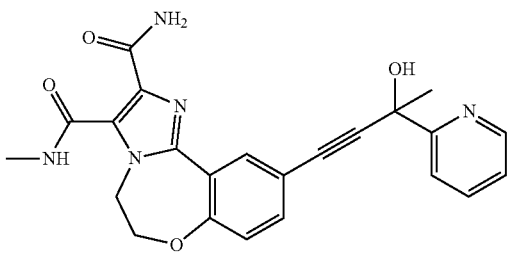 [SMILES: CNC(=O)c1c(C(N)=O)nc2n1CCOc1ccc(C#CC(C)(O)c3ccccn3)cc1-2]

10-bromo-N3-methyl-5,6-dihydrobenzo[f]imidazo[1,2-d][1,4]oxazepine-2,3-dicarboxamide was reacted with 2-(pyridin-2-yl)but-3-yn-2-ol via General Procedure E to yield 14 mg (17%) of (±)-10-[3-hydroxy-3-(2-pyridyl)but-1-ynyl]-N3-methyl-5,6-dihydroimidazo[1,2-d][1,4]benzoxazepine-2,3-dicarboxamide.

M+1=432; 1H NMR (500 MHz, DMSO) δ 11.08 (q, J=4.4 Hz, 1H), 8.59-8.55 (m, 1H), 8.53 (d, J=2.2 Hz, 1H), 8.37 (s, 1H), 7.90 (s, 1H), 7.88-7.82 (m, 1H), 7.77 (d, J=7.9 Hz, 1H), 7.37 (dd, J=8.5, 2.2 Hz, 1H), 7.35-7.30 (m, 1H), 7.04 (d, J=8.5 Hz, 1H), 6.35 (s, 1H), 4.98-4.93 (m, 2H), 4.53-4.48 (m, 2H), 2.80 (d, J=4.6 Hz, 3H), 1.82 (s, 3H).

Example 384

Synthesis of (±)-10-(3-hydroxy-4-methoxy-3-methyl-but-1-ynyl)-5,6,7,12-tetrahydro-5,7-methanobenzo[c]imidazo[1,2-a]azepine-2-carboxamide

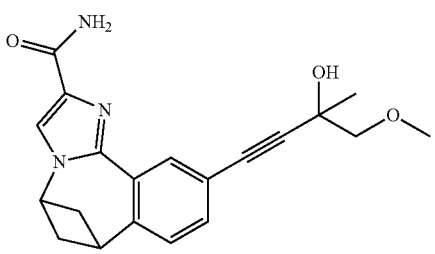 [SMILES: COCC(C)(O)C#Cc1ccc2c(c1)-c1nc(C(N)=O)cn1C1CC2C1]

10-bromo-6,7-dihydro-5H-5,7-methanobenzo[c]imidazo[1,2-a]azepine-2-carboxamide was reacted with 1-methoxy-2-methylbut-3-yn-2-ol via General Procedure E to afford 145 mg (87%) of the title compound.

M+1=352; $^1$H NMR (400 MHz, DMSO) δ 8.62 (s, 1H), 7.84 (s, 1H), 7.54 (s, 1H), 7.33-7.19 (m, 2H), 7.13 (s, 1H), 5.61 (s, 1H), 4.98-4.85 (m, 1H), 3.78-3.64 (m, 1H), 3.46-3.36 (m, 5H), 3.15-2.98 (m, 2H), 1.71-1.57 (m, 2H), 1.44 (s, 3H).

Example 385

Synthesis of (±)-3-cyclopropyl-9-fluoro-10-[3-hydroxy-3-(2-pyridyl)but-1-ynyl]-5,6-dihydroimidazo[1,2-d][1,4]benzoxazepine-2-carboxamide

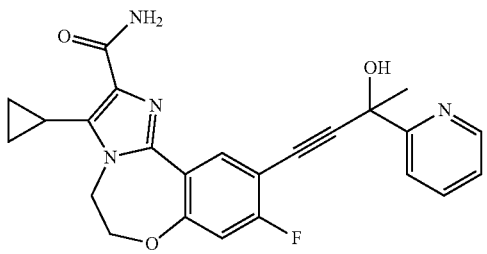 [SMILES: CC(O)(C#Cc1cc2c(cc1F)OCCn1c-2nc(C(N)=O)c1C1CC1)c1ccccn1]

10-bromo-3-cyclopropyl-9-fluoro-5,6-dihydrobenzo[f]imidazo[1,2-d][1,4]oxazepine-2-carboxamide was reacted with 2-(pyridin-2-yl)but-3-yn-2-ol via General Procedure E to yield 9.5 mg (16%) of (±)-3-cyclopropyl-9-fluoro-10-[3-hydroxy-3-(2-pyridyl)but-1-ynyl]-5,6-dihydroimidazo[1,2-d][1,4]benzoxazepine-2-carboxamide.

M+1=433; $^1$H NMR (500 MHz, DMSO) δ 8.60-8.51 (m, 2H), 7.86 (ddd, J=7.7, 1.8 Hz, 1H), 7.76 (d, J=7.9 Hz, 1H), 7.49 (d, J=1.8 Hz, 1H), 7.38-7.29 (m, 1H), 6.99 (d, J=6.7 Hz, 1H), 6.97 (d, J=1.8 Hz, 1H), 6.42 (s, 1H), 4.57-4.44 (m, 4H), 1.82 (s, 3H), 1.79-1.71 (m, 1H), 1.01-0.94 (m, 2H), 0.84-0.77 (m, 2H).

Example 386

Synthesis of 10-(3-hydroxy-3-methyl-but-1-ynyl)-5,6,7,12-tetrahydro-5,7-methanobenzo[c]imidazo[1,2-a]azepine-2-carboxamide

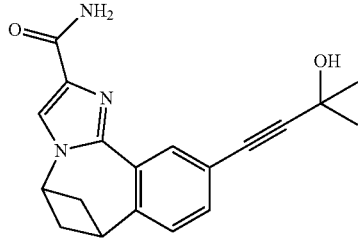 [SMILES: CC(C)(O)C#Cc1ccc2c(c1)-c1nc(C(N)=O)cn1C1CC2C1]

10-bromo-6,7-dihydro-5H-5,7-methanobenzo[c]imidazo[1,2-a]azepine-2-carboxamide was reacted with 2-Methyl-3-butyne-ol via General Procedure E to afford 148 mg (97%) of 10-(3-hydroxy-3-methyl-but-1-ynyl)-5,6,7,12-tetrahydro-5,7-methanobenzo[c]imidazo[1,2-a]azepine-2-carboxamide.

M+1=322; $^1$H NMR (400 MHz, DMSO) δ 8.62 (s, 1H), 7.84 (s, 1H), 7.54 (s, 1H), 7.33-7.20 (m, 2H), 7.13 (s, 1H), 5.50 (s, 1H), 4.92 (dd, J=10.6, 6.0 Hz, 1H), 3.78-3.63 (m, 1H), 3.14-2.99 (m, 2H), 1.73-1.62 (m, 2H), 1.49 (s, 6H).

Example 387

Synthesis of (±)-9-fluoro-10-[3-hydroxy-3-(2-pyridyl)but-1-ynyl]-N3-methyl-5,6-dihydroimidazo[1,2-d][1,4]benzoxazepine-2,3-dicarboxamide

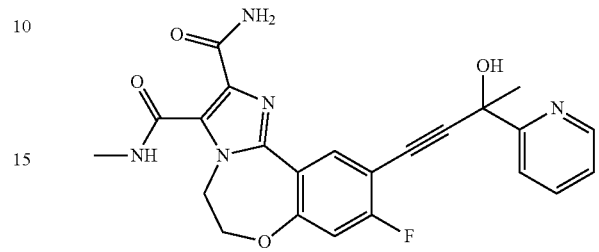

10-bromo-9-fluoro-N3-methyl-5,6-dihydrobenzo[f]imidazo[1,2-d][1,4]oxazepine-2,3-dicarboxamide was reacted with 2-(pyridin-2-yl)but-3-yn-2-ol via General Procedure E to yield 8.4 mg (10%) of (±)-9-fluoro-10-[3-hydroxy-3-(2-pyridyl)but-1-ynyl]-N3-methyl-5,6-dihydroimidazo[1,2-d][1,4]benzoxazepine-2,3-dicarboxamide.

M+1=450; $^1$H NMR (500 MHz, DMSO) δ 11.11 (q, J=4.5 Hz, 1H), 8.62 (d, J=8.4 Hz, 1H), 8.56 (d, J=4.5 Hz, 1H), 8.42 (s, 1H), 7.89 (s, 1H), 7.88-7.83 (m, 1H), 7.77 (d, J=7.9 Hz, 1H), 7.36-7.30 (m, 1H), 7.04 (d, J=10.5 Hz, 1H), 6.42 (s, 1H), 5.01-4.96 (m, 2H), 4.57-4.50 (m, 2H), 2.80 (d, J=4.6 Hz, 3H), 1.83 (s, 3H).

Example 388

Synthesis of (±)-10-(3,4-dihydroxy-3-methyl-but-1-ynyl)-5,6,7,12-tetrahydro-5,7-methanobenzo[c]imidazo[1,2-a]azepine-2-carboxamide

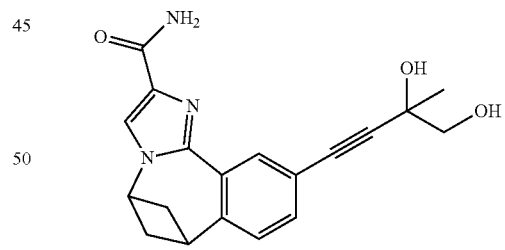

10-bromo-6,7-dihydro-5H-5,7-methanobenzo[c]imidazo[1,2-a]azepine-2-carboxamide was reacted with 2-methylbut-3-yne-1,2-diol via General Procedure E to yield 44 mg (28%) of (±)-10-(3,4-dihydroxy-3-methyl-but-1-ynyl)-5,6,7,12-tetrahydro-5,7-methanobenzo[c]imidazo[1,2-a]azepine-2-carboxamide.

M+1=338; $^1$H NMR (500 MHz, DMSO) δ 8.63 (s, 1H), 7.84 (s, 1H), 7.54 (s, 1H), 7.30-7.22 (m, 2H), 7.14 (s, 1H), 5.41 (s, 1H), 5.07-4.99 (m, 1H), 4.99-4.88 (m, 1H), 3.76-3.65 (m, 1H), 3.51-3.38 (m, 2H), 3.13-3.01 (m, 2H), 1.70-1.61 (m, 2H), 1.41 (s, 3H).

Example 389

Synthesis of 3-cyclopropyl-9-fluoro-10-[(3R)-3-hydroxy-3-(5-methyl-1,2,4-oxadiazol-3-yl)but-1-ynyl]-5,6-dihydroimidazo[1,2-d][1,4]benzoxazepine-2-carboxamide

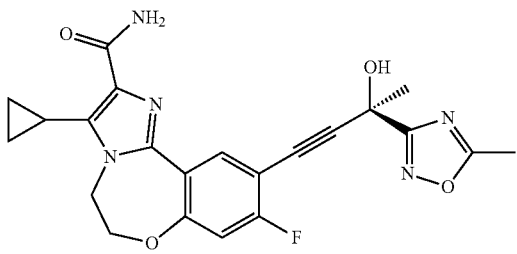 [SMILES: Cc1nc([C@](C)(O)C#Cc2cc3c(cc2F)OCCn2c-3nc(C(N)=O)c2C2CC2)no1]

10-bromo-3-cyclopropyl-9-fluoro-5,6-dihydrobenzo[f]imidazo[1,2-d][1,4]oxazepine-2-carboxamide was reacted with (R)-2-(5-methyl-1,2,4-oxadiazol-3-yl)but-3-yn-2-ol via General Procedure E to yield 8.2 mg (14%) of 3-cyclopropyl-9-fluoro-10-[(3R)-3-hydroxy-3-(5-methyl-1,2,4-oxadiazol-3-yl)but-1-ynyl]-5,6-dihydroimidazo[1,2-d][1,4]benzoxazepine-2-carboxamide.

M+1=438. $^1$H NMR (400 MHz, DMSO) δ 8.59 (d, J=8.4 Hz, 1H), 7.48 (s, 1H), 7.02 (d, J=10.5 Hz, 1H), 6.98 (s, 1H), 6.78 (s, 1H), 4.60-4.52 (m, 2H), 4.52-4.44 (m, 2H), 2.62 (s, 3H), 1.84 (s, 3H), 1.80-1.69 (m, 1H), 1.03-0.94 (m, 2H), 0.88-0.75 (m, 2H).

Example 390

Synthesis of 9-fluoro-10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide

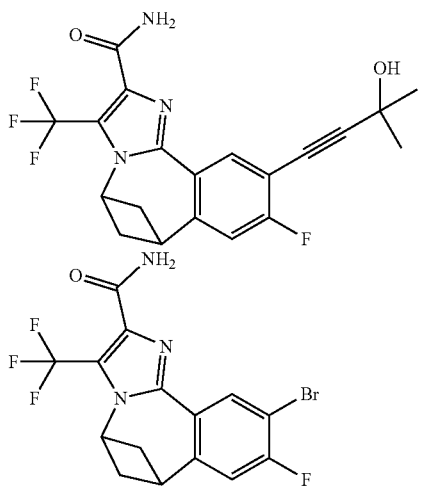

10-bromo-9-fluoro-6,7-dihydro-5H-5,7-methanobenzo[c]imidazo[1,2-a]azepine-2-carboxamide (350 mg) was subjected to conditions described in General Procedure J to afford 288 mg 10-bromo-9-fluoro-3-(trifluoromethyl)-6,7-dihydro-5H-5,7-methanobenzo[c]imidazo[1,2-a]azepine-2-carboxamide

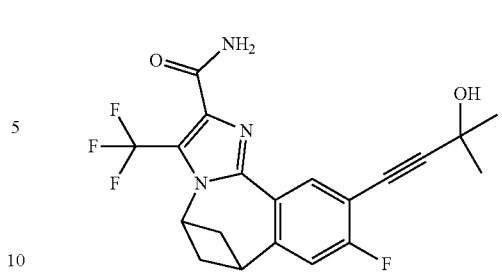

10-bromo-9-fluoro-3-(trifluoromethyl)-6,7-dihydro-5H-5,7-methanobenzo[c]imidazo[1,2-a]azepine-2-carboxamide was reacted 2-Methyl-3-butyne-ol via General Procedure E to afford 41 mg (50%) of 9-fluoro-10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide.

M+1=408; $^1$H NMR (400 MHz, DMSO) δ 8.73 (d, J=7.5 Hz, 1H), 7.99 (s, 1H), 7.56 (s, 1H), 7.35 (d, J=10.1 Hz, 1H), 5.59 (s, 1H), 5.05-4.88 (m, 1H), 3.81-3.65 (m, 1H), 3.27-3.12 (m, 2H), 1.82-1.71 (m, 2H), 1.50 (s, 6H).

Example 391

Synthesis of 10-bromo-3-(trifluoromethyl)-5,6-dihydrobenzo[f]imidazo[1,2-d][1,4]oxazepine-2-carboxamide

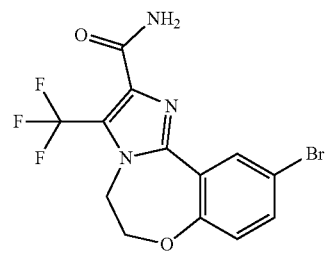 [SMILES: NC(=O)c1nc2n(c1C(F)(F)F)CCOc1ccc(Br)cc1-2]

10-bromo-5,6-dihydrobenzo[f]imidazo[1,2-d][1,4]oxazepine-2-carboxamide (410 mg) was subjected to conditions described in General Procedure J to afford 355 mg 10-bromo-3-(trifluoromethyl)-5,6-dihydrobenzo[f]imidazo[1,2-d][1,4]oxazepine-2-carboxamide.

Example 392

Synthesis of 10-(3-hydroxy-3-methyl-but-1-ynyl)-3-(trifluoromethyl)-5,6-dihydroimidazo[1,2-d][1,4]benzoxazepine-2-carboxamide

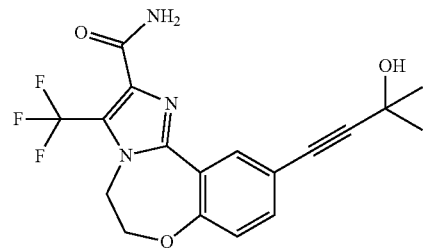 [SMILES: CC(C)(O)C#Cc1ccc2c(c1)-c1nc(C(N)=O)c(C(F)(F)F)n1CCO2]

10-bromo-3-(trifluoromethyl)-5,6-dihydrobenzo[f]imidazo[1,2-d][1,4]oxazepine-2-carboxamide was reacted with 2-Methyl-3-butyne-ol via General Procedure E to afford 27 mg (33%) of 10-(3-hydroxy-3-methyl-but-1-ynyl)-3-(trifluoromethyl)-5,6-dihydroimidazo[1,2-d][1,4]benzoxazepine-2-carboxamide.

M+1=380; $^1$H NMR (400 MHz, DMSO) δ 8.54 (s, 1H), 7.95 (s, 1H), 7.54 (s, 1H), 7.38 (d, J=7.3 Hz, 1H), 7.07 (d, J=8.5 Hz, 1H), 5.47 (s, 1H), 4.62-4.46 (m, 4H), 1.48 (s, 6H).

Example 393

Synthesis of 10-bromo-3-(trifluoromethyl)-6,7-dihydro-5H-5,7-methanobenzo[e]imidazo[1,2-a]azepine-2-carboxamide

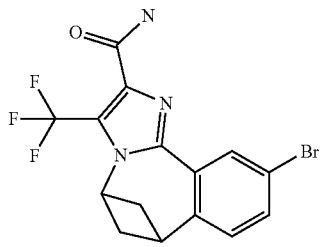 [SMILES: NC(=O)c1nc2n(c1C(F)(F)F)C1CC(C1)c1ccc(Br)cc1-2]

10-bromo-6,7-dihydro-5H-5,7-methanobenzo[c]imidazo[1,2-a]azepine-2-carboxamide carboxamide (400 mg) was subjected to conditions described in General Procedure J to afford 348 mg 10-bromo-3-(trifluoromethyl)-6,7-dihydro-5H-5,7-methanobenzo[c]imidazo[1,2-a]azepine-2-carboxamide.

Example 394

Synthesis of 10-[(3R)-3-hydroxy-3-(5-methylisoxazol-3-yl)but-1-ynyl]-3-(trifluoromethyl)-5,6,7,12-tetrahydro-5,7-methanobenzo[c]imidazo[1,2-a]azepine-2-carboxamide

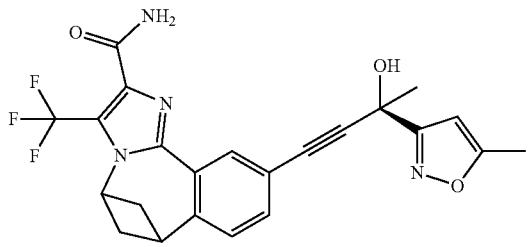 [SMILES: Cc1cc([C@](C)(O)C#Cc2ccc3c(c2)-c2nc(C(N)=O)c(C(F)(F)F)n2C2CC3C2)no1]

10-bromo-3-(trifluoromethyl)-5,6-dihydrobenzo[f]imidazo[1,2-d][1,4]oxazepine-2-carboxamide was reacted with (2R)-2-(5-methylisoxazol-3-yl)but-3-yn-2-ol via General Procedure E to afford 26.1 mg (27%) of 10-[(3R)-3-hydroxy-3-(5-methylisoxazol-3-yl)but-1-ynyl]-3-(trifluoromethyl)-5,6,7,12-tetrahydro-5,7-methanobenzo[c]imidazo[1,2-a]azepine-2-carboxamide.

M+1=457; 1H NMR (400 MHz, DMSO) δ 8.72 (s, 1H), 7.97 (s, 1H), 7.56 (s, 1H), 7.44-7.29 (m, 2H), 6.56 (s, 1H), 6.37 (s, 1H), 5.04-4.91 (m, 1H), 3.80-3.66 (m, 1H), 3.25-3.14 (m, 2H), 2.41 (s, 3H), 1.81 (s, 3H), 1.78-1.70 (m, 2H).

Example 395

Synthesis of 10-[(3R)-3-hydroxy-3-(5-methyl-1,2,4-oxadiazol-3-yl)but-1-ynyl]-3-(trifluoromethyl)-5,6,7,12-tetra hydro-5,7-methanobenzo[c]imidazo[1,2-a]azepine-2-carboxamide

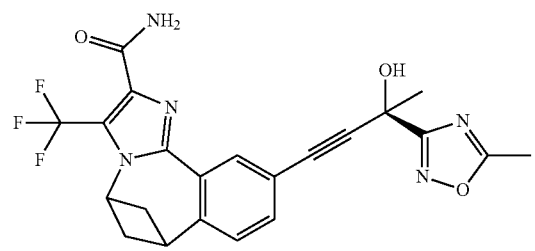 [SMILES: Cc1nc([C@](C)(O)C#Cc2ccc3c(c2)-c2nc(C(N)=O)c(C(F)(F)F)n2C2CC3C2)no1]

10-bromo-3-(trifluoromethyl)-5,6-dihydrobenzo[f]imidazo[1,2-d][1,4]oxazepine-2-carboxamide was reacted (2R)-2-(5-methyl-1,2,4-oxadiazol-3-yl)but-3-yn-2-ol via General Procedure E to afford 19.4 mg (21%) of 10-[(3R)-3-hydroxy-3-(5-methyl-1,2,4-oxadiazol-3-yl)but-1-ynyl]-3-(trifluoromethyl)-5,6,7,12-tetra hydro-5,7-methanobenzo[c]imidazo[1,2-a]azepine-2-carboxamide. M+1=458; $^1$H NMR (400 MHz, DMSO) δ 8.73 (s, 1H), 7.97 (s, 1H), 7.56 (s, 1H), 7.43-7.33 (m, 2H), 6.77 (s, 1H), 5.02-4.93 (m, 1H), 3.79-3.70 (m, 1H), 3.26-3.14 (m, 2H), 2.62 (s, 3H), 1.85 (s, 3H), 1.79-1.69 (m, 2H).

Example 396

Synthesis of 10-[(3R)-3-hydroxy-3-(5-methylisoxazol-3-yl)but-1-ynyl]-3-(trifluoromethyl)-5,6-dihydroimidazo[1,2-d][1,4]benzoxazepine-2-carboxamide

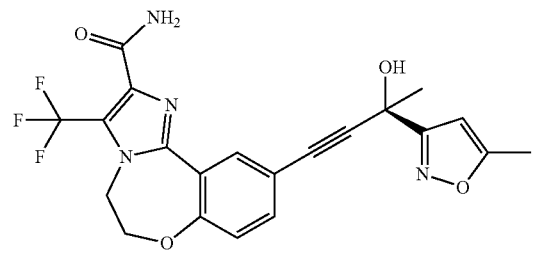 [SMILES: Cc1cc([C@](C)(O)C#Cc2ccc3c(c2)-c2nc(C(N)=O)c(C(F)(F)F)n2CCO3)no1]

10-bromo-3-(trifluoromethyl)-5,6-dihydrobenzo[f]imidazo[1,2-d][1,4]oxazepine-2-carboxamide was reacted with (2R)-2-(5-methylisoxazol-3-yl)but-3-yn-2-ol via General Procedure E to afford 19 mg (20%) of 10-[(3R)-3-hydroxy-3-(5-methylisoxazol-3-yl)but-1-ynyl]-3-(trifluoromethyl)-5,6-dihydroimidazo[1,2-d][1,4]benzoxazepine-2-carboxamide.

M+1=380; $^1$H NMR (400 MHz, DMSO) δ 8.57 (s, 1H), 7.96 (s, 1H), 7.54 (s, 1H), 7.43 (d, J=8.5 Hz, 1H), 7.09 (d, J=8.5 Hz, 1H), 6.52 (s, 1H), 6.36 (s, 1H), 4.60-4.49 (m, 4H), 2.41 (s, 3H), 1.80 (s, 3H).

Example 397

Synthesis of (±)-10-(3-hydroxy-3-pyrimidin-2-yl-but-1-ynyl)-5,6,7,12-tetrahydro-5,7-methanobenzo[c]imidazo[1,2-a]azepine-2-carboxamide

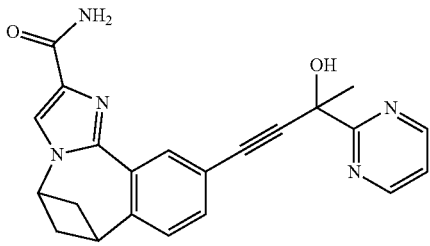 [SMILES: CC(O)(C#Cc1ccc2c(c1)-c1nc(C(N)=O)cn1C1CC2C1)c1ncccn1]

10-bromo-6,7-dihydro-5H-5,7-methanobenzo[c]imidazo[1,2-a]azepine-2-carboxamide was reacted with 2-pyrimidin-2-ylbut-3-yn-2-ol via General Procedure G to afford 108 mg (45%) of (±)-10-(3-hydroxy-3-pyrimidin-2-yl-but-1-ynyl)-5,6,7,12-tetrahydro-5,7-methanobenzo[c]imidazo[1,2-a]azepine-2-carboxamide.

M+1=386; $^1$H NMR (400 MHz, DMSO) δ 8.90 (d, J=4.9 Hz, 2H), 8.62 (s, 1H), 7.84 (s, 1H), 7.55 (s, 1H), 7.50 (t, J=4.8 Hz, 1H), 7.30-7.22 (m, 2H), 7.12 (s, 1H), 6.22 (s, 1H), 4.96-4.87 (m, 1H), 3.76-3.66 (m, 1H), 3.13-3.01 (m, 3H), 1.88 (s, 3H), 1.70-1.60 (m, 2H).

Example 398

Synthesis of 9-fluoro-10-(3-hydroxy-3-pyrimidin-2-yl-but-1-ynyl)-5,6,7,12-tetrahydro-5,7-methanobenzo[c]imidazo[1,2-a]azepine-2-carboxamide

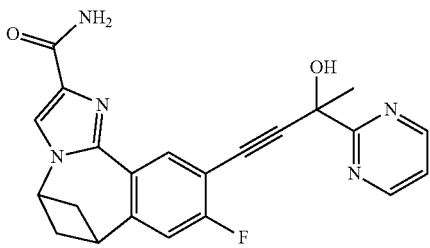 [SMILES: CC(O)(C#Cc1cc2c(cc1F)C1CC(C1)n1cc(C(N)=O)nc1-2)c1ncccn1]

10-bromo-9-fluoro-6,7-dihydro-5H-5,7-methanobenzo[c]imidazo[1,2-a]azepine-2-carboxamide was reacted with 2-pyrimidin-2-ylbut-3-yn-2-ol via General Procedure G to afford 84 mg (35%) of 9-fluoro-10-(3-hydroxy-3-pyrimidin-2-yl-but-1-ynyl)-5,6,7,12-tetrahydro-5,7-methanobenzo[c]imidazo[1,2-a]azepine-2-carboxamide.

M+1=404; $^1$H NMR (400 MHz, DMSO) δ 8.90 (d, J=4.8 Hz, 2H), 8.64 (d, J=7.6 Hz, 1H), 7.82 (s, 1H), 7.57 (s, 1H), 7.51 (t, J=4.8 Hz, 1H), 7.28 (d, J=10.2 Hz, 1H), 7.11 (s, 1H), 6.30 (s, 1H), 4.98-4.86 (m, 1H), 3.78-3.66 (m, 1H), 3.15-100 (m, 2H), 1.89 (s, 3H), 1.71-1.64 (m, 2H).

Example 399

Synthesis of (R)-9-fluoro-10-(3-hydroxy-3-(5-methylisoxazol-3-yl)but-1-yn-1-yl)-3-(trifluoromethyl)-6,7-dihydro-5H-5,7-methanobenzo[c]imidazo[1,2-a]azepine-2-carboxamide

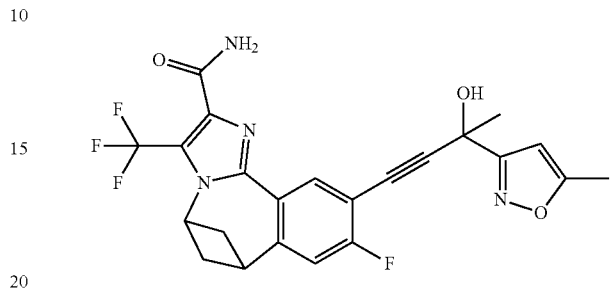

10-bromo-9-fluoro-3-(trifluoromethyl)-6,7-dihydro-5H-5,7-methanobenzo[c]imidazo[1,2-a]azepine-2-carboxamide was reacted with (2R)-2-(5-methylisoxazol-3-yl)but-3-yn-2-ol via General Procedure E to afford 38 mg (46%) of (R)-9-fluoro-10-(3-hydroxy-3-(5-methylisoxazol-3-yl)but-1-yn-1-yl)-3-(trifluoromethyl)-6,7-dihydro-5H-5,7-methanobenzo[c]imidazo[1,2-a]azepine-2-carboxamide.

M+1=475; $^1$H NMR (400 MHz, DMSO) δ 8.76 (d, J=7.4 Hz, 1H), 8.00 (s, 1H), 7.55 (s, 1H), 7.38 (d, J=10.0 Hz, 1H), 6.63 (s, 1H), 6.36 (s, 1H), 5.04-4.91 (m, 1H), 3.83-3.70 (m, 1H), 3.29-3.14 (m, 2H), 2.41 (s, 3H), 1.82 (s, 3H), 1.80-1.74 (m, 2H).

Example 400

Synthesis of 9-fluoro-10-[(3R)-3-hydroxy-3-(5-methyl-1,2,4-oxadiazol-3-yl)but-1-ynyl]-3-(trifluoromethyl)-5,6,7,12-tetrahydro-5,7-methanobenzo[c]imidazo[1,2-a]azepine-2-carboxamide

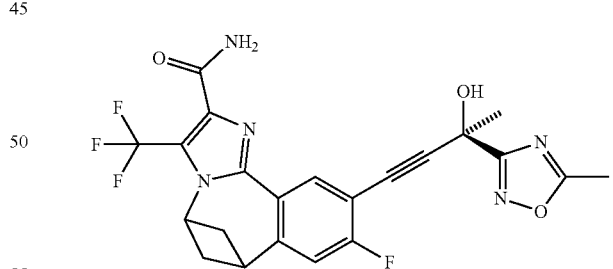

10-bromo-9-fluoro-3-(trifluoromethyl)-6,7-dihydro-5H-5,7-methanobenzo[c]imidazo[1,2-a]azepine-2-carboxamide was reacted with reacted (2R)-2-(5-methyl-1,2,4-oxadiazol-3-yl)but-3-yn-2-ol via General Procedure E to afford 25 mg (30%) of 9-fluoro-10-[(3R)-3-hydroxy-3-(5-methyl-1,2,4-oxadiazol-3-yl)but-1-ynyl]-3-(trifluoromethyl)-5,6,7,12-tetrahydro-5,7-methanobenzo[c]imidazo[1,2-a]azepine-2-carboxamide.

M+1=476; $^1$H NMR (400 MHz, DMSO) δ 8.77 (d, J=7.4 Hz, 1H), 7.99 (s, 1H), 7.55 (s, 1H), 7.39 (d, J=10.0 Hz, 1H), 6.85 (s, 1H), 5.03-4.89 (m, 1H), 3.80-3.71 (m, 1H), 3.27-3.14 (m, 2H), 2.63 (s, 3H), 1.86 (s, 4H), 1.81-1.73 (m, 3H).

Example 401

Synthesis of 10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide

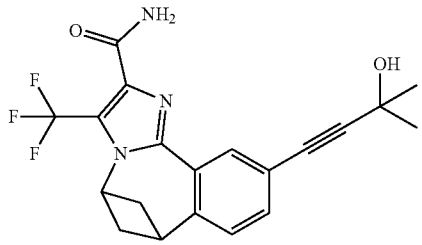 [SMILES: CC(C)(O)C#Cc1ccc2c(c1)-c1nc(C(N)=O)c(C(F)(F)F)n1C1CC2C1]

10-bromo-3-(trifluoromethyl)-5,6-dihydrobenzo[f]imidazo[1,2-d][1,4]oxazepine-2-carboxamide was reacted with 2-Methyl-3-butyne-ol via General Procedure E to afford 40.6 mg (58%) of 10-(3-hydroxy-3-methyl-but-1-ynyl)-3-(trifluoromethyl)-5,6,7,12-tetrahydro-5,7-methanobenzo[c]imidazo[1,2-a]azepine-2-carboxamide.

M+1=458; $^1$H NMR (400 MHz, DMSO) δ 8.73 (d, J=7.5 Hz, 1H), 7.99 (s, 1H), 7.56 (s, 1H), 7.35 (d, J=10.1 Hz, 1H), 5.59 (s, 1H), 5.05-4.88 (m, 1H), 3.81-3.65 (m, 1H), 3.27-3.12 (m, 2H), 1.82-1.71 (m, 2H), 1.50 (s, 6H).

Example 402

Synthesis of 10-bromo-N3-methyl-6,7-dihydro-5H-5,7-methanobenzo[c]imidazo[1,2-a]azepine-2,3-dicarboxamide

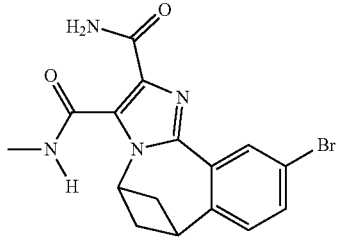 [SMILES: CNC(=O)c1c(C(N)=O)nc2n1C1CC(C1)c1ccc(Br)cc1-2]

10-bromo-6,7-dihydro-5H-5,7-methanobenzo[c]imidazo[1,2-a]azepine-2-carboxamide (5 g) was reacted similarly to the conditions described in example 6 to produce 4.56 g of methyl 10-bromo-2-carbamoyl-6,7-dihydro-5H-5,7-methanobenzo[c]imidazo[1,2-a]azepine-3-carboxylate. This intermediate was then subjected to General Procedure N to afford 1.91 g of 10-bromo-2-carbamoyl-6,7-dihydro-5H-5,7-methanobenzo[c]imidazo[1,2-a]azepine-3-carboxylic acid. This intermediate (0.5 g) was then reacted with N-Methylamine Hydrochloride similarly to the conditions described in Example 2 to produce 417 mg of 10-bromo-N3-methyl-6,7-dihydro-5H-5,7-methanobenzo[c]imidazo azepine-2,3-dicarboxamide as an orange solid.

Example 403

Synthesis of 10-[(3R)-3-hydroxy-3-(5-methylisoxazol-3-yl)but-1-ynyl]-N3-methyl-5,6,7,12-tetrahydro-5,7-methanobenzo[c]imidazo azepine-2,3-dicarboxamide

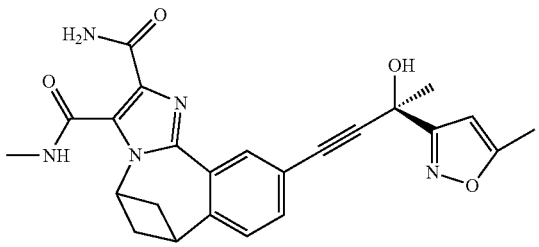

10-bromo-N3-methyl-6,7-dihydro-5H-5,7-methanobenzo[c]imidazo[1,2-a]azepine-2,3-dicarboxamide was reacted with (2R)-2-(5-methylisoxazol-3-yl)but-3-yn-2-ol via General Procedure E to afford 32 mg (39%) of 10-[(3R)-3-hydroxy-3-(5-methylisoxazol-3-yl)but-1-ynyl]-N3-methyl-5,6,7,12-tetrahydro-5,7-methanobenzo[c]imidazo[1,2-a]azepine-2,3-dicarboxamide.

M+1=446; $^1$H NMR (400 MHz, DMSO-d6) δ 10.49 (q, J=4.9 Hz, 1H), 8.80 (s, 1H), 8.24 (s, 1H), 7.75 (s, 1H), 7.38-7.28 (m, 2H), 6.56 (s, 1H), 6.37 (s, 1H), 6.08-5.98 (m, 1H), 3.72-3.63 (m, 1H), 2.78 (d, J=4.5 Hz, 3H), 2.41 (s, 3H), 1.82 (s, 3H), 1.70-1.60 (m, 2H).

Example 404

Synthesis of (±)-10-[3-hydroxy-3-(1H-1,2,4-triazol-3-yl)but-1-ynyl]-5,6,7,12-tetrahydro-5,7-methanobenzo[c]imidazo[1,2-a]azepine-2-carboxamide

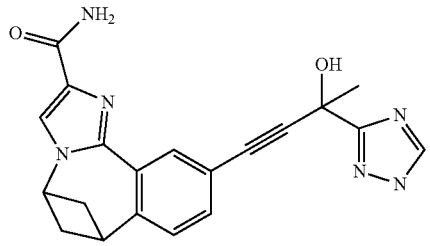 [SMILES: CC(O)(C#Cc1ccc2c(c1)-c1nc(C(N)=O)cn1C1CC2C1)c1nc[nH]n1]

10-bromo-6,7-dihydro-5H-5,7-methanobenzo[c]imidazo[1,2-a]azepine-2-carboxamide was reacted with 2-[1-(2-trimethylsilylethoxymethyl)-1,2,4-triazol-3-yl]but-3-yn-2-ol via General Procedure E to afford 50 mg (16%) of 10-(3-hydroxy-3-(14(2-(trimethylsilyl)ethoxy)methyl)-1H-1,2,4-triazol-3-yl)but-1-yn-1-yl)-6,7-dihydro-5H-5,7-methanobenzo[c]imidazo[1,2-a]azepine-2-carboxamide following reverse phase purification. This intermediate was subsequently reacted with tetrabutylammonium fluoride (1 mol/L) in THF (3 eq, 0.3 mmol) for 18 hours at 45° C. and purified via reverse phase hplc to afford 14 mg (38%) of (±)-10-[3-hydroxy-3-(1H-1,2,4-triazol-3-yl)but-1-ynyl]-5,6,7,12-tetrahydro-5,7-methanobenzo[c]imidazo[1,2-a]azepine-2-carboxamide.

M+1=375.

¹H NMR (400 MHz, DMSO-d6) δ 8.69-8.62 (m, 1H), 8.18 (s, 1H), 7.84 (s, 1H), 7.55 (s, 1H), 7.32-7.26 (m, 2H), 7.12 (s, 1H), 6.54 (s, 1H), 4.97-4.88 (m, 1H), 3.77-3.67 (m, 1H), 3.12-3.02 (m, 2H), 1.86 (s, 3H), 1.69-1.62 (m, 2H).

Example 405

Synthesis of 10-[(3R)-3-hydroxy-3-(5-methyl-1,2,4-oxadiazol-3-yl)but-1-ynyl]-N3-methyl-5,6,7,12-tetrahydro-5,7-methanobenzo[c]imidazo[1,2-a]azepine-2,3-dicarboxamide

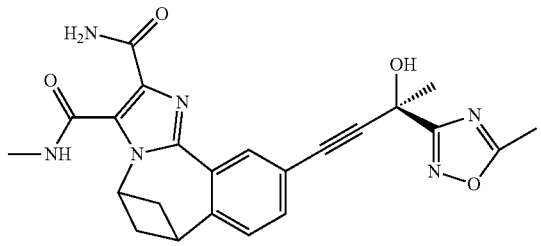

10-bromo-N3-methyl-6,7-dihydro-5H-5,7-methanobenzo [c]imidazo azepine-2,3-dicarboxamide was reacted (2R)-2-(5-methyl-1,2,4-oxadiazol-3-yl)but-3-yn-2-ol via General Procedure E to afford 32 mg (24%) of 10-[(3R)-3-hydroxy-3-(5-methyl-1,2,4-oxadiazol-3-yl)but-1-ynyl]-N3-methyl-5,6,7,12-tetrahydro-5,7-methanobenzo[c]imidazo[1,2-a] azepine-2,3-dicarboxamide. M+1=447.

¹H NMR (400 MHz, DMSO) δ 10.56-10.49 (q, J=4.4 Hz, 1H), 8.85-8.77 (s, 1H), 8.30-8.21 (s, 1H), 7.79-7.70 (s, 1H), 7.39-7.29 (m, 2H), 6.78-6.71 (s, 1H), 6.11-5.99 (m, 1H), 3.74-3.63 (m, 1H), 3.16-3.06 (m, 3H), 2.83-2.73 (d, J=4.5 Hz, 3H), 2.66-2.60 (s, 3H), 1.90-1.82 (s, 3H), 1.72-1.62 (m, 3H).

Example 406

Synthesis of 10-[(3R)-3-hydroxy-3-(5-methylisoxazol-3-yl)but-1-ynyl]-N3,N3-dimethyl-5,6,7,12-tetrahydro-5,7-methanobenzo[c]imidazo[1,2-a]azepine-2,3-dicarboxamide

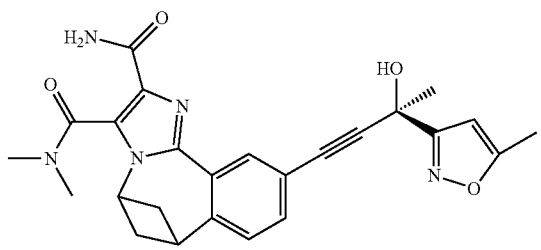

10-bromo-2-carbamoyl-6,7-dihydro-5H-5,7-methanobenzo[c]imidazo[1,2-a]azepine-3-carboxylic acid (0.1 g) was reacted with N,N-Dimethylamine Hydrochloride similarly to the conditions described in Example 2 to produce 10-bromo-N3,N3-dimethyl-6,7-dihydro-5H-5,7-methanobenzo[c]imidazo[1,2-a]azepine-2,3-dicarboxamide. This intermediate was then reacted with (2R)-2-(5-methylisoxazol-3-yl)but-3-yn-2-ol via General Procedure E to afford 21 mg (16%) of 10-[(3R)-3-hydroxy-3-(5-methylisoxazol-3-yl) but-1-ynyl]-N3,N3-dimethyl-5,6,7,12-tetrahydro-5,7-methanobenzo[c]imidazo[1,2-a]azepine-2,3-dicarboxamide.

M+1=460; ¹H NMR (400 MHz, DMSO) δ 8.75-8.65 (s, 1H), 7.74-7.63 (s, 1H), 7.37-7.28 (s, 2H), 7.27-7.19 (s, 1H), 6.58-6.50 (s, 1H), 6.39-6.33 (s, 1H), 4.63-4.49 (m, 1H), 3.77-3.66 (m, 1H), 3.16-3.04 (m, 2H), 3.03-2.98 (s, 3H), 2.85-2.79 (s, 3H), 2.46-2.40 (s, 3H), 1.86-1.79 (s, 3H), 1.74-1.66 (m, 2H).

Example 407

Synthesis of 3-[(dimethylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

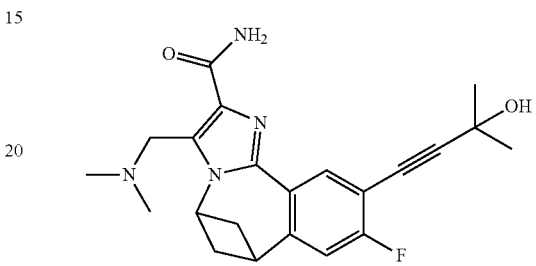

To a suspension of 10-bromo-9-fluoro-3-formyl-6,7-dihydro-5H-5,7-methanobenzo[c]imidazo[1,2-a]azepine-2-carboxamide (75 mg) in anhydrous N,N-Dimethylformamide was added acetic acid, dimethylamine hydrochloride and 200 mg powdered 4 angstrom molecular sieves. The reaction was stirred for 30 minutes before the addition of sodium cyanoborohydride then continued to stir at room temperature for 18 hours. The reaction mixture was then extracted with dichloromethane and saturated ammonium chloride. The organic layer was dried, filtered and concentrated to afford crude 10-bromo-3-((dimethylamino)methyl)-9-fluoro-6,7-dihydro-5H-5,7-methanobenzo[c]imidazo[1,2-a]azepine-2-carboxamide. This crude intermediate was directly reacted with 2-Methyl-3-butyne-ol via General Procedure E to afford 34 mg (41%) of 3-[(dimethylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide.

M+1=397; ¹H NMR (400 MHz, DMSO-d6) δ 8.70 (d, J=7.6 Hz, 1H), 7.64 (s, 1H), 7.26 (d, J=10.2 Hz, 1H), 7.09 (s, 1H), 5.57 (s, 1H), 5.06 (q, J=6.2 Hz, 1H), 3.86 (s, 2H), 3.70-3.62 (m, 1H), 3.17-3.03 (m, 3H), 2.12 (s, 6H), 1.73-1.58 (m, 2H), 1.50 (s, 5H).

Example 408

Synthesis of 9-fluoro-10-(3-hydroxy-3-methyl-but-1-ynyl)-3-[(4-methyl)piperazin-1-yl)methyl]-5,6,7,12-tetrahydro-5,7-methanobenzo[c]imidazo[1,2-a]azepine-2-carboxamide

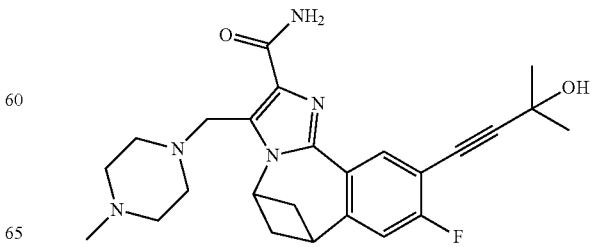

10-bromo-9-fluoro-3-formyl-6,7-dihydro-5H-5,7-methanobenzo[c]imidazo[1,2-a]azepine-2-carboxamide (75 mg) was reacted with N-Methylpiperazine similarly to as described elsewhere in this application to afford crude 10-bromo-9-fluoro-3((4-methylpiperazin-1-yl)methyl)-6,7-dihydro-5H-5,7-methanobenzo[c]imidazo[1,2-a]azepine-2-carboxamide which was directly reacted with 2-Methyl-3-butyne-ol via General Procedure E to afford 24 mg (26%) of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide.

M+1=452; $^1$H NMR (400 MHz, DMSO-d6) δ 8.69 (d, J=7.6 Hz, 1H), 7.63 (s, 1H), 7.26 (d, J=10.1 Hz, 1H), 7.08 (s, 1H), 5.57 (s, 1H), 5.08 (q, J=6.0 Hz, 1H), 3.96 (s, 2H), 3.71-3.62 (m, 1H), 3.15-3.03 (m, 2H), 2.38-2.33 (m, 4H), 2.25-2.20 (m, 4H), 2.11 (s, 3H), 1.68-1.59 (m, 2H), 1.50 (s, 6H).

Example 409

Synthesis of 10-[(3R)-3-hydroxy-3-(5-methylisoxazol-3-yl)but-1-ynyl]-N3-tetrahydropyran-4-yl-5,6,7,12-tetrahydro-5,7-methanobenzo[c]imidazo[1,2-a]azepine-2,3-dicarboxamide

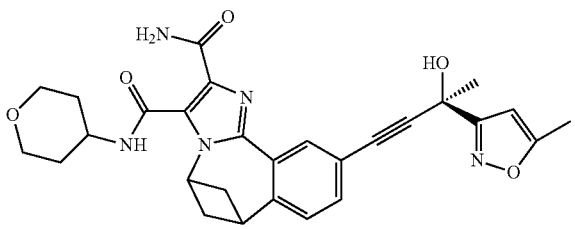 [SMILES: Cc1cc([C@](C)(O)C#Cc2ccc3c(c2)-c2nc(C(N)=O)c(C(=O)NC4CCOCC4)n2C2CC3C2)no1]

10-bromo-2-carbamoyl-6,7-dihydro-5H-5,7-methanobenzo[c]imidazo[1,2-a]azepine-3-carboxylic acid (0.1 g) was reacted with tetrahydro-2H-pyran-4-amine hydrochloride similarly to the conditions described in Example 2 to produce 10-bromo-N3-(tetrahydro-2H-pyran-4-yl)-6,7-dihydro-5H-5,7-methanobenzo[c]imidazo[1,2-a]azepine-2,3-dicarboxamide. This intermediate was then reacted with (2R)-2-(5-methylisoxazol-3-yl)but-3-yn-2-ol via General Procedure E to afford 5.7 mg (10%) of 10-[(3R)-3-hydroxy-3-(5-methylisoxazol-3-yl)but-1-ynyl]-N3-tetrahydropyran-4-yl-5,6,7,12-tetrahydro-5,7-methanobenzo[c]imidazo[1,2-a]azepine-2,3-dicarboxamide. M+1=516.

$^1$H NMR (400 MHz, DMSO-d6) δ 10.97 (d, J=7.1 Hz, 1H), 8.82 (s, 1H), 8.31 (s, 1H), 7.81 (s, 1H), 7.42-7.21 (m, 2H), 6.53 (s, 1H), 6.37 (s, 1H), 6.22-6.09 (m, 1H), 4.04-3.91 (m, 1H), 3.89-3.81 (m, 2H), 3.75-3.63 (m, 1H), 3.50-3.40 (m, 2H), 3.16-3.04 (m, 2H), 2.41 (s, 3H), 1.90-1.85 (m, 1H), 1.82 (s, 3H), 1.73-1.60 (m, 2H), 1.55-1.35 (m, 2H).

Example 410

Synthesis of 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6-dihydroimidazo[1,2-d][1,4]benzoxazepine-2-carboxamide

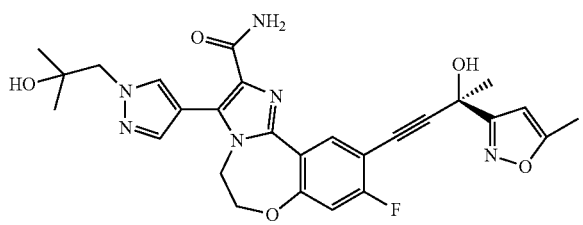 [SMILES: Cc1cc([C@](C)(O)C#Cc2cc3c(cc2F)OCCn2c-3nc(C(N)=O)c2-c2cnn(CC(C)(C)O)c2)no1]

10-bromo-9-fluoro-3-iodo-5,6-dihydrobenzo[f]imidazo[1,2-d][1,4]oxazepine-2-carboxamide was reacted with 2-methyl-1-[4-(4,4,5,5-tetramethyl-1,3,2-dioxaborolan-2-yl)pyrazol-1-yl]propan-2-ol similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[e]imidazo[1,2-a]azepine-2-carboxamide to produce crude 10-bromo-9-fluoro-3-(1-(2-hydroxy-2-methylpropyl)-1H-pyrazol-4-yl)-5,6-dihydrobenzo[f]imidazo[1,2-d][1,4]oxazepine-2-carboxamide. This intermediate was reacted with (2R)-2-(5-methylisoxazol-3-yl)but-3-yn-2-ol via General Procedure E to afford 25 mg (27%) of 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6-dihydroimidazo[1,2-d][1,4]benzoxazepine-2-carboxamide.

M+1=535; $^1$H NMR (400 MHz, DMSO-d6) δ 8.65 (d, J=8.4 Hz, 1H), 8.08 (s, 1H), 7.75 (s, 1H), 7.58 (s, 1H), 7.03 (d, J=10.5 Hz, 1H), 7.00 (s, 1H), 6.55 (s, 1H), 6.36 (s, 1H), 4.68 (s, 1H), 4.56-4.44 (m, 2H), 4.41-4.28 (m, 2H), 4.07 (s, 2H), 2.41 (s, 2H), 1.82 (s, 3H), 1.10 (s, 6H).

Example 411

Synthesis of 9-fluoro-10-(3-hydroxy-3-methyl-but-1-ynyl)-3-(pyrrolidin-1-ylmethyl)-5,6,7,12-tetrahydro-5,7-methanobenzo[c]imidazo[1,2-a]azepine-2-carboxamide

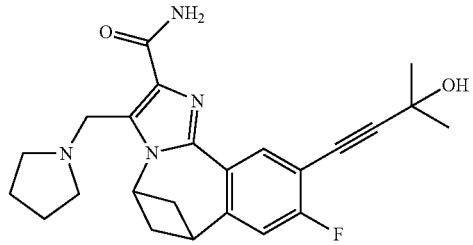 [SMILES: CC(C)(O)C#Cc1cc2c(cc1F)C1CC(C1)n1c-2nc(C(N)=O)c1CN1CCCC1]

10-bromo-9-fluoro-3-formyl-6,7-dihydro-5H-5,7-methanobenzo[c]imidazo[1,2-a]azepine-2-carboxamide (75 mg) was reacted with pyrrolidine similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 10-bromo-9-fluoro-3-(pyrrolidin-1-ylmethyl)-6,7-dihydro-5H-5,7-methanobenzo[c]imidazo[1,2-a]azepine-2-carboxamide which was directly reacted with 2-Methyl-3-butyne-ol via General Procedure E to afford 15 mg (17%) of 9-fluoro-10-(3-hydroxy-3-methyl-but-1-ynyl)-3-(pyrrolidin-1-ylmethyl)-5,6,7,12-tetrahydro-5,7-methanobenzo[c]imidazo[1,2-a]azepine-2-carboxamide. M+1=423.

$^1$H NMR (400 MHz, DMSO-d6) δ 8.69 (d, J=7.6 Hz, 1H), 7.64 (s, 1H), 7.25 (d, J=10.2 Hz, 1H), 7.03 (s, 1H), 5.53 (s, 1H), 5.11 (q, J=6.0 Hz, 1H), 4.07 (s, 2H), 3.66 (q, 1H), 3.20-3.02 (m, 2H), 2.48-2.38 (m, 4H), 1.72-1.57 (m, 6H), 1.50 (s, 6H).

Example 412

Synthesis of 9-fluoro-10-(3-hydroxy-3-methyl-but-1-ynyl)-3-[[isopropyl(methyl)amino]methyl]-5,6,7,12-tetrahydro-5,7-methanobenzo[c]imidazo azepine-2-carboxamide

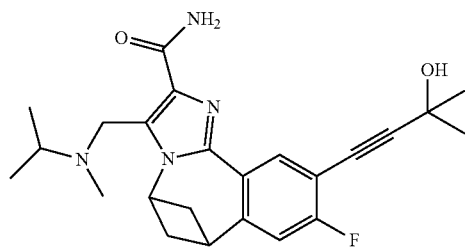 [SMILES: CC(C)N(C)Cc1c(C(N)=O)nc2n1C1CC(C1)c1cc(F)c(C#CC(C)(C)O)cc1-2]

10-bromo-9-fluoro-3-formyl-6,7-dihydro-5H-5,7-methanobenzo[c]imidazo[1,2-a]azepine-2-carboxamide (75 mg) was reacted with N-Isopropylmethylamine similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide afford 10-bromo-9-fluoro-3-((isopropyl(methyl)amino)methyl)-6,7-dihydro-5H-5,7-methanobenzo[c]imidazo[1,2-a]azepine-2-carboxamide which was directly reacted with 2-Methyl-3-butyne-ol via General Procedure E to afford 31 mg (35%) of 9-fluoro-10-(3-hydroxy-3-methyl-but-1-ynyl)-3-[[isopropyl(methyl)amino]methyl]-5,6,7,12-tetrahydro-5,7-methanobenzo[c]imidazo[1,2-a]azepine-2-carboxamide.

M+1=425; $^1$H NMR (400 MHz, DMSO-d6) δ 8.68 (d, J=7.6 Hz, 1H), 7.59 (s, 1H), 7.24 (d, J=10.1 Hz, 1H), 7.02 (s, 1H), 5.53 (s, 1H), 5.11 (q, J=6.2 Hz, 1H), 3.99 (s, 2H), 3.66 (q, J=8.5, 7.5 Hz, 1H), 3.16-3.04 (m, 2H), 2.73 (septet, J=6.5 Hz, 1H), 2.04 (s, 3H), 1.67-1.59 (m, 2H), 1.50 (s, 6H), 0.94 (d, J=6.6 Hz, 6H).

Example 413

Synthesis of 9-fluoro-10-(3-hydroxy-3-methyl-but-1-ynyl)-3-[(isopropylamino)methyl]-5,6,7,12-tetrahydro-5,7-methanobenzo[c]imidazo[1,2-a]azepine-2-carboxamide

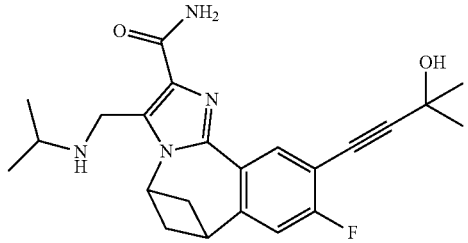 [SMILES: CC(C)NCc1c(C(N)=O)nc2n1C1CC(C1)c1cc(F)c(C#CC(C)(C)O)cc1-2]

10-bromo-9-fluoro-3-formyl-6,7-dihydro-5H-5,7-methanobenzo[c]imidazo[1,2-a]azepine-2-carboxamide (75 mg) was reacted with 2-aminopropane similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 10-bromo-9-fluoro-3-((isopropylamino)methyl)-6,7-dihydro-5H-5,7-methanobenzo[c]imidazo[1,2-a]azepine-2-carboxamide which was directly reacted with 2-Methyl-3-butyne-ol via General Procedure E to afford 34 mg (40%) of 9-fluoro-10-(3-hydroxy-3-methyl-but-1-ynyl)-3-[(isopropylamino)methyl]-5,6,7,12-tetrahydro-5,7-methanobenzo[c]imidazo[1,2-a]azepine-2-carboxamide. M+1=411.

$^1$H NMR (400 MHz, DMSO-d6) δ 8.69 (d, J=7.5 Hz, 1H), 7.60 (s, 1H), 7.24 (d, J=10.1 Hz, 1H), 7.05 (s, 1H), 5.53 (s, 1H), 5.10 (q, J=6.1 Hz, 1H), 4.08 (s, 2H), 3.73-3.59 (m, 1H), 3.18-3.03 (m, 3H), 2.70-2.55 (m, 1H), 1.73-1.59 (m, 2H), 1.50 (s, 5H), 0.96 (d, J=6.1 Hz, 6H).

Example 414

Synthesis of 3-[(4-acetylpiperazin-1-yl)methyl]-9-fluoro-10-(3-hydroxy-3-methyl-but-1-ynyl)-5,6,7,12-tetrahydro-5,7-methanobenzo[c]imidazo-1,2azepine-2-carboxamide

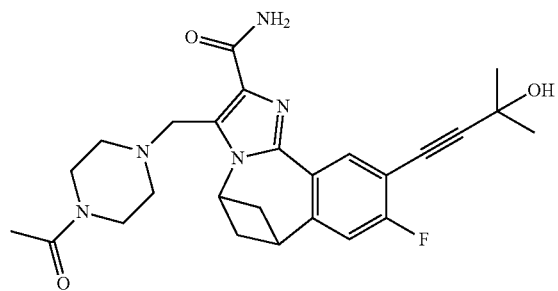 [SMILES: CC(=O)N1CCN(Cc2c(C(N)=O)nc3n2C2CC(C2)c2cc(F)c(C#CC(C)(C)O)cc2-3)CC1]

10-bromo-9-fluoro-3-formyl-6,7-dihydro-5H-5,7-methanobenzo[c]imidazo[1,2-a]azepine-2-carboxamide (75 mg) was reacted with N-acetylpiperazine similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 3-((4-acetylpiperazin-1-yl)methyl)-10-bromo-9-fluoro-6,7-dihydro-5H-5,7-methanobenzo[c]imidazo[1,2-a]azepine-2-carboxamide which was directly reacted with 2-Methyl-3-butyne-ol via General Procedure E to afford 41 mg (41%) of 3-[(4-acetylpiperazin-1-yl)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide. M+1=480.

¹H NMR (400 MHz, DMSO-d6) δ 8.69 (d, J=7.6 Hz, 1H), 7.61 (s, 1H), 7.25 (d, J=10.2 Hz, 1H), 7.07 (s, 1H), 5.53 (s, 1H), 5.10 (q, J=6.0 Hz, 1H), 4.00 (s, 2H), 3.70-3.63 (m, 1H), 3.38-3.30 (m, 4H), 3.10 (q, J=8.7 Hz, 2H), 2.38-2.28 (m, 4H), 1.95 (s, 3H), 1.70-1.62 (m, 2H), 1.50 (s, 6H).

Example 415

Synthesis of 9-fluoro-10-(3-hydroxy-3-methyl-but-1-ynyl)-3-[(2-methoxyethylamino)methyl]-5,6,7,12-tetrahydro-5,7-methanobenzo[c]imidazo[1,2-a]azepine-2-carboxamide

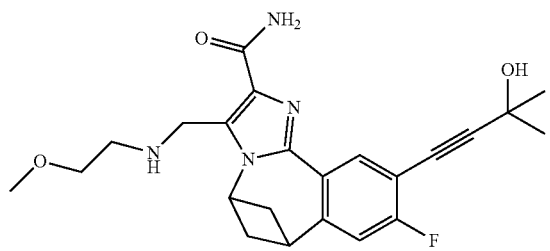 [SMILES: COCCNCc1c(C(N)=O)nc2n1C1CC(C1)c1cc(F)c(C#CC(C)(C)O)cc1-2]

10-bromo-9-fluoro-3-formyl-6,7-dihydro-5H-5,7-methanobenzo[c]imidazo[1,2-a]azepine-2-carboxamide (75 mg) was reacted with 2-methoxyethylamine similarly to as in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 10-bromo-9-fluoro-3-(((2-methoxyethyl)amino)methyl)-6,7-dihydro-5H-5,7-methanobenzo[c]imidazo[1,2-a]azepine-2-carboxamide which was directly reacted with 2-Methyl-3-butyne-ol via General Procedure E to afford 14 mg (16%) of 9-fluoro-10-(3-hydroxy-3-methyl-but-1-ynyl)-3-[(2-methoxyethylamino)methyl]-5,6,7,12-tetrahydro-5,7-methanobenzo[c]imidazo[1,2-a]azepine-2-carboxamide. M+1=427.

¹H NMR (400 MHz, DMSO-d6) δ 8.69 (d, J=7.6 Hz, 1H), 7.60 (s, 1H), 7.25 (d, J=10.2 Hz, 1H), 7.10-7.04 (m, 1H), 5.53 (s, 1H), 5.12-5.03 (m, 1H), 4.08 (s, 2H), 3.70-3.62 (m, 1H), 3.33 (t, J=5.6 Hz, 2H), 3.20 (s, 3H), 3.16-3.04 (m, 2H), 2.59 (t, J=5.6 Hz, 2H), 1.69-1.61 (m, 2H), 1.50 (s, 6H).

Example 416

Synthesis of 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide

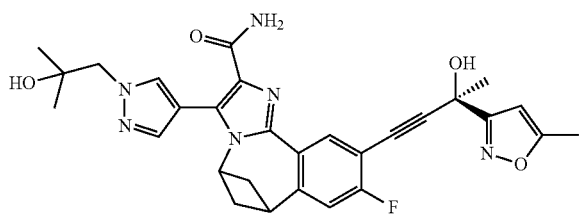 [SMILES: Cc1cc([C@](C)(O)C#Cc2cc3c(cc2F)C2CC(C2)n2c-3nc(C(N)=O)c2-c2cnn(CC(C)(C)O)c2)no1]

10-bromo-9-fluoro-3-iodo-6,7-dihydro-5H-5,7-methanobenzo[c]imidazo[1,2-a]azepine-2-carboxamide was reacted with 2-methyl-1-[4-(4,4,5,5-tetramethyl-1,3,2-dioxaborolan-2-yl)pyrazol-1-yl]propan-2-ol similarly to as described in Example 4 to produce crude 10-bromo-9-fluoro-3-(1-(2-hydroxy-2-methylpropyl)-1H-pyrazol-4-yl)-6,7-dihydro-5H-5,7-methanobenzo[c]imidazo[1,2-a]azepine-2-carboxamide. This intermediate was reacted with (2R)-2-(5-methylisoxazol-3-yl)but-3-yn-2-ol via General Procedure E to afford 11 mg (10%) of 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide. M+1=545; ¹H NMR (400 MHz, DMSO-d6) δ 8.77 (d, J=7.5 Hz, 1H), 7.90 (s, 1H), 7.55 (s, 1H), 7.53 (s, 1H), 7.29 (d, J=10.1 Hz, 1H), 6.97 (s, 1H), 6.58 (s, 1H), 6.37 (s, 1H), 4.85-4.76 (m, 1H), 4.68 (s, 1H), 4.07 (s, 2H), 3.15-3.05 (m, 2H), 2.42 (s, 3H), 1.83 (s, 3H), 1.77-1.68 (m, 2H), 1.10 (s, 6H).

Example 417

Synthesis of 3-[(cyclopropanecarbonylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

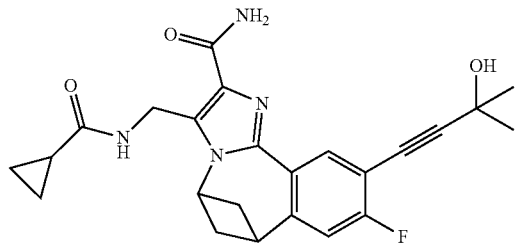 [SMILES: CC(C)(O)C#Cc1cc2c(cc1F)C1CC(C1)n1c-2nc(C(N)=O)c1CNC(=O)C1CC1]

10-bromo-9-fluoro-3-formyl-6,7-dihydro-5H-5,7-methanobenzo[c]imidazo[1,2-a]azepine-2-carboxamide (50 mg) was added into a saturated solution of ammonium acetate in Ethanol (2.7 mL) at which point sodium cyanoborohydride (3 eq) and 30% aqueous ammonia solution (1 mL) were added. The mixture was stirred at reflux for 1 hr, until reaction was deemed complete by LC-MS. The reaction was cooled to room temperature, concentrated to dryness and suspended in

669

Methanol. The slurry was loaded onto a biotage scx-2 cartridge, rinsed with Methanol and crude 3-(aminomethyl)-10-bromo-9-fluoro-6,7-dihydro-5H-5,7-methanobenzo[c]imidazo[1,2-a]azepine-2-carboxamide was then eluted with a 4N ammonia in methanol solution and concentrated to an orange oil. The crude intermediate was reacted with cyclopropane carboxylic acid similarly to as described in Example 2 to afford crude 10-bromo-3-(cyclopropanecarboxamidomethyl)-9-fluoro-6,7-dihydro-5H-5,7-methanobenzo[c]imidazo[1,2-a]azepine-2-carboxamide which was directly reacted with 2-Methyl-3-butyne-ol via General Procedure E to afford 12 mg (33%) of 3-[(cyclopropanecarbonylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide.

M+1=437; $^1$H NMR (400 MHz, DMSO-d6) δ 8.71 (d, J=7.6 Hz, 1H), 8.37 (t, J=5.3 Hz, 1H), 7.69 (s, 1H), 7.25 (d, J=10.2 Hz, 1H), 7.19 (s, 1H), 5.53 (s, 1H), 4.94-4.84 (m, 1H), 4.74 (d, J=5.2 Hz, 2H), 3.72-3.59 (m, 1H), 3.15-3.00 (m, 2H), 1.68-1.61 (m, 2H), 1.60-1.52 (m, 1H), 1.50 (s, 6H), 0.72-0.66 (m, 2H), 0.66-0.59 (m, 2H).

Example 418

Synthesis of 9-fluoro-10-(3-hydroxy-3-methyl-but-1-ynyl)-3-[[2-methoxyethyl(methyl)amino]methyl]-5,6,7,12-tetrahydro-5,7-methanobenzo[c]imidazo[1,2-a]azepine-2-carboxamide

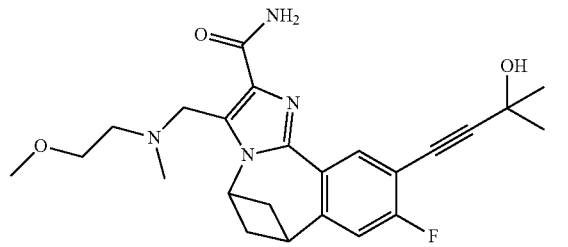 [SMILES: COCCN(C)Cc1c(C(N)=O)nc2n1C1CC(C1)c1cc(F)c(C#CC(C)(C)O)cc1-2]

10-bromo-9-fluoro-3-formyl-6,7-dihydro-5H-5,7-methanobenzo[c]imidazo[1,2-a]azepine-2-carboxamide (75 mg) was reacted with N-(methoxyethyl)methylamine similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 10-bromo-9-fluoro-3-(((2-methoxyethyl)(methyl)amino)methyl)-6,7-dihydro-5H-5,7-methanobenzo [c]imidazo[1,2-a]azepine-2-carboxamide which was directly reacted with 2-Methyl-3-butyne-ol via General Procedure E to afford 24 mg (26%) of 9-fluoro-10-(3-hydroxy-3-methyl-but-1-ynyl)-3-[[2-methoxyethyl(methyl)amino]methyl]-5,6,7,12-tetrahydro-5,7-methanobenzo[c]imidazo[1,2-a]azepine-2-carboxamide. M+1=441.

$^1$H NMR (400 MHz, DMSO-d6) δ 8.69 (d, J=7.7 Hz, 1H), 7.61 (s, 1H), 7.25 (d, J=10.1 Hz, 1H), 7.05 (s, 1H), 5.53 (s, 1H), 5.16-5.06 (m, 1H), 3.96 (s, 2H), 3.71-3.61 (m, 1H), 3.35 (t, J=5.9 Hz, 3H), 3.18 (s, 3H), 3.15-3.03 (m, 2H), 2.52-2.48 (m, 2H), 2.17 (s, 3H), 1.68-1.60 (m, 2H), 1.50 (s, 6H).

Example 419

Synthesis of (±)-9-fluoro-10-(3-hydroxy-3-methyl-but-1-ynyl)-3-[(3-hydroxypyrrolidin-1-yl)methyl]-5,6,7,12-tetrahydro-5,7-methanobenzo[c]imidazo[1,2-a]azepine-2-carboxamide

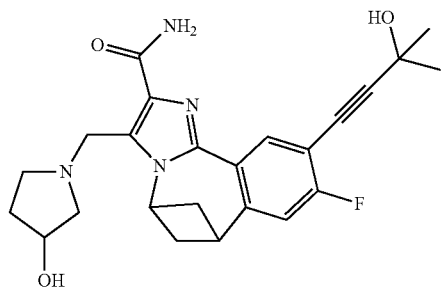 [SMILES: CC(C)(O)C#Cc1cc2c(cc1F)C1CC(C1)n1c-2nc(C(N)=O)c1CN1CCC(O)C1]

10-bromo-9-fluoro-3-formyl-6,7-dihydro-5H-5,7-methanobenzo[c]imidazo[1,2-a]azepine-2-carboxamide (75 mg) was reacted with DL-3-hydroxypyrrolidine similarly to as described in the synthesis of 9-fluoro-10-(3-hydroxy-3-methyl-but-1-ynyl)-3-[(4-methylpiperazin-1-yl)methyl]-5,6,7,12-tetrahydro-5,7-methanobenzo[c]imidazo[1,2-a]azepine-2-carboxamide to afford 10-bromo-9-fluoro-3((3-hydroxypyrrolidin-1-yl)methyl)-6,7-dihydro-5H-5,7-methanobenzo[c]imidazo[1,2-a]azepine-2-carboxamide which was directly reacted with 2-Methyl-3-butyne-ol via General Procedure E to afford 2.8 mg of (±)-9-fluoro-10-(3-hydroxy-3-methyl-but-1-ynyl)-3-[(3-hydroxypyrrolidin-1-yl)-methyl]-5,6,7,12-tetrahydro-5,7-methanobenzo[c]imidazo[1,2-a]azepine-2-carboxamide. M+1=439.

Example 420

Synthesis of 9-fluoro-10-[(3S)-3-hydroxy-3-(2-pyridyl)but-1-ynyl]-N3-methyl-5,6-dihydroimidazo[1,2-d][1,4]benzoxazepine-2,3-dicarboxamide

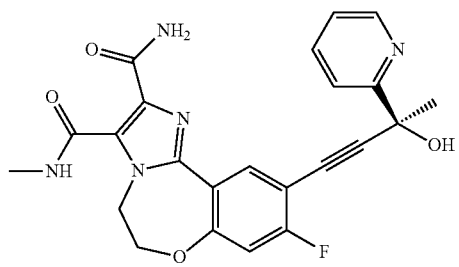 [SMILES: CNC(=O)c1c(C(N)=O)nc2n1CCOc1cc(F)c(C#C[C@](C)(O)c3ccccn3)cc1-2]

10-bromo-9-fluoro-N3-methyl-5,6-dihydroimidazo[1,2-d][1,4]benzoxazepine-2,3-dicarboxamide was reacted (2S)-2-(2-pyridyl)but-3-yn-2-ol via General Procedure E to afford 7.7 mg (9%) of 9-fluoro-10-[(3S)-3-hydroxy-3-(2-pyridyl)but-1-ynyl]-N3-methyl-5,6-dihydroimidazo[1,2-d][1,4]benzoxazepine-2,3-dicarboxamide. M+1=450.

$^1$H NMR (400 MHz, DMSO-d6) δ 11.08 (q, J=4.5 Hz, 1H), 8.60 (d, J=8.5 Hz, 1H), 8.58-8.53 (m, 1H), 8.38 (s, 1H), 7.85 (td, J=7.6, 1.8 Hz, 2H), 7.77 (d, J=8.0 Hz, 1H), 7.36-7.29 (m,

1H), 7.02 (d, J=10.6 Hz, 1H), 6.38 (s, 1H), 5.04-4.93 (m, 2H), 4.58-4.50 (m, 2H), 2.80 (d, J=4.5 Hz, 3H), 1.83 (s, 3H).

Example 421

Synthesis of 9-fluoro-10-[(3R)-3-hydroxy-3-(2-pyridyl)but-1-ynyl]-N3-methyl-5,6-dihydroimidazo[1,2-d][1,4]benzoxazepine-2,3-dicarboxamide

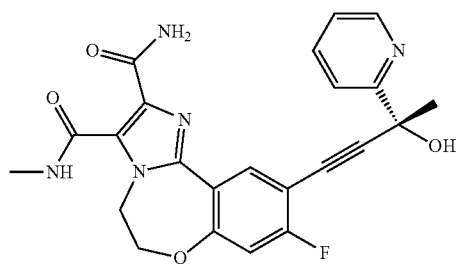 [SMILES: CNC(=O)c1c(C(N)=O)nc2n1CCOc1cc(F)c(C#C[C@@](C)(O)c3ccccn3)cc1-2]

10-bromo-9-fluoro-N3-methyl-5,6-dihydroimidazo[1,2-d][1,4]benzoxazepine-2,3-dicarboxamide was reacted (2R)-2-(2-pyridyl)but-3-yn-2-ol via General Procedure E to afford 8.9 mg (10%) of 9-fluoro-10-[(3R)-3-hydroxy-3-(2-pyridyl)but-1-ynyl]-N3-methyl-5,6-dihydroimidazo[1,2-d][1,4]benzoxazepine-2,3-dicarboxamide. M+1=450.

Example 422

Synthesis of 9-fluoro-10-(3-hydroxy-3-methyl-but-1-ynyl)-3-(1-hydroxy-1-methyl-ethyl)-5,6,7,12-tetrahydro-5,7-methanobenzo[c]imidazo[1,2-a]azepine-2-carboxamide

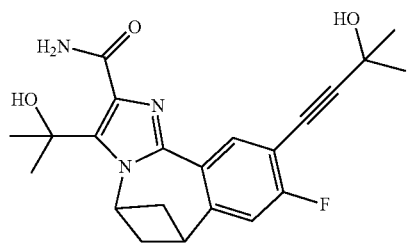 [SMILES: CC(C)(O)C#Cc1cc2c(cc1F)C1CC(C1)n1c-2nc(C(N)=O)c1C(C)(C)O]

Methyl 10-bromo-9-fluoro-6,7-dihydro-5H-5,7-methanobenzo[c]imidazo[1,2-a]azepine-2-carboxylate (0.3 g) was reacted with Acetone similar to as described in example 8 with non-critical modifications to produce methyl 10-bromo-9-fluoro-3-(2-hydroxypropan-2-yl)-6,7-dihydro-5H-5,7-methanobenzo[c]imidazo[1,2-a]azepine-2-carboxylate. This crude intermediate was reacted via General Procedure L to provide 10-bromo-9-fluoro-3-(2-hydroxypropan-2-yl)-6,7-dihydro-5H-5,7-methanobenzo[c]imidazo[1,2-a]azepine-2-carboxamide which was reacted as a crude with 2-Methyl-3-butyne-ol via General Procedure E to afford 23 mg (7%) of 9-fluoro-10-(3-hydroxy-3-methyl-but-1-ynyl)-3-(1-hydroxy-1-methyl-ethyl)-5,6,7,12-tetrahydro-5,7-methanobenzo[c]imidazo[1,2-a]azepine-2-carboxamide. M+1=398.
¹H NMR (400 MHz, DMSO-d6) δ 8.74 (d, J=7.6 Hz, 1H), 8.12 (s, 1H), 7.92 (s, 1H), 7.59 (s, 1H), 7.23 (d, J=10.1 Hz, 1H), 5.52 (s, 1H), 5.41-5.31 (m, 1H), 3.69-3.58 (m, 1H), 3.18-3.04 (m, 2H), 1.72-1.63 (m, 2H), 1.51 (d, J=10.6 Hz, 12H).

Example 423

Synthesis of 3-[(2-chlorophenyl)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

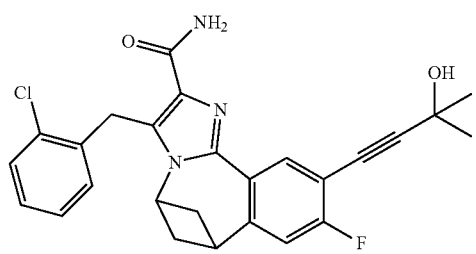 [SMILES: CC(C)(O)C#Cc1cc2c(cc1F)C1CC(C1)n1c-2nc(C(N)=O)c1Cc1ccccc1Cl]

Methyl 10-bromo-9-fluoro-6,7-dihydro-5H-5,7-methanobenzo[c]imidazo[1,2-a]azepine-2-carboxylate (0.3 g) was reacted with 2-Chlorobenzyl bromide similar to as described in example 8 with non-critical modifications to produce methyl 10-bromo-3-(2-chlorobenzyl)-9-fluoro-6,7-dihydro-5H-5,7-methanobenzo[c]imidazo[1,2-a]azepine-2-carboxylate. This crude intermediate was reacted via General Procedure L to provide 10-bromo-3-(2-chlorobenzyl)-9-fluoro-6,7-dihydro-5H-5,7-methanobenzo[c]imidazo[1,2-a]azepine-2-carboxamide which was reacted as a crude with 2-Methyl-3-butyne-ol via General Procedure E to afford 13 mg (3%) of 3-[(2-chlorophenyl)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide.
M+1=464; 1H NMR (400 MHz, DMSO-d6) δ 8.74 (d, J=7.6 Hz, 1H), 7.67 (s, 1H), 7.48 (dd, J=7.9, 1.3 Hz, 1H), 7.28-7.22 (m, 2H), 7.22-7.16 (m, 1H), 7.16-7.10 (m, 1H), 6.65 (dd, J=7.7, 1.7 Hz, 1H), 5.54 (s, 1H), 4.59 (s, 2H), 4.54-4.43 (m, 1H), 3.69-3.55 (m, 1H), 3.02-2.88 (m, 2H), 1.75-1.61 (m, 2H), 1.51 (s, 6H).

Example 424

Synthesis of 10-(3-hydroxy-3-methyl-but-1-ynyl)-N3-methyl-5,6,7,12-tetrahydro-5,7-methanobenzo[c]imidazo[1,2-a]azepine-2,3-dicarboxamide

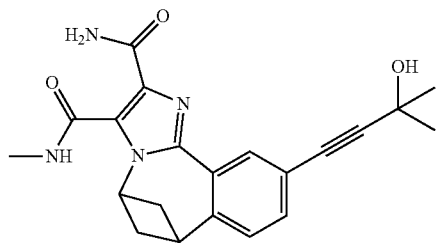 [SMILES: CNC(=O)c1c(C(N)=O)nc2n1C1CC(C1)c1ccc(C#CC(C)(C)O)cc1-2]

10-bromo-N3-methyl-6,7-dihydro-5H-5,7-methanobenzo[c]imidazo[1,2-a]azepine-2,3-dicarboxamide was reacted with 2-Methyl-3-butyne-ol via General Procedure E to afford 29 mg (48%) of 10-(3-hydroxy-3-methyl-but-1-ynyl)-N3- methyl-5,6,7,12-tetrahydro-5,7-methanobenzo[c]imidazo[1,2-a]azepine-2,3-dicarboxamide.

M+1=379; ¹H NMR (400 MHz, DMSO-d6) δ 10.53 (q, J=4.5 Hz, 1H), 8.78 (s, 1H), 8.22 (s, 1H), 7.73 (s, 1H), 7.31-7.26 (m, 2H), 6.10-6.03 (m, 1H), 5.45 (s, 1H), 3.70-3.62 (m, 1H), 3.17-3.05 (m, 2H), 2.78 (d, J=4.6 Hz, 3H), 1.73-1.58 (m, 2H), 1.50 (s, 6H).

Example 425

Synthesis of 10-[2-(1-hydroxycyclopentyl)ethynyl]-N3-methyl-5,6,7,12-tetrahydro-5,7-methanobenzo[c]imidazo[1,2-a]azepine-2,3-dicarboxamide

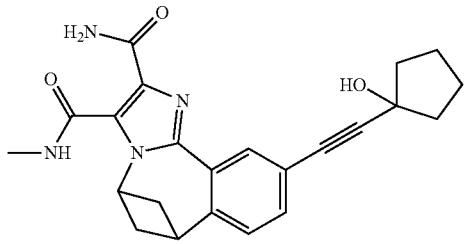 [SMILES: CNC(=O)c1c(C(N)=O)nc2n1C1CC(C1)c1ccc(C#CC3(O)CCCC3)cc1-2]

10-bromo-N3-methyl-6,7-dihydro-5H-5,7-methanobenzo[c]imidazo[1,2-a]azepine-2,3-dicarboxamide was reacted with 1-ethynylcyclopentanol via General Procedure E to afford 17 mg (26%) of 10-[2-(1-hydroxycyclopentyl)ethynyl]-N3-methyl-5,6,7,12-tetrahydro-5,7-methanobenzo[c]imidazo[1,2-a]azepine-2,3-dicarboxamide.

M+1=405; ¹H NMR (400 MHz, DMSO-d6) δ 10.53 (q, J=4.6 Hz, 1H), 8.78 (d, J=1.5 Hz, 1H), 8.22 (s, 1H), 7.73 (s, 1H), 7.34-7.24 (m, 2H), 6.12-6.03 (m, 1H), 5.31 (s, 1H), 3.72-3.59 (m, 1H), 3.17-3.02 (m, 2H), 2.78 (d, J=4.6 Hz, 3H), 2.06-1.56 (m, 9H).

Example 426

Synthesis of 10-bromo-9-fluoro-N3-methyl-6,7-dihydro-5H-5,7-methanobenzo[c]imidazo[1,2-a]azepine-2,3-dicarboxamide

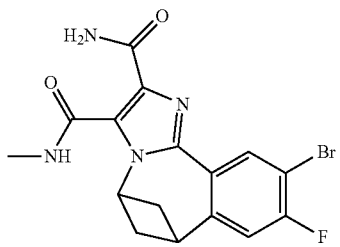 [SMILES: CNC(=O)c1c(C(N)=O)nc2n1C1CC(C1)c1cc(F)c(Br)cc1-2]

10-bromo-9-fluoro-3-iodo-6,7-dihydro-5H-5,7-methanobenzo[c]imidazo[1,2-a]azepine-2-carboxamide (2.5 g) was reacted similarly to the conditions described in example 6 to produce methyl 10-bromo-2-carbamoyl-6,7-dihydro-5H-5,7-methanobenzo[c]imidazo[1,2-a]azepine-3-carboxylate. This intermediate was then subjected to conditions in General Procedure N to afford 1.58 g of 10-bromo-2-carbamoyl-9-fluoro-6,7-dihydro-5H-5,7-methanobenzo[c]imidazo[1,2-a]azepine-3-carboxylic acid. This intermediate was then reacted with N-Methylamine Hydrochloride similarly to the conditions described in Example 2 to produce 500 mg of 10-bromo-9-fluoro-N3-methyl-6,7-dihydro-5H-5,7-methanobenzo[c]imidazo[1,2-a]azepine-2,3-dicarboxamide as a light yellow solid.

Example 427

Synthesis of 9-fluoro-10-(3-hydroxy-3-methyl-but-1-ynyl)-N3-methyl-5,6,7,12-tetrahydro-5,7-methanobenzo[c]imidazo[1,2-a]azepine-2,3-dicarboxamide

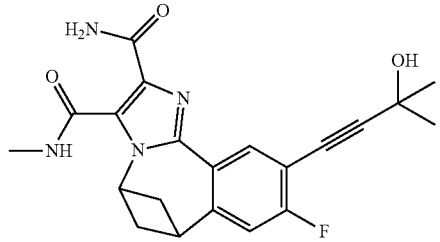 [SMILES: CNC(=O)c1c(C(N)=O)nc2n1C1CC(C1)c1cc(F)c(C#CC(C)(C)O)cc1-2]

10-bromo-9-fluoro-N3-methyl-6,7-dihydro-5H-5,7-methanobenzo[c]imidazo[1,2-a]azepine-2,3-dicarboxamide was reacted with 2-Methyl-3-butyne-ol via General Procedure E to afford 37 mg (37%) of 9-fluoro-10-(3-hydroxy-3-methyl-but-1-ynyl)-N3-methyl-5,6,7,12-tetrahydro-5,7-methanobenzo[c]imidazo[1,2-a]azepine-2,3-dicarboxamide. M+1=397.

¹H NMR (400 MHz, DMSO-d6) δ 10.60 (q, J=4.6 Hz, 1H), 8.83 (d, J=7.6 Hz, 1H), 8.28 (s, 1H), 7.74 (s, 1H), 7.29 (d, J=10.1 Hz, 1H), 6.17-6.04 (m, 1H), 5.53 (s, 1H), 3.74-3.59 (m, 1H), 3.22-3.03 (m, 2H), 2.78 (d, J=4.6 Hz, 3H), 1.75-1.62 (m, 2H), 1.51 (s, 6H).

Example 428

Synthesis of 10-bromo-3-iodo-6,7-dihydro-5H-5,7-methanobenzo[c]imidazo[1,2-a]azepine-2-carboxamide

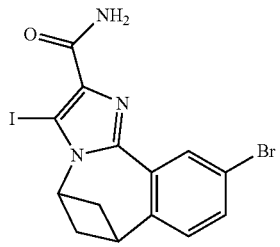 [SMILES: NC(=O)c1nc2n(c1I)C1CC(C1)c1ccc(Br)cc1-2]

10-bromo-9-fluoro-6,7-dihydro-5H-5,7-methanobenzo[c]imidazo[1,2-a]azepine-2-carboxamide (30 g) was reacted similarly to as described in for synthesis of 10-bromo-9-fluoro-3-iodo-6,7-dihydro-5H-5,7-methanobenzo[c]imidazo[1,2-a]azepine-2-carboxamide which afforded 29.6 g of 10-bromo-3-iodo-6,7-dihydro-5H-5,7-methanobenzo[c]imidazo[1,2-a]azepine-2-carboxamide as a dark orange solid.

Example 429

Synthesis of 10-[(3R)-3-hydroxy-3-(5-methylisoxazol-3-yl)but-1-ynyl]-3-[1-(2-hydroxy-2-methylpropyl)pyrazol-4-yl]-5,6,7,12-tetrahydro-5,7-methanobenzo[c]imidazo[1,2-a]azepine-2-carboxamide

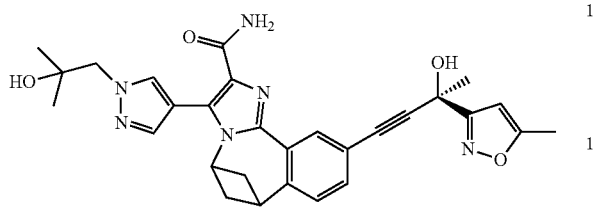

10-bromo-3-iodo-6,7-dihydro-5H-5,7-methanobenzo[c]imidazo[1,2-a]azepine-2-carboxamide was reacted with 2-methyl-1-[4-(4,4,5,5-tetramethyl-1,3,2-dioxaborolan-2-yl)pyrazol-1-yl]propan-2-ol similarly to as described in Example 4 to produce crude 10-bromo-3-(1-(2-hydroxy-2-methylpropyl)-1H-pyrazol-4-yl)-6,7-dihydro-5H-5,7-methanobenzo[c]imidazo[1,2-a]azepine-2-carboxamide. This intermediate was reacted with (2R)-2-(5-methylisoxazol-3-yl)but-3-yn-2-ol via General Procedure E to afford 39 mg (24%) of 10-[(3R)-3-hydroxy-3-(5-methylisoxazol-3-yl)but-1-ynyl]-3-[1-(2-hydroxy-2-methyl-propyl)pyrazol-4-yl]-5,6,7,12-tetrahydro-5,7-methanobenzo[c]imidazo[1,2-a]azepine-2-carboxamide. M+1=527.

1H NMR (400 MHz, DMSO-d6) δ 8.73 (s, 1H), 7.90 (s, 1H), 7.54 (s, 1H), 7.51 (s, 1H), 7.29 (s, 2H), 6.97 (s, 1H), 6.50 (s, 1H), 6.37 (s, 1H), 4.88-4.78 (m, 1H), 4.68 (s, 1H), 4.07 (s, 2H), 3.76-3.60 (m, 1H), 3.16-2.98 (m, 2H), 2.42 (s, 3H), 1.82 (s, 3H), 1.74-1.66 (m, 2H), 1.10 (s, 6H).

Example 430

Synthesis of 9-fluoro-10-[(3R)-3-hydroxy-3-(5-methyl-1,2,4-oxadiazol-3-yl)but-1-ynyl]-3-methyl-5,6,7,12-tetrahydro-5,7-methanobenzo[c]imidazo-1,2azepine-2-carboxamide

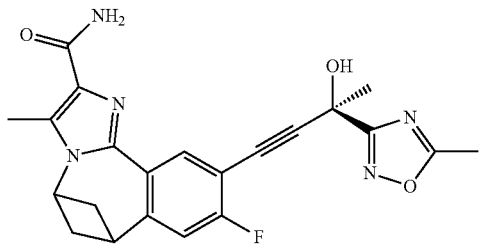

Methyl 10-bromo-9-fluoro-6,7-dihydro-5H-5,7-methanobenzo[c]imidazo[1,2-a]azepine-2-carboxylate (1 g) was reacted with iodomethane similar to as described in example 8 with non-critical modifications to produce methyl 10-bromo-9-fluoro-3-methyl-6,7-dihydro-5H-5,7-methanobenzo[c]imidazo[1,2-a]azepine-2-carboxylate. This crude intermediate (0.3 g) was reacted via General Procedure L to provide 10-bromo-9-fluoro-3-methyl-6,7-dihydro-5H-5,7-methanobenzo[c]imidazo[1,2-a]azepine-2-carboxamide. 144 mg of this crude intermediate was directly reacted with (2R)-2-(5-methyl-1,2,4-oxadiazol-3-yl)but-3-yn-2-ol via General Procedure E to afford 8.9 mg (5%) of 9-fluoro-10-[(3R)-3-hydroxy-3-(5-methyl-1,2,4-oxadiazol-3-yl)but-1-ynyl]-3-methyl-5,6,7,12-tetra hydro-5,7-methanobenzo[c]imidazo[1,2-a]azepine-2-carboxamide. M+1=422.

Example 431

Synthesis of 9-fluoro-10-[2-(1-hydroxycyclopentyl)ethynyl]-N3-methyl-5,6,7,12-tetrahydro-5,7-methanobenzo[c]imidazo[1,2-a]azepine-2,3-dicarboxamide

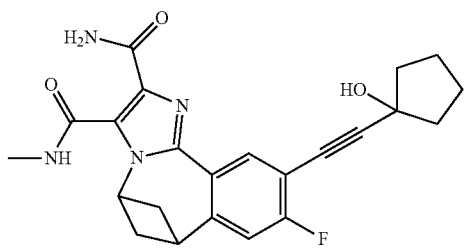 [SMILES: CNC(=O)c1c(C(N)=O)nc2n1C1CC(C1)c1cc(F)c(C#CC3(O)CCCC3)cc1-2]

10-bromo-9-fluoro-N3-methyl-6,7-dihydro-5H-5,7-methanobenzo[c]imidazo[1,2-a]azepine-2,3-dicarboxamide was reacted with 1-ethynylcyclopentanol via General Procedure E to afford 12 mg (11%) of 9-fluoro-10-[2-(1-hydroxycyclopentyl)ethynyl]-N3-methyl-5,6,7,12-tetrahydro-5,7-methanobenzo[c]imidazo[1,2-a]azepine-2,3-dicarboxamide. M+1=423.

1H NMR (400 MHz, DMSO-d6) δ 10.61 (q, J=4.5 Hz, 1H), 8.84 (d, J=7.6 Hz, 1H), 8.29 (s, 1H), 7.74 (s, 1H), 7.29 (d, J=10.0 Hz, 1H), 6.25-5.98 (m, 1H), 5.39 (s, 1H), 3.80-3.55 (m, 1H), 3.22-3.03 (m, 2H), 2.78 (d, J=4.5 Hz, 3H), 2.08-1.83 (m, 4H), 1.83-1.60 (m, 6H).

Example 432

Synthesis of 9-fluoro-10-[(3R)-3-hydroxy-3-(5-methylisoxazol-3-yl)but-1-ynyl]-3-methyl-5,6,7,12-tetrahydro-5,7-methanobenzo[c]imidazo[1,2-a]azepine-2-carboxamide

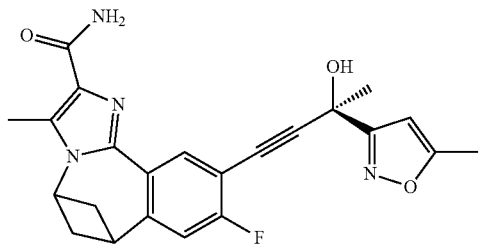

10-bromo-9-fluoro-3-methyl-5H-5,7methanobenzo[c]imidazo[1,2-a]azepine-2-carboxamide (144 mg) was reacted with (2R)-2-(5-methylisoxazol-3-yl)but-3-yn-2-ol via General Procedure E to afford 28 mg (16%) of 9-fluoro-10-[(3R)-3-hydroxy-3-(5-methylisoxazol-3-yl)but-1-ynyl]-3-methyl-5,6,7,12-tetrahydro-5,7-methanobenzo[c]imidazo[1,2-a]azepine-2-carboxamide. M+1=421.

¹H NMR (400 MHz, DMSO-d6) δ 8.68 (d, J=7.5 Hz, 1H), 7.49 (s, 1H), 7.25 (d, J=10.1 Hz, 1H), 6.98 (s, 1H), 6.56 (s, 1H), 6.35 (s, 1H), 4.93-4.77 (m, 1H), 3.75-3.62 (m, 1H), 3.18-3.05 (m, 2H), 2.52 (s, 4H), 2.41 (s, 2H), 1.82 (s, 3H), 1.78-1.63 (m, 2H).

Example 433

Synthesis of 9-[2-[(3R)-3-hydroxy-1-methyl-2-oxo-pyrrolidin-3-yl]ethynyl]-4,5-dihydro-[1]benzoxepino[5,4-d]thiazole-2-carboxamide

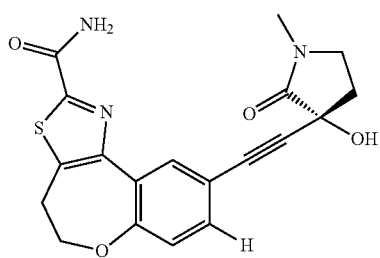

Methyl 9-bromo-4,5-dihydrobenzo[2,3]oxepino[4,5-d]thiazole-2-carboxylate was reacted with (3R)-3-ethynyl-3-hydroxy-1-methyl-pyrrolidin-2-one via General Procedure F followed by General Procedure M to afford 87 mg (43%) of 9-[2-[(3R)-3-hydroxy-1-methyl-2-oxo-pyrrolidin-3-yl]ethynyl]-4,5-dihydro-[1]benzoxepino[5,4-d]thiazole-2-carboxamide. M+1=384.

1H NMR (400 MHz, DMSO-d6) δ 8.63-8.58 (m, 1H), 8.40 (s, 1H), 7.84 (s, 1H), 7.30 (dd, J=8.3, 2.2 Hz, 1H), 7.07-7.02 (m, 1H), 6.37 (s, 1H), 4.39-4.32 (m, 2H), 3.45-3.39 (m, 2H), 3.38-3.32 (m, 2H), 180 (s, 3H), 2.48-2.40 (m, 1H), 2.24-2.14 (m, 1H).

Example 434

Synthesis of methyl 10-bromo-3-iodo-6,7-dihydro-5H-5,7-methanobenzo[c]imidazo[1,2-a]azepine-2-carboxylate

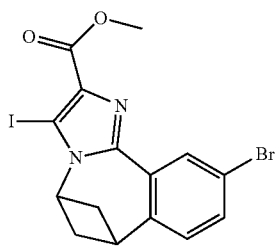 [SMILES: COC(=O)c1nc2n(c1I)C1CC(C1)c1ccc(Br)cc1-2]

Methyl 10-bromo-6,7-dihydro-5H-5,7-methanobenzo[c]imidazo[1,2-a]azepine-2-carboxylate (5 g) was subjected to General Procedure K (C—H halogenation) to afford 5 g of methyl 10-bromo-3-iodo-6,7-dihydro-5H-5,7-methanobenzo[c]imidazo[1,2-a]azepine-2-carboxylate as a yellow solid.

1H NMR (400 MHz, DMSO) δ 8.64 (s, 1H), 7.47 (d, J=8.0 Hz, 1H), 7.26 (d, J=8.1 Hz, 1H), 5.18 (dd, J=10.5, 6.5 Hz, 1H), 3.81 (s, 3H), 3.72-3.64 (m, 1H), 3.22-3.12 (m, 2H), 1.75-1.67 (m, 2H).

Example 435

Synthesis of methyl 10-bromo-9-fluoro-3-iodo-6,7-dihydro-5H-5,7-methanobenzo[c]imidazo[1,2-a]azepine-2-carboxylate

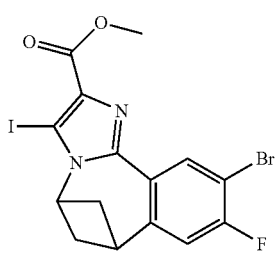 [SMILES: COC(=O)c1nc2n(c1I)C1CC(C1)c1cc(F)c(Br)cc1-2]

Methyl 10-bromo-9-fluoro-6,7-dihydro-5H-5,7-methanobenzo[c]imidazo[1,2-a]azepine-2-carboxylate (1 g) was subjected to General Procedure K (C—H halogenation) to afford 1.23 g of methyl 10-bromo-9-fluoro-3-iodo-6,7-dihydro-5H-5,7-methanobenzo[c]imidazo[1,2-a]azepine-2-carboxylate as a greenish brown solid.

Example 436

Synthesis of methyl 10-bromo-9-fluoro-3-dodo-5,6-dihydrobenzo[f]imidazo[1,2-d][1,4]oxazepine-2-carboxylate

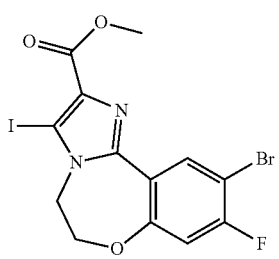 [SMILES: COC(=O)c1nc2n(c1I)CCOc1cc(F)c(Br)cc1-2]

Methyl 10-bromo-9-fluoro-5,6-dihydrobenzo[f]imidazo[1,2-d][1,4]oxazepine-2-carboxylate (1 g) was subjected to General Procedure K (C—H halogenation) to afford 1.37 g of methyl 10-bromo-9-fluoro-3-iodo-5,6-dihydrobenzo[f]imidazo[1,2-d][1,4]oxazepine-2-carboxylate as a dark brown solid.

Example 437

Synthesis of 10-[(3S)-3-hydroxy-3-(2-pyridyl)but-1-ynyl]-N3-methyl-5,6-dihydroimidazo[1,2-d][1,4]benzoxazepine-2,3-dicarboxamide

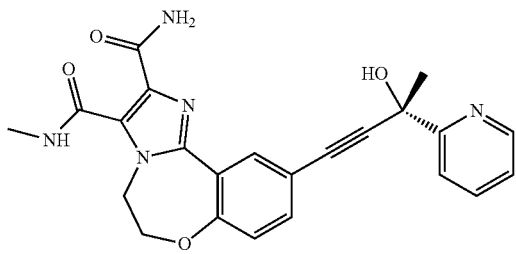 [SMILES: CNC(=O)c1c(C(N)=O)nc2n1CCOc1ccc(C#C[C@](C)(O)c3ccccn3)cc1-2]

10-bromo-N3-methyl-5,6-dihydrobenzo[f]imidazo[1,2-d][1,4]oxazepine-2,3-dicarboxamide was reacted with (2R)-2-(2-pyridyl)but-3-yn-2-ol via General Procedure G to afford 3.4 mg (6.1%) of 10-[(3S)-3-hydroxy-3-(2-pyridyl)but-1-ynyl]-N3-methyl-5,6-dihydroimidazo[1,2-d][1,4]benzoxazepine-2,3-dicarboxamide. M+1=432.0

Example 437.1

Synthesis of 10-[(3R)-3-hydroxy-3-(2-pyridyl)but-1-ynyl]-N3-methyl-5,6,7,12-tetrahydro-5,7-methanobenzo[c]imidazo[1,2-a]azepine-2,3-dicarboxamide

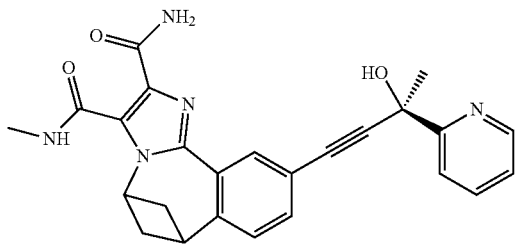 [SMILES: CNC(=O)c1c(C(N)=O)nc2n1C1CC(C1)c1ccc(C#C[C@@](C)(O)c3ccccn3)cc1-2]

10-bromo-N3-methyl-6,7-dihydro-5H-5,7-methanobenzo[c]imidazo[1,2-a]azepine-2,3-dicarboxamide was reacted with (2R)-2-(2-pyridyl)but-3-yn-2-ol via General Procedure G to afford 15 mg (19.0%) of 10-[(3R)-3-hydroxy-3-(2-pyridyl)but-1-ynyl]-N3-methyl-5,6,7,12-tetrahydro-5,7-methanobenzo[c]imidazo[1,2-a]azepine-2,3-dicarboxamide following reverse phase purification.

M+1=442.0; 1H NMR (400 MHz, DMSO-d6) δ 10.50 (q, J=4.6 Hz, 1H), 8.77 (d, J=1.5 Hz, 1H), 8.60-8.52 (m, 1H), 8.21 (s, 1H), 7.89-7.82 (m, 2H), 7.78 (d, J=7.9 Hz, 1H), 7.71 (s, 1H), 7.36-7.26 (m, 3H), 6.34 (s, 1H), 6.11-5.98 (m, 1H), 3.71-3.60 (m, 1H), 3.16-3.03 (m, 2H), 2.78 (d, J=4.5 Hz, 3H), 1.83 (s, 3H), 1.70-1.60 (m, 2H).

Example 438

Synthesis of 9-fluoro-10-[(3R)-3-hydroxy-3-(3-methylisoxazol-5-yl)but-1-ynyl]-5,6,7,12-tetrahydro-5,7-methanobenzo[c]imidazo[1,2-a]azepine-2-carboxamide

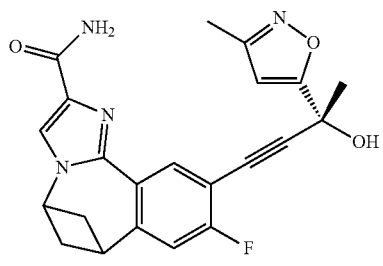 [SMILES: Cc1cc([C@](C)(O)C#Cc2cc3c(cc2F)C2CC(C2)n2cc(C(N)=O)nc2-3)on1]

10-bromo-9-fluoro-6,7-dihydro-5H-5,7-methanobenzo[c]imidazo[1,2-a]azepine-2-carboxamide was reacted with (2R)-2-(3-methylisoxazol-5-yl)but-3-yn-2-ol via General Procedure G to afford 102 mg (56.4%) of 9-fluoro-10-[(3R)-3-hydroxy-3-(3-methylisoxazol-5-yl)but-1-ynyl]-5,6,7,12-tetrahydro-5,7-methanobenzo[c]imidazo[1,2-a]azepine-2-carboxamide following reverse phase purification.

M+1=407.0; 1H NMR (400 MHz, DMSO-d6) δ 8.69 (d, J=7.5 Hz, 1H), 7.82 (s, 1H), 7.55 (s, 1H), 7.32 (d, J=10.2 Hz, 1H), 7.09 (s, 1H), 6.80 (s, 1H), 6.38 (s, 1H), 4.97-4.84 (m, 1H), 3.78-3.68 (m, 1H), 3.17-3.03 (m, 2H), 2.25 (s, 3H), 1.83 (s, 3H), 1.71-1.64 (m, 2H).

Example 439

Synthesis of 9-fluoro-10-[(3R)-3-hydroxy-3-(5-methyl-1,2,4-oxadiazol-3-yl)but-1-ynyl]-3-(3-methyl-1H-pyrazol-5-yl)-5,6-dihydroimidazo[1,2-d][1,4]benzoxazepine-2-carboxamide

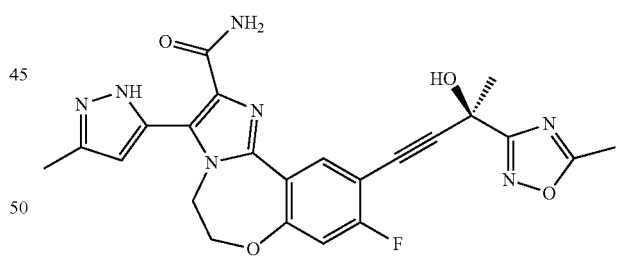

10-bromo-9-fluoro-3-iodo-5,6-dihydrobenzo[f]imidazo[1,2-d][1,4]oxazepine-2-carboxamide was reacted with (2-tert-butoxycarbonyl-5-methyl-pyrazol-3-yl)boronic acid similarly to as described in Example 4 to produce crude 10-bromo-9-fluoro-3-(3-methyl-1H-pyrazol-5-yl)-5,6dihydrobenzo[f]imidazo[1,2-d][1,4]oxazepine-2-carboxamide. 10-bromo-9-fluoro-3-(3-methyl-1H-pyrazol-5-yl)-5,6dihydrobenzo[f]imidazo[1,2-d][1,4]oxazepine-2-carboxamide was reacted with (2R)-2-(5-methyl-1,2,4-oxadiazol-3-yl)but-3-yn-2-ol via General Procedure E to afford 5.8 mg (6.6%) 9-fluoro-10-[(3R)-3-hydroxy-3-(5-methyl-1,2,4-oxadiazol-3-yl)but-1-ynyl]-3-(3-methyl-1H-pyrazol-5-yl)-5,6-dihydroimidazo[1,2-d][1,4]benzoxazepine-2-carboxamide following reverse phase purification. M+1=478.

Example 440

Synthesis of 3-(1-(2-hydroxy-2-methylpropyl)-1H-pyrazol-4-yl)-10-((1-hydroxycyclopentyl)ethynyl)-6,7-dihydro-5H-5,7-methanobenzo[c]imidazo[1,2-a]azepine-2-carboxamide

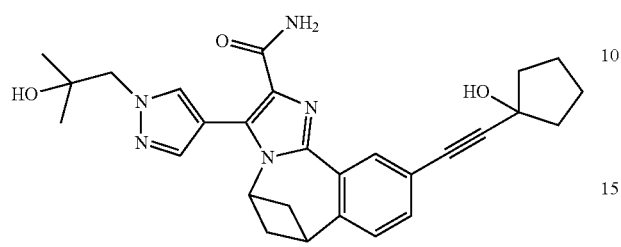

10-bromo-3-iodo-6,7-dihydro-5H-5,7-methanobenzo[c]imidazo[1,2-a]azepine-2-carboxamide was reacted with 2-methyl-1-[4-(4,4,5,5-tetramethyl-1,3,2-dioxaborolan-2-yl)pyrazol-1-yl]propan-2-ol similarly to as described in Example 4 to produce crude 10-bromo-3-(1-(2-hydroxy-2-methylpropyl)-1H-pyrazol-4-yl)-6,7-dihydro-5H-5,7-methanobenzo[c]imidazo[1,2-a]azepine-2-carboxamide.

10-bromo-3-(1-(2-hydroxy-2-methylpropyl)-1H-pyrazol-4-yl)-6,7-dihydro-5H-5,7 methanobenzo[c]imidazo[1,2-a]azepine-2-carboxamide was reacted with 1-ethynylcyclopentanol via General Procedure E to afford 20 mg (14.5%) of 3-(1-(2-hydroxy-2-methylpropyl)-1H-pyrazol-4-yl)-10-((1-hydroxycyclopentyl)ethynyl)-6,7-dihydro-5H-5,7-methanobenzo[c]imidazo[1,2-a]azepine-2-carboxamide following reverse phase purification. M+1=486.

1H NMR (400 MHz, DMSO-d6) δ 8.71 (s, 1H), 7.90 (s, 1H), 7.54 (s, 1H), 7.51 (s, 1H), 7.26 (s, 2H), 6.97 (s, 1H), 5.31 (s, 1H), 4.87-4.77 (m, 1H), 4.68 (s, 1H), 4.07 (s, 2H), 3.73-3.63 (m, 1H), 3.13-3.02 (m, 2H), 2.00-1.85 (m, 4H), 1.81-1.65 (m, 6H), 1.10 (s, 6H).

Example 441

Synthesis of 9-fluoro-10-[(3S)-3-hydroxy-3-(3-methylisoxazol-5-yl)but-1-ynyl]-5,6,7,12-tetrahydro-5,7-methanobenzo[c]imidazo[1,2-a]azepine-2-carboxamide

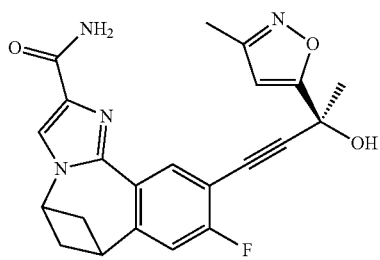 [SMILES: Cc1cc([C@@](C)(O)C#Cc2cc3c(cc2F)C2CC(C2)n2cc(C(N)=O)nc2-3)on1]

10-bromo-9-fluoro-6,7-dihydro-5H-5,7-methanobenzo[c]imidazo[1,2-a]azepine-2-carboxamide was reacted with (2S)-2-(3-methylisoxazol-5-yl)but-3-yn-2-ol via General Procedure G to afford 93 mg (51.4%) of 9-fluoro-10-[(3S)-3-hydroxy-3-(3-methylisoxazol-5-yl)but-1-ynyl]-5,6,7,12-tetrahydro-5,7-methanobenzo[c]imidazo[1,2-a]azepine-2-carboxamide following reverse phase purification. M+1=407.0

Example 442

Synthesis of 10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide and 10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide

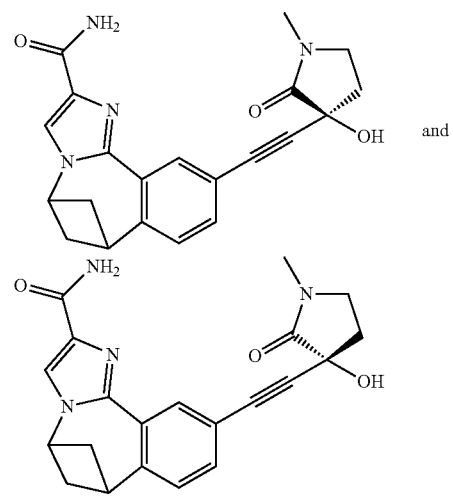

10-bromo-6,7-dihydro-5H-5,7-methanobenzo[c]imidazo[1,2-a]azepine-2-carboxamide was reacted with 3-ethynyl-3-hydroxy-1-methylpyrrolidin-2-one as described in General Procedure G without making critical modifications to afford 114 mg and 146 mg (55% overall yield) following reverse phase purification and chiral separation.

M+1=377.0; 1H NMR (400 MHz, DMSO-d6) δ 8.65 (s, 1H), 7.83 (s, 1H), 7.52 (s, 1H), 7.33-7.24 (coincident m, 2H), 7.08 (s, 1H), 6.44 (s, 1H), 4.97-4.88 (m, 1H), 3.77-3.67 (m, 1H), 3.41-3.33 (m, J=3.2 Hz, 5H), 3.14-3.02 (m, 2H), 2.81 (s, 3H), 2.50-2.39 (m, 1H), 2.26-2.14 (m, 1H), 1.70-1.62 (m, 2H).

Example 443

Synthesis of 9-fluoro-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide and 9-fluoro-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide

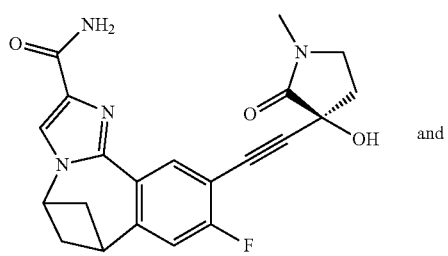

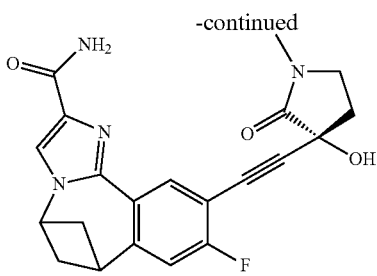

10-bromo-9-fluoro-6,7-dihydro-5H-5,7-methanobenzo[c]imidazo[1,2-a]azepine-2-carboxamide was reacted with 3-ethynyl-3-hydroxy-1-methylpyrrolidin-2-one as described in General Procedure G without making critical modifications to afford 146 mg and 144 mg (61% overall yield) following reverse phase purification and chiral separation.

M+1=395.0; 1H NMR (400 MHz, DMSO-d6) δ 8.68 (d, J=7.5 Hz, 1H), 7.82 (s, 1H), 7.55 (s, 1H), 7.30 (d, J=10.1 Hz, 1H), 7.08 (s, 1H), 6.53 (s, 1H), 4.99-4.80 (m, 1H), 3.79-3.64 (m, 1H), 3.42-332 (m, 2H), 3.19-103 (m, 2H), 2.81 (s, 3H), 2.49-2.41 (m, 1H), 2.28-2.16 (m, 1H), 1.75-1.62 (m, 2H).

Example 444

Synthesis of 9-fluoro-3-(formamidomethyl)-10-(3-hydroxy-3-methyl-but-1-ynyl)-5,6,7,12-tetrahydro-5,7-methanobenzo[c]imidazo[1,2-a]azepine-2-carboxamide

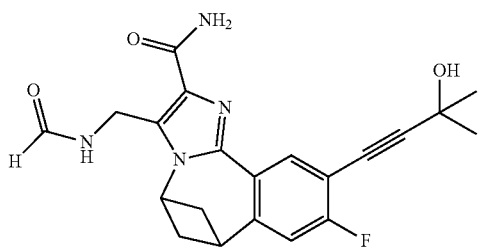 [SMILES: CC(C)(O)C#Cc1cc2c(cc1F)C1CC(C1)n1c-2nc(C(N)=O)c1CNC=O]

3-(aminomethyl)-10-bromo-9-fluoro-6,7-dihydro-5H-5,7-methanobenzo[c]imidazo[1,2-a]azepine-2-carboxamide was suspended in N,N-Dimethylformamide overnight to form crude 10-bromo-9-fluoro-3-(formamidomethyl)-6,7-dihydro-5H-5,7-methanobenzo[c]imidazo[1,2-a]azepine-2-carboxamide following extractive workup.

10-bromo-9-fluoro-3-(formamidomethyl)-6,7-dihydro-5H-5,7-methanobenzo[c]imidazo[1,2-a]azepine-2-carboxamide was reacted with 2-Methyl-3-butyne-ol via General Procedure E to afford 6.4 mg (3.2%) of 9-fluoro-3-(formamidomethyl)-10-(3-hydroxy-3-methyl-but-1-ynyl)-5,6,7,12-tetrahydro-5,7-methanobenzo[c]imidazo[1,2-a]azepine-2-carboxamide.

M+1=397.0; 1H NMR (400 MHz, DMSO-d6) δ 8.71 (d, J=7.5 Hz, 1H), 8.42-8.32 (m, 1H), 7.98 (s, 1H), 7.68 (s, 1H), 7.26 (d, J=10.2 Hz, 1H), 7.20 (s, 1H), 5.53 (s, 1H), 4.98-4.90 (m, 1H), 4.74 (d, J=5.5 Hz, 2H), 3.71-3.63 (m, 1H), 3.15-3.03 (m, 2H), 1.68-1.60 (m, 2H), 1.50 (s, 6H).

Example 445

Synthesis of 9-fluoro-10-[(3R)-3-hydroxy-3-pyrimidin-2-yl-but-1-ynyl]-3-methyl-5,6,7,12-tetrahydro-5,7-methanobenzo[c]imidazo[1,2-a]azepine-2-carboxamide

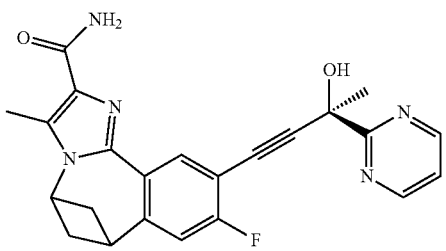 [SMILES: Cc1c(C(N)=O)nc2n1C1CC(C1)c1cc(F)c(C#C[C@@](C)(O)c3ncccn3)cc1-2]

10-bromo-9-fluoro-3-methyl-6,7-dihydro-5H-5,7methanobenzo[c]imidazo[1,2-a]azepine-2-carboxamide (144 mg) was reacted with (2R)-2-pyrimidin-2-ylbut-3-yn-2-ol via General Procedure F to afford 18 mg (19%) 9-fluoro-10-[(3R)-3-hydroxy-3-pyrimidin-2-yl-but-1-ynyl]-3-methyl-5,6,7,12-tetrahydro-5,7-methanobenzo[c]imidazo[1,2-a]azepine-2-carboxamide. M+1=418.0.

1H NMR (400 MHz, DMSO-d6) δ 8.89 (d, J=4.8 Hz, 2H), 8.65 (d, J=7.5 Hz, 1H), 7.51 (d, J=4.9 Hz, 1H), 7.48 (s, 1H), 7.23 (d, J=10.1 Hz, 1H), 6.96 (s, 1H), 6.23 (s, 1H), 4.89-4.78 (m, 1H), 3.73-3.61 (m, 1H), 3.17-3.02 (m, 1H), 2.52 (s, 3H), 1.89 (s, 3H), 1.73-1.63 (m, 2H).

Example 446

Synthesis of 9-fluoro-3-(1-hydroxycyclobutyl)-10-(3-hydroxy-3-methyl-but-1-ynyl)-5,6,7,12-tetrahydro-5,7-methanobenzo[c]imidazo[1,2-a]azepine-2-carboxamide

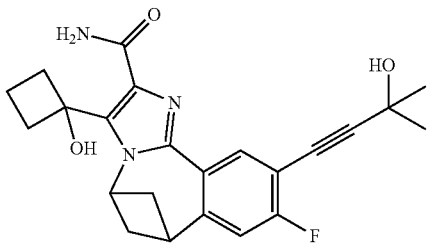 [SMILES: CC(C)(O)C#Cc1cc2c(cc1F)C1CC(C1)n1c-2nc(C(N)=O)c1C1(O)CCC1]

Methyl 10-bromo-9-fluoro-6,7-dihydro-5H-5,7-methanobenzo[c]imidazo[1,2-a]azepine-2-carboxylate (0.3 g) was reacted with cyclobutanone similar to as described in example 8 with non-critical modifications to produce methyl 10-bromo-9-fluoro-3-(1-hydroxycyclobutyl)-6,7-dihydro-5H-5,7-methanobenzo[c]imidazo[1,2-a]azepine-2-carboxylate. This crude intermediate was reacted via General Procedure L to provide 10-bromo-9-fluoro-3-(1-hydroxycyclobutyl)-6,7-dihydro-5H-5,7-methanobenzo[c]imidazo[1,2-a]azepine-2-carboxamide which was reacted as a crude with 2-Methyl-3-butyne-ol via General Procedure F to afford 5.2 mg (5.1%) of 9-fluoro-3-(1-hydroxycyclobutyl)-

10-(3-hydroxy-3-methyl-but-1-ynyl)-5,6,7,12-tetrahydro-5,7-methanobenzo[c]imidazo[1,2-a]azepine-2-carboxamide.
M+1=410.2.
1H NMR (400 MHz, DMSO-d6) δ 8.67 (d, J=7.7 Hz, 1H), 7.59 (s, 1H), 7.24 (d, J=10.1 Hz, 1H), 7.13 (s, 1H), 5.78 (s, 1H), 5.53 (s, 1H), 5.09-5.00 (m, 1H), 3.68-3.60 (m, 1H), 3.15-3.03 (m, 2H), 2.70-2.57 (m, 2H), 2.38-2.27 (m, 2H), 2.03-1.90 (m, 1H), 1.70-1.63 (m, 2H), 1.63-1.55 (m, 1H), 1.50 (s, 6H).

Example 447

Synthesis of 9-fluoro-10-[2-(1-hydroxycyclopentyl)ethynyl]-3-(1-hydroxy-1-methyl-ethyl)-5,6,7,12-tetrahydro-5,7-methanobenzo[c]imidazo[1,2-a]azepine-2-carboxamide

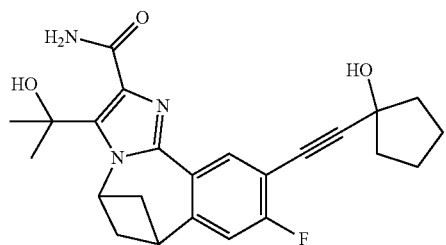 [SMILES: CC(C)(O)c1c(C(N)=O)nc2n1C1CC(C1)c1cc(F)c(C#CC3(O)CCCC3)cc1-2]

10-bromo-9-fluoro-3-(2-hydroxypropan-2-yl)-6,7-dihydro-5H-5,7-methanobenzo[c]imidazo[1,2-a]azepine-2-carboxamide was reacted with 1-ethynylcyclopentanol via General Procedure E to afford 8.9 mg (8.3%) of 9-fluoro-10-[2-(1-hydroxycyclopentyl)ethynyl]-3-(1-hydroxy-1-methyl-ethyl)-5,6,7,12-tetrahydro-5,7-methanobenzo[c]imidazo[1,2-a]azepine-2-carboxamide.
M+1=424.0; 1H NMR (400 MHz, DMSO-d6) δ 8.75 (d, J=7.6 Hz, 1H), 8.13 (s, 1H), 7.94 (s, 1H), 7.59 (s, 1H), 7.23 (d, J=10.0 Hz, 1H), 5.38 (s, 1H), 5.37-5.32 (m, 1H), 3.67-3.59 (m, 1H), 3.18-3.07 (m, 2H), 2.00-1.87 (m, 4H), 1.82-1.64 (m, 7H), 1.53 (s, 6H).

Example 448

Synthesis of 9-fluoro-3-(1-hydroxy-1-methyl-ethyl)-10-[2-[(3S)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide and 9-fluoro-3-(1-hydroxy-1-methyl-ethyl)-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide

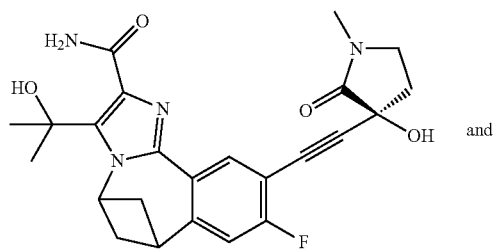 and

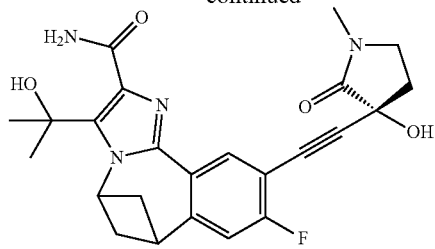

10-bromo-9-fluoro-3-(2-hydroxypropan-2-yl)-6,7-dihydro-5H-5,7-methanobenzo[c]imidazo[1,2-a]azepine-2-carboxamide was reacted with 3-ethynyl-3-hydroxy-1-methyl-pyrrolidin-2-one via General Procedure F to afford 16.3 and 17.4 mg (29.4% overall yield) following reverse phase purification and chiral separation.
M+1=453; 1H NMR (400 MHz, DMSO-d6) δ 8.77 (d, J=7.5 Hz, 1H), 8.14-8.08 (m, 1H), 7.89 (s, 1H), 7.58 (s, 1H), 7.26 (d, J=10.0 Hz, 1H), 6.51 (s, 1H), 5.41-5.32 (m, 1H), 3.69-3.60 (m, 1H), 3.42-3.29 (m, 2H), 3.18-3.06 (m, 2H), 2.81 (s, 3H), 2.50-2.40 (m, 1H), 2.27-2.16 (m, 1H), 1.73-1.65 (m, 2H), 1.53 (s, 6H).

Example 449

Synthesis of 9-fluoro-3-(1-hydroxy-1-methyl-ethyl)-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide

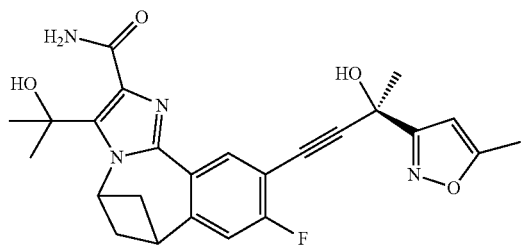 [SMILES: Cc1cc([C@](C)(O)C#Cc2cc3c(cc2F)C2CC(C2)n2c-3nc(C(N)=O)c2C(C)(C)O)no1]

10-bromo-9-fluoro-3-(2-hydroxypropan-2-yl)-6,7-dihydro-5H-5,7-methanobenzo[c]imidazo[1,2-a]azepine-2-carboxamide was reacted with (2R)-2-(5-methylisoxazol-3-yl)but-3-yn-2-ol via General Procedure E to afford 55 mg (47%) of 9-fluoro-3-(1-hydroxy-1-methyl-ethyl)-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide.
M+1=465.2; 1H NMR (400 MHz, DMSO-d6) δ 8.76 (d, J=7.5 Hz, 1H), 8.12 (s, 1H), 7.88 (s, 1H), 7.58 (s, 1H), 7.26 (d, J=10.0 Hz, 1H), 6.56 (s, 1H), 6.35 (s, 1H), 5.43-5.30 (m, 1H), 3.71-3.58 (m, 1H), 3.20-3.06 (m, 2H), 2.41 (s, 3H), 1.83 (s, 3H), 1.74-1.64 (m, 2H), 1.53 (s, 6H).

Example 450

Synthesis of 9-fluoro-10-[2-[(3S)-3-hydroxy-1-methyl-2-oxo-pyrrolidin-3-yl]ethynyl]-3-methyl-5,6,7,12-tetrahydro-5,7-methanobenzo [c]imidazo[1,2-a]azepine-2-carboxamide and 9-fluoro-10-[2-[(3R)-3-hydroxy-1-methyl-2-oxo-pyrrolidin-3-yl]ethynyl]-3-methyl-5,6,7,12-tetrahydro-5,7-methanobenzo[c]imidazo[1,2-a]azepine-2-carboxamide

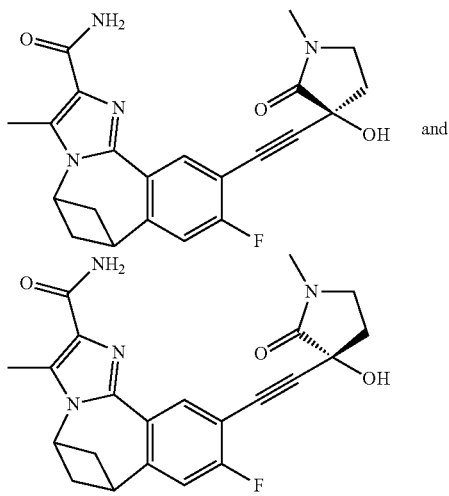

10-bromo-9-fluoro-3-methyl-6,7-dihydro-5H-5,7methanobenzo[c]imidazo[1,2-a]azepine-2-carboxamide (144 mg) was reacted with 3-ethynyl-3-hydroxy-1-methyl-pyrrolidin-2-one via General Procedure F to afford 20 mg and 17 mg (26% overall yield) following reverse phase purification and chiral separation.

M+1=409; $^1$H NMR (400 MHz, DMSO-d6) δ 8.69 (d, J=7.5 Hz, 1H), 7.49 (s, 1H), 7.26 (d, J=10.1 Hz, 1H), 6.98 (s, 1H), 6.51 (s, 1H), 4.89-4.80 (m, 1H), 3.72-3.63 (m, 1H), 3.40-3.33 (m, 2H), 3.15-3.06 (m, 2H), 2.81 (s, 3H), 2.52 (s, 3H), 2.46-2.40 (m, 1H), 2.26-2.17 (m, 1H), 1.73-1.65 (m, 2H).

Example 451

Synthesis of 9-fluoro-10-(3-hydroxy-3-methyl-but-1-ynyl)-3-(3-hydroxyoxetan-3-yl)-5,6,7,12-tetrahydro-5,7-methanobenzo[c]imidazo[1,2-a]azepine-2-carboxamide

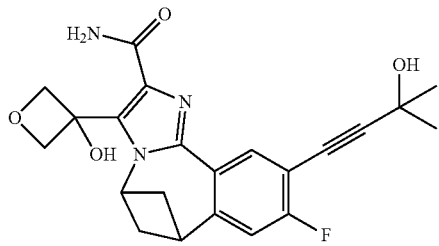 [SMILES: CC(C)(O)C#Cc1cc2c(cc1F)C1CC(C1)n1c-2nc(C(N)=O)c1C1(O)COC1]

Methyl 10-bromo-9-fluoro-6,7-dihydro-5H-5,7-methanobenzo[c]imidazo[1,2-a]azepine-2-carboxylate (0.3 g) was reacted with oxetan-3-one similar to as described in example 8 with non-critical modifications to produce methyl 10-bromo-9-fluoro-3-(3-hydroxyoxetan-3-yl)-6,7-dihydro-5H-5,7-methanobenzo[c]imidazo[1,2-a]azepine-2-carboxylate. This crude intermediate was reacted via General Procedure L to provide 10-bromo-9-fluoro-3-(3-hydroxyoxetan-3-yl)-6,7-dihydro-5H-5,7-methanobenzo[c]imidazo[1,2-a]azepine-2-carboxamide which was reacted as a crude with 2-Methyl-3-butyne-ol via General Procedure F to afford 23 mg (51.1%) 9-fluoro-10-(3-hydroxy-3-methyl-but-1-ynyl)-3-(3-hydroxyoxetan-3-yl)-5,6,7,12-tetrahydro-5,7-methanobenzo[c]imidazo[1,2-a]azepine-2-carboxamide.

M+1=412; $^1$H NMR (400 MHz, DMSO-d6) δ 8.71 (d, J=7.6 Hz, 1H), 7.71 (s, 1H), 7.25 (d, J=10.1 Hz, 1H), 7.15 (s, 1H), 6.55 (s, 1H), 5.53 (s, 1H), 4.92 (d, J=7.4 Hz, 2H), 4.66 (d, J=7.4 Hz, 2H), 4.41-4.31 (m, 1H), 3.72-3.61 (m, 1H), 3.15-3.02 (m, 2H), 1.76-1.66 (m, 2H), 1.50 (s, 6H).

Example 452

Synthesis of 3-[1-(cyclopropanecarbonyl)-3-hydroxy-azetidin-3-yl]-9-fluoro-10-(3-hydroxy-3-methyl-but-1-ynyl)-5,6,7,12-tetrahydro-5,7-methanobenzo[c]imidazo[1,2-a]azepine-2-carboxamide

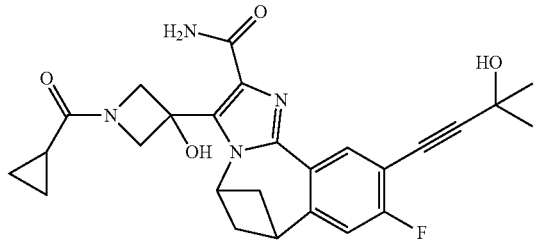 [SMILES: CC(C)(O)C#Cc1cc2c(cc1F)C1CC(C1)n1c-2nc(C(N)=O)c1C1(O)CN(C(=O)C2CC2)C1]

Methyl 10-bromo-9-fluoro-6,7-dihydro-5H-5,7-methanobenzo[c]imidazo[1,2-a]azepine-2-carboxylate (0.3 g) was reacted with tert-butyl 3-oxoazetidine-1-carboxylate similar to as described in example 8 with non-critical modifications to produce methyl 10-bromo-3-(1-(tert-butoxycarbonyl)-3-hydroxyazetidin-3-yl)-9-fluoro-6,7-dihydro-5H-5,7-methanobenzo[c]imidazo[1,2-a]azepine-2-carboxylate. This crude intermediate was reacted via General Procedure L then deprotected with 4N HCl in dioxane (5 eq) at room temperature to provide 10-bromo-9-fluoro-3-(3-hydroxyazetidin-3-yl)-6,7-dihydro-5H-5,7-methanobenzo[c]imidazo[1,2-a]azepine-2-carboxamide. 10-bromo-9-fluoro-3-(3-hydroxyazetidin-3-yl)-6,7-dihydro-5H-5,7-methanobenzo[c]imidazo[1,2-a]azepine-2-carboxamide was reacted with cyclopropane carboxylic acid similar to as described in Example 2 with non-critical modifications to afford crude 10-bromo-3-(1-(cyclopropanecarbonyl)-3-hydroxyazetidin-3-yl)-9-fluoro-6,7-dihydro-5H-5,7-methanobenzo[c]imidazo[1,2-a]azepine-2-carboxamide which was then reacted with 2-Methyl-3-butyne-ol via General Procedure F to afford 7.9 mg (71.8%) 3-[1-(cyclopropanecarbonyl)-3-hydroxy-azetidin-3-yl]-9-fluoro-10-(3-hydroxy-3-methyl-but-1-ynyl)-5,6,7,12-tetrahydro-5,7-methanobenzo[c]imidazo[1,2-a]azepine-2-carboxamide.

M+1=479; $^1$H NMR (400 MHz, DMSO-d6) δ 8.72 (d, J=7.6 Hz, 1H), 7.76 (s, 1H), 7.26 (d, J=10.1 Hz, 1H), 7.21 (s, 1H), 6.67 (s, 1H), 5.53 (s, 1H), 4.74 (d, J=9.8 Hz, 1H), 4.69-4.62 (m, 1H), 4.43 (d, J=9.7 Hz, 1H), 4.27 (d, J=10.8 Hz,

1H), 4.06 (d, J=10.8 Hz, 1H), 3.72-3.60 (m, 1H), 3.19-3.07 (m, 2H), 1.78-1.68 (m, 2H), 1.50 (s, 6H), 0.74-0.58 (m, 4H).

Example 453

Synthesis of 3-[(cyclobutanecarbonylamino)methyl]-9-fluoro-10-(3-hydroxy-3-methyl-but-1-ynyl)-5,6,7,12-tetra hydro-5,7-methanobenzo[c]imidazo[1,2-a]azepine-2-carboxamide

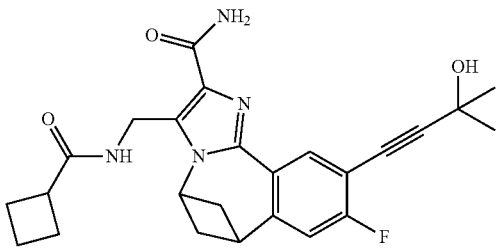 [SMILES: CC(C)(O)C#Cc1cc2c(cc1F)C1CC(C1)n1c-2nc(C(N)=O)c1CNC(=O)C1CCC1]

3-(Aminomethyl)-10-bromo-9-fluoro-6,7-dihydro-5H-5,7-methanobenzo[c]imidazo[1,2-a]azepine-2-carboxamide was reacted with cyclobutanecarboxylic acid similar to as described in example 2 with non-critical modifications to afford crude 10-bromo-3-(cyclobutanecarboxamidomethyl)-9-fluoro-6,7-dihydro-5H-5,7-methanobenzo[c]imidazo[1,2-a]azepine-2-carboxamide which was directly reacted with 2-methyl-3-butyne-ol via General Procedure F to afford 12 mg (29.3%) of 3-[(cyclobutanecarbonylamino)methyl]-9-fluoro-10-(3-hydroxy-3-methyl-but-1-ynyl)-5,6,7,12-tetra hydro-5,7-methanobenzo[c]imidazo[1,2-a]azepine-2-carboxamide.

M+1=451; $^1$H NMR (400 MHz, DMSO-d6) δ 8.70 (d, J=7.6 Hz, 1H), 8.00 (t, J=5.3 Hz, 1H), 7.67 (s, 1H), 7.24 (d, J=10.1 Hz, 1H), 7.17 (s, 1H), 5.53 (s, 1H), 4.89-4.81 (m, 1H), 4.74 (d, J=5.3 Hz, 2H), 3.70-3.61 (m, 1H), 3.12-3.02 (m, 2H), 3.01-2.92 (m, 1H), 2.16-2.06 (m, 2H), 2.01-1.92 (m, 2H), 1.88-1.70 (m, 2H), 1.66-1.58 (m, 2H), 1.50 (s, 6H).

Example 454

Synthesis of 10-[2-(1-hydroxycyclobutyl)ethynyl]-N3-methyl-5,6,7,12-tetrahydro-5,7-methanobenzo[c]imidazo[1,2-a]azepine-2,3-dicarboxamide

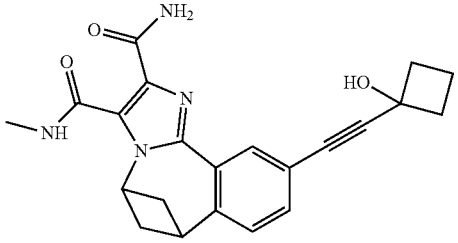 [SMILES: CNC(=O)c1c(C(N)=O)nc2n1C1CC(C1)c1ccc(C#CC3(O)CCC3)cc1-2]

10-bromo-N3-methyl-6,7-dihydro-5H-5,7-methanobenzo[c]imidazo[1,2-a]azepine-2,3-dicarboxamide was reacted with 1-ethynylcyclobutanol via General Procedure F to afford 48 mg (58%) of 10-[2-(1-hydroxycyclobutyl)ethynyl]-N3-methyl-5,6,7,12-tetrahydro-5,7-methanobenzo[c]imidazo[1,2-a]azepine-2,3-dicarboxamide following reverse phase purification. M+1=391.2; $^1$H NMR (400 MHz, DMSO-d6) δ 10.56 (q, J=4.7 Hz, 1H), 8.82 (d, J=1.7 Hz, 1H), 8.24 (s, 1H), 7.73 (s, 1H), 7.36-7.27 (m, 2H), 6.12-6.05 (m, 1H), 5.87 (s, 1H), 3.71-3.63 (m, 1H), 3.16-3.05 (m, 2H), 2.78 (d, J=4.6 Hz, 3H), 2.46-2.37 (m, 2H), 2.29-2.18 (m, 2H), 1.86-1.76 (m, 2H), 1.71-1.61 (m, 2H).

Example 455

Synthesis of 9-fluoro-10-[2-(1-hydroxycyclobutyl)ethynyl]-N3-methyl-5,6-dihydroimidazo[1,2-d][1,4]benzoxazepine-2,3-dicarboxamide

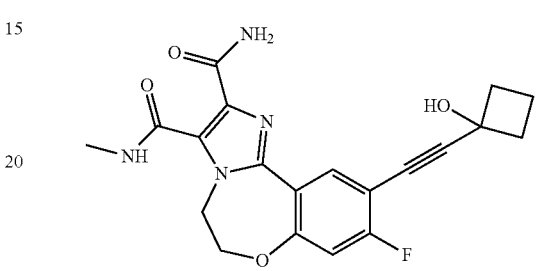

10-bromo-9-fluoro-N3-methyl-5,6-dihydrobenzo [f]imidazo[1,2-d][1,4]oxazepine-2,3-dicarboxamide was reacted with 1-ethynylcyclobutanol via General Procedure F to afford 26 mg (25%) of 9-fluoro-10-[2-(1-hydroxycyclobutyl)ethynyl]-N3-methyl-5,6-dihydroimidazo[1,2-d][1,4]benzoxazepine-2,3-dicarboxamide.

M+1=399; $^1$H NMR (400 MHz, DMSO-d6) δ 11.11 (q, J=4.6 Hz, 1H), 8.66 (d, J=8.4 Hz, 1H), 8.40 (s, 1H), 7.88 (s, 1H), 7.03 (d, J=10.5 Hz, 1H), 5.92 (s, 1H), 5.03-4.96 (m, 2H), 4.58-4.51 (m, 2H), 2.81 (d, J=4.5 Hz, 3H), 2.46-2.35 (m, 2H), 2.30-2.17 (m, 2H), 1.88-1.73 (m, 2H).

Example 456

Synthesis of 3-[(cyclopropanecarbonylamino)methyl]-9-fluoro-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide

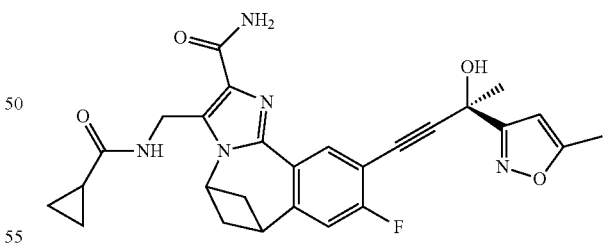

10-bromo-3-(cyclopropanecarboxamidomethyl)-9-fluoro-6,7-dihydro-5H-5,7-methanobenzo[c]imidazo[1,2-a]azepine-2-carboxamide was reacted with (2R)-2-(5-methylisoxazol-3-yl)but-3-yn-2-ol via General Procedure F to afford 7.7 mg (16.4%) of 3-[(cyclopropanecarbonylamino)methyl]-9-fluoro-10-[(3R)-3-hydroxy-3-(5-methylisoxazol-3-yl)but-1-ynyl]-5,6,7,12-tetrahydro-5,7-methanobenzo[c]imidazo[1,2-a]azepine-2-carboxamide.

M+1=504; $^1$H NMR (400 MHz, DMSO-d6) δ 8.73 (d, J=7.6 Hz, 1H), 8.37 (t, J=5.3 Hz, 1H), 4.93-4.85 (m, 1H), 4.74 (d, J=5.2 Hz, 2H), 3.71-3.64 (m, 1H), 3.13-3.01 (m, 2H), 2.41

(s, 3H), 1.83 (s, 2H), 1.68-1.61 (m, 2H), 1.60-1.53 (m, 1H), 0.72-0.66 (m, 2H), 0.65-0.58 (m, 2H).

Example 457

Synthesis of 9-fluoro-10-[2-(1-hydroxycyclobutyl)ethynyl]-5,6,7,12-tetrahydro-5,7-methanobenzo[c]imidazo[1,2-a]azepine-2-carboxamide

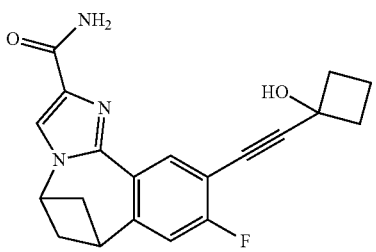 [SMILES: NC(=O)c1cn2c(n1)-c1cc(C#CC3(O)CCC3)c(F)cc1C1CC2C1]

10-bromo-9-fluoro-6,7-dihydro-5H-5,7-methanobenzo[c]imidazo[1,2-a]azepine-2-carboxamide was reacted with 1-ethynylcyclobutanol as described in General Procedure F without making critical modifications to afford 13 mg (12.4%) of 9-fluoro-10-[2-(1-hydroxycyclobutyl)ethynyl]-5,6,7,12-tetrahydro-5,7-methanobenzo[c]imidazo[1,2-a]azepine-2-carboxamide. M+1=352.2.

$^1$H NMR (400 MHz, DMSO-d6) δ 8.68 (d, J=7.6 Hz, 1H), 7.81 (s, 1H), 7.55 (s, 1H), 7.28 (d, J=10.2 Hz, 1H), 7.09 (s, 1H), 5.96 (s, 1H), 4.96-4.87 (m, 1H), 3.77-3.67 (m, 1H), 3.15-3.04 (m, 2H), 2.46-2.35 (m, 2H), 2.31-2.19 (m, 2H), 1.86-1.75 (m, 2H), 1.69 (d, J=11.6 Hz, 2H).

Example 458

Synthesis of 3-[(2,2-dimethylpropanoylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

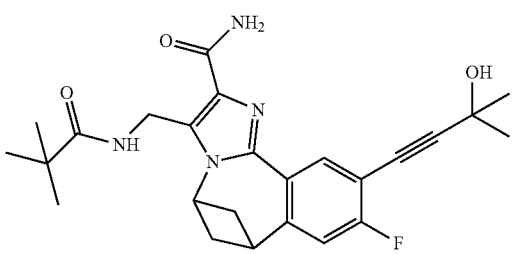 [SMILES: CC(C)(O)C#Cc1cc2c(cc1F)C1CC(C1)n1c-2nc(C(N)=O)c1CNC(=O)C(C)(C)C]

3-(aminomethyl)-10-bromo-9-fluoro-6,7-dihydro-5H-5,7-methanobenzo[c]imidazo[1,2-a]azepine-2-carboxamide was reacted with pivalic acid similarly to as described in Example 2 with non-critical modifications to afford crude 10-bromo-9-fluoro-3-(pivalamidomethyl)-6,7-dihydro-5H-5,7-methanobenzo[c]imidazo[1,2-a]azepine-2-carboxamide which was reacted directly with 2-methyl-3-butyne-ol via General Procedure F to afford 15 mg (37%) of 3-[(2,2-dimethylpropanoylamino)methyl]-9-fluoro-10-(3-hydroxy-3-methyl-but-1-ynyl)-5,6,7,12-tetrahydro-5,7-methanobenzo[c]imidazo[1,2-a]azepine-2-carboxamide. M+1=453.3.

1H NMR (400 MHz, DMSO-d6) δ 8.70 (d, J=7.6 Hz, 1H), 7.89 (t, J=5.2 Hz, 1H), 7.70 (s, 1H), 7.24 (d, J=10.1 Hz, 1H), 7.19 (s, 1H), 5.53 (s, 1H), 4.83-4.66 (m, 3H), 3.72-3.56 (m, 1H), 3.11-2.98 (m, 2H), 1.71-1.59 (m, 2H), 1.50 (s, 6H), 1.07 (s, 9H).

Example 459

Synthesis of 9-fluoro-3-[[(1-hydroxycyclopropanecarbonyl)amino]methyl]-10-(3-hydroxy-3-methyl-but-1-ynyl)-5,6,7,12-tetrahydro-5,7-methanobenzo[c]imidazo[1,2-a]azepine-2-carboxamide

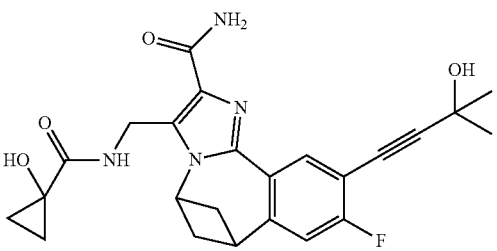 [SMILES: CC(C)(O)C#Cc1cc2c(cc1F)C1CC(C1)n1c-2nc(C(N)=O)c1CNC(=O)C1(O)CC1]

3-(aminomethyl)-10-bromo-9-fluoro-6,7-dihydro-5H-5,7-methanobenzo[c]imidazo[1,2-a]azepine-2-carboxamide was reacted with 1-hydroxy-1-cyclopropane carboxylic acid similarly to as described in example 2 with non-critical modifications to afford crude 10-bromo-9-fluoro-3-((1-hydroxycyclopropanecarboxamido)methyl)-6,7-dihydro-5H-5,7-methanobenzo[c]imidazo[1,2-a]azepine-2-carboxamide which was reacted directly with 2-methyl-3-butyne-ol via General Procedure F to afford 13 mg (32%) of 9-fluoro-3-[[(1-hydroxycyclopropanecarbonyl)amino]methyl]-10-(3-hydroxy-3-methyl-but-1-ynyl)-5,6,7,12-tetrahydro-5,7-methanobenzo[c]imidazo[1,2-a]azepine-2-carboxamide. M+1=453.2.

$^1$H NMR (400 MHz, DMSO-d6) δ 8.71 (d, J=7.6 Hz, 1H), 8.04 (t, J=6.0 Hz, 1H), 7.72 (s, 1H), 7.25 (d, J=10.3 Hz, 2H), 6.22 (s, 1H), 5.53 (s, 1H), 5.13-5.04 (m, 1H), 4.66 (d, J=6.0 Hz, 2H), 3.72-3.60 (m, 1H), 3.16-3.01 (m, 2H), 1.70-1.59 (m, 2H), 1.50 (s, 6H), 1.06-0.96 (m, 2H), 0.87-0.76 (m, 2H).

Example 460

Synthesis of 3-[[(2,2-difluorocyclopropanecarbonyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

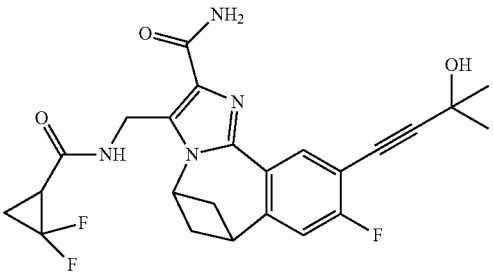 [SMILES: CC(C)(O)C#Cc1cc2c(cc1F)C1CC(C1)n1c-2nc(C(N)=O)c1CNC(=O)C1CC1(F)F]

3-(aminomethyl)-10-bromo-9-fluoro-6,7-dihydro-5H-5,7-methanobenzo[c]imidazo[1,2-a]azepine-2-carboxamide was reacted with 2,2-difluorocyclopropanecarboxylic acid similarly to as described in example 2 with non-critical modifications to afford crude 10-bromo-3-((2,2-difluorocyclopropanecarboxamido)methyl)-9-fluoro-6,7-dihydro-5H-5,7-methanobenzo[c]imidazo[1,2-a]azepine-2-carboxamide which was reacted directly with 2-methyl-3-butyne-ol via General Procedure F to afford 14 mg (33%) of 3-[[(2,2-difluorocyclopropanecarbonyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide M+1=473.2.

1H NMR (400 MHz, DMSO-d6) δ 8.71 (d, J=7.6 Hz, 1H), 8.65 (t, J=5.3 Hz, 1H), 7.70 (s, 1H), 7.25 (d, J=10.1 Hz, 1H), 7.22 (s, 1H), 5.53 (s, 1H), 4.92-4.85 (m, 1H), 4.80 (t, J=5.0 Hz, 2H), 3.70-3.61 (m, 1H), 3.13-2.97 (m, 2H), 2.63-2.55 (m, 1H), 1.97-1.88 (m, 1H), 1.87-1.77 (m, 1H), 1.69-1.58 (m, 2H), 1.50 (s, 6H).

Example 461

Synthesis of 9-fluoro-10-[2-(1-hydroxycyclobutyl)ethynyl]-N3-methyl-5,6,7,12-tetrahydro-5,7-methanobenzo[c]imidazo[1,2-a]azepine-2,3-dicarboxamide

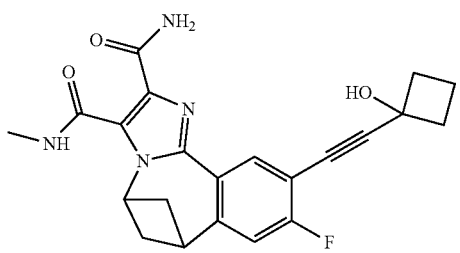 [SMILES: CNC(=O)c1c(C(N)=O)nc2n1C1CC(C1)c1cc(F)c(C#CC3(O)CCC3)cc1-2]

10-bromo-9-fluoro-N3-methyl-6,7-dihydro-5H-5,7-methanobenzo[e]imidazo[1,2-a]azepine-2,3-dicarboxamide was reacted with 1-ethynylcyclobutanol as described in General Procedure F without making critical modifications to afford 19.2 mg (24.6%) of 9-fluoro-10-[2-(1-hydroxycyclobutyl)ethynyl]-N3-methyl-5,6,7,12-tetrahydro-5,7-methanobenzo[c]imidazo[1,2-a]azepine-2,3-dicarboxamide. M+1=409.2.

1H NMR (400 MHz, DMSO-d6) δ 10.63 (q, J=4.6 Hz, 1H), 8.87 (d, J=7.6 Hz, 1H), 8.30 (s, 1H), 7.74 (s, 1H), 7.30 (d, J=10.0 Hz, 1H), 6.18-6.07 (m, 1H), 5.95 (s, 1H), 3.74-3.61 (m, 1H), 3.19-3.04 (m, 2H), 2.78 (d, J=4.6 Hz, 3H), 2.46-2.39 (m, 2H), 2.32-2.20 (m, 2H), 1.88-1.76 (m, 2H), 1.73-1.63 (m, 2H).

Example 462

Synthesis of 10-[2-(1-hydroxycyclobutyl)ethynyl]-5,6,7,12-tetrahydro-5,7-methanobenzo[c]imidazo[1,2-a]azepine-2-carboxamide

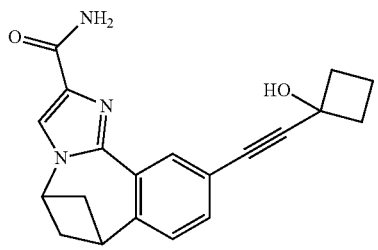 [SMILES: NC(=O)c1cn2c(n1)-c1cc(C#CC3(O)CCC3)ccc1C1CC2C1]

10-bromo-6,7-dihydro-5H-5,7-methanobenzo[c]imidazo[1,2-a]azepine-2-carboxamide was reacted with 1-ethynylcyclobutanol as described in General Procedure F without making critical modifications to afford 63 mg (60%) of 10-[2-(1-hydroxycyclobutyl)ethynyl]-5,6,7,12-tetrahydro-5,7-methanobenzo[c]imidazo[1,2-a]azepine-2-carboxamide. M+1=334.2.

1H NMR (400 MHz, DMSO-d6) δ 8.66 (s, 1H), 7.83 (s, 1H), 7.53 (s, 1H), 7.28 (s, 2H), 7.09 (s, 1H), 5.88 (s, 1H), 4.97-4.88 (m, 1H), 3.77-3.67 (m, 1H), 3.14-3.01 (m, 2H), 2.46-2.34 (m, 2H), 2.30-2.17 (m, 2H), 1.87-1.73 (m, 2H), 1.71-1.61 (m, 2H).

Example 463

Synthesis of 10-[2-(1-hydroxycyclobutyl)ethynyl]-N3-methyl-5,6-dihydroimidazo[1,2-d][1,4]benzoxazepine-2,3-dicarboxamide

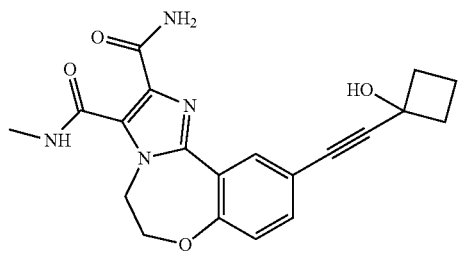 [SMILES: CNC(=O)c1c(C(N)=O)nc2n1CCOc1ccc(C#CC3(O)CCC3)cc1-2]

10-bromo-N3-methyl-5,6-dihydrobenzo[f]imidazo[1,2-d][1,4]oxazepine-2,3-dicarboxamide was reacted with 1-ethynylcyclobutanol as described in General Procedure F without making critical modifications to afford 48 mg (46.2%) of 10-[2-(1-hydroxycyclobutyl)ethynyl]-N3-methyl-5,6-dihydroimidazo[1,2-d][1,4]benzoxazepine-2,3-dicarboxamide. M+1=381.2.

1H NMR (400 MHz, DMSO-d6) δ 11.08 (q, J=4.5 Hz, 1H), 8.57 (d, J=2.2 Hz, 1H), 8.34 (s, 1H), 7.87 (s, 1H), 7.40 (dd, J=8.5, 2.2 Hz, 1H), 7.05 (d, J=8.5 Hz, 1H), 5.83 (s, 1H), 5.04-4.90 (m, 2H), 4.58-4.47 (m, 2H), 2.81 (d, J=4.6 Hz, 3H), 2.45-2.35 (m, 2H), 2.27-2.17 (m, 2H), 1.85-1.74 (m, 2H).

Example 464

Synthesis of 3-[[acetyl(isopropyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide

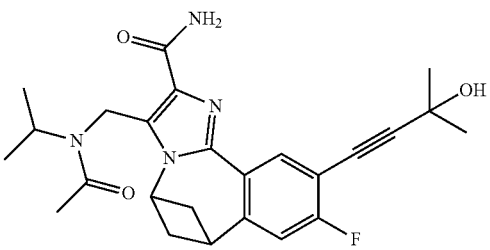 [SMILES: CC(=O)N(Cc1c(C(N)=O)nc2n1C1CC(C1)c1cc(F)c(C#CC(C)(C)O)cc1-2)C(C)C]

9-fluoro-10-(3-hydroxy-3-methylbut-1-yn-1-yl)-3-((isopropylamino)methyl)-6,7-dihydro-5H-5,7-methanobenzo[c]imidazo[1,2-a]azepine-2-carboxamide was reacted with acetic acid similarly to as described in example 2 without making critical modifications to afford 20 mg (61%) of 3-[[acetyl(isopropyl)amino]methyl]-9-fluoro-10-(3-hydroxy-3-methyl-but-1-ynyl)-5,6,7,12-tetrahydro-5,7-methanobenzo[c]imidazo[1,2-a]azepine-2-carboxamide. M+1=453.3.

1H NMR (400 MHz, DMSO-d6) δ 8.71 (d, J=7.6 Hz, 1H), 7.73 (s, 1H), 7.25 (d, J=10.0 Hz, 1H), 7.19 (s, 1H), 5.53 (s, 1H), 5.24 (s, 2H), 4.94-4.83 (m, 1H), 4.12-3.98 (m, 1H), 3.70-3.60 (m, 1H), 3.11-2.96 (m, 2H), 2.12 (s, 3H), 1.69-1.58 (m, 2H), 1.50 (s, 6H), 0.98 (d, J=6.8 Hz, 6H).

Example 465

Synthesis of 10-bromo-9-fluoro-3-(pyrrolidin-1-ylmethyl)-5,6-dihydrobenzo[f]imidazo[1,2-d][1,4]oxazepine-2-carboxamide

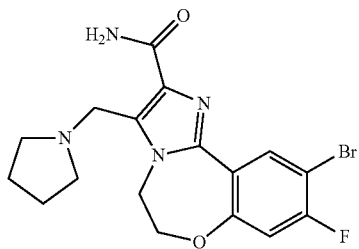 [SMILES: NC(=O)c1nc2n(c1CN1CCCC1)CCOc1cc(F)c(Br)cc1-2]

Into a 20-mL sealed tube was placed a suspension of 10-bromo-9-fluoro-2-iodo-5,6-dihydrobenzo[f]imidazo[1,2-d][1,4]oxazepine (300 mg, 0.77 mmol, 1.00 equiv), formaldehyde (37% in water, 312 mg, 4.00 equiv) and pyrrolidine (332 mg, 4.67 mmol, 6.00 equiv) in acetic acid (4 mL). The resulting mixture was stirred at 120° C. for 3 hours. The reaction mixture was cooled then extracted with Dichloromethane and a saturated ammonium chloride solution. The organic layer was then dried, filtered and concentrated to afford an orange oil. The oil was brought up in methanol and sonicated until a solid crashed out, which was collected by filtration to get 338 mg of light yellow solid. An additional 440 mg of a light orange solid was gained from concentration of the resultant mother liquor and trituration from water for an overall yield of 65% of 10-bromo-9-fluoro-2-iodo-3-(pyrrolidin-1-ylmethyl)-5,6-dihydrobenzo[f]imidazo[1,2-d][1,4]oxazepine.

10-Bromo-9-fluoro-3-(pyrrolidin-1-ylmethyl)-5,6-dihydrobenzo[f]imidazo[1,2-d][1,4]oxazepine-2-carboxamide was prepared similarly to as described in example 10 with non-critical modifications to afford 580 mg (90%) of 10-bromo-9-fluoro-3-(pyrrolidin-1-ylmethyl)-5,6-dihydrobenzo[f]imidazo[1,2-d][1,4]oxazepine-2-carboxamide.

Example 466

Synthesis of 9-fluoro-10-[(3R)-3-hydroxy-3-(5-methyl-1,2,4-oxadiazol-3-yl)but-1-ynyl]-3-(pyrrolidin-1-ylmethyl)-5,6-dihydroimidazo[1,2-d][1,4]benzoxazepine-2-carboxamide

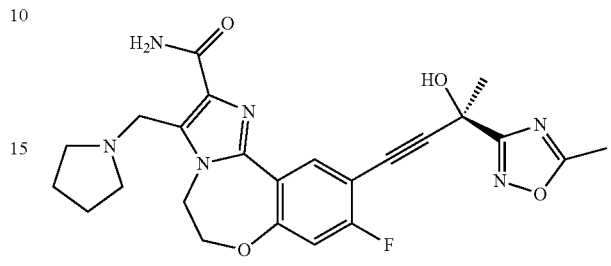

10-bromo-9-fluoro-3-(pyrrolidin-1-ylmethyl)-5,6-dihydrobenzo[f]imidazo[1,2-d][1,4]oxazepine-2-carboxamide was reacted with (2R)-2-(5-methyl-1,2,4-oxadiazol-3-yl)but-3-yn-2-ol similarly to as described in General Procedure F with non-critical modifications to afford 9.8 mg (10.4%) of 9-fluoro-10-[(3R)-3-hydroxy-3-(5-methyl-1,2,4-oxadiazol-3-yl)but-1-ynyl]-3-(pyrrolidin-1-ylmethyl)-5,6-dihydroimidazo[1,2-d][1,4]benzoxazepine-2-carboxamide. M+1=481.2.

1H NMR (400 MHz, DMSO-d6) δ 8.59 (d, J=8.5 Hz, 1H), 7.58 (s, 1H), 7.06 (s, 1H), 7.02 (d, J=10.4 Hz, 1H), 6.75 (s, 1H), 4.57-4.45 (m, 4H), 4.07 (s, 2H), 2.62 (s, 3H), 2.49-2.43 (m, 4H), 1.85 (s, 3H), 1.70-1.62 (m, 4H).

Example 467

Synthesis of 9-fluoro-10-[(3R)-3-hydroxy-3-(5-methylisoxazol-3-yl)but-1-ynyl]-3-(pyrrolidin-1-ylmethyl)-5,6-dihydroimidazo[1,2-d][1,4]benzoxazepine-2-carboxamide

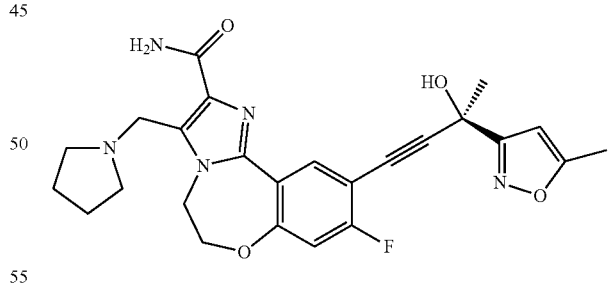

10-bromo-9-fluoro-3-(pyrrolidin-1-ylmethyl)-5,6-dihydrobenzo[f]imidazo[1,2-d][1,4]oxazepine-2-carboxamide was reacted with (2R)-2-(5-methylisoxazol-3-yl)but-3-yn-2-ol similarly to as described in General Procedure F with non-critical modifications to afford 26 mg (28%) of 9-fluoro-10-[(3R)-3-hydroxy-3-(5-methylisoxazol-3-yl)but-1-ynyl]-3-(pyrrolidin-1-ylmethyl)-5,6-dihydroimidazo[1,2-d][1,4]benzoxazepine-2-carboxamide. M+1=480.3.

1H NMR (400 MHz, DMSO-d6) δ 10.64 (s, 1H), 8.65 (d, J=8.4 Hz, 1H), 8.06 (s, 1H), 7.58 (s, 1H), 7.29 (s, 1H), 7.16 (s, 1H), 7.08-7.02 (m, 2H), 6.55 (s, 1H), 6.35 (s, 1H), 4.75 (d,

J=5.4 Hz, 2H), 4.63-4.54 (m, 4H), 3.48-3.43 (m, 2H), 3.26-3.20 (m, 2H), 2.41 (s, 3H), 2.07-2.02 (m, 2H), 1.94-1.89 (m, 2H), 1.82 (s, 3H).

Example 468

Synthesis of 9-fluoro-10-[2-[(3R)-3-hydroxy-1-methyl-2-oxo-pyrrolidin-3-yl]ethynyl]-3-(pyrrolidin-1-ylmethyl)-5,6-dihydroimidazo[1,2-d][1,4]benzoxazepine-2-carboxamide

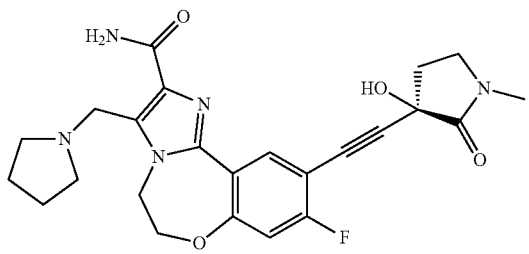 [SMILES: CN1CC[C@@](O)(C#Cc2cc3c(cc2F)OCCn2c-3nc(C(N)=O)c2CN2CCCC2)C1=O]

10-bromo-9-fluoro-3-(pyrrolidin-1-ylmethyl)-5,6-dihydrobenzo[f]imidazo[1,2-d][1,4]oxazepine-2-carboxamide was reacted with (3R)-3-ethynyl-3-hydroxy-1-methyl-pyrrolidin-2-one similarly to as described in General Procedure F with non-critical modifications to afford 3 mg (3.3%) of 9-fluoro-10-[2-[(3R)-3-hydroxy-1-methyl-2-oxo-pyrrolidin-3-yl]ethynyl]-3-(pyrrolidin-1-ylmethyl)-5,6-dihydroimidazo[1,2-d][1,4]benzoxazepine-2-carboxamide. M+1=468.2.

Example 469

Synthesis of methyl 10-bromo-3-formyl-6,7-dihydro-5H-5,7-methanobenzo[c]imidazo[1,2-a]azepine-2-carboxylate

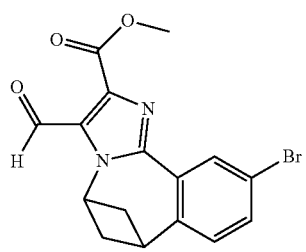 [SMILES: COC(=O)c1nc2n(c1C=O)C1CC(C1)c1ccc(Br)cc1-2]

Methyl 10-bromo-6,7-dihydro-5H-5,7-methanobenzo[c]imidazo[1,2-a]azepine-2-carboxylate (4 g) was reacted with ethyl formate similarly to as described in example 8 with non-critical modifications to afford 3.2 g (74%) of methyl 10-bromo-3-formyl-6,7-dihydro-5H-5,7-methanobenzo[c]imidazo[1,2-a]azepine-2-carboxylate as a yellow solid.

Example 470

Synthesis of 10-[2-[(3R)-3-hydroxy-1-methyl-2-oxo-pyrrolidin-3-yl]ethynyl]-3-[(2-methylbenzimidazol-1-yl)methyl]-5,6,7,12-tetrahydro-5,7-methanobenzo[c]imidazo[1,2-a]azepine-2-carboxamide

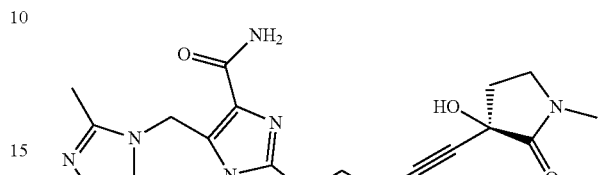

10-bromo-3-formyl-6,7-dihydro-5H-5,7-methanobenzo[c]imidazo[1,2-a]azepine-2-carboxylate was subjected to General Procedure O (ketone/aldehyde reduction) to afford crude methyl 10-bromo-3-(hydroxymethyl)-6,7-dihydro-5H-5,7-methanobenzo[c]imidazo[1,2-a]azepine-2-carboxylate. To a reaction flask was placed a solution of methyl 10-bromo-3-(hydroxymethyl)-6,7-dihydro-5H-5,7-methanobenzo[c]imidazo[1,2-a]azepine-2-carboxylate (1 eq), 2-methylbenzimidazole (1.05 eq) and triphenylphosphine (1.20 equiv) in tetrahydrofuran. This was followed by the addition of di-tert-butylazodicarboxylate (1.1 eq) in Tetrahydrofuran (1.0 mL) dropwise with stirring at 0° C. The resulting solution was stirred for 3 hours at room temperature. The resulting mixture was extracted with dichloromethane and saturated ammonium chloride. The residue was purified by flash column chromatography to afford 114 mg (43%) of methyl 10-bromo-3-((2-methyl-1H-benzo[d]imidazol-1-yl)methyl)-6,7-dihydro-5H-5,7-methanobenzo[c]imidazo[1,2-a]azepine-2-carboxylate as a light yellow oil. 10-bromo-3((2-methyl-1H-benzo[d]imidazol-1-yl)methyl)-6,7-dihydro-5H-5,7-methanobenzo[c]imidazo[1,2-a]azepine-2-carboxylate was subjected to General Procedure L to afford 89 mg (81%) of 10-bromo-3((2-methyl-1H-benzo[d]imidazol-1-yl)methyl)-6,7-dihydro-5H-5,7-methanobenzo[c]imidazo[1,2-a]azepine-2-carboxamide as a white solid. 10-bromo-3((2-methyl-1H-benzo[d]imidazol-1-yl)methyl)-6,7-dihydro-5H-5,7-methanobenzo[c]imidazo[1,2-a]azepine-2-carboxamide was reacted with (3R)-3-ethynyl-3-hydroxy-1-methyl-pyrrolidin-2-one similarly to as described in General Procedure F with non-critical modifications to afford 6.8 mg (15.1%) of 10-[2-[(3R)-3-hydroxy-1-methyl-2-oxo-pyrrolidin-3-yl]ethynyl]-3-[(2-methylbenzimidazol-1-yl)methyl]-5,6,7,12-tetrahydro-5,7-methanobenzo[c]imidazo[1,2-a]azepine-2-carboxamide.

M+1=521.0; $^1$H NMR (400 MHz, DMSO-d6) δ 8.74 (d, J=1.8 Hz, 1H), 7.88 (s, 1H), 7.52-7.47 (m, 1H), 7.38 (s, 1H), 7.27 (dd, J=7.8, 1.8 Hz, 1H), 7.21 (d, J=7.9 Hz, 1H), 7.15-7.02 (m, 3H), 6.44 (s, 1H), 6.01 (s, 2H), 4.55-4.46 (m, 1H), 3.57-3.49 (m, 1H), 3.40-3.34 (m, 2H), 2.81 (s, 3H), 2.79-2.70 (m, 2H), 2.52 (s, 3H), 2.44-2.42 (m, 1H), 2.24-2.16 (m, 1H), 1.38-1.30 (m, 2H).

Example 471

Synthesis of 10-[2-[(3R)-3-hydroxy-1-methyl-2-oxo-pyrrolidin-3-yl]ethynyl]-3-(pyrrolidin-1-ylmethyl)-5,6,7,12-tetrahydro-5,7-methanobenzo[c]imidazo[1,2-a]azepine-2-carboxamide

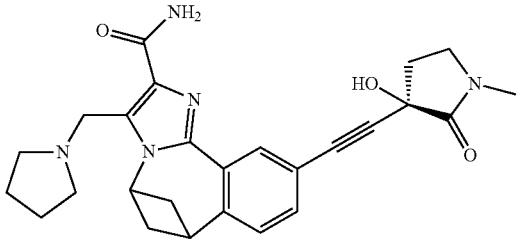 [SMILES: CN1CC[C@@](O)(C#Cc2ccc3c(c2)-c2nc(C(N)=O)c(CN4CCCC4)n2C2CC3C2)C1=O]

Methyl 10-bromo-3-formyl-6,7-dihydro-5H-5,7-methanobenzo[c]imidazo[1,2-a]azepine-2-carboxylate was reacted with pyrrolidine similarly to as described in Example 7 to afford 320 mg (70%) of methyl 10-bromo-3-(pyrrolidin-1-ylmethyl)-6,7-dihydro-5H-5,7-methanobenzo[c]imidazo[1,2-a]azepine-2-carboxylate as a white solid. methyl 10-bromo-3-(pyrrolidin-1-ylmethyl)-6,7-dihydro-5H-5,7-methanobenzo[c]imidazo[1,2-a]azepine-2-carboxylate was subjected to General Procedure L to afford 130 mg (47%) of 10-bromo-3-(pyrrolidin-1-ylmethyl)-6,7-dihydro-5H-5,7-methanobenzo[c]imidazo[1,2-a]azepine-2-carboxamide. 10-bromo-3-(pyrrolidin-1-ylmethyl)-6,7-dihydro-5H-5,7-methanobenzo[c]imidazo[1,2-a]azepine-2-carboxamide was reacted with (3R)-3-ethynyl-3-hydroxy-1-methyl-pyrrolidin-2-one similarly to as described in General Procedure F with non-critical modifications to afford 14 mg (19%) of 10-[2-[(3R)-3-hydroxy-1-methyl-2-oxo-pyrrolidin-3-yl]ethynyl]-3-(pyrrolidin-1-ylmethyl)-5,6,7,12-tetrahydro-5,7-methanobenzo[c]imidazo[1,2-a]azepine-2-carboxamide.

M+1=460; $^1$H NMR (400 MHz, DMSO-d6) δ 8.68 (d, J=1.3 Hz, 1H), 7.56 (s, 1H), 7.30-7.24 (m, 2H), 7.03 (s, 1H), 6.43 (s, 1H), 5.17-5.08 (m, 1H), 4.08 (s, 2H), 3.70-3.64 (m, 1H), 3.40-3.33 (m, 2H), 3.15-3.03 (m, 2H), 2.81 (s, 3H), 2.48-2.42 (m, 4H), 2.26-2.14 (m, 1H), 1.67-1.58 (m, 5H).

Example 472

Synthesis of 4,4-difluoro-9-[2-[(3R)-3-hydroxy-1-methyl-2-oxo-pyrrolidin-3-yl]ethynyl]-5H-[1]benzoxepino[5,4-d]thiazole-2-carboxamide

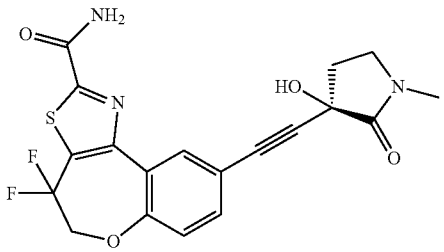

Methyl 9-bromo-4,4-difluoro-4,5-dihydrobenzo[2,3]oxepino[4,5-d]thiazole-2-carboxylate was reacted with (3R)-3-ethynyl-3-hydroxy-1-methyl-pyrrolidin-2-one similarly to as described in General Procedure F with non-critical modifications to afford crude (R)-methyl 4,4-difluoro-9-((3-hydroxy-1-methyl-2-oxopyrrolidin-3-yl)ethynyl)-4,5-dihydrobenzo[2,3]oxepino[4,5-d]thiazole-2-carboxylate. Crude (R)-methyl 4,4-difluoro-9-((3-hydroxy-1-methyl-2-oxopyrrolidin-3-yl)ethynyl)-4,5-dihydrobenzo[2,3]oxepino[4,5-d]thiazole-2-carboxylate was subjected to General Procedure M to afford 21.2 mg (38%) of 4,4-difluoro-9-[2-[(3R)-3-hydroxy-1-methyl-2-oxo-pyrrolidin-3-yl]ethynyl]-5H-[1]benzoxepino[5,4-d]thiazole-2-carboxamide.

M+1=420; $^1$H NMR (400 MHz, DMSO-d6) δ 8.73 (s, 1H), 8.63 (d, J=2.2 Hz, 1H), 8.15 (s, 1H), 7.49 (dd, J=8.4, 2.2 Hz, 1H), 7.24 (d, J=8.4 Hz, 1H), 6.43 (s, 1H), 4.76 (t, J=10.6 Hz, 2H), 3.43-3.29 (m, 2H), 2.81 (s, 2H), 2.46 (ddd, J=12.8, 6.4, 5.1 Hz, 1H), 2.26-2.15 (m, 1H).

Example 473

Synthesis of 3-cyclopropyl-9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide

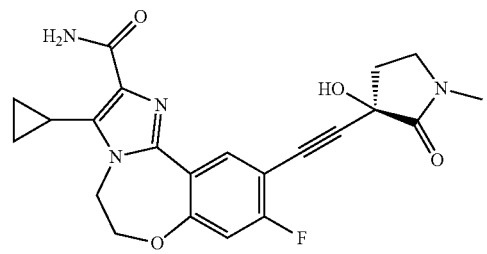 [SMILES: CN1CC[C@@](O)(C#Cc2cc3c(cc2F)OCCn2c-3nc(C(N)=O)c2C2CC2)C1=O]

10-bromo-3-cyclopropyl-9-fluoro-5,6-dihydrobenzo[f]imidazo[1,2-d][1,4]oxazepine-2-carboxamide was reacted with (3R)-3-ethynyl-3-hydroxy-1-methyl-pyrrolidin-2-one similarly to as described in General Procedure F with non-critical modifications to afford 14.2 mg (31%) of 3-cyclopropyl-9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide. M+1=425.0.

1H NMR (400 MHz, DMSO-d6) δ 8.57 (d, J=8.5 Hz, 1H), 7.45 (s, 1H), 7.00 (d, J=10.6 Hz, 1H), 6.93 (s, 1H), 6.46 (s, 1H), 4.59-4.43 (m, 4H), 3.42-3.28 (m, 2H), 2.80 (s, 3H), 2.49-2.38 (m, 1H), 2.26-2.14 (m, 1H), 1.81-1.69 (m, 1H), 1.03-0.93 (m, 2H), 0.87-0.78 (m, 2H).

Example 474

Synthesis of 10-[2-[(3R)-3-hydroxy-1-methyl-2-oxo-pyrrolidin-3-yl]ethynyl]-N3-methyl-5,6-dihydroimidazo[1,2-d][1,4]benzoxazepine-2,3-dicarboxamide

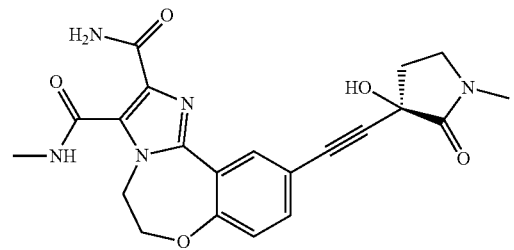

10-bromo-N3-methyl-5,6-dihydroimidazo[1,2-d][1,4] benzoxazepine-2,3-dicarboxamide was reacted with (3R)-3-ethynyl-3-hydroxy-1-methyl-pyrrolidin-2-one similarly to as described in General Procedure F with non-critical modifications to afford 4.4 mg (9%) of 10-[2-[(3R)-3-hydroxy-1-methyl-2-oxo-pyrrolidin-3-yl]ethynyl]-N3-methyl-5,6-dihydroimidazo[1,2-d][1,4]benzoxazepine-2,3-dicarboxamide. M+1=424.0.

Example 475

Synthesis of 10-[2-[(3R)-3-hydroxy-1-methyl-2-oxo-pyrrolidin-3-yl]ethynyl]-3-(trifluoromethyl)-5,6-dihydroimidazo[1,2-d][1,4]benzoxazepine-2-carboxamide

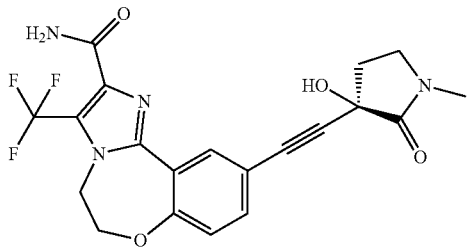 [SMILES: CN1CC[C@@](O)(C#Cc2ccc3c(c2)-c2nc(C(N)=O)c(C(F)(F)F)n2CCO3)C1=O]

10-bromo-3-(trifluoromethyl)-5,6-dihydroimidazo[1,2-d][1,4]benzoxazepine-2-carboxamide was reacted with (3R)-3-ethynyl-3-hydroxy-1-methyl-pyrrolidin-2-one similarly to as described in General Procedure F with non-critical modifications to afford 56 mg (48.3%) of 10-[2-[(3R)-3-hydroxy-1-methyl-2-oxo-pyrrolidin-3-yl]ethynyl]-3-(trifluoromethyl)-5,6-dihydroimidazo[1,2-d][1,4]benzoxazepine-2-carboxamide.

M+1=435; $^1$H NMR (400 MHz, DMSO-d6) δ 8.57 (d, J=2.2 Hz, 1H), 7.91 (s, 1H), 7.49 (s, 1H), 7.42 (dd, J=8.5, 2.2 Hz, 1H), 7.09 (d, J=8.5 Hz, 1H), 6.41 (s, 1H), 4.61-4.48 (m, 4H), 3.40-3.30 (m, 2H), 2.80 (s, 2H), 2.50-2.38 (m, 1H), 2.24-2.12 (m, 1H).

Example 476

Synthesis of 10-[2-[(3R)-3-hydroxy-1-methyl-2-oxo-pyrrolidin-3-yl]ethynyl]-N3-isopropyl-5,6-dihydroimidazo[1,2-d][1,4]benzoxazepine-2,3-dicarboxamide

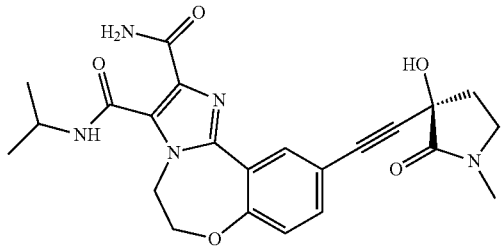 [SMILES: CC(C)NC(=O)c1c(C(N)=O)nc2n1CCOc1ccc(C#C[C@]3(O)CCN(C)C3=O)cc1-2]

10-bromo-2-carbamoyl-5,6-dihydrobenzo[f]imidazo[1,2-d][1,4]oxazepine-3-carboxyl is acid was reacted with 2-aminopropane similarly to as described in example 2 with non-critical modifications to afford 112 mg (67%) 10-bromo-N3-isopropyl-5,6-dihydrobenzo[f]imidazo[1,2-d][1,4]oxazepine-2,3-dicarboxamide. 10-bromo-N3-isopropyl-5,6-dihydrobenzo[f]imidazo[1,2-d][1,4]oxazepine-2,3-dicarboxamide was reacted with (3R)-3-ethynyl-3-hydroxy-1-methyl-pyrrolidin-2-one similarly to as described in General Procedure F with non-critical modifications to afford 16 mg (12.2%) 10-[2-[(3R)-3-hydroxy-1-methyl-2-oxo-pyrrolidin-3-yl]ethynyl]-N3-isopropyl-5,6-dihydroimidazo[1,2-d][1,4]benzoxazepine-2,3-dicarboxamide.

M+1=452; $^1$H NMR (400 MHz, DMSO-d6) δ 11.21 (d, J=6.9 Hz, 1H), 8.55 (d, J=2.2 Hz, 1H), 8.30 (s, 1H), 7.83 (s, 1H), 7.39 (dd, J=8.5, 2.2 Hz, 1H), 7.06 (d, J=8.5 Hz, 1H), 6.39 (s, 1H), 5.02-4.95 (m, 2H), 4.55-4.48 (m, 2H), 4.04-3.93 (m, 1H), 3.39-3.32 (m, 1H), 2.80 (s, 3H), 2.48-2.39 (m, 1H), 2.24-2.13 (m, 1H), 1.17 (d, J=6.6 Hz, 6H).

Example 477

Synthesis of 10-[2-[(3R)-3-hydroxy-1-methyl-2-oxo-pyrrolidin-3-yl]ethynyl]-N3-tetrahydropyran-4-yl-5,6-dihydroimidazo[1,2-d][1,4]benzoxazepine-2,3-dicarboxamide

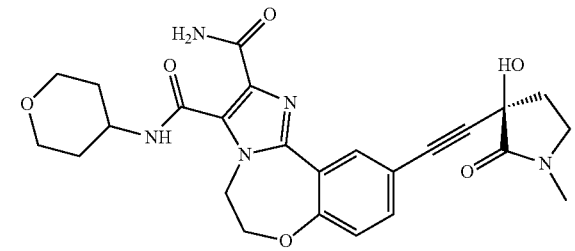 [SMILES: CN1CC[C@@](O)(C#Cc2ccc3c(c2)-c2nc(C(N)=O)c(C(=O)NC4CCOCC4)n2CCO3)C1=O]

10-bromo-2-carbamoyl-5,6-dihydrobenzo[f]imidazo[1,2-d][1,4]oxazepine-3-carboxylic acid was reacted with tetrahydro-pyran-4-ylamine hydrochloride similarly to as described in example 2 with non-critical modifications to afford 117 mg (63%) 10-bromo-N3-tetrahydropyran-4-yl-5,6-dihydroimidazo[1,2-d][1,4]benzoxazepine-2,3-dicarboxamide. 10-bromo-N3-tetrahydropyran-4-yl-5,6-dihydroimidazo[1,2-d][1,4]benzoxazepine-2,3-dicarboxamide was reacted with (3R)-3-ethynyl-3-hydroxy-1-methyl-pyrrolidin-2-one similarly to as described in General Procedure F with non-critical modifications to afford 14 mg (11%) of 10-[2-[(3R)-3-hydroxy-1-methyl-2-oxo-pyrrolidin-3-yl]ethynyl]-N3-tetrahydropyran-4-yl-5,6-dihydroimidazo[1,2-d][1,4]benzoxazepine-2,3-dicarboxamide.

M+1=494; $^1$H NMR (400 MHz, DMSO-d6) δ 11.42 (d, J=7.0 Hz, 1H), 8.56 (d, J=2.2 Hz, 1H), 8.35 (s, 1H), 7.89 (s, 1H), 7.40 (dd, J=8.5, 2.2 Hz, 1H), 7.06 (d, J=8.5 Hz, 1H), 6.39 (s, 1H), 5.02-4.95 (m, 2H), 4.55-4.48 (m, 2H), 3.90-3.80 (m, 2H), 3.52-3.41 (m, 2H), 3.40-3.31 (m, 2H), 3.30-3.23 (m, 1H), 2.80 (s, 3H), 2.50-2.38 (m, 1H), 2.25-2.13 (m, 1H), 1.91-1.83 (m, 2H), 1.54-1.40 (m, 2H).

Example 478

Synthesis of 3-[(2-chlorophenoxy)methyl]-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide

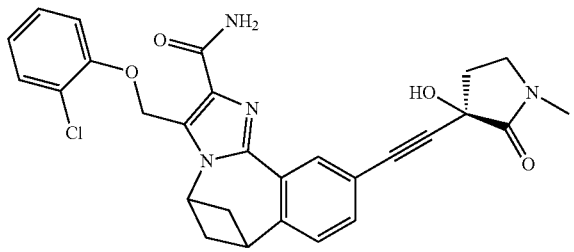 [SMILES: CN1CC[C@@](O)(C#Cc2ccc3c(c2)-c2nc(C(N)=O)c(COc4ccccc4Cl)n2C2CC3C2)C1=O]

To a solution of methyl 10-bromo-3-(hydroxymethyl)-6,7-dihydro-5H-5,7-methanobenzo[c]imidazo[1,2-a]azepine-2-carboxylate in dichloromethane (1 eq) was added phosphorus tribromide. After 20 minutes of stirring at room temperature, the reaction was extracted with a saturated ammonium chloride solution and the organic layer was dried, filtered and concentrated to afford crude methyl 10-bromo-3-(bromomethyl)-6,7-dihydro-5H-5,7-methanobenzo[c]imidazo[1,2-a]azepine-2-carboxylate. To this intermediate in a solution of N,N-dimethylformamide (5 mL/mmol) was added 2-chlorophenol (2 eq) and cesium carbonate (1.5 eq). The reaction was stirred at 50° C. and monitored by LC-MS until complete, whereupon the reaction mixture was extracted with dichloromethane and a saturated ammonium chloride solution and the organic layer was dried, filtered and concentrated to afford 147 mg (59%) crude methyl 10-bromo-3-((2-chlorophenoxy)methyl)-6,7-dihydro-5H-5,7-methanobenzo[c]imidazo[1,2-a]azepine-2-carboxylate. Methyl 10-bromo-3-((2-chlorophenoxy)methyl)-6,7-dihydro-5H-5,7-methanobenzo[c]imidazo[1,2-a]azepine-2-carboxylate was subjected to General Procedure L to afford 124 mg (91%) of 10-bromo-3-((2-chlorophenoxy)methyl)-6,7-dihydro-5H-5,7-methanobenzo[c]imidazo[1,2-a]azepine-2-carboxamide, 50 mg of which was directly reacted with (3R)-3-ethynyl-3-hydroxy-1-methyl-pyrrolidin-2-one similarly to as described in General Procedure F with non-critical modifications to afford 31 mg (55.4%) of 3-[(2-chlorophenoxy)methyl]-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide.

M+1=517; $^1$H NMR (400 MHz, DMSO-d6) δ 8.71 (t, J=1.1 Hz, 1H), 7.78 (s, 1H), 7.49-7.37 (m, 2H), 7.35-7.21 (m, 4H), 6.95 (td, J=7.6, 1.3 Hz, 1H), 6.43 (s, 1H), 5.74 (s, 2H), 5.12-4.96 (m, 1H), 3.76-3.66 (m, 1H), 3.40-3.33 (m, 2H), 3.19-3.07 (m, 2H), 2.81 (s, 3H), 2.48-2.39 (m, 1H), 2.26-2.15 (m, 1H), 1.68-1.60 (m, 2H).

Example 479

Synthesis of 10-[(3R)-3-hydroxy-3-(5-methylisoxazol-3-yl)but-1-ynyl]-3-(pyrrolidin-1-ylmethyl)-5,6,7,12-tetrahydro-5,7-methanobenzo[c]imidazo[1,2-a]azepine-2-carboxamide

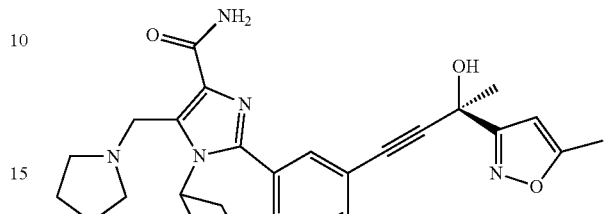

10-bromo-3-(pyrrolidin-1-ylmethyl)-6,7-dihydro-5H-5,7-methanobenzo[c]imidazo[1,2-a]azepine-2-carboxamide was reacted with (2R)-2-(5-methylisoxazol-3-yl)but-3-yn-2-ol similarly to as described in General Procedure F with non-critical modifications to afford 12 mg (16%) of 10-[(3R)-3-hydroxy-3-(5-methylisoxazol-3-yl)but-1-ynyl]-3-(pyrrolidin-1-ylmethyl)-5,6,7,12-tetrahydro-5,7-methanobenzo[c]imidazo[1,2-a]azepine-2-carboxamide.

M+1=472; $^1$H NMR (400 MHz, DMSO-d6) δ 8.68 (s, 1H), 8.27 (s, 1H), 7.56 (s, 1H), 7.27 (d, J=1.0 Hz, 2H), 7.02 (s, 1H), 6.36 (s, 1H), 5.19-5.04 (m, 1H), 4.08 (s, 2H), 3.72-3.61 (m, 1H), 3.14-3.05 (m, 1H), 2.47-2.42 (m, 4H), 2.41 (s, 3H), 1.81 (s, 3H), 1.68-1.55 (m, 6H).

Example 480

Synthesis of 8-fluoro-9-[(3R)-3-hydroxy-3-(5-methylisoxazol-3-yl)but-1-ynyl]-4,5-dihydrothieno[3,2-d][1]benz oxepine-2-carboxamide

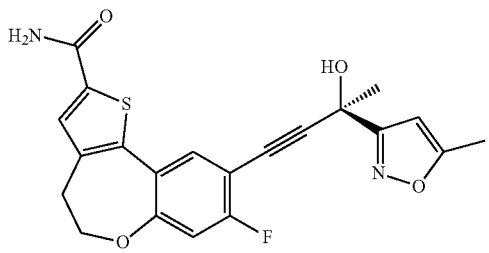 [SMILES: Cc1cc([C@](C)(O)C#Cc2cc3c(cc2F)OCCc2cc(C(N)=O)sc2-3)no1]

Methyl 9-bromo-8-fluoro-4,5-dihydrobenzo[b]thieno[2,3-d]oxepine-2-carboxylate was subjected to General Procedure L to afford 484 mg 9-bromo-8-fluoro-4,5-dihydrobenzo[b]thieno[2,3-d]oxepine-2-carboxamide in quantitative yield. 9-bromo-8-fluoro-4,5-dihydrobenzo[b]thieno[2,3-d]oxepine-2-carboxamide (0.1 g) was reacted with (2R)-2-(5-methylisoxazol-3-yl)but-3-yn-2-ol similarly to as described in General Procedure F with non-critical modifications to afford 50 mg (41%) of 8-fluoro-9-[(3R)-3-hydroxy-3-(5-methylisoxazol-3-yl)but-1-ynyl]-4,5-dihydrothieno[3,2-d][1]benz oxepine-2-carboxamide. M+1=413; $^1$H NMR (400 MHz, DMSO-d6) δ 7.95 (s, 1H), 7.70 (d, J=7.8 Hz, 1H), 7.59 (s, 1H), 7.43 (s, 1H), 7.03 (d, J=10.4 Hz, 1H), 6.55 (s, 1H), 6.35 (d, J=1.0 Hz, 1H), 4.34 (t, J=5.6, 4.5 Hz, 2H), 3.18 (t, J=5.1 Hz, 2H), 2.41 (d, J=1.0 Hz, 3H), 1.80 (s, 3H).

Example 481

Synthesis of 8-fluoro-9-[2-[(3R)-3-hydroxy-1-methyl-2-oxo-pyrrolidin-3-yl]ethynyl]-4,5-dihydrothieno[3,2-d][1]benzoxepine-2-carboxamide

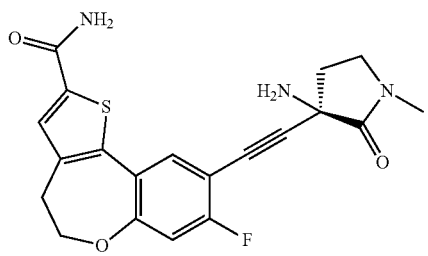 [SMILES: CN1CC[C@@](N)(C#Cc2cc3c(cc2F)OCCc2cc(C(N)=O)sc2-3)C1=O]

Methyl 9-bromo-8-fluoro-4,5-dihydrobenzo[b]thieno[2,3-d]oxepine-2-carboxylate was reacted with (3R)-3-ethynyl-3-hydroxy-1-methyl-pyrrolidin-2-one similarly to as described in General Procedure F with non-critical modifications to afford (R)-methyl 8-fluoro-9-((3-hydroxy-1-methyl-2-oxopyrrolidin-3-yl)ethynyl)-4,5-dihydrobenzo[b]thieno[2,3-d]oxepine-2-carboxylate. Crude (R)-methyl 8-fluoro-9-((3-hydroxy-1-methyl-2-oxopyrrolidin-3-yl)ethynyl)-4,5-dihydrobenzo[b]thieno[2,3-d]oxepine-2-carboxylate was to General Procedure M subjected to afford 26 mg (21%) of 8-fluoro-9-[2-[(3R)-3-hydroxy-1-methyl-2-oxo-pyrrolidin-3-yl]ethynyl]-4,5-dihydrothieno[3,2-d][1]benzoxepine-2-carboxamide.

M+1=401; $^1$H NMR (400 MHz, DMSO-d6) δ 7.96 (s, 1H), 7.71 (d, J=7.8 Hz, 1H), 7.59 (s, 1H), 7.43 (s, 1H), 7.03 (d, J=10.5 Hz, 1H), 6.51 (s, 1H), 4.34 (t, J=5.6, 4.5 Hz, 2H), 3.42-3.25 (m, 3H), 3.18 (t, J=5.1 Hz, 2H), 2.80 (s, 2H), 2.51-2.40 (m, 1H), 2.24-2.13 (m, 1H).

Example 482

Synthesis of 10-[2-[(3R)-3-hydroxy-1-methyl-2-oxo-3-piperidyl]ethynyl]-N3-tetrahydropyran-4-yl-5,6-dihydroimidazo[1,2-d][1,4]benzoxazepine-2,3-dicarboxamide

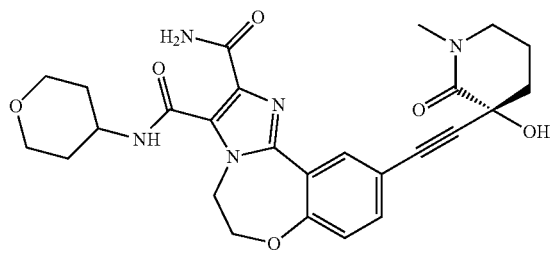 [SMILES: CN1CCC[C@@](O)(C#Cc2ccc3c(c2)-c2nc(C(N)=O)c(C(=O)NC4CCOCC4)n2CCO3)C1=O]

10-bromo-N3-tetrahydropyran-4-yl-5,6-dihydroimidazo[1,2-d][1,4]benzoxazepine-2,3-dicarboxamide was reacted with (3R)-3-ethynyl-3-hydroxy-1-methyl-piperidin-2-one similarly to as described in General Procedure F with non-critical modifications to afford 22 mg (25.3%) of 10-[2-[(3R)-3-hydroxy-1-methyl-2-oxo-3-piperidyl]ethynyl]-N3-tetrahydropyran-4-yl-5,6-dihydroimidazo[1,2-d][1,4]benzoxazepine-2,3-dicarboxamide.

M+1=508; $^1$H NMR (400 MHz, DMSO-d6) δ 11.43 (d, J=7.0 Hz, 1H), 8.54 (d, J=2.2 Hz, 1H), 8.36 (s, 1H), 7.91 (s, 1H), 7.39 (dd, J=8.5, 2.2 Hz, 1H), 7.06 (d, J=8.5 Hz, 1H), 6.02 (s, 1H), 5.02-4.94 (m, 2H), 4.55-4.49 (m, 2H), 4.01-3.95 (m, 1H), 3.89-3.81 (m, 3H), 3.52-3.40 (m, 3H), 3.36-3.32 (m, 1H), 2.86 (s, 3H), 1.90-1.83 (m, 4H), 1.51-1.43 (m, 3H).

Example 483

Synthesis of 4,4,8-trifluoro-9-[2-[(3R)-3-hydroxy-1-methyl-2-oxo-pyrrolidin-3-yl]ethynyl]-5H-[1]benzoxepino[5,4-d]thiazole-2-carboxamide

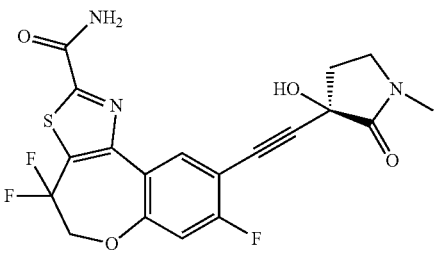 [SMILES: CN1CC[C@@](O)(C#Cc2cc3c(cc2F)OCC(F)(F)c2sc(C(N)=O)nc2-3)C1=O]

Ethyl 9-bromo-8-fluoro-4-oxo-4,5-dihydrobenzo[2,3]oxepino[4,5-d]thiazole-2-carboxylate was subjected to General Procedure P to afford 400 mg (95%) of ethyl 9-bromo-4,4,8-trifluoro-4,5-dihydrobenzo[2,3]oxepino[4,5-d]thiazole-2-carboxylate. Ethyl 9-bromo-4,4,8-trifluoro-4,5-dihydrobenzo[2,3]oxepino[4,5-d]thiazole-2-carboxylate was reacted with (3R)-3-ethynyl-3-hydroxy-1-methyl-pyrrolidin-2-one similarly to as described in General Procedure F with non-critical modifications to afford (R)-ethyl 4,4,8-trifluoro-9-((3-hydroxy-1-methyl-2-oxopyrrolidin-3-yl)ethynyl)-4,5-dihydrobenzo[2,3]oxepin o[4,5-d]thiazole-2-carboxylate. Crude (R)-ethyl 4,4,8-trifluoro-9-((3-hydroxy-1-methyl-2-oxopyrrolidin-3-yl)ethynyl)-4,5-dihydrobenzo[2,3]oxepin o[4,5-d]thiazole-2-carboxylate was subjected to General Procedure P to afford 190 mg (44.4%) of 4,4,8-trifluoro-9-[2-[(3R)-3-hydroxy-1-methyl-2-oxo-pyrrolidin-3-yl]ethynyl]-5H-[1]benzoxepino[5,4-d]thiazole-2-carboxamide. M+1=438.0.

1H NMR (400 MHz, DMSO-d6) δ 8.77 (s, 1H), 8.71 (d, J=8.3 Hz, 1H), 8.15 (s, 1H), 7.28 (d, J=10.0 Hz, 1H), 6.51 (s, 1H), 4.81 (t, J=10.4 Hz, 2H), 3.41-3.33 (m, 2H), 2.81 (s, 3H), 2.47-2.42 (m, 1H), 2.27-2.18 (m, 1H).

Example 484

Synthesis of (R)-4,4-difluoro-9-((3-hydroxy-2-oxopyrrolidin-3-yl)ethynyl)-4,5-dihydrobenzo[2,3]oxepino[4,5-d]thiazole-2-carboxamide and (S)-4,4-difluoro-9-((3-hydroxy-2-oxopyrrolidin-3-yl)ethynyl)-4,5-dihydrobenzo[2,3]oxepino[4,5-d]thiazole-2-carboxamide

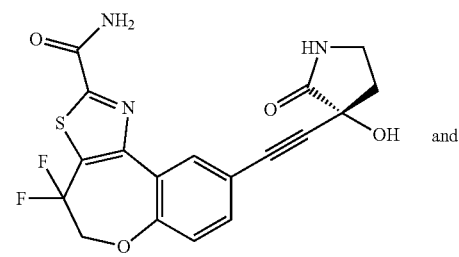

and

707
-continued

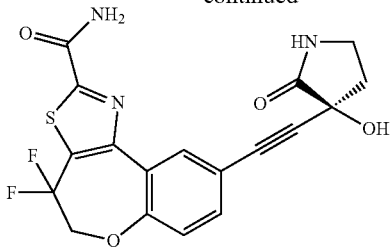

Methyl 9-bromo-4,4-difluoro-5H-[1]benzoxepino[5,4-d]thiazole-2-carboxylate was reacted with (3R)-3-ethynyl-3-hydroxy-pyrrolidin-2-one similarly to as described in General Procedure F with non-critical modifications to methyl 4,4-difluoro-9-((3-hydroxy-1-methyl-2-oxopyrrolidin-3-yl)ethynyl)-4,5-dihydrobenzo[2,3]oxepino[4,5-d]thiazole-2-carboxylate. Crude methyl 4,4-difluoro-9-((3-hydroxy-1-methyl-2-oxopyrrolidin-3-yl)ethynyl)-4,5-dihydrobenzo[2,3]oxepino[4,5-d]thiazole-2-carboxylate was subjected to General Procedure M to afford 8.1 mg and 28.5 mg (53% overall yield) following reverse phase purification and chiral separation. M+1=406.0.

1H NMR (400 MHz, DMSO-d6) δ 8.74 (s, 1H), 8.63 (d, J=2.2 Hz, 1H), 8.14 (s, 1H), 7.99 (s, 1H), 7.50 (dd, J=8.4, 2.2 Hz, 1H), 7.25 (d, J=8.4 Hz, 1H), 6.32 (s, 1H), 4.76 (t, J=10.6 Hz, 2H), 3.28-3.22 (m, 3H), 2.48-2.42 (m, 1H), 2.27-2.18 (m, 1H).

Example 485

Synthesis of (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

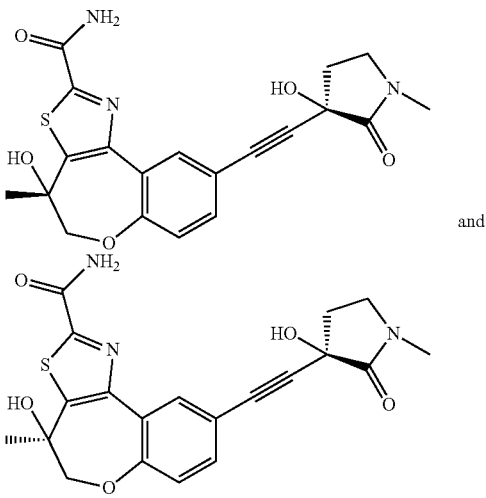

Methyl 9-bromo-4-hydroxy-4-methyl-4,5-dihydrobenzo[2,3]oxepino[4,5-d]thiazole-2-carboxylate (0.11 g) was reacted with (3R)-3-ethynyl-3-hydroxy-1-methyl-pyrrolidin-2-one similarly to as described in General Procedure F with non-critical modifications to afford methyl 4-hydroxy-

708

9-(((R)-3-hydroxy-1-methyl-2-oxopyrrolidin-3-yl)ethynyl)-4-methyl-4,5-dihydrobenzo[2,3]oxepino[4,5-d]thiazole-2-carboxylate which was directly subjected to conditions described in General Procedure M to afford 5 mg and 5.6 mg (9% overall yield) after reverse phase purification then chiral separation. The absolute stereochemistry at the 4-hydroxyl substitution position for each isomer was not determined. M+1=414.0.

Compound 1 $^1$H NMR (400 MHz, DMSO-d6) δ 8.59 (d, J=2.2 Hz, 1H), 8.43 (s, 1H), 7.86 (s, 1H), 7.34 (dd, J=8.3, 2.2 Hz, 1H), 7.09 (d, J=8.4 Hz, 1H), 6.38 (s, 1H), 6.24 (s, 1H), 4.21 (d, J=11.8 Hz, 1H), 4.01 (d, J=11.8 Hz, 1H), 3.39-3.32 (m, 2H), 2.80 (s, 3H), 2.47-2.40 (m, 1H), 2.23-2.14 (m, 1H), 1.57 (s, 3H).

Compound 2 1H NMR (400 MHz, DMSO-d6) δ 8.59 (d, J=2.2 Hz, 1H), 8.43 (s, 1H), 7.86 (s, 1H), 7.34 (dd, J=8.3, 2.2 Hz, 1H), 7.09 (d, J=8.4 Hz, 1H), 6.38 (s, 1H), 6.24 (s, 1H), 4.21 (d, J=11.7 Hz, 1H), 4.01 (d, J=11.7 Hz, 1H), 3.38-3.32 (m, 2H), 2.80 (s, 3H), 2.49-2.41 (m, 1H), 2.23-2.15 (m, 1H), 2.23-2.15 (m, 1H), 1.57 (s, 3H).

Example 486

Synthesis of (R)-4-fluoro-9-4(R)-3-hydroxy-1-methyl-2-oxopyrrolidin-3-yl)ethynyl)-4,5-dihydrobenzo[2,3]oxepino[4,5-d]thiazole-2-carboxamide and (S)-4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide

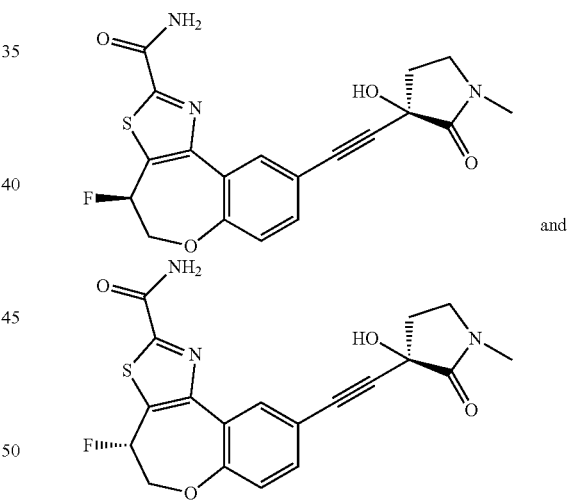

Methyl 9-bromo-4-hydroxy-4,5-dihydro-[1]benzoxepino[5,4-d]thiazole-2-carboxylate was reacted similarly to as described in General Procedure P with non-critical modifications to afford 142 mg (94%) of methyl 9-bromo-4-fluoro-4,5-dihydro-[1]benzoxepino[5,4-d]thiazole-2-carboxylate.

Methyl 9-bromo-4-fluoro-4,5-dihydro-[1]benzoxepino[5,4-d]thiazole-2-carboxylate was reacted with (3R)-3-ethynyl-3-hydroxy-1-methyl-pyrrolidin-2-one similarly to as described in General Procedure F with non-critical modifications to afford methyl 4-fluoro-9-[2-[(3R)-3-hydroxy-1-methyl-2-oxo-pyrrolidin-3-yl]ethynyl]-4,5-dihydro-[1]benzoxepino[5,4-d]thiazole-2-carboxylate which was directed subjected to General Procedure M to afford 29 mg and 30 mg (37% overall yield) after reverse phase purification then chiral separation. The absolute stereochemistry at the 4-fluorine substitution position for each isomer was not determined.

Compound 1 $^1$H NMR (400 MHz, DMSO-d6) δ 8.60 (d, J=2.1 Hz, 1H), 8.58 (s, 1H), 8.01 (s, 1H), 7.43 (dd, J=8.4, 2.2 Hz, 1H), 7.18 (d, J=8.4 Hz, 1H), 6.41 (d, J=1.5 Hz, 1H), 6.30-6.15 (m, 1H), 4.89-4.79 (m, 1H), 4.27-4.13 (m, 1H), 3.40-3.33 (m, 2H), 2.80 (s, 3H), 2.47-2.41 (m, 1H), 2.24-2.16 (m, 1H).

Compound 2 $^1$H NMR (400 MHz, DMSO-d6) δ 8.59 (d, J=2.2 Hz, 1H), 8.58 (s, 1H), 8.01 (s, 1H), 7.43 (dd, J=8.3, 2.2 Hz, 1H), 7.18 (d, J=8.4 Hz, 1H), 6.41 (d, J=1.2 Hz, 1H), 6.32-6.14 (m, 1H), 4.91-4.79 (m, 1H), 4.28-4.12 (m, 1H), 3.39-3.33 (m, 2H), 2.80 (s, 3H), 2.48-2.41 (m, 1H), 2.25-2.15 (m, 1H).

Example 487

Synthesis of (S)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide and (R)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide

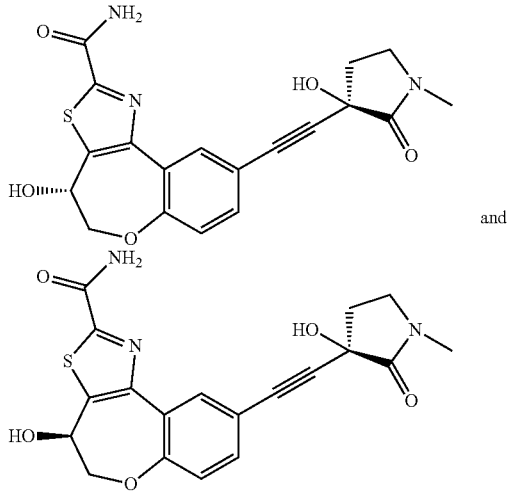

and

Methyl 9-bromo-4-oxo-[1]benzoxepino[5,4-d]thiazole-2-carboxylate (0.37 g) was subjected to General Procedure 0 to afford 280 mg (75%) of methyl 9-bromo-4-hydroxy-4,5-dihydro-[1]benzoxepino[5,4-d]thiazole-2-carboxylate. Methyl 9-bromo-4-hydroxy-4,5-dihydro-[1]benzoxepino[5,4-d]thiazole-2-carboxylate (128 mg) was reacted with (3R)-3-ethynyl-3-hydroxy-1-methyl-pyrrolidin-2-one similarly to as described in General Procedure F with non-critical modifications to afford methyl 4-hydroxy-9-[2-[(3R)-3-hydroxy-1-methyl-2-oxo-pyrrolidin-3-yl]ethynyl]-4,5-dihydro-[1]benzoxepino[5,4-d]thiazole-2-carboxylate which was directed subjected to General Procedure M to afford 25 mg and 7.9 mg (26% overall yield) after reverse phase purification then chiral separation. The absolute stereochemistry at the 4-hydroxyl substitution position for each isomer was not determined.

Compound 1 1H NMR (400 MHz, DMSO-d6) δ 8.59 (d, J=2.2 Hz, 1H), 8.44 (s, 1H), 7.87 (s, 1H), 7.34 (dd, J=8.3, 2.2 Hz, 1H), 7.09 (d, J=8.3 Hz, 1H), 6.38 (s, 1H), 6.35 (d, J=7.3 Hz, 1H), 5.16-5.07 (m, 1H), 4.38-4.30 (m, 1H), 4.17-4.07 (m, 1H), 3.37-3.33 (m, 2H), 2.80 (s, 3H), 2.48-2.41 (m, 1H), 2.23-2.15 (m, 1H).

Compound 2 analytical data was not collected.

Example 488

Synthesis of (S)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide and (R)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide

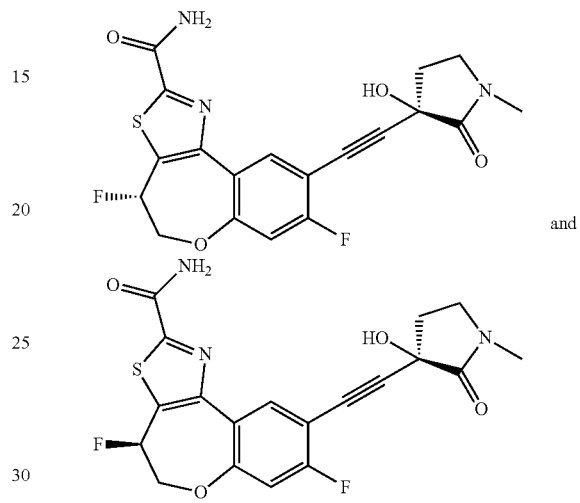

and

Ethyl 9-bromo-8-fluoro-4-oxo-4,5-dihydrobenzo[2,3]oxepino[4,5-d]thiazole-2-carboxylate was subjected to General Procedure Ketone/Aldehyde Reduction to afford 141 mg (94%) ethyl 9-bromo-8-fluoro-4-hydroxy-4,5-dihydro-[1]benzoxepino[5,4-d]thiazole-2-carboxylate. Ethyl 9-bromo-8-fluoro-4-hydroxy-4,5-dihydro-[1]benzoxepino[5,4-d]thiazole-2-carboxylate was reacted similarly to as described in General Procedure P with non-critical modifications to afford 105 mg (74%) of ethyl 9-bromo-4,8-difluoro-4,5-dihydro-[1]benzoxepino[5,4-d]thiazole-2-carboxylate. Ethyl 9-bromo-4,8-difluoro-4,5-dihydro-[1]benzoxepino[5,4-d]thiazole-2-carboxylate (105 mg) was reacted with (3R)-3-ethynyl-3-hydroxy-1-methyl-pyrrolidin-2-one similarly to as described in General Procedure F with non-critical modifications to afford methyl 4-hydroxy-9-[2-[(3R)-3-hydroxy-1-methyl-2-oxo-pyrrolidin-3-yl]ethynyl]-4,5-dihydro-[1]benzoxepino[5,4-d]thiazole-2-carboxylate which was directed subjected to General Procedure M to afford 14.2 mg and 12.4 mg (24% overall yield) after reverse phase purification then chiral separation. The absolute stereochemistry at the 4-fluorine substitution position for each isomer was not determined.

Compound 1 NMR (400 MHz, DMSO-d6) δ 8.67 (d, J=8.4 Hz, 1H), 8.63 (s, 1H), 8.02 (s, 1H), 7.19 (d, J=10.2 Hz, 1H), 6.49 (s, 1H), 6.31-6.16 (m, 1H), 4.93-4.81 (m, 1H), 4.36-4.20 (m, 1H), 3.41-3.33 (m, 2H), 2.81 (s, 3H), 2.48-2.41 (m, 1H), 2.27-2.17 (m, 1H).

Compound 1 $^1$H NMR (400 MHz, DMSO-d6) δ 8.68 (d, J=8.3 Hz, 1H), 8.62 (s, 1H), 8.02 (s, 1H), 7.19 (d, J=10.2 Hz, 1H), 6.49 (s, 1H), 6.31-6.16 (m, 1H), 4.91-4.82 (m, 1H), 4.35-4.20 (m, 1H), 3.39-3.33 (m, 2H), 2.81 (s, 3H), 2.48-2.42 (m, 1H), 2.26-2.18 (m, 1H).

Example 489

Synthesis of (R)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (S)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

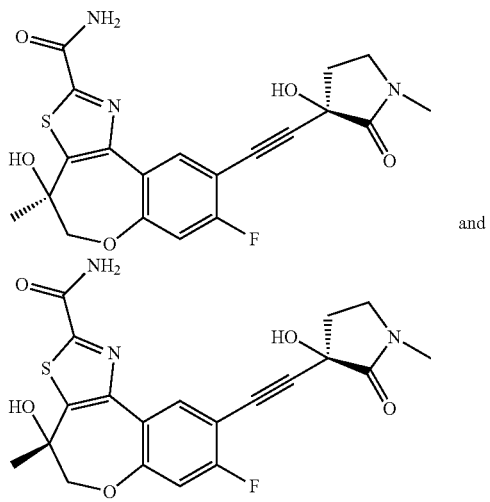

and

Ethyl 9-bromo-8-fluoro-4-oxo-[1]benzoxepino[5,4-d]thiazole-2-carboxylate (415 mg) was reacted with methylmagnesium bromide similarly to as described in the synthesis of 4-Hydroxy-9-(3-hydroxy-3-methyl-but-1-ynyl)-4-methyl-4,5-dihydro-6-oxa-3-thia-1-aza-benzo{e}azulene-2-carboxylic amide with non-critical modifications to afford ethyl 9-bromo-8-fluoro-4-hydroxy-4-methyl-5H-[1]benzoxepino[5,4-d]thiazole-2-carboxylate. Ethyl 9-bromo-8-fluoro-4-hydroxy-4-methyl-5H-[1]benzoxepino[5,4-d]thiazole-2-carboxylate (272 mg) was reacted with (3R)-3-ethynyl-3-hydroxy-1-methyl-pyrrolidin-2-one similarly to as described in General Procedure F with non-critical modifications to afford ethyl 8-fluoro-4-hydroxy-9-[2-[(3R)-3-hydroxy-1-methyl-2-oxo-pyrrolidin-3-yl]ethynyl]-4-methyl-5H-[1]benzoxepino[5,4-d]thiazole-2-carboxylate which was directed subjected to General Procedure M to afford 23.3 mg and 27.4 mg (17.4% overall yield) after reverse phase purification then chiral separation. The absolute stereochemistry at the 4-hydroxyl substitution position for each isomer was not determined Compound 1 $^1$H NMR (400 MHz, DMSO-d6) δ 8.67 (d, J=8.5 Hz, 1H), 8.52 (s, 1H), 7.90 (s, 1H), 7.10 (d, J=10.3 Hz, 1H), 6.51 (s, 1H), 6.30 (s, 1H), 4.24 (d, J=11.8 Hz, 1H), 4.06 (d, J=11.8 Hz, 1H), 3.42-3.35 (m, 2H), 2.80 (s, 3H), 2.48-2.41 (m, 1H), 2.26-2.17 (m, 1H), 1.56 (s, 3H).

Compound 2 NMR (400 MHz, DMSO-d6) δ 8.67 (d, J=8.5 Hz, 1H), 8.52 (s, 1H), 7.90 (s, 1H), 7.10 (d, J=10.3 Hz, 1H), 6.52 (s, 1H), 6.31 (s, 1H), 4.24 (d, J=11.8 Hz, 1H), 4.06 (d, J=11.8 Hz, 1H), 3.44-3.39 (m, 2H), 2.80 (s, 3H), 2.49-2.40 (m, 1H), 2.26-2.17 (m, 1H), 1.56 (s, 3H).

Example 490

Synthesis of (S)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (R)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

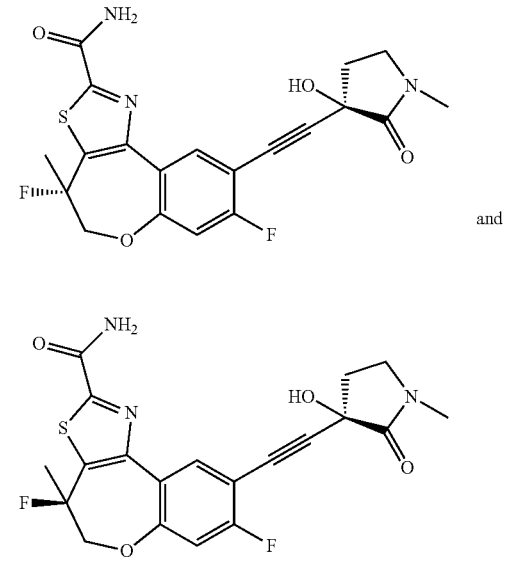

and

Ethyl 9-bromo-8-fluoro-4-hydroxy-4-methyl-5H-[1]benzoxepino[5,4-d]thiazole-2-carboxylate (170 mg) was reacted similarly to as described in General Procedure P with non-critical modifications to afford 130 mg (76%) of ethyl 9-bromo-4,8-difluoro-4-methyl-5H-[1]benzoxepino[5,4-d]thiazole-2-carboxylate. Ethyl 9-bromo-4,8-difluoro-4-methyl-5H-[1]benzoxepino[5,4-d]thiazole-2-carboxylate (122 mg) was reacted with (3R)-3-ethynyl-3-hydroxy-1-methyl-pyrrolidin-2-one similarly to as described in General Procedure F with non-critical modifications to afford ethyl 4,8-difluoro-9-[2-[(3R)-3-hydroxy-1-methyl-2-oxo-pyrrolidin-3-yl]ethynyl]-4-methyl-5H-[1]benzoxepino[5,4-d]thiazole-2-carboxylate which was directed subjected to General Procedure M to afford 7.2 mg and 6.9 mg (11% overall yield) after reverse phase purification then chiral separation. The absolute stereochemistry at the 4-fluorine substitution position for each isomer was not determined.

Compound 1 $^1$H NMR (400 MHz, DMSO-d6) δ 8.65 (d, J=8.4 Hz, 1H), 8.61 (s, 1H), 8.00 (s, 1H), 7.18 (d, J=10.1 Hz, 1H), 6.49 (s, 1H), 4.70-4.59 (m, 1H), 4.42-4.29 (m, 1H), 3.40-3.32 (m, 2H), 2.80 (s, 3H), 2.47-2.42 (m, 1H), 2.26-2.18 (m, 1H), 1.79 (d, J=20.5 Hz, 3H).

Compound 2 $^1$H NMR (400 MHz, DMSO-d6) δ 8.65 (d, J=8.3 Hz, 1H), 8.61 (s, 1H), 8.00 (s, 1H), 7.18 (d, J=10.1 Hz, 1H), 6.49 (s, 1H), 4.70-4.59 (m, 1H), 4.43-4.28 (m, 1H), 3.41-3.33 (m, 2H), 2.80 (s, 3H), 2.51-2.40 (m, 1H), 2.28-2.16 (m, 1H), 1.79 (d, J=20.5 Hz, 3H).

Example 491

Synthesis of N3-cyclopropyl-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2,3-dicarboxamide

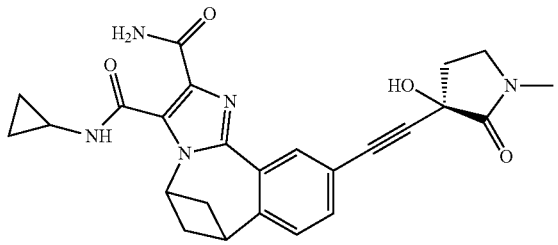 [SMILES: CN1CC[C@@](O)(C#Cc2ccc3c(c2)-c2nc(C(N)=O)c(C(=O)NC4CC4)n2C2CC3C2)C1=O]

10-bromo-2-carbamoyl-6,7-dihydro-5H-5,7-methanobenzo[c]imidazo[1,2-a]azepine-3-carboxylic acid was reacted with cyclopropylamine similarly to as described in example 2 with non-critical modifications to afford 141 mg (85%) 10-bromo-N3-cyclopropyl-6,7-dihydro-5H-5,7-methanobenzo[c]imidazo[1,2-a]azepine-2,3-dicarboxamide. 10-bromo-N3-cyclopropyl-6,7-dihydro-5H-5,7-methanobenzo[c]imidazo[1,2-a]azepine-2,3-dicarboxamide was reacted with (3R)-3-ethynyl-3-hydroxy-1-methyl-pyrrolidin-2-one similarly to as described in General Procedure F with non-critical modifications to afford 29 mg (18%) of N3-cyclopropyl-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2,3-dicarboxamide.

M+1=460; $^1$H NMR (400 MHz, DMSO-d6) δ 10.79 (d, J=4.3 Hz, 1H), 8.80 (d, J=1.6 Hz, 1H), 8.23 (s, 1H), 7.73 (s, 1H), 7.37-7.28 (m, 2H), 6.43 (s, 1H), 6.15-6.06 (m, 1H), 3.73-3.63 (m, 1H), 3.40-3.33 (m, 2H), 3.17-3.06 (m, 2H), 2.87-2.82 (m, 1H), 2.81 (s, 3H), 2.49-2.41 (m, 1H), 2.25-2.15 (m, 1H), 1.71-1.61 (m, 2H), 0.76-0.69 (m, 2H), 0.53-0.46 (m, 2H).

Example 492

Synthesis of 10-[2-[(3R)-3-hydroxy-1-methyl-2-oxo-pyrrolidin-3-yl]ethynyl]-N3-isopropyl-5,6,7,12-tetrahydro-5,7-methanobenzo[c]imidazo[1,2-a]azepine-2,3-dicarboxamide

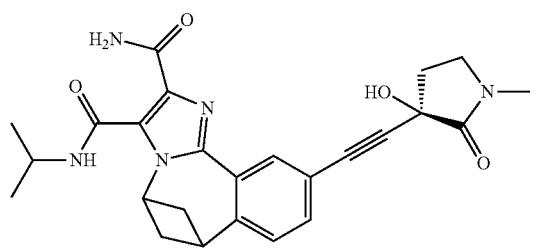 [SMILES: CC(C)NC(=O)c1c(C(N)=O)nc2n1C1CC(C1)c1ccc(C#C[C@]3(O)CCN(C)C3=O)cc1-2]

10-bromo-2-carbamoyl-6,7-dihydro-5H-5,7-methanobenzo[c]imidazo[1,2-a]azepine-3-carboxylic acid was reacted with isopropylamine similarly to as described in example 2 with non-critical modifications to afford 166 mg (99%) 10-bromo-N3-isopropyl-6,7-dihydro-5H-5,7-methanobenzo[c]imidazo[1,2-a]azepine-2,3-dicarboxamide. 10-bromo-N3-isopropyl-6,7-dihydro-5H-5,7-methanobenzo[c]imidazo[1,2-a]azepine-2,3-dicarboxamide was reacted with (3R)-3-ethynyl-3-hydroxy-1-methyl-pyrrolidin-2-one similarly to as described in General Procedure F with non-critical modifications to afford 43 mg (23%) of 10-[2-[(3R)-3-hydroxy-1-methyl-2-oxo-pyrrolidin-3-yl]ethynyl]-N3-isopropyl-5,6,7,12-tetrahydro-5,7-methanobenzo[c]imidazo[1,2-a]azepine-2,3-dicarboxamide.

M+1=462.2; $^1$H NMR (400 MHz, DMSO-d6) δ 10.77 (d, J=7.1 Hz, 1H), 8.81 (d, J=1.6 Hz, 1H), 8.24 (s, 1H), 7.73 (s, 1H), 7.37-7.27 (m, 2H), 6.22-6.12 (m, 1H), 4.03-3.93 (m, 1H), 3.40-3.31 (m, 2H), 3.17-3.05 (m, 2H), 2.81 (s, 3H), 2.48-2.42 (m, 1H), 2.24-2.16 (m, 1H), 2.08 (s, 1H), 1.70-1.62 (m, 2H), 1.16 (d, J=6.6 Hz, 6H).

Example 493

Synthesis of 10-[2-[(3R)-3-hydroxy-1-methyl-2-oxo-pyrrolidin-3-yl]ethynyl]-N3-methyl-5,6,7,12-tetrahydro-5,7-methanobenzo[c]imidazo[1,2-a]azepine-2,3-dicarboxamide

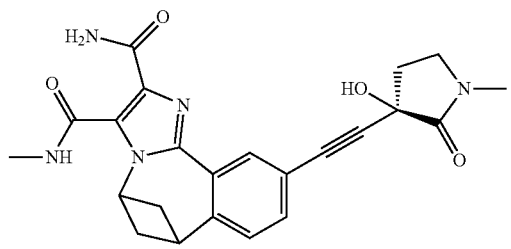

10-bromo-N3-methyl-6,7-dihydro-5H-5,7-methanobenzo[c]imidazo[1,2-a]azepine-2,3-dicarboxamide was reacted with (3R)-3-ethynyl-3-hydroxy-1-methyl-pyrrolidin-2-one similarly to as described in General Procedure F with non-critical modifications to afford 44 mg (32%) of 10-[2-[(3R)-3-hydroxy-1-methyl-2-oxo-pyrrolidin-3-yl]ethynyl]-N3-methyl-5,6,7,12-tetrahydro-5,7-methanobenzo[e]imidazo[1,2-a]azepine-2,3-dicarboxamide.

M+1=434; NMR (400 MHz, DMSO-d6) δ 10.51 (q, J=4.5 Hz, 1H), 8.81 (d, J=1.6 Hz, 1H), 8.21 (s, 1H), 7.72 (s, 1H), 7.39-7.26 (m, 2H), 6.44 (s, 1H), 6.13-6.00 (m, 1H), 3.73-3.61 (m, 1H), 3.40-3.34 (m, 2H), 3.17-3.06 (m, 2H), 2.81 (s, 3H), 2.78 (d, J=4.6 Hz, 3H), 2.49-2.41 (m, 1H), 2.25-2.15 (m, 1H), 1.69-1.62 (m, 2H).

Example 494

Synthesis of (S)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide and (R)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide

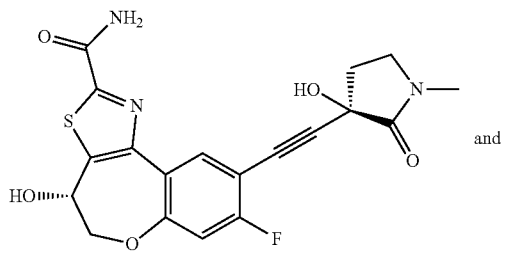

and

-continued

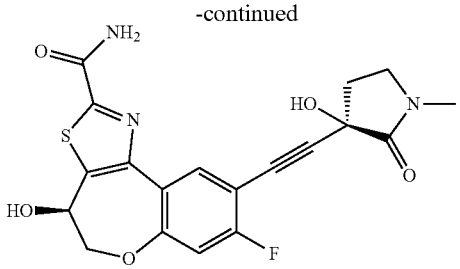

Ethyl 9-bromo-8-fluoro-4-hydroxy-4,5-dihydrobenzo[2,3]oxepino[4,5-d]thiazole-2-carboxylate was reacted with (3R)-3-ethynyl-3-hydroxy-1-methyl-pyrrolidin-2-one similarly to as described in General Procedure F to afford ethyl 8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxylate which was directed subjected to General Procedure M to afford 12.9 mg and 17.1 mg (22% overall yield) after reverse phase purification then chiral separation. The absolute stereochemistry at the 4-hydroxyl substitution position for each isomer was not determined.

Compound 1 $^1$H NMR (400 MHz, DMSO-d6) δ 8.66 (d, J=8.5 Hz, 1H), 8.49 (s, 1H), 7.88 (s, 1H), 7.08 (d, J=10.4 Hz, 1H), 6.47 (s, 1H), 6.38 (d, J=7.1 Hz, 1H), 5.15-5.07 (m, 1H), 4.40-4.33 (m, 1H), 4.21-4.14 (m, 1H), 3.41-3.34 (m, 2H), 2.80 (s, 3H), 2.48-2.41 (m, 1H), 2.26-2.17 (m, 1H).

Compound 2 $^1$H NMR (400 MHz, DMSO-d6) δ 8.66 (d, J=8.5 Hz, 1H), 8.49 (s, 1H), 7.88 (s, 1H), 7.08 (d, J=10.3 Hz, 1H), 6.47 (s, 1H), 6.38 (d, J=7.1 Hz, 1H), 5.16-5.07 (m, 1H), 4.41-4.32 (m, 1H), 4.22-4.12 (m, 1H), 3.43-3.29 (m, 2H), 2.80 (s, 3H), 2.51-2.40 (m, 1H), 2.27-2.15 (m, 1H).

Example 495

Synthesis of 10-[3-hydroxy-3-(5-methyloxazol-2-yl)but-1-ynyl]-5,6,7,12-tetrahydro-5,7-methanobenzo[c]imidazo[1,2-a]azepine-2-carboxamide and 10-[(3R)-3-hydroxy-3-(5-methyloxazol-2-yl)but-1-ynyl]-5,6,7,12-tetrahydro-5,7-methanobenzo[c]imidazo[1,2-a]azepine-2-carboxamide

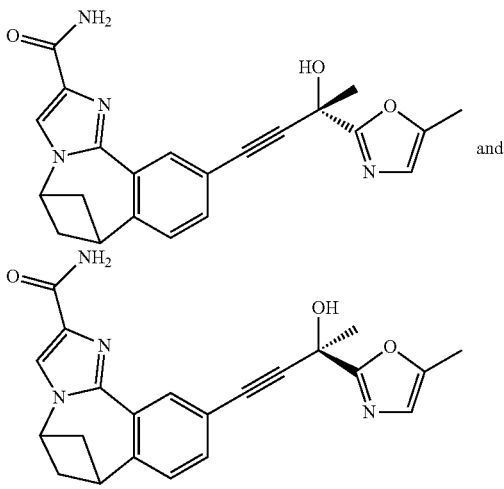

10-bromo-6,7-dihydro-5H-5,7-methanobenzo[c]imidazo[1,2-a]azepine-2-carboxamide was reacted with 2-(5-methyloxazol-2-yl)but-3-yn-2-ol as described in General Procedure G without making critical modifications to afford 79 mg and 32 mg (73% overall yield) following reverse phase purification and chiral separation. The absolute stereochemistry at propargyl alcohol stereocenter for each isomer was not determined.

Compound 1 $^1$H NMR (400 MHz, DMSO-d6) δ 8.71 (d, J=8.5 Hz, 1H), 8.48 (s, 1H), 7.85 (s, 1H), 7.06 (d, J=10.3 Hz, 1H), 6.45 (s, 1H), 6.20 (s, 1H), 4.45 (d, J=12.1 Hz, 1H), 4.02 (d, J=12.0 Hz, 1H), 3.41-3.32 (m, 2H), 2.80 (s, 3H), 2.48-2.41 (m, 1H), 2.26-2.17 (m, 1H), 2.03-1.94 (m, 1H), 0.99 (d, J=6.8 Hz, 3H), 0.89 (d, J=7.0 Hz, 3H).

Compound 2 1H NMR (400 MHz, DMSO-d6) δ 8.70 (d, J=8.5 Hz, 1H), 8.48 (s, 1H), 7.85 (s, 1H), 7.06 (d, J=10.3 Hz, 1H), 6.46 (s, 1H), 6.18 (s, 1H), 4.45 (d, J=12.0 Hz, 1H), 4.02 (d, J=12.0 Hz, 1H), 3.43-3.33 (m, 2H), 2.80 (s, 3H), 2.47-2.41 (m, 1H), 2.26-2.17 (m, 1H), 2.04-1.94 (m, 1H), 0.99 (d, J=6.8 Hz, 3H), 0.89 (d, J=6.9 Hz, 3H).

Example 496

Synthesis of (S)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide and (R)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide

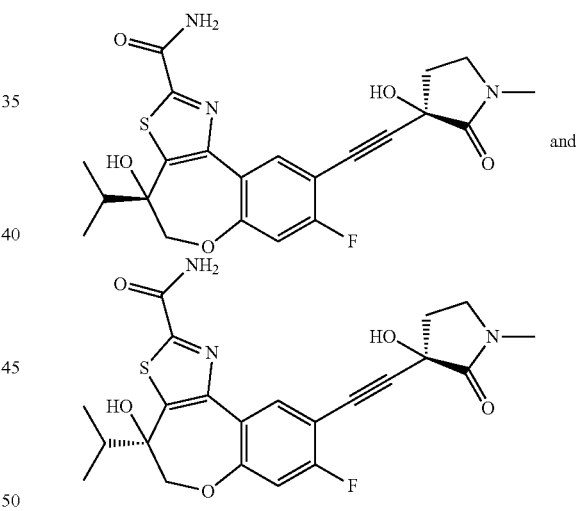

Ethyl 9-bromo-8-fluoro-4-oxo-[1]benzoxepino[5,4-d]thiazole-2-carboxylate (133 mg) was reacted with isopropylmagnesium bromide similarly to as described in the synthesis of 4-Hydroxy-9-(3-hydroxy-3-methyl-but-1-ynyl)-4-methyl-4,5-dihydro-6-oxa-3-thia-1-aza-benzo {e}azulene-2-carboxylic amide with non-critical modifications to afford ethyl 9-bromo-8-fluoro-4-hydroxy-4-isopropyl-5H-[1]benzoxepino[5,4-d]thiazole-2-carboxylate. Ethyl 9-bromo-8-fluoro-4-hydroxy-4-isopropyl-5H-[1]benzoxepino[5,4-d]thiazole-2-carboxylate (80 mg) was reacted with (3R)-3-ethynyl-3-hydroxy-1-methyl-pyrrolidin-2-one similarly to as described in General Procedure F with non-critical modifications to afford ethyl 8-fluoro-4-hydroxy-9-[2-[(3R)-3-hydroxy-1-methyl-2-oxo-pyrrolidin-3-yl]ethynyl]-4-isopropyl-5H-[1]benzoxepino[5,4-d]thiazole-2-carboxylate which was directed subjected to General Procedure M to afford 12 mg and 13 mg (29% overall yield) after reverse phase purification then chiral separation. The absolute stereochemistry at the 4-hydroxyl substitution position for each isomer was not determined.

M+1=460; $^1$H NMR (400 MHz, DMSO-d6) δ 8.70 (d, J=8.5 Hz, 1H), 8.48 (s, 1H), 7.85 (s, 1H), 7.06 (d, J=10.3 Hz, 1H), 6.46 (s, 1H), 6.18 (s, 1H), 4.45 (d, J=12.0 Hz, 1H), 4.02 (d, J=12.0 Hz, 1H), 3.43-3.33 (m, 2H), 2.80 (s, 3H), 2.47-2.41 (m, 1H), 2.26-2.17 (m, 1H), 2.04-1.94 (m, 1H), 0.99 (d, J=6.8 Hz, 3H), 0.89 (d, J=6.9 Hz, 3H).

Example 497

Synthesis of 10-bromo-9-fluoro-3-(3-(pyridin-3-yl)-1H-1,2,4-triazol-5-yl)-5,6-dihydrobenzo[f]imidazo[1,2-d][1,4]oxazepine-2-carboxamide

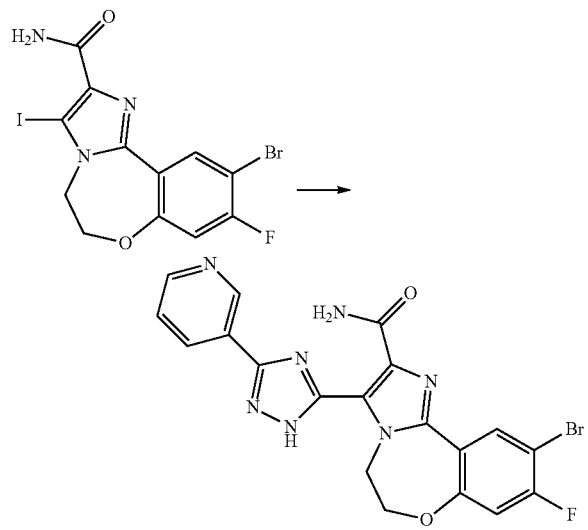

10-bromo-9-fluoro-3-(3-(pyridin-3-yl)-1H-1,2,4-triazol-5-yl)-5,6-dihydrobenzo[f]imidazo[1,2-d][1,4]oxazepine-2-carboxamide was prepared similarly according to Procedure I. Pyridine-3-carboximidamide hydrochloride was reacted with 10-bromo-9-fluoro-3-iodo-5,6-dihydroimidazo[1,2-d][1,4]benzoxazepine-2-carboxamide then hydrazine to afford 125 mg (24% yield) of the title compound.

Example 498

Synthesis of 9-fluoro-10-(3-hydroxy-3-methyl-but-1-ynyl)-3-[3-(3-pyridyl)-1H-1,2,4-triazol-5-yl]-5,6-dihydroimidazo[1,2-d][1,4]benzoxazepine-2-carboxamide

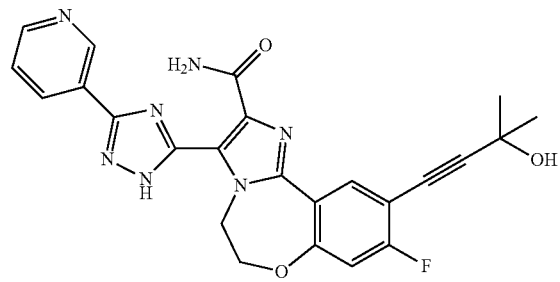 [SMILES: CC(C)(O)C#Cc1cc2c(cc1F)OCCn1c-2nc(C(N)=O)c1-c1nc(-c2cccnc2)n[nH]1]

9-fluoro-10-(3-hydroxy-3-methyl-but-1-ynyl)-3-[3-(3-pyridyl)-1H-1,2,4-triazol-5-yl]-5,6-dihydroimidazo[1,2-d][1,4]benzoxazepine-2-carboxamide was prepared similarly according to General Procedure G with slight modifications. The crude was purified by reverse-phase HPLC to afford 6.3 mg of the titled compound (12.6% yield). M+1=474.0. $^1$H NMR (400 MHz, DMSO) δ 16.05-15.24 (m, 1H), 9.31 (s, 1H), 8.71 (d, J=8.5 Hz, 1H), 8.67 (d, J=4.6 Hz, 1H), 8.57 (br s, 1H), 8.43 (d, J=8.2 Hz, 1H), 8.00 (br s, 1H), 7.56 (dd, J=7.8, 4.9 Hz, 1H), 7.08 (d, J=10.5 Hz, 1H), 5.56 (s, 1H), 5.25-5.11 (m, 2H), 4.70-4.63 (m, 2H), 1.51 (s, 6H).

Example 499

Synthesis of (±)-methyl 10-bromo-9-fluoro-3-(hydroxy(1-methyl-1H-pyrazol-5-yl)methyl)-5,6-dihydrobenzo[f]imidazo[1,2-d][1,4]oxazepine-2-carboxylate

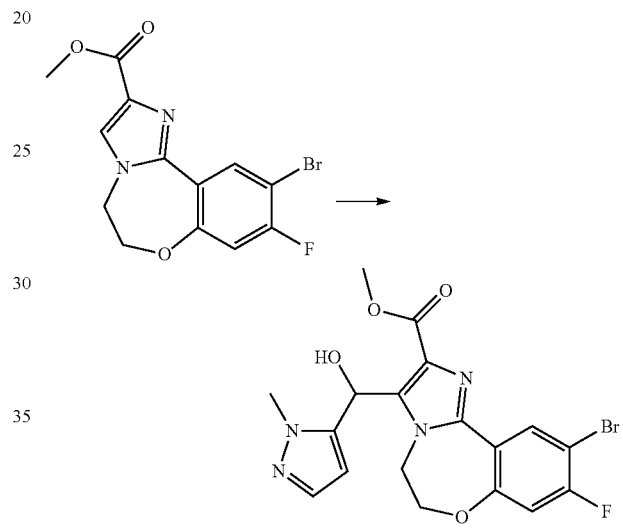

Methyl 10-bromo-9-fluoro-3-(hydroxy(1-methyl-1H-pyrazol-5-yl)methyl)-5,6-dihydrobenzo[f]imidazo[1,2-d][1,4]oxazepine-2-carboxylate was prepared similarly according to the procedure in Example 9. Methyl 10-bromo-9-fluoro-5,6-dihydroimidazo[1,2-d][1,4]benzoxazepine-2-carboxylate was reacted with 1-methylpyrazole-5-carbaldehyde to afford 219 mg (33% yield) of the title compound.

Example 500

Synthesis of (±)-10-bromo-9-fluoro-3-(hydroxy(1-methyl-1H-pyrazol-5-yl)methyl)-5,6-dihydrobenzo[f]imidazo[1,2-d][1,4]oxazepine-2-carboxylic acid

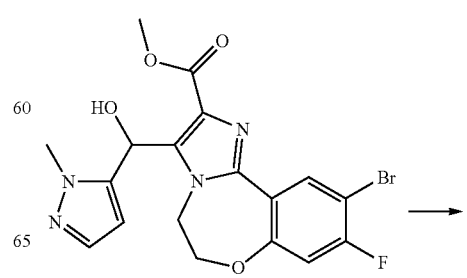

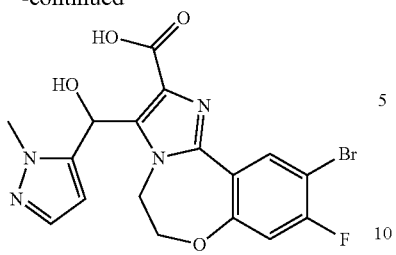

10-bromo-9-fluoro-3-(hydroxy(1-methyl-1H-pyrazol-5-yl)methyl)-5,6-dihydrobenzo[f]imidazo[1,2-d][1,4]oxazepine-2-carboxylic acid was prepared similarly according to the procedure for the synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid. methyl 10-bromo-9-fluoro-3-[hydroxy-(2-methylpyrazol-3-yl)methyl]-5,6-dihydroimidazo[1,2-d][1,4]benzoxazepine-2-carboxylate was reacted with lithium hydroxide to afford 160 mg (87% yield) of the title compound.

Example 501

Synthesis of (±)-10-bromo-9-fluoro-3-[hydroxy-(2-methylpyrazol-3-yl)methyl]-5,6-dihydroimidazo[1,2-d][1,4]benzoxazepine-2-carboxamide

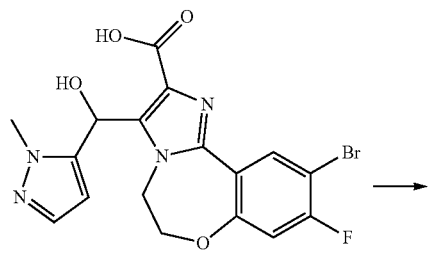

10-bromo-9-fluoro-3-[hydroxy-(2-methylpyrazol-3-yl)methyl]-5,6-dihydroimidazo[1,2-d][1,4]benzoxazepine-2-carboxamide was prepared similarly according to the procedure in Example 2.

10-bromo-9-fluoro-3-(hydroxy(1-methyl-1H-pyrazol-5-yl)methyl)-5,6-dihydrobenzo[f]imidazo[1,2-d][1,4]oxazepine-2-carboxylic acid was reacted with ammonium chloride and purified by flash chromatography to afford 79 mg (50% yield) of the title compound.

Example 502

Synthesis of (±)-9-fluoro-10-(3-hydroxy-3-methyl-but-1-ynyl)-3-[hydroxy-(2-methylpyrazol-3-yl)methyl]-5,6-dihydroimidazo[1,2-d][1,4]benzoxazepine-2-carboxamide

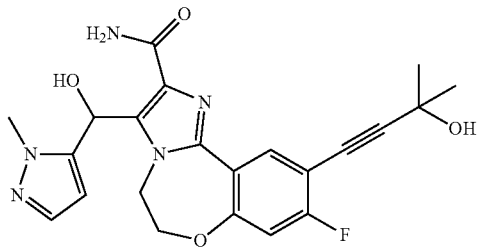 [SMILES: Cn1nccc1C(O)c1c(C(N)=O)nc2n1CCOc1cc(F)c(C#CC(C)(C)O)cc1-2]

9-fluoro-10-(3-hydroxy-3-methyl-but-1-ynyl)-3-[hydroxy-(2-methylpyrazol-3-yl)methyl]-5,6-dihydroimidazo[1,2-d][1,4]benzoxazepine-2-carboxamide was prepared similarly was prepared similarly according to General Procedure G with slight modifications. 10-bromo-9-fluoro-3-[hydroxy-(2-methylpyrazol-3-yl)methyl]-5,6-dihydroimidazo[1,2-d][1,4]benzoxazepine-2-carboxamide was reacted with 2-methyl-3-butyne-ol to afford 12.9 mg of the titled compound (35.6% yield). M+1=440.0. $^1$H NMR (500 MHz, DMSO-d6) δ 8.60 (d, J=8.4 Hz, 1H), 8.02-7.91 (m, 1H), 7.53-7.46 (m, 1H), 7.28 (d, J=1.9 Hz, 1H), 7.24 (d, J=6.2 Hz, 1H), 7.01 (d, J=10.6 Hz, 1H), 6.80 (d, J=6.1 Hz, 1H), 5.88 (d, J=1.8 Hz, 1H), 5.55 (s, 1H), 4.65-4.51 (m, 1H), 4.51-4.41 (m, 2H), 4.41-4.30 (m, 1H), 3.85 (s, 3H), 1.49 (s, 6H).

Example 503

Synthesis of (±)-9-fluoro-10-(3-hydroxy-3-(pyridin-2-yl)but-1-yn-1-yl)-6,7-dihydro-5H-5,7-methanobenzo[c]imidazo[1,2-a]azepine-2-carboxamide

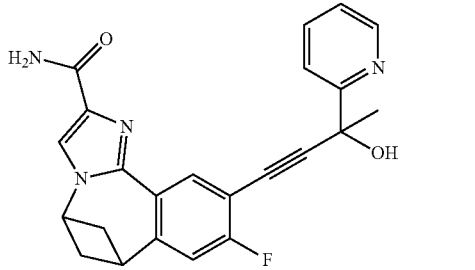 [SMILES: CC(O)(C#Cc1cc2c(cc1F)C1CC(C1)n1cc(C(N)=O)nc1-2)c1ccccn1]

9-fluoro-10-(3-hydroxy-3-(pyridin-2-yl)but-1-yn-1-yl)-6,7-dihydro-5H-5,7-methanobenzo[c]imidazo[1,2-a]azepine-2-carboxamide was prepared similarly according to General Procedure G with slight modifications. 10-bromo-9-fluoro-6,7-dihydro-5H-5,7-methanobenzo[c]imidazo[1,2-a]azepine-2-carboxamide was reacted with 2-(2-pyridyl)but-3-yn-2-ol to afford 7.5 mg of the titled compound (6.3% yield). M+1=403.1. $^1$H NMR (400 MHz, DMSO) δ 8.64 (d, J=7.6 Hz, 1H), 8.58 (d, J=4.6 Hz, 1H), 7.90-7.84 (m, 1H), 7.82 (s, 1H), 737 (d, J=7.9 Hz, 1H), 7.57 (br s, 1H), 7.38-7.32 (m, 1H),

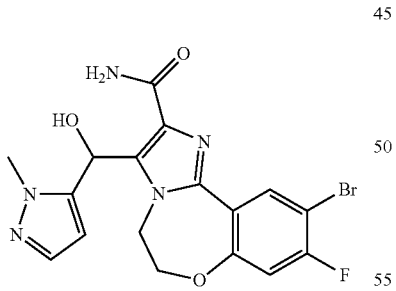

7.29 (d, J=10.1 Hz, 1H), 7.11 (br s, 1H), 6.47 (s, 1H), 4.94-4.87 (m, 1H), 3.75-3.67 (m, 1H), 3.14-3.03 (m, 2H), 1.83 (s, 3H), 1.71-1.64 (m, 2H).

Example 504

Synthesis of (±)-Methyl 10-bromo-3-((3,5-difluorophenyl)(hydroxy)methyl)-9-fluoro-5,6-dihydrobenzo[f]imidazo[1,2-d][1,4]oxazepine-2-carboxylate

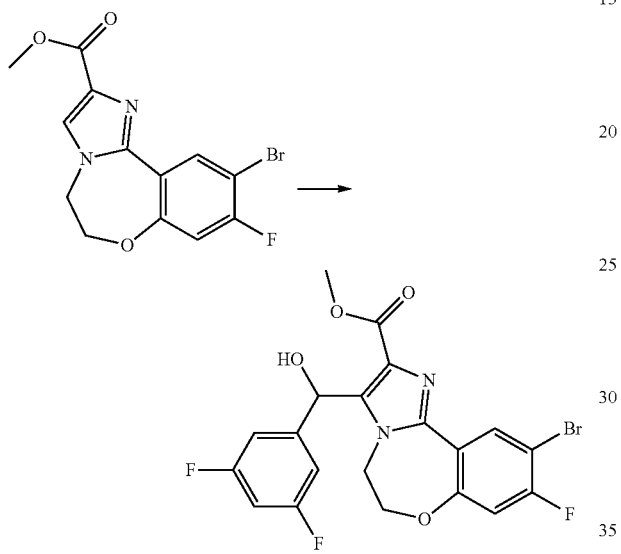

Methyl 10-bromo-3-((3,5-difluorophenyl)(hydroxy)methyl)-9-fluoro-5,6-dihydrobenzo[f]imidazo[1,2-d][1,4]oxazepine-2-carboxylate was prepared similarly according to the procedure in Example 9. Methyl 10-bromo-9-fluoro-5,6-dihydrobenzo[f]imidazo[1,2-d][1,4]oxazepine-2-carboxylate was reacted with 3,5-difluorobenzaldehyde to afford 291 mg (69% yield) of the title compound.

Example 505

Synthesis of (±)-10-bromo-3-((3,5-difluorophenyl)(hydroxy)methyl)-9-fluoro-5,6-dihydrobenzo[f]imidazo[1,2-d][1,4]oxazepine-2-carboxylic acid

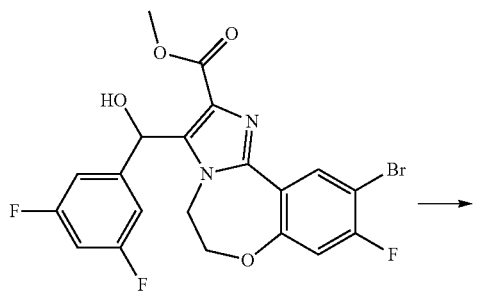

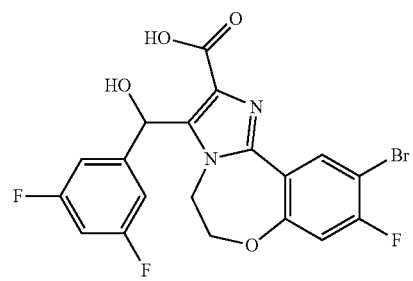

10-bromo-3-((3,5-difluorophenyl)(hydroxy)methyl)-9-fluoro-5,6-dihydrobenzo[f]imidazo[1,2-d][1,4]oxazepine-2-carboxylic acid was prepared similarly according to the procedure for the synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid. Methyl 10-bromo-3-((3,5-difluorophenyl)(hydroxy)methyl)-9-fluoro-5,6-dihydrobenzo[f]imidazo[1,2-d][1,4]oxazepine-2-carboxylate was reacted with lithium hydroxide to the crude title compound which was carried forward without further purification.

Example 506

Synthesis of (±)-10-bromo-3-((3,5-difluorophenyl)(hydroxy)methyl)-9-fluoro-5,6-dihydrobenzo[f]imidazo[1,2-d][1,4]oxazepine-2-carboxamide

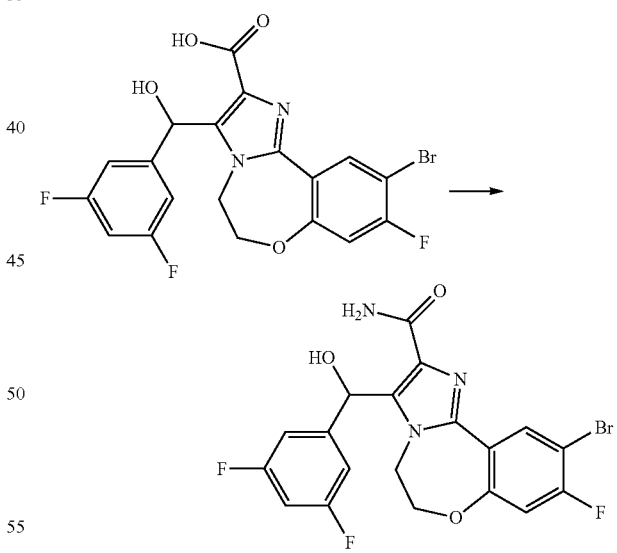

10-bromo-3-((3,5-difluorophenyl)(hydroxy)methyl)-9-fluoro-5,6-dihydrobenzo[f]imidazo[1,2-d][1,4]oxazepine-2-carboxamide was prepared similarly according to the procedure in Example 2.

10-bromo-3-((3,5-difluorophenyl)(hydroxy)methyl)-9-fluoro-5,6-dihydrobenzo[f]imidazo[1,2-d][1,4]oxazepine-2-carboxylic acid was reacted with ammonium chloride and purified by flash chromatography to afford 57 mg (45% yield) of the title compound.

Example 507

Synthesis of (±)-3-((3,5-difluorophenyl)(hydroxy)methyl)-9-fluoro-10-(3-hydroxy-3-methylbut-1-yn-1-yl)-5,6-dihydrobenzo[f]imidazo[1,2-d][1,4]oxazepine-2-carboxamide

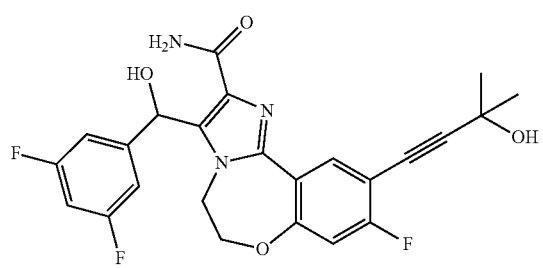 [SMILES: CC(C)(O)C#Cc1cc2c(cc1F)OCCn1c-2nc(C(N)=O)c1C(O)c1cc(F)cc(F)c1]

3-((3,5-difluorophenyl)(hydroxy)methyl)-9-fluoro-10-(3-hydroxy-3-methylbut-1-yn-1-yl)-5,6-dihydrobenzo[f]imidazo[1,2-d][1,4]oxazepine-2-carboxamide was prepared similarly according to General Procedure G with slight modifications. 10-bromo-3-((3,5-difluorophenyl)(hydroxy)methyl)-9-fluoro-5,6-dihydrobenzo[f]imidazo[1,2-d][1,4]oxazepine-2-carboxamide was reacted with 3-methyl-1-butyne-3-ol to afford 25.7 mg of the titled compound (45% yield). M+1=472.1. 1H NMR (400 MHz, DMSO) δ 8.57 (d, J=8.4 Hz, 1H), 7.94 (br s, 1H), 7.47 (br s, 1H), 7.18-7.06 (m, 2H), 7.05-7.00 (m, 2H), 6.98 (d, J=10.6 Hz, 1H), 6.91-6.85 (m, 1H), 5.54 (s, 1H), 4.58-4.49 (m, 1H), 4.48-4.36 (m, 2H), 4.11-3.92 (m, 1H), 1.49 (s, 6H).

Example 508

Synthesis of (±)-9-fluoro-10-(3-hydroxy-3-(14(2-(trimethylsilyl)ethoxy)methyl)-1H-1,2,4-triazol-3-yl)but-1-yn-1-yl)-6,7-dihydro-5H-5,7-methanobenzo[c]imidazo[1,2-a]azepine-2-carboxamide

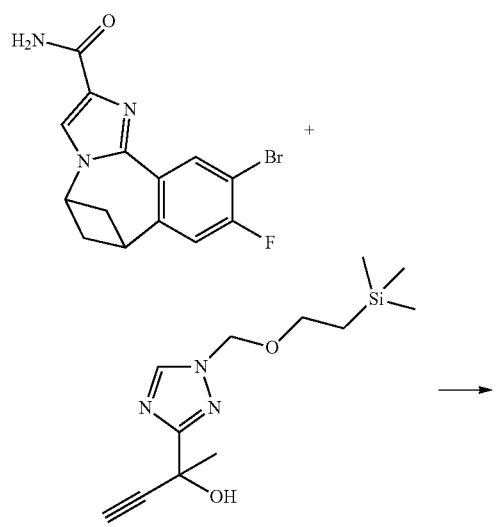

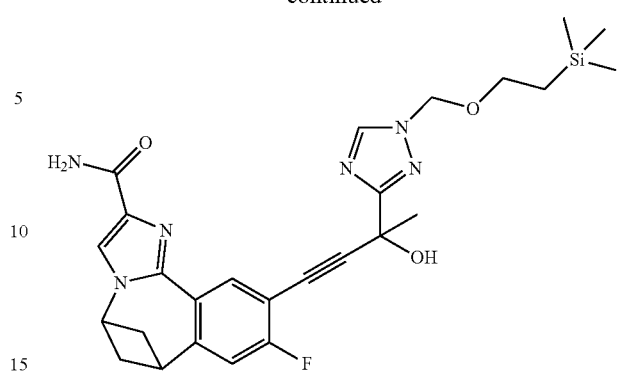

9-fluoro-10-(3-hydroxy-3-(14(2-(trimethylsilyl)ethoxy)methyl)-1H-1,2,4-triazol-3-yl) but-1-yn-1-yl)-6,7-dihydro-5H-5,7-methanobenzo[c]imidazo[1,2-a]azepine-2-carboxamide was prepared similarly according to General Procedure G with slight modifications. 10-bromo-9-fluoro-6,7-dihydro-5H-5,7-methanobenzo[c]imidazo[1,2-a]azepine-2-carboxamide was reacted with 2-[1-(2-trimethylsilylethoxymethyl)-1,2,4-triazol-3-yl]but-3-yn-2-ol to afford the title compound which was carried forward without further purification. Reaction did not go to completion.

Example 509

Synthesis of (±)-9-fluoro-10-(3-hydroxy-3-(1H-1,2,4-triazol-3-yl)but-1-yn-1-yl)-6,7-dihydro-5H-5,7-methanobenzo[c]imidazo[1,2-a]azepine-2-carboxamide

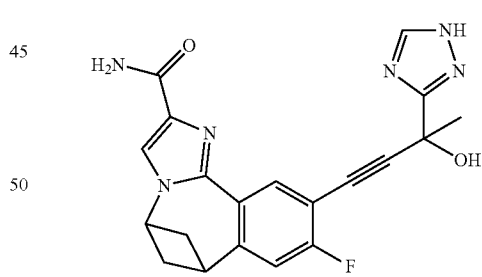

9-fluoro-10-(3-hydroxy-3-(14(2-(trimethylsilyl)ethoxy)methyl)-1H-1,2,4-triazol-3-yl) but-1-yn-1-yl)-6,7-dihydro-5H-5,7-methanobenzo[c]imidazo[1,2-a]azepine-2-carboxamide was dissolved in methylene chloride (0.7 mL) and trifluoroacetic acid (30 equiv., 0.5 mL) and stirred at room temperature for 6 h. Complete deprotection was observed by LC/MS. The crude was purified by reverse-phase HPLC to afford 1.1 mg (1.1% yield) of the title compound. M+1=393.1.

Example 510

Synthesis of (R)-9-fluoro-10-(3-hydroxy-4-methoxy-3-methylbut-1-yn-1-yl)-6,7-dihydro-5H-5,7-methanobenzo[c]imidazo[1,2-a]azepine-2-carboxamide and (S)-9-fluoro-10-(3-hydroxy-4-methoxy-3-methylbut-1-yn-1-yl)-6,7-dihydro-5H-5,7-methanobenzo[c]imidazo[1,2-a]azepine-2-carboxamide

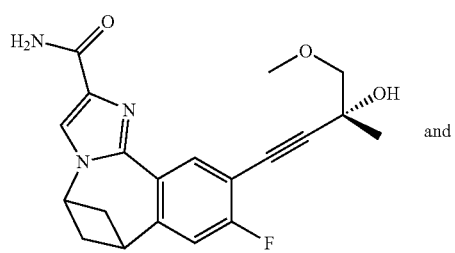

and

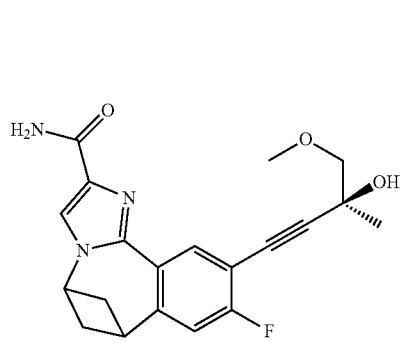

(R)-9-fluoro-10-(3-hydroxy-4-methoxy-3-methylbut-1-yn-1-yl)-6,7-dihydro-5H-5,7-methanobenzo[e]imidazo[1,2-a]azepine-2-carboxamide and (S)-9-fluoro-10-(3-hydroxy-4-methoxy-3-methylbut-1-yn-1-yl)-6,7-dihydro-5H-5,7-methanobenzo[c]imidazo[1,2-a]azepine-2-carboxamide were prepared similarly according to General Procedure G with slight modifications. 10-bromo-9-fluoro-6,7-dihydro-5H-5,7-methanobenzo[c]imidazo[1,2-a]azepine-2-carboxamide was reacted with 1-methoxy-2-methyl-but-3-yn-2-ol to afford 58.1 mg (53% yield). The enantiomers were separated by chiral SFC to afford 20.1 mg of Compound 1 and 19.6 mg of Compound 2. M+1=370.1. 1H NMR (400 MHz, DMSO) δ 8.65 (d, J=7.6 Hz, 1H), 7.83 (s, 1H), 7.56 (br s, 1H), 7.29 (d, J=10.2 Hz, 1H), 7.13 (br s, 1H), 5.69 (s, 1H), 4.94-4.88 (m, 1H), 3.75-3.67 (m, 1H), 3.44 (d, J=9.7 Hz, 1H), 3.38 (d, J=9.4 Hz, 1H), 3.38 (s, 3H), 3.14-3.04 (m, 2H), 1.72-1.64 (m, 2H), 1.45 (s, 3H).

Example 511

Synthesis of (R)-9-fluoro-3-(hydroxy(1-methyl-1H-pyrazol-4-yl)methyl)-10-(3-hydroxy-3-methylbut-1-yn-1-yl)-5,6-dihydrobenzo[f]imidazo[1,2-d][1,4]oxazepine-2-carboxamide and (S)-9-fluoro-3-(hydroxy(1-methyl-1H-pyrazol-4-yl)methyl)-10-(3-hydroxy-3-methylbut-1-yn-1-yl)-5,6-dihydrobenzo[f]imidazo[1,2-d][1,4]oxazepine-2-carboxamide

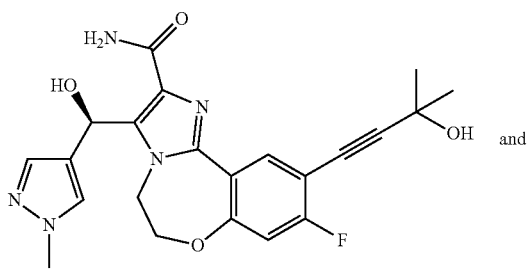

and

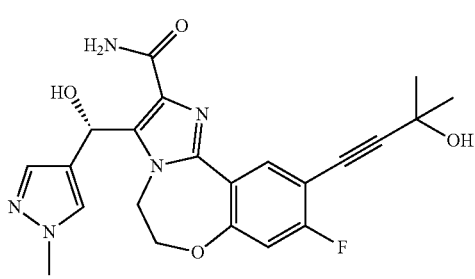 [SMILES: Cc1nn(C)cc1C(O)c1c(C(N)=O)nc2n1CCOc1cc(F)c(C#CC(C)(C)O)cc1-2]

(R)-9-fluoro-3-(hydroxy(1-methyl-1H-pyrazol-4-yl)methyl)-10-(3-hydroxy-3-methyl but-1-yn-1-yl)-5,6-dihydrobenzo[f]imidazo[1,2-d][1,4]oxazepine-2-carboxamide AND (S)-9-fluoro-3-(hydroxy(1-methyl-1H-pyrazol-4-yl)methyl)-10-(3-hydroxy-3-methylbut-1-yn-1-yl)-5,6-dihydrobenzo[f]imidazo[1,2-d][1,4]oxazepine-2-carboxamide were prepared similarly according to General Procedure G with slight modifications. 10-bromo-9-fluoro-3-[hydroxy-(1-methylpyrazol-4-yl)methyl]-5,6-dihydroimidazo[1,2-d][1,4]benz oxazepine-2-carboxamide was reacted with 2-methyl-3-butyne-ol to afford 24.8 mg (30% yield). The enantiomers were separated by chiral SFC to afford 5.9 mg of Compound 1 and 6.2 mg of the Compound 2. The absolute stereochemistry for each isomer was not determined. M+1=422; 1H NMR (400 MHz, DMSO) δ 8.57 (d, J=8.5 Hz, 1H), 7.87 (br s, 1H), 7.44 (s, 1H), 7.40 (br s, 1H), 7.26 (s, 1H), 6.99 (d, J=10.5 Hz, 1H), 6.85 (d, J=6.4 Hz, 1H), 6.57 (d, J=6.3 Hz, 1H), 5.54 (s, 1H), 4.58-4.37 (m, 3H), 4.36-4.26 (m, 1H), 3.75 (s, 3H), 1.49 (s, 6H).

Example 512

Synthesis of (±)-methyl 10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxylate

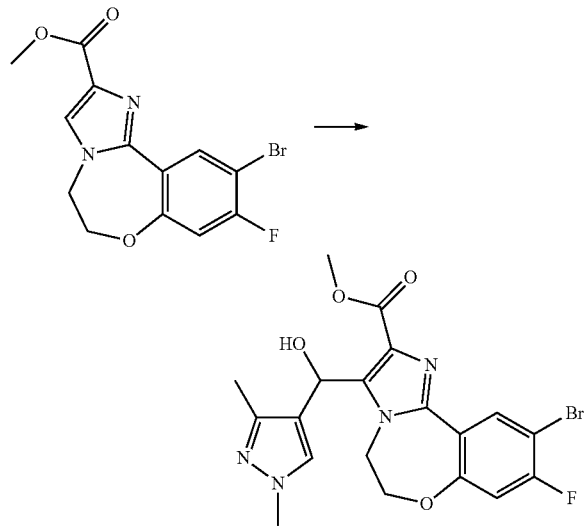

Methyl 10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxylate was prepared similarly according to the procedure in Example 9. methyl 10-bromo-9-fluoro-5,6-dihydroimidazo[1,2-d][1,4]benzoxazepine-2-carboxylate was reacted with 1,3-dimethyl-1 h-pyrazole-4-carbaldehyde to afford the crude title compound which was carried forward without further purification.

Example 513

Synthesis of (±)-10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxylic acid

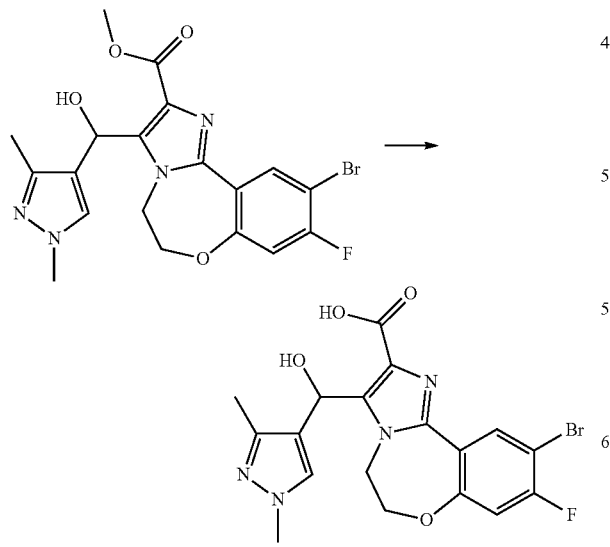

10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxylic acid was prepared similarly according to the procedure for the synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid. methyl 10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxylate was reacted with lithium hydroxide to the crude title compound which was carried forward without further purification.

Synthesis of 10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxamide

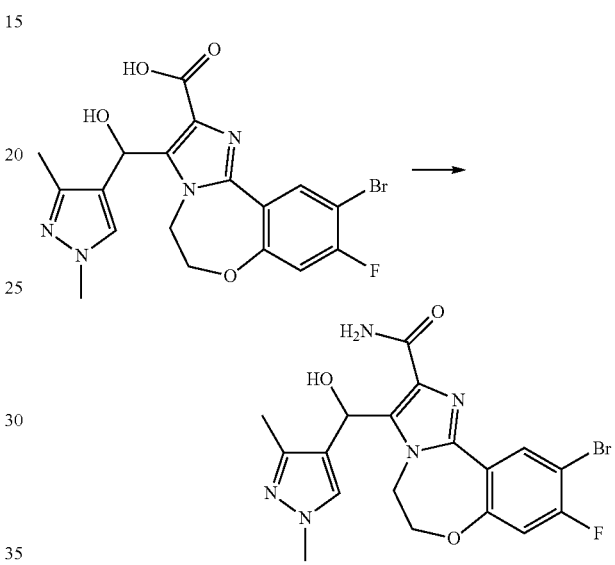

10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxamide was prepared similarly according to the procedure in Example 2. 10-bromo-3((1,3-dimethyl-1H-pyrazol-4-yl)(hydroxy)methyl)-9-fluoro-5,6-dihydrobenzo[f]imidazo[1,2-d][1,4]oxazepine-2-carboxylic acid was reacted with ammonium chloride and purified by flash chromatography to afford 134 mg (68% yield) of the title compound.

Example 514

Synthesis of (±)-3-((1,3-dimethyl-1H-pyrazol-4-yl)(hydroxy)methyl)-9-fluoro-10-(3-hydroxy-3-methyl-but-1-yn-1-yl)-5,6-dihydrobenzo[f]imidazo[1,2-d][1,4]oxazepine-2-carboxamide

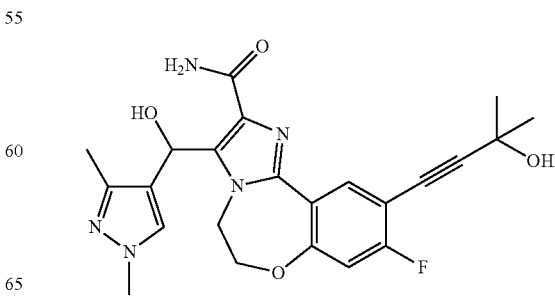

3-((1,3-dimethyl-1H-pyrazol-4-yl)(hydroxy)methyl)-9-fluoro-10-(3-hydroxy-3-methylbut-1-yn-1-yl)-5,6-dihydrobenzo[f]imidazo[1,2-d][1,4]oxazepine-2-carboxamide was prepared similarly according to General Procedure G with slight modifications. 10-bromo-3-((1,3-dimethyl-1H-pyrazol-4-yl)(hydroxy)methyl)-9-fluoro-5,6-dihydrobenzo[f]imidazo[1,2-d][1,4]oxazepine-2-carboxamide was reacted with 3-methyl-1-butyne-3-ol to afford 11.3 mg of the titled compound (19% yield). M+1=436.1. 1H NMR (400 MHz, DMSO) δ 8.58 (d, J=8.5 Hz, 1H), 7.87 (br s, 1H), 7.40 (br s, 1H), 7.25 (s, 1H), 6.99 (d, J=10.5 Hz, 1H), 6.72 (d, J=6.3 Hz, 1H), 6.52 (d, J=6.2 Hz, 1H), 5.54 (s, 1H), 4.58-4.25 (m, 4H), 3.65 (s, 3H), 2.06 (s, 3H), 1.49 (s, 6H).

Example 515

Synthesis of (±)-methyl 10-bromo-9-fluoro-3-[hydroxy-(4-methylthiazol-5-yl)methyl]-5,6-dihydroimidazo[1,2-d][1,4]benzoxazepine-2-carboxylate

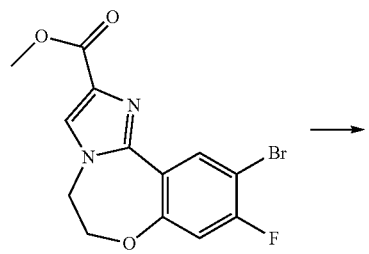

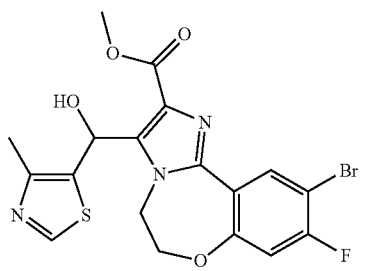

methyl 10-bromo-9-fluoro-3-[hydroxy-(4-methylthiazol-5-yl)methyl]-5,6-dihydroimidazo[1,2-d][1,4]benzoxazepine-2-carboxylate was prepared similarly according to the procedure in Example 9. Methyl 10-bromo-9-fluoro-5,6-dihydroimidazo[1,2-d][1,4]benzoxazepine-2-carboxylate was reacted with 4-methylthiazole-5-carboxaldehyde to afford the crude title compound which was carried forward without further purification.

Example 516

Synthesis of (±)-10-bromo-9-fluoro-3-[hydroxy-(4-methylthiazol-5-yl)methyl]-5,6-dihydroimidazo[1,2-d][1,4]benzoxazepine-2-carboxylic acid

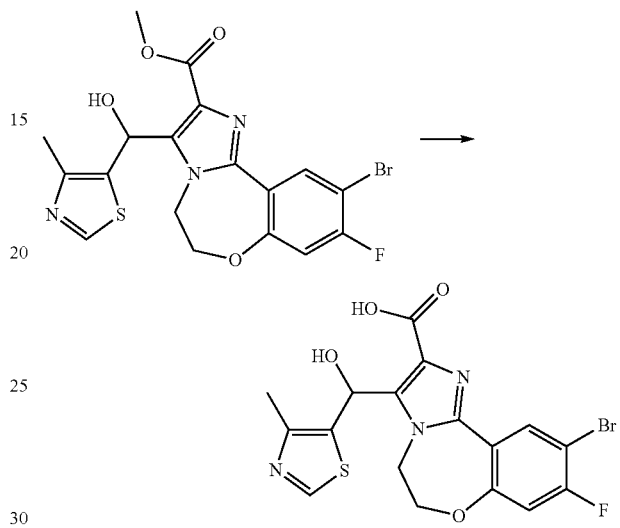

10-bromo-9-fluoro-3-[hydroxy-(4-methylthiazol-5-yl)methyl]-5,6-dihydroimidazo[1,2-d][1,4]benzoxazepine-2-carboxylic acid was prepared similarly according to the procedure for the synthesis of 10-bromo-9-fluoro-3-(hydroxy(3-(trifluoromethyl)phenyl)methyl)-5,6-dihydrobenzo[f]imidazo[1,2-d][1,4]oxazepine-2-carboxylic acid. Methyl 10-bromo-9-fluoro-3-[hydroxy-(4-methylthiazol-5-yl)methyl]-5,6-dihydroimidazo[1,2-d][1,4]benzoxazepine-2-carboxylate was reacted with lithium hydroxide to the crude title compound which was carried forward without further purification.

Example 517

Synthesis of (±)-10-bromo-9-fluoro-3-[hydroxy-(4-methylthiazol-5-yl)methyl]-5,6-dihydroimidazo[1,2-d][1,4]benzoxazepine-2-carboxamide

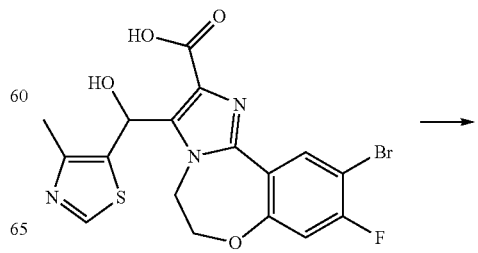

731
-continued

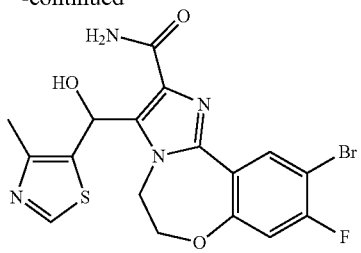

10-bromo-9-fluoro-3-[hydroxy-(4-methylthiazol-5-yl)methyl]-5,6-dihydroimidazo[1,2-d][1,4]benzoxazepine-2-carboxamide was prepared similarly according to the procedure in Example 2.

10-bromo-9-fluoro-3-[hydroxy-(4-methylthiazol-5-yl)methyl]-5,6-dihydroimidazo[1,2-d][1,4]benzoxazepine-2-carboxylic acid was reacted with ammonium chloride and purified by flash chromatography to afford 30.4 mg (15% yield) of the title compound.

Example 518

Synthesis of (±)-9-fluoro-3-(hydroxy(4-methylthiazol-5-yl)methyl)-10-(3-hydroxy-3-methylbut-1-yn-1-yl)-5,6-dihydrobenzo[f]imidazo[1,2-d][1,4]oxazepine-2-carboxamide

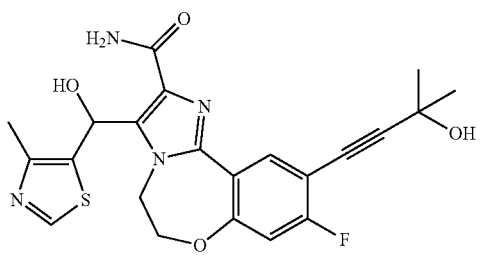 [SMILES: Cc1ncsc1C(O)c1c(C(N)=O)nc2n1CCOc1cc(F)c(C#CC(C)(C)O)cc1-2]

9-fluoro-3-(hydroxy(4-methylthiazol-5-yl)methyl)-10-(3-hydroxy-3-methylbut-1-yn-1-yl)-5,6-dihydrobenzo[f]imidazo[1,2-d][1,4]oxazepine-2-carboxamide was prepared similarly according to General Procedure G with slight modifications. 10-bromo-9-fluoro-3-[hydroxy-(4-methylthiazol-5-yl)methyl]-5,6-dihydroimidazo[1,2-d][1,4]benzoxazepine-2-carboxamide was reacted with 3-methyl-1-butyne-3-ol to afford 5.4 mg of the titled compound (18% yield). M+1=457.1. 1H NMR (400 MHz, DMSO) δ 8.87 (s, 1H), 8.58 (d, J=8.3 Hz, 1H), 8.01 (br s, 1H), 7.59-7.53 (m, 2H), 7.00 (d, J=10.5 Hz, 1H), 6.94 (d, J=6.3 Hz, 1H), 5.54 (s, 1H), 4.57-4.48 (m, 1H), 4.48-4.36 (m, 2H), 4.31-4.22 (m, 1H), 2.25 (s, 3H), 1.49 (s, 6H).

732
Example 519

Synthesis of 10-bromo-3-(3-cyclopropyl-1,2,4-oxadiazol-5-yl)-9-fluoro-5,6-dihydrobenzo[f]imidazo[1,2-d][1,4]oxazepine-2-carboxamide 10-bromo-3-(3-cyclopropyl-1,2,4-oxadiazol-5-yl)-9-fluoro-5,6-dihydrobenzo[f]imidazo[1,2-d][1,4]oxazepine-2-carboxamide was prepared similarly according to Procedure I.

Cyclopropylcarboxamidine hydrochloride was reacted with 10-bromo-9-fluoro-3-iodo-5,6-dihydroimidazo[1,2-d][1,4]benzoxazepine-2-carboxamide then hydroxylamine hydrochloride to afford the title compound which was carried forward without purification.

Example 520

Synthesis of 3-(3-cyclopropyl-1,2,4-oxadiazol-5-yl)-9-fluoro-10-(3-hydroxy-3-methyl-but-1-ynyl)-5,6-dihydroimidazo[1,2-d][1,4]benzoxazepine-2-carboxamide

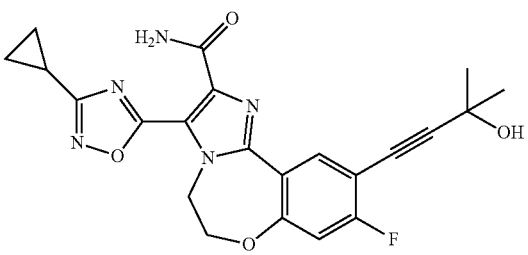 [SMILES: CC(C)(O)C#Cc1cc2c(cc1F)OCCn1c-2nc(C(N)=O)c1-c1nc(C2CC2)no1]

3-(3-cyclopropyl-1,2,4-oxadiazol-5-yl)-9-fluoro-10-(3-hydroxy-3-methyl-but-1-ynyl)-5,6-dihydroimidazo[1,2-d][1,4]benzoxazepine-2-carboxamide was prepared similarly according to General Procedure G with slight modifications. 10-bromo-3-(3-cyclopropyl-1,2,4-oxadiazol-5-yl)-9-fluoro- 5,6-dihydroimidazo[1,2-d][1,4]benzoxazepine-2-carboxamide was reacted with 3-methyl-1-butyne-3-ol to afford 26 mg of the titled compound (28.6% yield). M+1=438.0. 1H NMR (400 MHz, DMSO-d6) δ 8.63 (d, J=8.3 Hz, 1H), 7.99 (br s, 1H), 7.52 (br s, 1H), 7.07 (d, J=10.5 Hz, 1H), 5.56 (s, 1H), 4.58-4.51 (m, 4H), 2.28-2.19 (m, 1H), 1.49 (s, 6H), 1.19-1.09 (m, 2H), 1.03-0.97 (m, 2H).

Example 521

Synthesis of 10-bromo-3-(3-cyclopropyl-1H-1,2,4-triazol-5-yl)-5,6-dihydrobenzo[f]imidazo[1,2-d][1,4]oxazepine-2-carboxamide

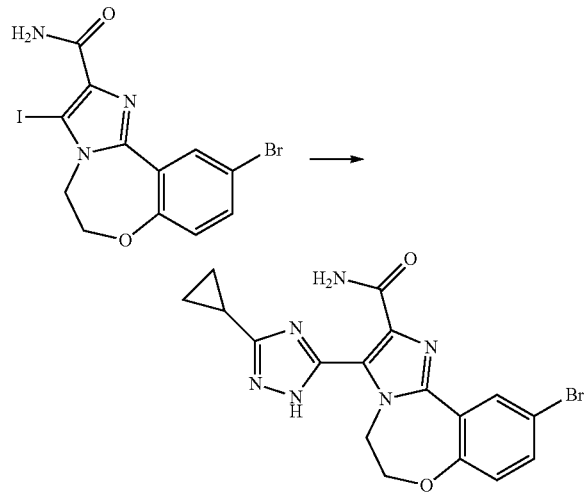

10-bromo-3-(3-cyclopropyl-1H-1,2,4-triazol-5-yl)-5,6-dihydrobenzo[f]imidazo[1,2-d][1,4]oxazepine-2-carboxamide was prepared similarly according to Procedure I. Cyclopropylcarboxamidine hydrochloride was reacted with 10-bromo-3-iodo-5,6-dihydroimidazo[1,2-d][1,4]benzoxazepine-2-carboxamide then hydrazine. The completed reaction was then diluted with methylene chloride and filtered over celite to afford 83 mg (31% yield) of the title compound.

Example 522

Synthesis of 3-(3-cyclopropyl-1H-1,2,4-triazol-5-yl)-10-(3-hydroxy-3-methyl-but-1-ynyl)-5,6-dihydroimidazo[1,2-d][1,4]benzoxazepine-2-carboxamide

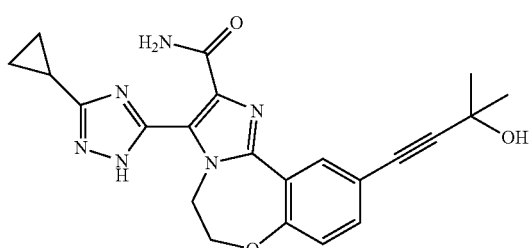

3-(3-cyclopropyl-1H-1,2,4-triazol-5-yl)-10-(3-hydroxy-3-methyl-but-1-ynyl)-5,6-dihydroimidazo[1,2-d][1,4]benzoxazepine-2-carboxamide was prepared similarly to General Procedure G with slight modifications. 10-bromo-3-(3-cyclopropyl-1H-1,2,4-triazol-5-yl)-5,6-dihydroimidazo[1,2-d][1,4]benzoxazepine-2-carboxamide was reacted with 3-methyl-1-butyne-3-ol to afford 5.5 mg (6.6% yield). M+1=419.0.

Example 523

Synthesis of 10-bromo-3-(3-cyclopropyl-1,2,4-oxadiazol-5-yl)-9-fluoro-6,7-dihydro-5H-5,7-methanobenzo[c]imidazo[1,2-a]azepine-2-carboxamide

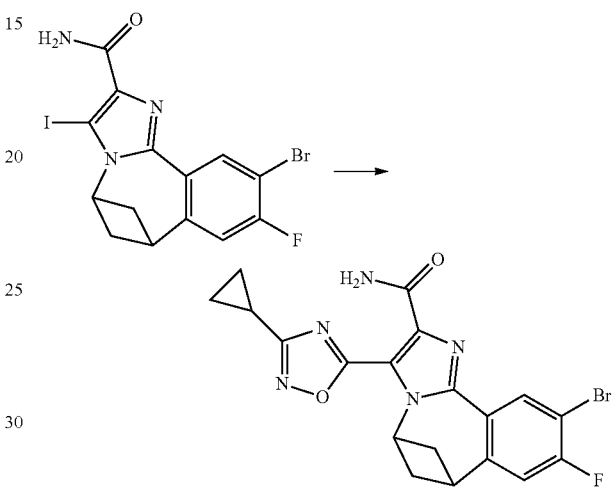

10-bromo-3-(3-cyclopropyl-1,2,4-oxadiazol-5-yl)-9-fluoro-6,7-dihydro-5H-5,7-methanobenzo[c]imidazo[1,2-a]azepine-2-carboxamide was prepared similarly according to Procedure I. Cyclopropylcarboxamidine hydrochloride was reacted with 10-bromo-9-fluoro-3-iodo-6,7-dihydro-5H-5,7-methanobenzo[c]imidazo[1,2-a]azepine-2-carboxamide then hydroxylamine hydrochloride to afford 164 mg (56% yield) of the title compound.

Example 524

Synthesis of 3-(3-cyclopropyl-1,2,4-oxadiazol-5-yl)-9-fluoro-10-(3-hydroxy-3-methyl-but-1-ynyl)-5,6,7,12-tetrahydro-5,7-methanobenzo[c]imidazo[1,2-a]azepine-2-carboxamide

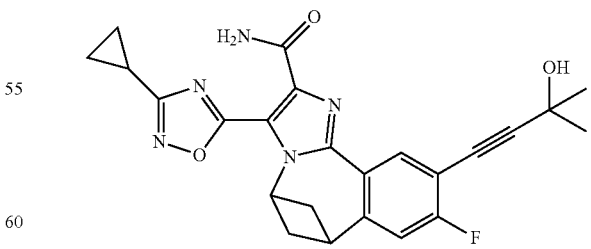

3-(3-cyclopropyl-1,2,4-oxadiazol-5-yl)-9-fluoro-10-(3-hydroxy-3-methyl-but-1-ynyl)-5,6,7,12-tetrahydro-5,7-methanobenzo[c]imidazo[1,2-a]azepine-2-carboxamide was prepared similarly according to General Procedure G with slight modifications. 10-bromo-3-(3-cyclopropyl-1,2,4-oxadiazol-5-yl)-9-fluoro-6,7-dihydro-5H-5,7-methanobenzo[c]imidazo[1,2-a]azepine-2-carboxamide was reacted with 3-methyl-1-butyne-3-ol to afford 8.0 mg of the titled compound (9.9% yield). M+1=448; $^1$H NMR (400 MHz, DMSO-d6) δ 8.78 (d, J=7.5 Hz, 1H), 7.97 (br s, 1H), 7.49 (br s, 1H), 7.35 (d, J=10.1 Hz, 1H), 5.60 (s, 1H), 5.04-4.89 (m, 1H), 3.75-3.67 (m, 1H), 3.23-3.01 (m, 2H), 2.23 (tt, J=8.4, 4.8 Hz, 1H), 1.82-1.66 (m, 2H), 1.51 (s, 6H), 1.23-1.05 (m, 2H), 1.05-0.92 (m, 2H).

Example 525

Synthesis of 10-bromo-3-(3-cyclopropyl-1H-1,2,4-triazol-5-yl)-9-fluoro-6,7-dihydro-5H-5,7-methanobenzo[c]imidazo[1,2-a]azepine-2-carboxamide

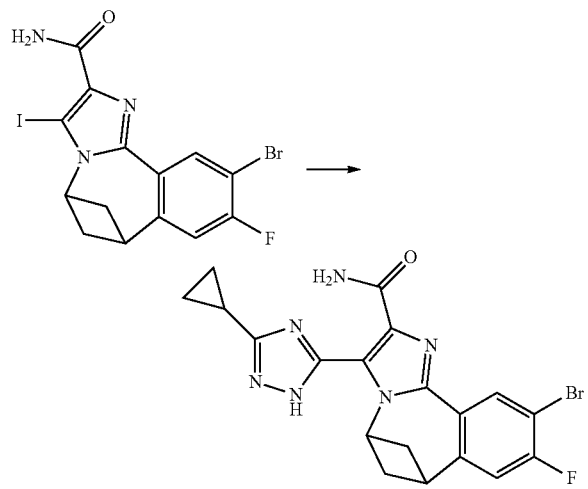

10-bromo-3-(3-cyclopropyl-1H-1,2,4-triazol-5-yl)-9-fluoro-6,7-dihydro-5H-5,7-methanobenzo[c]imidazo[1,2-a]azepine-2-carboxamide was prepared similarly according to Procedure I. Cyclopropylcarboxamidine hydrochloride was reacted with 10-bromo-9-fluoro-3-iodo-6,7-dihydro-5H-5,7-methanobenzo[c]imidazo[1,2-a]azepine-2-carboxamide then hydrazine to afford the title compound which was carried forward without purification.

Example 526

Synthesis of (±)-3-(3-cyclopropyl-1H-1,2,4-triazol-5-yl)-10-(3,4-dihydroxy-3-methyl-but-1-ynyl)-9-fluoro-5,6,7,12-tetrahydro-5,7-methanobenzo[c]imidazo[1,2-a]azepine-2-carboxamide

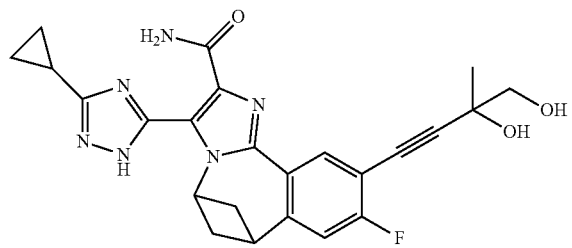 [SMILES: CC(O)(C#Cc1cc2c(cc1F)C1CC(C1)n1c-2nc(C(N)=O)c1-c1nc(C2CC2)n[nH]1)CO]

3-(3-cyclopropyl-1H-1,2,4-triazol-5-yl)-10-(3,4-dihydroxy-3-methyl-but-1-ynyl)-9-fluoro-5,6,7,12-tetrahydro-5,7-methanobenzo[c]imidazo[1,2-a]azepine-2-carboxamide was prepared similarly according to General Procedure E with slight modification. 10-bromo-3-(3-cyclopropyl-1H-1,2,4-triazol-5-yl)-9-fluoro-6,7-dihydro-5H-5,7-methanobenzo[c]imidazo[1,2-a]azepine-2-carboxamide was reacted with 2-methylbut-3-yne-1,2-diol in a solution of DMF (1.3 mL/mmol) and diisopropylamine (2.6 mL/mmol) to afford 7.7 mg (9.2% yield). M+1=463.2.

Example 527

Synthesis of 10-bromo-9-fluoro-3-(3-(pyridin-3-yl)-1H-1,2,4-triazol-5-yl)-6,7-dihydro-5H-5,7-methanobenzo[c]imidazo[1,2-a]azepine-2-carboxamide

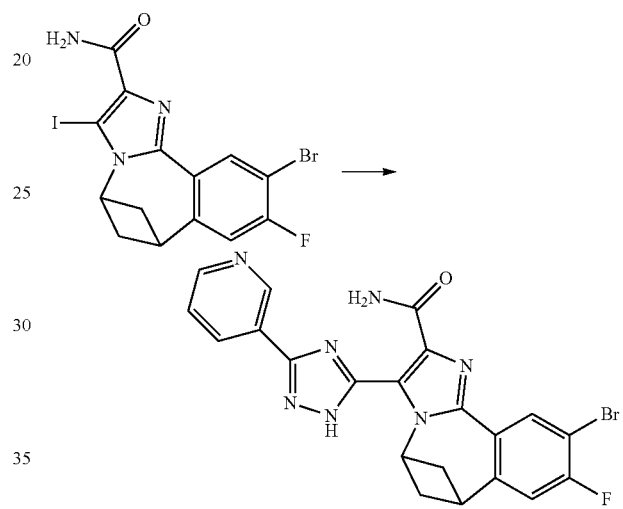

10-bromo-9-fluoro-3-(3-(pyridin-3-yl)-1H-1,2,4-triazol-5-yl)-5,6-dihydrobenzo[f]imidazo[1,2-d][1,4]oxazepine-2-carboxamide was prepared similarly according to Procedure I. Pyridine-3-carboximidamide hydrochloride was reacted with 10-bromo-9-fluoro-3-iodo-6,7-dihydro-5H-5,7-methanobenzo[c]imidazo[1,2-a]azepine-2-carboxamide then hydrazine. The completed reaction was then diluted with methylene chloride and filtered over celite to afford 37 mg (35% yield) of the title compound.

Example 530

Synthesis of 9-fluoro-10-(3-hydroxy-3-methyl-but-1-ynyl)-3-[3-(3-pyridyl)-1H-1,2,4-triazol-5-yl]-5,6,7,12-tetrahydro-5,7-methanobenzo[c]imidazo[1,2-a]azepine-2-carboxamide

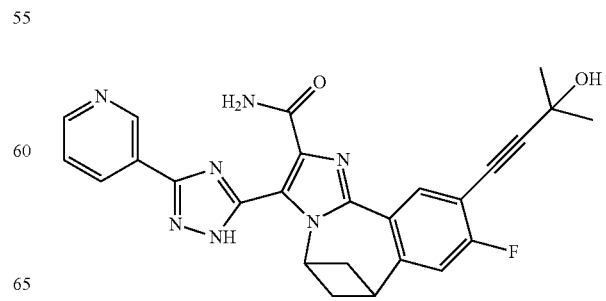

9-fluoro-10-(3-hydroxy-3-methyl-but-1-ynyl)-3-[3-(3-pyridyl)-1H-1,2,4-triazol-5-yl]-5,6,7,12-tetrahydro-5,7-methanobenzo[c]imidazo[1,2-a]azepine-2-carboxamide was prepared similarly according to General Procedure E slight modification. 10-bromo-9-fluoro-3-(3-(pyridin-3-yl)-1H-1,2,4-triazol-5-yl)-6,7-dihydro-5H-5,7-methanobenzo[c]imidazo[1,2-a]azepine-2-carboxamide was reacted with 2-methyl-3-butyne-ol in a solution of DMF (1.3 mL/mmol) and diisopropylamine (2.6 mL/mmol) to afford 17 mg of the titled compound (44.6% yield). M+1=484.0. $^1$H NMR (400 MHz, DMSO-d6) δ 9.27 (s, 1H), 8.88 (d, J=7.6 Hz, 1H), 8.66 (d, J=4.8 Hz, 1H), 8.56 (br s, 1H), 8.40 (d, J=7.8 Hz, 1H), 7.83 (br s, 1H), 7.55 (dd, J=7.7, 4.9 Hz, 1H), 7.34 (d, J=10.0 Hz, 1H), 6.24 (br s, 1H), 5.60 (s, 1H), 3.77-3.68 (m, 1H), 3.26-3.12 (m, 2H), 1.89-1.72 (m, 2H), 1.52 (s, 6H).

Example 531

Synthesis of 10-bromo-3-(3-cyclopropyl-1H-1,2,4-triazol-5-yl)-9-fluoro-5,6-dihydrobenzo[f]imidazo[1,2-d][1,4]oxazepine-2-carboxamide

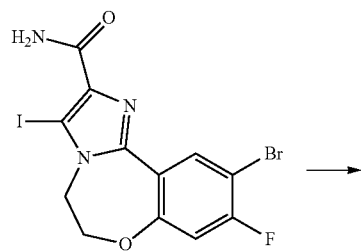

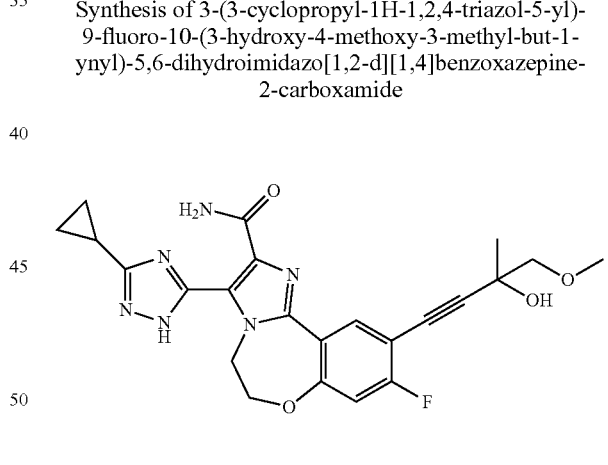

10-bromo-3-(3-cyclopropyl-1H-1,2,4-triazol-5-yl)-9-fluoro-5,6-dihydrobenzo[f]imidazo[1,2-d][1,4]oxazepine-2-carboxamide was prepared similarly according to Procedure I. Cyclopropylcarboxamidine hydrochloride was reacted with 10-bromo-9-fluoro-3-iodo-5,6-dihydrobenzo[f]imidazo[1,2-d][1,4]oxazepine-2-carboxamide then hydrazine. The completed reaction was then diluted with methylene chloride and filtered over celite to afford 334 mg (70% yield) of the title compound.

Example 532

Synthesis of (±)-3-(3-cyclopropyl-1H-1,2,4-triazol-5-yl)-10-(3,4-dihydroxy-3-methyl-but-1-ynyl)-9-fluoro-5,6-dihydroimidazo[1,2-d][1,4]benzoxazepine-2-carboxamide

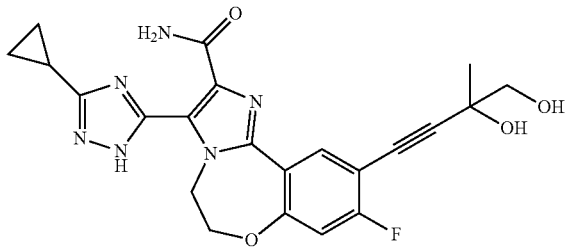 [SMILES: CC(O)(C#Cc1cc2c(cc1F)OCCn1c-2nc(C(N)=O)c1-c1nc(C2CC2)n[nH]1)CO]

3-(3-cyclopropyl-1H-1,2,4-triazol-5-yl)-10-(3,4-dihydroxy-3-methyl-but-1-ynyl)-9-fluoro-5,6-dihydroimidazo[1,2-d][1,4]benzoxazepine-2-carboxamide was prepared similarly according to General Procedure E with slight modification. 10-bromo-3-(3-cyclopropyl-1H-1,2,4-triazol-5-yl)-9-fluoro-5,6-dihydroimidazo[1,2-d][1,4]benzoxazepine-2-carboxamide was reacted with 2-methylbut-3-yne-1,2-diol in a solution of DMF (1.3 mL/mmol) and diisopropylamine (2.6 mL/mmol) to afford 30 mg of the titled compound (47.1% yield). M+1=453.0.

Example 533

Synthesis of 3-(3-cyclopropyl-1H-1,2,4-triazol-5-yl)-9-fluoro-10-(3-hydroxy-4-methoxy-3-methyl-but-1-ynyl)-5,6-dihydroimidazo[1,2-d][1,4]benzoxazepine-2-carboxamide 3-(3-cyclopropyl-1H-1,2,4-triazol-5-yl)-9-fluoro-10-(3-hydroxy-4-methoxy-3-methyl-but-1-ynyl)-5,6-dihydroimidazo[1,2-d][1,4]benzoxazepine-2-carboxamide was prepared similarly according to General Procedure E with slight modification. 10-bromo-3-(3-cyclopropyl-1H-1,2,4-triazol-5-yl)-9-fluoro-5,6-dihydroimidazo[1,2-d][1,4]benzoxazepine-2-carboxamide was reacted with 1-methoxy-2-methyl-but-3-yn-2-ol in a solution of DMF (1.3 mL/mmol) and diisopropylamine (2.6 mL/mmol) to afford 17 mg of the titled compound (26.3% yield). M+1=467.2. $^1$H NMR (400 MHz, DMSO-d6) δ 8.65 (d, J=8.3 Hz, 1H), 8.38 (br s, 1H), 7.79 (br s, 1H), 7.05 (d, J=10.4 Hz, 1H), 5.66 (s, 1H), 5.00-4.81 (m, 2H), 4.65-4.52 (m, 2H), 3.47-3.34 (m, 2H), 3.37 (s, 3H), 2.13-2.04 (m, 1H), 1.45 (s, 3H), 1.03-0.95 (m, 2H), 0.93-0.87 (m, 2H).

Example 534

Synthesis of methyl (±)-10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxylate

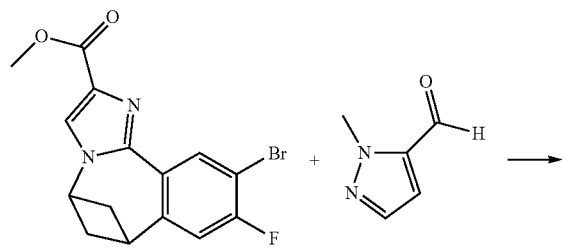

Methyl 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 1-methylpyrazole-5-carbaldehyde to afford 342 mg (87% yield) of the title compound.

Example 535

Synthesis of (±)-10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide

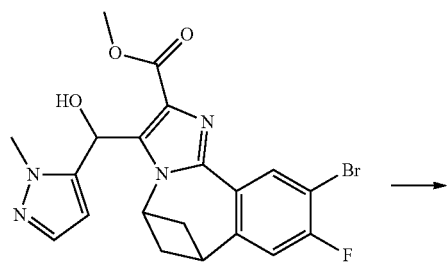

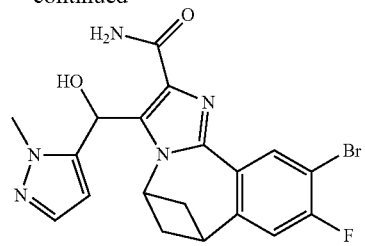

10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxylate was reacted with sodium methoxide and formamide to afford 131 mg (90% yield) of the title compound.

Example 536

Synthesis of (±)-9-fluoro-10-(3-hydroxy-3-methyl-but-1-ynyl)-3-[hydroxy-(2-methylpyrazol-3-yl)methyl]-5,6,7,12-tetrahydro-5,7-methanobenzo[c]imidazo[1,2-a]azepine-2-carboxamide

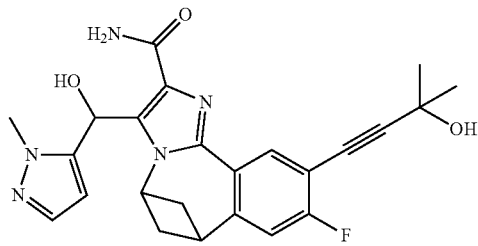 [SMILES: Cn1nccc1C(O)c1c(C(N)=O)nc2n1C1CC(C1)c1cc(F)c(C#CC(C)(C)O)cc1-2]

9-fluoro-10-(3-hydroxy-3-methyl-but-1-ynyl)-3-[hydroxy-(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (16 mL/mmol) to afford 99.7 mg of the titled compound (76.1% yield). M+1=450.2. $^1$H NMR (400 MHz, DMSO-d6) δ 8.76 (d, J=7.6 Hz, 1H), 7.90 (br s, 1H), 7.39 (br s, 1H), 7.31-7.21 (m, 2H), 7.07 (d, J=6.1 Hz, 1H), 6.90 (d, J=6.1 Hz, 1H), 5.68 (d, J=1.8 Hz, 1H), 5.54 (s, 1H), 5.17 (td, J=6.7, 4.2 Hz, 1H), 3.86 (s, 3H), 3.68-3.58 (m, 1H), 3.09-2.91 (m, 2H), 1.75 (dd, J=11.9, 7.0 Hz, 1H), 1.63 (dd, J=12.1, 6.9 Hz, 1H), 1.51 (s, 6H).

Example 537

Synthesis of 2-(5-bromo-2-fluorophenyl)-1H-imidazole

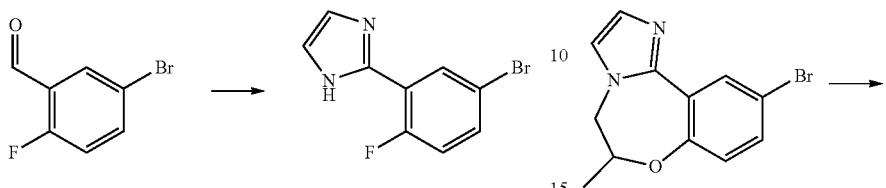

To a solution of 5-bromo-2-fluoro-benzaldehyde (0.292 mL, 500 mg, 2.4629 mmol) in isopropanol (2.46 mL) and water (2.46 mL) was added ammonium acetate (9.0 equiv., 1760 mg, 22.166 mmol) followed by glyoxal (40 mass %) in H$_2$O (approx 8.8 M) (1.6 equiv., 0.45 mL, 3.9407 mmol) dropwise. The reaction was stirred at room temperature for 16 h. Complete consumption of starting material was observed by LC/MS. The reaction mixture was diluted with isopropanol and filtered. The filtrated was concentrated in vacuo then extracted 3× with water and methylene chloride. The organic layers were combined, dried with sodium sulfate, and concentrated. The crude material was purified by flash chromatography (5-100% EtOAc with 1% triethylamine in heptanes) to afford 205.1 mg (35% yield) of the title compound.

Example 538

Synthesis of (±)-10-bromo-6-methyl-5,6-dihydrobenzo[f]imidazo[1,2-d][1,4]oxazepine

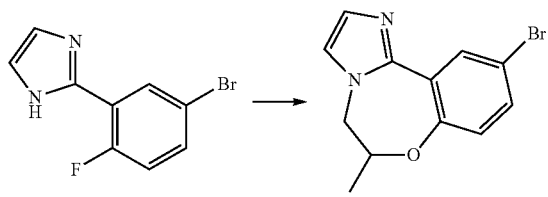 [SMILES: Fc1ccc(Br)cc1-c1ncc[nH]1 ; CC1Cn2ccnc2-c2cc(Br)ccc2O1]

To a solution of 2-(5-bromo-2-fluoro-phenyl)-1H-imidazole (250 mg, 1.0371 mmol) in dimethylformamide (3.0 mL) was added sodium hydride (1.1 equiv., 45.6 mg, 1.1408 mmol) at 0° C. The reaction was stirred at this temperature for 10 minutes, then (+/−)-propylene oxide (1.2 equiv., 0.09 mL, 1.2445 mmol) was added and the mixture was allowed to warm up to room temperature. The reaction was then heated to 95° C. for 6 h. The reaction mixture was cooled to room temperature and quenched with saturated aqueous ammonium chloride. The solution was extracted 3× with methylene chloride. The organic layers were combined, dried with sodium sulfate, and concentrated in vacuo. The crude was purified by flash chromatography (5-100% EtOAc in heptanes) to afford 188 mg (65% yield) of an orange solid.

Example 539

Synthesis of (±)-10-bromo-2,3-diiodo-6-methyl-5,6-dihydrobenzo[f]imidazo[1,2-d][1,4]oxazepine

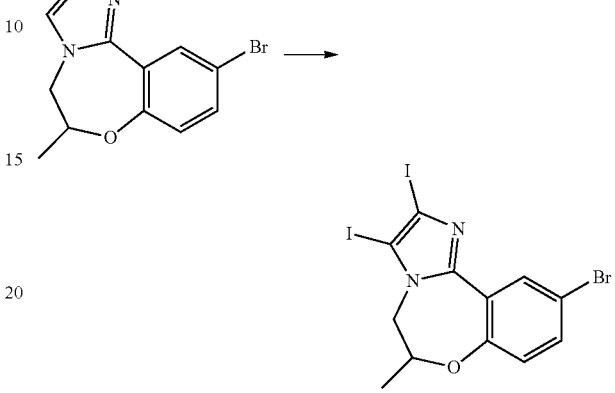

10-bromo-2,3-diiodo-6-methyl-5,6-dihydrobenzo[f]imidazo[1,2-d][1,4]oxazepine was prepared similarly according to 9-bromo-2,3-diiodo-4,5-dihydro-6-oxa-1,3a-diaza-benzo[e]azulene. 10-bromo-6-methyl-5,6-dihydrobenzo[f]imidazo[1,2-d][1,4]oxazepine was reacted with N-iodosuccinimide to afford 324 mg (90% yield) of a yellow solid.

Example 540

Synthesis of 10-bromo-2-iodo-6-methyl-5,6-dihydrobenzo[f]imidazo[1,2-d][1,4]oxazepine

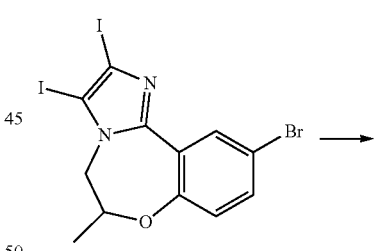

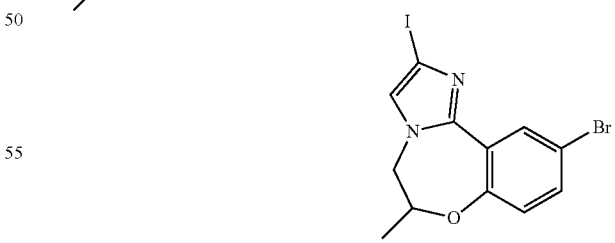

10-bromo-2-iodo-6-methyl-5,6-dihydrobenzo[f]imidazo[1,2-d][1,4]oxazepine was prepared similarly according to 9-bromo-2,3-diiodo-4,5-dihydro-6-oxa-1,3a-diaza-benzo[e]azulene.

10-bromo-2,3-diiodo-6-methyl-5,6-dihydrobenzo[f]imidazo[1,2-d][1,4]oxazepine was reacted with ethylmagnesium bromide to afford 169 mg (68% yield) of a beige solid.

Example 541

Synthesis of (±)-10-bromo-6-methyl-5,6-dihydrobenzo[f]imidazo[1,2-d][1,4]oxazepine-2-carboxamide

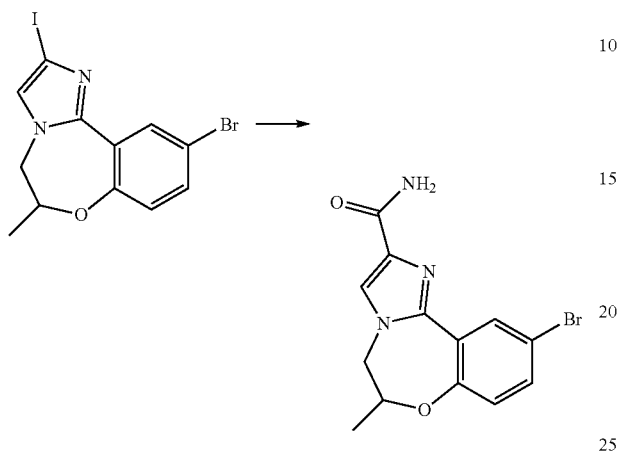

10-bromo-6-methyl-5,6-dihydrobenzo[f]imidazo[1,2-d][1,4]oxazepine-2-carboxamide was prepared similarly according to the procedure in example 10. 10-bromo-2-iodo-6-methyl-5,6-dihydrobenzo[f]imidazo[1,2-d][1,4]oxazepine was reacted with carbon monoxide and hexamethyldisilazane to afford the title compound which was carried forward crude without further purification.

Example 542

Synthesis of (S)-10-(3-hydroxy-3-methylbut-1-yn-1-yl)-6-methyl-5,6-dihydrobenzo[f]imidazo[1,2-d][1,4]oxazepine-2-carboxamide and (R)-10-(3-hydroxy-3-methylbut-1-yn-1-yl)-6-methyl-5,6-dihydrobenzo[f]imidazo[1,2-d][1,4]oxazepine-2-carboxamide

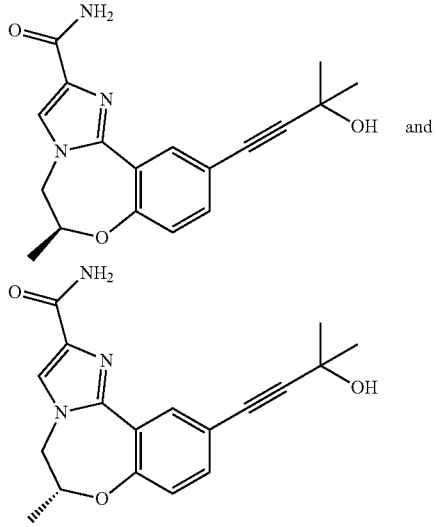

(S)-10-(3-hydroxy-3-methylbut-1-yn-1-yl)-6-methyl-5,6-dihydrobenzo[f]imidazo[1,2-d][1,4]oxazepine-2-carboxamide and (R)-10-(3-hydroxy-3-methylbut-1-yn-1-yl)-6-methyl-5,6-dihydrobenzo[f]imidazo[1,2-d][1,4]oxazepine-2-carboxamide were prepared similarly according to General Procedure E with slight modification. 10-bromo-6-methyl-5,6-dihydroimidazo[1,2-d][1,4]benzoxazepine-2-carboxamide was reacted with 3-methyl-1-butyne-3-ol in a solution of DMF (1.3 mL/mmol) and diisopropylamine (2.6 mL/mmol) to afford 87 mg of a mixture of the titled compounds (64.3% yield). The enantiomers were separated by chiral SFC to afford 29 mg of Compound 1 and 30 mg of Compound 2. The absolute stereochemistry for each isomer was not determined. M+1=326.2. $^1$H NMR (400 MHz, DMSO-d6) δ 8.40 (d, J=2.1 Hz, 1H), 7.74 (s, 1H), 7.51 (br s, 1H), 7.29 (dd, J=8.5, 2.1 Hz, 1H), 7.12 (br s, 1H), 6.99 (d, J=8.4 Hz, 1H), 5.43 (s, 1H), 4.59-4.46 (m, 2H), 4.25 (dd, J=14.8, 8.2 Hz, 1H), 1.47 (s, 6H), 1.40 (d, J=6.4 Hz, 3H).

Example 543

Synthesis of methyl 10-bromo-9-fluoro-3-((1-methyl-1H-pyrazol-5-yl)methyl)-6,7-dihydro-5H-5,7-methanobenzo[c]imidazo[1,2-a]azepine-2-carboxylate

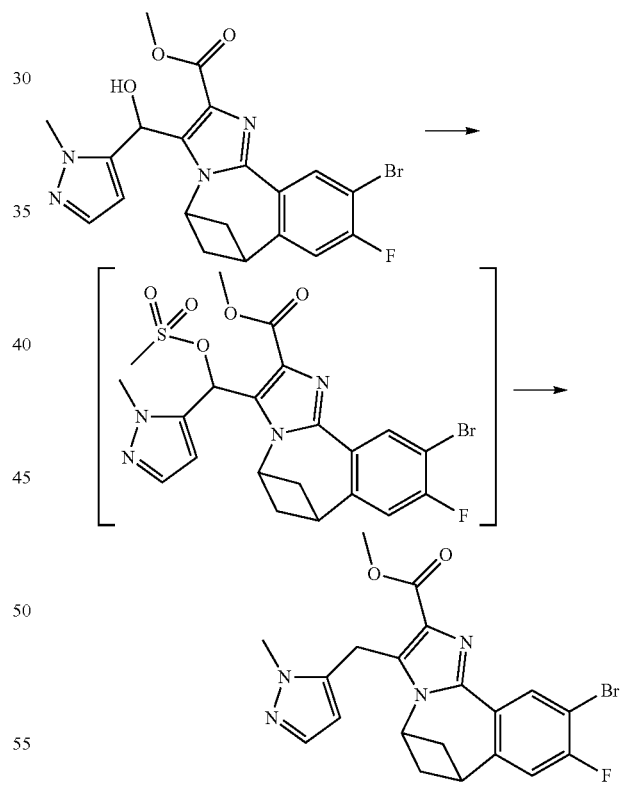

To a solution of methyl 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxylate (140 mg, 0.3035 mmol) in dichloromethane (0.91 mL) was added triethylamine (4.0 equiv., 0.171 mL, 1.214 mmol) followed by methanesulfonyl chloride (1.2 equiv., 0.029 mL, 0.3642 mmol). The reaction was stirred at room temperature until LC/MS analysis indicated complete consumption of starting material.

The solution was then concentrated in vacuo, and used crude in the following step. The crude material was dissolved in ethyl acetate (2.72 mL) in a vial equipped with a septum cap. 10% palladium on carbon (0.18 equiv., 58.32 mg, 0.05480 mmol) was added and the vial was purged with nitrogen. A hydrogen balloon was fixed to the vial and the vial was purged with hydrogen for 5 minutes. The reaction was then stirred at room temperature for 1 hour. LC/MS indicated complete consumption of the starting material. The solution was diluted with DMF and filtered over celite. The filtrate was concentrated in vacuo to afford 120 mg (89% yield over 2 steps) of crude material and carried forward without further purification.

Example 544

Synthesis of 10-bromo-9-fluoro-3-((1-methyl-1H-pyrazol-5-yl)methyl)-6,7-dihydro-5H-5,7-methanobenzo[c]imidazo[1,2-a]azepine-2-carboxamide

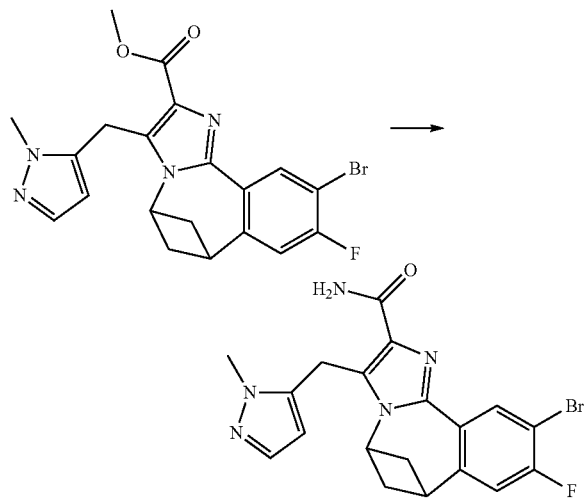

10-bromo-9-fluoro-3-((1-methyl-1H-pyrazol-5-yl)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3((1-methyl-1H-pyrazol-5-yl)methyl)-6,7-dihydro-5H-5,7-methanobenzo[c]imidazo[1,2-a]azepine-2-carboxylate was reacted with sodium methoxide and formamide to afford 66 mg (57% yield) of the title compound.

Example 545

Synthesis of 9-fluoro-10-(3-hydroxy-3-methyl-but-1-ynyl)-3-[(2-methylpyrazol-3-yl)methyl]-5,6,7,12-tetrahydro-5,7-methanobenzo[c]imidazo[1,2-a]azepine-2-carboxamide

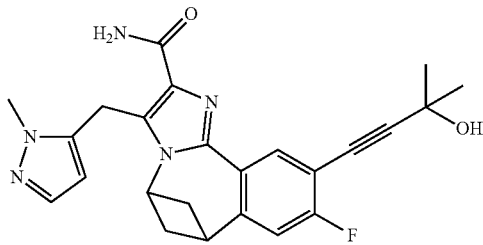 [SMILES: Cn1nccc1Cc1c(C(N)=O)nc2n1C1CC(C1)c1cc(F)c(C#CC(C)(C)O)cc1-2]

9-fluoro-10-(3-hydroxy-3-methyl-but-1-ynyl)-3-[(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modifications. 10-bromo-9-fluoro-3((1-methyl-1H-pyrazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 40.6 mg of the titled compound (61.1% yield). M+1=434.2. 1H NMR (400 MHz, DMSO-d6) δ 8.72 (d, J=7.6 Hz, 1H), 7.66 (br s, 1H), 7.25 (d, J=10.2 Hz, 1H), 7.22 (d, J=1.9 Hz, 1H), 7.14 (br s, 1H), 5.59 (d, J=1.7 Hz, 1H), 5.54 (s, 1H), 4.76-4.67 (m, 1H), 4.56 (s, 2H), 3.81 (s, 3H), 3.69-3.58 (m, 1H), 3.08-2.93 (m, 2H), 1.73-1.61 (m, 2H), 1.50 (s, 6H).

Example 546

Synthesis of 3-(3-cyclopropyl-1H-1,2,4-triazol-5-yl)-9-fluoro-10-(3-hydroxy-3-methyl-but-1-ynyl)-5,6,7,12-tetra hydro-5,7-methanobenzo[c]imidazo[1,2-a]azepine-2-carboxamide

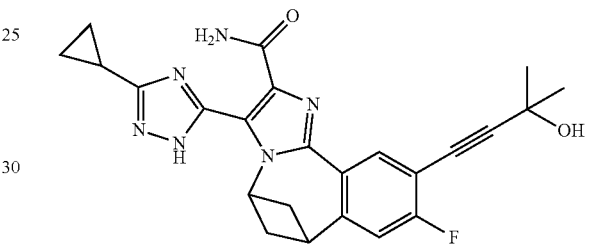

3-(3-cyclopropyl-1H-1,2,4-triazol-5-yl)-9-fluoro-10-(3-hydroxy-3-methyl-but-1-ynyl)-5,6,7,12-tetrahydro-5,7-methanobenzo[c]imidazo[1,2-a]azepine-2-carboxamide was prepared similarly according to General Procedure E with slight modification. 10-bromo-3-(3-cyclopropyl-1H-1,2,4-triazol-5-yl)-9-fluoro-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 40 mg of the titled compound (47.1% yield). M+1=447.2. 1H NMR (400 MHz, DMSO-d6) δ 8.82 (d, J=7.6 Hz, 1H), 8.32 (br s, 1H), 8.21 (br s, 1H), 7.59 (br s, 1H), 7.30 (d, J=10.1 Hz, 1H), 5.90-5.72 (m, 1H), 3.74-3.64 (m, 1H), 3.17 (s, 1H), 3.16-3.06 (m, 2H), 2.08 (tt, J=8.4, 4.9 Hz, 1H), 1.76-1.69 (m, 2H), 1.51 (s, 6H), 1.04-0.96 (m, 2H), 0.92-0.86 (m, 2H).

Example 547

Synthesis of (±)-Methyl 10-bromo-3-(hydroxy(1-methyl-1H-pyrazol-5-yl)methyl)-6,7-dihydro-5H-5,7-methanobenzo[c]imidazo[1,2-a]azepine-2-carboxylate

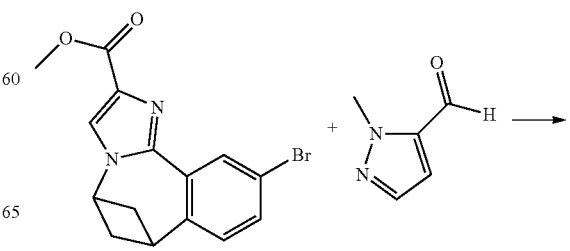

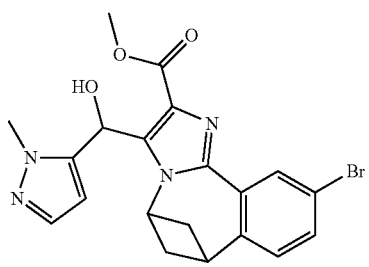

Methyl 10-bromo-3-(hydroxy(1-methyl-1H-pyrazol-5-yl)methyl)-6,7-dihydro-5H-5,7-methanobenzo[c]imidazo[1,2-a]azepine-2-carboxylate was prepared similarly according to the procedure in Example 9. Methyl 10-bromo-6,7-dihydro-5H-5,7-methanobenzo[c]imidazo[1,2-a]azepine-2-carboxylate was reacted with 1-methylpyrazole-5-carbaldehyde to afford 385 mg (59% yield) of the title compound.

Example 548

Synthesis of 10-bromo-3-(hydroxy(1-methyl-1H-pyrazol-5-yl)methyl)-6,7-dihydro-5H-5,7-methanobenzo[c]imidazo[1,2-a]azepine-2-carboxamide

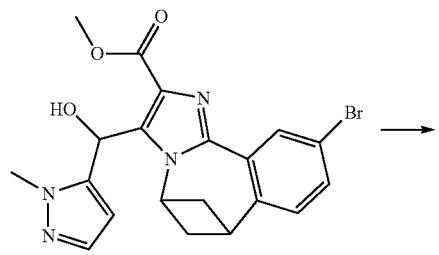

10-Bromo-3-(hydroxy(1-methyl-1H-pyrazol-5-yl)methyl)-6,7-dihydro-5H-5,7-methanobenzo[c]imidazo[1,2-a]azepine-2-carboxamide was prepared similarly to as described in General Procedure L. Methyl 10-bromo-3-(hydroxy(1-methyl-1H-pyrazol-5-yl)methyl)-6,7-dihydro-5H-5,7-methanobenzo[c]imidazo[1,2-a]azepine-2-carboxylate was reacted with sodium methoxide and formamide to afford 181 mg (94% yield) of the title compound.

Example 549

Synthesis of (±)-10-(3-hydroxy-3-methyl-but-1-ynyl)-3-[hydroxy-(2-methylpyrazol-3-yl)methyl]-5,6,7,12-tetrahydro-5,7-methanobenzo[c]imidazo[1,2-a]azepine-2-carboxamide

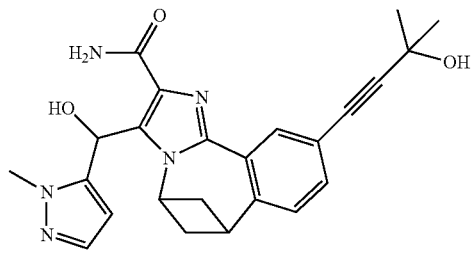 [SMILES: Cn1nccc1C(O)c1c(C(N)=O)nc2n1C1CC(C1)c1ccc(C#CC(C)(C)O)cc1-2]

10-(3-hydroxy-3-methyl-but-1-ynyl)-3-[hydroxy-(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-3-(hydroxy(1-methyl-1H-pyrazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 27.8 mg of the titled compound (34.5% yield). M+1=432.2. $^1$H NMR (400 MHz, DMSO-d6) δ 832 (s, 1H), 7.86 (br s, 1H), 7.40 (br s, 1H), 7.30-7.23 (m, 3H), 7.08 (d, J=6.1 Hz, 1H), 6.90 (d, J=6.2 Hz, 1H), 5.68 (d, J=1.7 Hz, 1H), 5.45 (s, 1H), 5.23-5.14 (m, 1H), 3.87 (s, 3H), 3.67-3.59 (m, 1H), 3.08-2.88 (m, 2H), 1.72 (dd, J=11.9, 7.1 Hz, 1H), 1.60 (dd, J=11.7, 7.0 Hz, 1H), 1.50 (s, 6H).

Example 550

Synthesis of Methyl 10-bromo-3-((1-methyl-1H-pyrazol-5-yl)methyl)-6,7-dihydro-5H-5,7-methanobenzo[c]imidazo[1,2-a]azepine-2-carboxylate

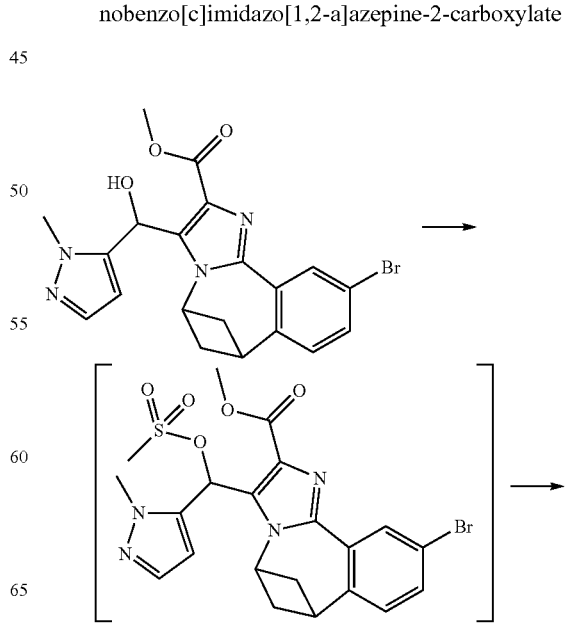

749
-continued

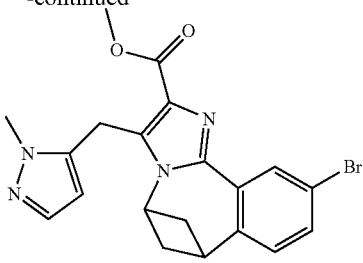

methyl 10-bromo-3-((1-methyl-1H-pyrazol-5-yl)methyl)-6,7-dihydro-5H-5,7-methanobenzo[c]imidazo[1,2-a]azepine-2-carboxylate was prepared similarly to methyl 10-bromo-9-fluoro-3((1-methyl-1H-pyrazol-5-yl)methyl)-6,7-dihydro-5H-5,7-methanobenzo[c]imidazo[1,2-a]azepine-2-carboxylate. Methyl 10-bromo-3-(hydroxy(1-methyl-1H-pyrazol-5-yl)methyl)-6,7-dihydro-5H-5,7-methanobenzo[c]imidazo[1,2-a]azepine-2-carboxylate was reacted with methanesulfonyl chloride followed by palladium on carbon and hydrogen to afford 140 mg (98% crude yield) of the titled crude product which was carried forward without further purification.

Example 551

Synthesis of 10-bromo-3-((1-methyl-1H-pyrazol-5-yl)methyl)-6,7-dihydro-5H-5,7-methanobenzo[c]imidazo[1,2-a]azepine-2-carboxamide

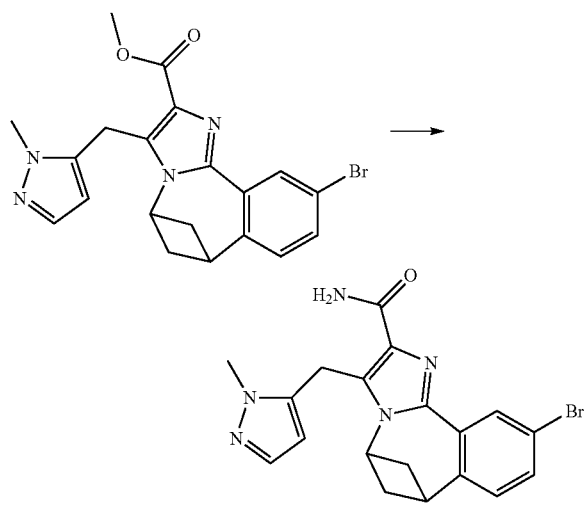

10-bromo-3-((1-methyl-1H-pyrazol-5-yl)methyl)-6,7-dihydro-5H-5,7-methanobenzo[c]imidazo[1,2-a]azepine-2-carboxamide was prepared similarly to as described in General Procedure L. Methyl 10-bromo-3-((1-methyl-1H-pyrazol-5-yl)methyl)-6,7-dihydro-5H-5,7-methanobenzo[c]imidazo[1,2-a]azepine-2-carboxylate was reacted with sodium methoxide and formamide to afford 150 mg (110% crude yield) of the crude title compound which was carried forward without further purification.

750

Example 552

Synthesis of 10-[(3R)-3-hydroxy-3-(5-methyl-1,2,4-oxadiazol-3-yl)but-1-ynyl]-3-[(2-methylpyrazol-3-yl)methyl]-5,6,7,12-tetrahydro-5,7-methanobenzo[c]imidazo[1,2-a]azepine-2-carboxamide

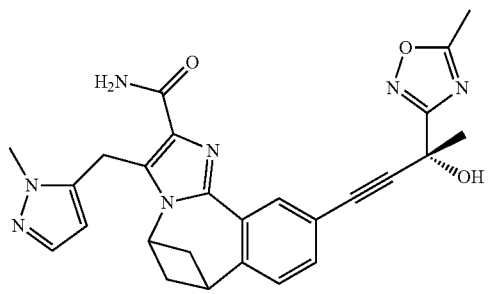

10-[(3R)-3-hydroxy-3-(5-methyl-1,2,4-oxadiazol-3-yl)but-1-ynyl]-3-[(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-3((1-methyl-1H-pyrazol-5-yl)methyl)-6,7-dihydro-5H-5,7-methanobenzo[c]imidazo[1,2-a]azepine-2-carboxamide was reacted with (2R)-2-(5-methyl-1,2,4-oxadiazol-3-yl)but-3-yn-2-ol in a solution of DMF (1.3 mL/mmol) and diisopropylamine (2.6 mL/mmol) to afford 6.7 mg of the titled compound (14% yield). M+1=484.3. 1H NMR (400 MHz, DMSO-d6) δ 8.72 (s, 1H), 7.63 (br s, 1H), 7.28 (s, 2H), 7.22 (d, J=1.8 Hz, 1H), 7.14 (br s, 1H), 6.70 (s, 1H), 5.59 (d, J=1.5 Hz, 1H), 4.76-4.70 (m, 1H), 4.57 (s, 2H), 3.81 (s, 3H), 3.69-3.61 (m, 1H), 3.06-2.94 (m, 2H), 2.62 (s, 3H), 1.86 (s, 3H), 1.70-1.61 (m, 2H).

Example 553

Synthesis of 10-(3-hydroxy-3-methyl-but-1-ynyl)-3-[(2-methylpyrazol-3-yl)methyl]-5,6,7,12-tetrahydro-5,7-methanobenzo[c]imidazo[1,2-a]azepine-2-carboxamide

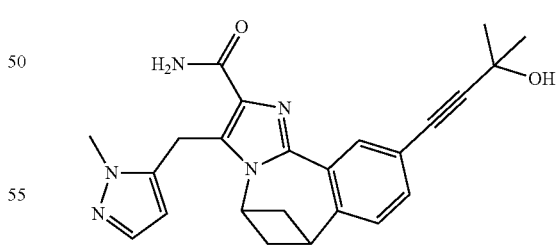

10-(3-hydroxy-3-methyl-but-1-ynyl)-3-[(2-methylpyrazol-3-yl)methyl]-5,6,7,12-tetra hydro-5,7-methanobenzo[c]imidazo[1,2-a]azepine-2-carboxamide was prepared similarly according to General Procedure E with slight modification. 10-bromo-3-((1-methyl-1H-pyrazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 22.8 mg (37.7% yield). M+1=416.2. 1H NMR (400 MHz, DMSO-d6) δ 8.68 (s, 1H), 7.62 (br s, 1H), 7.26-7.23 (m, 2H), 7.22 (d, J=1.9 Hz, 1H), 7.14 (br s, 1H), 5.59 (d, J=1.7 Hz, 1H), 5.45 (s, 1H), 4.77-4.69 (m, 1H), 4.57 (s, 2H), 3.81 (s, 3H), 3.69-3.58 (m, 1H), 3.09-2.93 (m, 2H), 1.68-1.61 (m, 2H), 1.49 (s, 6H).

Example 554

Synthesis of Methyl 10-bromo-9-fluoro-3((1-methyl-1H-pyrazol-5-yl)methyl)-5,6-dihydrobenzo[f]imidazo[1,2-d][1,4]oxazepine-2-carboxylate

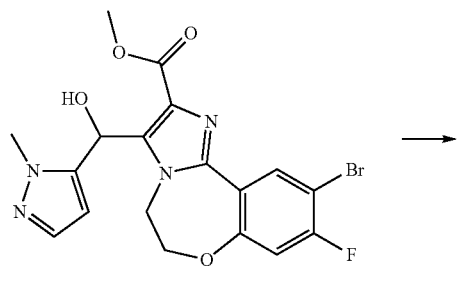

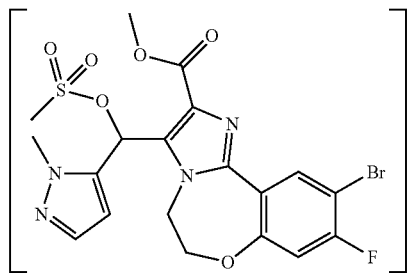

Methyl 10-bromo-9-fluoro-3-((1-methyl-1H-pyrazol-5-yl)methyl)-5,6-dihydrobenzo[f]imidazo[1,2-d][1,4]oxazepine-2-carboxylate was prepared similarly to methyl 10-bromo-9-fluoro-3-((1-methyl-1H-pyrazol-5-yl)methyl)-6,7-dihydro-5H-5,7-methanobenzo[c]imidazo[1,2-a]azepine-2-carboxylate. Methyl 10-bromo-9-fluoro-3-(hydroxy(1-methyl-1H-pyrazol-5-yl)methyl)-5,6-dihydrobenzo[f]imidazo[1,2-d][1,4]oxazepine-2-carboxylate was reacted with methanesulfonyl chloride followed by palladium on carbon and hydrogen to afford 105 mg (85% crude yield) of the titled crude product which was carried forward without further purification.

Example 555

Synthesis of 10-bromo-9-fluoro-3-((1-methyl-1H-pyrazol-5-yl)methyl)-5,6-dihydrobenzo[f]imidazo[1,2-d][1,4]oxazepine-2-carboxamide

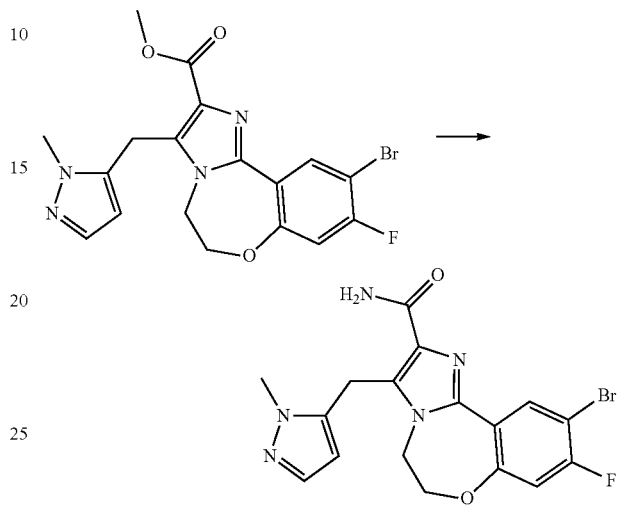

10-bromo-9-fluoro-3-((1-methyl-1H-pyrazol-5-yl)methyl)-5,6-dihydrobenzo[f]imidazo[1,2-d][1,4]oxazepine-2-carboxamide was prepared similarly to as described in General Procedure L. Methyl 10-bromo-9-fluoro-3-((1-methyl-1H-pyrazol-5-yl)methyl)-5,6-dihydrobenzo[f]imidazo[1,2-d][1,4]oxazepine-2-carboxylate was reacted with sodium methoxide and formamide to afford 11 mg (11% crude yield) of the crude title compound which was carried forward without further purification.

Example 556

Synthesis of 9-fluoro-10-(3-hydroxy-3-methyl-but-1-ynyl)-3-[(2-methylpyrazol-3-yl)methyl]-5,6-dihydroimidazo[1,2-d][1,4]benzoxazepine-2-carboxamide

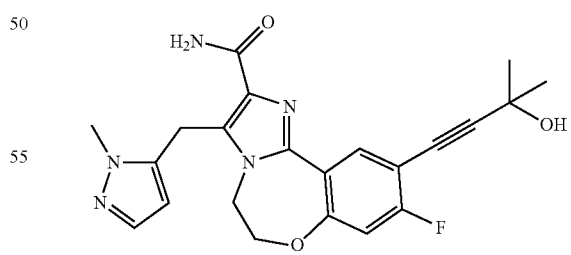

9-fluoro-10-(3-hydroxy-3-methyl-but-1-ynyl)-3-[(2-methylpyrazol-3-yl)methyl]-5,6-dihydroimidazo[1,2-d][1,4]benzoxazepine-2-carboxamide was prepared similarly according to General Procedure E with slight modification. 10-bromo-9-fluoro-3-[(2-methylpyrazol-3-yl)methyl]-5,6-dihydroimidazo[1,2-d][1,4]benzoxazepine-2-carboxamide was reacted with 3-methyl-1-butyne-3-ol in a solution of DMF (1.3 mL/mmol) and diisopropylamine (2.6 mL/mmol) to afford 2.5 mg (23% yield). M+1=424.2.

Example 557

Synthesis of 10-bromo-3-(3-cyclopropyl-1H-1,2,4-triazol-5-yl)-9-fluoro-5,6-dihydrobenzo[f]imidazo[1,2-d][1,4]oxazepine-2-carboxamide

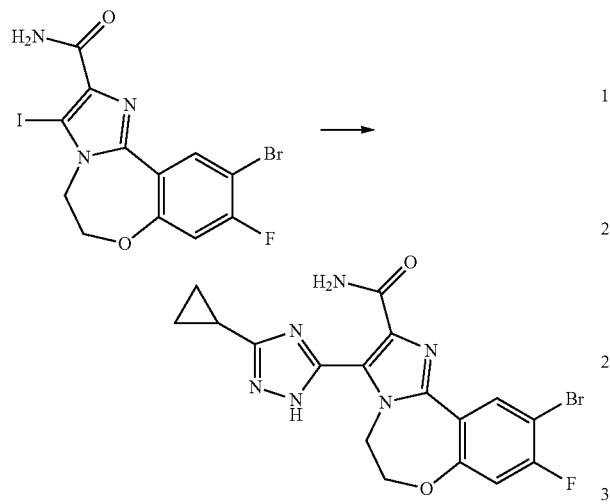

10-bromo-3-(3-cyclopropyl-1H-1,2,4-triazol-5-yl)-9-fluoro-5,6-dihydrobenzo[f]imidazo[1,2-d][1,4]oxazepine-2-carboxamide was prepared similarly according to Procedure I. Cyclopropylcarboxamidine hydrochloride was reacted with 10-bromo-9-fluoro-3-iodo-5,6-dihydrobenzo[f]imidazo[1,2-d][1,4]oxazepine-2-carboxamide then hydrazine to afford 102 mg (35% yield) of the title compound.

Example 558

Synthesis of 3-(3-cyclopropyl-1H-1,2,4-triazol-5-yl)-9-fluoro-10-[(3R)-3-hydroxy-3-pyrimidin-2-yl-but-1-ynyl]-5,6-dihydroimidazo[1,2-d][1,4]benzoxazepine-2-carboxamide

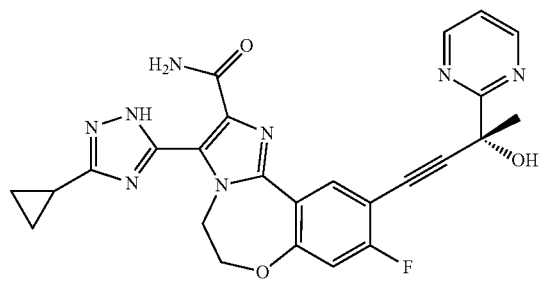 [SMILES: C[C@@](O)(C#Cc1cc2c(cc1F)OCCn1c-2nc(C(N)=O)c1-c1nc(C2CC2)n[nH]1)c1ncccn1]

3-(3-cyclopropyl-1H-1,2,4-triazol-5-yl)-9-fluoro-10-[(3R)-3-hydroxy-3-pyrimidin-2-yl-but-1-ynyl]-5,6-dihydroimidazo[1,2-d][1,4]benzoxazepine-2-carboxamide was prepared similarly according to General Procedure E with slight modification. 10-bromo-3-(3-cyclopropyl-1H-1,2,4-triazol-5-yl)-9-fluoro-5,6-dihydroimidazo[1,2-d][1,4]benzoxazepine-2-carboxamide was reacted with (2R)-2-pyrimidin-2-ylbut-3-yn-2-ol in a solution of DMF (1.3 mL/mmol) and diisopropylamine (2.6 mL/mmol) to afford 47 mg of the titled compound (40% yield). M+1=501.2. 1H NMR (400 MHz, DMSO-d6) δ 8.89 (d, J=4.8 Hz, 2H), 8.64 (d, J=8.4 Hz, 1H), 8.35 (br s, 1H), 7.74 (br s, 1H), 7.50 (t, J=4.8 Hz, 1H), 7.03 (d, J=10.5 Hz, 1H), 6.21 (s, 1H), 5.04-4.80 (m, 2H), 4.63-4.54 (m, 2H), 2.13-2.04 (m, 1H), 1.89 (s, 3H), 1.03-0.95 (m, 2H), 0.93-0.87 (m, 2H).

Example 559

Synthesis of (±)-methyl 10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxylate

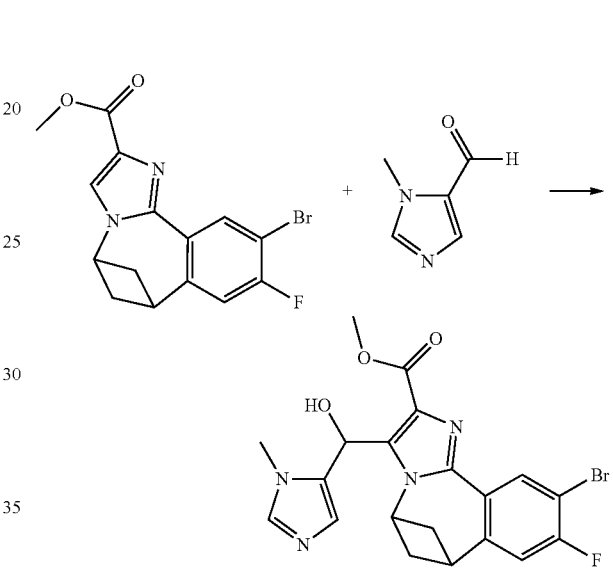

Methyl 10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 1-methylpyrazole-5-carbaldehyde to afford 491 mg (75% yield) of the title compound.

Example 560

Synthesis of (±)-10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxamide

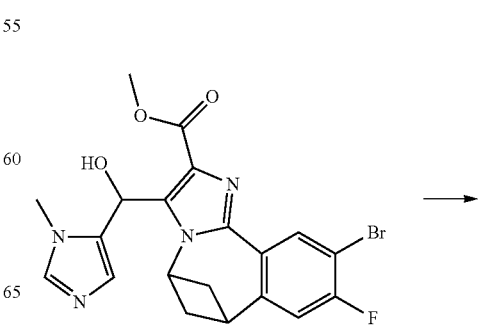

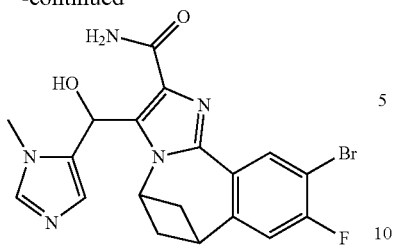

10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxylate was reacted with sodium methoxide and formamide to afford 127 mg (66% yield) of the crude title compound which was carried forward without further purification.

Example 561

Synthesis of (±)-9-fluoro-10-(3-hydroxy-3-methyl-but-1-ynyl)-3-[hydroxy-(3-methylimidazol-4-yl)methyl]-5,6,7,12-tetrahydro-5,7-methanobenzo[c]imidazo[1,2-a]azepine-2-carboxamide

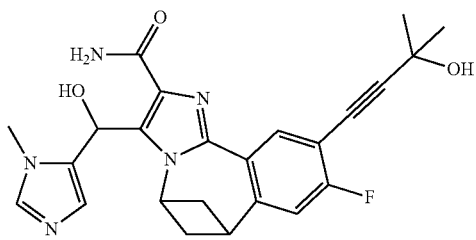 [SMILES: Cn1cncc1C(O)c1c(C(N)=O)nc2n1C1CC(C1)c1cc(F)c(C#CC(C)(C)O)cc1-2]

9-fluoro-10-(3-hydroxy-3-methyl-but-1-ynyl)-3-[hydroxy-(3-methylimidazol-4-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 6.9 mg (11% yield). M+1=450.0. 1H NMR (400 MHz, DMSO-d6) δ 8.76 (d, J=7.6 Hz, 1H), 7.89 (br s, 1H), 7.57 (s, 1H), 7.37 (br s, 1H), 7.27 (d, J=10.2 Hz, 1H), 6.94 (d, J=6.2 Hz, 1H), 6.78 (d, J=6.2 Hz, 1H), 6.23 (s, 1H), 5.54 (s, 1H), 5.21 (td, J=6.6, 4.4 Hz, 1H), 3.69 (s, 3H), 3.64 (td, J=7.2, 6.7, 3.7 Hz, 1H), 3.02 (ddd, J=9.3, 7.3, 4.6 Hz, 2H), 1.79 (dd, J=12.0, 6.9 Hz, 1H), 1.62 (dd, J=12.0, 6.8 Hz, 1H), 1.51 (s, 6H).

Example 562

Synthesis of 3-(3-cyclopropyl-1H-1,2,4-triazol-5-yl)-10-[(3R)-3-hydroxy-3-pyrimidin-2-yl-but-1-ynyl]-5,6-dihydroimidazo[1,2-d][1,4]benzoxazepine-2-carboxamide

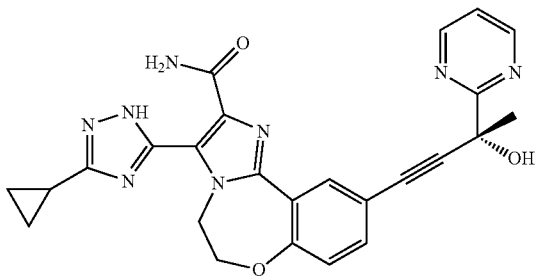 [SMILES: C[C@@](O)(C#Cc1ccc2c(c1)-c1nc(C(N)=O)c(-c3nc(C4CC4)n[nH]3)n1CCO2)c1ncccn1]

3-(3-cyclopropyl-1H-1,2,4-triazol-5-yl)-10-[(3R)-3-hydroxy-3-pyrimidin-2-yl-but-1-ynyl]-5,6-dihydroimidazo[1,2-d][1,4]benzoxazepine-2-carboxamide was prepared similarly according to General Procedure E with slight modification. 10-bromo-3-(3-cyclopropyl-1H-1,2,4-triazol-5-yl)-5,6-dihydroimidazo[1,2-d][1,4]benzoxazepine-2-carboxamide was reacted with (2R)-2-pyrimidin-2-ylbut-3-yn-2-ol in a solution of DMF (1.3 mL/mmol) and diisopropylamine (2.6 mL/mmol) to afford 36.7 mg (41.6% yield). M+1=483.2. 1H NMR (400 MHz, DMSO-d6) δ 8.89 (d, J=4.8 Hz, 2H), 8.57 (d, J=2.2 Hz, 1H), 8.30 (br s, 1H), 7.72 (br s, 1H), 7.49 (t, J=4.8 Hz, 1H), 7.35 (dd, J=8.5, 2.3 Hz, 1H), 7.05 (d, J=8.5 Hz, 1H), 6.14 (s, 1H), 5.00-4.77 (m, 2H), 4.58-4.50 (m, 2H), 2.13-2.03 (m, 1H), 1.88 (s, 3H), 1.03-0.96 (m, 2H), 0.94-0.86 (m, 2H).

Example 563

Synthesis of (±)-Methyl 10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxylate

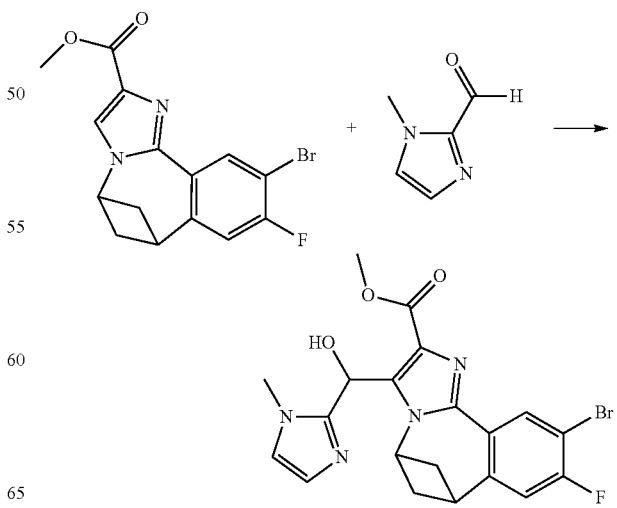

Methyl 10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 1-methylpyrazole-5-carbaldehyde to afford 433 mg (66% yield) of the title compound.

Example 564

Synthesis of (±)-10-bromo-9-fluoro-3-(hydroxy(1-methyl-1H-imidazol-2-yl)methyl)-6,7-dihydro-5H-5,7-methanobenzo[c]imidazo azepine-2-carboxamide

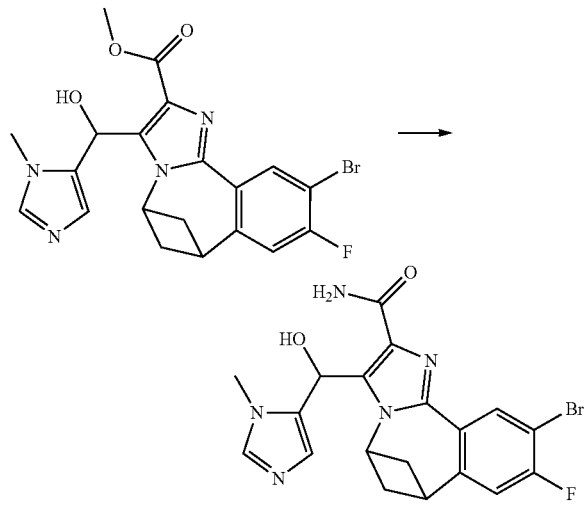

10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxylate was reacted with sodium methoxide and formamide to afford 120 mg (62% yield) of the crude title compound which was carried forward without further purification.

Example 565

Synthesis of (±)-9-fluoro-10-[2-(1-hydroxycyclopentyl)ethynyl]-3-[hydroxy-(1-methylimidazol-2-yl)methyl]-5,6,7,12-tetrahydro-5,7-methanobenzo[c]imidazo[1,2-a]azepine-2-carboxamide

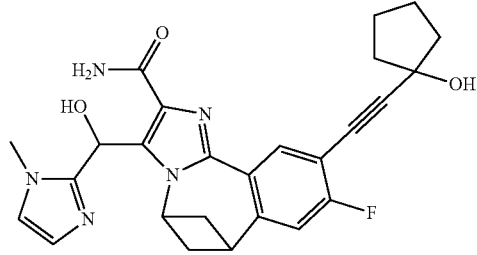 [SMILES: Cn1ccnc1C(O)c1c(C(N)=O)nc2n1C1CC(C1)c1cc(F)c(C#CC3(O)CCCC3)cc1-2]

9-fluoro-10-[2-(1-hydroxycyclopentyl)ethynyl]-3-[hydroxy-(1-methylimidazol-2-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxamide was reacted with 1-ethynylcyclopentanol in a solution of DMF (1.3 mL/mmol) and diisopropylamine (2.6 mL/mmol) to afford 22.5 mg of the titled compound (35.2% yield). M+1=476.3. 1H NMR (400 MHz, DMSO-d6) δ 8.75 (d, J=7.7 Hz, 1H), 7.79 (br s, 1H), 7.33-7.19 (m, 2H), 7.11-7.06 (m, 1H), 7.01 (s, 1H), 6.79 (br s, 1H), 6.69 (d, J=1.1 Hz, 1H), 5.39 (s, 1H), 5.38-5.35 (m, 1H), 3.74 (s, 3H), 3.67-3.55 (m, 1H), 3.05-2.93 (m, 2H), 2.00-1.87 (m, 4H), 1.82-1.66 (m, 5H), 1.62 (dd, J=12.0, 6.6 Hz, 1H).

Example 566

Synthesis of (±)-9-fluoro-10-(3-hydroxy-3-methyl-but-1-ynyl)-3-[hydroxy-(1-methylimidazol-2-yl)methyl]-5,6,7,12-tetrahydro-5,7-methanobenzo[c]imidazo[1,2-a]azepine-2-carboxamide

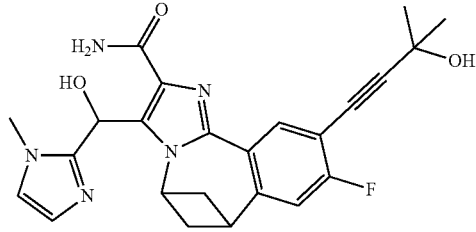 [SMILES: Cn1ccnc1C(O)c1c(C(N)=O)nc2n1C1CC(C1)c1cc(F)c(C#CC(C)(C)O)cc1-2]

9-fluoro-10-(3-hydroxy-3-methyl-but-1-ynyl)-3-[hydroxy-(1-methylimidazol-2-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-imidazol-2-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford 20.3 mg of the titled compound (33.6% yield). M+1=450.2. 1H NMR (400 MHz, DMSO-d6) δ 8.75 (d, J=7.6 Hz, 1H), 7.78 (br s, 1H), 7.30-7.21 (m, 2H), 7.13-7.05 (m, 1H), 7.01 (d, J=5.5 Hz, 1H), 6.78 (d, J=5.4 Hz, 1H), 6.69 (d, J=1.1 Hz, 1H), 5.53 (s, 1H), 5.38 (td, J=6.8, 4.1 Hz, 1H), 3.74 (s, 3H), 3.65-3.57 (m, 1H), 3.04-2.94 (m, 2H), 1.72 (dd, J=11.9, 6.9 Hz, 1H), 1.61 (dd, J=11.9, 7.2 Hz, 1H), 1.51 (s, 6H).

Example 567

Synthesis of (±)-9-fluoro-10-[2-(1-hydroxycyclopentyl)ethynyl]-3-[hydroxy-(3-methylimidazol-4-yl)methyl]-5,6,7,12-tetrahydro-5,7-methanobenzo[c]imidazo[1,2-a]azepine-2-carboxamide

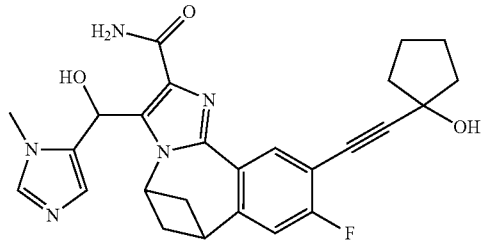 [SMILES: Cn1cncc1C(O)c1c(C(N)=O)nc2n1C1CC(C1)c1cc(F)c(C#CC3(O)CCCC3)cc1-2]

9-fluoro-10-[2-(1-hydroxycyclopentyl)ethynyl]-3-[hydroxy-(3-methylimidazol-4-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-imidazol-5-yl)methyl)-6,7-dihydro-5H-5,7-methanobenzo[c]imidazo[1,2-a]azepine-2-carboxamide was reacted with 1-ethynylcyclopentanol in a solution of DMF (1.3 mL/mmol) and diisopropylamine (2.6 mL/mmol) to afford 10.8 mg of the titled compound (17% yield). M+1=476.3. $^1$H NMR (400 MHz, DMSO-d6) δ 8.77 (d, J=7.7 Hz, 1H), 7.89 (br s, 1H), 7.57 (s, 1H), 7.37 (br s, 1H), 7.27 (d, J=10.2 Hz, 1H), 6.95 (d, J=6.3 Hz, 1H), 6.78 (d, J=6.2 Hz, 1H), 6.23 (s, 3H), 5.40 (s, 1H), 5.25-5.17 (m, 1H), 3.69 (s, 3H), 3.67-3.60 (m, 1H), 3.09-2.93 (m, 2H), 2.00-1.88 (m, 4H), 1.84-1.66 (m, 5H), 1.62 (dd, J=11.7, 6.9 Hz, 1H).

Example 568

Synthesis of 9-fluoro-10-[2-(3-hydroxy-1-methyl-2-oxo-pyrrolidin-3-yl)ethynyl]-3-[(2-methylpyrazol-3-yl)methyl]-5,6,7,12-tetrahydro-5,7-methanobenzo[c]imidazo[1,2-a]azepine-2-carboxamide

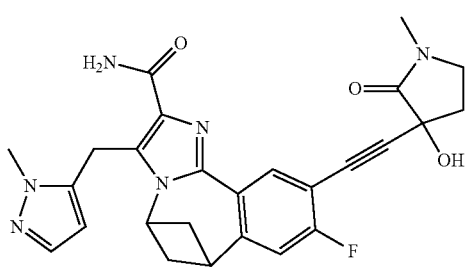 [SMILES: CN1CCC(O)(C#Cc2cc3c(cc2F)C2CC(C2)n2c-3nc(C(N)=O)c2Cc2ccnn2C)C1=O]

9-fluoro-10-[2-(3-hydroxy-1-methyl-2-oxo-pyrrolidin-3-yl)ethynyl]-3-[(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-((1-methyl-1H-pyrazol-5-yl)methyl)-6,7-dihydro-5H-5,7-methanobenzo[c]imidazo[1,2-a]azepine-2-carboxamide was reacted with 3-ethynyl-3-hydroxy-1-methyl-pyrrolidin-2-one in a solution of DMF (1.3 mL/mmol) and diisopropylamine (2.6 mL/mmol) to afford 18.7 mg of the titled compound (47.1% yield). M+1=489.2. 1H NMR (400 MHz, DMSO-d6) δ 8.75 (d, J=7.6 Hz, 1H), 7.67 (br s, 1H), 7.28 (d, J=10.1 Hz, 1H), 7.22 (d, J=1.8 Hz, 1H), 7.14 (br s, 1H), 6.52 (s, 1H), 5.59 (d, J=1.7 Hz, 1H), 4.76-4.68 (m, 1H), 4.56 (s, 2H), 3.81 (s, 3H), 3.69-3.60 (m, 1H), 3.42-3.32 (m, 2H), 3.06-2.96 (m, 2H), 2.81 (s, 3H), 2.48-2.40 (m, 1H), 2.22 (dt, J=12.9, 7.1 Hz, 1H), 1.73-1.64 (m, 2H).

Example 569

Synthesis of 9-fluoro-10-[2-(1-hydroxycyclopentyl)ethynyl]-3-[hydroxy-(2-methylpyrazol-3-yl)methyl]-5,6,7,12-tetrahydro-5,7-methanobenzo[c]imidazo[1,2-a]azepine-2-carboxamide

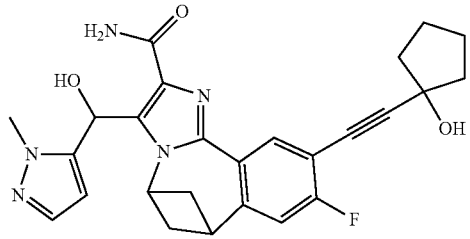 [SMILES: Cn1nccc1C(O)c1c(C(N)=O)nc2n1C1CC(C1)c1cc(F)c(C#CC3(O)CCCC3)cc1-2]

9-fluoro-10-[2-(1-hydroxycyclopentyl)ethynyl]-3-[hydroxy-(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide was reacted with 1-ethynylcyclopentanol in a solution of DMF (1.3 mL/mmol) and diisopropylamine (2.6 mL/mmol) to afford 18.2 mg of the titled compound (42.7% yield). M+1=476.2. 1H NMR (400 MHz, DMSO-d6) δ 8.77 (d, J=7.6 Hz, 1H), 7.91 (br s, 1H), 7.39 (br s, 1H), 7.30-7.24 (m, 2H), 7.08 (d, J=5.6 Hz, 1H), 6.89 (d, J=5.5 Hz, 1H), 5.70-5.65 (m, 1H), 5.40 (s, 1H), 5.21-5.13 (m, 1H), 3.86 (s, 3H), 3.69-3.58 (m, 1H), 3.10-2.93 (m, 2H), 2.02-1.85 (m, J=5.1, 4.1 Hz, 4H), 1.83-1.57 (m, 6H).

Example 570

Synthesis of a mixture of stereoisomers of 3,10-bis[2-(3-hydroxy-1-methyl-2-oxo-pyrrolidin-3-yl)ethynyl]-5,6,7,12-tetrahydro-5,7-methanobenzo[c]imidazo[1,2-a]azepine-2-carboxamide

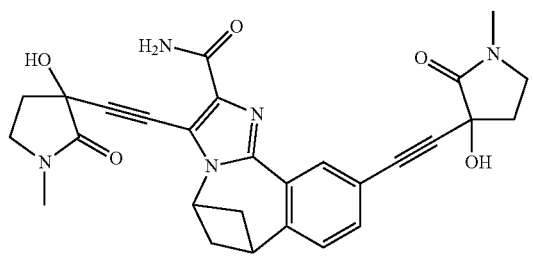 [SMILES: CN1CCC(O)(C#Cc2ccc3c(c2)-c2nc(C(N)=O)c(C#CC4(O)CCN(C)C4=O)n2C2CC3C2)C1=O]

3,10-bis[2-(3-hydroxy-1-methyl-2-oxo-pyrrolidin-3-yl)ethynyl]-5,6,7,12-tetrahydro-5,7-methanobenzo[c]imidazo[1,2-a]azepine-2-carboxamide was prepared similarly according to General Procedure E with slight modification. 10-bromo-3-iodo-6,7-dihydro-5H-5,7-methanobenzo[c]imidazo[1,2-a]azepine-2-carboxamide was reacted with racemic 3-ethynyl-3-hydroxy-1-methyl-pyrrolidin-2-one in a solution of DMF (1.3 mL/mmol) and diisopropylamine (2.6 mL/mmol) to afford 18.6 mg of the titled compound as a mixture of stereoisomers (31% yield). M+1=514.3. $^1$H NMR (400 MHz, DMSO-d6) δ 8.68 (s, 1H), 7.59 (br s, 1H), 7.38-

7.29 (m, 2H), 7.20 (br s, 1H), 6.58 (s, 1H), 6.44 (s, 1H), 5.15-5.05 (m, 1H), 3.78-3.70 (m, 1H), 3.45-3.33 (m, 4H), 3.18-3.06 (m, 2H), 2.81 (s, 3H), 2.80 (s, 3H), 2.48-2.37 (m, 2H), 2.24-2.14 (m, 2H), 1.75-1.62 (m, 2H).

Example 571

Synthesis of Methyl 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxylate

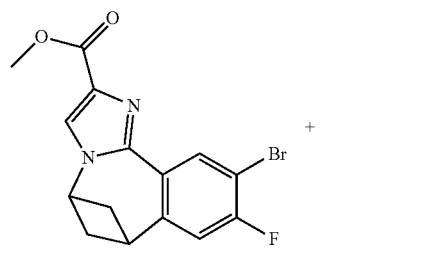
+
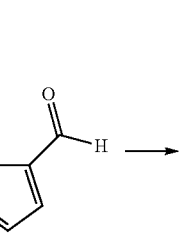
→
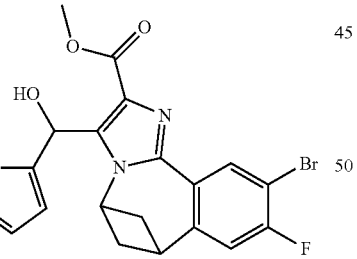

Methyl 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 2-tetrahydropyran-2-ylpyrazole-3-carbaldehyde to afford 329 mg (43% yield) of the title compound.

Example 572

Synthesis of 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxamide

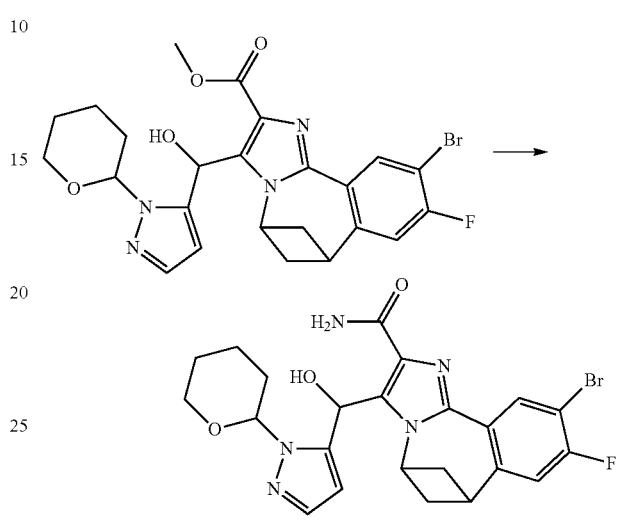

10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxylate was reacted with sodium methoxide and formamide to afford the crude title compound which was carried forward without further purification.

Example 573

Synthesis of (±)-9-fluoro-3-(hydroxy(1-(tetrahydro-2H-pyran-2-yl)-1H-pyrazol-5-yl)methyl)-10-(3-hydroxy-3-methylbut-1-yn-1-yl)-6,7-dihydro-5H-5,7-methanobenzo[c]imidazo[1,2-a]azepine-2-carboxamide

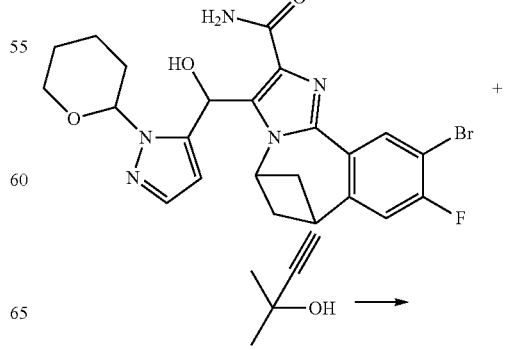
+

-continued

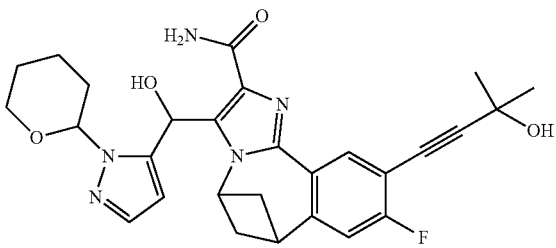

9-Fluoro-3-(hydroxy(1-(tetrahydro-2H-pyran-2-yl)-1H-pyrazol-5-yl)methyl)-10-(3-hydroxy-3-methylbut-1-yn-1-yl)-6,7-dihydro-5H-5,7-methanobenzo[c]imidazo[1,2-a]azepine-2-carboxamide was prepared similarly according to General Procedure E with slight modification. 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford the title compound which was carried forward to the next step without further purification.

Example 574

Synthesis of (±)-9-fluoro-10-(3-hydroxy-3-methyl-but-1-ynyl)-3-[hydroxy(1H-pyrazol-5-yl)methyl]-5,6,7,12-tetrahydro-5,7-methanobenzo[c]imidazo[1,2-a]azepine-2-carboxamide

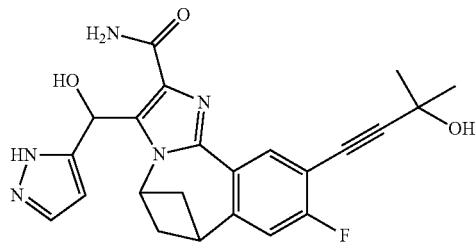 [SMILES: CC(C)(O)C#Cc1cc2c(cc1F)C1CC(C1)n1c-2nc(C(N)=O)c1C(O)c1ccn[nH]1]

9-fluoro-3-(hydroxy(1-(tetrahydro-2H-pyran-2-yl)-1H-pyrazol-5-yl)methyl)-10-(3-hydroxy-3-methylbut-1-yn-1-yl)-6,7-dihydro-5H-5,7-methanobenzo[c]imidazo[1,2-a]azepine-2-carboxamide (35 mg, 0.0674 mmol) was dissolved in methanol (0.27 mL). Hydrogen chloride (4.0 mol/L) in dioxane (4.0 equiv., 0.067 mL, 0.2694 mmol) was added and the reaction was stirred at room temperature for 45 minutes. The solution was evaporated in vacuo and purified by reverse-phase HPLC to afford 3.4 mg (12% yield) of the title compound. M+1=436.2.

Example 575

Synthesis of 9-fluoro-3-(hydroxy(1-(tetrahydro-2H-pyran-2-yl)-1H-pyrazol-5-yl)methyl)-10-((1-hydroxycyclopentyl)ethynyl)-6,7-dihydro-5H-5,7-methanobenzo[c]imidazo[1,2-a]azepine-2-carboxamide

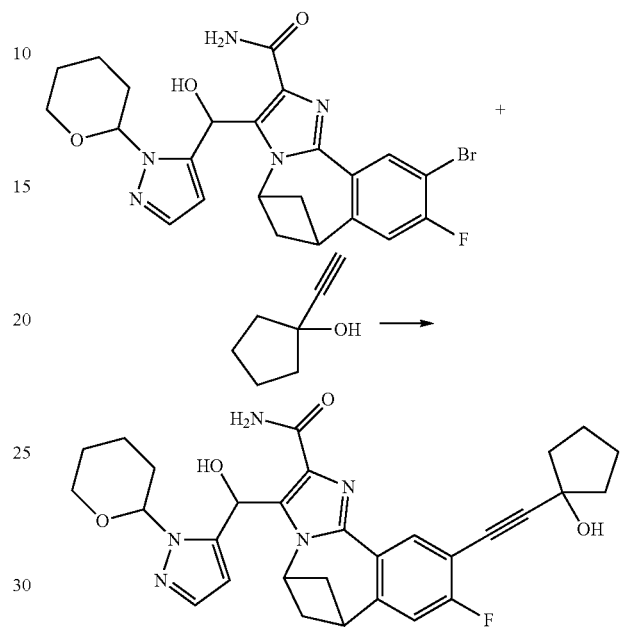

9-fluoro-3-(hydroxy(1-(tetrahydro-2H-pyran-2-yl)-1H-pyrazol-5-yl)methyl)-10-((1-hydroxycyclopentyl)ethynyl)-6,7-dihydro-5H-5,7-methanobenzo[c]imidazo[1,2-a]azepine-2-carboxamide was prepared similarly according to General Procedure E with slight modification. 10-bromo-9-fluoro-3-(hydroxy(1-(tetrahydro-2H-pyran-2-yl)-1H-pyrazol-5-yl)methyl)-6,7-dihydro-5H-5,7-methanobenzo[c]imidazo[1,2-a]azepine-2-carboxamide was reacted with 1-ethynylcyclopentanol in a solution of DMF (1.3 mL/mmol) and diisopropylamine (2.6 mL/mmol) to afford the title compound which was carried forward to the next step without further purification.

Example 576

Synthesis of (±)-9-fluoro-10-[2-(1-hydroxycyclopentyl)ethynyl]-3-[hydroxy(1H-pyrazol-5-yl)methyl]-5,6,7,12-tetrahydro-5,7-methanobenzo[c]imidazo[1,2-a]azepine-2-carboxamide

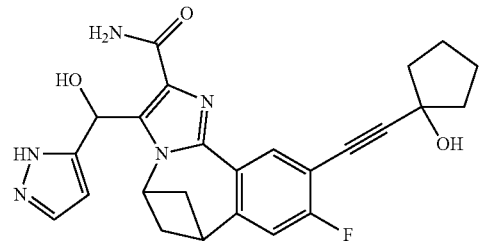 [SMILES: NC(=O)c1nc2n(c1C(O)c1ccn[nH]1)C1CC(C1)c1cc(F)c(C#CC3(O)CCCC3)cc1-2]

9-fluoro-10-[2-(1-hydroxycyclopentyl)ethynyl]-3-[hydroxy(1H-pyrazol-5-yl)methyl]-5,6,7,12-tetrahydro-5,7-methanobenzo[c]imidazo[1,2-a]azepine-2-carboxamide was prepared 9-fluoro-10-(3-hydroxy-3-methyl-but-1-ynyl)-3-

[hydroxy(1H-pyrazol-5-yl)methyl]-5,6,7,12-tetrahydro-5,7-methanobenzo[c]imidazo[1,2-a]azepine-2-carboxamide. 9-fluoro-3-(hydroxy(1-(tetrahydro-2H-pyran-2-yl)-1H-pyrazol-5-yl)methyl)-10-((1-hydroxycyclopentyl)ethynyl)-6,7-dihydro-5H-5,7-methanobenzo[c]imidazo[1,2-a]azepine-2-carboxamide was reacted with hydrogen chloride to afford 4.1 mg (13% yield) of the title compound. M+1=462.2.

Example 577

Synthesis of 9-fluoro-10-[(3R)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide and 9-fluoro-10-[(3S)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide

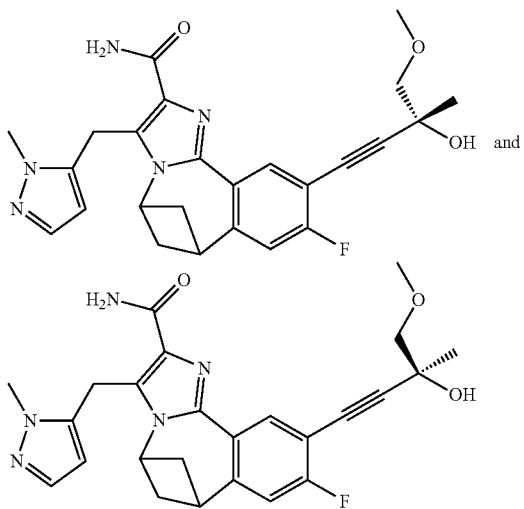

9-fluoro-10-[(3R)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide AND 9-fluoro-10-[(3S)-3-hydroxy-4-methoxy-3-methyl-but-1-ynyl]-3-[(2-methylpyrazol-3-yl)methyl]-5,6,7,12-tetrahydro-5,7-methanobenzo[c]imidazo[1,2-a]azepine-2-carboxamide were prepared similarly according to General Procedure E with slight modification. 10-bromo-9-fluoro-3((1-methyl-1H-pyrazol-5-yl)methyl)-6,7-dihydro-5H-5,7-methanobenzo[c]imidazo[1,2-a]azepine-2-carboxamide was reacted with 1-methoxy-2-methyl-but-3-yn-2-ol in a solution of DMF (1.3 mL/mmol) and diisopropylamine (2.6 mL/mmol) to afford 32.4 mg (85.9% yield) of the racemic compound. The enantiomers were separated by chiral SFC to afford 7.2 mg of Compound 1 and 7.4 mg of Compound 2. The stereochemistry of the propargyl alcohol position for each isomer was not determined. M+1=464.3. 1H NMR (400 MHz, DMSO-d6) δ 8.72 (d, J=7.6 Hz, 1H), 7.65 (br s, 1H), 7.25 (d, J=10.2 Hz, 1H), 7.22 (d, J=1.9 Hz, 1H), 7.15 (br s, 1H), 5.64 (s, 1H), 5.59 (d, J=1.5 Hz, 1H), 4.76-4.67 (m, 1H), 4.56 (s, 2H), 3.81 (s, 3H), 3.68-3.61 (m, 1H), 3.44 (d, J=9.5 Hz, 1H), 3.39 (d, J=9.5 Hz, 1H), 3.38 (s, 3H), 3.06-2.92 (m, 2H), 1.73-1.59 (m, 2H), 1.46 (s, 3H).

Example 578

Synthesis of 9-fluoro-3-((S)-hydroxy(1-methyl-1H-pyrazol-5-yl)methyl)-10-((R)-3-hydroxy-4-methoxy-3-methylbut-1-yn-1-yl)-6,7-dihydro-5H-5,7-methanobenzo[c]imidazo[1,2-a]azepine-2-carboxamide AND 9-fluoro-3-((S)-hydroxy(1-methyl-1H-pyrazol-5-yl)methyl)-10-((S)-3-hydroxy-4-methoxy-3-methyl but-1-yn-1-yl)-6,7-dihydro-5H-5,7-methanobenzo[c]imidazo[1,2-a]azepine-2-carboxamide AND 9-fluoro-3((R)-hydroxy(1-methyl-1H-pyrazol-5-yl)methyl)-10-((R)-3-hydroxy-4-methoxy-3-methylbut-1-yn-1-yl)-6,7-dihydro-5H-5,7-methanobenzo[c]imidazo[1,2-a]azepine-2-carboxamide AND 9-fluoro-3((R)-hydroxy(1-methyl-1H-pyrazol-5-yl)methyl)-10-((S)-3-hydroxy-4-methoxy-3-methylbut-1-yn-1-yl)-6,7-dihydro-5H-5,7-methanobenzo[c]imidazo[1,2-a]azepine-2-carboxamide

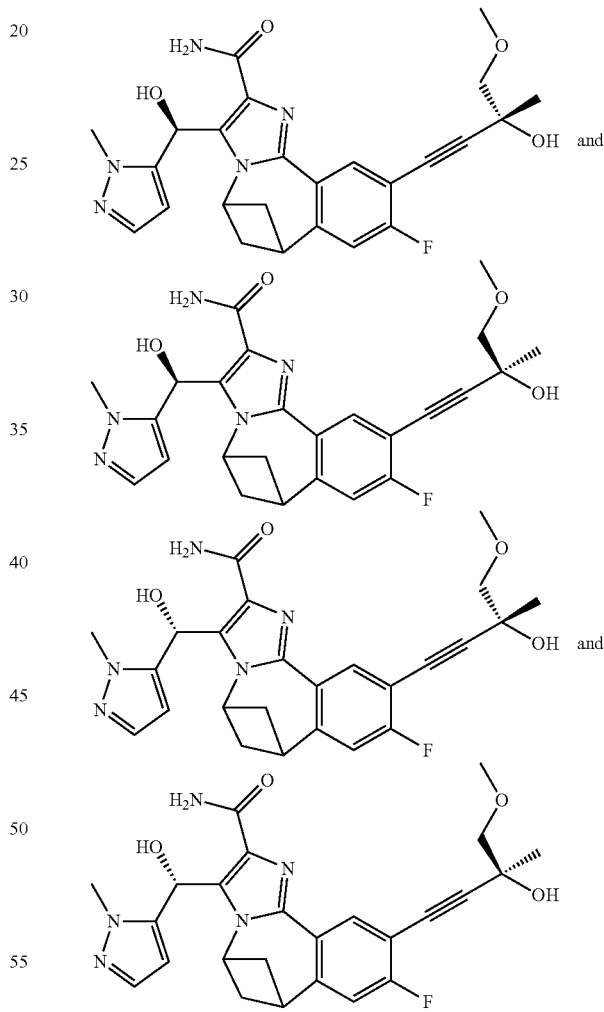

9-fluoro-3-((S)-hydroxy(1-methyl-1H-pyrazol-5-yl)methyl)-10-((R)-3-hydroxy-4-methoxy 3-methylbut-1-yn-1-yl)-6,7-dihydro-5H-5,7-methanobenzo[c]imidazo[1,2-a]azepine-2-carboxamide AND 9-fluoro-3-((S)-hydroxy(1-methyl-1H-pyrazol-5-yl)methyl)-10-((S)-3-hydroxy-4-methoxy-3-methyl but-1-yn-1-yl)-6,7-dihydro-5H-5,7-methanobenzo[c]imidazo[1,2-a]azepine-2-carboxamide AND 9-fluoro-3((R)-hydroxy(1-methyl-1H-pyrazol-5-yl)methyl)-10-((R)-3-hydroxy-4-methoxy-3-methylbut-1-yn- 1-yl)-6,7-dihydro-5H-5,7-methanobenzo[c]imidazo[1,2-a] azepine-2-carboxamide AND 9-fluoro-3((R)-hydroxy(1-methyl-1H-pyrazol-5-yl)methyl)-10-((S)-3-hydroxy-4-methoxy-3-methylbut-1-yn-1-yl)-6,7-dihydro-5H-5,7-methanobenzo[c]imidazo[1,2-a]azepine-2-carboxamide were prepared similarly according to General Procedure E with slight modification. 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide was reacted with 1-methoxy-2-methyl-but-3-yn-2-ol in a solution of DMF (1.3 mL/mmol) and diisopropylamine (2.6 mL/mmol) to afford the racemic compound. The diastereomers and enantiomers were separated by chiral SFC to afford 5.1 mg Compound 1, 5.0 mg Compound 2, 4.3 mg Compound 3 and 4.2 mg Compound 4. The absolute and relative stereochemistry for each isomer was not determined.

Compound 1 M+1=480.2. $^1$H NMR (400 MHz, DMSO-d6) δ 8.76 (d, J=7.6 Hz, 1H), 7.89 (br s, 1H), 7.39 (br s, 1H), 7.27 (d, J=102 Hz, 1H), 7.25 (d, J=1.8 Hz, 1H), 7.07 (d, J=6.1 Hz, 1H), 6.90 (d, J=6.0 Hz, 1H), 5.68 (d, J=1.9 Hz, 1H), 5.64 (s, 1H), 5.22-5.14 (m, 1H), 3.86 (s, 3H), 3.70-3.55 (m, 1H), 3.45 (d, J=9.5 Hz, 1H), 3.39 (d, J=9.5 Hz, 2H), 3.39 (s, 3H), 3.09-2.88 (m, 2H), 1.82-1.68 (m, 1H), 1.68-1.56 (m, 1H), 1.46 (s, 3H).

Compound 2: $^1$H NMR (400 MHz, DMSO-d6) δ 8.76 (d, J=7.6 Hz, 1H), 7.89 (br s, 1H), 7.39 (br s, 1H), 7.27 (d, J=10.2 Hz, 1H), 7.25 (d, J=2.0 Hz, 1H), 7.07 (d, J=6.0 Hz, 1H), 6.90 (d, J=6.0 Hz, 1H), 5.68 (d, J=2.0 Hz, 1H), 5.64 (s, 1H), 5.22-5.14 (m, 1H), 3.86 (s, 3H), 3.68-3.58 (m, 1H), 3.45 (d, J=9.5 Hz, 1H), 3.39 (d, J=9.4 Hz, 1H), 3.39 (s, 3H), 3.10-2.92 (m, 2H), 1.79-1.70 (m, 1H), 1.68-1.59 (m, 2H), 1.46 (s, 3H).

Compound 1 and Compound 2: M+1=480.2

Example 579

Synthesis of 9-fluoro-3((S)-hydroxy(1-methyl-1H-pyrazol-5-yl)methyl)-10-(((R)-3-hydroxy-1-methyl-2-oxopyrrolidin-3-yl)ethynyl)-6,7-dihydro-5H-5,7-methanobenzo[c]imidazo[1,2-a]azepine-2-carboxamide and 9-fluoro-3((R)-hydroxy(1-methyl-1H-pyrazol-5-yl)methyl)-10-(((R)-3-hydroxy-1-methyl-2-oxopyrrolidin-3-yl)ethynyl)-6,7-dihydro-5H-5,7-methanobenzo[c]imidazo[1,2-a]azepine-2-carboxamide and 9-fluoro-3-((S)-hydroxy(1-methyl-1H-pyrazol-5-yl)methyl)-10-(((S)-3-hydroxy-1-methyl-2-oxopyrrolidin-3-yl)ethynyl)-6,7-dihydro-5H-5,7-methanobenzo[c]imidazo[1,2-a]azepine-2-carboxamide and 9-fluoro-3-((R)-hydroxy(1-methyl-1H-pyrazol-5-yl)methyl)-10-(((S)-3-hydroxy-1-methyl-2-oxopyrrolidin-3-yl)ethynyl)-6,7-dihydro-5H-5,7-methanobenzo[c]imidazo[1,2-a]azepine-2-carboxamide

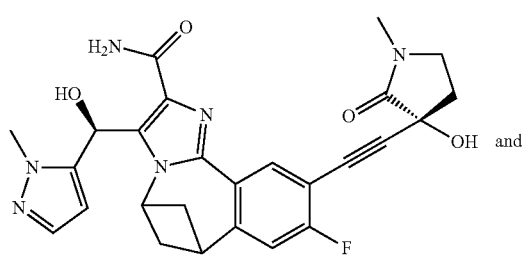

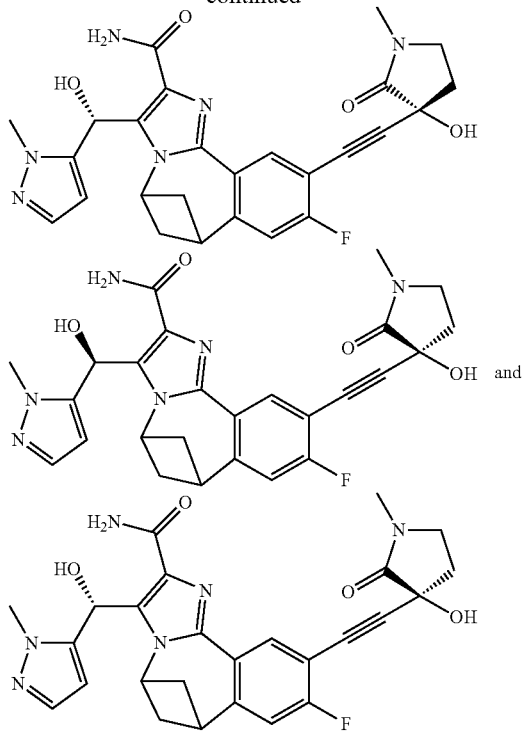

9-fluoro-3-((S)-hydroxy(1-methyl-4H-pyrazol-5-yl)methyl)-10-(4R)-3-hydroxy-1-methyl-2-oxopyrrolidin-3-yl) ethynyl)-6,7-dihydro-5H-5,7-methanobenzo[c]imidazo-1,2azepine-2-carboxamide and 9-fluoro-3((R)-hydroxy(1-methyl-1H-pyrazol-5-yl)methyl)-10-(((R)-3-hydroxy-1-methyl-2-oxopyrrolidin-3-yl)ethynyl)-6,7-dihydro-5H-5,7-methanobenzo[c]imidazo[1,2-a]azepine-2-carboxamide and 9-fluoro-3-((S)-hydroxy(1-methyl-1H-pyrazol-5-yl)methyl)-10-(((S)-3-hydroxy-1-methyl-2-oxopyrrolidin-3-yl) ethynyl)-6,7-dihydro-5H-5,7-methanobenzo[c]imidazo[1,2-a]azepine-2-carboxamide and 9-fluoro-3-((R)-hydroxy(1-methyl-1H-pyrazol-5-yl)methyl)-10-(((S)-3-hydroxy-1-methyl-2-oxopyrrolidin-3-yl)ethynyl)-6,7-dihydro-5H-5,7-methanobenzo[c]imidazo[1,2-a]azepine-2-carboxamide were prepared similarly according to General Procedure E with slight modification. 10-bromo-9-fluoro-3-(hydroxy(1-methyl-1H-pyrazol-5-yl)methyl)-6,7-dihydro-5H-5,7-methanobenzo[c]imidazo[1,2-a]azepine-2-carboxamide was reacted with 3-ethynyl-3-hydroxy-1-methyl-pyrrolidin-2-one in a solution of DMF (1.3 mL/mmol) and diisopropylamine (2.6 mL/mmol) to afford the racemic compound. The diastereoisomers and enantiomers were separated by chiral SFC to afford 5.9 mg Compound 1, 6.0 mg Compound 2, 5.2 mg Compound 3 and 4.7 mg Compound 4.

Compound 1: M+1=505.2. $^1$H NMR (400 MHz, DMSO-d6) δ 8.79 (d, J=7.5 Hz, 1H), 7.90 (br s, 1H), 7.38 (br s, 1H), 7.30 (d, J=10.1 Hz, 1H), 7.25 (d, J=2.0 Hz, 1H), 7.07 (d, J=6.2 Hz, 1H), 6.90 (d, J=6.1 Hz, 1H), 6.52 (s, 1H), 5.68 (d, J=2.3 Hz, 1H), 5.22-5.13 (m, 1H), 3.86 (s, 3H), 3.69-3.59 (m, 1H), 3.42-3.33 (m, 2H), 3.09-2.92 (m, 2H), 2.81 (s, 3H), 2.50-2.40 (m, 1H), 2.28-2.17 (m, 1H), 1.81-1.71 (m, 1H), 1.68-1.58 (m, 1H).

Compound 2: M+1=505.2. $^1$H NMR (400 MHz, DMSO-d6) δ 8.79 (d, J=7.5 Hz, 1H), 7.91 (br s, 1H), 7.38 (br s, 1H), 7.30 (d, J=10.1 Hz, 1H), 7.25 (d, J=2.2 Hz, 1H), 7.07 (d, J=6.0 Hz, 1H), 6.90 (d, J=6.1 Hz, 1H), 6.52 (s, 1H), 5.68 (d, J=1.8 Hz, 1H), 5.25-5.10 (m, 1H), 3.86 (s, 3H), 3.70-3.58 (m, 1H), 3.45-3.32 (m, 2H), 3.11-2.90 (m, 2H), 2.81 (s, 3H), 2.48-2.40 (m, 1H), 2.28-2.16 (m, 1H), 1.82-1.70 (m, 1H), 1.69-1.56 (m, 1H).

Compound 3: M+1=505.3. $^1$H NMR (400 MHz, DMSO-d6) δ 8.79 (d, J=7.5 Hz, 1H), 7.91 (br s, 1H), 7.38 (br s, 1H), 7.30 (d, J=10.1 Hz, 1H), 7.25 (d, J=1.9 Hz, 1H), 7.07 (d, J=6.1 Hz, 1H), 6.90 (d, J=6.0 Hz, 1H), 6.52 (s, 1H), 5.68 (d, J=1.9 Hz, 1H), 5.22-5.08 (m, 1H), 3.86 (s, 3H), 3.72-3.55 (m, 1H), 3.46-3.32 (m, 2H), 3.15-2.89 (m, 2H), 2.81 (s, 3H), 2.45-2.38 (m, 1H), 2.28-2.13 (m, 1H), 1.87-1.69 (m, 1H), 1.69-1.55 (m, 1H).

Compound 4: M+1=505.3. $^1$H NMR (400 MHz, DMSO-d6) δ 8.79 (d, J=7.5 Hz, 1H), 7.91 (br s, 1H), 7.38 (br s, 1H), 7.30 (d, J=10.0 Hz, 1H), 7.25 (d, J=2.4 Hz, 1H), 7.07 (d, J=6.1 Hz, 1H), 6.90 (d, J=6.1 Hz, 1H), 6.52 (s, 1H), 5.68 (d, J=2.5 Hz, 1H), 5.25-5.08 (m, 1H), 3.86 (s, 3H), 3.69-3.58 (m, 1H), 3.43-3.32 (m, 2H), 3.11-2.92 (m, 2H), 2.81 (s, 3H), 2.48-2.40 (m, 1H), 2.29-2.16 (m, 1H), 1.82-1.70 (m, 1H), 1.69-1.57 (m, 1H).

Example 580

Synthesis of Methyl 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxylate

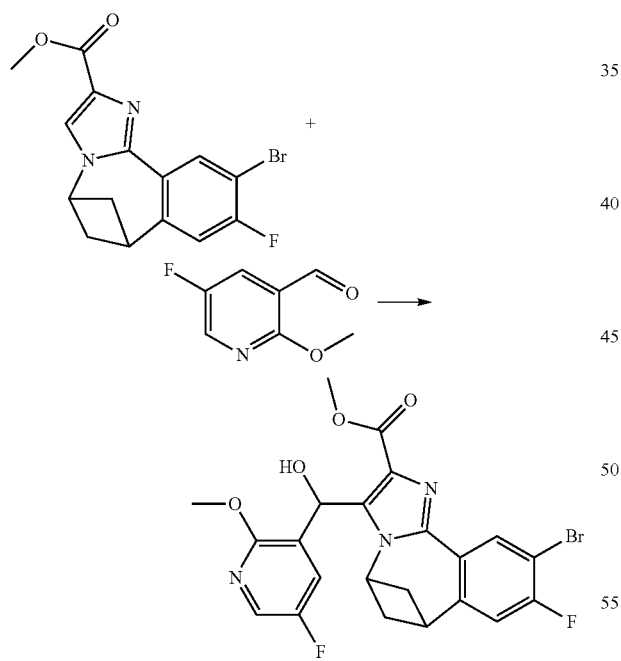

Methyl 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 5-fluoro-2-methoxy-pyridine-3-carbaldehyde to afford 196 mg (68% yield) of the title compound.

Example 581

Synthesis of 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxamide

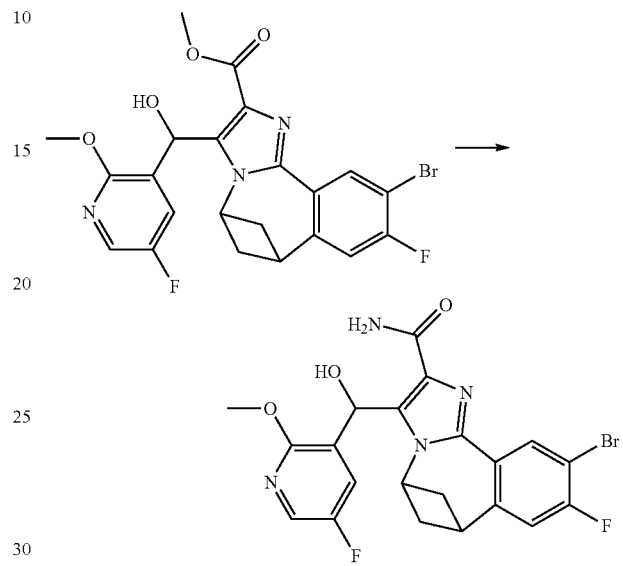

10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxamide was prepared similarly to as described in General Procedure L. Methyl 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxylate was reacted with sodium methoxide and formamide to afford the crude title compound which was carried forward without further purification.

Example 582

Synthesis of 9-fluoro-3-[(5-fluoro-2-methoxy-3-pyridyl)-hydroxy-methyl]-10-(3-hydroxy-3-methyl-but-1-ynyl)-5,6,7,12-tetrahydro-5,7-methanobenzo[c]imidazo[1,2-a]azepine-2-carboxamide and 9-fluoro-3-[(5-fluoro-2-methoxy-3-pyridyl)-hydroxy-methyl]-10-(3-hydroxy-3-methyl-but-1-ynyl)-5,6,7,12-tetrahydro-5,7-methanobenzo[c]imidazo[1,2-a]azepine-2-carboxamide

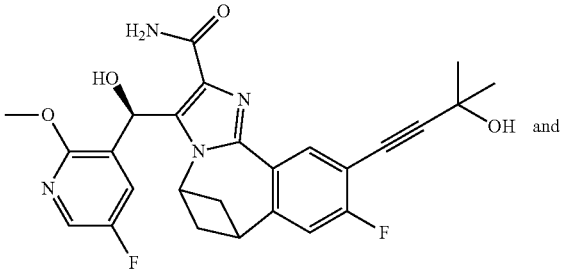 and

-continued

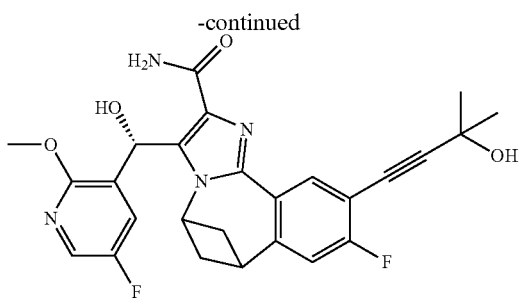

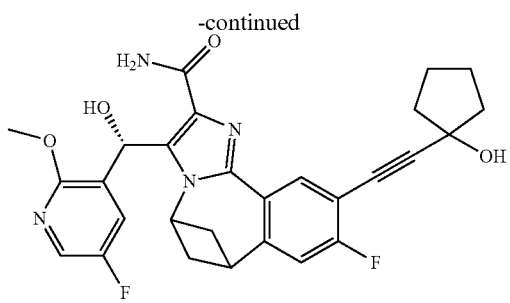

9-fluoro-3-[(5-fluoro-2-methoxy-3-pyridyl)-hydroxy-methyl]-10-(3-hydroxy-3-methyl-but-1-ynyl)-5,6,7,12-tetrahydro-5,7-methanobenzo[c]imidazo[1,2-a]azepine-2-carboxamide AND 9-fluoro-3-[(5-fluoro-2-methoxy-3-pyridyl)-hydroxy-methyl]-10-(3-hydroxy-3-methyl-but-1-ynyl)-5,6,7,12-tetrahydro-5,7-methanobenzo [c]imidazo[1,2-a]azepine-2-carboxamide were prepared similarly according to General Procedure E with slight modification. 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxamide was reacted with 3-methyl-1-butyne-3-ol in a solution of DMF (1.3 mL/mmol) and diisopropylamine (2.6 mL/mmol) to afford a racemic mixture of the titled compounds. The enantiomers were separated by chiral SFC to afford 26.9 mg of Compound 1 and 24.9 mg of Compound 2. The stereochemistry at the benzylic alcohol stereocenter for each isomer was not determined. M+1=495.2. 1H NMR (400 MHz, DMSO-d6) δ 8.72 (d, J=7.6 Hz, 1H), 8.04 (d, J=3.0 Hz, 1H), 7.98 (br s, 1H), 7.71 (dd, J=9.0, 3.0 Hz, 1H), 7.63 (d, J=8.8 Hz, 1H), 7.54 (br s, 1H), 7.25 (d, J=10.1 Hz, 1H), 6.33 (d, J=8.7 Hz, 1H), 5.53 (s, 1H), 5.26-5.16 (m, 1H), 3.76 (s, 3H), 3.69-3.61 (m, 1H), 3.17 (ddd, J=12.0, 7.4, 7.4 Hz, 1H), 3.03 (ddd, J=11.9, 7.5, 7.5 Hz, 1H), 1.71-1.57 (m, 2H), 1.50 (s, 6H).

Example 583

Synthesis of 9-fluoro-3-[(5-fluoro-2-methoxy-3-pyridyl)-(R)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide and 9-fluoro-3-[(5-fluoro-2-methoxy-3-pyridyl)-(S)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide

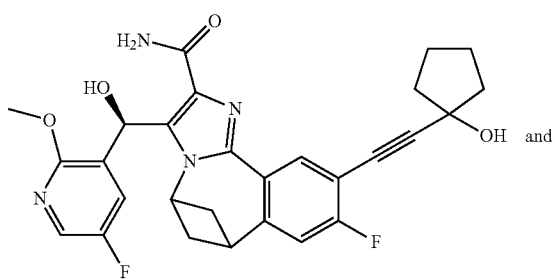 and 9-fluoro-3-[(5-fluoro-2-methoxy-3-pyridyl)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide AND 9-fluoro-3-[(5-fluoro-2-methoxy-3-pyridyl)-hydroxy-methyl]-10-[2-(1-hydroxycyclopentyl)ethynyl]-5,6,7,12-tetrahydro-5,7-methanobenzo[c]imidazo[1,2-a]azepine-2-carboxamide were prepared similarly according to General Procedure E with slight modification. 10-bromo-9-fluoro-3-((5-fluoro-2-methoxypyridin-3-yl)(hydroxy)methyl)-6,7-dihydro-5H-5,7-methanobenzo[c]imidazo[1,2-a]azepine-2-carboxamide was reacted with 1-ethynylcyclopentanol in a solution of DMF (1.3 mL/mmol) and diisopropylamine (2.6 mL/mmol) to afford the racemic compound. The enantiomers were separated by chiral SFC to afford 23.5 mg of Compound 1 and 11.9 mg of Compound 2. The stereochemistry at the benzylic alcohol stereocenter for each isomer was not determined. M+1=521.3. 1H NMR (400 MHz, DMSO-d6) δ 8.73 (d, J=7.6 Hz, 1H), 8.04 (d, J=3.0 Hz, 1H), 7.98 (br s, 1H), 7.71 (dd, J=9.0, 3.0 Hz, 1H), 7.64 (d, J=8.8 Hz, 1H), 7.54 (br s, 1H), 7.25 (d, J=10.1 Hz, 1H), 6.33 (d, J=8.8 Hz, 1H), 5.39 (s, 1H), 5.24-5.18 (m, 1H), 3.76 (s, 3H), 3.69-3.60 (m, 1H), 3.22-3.13 (m, 1H), 3.09-2.97 (m, 1H), 2.00-1.86 (m, 4H), 1.82-1.57 (m, 6H).

Example 584

Synthesis of 9-fluoro-10-[(3S)-3-hydroxy-3-(5-methylisoxazol-3-yl)but-1-ynyl]-5,6,7,12-tetrahydro-5,7-methanobenzo[c]imidazo[1,2-a]azepine-2-carboxamide

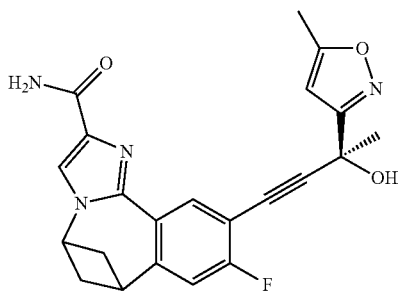 [SMILES: Cc1cc([C@@](C)(O)C#Cc2cc3c(cc2F)C2CC(C2)n2cc(C(N)=O)nc2-3)no1]

9-fluoro-10-[(3S)-3-hydroxy-3-(5-methylisoxazol-3-yl)but-1-ynyl]-5,6,7,12-tetrahydro-5,7-methanobenzo[c]imidazo[1,2-a]azepine-2-carboxamide was prepared similarly according to General Procedure E with slight modification. 10-bromo-9-fluoro-6,7-dihydro-5H-5,7-methanobenzo[c]imidazo[1,2-a]azepine-2-carboxamide was reacted with (2S)-2-(5-methylisoxazol-3-yl)but-3-yn-2-ol in a solution of DMF (1.3 mL/mmol) and diisopropylamine (2.6 mL/mmol) to afford 45.7 mg of the titled compound (75.6% yield). M+1=407.2. 1H NMR (400 MHz, DMSO-d6) δ 8.67 (d, J=7.5 Hz, 1H), 7.82 (s, 1H), 7.54 (br s, 1H), 7.30 (d, J=10.1 Hz, 1H), 7.08 (br s, 1H), 6.59 (s, 1H), 6.35 (s, 1H), 4.96-4.88 (m, 1H), 3.77-3.68 (m, 1H), 3.16-3.03 (m, 2H), 2.41 (s, 3H), 1.82 (s, 3H), 1.76-1.57 (m, 2H).

Example 585

Synthesis of (±)-Methyl 10-bromo-3-((1-(tert-butoxycarbonyl)azetidin-3-yl)(hydroxy)methyl)-9-fluoro-6,7-dihydro-5H-5,7-methanobenzo[c]imidazo[1,2-a]azepine-2-carboxylate

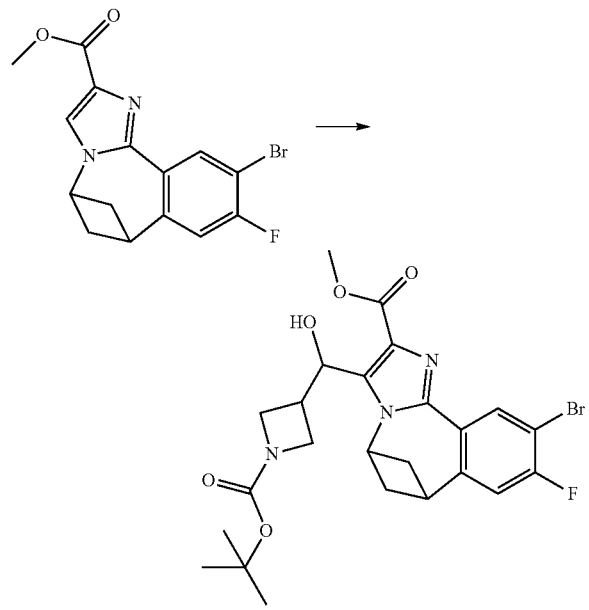

Methyl 10-bromo-3-((1-(tert-butoxycarbonyl)azetidin-3-yl)(hydroxy)methyl)-9-fluoro-6,7-dihydro-5H-5,7-methanobenzo[c]imidazo[1,2-a]azepine-2-carboxylate was prepared similarly according to the procedure in Example 9. Methyl 10-bromo-9-fluoro-6,7-dihydro-5H-5,7-methanobenzo[c]imidazo[1,2-a]azepine-2-carboxylate was reacted with 1-boc-3-azetidinecarboxaldehyde to afford 479 mg (63% yield) of the title compound.

Example 586

Synthesis of tert-butyl (±)-3-((10-bromo-2-carbamoyl-9-fluoro-6,7-dihydro-5H-5,7-methanobenzo[c]imidazo[1,2-a]azepin-3-yl)(hydroxy)methyl)azetidine-1-carboxylate

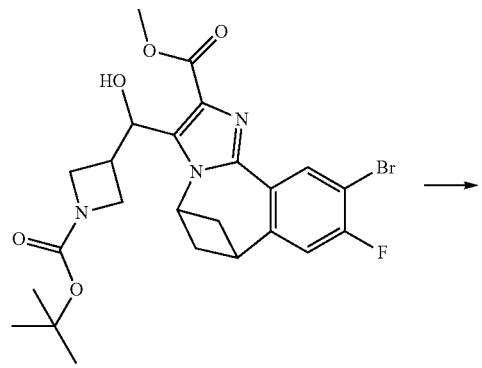

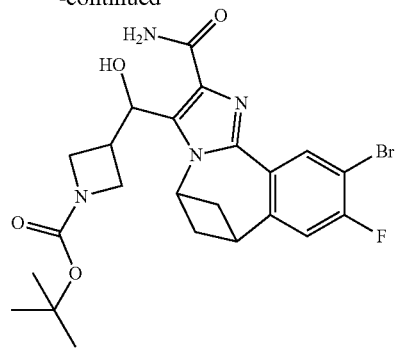

tert-butyl 3-((10-bromo-2-carbamoyl-9-fluoro-6,7-dihydro-5H-5,7-methanobenzo[c]imidazo[1,2-a]azepin-3-yl)(hydroxy)methyl)azetidine-1-carboxylate was prepared similarly to as described in General Procedure L. Methyl 10-bromo-3-((1-(tert-butoxycarbonyl)azetidin-3-yl)(hydroxy)methyl)-9-fluoro-6,7-dihydro-5H-5,7-methanobenzo[c]imidazo[1,2-a]azepine-2-carboxylate was reacted with sodium methoxide and formamide to afford 160 mg (82% yield) of the title compound.

Example 587

Synthesis of tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-(R)-hydroxy-methyl]azetidine-1-carboxylate and tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-(S)-hydroxy-methyl]azetidine-1-carboxylate

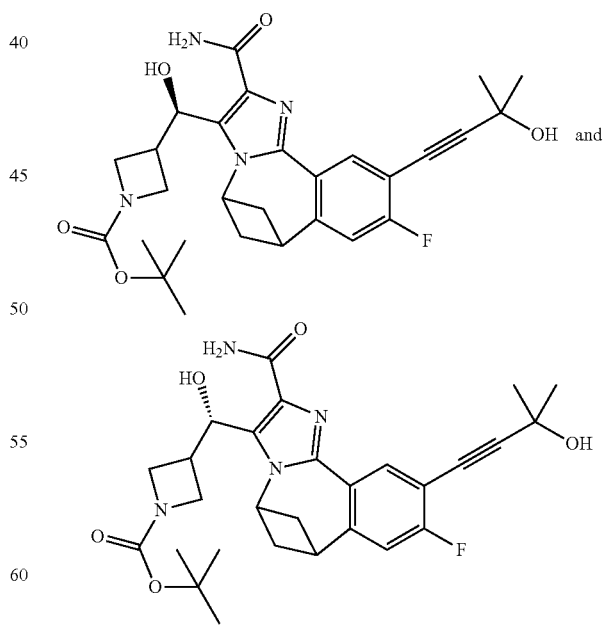

tert-butyl 3-[[2-carbamoyl-9-fluoro-10-(3-hydroxy-3-methyl-but-1-ynyl)-5,6,7,12-tetrahydro-5,7-methanobenzo[c]imidazo[1,2-a]azepin-3-yl]-hydroxy-methyl]azetidine-1-carboxylate AND tert-butyl 3-[[2-carbamoyl-9-fluoro-10-(3- hydroxy-3-methyl-but-1-ynyl)-5,6,7,12-tetrahydro-5,7-methanobenzo[c]imidazo[1,2-a]azepin-3-yl]-hydroxymethyl]azetidine-1-carboxylate were prepared similarly according to General Procedure E with slight modification. tert-butyl 3-((10-bromo-2-carbamoyl-9-fluoro-6,7-dihydro-5H-5,7-methanobenzo[c]imidazo[1,2-a]azepin-3-yl)(hydroxy)methyl)azetidine-1-carboxylate was reacted with 3-methyl-1-butyne-3-ol in a solution of DMF (1.3 mL/mmol) and diisopropylamine (2.6 mL/mmol) to afford a racemic mixture of the titled compounds. The enantiomers were separated by chiral SFC to afford 30.6 mg of Compound 1 and 30.2 mg Compound 2. The stereochemistry at the benzylic alcohol stereocenter position for each isomer was not determined. M+1=525.3. 1H NMR (400 MHz, DMSO-d6) δ 8.72 (d, J=7.5 Hz, 1H), 7.90 (be s, 1H), 7.40 (be s, 1H), 7.25 (d, J=10.2 Hz, 1H), 6.82-6.63 (m, 1H), 5.70-5.56 (m, 1H), 5.53 (s, 1H), 5.34-5.25 (m, 1H), 3.91-3.81 (m, 1H), 3.81-3.73 (m, 1H), 3.71-3.59 (m, 2H), 3.59-3.49 (m, 1H), 3.16-3.04 (m, 2H), 2.80-2.70 (m, 1H), 1.75-1.59 (m, 2H), 1.50 (s, 6H), 1.36 (s, 9H).

Example 588

Synthesis of 3-[hydroxy-(2-methylpyrazol-3-yl)methyl]-10-(3-(R)-hydroxy-3-pyrimidin-2-yl-but-1-ynyl)-5,6,7,12-tetrahydro-5,7-methanobenzo[c]imidazo[1,2-a]azepine-2-carboxamide

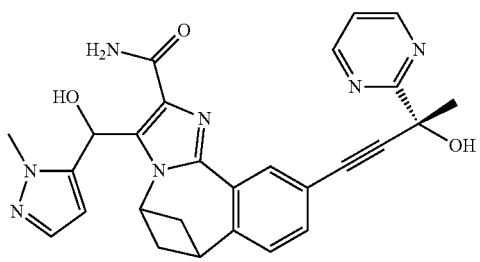 [SMILES: Cn1nccc1C(O)c1c(C(N)=O)nc2n1C1CC(C1)c1ccc(C#C[C@@](C)(O)c3ncccn3)cc1-2]

3-[hydroxy-(2-methylpyrazol-3-yl)methyl]-10-(3-hydroxy-3-pyrimidin-2-yl-but-1-ynyl)-5,6,7,12-tetrahydro-5,7-methanobenzo[c]imidazo[1,2-a]azepine-2-carboxamide was prepared similarly according to General Procedure E with slight modification. 10-bromo-3-(hydroxy(1-methyl-1H-pyrazol-5-yl)methyl)-6,7-dihydro-5H-5,7-methanobenzo[c]imidazo[1,2-a]azepine-2-carboxamide was reacted with (2R)-2-pyrimidin-2-ylbut-3-yn-2-ol in a solution of DMF (1.3 mL/mmol) and diisopropylamine (2.6 mL/mmol) to afford the racemic compound. The diastereomers were separated by chiral SFC to afford 6.4 mg of the title compound. The other diastereomer was not deemed pure enough for submission.

M+1=496.3. 1H NMR (400 MHz, DMSO-d6) δ 8.89 (d, J=4.9 Hz, 2H), 8.72 (s, 1H), 7.86 (br s, 1H), 7.50 (dd, J=4.9, 4.9 Hz 1H), 7.37 (br s, 1H), 7.26 (s, 2H), 7.25 (d, J=1.9 Hz, 1H), 7.08 (d, J=6.1 Hz, 1H), 6.90 (d, J=5.9 Hz, 1H), 6.16 (s, 1H), 5.68 (d, J=1.8 Hz, 1H), 5.22-5.15 (m, 1H), 3.86 (s, 3H), 3.67-3.59 (m, 1H), 3.09-2.91 (m, 2H), 1.89 (s, 3H), 1.77-1.66 (m, 1H), 1.64-1.54 (m, 1H).

Example 589

Synthesis of 10-[3-hydroxy-3-(5-methyl-1,2,4-oxadiazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide

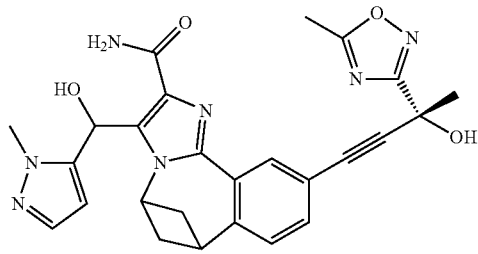 [SMILES: Cc1nc([C@](C)(O)C#Cc2ccc3c(c2)-c2nc(C(N)=O)c(C(O)c4ccnn4C)n2C2CC3C2)no1]

10-[3-hydroxy-3-(5-methyl-1,2,4-oxadiazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-3-(hydroxy (1-methyl-1H-pyrazol-5-yl)methyl)-6,7-dihydro-5H-5,7-methanobenzo[c]imidazo[1,2-a]azepine-2-carboxamide was reacted with (2R)-2-(5-methyl-1,2,4-oxadiazol-3-yl)but-3-yn-2-ol in a solution of DMF (1.3 mL/mmol) and diisopropylamine (2.6 mL/mmol) to afford the racemic compound. The enantiomers were separated by chiral SFC to afford 1.9 mg of the title compound. M+1=500.3.

Example 590

Synthesis of 10-[3-(R)-hydroxy-3-(5-methylisoxazol-3-yl)but-1-ynyl]-3-(S)-[hydroxy-(2-methylpyrazol-3-yl)methyl]-5,6,7,12-tetrahydro-5,7-methanobenzo[c]imidazo[1,2-a]azepine-2-carboxamide and 10-[3-(R)-hydroxy-3-(5-methylisoxazol-3-yl)but-1-ynyl]-3-(R)-[hydroxy-(2-methylpyrazol-3-yl)methyl]-5,6,7,12-tetrahydro-5,7-methanobenzo[c]imidazo[1,2-a]azepine-2-carboxamide

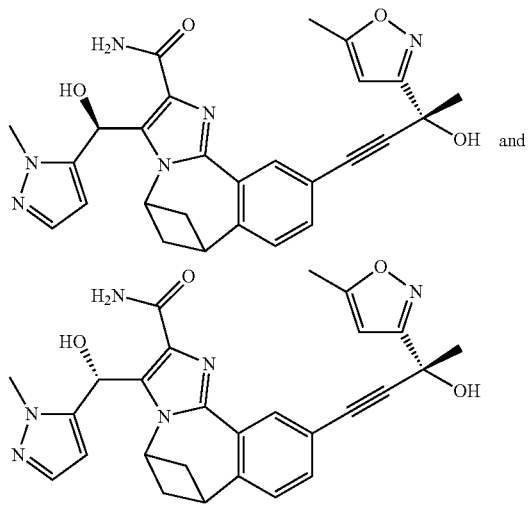

10-[3-hydroxy-3-(5-methylisoxazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide AND 10-[3-hydroxy-3-(5-methylisoxazol-3-yl)but-1-ynyl]-3-[hydroxy-(2-methylpyrazol-3-yl)methyl]-5,6,7,12-tetrahydro-5,7-methanobenzo[c]imidazo[1,2-a]azepine-2-carboxamide were prepared similarly according to General Procedure E with slight modification. 10-bromo-3-(hydroxy(1-methyl-1H-pyrazol-5-yl)methyl)-6,7-dihydro-5H-5,7-methanobenzo[c]imidazo[1,2-a]azepine-2-carboxamide was reacted with (2R)-2-(5-methylisoxazol-3-yl)but-3-yn-2-ol in a solution of DMF (1.3 mL/mmol) and diisopropylamine (2.6 mL/mmol) to afford a racemic mixture of the titled compounds. The enantiomers were separated by chiral SFC to afford 5.3 mg of Compound 1 and 5.4 mg of Compound 2. The stereochemistry at the benzylic alcohol stereocenter for each isomer was not determined.

Compound 1: M+1=499.3. $^1$H NMR (400 MHz, DMSO-d6) δ 8.75 (s, 1H), 7.87 (br s, 1H), 7.39 (br s, 1H), 7.34-7.23 (m, 3H), 7.08 (d, J=6.1 Hz, 1H), 6.91 (d, J=6.1 Hz, 1H), 6.50 (s, 1H), 6.37 (s, 1H), 5.70-5.67 (m, 1H), 5.23-5.15 (m, 1H), 3.87 (s, 3H), 3.68-3.60 (m, 1H), 3.07-2.92 (m, 2H), 2.41 (s, 3H), 1.82 (s, 3H), 1.77-1.66 (m, 1H), 1.66-1.55 (m, 1H).

Compound 2: M+1=499.3. $^1$H NMR (400 MHz, DMSO-d6) δ 8.77-8.73 (m, 1H), 7.87 (br s, 1H), 7.39 (br s, 1H), 7.34-7.21 (m, 3H), 7.08 (d, J=6.1 Hz, 1H), 6.91 (d, J=6.1 Hz, 1H), 6.50 (s, 1H), 6.38-6.35 (m, 1H), 5.68 (d, J=1.9 Hz, 1H), 5.23-5.15 (m, 1H), 3.87 (s, 3H), 3.69-3.58 (m, 1H), 3.09-2.91 (m, 2H), 2.41 (s, 3H), 1.82 (s, 3H), 1.78-1.66 (m, 1H), 1.66-1.56 (m, 1H).

Example 591

Synthesis of 10-[(3R)-3-hydroxy-3-pyrimidin-2-yl-but-1-ynyl]-3-[(2-methylpyrazol-3-yl)methyl]-5,6,7,12-tetrahydro-5,7-methanobenzo[c]imidazo[1,2-a]azepine-2-carboxamide

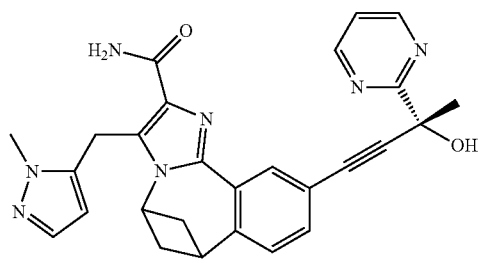 [SMILES: Cn1nccc1Cc1c(C(N)=O)nc2n1C1CC(C1)c1ccc(C#C[C@@](C)(O)c3ncccn3)cc1-2]

10-[(3R)-3-hydroxy-3-pyrimidin-2-yl-but-1-ynyl]-3-[(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-3-(hydroxy(1-methyl-1H-pyrazol-5-yl)methyl)-6,7-dihydro-5H-5,7-methanobenzo[c]imidazo[1,2-a]azepine-2-carboxamide was reacted with (2R)-2-pyrimidin-2-ylbut-3-yn-2-ol in a solution of DMF (1.3 mL/mmol) and diisopropylamine (2.6 mL/mmol) to afford 22.9 mg of the titled compound (49.2% yield). M+1=480.3. 1H NMR (400 MHz, DMSO-d6) δ 8.89 (d, J=4.8 Hz, 2H), 8.68 (s, 1H), 7.63 (br s, 1H), 7.50 (t, J=4.8 Hz, 1H), 7.28-7.23 (m, 1H), 7.22 (d, J=1.5 Hz, 1H), 7.13 (br s, 1H), 6.16 (s, 1H), 5.59 (s, 1H), 4.76-4.69 (m, 1H), 4.57 (s, 2H), 3.81 (s, 3H), 3.68-3.59 (m, 1H), 3.05-2.92 (m, 2H), 1.89 (s, 3H), 1.70-1.58 (m, 2H).

Example 592

Synthesis of 10-[(3R)-3-hydroxy-3-(5-methylisoxazol-3-yl)but-1-ynyl]-3-[(2-methylpyrazol-3-yl)methyl]-5,6,7,12-tetrahydro-5,7-methanobenzo[c]imidazo[1,2-a]azepine-2-carboxamide

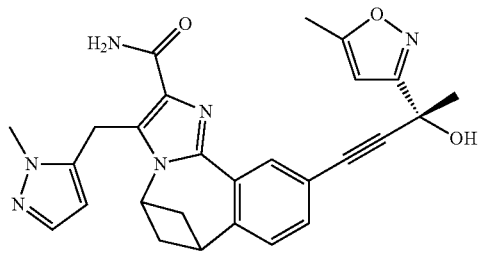 [SMILES: Cc1cc([C@](C)(O)C#Cc2ccc3c(c2)-c2nc(C(N)=O)c(Cc4ccnn4C)n2C2CC3C2)no1]

10-[(3R)-3-hydroxy-3-(5-methylisoxazol-3-yl)but-1-ynyl]-3-[(2-methylpyrazol-3-yl)methyl]-5,6,7,12-tetrahydro-5,7-methanobenzo[c]imidazo[1,2-a]azepine-2-carboxamide was prepared similarly according to General Procedure E with slight modification. 10-bromo-3-(hydroxy(1-methyl-1H-pyrazol-5-yl)methyl)-6,7-dihydro-5H-5,7-methanobenzo[c]imidazo[1,2-a]azepine-2-carboxamide was reacted with (2R)-2-(5-methylisoxazol-3-yl)but-3-yn-2-ol in a solution of DMF (1.3 mL/mmol) and diisopropylamine (2.6 mL/mmol) to afford 15.3 mg of the titled compound (32.7% yield). M+1=483.3. 1H NMR (400 MHz, DMSO-d6) δ 8.71 (s, 1H), 7.63 (br s, 1H), 7.28 (s, 2H), 7.22 (d, J=1.6 Hz, 1H), 7.14 (br s, 1H), 6.50 (s, 1H), 6.36 (s, 1H), 5.59 (s, 1H), 4.77-4.70 (m, 1H), 4.57 (s, 2H), 3.81 (s, 3H), 3.70-3.61 (m, 1H), 3.06-2.94 (m, 2H), 2.41 (s, 3H), 1.82 (s, 3H), 1.70-1.60 (m, 2H).

Example 593

Synthesis of Methyl 10-bromo-3-(2-(cyclopropanecarbonyl)hydrazinecarbonyl)-6,7-dihydro-5H-5,7-methanobenzo[c]imidazo[1,2-a]azepine-2-carboxylate

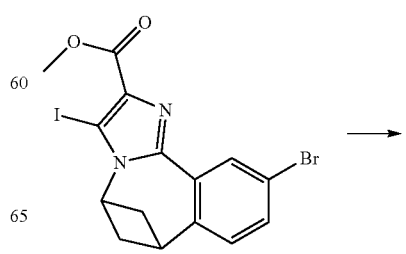

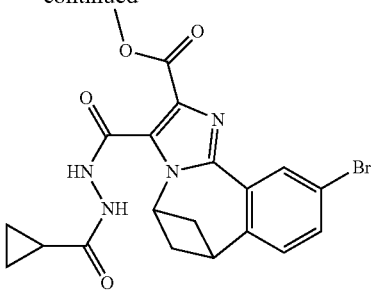

Methyl 10-bromo-3-iodo-6,7-dihydro-5H-5,7-methanobenzo[c]imidazo[1,2-a]azepine-2-carboxylate (100 mg, 0.2178 mmol) and cyclopropanecarbohydrazide (1.5 equiv., 34.43 mg, 0.3267 mmol) were dissolved in dry N,N-dimethylformamide (0.87 mL) and triethylamine (0.13 mL). The solution was sparged with nitrogen. Palladium(II) acetate (0.05 equiv., 2.5 mg, 0.01089 mmol) and xantphos (0.05000, 6.430 mg, 0.01089 mmol) were added and the solution was purged and fixed with a CO balloon. The reaction was heated to 80° C. for 2 h. The reaction was monitored by LC/MS for consumption of starting material. The reaction was cooled to room temperature and diluted with methylene chloride. Saturated aqueous sodium bicarbonate was added and the mixture was extracted twice with methylene chloride. The organic layers were combined, dried with sodium sulfate and concentrated. Purified by flash chromatography (10-100% EtOAc in heptanes) to afford 26 mg (26% yield) of a white solid.

Example 594

Synthesis of Methyl 10-bromo-3-(5-cyclopropyl-1,3,4-thiadiazol-2-yl)-6,7-dihydro-5H-5,7-methanobenzo[c]imidazo[1,2-a]azepine-2-carboxylate

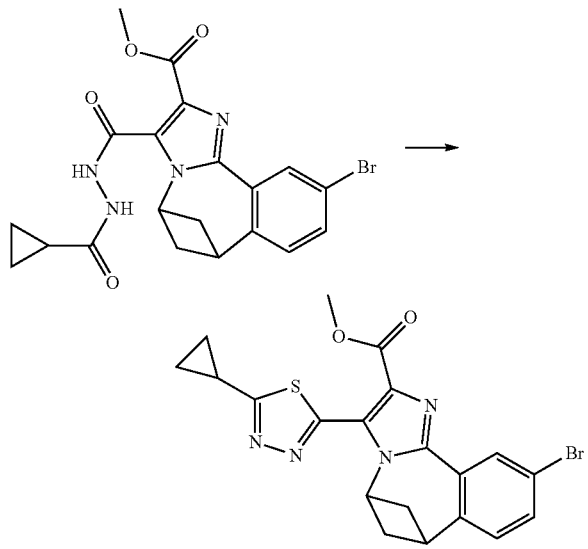

Methyl 10-bromo-3-(2-(cyclopropanecarbonyl)hydrazinecarbonyl)-6,7-dihydro-5H-5,7-methanobenzo[c]imidazo[1,2-a]azepine-2-carboxylate was dissolved in toluene (0.56 mL) and treated with Lawesson's reagent (1.3 equiv., 29.8 mg, 0.07359 mmol). The reaction was heated to reflux until judged complete by LC/MS analysis. The solution was cooled to room temperature. Water was added and the solution was extracted 2× with methylene chloride. The organic layers were combined, dried with sodium sulfate and concentrated in vacuo. The crude material was carried forward without further purification.

Example 595

Synthesis of 10-bromo-3-(5-cyclopropyl-1,3,4-thiadiazol-2-yl)-6,7-dihydro-5H-5,7-methanobenzo[c]imidazo[1,2-a]azepine-2-carboxamide

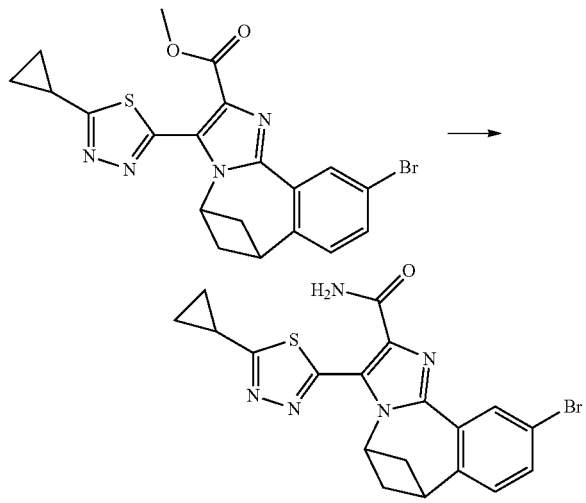

10-bromo-3-(5-cyclopropyl-1,3,4-thiadiazol-2-yl)-6,7-dihydro-5H-5,7-methanobenzo [c]imidazo[1,2-a]azepine-2-carboxamide was prepared similarly to as described in General Procedure L Methyl 10-bromo-3-(5-cyclopropyl-1,3,4-thiadiazol-2-yl)-6,7-dihydro-5H-5,7-methanobenzo[c]imidazo[1,2-a]azepine-2-carboxylate was reacted with sodium methoxide and formamide to afford the crude title compound which was carried forward without further purification.

Example 596

Synthesis of 3-(5-cyclopropyl-1,3,4-thiadiazol-2-yl)-10-(3-hydroxy-3-methyl-but-1-ynyl)-5,6,7,12-tetrahydro-5,7-methanobenzo[c]imidazo[1,2-a]azepine-2-carboxamide

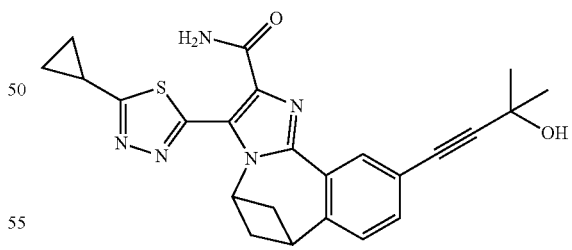

3-(5-cyclopropyl-1,3,4-thiadiazol-2-yl)-10-(3-hydroxy-3-methyl-but-1-ynyl)-5,6,7,12-tetrahydro-5,7-methanobenzo[c]imidazo[1,2-a]azepine-2-carboxamide was prepared similarly according to General Procedure E with slight modification 10-bromo-3-(5-cyclopropyl-1,3,4-thiadiazol-2-yl)-6,7-dihydro-5H-5,7-methanobenzo[c]imidazo[1,2-a]azepine-2-carboxamide was reacted with 2-methyl-3-butyn-2-ol in a solution of DMF (1.3 mL/mmol) and diisopropylamine (2.6 mL/mmol) to afford 10.8 mg of the titled compound (44.7% yield). M+1=446.2. 1H NMR (400

MHz, DMSO-d6) δ 8.78 (s, 1H), 7.92 (br s, 1H), 7.40 (br s, 1H), 7.34-7.29 (m, 2H), 5.48 (s, 1H), 5.24-5.17 (m, 1H), 3.73-3.66 (m, 1H), 3.15-3.04 (m, 2H), 2.61 (tt, J=8.2, 4.8 Hz, 1H), 1.76-1.68 (m, 2H), 1.32-1.24 (m, 2H), 1.14-1.08 (m, 2H).

Example 597

Synthesis of Methyl 10-bromo-3-(difluoromethyl)-6,7-dihydro-5H-5,7-methanobenzo[c]imidazo[1,2-a]azepine-2-carboxylate

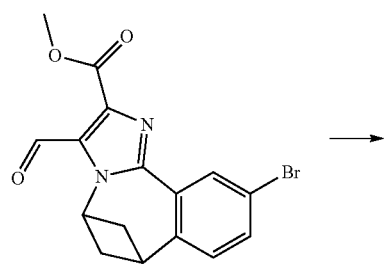

→

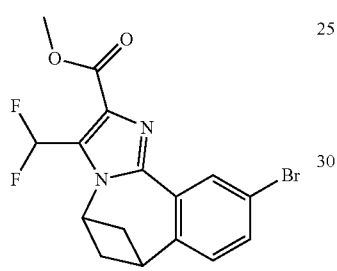

To a solution of methyl 10-bromo-3-formyl-6,7-dihydro-5H-5,7-methanobenzo[c]imidazo[1,2-a]azepine-2-carboxylate (150 mg, 0.4153 mmol) in methylene chloride (0.41 mL) at −78° C. was added DAST (5.0 equiv., 0.274 mL, 2.076 mmol) dropwise. The solution was stirred for 15 minutes then warmed to room temperature and stirred overnight. The vial was cooled to 0° C. and quenched dropwise, very slowly, with an aqueous saturated sodium bicarbonate solution. The reaction mixture was extracted 2× with methylene chloride and dried with sodium sulfate. The crude was purified by flash chromatography (iPrOAc in heptanes) to afford 71 mg (45% yield) of a white solid.

Example 598

Synthesis of 10-bromo-3-(difluoromethyl)-6,7-dihydro-5H-5,7-methanobenzo[c]imidazo[1,2-a]azepine-2-carboxamide

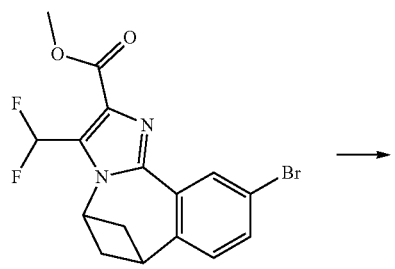

→

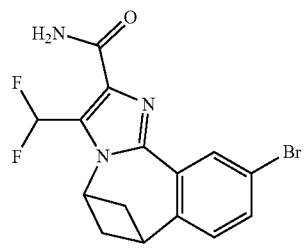

10-bromo-3-(difluoromethyl)-6,7-dihydro-5H-5,7-methanobenzo[c]imidazo[1,2-a]azepine-2-carboxamide was prepared similarly to as described in General Procedure L Methyl 10-bromo-3-(difluoromethyl)-6,7-dihydro-5H-5,7-methanobenzo[c]imidazo[1,2-a]azepine-2-carboxylate was reacted with sodium methoxide and formamide to afford 70.2 mg (100% yield) of the crude title compound which was carried forward without further purification.

Example 599

Synthesis of 3-(difluoromethyl)-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide

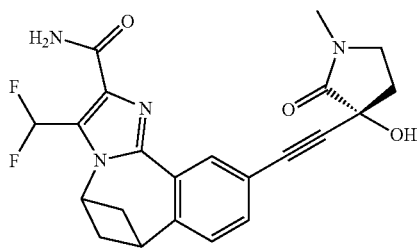 [SMILES: CN1CC[C@@](O)(C#Cc2ccc3c(c2)-c2nc(C(N)=O)c(C(F)F)n2C2CC3C2)C1=O]

3-(difluoromethyl)-10-[2-[(3R)-3-hydroxy-1-methyl-2-oxo-pyrrolidin-3-yl]ethynyl]-5,6,7,12-tetrahydro-5,7-methanobenzo[c]imidazo[1,2-a]azepine-2-carboxamide was prepared similarly according to General Procedure E with slight modification. 10-bromo-3-(difluoromethyl)-6,7-dihydro-5H-5,7-methanobenzo[c]imidazo[1,2-a]azepine-2-carboxamide was reacted with (3R)-3-ethynyl-3-hydroxy-1-methyl-pyrrolidin-2-one in a solution of DMF (1.3 mL/mmol) and diisopropylamine (2.6 mL/mmol) to afford 36.3 mg of the titled compound (44.7% yield). M+1=427.2. 1H NMR (400 MHz, DMSO-d6) δ 8.77 (d, J=1.5 Hz, 1H), 8.01 (br s, 1H), 7.81 (t, J=52.9 Hz, 1H), 7.57 (br s, 1H), 737 (dd, J=7.8, 1.7 Hz, 1H), 7.34 (d, J=7.8 Hz, 1H), 6.44 (s, 1H), 5.17-5.03 (m, 1H), 3.79-3.68 (m, 1H), 3.41-3.33 (m, 1H), 3.25-3.14 (m, 2H), 2.81 (s, 3H), 2.47-2.40 (m, 1H), 2.20 (dt, J=12.7, 7.2 Hz, 1H), 1.78-1.70 (m, 2H).

Example 600

Synthesis of 10-[2-[(3R)-3-hydroxy-1-methyl-2-oxo-pyrrolidin-3-yl]ethynyl]-3-(trifluoromethyl)-5,6,7,12-tetrahydro-5,7-methanobenzo[c]imidazo[1,2-a]azepine-2-carboxamide

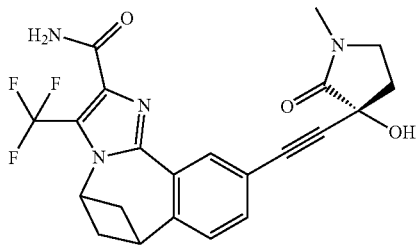 [SMILES: CN1CC[C@@](O)(C#Cc2ccc3c(c2)-c2nc(C(N)=O)c(C(F)(F)F)n2C2CC3C2)C1=O]

10-[2-[(3R)-3-hydroxy-1-methyl-2-oxo-pyrrolidin-3-yl]ethynyl]-3-(trifluoromethyl)-5,6,7,12-tetrahydro-5,7-methanobenzo[c]imidazo[1,2-a]azepine-2-carboxamide was prepared similarly according to General Procedure E with slight modification. 10-bromo-3-(trifluoromethyl)-6,7-dihydro-5H-5,7-methanobenzo[c]imidazo[1,2-a]azepine-2-carboxamide was reacted with (3R)-3-ethynyl-3-hydroxy-1-methyl-pyrrolidin-2-one in a solution of DMF (1.3 mL/mmol) and diisopropylamine (2.6 mL/mmol) to afford 24.1 mg of the titled compound (26.2% yield). M+1=445.2. 1H NMR (400 MHz, DMSO-d6) δ 8.72 (d, J=1.6 Hz, 1H), 7.93 (br s, 1H), 7.51 (br s, 1H), 7.38 (dd, J=7.8, 1.7 Hz, 1H), 7.35 (d, J=7.8 Hz, 1H), 6.48 (br s, 1H), 5.02-4.94 (m, 1H), 3.78-3.70 (m, 1H), 3.41-3.33 (m, 2H), 3.25-3.15 (m, 2H), 2.81 (s, 3H), 2.47-2.40 (m, 1H), 2.19 (dt, J=13.0, 7.1 Hz, 1H), 1.78-1.70 (m, 2H).

Example 601

Synthesis of ethyl 2-bromo-3-fluoro-8-oxo-6,7,8,9-tetrahydro-5H-5,7-methanobenzo[7]annulene-9-carboxylate

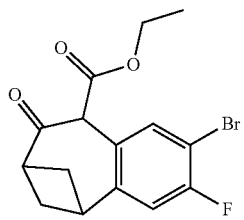 [SMILES: CCOC(=O)C1C(=O)C2CC(C2)c2cc(F)c(Br)cc21]

To a solution of 6-bromo-7-fluoro-2,3-dihydro-1,3-methanonaphthalen-4(1H)-one (9.00 g, 35.3 mmol) in dry dichloromethane (180 mL) at 0° C. was introduced triethyloxonium tetrafluoroborate (141 mL of a 1.0M solution in dichloromethane, 141 mmol) dropwise over 15 minutes. A solution of ethyl diazoacetate (8.05 g in 75 mL dry dichloromethane, 70.6 mmol) was then added slowly over 20 minutes ensuring the reaction temperature did not rise >3° C. After 30 minutes, the reaction mixture was allowed to warm to room temperature for 16 hr. The solution was then re-cooled to 0° C. and re-treated with triethyloxonium tetrafluoroborate (141 mL of a 1.0M solution in dichloromethane, 141 mmol) and ethyl diazoacetate (8.05 g in 75 mL dry dichloromethane, 70.6 mmol) as described for the first treatment. After warming to room temperature for 5½ hours, the reaction mixture was washed with saturated aqueous sodium bicarbonate (3×100 mL washes), the organic phase dried over sodium sulfate and filtered under vacuum through a Celite 0 pad. The filtrate was adsorbed onto silica gel in vacuo and purified by silica gel flash column chromatography (heptanes/ethyl acetate gradient elution of increasing polarity) to furnish the title compound (8.70 g, 25.50 mmol, 72%) as a colorless solid: ¹H NMR (500 MHz, CDCl₃) δ 1.27 (t, J=7.09 Hz, 4H) 1.84 (dd, J=11.66, 6.62 Hz, 1H) 2.32 (dd, J=12.93, 6.94 Hz, 1H) 2.80 (dt, J=12.61, 7.88 Hz, 1H) 3.04 (dt, J=11.90, 8.55 Hz, 1H) 3.38 (ddd, J=8.83, 7.57, 3.78 Hz, 1H) 3.45 (td, J=8.20, 3.78 Hz, 1H) 4.18-4.29 (m, 2H) 4.78 (s, 1H) 6.88 (d, J=9.14 Hz, 1H) 7.48 (d, J=6.94 Hz, 1H); M+23=363/365.

Example 602

Synthesis of 2-bromo-3-fluoro-6,7-dihydro-5H-5,7-methanobenzo[7]annulen-8(9H)-one

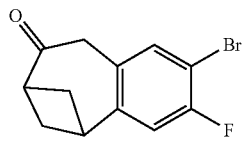 [SMILES: O=C1Cc2cc(Br)c(F)cc2C2CC1C2]

A solution of ethyl 2-bromo-3-fluoro-8-oxo-6,7,8,9-tetrahydro-5H-5,7-methanobenzo[7]annulene-9-carboxylate (5.00 g, 14.7 mmol) in dimethylsulfoxide (60 mL) and brine (10 mL of saturated brine) was prepared and nitrogen gas bubbled through for 5 minutes. The resulting slurry was warmed to 145° C. for 8 hr under an atmosphere of nitrogen. Evaporation of the reaction mixture (high vacuum distillation) furnished a yellow syrupy residue which was diluted with ethyl acetate (50 mL) and washed with water (2×25 mL) and brine (10 mL). The organic extract was dried over sodium sulfate, filtered and the filtrate evaporated in vacuo to furnish the title compound (3.89 g, 14.5 mmol, 99%) as a pale yellow waxy solid: ¹H NMR (500 MHz, CDCl₃) δ 2.08-2.15 (m, 2H), 2.88-2.96 (m, 2H), 3.26 (td, J=8.20, 3.47 Hz, 1H), 3.49 (td, J=8.28, 3.63 Hz, 1H), 4.12 (s, 2H), 6.85 (d, J=9.14 Hz, 1H), 7.35 (d, J=6.94 Hz, 1H).

Example 603

Synthesis 2,9-dibromo-3-fluoro-6,7-dihydro-5H-5,7-methanobenzo[7]annulen-8(9H)-one

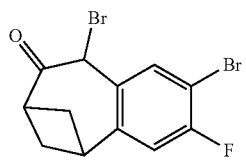 [SMILES: O=C1C2CC(C2)c2cc(F)c(Br)cc2C1Br]

To a solution 2-bromo-3-fluoro-6,7-dihydro-5H-5,7-methanobenzo[7]annulen-8(9H)-one (1.69 g, 5.3 mmol) in a solution of cyclohexane (20 mL) and benzene (10 mL), was introduced 1,3-dibromo-4,4-dimethylhydantoin (2.29 g, 8.0 mmol) and 2,2'-azobis(2-methylpropionitrile) (0.175 g, 1.07 mmol). The solution was warmed to 81° C. under an atmosphere of nitrogen for 80 minutes then cooled to room temperature. After filtration through a pad of Celite®, the filtrate was evaporated in vacuo to furnish the crude title compound (2.89 g at 65% purity LC-UV$_{215}$) as a yellow oil. The crude product was carried through to the next synthetic step without additional purification, but a small portion was subjected to silica gel flash column chromatography (heptanes/ethyl acetate gradient of increasing polarity) to furnish a sample suitable for characterization/analysis: $^1$H NMR (500 MHz, CDCl$_3$) δ 1.83 (dd, J=11.66, 6.62 Hz, 1H), 2.89 (dt, J=12.61, 8.04 Hz, 1H), 3.08 (ddd, J=11.82, 8.67, 8.51 Hz, 1H), 3.20 (dd, J=12.61, 6.62 Hz, 1H), 3.44-3.54 (m, 2H), 5.65 (s, 1H), 6.89 (d, J=9.14 Hz, 1H), 7.69 (d, J=6.62 Hz, 1H).

Example 604

Synthesis of 2-bromo-3-fluoro-6,7-dihydro-5H-5,7-methanobenzo[7]annulene-8,9-dione

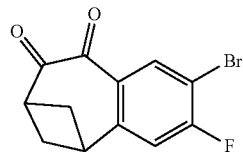 [SMILES: O=C1C(=O)C2CC(C2)c2cc(F)c(Br)cc21]

A solution of 2,9-dibromo-3-fluoro-6,7-dihydro-5H-5,7-methanobenzo[7]annulen-8(9H)-one (1.04 g at 65% purity LC-UV$_{215}$) in dimethylsulfoxide (15 mL) was warmed to 80° C. for 1 hr. Evaporation of the reaction mixture (high vacuum distillation) furnished the crude title compound (0.87 g at 72% purity LC-UV$_{215}$) as a golden-brown syrup which was carried through to the next synthetic step without purification. $^1$H NMR (500 MHz, CDCl$_3$) δ 2.25-2.30 (m, 2H), 3.12-3.18 (m, 2H), 3.48-3.51 (m, 1H), 3.61-3.65 (m, 1H), 6.94 (d, J=8.2 Hz, 1H), 8.55 (d, J=6.6 Hz, 1H); M+1=305/307.

Example 605

Synthesis of ethyl 9-bromo-8-fluoro-3,4,5,6-tetrahydro-4,6-methanobenzo[3,4]cyclohepta[1,2-d]imidazole-2-carboxylate

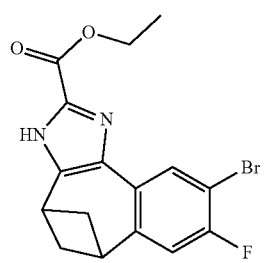 [SMILES: CCOC(=O)c1nc2c([nH]1)C1CC(C1)c1cc(F)c(Br)cc1-2]

To a solution of 2-bromo-3-fluoro-6,7-dihydro-5H-5,7-methanobenzo[7]annulene-8,9-dione (100 mg at 72% purity LC-UV$_{215}$) in tetrahydrofuran (1 mL) was introduced ethyl glyoxylate (115 mg of a 50% solution in toluene diluted in 1 mL tetrahydrofuran, 0.56 mmol) followed by ammonium acetate (269 mg in 2 mL methanol, 3.53 mmol). After 24 hr at room temperature, the reaction mixture was evaporated in vacuo and the residue was slurried in 4:1 water/acetonitrile (3 mL) with sonnication. The resulting solid was collected by vacuum filtration, washed on the filter with 9:1 acetonitrile/water (0.3 mL) and air dried on the filter to furnish the title compound (80 mg, 0.22 mmol, 88%) as a colorless solid: $^1$H NMR (500 MHz, CDCl$_3$) δ 1.46 (t, J=7.09 Hz, 3H), 1.75 (d, J=10.09 Hz, 2H), 2.88-3.00 (m, 2H), 3.39-3.48 (m, 1H), 3.61 (td, J=8.20, 3.78 Hz, 1H), 4.49 (q, J=6.94 Hz, 2H), 6.88 (d, J=9.14 Hz, 1H), 8.68 (d, J=7.57 Hz, 1H), 10.17 (br. s., 1H); M+1=365/367

Example 606

Synthesis of 9-bromo-8-fluoro-3,4,5,6-tetrahydro-4,6-methanobenzo[3,4]cyclohepta[1,2-d]imidazole-2-carboxamide

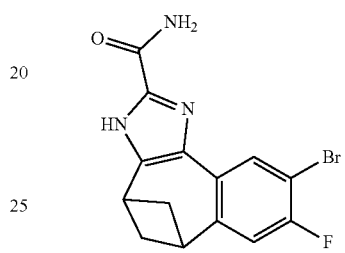

A solution of ethyl 9-bromo-8-fluoro-3,4,5,6-tetrahydro-4,6-methanobenzo[3,4]cyclohepta[1,2-d]imidazole-2-carboxylate (80 mg, 0.22 mmol) in methanolic ammonia (10 mL of a 7M ammonia solution in methanol) was warmed to 40° C. for 3d in a pressure tube. Evaporation of the reaction mixture in vacuo furnished the title compound (77 mg, 0.22 mmol, 100%) as a colorless solid: $^1$H NMR (500 MHz, d4-methanol) δ 1.62-1.69 (m, 2H), 2.92-3.01 (m, 2H), 3.45-3.50 (m, 1H), 3.65-3.72 (m, 1H), 6.97-7.02 (m, 1H), 8.42-8.50 (m, 1H); M+1=336/338.

Example 608

Synthesis of 8-fluoro-9-(3-hydroxy-3-methylbut-1-yn-1-yl)-3,4,5,6-tetrahydro-4,6-methanobenzo[3,4]cyclohept a[1,2-d]imidazole-2-carboxamide

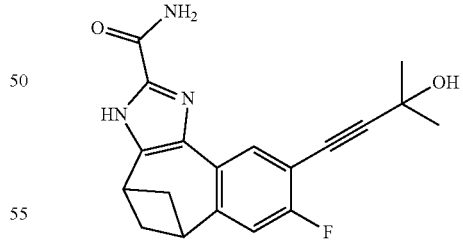

Into a pressure tube containing a solution 9-bromo-8-fluoro-3,4,5,6-tetrahydro-4,6-methanobenzo[3,4]cyclohepta [1,2-d]imidazole-2-carboxamide (47 mg, 0.14 mmol) in 1:1 N,N-dimethylformamide/triethylamine (0.8 mL) was introduced 2-methyl-3-butyn-2-ol (235 mg, 2.80 mmol), copper (I) iodide (2 mg, 0.01) and nitrogen gas bubbled through the solution for 3 minutes. Bis(triphenylphosphine)palladium(II) chloride (10 mg, 0.01 mmol) was added and nitrogen bubbling continued a further two minutes before the pressure tube was closed under nitrogen. The reaction mixture was warmed to 80° C. for 8 hr. After cooling to room temperature, the reaction mixture was evaporated in vacuo and the residue re-dissolved in ethyl acetate (15 mL). This solution was washed with water (2×5 mL) and brine (5 mL). The organic extract was dried over sodium sulfate, filtered and the filtrate absorbed onto silica gel. Purification by silica gel flash column chromatography (eluent: dichloromethane containing a 0-8% gradient of methanol) furnished partially purified product as a brown oil. After several acetonitile solubilisation-evaporation (in vacuo) cycles, a grey-brown solid was obtained which was slurried in acetonitrile (0.4 mL) and collected by filtration to furnish the title compound (13 mg, 0.038 mmol, 27%) as a grey solid: $^1$H NMR (500 MHz, d4-methanol) δ 1.59 (s, 6H), 1.63 (d, J=11.03 Hz, 2H), 2.85-2.95 (m, 2H), 3.44 (td, J=6.94, 3.78 Hz, 1H), 3.63 (td, J=8.04, 3.78 Hz, 1H), 6.86 (d, J=10.40 Hz, 1H), 8.25 (d, J=7.57 Hz, 1H); M+1=340.

Example 609

Synthesis of 3-fluoro-2-(trimethylstannyl)-6,7-dihydro-5H-5,7-methanobenzo[7]annulen-8(9H)-one

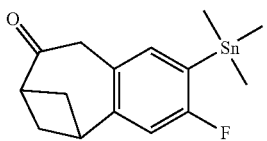 [SMILES: [CH3][Sn]([CH3])([CH3])[c]1cc2c(cc1F)C1CC(C1)C(=O)C2]

To a solution of 2-bromo-3-fluoro-6,7-dihydro-5H-5,7-methanobenzo[7]annulen-8(9H)-one (1.578 g, 5.86 mmol) in anhydrous 1,4-dioxane (20 mL) was introduced hexamethylditin (3.842 g, 11.73 mmol). The solution was de-oxygenated by nitrogen bubbling for 5 minutes, bis(triphenylphosphine)palladium(II)dichloride (0.41 g, 0.58 mmol) added and the reaction mixture warmed to 100° C. for 40 hr under an atmosphere of nitrogen. Following evaporation of the reaction mixture in vacuo, the residual syrup was subjected to and high vacuum (bulb-to-bulb) distillation to remove unreacted hexamethylditin. The residual syrup was diluted with chloroform (20 mL) and filtered through a Celite® plug. Evaporation of the filtrate furnished the crude title compound (3.111 g at 37% purity LC-MS UV$_{215}$) which was carried on to the next synthetic step without additional purification. For characterization purposes, the crude product (20 mg) was purified by silica gel flash column chromatography (eluent: heptane/ethyl acetate gradient) to furnish the title compound as a colorless oil: $^1$H NMR of major tin isotope (500 MHz, CDCl$_3$) δ 0.35 (s, 9H) 2.10-2.17 (m, 2H) 2.85-2.94 (m, 2H) 3.24 (td, J=8.12, 3.63 Hz, 1H) 3.48 (td, J=8.20, 3.78 Hz, 1H) 4.15 (s, 2H) 6.73 (d, J=7.25 Hz, 1H) 7.13 (d, J=4.10 Hz, 1H).

Example 610

Synthesis of 3-fluoro-2-iodo-6,7-dihydro-5H-5,7-methanobenzo[7]annulen-8(9H)-one

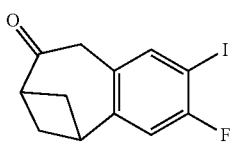 [SMILES: O=C1Cc2cc(I)c(F)cc2C2CC1C2]

To a rapidly stirred solution of crude of 3-fluoro-2-(trimethylstannyl)-6,7-dihydro-5H-5,7-methanobenzo[7]annulen-8(9H)-one (3.09 g at 37% purity LCMS-UV$_{215}$) in chloroform (20 mL) at room temperature was introduced dropwise a solution of iodine (1.488 g, 5.86 mmol, 1.0 equivalent with respect to number of moles 5-bromo-4-fluorotricyclo[8.1.1.0$^{2,7}$]dodeca-2(7),3,5-trien-9-one used for stannane synthesis in previous synthetic step, as a saturated solution in chloroform). Following addition of the iodine solution, the reaction mixture was evaporated directly onto silica gel in vacuo. The dry-loaded material was purified by silica gel flash column chromatography (eluent: heptane/ethyl acetate gradient) to furnish the title compound (0.835 g, 2.64 mmol, 45% over 2 steps) as a yellow oil: $^1$H NMR (500 MHz, CDCl$_3$) δ 2.08-2.14 (m, 2H), 2.87-2.96 (m, 2H), 3.22-3.28 (m, 1H), 3.48 (td, J=8.28, 3.63 Hz, 1H), 4.11 (s, 2H), 6.78 (d, J=8.51 Hz, 1H), 7.53 (d, J=6.31 Hz, 1H); M+H=317

Example 611

Synthesis of 9-bromo-3-fluoro-2-iodo-6,7-dihydro-5H-5,7-methanobenzo[7]annulen-8(9H)-one

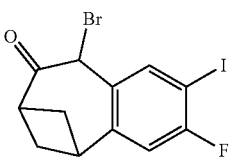 [SMILES: O=C1C2CC(C2)c2cc(F)c(I)cc2C1Br]

To a solution of 3-fluoro-2-iodo-6,7-dihydro-5H-5,7-methanobenzo[7]annulen-8(9H)-one (0.835 g, 2.64 mmol) in a solution of cyclohexane (15 mL) and benzene (8 mL) in a pressure tube were introduced 1,3-dibromo-4,4-dimethylhydantoin (1.133 g, 3.96 mmol) and 2,2'-azobis(2-methylpropionitrile) (0.087 g, 0.53 mmol). The reaction mixture was warmed to 81° C. under an atmosphere of nitrogen for 1 hr. After cooling to room temperature, the reaction mixture was filtered, and the filtrate concentrated in vacuo to furnish the crude title compound (1.400 g at 87% purity LC-UV$_{215}$) as a pale yellow oil containing residual cyclohexane. The crude product was carried through to the next synthetic step without purification.

Example 612

Synthesis of 3-fluoro-2-iodo-6,7-dihydro-5H-5,7-methanobenzo[7]annulene-8,9-dione

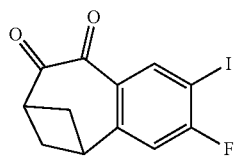 [SMILES: O=C1C(=O)C2CC(C2)c2cc(F)c(I)cc21]

A solution of crude 9-bromo-3-fluoro-2-iodo-6,7-dihydro-5H-5,7-methanobenzo[7]annulen-8(9H)-one (1.400 g at 87% purity LCMS-UV$_{215}$) in dimethylsulfoxide (15 mL) was warmed to 80° C. for 1 hr under an atmosphere of nitrogen. Evaporation in vacuo furnished the crude title compound (2.855 g) containing residual DMSO as a golden-brown oil which was carried through to the next synthetic step without further purification: $^1$H NMR (500 MHz, CDCl$_3$) δ 2.25-2.30 (m, 2H), 3.12-3.18 (m, 2H), 3.48-3.51 (m, 1H), 3.61-3.65 (m, 1H), 6.94 (d, J=8.2 Hz, 1H), 8.55 (d, J=6.6 Hz, 1H).

Example 613

Synthesis of ethyl 8-fluoro-9-iodo-3,4,5,6-tetrahydro-4,6-methanobenzo[3,4]cyclohepta[1,2-d]imidazole-2-carboxylate

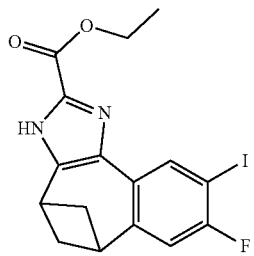 [SMILES: CCOC(=O)c1nc2c([nH]1)C1CC(C1)c1cc(F)c(I)cc1-2]

To a solution of 3-fluoro-2-iodo-6,7-dihydro-5H-5,7-methanobenzo[7]annulene-8,9-dione (2.855 g containing DMSO) in tetrahydrofuran (8 mL) was introduced ethyl glyoxylate (860 mg of a 50% solution in toluene, 4.21 mmol). A solution of ammonium acetate (2.00 g in 7 mL methanol, 26.33 mmol) was then added and the reaction mixture stirred at room temperature for 16 hr. After concentrating the reaction mixture in vacuo, the residue was re-slurried in ethyl acetate (25 mL) and washed with saturated aqueous sodium bicarbonate (5 ml), water (3×5 mL) and brine (5 mL). The organic extract was dried over sodium sulfate, filtered and evaporated to furnish the crude title compound (0.951 g at 69% purity LC-UV$_{215}$) as a tan solid: M+1=413 This material was carried forward to the next synthetic step without further purification.

Example 614

Synthesis of 8-fluoro-9-iodo-3,4,5,6-tetrahydro-4,6-methanobenzo[3,4]cyclohepta[1,2-d]imidazole-2-carboxamide

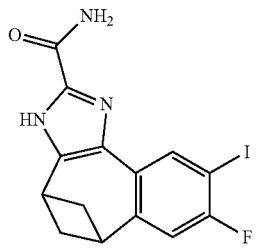 [SMILES: NC(=O)c1nc2c([nH]1)C1CC(C1)c1cc(F)c(I)cc1-2]

A solution of ethyl 8-fluoro-9-iodo-3,4,5,6-tetrahydro-4,6-methanobenzo[3,4]cyclohepta[1,2-d]imidazole-2-carboxylate (302 mg at 69% purity) in methanolic ammonia (7 mL of a 7.0M solution of ammonia in methanol, 49.0 mmol) was warmed to 44° C. for 72 hr in a pressure tube. After cooling to room temperature, the precipitous solution was evaporated to dryness in vacuo. The residue was re-suspended in methanol (1 mL) and the solid collected by filtration to furnish the title compound (155 mg, 0.40 mmol, 78%) as an off-white powder: $^1$H NMR (500 MHz, d6-DMSO) δ 1.47-1.49 (m, 2H), 2.83-2.91 (m, 2H), 3.40-3.44 (m, 1H), 3.60-3.68 (m, 1H), 7.10 (d, J=9.2 Hz, 1H), 7.42 (br. s, 1H), 7.82 (br, s, 1H), 8.64 (d, J=6.9 Hz, 1H), 13.08 (br. s, 1H); M+H=384

Example 615

Synthesis of (R)-8-fluoro-9-(3-hydroxy-3-(5-methyl-isoxazol-3-yl)but-1-yn-1-yl)-3,4,5,6-tetrahydro-4,6-methanobenzo[3,4]cyclohepta[1,2-d]imidazole-2-carboxamide

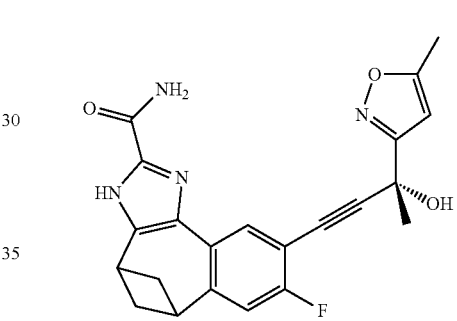

Into a pressure tube containing a solution of 8-fluoro-9-iodo-3,4,5,6-tetrahydro-4,6-methanobenzo[3,4]cyclohepta[1,2-d]imidazole-2-carboxamide (80 mg, 0.21 mmol) in piperidine (2 mL) was introduced (2R)-2-(5-methyl-1,2-oxazol-3-yl)but-3-yn-2-ol (158 mg, 1.04 mmol) and copper(I) iodide (2 mg, 0.01 mmol). The resulting solution was de-oxygenated by nitrogen bubbling for five minutes following which tetrakis(triphenylphosphine)palladium(0) (12 mg, 0.01 mmol) was added. Nitrogen bubbling was continued for a further two minutes and the pressure tube closed under an atmosphere of nitrogen. The reaction mixture was warmed to 40° C. for 2 hr. After concentration of the reaction mixture in vacuo, the residue was slurried in ethyl acetate (25 mL) and washed with saturated aqueous sodium bicarbonate (5 mL), water (5 mL) and brine (5 mL). The organic extract was dried over sodium sulfate, filtered and the filtrate evaporated onto silica gel (~1.0 g) in vacuo. The dry-loaded material was purified by silica gel flash column chromatography (eluent: DCM containing a 0-4% gradient of 7M ammonia in methanol) to furnish the title compound (27 mg, 0.066 mmol, 31%) as a rusty-brown solid: $^1$H NMR (500 MHz, d4-methanol) δ 1.63 (d, J=11.03 Hz, 2H), 1.90 (s, 3H), 2.45 (s, 3H), 2.91-3.00 (m, 2H), 3.46 (td, J=7.09, 4.10 Hz, 1H), 3.66 (td, J=8.12, 3.94 Hz, 1H), 6.33 (s, 1H), 6.94 (d, J=10.09 Hz, 1H), 8.31 (d, J=7.25 Hz, 1H); M+1=407.

Example 616

Synthesis of (R)-8-fluoro-9-(3-hydroxy-3-(pyrimidin-2-yl)but-1-yn-1-yl)-3,4,5,6-tetrahydro-4,6-methanobenzo[3,4]cyclohepta[1,2-d]imidazole-2-carboxamide

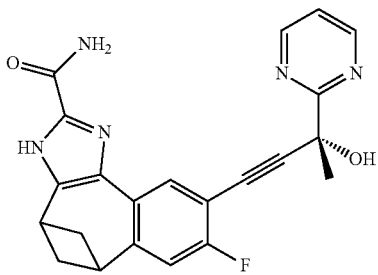 [SMILES: C[C@@](O)(C#Cc1cc2c(cc1F)C1CC(C1)c1[nH]c(C(N)=O)nc1-2)c1ncccn1]

Into a pressure tube containing a solution of 8-fluoro-9-iodo-3,4,5,6-tetrahydro-4,6-methanobenzo[3,4]cyclohepta[1,2-d]imidazole-2-carboxamide (73 mg, 0.19 mmol) in piperidine (2 mL) was introduced (2R)-2-(pyrimidin-2-yl)but-3-yn-2-ol (140 mg, 0.95 mmol) and copper(I) iodide (2 mg, 0.01 mmol). The resulting solution was de-oxygenated by nitrogen bubbling for five minutes then tetrakis(triphenylphosphine)palladium(0) (11 mg, 0.01 mmol) was added. Nitrogen bubbling was continued for a further two minutes and the pressure tube closed under an atmosphere of nitrogen. The reaction mixture was warmed to 40° C. for 6 hr. After concentration of the reaction mixture in vacuo, the residue was slurried in ethyl acetate (20 mL) and washed with saturated aqueous sodium bicarbonate (2×5 mL), water (2×5 mL) and brine (5 mL). The organic extract was dried over sodium sulfate, filtered and the filtrate evaporated onto silica gel (~1.0 g) in vacuo. Purification of the dry-loaded material by silica gel flash column chromatography (eluent: DCM containing a 0-8% gradient of 7M ammonia in methanol) furnished the title compound (35 mg, 0.087 mmol, 46%) as a colorless solid: $^1$H NMR (500 MHz, d4-methanol) δ 1.64 (d, J=9.77 Hz, 2H), 1.97 (s, 3H), 2.96 (qd, J=7.88, 2.84 Hz, 2H), 3.43-3.50 (m, 1H), 3.66 (td, J=8.12, 4.26 Hz, 1H), 6.91 (d, J=10.09 Hz, 1H), 7.46 (t, J=4.89 Hz, 1H), 8.32 (d, J=7.57 Hz, 1H), 8.86 (d, J=5.04 Hz, 2H); M+H=404.

Example 617

Synthesis of ethyl 8-fluoro-9-iodo-3-methyl-3,4,5,6-tetrahydro-4,6methanobenzo[3,4]cyclohepta[1,2-d]imidazole-2-carboxylate

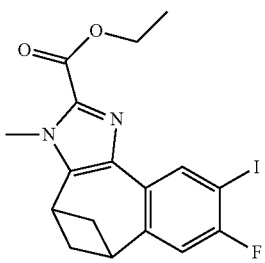 [SMILES: CCOC(=O)c1nc2c(n1C)C1CC(C1)c1cc(F)c(I)cc1-2]

To a pressure tube containing a solution of ethyl 8-fluoro-9-iodo-3,4,5,6-tetrahydro-4,6-methanobenzo[3,4]cyclohepta[1,2-d]imidazole-2-carboxylate (400 mg at 69% purity) in N,N-dimethylformamide (0.5 mL) was introduced potassium carbonate (134 mg, 0.97 mmol) and methyl iodide (207 mg, 1.46 mol). The pressure tube was closed under an atmosphere of nitrogen and the reaction mixture warmed to 40° C. for 2.5 hr and room temperature for 12 hr. After concentrating the reaction mixture in vacuo, the residue was suspended in ethyl acetate (30 mL) and washed with saturated aqueous sodium bicarbonate (2×10 m), water (2×10 ml) and brine (10 mL). The organic extract was dried over sodium sulfate, filtered and evaporated in vacuo to furnish the crude title compound (389 mg of 77% purity LCMS-UV$_{215}$) as an orange-brown sticky solid which was used for the next step without further purification. For characterisation purposes, some of the crude product was taken and suspended in ethyl acetate by sonnication and the product, an off-white solid, collected by filtration: $^1$H NMR (500 MHz, CDCl$_3$) δ 1.48 (t, J=7.09 Hz, 3H), 1.69-1.74 (m, 2H), 2.92-3.00 (m, 2H), 3.50 (td, J=7.57, 3.78 Hz, 1H), 3.56 (td, J=8.35, 3.78 Hz, 1H), 3.94 (s, 3H), 4.46 (q, J=7.15 Hz, 2H), 6.79 (d, J=8.83 Hz, 1H), 8.83 (d, J=6.62 Hz, 1H); M+1=427.

Example 618

Synthesis of 8-fluoro-9-iodo-3-methyl-3,4,5,6-tetrahydro-4,6-methanobenzo[3,4]cyclohepta[1,2-d]imidazole-2-carboxamide

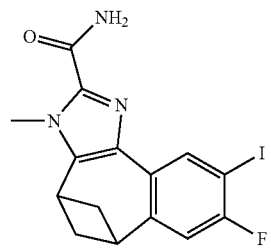 [SMILES: Cn1c(C(N)=O)nc2c1C1CC(C1)c1cc(F)c(I)cc1-2]

A pressure tube containing a solution of ethyl 8-fluoro-9-iodo-3-methyl-3,4,5,6-tetrahydro-4,6 methanobenzo[3,4]cyclohepta[1,2-d]imidazole-2-carboxylate (389 mg at 77% purity LCMS-UV$_{215}$) in methanolic ammonia (6 mL of 7.0M ammonia in methanol) was warmed to 44° C. for 48 hr. After cooling to room temperature, a 0.5 mL aliquot of the precipitous solution was sampled and the solid collected by filtration. The filtrate was pooled back into the reaction mixture and concentrated in vacuo to furnish the crude title compound (329 mg at 77% purity LCMS-UV$_{215}$) as a tan solid which was used for the next step without further purification. The colourless solid isolated by filtration for characterisation purposes was analysed: $^1$H NMR (500 MHz, CDCl$_3$) δ 1.69-1.74 (m, 2H), 2.92-3.00 (m, 2H), 3.47 (td, J=7.49, 3.63 Hz, 1H), 3.57 (td, J=8.28, 3.63 Hz, 1H), 4.00 (s, 3H), 5.39 (br. s., 1H), 6.81 (d, J=8.51 Hz, 1H), 7.36 (br. s., 1H), 8.73 (d, J=6.94 Hz, 1H); M+H=398.

Example 619

Synthesis of (R)-8-fluoro-9-(3-hydroxy-3-(5-methyl-1,2,4-oxadiazol-3-yl)but-1-yn-1-yl)-3-methyl-3,4,5,6-tetrahydro-4,6-methanobenzo[3,4]cyclohepta[1,2-d]imidazole-2-carboxamide

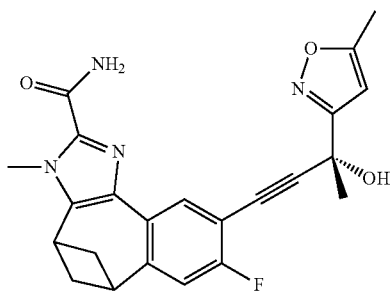

Into a pressure tube containing a solution of 8-fluoro-9-iodo-3-methyl-3,4,5,6-tetrahydro-4,6-methanobenzo[3,4]cyclohepta[1,2-d]imidazole-2-carboxamide (110 mg at 77% purity LCMS-UV$_{215}$) in piperidine (2 mL) was introduced (2R)-2-(5-methyl-1,2,4-oxadiazol-3-yl)but-3-yn-2-ol* (211 mg, 1.39 mmol) and copper(I) iodide (3 mg, 0.01 mmol). The solution was de-oxygenated by nitrogen bubbling for five minutes, then tetrakis(triphenylphosphine)palladium(0) (16 mg, 0.01 mmol) added and bubbling continued for a further two minutes. The pressure tube was closed under an atmosphere of nitrogen and the reaction mixture warmed to 40° C. for 3 hr. After concentration of the reaction mixture in vacuo, the residue was slurried in ethyl acetate (25 mL) and washed with saturated aqueous sodium bicarbonate (5 mL), water (5 mL) and brine (5 ml). The organic extract was dried over sodium sulfate, filtered and evaporated in vacuo. Purification of the residue by silica gel flash column chromatography (eluent: dichloromethane containing a 0-4% gradient of 7M ammonia in methanol) furnished a waxy tan solid which was slurried in acetonitrile (0.3 mL) with sonication, and the precipitate collected by filtration to furnish the title compound (53 mg, 0.126 mmol, 60%) as an off-white solid: $^1$H NMR (250 MHz, 9:1 CDCl$_3$/d4-methanol) δ 1.57-1.68 (m, 2H), 1.93 (s, 3H), 2.56 (s, 3H), 2.90 (qd, J=7.97, 3.20 Hz, 2H), 3.38-3.46 (m, 1H), 3.48-3.55 (m, 1H), 3.91 (s, 3H), 6.76 (d, J=10.05 Hz, 1H), 8.38 (d, J=7.31 Hz, 1H); M+1=422.

Example 620

Synthesis of 8-fluoro-9-(3-hydroxy-3-methylbut-1-yn-1-yl)-3-methyl-3,4,5,6-tetrahydro-4,6-methanobenzo[3,4]cyclohepta[1,2-d]imidazole-2-carboxamide

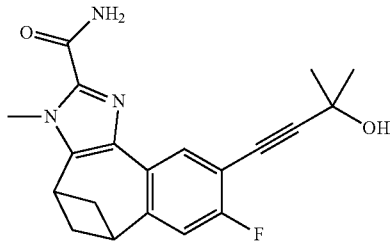 [SMILES: Cn1c(C(N)=O)nc2c1C1CC(C1)c1cc(F)c(C#CC(C)(C)O)cc1-2]

Into a pressure tube containing a solution of 8-fluoro-9-iodo-3-methyl-3,4,5,6-tetrahydro-4,6-methanobenzo[3,4]cyclohepta[1,2-d]imidazole-2-carboxamide (110 mg at 77% purity LCMS-UV$_{215}$) in piperidine (2 mL) was introduced 2-methyl-3-butyn-2-ol (117 mg, 1.39 mmol) and copper(I) iodide (3 mg, 0.01 mmol). The solution was de-oxygenated by nitrogen bubbling for five minutes, then tetrakis(triphenylphosphine)palladium(0) (16 mg, 0.01 mmol) added and bubbling continued for a further two minutes. The pressure tube was closed under an atmosphere of nitrogen and the reaction mixture warmed to 40° C. for 3 hr. After concentration of the reaction mixture in vacuo, the residue was slurried in ethyl acetate (25 mL) and washed with saturated aqueous sodium bicarbonate (5 mL), water (5 mL) and brine (5 ml). The organic extract was dried over sodium sulfate, filtered and evaporated in vacuo. Purification of the residue by silica gel flash column chromatography (eluent: dichloromethane containing a 0-4% gradient of 7M ammonia in methanol) furnished a waxy tan solid which was slurried in acetonitrile (0.3 mL) with sonication, and the precipitate collected by filtration to furnish the title compound (39 mg, 0.11 mmol, 52%) as a colorless solid: $^1$H NMR (500 MHz, d6-DMSO) δ 1.49 (s, 6H), 1.51 (d, J=10.40 Hz, 2H), 2.93 (qd, J=7.88, 2.84 Hz, 2H), 3.54 (td, J=7.09, 4.10 Hz, 1H), 3.65 (td, J=8.28, 3.31 Hz, 1H), 3.89 (s, 3H), 5.55 (s, 1H), 7.11 (d, J=10.72 Hz, 1H), 7.42 (s, 1H), 7.89 (s, 1H), 8.34 (d, J=7.57 Hz, 1H); M+H=354.

Example 621

Synthesis of (R)-8-fluoro-9-(3-hydroxy-3-(pyrimidin-2-yl)but-1-yn-1-yl)-3-methyl-3,4,5,6-tetrahydro-4,6-methanobenzo[3,4]cyclohepta[1,2-d]imidazole-2-carboxamide

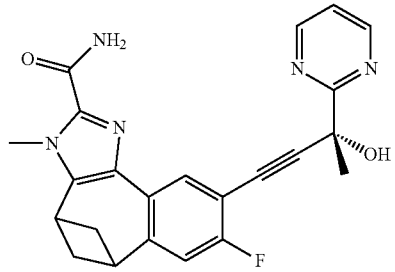 [SMILES: Cn1c(C(N)=O)nc2c1C1CC(C1)c1cc(F)c(C#C[C@@](C)(O)c3ncccn3)cc1-2]

Into a pressure tube containing a solution of 8-fluoro-9-iodo-3-methyl-3,4,5,6-tetrahydro-4,6-methanobenzo[3,4]cyclohepta[1,2-d]imidazole-2-carboxamide (110 mg at 77% purity LCMS-UV$_{215}$) in piperidine (2 mL) was introduced (2R)-2-(pyrimidin-2-yl)but-3-yn-2-ol (205 mg, 1.39 mmol) and copper(I) iodide (3 mg, 0.01 mmol). The solution was de-oxygenated by nitrogen bubbling for five minutes, then tetrakis(triphenylphosphine)palladium(0) (16 mg, 0.01 mmol) added and bubbling continued for a further two minutes. The pressure tube was closed under an atmosphere of nitrogen and the reaction mixture warmed to 40° C. for 3 hr. After concentration of the reaction mixture in vacuo, the residue was slurried in ethyl acetate (25 mL) and washed with saturated aqueous sodium bicarbonate (5 mL), water (5 mL) and brine (5 ml). The organic extract was dried over sodium sulfate, filtered and evaporated in vacuo. Purification of the residue by silica gel flash column chromatography (eluent: dichloromethane containing a 0-3% gradient of 7M ammonia in methanol) furnished a pale yellow solid which was slurried in acetonitrile (0.3 mL) with sonication, and the precipitate collected by filtration to furnish the title compound (32 mg, 0.077 mmol, 37%) as a colorless solid: $^1$H NMR (500 MHz, CDCl$_3$) δ 1.68-1.74 (m, 2H), 2.06 (s, 3H), 2.94 (qd, J=7.99, 3.15 Hz, 2H), 3.45 (td, J=7.17, 3.94 Hz, 1H), 3.56 (td, J=8.04, 3.78 Hz, 1H), 3.99 (s, 3H), 5.26 (s, 1H), 5.32 (br. s., 1H), 6.78 (d, J=9.77 Hz, 1H), 7.32 (t, J=4.89 Hz, 1H), 7.36-7.47 (m, 1H), 8.44 (d, J=7.25 Hz, 1H), 8.84 (d, J=4.73 Hz, 2H); M+H=418.

Example 622

Synthesis of (R)-8-fluoro-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide and (S)-8-fluoro-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide

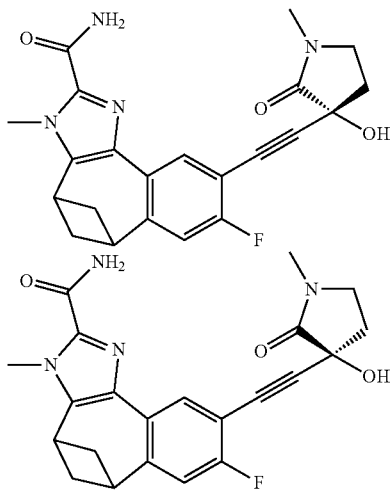

Into a pressure tube containing a solution of 8-fluoro-9-iodo-3-methyl-3,4,5,6-tetrahydro-4,6-methanobenzo[3,4]cyclohepta[1,2-d]imidazole-2-carboxamide (134 mg, 0.31 mmol) in piperidine (3 mL) was introduced 3-ethynyl-3-hydroxy-1-methylpyrrolidin-2-one* (141 mg, 1.01 mmol) and copper(I) iodide (3 mg, 0.01 mmol). The solution was deoxygenated by nitrogen bubbling for five minutes, then tetrakis(triphenylphosphine)palladium(0) (19 mg, 0.02 mmol) added and bubbling continued for a further two minutes. The pressure tube was closed under an atmosphere of nitrogen and the reaction mixture warmed to 55° C. for 3 hr. After concentration of the reaction mixture in vacuo, the residue was slurried in ethyl acetate (25 mL) and washed with saturated aqueous sodium bicarbonate (10 mL), water (10 mL) and brine (5 ml). The organic extract was dried over sodium sulfate, filtered and evaporated in vacuo. After re-dissolving in acetonitrile (10 ml), the solution was re-evaporated in vacuo to furnish a brown solid. The solid was suspended in acetonitrile and the slurry sonnicated for several minutes. Collection of the solid by vacuum filtration and washing on the filter with acetonitrile (0.2 mL) furnished the title compound. The filtrate was adsorbed onto silica gel in vacuo and purified by silica gel flash column chromatography (eluent: dichloromethane containing 0-4% methanol) and product containing fractions combined and concentrated in vacuo. The residue was suspended in acetonitrile (0.2 mL), filtered and washed on the filter with additional acetonitrile (4 drops) to surrender a second batch of the title compound. Both product batches were combined to give the racemic title compound (85 mg, 0.21 mmol, 68%) as an off-white solid: $^1$H NMR (500 MHz, CDCl$_3$) delta 1.66-1.75 (m, 2H), 2.39 (dt, J=12.77, 8.28 Hz, 1H), 2.65-2.73 (m, 1H), 2.90-3.01 (m, 5H), 3.39 (td, J=9.14, 2.52 Hz, 1H), 3.46 (td, J=7.49, 3.63 Hz, 1H), 3.50-3.61 (m, 2H), 3.85 (br. s., 1H), 3.99 (s, 3H), 5.65 (br. s., 1H), 6.81 (d, J=10.09 Hz, 1H), 7.39-7.48 (m, 1H), 7.44 (br. s., 1H), 8.44 (d, J=7.57 Hz, 1H); M+1=409. The enantiomers were separated by chiral HPLC. The absolute stereochemistry at the propargyl alcohol stereocenter was not determined.

Example 623

Synthesis of ethyl 8-fluoro-9-iodo-3-((1-methyl-1H-pyrazol-5-yl)methyl)-3,4,5,6-tetrahydro-4,6-methanobenzo[3,4]cyclohepta[1,2-d]imidazole-2-carboxylate

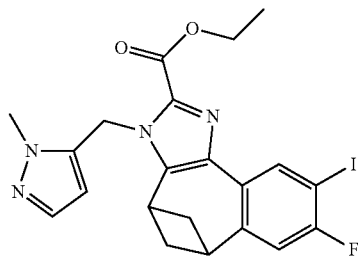 [SMILES: CCOC(=O)c1nc2c(n1Cc1ccnn1C)C1CC(C1)c1cc(F)c(I)cc1-2]

To a mixture of ethyl 8-fluoro-9-iodo-3,4,5,6-tetrahydro-4,6-methanobenzo[3,4]cyclohepta[1,2-d]imidazole-2-carboxylate (100 mg at 69% purity LCMS-UV$_{215}$), potassium carbonate (50 mg, 0.36 mmol) and sodium iodide (73 mg, 0.48 mmol) was introduced a solution of 5-(chloromethyl)-1-methylpyrazole (64 mg, 0.48 mmol) in N,N-dimethylformamide (5 mL). After warming to 50° C. for 4 hr the reaction mixture was evaporated in vacuo. The residue was suspended in ethyl acetate (40 mL), washed with saturated aqueous sodium bicarbonate (2×10 mL), water (2×10 mL) and brine (10 mL) and the organic extract dried over sodium sulfate. Following filtration, the filtrate was evaporated onto silica gel in vacuo and the dry-loaded material purified by silica gel flash column chromatography (eluent: heptanes/ethyl acetate gradient). The title compound (78 mg, 0.15 mmol, 88%) was furnished as a colorless oil: $^1$H NMR (500 MHz, CDCl$_3$) δ 1.45 (t, J=7.3 Hz, 3H), 1.67-1.74 (m, 2H), 2.92 (dq, J=8.2, 2.8 Hz, 2H), 3.38 (dt, J=7.3, 3.8 Hz, 1H), 3.58 (dt, J=8.2, 3.8 Hz, 1H), 3.92 (s, 3H), 4.42 (q, J=6.9 Hz, 2H), 5.59 (d, J=1.6 Hz, 1H), 5.74 (s, 2H), 6.82 (d, J=8.9 Hz, 1H), 7.34 (d, J=1.8 Hz, 1H), 8.86 (d, J=6.9 Hz, 1H); M+1=507.

Example 624

Synthesis of 8-fluoro-9-iodo-3((1-methyl-1H-pyrazol-5-yl)methyl)-3,4,5,6-tetrahydro-4,6-methanobenzo[3,4]cyclohepta[1,2-d]imidazole-2-carboxamide

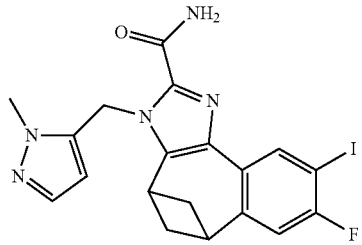 [SMILES: Cn1nccc1Cn1c(C(N)=O)nc2c1C1CC(C1)c1cc(F)c(I)cc1-2]

A pressure tube containing a solution of ethyl 8-fluoro-9-iodo-3-((1-methyl-1H-pyrazol-5-yl)methyl)-3,4,5,6-tetrahydro-4,6-methanobenzo[3,4]cyclohepta[1,2-d]imidazole-2-carboxylate (77 mg, 0.15 mmol) in methanolic ammonia (5 mL of 7.0M ammonia in methanol) was warmed to 44° C. for 48 hr. Evaporation of the reaction mixture furnished the title compound (67 mg, 0.14 mmol, 93%) as a colorless solid: $^1$H NMR (500 MHz, d4-methanol) δ 1.65 (d, J=11.35 Hz, 2H), 2.93-3.02 (m, 2H), 3.47-3.53 (m, 1H), 3.64 (td, J=8.04, 4.10 Hz, 1H), 3.89 (s, 3H), 5.61 (d, J=1.89 Hz, 1H), 5.88 (s, 2H), 6.93 (d, J=8.83 Hz, 1H), 7.30 (d, J=1.89 Hz, 1H), 8.79 (d, J=6.94 Hz, 1H); M+H=478.

Example 625

Synthesis of 8-fluoro-9-(3-hydroxy-3-methylbut-1-yn-1-yl)-3-((1-methyl-1H-pyrazol-5-yl)methyl)-3,4,5,6-tetrahydro-4,6-methanobenzo[3,4]cyclohepta[1,2-d]imidazole-2-carboxamide

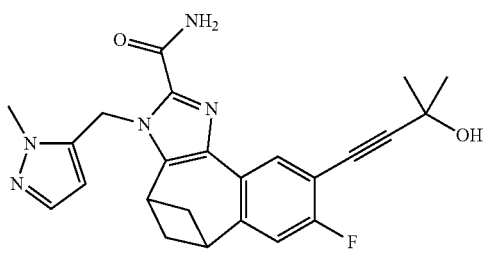 [SMILES: Cn1nccc1Cn1c(C(N)=O)nc2c1C1CC(C1)c1cc(F)c(C#CC(C)(C)O)cc1-2]

To a solution of 8-fluoro-9-iodo-3-((1-methyl-1H-pyrazol-5-yl)methyl)-3,4,5,6-tetrahydro-4,6-methanobenzo[3,4]cyclohepta[1,2-d]imidazole-2-carboxamide (67 mg, 0.14 mmol) in piperidine (2 mL) was introduced 2-methyl-3-butyn-2-ol (68 mg, 0.81 mmol) and copper(I) iodide (2 mg, 0.01 mmol). The solution was de-oxygenated by nitrogen bubbling for five minutes, then tetrakis(triphenylphosphine)palladium(0) (9 mg, 0.01 mmol) added and bubbling continued for a further two minutes. The pressure tube was closed under an atmosphere of nitrogen and the reaction mixture warmed to 50° C. for 4 hr. After evaporation of the reaction mixture in vacuo, the residue was suspended in ethyl acetate (30 mL) and washed with saturated aqueous sodium bicarbonate (2×10 mL), water (2×10 mL) and brine (10 mL). The organic extract was dried over sodium sulfate, filtered and the filtrate adsorbed onto silica gel in vacuo. Purification of the dry-loaded material by silica gel flash column chromatography (eluent: dichloromethane containing a 0-4% gradient of 7M ammonia in methanol) furnished the title compound (47 mg, 0.11 mmol, 78%) as off-white fine crystals: $^1$H NMR (500 MHz, CDCl$_3$) δ 1.64-1.72 (m, 8H), 2.43 (br. s., 1H), 2.90 (qd, J=7.93, 3.00 Hz, 2H), 3.31-3.40 (m, 1H), 3.54-3.61 (m, 1H), 3.92 (br. s., 3H), 5.49 (br. s., 1H), 5.87 (s, 2H), 6.83 (d, J=10.09 Hz, 1H), 7.42 (br. s., 1H), 8.42 (d, J=7.57 Hz, 1H); M+1=434.

Example 626

Synthesis of ethyl 3-(2-chlorobenzyl)-8-fluoro-9-iodo-3,4,5,6-tetrahydro-4,6-methanobenzo[3,4]cyclohepta[1,2-d]imidazole-2-carboxylate

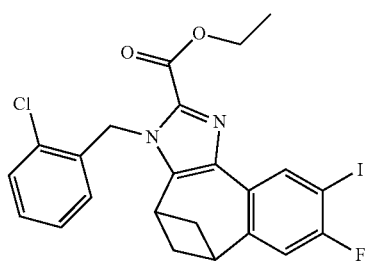 [SMILES: CCOC(=O)c1nc2c(n1Cc1ccccc1Cl)C1CC(C1)c1cc(F)c(I)cc1-2]

To a solution of 8-fluoro-9-iodo-3,4,5,6-tetrahydro-4,6-methanobenzo[3,4]cyclohepta[1,2-d]imidazole-2-carboxylate (100 mg at 69% purity LCMS-UV$_{215}$) in N,N-dimethylformamide (5 mL) was introduced potassium carbonate (50 mg, 0.36 mmol) and 2-chlorobenzyl bromide (75 mg, 0.36 mmol). After warming to 44° C. for 20 hr, the reaction mixture was evaporated in vacuo and the residue suspended in ethyl acetate (35 mL). The suspension was washed with saturated aqueous sodium bicarbonate (2×10 mL), water (2×15 mL) and brine (1×10 mL), then the organic extract dried over sodium sulfate. Following filtration, the organic extract was concentrated in vacuo and the resulting solid residue was slurried in diethyl ether (0.3 mL) with sonnication. Filtration of the slurry furnished the title compound (89 mg, 0.17 mmol, 100%) as a colorless solid: $^1$H NMR (500 MHz, CDCl$_3$) δ 1.42 (t, J=7.09 Hz, 3H), 1.62-1.69 (m, 2H), 2.79-2.87 (m, 2H), 3.22 (td, J=7.41, 3.78 Hz, 1H), 3.54 (td, J=8.28, 3.94 Hz, 1H), 4.41 (q, J=7.25 Hz, 2H), 5.78 (s, 2H), 6.35 (d, J=7.88 Hz, 1H), 6.81 (d, J=8.51 Hz, 1H), 7.11 (td, J=7.57, 0.95 Hz, 1H), 7.22 (t, J=7.72 Hz, 1H), 7.42 (dd, J=7.88, 0.95 Hz, 1H), 8.92 (d, J=6.62 Hz, 1H); M+1=537/539.

Example 627

Synthesis of 3-(2-chlorobenzyl)-8-fluoro-9-iodo-3,4,5,6-tetrahydro-4,6-methanobenzo[3,4]cyclohepta[1,2-d]imidazole-2-carboxamide

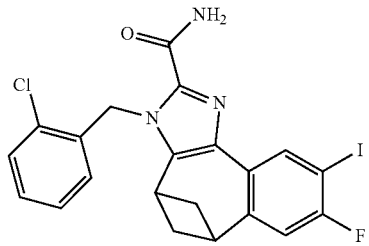 [SMILES: NC(=O)c1nc2c(n1Cc1ccccc1Cl)C1CC(C1)c1cc(F)c(I)cc1-2]

A pressure tube containing a solution of ethyl 3-(2-chlorobenzyl)-8-fluoro-9-iodo-3,4,5,6-tetrahydro-4,6-methanobenzo[3,4]cyclohepta[1,2-d]imidazole-2-carboxylate (89 mg, 0.17 mmol) in methanolic ammonia (5 mL of 7.0M ammonia in methanol) was warmed to 44° C. for 36 hr. Evaporation of the reaction mixture furnished the title compound (86 mg, 0.17 mmol, 100%) as a colorless solid: $^1$H NMR (500 MHz, CDCl$_3$) δ 1.63 (d, J=11.35 Hz, 1H), 2.81 (dd, J=7.72, 3.00 Hz, 2H), 3.14-3.23 (m, 1H), 3.54 (td, J=8.43, 4.26 Hz, 1H), 5.39 (br. s, 1H), 5.92 (s, 1H), 6.42 (d, J=7.57 Hz, 1H), 6.82 (d, J=8.83 Hz, 1H), 7.09-7.15 (m, 1H), 7.17-7.23 (m, 1H), 7.41 (d, J=0.95 Hz, 1H), 7.44-7.66 (m, 1H), 8.83 (d, J=6.94 Hz, 1H); M+1=530/532.

Example 628

Synthesis of 3-(2-chlorobenzyl)-8-fluoro-9-(3-hydroxy-3-methylbut-1-yn-1-yl)-3,4,5,6-tetrahydro-4,6-methanobenzo[3,4]cyclohepta[1,2-c]imidazole-2-carboxamide

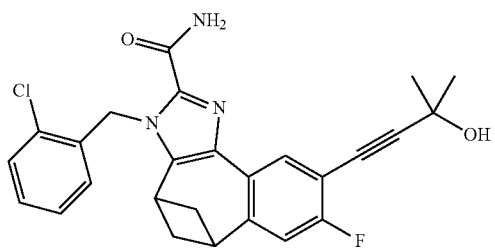 [SMILES: CC(C)(O)C#Cc1cc2c(cc1F)C1CC(C1)c1c-2nc(C(N)=O)n1Cc1ccccc1Cl]

To a solution of 3-(2-chlorobenzyl)-8-fluoro-9-iodo-3,4,5,6-tetrahydro-4,6-methanobenzo[3,4]cyclohepta[1,2-d]imidazole-2-carboxamide (86 mg, 0.17 mmol) in piperidine (2 mL) was introduced 2-methyl-3-butyn-2-ol (71 mg, 0.84 mmol) and copper(I) iodide (2 mg, 0.01 mmol). The solution was de-oxygenated by nitrogen bubbling for five minutes, then tetrakis(triphenylphosphine)palladium(0) (10 mg, 0.01 mmol) added and bubbling continued for a further two minutes. The pressure tube was closed under an atmosphere of nitrogen and the reaction mixture warmed to 50° C. for 4 hr. After evaporation of the reaction mixture in vacuo, the residue was suspended in ethyl acetate (30 mL) and washed with saturated aqueous sodium bicarbonate (2×10 mL), water (2×10 mL) and brine (10 mL). The organic extract was dried over sodium sulfate, filtered, and the filtrate adsorbed onto silica gel in vacuo. Partial purification of the dry-loaded material by silica gel flash column chromatography (eluent: heptane/ethyl acetate gradient) was followed by suspension of the product in acetonitrile/water (9:1, 0.6 mL). Filtration furnished the title compound (31 mg, 0.07 mmol, 41%) as a colorless solid: $^1$H NMR (500 MHz, CDCl$_3$) δ 1.61-1.66 (m, 2H), 1.68 (s, 6H), 2.15 (br. s., 1H), 2.76-2.85 (m, 2H), 3.17 (td, J=7.33, 3.63 Hz, 1H), 3.54 (td, J=8.28, 3.63 Hz, 1H), 5.34-5.40 (m, 1H), 5.90 (s, 2H), 6.41-6.46 (m, 1H), 6.83 (d, J=9.77 Hz, 1H), 7.12 (dd, J=15.29, 1.10 Hz, 1H), 7.16-7.22 (m, 1H), 7.38-7.45 (m, 2H), 8.46 (d, J=7.57 Hz, 1H); M+1=464/466.

Example 629

Synthesis of ethyl 3-(difluoromethyl)-8-fluoro-9-iodo-3,4,5,6-tetrahydro-4,6-methanobenzo[3,4]cyclohepta[1,2-d]imidazole-2-carboxylate

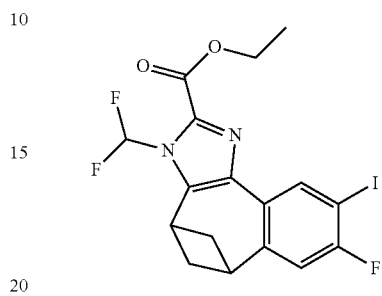

To a pressure tube containing a solution of 8-fluoro-9-iodo-3,4,5,6-tetrahydro-4,6-methanobenzo[3,4]cyclohepta[1,2-d]imidazole-2-carboxylate (100 mg at 69% purity LCMS-UV$_{215}$) in N,N-dimethylformamide (5 mL) was introduced cesium carbonate (79 mg, 0.24 mmol) and methyl chlorodifluoroacetate (825 mg, 5.71 mmol). The reaction mixture was warmed from 50° C. to 100° C. in 25° C. steps with 1 hr at each temperature. After cooling to room temperature, the reaction mixture was concentrated in vacuo and re-suspended in ethyl acetate (20 mL). Following filtration, the filtrate was adsorbed onto silica gel in vacuo and the dry-loaded material purified by silica gel flash column chromatography to furnish the title compound (12 mg at 52% purity LCMS-UV$_{215}$). This compound was carried through to the next synthetic step without further purification. M+H=463.

Example 630

Synthesis of 3-(difluoromethyl)-8-fluoro-9-iodo-3,4,5,6-tetrahydro-4,6-methanobenzo[3,4]cyclohepta[1,2-d]imidazole-2-carboxamide

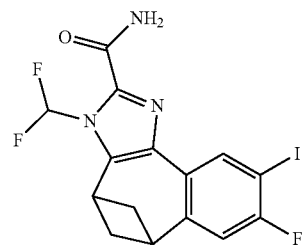 [SMILES: NC(=O)c1nc2c(n1C(F)F)C1CC(C1)c1cc(F)c(I)cc1-2]

A pressure tube containing a solution of ethyl 3-(difluoromethyl)-8-fluoro-9-iodo-3,4,5,6-tetrahydro-4,6-methanobenzo[3,4]cyclohepta[1,2-d]imidazole-2-carboxylate (11 mg, at 52% purity LCMS-UV$_{215}$) in methanolic ammonia (5 mL of 7.0M ammonia in methanol) was warmed to 44° C. for 36 hr. Evaporation of the reaction mixture furnished the title compound (12 mg at 80% purity LCMS-UV$_{215}$) as a colorless solid which was carried through to the next synthetic step without purification: $^1$H NMR (500 MHz, CDCl$_3$) δ 1.70-1.16 (m, 2H), 2.95-3.02 (m, 2H), 3.59 (td, J=8.2, 3.5 Hz, 1H), 3.86-3.91 (m, 1H), 5.58 (br. s, 1H), 6.86 (d, J=8.6 Hz, 1H), 7.40 (br. s, 1H), 8.71 (d, J=6.6 Hz, 1H), 8.75 (t, J=58.6 Hz, 1H); M+H=434.

Example 631

Synthesis 3-(difluoromethyl)-8-fluoro-9-(3-hydroxy-3-methylbut-1-yn-1-yl)-3,4,5,6-tetrahydro-4,6-methanobenzo[3,4]cyclohepta[1,2-d]imidazole-2-carboxamide

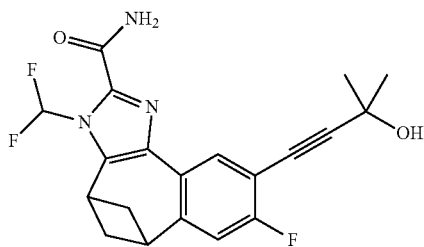 [SMILES: CC(C)(O)C#Cc1cc2c(cc1F)C1CC(C1)c1c-2nc(C(N)=O)n1C(F)F]

To a solution of -(difluoromethyl)-8-fluoro-9-iodo-3,4,5,6-tetrahydro-4,6-methanobenzo[3,4]cyclohepta[1,2-d]imidazole-2-carboxamide (12 mg at 80% purity LCMS-UV$_{215}$) in piperidine (0.5 mL) was introduced 2-methyl-3-butyn-2-ol (12 mg, 0.14 mmol) and copper(I) iodide (0.3 mg, 0.001 mmol). The solution was de-oxygenated by nitrogen bubbling for five minutes, then tetrakis(triphenylphosphine)palladium(0) (0.6 mg, 0.001 mmol) added and bubbling continued for a further two minutes. The pressure tube was closed under an atmosphere of nitrogen and the reaction mixture warmed to 40° C. for 2 hr. After evaporation of the reaction mixture in vacuo, the residue was suspended in ethyl acetate (20 mL) and washed with saturated aqueous sodium bicarbonate (2×7 mL), water (2×7 mL) and brine (7 mL). The organic extract was dried over sodium sulfate, filtered, and the filtrate adsorbed onto silica gel in vacuo. Partial purification of the dry-loaded material by silica gel flash column chromatography (eluent: heptane/ethyl acetate gradient) was followed by suspension of the product in acetonitrile/water (3:1, 0.4 mL). Filtration furnished the title compound (4.5 mg, 0.011 mmol, 6% over 3 steps) as a colorless solid: $^1$H NMR (500 MHz, CDCl$_3$) δ 1.67 (s, 6H), 1.73 (d, J=11.35 Hz, 2H), 2.93-3.04 (m, 2H), 3.60 (td, J=7.96, 3.31 Hz, 1H), 3.84-3.92 (m, 1H), 5.56 (br. s., 1H), 6.87 (d, J=10.09 Hz, 1H), 7.42 (br. s., 1H), 8.40 (d, J=7.57 Hz, 1H), 8.75 (t, J=58.40 Hz, 1H); M+H=390.

Example 632

Synthesis of ethyl 9-iodo-3-methyl-3,4,5,6-tetrahydro-4,6-methanobenzo[3,4]cyclohepta[1,2-d]imidazole-2-carboxylate

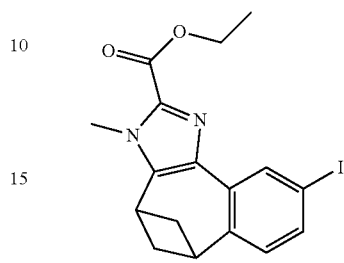

To a solution of ethyl 9-iodo-3,4,5,6-tetrahydro-4,6-methanobenzo[3,4]cyclohepta[1,2-d]imidazole-2-carboxylate (500 mg, 1.27 mmol) in N,N-dimethylformamide (5 mL) was introduced potassium carbonate (175 mg, 1.27 mmol) and methyl iodide (270 mg, 1.90 mmol). The reaction mixture was warmed to 40° C. for 3 hr. After concentration of the reaction mixture in vacuo, the residue was suspended in ethyl acetate (50 mL) and washed with saturated aqueous sodium bicarbonate (2×10 mL), water (10 mL) and brine (10 mL). The organic extract was filtered at this stage to furnish the title compound (94 mg, 0.23 mmol) as a colorless solid of high purity. Following drying over sodium sulfate, the filtrate was re-filtered and concentrated in vacuo to furnish additional title compound of slightly lower purity (395 mg at 93% purity LC-UV$_{215}$). This material was carried through to the next synthetic step without further purification. The higher purity batch was analysed for characterisation purposes: $^1$H NMR (500 MHz, CDCl$_3$) δ 1.49 (t, J=7.09 Hz, 3H), 1.68-1.74 (m, 2H), 2.89-2.99 (m, 2H), 3.50 (td, J=7.49, 3.94 Hz, 1H), 3.60 (td, J=8.28, 3.63 Hz, 1H), 3.95 (s, 3H), 4.47 (q, J=7.04 Hz, 2H), 6.80 (d, J=7.88 Hz, 1H), 7.41 (dd, J=7.88, 1.89 Hz, 1H), 8.82 (s, 1H); M+1=409.

Example 633

Synthesis of 9-iodo-3-methyl-3,4,5,6-tetrahydro-4,6-methanobenzo[3,4]cyclohepta[1,2-d]imidazole-2-carboxamide

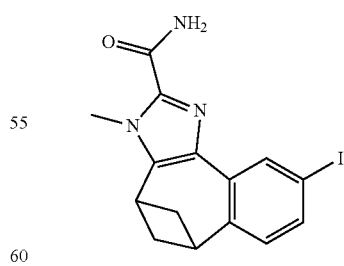

A pressure tube containing a solution of ethyl 9-iodo-3-methyl-3,4,5,6-tetrahydro-4,6-methanobenzo[3,4]cyclohepta[1,2-d]imidazole-2-carboxylato (489 mg, 1.20 mmol) in methanolic ammonia (10 mL of 7.0M ammonia in methanol) was warmed to 45° C. for 24 hr. Evaporation of the reaction mixture furnished the title compound (435 mg, 1.15 mmol, 96%) as a colorless solid: ¹H NMR (500 MHz, d6-DMSO) 61.48 (d, J=10.09 Hz, 2H), 2.90 (qd, J=7.72, 3.00 Hz, 2H), 3.51-3.56 (m, 1H), 3.57-3.63 (m, 1H), 3.90 (s, 3H), 6.92 (d, J=7.88 Hz, 1H), 7.37 (dd, J=7.88, 1.89 Hz, 1H), 7.42 (br. s., 1H), 7.89 (br. s., 1H), 8.64 (d, J=1.58 Hz, 1H); M+H=380.

Example 634

Synthesis of 9-(3-hydroxy-3-methylbut-1-yn-1-yl)-3-methyl-3,4,5,6-tetrahydro-4,6-methanobenzo[3,4]cyclohepta[1,2-d]imidazole-2-carboxamide

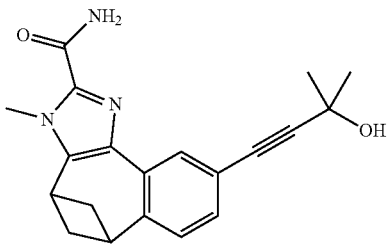 [SMILES: Cn1c(C(N)=O)nc2c1C1CC(C1)c1ccc(C#CC(C)(C)O)cc1-2]

To a solution 9-iodo-3-methyl-3,4,5,6-tetrahydro-4,6-methanobenzo[3,4]cyclohepta[1,2-d]imidazole-2-carboxamide (100 mg, 0.26 mmol) in piperidine (2 mL) was introduced 2-methyl-3-butyn-2-ol (89 mg, 1.05 mmol) and copper(I) iodide (2.5 mg, 0.01 mmol). The solution was de-oxygenated by nitrogen bubbling for five minutes, then tetrakis(triphenylphosphine)palladium(0) (15 mg, 0.01 mmol) added and bubbling continued for a further two minutes. The pressure tube was closed under an atmosphere of nitrogen and the reaction mixture warmed to 40° C. for 2.5 hr. After evaporation of the reaction mixture in vacuo, the residue was suspended in ethyl acetate (25 mL) and washed with saturated aqueous sodium bicarbonate (6 mL), water (2×10 mL) and brine (5 mL). The organic extract was dried over sodium sulfate, filtered, and the filtrate adsorbed onto silica gel in vacuo. Purification of the dry-loaded material by silica gel flash column chromatography (eluent: heptane/ethyl acetate gradient) was followed by suspension of the product in acetonitrile (0.6 mL). The solid was collected by filtration to furnish the title compound (4.5 mg, 0.011 mmol, 4%) as a colorless solid: ¹H NMR (500 MHz, CDCl₃) delta 1.65 (s, 6H), 1.71 (d, J=9.46 Hz, 2H), 2.15 (br. s., 1H), 2.91-3.00 (m, 2H), 3.48 (td, J=7.41, 3.78 Hz, 1H), 3.65 (td, J=8.04, 3.47 Hz, 1H), 4.01 (s, 3H), 5.37 (br. s., 1H), 7.03 (d, J=7.57 Hz, 1H), 7.14 (dd, J=7.72, 1.42 Hz, 1H), 7.49 (br. s., 1H), 8.47 (br. s., 1H); LC-MS: m/z=+336.10 (M+H)+

Example 635

Synthesis of (R)-9-(3-hydroxy-3-(5-methyl-1,2,4-oxadiazol-3-yl)but-1-yn-1-yl)-3-methyl-3,4,5,6-tetrahydro-4,6-methanobenzo[3,4]cyclohepta[1,2-d]imidazole-2-carboxamide

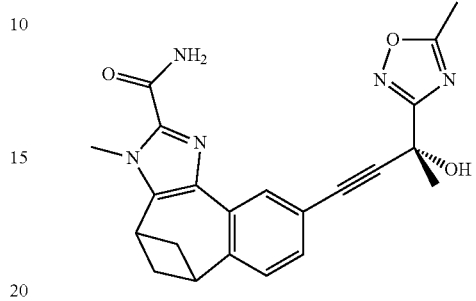

To a solution 9-iodo-3-methyl-3,4,5,6-tetrahydro-4,6-methanobenzo[3,4]cyclohepta[1,2-d]imidazole-2-carboxamide (100 mg, 0.26 mmol) in piperidine (2 mL) was introduced (2R)-2-(5-methyl-1,2,4-oxadiazol-3-yl)but-3-yn-2-ol (160 mg, 1.05 mmol) and copper(I) iodide (2.5 mg, 0.01 mmol). The solution was de-oxygenated by nitrogen bubbling for five minutes, then tetrakis(triphenylphosphine)palladium(0) (15 mg, 0.01 mmol) added and bubbling continued for a further two minutes. The pressure tube was closed under an atmosphere of nitrogen and the reaction mixture warmed to 40° C. for 2.5 hr. After evaporation of the reaction mixture in vacuo, the residue was suspended in ethyl acetate (25 mL) and washed with saturated aqueous sodium bicarbonate (6 mL), water (2×10 mL) and brine (5 mL). The organic extract was dried over sodium sulfate, filtered, and the filtrate adsorbed onto silica gel in vacuo. Purification of the dry-loaded material by silica gel flash column chromatography (eluent: heptane/ethyl acetate gradient) was followed by suspension of the product in acetonitrile (0.8 mL). The solid was collected by filtration to furnish the title compound (80 mg, 0.20 mmol, 77%) as a colorless solid: ¹H NMR (500 MHz, CDCl₃) δ 1.61-1.73 (m, 2H), 2.05 (s, 3H), 2.65 (s, 3H), 2.94 (q, J=8.62 Hz, 2H), 3.47 (td, J=7.25, 3.47 Hz, 1H), 3.57-3.70 (m, 2H), 4.01 (s, 3H), 5.57 (br. s., 1H), 7.02 (d, J=7.88 Hz, 1H), 7.17 (d, J=7.88 Hz, 1H), 7.70 (br. s., 1H), 8.51 (s, 1H); M+H=404.

Example 636

Synthesis of (R)-9-(3-hydroxy-3-(pyrimidin-2-yl)but-1-yn-1-yl)-3-methyl-3,4,5,6-tetrahydro-4,6-methanobenzo[3,4]cyclohepta[1,2-d]imidazole-2-carboxamide

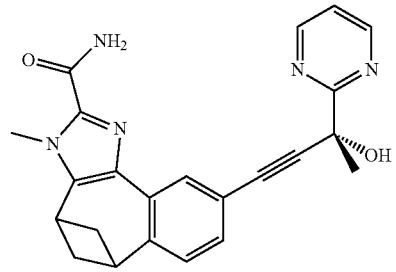 [SMILES: Cn1c(C(N)=O)nc2c1C1CC(C1)c1ccc(C#C[C@@](C)(O)c3ncccn3)cc1-2]

To a solution 9-iodo-3-methyl-3,4,5,6-tetrahydro-4,6-methanobenzo[3,4]cyclohepta[1,2-d]imidazole-2-carboxamide (100 mg, 0.26 mmol) in piperidine (2 mL) was introduced (2R)-2-(pyrimidin-2-yl)but-3-yn-2-ol (156 mg, 1.05 mmol) and copper(I) iodide (2.5 mg, 0.01 mmol). The solution was de-oxygenated by nitrogen bubbling for five minutes, then tetrakis(triphenylphosphine)palladium(0) (15 mg, 0.01 mmol) added and bubbling continued for a further two minutes. The pressure tube was closed under an atmosphere of nitrogen and the reaction mixture warmed to 40° C. for 2.5 hr. After evaporation of the reaction mixture in vacuo, the residue was suspended in ethyl acetate (25 mL) and washed with saturated aqueous sodium bicarbonate (6 mL), water (2×10 mL) and brine (5 mL). The organic extract was dried over sodium sulfate, filtered, and the filtrate adsorbed onto silica gel in vacuo. Purification of the dry-loaded material by silica gel flash column chromatography (eluent: heptane/ethyl acetate gradient) was followed by suspension of the product in acetonitrile (0.8 mL). The solid was collected by filtration to furnish the title compound (51 mg, 0.13 mmol, 50%) as an off-white solid: $^1$H NMR (500 MHz, CDCl$_3$) δ 1.69 (d, J=10.72 Hz, 2H), 2.06 (br. s., 2H), 2.93 (qd, J=7.99, 3.15 Hz, 2H), 3.46 (td, J=7.25, 3.78 Hz, 1H), 3.62 (td, J=8.12, 3.63 Hz, 1H), 3.99 (s, 3H), 5.16-5.44 (m, 2H), 6.99 (d, J=7.57 Hz, 1H), 7.15 (d, J=7.57 Hz, 1H), 7.33 (br. s., 1H), 7.52 (br. s., 1H), 8.49 (s, 1H), 8.85 (br. s., 2H); M+H=400.

Example 637

Synthesis of (R)-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide and (S)-9-((3-hydroxy-1-methyl-2-oxopyrrolidin-3-yl)ethynyl)-3-methyl-3,4,5,6-tetrahydro-4,6-methanobenzo[3,4]cyclohepta[1,2-d]imidazole-2-carboxamide

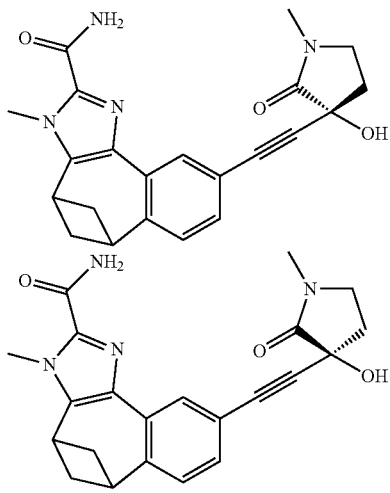

To a solution 9-iodo-3-methyl-3,4,5,6-tetrahydro-4,6-methanobenzo[3,4]cyclohepta[1,2-d]imidazole-2-carboxamide (110 mg, 0.29 mmol) in piperidine (3 mL) was introduced 3-ethynyl-3-hydroxy-1-methylpyrrolidin-2-one*(121 mg, 0.87 mmol) and copper(I) iodide (3 mg, 0.01 mmol). The solution was de-oxygenated by nitrogen bubbling for five minutes, then tetrakis(triphenylphosphine)palladium(0) (17 mg, 0.01 mmol) added and bubbling continued for a further two minutes. The pressure tube was closed under an atmosphere of nitrogen and the reaction mixture warmed to 40° C. for 2.5 hr. After evaporation of the reaction mixture in vacuo, the residue was suspended in ethyl acetate (25 mL) and washed with saturated aqueous sodium bicarbonate (6 mL), water (2×10 mL) and brine (5 mL). The organic extract was dried over sodium sulfate, filtered, and the filtrate adsorbed onto silica gel in vacuo. Purification of the dry-loaded material by silica gel flash column chromatography (eluent: heptane/ethyl acetate gradient) furnished the racemic title compound (107 mg, 0.27 mmol, 93%) as an orange-brown foam. This sample was subjected to resolution by chiral-LC (Column: Chiralpak AD 25 cm, eluent: ethanol) to furnish the title compounds as single isomers (27 mg, 0.07 mmol, 24%). The absolute stereochemistry at the propargyl alcohol stereocenter for each isomer was not determined.

$^1$H NMR (500 MHz, CDCl$_3$) delta 1.63-1.74 (m, 2H), 2.41 (dt, J=12.69, 8.32 Hz, 1H), 2.68 (ddd, J=12.69, 6.86, 2.52 Hz, 1H), 2.94 (quin, J=7.96 Hz, 2H), 2.99 (s, 3H), 3.41 (td, J=9.06, 2.68 Hz, 1H), 3.47 (td, J=7.33, 3.94 Hz, 1H), 3.51-3.57 (m, 1H), 3.64 (td, J=8.04, 3.47 Hz, 1H), 4.00 (s, 3H), 4.26 (br. s., 1H), 6.05 (br. s., 1H), 7.02 (d, J=7.88 Hz, 1H), 7.17 (dd, J=7.72, 1.73 Hz, 1H), 7.63 (br. s., 1H), 8.51 (s, 1H); LC-MS: m/z=+391.10 (M+H)+

Example 638

Synthesis of ethyl 9-iodo-3-((1-methyl-1H-indazol-3-yl)methyl)-3,4,5,6-tetrahydro-4,6-methanobenzo[3,4]cyclohepta[1,2-d]imidazole-2-carboxylate

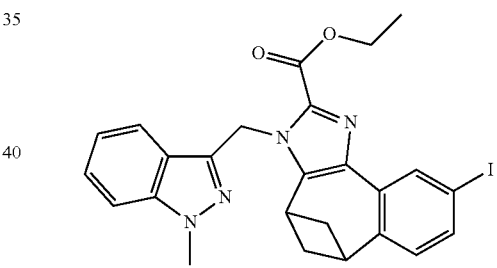

To a mixture of ethyl 9-iodo-3,4,5,6-tetrahydro-4,6-methanobenzo[3,4]cyclohepta[1,2-d]imidazole-2-carboxylate (150 mg, 0.38 mmol), potassium carbonate (79 mg, 0.57 mmol) and sodium iodide (114 mg, 0.76 mmol) was introduced a solution of 3-(chloromethyl)-1-methyl-1H-indazole (137 mg, 0.76 mmol) in N,N-dimethylformamide (5 mL). After warming to 50° C. for 2 hr the reaction mixture was evaporated in vacuo. The residue was suspended in ethyl acetate (40 mL), washed with saturated aqueous sodium bicarbonate (15 mL). After washing the basic aqueous extract with ethyl acetate (3×10 ml), all the organic extracts were combined, washed with water (15 mL) and brine (15 mL), and dried over sodium sulfate. Following filtration of the ethyl acetate extract, the filtrate was evaporated onto silica gel in vacuo. The dry-loaded material was purified by silica gel flash column chromatography (eluent: heptanes/ethyl acetate gradient) to furnish the title compound (198 mg, 0.37 mmol, 97%) as a colorless solid: $^1$H NMR (500 MHz, CDCl$_3$) δ1.48 (t, J=7.2 Hz, 3H), 1.55-1.57 (m, 2H), 2.79 (dq, J=8.2, 2.8 Hz, 2H), 3.53 (td, J=7.9, 3.8 Hz, 1H), 3.73 (td, J=7.6, 4.1 Hz, 1H), 3.99 (s, 3H), 4.50 (q, J=7.2 Hz, 2H), 6.13 (s, 2H), 6.77 (d, J=7.8 Hz, 1H), 7.05 (ddd, J=7.9, 6.3, 1.3 Hz, 1H), 7.32-7.34 (m, 3H), 7.41 (dd, J=7.9, 1.9 Hz, 1H), 8.89 (s, 1H); M+H=539.

Example 639

Synthesis of 9-iodo-3-((1-methyl-1H-indazol-3-yl)methyl)-3,4,5,6-tetrahydro-4,6-methanobenzo[3,4]cyclohepta[1,2-d]imidazole-2-carboxamide

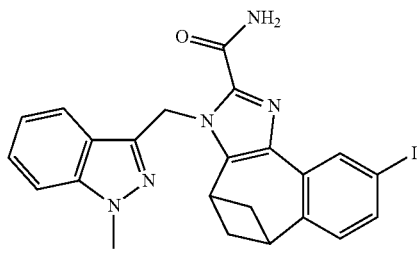 [SMILES: Cn1nc(Cn2c(C(N)=O)nc3c2C2CC(C2)c2ccc(I)cc2-3)c2ccccc21]

A pressure tube containing a solution of ethyl 9-iodo-3-((1-methyl-1H-indazol-3-yl)methyl)-3,4,5,6-tetrahydro-4,6-methanobenzo[3,4]cyclohepta[1,2-d]imidazole-2-carboxylate (198 mg, 0.37 mmol) in methanolic ammonia (7 mL of 7.0M ammonia in methanol) was warmed to 50° C. for 8 days. After evaporation of the reaction mixture in vacuo, the residue was suspended in methanol (0.8 mL) and the solid collected by vacuum filtration to furnish the title compound as an off-white solid (164 mg, 0.32 mmol, 86%): $^1$H NMR (250 MHz, CDCl$_3$) δ1.48-1.57 (m, 2H), 2.71-2.87 (m, 2H), 3.52 (td, J=8.15, 4.42 Hz, 1H), 3.79 (td, J=7.54, 3.81 Hz, 1H), 3.99 (s, 3H), 5.44 (br. s., 3H), 6.24 (s, 2H), 6.78 (d, J=7.92 Hz, 1H), 7.03-7.11 (m, 1H), 7.31-7.41 (m, 3H), 7.53 (dt, J=8.22, 0.91 Hz, 1H), 8.71 (d, J=1.83 Hz, 1H); M+H=510.

Example 640

Synthesis of (R)-9-((3-hydroxy-1-methyl-2-oxopyrrolidin-3-yl)ethynyl)-3-((1-methyl-1H-indazol-3-yl)methyl)-3,4,5,6-tetrahydro-4,6-methanobenzo[3,4]cyclohepta[1,2-d]imidazole-2-carboxamide and (S)-9-((3-hydroxy-1-methyl-2-oxopyrrolidin-3-yl)ethynyl)-3-((1-methyl-1H-indazol-3-yl)methyl)-3,4,5,6-tetrahydro-4,6-methanobenzo[3,4]cyclohepta[1,2-d]imidazole-2-carboxamide

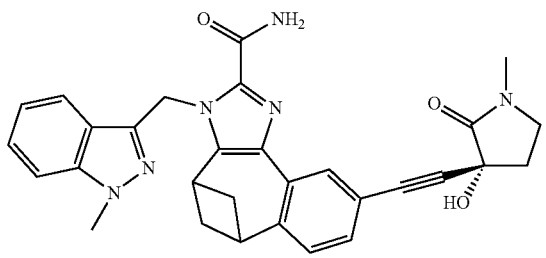

-continued

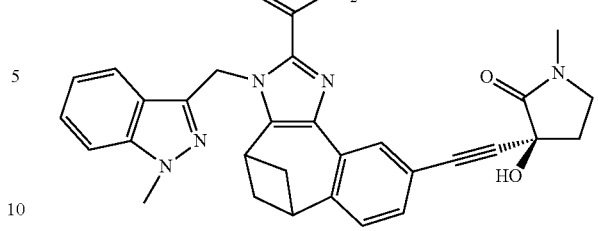

To a solution of -iodo-3-((1-methyl-1H-indazol-3-yl)methyl)-3,4,5,6-tetrahydro-4,6-methanobenzo[3,4]cyclohepta[1,2-d]imidazole-2-carboxamide (164 mg, 0.32 mmol) in piperidine (4 mL) was introduced 3-ethynyl-3-hydroxy-1-methylpyrrolidin-2-one (134 mg, 0.97 mmol) and copper(I) iodide (3 mg, 0.01 mmol). The solution was de-oxygenated by nitrogen bubbling for five minutes, then tetrakis(triphenylphosphine)palladium(0) (19 mg, 0.02 mmol) added and bubbling continued for a further two minutes. The pressure tube was closed under an atmosphere of nitrogen and the reaction mixture warmed to 40° C. for 3 hr. After evaporation of the reaction mixture in vacuo, the residue was suspended in ethyl acetate (40 mL) and washed with saturated aqueous sodium bicarbonate (2×10 mL), water (2×10 mL) and brine (10 mL). The organic extract was dried over sodium sulfate, filtered, and the filtrate adsorbed onto silica gel in vacuo. Following purification of the dry-loaded material by silica gel flash column chromatography (eluent: dichloromethane containing a 0-6% gradient of 7M ammonia in methanol), the partially purified product was suspended in acetonitrile (0.5 mL) and the resulting solid collected by filtration to furnish the racemic title compound (46 mg, 0.09 mmol, 28%) as a colourless solid. This sample was subjected to resolution by chiral-SFC (25 cm Phenomenex Lux Cellulose-2 column, 85:15 carbon dioxide/methanol) to furnish the title compounds (17 mg, 0.033 mmol, 10%) as a colorless solids. The absolute stereochemistry at the propargyl alcohol stereocenter for each isomer was not determined. $^1$H NMR (500 MHz, CDCl$_3$) δ 2.36 (dt, J=12.7, 8.6 Hz, 1H), 2.69 (dd, J=12.4, 5.2 Hz, 1H), 2.78-2.86 (m, 2H), 2.97 (s, 3H), 3.33-3.42 (m, 2H), 3.54-3.63 (m, 2H), 3.80-3.88 (m, 1H), 3.98 (s, 3H), 5.55 (s, 1H), 6.26 (s, 2H), 7.00 (d, J=7.8 Hz, 1H), 7.08 (t, J=7.3 Hz, 1H), 7.16 (d, J=7.2 Hz, 1H), 7.29-7.39 (m, 2H), 7.57 (d, J=8.2 Hz, 1H), 8.62 (s, 1H); M+H=521.

Example 641

Synthesis of 2-bromo-8-chloro-3-fluoro-6,7-dihydro-5H-5,7-methanobenzo[7]annulene-9-carbaldehyde

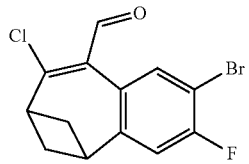 [SMILES: O=CC1=C(Cl)C2CC(C2)c2cc(F)c(Br)cc21]

To anhydrous N,N-dimethylformamide (0.1 mL) at 0-5° C. under an atmosphere of nitrogen was introduced phosphorous oxychloride (0.09 mL, 0.94 mmol) dropwise over 10 minutes and the reaction mixture warmed to room temperature for 1 hr. The reaction mixture was cooled to +5-10° C. and a solution of 2-bromo-3-fluoro-6,7-dihydro-5H-5,7-methanobenzo[7]annulen-8(9H)-one (100 mg, 0.37 mmol) in anhydrous N,N-dimethylformamide (0.2 mL) introduced. After 1 hr at this temperature, the reaction mixture was warmed to 72° C. for 3.5 hr. After cooling to room temperature, ice-water (~5 mL) was introduced and the aqueous solution extracted with ethyl acetate (2×5 mL). The combined ethyl acetate extracts were dried over sodium sulfate, filtered and evaporated in vacuo to furnish the crude title compound (125 mg at 79% purity LC-MS (UV$_{215}$) as an orange wax. This compound was carried through to the next synthetic step without further purification: $^1$H NMR (500 MHz, CDCl$_3$) δ1.66-1.74 (m, 2H), 2.76-2.84 (m, 2H), 3.36 (td, J=7.88, 4.10 Hz, 1H), 3.48 (td, J=7.88, 4.10 Hz, 1H), 6.91 (d, J=8.83 Hz, 1H), 7.96 (d, J=7.25 Hz, 1H), 10.33 (s, 1H)

Example 642

Synthesis of ethyl 9-bromo-8-fluoro-5,6-dihydro-4H-4,6-methanobenzo[3,4]cyclohepta[1,2-b]thiophene-2-carboxylate

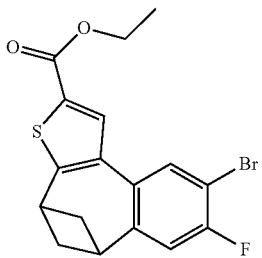 [SMILES: CCOC(=O)c1cc2c(s1)C1CC(C1)c1cc(F)c(Br)cc1-2]

Into a pressure tube containing a solution of 2-bromo-8-chloro-3-fluoro-6,7-dihydro-5H-5,7-methanobenzo[7]annulene-9-carbaldehyde (125 mg at 79% purity LCMS-UV$_{215}$) in anhydrous N,N-dimethylformamide (0.5 mL) was introduced ethyl mercaptoacetate (46 mg, 0.38 mmol as a solution in 0.5 mL of anhydrous N,N-dimethylformamide) and finely powdered potassium carbonate (53 mg, 0.38 mmol). After warming to 60° C. for 4 hr, the reaction mixture was concentrated in vacuo, the residue suspended in ethyl acetate (15 mL) and washed with water (2×10 ml) and brine (10 ml). The organic extract was dried over sodium sulfate, filtered and the filtrate adsorbed onto silica gel in vacuo. Purification of the dry-loaded material by silica gel flash column chromatography (eluent: heptane/ethyl acetate gradient) furnished the title compound (39 mg, 0.10 mmol, 27% over 2 steps) as a colorless solid: $^1$H NMR (500 MHz, CDCl$_3$) δ 1.40 (t, J=7.09 Hz, 3H), 1.71 (d, J=8.83 Hz, 2H), 2.86-2.95 (m, 2H), 3.57 (m, 2H), 4.37 (q, J=7.04 Hz, 2H), 6.91 (dd, J=9.14, 2.21 Hz, 1H), 8.06 (dd, J=6.94, 2.21 Hz, 1H), 8.22 (d, J=1.89 Hz, 1H); M+1=381/383.

Example 643

Synthesis of 9-bromo-8-fluoro-5,6-dihydro-4H-4,6-methanobenzo[3,4]cyclohepta[1,2-b]thiophene-2-carboxamide

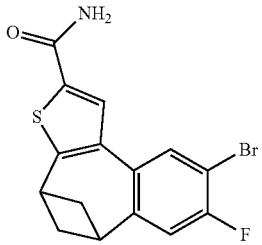 [SMILES: NC(=O)c1cc2c(s1)C1CC(C1)c1cc(F)c(Br)cc1-2]

A pressure tube containing a solution of ethyl 9-bromo-8-fluoro-5,6-dihydro-4H-4,6-methanobenzo[3,4]cyclohepta[1,2-b]thiophene-2-carboxylate (32 mg, 0.08 mmol) in methanolic ammonia (5 mL of 7.0M ammonia in methanol) was warmed to 45° C. for two weeks. Evaporation of the reaction mixture furnished the title compound (31 mg, 0.08 mmol, 100%) as a pale brown solid: $^1$H NMR (500 MHz, d4-methanol) delta 1.61-1.68 (m, 2H), 2.93-3.02 (m, 2H), 3.59 (td, J=7.33, 4.26 Hz, 1H), 3.67 (td, J=8.04, 3.78 Hz, 1H), 7.05 (d, J=9.46 Hz, 1H), 8.18 (d, J=6.94 Hz, 1H), 8.39 (s, 1H); M+1=352/354.

Example 644

Synthesis of 8-fluoro-9-(3-hydroxy-3-methylbut-1-yn-1-yl)-5,6-dihydro-4H-4,6-methanobenzo[3,4]cyclohepta[1,2-b]thiophene-2-carboxamide

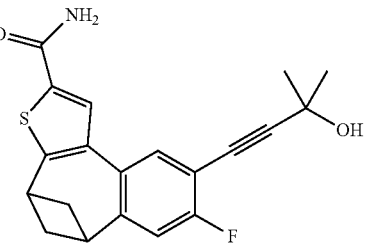

Into a pressure tube containing a solution of 9-bromo-8-fluoro-5,6-dihydro-4H-4,6-methanobenzo[3,4]cyclohepta[1,2-b]thiophene-2-carboxamide (31 mg, 0.08 mmol) in 1:1 N,N-dimethylformamide/triethylamine (0.8 mL) was introduced 2-methyl-3-butyn-2-ol (181 mg, 2.16 mmol), copper (I) iodide (2 mg, 0.01) and nitrogen gas bubbled through the solution for 3 minutes. Bis(triphenylphosphine)palladium(II) chloride (8 mg, 0.01 mmol) was added and nitrogen bubbling continued a further two minutes before the pressure tube was closed under nitrogen. The reaction mixture was warmed to 80° C. for 20 hr, re-treated with 2-methyl-3-butyn-2-ol (181 mg, 2.16 mmol), copper(I) iodide (2 mg, 0.01) and bis(triphenylphosphine)palladium(II) chloride (8 mg, 0.01 mmol) and warmed to 100° C. for an additional 7 hr. After cooling to room temperature, the reaction mixture was evaporated in vacuo and the residue re-dissolved in ethyl acetate (20 mL). This solution was washed with saturated aqueous sodium bicarbonate (10 mL), water (10 mL) and brine (5 mL). The organic extract was dried over sodium sulfate, filtered and the filtrate adsorbed onto silica gel. Purification by silica gel flash column chromatography (eluent:heptane/ethyl acetate) furnished partially purified product as a brown solid. After several acetonitile solubilisation-evaporation (in vacuo) cycles, the resulting solid residue was slurried in acetonitrile (1.0 mL) and collected by filtration to furnish the title compound (17 mg, 0.05 mmol, 62%) as a pale-brown solid: $^1$H NMR (500 MHz, CDCl$_3$) δ1.68 (s, 6H), 1.71-1.73 (m, 2H), 2.87-2.96 (m, 2H), 3.53-3.62 (m, 2H), 6.87 (d, J=10.09 Hz, 1H), 7.92 (d, J=6.94 Hz, 1H), 8.06 (s, 1H); M+H=356.

Example 645

Synthesis of 9-bromo-4,5-dihydrobenzo[b]pyrazolo [1,5-d][1,4]oxazepine-2-carboxamide

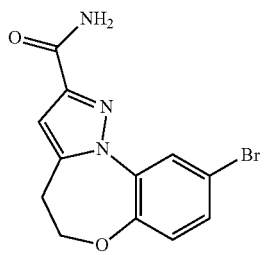 [SMILES: NC(=O)c1cc2n(n1)-c1cc(Br)ccc1OCC2]

A suspension of ethyl 9-bromo-4,5-dihydrobenzo[b]pyrazolo[1,5-d][1,4]oxazepine-2-carboxylate (compound 61-4, page 196, WO 2011/036280) (0.3 g, 0.89 mmol) in 7 M ammonia solution (in methanol, 4 ml) was heated in a microwave apparatus to 120-125° C. for 2.5 hours. After cooling the mixture was left at room temperature for 18 hours before the solvent was removed in vacuo and the residue was then taken up in tetrahydrofuran and pre-absorbed onto a small amount of silica. Purification by FCC (silica, 20-100% ethyl acetate in heptane) gave 245 mg (89%) of the title compound. $^1$H NMR (250 MHz, DMSO-d6) δ ppm 3.18 (2H, t, J=5.79 Hz), 4.46 (2H, t, J=5.79 Hz), 6.71 (1H, s), 7.18 (1H, dd, J=8.60, 0.69 Hz), 7.39 (1H, br, s.), 7.51 (1H, ddd, J=8.68, 2.44, 0.76 Hz), 7.84 (1H, br. s.), 8.19 (1H, dd, J=2.44, 0.76 Hz)); M+1=308/310.

Example 646

Synthesis of 9-(3-hydroxy-3-methylbut-1-yn-1-yl)-4, 5-dihydrobenzo[b]pyrazolo[1,5-d][1,4]oxazepine-2-carboxamide

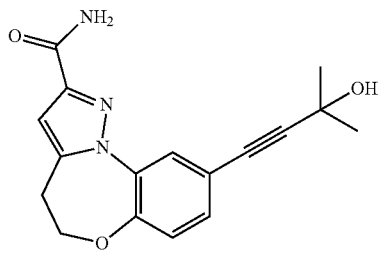

A mixture of 9-bromo-4,5-dihydrobenzo[b]pyrazolo[1,5-d][1,4]oxazepine-2-carboxamide
(100 mg, 0.32 mmol), 2-methylbut-3-yn-2-ol (300 µl, 3.07 mmol) and copper(I) iodide (10 mg, 0.05 mmol) in piperidine (1.5 ml) was sonicated under a stream of argon for 15 minutes. After addition of tetrakis(triphenylphosphine)palladium (0) (38 mg, 0.03 mmol) the mixture was heated at 60° C. for 18 hours before the being concentrated. The residue was taken up in ethyl acetate (300 ml) and washed with 1 M hydrochloric acid (50 ml), water (50 ml) and brine (50 ml), dried over MgSO$_4$, filtered and pre-absorbed onto a small amount of silica. Purification by FCC (silica, 0-3% methanol in dichloromethane) provided a crude product, which was further purified by prep HPLC to give 70 mg (69%) of the title compound. $^1$H NMR (500 MHz, DMSO-d6) δ ppm 1.47 (6H, s), 3.16 (2H, t, J=5.72 Hz), 4.48 (2H, t, J=5.87 Hz), 5.49 (1H, s), 6.71 (1H, s), 7.19 (1H, d, J=8.39 Hz), 7.33 (1H, dd, J=8.39, 2.14 Hz), 7.35 (1H, s), 7.79 (1H, s), 7.98 (1H, d, J=1.98 Hz); M+H=312.

Example 647

Synthesis of 1-(but-3-yn-1-yloxy)-4-iodo-2-nitrobenzene

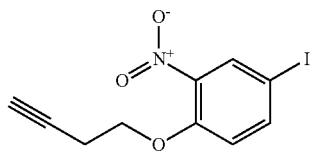

A mixture of 1-fluoro-4-iodo-2-nitro-benzene (5.0 g, 0.02 mol), 3-butyn-1-ol (1.57 ml, 0.02 mol) and potassium carbonate (2.86 g, 0.02 mol) in N,N-dimethylformamide (20 ml) was heated to 100° C. for 18 hours. After cooling the mixture was distributed between ethyl acetate (400 ml) and water (100 ml). The organic layer was separated, washed with water (2×100 ml) and brine (100 ml), dried over MgSO$_4$, filtered and pre-absorbed onto a small amount of silica. Purification by FCC (silica, 0-15% ethyl acetate in heptanes) provided 3.7 g (56%) of the title compound. $^1$H NMR (250 MHz, CDCl$_3$) δ ppm 2.06 (1H, t, J=2.66 Hz), 2.75 (2H, td, J=7.16, 2.74 Hz), 4.22 (2H, t, J=7.08 Hz), 6.88 (1H, d, J=8.83 Hz), 7.81 (1H, dd, J=8.83, 2.28 Hz), 8.11 (1H, d, J=2.28 Hz).

Example 648

Synthesis of 2-(but-3-yn-1-yloxy)-5-iodoanline

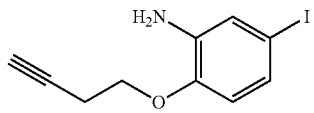

A suspension of 1-(but-3-yn-1-yloxy)-4-iodo-2-nitrobenzene (3.7 g, 11.67 mmol) in ethanol (50 ml) and acetic acid (3 ml) was heated at 60° C. until all solid material dissolved. After addition of iron powder (4.0 g, 72.0 mmol) and iron(III) chloride hexahydrate (0.41 g, 1.52 mmol) the mixture was stirred under reflux for 18 hours. After cooling to room temperature the mixture was diluted with ethyl acetate (500 ml) and filtered through Celite. The filtrate and washings were combined and concentrated in vacuo before being taken up in ethyl acetate (150 ml) and pre-absorbed onto silica. The residue was purified by FCC (silica, 0-20% ethyl acetate in heptane) to give 2.9 g (87%) of the title compound. $^1$H NMR (500 MHz, CDCl$_3$) δ ppm 2.04 (1H, t, J=2.67 Hz), 2.70 (2H, td, J=6.75, 2.67 Hz), 4.05 (2H, b.s.), 4.10 (2H, t, J=6.79 Hz), 6.54 (1H, d, J=8.39 Hz), 7.01 (1H, dd, J=8.39, 2.14 Hz), 7.04 (1H, d, J=2.14 Hz); M+1=288.

Example 649

Synthesis of ethyl 2-{2-[2-(but-3-yn-1-yloxy)-5-iodophenyl]hydrazin-1-ylidene}-2-chloroacetate

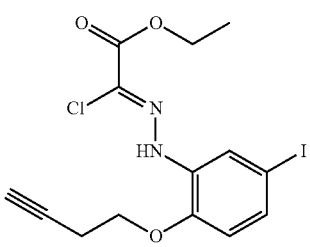 [SMILES: C#CCCOc1ccc(I)cc1N/N=C(\Cl)C(=O)OCC]

A mixture of sodium acetate (1.29 g, 15.7 mmol) and 2-chloro-3-oxo-butyric acid ethyl ester (1.4 ml, 10.0 mmol) in ethanol (125 ml) was stirred at room temperature for 1 hours and then cooled to 0° C. In a separate flask a mixture of 2-(but-3-yn-1-yloxy)-5-iodoaniline (2.81 g, 9.79 mmol) in hydrochloric acid (6 M, 6.8 ml) and tetrahydrofuran (2 ml) was cooled to 0° C. before a solution of sodium nitrite (685 mg, 9.79 mmol) in water (~10 ml) was added slowly. After stirring for 30 minutes in the cold the diazonium salt mixture was washed into the ethanol solution with a small amount of water. The resulting solution was stirred for one hour at 0° C. before being added to water (600 ml) and ethyl acetate (200 ml). After separation the aqueous layer was further extracted with ethyl acetate (2×200 ml) and the combined extracts were washed with brine (200 ml), dried over MgSO₄, filtered and concentrated. The residue was co-evaporated with ethyl acetate (2×) to give 3.96 g (96%) of the title compound as a crystalline solid. ¹H NMR (500 MHz, CDCl₃) δ ppm 1.43 (3H, t, J=7.17 Hz), 2.06 (1H, t, J=2.67 Hz), 2.73 (2H, td, J=6.49, 2.59 Hz), 4.17 (2H, t, J=6.48 Hz), 4.41 (2H, q, J=7.17 Hz), 6.64 (1H, d, J=8.39 Hz), 7.27 (1H, dd, J=8.70, 2.14 Hz), 7.82 (1H, d, J=2.14 Hz), 8.81 (1H, s); M+23=443.

Example 650

Synthesis of ethyl 9-iodo-4,5-dihydrobenzo[b]pyrazolo[1,5-d][1,4]oxazepine-2-carboxylate

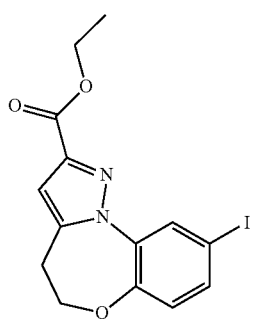 [SMILES: CCOC(=O)c1cc2n(n1)-c1cc(I)ccc1OCC2]

To a solution of ethyl 2-{2-[2-(but-3-yn-1-yloxy)-5-iodophenyl]hydrazin-1-ylidene}-2-chloroacetate (3.9 g, 9.27 mmol) in toluene (800 ml) was added triethylamine (13 ml, 9.32 mmol) and the mixture was then stirred under reflux (heating block at 125° C.) for 18 hours. After cooling to ambient temperature water (100 ml) and ethyl acetate (100 ml) were added and the mixture was transferred into a separation flask. The organic layer was separated, washed with brine (200 ml), dried over MgSO₄, filtered and pre-absorbed onto a small amount of silica. Purification by FCC (silica, 0-20% ethyl acetate in heptane) provided 2.63 g (74%) of the title compound as crystalline solid. ¹H NMR (500 MHz, CDCl₃) δ ppm 1.43 (3H, t, J=7.17 Hz), 3.09 (2H, t, J=6.03 Hz), 4.45 (2H, q, J=7.17 Hz), 4.53 (2H, t, J=6.10 Hz), 6.81 (1H, s), 6.93 (1H, d, J=8.54 Hz), 7.61 (1H, dd, J=8.54, 2.14 Hz), 8.28 (1H, d, J=2.14 Hz);); M+1=385

Example 651

Synthesis of 9-iodo-4,5-dihydrobenzo[b]pyrazolo[1,5-d][1,4]oxazepine-2-carboxamide

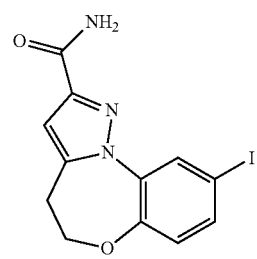 [SMILES: NC(=O)c1cc2n(n1)-c1cc(I)ccc1OCC2]

A suspension of ethyl 9-iodo-4,5-dihydrobenzo[b]pyrazolo[1,5-d][1,4]oxazepine-2-carboxylate (300 mg, 0.78 mmol) in 7 M ammonia solution (in methanol, 3 ml) was heated in a microwave apparatus to 130° C. for 70 minutes. After cooling the volatiles were removed in vacuo and the residue was purified by FCC (silica, 20-100% ethyl acetate in heptane) to give 99 mg (36%) of the title compound as an off-white solid. ¹H NMR (DMSO, 500 MHz) δ 3.17 (2H, t, J=5.8 Hz), 4.47 (2H, t, J=5.9 Hz), 6.71 (1H, s), 7.03 (1H, d, J=8.5 Hz), 7.36 (1H, s), 7.66 (1H, dd, J=8.5, 2.2 Hz), 7.81 (1H, s), 8.29 (1H, d, J=2.2 Hz); M+1=356

Example 652

Synthesis of (R)-9-(3-hydroxy-3-(5-methyl-1,2,4-oxadiazol-3-yl)but-1-yn-1-yl)-4,5-dihydrobenzo[b]pyrazolo[1,5-d][1,4]oxazepine-2-carboxamide

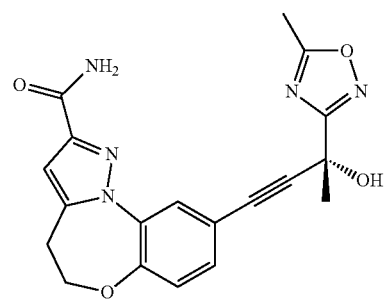 [SMILES: Cc1nc([C@](C)(O)C#Cc2ccc3c(c2)-n2nc(C(N)=O)cc2CCO3)no1]

A mixture of 9-iodo-4,5-dihydrobenzo[b]pyrazolo[1,5-d][1,4]oxazepine-2-carboxamide (100 mg, 0.28 mmol), (R)-2-(5-methyl-[1,2,4]oxadiazol-3-yl)-but-3-yn-2-ol (70 mg, 0.46 mmol), and copper(I) iodide (10 mg, 0.05 mmol) in piperidine (1.5 ml) was sonicated under a stream of argon for 15 minutes. After the addition of tetrakis(triphenylphosphine)palladium (0) (40 mg, 0.035 mmol) the mixture was heated at 60° C. for 3 hours before the being concentrated. The residue was taken up in ethyl acetate (100 ml) and pre-absorbed onto a small amount of silica. Purification by FCC (silica, 0-10% methanol in dichloromethane) gave a solid residue, which was re-crystallised from heptane/dichloromethane (~10 ml, 2/1). Filtration and drying of the crystalline material under high vacuum provided 53 mg (40%) of the title compound. $^1$H NMR (500 MHz, DMSO-d6) δ ppm 1.83 (3H, s), 2.61 (3H, s), 3.17 (2H, t, J=5.80 Hz), 4.49 (2H, t, 0.1=5.80 Hz), 6.71 (1H, s), 6.74 (1H, s), 7.22 (1H, d, J=8.39 Hz), 7.35 (1H, s), 7.38 (1H, dd, J=8.32, 2.06 Hz), 7.81 (1H, s), 8.03 (1H, d, J=1.98 Hz); M+1=380.

Example 653

Synthesis of ethyl 4,4-dibromo-9-iodo-4,5-dihydrobenzo[b]pyrazolo[1,5-d][1,4]oxazepine-2-carboxylate

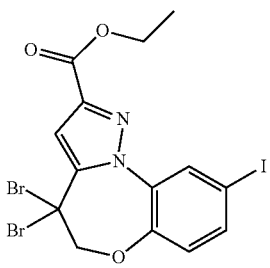 [SMILES: CCOC(=O)c1cc2n(n1)-c1cc(I)ccc1OCC2(Br)Br]

A suspension of ethyl 9-iodo-4,5-dihydrobenzo[b]pyrazolo[1,5-d][1,4]oxazepine-2-carboxylate (1.22 g, 6.87 mmol), N-bromosuccinimide (1.22 g, 6.87 mmol) and dibenzoyl peroxide (70%, 0.11 g, 0.31 mmol) in carbon tetrachloride (50 ml) was heated to 75° C. before azobisisobutyronitrile (51 mg, 0.31 mmol) was added. The temperature was increased to a gentle reflux and the mixture was stirred for 3 hours. More N-bromosuccinimide (601 mg, 3.38 mmol) followed by dibenzoyl peroxide (70%, 0.11 g, 0.31 mmol) and azobisisobutyronitrile (51 mg, 0.31 mmol) were added and the stirring under reflux was continued for an additional 5 hours. After cooling the solvent was removed in vacuo. The residue was taken up in ethyl acetate (300 ml), washed with water (50 ml) and brine (50 ml), dried over MgSO$_4$, filtered and then pre-absorbed onto a small amount of silica. Purification by FCC (silica, 0-10% ethyl acetate in heptane) provided 935 mg (47%) of the title compound as colourless, crystalline solid. $^1$H NMR (500 MHz, CDCl$_3$) δ ppm 1.46 (3H, t, J=7.10 Hz), 4.47 (2H, q, J=7.17 Hz), 4.79 (2H, s), 6.94 (1H, d, J=8.39 Hz), 7.55 (1H, s), 7.60 (1H, dd, J=8.55, 2.14 Hz), 8.65 (1H, d, J=1.98 Hz); M+1=543.

Example 654

Synthesis of ethyl 9-iodo-4-oxo-4,5-dihydrobenzo[b]pyrazolo[1,5-d][1,4]oxazepine-2-carboxylate

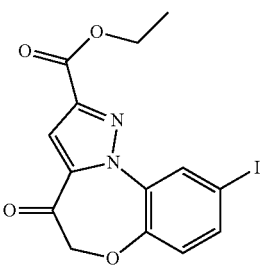 [SMILES: CCOC(=O)c1cc2n(n1)-c1cc(I)ccc1OCC2=O]

A solution of ethyl 4,4-dibromo-9-iodo-4,5-dihydrobenzo[b]pyrazolo[1,5-d][1,4]oxazepine-2-carboxylate (0.93 g, 1.71 mmol) in acetone (40 ml) and water (10 ml) was treated with silver(I) nitrate (0.78 g, 4.59 mmol) and then stirred at room temperature for 2 hours. The solids were removed by filtration through celite and carefully washed with acetone (3×50 ml). The filtrate and washings were combined and concentrated in vacuo before the residue was distributed between ethyl acetate (300 ml) and brine (100 ml). The organic layer was separated, dried over MgSO$_4$, filtered and concentrated. The residue was purified by FCC (silica, 0-20% ethyl acetate in heptane) to give 0.54 g (79%) of the title compound as crystalline solid. $^1$H-NMR (500 MHz, CDCl$_3$) δ ppm 1.45 (3H, t, J=7.10 Hz), 4.48 (2H, q, J=7.17 Hz), 4.78 (2H, s), 7.06 (1H, d, J=8.39 Hz), 7.67 (1H, s), 7.70 (1H, dd, J=8.54, 2.14 Hz), 8.44 (1H, d, J=2.14 Hz); M+1=399.

Example 655

Synthesis of ethyl 4,4-difluoro-9-iodo-4,5-dihydrobenzo[b]pyrazolo[1,5-d][1,4]oxazepine-2-carboxylate

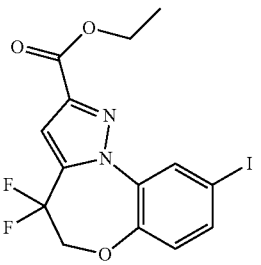 [SMILES: CCOC(=O)c1cc2n(n1)-c1cc(I)ccc1OCC2(F)F]

To a solution of ethyl 9-iodo-4-oxo-4,5-dihydrobenzo[b]pyrazolo[1,5-d][1,4]oxazepine-2-carboxylate (334 mg, 0.84 mmol) in dry dichloromethane (15 ml) was added diethylaminosulfur trifluoride (500 μl, 3.78 mmol) and the mixture was stirred for 3 days at room temperature. The mixture was distributed between dichloromethane (300 ml) and saturated NaHCO$_3$ solution (100 ml). After separation the organic layer was washed with brine (50 ml), dried over MgSO$_4$, filtered and concentrated. The residue was purified by FCC (silica, 0-10% ethyl acetate in heptane) to provide 88 mg (25%) of the title compound as a light yellow, crystalline solid. $^1$H NMR (500 MHz, CDCl$_3$) δ ppm 1.45 (3H, t, J=7.17 Hz), 4.48 (2H, q, J=7.12 Hz), 4.59 (2H, t, J=11.90 Hz), 6.99 (1H, d, J=8.54 Hz), 7.34-7.36 (1H, m), 7.64 (1H, dd, J=8.54, 2.14 Hz), 8.53 (1H, d, J=1.98 Hz); M+23=443.

Example 656

Synthesis of 4,4-difluoro-9-iodo-4,5-dihydrobenzo[b]pyrazolo[1,5-d][1,4]oxazepine-2-carboxamide

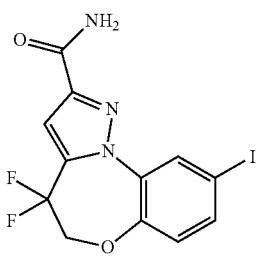 [SMILES: NC(=O)c1cc2n(n1)-c1cc(I)ccc1OCC2(F)F]

A suspension of ethyl 4,4-difluoro-9-iodo-4,5-dihydrobenzo[b]pyrazolo[1,5-d][1,4]oxazepine-2-carboxylate (140 mg, 0.33 mmol) in ammonia in methanol (7M, 3 ml) was heated in a microwave apparatus to 130° C. for 2 hours. After cooling the solvent was removed in vacuo and the residue was washed with a small amount of methanol (3 ml). The solid was collected and dried to give 98 mg (75%) of the title compound. The washings were concentrated and the residue was purified by FCC (silica, 20-60% ethyl acetate in heptanes) to give further 25 mg (19%) of the title compound as an off-white solid. $^1$H NMR (500 MHz, DMSO-d6) δ ppm 4.81 (2H, t, J=11.75 Hz), 7.12 (1H, d, J=8.55 Hz), 7.33-7.34 (1H, m), 7.63 (1H, s), 7.71 (1H, dd, J=8.54, 2.14 Hz), 8.19 (1H, br. s.), 8.67 (1H, d, J=1.98 Hz); M+1=392.

Example 657

Synthesis of (R)-4,4-difluoro-9-(3-hydroxy-3-(5-methylisoxazol-3-yl)but-1-yn-1-yl)-4,5-dihydrobenzo[b]pyrazolo[1,5-d][1,4]oxazepine-2-carboxamide

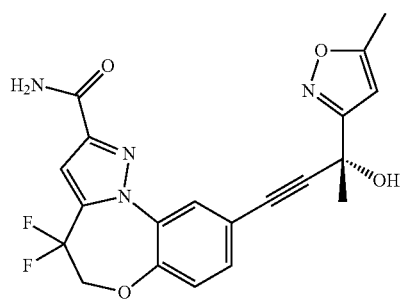 [SMILES: Cc1cc([C@](C)(O)C#Cc2ccc3c(c2)-n2nc(C(N)=O)cc2C(F)(F)CO3)no1]

To a pressure tube was added 4,4-difluoro-9-iodo-4,5-dihydrobenzo[b]pyrazolo[1,5-d][1,4]oxazepine-2-carboxamide (65 mg, 0.17 mmol) followed by piperidine (1.5 ml), tetrakis(triphenylphosphine)palladium (0) (19.2 mg, 0.02 mmol), copper(I) iodide (3.2 mg, 0.02 mmol) and (2R)-2-(5-methyl-1,2-oxazol-3-yl)but-3-yn-2-ol (38 mg, 0.25 mmol). The reaction vessel was sealed and heated at 60° C. for 40 minutes. The reaction mixture was cooled and concentrated in vacuo. and then co-evaporated with dichloromethane (2×10 ml). The crude material was purified by FCC (silica, 1-8% methanol in dichloromethane) to provide 34 mg (49%) of the title compound as a pale brown solid. $^1$H-NMR (500 MHz, DMSO-d6): 1.81 (3H, s), 2.41 (3H, d, J=0.7 Hz), 4.85 (2H, t, J=11.7 Hz), 6.36 (1H, d, J=0.8 Hz), 6.56 (1H, s), 7.33 (1H, d, J=8.4 Hz), 7.35 (1H, s), 7.43 (1H, dd, J=8.4, 2.0 Hz), 7.60 (1H, s), 8.16 (1H, s), 8.37 (1H, d, J=2.0 Hz); M+23=437.

Example 658

Synthesis of (R)-9-(3-hydroxy-3-(5-methylisoxazol-3-yl)but-1-yn-1-yl)-4,5-dihydrobenzo[b]pyrazolo[1,5-d][1,4]oxazepine-2-carboxamide

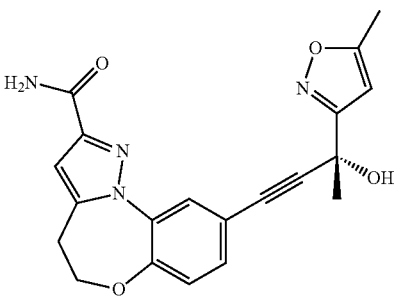 [SMILES: Cc1cc([C@](C)(O)C#Cc2ccc3c(c2)-n2nc(C(N)=O)cc2CCO3)no1]

To a pressure tube was added 9-iodo-4,5-dihydrobenzo[b]pyrazolo[1,5-d][1,4]oxazepine-2-carboxamide (99 mg, 0.28 mmol) followed by piperidine (2.0 mL), tetrakis(triphenylphosphine)palladium (0) (32 mg, 0.03 mmol), copper(I) iodide (5 mg, 0.03 mmol) and (2R)-2-(5-methyl-1,2-oxazol-3-yl)but-3-yn-2-ol (63 mg, 0.42 mmol). The reaction vessel was sealed and heated at 60° C. for 30 minutes. The reaction mixture was cooled and concentrated in vacuo. and then co-evaporated with dichloromethane (2×10 ml). The crude material was purified by FCC (silica, 2-8% methanol in dichloromethane) to provide 59 mg (56%) of the title compound as a pale brown solid. $^1$H NMR (DMSO, 500 MHz) δ 1.80 (3H, s), 2.41 (3H, s), 3.17 (2H, t, J=5.8 Hz), 4.49 (2H, t, J=5.8 Hz), 6.32-6.39 (1H, m), 6.52 (1H, s), 6.72 (1H, s), 7.21 (1H, d, J=8.4 Hz), 7.34 (1H, s), 7.37 (1H, dd, J=8.4, 2.1 Hz), 7.79 (1H, s), 8.02 (1H, d, J=2.1 Hz); M+23=401.

Example 659

Synthesis of (R)-9-((3-hydroxy-1-methyl-2-oxopyrrolidin-3-yl)ethynyl)-4,5-dihydrobenzo[b]pyrazolo[1,5-d][1,4]oxazepine-2-carboxamide and (S)-9-((3-hydroxy-1-methyl-2-oxopyrrolidin-3-yl)ethynyl)-4,5-dihydrobenzo[b]pyrazolo[1,5-d][1,4]oxazepine-2-carboxamide

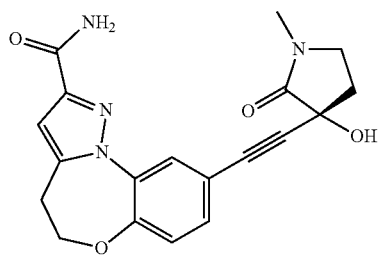

-continued

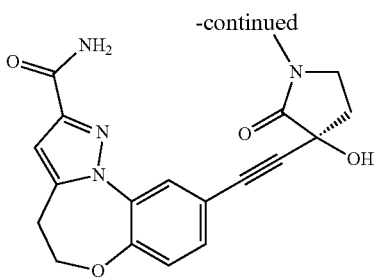

A suspension of 9-iodo-4,5-dihydrobenzo[b]pyrazolo[1,5-d][1,4]oxazepine-2-carboxamide (150 mg, 0.42 mmol), (rac)-3-ethynyl-3-hydroxy-1-methyl-pyrrolidin-2-one (100 mg, 0.72 mmol) and copper(I) iodide (20 mg, 0.11 mmol) in piperidine (2 ml) was sonicated under a stream of nitrogen for 15 minutes. Tetrakis(triphenylphosphine)palladium (0) (50 mg, 0.04 mmol) was added and the mixture was stirred for 2 hours at 60° C. After cooling the volatiles were removed in vacuo and the residue was taken up in ethyl acetate (100 ml) and pre-absorbed onto silica. Purification by FCC (silica, 0-10% methanol in dichloromethane) provided a crude material, which was further purified by re-crystallisation from heptane/dichloromethane (1:1, ~15 ml) to give 145 mg (94%) of the racemic title compound. $^1$H NMR (500 MHz, MeOH-d4) δ ppm 2.30 (1H, dt, J=12.82, 7.55 Hz), 2.57 (1H, ddd, J=12.89, 6.41, 4.50 Hz), 2.92 (3H, s), 3.14-3.19 (2H, m), 3.44-3.49 (2H, m), 4.49-4.54 (2H, m), 6.77 (1H, s), 7.17 (1H, d, J=8.39 Hz), 7.40 (1H, dd, J=8.39, 1.98 Hz), 8.09 (1H, d, J=1.98 Hz); M+23=389. Both enantiomers were separated by SFC (Chiralcel OD-H 25 cm; 16% methanol: 84% $CO_2$; flow rate: 15 ml/min). The absolute stereochemistry at the propargyl alcohol for each isomer was not determined.

Example 660

Synthesis of (R)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide and (S)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide

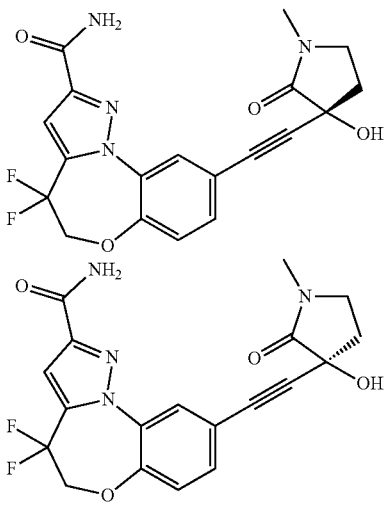

A mixture of 4,4-difluoro-9-iodo-4,5-dihydrobenzo[b]pyrazolo[1,5-d][1,4]oxazepine-2-carboxamide (75% pure, 96 mg, 0.18 mmol), (rac)-3-ethynyl-3-hydroxy-1-methyl-pyrrolidin-2-one (50 mg, 0.36 mmol) and copper(I) iodide (10 mg, 0.05 mmol) in piperidine (1 ml) was sonicated under a stream of nitrogen for 15 minutes. Tetrakis(triphenylphosphine)palladium (0) (50 mg, 0.04 mmol) was added and the mixture was stirred for 2 hours at 60° C. After cooling the volatiles were removed in vacuo and the residue was taken up in ethyl acetate (100 ml) and pre-absorbed onto silica. Purification by FCC (silica, 0-10% methanol in dichloromethane) provided 93 mg (81% pure, quant) of racemic title compound. $^1$H NMR (500 MHz, MeOH-d4) δ ppm 2.32 (1H, dt, J=13.05, 7.44 Hz), 2.59 (1H, ddd, J=12.93, 6.29, 4.73 Hz), 2.93 (3H, s), 3.46-3.50 (2H, m), 4.69 (2H, t, 0.1=11.75 Hz), 7.28 (1H, d, J=8.24 Hz), 7.32-7.34 (1H, m), 7.45 (1H, dd, J=8.39, 2.14 Hz), 8.42 (1H, d, J=1.83 Hz); LC-MS: m/z=425.1 (M+Na)$^+$. Both enantiomers were separated by SFC (Chiralcel OD-H 25 cm; 16% methanol: 84% $CO_2$; flow rate: 15 ml/min). The absolute stereochemistry at the propargyl alcohol for each isomer was not determined.

Scheme for the preparation of 9-iodo-5H-spiro[benzo[b]pyrazolo[1,5-d][1,4]oxazepine-4,1'-cyclopropane]-2-carboxamide

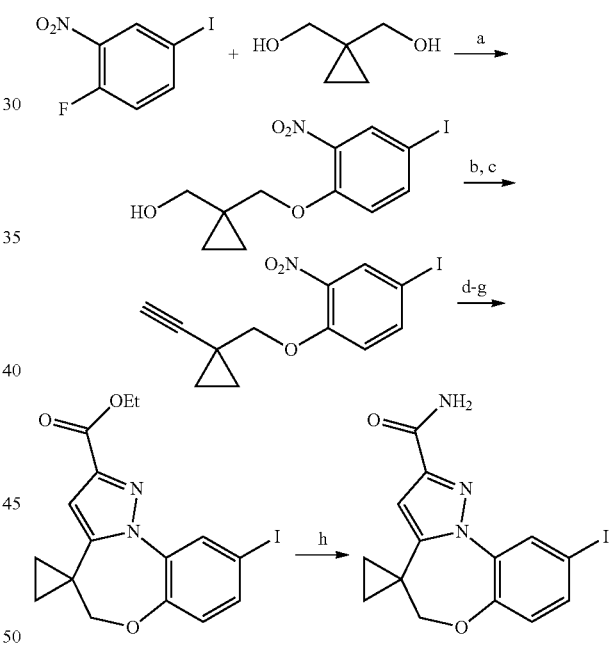

Reagents and Conditions:
a) $K_2CO_3$, DMF, XX° C., 71% yield; b) pyridinium chlorochromate, $CH_2Cl_2$; c) dimethyl (1-diazo-2-oxopropyl)phosphonate, $K_2CO_3$, MeOH, 69% over two steps; d) Fe, $FeCl_3 \cdot 6H_2O$, AcOH, 70° C.; e) $NaNO_2$, HCl (aq); f) ethyl 2-chloroacetoacetate, EtOH; g) triethylamine, toluene, 125° C., 62% yield; h) $NH_3$, dioxane, 110° C.

Example 666

Synthesis of (1-((4-iodo-2-nitrophenoxy)methyl)cyclopropyl)methanol

A solution of 1-fluoro-4-iodo-2-nitrobenzene (2.50 g, 9.4 mmol) in DMF (30 mL) was treated with 1-(hydroxymethyl)cyclopropylmethanol (1.91 g, 19 mmol) and $K_2CO_3$ (2.6 g, 19 mmol) and the mixture was heated at 50° C. for 8 hours. TLC indicated complete consumption of the arylfluoride. The mixture was diluted with water and extracted with ethyl acetate. The combined organics were washed with brine, dried over sodium sulfate and concentrated by rotoevaporation. Purification by flash column chromatography (EtOAc in heptanes) gave the titled compound as a light yellow solid (2.31 g, 71% yield). 1H NMR (400 MHz, DMSO) δ 8.15 (d, J=2.2 Hz, 1H), 7.92 (dd, J=8.8, 2.2 Hz, 1H), 7.17 (d, J=8.9 Hz, 1H), 4.60 (t, J=5.6 Hz, 1H), 4.05 (s, 2H), 3.36 (d, J=5.6 Hz, 2H), 0.50 (s, 4H).

Example 667

Synthesis of 1-((1-ethynylcyclopropyl)methoxy)-4-iodo-2-nitrobenzene

A solution of (1-((4-iodo-2-nitrophenoxy)methyl)cyclopropyl)methanol (750 mg, 2.15 mmol) in 5 mL $CH_2Cl_2$ was treated portionwise with pyridinium chlorochromate (PCC, 615 mg, 2.8 mmol). After 1 hour, an additional 615 mg of PCC was added. The mixture was diluted with 100 mL of EtOAc and filtered through a plug of celite/silica (EtOAc wash). Concentration gave a light yellow oil of the aldehyde. A crude solution of the aldehyde in methanol (5 mL) was treated with $K_2CO_3$ (599 mg, 4.3 mmol) followed by dimethyl (1-diazo-2-oxopropyl)phosphonate (0.43 mL, 550 mg, 2.9 mmol) at 0° C. The mixture was allowed to warm to room temperature at which time incomplete conversion of the starting material was observed by TLC. An additional 200 mg of dimethyl (1-diazo-2-oxopropyl)phosphonate was added and the mixture was stirred at room temperature overnight. The methanol was removed and the residue was diluted with water and extracted with ethyl acetate. The combined organics were washed with brine, dried over sodium sulfate and concentrated by rotoevaporation. Purification by flash column chromatography (isco, 5-25% EtOAc in heptanes) gave 505 mg of the titled compound as an off-white solid (69% over two steps). $^1$H NMR (400 MHz, DMSO) δ 8.16 (d, J=2.2 Hz, 1H), 7.93 (dd, J=8.8, 2.2 Hz, 1H), 7.16 (d, J=8.9 Hz, 1H), 4.09 (s, 2H), 2.78 (s, 1H), 0.98-0.89 (m, 4H).

Example 668

Synthesis of ethyl 9-iodo-5H-spiro[benzo[b]pyrazolo[1,5-d][1,4]oxazepine-4,1'-cyclopropane]-2-carboxylate A suspension of 1((1-ethynylcyclopropyl)methoxy)-4-iodo-2-nitrobenzene (500 mg, 1.47 mmol) in EtOH was treated with acetic acid then iron powder. FeCl3-6H2O was added and the mixture sealed and heated at 70° C. (periodic sonication). After 2 hours, TLC and LCMS indicated complete conversion. The mixture was diluted with ~100 mL of ethylacetate and filtered through a plug of celite and silica. The resulting aniline was used in the next steps without further purification. The crude aniline was suspended in 2 mL THF and treated with 2 mL of a 1:1 mix of concentrated HCl:water at 0° C. After 2 min, a solution of $NaNO_2$ (111 mg, 1.62 mmol) in 0.5 mL, water was added and the mixture rapidly stirred (periodic sonication). In a second flask, ethyl-2-chloroacetoacetate (266 mg, 1.62 mmol) and sodium acetate (195 mg, 2.35 mmol) were stirred in 7 mL of ethanol at room temperature. After 30 min, the solution of the diazo-compound was decanted over (water rinsing) at 0° C. The mixture was stirred at 0° C. for 30 min, then room temperature for 30 min (complete conversion to the chlorohydrazone by LCMS, very non-polar). The mixture was diluted with water and extracted with ethyl acetate. The combined organics were washed with brine, dried over sodium sulfate and concentrated by rotoevaporation to give a light yellow solid which was used in the next step without purification. The crude chlorohydrazone (547 mg, 1.23 mmol) was dissolved in triethylamine 1.3 mL) and toluene (11.5 mL) in a mw vial and heated at 125° C. (sand bath temp) overnight. LCMS indicated good, clean conversion to the titled compound. The mixture was diluted with water and extracted with ethyl acetate. The combined organics were washed with brine, dried over sodium sulfate and concentrated by rotoevaporation. Purification by FCC (5-50% EtOAc in heptanes) gave 313 mg of a sticky red/orange oil (62% yield). $^1$H NMR (400 MHz, DMSO) δ 8.22 (d, J=2.1 Hz, 1H), 7.67 (dd, J=8.4, 2.2 Hz, 1H), 7.03 (d, J=8.5 Hz, 1H), 6.72 (s, 1H), 4.32 (q, J=7.1 Hz, 2H), 4.25 (s, 2H), 1.31 (t, J=7.0 Hz, 3H), 1.09-0.94 (m, 4H).

Example 669

Synthesis of 9-iodo-5H-spiro[benzo[b]pyrazolo[1,5-d][1,4]oxazepine-4,1'-cyclopropane]-2-carboxamide A solution of ethyl 9-iodo-5H-spiro[benzo[b]pyrazolo[1,5-d][1,4]oxazepine-4,1'-cyclopropane]-2-carboxylate (313 mg, 0.76 mmol) in ammonium hydroxide (3 mL) and dioxane (2 mL) was sealed in a 20 mL microwave vial and heated at 110° C. behind a blast shield. The mixture was cooled to room temperature, diluted with ethyl acetate and water and washed with sodium bicarbonate solution. The organics were dried over sodium sulfate and concentrated by rotoevaporation to give the titled compound which was used without purification in subsequent operations. $^1$H NMR (400 MHz, DMSO) δ 8.44 (d, J=2.1 Hz, 1H), 7.83 (br s, 1H), 7.61 (dd, J=8.5, 2.2 Hz, 1H), 7.33 (br s, 1H), 6.99 (d, J=8.5 Hz, 1H), 6.55 (s, 1H), 4.22 (s, 2H), 1.10-0.96 (m, 4H).

Example 670

Synthesis of (R)-9-((3-hydroxy-1-methyl-2-oxopyrrolidin-3-yl)ethynyl)-5H-spiro[benzo[b]pyrazolo[1,5-d][1,4]oxazepine-4,1'-cyclopropane]-2-carboxamide

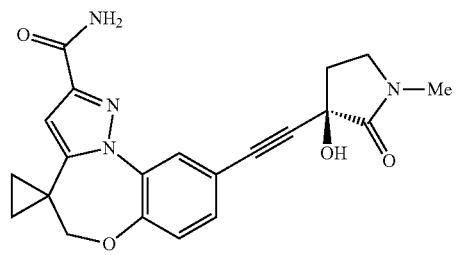 [SMILES: CN1CC[C@@](O)(C#Cc2ccc3c(c2)-n2nc(C(N)=O)cc2C2(CC2)CO3)C1=O]

A solution of ethyl 9-iodo-5H-spiro[benzo[b]pyrazolo[1,5-d][1,4]oxazepine-4,1'-cyclopropane]-2-carboxylate (28 mg, 0.068 mmol) in 2 mL of DMF was treated sequentially with formamidine (0.2 mL) and 25 wt % sodium methoxide in methanol (0.1 mL). The mixture was stirred at room temperature overnight (complete conversion of starting material by LCMS). The mixture was diluted with ammonium chloride solution and extracted with ethyl acetate. The combined organics were dried over sodium sulfate and concentrated by rotoevaporation. Similar to as described elsewhere in the application the crude amide was dissolved in dissolved in DMF/TEA (0.75 mL/0.25 mL) and the mixture sparged with nitrogen. Solid bis(triphenylphosphine)palladium(II)dichloride (4.8 mg, 0.00068 mmol), cuprous iodide (1.3 mg, 0.0068 mmol) and (3R)-3-ethynyl-3-hydroxy-1-methyl-pyrrolidin-2-one (24 mg. 0.17 mmol) was added and the MW vial was sealed. The mixture was heated at 80° C. (sand bath). Complete conversion at 30 min. Purification by reverse phase HPLC gave 7.2 mg of the titled compound as a colorless solid (27% yield).

M+1=393.2; $^1$H NMR (400 MHz, DMSO) δ 8.16 (d, J=2.0 Hz, 1H), 7.81 (s, 1H), 7.37-7.28 (overlapping m, 2H), 7.19 (d, J=8.4 Hz, 1H), 6.56 (s, 1H), 6.44 (s, 1H), 4.25 (s, 2H), 3.38-3.20 (m, 2H), 2.80 (s, 3H), 2.44 (m, 1H), 2.18 (dt, J=13.1, 7.2 Hz, 1H), 1.11-0.95 (m, 4H).

Example 671

Synthesis of 10-bromo-3-(2-chlorobenzyl)-6,7-dihydro-5H-5,7-methanobenzo[c]imidazo[1,2-a]azepine-2-carboxamide

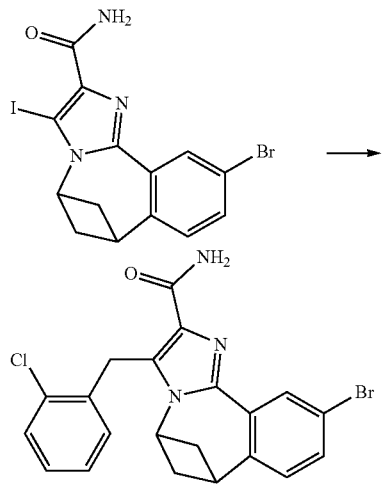

A solution of methyl 10-bromo-3-iodo-6,7-dihydro-5H-5,7-methanobenzo[c]imidazo[1,2-a]azepine-2-carboxylate (150 mg, 0.33 mmol) in dry dimethylacetamide (DMA, 1.0 mL) was sparged with nitrogen gas and treated with PdCl$_2$-[P(o-Tol)$_3$]$_2$ (27 mg, 0.033 mmol). A degassed solution of 2-chlorobenzylzinc bromide (0.61 M, 0.96 mL, 0.59 mmol) was added over 5 min dropwise. The flask was sealed under nitrogen and heated at 50° C. An additional 0.5 mL, of the zinc reagent was added under nitrogen sparge. After 30 min, LCMS indicated complete consumption. The mixture was diluted with ammonium chloride and extracted with ethyl acetate. The combined organics were washed with brine, dried over sodium sulfate and concentrated by rotoevaporation. The crude residue was dissolved in DMF (2 mL) and treated with formamide (1 mL) then sodium methoxide (0.5 mL, 25 wt % in methanol). After 20 min at 50° C., complete conversion to the amide was evident by LCMS. The mixture was diluted with water and extracted with ethyl acetate. The combined organics were washed with brine, dried over sodium sulfate and concentrated by rotoevaporation. The amide was used in subsequent steps without further purification.

Example 672

Synthesis of (R)-3-(2-chlorobenzyl)-10-((3-hydroxy-1-methyl-2-oxopyrrolidin-3-yl)ethynyl)-6,7-dihydro-5H-5,7-methanobenzo[c]imidazo[1,2-a]azepine-2-carboxamide and (S)-3-(2-chlorobenzyl)-10-((3-hydroxy-1-methyl-2-oxopyrrolidin-3-yl)ethynyl)-6,7-dihydro-5H-5,7-methanobenzo[c]imidazo[1,2-a]azepine-2-carboxamide

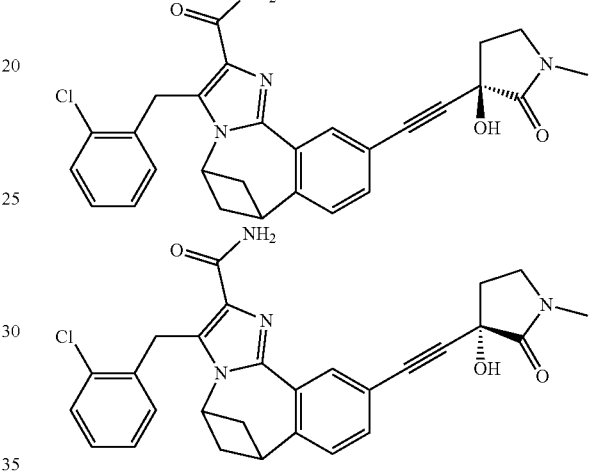

Similar to as described in General Procedure F, 10-bromo-3-(2-chlorobenzyl)-6,7-dihydro-5H-5,7-methanobenzo[c]imidazo[1,2-a]azepine-2-carboxamide to give the titled compounds after purification by chiral SFC (Cel-1 @ 40% methanol with 0.1% NH$_4$OH). LCMS and $^1$H NMR of the two enantiomers were identical.

M+1=501.2. $^1$H NMR (400 MHz, DMSO) δ 8.74 (s, 1H), 7.65 (br s, 1H), 7.48 (m, 1H), 7.31-7.10 (overlapping m, 4H), 6.65 (m, 1H), 6.44 (s, 1H), 4.60 (s, 2H), 4.49 (m, 1H), 3.62 (m, 1H), 3.36 (m, 2H), 2.93 (m, 2H), 2.81 (s, 3H), 2.45 (m, 1H), 2.21 (m, 1H), 1.64 (m, 2H).

Example 674

Synthesis of 10-bromo-3-((3-methyloxetan-3-yl)methyl)-6,7-dihydro-5H-5,7-methanobenzo[c]imidazo[1,2-a]azepine-2-carboxamide

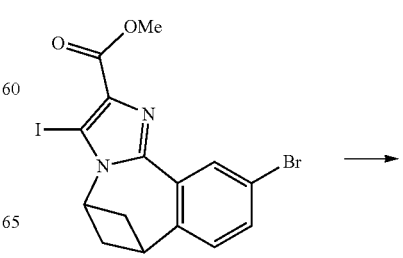

-continued

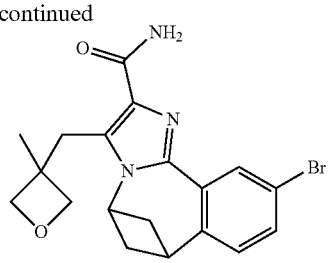

A solution of methyl 10-bromo-3-iodo-6,7-dihydro-5H-5,7-methanobenzo[c]imidazo[1,2-a]azepine-2-carboxylate (75 mg, 0.16 mmol) in 1 mL DMA was sparged with nitrogen and treated with ((3-methyloxetan-3-yl)methyl)zinc(II) iodide (1.11 mL, 0.59 M, 0.65 mmol) reagent while nitrogen was sparging. After 1 min, solid Pd(PPh$_3$)$_4$ (ca. 10 mol %) was added and the mixture stirred at 90° C. overnight. The mixture was diluted with ammonium chloride and extracted with ethyl acetate. The combined organics were washed with brine, dried over sodium sulfate and concentrated by rotoevaporation. Purification by flash column chromatography (12 g isco, 10-100% EtOAc) gave 27 mg of methyl 10-bromo-3-((3-methyloxetan-3-yl)methyl)-6,7-dihydro-5H-5,7-methanobenzo[c]imidazo[1,2-a]azepine-2-carboxylate. This product was taken up in 1 mL of DMF and treated with 0.2 mL formamide then 0.2 mL of 25% wt NaOMe in MeOH. After 1 hour at room temp, the mixture was diluted with ammonium chloride and extracted with ethyl acetate. The combined organics were washed with brine, dried over sodium sulfate and concentrated by rotoevaporation. This material was used in subsequent operations without further purification.

Example 675

Synthesis of (R)-10-(3-hydroxy-3-(5-methylisoxazol-3-yl)but-1-yn-1-yl)-3-((3-methyloxetan-3-yl)methyl)-6,7-dihydro-5H-5,7-methanobenzo[c]imidazo[1,2-a]azepine-2-carboxamide

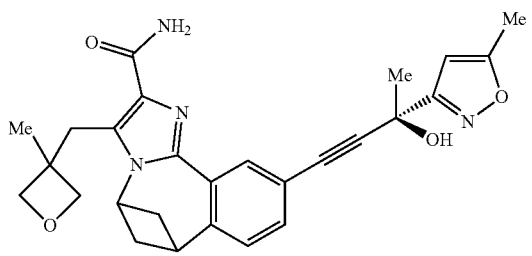 [SMILES: Cc1cc([C@](C)(O)C#Cc2ccc3c(c2)-c2nc(C(N)=O)c(CC4(C)COC4)n2C2CC3C2)no1]

Similar to as described in General Procedure E, 10-bromo-3-((3-methyloxetan-3-yl)methyl)-6,7-dihydro-5H-5,7-methanobenzo[c]imidazo[1,2-a]azepine-2-carboxamide was reacted with (R)-2-(5-methylisoxazol-3-yl)but-3-yn-2-ol to give the titled compound.

M+1=473; $^1$H NMR (400 MHz, DMSO) δ 8.71 (s, 1H), 7.61 (br s, 1H), 7.28 (overlapping s, 2H), 7.07 (br s, 1H), 6.49 (s, 1H), 6.36 (s, 1H), 4.87 (m, 1H), 4.44 (d, J=5.7 Hz, 2H), 4.05 (d, J=5.6 Hz, 2H), 3.63 (m, 1H), 3.07 (m, 2H), 2.41 (s, 3H), 1.82 (s, 3H), 1.65 (m, 2H), 1.29 (s, 3H).

Example 676

Synthesis of 10-bromo-3-cyclopropyl-9-fluoro-6,7-dihydro-5H-5,7-methanobenzo[c]imidazo[1,2-a]azepine-2-carboxamide

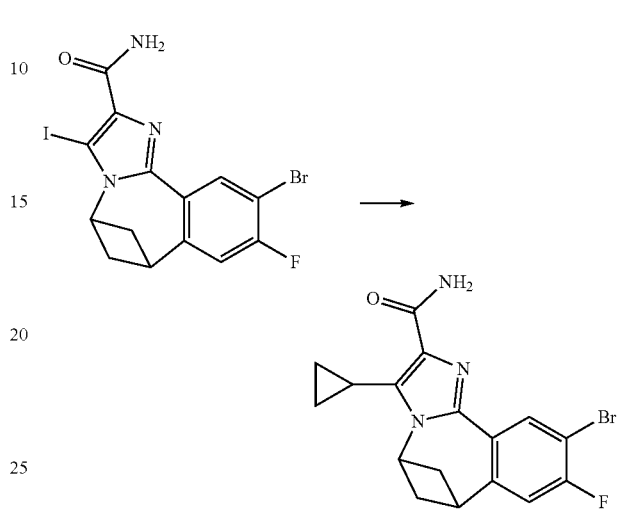

A solution of 10-bromo-9-fluoro-3-iodo-6,7-dihydro-5H-5,7-methanobenzo[c]imidazo[1,2-a]azepine-2-carboxamide (2.0 g, 4.3 mmol) in 15 mL dry DMA with PdCl$_2$-[P(o-Tol)$_3$]$_2$ (210 mg, 0.26 mmol) was sparged with nitrogen gas then treated with a solution of cyclopropylzinc bromide (19 mL, 9.5 mmol, 0.5 M in THF) over 10 min. The mixture was heated at 50° C. for 40 min at which time 10 mL of additional zinc reagent (5 mmols, 1.16 eq) was added at 50° C. with sparging nitrogen. After 15 min, an additional 6 mL of zinc reagent was added. The mixture was cooled to room temp and treated with ~5 mL of ammonium chloride. The mixture was diluted with water and extracted with ethyl acetate. The combined organics were washed with brine, dried over sodium sulfate and concentrated by rotoevaporation. The mixture was dissolved in DMF and purified by RPHPLC. The resultant solid was used in subsequent operations without further purification.

Example 677

Synthesis of 3-cyclopropyl-9-fluoro-10-(3-hydroxy-3-methylbut-1-yn-1-yl)-6,7-dihydro-5H-5,7-methanobenzo[c]imidazo[1,2-a]azepine-2-carboxamide

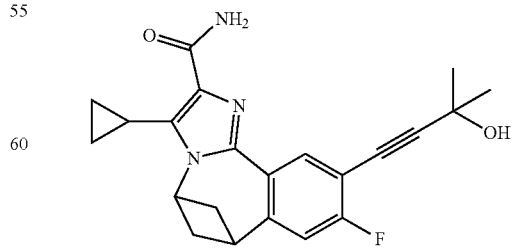

Similar to as described in General Procedure E, 10-bromo-3-cyclopropyl-9-fluoro-6,7-dihydro-5H-5,7-methanobenzo

[c]imidazo[1,2-a]azepine-2-carboxamide was reacted with 2-methylbut-3-yn-2-ol to give the titled compound.

M+1=380; $^1$H NMR (400 MHz, DMSO) δ 8.66 (d, J=7.5 Hz, 1H), 7.48 (br s, 1H), 7.24 (d, J=10.1 Hz, 1H), 6.97 (br s, 1H), 5.56 (s, 1H), 5.26 (m, 1H), 3.67 (m, 1H), 3.13 (m, 2H), 1.79-1.59 (overlapping m, 3H), 1.49 (s, 6H), 0.99 (m, 2H), 0.67 (m, 2H).

Example 678

Synthesis of (±)-3-cyclopropyl-9-fluoro-10-(3-hydroxy-4-methoxy-3-methylbut-1-yn-1-yl)-6,7-dihydro-5H-5,7-methanobenzo[c]imidazo[1,2-a]azepine-2-carboxamide

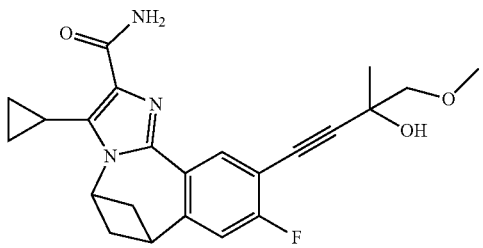 [SMILES: COCC(C)(O)C#Cc1cc2c(cc1F)C1CC(C1)n1c-2nc(C(N)=O)c1C1CC1]

Similar to as described in General Procedure G, 10-bromo-3-cyclopropyl-9-fluoro-6,7-dihydro-5H-5,7-methanobenzo[c]imidazo[1,2-a]azepine-2-carboxamide was reacted with 1-methoxy-2-methylbut-3-yn-2-ol to give the titled compound. MS+410.2. $^1$H NMR (400 MHz, DMSO) δ 8.66 (d, J=7.5 Hz, 1H), 7.47 (br s, 1H), 7.25 (d, J=10.1 Hz, 1H), 6.98 (br s, 1H), 5.68 (s, 1H), 5.26 (m, 1H), 3.68 (m, 1H), 3.39 (m, 2H), 3.37 (s, 3H), 3.14 (m, 2H), 1.81-1.59 (overlapping m, 3H), 1.45 (s, 3H), 0.99 (m, 2H), 0.67 (m, 2H).

Example 679

Synthesis of (R)-3-cyclopropyl-9-fluoro-10-(3-hydroxy-3-(5-methylisoxazol-3-yl)but-1-yn-1-yl)-6,7-dihydro-5H-5,7-methanobenzo[c]imidazo[1,2-a]azepine-2-carboxamide

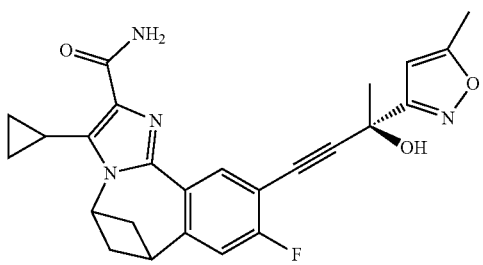 [SMILES: Cc1cc([C@](C)(O)C#Cc2cc3c(cc2F)C2CC(C2)n2c-3nc(C(N)=O)c2C2CC2)no1]

Similar to as described in General Procedure E, 10-bromo-3-cyclopropyl-9-fluoro-6,7-dihydro-5H-5,7-methanobenzo[c]imidazo[1,2-a]azepine-2-carboxamide was reacted with (R)-2-(5-methylisoxazol-3-yl)but-3-yn-2-ol to give the titled compound. MS+447.2. $^1$H NMR (400 MHz, DMSO) δ 8.68 (d, J=7.5 Hz, 1H), 7.45 (br s, 1H), 7.26 (d, J=10.1 Hz, 1H), 6.92 (br s, 1H), 6.57 (s, 1H), 6.35 (s, 1H), 5.26 (m, 1H), 3.68 (m, 1H), 3.14 (m, 1H), 2.41 (s, 3H), 1.82 (s, 3H), 1.77-1.61 (overlapping m, 3H), 0.99 (m, 1H), 0.68 (m, 1H).

Example 680

Synthesis of (R)-3-cyclopropyl-10-(3-hydroxy-3-(5-methylisoxazol-3-yl)but-1-yn-1-yl)-5,6-dihydrobenzo[f]imidazo[1,2-d][1,4]oxazepine-2-carboxamide

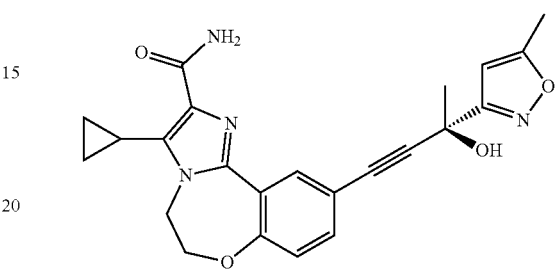

Similar to as described in General Procedure G, 10-bromo-3-cyclopropyl-5,6-dihydrobenzo[f]imidazo[1,2-d][1,4]oxazepine-2-carboxamide was reacted with (R)-2-(5-methylisoxazol-3-yl)but-3-yn-2-ol to give the titled compound. MS+419.2. $^1$H NMR (400 MHz, DMSO) δ 8.52 (d, J=2.2 Hz, 1H), 7.42 (br s, 1H), 7.31 (dd, J=8.5, 2.2 Hz, 1H), 7.02 (d, J=8.5 Hz, 1H), 6.95 (br s, 1H), 6.45 (s, 1H), 6.35 (s, 1H), 4.50 (m, 4H), 2.40 (s, 3H), 1.80 (s, 3H), 1.76 (m, 1H), 0.98 (m, 2H), 0.84 (m, 2H).

Example 681

Synthesis of (S)-3-cyclopropyl-9-fluoro-10-((3-hydroxy-1-methyl-2-oxopyrrolidin-3-yl)ethynyl)-6,7-dihydro-5H-5,7-methanobenzo[c]imidazo[1,2-a]azepine-2-carboxamide and (R)-3-cyclopropyl-9-fluoro-10-((3-hydroxy-1-methyl-2-oxopyrrolidin-3-yl)ethynyl)-6,7-dihydro-5H-5,7-methanobenzo[c]imidazo[1,2-a]azepine-2-carboxamide

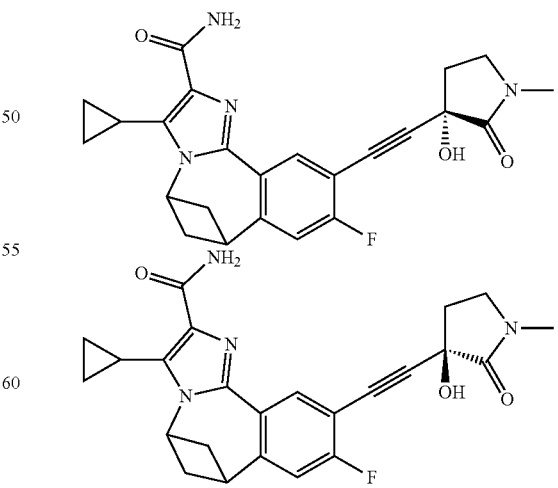

Similar to as described in General Procedure E, 10-bromo-3-cyclopropyl-9-fluoro-6,7-dihydro-5H-5,7-methanobenzo

[c]imidazo[1,2-a]azepine-2-carboxamide was reacted with 3-ethynyl-3-hydroxy-1-methylpyrrolidin-2-one to give the titled compounds after purification by chiral SFC (chiralpak AD, MeOH/NH₄OH). LCMS and ¹H NMR of the two enantiomers were identical.

M+1=435; ¹H NMR (400 MHz, DMSO) 8.68 (d, J=7.6 Hz, 1H), 7.45 (br s, 1H), 7.26 (d, J=10.2 Hz, 1H), 6.92 (br s, 1H), 6.51 (s, 1H), 5.26 (m, 1H), 3.68 (m, 1H), 3.41-3.31 (overlapping m, 2H), 3.14 (m, 2H), 2.81 (s, 3H), 2.45 (m, 1H), 2.21 (m, 1H), 1.77-1.67 (overlapping m, 3H), 0.99 (m, 2H), 0.68 (m, 2H).

Example 682

Synthesis of (S)-3-cyclopropyl-9-fluoro-10-((3-hydroxy-2-oxopyrrolidin-3-yl)ethynyl)-6,7-dihydro-5H-5,7-methanobenzo[c]imidazo[1,2-a]azepine-2-carboxamide and (R)-3-cyclopropyl-9-fluoro-10-((3-hydroxy-2-oxopyrrolidin-3-yl)ethynyl)-6,7-dihydro-5H-5,7-methanobenzo[c]imidazo[1,2-a]azepine-2-carboxamide

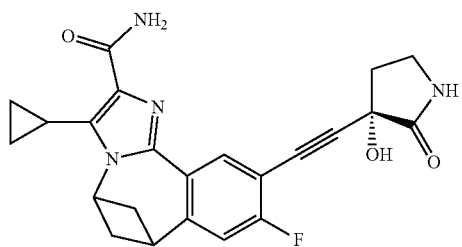

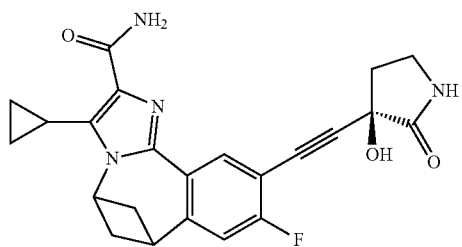

Similar to as described in General Procedure G, 10-bromo-3-cyclopropyl-9-fluoro-6,7-dihydro-5H-5,7-methanobenzo[c]imidazo[1,2-a]azepine-2-carboxamide was reacted with 3-ethynyl-3-hydroxypyrrolidin-2-one to give the titled compounds after purification by chiral SFC (chiralpak AS, MeOH/NH₄OH). LCMS and ¹H NMR of the two enantiomers were identical.

M+1=421; ¹H NMR (400 MHz, DMSO) δ 8.69 (d, J=7.6 Hz, 1H), 8.02 (s, 1H), 7.46 (br s, 1H), 7.26 (d, J=10.1 Hz, 1H), 6.91 (br s, 1H), 6.40 (s, 1H), 5.26 (m, 1H), 3.67 (m, 1H), 3.29-3.18 (overlapping m, 3H), 3.14 (m, 2H), 2.50 (m, 1H), 2.23 (m, 1H), 1.79-1.63 (overlapping m, 3H), 0.99 (m, 2H), 0.67 (m, 2H).

Example 683

Synthesis of tert-butyl 3-(10-bromo-2-carbamoyl-6,7-dihydro-5H-5,7-methanobenzo[c]imidazo[1,2-a]azepin-3-yl)azetidine-1-carboxylate

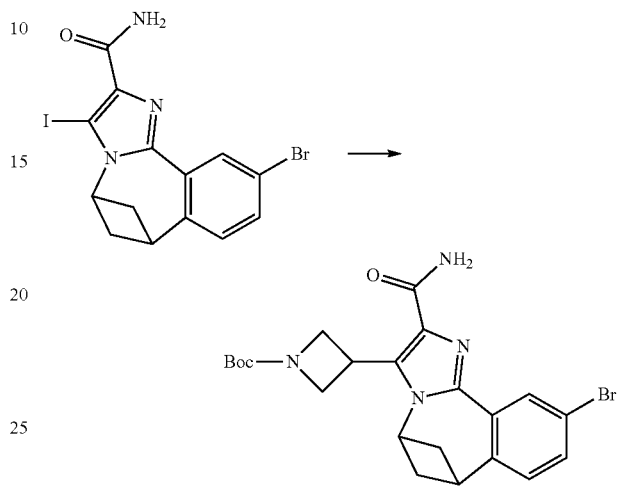

Similar to as described for 10-bromo-3-cyclopropyl-9-fluoro-6,7-dihydro-5H-5,7-methanobenzo[c]imidazo[1,2-a]azepine-2-carboxamide above, 10-bromo-3-iodo-6,7-dihydro-5H-5,7-methanobenzo[c]imidazo[1,2-a]azepine-2-carboxamide was coupled with (1-(tert-butoxycarbonyl)azetidin-3-yl)zinc(II) iodide to give the titled compound after purification by flash column chromatography.

Example 684

Synthesis of tert-butyl 3-(2-carbamoyl-9-fluoro-10-(3-hydroxy-3-methylbut-1-yn-1-yl)-6,7-dihydro-5H-5,7-methanobenzo[c]imidazo[1,2-a]azepin-3-yl)azetidine-1-carboxylate

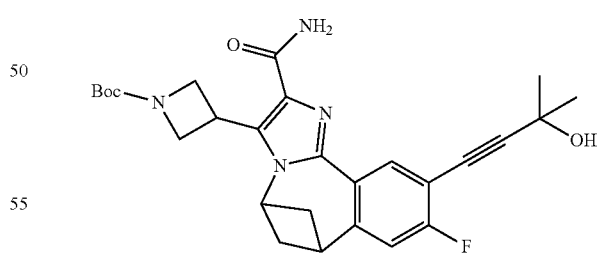

Similar to as described in General Procedure E, tert-butyl 3-(10-bromo-2-carbamoyl-9-fluoro-6,7-dihydro-5H-5,7-methanobenzo[c]imidazo[1,2-a]azepin-3-yl)azetidine-1-carboxylate was reacted with 2-methylbut-3-yn-2-ol to give the titled compound.

M-tBu=439. ¹H NMR (400 MHz, DMSO) δ 8.72 (d, J=7.5 Hz, 0H), 7.71 (br s, 1H), 7.26 (d, J=10.0 Hz, 1H), 7.16 (br s, 1H), 5.57 (s, 1H), 4.87 (m, 1H), 4.53 (m, 1H), 4.16 (m, 1H), 4.03 (m, 1H), 3.67 (m, 1H), 3.12 (m, 2H), 1.74 (d, J=11.0 Hz, 2H), 1.50 (s, 6H), 1.40 (s, 9H).

Example 685

Synthesis of 3-(1-acetylazetidin-3-yl)-10-((1-hydroxycyclopentyl)ethynyl)-6,7-dihydro-5H-5,7-methanobenzo[c]imidazo[1,2-a]azepine-2-carboxamide

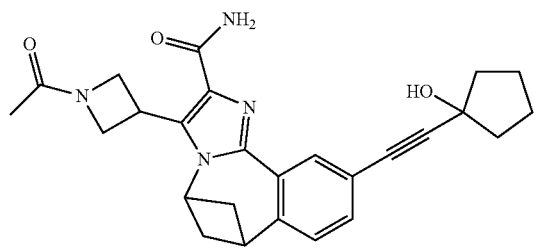 [SMILES: CC(=O)N1CC(c2c(C(N)=O)nc3n2C2CC(C2)c2ccc(C#CC4(O)CCCC4)cc2-3)C1]

Similar to as described in General Procedure E, 3-(1-acetylazetidin-3-yl)-10-bromo-6,7-dihydro-5H-5,7-methanobenzo[c]imidazo[1,2-a]azepine-2-carboxamide was reacted with 1-ethynylcyclopentanol to give the titled compound.

M+1=445.3; $^1$H NMR (400 MHz, DMSO) δ 8.69 (s, 1H), 7.66 (br s, 1H), 7.24 (overlapping s, 2H), 7.13 (br s, 1H), 5.30 (s, 1H), 4.89 (m, 1H), 4.61 (m, H), 4.44 (m, 1H), 4.28 (m, 1H), 4.18 (m, 1H), 3.94 (m, 1H), 3.67 (m, 1H), 3.13 (m, 2H), 1.91 (overlapping m, 3H), 1.78 (s, 3H), 1.71 (overlapping m, 4H).

Example 686

Synthesis of (R)-3-(1-(cyclopropanecarbonyl)azetidin-3-yl)-10-((3-hydroxy-1-methyl-2-oxopyrrolidin-3-yl)ethynyl)-6,7-dihydro-5H-5,7-methanobenzo[c]imidazo[1,2-a]azepine-2-carboxamide and (S)-3-(1-(cyclopropanecarbonyl)azetidin-3-yl)-10-((3-hydroxy-1-methyl-2-oxopyrrolidin-3-yl)ethynyl)-6,7-dihydro-5H-5,7-methanobenzo[c]imidazo[1,2-a]azepine-2-carboxamide

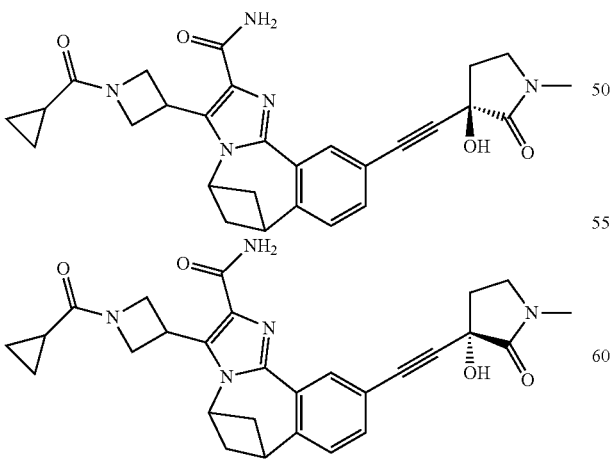

Similar to as described in General Procedure G, 3-(1-acetylazetidin-3-yl)-10-bromo-6,7-dihydro-5H-5,7-methanobenzo[c]imidazo[1,2-a]azepine-2-carboxamide was reacted with 3-ethynyl-3-hydroxy-1-methylpyrrolidin-2-one to give the titled compounds after chiral SFC (chiralpak AD, MeOH/NH$_4$OH). LCMS and $^1$H NMR of the two enantiomers were identical.

M+1=500.3; $^1$H NMR (400 MHz, DMSO) δ 8.71 (s, 1H), 7.66 (br s, 1H), 7.28 (overlapping s, 2H), 7.14 (br s, 1H), 6.43 (s, 1H), 4.89 (m, 1H), 4.76-4.51 (overlapping m, 2H), 4.42 (t, J=7.1 Hz, 1H), 4.20 (t, J=9.1 Hz, 1H), 3.99 (t, J=8.1 Hz, 1H), 3.69 (m, 1H), 3.36 (t, J=6.5 Hz, 2H), 3.12 (m, 1H), 2.81 (s, 3H), 2.45 (m, 1H), 2.20 (m, 1H), 1.76-1.66 (m, 2H), 1.54 (p, J=6.2 Hz, 1H), 0.72 (m, 4H).

Example 687

Synthesis of (R)-9-fluoro-10-(3-hydroxy-3-(pyridin-2-yl)but-1-yn-1-yl)-6,7-dihydro-5H-5,7-methanobenzo[c]imidazo[1,2-a]azepine-2-carboxamide

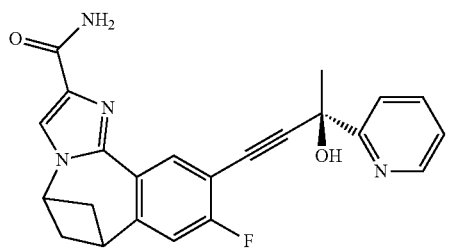 [SMILES: C[C@@](O)(C#Cc1cc2c(cc1F)C1CC(C1)n1cc(C(N)=O)nc1-2)c1ccccn1]

Similar to as described in General Procedure F, reaction of 10-bromo-9-fluoro-6,7-dihydro-5H-5,7-methanobenzo[c]imidazo[1,2-a]azepine-2-carboxamide with (R)-2-(pyridin-2-yl)but-3-yn-2-ol gave the titled compound.

M+H=403.2. $^1$H NMR (400 MHz, DMSO) δ 8.64 (d, J=7.6 Hz, 1H), 8.57 (m, 1H), 7.86 (m, 1H), 7.81 (s, 1H), 7.77 (d, J=7.9 Hz, 1H), 7.54 (br s, 1H), 7.34 (dd, J=7.1, 5.1 Hz, 1H), 7.27 (d, J=10.2 Hz, 1H), 7.07 (br s, 1H), 6.43 (s, 1H), 4.91 (m, 1H), 3.71 (m, 1H), 3.08 (m, 1H), 1.84 (s, 3H), 1.68 (m, 2H).

Example 688

Synthesis of 10-((1-hydroxycyclohexyl)ethynyl)-N3-methyl-5,6-dihydrobenzo[f]imidazo[1,2-d][1,4]oxazepine-2,3-dicarboxamide

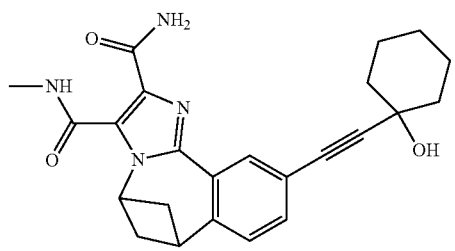 [SMILES: CNC(=O)c1c(C(N)=O)nc2n1C1CC(C1)c1ccc(C#CC3(O)CCCCC3)cc1-2]

Similar to as described in General Procedure E, reaction of 10-bromo-N3-methyl-5,6-dihydrobenzo[f]imidazo[1,2-d]

[1,4]oxazepine-2,3-dicarboxamide with 1-ethynylcyclohexanol gave the titled compound. M+H=409.2.

Example 689

Synthesis of (R)-2',2'-difluoro-9-(((R)-3-hydroxy-1-methyl-2-oxopyrrolidin-3-yl)ethynyl)-5H-spiro[benzo[2,3]oxepino[4,5-d]thiazole-4,1'-cyclopropane]-2-carboxamide and (S)-2',2'-difluoro-9-(((R)-3-hydroxy-1-methyl-2-oxopyrrolidin-3-yl)ethynyl)-5H-spiro[benzo[2,3]oxepino[4,5-d]thiazole-4,1'-cyclopropane]-2-carboxamide

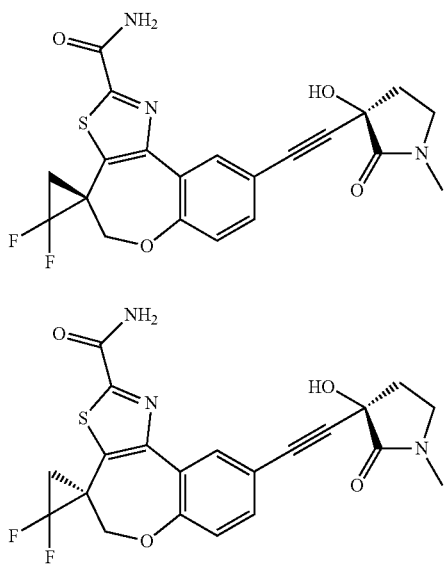 [SMILES: CN1CC[C@@](O)(C#Cc2ccc3c(c2)-c2nc(C(N)=O)sc2[C@@]2(CO3)CC2(F)F)C1=O ; CN1CC[C@@](O)(C#Cc2ccc3c(c2)-c2nc(C(N)=O)sc2[C@]2(CO3)CC2(F)F)C1=O]

Similar to as described in General Procedure G, ethyl 9-bromo-2',2'-difluoro-5H-spiro[benzo[2,3]oxepino[4,5-d]thiazole-4,1'-cyclopropane]-2-carboxylate was reacted with (R)-3-ethynyl-3-hydroxy-1-methylpyrrolidin-2-one to give a diasteromeric mixture of ethyl 2',2'-difluoro-9-(((R)-3-hydroxy-1-methyl-2-oxopyrrolidin-3-yl)ethynyl)-5H-spiro[benzo[2,3]oxepino[4,5-d]thiazole-4,1'-cyclopropane]-2-carboxylate. Following aminolysis of the ethyl ester (similar to as described in General Procedure M) a mixture of the titled compounds was obtained and separated by chiral Prep HPLC. The stereochemistry at the spirocyclic ring juncture for each isomer was not determined.

Compound 1: colorless solid; $t_R$=11.2 min (CHIRLPAK AD-3, 25° C., UV-254 nm Hex:EtOH=60:40, 1.0 ml/min); LC-MS (ES, m/z) 446 [M+1]⁺; NMR (400 MHz, CD₃OD) δ: 8.68 (d, J=2.0 Hz, 1H), 7.28 (dd, J=2.0, 8.4 Hz, 1H), 6.96 (d, J=8.4 Hz, 1H), 4.30-4.20 (m, 2H), 3.39-3.32 (m, 2H), 2.81 (s, 3H), 2.53-2.45 (m, 1H), 2.24-2.19 (m, 2H), 1.96-1.88 (m, 1H).

Compound 2: colorless solid; $t_R$=17.1 min (CHIRLPAK AD-3, 25° C., UV-254 nm Hex:EtOH=60:40, 1.0 ml/min); LC-MS (ES, m/z) 446 [M+1]⁺; NMR (400 MHz, CD₃OD) δ: 8.68 (d, J=2.0 Hz, 1H), 7.28 (dd, J=2.0, 8.4 Hz, 1H), 6.96 (d, J=8.4 Hz, 1H), 4.30-4.20 (m, 2H), 3.39-3.32 (m, 2H), 2.81 (s, 3H), 2.53-2.45 (m, 1H), 2.24-2.19 (m, 2H), 1.96-1.88 (m, 1H).

Example 690

Synthesis of 9-((R)-3-hydroxy-3-(pyridin-2-yl)but-1-yn-1-yl)-4-methyl-4,5-dihydrobenzo[2,3]oxepino[4,5-d]thiazole-2-carboxamide

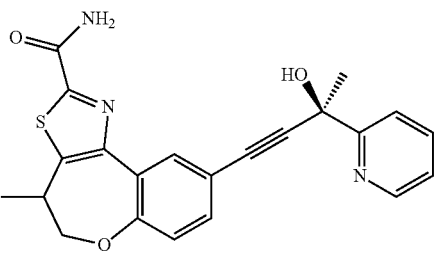 [SMILES: CC1COc2ccc(C#C[C@@](C)(O)c3ccccn3)cc2-c2nc(C(N)=O)sc21]

Similar to as described in General Procedure G, ethyl 9-bromo-4-methyl-4,5-dihydrobenzo[2,3]oxepino[4,5-d]thiazole-2-carboxylate was reacted with (R)-2-(pyridin-2-yl)but-3-yn-2-ol to give a diasteromeric mixture of ethyl 94(R)-3-hydroxy-3-(pyridin-2-yl)but-1-yn-1-yl)-4-methyl-4,5-dihydrobenzo[2,3]oxepino[4,5-d]thiazole-2-carboxylate. Following aminolysis of the ethyl ester (similar to as described in General Procedure M) a diasteromeric mixture of the titled compounds was obtained and separated by Prep HPLC.

off-white solid; LC-MS (ES, m/z) 406 [M+1]⁺; ¹H NMR (300 MHz, CD₃OD) δ: 8.72 (d, J=2.0 Hz, 1H), 8.57 (m, 1H), 7.92 (m, 2H), 7.38-7.32 (m, 2H), 7.03 (d, J=8.4 Hz, 1H), 4.30-4.25 (m, 2H), 3.70-3.60 (m, 1H), 1.90 (s, 3H), 1.48 (d, J=7.2 Hz, 3H).

Example 691

Synthesis of (R)-9-(((R)-3-hydroxy-2-oxopyrrolidin-3-yl)ethynyl)-4-methyl-4,5-dihydrobenzo[2,3]oxepino[4,5-d]thiazole-2-carboxamide and (S)-9-(((R)-3-hydroxy-2-oxopyrrolidin-3-yl)ethynyl)-4-methyl-4,5-dihydrobenzo[2,3]oxepino[4,5-d]thiazole-2-carboxamide

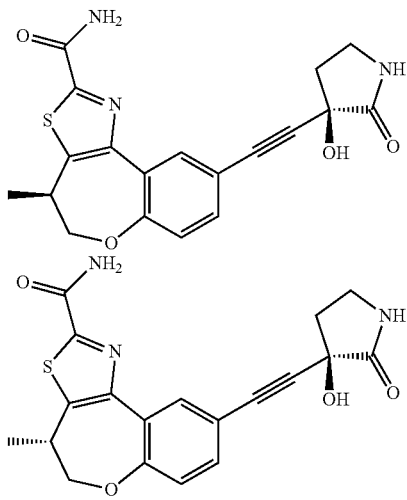

Similar to as described in General Procedure G, racemic ethyl 9-bromo-4-methyl-4,5-dihydrobenzo[2,3]oxepino[4,5-d]thiazole-2-carboxylate was reacted with (R)-3-ethynyl-3-hydroxypyrrolidin-2-one to give a diasteromeric mixture of ethyl 9-(((R)-3-hydroxy-2-oxopyrrolidin-3-yl)ethynyl)-4-methyl-4,5-dihydrobenzo[2,3]oxepino[4,5-d]thiazole-2-carboxylate. Following aminolysis of the ethyl ester (similar to as described in General Procedure M) a diasteromeric mixture of the titled compounds was separated by chiral prep HPLC. The absolute stereochemistry at the methyl stereocenter for each isomer was not determined.

Compound 1: colorless solid; $t_R$=8.5 min (CHIRLPAK IA, 25° C., UV-254 nm MTBE:IPA=85:15, 1.0 ml/min); LC-MS (ES, m/z) 384 [M+1]$^+$; $^1$H NMR (300 MHz, DMSO-d$_6$) δ: 8.61 (d, J=2.1 Hz, 1H), 8.44 (s, 1H), 7.99 (s, 1H), 7.86 (s, 1H), 7.31 (dd, J=2.1, 8.1 Hz, 1H), 7.07 (d, J=8.1 Hz, 1H), 6.30 (s, 1H), 4.30-4.20 (m, 2H), 3.70-3.59 (m, 1H), 3.24 (t, J=6.6 Hz, 2H), 2.50-2.40 (m, 1H), 2.24-2.19 (m, 1H), 1.37 (d, J=6.6 Hz, 3H).

Compound 2: colorless solid; $t_R$=12.6 min (CHIRLPAK IA, 25° C., UV-254 nm MTBE:IPA=85:15, 1.0 ml/min); LC-MS (ES, m/z) 384 [M+1]$^+$; $^1$H NMR (300 MHz, DMSO-d$_6$) δ: 8.61 (d, J=2.1 Hz, 1H), 8.44 (s, 1H), 7.99 (s, 1H), 7.86 (s, 1H), 7.31 (dd, J=2.1, 8.1 Hz, 1H), 7.07 (d, J=8.1 Hz, 1H), 6.30 (s, 1H), 4.30-4.20 (m, 2H), 3.70-3.59 (m, 1H), 3.24 (t, J=6.6 Hz, 2H), 2.50-2.40 (m, 1H), 2.24-2.19 (m, 1H), 1.37 (d, J=6.6 Hz, 3H).

Example 692

Synthesis of 8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide

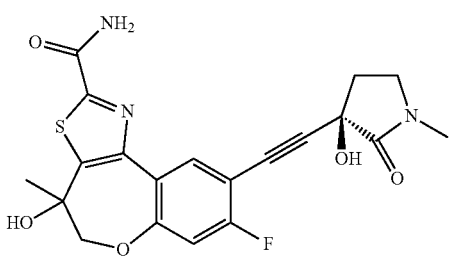

Similar to as described in General Procedure G, racemic ethyl 9-bromo-8-fluoro-4-hydroxy-4-methyl-4,5-dihydrobenzo[2,3]oxepino[4,5-d]thiazole-2-carboxylate was reacted with (R)-3-ethynyl-3-hydroxy-1-methylpyrrolidin-2-one to give a diasteromeric mixture of ethyl 8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxylate. Following aminolysis of the ethyl ester (similar to as described in General Procedure M) a diasteromeric mixture of the titled compounds was obtained after purification by prep HPLC.

colorless solid; LC-MS (ES, m/z) 432 [M+1]$^+$; $^1$H NMR (300 MHz, CD$_3$OD) δ: 8.74 (d, J=8.1 Hz, 1H), 6.91 (d, J=9.9 Hz, 1H), 4.25 (d, J=11.4 Hz, 1H), 4.13 (d, J=11.4 Hz, 1H), 3.50-3.46 (m, 2H), 2.94 (s, 3H), 2.63-2.58 (m, 1H), 2.37-2.29 (m, 1H), 1.66 (s, 3H).

Example 693

Synthesis of 4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide

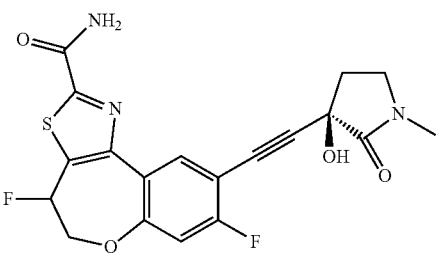 [SMILES: CN1CC[C@@](O)(C#Cc2cc3c(cc2F)OCC(F)c2sc(C(N)=O)nc2-3)C1=O]

Similar to as described in General Procedure G, racemic ethyl 9-bromo-4,8-difluoro-4,5-dihydrobenzo[2,3]oxepino[4,5-d]thiazole-2-carboxylate was reacted with (R)-3-ethynyl-3-hydroxy-1-methylpyrrolidin-2-one to give a diasteromeric mixture of ethyl 4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxylate. Following aminolysis of the ethyl ester (similar to as described in General Procedure M) a diasteromeric mixture of the titled compounds was obtained after purification by prep HPLC.

colorless solid; LC-MS (ES, m/z) 420 [M+1]$^+$; NMR (300 MHz, CD$_3$OD) δ: 8.73 (d, J=8.1 Hz, 1H), 6.99 (d, J=9.9 Hz, 1H), 6.07 (dd, 2.1, 48.3 Hz, 1H), 4.81-4.79 (m, 1H), 4.31-4.18 (m, 1H), 3.50-3.46 (m, 2H), 2.94 (s, 3H), 2.63-2.58 (m, 1H), 2.37-2.29 (m, 1H).

Example 694

Synthesis of (R)-9-((3-hydroxy-1-methyl-2-oxopyrrolidin-3-yl)ethynyl)-5H-spiro[benzo[2,3]oxepino[4,5-d]thiazole-4,2'-[1,3]dioxolane]-2-carboxamide

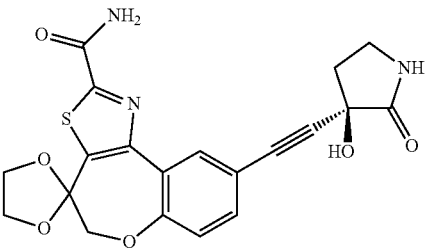 [SMILES: NC(=O)c1nc2c(s1)C1(COc3ccc(C#C[C@]4(O)CCNC4=O)cc3-2)OCCO1]

Similar to as described in General Procedure G, ethyl 9-bromo-5H-spiro[benzo[2,3]oxepino[4,5-d]thiazole-4,2'-[1,3]dioxolane]-2-carboxylate was reacted with (R)-3-ethynyl-3-hydroxy-1-methylpyrrolidin-2-one to give a diasteromeric mixture of (R)-ethyl 9-((3-hydroxy-1-methyl-2-oxopyrrolidin-3-yl)ethynyl)-5H-spiro[benzo[2,3]oxepino[4,5-d]thiazole-4,2'-[1,3]dioxolane]-2-carboxylate. Following aminolysis of the ethyl ester (similar to as described in General Procedure M) the titled compound was obtained after purification by prep HPLC light yellow solid; LC-MS (ES, m/z) 442 [M+1]$^+$, 459 [M+NH$_4$]$^+$; $^1$H NMR (300 MHz, CD$_3$OD) δ: 8.69 (d, J=2.1

Hz, 1H), 7.44 (dd, J=2.1, 8.4 Hz, 1H), 7.12 (d, 8.4 Hz, 1H), 4.33-4.19 (m, 6H), 3.54-3.46 (m, 2H), 2.96 (s, 3H), 2.66-2.58 (m, 1H), 2.37-2.29 (m, 1H).

Example 695

Synthesis of 4-hydroxy-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide

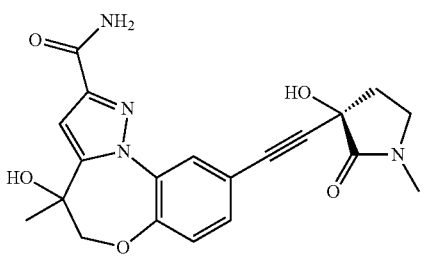

Similar to as described in General Procedure G, racemic 9-iodo-4-hydroxy-4-methyl-4,5-dihydrobenzo[b]pyrazolo[1,5-d][1,4]oxazepine-2-carboxamide was reacted with (R)-3-ethynyl-3-hydroxy-1-methylpyrrolidin-2-one to give a diasteromeric mixture of the titled compound after purification by prep HPLC.

colorless solid; LC-MS (ES, m/z) 397 [M+1]$^+$; $^1$H NMR (400 MHz, CD$_3$OD) δ: 8.21 (d, J=2.0 Hz, 1H), 7.25 (dd, J=2.0, 8.4 Hz, 1H), 7.05 (d, 8.4 Hz, 1H), 6.91 (s, 1H), 4.19 (s, 2H), 3.39-3.32 (m, 2H), 2.83 (s, 3H), 2.51-2.46 (m, 1H), 2.25-2.19 (m, 1H), 1.49 (s, 3H).

Example 696

Synthesis of 4-fluoro-9-((R)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide

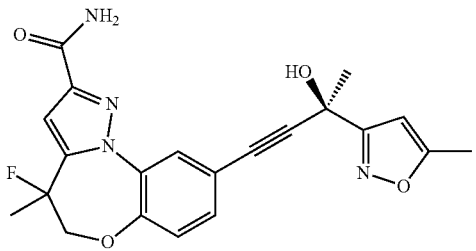

Similar to as described in General Procedure G, racemic 9-iodo-4-fluoro-4-methyl-4,5-dihydrobenzo[b]pyrazolo[1,5-d][1,4]oxazepine-2-carboxamide was reacted with (R)-2-(5-methylisoxazol-3-yl)but-3-yn-2-ol to give a diasteromeric mixture of the titled compound after purification by prep HPLC.

white solid; LC-MS (ES, m/z) 411 [M+1]$^+$; $^1$H NMR (400 MHz, CD$_3$OD) δ: 8.16 (d, J=2.1 Hz, 1H), 7.46 (dd, J=2.1, 8.4 Hz, 1H), 7.26 (d, J=8.1 Hz, 1H), 7.18 (d, J=2.4 Hz, 1H), 6.33 (s, 1H), 4.72-4.47 (m, 2H), 2.47 (s, 3H), 2.07 (s, 3H), 1.80 (d, J=8.4 Hz, 3H).

Example 697

Synthesis of (R)-9-(((R)-3-hydroxy-1-methyl-2-oxopyrrolidin-3-yl)ethynyl)-N3,4-dimethyl-4,5-dihydrobenzo[b]pyrazolo[1,5-d][1,4]oxazepine-2,3-dicarboxamide and (S)-9-(((R)-3-hydroxy-1-methyl-2-oxopyrrolidin-3-yl)ethynyl)-N3,4-dimethyl-4,5-dihydrobenzo[b]pyrazolo[1,5-d][1,4]oxazepine-2,3-dicarboxamide

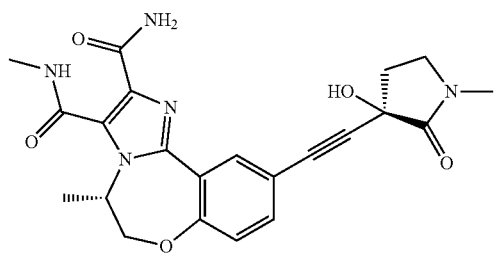

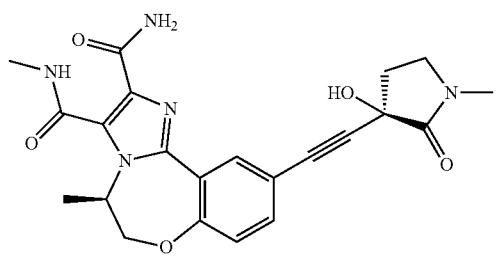

Similar to as described in General Procedure G, racemic 9-iodo-N3,4-dimethyl-4,5-dihydrobenzo[b]pyrazolo[1,5-d][1,4]oxazepine-2,3-dicarboxamide was reacted with (R)-3-ethynyl-3-hydroxypyrrolidin-2-one to give a mixture of titled compounds that were separated by chiral prep HPLC. The absolute stereochemistry at the methyl stereocenter for each isomer was not determined.

Compound 1: white solid; t$_R$=4.7 min (CHIRLPAK OJ-3, 25° C., UV-254 nm Hex: EtOH=60:40, 1.0 ml/min); LC-MS (ES, m/z): 438 [M+1]$^+$; $^1$H NMR (300 MHz, CD$_3$OD) δ: 8.55 (d, J=2.1 Hz, 1H), 7.38 (dd, J=2.1, 8.4 Hz, 1H), 7.15 (d, J=8.4 Hz, 1H), 4.71-4.62 (m, 1H), 4.52-4.49 (m, 1H), 4.38-4.35 (m, 1H), 3.52-3.46 (m, 2H), 2.95 (s, 3H), 2.92 (s, 3H), 2.64-2.55 (m, 1H), 2.38-2.29 (m, 1H), 1.34 (d, J=8.4 Hz, 3H).

Compound 2: white solid; t$_R$=8.2 min (CHIRLPAK OJ-3, 25° C., UV-254 nm Hex:EtOH=60:40, 1.0 ml/min); LC-MS (ES, m/z): 438 [M+1]$^+$; NMR (300 MHz, CD$_3$OD) δ: 8.55 (d, J=2.1 Hz, 1H), 7.38 (dd, J=2.1, 8.4 Hz, 1H), 7.15 (d, J=8.4 Hz, 1H), 4.71-4.62 (m, 1H), 4.52-4.49 (m, 1H), 4.38-4.35 (m, 1H), 3.52-3.46 (m, 2H), 2.95 (s, 3H), 2.92 (s, 3H), 2.64-2.55 (m, 1H), 2.38-2.29 (m, 1H), 1.34 (d, J=8.4 Hz, 3H).

Example 698

Synthesis of (R)-9-((R)-3-hydroxy-3-(5-methylisoxazol-3-yl)but-1-yn-1-yl)-N3,4-dimethyl-4,5-dihydrobenzo[b]pyrazolo[1,5-d][1,4]oxazepine-2,3-dicarboxamide and (S)-9-((R)-3-hydroxy-3-(5-methylisoxazol-3-yl)but-1-yn-1-yl)-N3,4-dimethyl-4,5-dihydrobenzo[b]pyrazolo[1,5-d][1,4]oxazepine-2,3-dicarboxamide

Example 699

Synthesis of (R)-9-(((R)-3-hydroxy-1-methyl-2-oxopyrrolidin-3-yl)ethynyl)-4-methyl-3-(trifluoromethyl)-4,5-dihydrobenzo[b]pyrazolo[1,5-d][1,4]oxazepine-2-carboxamide and (S)-9-4(R)-3-hydroxy-1-methyl-2-oxopyrrolidin-3-yl)ethynyl)-4-methyl-3-(trifluoromethyl)-4,5-dihydrobenzo[b]pyrazolo[1,5-d][1,4]oxazepine-2-carboxamide

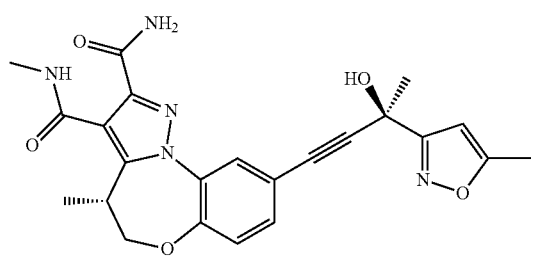

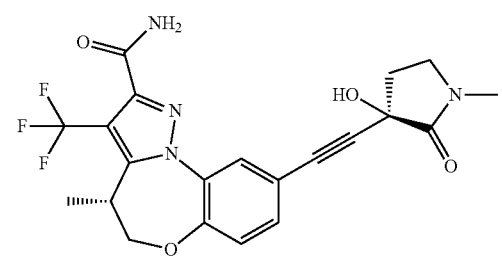

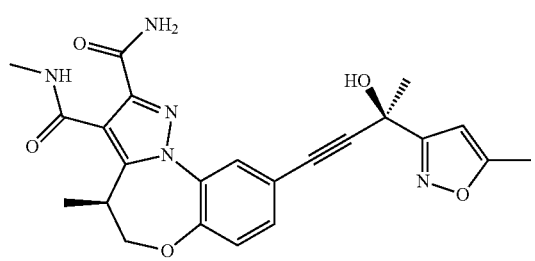

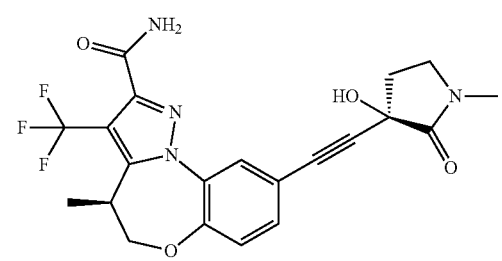

Similar to as described in General Procedure G, racemic 9-iodo-N3,4-dimethyl-4,5-dihydrobenzo[b]pyrazolo[1,5-d][1,4]oxazepine-2,3-dicarboxamide was reacted with (R)-2-(5-methylisoxazol-3-yl)but-3-yn-2-ol to give a mixture of titled compounds that were separated by chiral prep HPLC. The absolute stereochemistry at the methyl stereocenter for each isomer was not determined.

Compound 1: white solid. $t_R$=5.6 min (Lux Cellulose-4, 25° C., UV-254 nm Hex:EtOH=60:40, 1.0 ml/min); LC-MS (ES, m/z): 450 [M+1]+; 1H NMR (300 MHz, CD3OD) δ: 8.55 (d, J=2.1 Hz, 1H), 7.38 (dd, J=2.1, 8.4 Hz, 1H), 7.15 (d, J=8.4 Hz, 1H), 6.32 (s, 1H), 4.71-4.62 (m, 1H), 4.52-4.49 (m, 1H), 4.39-4.35 (m, 1H), 2.92 (s, 3H), 2.46 (s, 3H), 1.90 (s, 3H), 1.34 (d, J=8.4 Hz, 3H).

Compound 2: white solid; $t_R$=9.8 min (Lux Cellulose-4, 25° C., UV-254 nm Hex:EtOH=60:40, 1.0 ml/min); LC-MS (ES, m/z): 450 [M+1]+; 1H NMR (300 MHz, CD3OD) δ: 8.55 (d, J=2.1 Hz, 1H), 7.38 (dd, J=2.1, 8.4 Hz, 1H), 7.15 (d, J=8.4 Hz, 1H), 6.32 (s, 1H), 4.71-4.62 (m, 1H), 4.52-4.49 (m, 1H), 4.39-4.35 (m, 1H), 2.92 (s, 3H), 2.46 (s, 3H), 1.90 (s, 3H), 1.34 (d, J=8.4 Hz, 3H).

Similar to as described in General Procedure G, racemic 9-iodo-4-methyl-3-(trifluoromethyl)-4,5-dihydrobenzo[b]pyrazolo[1,5-d][1,4]oxazepine-2-carboxamide was reacted with (R)-3-ethynyl-3-hydroxy-1-methylpyrrolidin-2-one to give a mixture of titled compounds that were separated by chiral prep HPLC. The absolute stereochemistry at the methyl stereocenter for each isomer was not determined.

Compound 1: white solid; $t_R$=21.7 min (Chiralpak IC-3, 25° C., UV-254 nm Hex:EtOH=60:40, 1.0 ml/min); LC-MS (ES, m/z): 449 [M+1]+; NMR (300 MHz, CD3OD) δ: 8.53 (d, J=1.8 Hz, 1H), 7.40 (dd, J=1.8, 8.4 Hz, 1H), 7.17 (d, J=8.4 Hz, 1H), 4.58-4.50 (m, 1H), 4.41-4.36 (m, 1H), 3.91-3.83 (m, 1H), 3.51-3.44 (m, 2H), 2.93 (s, 3H), 2.65-2.56 (m, 1H), 2.38-2.27 (m, 1H), 1.36 (d, J=7.2 Hz, 3H).

Compound 2: white solid; $t_R$=25.9 min (Chiralpak IC-3, 25° C., UV-254 nm Hex:EtOH=60:40, 1.0 ml/min); LC-MS (ES, m/z): 449 [M+1]+; NMR (300 MHz, CD3OD) δ: 8.53 (d, J=1.8 Hz, 1H), 7.40 (dd, J=1.8, 8.4 Hz, 1H), 7.17 (d, J=8.4 Hz, 1H), 4.58-4.50 (m, 1H), 4.41-4.36 (m, 1H), 3.91-3.83 (m, 1H), 3.51-3.44 (m, 2H), 2.93 (s, 3H), 2.65-2.56 (m, 1H), 2.38-2.27 (m, 1H), 1.36 (d, J=7.2 Hz, 3H).

Example 700

Synthesis of (R)-4-hydroxy-9-(((R)-3-hydroxy-1-methyl-2-oxopyrrolidin-3-yl)ethynyl)-4-methyl-3-(trifluoromethyl)-4,5-dihydrobenzo[b]pyrazolo[1,5-d][1,4]oxazepine-2-carboxamide and (S)-4-hydroxy-9-(((R)-3-hydroxy-1-methyl-2-oxopyrrolidin-3-yl)ethynyl)-4-methyl-3-(trifluoromethyl)-4,5-dihydrobenzo[b]pyrazolo[1,5-d][1,4]oxazepine-2-carboxamide

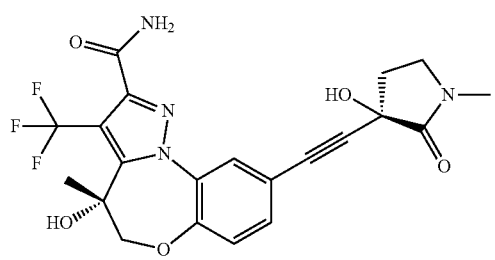

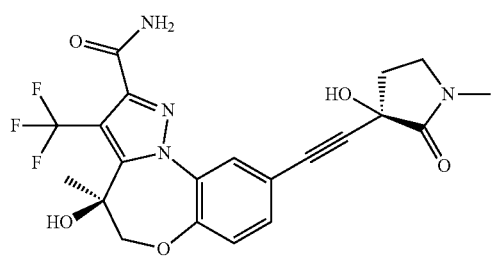

Similar to as described in General Procedure G, racemic 9-iodo-4-hydroxy-4-methyl-3-(trifluoromethyl)-4,5-dihydrobenzo[b]pyrazolo[1,5-d][1,4]oxazepine-2-carboxamide was reacted with (R)-3-ethynyl-3-hydroxy-1-methylpyrrolidin-2-one to give a mixture of titled compounds that were separated by chiral prep HPLC. The stereochemistry at the methyl stereocenter for each isomer was not determined.

Compound 1: white solid; $t_R$=8.6 min (Chiralpak IA, 25° C., UV-254 nm MTBE EtOH=90:10, 1.0 ml/min); LC-MS (ES, m/z): 465 [M+1]$^+$; $^1$H NMR (300 MHz, CD$_3$OD) δ: 7.90 (d, J=2.1 Hz, 1H), 7.24 (dd, J=2.1, 8.4 Hz, 1H), 6.98 (d, J=8.4 Hz, 1H), 3.87 (d, J=12.3 Hz, 1H), 3.72 (d, J=12.3 Hz, 1H), 3.40-3.33 (m, 2H), 2.82 (s, 3H), 2.51-2.43 (m, 1H), 2.23-2.16 (m, 1H), 1.65 (s, 3H).

Compound 2: white solid; $t_R$=10.7 min (Chiralpak IA, 25° C., UV-254 nm MTBE:EtOH=90:10, 1.0 ml/min); LC-MS (ES, m/z): 465 [M+1]$^+$; $^1$H NMR (300 MHz, CD$_3$OD) δ: 7.90 (d, J=2.1 Hz, 1H), 7.24 (dd, J=2.1, 8.4 Hz, 1H), 6.98 (d, J=8.4 Hz, 1H), 3.87 (d, J=12.3 Hz, 1H), 3.72 (d, J=12.3 Hz, 1H), 3.40-3.33 (m, 2H), 2.82 (s, 3H), 2.51-2.43 (m, 1H), 2.23-2.16 (m, 1H), 1.65 (s, 3H).

Example 701

Synthesis of (R)-4,4-difluoro-9-((3-hydroxy-2-oxopyrrolidin-3-yl)ethynyl)-4,5-dihydrobenzo[b]pyrazolo[1,5-d][1,4]oxazepine-2-carboxamide

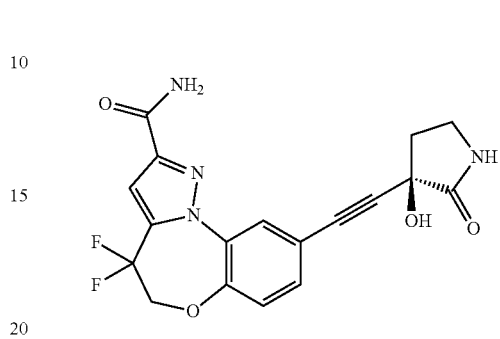

Similar to as described in General Procedure G, 9-iodo-4,4-difluoro-4,5-dihydrobenzo[b]pyrazolo[1,5-d][1,4]oxazepine-2-carboxamide was reacted with (R)-3-ethynyl-3-hydroxypyrrolidin-2-one to give a mixture of titled compound after purification by prep HPLC.

white solid; LC-MS (ES, m/z): 411 [M+23]$^+$; $^1$H NMR (300 MHz, CD$_3$OD) δ: 8.46 (d, J=1.8 Hz, 1H), 7.49 (dd, J=1.8, 8.4 Hz, 1H), 7.36 (s, 1H), 7.32 (d, J=8.4 Hz, 1H), 4.73 (t, J=11.7 Hz, 2H), 3.47-3.41 (m, 2H), 3.69-3.61 (m, 1H), 2.44-2.35 (m, 1H).

Example 702

Synthesis of (R)-4,4-difluoro-9-(3-hydroxy-3-(pyridazin-3-yl)but-1-yn-1-yl)-4,5-dihydrobenzo[b]pyrazolo[1,5-d][1,4]oxazepine-2-carboxamide

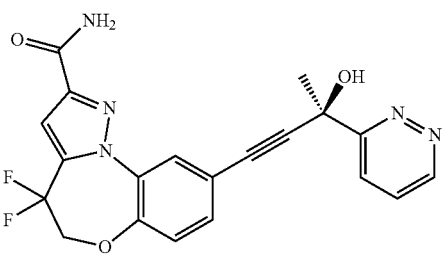 [SMILES: C[C@@](O)(C#Cc1ccc2c(c1)-n1nc(C(N)=O)cc1C(F)(F)CO2)c1cccnn1]

Similar to as described in General Procedure G, 9-iodo-4,4-difluoro-4,5-dihydrobenzo[b]pyrazolo[1,5-d][1,4]oxazepine-2-carboxamide was reacted with (R)-2-(pyridazin-3-yl)but-3-yn-2-ol to give a mixture of titled compound after purification by prep HPLC.

light yellow solid; LC-MS (ES, m/z): 412 [M+1]$^+$; $^1$H NMR (300 MHz, CD$_3$OD) δ: 9.16 (dd, J=0.6, 5.1 Hz, 1H), 8.42 (d, J=1.8 Hz, 1H), 8.14 (dd, J=1.8, 8.4 Hz, 1H), 7.81 (d, J=4.8 Hz, 1H), 7.78 (d, J=4.8 Hz, 1H), 7.46 (dd, J=1.8, 8.4 Hz, 1H), 7.34-7.27 (m, 2H), 4.70 (t, J=12.0 Hz, 2H), 2.00 (s, 3H).

Example 703

Synthesis of (R)-9-((3-hydroxy-1-trideuteromethyl-2-oxopyrrolidin-3-yl)ethynyl)-4,5-dihydrobenzo[b]pyrazolo[1,5-d][1,4]oxazepine-2-carboxamide and (S)-9-((3-hydroxy-1-trideuteromethyl-2-oxopyrrolidin-3-yl)ethynyl)-4,5-dihydrobenzo[b]pyrazolo[1,5-d][1,4]oxazepine-2-carboxamide

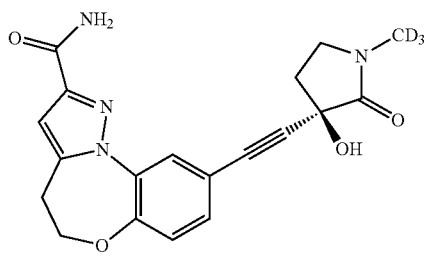

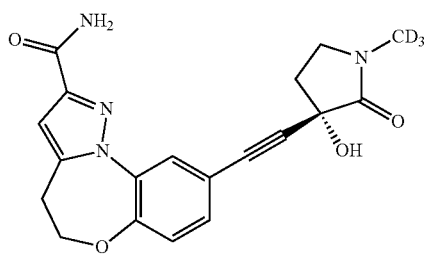

Similar to as described in General Procedure G, 9-iodo-4,5-dihydrobenzo[b]pyrazolo[1,5-d][1,4]oxazepine-2-carboxamide was reacted with 3-ethynyl-3-hydroxy-1-trideuteromethylpyrrolidin-2-one to give the titled compounds after purification by chiral prep HPLC.

Compound 1: white solid; $t_R$=2.8 min (Chiralpak IA-3, 25° C., UV-254 nm Hex:EtOH=55:45, 1.0 ml/min); LC-MS (ES, m/z): 370 [M+1]$^+$, 387 [M+NH$_4$]$^+$; $^1$H NMR (300 MHz, CD$_3$OD) δ: 8.10 (d, J=1.8 Hz, 1H), 7.41 (dd, J=1.8, 8.4 Hz, 1H), 7.18 (d, J=8.4 Hz, 1H), 6.82 (s, 1H), 4.53 (t, J=6.0 Hz, 2H), 3.49-3.45 (m, 2H), 3.18 (t, J=6.0 Hz, 2H), 2.61-2.56 (m, 1H), 2.34-2.27 (m, 1H).

Compound 2: off-white solid; $t_R$=5.7 min (Chiralpak IA-3, 25° C., UV-254 nm Hex:EtOH=55:45, 1.0 ml/min); LC-MS (ES, m/z): 370 [M+1]$^+$, 387 [M+NH$_4$]$^+$; $^1$H NMR (300 MHz, CD$_3$OD) δ: 8.10 (d, J=1.8 Hz, 1H), 7.41 (dd, J=1.8, 8.4 Hz, 1H), 7.18 (d, J=8.4 Hz, 1H), 6.82 (s, 1H), 4.53 (t, J=6.0 Hz, 2H), 3.49-3.45 (m, 2H), 3.18 (t, J=6.0 Hz, 2H), 2.61-2.56 (m, 1H), 2.34-2.27 (m, 1H).

Example 704

Synthesis of (R)-3-chloro-9-((3-hydroxy-1-methyl-2-oxopyrrolidin-3-yl)ethynyl)-4,5-dihydrobenzo[b]pyrazolo[1,5-d][1,4]oxazepine-2-carboxamide

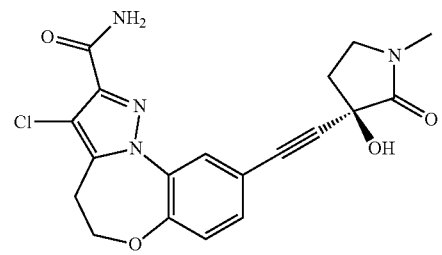 [SMILES: CN1CC[C@@](O)(C#Cc2ccc3c(c2)-n2nc(C(N)=O)c(Cl)c2CCO3)C1=O]

Similar to as described in General Procedure G, racemic ethyl 3-chloro-9-iodo-4,5-dihydrobenzo[b]pyrazolo[1,5-d][1,4]oxazepine-2-carboxylate was reacted with (R)-3-ethynyl-3-hydroxy-1-methylpyrrolidin-2-one to give a diastereomeric mixture of (R)-ethyl 3-chloro-9-((3-hydroxy-1-methyl-2-oxopyrrolidin-3-yl)ethynyl)-4,5-dihydrobenzo[b]pyrazolo[1,5-d][1,4]oxazepine-2-carboxylate. Following aminolysis of the ethyl ester (similar to as described in General Procedure M) the titled compound was obtained after purification by prep HPLC.

white solid; LC-MS (ES, m/z): 401 [M+1]$^+$; $^1$H NMR (400 MHz, CD$_3$OD) δ: 8.12 (d, J=2.0 Hz, 1H), 7.31 (dd, J=2.0, 8.4 Hz, 1H), 7.07 (d, J=8.4 Hz, 1H), 4.42 (t, J=6.0 Hz, 2H), 3.40-3.36 (m, 2H), 3.11 (t, J=6.0 Hz, 2H), 2.49-2.41 (m, 1H), 2.21-2.18 (m, 1H).

Example 705

Synthesis of (S)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide and (R)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide

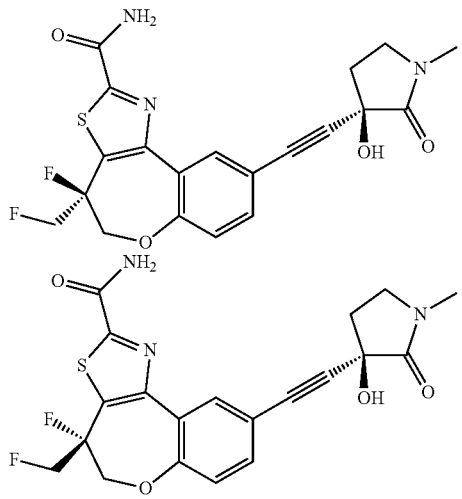

Similar to as described in General Procedure G, racemic ethyl 4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxylate was reacted with (R)-3-ethynyl-3-hydroxy-1-methylpyrrolidin-2-one to give a diasteromeric mixture of ethyl 4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxylate. Following aminolysis of the ethyl ester (similar to as described in General Procedure M) a diasteromeric mixture of the titled compounds was separated by chiral prep HPLC. The absolute stereochemistry at the fluorine stereocenter for each isomer was not determined.

Compound 1: off-white solid; $t_R$=7.2 min (Chiralpak OJ-3, 25° C., UV-254 nm Hex:EtOH=60:40, 1.0 ml/min); LC-MS (ES, m/z): 434 [M+1]$^+$; $^1$H NMR (300 MHz, CD$_3$OD) δ: 8.73 (d, J=2.1 Hz, 1H), 7.46 (dd, J=2.1, 8.4 Hz, 1H), 7.15 (d, J=8.4 Hz, 1H), 4.95-4.90 (m, 1H), 4.82-4.68 (m, 2H), 2.93 (s, 3H), 2.65-2.58 (m, 1H), 2.38-2.29 (m, 1H).

Compound 2: off-white solid; $t_R$=12.6 min (Chiralpak OJ-3, 25° C., UV-254 nm Hex:EtOH=60:40, 1.0 ml/min); LC-MS (ES, m/z): 434 [M+1]$^+$; $^1$H NMR (300 MHz, CD$_3$OD) δ: 8.73 (d, J=2.1 Hz, 1H), 7.46 (dd, J=2.1, 8.4 Hz, 1H), 7.15 (d, J=8.4 Hz, 1H), 4.95-4.90 (m, 1H), 4.82-4.68 (m, 2H), 2.93 (s, 3H), 2.65-2.58 (m, 1H), 2.38-2.29 (m, 1H).

Example 706

Synthesis of (S)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide and (R)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide

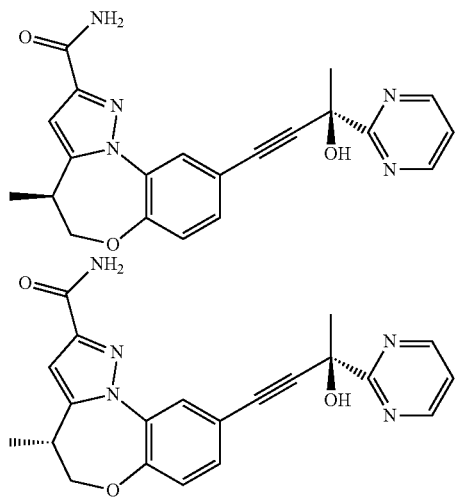

Similar to as described in General Procedure G, racemic 9-iodo-4-methyl-4,5-dihydrobenzo[b]pyrazolo[1,5-d][1,4]oxazepine-2-carboxamide was reacted with (R)-2-(pyrimidin-2-yl)but-3-yn-2-ol to give a mixture of titled compounds that were separated by chiral prep HPLC. The absolute stereochemistry at the methyl stereocenter for each isomer was not determined.

Compound 1: light yellow white solid; $t_R$=24.1 min (Chiralpak IC, 25° C., UV-254 nm Hex (0.1% TEA) EtOH=50:50, 1.0 ml/min); LC-MS (ES, m/z): 390 [M+1]$^+$; $^1$H NMR (300 MHz, CD$_3$OD) δ: 8.56 (d, J=4.8 Hz, 2H), 8.01 (d, J=2.1 Hz, 1H), 7.46 (t, J=4.8 Hz, 1H), 7.39 (dd, J=2.1, 8.4 Hz, 1H), 7.17 (d, J=8.4 Hz, 1H), 6.79 (s, 1H), 4.52-4.46 (dd, J=5.4, 10.8 Hz, 1H), 4.23-4.18 (t, J=10.8 Hz, 1H), 3.28-3.25 (m, 1H), 1.95 (s, 3H), 1.28 (d, J=7.8 Hz, 3H).

Compound 2: off-white solid; $t_R$=31.9 min (Chiralpak IC, 25° C., UV-254 nm Hex (0.1% TEA): EtOH=50:50, 1.0 ml/min); LC-MS (ES, m/z): 390 [M+1]$^+$; $^1$H NMR (300 MHz, CD$_3$OD) δ: 8.56 (d, J=4.8 Hz, 2H), 8.01 (d, J=2.1 Hz, 1H), 7.46 (t, J=4.8 Hz, 1H), 7.39 (dd, J=2.1, 8.4 Hz, 1H), 7.17 (d, J=8.4 Hz, 1H), 6.79 (s, 1H), 4.52-4.46 (dd, J=5.4, 10.8 Hz, 1H), 4.23-4.18 (t, J=10.8 Hz, 1H), 3.28-3.25 (m, 1H), 1.95 (s, 3H), 1.28 (d, J=7.8 Hz, 3H).

Example 707

Synthesis of 9-((3-hydroxy-5-methyl-2-oxopyrrolidin-3-yl)ethynyl)-4,5-dihydrobenzo[b]pyrazolo[1,5-d][1,4]oxazepine-2-carboxamide

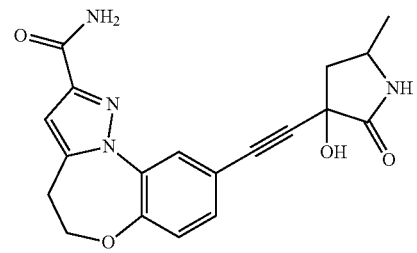 [SMILES: CC1CC(O)(C#Cc2ccc3c(c2)-n2nc(C(N)=O)cc2CCO3)C(=O)N1]

Similar to as described in General Procedure G, 9-iodo-4,5-dihydrobenzo[b]pyrazolo[1,5-d][1,4]oxazepine-2-carboxamide was reacted with a ~1:1 diastereomeric mixture of 3-ethynyl-3-hydroxy-5-methylpyrrolidin-2-one to give a mixture of titled compounds after purification by HPLC.

white solid; LC-MS (ES, m/z): 367 [M+1]$^+$; $^1$H NMR (300 MHz, CD$_3$OD) δ: 8.13-8.10 (m, 1H), 7.48-7.40 (m, 1H), 7.22-7.20 (m, 1H), 6.79 (s, 1H), 4.55 (t, J=6.0 Hz, 2H), 3.90-3.78 (m, 1H), 3.20 (t, J=6.0 Hz, 2H), 2.81-2.74 (m, 0.5H), 2.60-2.54 (m, 0.5H), 2.23-2.18 (m, 0.5H), 1.94-1.85 (m, 0.5H), 1.32-1.25 (m, 3H).

Example 708

Synthesis of 9-((2-fluoro-1-hydroxycyclopentyl)ethynyl)-4,5-dihydrobenzo[b]pyrazolo[1,5-d][1,4]oxazepine-2-carboxamide

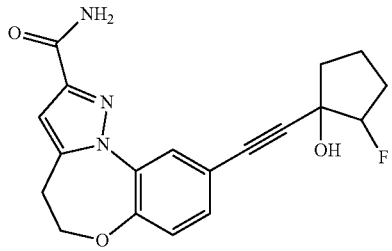 [SMILES: NC(=O)c1cc2n(n1)-c1cc(C#CC3(O)CCCC3F)ccc1OCC2]

Similar to as described in General Procedure G, 9-iodo-4,5-dihydrobenzo[b]pyrazolo[1,5-d][1,4]oxazepine-2-carboxamide was reacted with a 1-ethynyl-2-fluorocyclopentanol to give a mixture of titled compounds after purification by HPLC.

white solid; LC-MS (ES, m/z): 356 [M+1]+; 1H NMR (300 MHz, CD3OD) δ: 8.05 (d, J=2.1 Hz, 1H), 7.39 (dd, J=2.1, 8.4 Hz, 1H), 7.19 (d, J=8.4 Hz, 1H), 6.79 (s, 1H), 4.98-4.93 (m, 0.5H), 4.78-4.75 (m, 0.5H), 4.55 (t, J=6.0 Hz, 2H), 3.19 (t, J=6.0 Hz, 2H), 2.30-1.75 (m, 6H).

Example 709

Synthesis of 94(1,2-dihydroxycyclopentyl)ethynyl)-4,5-dihydrobenzo[b]pyrazolo[1,5-d][1,4]oxazepine-2-carboxamide

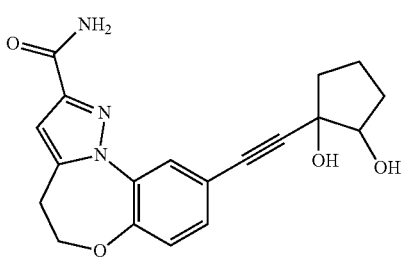

Similar to as described in General Procedure G, 9-iodo-4,5-dihydrobenzo[b]pyrazolo[1,5-d][1,4]oxazepine-2-carboxamide was reacted with 1-ethynylcyclopentane-1,2-diol to give a mixture of titled compounds after purification by HPLC.

white solid; LC-MS (ES, m/z): 354 [M+1]+; 1H NMR (300 MHz, CD3OD) δ: 8.03 (d, J=1.8 Hz, 1H), 7.39 (dd, J=1.8, 8.4 Hz, 1H), 7.17 (d, J=8.4 Hz, 1H), 6.78 (s, 1H), 4.53 (t, J=6.0 Hz, 2H), 4.09 (t, J=6.6 Hz, 1H), 3.17 (t, J=6.0 Hz, 2H), 2.13-2.02 (m, 3H), 1.96-1.60 (m, 3H).

Example 710

Synthesis of 9-(3-hydroxy-3-(tetrahydrofuran-2-yl)but-1-yn-1-yl)-4,5-dihydrobenzo[b]pyrazolo[1,5-d][1,4]oxazepine-2-carboxamide

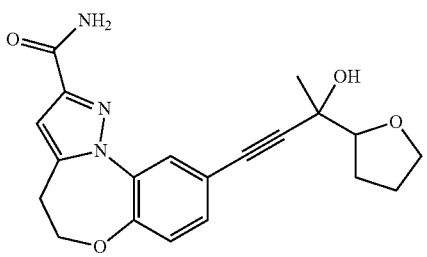 [SMILES: CC(O)(C#Cc1ccc2c(c1)-n1nc(C(N)=O)cc1CCO2)C1CCCO1]

Similar to as described in General Procedure G, 9-iodo-4,5-dihydrobenzo[b]pyrazolo[1,5-d][1,4]oxazepine-2-carboxamide was reacted with 2-(tetrahydrofuran-2-yl)but-3-yn-2-ol to give a mixture of titled compounds after purification by HPLC.

white solid; LC-MS (ES, m/z): 368 [M+1]+, 385 [M+NH4]+; 1H NMR (300 MHz, CD3OD) δ: 8.03 (d, J=1.8 Hz, 1H), 7.39 (dd, J=1.8, 8.4 Hz, 1H), 7.17 (d, J=8.4 Hz, 1H), 6.78 (s, 1H), 4.53 (t, J=6.0 Hz, 2H), 4.00-3.80 (m, 4H), 3.17 (t, J=6.0 Hz, 2H), 2.20-1.89 (m, 4H), 1.56 (s, 2.0H), 1.52 (s, 1.0H).

Example 711

Synthesis of (R)-4,4-difluoro-9-((3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide

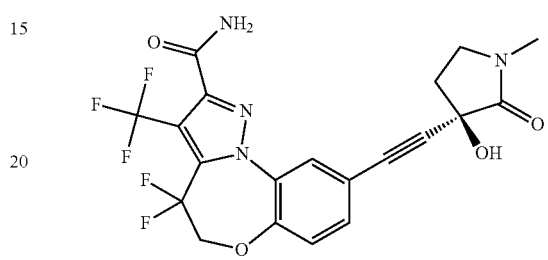

Similar to as described in General Procedure G, 4,4-difluoro-9-iodo-3-(trifluoromethyl)-4,5-dihydrobenzo[b]pyrazolo[1,5-d][1,4]oxazepine-2-carboxamide was reacted with (R)-3-ethynyl-3-hydroxy-1-methylpyrrolidin-2-one to give a titled compound after purification by HPLC.

white solid; LC-MS (ES, m/z): 471 [M+1]+, 488 [M+NH4]+; 1H NMR (300 MHz, CD3OD) δ: 8.50 (d, J=1.8 Hz, 1H), 7.50 (dd, J=1.8, 8.4 Hz, 1H), 7.31 (d, J=8.4 Hz, 1H), 4.72 (t, J=12.0 Hz, 2H), 3.50-3.45 (m, 2H), 2.93 (s, 3H), 2.61-2.54 (m, 1H), 2.38-2.25 (m, 1H).

Example 712

NIK Enzyme Inhibition Assay: The ability of the nuclear factor-kappa B (NF-kB)-inducing kinase (NIK) to catalyze the hydrolysis of adenosine-5'-triphosphate (ATP) was monitored using the Transcreener ADP (adenosine-5'-diphosphate) assay (BellBrook Labs). Purified NIK (0.2-1 nM) derived from a baculovirus-infected insect cell expression system was incubated with test compounds for 1-3.5 hours in 50 mM 2-[4-(2-hydroxyethyl)piperazin-1-yl]ethanesulfonic acid buffer (pH 7.2) containing 10 mM MgCl2, 2 mM dithiothreitol, 10 uM ATP, 0.01% Triton X-100, 0.1% gamma-globulins from bovine blood, 1% dimethylsulfoxide (DMSO), 12 ug/mL ADP antibody and 4 nM ADP-AlexaFluor® 633 tracer. Reactions were quenched by the addition of 20 mM 2,2',2'',2'''-(ethane-1,2-diyldinitrilo)tetraacetic acid and 0.01% Brij 35. The tracer bound to the antibody was displaced by the ADP generated during the NIK reaction, which causes a decrease in fluorescence polarization that was measured by laser excitation at 633 nm with a Fluorescence Correlation Spectroscopy Plus reader (Evotec AG). Equilibrium dissociation constant (KO values for NIK inhibitors are calculated from plots of activity vs. inhibitor concentration using Morrison's quadratic equation that accounts for the potential of tight binding, and by also applying the conversion factor that accounted for competitive inhibition and the concentration of substrate used in the assay relative to its Michaelis constant ($K_m$). The compounds in listed in Table 1 have the corresponding inhibitory value (NIK ADP-FP, Ki in micromolar) for NIK described in Table 2 below.

TABLE 2

| No. | NIK ADP-FP (Ki uM) | REL-A HeLa Transloc Assay (IC50) [uM] | p52 HeLa Transloc Assay (IC50) [uM] |
|---|---|---|---|
| 1 | 0.052 | | |
| 2 | 0.319 | | |
| 3 | 0.033 | | |
| 4 | 0.004 | | |
| 5 | 0.034 | | |
| 6 | 0.0003 | 20 | 0.135 |
| 7 | 0.0002 | 20 | 0.0395 |
| 8 | 0.001 | 20 | 0.672 |
| 9 | 0.216 | | |
| 10 | 0.096 | | |
| 11 | 0.416 | | |
| 12 | 0.093 | | |
| 13 | 0.85 | | |
| 14 | 0.864 | | |
| 15 | 0.036 | | |
| 16 | 0.025 | | |
| 17 | 0.010 | | |
| 18 | >5 | | |
| 19 | >5 | | |
| 20 | 0.771 | | |
| 21 | 0.094 | | |
| 22 | 0.97 | | |
| 23 | >5 | | |
| 24 | 0.011 | | |
| 25 | 0.012 | | |
| 26 | 0.21 | | |
| 27 | 0.057 | | |
| 28 | >5 | | |
| 29 | >5 | | |
| 30 | >5 | | |
| 31 | >5 | | |
| 32 | 0.002 | | |
| 33 | 0.172 | | |
| 34 | 0.025 | | |
| 35 | 0.003 | | |
| 36 | 0.037 | | |
| 37 | 0.003 | | |
| 38 | 0.062 | | |
| 39 | 0.0006 | 20 | 0.038 |
| 40 | 0.0002 | 20 | 0.068 |
| 41 | 0.003 | 20 | 0.237 |
| 42 | 0.032 | | |
| 43 | 0.403 | | |
| 44 | 0.010 | | |
| 45 | 0.0054 | | |
| 46 | 0.239 | | |
| 47 | 0.212 | | |
| 48 | 0.018 | | |
| 49 | 0.023 | | |
| 50 | 2 | | |
| 51 | 0.721 | | |
| 52 | 3.6 | | |
| 53 | 0.105 | | |
| 54 | 0.024 | | |
| 55 | 0.018 | | |
| 56 | 2 | | |
| 57 | 0.049 | | |
| 58 | 3.6 | | |
| 59 | 0.006 | | |
| 60 | 0.025 | | |
| 61 | 0.105 | | |
| 62 | >5 | | |
| 63 | >5 | | |
| 64 | >5 | | |
| 65 | 0.001 | 20 | 0.43 |
| 66 | 0.088 | | |
| 67 | 0.048 | | |
| 68 | 0.879 | | |
| 69 | 0.041 | | |
| 70 | 0.014 | | |
| 71 | 0.005 | | |
| 72 | 0.354 | | |
| 73 | 1.1 | | |
| 74 | 0.010 | | |
| 75 | 0.008 | 20 | 3.8 |
| 76 | 2.3 | | |
| 77 | 1.2 | | |
| 78 | 0.060 | | |
| 79 | 0.453 | | |
| 80 | 0.005 | | |
| 81 | 0.008 | | |
| 82 | 0.158 | | |
| 83 | 0.109 | | |
| 84 | 0.006 | | |
| 85 | 0.0004 | 20 | 0.077 |
| 86 | 0.142 | | |
| 87 | 0.037 | | |
| 88 | 0.068 | | |
| 89 | 0.003 | 20 | 1.1 |
| 90 | 0.005 | 20 | 0.807 |
| 91 | 0.004 | | |
| 92 | 1.4 | | |
| 93 | 0.007 | 20 | 0.344 |
| 94 | 0.854 | | |
| 95 | 0.304 | | |
| 96 | 0.0003 | 20 | 0.104 |
| 97 | 0.007 | | |
| 98 | 0.002 | 20 | 0.237 |
| 99 | 0.001 | 20 | 0.0625 |
| 100 | 0.148 | | |
| 101 | 3.5 | | |
| 102 | >5 | | |
| 103 | 0.002 | 20 | 0.104 |
| 104 | 0.022 | | |
| 105 | 0.289 | | |
| 106 | 0.010 | | |
| 107 | 0.001 | 20 | 0.0831 |
| 108 | 0.004 | 20 | |
| 109 | 0.002 | | 0.272 |
| 110 | 0.023 | | |
| 111 | 0.007 | | |
| 112 | 0.003 | 20 | 0.142 |
| 113 | 0.020 | | |
| 114 | 0.073 | | |
| 115 | 0.022 | | |
| 116 | 0.003 | | |
| 117 | 0.005 | | |
| 118 | 0.035 | | |
| 119 | >5 | | |
| 120 | 3.4 | | |
| 121 | 0.001 | 20 | 0.171 |
| 122 | 0.002 | | |
| 123 | 0.003 | | |
| 124 | 0.007 | | |
| 125 | 0.003 | | 0.552 |
| 126 | 0.002 | | 0.112 |
| 127 | 0.635 | | |
| 128 | 0.003 | | 0.792 |
| 129 | 0.003 | | 0.059 |
| 130 | 0.502 | | |
| 131 | 0.083 | | |
| 132 | 2.3 | | |
| 133 | 0.004 | | |
| 134 | 4 | | |
| 135 | 0.377 | | |
| 136 | >5 | | |
| 137 | 0.008 | | 0.683 |
| 138 | 0.051 | | |
| 139 | 0.010 | | |
| 140 | 0.002 | | |
| 141 | 0.005 | | |
| 142 | 0.142 | | |
| 143 | 0.016 | | |
| 144 | 0.002 | | 0.483 |
| 145 | 1.3 | | |
| 146 | 4.9 | | |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 147 | 0.019 | | 0.344 |
| 148 | 0.003 | | |
| 149 | 0.014 | | |
| 150 | 0.0003 | 20 | 0.0811 |
| 151 | 0.0031 | | 0.424 |
| 152 | 0.0051 | | |
| 153 | 0.021 | | |
| 154 | 3.9 | | |
| 155 | >5 | | |
| 156 | 0.155 | | |
| 157 | 0.0029 | | |
| 158 | 0.0059 | | |
| 159 | >5 | | |
| 160 | 0.0068 | | |
| 161 | 0.0072 | | |
| 162 | 0.027 | | |
| 163 | | | |
| 164 | 0.014 or >5 | >20 | 2.1 |
| 165 | 0.082 | | |
| 166 | 0.033 | | |
| 167 | 0.033 | | |
| 168 | 0.014 or >5 | | |
| 169 | 0.023 | | |
| 170 | 0.012 | | |
| 171 | >5 | | |
| 172 | 0.00040 | >20 | 1.2 |
| 173 | 0.098 | | |
| 174 | 0.0071 | | |
| 175 | 0.0015 | | |
| 176 | 0.0043 | >20 | 1.4 |
| 177 | 0.0097 | | |
| 178 | 0.037 | | |
| 179 | 0.022 | | |
| 180 | 0.0012 | >20 | 0.87 |
| 181 | 0.036 | | |
| 182 | 0.0021 | | |
| 183 | 0.0033 | | |
| 184 | 0.0015 | >20 | 2.4 |
| 185 | >5 | | |
| 186 | >5 | | |
| 187 | 0.0009 | >20 | 1.5 |
| 188 | 0.19 | | |
| 189 | 0.0024 | >20 | 0.594 |
| 190 | >5 | | |
| 191 | 0.0191 | | |
| 192 | 0.0032 | >20 | 16 |
| 193 | 0.0077 | >20 | 1.8 |
| 194 | 0.014 | | |
| 195 | 0.0037 | >20 | 2.4 |
| 196 | 0.0065 | | |
| 197 | 0.0095 | >20 | 2.6 |
| 198 | 0.54 | | |
| 199 | 0.0005 | 15.1 | 0.511 |
| 200 | 0.0013 | >20 | 1.4 |
| 201 | 0.0049 | >20 | 4.5 |
| 202 | 0.0083 | | |
| 203 | 0.0069 | | |
| 204 | 0.0017 | >20 | 0.638 |
| 205 | 0.0072 | >20 | 2.3 |
| 206 | 0.026 | >20 | 4.4 |
| 207 | 0.00077 | | |
| 208 | 0.0026 | | |
| 209 | 0.00061 | 1.8 | 1.3 |
| 210 | 0.018 | | |
| 211 | 0.0021 | 17.5 | 3.8 |
| 212 | 0.030 | | |
| 213 | 0.009 | | |
| 214 | 0.6 | | |
| 215 | 0.12 | | |
| 216 | 0.0011 | 20 | 0.284 |
| 217 | 0.00068 | | |
| 218 | 0.00031 | >20 | 0.44 |
| 219 | 0.0012 | >20 | 0.74 |
| 220 | 0.0072 | | |
| 221 | 0.00127 | >20 | 1.8 |
| 222 | 0.027 | | |
| 223 | 0.16 | | |
| 224 | 0.042 | | |
| 225 | 0.026 | | |
| 226 | 0.00053 | >20 | 0.45 |
| 227 | 0.000040 | >20 | 0.3 |
| 228 | 0.001 | >20 | 4.1 |
| 229 | 2.5 | | |
| 230 | 0.079 or 0.025 | | |
| 231 | >5 | | |
| 232 | 0.079 or 0.025 | | |
| 233 | 0.0022 | >20 | 2 |
| 234 | 0.0019 | >20 | 1.7 |
| 235 | 0.0057 | | |
| 236 | 0.056 | | |
| 237 | 0.00071 | >20 | 1.9 |
| 238 | 0.0021 | >20 | 1.4 |
| 239 | 0.23 | | |
| 240 | 0.043 | | |
| 241 | 0.98 | | |
| 242 | 0.00084 | >20 | 0.4 |
| 243 | | | |
| 244 | 0.62 or 1 | | |
| 245 | 1 or 0.62 | | |
| 246 | 0.0024 | | |
| 247 | 0.0013 | >20 | 3.6 |
| 248 | 0.0005 | >20 | 1.4 |
| 249 | 0.0021 | | |
| 250 | 0.00012 | >20 | 0.736 |
| 251 | 0.00107 | >20 | 0.709 |
| 252 | 0.025 | | |
| 253 | | | |
| 254 | 0.00033 or 0.0011 | 20 | 0.262 or 2 |
| 255 | | | |
| 256 | 0.0031 or 0.0025 | >20 | 2.9 or 2 |
| 257 | 0.00033 or 0.0011 | 20 | 0.262 or 2 |
| 258 | 0.0031 or 0.0025 | >20 | 2.9 or 2 |
| 259 | 0.0066 | | |
| 260 | 0.0012 | >20 | 4.8 |
| 261 | 0.024 | | |
| 262 | 0.0022 | >20 | 0.358 |
| 263 | 0.00024 | | |
| 264 | 0.21 | | |
| 265 | 0.00059 | >20 | 0.934 |
| 266 | 0.0040 | | |
| 267 | 0.028 | | |
| 268 | >5 or 0.019 or 0.04 | | |
| 269 | 0.0002 | >20 | 0.477 |
| 270 | 0.0078 | | |
| 271 | 0.0026 | >20 | 1.7 |
| 272 | 0.0007 | >20 | 1.1 |
| 273 | 0.00012 | >20 | 0.375 |
| 274 | 0.0013 | >20 | 0.385 |
| 275 | 0.068 | | |
| 276 | 0.000055 | 20 | 0.0946 |
| 277 | 0.0047 | >20 | 1.6 |
| 278 | 0.011 | | |
| 279 | 0.0072 | >20 | 2.1 |
| 280 | 0.014 | | |
| 281 | 0.0005 | >20 | 0.835 |
| 282 | 0.0078 | >20 | 0.286 |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 283 | 0.00016 | 20 | 0.881 |
| 284 | 0.031 | | |
| 285 | >5 | | |
| 286 | 0.0021 | >20 | 0.83 |
| 287 | 0.0024 | >20 | 0.675 |
| 288 | 0.0087 | >20 | 2.5 |
| 289 | 0.0046 | >20 | 2.7 |
| 290 | >5 | | |
| 291 | 0.001 | | |
| 292 | 0.0013 | | |
| 293 | 0.21 | | |
| 294 | 0.95 | | |
| 295 | 0.0088 | | |
| 296 | 1 | | |
| 297 | >1.2 | | |
| 298 | >1.2 | | |
| 299 | 0.0012 | 20 | 1.5 |
| 300 | 0.0025 | >20 | 3 |
| 301 | 0.27 | | |
| 302 | 0.006 | | |
| 303 | 0.0061 | | |
| 304 | 0.0045 | >20 | 1.1 |
| 305 | >1.2 | | |
| 306 | 0.017 | | |
| 307 | 0.012 | | |
| 308 | 0.0013 | 20 | 1.5 |
| 309 | 0.022 | | |
| 310 | 0.013 | >20 | 2.6 |
| 311 | 0.016 | | |
| 312 | 0.0057 or >1.2 | | |
| 313 | 0.0057 or >1.2 | | |
| 314 | 0.0067 | | |
| 315 | | | |
| 316 | >1.2, 0.015, 0.0041 or 1.2 | | |
| 317 | >1.2, 0.015, 0.0041 or 1.2 | | |
| 318 | | | |
| 319 | 0.00099, 0.006, 0.25, >1.2 | | |
| 320 | 0.0049 | | |
| 321 | 0.012 | >20 | 3 |
| 322 | 0.00099, 0.006, 0.25, >1.2 | | |
| 323 | 0.0274 | | |
| 324 | 0.0089 | >20 | 1.1 |
| 325 | >1.2 | | |
| 326 | 0.0057 | 5.6 | 1.2 |
| 327 | 0.00685 | >20 | 7.8 |
| 328 | 0.00099, 0.006, 0.25 or >1.2 | | |
| 329 | 0.00099, 0.006, 0.25 or >1.2 | | |
| 330 | >1.2 | | |
| 331 | 0.0029 | >20 | 1 |
| 332 | >1.2 | | |
| 333 | 0.0056 | >20 | 2.2 |
| 334 | >1.2, 0.015, 0.0041 or 1.2 | | |
| 335 | >1.2, 0.015, 0.0041 or 1.2 | | |
| 336 | | | |
| 337 | 0.27 | | |
| 338 | 0.0015 | >20 | 3 |
| 339 | 0.007 | >20 | 2.6 |
| 340 | 0.0052 | | |
| 341 | 1 | | |
| 342 | 1.4 | | |
| 343 | 0.088 | | |
| 344 | | | |
| 345 | 0.019 or 0.014 | | |
| 346 | 0.0136 | | |
| 347 | | | |
| 348 | 0.0089 or 0.0034 | | |
| 349 | 0.0089 or 0.0034 | | |
| 350 | 0.011 | | |
| 351 | 0.12 | | |
| 352 | | | |
| 353 | 0.035 or 0.0077 | | |
| 354 | 0.035 or 0.0077 | | |
| 355 | 0.00614 | | |
| 356 | 0.0029 | | |
| 357 | | | |
| 358 | 0.0001 or 0.0011 | 1.1 or >20 | 1.2 |
| 359 | 0.0001 or 0.0011 | 1.1 or >20 | 1.2 |
| 360 | 0.0084 | | |
| 361 | 0.0002 | >20 | 0.409 |
| 362 | 0.0007 | >20 | 0.143 |
| 363 | 0.0033 | >20 | 0.66 |
| 364 | 0.00053 | >20 | 0.985 |
| 365 | 0.017 | | |
| 366 | 0.0046 | | |
| 367 | 0.0031 | | |
| 368 | 0.0004 | >20 | 0.342 |
| 369 | 0.0037 | >20 | 3.7 |
| 370 | 0.0022 | >20 | 0.727 |
| 371 | 0.0025 | >20 | 1.9 |
| 372 | >1.2 | | |
| 373 | 0.47 | | |
| 374 | 0.093 | | |
| 375 | 0.082 | | |
| 376 | 0.020 | | |
| 377 | 0.14 | | |
| 378 | 0.0013 | | |
| 379 | 0.0002 | >20 | 1.7 |
| 380 | | | |
| 381 | 0.0005 or 0.37 | >20 | 0.285 |
| 382 | 0.0005 or 0.37 | | |
| 383 | 0.11 | | |
| 384 | 0.013 | | |
| 385 | 0.21 | | |
| 386 | 0.064 | | |
| 387 | 0.003 | | |
| 388 | 0.23 | | |
| 389 | 0.20 | | |
| 390 | 0.003 | 9.5 | 1.5 |
| 391 | 0.0020 | 20 | 0.0368 |
| 392 | 0.0036 | | |
| 393 | >1.2 | | |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 394 | 0.18 | | |
| 395 | 0.17 | | |
| 396 | 0.026 | | |
| 397 | 0.0045 | | |
| 398 | 0.0061 | | |
| 399 | 0.00087 | >20 | 2.9 |
| 400 | 0.010 | | |
| 401 | | | |
| 402 | 0.15 or 0.8 | | |
| 403 | 0.0030 | | |
| 404 | 0.14 or 0.8 | | |
| 405 | 0.0089 | | |
| 406 | <0.00010 | >20 | 0.0761 |
| 407 | 0.017 | | |
| 408 | | | |
| 409 | 0.011 or 0.072 | | |
| 410 | 0.011 or 0.072 | | |
| 411 | 0.0003 | 20 | 0.0732 |
| 412 | | | |
| 413 | 0.0086 or 0.03 | | |
| 414 | 0.0075 | | |
| 415 | 0.0011 | >20 | 0.979 |
| 416 | 0.00071 | >20 | 3.2 |
| 417 | 0.0086 or 0.03 | | |
| 418 | 0.0019 | >20 | 0.515 |
| 419 | 0.0005 | >20 | 0.317 |
| 420 | 0.00072 | >20 | 0.442 |
| 421 | 0.0012 | >20 | 0.316 |
| 422 | 0.00073 | >20 | 0.406 |
| 423 | 0.0011 | >20 | 0.407 |
| 424 | 0.012 | >20 | 3.2 |
| 425 | 0.0069 | | |
| 426 | 0.0018 | >20 | 0.406 |
| 427 | 0.0024 | >20 | 0.453 |
| 428 | >1.2 | | |
| 429 | 0.042 | | |
| 430 | 0.0069 | | |
| 431 | | | |
| 432 | | | |
| 433 | | | |
| 434 | | | |
| 435 | 0.002 or 0.001 | | |
| 436 | | | |
| 437 | 0.001 or 0.006 | | |
| 438 | 0.002 or 0.001 | | |
| 439 | 0.001 or 0.006 | | |
| 440 | | | |
| 441 | 0.0007 or 0.0003 | | |
| 442 | 0.0007 or 0.0003 | | |
| 443 | | | |
| 444 | 0.003 or 0.29 | | |
| 445 | | | |
| 446 | >1.2 | | |
| 447 | 0.38 | | |
| 448 | 0.0056 | | |
| 449 | 0.024 | | |
| 450 | 0.0046 | >20 | 0.459 |
| 451 | | | |
| 452 | 0.0031 or 0.29 | | |
| 453 | | | |
| 454 | | | |
| 455 | | | |
| 456 | 0.017 or >1.2 | | |
| 457 | 0.003 or 0.29 | | |
| 458 | 0.0031 or 0.29 | 20 | 0.369 |
| 459 | 0.012 or >1.2 | >20 | 1 |
| 460 | 0.00083 | >20 | 0.252 |
| 461 | | | |
| 462 | 0.0013 or 0.00056 | >20 | 0.72 or 3.2 |
| 463 | | | |
| 464 | 0.0044 or 0.020 | >20 | 0.445 or 2.2 |
| 465 | 0.0013 or 0.00056 | >20 | 3.2 or 0.72 |
| 466 | 0.0044 or 0.020 | >20 | 0.445 or 2.2 |
| 467 | | | |
| 468 | 0.0048 or 0.024 | >20 | 2.6 or 6.9 |
| 469 | 0.0048 or 0.024 | >20 | 2.6 or 6.9 |
| 470 | | | |
| 471 | 0.044 or 0.0076 | | |
| 472 | 0.044 or 0.0076 | | |
| 473 | | | |
| 474 | 0.015, >1.2, 0.14 or 0.015 | | |
| 475 | | | |
| 476 | 0.0024 or 0.0019 | >20 | 0.51 or 1.6 |
| 477 | | | |
| 478 | 0.0051 or 0.0062 | | |
| 479 | | | |
| 480 | 0.0035 or 0.031 | >20 | 0.379 |
| 481 | | | |
| 482 | 0.047 or 0.012 | | |
| 483 | 0.015, >1.2, 0.14 or 0.015 | 15.3 | 0.682 |
| 484 | 0.015, >1.2, 0.14 or 0.015 | | |
| 485 | 0.015, >1.2, 0.14 or 0.015 | | |
| 486 | 0.0019 | >20 | 0.51 |
| 487 | 0.0051 or 0.0063 | | |
| 488 | 0.031 | | |
| 489 | 0.047 or 0.012 | | |
| 490 | | | |
| 491 | 0.0021 | | |
| 492 | | | |
| 493 | 0.0040 or 0.00086 | >20 | 0.198 or 0.0912 |
| 494 | | | |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 495 | | | |
| 496 | 0.0012 or 0.0018 | >20 | 0.237 or 0.225 |
| 497 | 0.039 | | |
| 498 | | | |
| 499 | 0.056 or 0.014 | | |
| 500 | 0.0021 | >20 | 0.381 |
| 501 | 0.0040 or 0.00086 | >20 | 0.198 or 0.0912 |
| 502 | 0.0012 | >20 | 0.225 |
| 503 | 0.0098 or 1.2 | | |
| 504 | 0.056 or 0.014 | | |
| 505 | | | |
| 506 | 0.0028 or 0.0029 | | |
| 507 | | | |
| 508 | 0.0042 or 0.010 | | |
| 509 | 0.0017 | >20 | 0.184 |
| 510 | | | |
| 511 | 0.0032 or 0.0085 | >20 | 0.333 or 1 |
| 512 | | | |
| 513 | 0.0082 or 0.0004 | >20 | 0.236 or 1.9 |
| 514 | 0.0012 | >20 | 0.543 |
| 515 | 0.0028 or 0.0029 | | |
| 516 | 0.0042 or 0.010 | | |
| 517 | >1.2 or 0.534 | | |
| 518 | 0.0032 or 0.00846 | >20 | 0.333 or 1 |
| 519 | 0.0082 or 0.0004 | >20 | 0.236 or 1.9 |
| 520 | | | |
| 521 | 0.91 or 0.022 | | |
| 522 | 0.91 or 0.022 | | |
| 523 | | | |
| 524 | 0.005 or 0.00081 | | |
| 525 | | | |
| 526 | 0.0024 or 0.00073 | | |
| 527 | 0.0008 | | |
| 528 | | | |
| 529 | 0.003 or 0.016 | | |
| 530 | | | |
| 531 | 0.028 or 0.025 | | |
| 532 | | | |
| 533 | 0.0031 or 0.0023 | | |
| 534 | 0.0015 | | |
| 535 | 0.005 or 0.00081 | | |
| 536 | 0.0024 or 0.00073 | | |
| 537 | 0.003 or 0.016 | | |
| 538 | 0.028 or 0.025 | | |
| 539 | 0.0031 or 0.0023 | | |
| 540 | | | |
| 541 | 0.019 or 0.011 | | |
| 542 | | | |
| 543 | 0.0115 or 0.00068 | | |
| 544 | | | |
| 545 | 0.00076 or 0.00098 | | |
| 546 | | | |
| 547 | 0.0022 or 0.0012 | | |
| 548 | 0.0014 | | |
| 549 | 0.00076 or 0.00098 | | |
| 550 | 0.0022 or 0.0012 | | |
| 551 | | | |
| 552 | 0.0001 or 0.00089 | | |
| 553 | 0.0012 | | |
| 554 | | | |
| 555 | 0.0012 or 0.0023 | | |
| 556 | | | |
| 557 | 0.00039 or 0.0016 | | |
| 558 | | | |
| 559 | 0.014 or 0.042 | | |
| 560 | 0.019 or 0.011 | | |
| 561 | 0.012 or 0.000684 | | |
| 562 | 0.0001 or 0.00089 | | |
| 563 | 0.0012 or 0.0023 | | |
| 564 | 0.00039 or 0.0016 | | |
| 565 | 0.014 or 0.042 | | |
| 566 | | | |
| 567 | 0.0010 or 0.0013 | | |
| 568 | 0.0026 | | |
| 569 | | | |
| 570 | 0.00077 or 0.0023 | | |
| 571 | 0.00096 | | |
| 572 | 0.0010 or 0.0013 | | |
| 573 | 0.00077 or 0.0023 | | |
| 574 | 0.0017 or >1.2 | | |
| 575 | >1.2 or 0.53 | | |
| 576 | 0.0017 or >1.2 | | |
| 577 | | | |
| 578 | | | |
| 579 | | | |
| 580 | 0.0026 | | |
| 581 | 0.0010 | | |
| 582 | 0.0033 | | |
| 583 | 0.026 | | |
| 584 | | | |
| 585 | 0.014 or 0.016 | | |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 586 | 0.014 or 0.016 | | |
| 587 | | | |
| 588 | 0.0063 or 0.0032 | | |
| 589 | 0.0063 or 0.0032 | | |
| 590 | 0.024 | | |
| 591 | | | |
| 592 | 0.46 or 1.2 | | |
| 593 | 0.46 or 1.2 | | |
| 594 | | | |
| 595 | >1.2 or 1.3 | | |
| 596 | >1.2 or 1.3 | | |
| 597 | 0.28 | | |
| 598 | | | |
| 599 | | | |
| 600 | | | |
| 601 | 0.0017 or 0.25 | | |
| 602 | 0.0017 or 0.25 | | |
| 603 | | | |
| 604 | 0.54 or 0.026 | | |
| 605 | 0.54 or 0.026 | | |
| 606 | | | |
| 607 | 0.11 or 0.0081 | | |
| 608 | 0.11 or 0.0081 | | |
| 609 | 0.00094 | | |
| 610 | 0.0018 | | |
| 611 | | | |
| 612 | 0.0032 or 0.013 | | |
| 613 | 0.00323 or 0.013 | | |
| 614 | | | |
| 615 | | | |
| 616 | | | |
| 617 | | | |
| 618 | 0.01 or 0.056 | | |
| 619 | 0.01 or 0.056 | | |
| 620 | | | |
| 621 | 0.00099 or 0.00097 | | |
| 622 | 0.00099 or 0.00097 | | |
| 623 | | | |
| 624 | 0.003 or 0.0009 | | |
| 625 | 0.003 or 0.0009 | | |
| 626 | | | |
| 627 | 0.0068 | | |
| 628 | | | |
| 629 | 0.023 or 0.025 | | |
| 630 | 0.023 or 0.025 | | |
| 631 | | | |
| 632 | 0.032 or 0.13 | | |
| 633 | 0.032 or 0.13 | | |
| 634 | | | |
| 635 | 0.073 or 0.062 | | |
| 636 | 0.073 or 0.062 | | |
| 637 | 0.007 | | |
| 638 | | | |
| 639 | | | |
| 640 | 0.004 | | |
| 641 | 0.0002 | | |
| 642 | 0.00097 | | |
| 643 | | | |
| 644 | 0.004 or 0.0007 | | |
| 645 | 0.004 or 0.0007 | | |
| 646 | | | |
| 647 | 0.0004 or 0.0006 | | |
| 648 | 0.0004 or 0.0006 | | |
| 649 | | | |
| 650 | 0.0015 or 0.0012 | | |
| 651 | 0.0015 or 0.0012 | | |
| 652 | 0.016 | | |
| 653 | 0.027 | | |
| 654 | 0.015 | | |
| 655 | | | |
| 656 | 0.001 or 0.00058 | | |
| 657 | 0.001 or 0.00058 | | |
| 658 | | | |
| 659 | 1.6 or 0.00029 | | |
| 660 | 1.6 or 0.00029 | | |
| 661 | | | |
| 662 | 0.0017 or 0.014 | | |
| 663 | 0.0017 or 0.014 | | |
| 664 | 0.00078 | | |
| 665 | | | |
| 666 | | | |
| 667 | 0.001 or 0.16 | | |
| 668 | 0.001 or 0.16 | | |
| 669 | | | |
| 670 | 1.2 or 0.0022 | | |
| 671 | 1.2 or 0.02 | | |
| 672 | 0.79 | | |
| 673 | 0.045 | | |
| 674 | 0.0011 | | |
| 675 | 0.0066 | | |
| 676 | | | |
| 677 | 0.00094 or 0.083 | | |
| 678 | 0.00094 or 0.083 | | |
| 679 | | | |
| 680 | 0.00033 or >1.2 | | |
| 681 | 0.00033 or >1.2 | | |
| 682 | 0.00094 or 0.083 | | |

TABLE 2-continued

| No. | NIK ADP-FP (Ki uM) | REL-A HeLa Transloc Assay (IC50) [uM] | p52 HeLa Transloc Assay (IC50) [uM] |
|---|---|---|---|
| 683 | | | |
| 684 | 0.00033 or >1.2 | | |
| 685 | 1.6 | | |
| 686 | 0.00082 | | |
| 687 | | | |
| 688 | 0.00058 or 0.00093 | | |
| 689 | 0.00058 or 0.00093 | | |
| 690 | | | |
| 691 | 0.066 | 0.024 | |
| 692 | 0.0663 | 0.024 | |
| 693 | | | |
| 694 | 1.8 or 1.1 | | |
| 695 | 1.8 or 1.1 | | |
| 696 | 1 | | |
| 697 | >1.2 | | |
| 698 | 2.1 | | |
| 699 | 0.065 | | |
| 700 | 0.0012 | | |
| 701 | 0.00054 | | |
| 702 | 0.0042 | | |
| 703 | | | |
| 704 | 0.27 or 0.5 | | |
| 705 | 0.27 or 0.5 | | |
| 706 | 0.43 | | |
| 707 | 0.004 | | |
| 708 | 0.0019 | | |
| 709 | | | |
| 710 | 1.8 or 1.1 | | |
| 711 | 1.8 or 1.1 | | |
| 712 | 1 | | |
| 713 | >1.2 | | |
| 714 | 0.0033 | | |
| 715 | 0.10 | | |
| 716 | 0.008 | | |
| 717 | 0.0005 | | |
| 718 | 0.0003 | | |
| 719 | 0.0004 | | |
| 720 | 0.001 | | |

Example 713

Cellular Assay

Several Assays were Developed to Profile the Cellular Activities of NIK Inhibitors (1) The first assay that can be used to profile whether a test compound can inhibit the NF-kB signally through NIK inhibition without affecting cell viability. In this assay, human embryonic kidney 293 cells are stably transfected with a tetracycline-inducible NIK DNA construct containing a cytomegalovirus promoter plus two reporter DNA constructs. One reporter encodes firefly luciferase under the control of three repeats of an NF-kB response element from the ELAM-1 gene and reflects the level of NIK activity in the cells, whereas the other reporter constitutively expresses Renilla luciferase under the control of the herpes simplex virus thymidine kinase promoter and serves as a general measure of cell viability. Cells are incubated with different concentrations of compounds (0.2% DMSO final) in medium containing 1 ug/mL doxycycline and 10% tet-system approved fetal bovine serum (Clontech) for 24 hours, after which the reporters' signals are detected using the Dual Glo luciferase detection system (Promega) according to the vendor's protocol.

(2) A second set of cell assay are used to define the selectivity of NIK inhibitors toward inhibition of classical vs. non-classical NF-kB signaling and rely on quantification of the nuclear translocation of p52 (NF-kB2) and REL-A (p65) using high content cellular imaging. For the p52 (non-classical NF-kB signaling) nuclear translocation assay, HeLa cells are treated with different concentrations of compounds (0.2% DMSO final) in medium containing 10% fetal bovine serum and then stimulated with 100 ng/mL, of an anti-lymphotoxin beta receptor antibody (R&D Systems) for 5 hours. In the REL-A nuclear translocation assay, HeLa cells are incubated with compounds (0.2% DMSO final) for 4.5 hours in medium containing 10% fetal bovine serum before stimulating them with 10 ng/mL tumor necrosis factor (TNF)-α (R&D Systems) for 30 minutes. Cells are fixed with 4% paraformaldehyde, permeabilized by adding 0.1% Triton X-100 in phosphate buffered saline, and then are incubated with either 2 ug/mL anti-p52 antibody (Millipore) or 400 ng/mL anti-REL-A (p65) antibody (Santa Cruz Biotechnology). Finally, the cells are incubated with an Alexa488-labeled secondary antibody (Invitrogen) and DRAQ5 DNA stain (Biostatus). Imaging is carried out using an Opera reader (Perkin Elmer) and data are analyzed with the aid of Acapella software (Perkin Elmer). The p52 or REL-A translocation into the nucleus is quantified by the ratio of the nuclear to cytoplasmic signal intensity. The concentration of inhibitor required for 50% inhibition ($IC_{50}$ values) in these cell assays are derived from the plots of signal vs. inhibitor concentration. The compounds in listed in Table 1 have the corresponding inhibitory value ($IC_{50}$ in micromolar) for NIK p52 Translocation Assay as set forth in Table 2.

The compounds in listed in Table 1 has the corresponding inhibitory value ($IC_{50}$ in micromolar) for NIK RelA Translocation Assay as set forth in Table 2.

We claim:

1. A compound of Formula I, or a pharmaceutically acceptable salt thereof

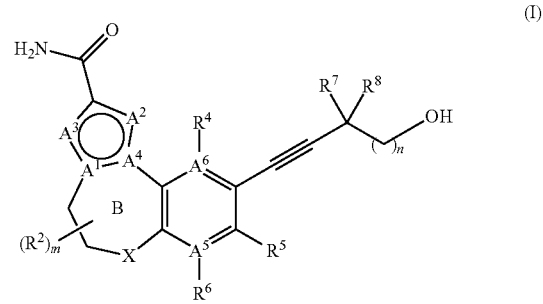

wherein $A^1$, $A^2$, $A^3$ and $A^4$ are selected from group consisting of:
$A^1$, $A^2$, $A^3$ are each N and $A^4$ is C;
$A^1$ and $A^2$ are each N, $A^3$ is $C(R^{A3})$ and $A^4$ is C;
$A^1$ is C, $A^2$ is N, $A^3$ is $N(R^{N3})$ and $A^4$ is C;
$A^1$ is C, $A^2$ is $N(R^{N2})$, $A^3$ is N and $A^4$ is C, wherein $R^{N2}$ is hydrogen, $C_{1-3}$ alkyl, $C_{1-3}$ haloalkyl, $C_{1-3}$ alkyl-C(=O)— or $C_{1-3}$ haloalkyl-C(=O)—;

$A^1$ is C and one of $A^2$ and $A^3$ is N and the other is S and $A^4$ is C;

$A^1$ is C, $A^2$ is S, $A^3$ is $C(R^{43})$ and $A^4$ is C;

$A^1$ is C, $A^2$ is N, $A^3$ and $A^4$ is N;

$A^1$ is C, $A^2$ is N, $A^3$ is $C(R^{43})$ and $A^4$ is N;

$A^1$ is C, $A^2$ is $C(R^{c2})$, $A^3$ is S and $A^4$ is C, wherein IC is hydrogen, halogen, $C_{1-3}$ alkyl, $C_{1-3}$ haloalkyl, $C_{1-3}$ alkyl-$C(=O)$— or $C_{1-3}$ haloalkyl-$C(=O)$—; and $A^1$ is C, $A^2$ and $A^3$ and $A^4$ are each N;

$A^5$ and $A^6$ are each independently C;

X is O;

m is an integer from 0 to 4;

$R^1$, $R^2$ and e and $R^{N3}$ at each occurrence each is independently selected from the group consisting of hydrogen, —F, —Cl, —Br, —I, —$(X^1)_{0-1}$—CN, —$(X^1)_{0-1}$—$NO_2$, —$(X^1)_{0-1}$—$SF_5$, —$(X^1)_{0-1}$—OH, —$(X^1)_{0-1}$—$NH_2$, —$(X^1)_{0-1}$—$N(H)(R^{1a})$, —$(X^1)_{0-1}$—$N(R^{1b})(R^{1a})$, —$(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, —$(X^1)_{0-1}$—$C_{1-6}$ alkyl, —$(X^1)_{0-1}$—$C_{3-10}$ cycloalkyl, —$(X^1)_{0-1}$—$C_{2-9}$ heterocycloalkyl, —$(X^1)_{0-1}$-5-10 membered heteroaryl, —$(X^1)_{0-1}$-6-10 membered aryl, —$C(=O)(X^1)_1$—$C_{3-10}$ cycloalkyl, —$C(=O)(X^1)_1$—$C_{2-9}$ heterocycloalkyl, =O, —$(X^1)_{0-1}$—$C(=Y^1)N(H)(R^{1a})$, —$(X^1)_{0-1}$—$C(=Y^1)NH_2$, —$(X^1)_{0-1}$—$C(=Y^1)N(R^{1a})(R^{1b})$, —$(X^1)_{0-1}$—$C(Y^1)OR^{1a}$, —$(X^1)_{0-1}$—$C(=Y^1)OH$, —$(X^1)_{0-1}$—$N(H)C(=Y^1)(R^{1a})$, $(X^1)_{0-1}$—$N(R^{1b})C(Y^1)(R^{1a})$, —$(X^1)_{0-1}$—$N(R^{1b})C(=Y^1)(H)$, —$(X^1)_{0-1}$—$N(H)C(=Y^1)OR^{1a}$, —$(X^1)_{0-1}$—$N(R^{1b})C(=Y^1)OR^{1a}$, —$(X^1)_{0-1}$—$S(O)_{1-2}R^{1a}$, —$(X^1)_{0-1}$—$N(H)S(O)_{1-2}R^{1a}$, —$(X^1)_{0-1}$—$N(R^{1b})S(O)_{1-2}R^{1a}$, —$(X^1)_{0-1}$—$S(O)_{0-1}N(H)(R^{1a})$, —$(X^1)_{0-1}$—$S(O)_{0-1}N(R^{1b})(R^{1a})$, —$(X^1)_{0-1}$—$S(O)_{0-1}NH_2$, —$(X^1)_{0-1}$—$S(=O)(=NR^{1b})R^{1a}$, $(X^1)_{0-1}C(=Y^1)H$, —$(X^1)_{0-1}$—$C(=NOH)R^{1a}$, —$(X^1)_{0-1}$—$C(=NOR^{1b})R^{1a}$, —$(X^1)_{0-1}$—$NHC(=Y^1)N(H)(R^{1a})$, —$(X^1)_{0-1}$—$NHC(=Y^1)NH_2$, —$(X^1)_{0-1}$—$NHC(=Y^1)N(R^{1b})(R^{1a})$, —$(X^1)_{0-1}$—$N(R^{1a})C(=Y^1)N(H)(R^{1a})$, —$(X^1)_{0-1}$—$N(R^{1a})C(=Y^1)N(R^{1a})(R^{1a})$, —$(X^1)_{0-1}$—$N(R^{1a})C(=Y^1)NH_2$, —$(X^1)_{0-1}$—$OC(=Y^1)R^{1a}$, —$(X^1)_{0-1}$—$OC(=Y^1)H$, —$(X^1)_{0-1}$—$OC(=Y^1)OR^{1a}$, —$(X^1)_{0-1}$—$OP(=Y^1)(OR^{1a})(OR^{1b})$, —$(X^1)$—$SC(=Y^1)OR^{1a}$ and —$(X^1)$—$SC(=Y^1)N(R^{1a})(R^{1b})$ wherein $X^1$ is selected from the group consisting of $C_{1-4}$ alkylene, $C_{1-4}$ haloalkylene, $C_{1-4}$ heteroalkylene, $C_{2-4}$ alkenylene, $C_{2-4}$ alkynylene, $C_{1-4}$ alkyleneoxy, $C_{3-7}$ cycloalkylene and $C_{2-6}$ heterocycloalkylene, phenylene, 5-6 membered heteroarylene, $R^{1a}$ and $R^{1b}$ are each independently selected from the group consisting of $C_{1-6}$ alkyl, $C_{1-6}$ haloalkyl, $C_{1-6}$ heteroalkyl, $C_{3-7}$ cycloalkyl, $C_{3-7}$ cycloalkyl-$C_{1-4}$ alkyl, $C_{2-6}$ heterocycloalkyl, $C_{2-6}$ heterocycloalkyl-$C_{1-4}$ alkyl, 5-6 membered heteroaryl, 5-6 membered heteroaryl-$C_{1-4}$ alkyl, $C_6$ aryl, $C_6$ aryl-$C_{1-4}$ alkyl and benzyl, or $R^{1a}$ and $R^{1b}$ when attached to the same nitrogen atom are optionally combined to form a 3 to 7 membered heterocyclic ring comprising 0-2 additional heteroatoms selected from N, O and S; $Y^1$ is O, $NR^{1d}$ or S wherein $R^{1d}$ is hydrogen or $C_{1-6}$ alkyl; wherein any portion of $R^1$, $R^2$ and $R^{43}$ and $R^{N3}$ substituent at each occurrence is each independently further substituted with from 0 to 4 $R^{1/2}$ substituents selected from the group consisting of —F, —Cl, —Br, —I, —CN, —$NO_2$, —$SF_5$, —OH, —$NH_2$, —$N(C_{1-6}$ alkyl$)_2$, —$NH(C_{1-6}$ alkyl), —$CF_3$, =O, $C_{1-6}$ alkyl, $C_{1-6}$ haloalkyl, $C_{1-6}$ hydroxyalkyl, $C_{1-6}$ heteroalkyl, $C_{1-6}$ alkoxy, $C_{1-6}$ alkylthio, $C_{3-7}$ cycloalkyl, $C_{2-6}$ heterocycloalkyl, —$C(=O)N(H)(C_{1-6}$ (halo)alkyl), —$C(=O)N(C_{1-6}$ (halo)alkyl$)_2$, —$C(=O)NH_2$, —$C(=O)OC_{1-6}$ (halo)alkyl, —$C(=O)OH$, —$N(H)C(=O)(C_{1-6}$ (halo)alkyl), —$N(C_{1-6}$ (halo)alkyl)$C(=O)(C_{1-6}$ (halo)alkyl), —$N(H)C(=O)OC_{1-6}$ (halo)alkyl, —$N(C_{1-6}$ (halo)alkyl)$C(=O)OC_{1-6}$ (halo)alkyl, —$S(O)_{1-2}C_{1-6}$ (halo)alkyl, —$N(H)S(O)_{1-2}C_{1-6}$ (halo)alkyl, —$N(C_{1-6}$ (halo)alkyl)$S(O)_{1-2}C_{1-6}$ (halo)alkyl, —$S(O)_{0-1}N(H)(C_{1-6}$ (halo)alkyl), —$S(O)_{0-1}N(C_{1-6}$ (halo)alkyl$)_2$, —$S(O)_{0-1}NH_2$, —$C(=O)C_{1-6}$ (halo)alkyl, —$C(=O)$ $C_{3-7}$ cycloalkyl, —$C(=NOH)C_{1-6}$ (halo)alkyl, —$C(=NOC_{1-6}$ alkyl$)C_{1-6}$ (halo)alkyl, —$NHC(=O)N(H)(C_{1-6}$ (halo)alkyl), —$NHC(=O)N(C_{1-6}$ (halo)alkyl$)_2$, —$NHC(=O)NH_2$, —$N(C_{1-6}$ (halo)alkyl)$C(=O)N(H)(C_{1-6}$ (halo)alkyl), —$N(C_{1-6}$ (halo)alkyl)$C(=O)NH_2$, —$OC(=O)C_{1-6}$ (halo)alkyl, —$OC(=O)OC_{1-6}$ (halo)alkyl, —$OP(=O)(OC_{1-6}$ (halo)alkyl$)_2$, —$SC(=O)OC_{1-6}$ (halo)alkyl and —$SC(=O)N(C_{1-6}$ (halo)alkyl$)_2$, wherein any two $R^2$ substituents attached to the same or different ring vertices in the B ring or a $R^1$ and $R^2$ substituents attached to different ring vertices in the B ring are optionally combined to form a 3 to 6-membered carbocyclic or heterocyclic ring comprising 1 to 2 heteroatoms selected from N, O and S, wherein said 3 to 6-membered carbocyclic or heterocyclic ring is optionally substituted with 1 to 2 $R^{1/2}$ substituents;

$R^4$ and $R^6$ are each independently absent if attached to a nitrogen atom or selected from the group consisting of hydrogen, $C_{1-3}$ alkyl, $C_{1-3}$ haloalkyl, $C_{1-3}$ alkyl-$C(=O)$— or $C_{1-3}$ haloalkyl-$C(=O)$—, $C_{1-3}$ alkoxy, $C_{1-3}$ alkylamino, $C_{1-3}$ dialkylamino, $C_{1-3}$ alkylthio, $NH_2$, OH, F, Cl, Br, I, CN and $NO_2$;

$R^5$ is selected from the group consisting of hydrogen, $C_{1-3}$ alkyl, $C_{1-3}$ haloalkyl, $C_{1-3}$ alkyl-$C(=O)$— or $C_{1-3}$ haloalkyl-$C(=O)$—, $C_{1-3}$ alkoxy, $C_{1-3}$ alkylamino, $C_{1-3}$ dialkylamino, $C_{1-3}$ alkylthio, $NH_2$, OH, F, Cl, Br, I, CN and $NO_2$, $R^7$ at each occurrence is independently selected from the group consisting of hydrogen, $C_{1-6}$alkyl, $C_{1-6}$ haloalkyl, $C_{3-10}$ cycloalkyl, $C_{2-9}$ heterocycloalkyl, 6-10 membered aryl, 5-10 membered heteroaryl, —$C(=O)R^{7a}$, —$C(=O)H$, —$C(=O)OR^{7a}$ or —$C(=O)NR^{7a}R^{7b}$, wherein $R^{7a}$ and $R^{7b}$ at each occurrence is independently selected from the group consisting of hydrogen, $C_{1-6}$ alkyl, $C_{2-6}$ alkenyl, $C_{2-6}$ alkynyl, $C_{1-6}$ heteroalkyl, $C_{3-10}$ cycloalkyl, $C_{2-9}$ heterocycloalkyl, —$(C_{1-6}$ alkylene)-$(C_{3-10}$ cycloalkyl), —$(C_{1-6}$ alkylene)-$(C_{2-9}$ heterocycloalkyl), —$(C_{1-6}$ alkylene)-(6-membered aryl) and —$(C_{1-6}$ alkylene)-(5-6 membered heteroaryl), and wherein $R^{7a}$ and $R^{7b}$, when attached to the same nitrogen atom, are optionally combined to form a $C_{2-9}$ heterocycloalkyl further comprising 0-2 additional heteroatoms selected from N, O and S;

$R^8$ at each occurrence is independently selected from the group consisting of hydrogen, $C_{1-6}$ alkyl, $C_{1-6}$ haloalkyl or —$CH_2$—OH; or alternatively $R^7$ and $R^8$ are combined to form a $C_{3-10}$ cycloalkyl, $C_{2-9}$ heterocycloalkyl, wherein optionally fused to said $C_{3-10}$ cycloalkyl and $C_{2-9}$ heterocycloalkyl is a 6 membered aryl, 5-6 membered heteroaryl ring or 3-6 membered heterocycloalkyl ring; and wherein the $R^7$ substituent, either alone or as combined with $R^8$, are optionally substituted with 1 to 5 $R^{R7/8}$ substituents selected from the group consisting of F, Cl, Br, I, —OH, —$NH_2$, —SH, —$CF_3$, —$OCF_3$, —$SF_5$, —$OCH_3$, $C_{1-6}$ alkyl, $CD_3$, $C_{1-6}$ haloalkyl, $C_{1-6}$ heteroalkyl, $C_{1-6}$ alkoxy, $C_{1-6}$ alkylthio, $C_{3-5}$ cycloalkyl and $C_{2-5}$ heterocycloalkyl, =O, —$(X^7)_{0-1}$—CN, —$(X^7)_{0-1}$—$NO_2$, —$(X^7)_{0-1}$—$N_3$, —$(X^7)_{0-1}$—OH, —$(X^7)_{0-1}$—H, —$(X^7)_{0-1}$—$OR^{R7}$, —$(X^7)_{0-1}$—$N(H)R^{R7}$, —$(X^7)_{0-1}$—$N(H)_2$, —$(X^7)_{0-1}$—$N(R^{R7})_2$, —$(X^7)_{0-1}$—$SR^{R7}$, —$(X^7)_{0-1}$—SH, —$(X^7)_{0-1}$—C(O)$R^{R7}$, —$(X^7)_{0-1}$—C(O)H, —$(X^7)_{0-1}$—S(O)$_2R^{R7}$, —$(X^7)_{0-1}$—S(O)$R^{R7}$, —$(X^7)_{0-1}$—N(H)S(O)$_2R^{R7}$, —$(X^7)_{0-1}$—N($R^{R7}$)S(O)$_2R^{R7}$, —$(X^7)_{0-1}$—OC(O)$R^{R7}$, —$(X^7)_{0-1}$—N(H)C(O)$OR^{R7}$, —$(X^7)_{0-1}$—N($R^{R7}$)C(O)$OR^{R7}$, —$(X^7)_{0-1}$—C(=O)$OR^{R7}$, —$(X^7)_{0-1}$—C(=O)OH, —$(X^7)_{0-1}$—C(=O)N(H)$R^{R7}$, —$(X^7)_{0-1}$—C(=O)N($R^{R7}$)$R^{R7}$, —$(X^7)_{0-1}$—N(H)C(=O)$R^{R7}$, —$(X^7)_{0-1}$—N($R^{R7}$)C(=O)$R^{R7}$, —$(X^7)_{0-1}$—N(H)C(=O)$OR^{R7}$ and —$(X^7)_{0-1}$—N($R^{R7}$)C(=O)$OR^{R7}$, wherein $X^7$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{2-6}$ heterocycloalkylene, and $R^{R7}$ at each occurrence is independently selected from the group consisting of $C_{1-6}$ alkyl, $C_{1-6}$ haloalkyl, $C_{1-6}$ heteroalkyl, $C_{2-6}$ alkenyl, $C_{2-6}$ alkynyl, $C_{3-7}$ cycloalkyl and $C_{2-6}$ heterocycloalkyl; and the subscript n is an integer from 0 to 1.

2. The compound of claim 1, wherein said compound having Formula I is selected from the subformula group consisting of

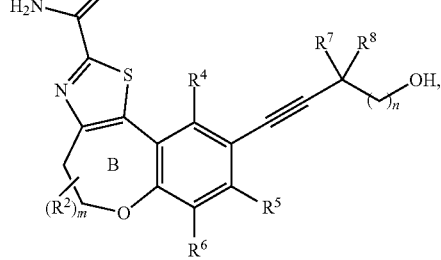
(I-A$^1$)

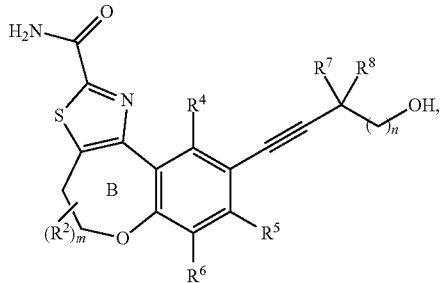
(I-A$^2$)

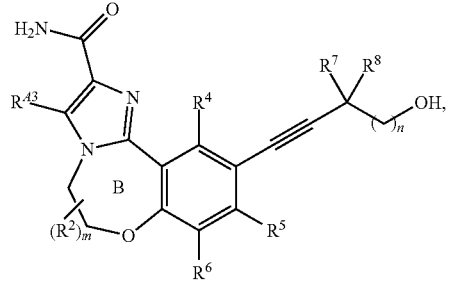
(I-A$^3$)

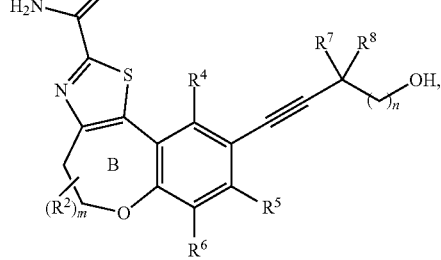
(I-A$^4$)

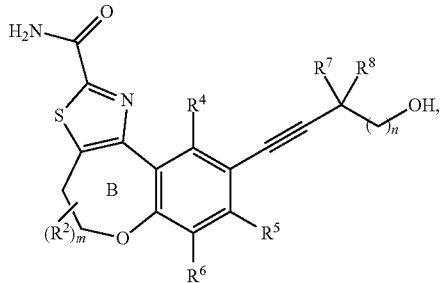
(I-A$^5$)

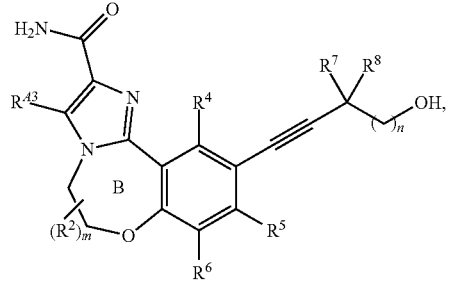
(I-A$^6$)

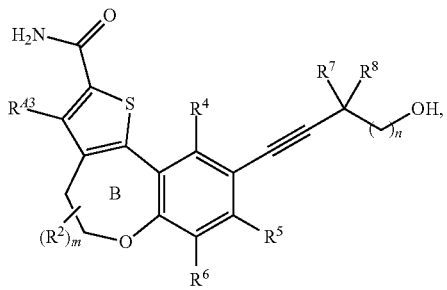
(I-A$^7$)

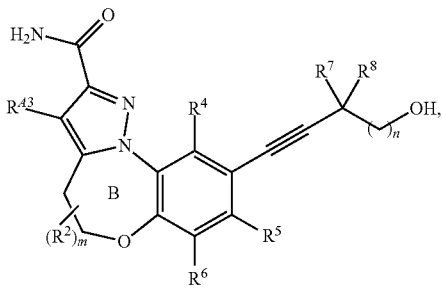
(I-A$^8$)

-continued

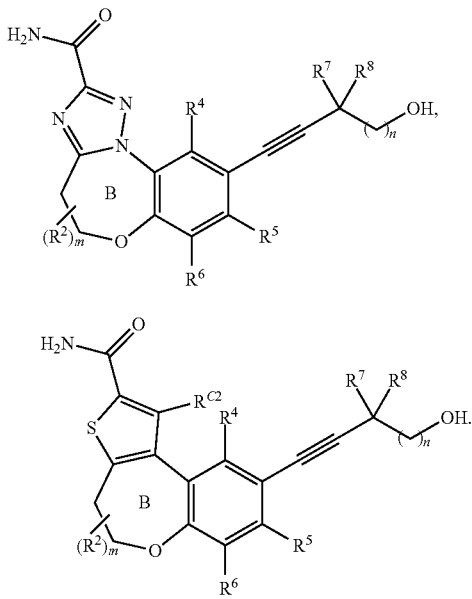

(I-A$^9$)

(I-A$^{10}$)

3. The compound of claim 1, wherein A$^1$ and A$^2$ are each N, A$^3$ is C(R$^{43}$) and A$^4$ is C, wherein cis optionally substituted and selected from the group consisting of hydrogen, —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, (X$^1$)$_{0-1}$—C(Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^1$a)(OR$^{1b}$), —(X$^1$)—SC(=Y$^1$)OR$^{1a}$ and —(X$^1$)—SC(=Y$^1$)N(R$^{1a}$)(R$^{1b}$);

R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy and C$_{1-6}$ alkylthio; and m is 0 to 4.

4. The compound of claim 3, wherein m is 0-2 and R$^{43}$ is other than hydrogen.

5. The compound of claim 1, wherein A$^1$ and A$^2$ are each N, A$^3$ is C(R$^{43}$) and A$^4$ is C, wherein m is 0 to 4; R$^2$ is optionally substituted and selected from the group consisting of hydrogen, —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, (X$^1$)$_{0-1}$—C(Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$);

R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy and C$_{1-6}$ alkylthio; and m is from 0 to 4.

6. The compound of claim 5, wherein m is 1-2.

7. The compound of claim 1, wherein A$^1$ and A$^4$ are each C, A$^2$ is N and A$^3$ is N(R$^{N3}$); wherein R$^{N3}$ is optionally substituted and selected from the group consisting of consisting of hydrogen, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), (X$^1$)$_{01}$Y$^1$)OR$^{1a}$, —(X$^1$)$_{0-1}$—C(=Y$^1$)OH, —(X$^1$)$_{0-1}$—N(H)C(=Y$^1$)(R$^{1a}$), (X$^1$)$_{0-1}$N(R$^{1b}$)C(Y$^1$)(R$^{1a}$), (X$^1$)$_{0-1}$N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{01}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, (X$^1$)$_{0-1}$—C(Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$);

R$^2$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy and C$_{1-6}$ alkylthio; and m is from 0 to 4.

8. The compound of claim 7, wherein m is 0-2 and R$^{N3}$ is other than hydrogen.

9. The compound of claim 1, wherein A$^1$ and A$^4$ are each C, A$^2$ is N and A$^3$ is N(R$^{N3}$); wherein m is from 0 to 4; R$^2$ is optionally substituted and selected from the group consisting of consisting of —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$); and R$^{N3}$ is optionally substituted and selected from the group consisting of hydrogen, —F, —Cl, —Br, —I, —CN, —NO$_2$, —SF$_5$, —OH, —NH$_2$, —N(H)(R$^{1a}$), —N(R$^{1b}$)(R$^{1a}$), —CF$_3$, C$_{1-6}$ alkyl, C$_{1-6}$ haloalkyl, C$_{1-6}$ heteroalkyl, C$_{1-6}$ alkoxy, and C$_{1-6}$ alkylthio.

10. The compound of claim 9, wherein m is 1-2.

11. The compound of claim 1, wherein in compounds of Formula I or a subformula thereof, A$^1$ is C, A$^2$ and A$^4$ are each N and A$^3$ is C(R$^{43}$); wherein R$^{43}$ is optionally substituted and selected from the group consisting of consisting of hydrogen, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{1-6}$ alkyl, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{12}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$).

12. The compound of claim 11, wherein in compound of Formula I or a subformula thereof, m is 0-2 and R$^{N3}$ is other than hydrogen.

13. The compound of claim 1, wherein in compounds of Formula I or a subformula thereof, A$^1$ is C, A$^2$ and A$^4$ are each N and A$^3$ is C(R$^{43}$), wherein m is from 0 to 4; R$^2$ is optionally substituted and selected from the group consisting of consisting of —F, —Cl, —Br, —I, —(X$^1$)$_{0-1}$—CN, —(X$^1$)$_{0-1}$—NO$_2$, —(X$^1$)$_{0-1}$—SF$_5$, —(X$^1$)$_{0-1}$—OH, —(X$^1$)$_{0-1}$—NH$_2$, —(X$^1$)$_{0-1}$—N(H)(R$^{1a}$), —(X$^1$)$_{0-1}$—N(R$^{1b}$)(R$^{1a}$), —(X$^1$)$_{0-1}$—CF$_3$, C$_{1-6}$ alkyl, C$_{1-6}$ haloalkyl, C$_{1-6}$ heteroalkyl, C$_{1-6}$ alkoxy, C$_{1-6}$ alkylthio, —(X$^1$)$_{0-1}$—C$_{3-10}$ cycloalkyl, —(X$^1$)$_{0-1}$—C$_{2-9}$ heterocycloalkyl, —(X$^1$)$_{0-1}$-5-10 membered heteroaryl, —(X$^1$)$_{0-1}$-6-10 membered aryl, —(X$^1$)$_{0-1}$—C(=Y$^1$)N(H)(R$^{1a}$), —(X$^1$)$_{0-1}$—C(=Y$^1$)NH$_2$, —(X$^1$)$_{0-1}$—C(=Y$^1$)N(R$^{1a}$)(R$^{1b}$), —(X$^1$)$_{0-1}$—C(=Y$^1$)OR$^{1a}$, —(X$^1$)$_{0-1}$—C(=Y$^1$)OH, —(X$^1$)$_{0-1}$—N(H)C(=Y$^1$)(R$^{1a}$), —(X$^1$)$_{0-1}$—N(R$^{1b}$)C(=Y$^1$)(R$^{1a}$), —(X$^1$)$_{0-1}$—N(R$^{1b}$)C(=Y$^1$)(H), —(X$^1$)$_{0-1}$—N(H)C(=Y$^1$)OR$^{1a}$, —(X$^1$)$_{0-1}$—N(R$^{1b}$)C(=Y$^1$)OR$^{1a}$, —(X$^1$)$_{0-1}$—S(O)$_{1-2}$R$^{1a}$, —(X$^1$)$_{0-1}$—N(H)S(O)$_{1-2}$R$^{1a}$, —(X$^1$)$_{0-1}$—N(R$^{1b}$)S(O)$_{1-2}$R$^{1a}$, —(X$^1$)$_{0-1}$—S(O)$_{0-1}$N(H)(R$^{1a}$), —(X$^1$)$_{0-1}$—S(O)$_{0-1}$N(R$^{1b}$)(R$^{1a}$), —(X$^1$)$_{0-1}$—S(O)$_{0-1}$NH$_2$, —(X$^1$)$_{0-1}$—S(=O)(=NR$^{1b}$)R$^{1a}$, —(X$^1$)$_{0-1}$—C(=Y$^1$)R$^{1a}$, —(X$^1$)$_{0-1}$—C(=Y$^1$)H, —(X$^1$)$_{0-1}$—C(=NOH)R$^{1a}$, —(X$^1$)$_{0-1}$—C(=NOR$^{1b}$)R$^{1a}$, —(X$^1$)$_{0-1}$—NHC(=Y$^1$)N(H)(R$^{1a}$), —(X$^1$)$_{0-1}$—NHC(=Y$^1$)NH$_2$, —(X$^1$)$_{0-1}$—NHC(=Y$^1$)N(R$^{1b}$)(R$^{1a}$), —(X$^1$)$_{0-1}$—N(R$^{1a}$)C(=Y$^1$)N(H)(R$^{1a}$), —(X$^1$)$_{0-1}$—N(R$^{1a}$)C(=Y$^1$)N(R$^{1a}$)(R$^{1a}$), —(X$^1$)$_{0-1}$—N(R$^{1a}$)C(=Y$^1$)NH$_2$, —(X$^1$)$_{0-1}$—OC(=Y$^1$)R$^{1a}$, —(X$^1$)$_{0-1}$—OC(=Y$^1$)H, —(X$^1$)$_{0-1}$—OC(=Y$^1$)OR$^{1a}$, —(X$^1$)$_{0-1}$—OP(=Y$^1$)(OR$^{1a}$)(OR$^{1b}$), —(X$^1$)—SC(=Y$^1$)OR$^{1a}$ and —(X$^1$)—SC(=Y$^1$)N(R$^{1a}$)(R$^{1b}$).

14. The compound of claim 13, wherein in compound of Formula I or a subformula thereof, m is 1-2.

15. The compound of claim 1, wherein R$^7$ at each occurrence is optionally substituted and independently selected from the group consisting of hydrogen, C$_{1-6}$ alkyl, C$_{1-6}$ haloalkyl, 3-10 membered heterocycloalkyl, 5-10 membered heteroaryl or —C(=O)NR$^{7a}$R$^{7b}$; and R$^8$ at each occurrence is independently selected from the group consisting of hydrogen C$_{1-6}$ alkyl, C$_{1-6}$ haloalkyl or and —CH$_2$—OH.

16. The compound of claim 15, wherein R$^7$ is optionally substituted and selected from the group consisting of: furan, oxazole, isoxazole, oxadiazole, pyrrole, pyrazole, imidazole, triazole, tetrazole, thiazole, thiadiazole, thiophene, pyridine, pyrimidine, pyridazine, pyrazine, indole, indazole, indole, 1H-pyrrolo[2,3-b]pyridine, 1H-pyrrolo[2,3-c]pyridine, 1H-pyrrolo[3,2-c]pyridine, 1H-pyrrolo[3,2-b]pyridine, 5H-pyrrolo[3,2-d]pyrimidine, 7H-pyrrolo[2,3-d]pyrimidine, 5H-pyrrolo[2,3-b]pyrazine, benzimidazole, benzofuran and benzothiophene.

17. The compound of claim 16, wherein R is optionally substituted and selected from the group consisting of: oxazole, isoxazole, 1,2,4-oxadiazole, 1,2,5-oxadiazole, thiazole, thiazole, 1,3,4-thiadiazole, imidazole, pyrazole, triazole, pyrimidine, pyridazine, pyrazine, pyridine, 2H-1,2,3-triazole, and 1H-1,2,4-triazole.

18. The compound of claim 15, wherein R$^7$ is optionally substituted with from 1 to 5 substituents selected from the group consisting of F, Cl, Br, —OH, C$_{1-6}$ alkyl, C$_{1-6}$ haloalkyl, —(X$^7$)$_{0-1}$—CN, —(X$^7$)$_{0-1}$—OH, —(X$^7$)$_{0-1}$—H and —(X$^7$)$_{0-1}$—OR$^a$.

19. The compound of claim 15, wherein R$^7$ is selected from the group consisting of:

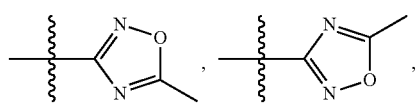

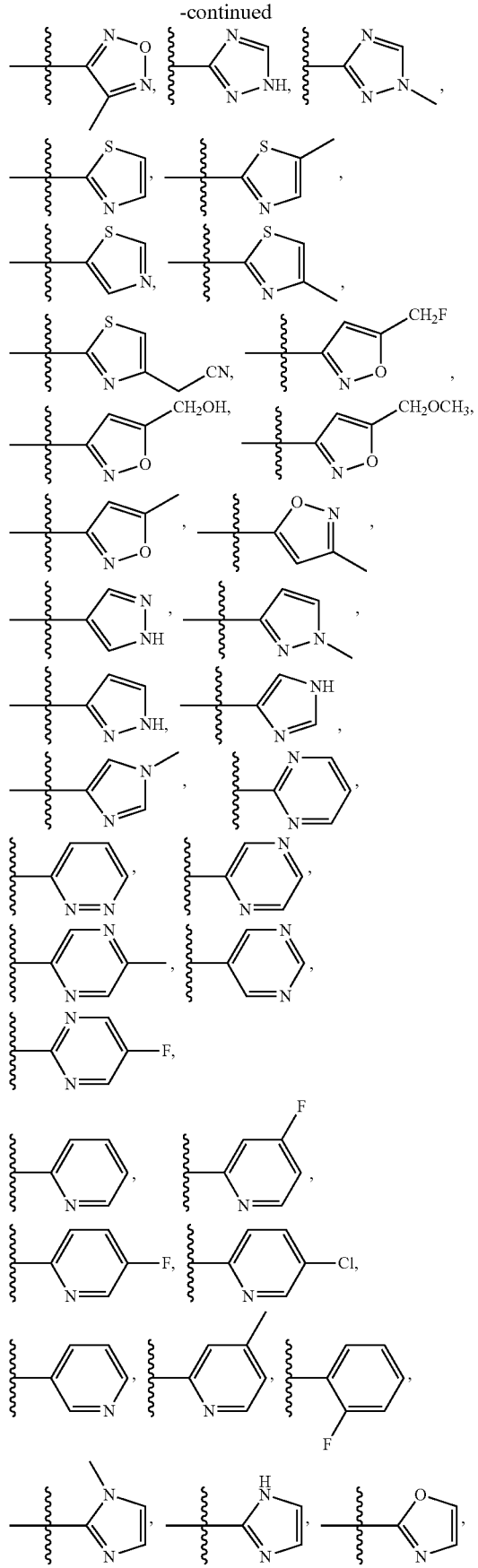
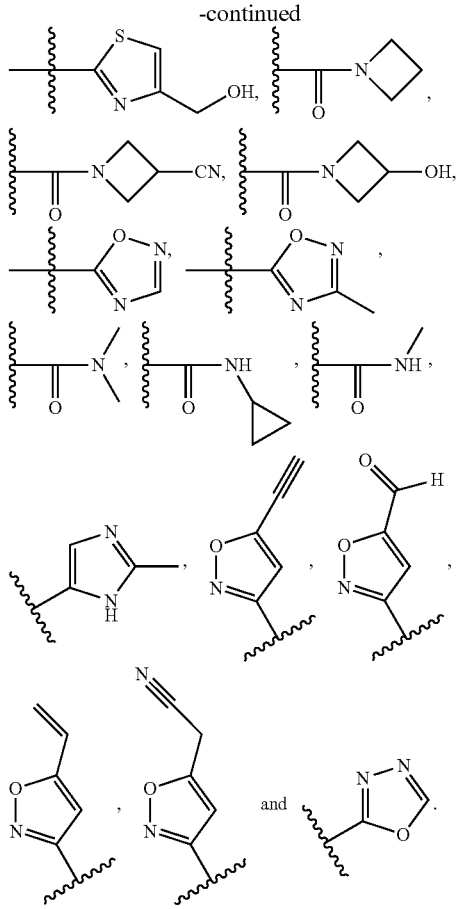

20. The compound of claim 15, wherein $R^7$ is selected from the group consisting of methyl, ethyl, hydroxymethyl, fluoromethyl, difluoromethyl, trifluoromethyl, methoxymethyl, cyanomethyl, cyclopropyl, 3-hydroxycyclobut-1-yl cyclopropylmethyl, isopropyl and 1-hydroxyeth-1-yl.

21. The compound of claim 1, wherein $R^7$ and $R^8$ are combined with the carbon atom to each is attached to form an optionally substituted $C_{3-10}$ cycloalkyl or $C_{2-9}$ heterocycloalkyl, and wherein optionally fused to said $C_{3-10}$ cycloalkyl and $C_{2-9}$ heterocycloalkyl is a 6 membered aryl or 5-6 membered heteroaryl ring.

22. The compound of claim 21, wherein $R^7$ and $R^8$ are combined with the carbon atom in Formula I (denoted as "*C" below) to which each is attached to form a ring selected from the group consisting of:

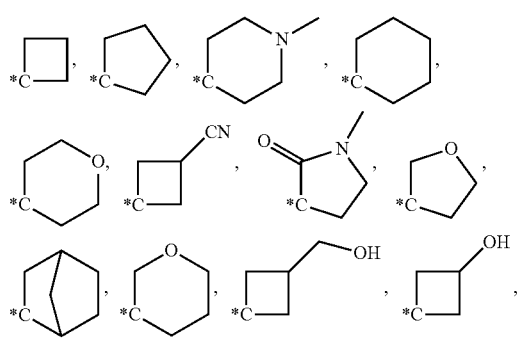

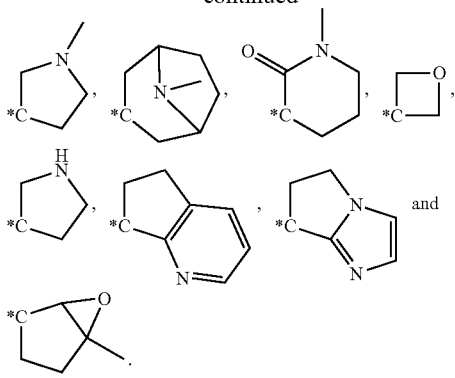

23. The compound of claim 1, wherein n is 0.

24. The compound of claim 1, wherein $R^4$, $R^5$ and $R^6$ are each independently selected from the group consisting of hydrogen, methyl, trifluoromethyl, methoxy, OH, F, Cl, Br, I, CN and $NO_2$.

25. The compound of claim 1, wherein m is 0 and $R^{A3}$ and $R^{N3'}$, if present, is hydrogen.

26. The compound of claim 1, wherein m is 0 and $R^{A3}$ and $R^{N3}$, if present, is selected from the group consisting of —F, —Cl, —Br, —I, $-(X^1)_{0-1}$—CN, $-(X^1)_{0-1}$—$SF_5$, $-(X^1)_{0-1}$—OH, $-(X^1)_{0-1}$—$NH_2$, $-(X^1)_{0-1}$—N(H)($R^{1a}$), $-(X^1)_{0-1}$—N($R^{1b}$)($R^{1a}$), $-(X^1)_{0-1}$—$CF_3$, $C_{1-6}$ alkyl, $C_{1-6}$ haloalkyl, $C_{1-6}$ heteroalkyl, $C_{1-6}$ alkoxy, $C_{1-6}$ alkylthio, $-(X^1)_{0-1}$—$C_{3-10}$ cycloalkyl, $-(X^1)_{0-1}$—$C_{2-9}$ heterocycloalkyl, $-(X^1)_{0-1}$-5-10 membered heteroaryl, $-(X^1)_{0-1}$-6-10 membered aryl, $-(X^1)_{0-1}$—C(=$Y^1$)N(H)($R^{1a}$), $-(X^1)_{0-1}$—C(=$Y^1$)$NH_2$, $-(X^1)_{0-1}$—C(=$Y^1$)N($R^{1a}$)($R^{1b}$), $(X^1)_{0-1}$—C(=$Y^1$)$OR^{1a}$ and $-(X^1)_{0-1}$—C(=$Y^1$)OH.

27. The compound of claim 1, wherein $R^1$, $R^2$, in its first occurrence, $R^{A3}$ and $R^{N3}$, each if present, is independently selected from the group consisting of:

875
-continued

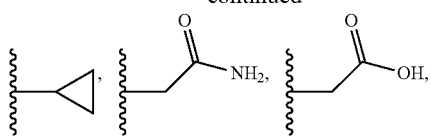

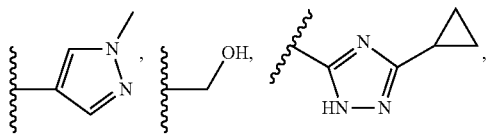

876
-continued

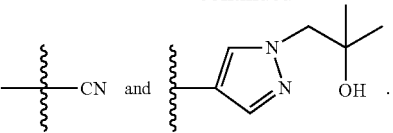

28. A pharmaceutical composition comprising a compound of claim 1 and at least one pharmaceutically acceptable carrier, diluent or excipient.

29. The compound of Formula I of claim 1, selected from the group of Table 1A, and pharmaceutically acceptable salts thereof:

TABLE 1A

| No. | Structure | Name |
|---|---|---|
| 1 | 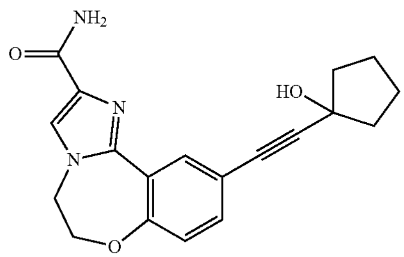 [SMILES: NC(=O)c1cn2c(n1)-c1cc(C#CC3(O)CCCC3)ccc1OCC2] | 9-(1-hydroxy-cyclopentylethynyl)-4,5-dihydro-6-oxa-1,3a-diaza-benzo[e]azulene-2-carboxylic acid amide |
| 2 | 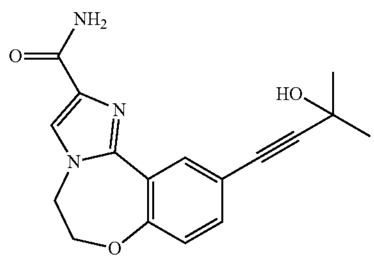 [SMILES: CC(C)(O)C#Cc1ccc2c(c1)-c1nc(C(N)=O)cn1CCO2] | 9-(3-hydroxy-3-methyl-but-1-ynyl)-4,5-dihydro-6-oxa-1,3a-diaza-benzo[e]azulene-2-carboxylic acid amide |
| 3 | 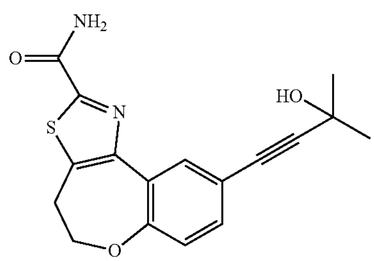 [SMILES: CC(C)(O)C#Cc1ccc2c(c1)-c1nc(C(N)=O)sc1CCO2] | 9-(3-hydroxy-3-methyl-but-1-ynyl)-4,5-dihydro-6-oxa-3-thia-1-aza-benzo[e]azulene-2-carboxylic acid amide |
| 4 | 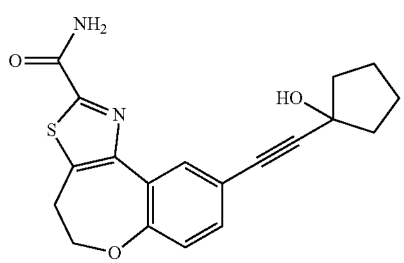 [SMILES: NC(=O)c1nc2c(s1)CCOc1ccc(C#CC3(O)CCCC3)cc1-2] | 9-(1-hydroxy-cyclopentylethynyl)-4,5-dihydro-6-oxa-3-thia-1-aza-benzo[e]azulene-2-carboxylic acid amide |

TABLE 1A-continued

| No. | Structure | Name |
|---|---|---|
| 5 | 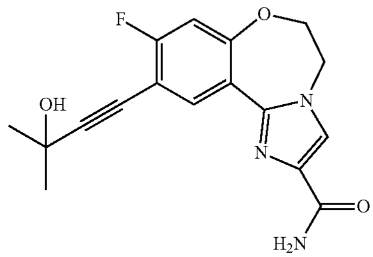 [SMILES: CC(C)(O)C#Cc1cc2c(cc1F)OCCn1cc(C(N)=O)nc1-2] | 8-fluoro-9-(3-hydroxy-3-methyl-but-1-ynyl)-4,5-dihydro-6-oxa-1,3a-diaza-benzo[e]azulene-2-carboxylic acid amide |
| 6 | 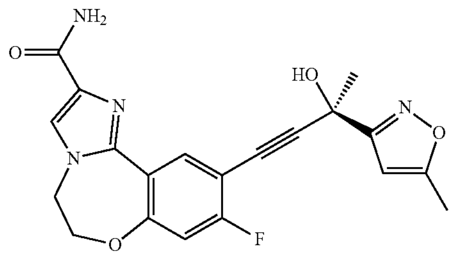 [SMILES: Cc1cc([C@](C)(O)C#Cc2cc3c(cc2F)OCCn2cc(C(N)=O)nc2-3)no1] | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 7 | 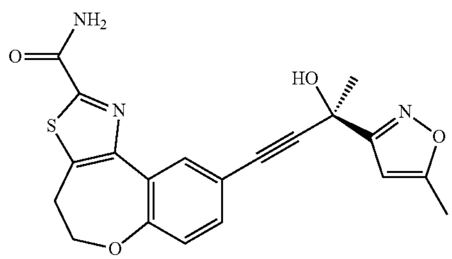 [SMILES: Cc1cc([C@](C)(O)C#Cc2ccc3c(c2)-c2nc(C(N)=O)sc2CCO3)no1] | 9-[(R)-3-hydroxy-3-(5-methyl-isoxazol-3-yl)-but-1-ynyl]-4,5-dihydro-6-oxa-3-thia-1-aza-benzo[e]azulene-2-carboxylic acid amide |
| 8 | 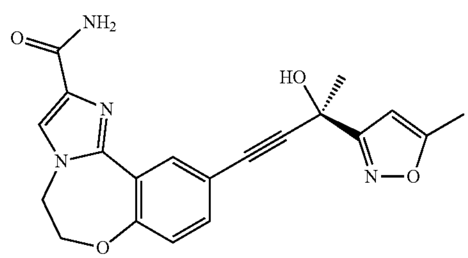 [SMILES: Cc1cc([C@](C)(O)C#Cc2ccc3c(c2)-c2nc(C(N)=O)cn2CCO3)no1] | 9-[(R)-3-Hydroxy-3-(5-methyl-isoxazol-3-yl)-but-1-ynyl]-4,5-dihydro-6-oxa-1,3a-diaza-benzo[e]azulene-2-carboxylic acid amide |
| 9 | 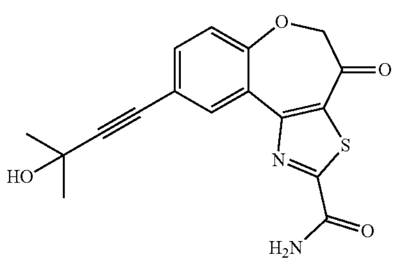 [SMILES: CC(C)(O)C#Cc1ccc2c(c1)-c1nc(C(N)=O)sc1C(=O)CO2] | 9-(3-hydroxy-3-methyl-but-1-ynyl)-4-oxo-4,5-dihydro-6-oxa-3-thia-1-aza-benzo[e]azulene-2-carboxylic acid amide |
| 10 | 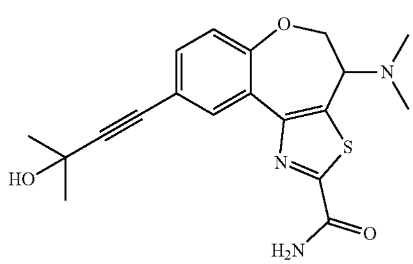 [SMILES: CN(C)C1COc2ccc(C#CC(C)(C)O)cc2-c2nc(C(N)=O)sc21] | 4-dimethylamino-9-(3-hydroxy-3-methyl-but-1-ynyl)-4,5-dihydro-6-oxa-3-thia-1-aza-benzo[e]azulene-2-carboxylic acid amide |

TABLE 1A-continued

| No. | Structure | Name |
|---|---|---|
| 11 | 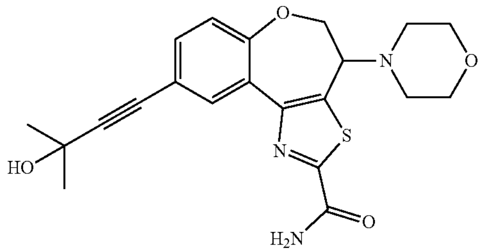 [SMILES: CC(C)(O)C#Cc1ccc2c(c1)-c1nc(C(N)=O)sc1C(N1CCOCC1)CO2] | 9-(3-hydroxy-3-methyl-but-1-ynyl)-4-morpholin-4-yl-4,5-dihydro-6-oxa-3-thia-1-aza-benzo[e]azulene-2-carboxylic acid amide |
| 12 | 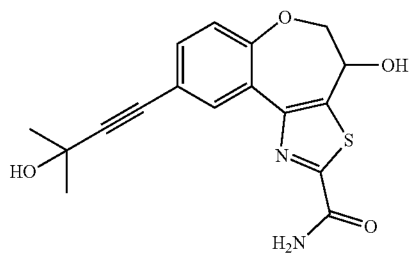 [SMILES: CC(C)(O)C#Cc1ccc2c(c1)-c1nc(C(N)=O)sc1C(O)CO2] | 4-hydroxy-9-(3-hydroxy-3-methyl-but-1-ynyl)-4,5-dihydro-6-oxa-3-thia-1-aza-benzo[e]azulene-2-carboxylic acid amide |
| 13 | 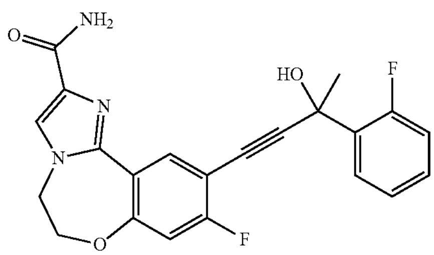 [SMILES: CC(O)(C#Cc1cc2c(cc1F)OCCn1cc(C(N)=O)nc1-2)c1ccccc1F] | 8-fluoro-9-[3-(2-fluoro-phenyl)-3-hydroxy-but-1-ynyl]-4,5-dihydro-6-oxa-1,3a-diaza-benzo[e]azulene-2-carboxylic acid amide |
| 14 | 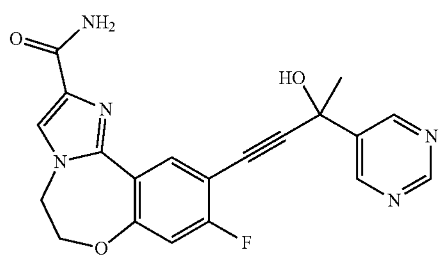 [SMILES: CC(O)(C#Cc1cc2c(cc1F)OCCn1cc(C(N)=O)nc1-2)c1cncnc1] | 8-Fluoro-9-(3-hydroxy-3-pyrimidin-5-yl-but-1-ynyl)-4,5-dihydro-6-oxa-1,3a-diaza-benzo[e]azulene-2-carboxylic acid amide |
| 15 | 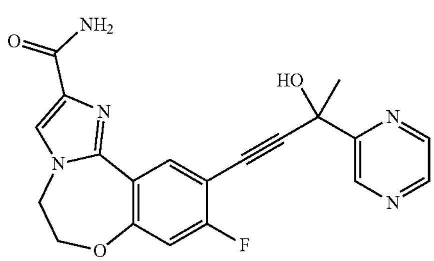 [SMILES: CC(O)(C#Cc1cc2c(cc1F)OCCn1cc(C(N)=O)nc1-2)c1cnccn1] | 8-fluoro-9-(3-hydroxy-3-pyrazin-2-yl-but-1-ynyl)-4,5-dihydro-6-oxa-1,3a-diaza-benzo[e]azulene-2-carboxylic acid amide |
| 16 | 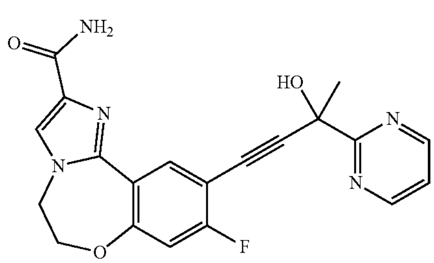 [SMILES: CC(O)(C#Cc1cc2c(cc1F)OCCn1cc(C(N)=O)nc1-2)c1ncccn1] | 8-fluoro-9-(3-hydroxy-3-pyrimidin-2-yl-but-1-ynyl)-4,5-dihydro-6-oxa-1,3a-diaza-benzo[e]azulene-2-carboxylic acid amide |

TABLE 1A-continued

| No. | Structure | Name |
| --- | --- | --- |
| 17 | 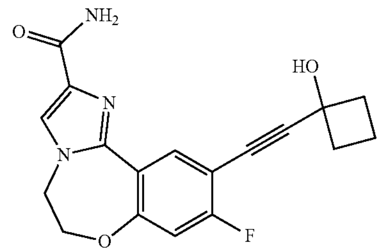 [SMILES: NC(=O)c1cn2c(n1)-c1cc(C#CC3(O)CCC3)c(F)cc1OCC2] | 8-fluoro-9-(1-hydroxy-cyclobutylethynyl)-4,5-dihydro-6-oxa-1,3a-diaza-benzo[e]azulene-2-carboxylic acid amide |
| 18 | 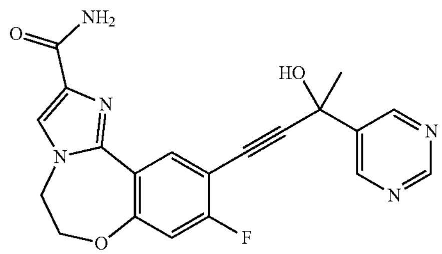 [SMILES: CC(O)(C#Cc1cc2c(cc1F)OCCn1cc(C(N)=O)nc1-2)c1cncnc1] | 8-fluoro-9-(3-hydroxy-3-pyrimidin-5-yl-but-1-ynyl)-4,5-dihydro-6-oxa-1,3a-diaza-benzo[e]azulene-2-carboxylic acid amide |
| 19 | 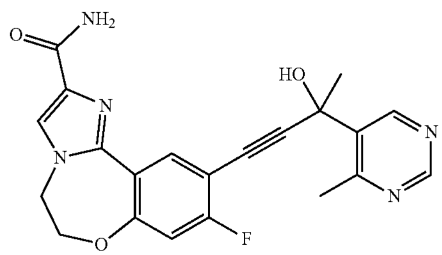 [SMILES: Cc1ncncc1C(C)(O)C#Cc1cc2c(cc1F)OCCn1cc(C(N)=O)nc1-2] | 8-fluoro-9-[3-hydroxy-3-(2-methyl-pyridin-3-yl)-but-1-ynyl]-4,5-dihydro-6-oxa-1,3a-diaza-benzo[e]azulene-2-carboxylic acid amide |
| 20 | 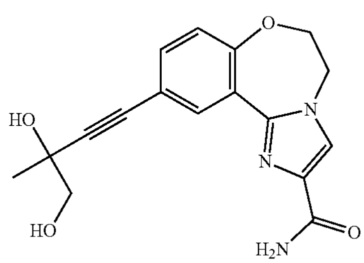 [SMILES: CC(O)(C#Cc1ccc2c(c1)-c1nc(C(N)=O)cn1CCO2)CO] | 9-(3,4-dihydroxy-3-methyl-but-1-ynyl)-4,5-dihydro-6-oxa-1,3a-diaza-benzo[e]azulene-2-carboxylic acid amide |
| 21 | 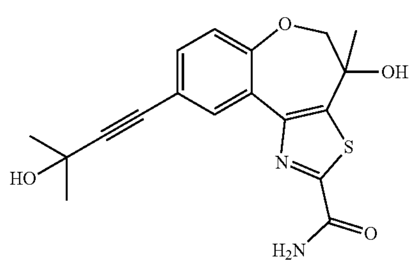 [SMILES: CC(C)(O)C#Cc1ccc2c(c1)-c1nc(C(N)=O)sc1C(C)(O)CO2] | 4-hydroxy-9-(3-hydroxy-3-methyl-but-1-ynyl)-4-methyl-4,5-dihydro-6-oxa-3-thia-1-aza-benzo[e]azulene-2-carboxylic acid amide |
| 22 | 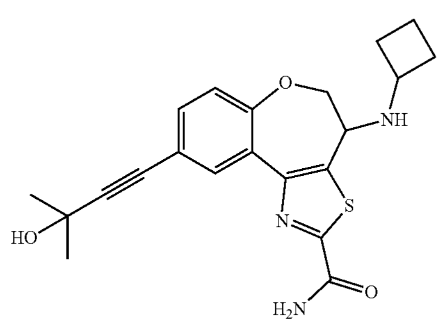 [SMILES: CC(C)(O)C#Cc1ccc2c(c1)-c1nc(C(N)=O)sc1C(NC1CCC1)CO2] | 4-cyclobutylamino-9-(3-hydroxy-3-methyl-but-1-ynyl)-4,5-dihydro-6-oxa-3-thia-1-aza-benzo[e]azulene-2-carboxylic acid amide |

TABLE 1A-continued

| No. | Structure | Name |
|---|---|---|
| 23 | 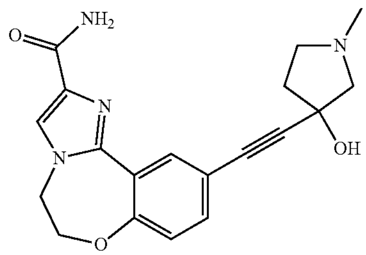 [SMILES: CN1CCC(O)(C#Cc2ccc3c(c2)-c2nc(C(N)=O)cn2CCO3)C1] | 9-(3-hydroxy-1-methyl-pyrrolidin-3-ylethynyl)-4,5-dihydro-6-oxa-1,3a-diaza-benzo[e]azulene-2-carboxylic acid amide |
| 24 | 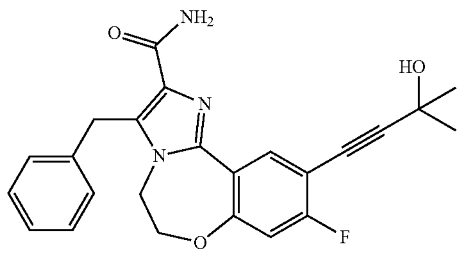 [SMILES: CC(C)(O)C#Cc1cc2c(cc1F)OCCn1c-2nc(C(N)=O)c1Cc1ccccc1] | 3-benzyl-8-fluoro-9-(3-hydroxy-3-methyl-but-1-ynyl)-4,5-dihydro-6-oxa-1,3a-diaza-benzo[e]azulene-2-carboxylic acid amide |
| 25 | 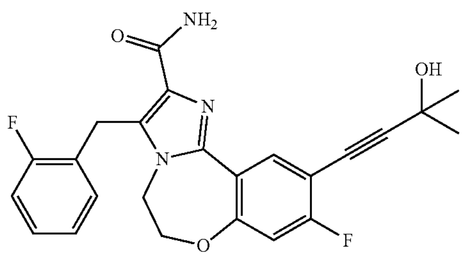 [SMILES: CC(C)(O)C#Cc1cc2c(cc1F)OCCn1c-2nc(C(N)=O)c1Cc1ccccc1F] | 8-fluoro-3-(2-fluoro-benzyl)-9-(3-hydroxy-3-methyl-but-1-ynyl)-4,5-dihydro-6-oxa-1,3a-diaza-benzo[e]azulene-2-carboxylic acid amide |
| 26 | 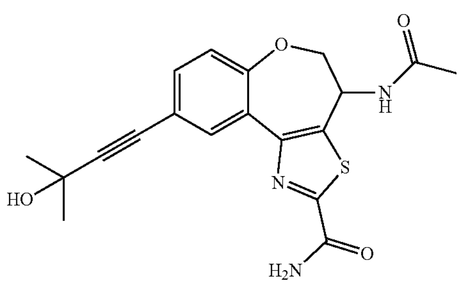 [SMILES: CC(=O)NC1COc2ccc(C#CC(C)(C)O)cc2-c2nc(C(N)=O)sc21] | 4-acetylamino-9-(3-hydroxy-3-methyl-but-1-ynyl)-4,5-dihydro-6-oxa-3-thia-1-aza-benzo[e]azulene-2-carboxylic acid amide |
| 27 | 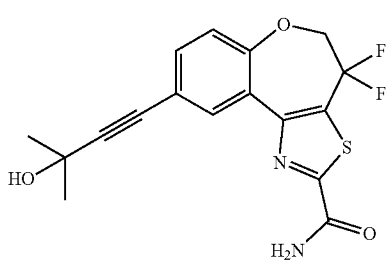 [SMILES: CC(C)(O)C#Cc1ccc2c(c1)-c1nc(C(N)=O)sc1C(F)(F)CO2] | 4,4-difluoro-9-(3-hydroxy-3-methyl-but-1-ynyl)-4,5-dihydro-6-oxa-3-thia-1-aza-benzo[e]azulene-2-carboxylic acid amide |
| 28 | 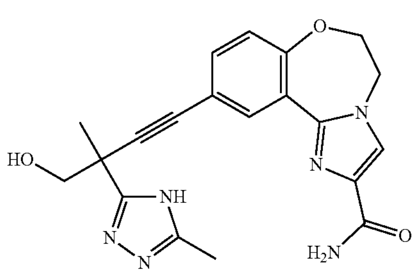 [SMILES: Cc1nnc(C(C)(C#Cc2ccc3c(c2)-c2nc(C(N)=O)cn2CCO3)CO)[nH]1] | 9-[4-hydroxy-3-methyl-3-(5-methyl-4H-[1,2,4]triazol-3-yl)-but-1-ynyl]-4,5-dihydro-6-oxa-1,3a-diaza-benzo[e]azulene-2-carboxylic acid amide |

TABLE 1A-continued

| No. | Structure | Name |
|---|---|---|
| 29 | 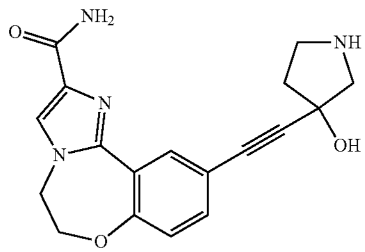 [SMILES: NC(=O)c1cn2c(n1)-c1cc(C#CC3(O)CCNC3)ccc1OCC2] | 9-(3-hydroxy-pyrrolidin-3-ylethynyl)-4,5-dihydro-6-oxa-1,3a-diaza-benzo[e]azulene-2-carboxylic acid amide |
| 30 | 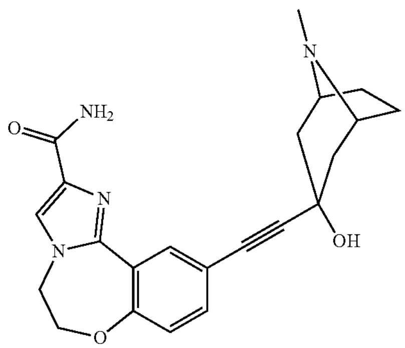 [SMILES: CN1C2CCC1CC(O)(C#Cc1ccc3c(c1)-c1nc(C(N)=O)cn1CCO3)C2] | 9-(3-hydroxy-8-methyl-8-aza-bicyclo[3.2.1]oct-3-ylethynyl)-4,5-dihydro-6-oxa-1,3a-diaza-benzo[e]azulene-2-carboxylic acid amide |
| 31 | 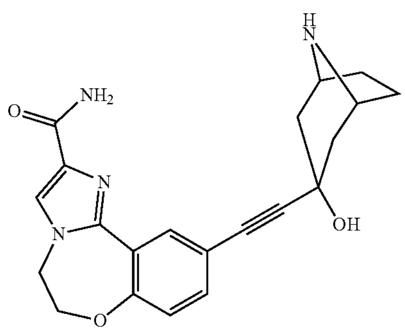 [SMILES: NC(=O)c1cn2c(n1)-c1cc(C#CC3(O)CC4CCC(C3)N4)ccc1OCC2] | 9-(3-hydroxy-8-aza-bicyclo[3.2.1]oct-3-ylethynyl)-4,5-dihydro-6-oxa-1,3a-diaza-benzo[e]azulene-2-carboxylic acid amide |
| 32 | 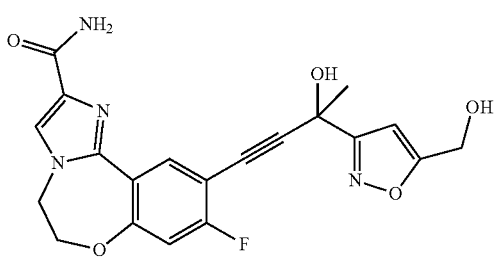 [SMILES: CC(O)(C#Cc1cc2c(cc1F)OCCn1cc(C(N)=O)nc1-2)c1cc(CO)on1] | 8-fluoro-9-[3-hydroxy-3-(5-hydroxymethyl-isoxazol-3-yl)-but-1-ynyl]-4,5-dihydro-6-oxa-1,3a-diaza-benzo[e]azulene-2-carboxylic acid amide |
| 33 | 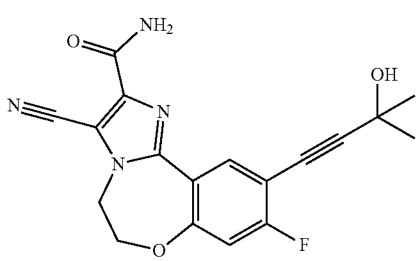 [SMILES: CC(C)(O)C#Cc1cc2c(cc1F)OCCn1c-2nc(C(N)=O)c1C#N] | 3-cyano-8-fluoro-9-(3-hydroxy-3-methyl-but-1-ynyl)-4,5-dihydro-6-oxa-1,3a-diaza-benzo[e]azulene-2-carboxylic acid amide |

TABLE 1A-continued

| No. | Structure | Name |
|---|---|---|
| 34 | 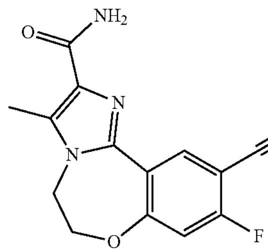 | 8-fluoro-9-(3-hydroxy-3-methyl-but-1-ynyl)-3-methyl-4,5-dihydro-6-oxa-1,3a-diaza-benzo[e]azulene-2-carboxylic acid amide |
| 35 | 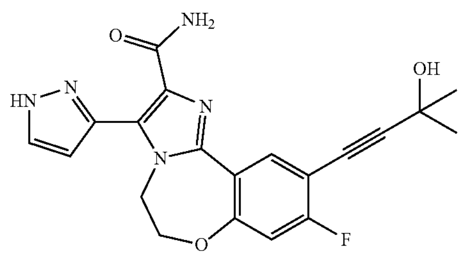 | 8-fluoro-9-(3-hydroxy-3-methyl-but-1-ynyl)-3-(1H-pyrazol-3-yl)-4,5-dihydro-6-oxa-1,3a-diaza-benzo[e]azulene-2-carboxylic acid amide |
| 36 | 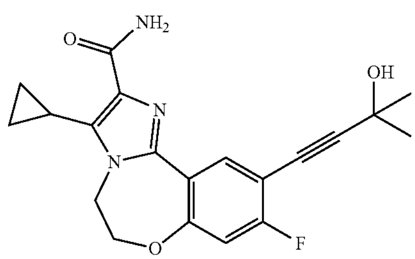 [SMILES: CC(C)(O)C#Cc1cc2c(cc1F)OCCn1c-2nc(C(N)=O)c1C1CC1] | 3-cyclopropyl-8-fluoro-9-(3-hydroxy-3-methyl-but-1-ynyl)-4,5-dihydro-6-oxa-1,3a-diaza-benzo[e]azulene-2-carboxylic acid amide |
| 38 | 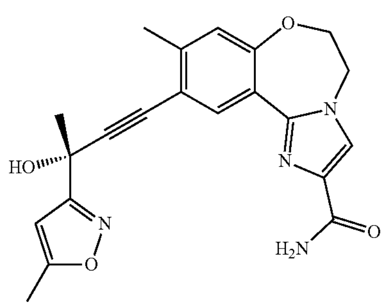 [SMILES: Cc1cc([C@](C)(O)C#Cc2cc3c(cc2C)OCCn2cc(C(N)=O)nc2-3)no1] | 9-[(R)-3-hydroxy-3-(5-methyl-isoxazol-3-yl)-but-1-ynyl]-8-methyl-4,5-dihydro-6-oxa-1,3a-diaza-benzo[e]azulene-2-carboxylic acid amide |
| 39 | 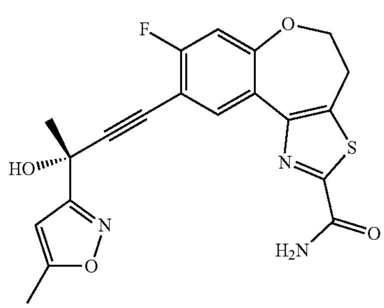 [SMILES: Cc1cc([C@](C)(O)C#Cc2cc3c(cc2F)OCCc2sc(C(N)=O)nc2-3)no1] | 8-fluoro-9-[(R)-3-hydroxy-3-(5-methyl-isoxazol-3-yl)-but-1-ynyl]-4,5-dihydro-6-oxa-3-thia-1-aza-benzo[e]azulene-2-carboxylic acid amide |

TABLE 1A-continued

| No. | Structure | Name |
|---|---|---|
| 40 | 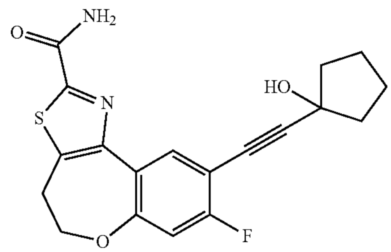 [SMILES: NC(=O)c1nc2c(s1)CCOc1cc(F)c(C#CC3(O)CCCC3)cc1-2] | 8-fluoro-9-(1-hydroxy-cyclopentylethynyl)-4,5-dihydro-6-oxa-3-thia-1-aza-benzo[e]azulene-2-carboxylic acid amide |
| 41 | 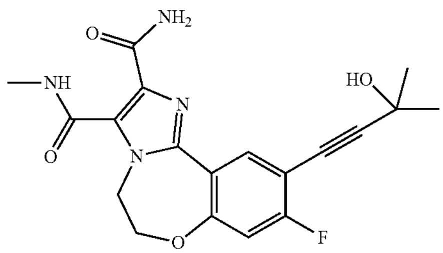 [SMILES: CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-methylamide |
| 42 | 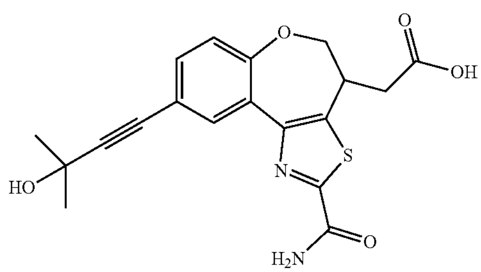 [SMILES: CC(C)(O)C#Cc1ccc2c(c1)-c1nc(C(N)=O)sc1C(CC(=O)O)CO2] | [2-carbamoyl-9-(3-hydroxy-3-methyl-but-1-ynyl)-4,5-dihydro-6-oxa-3-thia-1-aza-benzo[e]azulen-4-yl]-acetic acid |
| 43 | 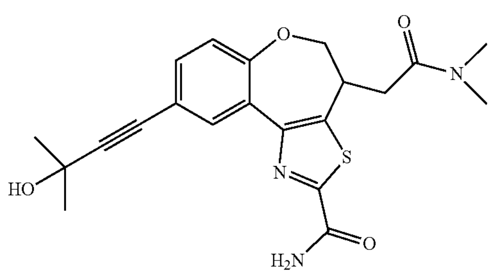 [SMILES: CN(C)C(=O)CC1COc2ccc(C#CC(C)(C)O)cc2-c2nc(C(N)=O)sc21] | 4-dimethylcarbamoylmethyl-9-(3-hydroxy-3-methyl-but-1-ynyl)-4,5-dihydro-6-oxa-3-thia-1-aza-benzo[e]azulene-2-carboxylic acid amide |
| 44 | 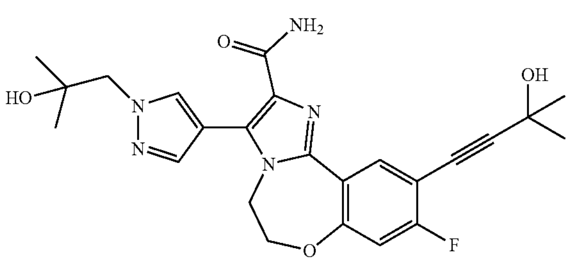 [SMILES: CC(C)(O)C#Cc1cc2c(cc1F)OCCn1c-2nc(C(N)=O)c1-c1cnn(CC(C)(C)O)c1] | 8-fluoro-9-(3-hydroxy-3-methyl-but-1-ynyl)-3-[1-(2-hydroxy-2-methyl-propyl)-1H-pyrazol-4-yl]-4,5-dihydro-6-oxa-1,3a-diaza-benzo[e]azulene-2-carboxylic acid amide |
| 45 | 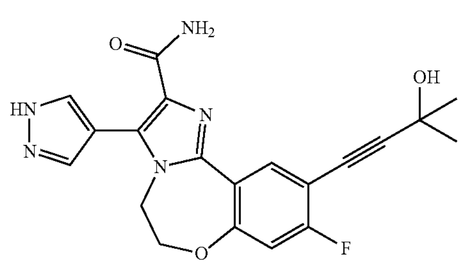 [SMILES: CC(C)(O)C#Cc1cc2c(cc1F)OCCn1c-2nc(C(N)=O)c1-c1cn[nH]c1] | 8-fluoro-9-(3-hydroxy-3-methyl-but-1-ynyl)-3-(1H-pyrazol-4-yl)-4,5-dihydro-6-oxa-1,3a-diaza-benzo[e]azulene-2-carboxylic acid amide |

TABLE 1A-continued

| No. | Structure | Name |
|---|---|---|
| 46 | 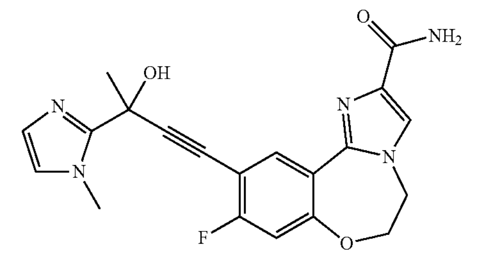 [SMILES: Cn1ccnc1C(C)(O)C#Cc1cc2c(cc1F)OCCn1cc(C(N)=O)nc1-2] | 8-fluoro-9-[3-hydroxy-3-(1-methyl-1H-imidazol-2-yl)-but-1-ynyl]-4,5-dihydro-6-oxa-1,3a-diaza-benzo[e]azulene-2-carboxylic acid amide |
| 47 | 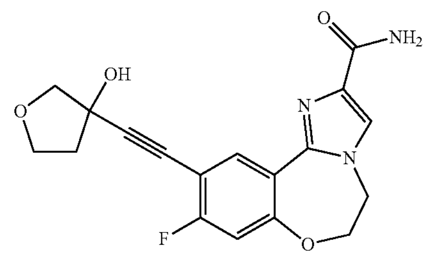 [SMILES: NC(=O)c1cn2c(n1)-c1cc(C#CC3(O)CCOC3)c(F)cc1OCC2] | 8-fluoro-9-(3-hydroxy-tetrahydro-furan-3-ylethynyl)-4,5-dihydro-6-oxa-1,3a-diaza-benzo[e]azulene-2-carboxylic acid amide |
| 48 | 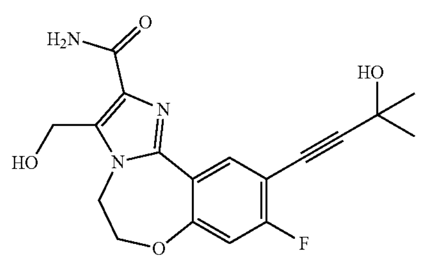 [SMILES: CC(C)(O)C#Cc1cc2c(cc1F)OCCn1c-2nc(C(N)=O)c1CO] | 8-fluoro-3-hydroxymethyl-9-(3-hydroxy-3-methyl-but-1-ynyl)-4,5-dihydro-6-oxa-1,3a-diaza-benzo[e]azulene-2-carboxylic acid amide |
| 49 | 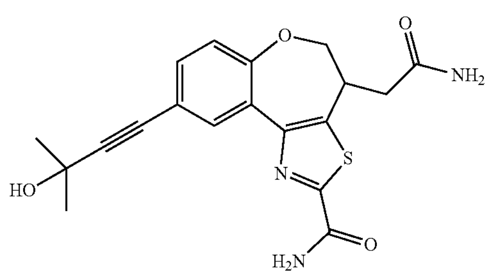 [SMILES: CC(C)(O)C#Cc1ccc2c(c1)-c1nc(C(N)=O)sc1C(CC(N)=O)CO2] | 4-carbamoylmethyl-9-(3-hydroxy-3-methyl-but-1-ynyl)-4,5-dihydro-6-oxa-3-thia-1-aza-benzo[e]azulene-2-carboxylic acid amide |
| 50 | 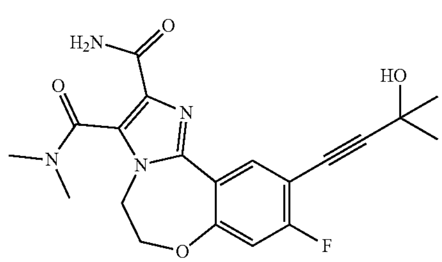 [SMILES: CN(C)C(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-dimethylamide |
| 51 | 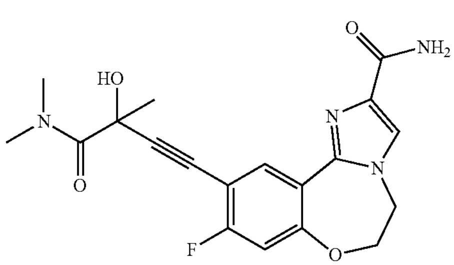 [SMILES: CN(C)C(=O)C(C)(O)C#Cc1cc2c(cc1F)OCCn1cc(C(N)=O)nc1-2] | 9-(3-dimethylcarbamoyl-3-hydroxy-but-1-ynyl)-8-fluoro-4,5-dihydro-6-oxa-1,3a-diaza-benzo[e]azulene-2-carboxylic acid amide |

TABLE 1A-continued

| No. | Structure | Name |
|---|---|---|
| 52 | 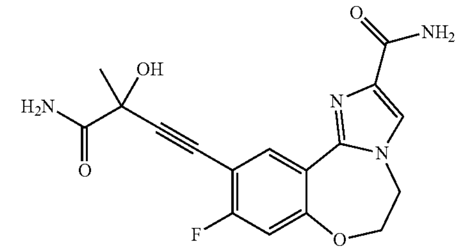 [SMILES: CC(O)(C#Cc1cc2c(cc1F)OCCn1cc(C(N)=O)nc1-2)C(N)=O] | 9-(3-carbamoyl-3-hydroxy-but-1-ynyl)-8-fluoro-4,5-dihydro-6-oxa-1,3a-diaza-benzo[e]azulene-2-carboxylic acid amide |
| 53 | 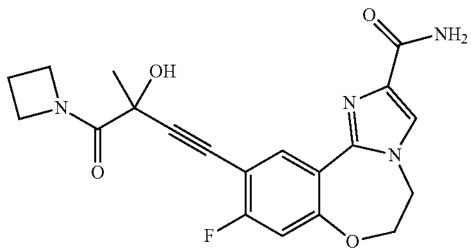 [SMILES: CC(O)(C#Cc1cc2c(cc1F)OCCn1cc(C(N)=O)nc1-2)C(=O)N1CCC1] | 9-(4-azetidin-1-yl-3-hydroxy-3-methyl-4-oxo-but-1-ynyl)-8-fluoro-4,5-dihydro-6-oxa-1,3a-diaza-benzo[e]azulene-2-carboxylic acid amide |
| 54 | 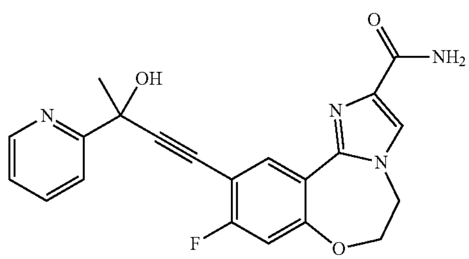 [SMILES: CC(O)(C#Cc1cc2c(cc1F)OCCn1cc(C(N)=O)nc1-2)c1ccccn1] | 8-fluoro-9-(3-hydroxy-3-pyridin-2-yl-but-1-ynyl)-4,5-dihydro-6-oxa-1,3a-diaza-benzo[e]azulene-2-carboxylic acid amide |
| 55 | 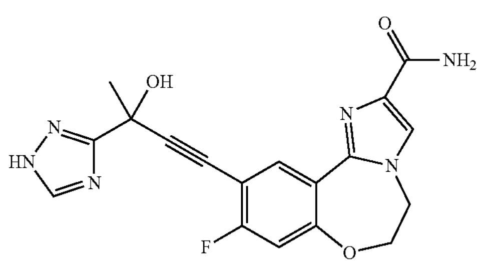 [SMILES: CC(O)(C#Cc1cc2c(cc1F)OCCn1cc(C(N)=O)nc1-2)c1nc[nH]n1] | 8-fluoro-9-[3-hydroxy-3-(1H-[1,2,4]triazol-3-yl)-but-1-ynyl]-4,5-dihydro-6-oxa-1,3a-diaza-benzo[e]azulene-2-carboxylic acid amide |
| 56 | 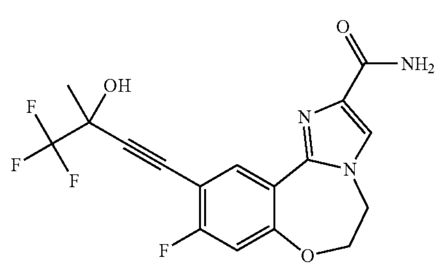 [SMILES: CC(O)(C#Cc1cc2c(cc1F)OCCn1cc(C(N)=O)nc1-2)C(F)(F)F] | 8-fluoro-9-(4,4,4-trifluoro-3-hydroxy-3-methyl-but-1-ynyl)-4,5-dihydro-6-oxa-1,3a-diaza-benzo[e]azulene-2-carboxylic acid amide |
| 57 | 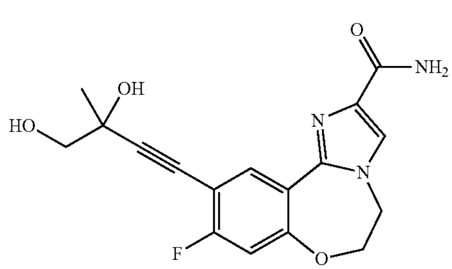 [SMILES: CC(O)(C#Cc1cc2c(cc1F)OCCn1cc(C(N)=O)nc1-2)CO] | 9-(3,4-dihydroxy-3-methyl-but-1-ynyl)-8-fluoro-4,5-dihydro-6-oxa-1,3a-diaza-benzo[e]azulene-2-carboxylic acid amide |

TABLE 1A-continued

| No. | Structure | Name |
|---|---|---|
| 58 | 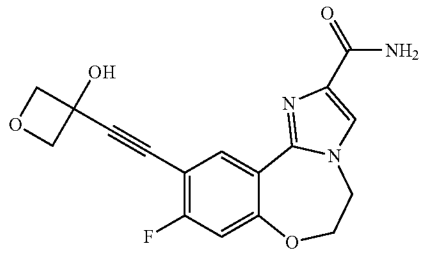 [SMILES: NC(=O)c1cn2c(n1)-c1cc(C#CC3(O)COC3)c(F)cc1OCC2] | 8-fluoro-9-(3-hydroxy-oxetan-3-ylethynyl)-4,5-dihydro-6-oxa-1,3a-diaza-benzo[e]azulene-2-carboxylic acid amide |
| 59 | 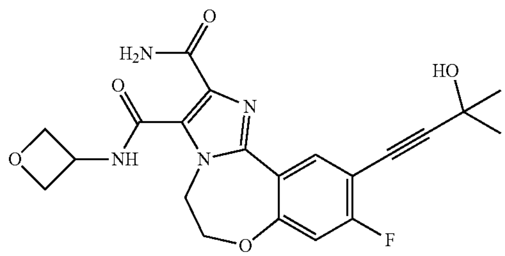 [SMILES: CC(C)(O)C#Cc1cc2c(cc1F)OCCn1c-2nc(C(N)=O)c1C(=O)NC1COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-oxetan-3-ylamide |
| 60 | 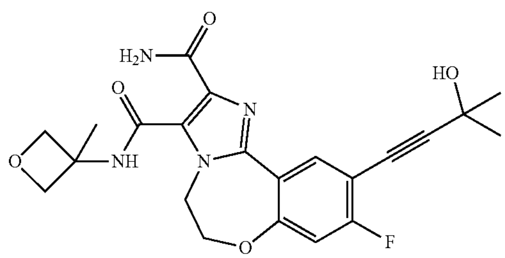 [SMILES: CC(C)(O)C#Cc1cc2c(cc1F)OCCn1c-2nc(C(N)=O)c1C(=O)NC1(C)COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(3-methyl-oxetan-3-yl)-amide] |
| 61 | 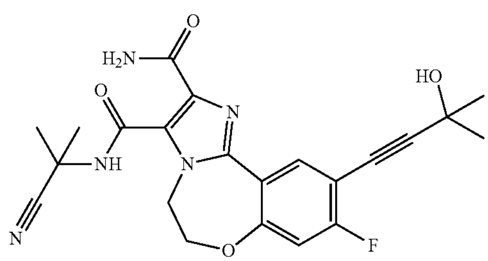 [SMILES: CC(C)(O)C#Cc1cc2c(cc1F)OCCn1c-2nc(C(N)=O)c1C(=O)NC(C)(C)C#N] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(cyano-dimethyl-methyl)-amide] |
| 62 | 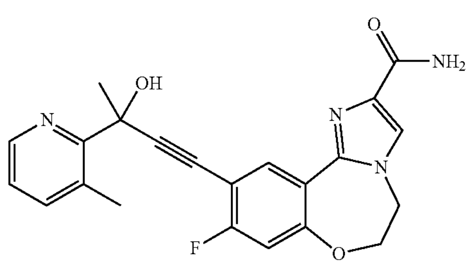 [SMILES: Cc1cccnc1C(C)(O)C#Cc1cc2c(cc1F)OCCn1cc(C(N)=O)nc1-2] | 8-fluoro-9-[3-hydroxy-3-(3-methyl-pyridin-2-yl)-but-1-ynyl]-4,5-dihydro-6-oxa-1,3a-diaza-benzo[e]azulene-2-carboxylic acid amide |
| 63 | 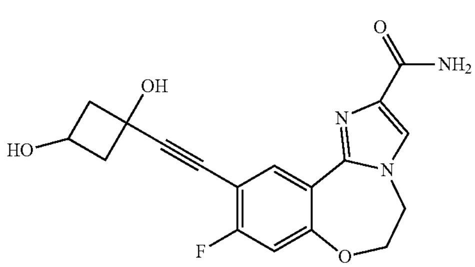 [SMILES: NC(=O)c1cn2c(n1)-c1cc(C#CC3(O)CC(O)C3)c(F)cc1OCC2] | 9-(1,3-dihydroxy-cyclobutylethynyl)-8-fluoro-4,5-dihydro-6-oxa-1,3a-diaza-benzo[e]azulene-2-carboxylic acid amide |

TABLE 1A-continued

| No. | Structure | Name |
|---|---|---|
| 64 | 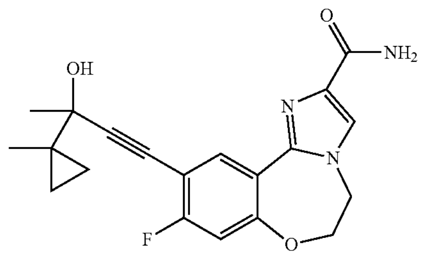 [SMILES: CC(O)(C#Cc1cc2c(cc1F)OCCn1cc(C(N)=O)nc1-2)C1(C)CC1] | 8-fluoro-9-[3-hydroxy-3-(1-methyl-cyclopropyl)-but-1-ynyl]-4,5-dihydro-6-oxa-1,3a-diaza-benzo[e]azulene-2-carboxylic acid amide |
| 65 | 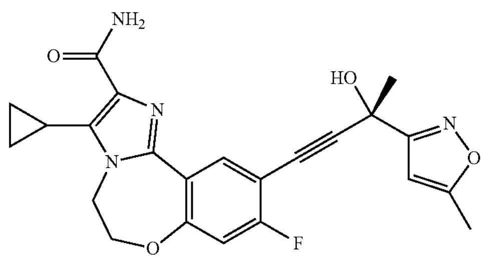 [SMILES: Cc1cc([C@@](C)(O)C#Cc2cc3c(cc2F)OCCn2c-3nc(C(N)=O)c2C2CC2)no1] | 3-cyclopropyl-8-fluoro-9-[(S)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 66 | 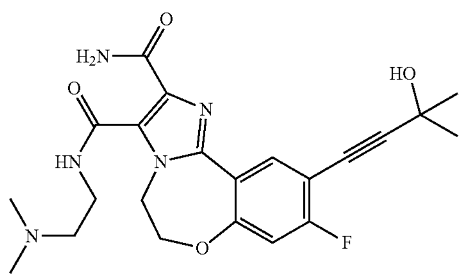 [SMILES: CN(C)CCNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-dimethylamino-ethyl)-amide] |
| 67 | 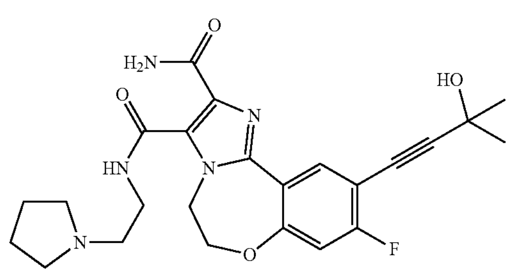 [SMILES: CC(C)(O)C#Cc1cc2c(cc1F)OCCn1c-2nc(C(N)=O)c1C(=O)NCCN1CCCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-pyrrolidin-1-yl-ethyl)-amide] |
| 68 | 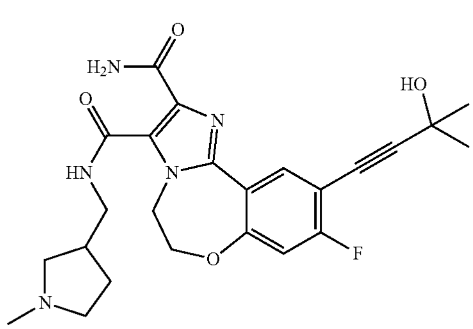 [SMILES: CN1CCC(CNC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-3-ylmethyl)-amide] |

TABLE 1A-continued

| No. | Structure | Name |
|---|---|---|
| 69 | 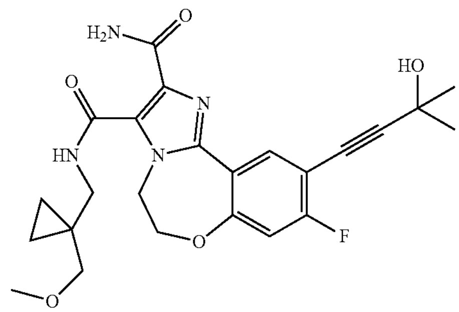 [SMILES: COCC1(CNC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methoxymethyl-cyclopropylmethyl)-amide] |
| 70 | 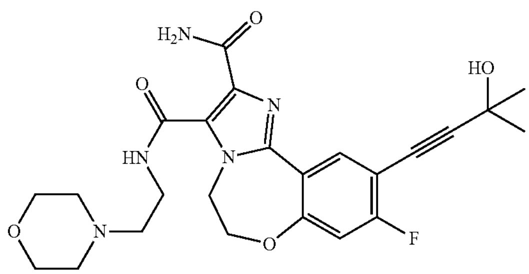 [SMILES: CC(C)(O)C#Cc1cc2c(cc1F)OCCn1c-2nc(C(N)=O)c1C(=O)NCCN1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-morpholin-4-yl-ethyl)-amide] |
| 71 | 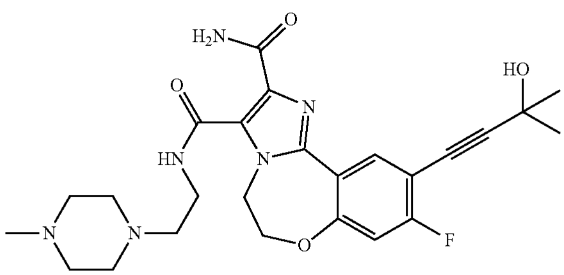 [SMILES: CN1CCN(CCNC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-{[2-(4-methyl-piperazin-1-yl)-ethyl]-amide} |
| 72 | 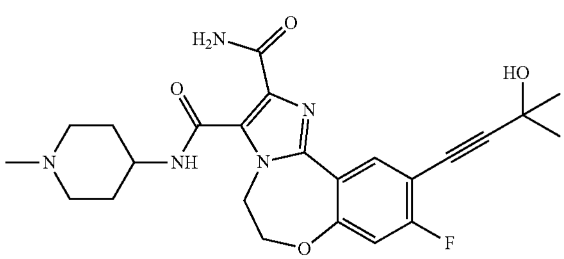 [SMILES: CN1CCC(NC(=O)c2c(C(N)=O)nc3n2CCOc2cc(F)c(C#CC(C)(C)O)cc2-3)CC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-piperidin-4-yl)-amide] |
| 73 | 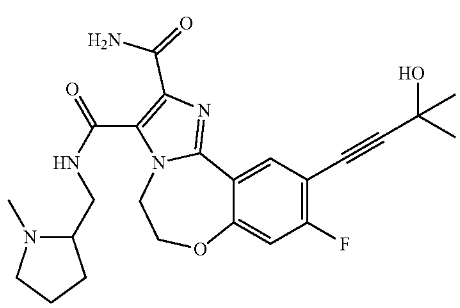 [SMILES: CN1CCCC1CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-2-ylmethyl)-amide] |

TABLE 1A-continued

| No. | Structure | Name |
|---|---|---|
| 74 | 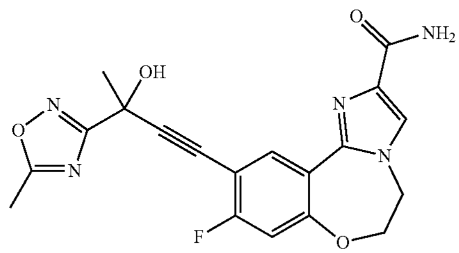 [SMILES: Cc1nc(C(C)(O)C#Cc2cc3c(cc2F)OCCn2cc(C(N)=O)nc2-3)no1] | 8-fluoro-9-[3-hydroxy-3-(5-methyl-[1,2,4]oxadiazol-3-yl)-but-1-ynyl]-4,5-dihydro-6-oxa-1,3a-diaza-benzo[e]azulene-2-carboxylic acid amide |
| 75 | 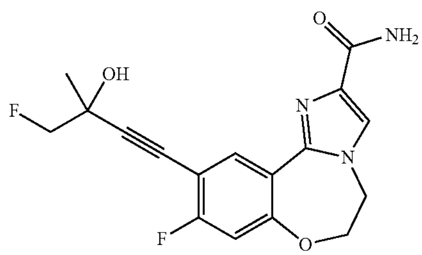 [SMILES: CC(O)(C#Cc1cc2c(cc1F)OCCn1cc(C(N)=O)nc1-2)CF] | 8-fluoro-9-(4-fluoro-3-hydroxy-3-methyl-but-1-ynyl)-4,5-dihydro-6-oxa-1,3a-diaza-benzo[e]azulene-2-carboxylic acid amide |
| 76 | 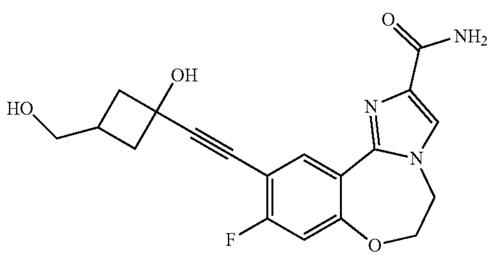 [SMILES: NC(=O)c1cn2c(n1)-c1cc(C#CC3(O)CC(CO)C3)c(F)cc1OCC2] | 8-fluoro-9-(1-hydroxy-3-hydroxymethyl-cyclobutylethynyl)-4,5-dihydro-6-oxa-1,3a-diaza-benzo[e]azulene-2-carboxylic acid amide |
| 77 | 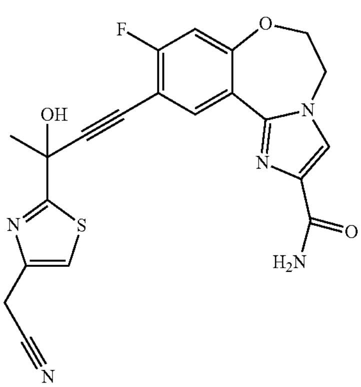 [SMILES: CC(O)(C#Cc1cc2c(cc1F)OCCn1cc(C(N)=O)nc1-2)c1nc(CC#N)cs1] | 9-[3-(4-cyanomethyl-thiazol-2-yl)-3-hydroxy-but-1-ynyl]-8-fluoro-4,5-dihydro-6-oxa-1,3a-diaza-benzo[e]azulene-2-carboxylic acid amide |
| 78 | 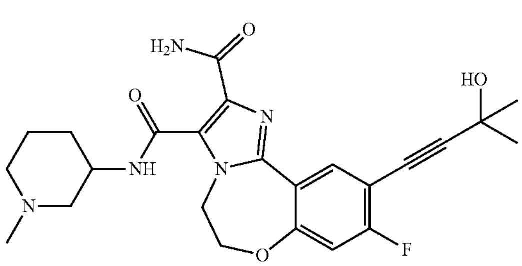 [SMILES: CN1CCCC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-piperidin-3-yl)-amide] |

TABLE 1A-continued

| No. | Structure | Name |
|---|---|---|
| 79 | 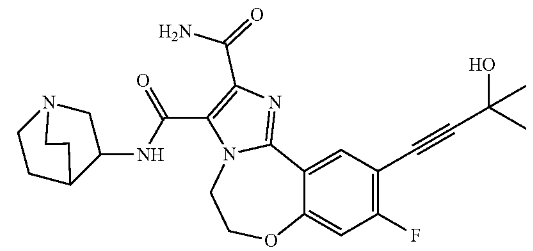 [SMILES: CC(C)(O)C#Cc1cc2c(cc1F)OCCn1c-2nc(C(N)=O)c1C(=O)NC1CN2CCC1CC2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-aza-bicyclo[2.2.2]oct-3-yl)-amide] |
| 80 | 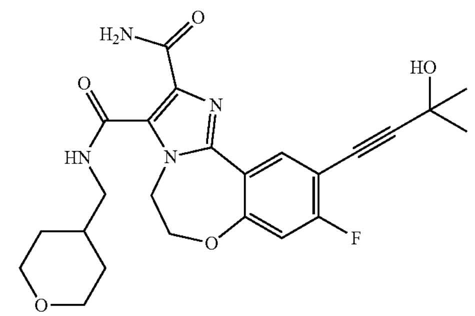 [SMILES: CC(C)(O)C#Cc1cc2c(cc1F)OCCn1c-2nc(C(N)=O)c1C(=O)NCC1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-pyran-4-ylmethyl)-amide] |
| 81 | 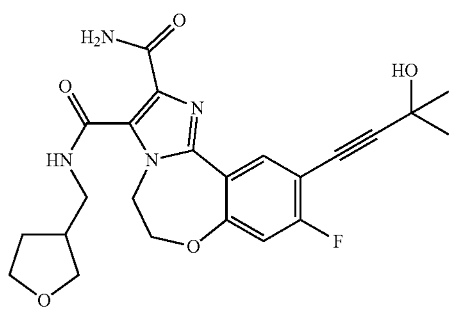 [SMILES: CC(C)(O)C#Cc1cc2c(cc1F)OCCn1c-2nc(C(N)=O)c1C(=O)NCC1CCOC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-furan-3-ylmethyl)-amide] |
| 82 | 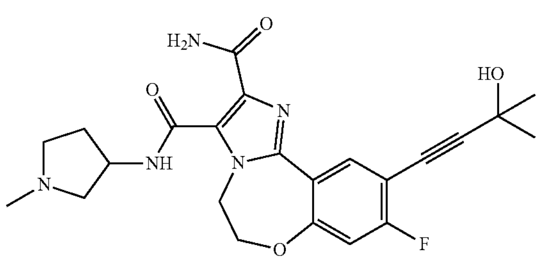 [SMILES: CN1CCC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-pyrrolidin-3-yl)-amide] |
| 83 | 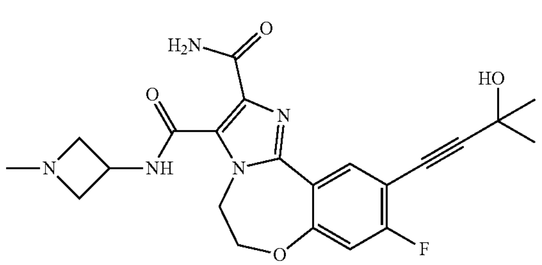 [SMILES: CN1CC(NC(=O)c2c(C(N)=O)nc3n2CCOc2cc(F)c(C#CC(C)(C)O)cc2-3)C1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(1-methyl-azetidin-3-yl)-amide] |

TABLE 1A-continued

| No. | Structure | Name |
|---|---|---|
| 84 | 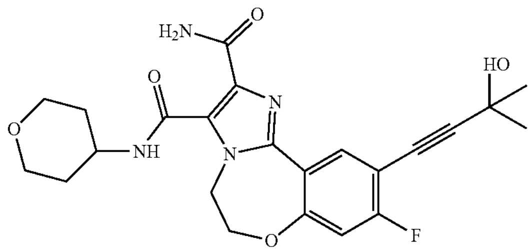 [SMILES: CC(C)(O)C#Cc1cc2c(cc1F)OCCn1c-2nc(C(N)=O)c1C(=O)NC1CCOCC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-pyran-4-yl)-amide] |
| 85 | 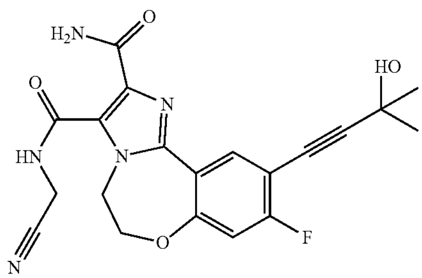 [SMILES: CC(C)(O)C#Cc1cc2c(cc1F)OCCn1c-2nc(C(N)=O)c1C(=O)NCC#N] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-cyanomethyl-amide |
| 86 | 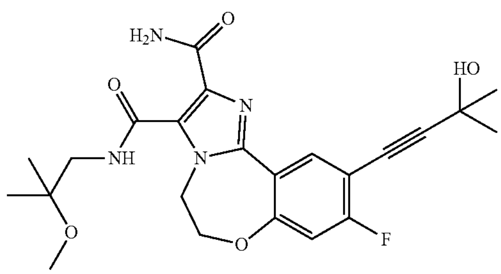 [SMILES: COC(C)(C)CNC(=O)c1c(C(N)=O)nc2n1CCOc1cc(F)c(C#CC(C)(C)O)cc1-2] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(2-methoxy-2-methyl-propyl)-amide] |
| 87 | 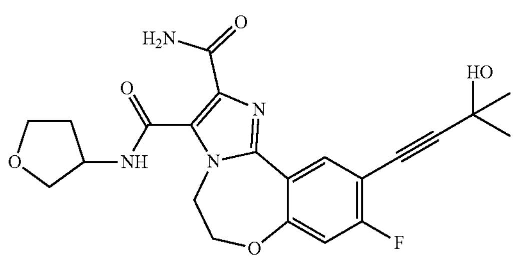 [SMILES: CC(C)(O)C#Cc1cc2c(cc1F)OCCn1c-2nc(C(N)=O)c1C(=O)NC1CCOC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(tetrahydro-furan-3-yl)-amide] |
| 88 | 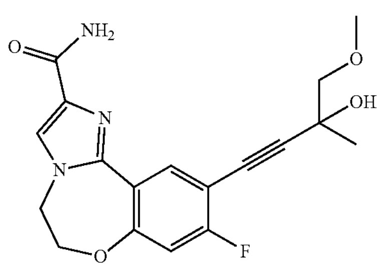 [SMILES: COCC(C)(O)C#Cc1cc2c(cc1F)OCCn1cc(C(N)=O)nc1-2] | 8-fluoro-9-(3-hydroxy-4-methoxy-3-methyl-but-1-ynyl)-4,5-dihydro-6-oxa-1,3a-diaza-benzo[e]azulene-2-carboxylic acid amide |
| 89 | 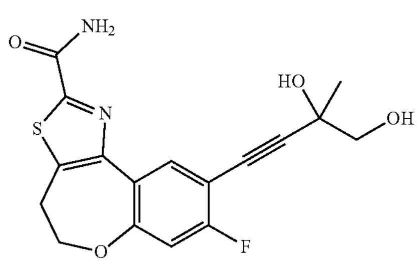 [SMILES: CC(O)(C#Cc1cc2c(cc1F)OCCc1sc(C(N)=O)nc1-2)CO] | 9-(3,4-dihydroxy-3-methyl-but-1-ynyl)-8-fluoro-4,5-dihydro-6-oxa-3-thia-1-aza-benzo[e]azulene-2-carboxylic acid amide |

TABLE 1A-continued

| No. | Structure | Name |
|---|---|---|
| 90 | 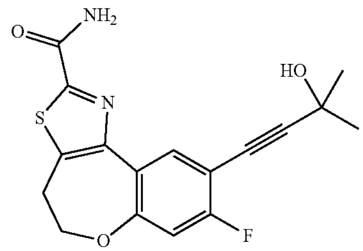 [SMILES: CC(C)(O)C#Cc1cc2c(cc1F)OCCc1sc(C(N)=O)nc1-2] | 8-fluoro-9-(3-hydroxy-3-methyl-but-1-ynyl)-4,5-dihydro-6-oxa-3-thia-1-aza-benzo[e]azulene-2-carboxylic acid amide |
| 91 | 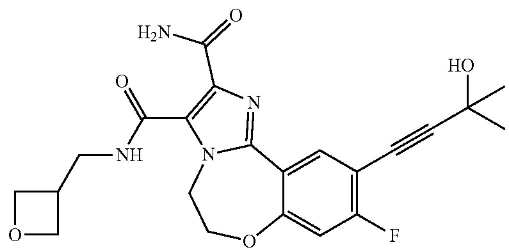 [SMILES: CC(C)(O)C#Cc1cc2c(cc1F)OCCn1c-2nc(C(N)=O)c1C(=O)NCC1COC1] | 8-fluoro-9-(3-hydroxy-3-methyl-but-1-ynyl)-4,5-dihydro-6-oxa-1,3a-diaza-benzo[e]azulene-2,3-dicarboxylic acid 2-amide 3-[(oxetan-3-ylmethyl)-amide] |
| 92 | 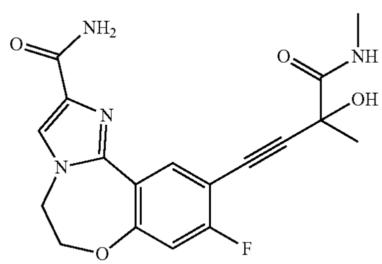 [SMILES: CNC(=O)C(C)(O)C#Cc1cc2c(cc1F)OCCn1cc(C(N)=O)nc1-2] | 8-fluoro-9-(3-hydroxy-3-methylcarbamoyl-but-1-ynyl)-4,5-dihydro-6-oxa-1,3a-diaza-benzo[e]azulene-2-carboxylic acid amide |
| 93 | 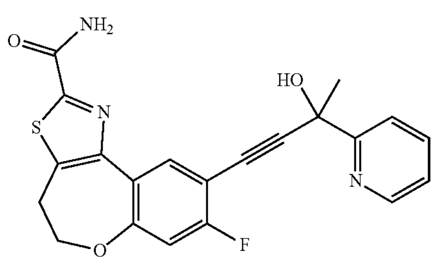 [SMILES: CC(O)(C#Cc1cc2c(cc1F)OCCc1sc(C(N)=O)nc1-2)c1ccccn1] | 8-fluoro-9-(3-hydroxy-3-pyridin-2-yl-but-1-ynyl)-4,5-dihydro-6-oxa-3-thia-1-aza-benzo[e]azulene-2-carboxylic acid amide |
| 94 | 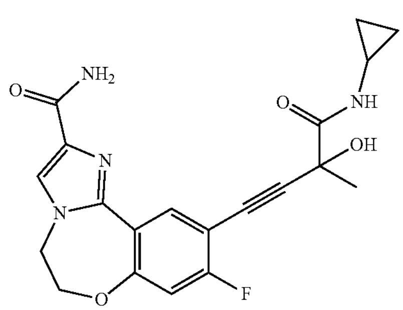 [SMILES: CC(O)(C#Cc1cc2c(cc1F)OCCn1cc(C(N)=O)nc1-2)C(=O)NC1CC1] | 9-(3-cyclopropylcarbamoyl-3-hydroxy-but-1-ynyl)-8-fluoro-4,5-dihydro-6-oxa-1,3a-diaza-benzo[e]azulene-2-carboxylic acid amide |

TABLE 1A-continued

| No. | Structure | Name |
|---|---|---|
| 95 | 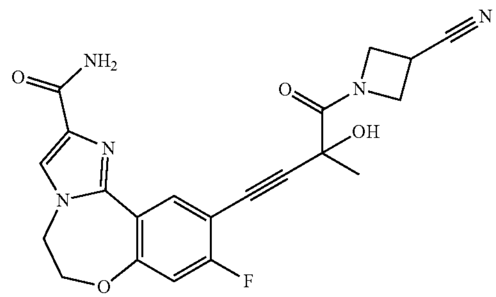 [SMILES: CC(O)(C#Cc1cc2c(cc1F)OCCn1cc(C(N)=O)nc1-2)C(=O)N1CC(C#N)C1] | 9-[4-(3-cyano-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide |
| 96 | 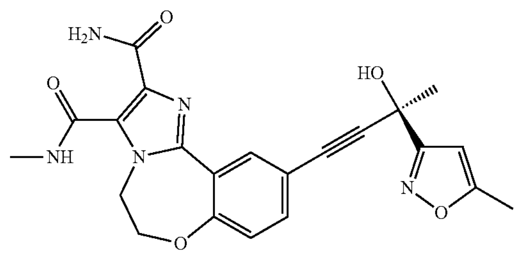 | 9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-methylamide |
| 97 | 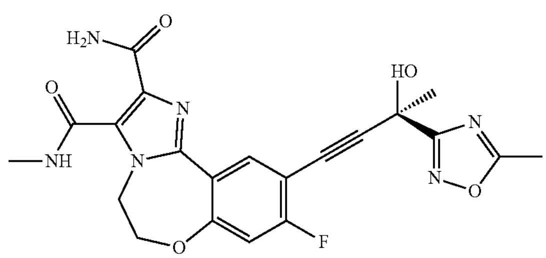 | 8-fluoro-9-[(R)-3-hydroxy-3-(5-methyl-[1,2,4]oxadiazol-3-yl)-but-1-ynyl]-4,5-dihydro-6-oxa-1,3a-diaza-benzo[e]azulene-2,3-dicarboxylic acid 2-amide 3-methylamide |
| 98 | 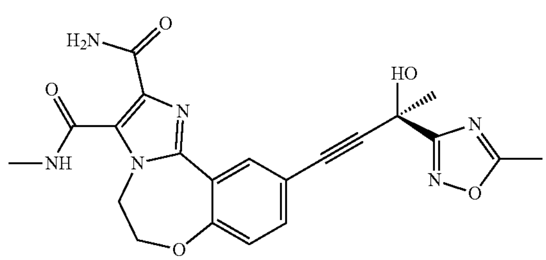 | 9-[(R)-3-hydroxy-3-(5-methyl-[1,2,4]oxadiazol-3-yl)-but-1-ynyl]-4,5-dihydro-6-oxa-1,3a-diaza-benzo[e]azulene-2,3-dicarboxylic acid 2-amide 3-methylamide |
| 99 | 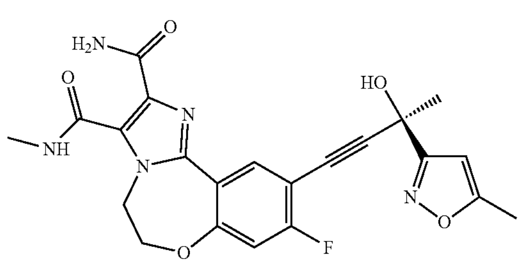 | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-methylamide |
| 100 | 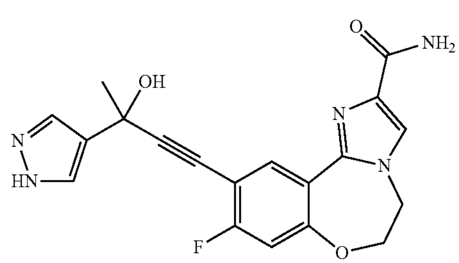 [SMILES: CC(O)(C#Cc1cc2c(cc1F)OCCn1cc(C(N)=O)nc1-2)c1cn[nH]c1] | 8-fluoro-9-[3-hydroxy-3-(1H-pyrazol-4-yl)-but-1-ynyl]-4,5-dihydro-6-oxa-1,3a-diaza-benzo[e]azulene-2-carboxylic acid amide |

TABLE 1A-continued

| No. | Structure | Name |
|---|---|---|
| 101 | 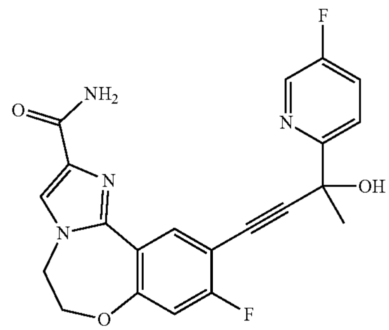 [SMILES: CC(O)(C#Cc1cc2c(cc1F)OCCn1cc(C(N)=O)nc1-2)c1ccc(F)cn1] | 8-fluoro-9-[3-(5-fluoro-pyridin-2-yl)-3-hydroxy-but-1-ynyl]-4,5-dihydro-6-oxa-1,3a-diaza-benzo[e]azulene-2-carboxylic acid amide |
| 102 | 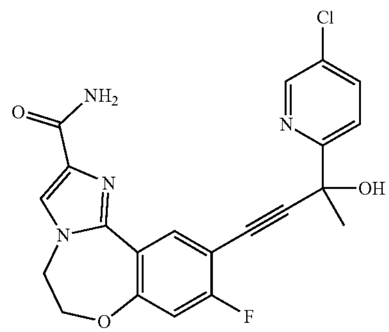 [SMILES: CC(O)(C#Cc1cc2c(cc1F)OCCn1cc(C(N)=O)nc1-2)c1ccc(Cl)cn1] | 9-[3-(5-chloro-pyridin-2-yl)-3-hydroxy-but-1-ynyl]-8-fluoro-4,5-dihydro-6-oxa-1,3a-diaza-benzo[e]azulene-2-carboxylic acid amide |
| 103 | 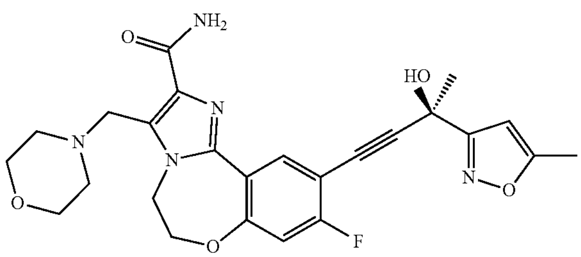 [SMILES: Cc1cc([C@](C)(O)C#Cc2cc3c(cc2F)OCCn2c-3nc(C(N)=O)c2CN2CCOCC2)no1] | 9-[(R)-3-hydroxy-3-(5-methyl-isoxazol-3-yl)-but-1-ynyl]-3-morpholin-4-ylmethyl-4,5-dihydro-6-oxa-1,3a-diaza-benzo[e]azulene-2-carboxylic acid amide |
| 104 | 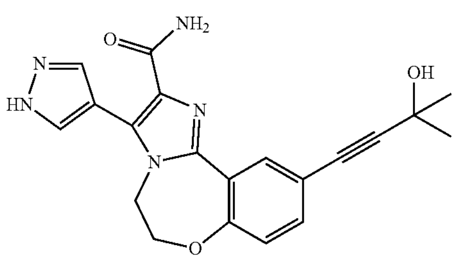 [SMILES: CC(C)(O)C#Cc1ccc2c(c1)-c1nc(C(N)=O)c(-c3cn[nH]c3)n1CCO2] | 9-(3-hydroxy-3-methyl-but-1-ynyl)-3-(1H-pyrazol-4-yl)-4,5-dihydro-6-oxa-1,3a-diaza-benzo[e]azulene-2-carboxylic acid amide |
| 105 | 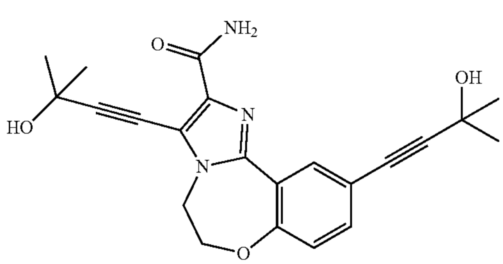 [SMILES: CC(C)(O)C#Cc1ccc2c(c1)-c1nc(C(N)=O)c(C#CC(C)(C)O)n1CCO2] | 3,9-bis-(3-hydroxy-3-methyl-but-1-ynyl)-4,5-dihydro-6-oxa-1,3a-diaza-benzo[e]azulene-2-carboxylic acid amide |

TABLE 1A-continued

| No. | Structure | Name |
|---|---|---|
| 106 | 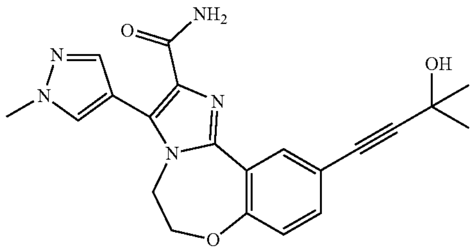 [SMILES: Cn1cc(-c2c(C(N)=O)nc3n2CCOc2ccc(C#CC(C)(C)O)cc2-3)cn1] | 9-(3-hydroxy-3-methyl-but-1-ynyl)-3-(1-methyl-1H-pyrazol-4-yl)-4,5-dihydro-6-oxa-1,3a-diaza-benzo[e]azulene-2-carboxylic acid amide |
| 107 | 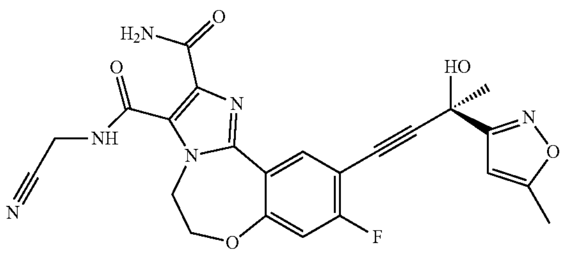 [SMILES: Cc1cc([C@](C)(O)C#Cc2cc3c(cc2F)OCCn2c-3nc(C(N)=O)c2C(=O)NCC#N)no1] | 8-fluoro-9-[(R)-3-hydroxy-3-(5-methyl-isoxazol-3-yl)-but-1-ynyl]-4,5-dihydro-6-oxa-1,3a-diaza-benzo[e]azulene-2,3-dicarboxylic acid 2-amide 3-cyanomethyl-amide |
| 108 | 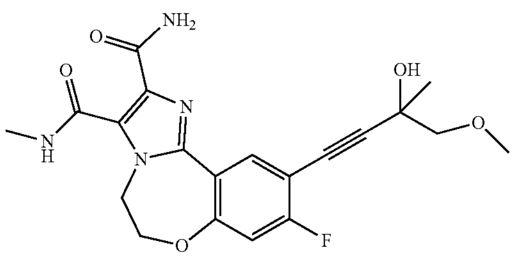 | 8-fluoro-9-(3-hydroxy-4-methoxy-3-methyl-but-1-ynyl)-4,5-dihydro-6-oxa-1,3a-diaza-benzo[e]azulene-2,3-dicarboxylic acid 2-amide 3-methylamide |
| 109 | 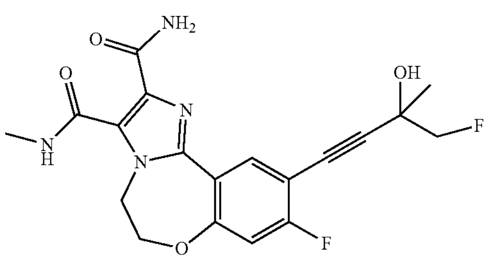 [SMILES: CNC(=O)c1c(C(N)=O)nc2n1CCOc1cc(F)c(C#CC(C)(O)CF)cc1-2] | 8-fluoro-9-(4-fluoro-3-hydroxy-3-methyl-but-1-ynyl)-4,5-dihydro-6-oxa-1,3a-diaza-benzo[e]azulene-2,3-dicarboxylic acid 2-amide 3-methylamide |
| 110 | 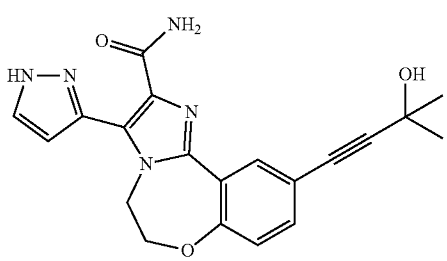 [SMILES: CC(C)(O)C#Cc1ccc2c(c1)-c1nc(C(N)=O)c(-c3cc[nH]n3)n1CCO2] | 9-(3-hydroxy-3-methyl-but-1-ynyl)-3-(1H-pyrazol-3-yl)-4,5-dihydro-6-oxa-1,3a-diaza-benzo[e]azulene-2-carboxylic acid amide |
| 111 | 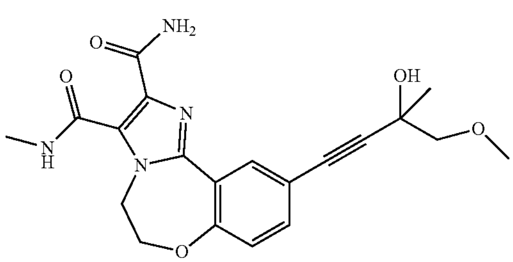 | 9-(3-hydroxy-4-methoxy-3-methyl-but-1-ynyl)-4,5-dihydro-6-oxa-1,3a-diaza-benzo[e]azulene-2,3-dicarboxylic acid 2-amide 3-methylamide |

TABLE 1A-continued

| No. | Structure | Name |
| --- | --- | --- |
| 112 | 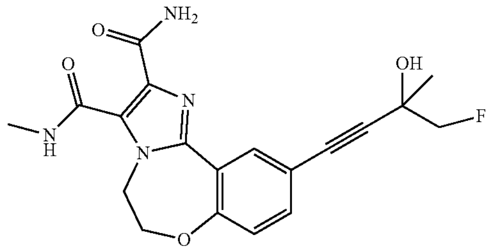 [SMILES: CNC(=O)c1c(C(N)=O)nc2n1CCOc1ccc(C#CC(C)(O)CF)cc1-2] | 9-(4-fluoro-3-hydroxy-3-methyl-but-1-ynyl)-4,5-dihydro-6-oxa-1,3a-diaza-benzo[e]azulene-2,3-dicarboxylic acid 2-amide 3-methylamide |
| 113 | 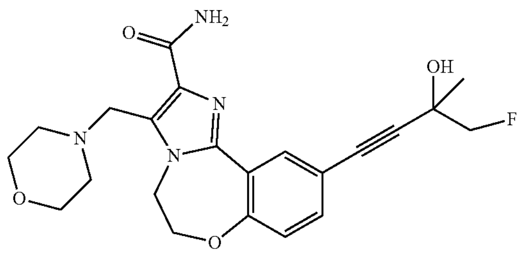 [SMILES: CC(O)(C#Cc1ccc2c(c1)-c1nc(C(N)=O)c(CN3CCOCC3)n1CCO2)CF] | 9-(4-fluoro-3-hydroxy-3-methyl-but-1-ynyl)-3-morpholin-4-ylmethyl-4,5-dihydro-6-oxa-1,3a-diaza-benzo[e]azulene-2-carboxylic acid amide |
| 114 | 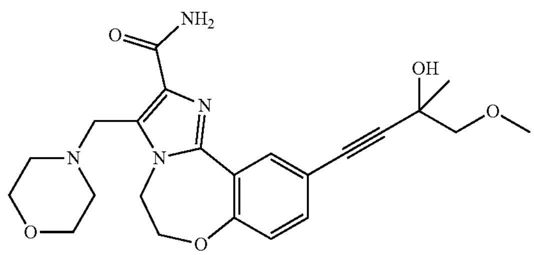 [SMILES: COCC(C)(O)C#Cc1ccc2c(c1)-c1nc(C(N)=O)c(CN3CCOCC3)n1CCO2] | 9-(3-hydroxy-4-methoxy-3-methyl-but-1-ynyl)-3-morpholin-4-ylmethyl-4,5-dihydro-6-oxa-1,3a-diaza-benzo[e]azulene-2-carboxylic acid amide |
| 115 | 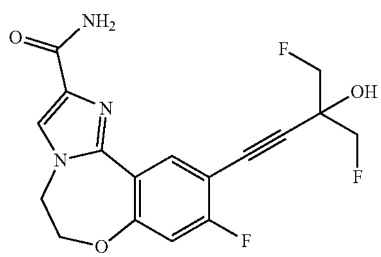 [SMILES: NC(=O)c1cn2c(n1)-c1cc(C#CC(O)(CF)CF)c(F)cc1OCC2] | 8-fluoro-9-(4-fluoro-3-fluoromethyl-3-hydroxy-but-1-ynyl)-4,5-dihydro-6-oxa-1,3a-diaza-benzo[e]azulene-2-carboxylic acid amide |
| 116 | 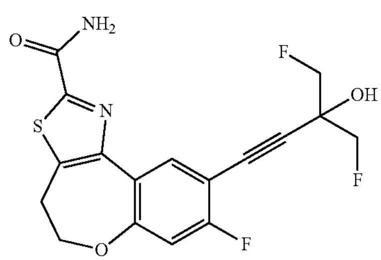 [SMILES: NC(=O)c1nc2c(s1)CCOc1cc(F)c(C#CC(O)(CF)CF)cc1-2] | 8-fluoro-9-(4-fluoro-3-fluoromethyl-3-hydroxy-but-1-ynyl)-4,5-dihydro-6-oxa-3-thia-1-aza-benzo[e]azulene-2-carboxylic acid amide |
| 117 | 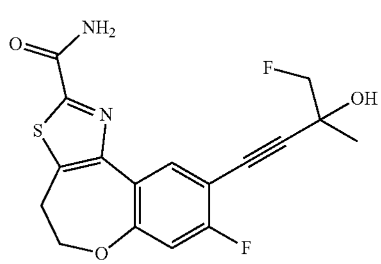 [SMILES: CC(O)(C#Cc1cc2c(cc1F)OCCc1sc(C(N)=O)nc1-2)CF] | 8-fluoro-9-(4-fluoro-3-hydroxy-3-methyl-but-1-ynyl)-4,5-dihydro-6-oxa-3-thia-1-aza-benzo[e]azulene-2-carboxylic acid amide |

TABLE 1A-continued

| No. | Structure | Name |
|---|---|---|
| 118 | 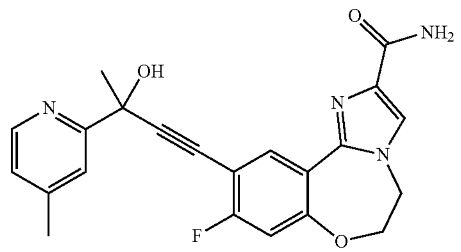 [SMILES: Cc1ccnc(C(C)(O)C#Cc2cc3c(cc2F)OCCn2cc(C(N)=O)nc2-3)c1] | 8-fluoro-9-[3-hydroxy-3-(4-methyl-pyridin-2-yl)-but-1-ynyl]-4,5-dihydro-6-oxa-1,3a-diaza-benzo[e]azulene-2-carboxylic acid amide |
| 119 | 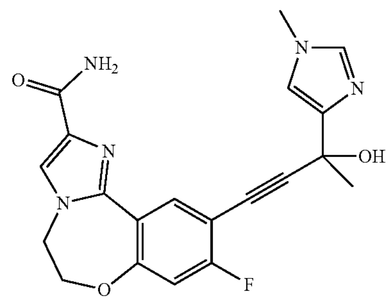 [SMILES: Cn1cnc(C(C)(O)C#Cc2cc3c(cc2F)OCCn2cc(C(N)=O)nc2-3)c1] | 8-fluoro-9-[3-hydroxy-3-(1-methyl-1H-imidazol-4-yl)-but-1-ynyl]-4,5-dihydro-6-oxa-1,3a-diaza-benzo[e]azulene-2-carboxylic acid amide |
| 120 | 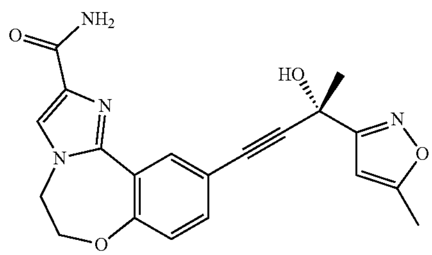 [SMILES: Cc1cc([C@@](C)(O)C#Cc2ccc3c(c2)-c2nc(C(N)=O)cn2CCO3)no1] | 9-[(S)-3-hydroxy-3-(5-methyl-isoxazol-3-yl)-but-1-ynyl]-4,5-dihydro-6-oxa-1,3a-diaza-benzo[e]azulene-2-carboxylic acid amide |
| 121 | 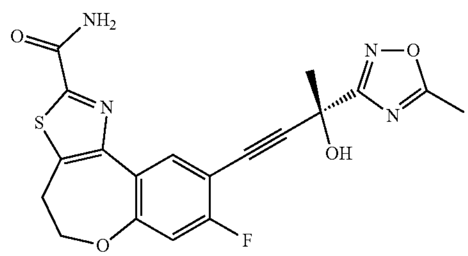 [SMILES: Cc1nc([C@](C)(O)C#Cc2cc3c(cc2F)OCCc2sc(C(N)=O)nc2-3)no1] | 8-fluoro-9-[(R)-3-hydroxy-3-(5-methyl-[1,2,4]oxadiazol-3-yl)-but-1-ynyl]-4,5-dihydro-6-oxa-3-thia-1-aza-benzo[e]azulene-2-carboxylic acid amide |
| 122 | 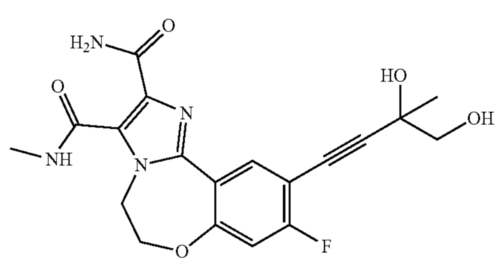 [SMILES: CNC(=O)c1c(C(N)=O)nc2n1CCOc1cc(F)c(C#CC(C)(O)CO)cc1-2] | 9-(3,4-dihydroxy-3-methyl-but-1-ynyl)-8-fluoro-4,5-dihydro-6-oxa-1,3a-diaza-benzo[e]azulene-2,3-dicarboxylic acid 2-amide 3-methylamide |
| 123 | 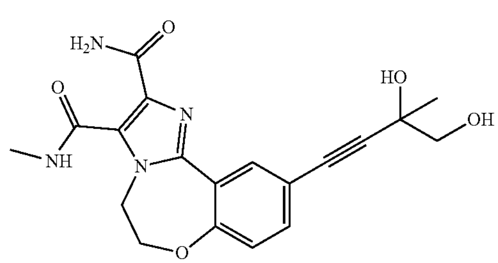 [SMILES: CNC(=O)c1c(C(N)=O)nc2n1CCOc1ccc(C#CC(C)(O)CO)cc1-2] | 9-(3,4-dihydroxy-3-methyl-but-1-ynyl)-4,5-dihydro-6-oxa-1,3a-diaza-benzo[e]azulene-2,3-dicarboxylic acid 2-amide 3-methylamide |

TABLE 1A-continued

| No. | Structure | Name |
|---|---|---|
| 124 | 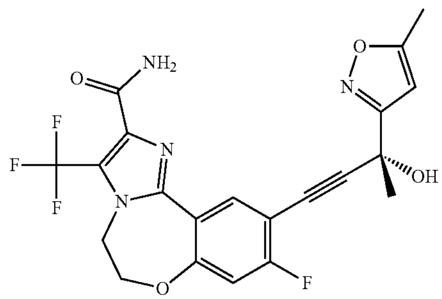 [SMILES: Cc1cc([C@](C)(O)C#Cc2cc3c(cc2F)OCCn2c-3nc(C(N)=O)c2C(F)(F)F)no1] | 8-fluoro-9-[(R)-3-hydroxy-3-(5-methyl-isoxazol-3-yl)-but-1-ynyl]-3-trifluoromethyl-4,5-dihydro-6-oxa-1,3a-diaza-benzo[e]azulene-2-carboxylic acid amide |
| 126 | 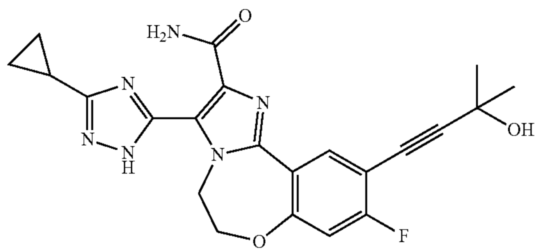 [SMILES: CC(C)(O)C#Cc1cc2c(cc1F)OCCn1c-2nc(C(N)=O)c1-c1nc(C2CC2)n[nH]1] | 3-(5-cyclopropyl-2H-[1,2,4]triazol-3-yl)-8-fluoro-9-(3-hydroxy-3-methyl-but-1-ynyl)-4,5-dihydro-6-oxa-1,3a-diaza-benzo[e]azulene-2-carboxylic acid amide |
| 127 | 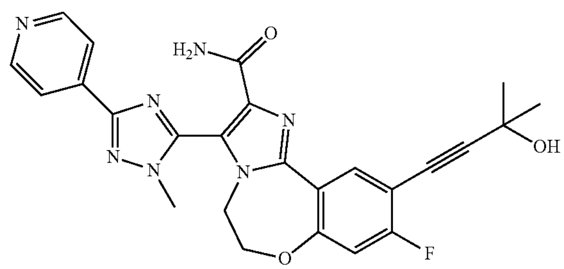 [SMILES: Cn1nc(-c2ccncc2)nc1-c1c(C(N)=O)nc2n1CCOc1cc(F)c(C#CC(C)(C)O)cc1-2] | 8-fluoro-9-(3-hydroxy-3-methyl-but-1-ynyl)-3-(2-methyl-5-pyridin-4-yl-2H-[1,2,4]triazol-3-yl)-4,5-dihydro-6-oxa-1,3a-diaza-benzo[e]azulene-2-carboxylic acid amide |
| 130 | 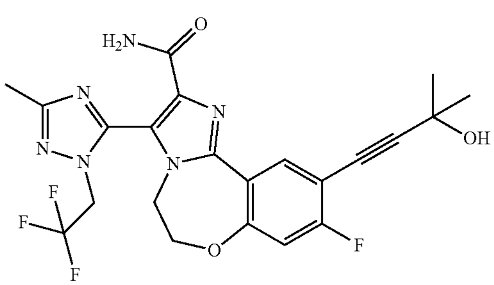 [SMILES: Cc1nc(-c2c(C(N)=O)nc3n2CCOc2cc(F)c(C#CC(C)(C)O)cc2-3)n(CC(F)(F)F)n1] | 8-fluoro-9-(3-hydroxy-3-methyl-but-1-ynyl)-3-[5-methyl-2-(2,2,2-trifluoro-ethyl)-2H-[1,2,4]triazol-3-yl]-4,5-dihydro-6-oxa-1,3a-diaza-benzo[e]azulene-2-carboxylic acid amide |
| 131 | 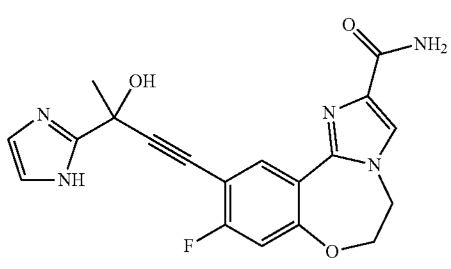 [SMILES: CC(O)(C#Cc1cc2c(cc1F)OCCn1cc(C(N)=O)nc1-2)c1ncc[nH]1] | 8-fluoro-9-[3-hydroxy-3-(1H-imidazol-2-yl)-but-1-ynyl]-4,5-dihydro-6-oxa-1,3a-diaza-benzo[e]azulene-2-carboxylic acid amide |

TABLE 1A-continued

| No. | Structure | Name |
|---|---|---|
| 132 | 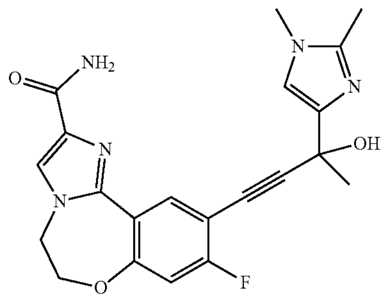 [SMILES: Cc1nc(C(C)(O)C#Cc2cc3c(cc2F)OCCn2cc(C(N)=O)nc2-3)cn1C] | 9-[3-(1,2-dimethyl-1H-imidazol-4-yl)-3-hydroxy-but-1-ynyl]-8-fluoro-4,5-dihydro-6-oxa-1,3a-diaza-benzo[e]azulene-2-carboxylic acid amide |
| 133 | 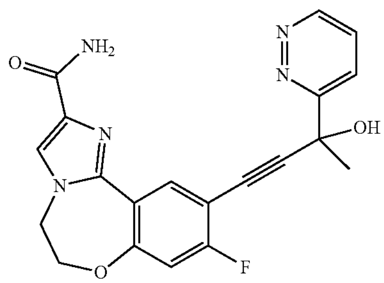 [SMILES: CC(O)(C#Cc1cc2c(cc1F)OCCn1cc(C(N)=O)nc1-2)c1cccnn1] | 8-fluoro-9-(3-hydroxy-3-pyridazin-3-yl-but-1-ynyl)-4,5-dihydro-6-oxa-1,3a-diaza-benzo[e]azulene-2-carboxylic acid amide |
| 134 | 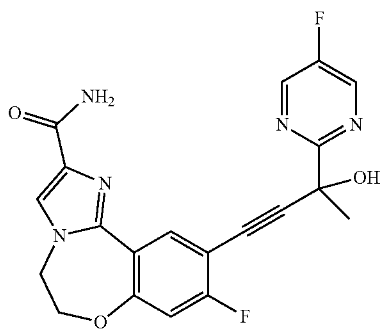 [SMILES: CC(O)(C#Cc1cc2c(cc1F)OCCn1cc(C(N)=O)nc1-2)c1ncc(F)cn1] | 8-fluoro-9-[3-(5-fluoro-pyrimidin-2-yl)-3-hydroxy-but-1-ynyl]-4,5-dihydro-6-oxa-1,3a-diaza-benzo[e]azulene-2-carboxylic acid amide |
| 135 | 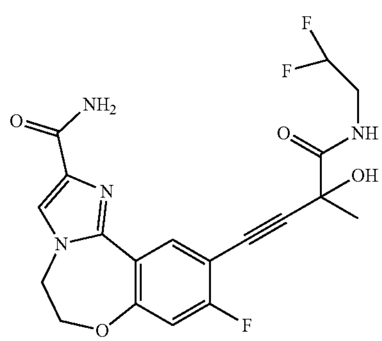 [SMILES: CC(O)(C#Cc1cc2c(cc1F)OCCn1cc(C(N)=O)nc1-2)C(=O)NCC(F)F] | 9-[3-(2,2-difluoro-ethylcarbamoyl)-3-hydroxy-but-1-ynyl]-8-fluoro-4,5-dihydro-6-oxa-1,3a-diaza-benzo[e]azulene-2-carboxylic acid amide |
| 136 | 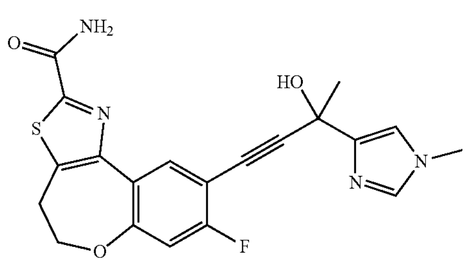 [SMILES: Cn1cnc(C(C)(O)C#Cc2cc3c(cc2F)OCCc2sc(C(N)=O)nc2-3)c1] | 8-fluoro-9-[3-hydroxy-3-(1-methyl-1H-imidazol-4-yl)-but-1-ynyl]-4,5-dihydro-6-oxa-3-thia-1-aza-benzo[e]azulene-2-carboxylic acid amide |

TABLE 1A-continued

| No. | Structure | Name |
|---|---|---|
| 140 | 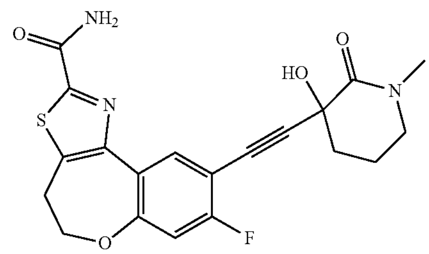 [SMILES: CN1CCCC(O)(C#Cc2cc3c(cc2F)OCCc2sc(C(N)=O)nc2-3)C1=O] | 8-fluoro-9-(3-hydroxy-1-methyl-2-oxo-piperidin-3-ylethynyl)-4,5-dihydro-6-oxa-3-thia-1-aza-benzo[e]azulene-2-carboxylic acid amide |
| 141 | 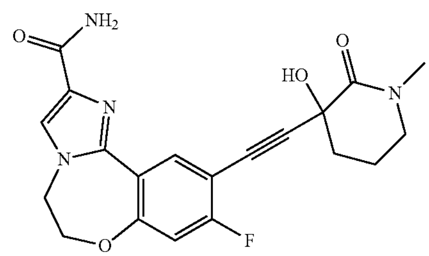 [SMILES: CN1CCCC(O)(C#Cc2cc3c(cc2F)OCCn2cc(C(N)=O)nc2-3)C1=O] | 8-fluoro-9-(3-hydroxy-1-methyl-2-oxo-piperidin-3-ylethynyl)-4,5-dihydro-6-oxa-1,3a-diaza-benzo[e]azulene-2-carboxylic acid amide |
| 142 | 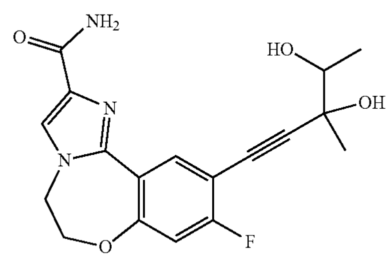 [SMILES: CC(O)C(C)(O)C#Cc1cc2c(cc1F)OCCn1cc(C(N)=O)nc1-2] | 9-(3,4-dihydroxy-3-methyl-pent-1-ynyl)-8-fluoro-4,5-dihydro-6-oxa-1,3a-diaza-benzo[e]azulene-2-carboxylic acid amide |
| 143 | 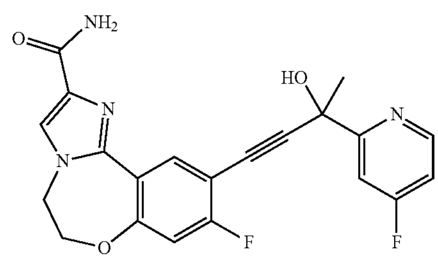 [SMILES: CC(O)(C#Cc1cc2c(cc1F)OCCn1cc(C(N)=O)nc1-2)c1cc(F)ccn1] | 8-fluoro-9-[3-(4-fluoro-pyridin-2-yl)-3-hydroxy-but-1-ynyl]-4,5-dihydro-6-oxa-1,3a-diaza-benzo[e]azulene-2-carboxylic acid amide |
| 144 | 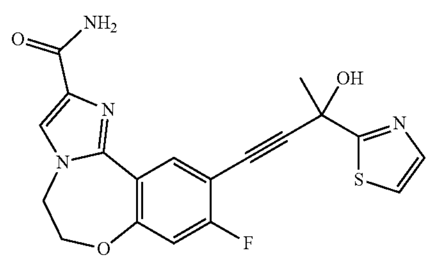 [SMILES: CC(O)(C#Cc1cc2c(cc1F)OCCn1cc(C(N)=O)nc1-2)c1nccs1] | 8-fluoro-9-(3-hydroxy-3-thiazol-2-yl-but-1-ynyl)-4,5-dihydro-6-oxa-1,3a-diaza-benzo[e]azulene-2-carboxylic acid amide |
| 145 | 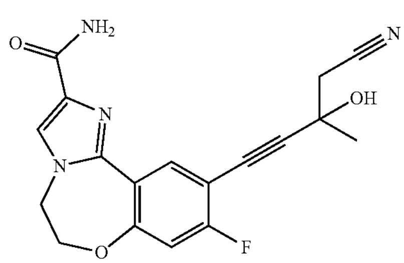 [SMILES: CC(O)(C#Cc1cc2c(cc1F)OCCn1cc(C(N)=O)nc1-2)CC#N] | 9-(4-cyano-3-hydroxy-3-methyl-but-1-ynyl)-8-fluoro-4,5-dihydro-6-oxa-1,3a-diaza-benzo[e]azulene-2-carboxylic acid amide |

TABLE 1A-continued

| No. | Structure | Name |
|---|---|---|
| 146 | 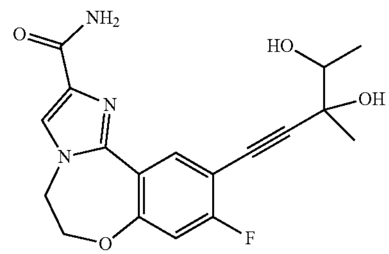 [SMILES: CC(O)C(C)(O)C#Cc1cc2c(cc1F)OCCn1cc(C(N)=O)nc1-2] | 9-(3,4-dihydroxy-3-methyl-pent-1-ynyl)-8-fluoro-4,5-dihydro-6-oxa-1,3a-diaza-benzo[e]azulene-2-carboxylic acid amide |
| 147 | 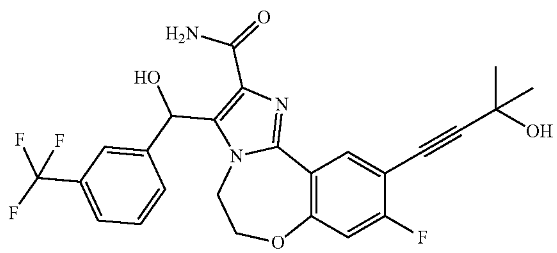 [SMILES: CC(C)(O)C#Cc1cc2c(cc1F)OCCn1c-2nc(C(N)=O)c1C(O)c1cccc(C(F)(F)F)c1] | 8-fluoro-9-(3-hydroxy-3-methyl-but-1-ynyl)-3-[hydroxy-(3-trifluoromethyl-phenyl)-methyl]-4,5-dihydro-6-oxa-1,3a-diaza-benzo[e]azulene-2-carboxylic acid amide |
| 152 | 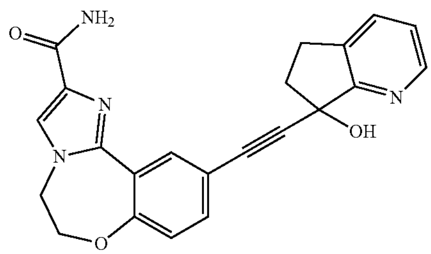 [SMILES: NC(=O)c1cn2c(n1)-c1cc(C#CC3(O)CCc4cccnc43)ccc1OCC2] | 9-(7-hydroxy-6,7-dihydro-5H-[1]pyrindin-7-ylethynyl)-4,5-dihydro-6-oxa-1,3a-diaza-benzo[e]azulene-2-carboxylic acid amide |
| 154 | 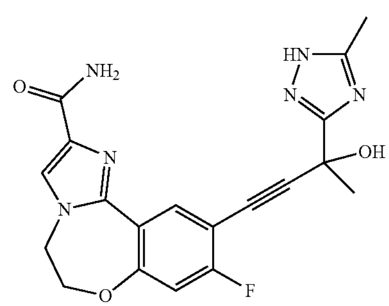 [SMILES: Cc1nc(C(C)(O)C#Cc2cc3c(cc2F)OCCn2cc(C(N)=O)nc2-3)n[nH]1] | 8-fluoro-9-[3-hydroxy-3-(5-methyl-1H-[1,2,4]triazol-3-yl)-but-1-ynyl]-4,5-dihydro-6-oxa-1,3a-diaza-benzo[e]azulene-2-carboxylic acid amide |
| 155 | 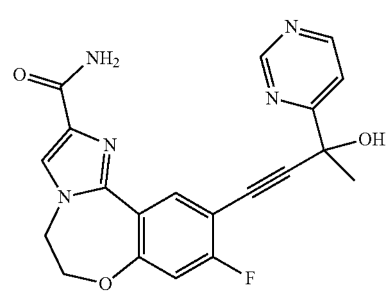 [SMILES: CC(O)(C#Cc1cc2c(cc1F)OCCn1cc(C(N)=O)nc1-2)c1ccncn1] | 8-fluoro-9-(3-hydroxy-3-pyrimidin-4-yl-but-1-ynyl)-4,5-dihydro-6-oxa-1,3a-diaza-benzo[e]azulene-2-carboxylic acid amide |

TABLE 1A-continued

| No. | Structure | Name |
|---|---|---|
| 156 | 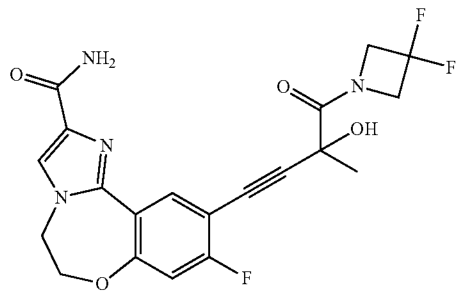 [SMILES: CC(O)(C#Cc1cc2c(cc1F)OCCn1cc(C(N)=O)nc1-2)C(=O)N1CC(F)(F)C1] | 9-[4-(3,3-difluoro-azetidin-1-yl)-3-hydroxy-3-methyl-4-oxo-but-1-ynyl]-8-fluoro-4,5-dihydro-6-oxa-1,3a-diaza-benzo[e]azulene-2-carboxylic acid amide |
| 157 | 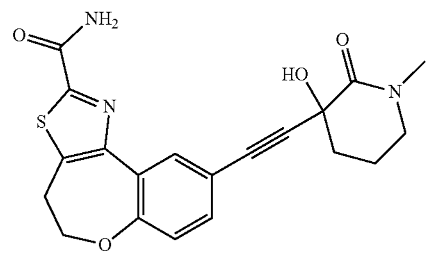 [SMILES: CN1CCCC(O)(C#Cc2ccc3c(c2)-c2nc(C(N)=O)sc2CCO3)C1=O] | 9-[2-(3-hydroxy-1-methyl-2-oxo-3-piperidyl)ethynyl]-4,5-dihydro-[1]benzoxepino[5,4-d]thiazole-2-carboxamide |
| 158 | 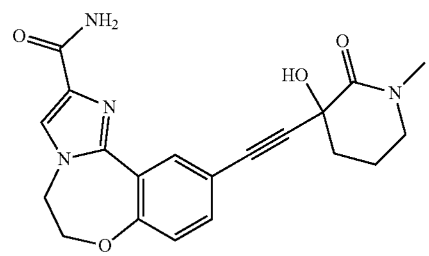 [SMILES: CN1CCCC(O)(C#Cc2ccc3c(c2)-c2nc(C(N)=O)cn2CCO3)C1=O] | 10-[2-(3-hydroxy-1-methyl-2-oxo-3-piperidyl)ethynyl]-5,6-dihydroimidazo[1,2-d][1,4]benzoxazepine-2-carboxamide |
| 159 | 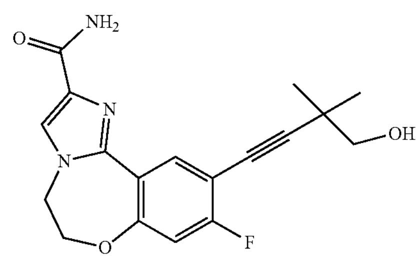 [SMILES: CC(C)(C#Cc1cc2c(cc1F)OCCn1cc(C(N)=O)nc1-2)CO] | 9-fluoro-10-(4-hydroxy-3,3-dimethyl-but-1-ynyl)-5,6-dihydroimidazo[1,2-d][1,4]benzoxazepine-2-carboxamide |
| 161 | 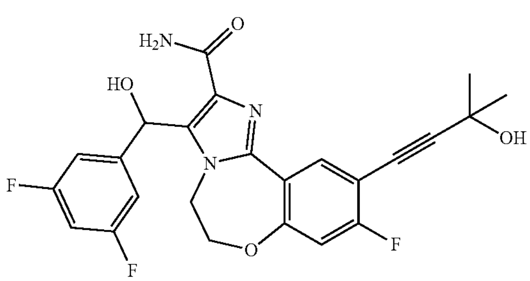 [SMILES: CC(C)(O)C#Cc1cc2c(cc1F)OCCn1c-2nc(C(N)=O)c1C(O)c1cc(F)cc(F)c1] | 3-[(3,5-difluorophenyl)-hydroxy-methyl]-9-fluoro-10-(3-hydroxy-3-methyl-but-1-ynyl)-5,6-dihydroimidazo[1,2-d][1,4]benzoxazepine-2-carboxamide |
| 165 | 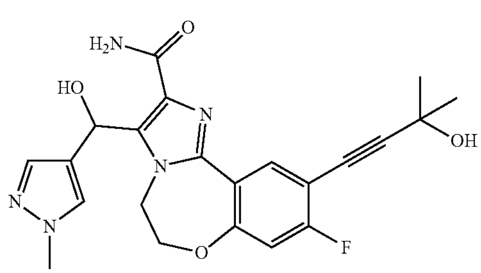 [SMILES: Cn1cc(C(O)c2c(C(N)=O)nc3n2CCOc2cc(F)c(C#CC(C)(C)O)cc2-3)cn1] | 9-fluoro-10-(3-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |

TABLE 1A-continued

| No. | Structure | Name |
|---|---|---|
| 166 | 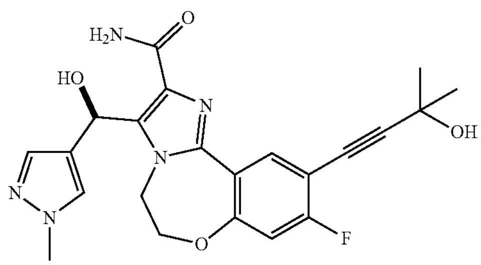 [SMILES: Cn1cc([C@@H](O)c2c(C(N)=O)nc3n2CCOc2cc(F)c(C#CC(C)(C)O)cc2-3)cn1] | 9-fluoro-10-(3-(R)-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |
| 167 | 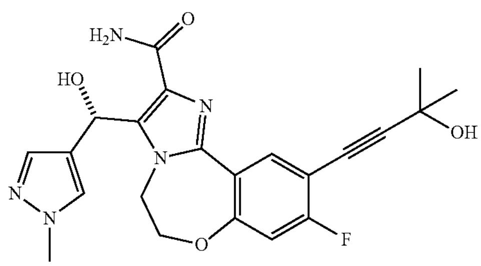 | 9-fluoro-10-(3-(S)-hydroxy-3-methyl-but-1-ynyl)-3-[hydroxy-(1-methylpyrazol-4-yl)methyl]-5,6-dihydroimidazo[1,2-d][1,4]benzoxazepine-2-carboxamide |
| 169 | 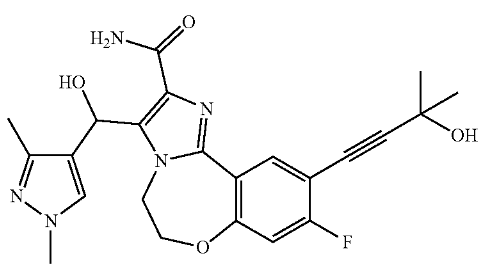 [SMILES: Cc1nn(C)cc1C(O)c1c(C(N)=O)nc2n1CCOc1cc(F)c(C#CC(C)(C)O)cc1-2] | 3-[(1,3-dimethylpyrazol-4-yl)-hydroxy-methyl]-9-fluoro-10-(3-hydroxy-3-methyl-but-1-ynyl)-5,6-dihydroimidazo[1,2-d][1,4]benzoxazepine-2-carboxamide |
| 170 | 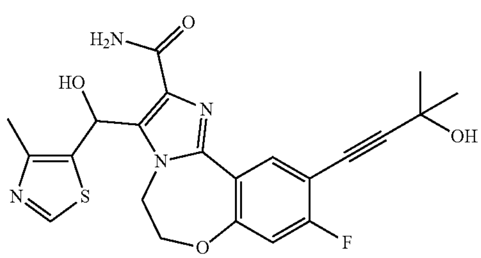 [SMILES: Cc1ncsc1C(O)c1c(C(N)=O)nc2n1CCOc1cc(F)c(C#CC(C)(C)O)cc1-2] | 9-fluoro-10-(3-hydroxy-3-methyl-but-1-ynyl)-3-[hydroxy-(4-methylthiazol-5-yl)methyl]-5,6-dihydroimidazo[1,2-d][1,4]benzoxazepine-2-carboxamide |
| 171 | 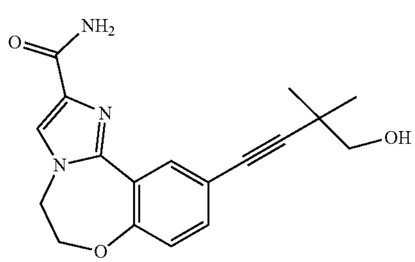 [SMILES: CC(C)(C#Cc1ccc2c(c1)-c1nc(C(N)=O)cn1CCO2)CO] | 10-(4-hydroxy-3,3-dimethyl-but-1-ynyl)-5,6-dihydroimidazo[1,2-d][1,4]benzoxazepine-2-carboxamide |
| 172 | 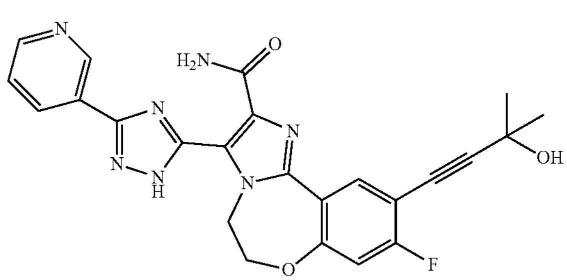 [SMILES: CC(C)(O)C#Cc1cc2c(cc1F)OCCn1c-2nc(C(N)=O)c1-c1nc(-c2cccnc2)n[nH]1] | 9-fluoro-10-(3-hydroxy-3-methyl-but-1-ynyl)-3-[3-(3-pyridyl)-1H-1,2,4-triazol-5-yl]-5,6-dihydroimidazo[1,2-d][1,4]benzoxazepine-2-carboxamide |

TABLE 1A-continued

| No. | Structure | Name |
|---|---|---|
| 173 | 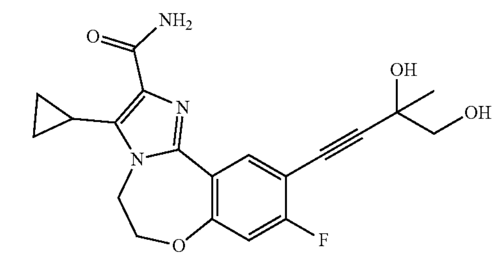 [SMILES: CC(O)(C#Cc1cc2c(cc1F)OCCn1c-2nc(C(N)=O)c1C1CC1)CO] | 3-cyclopropyl-10-(3,4-dihydroxy-3-methyl-but-1-ynyl)-9-fluoro-5,6-dihydroimidazo[1,2-d][1,4]benzoxazepine-2-carboxamide |
| 176 | 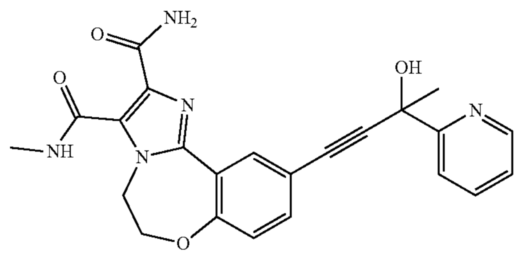 [SMILES: CNC(=O)c1c(C(N)=O)nc2n1CCOc1ccc(C#CC(C)(O)c3ccccn3)cc1-2] | 10-[3-hydroxy-3-(2-pyridyl)but-1-ynyl]-N3-methyl-5,6-dihydroimidazo[1,2-d][1,4]benzoxazepine-2,3-dicarboxamide |
| 178 | 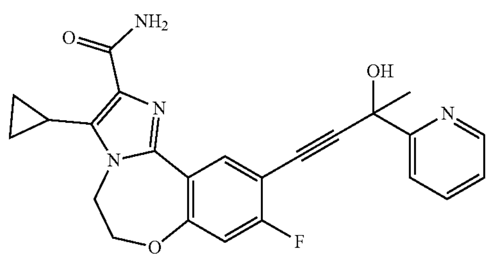 [SMILES: CC(O)(C#Cc1cc2c(cc1F)OCCn1c-2nc(C(N)=O)c1C1CC1)c1ccccn1] | 3-cyclopropyl-9-fluoro-10-[3-hydroxy-3-(2-pyridyl)but-1-ynyl]-5,6-dihydroimidazo[1,2-d][1,4]benzoxazepine-2-carboxamide |
| 180 | 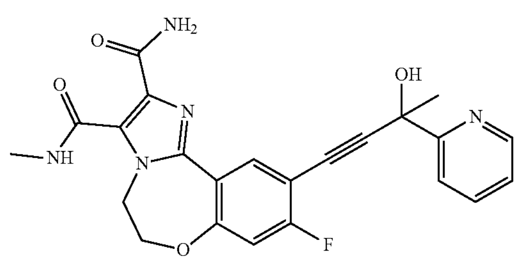 [SMILES: CNC(=O)c1c(C(N)=O)nc2n1CCOc1cc(F)c(C#CC(C)(O)c3ccccn3)cc1-2] | 9-fluoro-10-[3-hydroxy-3-(2-pyridyl)but-1-ynyl]-N3-meth-5,6-dihydroimidazo[1,2-d][1,4]benzoxazepine-2,3-dicarboxamide |
| 182 | 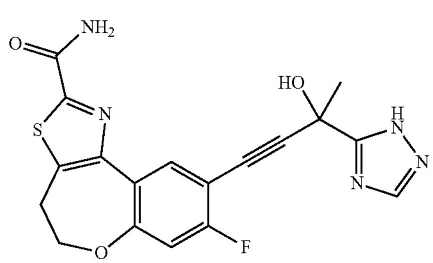 [SMILES: CC(O)(C#Cc1cc2c(cc1F)OCCc1sc(C(N)=O)nc1-2)c1ncn[nH]1] | 8-fluoro-9-[3-hydroxy-3-(1H-1,2,4-triazol-5-yl)but-1-ynyl]-4,5-dihydro-[1]benzoxepino[5,4-d]thiazole-2-carboxamide |
| 183 | 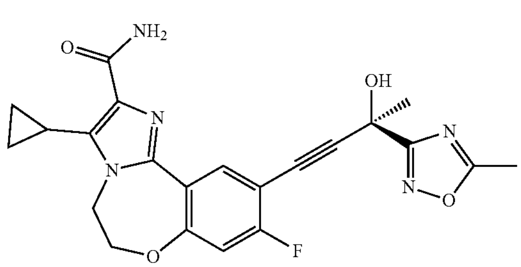 [SMILES: Cc1nc([C@](C)(O)C#Cc2cc3c(cc2F)OCCn2c-3nc(C(N)=O)c2C2CC2)no1] | 3-cyclopropyl-9-fluoro-10-[(3R)-3-hydroxy-3-(5-methyl-1,2,4-oxadiazol-3-yl)but-1-ynyl]-5,6-dihydroimidazo[1,2-d][1,4]benzoxazepine-2-carboxamide |

TABLE 1A-continued

| No. | Structure | Name |
|---|---|---|
| 184 | 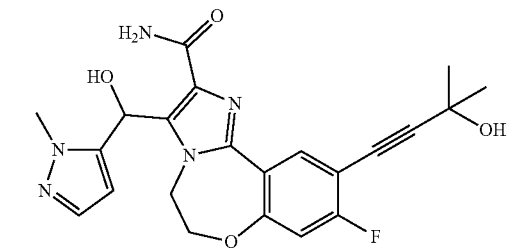 [SMILES: Cn1nccc1C(O)c1c(C(N)=O)nc2n1CCOc1cc(F)c(C#CC(C)(C)O)cc1-2] | 9-fluoro-10-(3-hydroxy-3-methyl-but-1-ynyl)-3-[hydroxy-(2-methylpyrazol-3-yl)methyl]-5,6-dihydroimidazo[1,2-d][1,4]benzoxazepine-2-carboxamide |
| 185 | 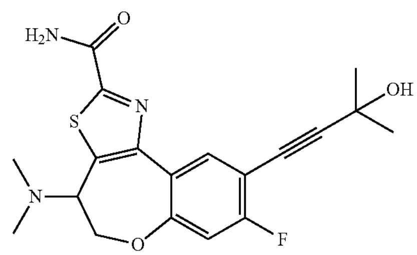 [SMILES: CN(C)C1COc2cc(F)c(C#CC(C)(C)O)cc2-c2nc(C(N)=O)sc21] | 4-(dimethylamino)-8-fluoro-9-(3-hydroxy-3-methyl-but-1-ynyl)-4,5-dihydro-[1]benzoxepino[5,4-d]thiazole-2-carboxamide |
| 186 | 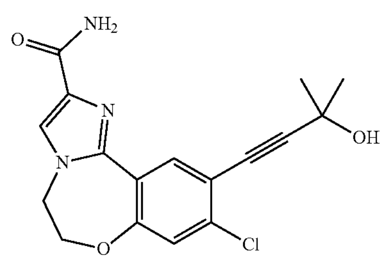 [SMILES: CC(C)(O)C#Cc1cc2c(cc1Cl)OCCn1cc(C(N)=O)nc1-2] | 9-chloro-10-(3-hydroxy-3-methyl-but-1-ynyl)-5,6-dihydroimidazo[1,2-d][1,4]benzoxazepine-2-carboxamide |
| 187 | 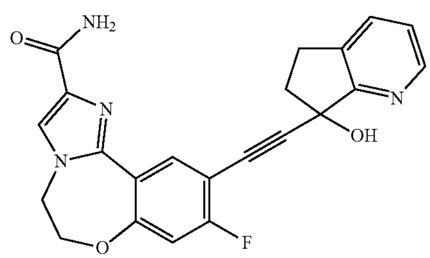 [SMILES: NC(=O)c1cn2c(n1)-c1cc(C#CC3(O)CCc4cccnc43)c(F)cc1OCC2] | 9-fluoro-10-[2-(7-hydroxy-5,6-dihydrocyclopenta[b]pyridin-7-yl)ethynyl]-5,6-dihydroimidazo[1,2-d][1,4]benzoxazepine-2-carboxamide |
| 188 | 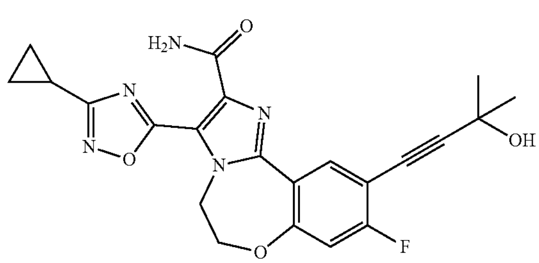 [SMILES: CC(C)(O)C#Cc1cc2c(cc1F)OCCn1c-2nc(C(N)=O)c1-c1nc(C2CC2)no1] | 3-(3-cyclopropyl-1,2,4-oxadiazol-5-yl)-9-fluoro-10-(3-hydroxy-3-methyl-but-1-ynyl)-5,6-dihydroimidazo[1,2-d][1,4]benzoxazepine-2-carboxamide |
| 189 | 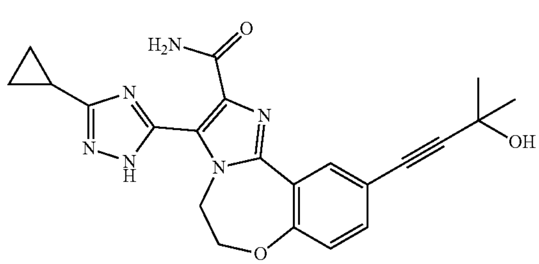 [SMILES: CC(C)(O)C#Cc1ccc2c(c1)-c1nc(C(N)=O)c(-c3nc(C4CC4)n[nH]3)n1CCO2] | 3-(3-cyclopropyl-1H-1,2,4-triazol-5-yl)-10-(3-hydroxy-3-methyl-but-1-ynyl)-5,6-dihydroimidazo[1,2-d][1,4]benzoxazepine-2-carboxamide |

TABLE 1A-continued

| No. | Structure | Name |
| --- | --- | --- |
| 190 | 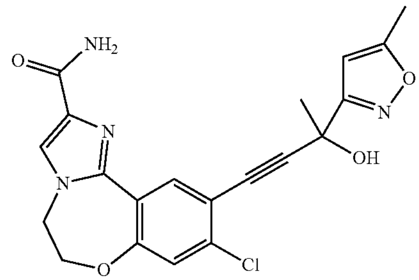 [SMILES: Cc1cc(C(C)(O)C#Cc2cc3c(cc2Cl)OCCn2cc(C(N)=O)nc2-3)no1] | 9-chloro-10-[3-hydroxy-3-(5-methylisoxazol-3-yl)but-1-ynyl]-5,6-dihydroimidazo[1,2-d][1,4]benzoxazepine-2-carboxamide |
| 192 | 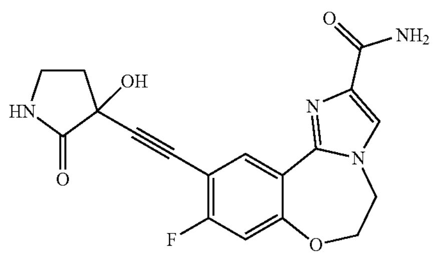 [SMILES: NC(=O)c1cn2c(n1)-c1cc(C#CC3(O)CCNC3=O)c(F)cc1OCC2] | 9-fluoro-10-[2-(3-hydroxy-2-oxo-pyrrolidin-3-yl)ethynyl]-5,6-dihydroimidazo[1,2-d][1,4]benzoxazepine-2-carboxamide |
| 198 | 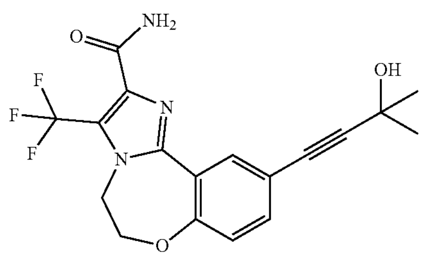 [SMILES: CC(C)(O)C#Cc1ccc2c(c1)-c1nc(C(N)=O)c(C(F)(F)F)n1CCO2] | 10-(3-hydroxy-3-methyl-but-1-ynyl)-3-(trifluoromethyl)-5,6-dihydroimidazo[1,2-d][1,4]benzoxazepine-2-carboxamide |
| 201 | 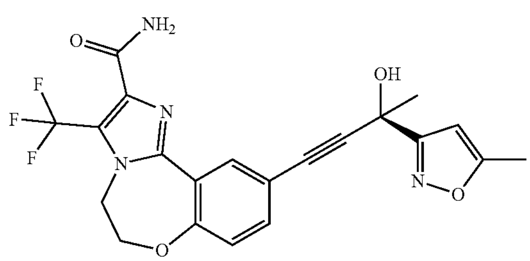 [SMILES: Cc1cc([C@](C)(O)C#Cc2ccc3c(c2)-c2nc(C(N)=O)c(C(F)(F)F)n2CCO3)no1] | 10-[(3R)-3-hydroxy-3-(5-methylisoxazol-3-yl)but-1-ynyl]-3-(trifluoromethyl)-5,6-dihydroimidazo[1,2-d][1,4]benzoxazepine-2-carboxamide |
| 208 | 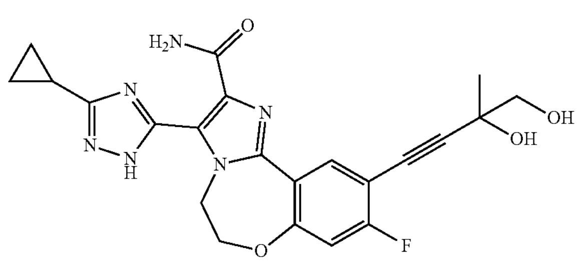 [SMILES: CC(O)(C#Cc1cc2c(cc1F)OCCn1c-2nc(C(N)=O)c1-c1nc(C2CC2)n[nH]1)CO] | 3-(3-cyclopropyl-1H-1,2,4-triazol-5-yl)-10-(3,4-dihydroxy-3-methyl-but-1-ynyl)-9-fluoro-5,6-dihydroimidazo[1,2-d][1,4]benzoxazepine-2-carboxamide |
| 213 | 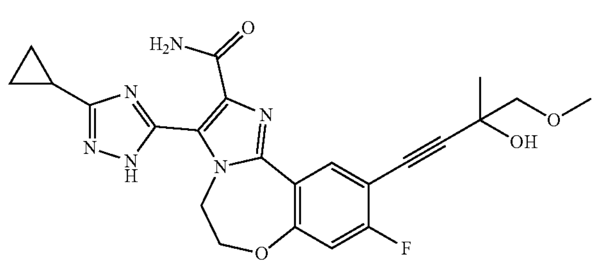 [SMILES: COCC(C)(O)C#Cc1cc2c(cc1F)OCCn1c-2nc(C(N)=O)c1-c1nc(C2CC2)n[nH]1] | 3-(3-cyclopropyl-1H-1,2,4-triazol-5-yl)-9-fluoro-10-(3-hydroxy-4-methoxy-3-methyl-but-1-ynyl)-5,6-dihydroimidazo[1,2-d][1,4]benzoxazepine-2-carboxamide |

TABLE 1A-continued

| No. | Structure | Name |
|---|---|---|
| 221 | 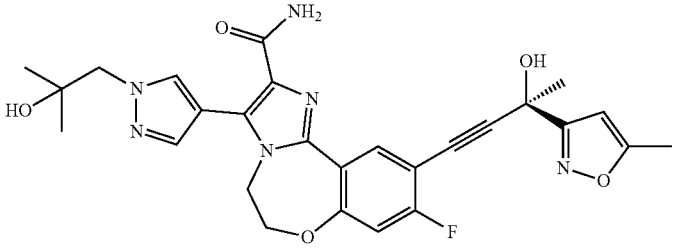 [SMILES: Cc1cc([C@](C)(O)C#Cc2cc3c(cc2F)OCCn2c-3nc(C(N)=O)c2-c2cnn(CC(C)(C)O)c2)no1] | 9-fluoro-10-[(3R)-3-hydroxy-3-(5-methylisoxazol-3-yl)but-1-ynyl]-3-[1-(2-hydroxy-2-methyl-propyl)pyrazol-4-yl]-5,6-dihydroimidazo[1,2-d][1,4]benzoxazepine-2-carboxamide |
| 226 | 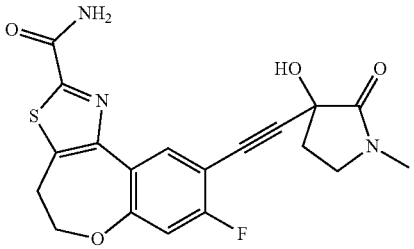 [SMILES: CN1CCC(O)(C#Cc2cc3c(cc2F)OCCc2sc(C(N)=O)nc2-3)C1=O] | 8-fluoro-9-[2-(3-hydroxy-1-methyl-2-oxo-pyrrolidin-3-yl)ethynyl]-4,5-dihydro-[1]benzoxepino[5,4-d]thiazole-2-carboxamide |
| 227 | 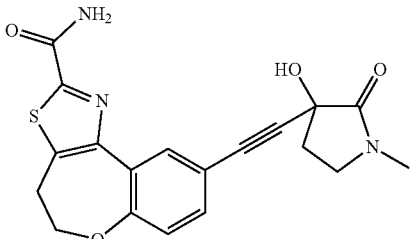 | 9-[2-(3-hydroxy-1-methyl-2-oxo-pyrrolidin-3-yl)ethynyl]-4,5-dihydro-[1]benzoxepino[5,4-d]thiazole-2-carboxamide |
| 228 | 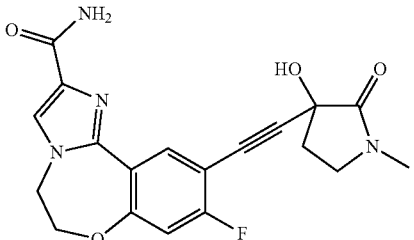 | 9-fluoro-10-[2-(3-hydroxy-1-methyl-2-oxo-pyrrolidin-3-yl)ethynyl]-5,6-dihydroimidazo[1,2-d][1,4]benzoxazepine-2-carboxamide |
| 229 | 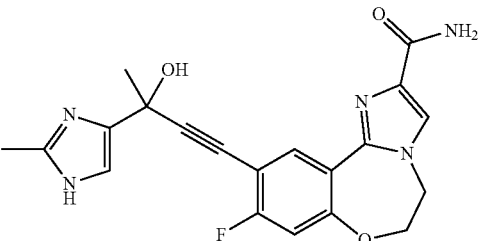 | 9-fluoro-10-[3-hydroxy-3-(2-methyl-1H-imidazol-4-yl)but-1-ynyl]-5,6-dihydroimidazo[1,2-d][1,4]benzoxazepine-2-carboxamide |
| 230 | 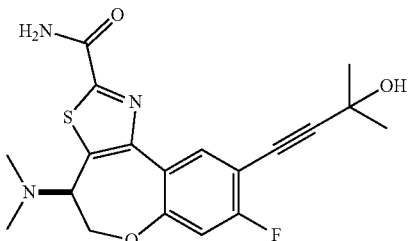 | 4-(R)-(dimethylamino)-8-fluoro-9-(3-hydroxy-3-methyl-but-1-ynyl)-4,5-dihydro-[1]benzoxepino[5,4-d]thiazole-2-carboxamide |

TABLE 1A-continued

| No. | Structure | Name |
|---|---|---|
| 231 | 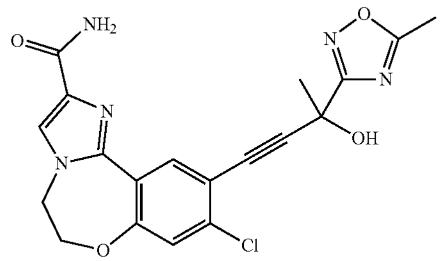 [SMILES: Cc1nc(C(C)(O)C#Cc2cc3c(cc2Cl)OCCn2cc(C(N)=O)nc2-3)no1] | 9-chloro-10-[3-hydroxy-3-(5-methyl-1,2,4-oxadiazol-3-yl)but-1-ynyl]-5,6-dihydroimidazo[1,2-d][1,4]benzoxazepine-2-carboxamide |
| 232 | 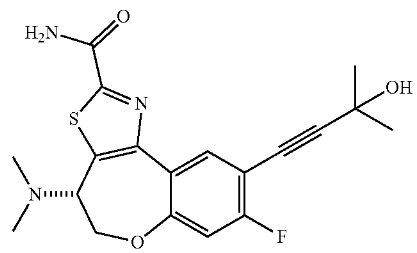 [SMILES: CN(C)[C@H]1COc2cc(F)c(C#CC(C)(C)O)cc2-c2nc(C(N)=O)sc21] | 4-(S)-(dimethylamino)-8-fluoro-9-(3-hydroxy-3-methyl-but-1-ynyl)-4,5-dihydro-[1]benzoxepino[5,4-d]thiazole-2-carboxamide |
| 233 | 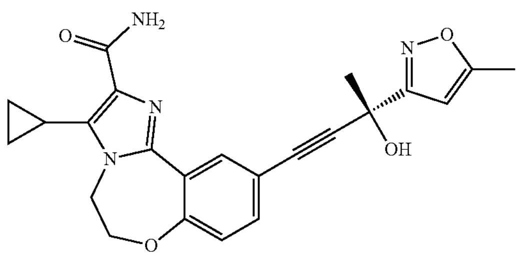 [SMILES: Cc1cc([C@](C)(O)C#Cc2ccc3c(c2)-c2nc(C(N)=O)c(C4CC4)n2CCO3)no1] | 3-cyclopropyl-10-[(3R)-3-hydroxy-3-(5-methylisoxazol-3-yl)but-1-ynyl]-5,6-dihydroimidazo[1,2-d][1,4]benzoxazepine-2-carboxamide |
| 235 | 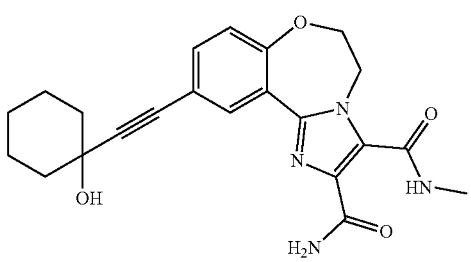 [SMILES: CNC(=O)c1c(C(N)=O)nc2n1CCOc1ccc(C#CC3(O)CCCCC3)cc1-2] | 10-[2-(1-hydroxycyclohexyl)ethynyl]-N3-methyl-5,6-dihydroimidazo[1,2-d][1,4]benzoxazepine-2,3-dicarboxamide |
| 241 | 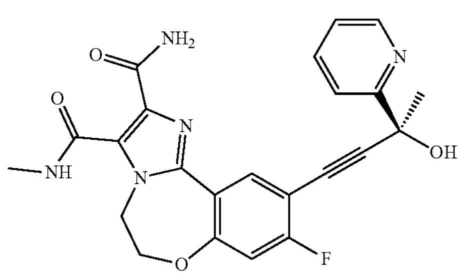 [SMILES: CNC(=O)c1c(C(N)=O)nc2n1CCOc1cc(F)c(C#C[C@](C)(O)c3ccccn3)cc1-2] | 9-fluoro-10-[(3S)-3-hydroxy-3-(2-pyridyl)but-1-ynyl]-N3-methyl-5,6-dihydroimidazo[1,2-d][1,4]benzoxazepine-2,3-dicarboxamide |
| 242 | 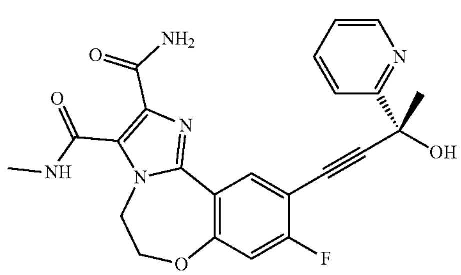 [SMILES: CNC(=O)c1c(C(N)=O)nc2n1CCOc1cc(F)c(C#C[C@@](C)(O)c3ccccn3)cc1-2] | 9-fluoro-10-[(3R)-3-hydroxy-3-(2-pyridyl)but-1-ynyl]-N3-methyl-5,6-dihydroimidazo[1,2-d][1,4]benzoxazepine-2,3-dicarboxamide |

TABLE 1A-continued

| No. | Structure | Name |
| --- | --- | --- |
| 243 | 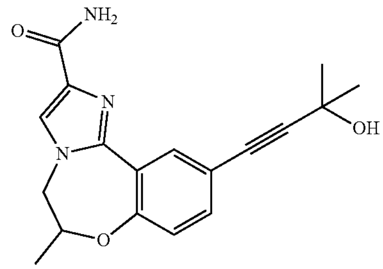 [SMILES: CC1Cn2cc(C(N)=O)nc2-c2cc(C#CC(C)(C)O)ccc2O1] | 10-(3-hydroxy-3-methyl-but-1-ynyl)-6-methyl-5,6-dihydroimidazo[1,2-d][1,4]benzoxazepine-2-carboxamide |
| 244 | 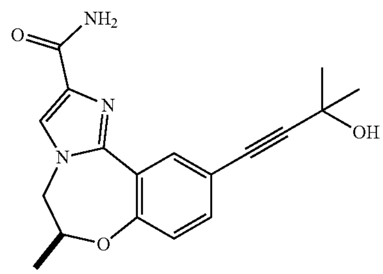 [SMILES: C[C@H]1Cn2cc(C(N)=O)nc2-c2cc(C#CC(C)(C)O)ccc2O1] | 10-(3-hydroxy-3-methyl-but-1-ynyl)-6-(S)-methyl-5,6-dihydroimidazo[1,2-d][1,4]benzoxazepine-2-carboxamide |
| 245 | 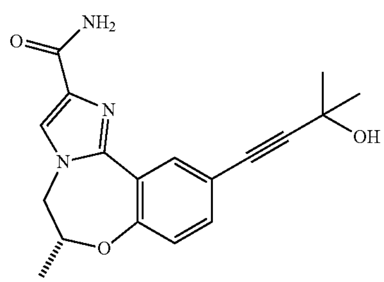 [SMILES: C[C@@H]1Cn2cc(C(N)=O)nc2-c2cc(C#CC(C)(C)O)ccc2O1] | 10-(3-hydroxy-3-methyl-but-1-ynyl)-6-(R)-methyl-5,6-dihydroimidazo[1,2-d][1,4]benzoxazepine-2-carboxamide |
| 252 | 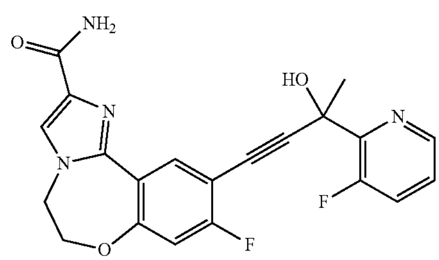 [SMILES: CC(O)(C#Cc1cc2c(cc1F)OCCn1cc(C(N)=O)nc1-2)c1ncccc1F] | 9-fluoro-10-[3-(3-fluoro-2-pyridyl)-3-hydroxy-but-1-ynyl]-5,6-dihydroimidazo[1,2-d][1,4]benzoxazepine-2-carboxamide |
| 253 | 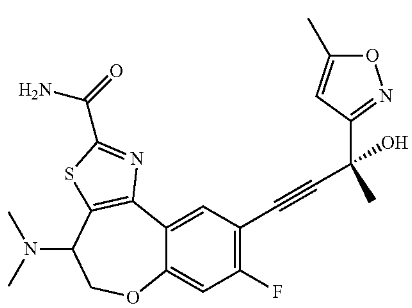 | 4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |

TABLE 1A-continued

| No. | Structure | Name |
|---|---|---|
| 254 | 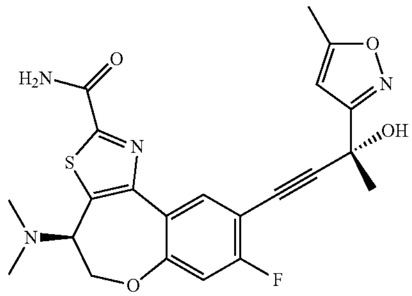 [SMILES: Cc1cc([C@](C)(O)C#Cc2cc3c(cc2F)OC[C@@H](N(C)C)c2sc(C(N)=O)nc2-3)no1] | (R)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 255 | 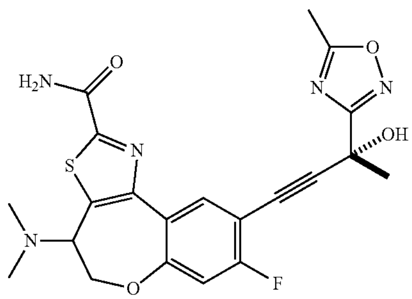 [SMILES: Cc1nc([C@](C)(O)C#Cc2cc3c(cc2F)OCC(N(C)C)c2sc(C(N)=O)nc2-3)no1] | 4-(dimethylamino)-8-fluoro-9-[(R)-3-hydroxy-3-(5-methyl-1,2,4-oxadiazol-3-yl)but-1-ynyl]-4,5-dihydro-[1]benzoxepino[5,4-d]thiazole-2-carboxamide |
| 256 | 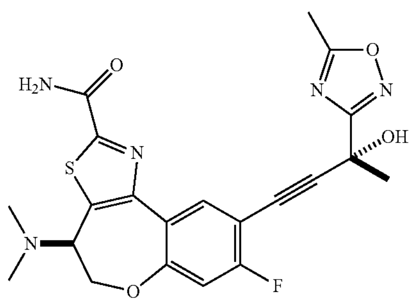 [SMILES: Cc1nc([C@](C)(O)C#Cc2cc3c(cc2F)OC[C@@H](N(C)C)c2sc(C(N)=O)nc2-3)no1] | (R)-4-(dimethylamino)-8-fluoro-9-[(R)-3-hydroxy-3-(5-methyl-1,2,4-oxadiazol-3-yl)but-1-ynyl]-4,5-dihydro-[1]benzoxepino[5,4-d]thiazole-2-carboxamide |
| 257 | 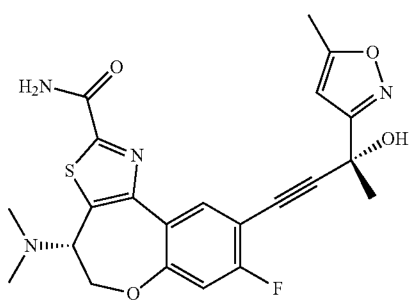 [SMILES: Cc1cc([C@](C)(O)C#Cc2cc3c(cc2F)OC[C@H](N(C)C)c2sc(C(N)=O)nc2-3)no1] | (S)-4-(dimethylamino)-8-fluoro-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 258 | 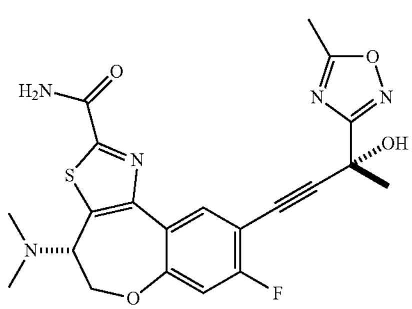 | (S)-4-(dimethylamino)-8-fluoro-9-[3-(R)-hydroxy-3-(5-methyl-1,2,4-oxadiazol-3-yl)but-1-ynyl]-4,5-dihydro-[1]benzoxepino[5,4-d]thiazole-2-carboxamide |

TABLE 1A-continued

| No. | Structure | Name |
|---|---|---|
| 263 | 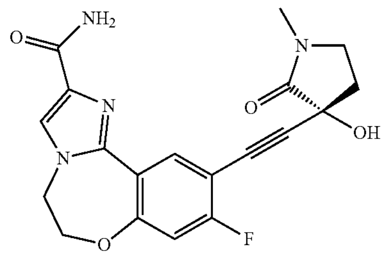 [SMILES: CN1CC[C@@](O)(C#Cc2cc3c(cc2F)OCCn2cc(C(N)=O)nc2-3)C1=O] | 9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide |
| 264 | 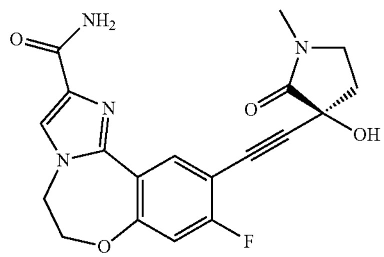 [SMILES: CN1CC[C@](O)(C#Cc2cc3c(cc2F)OCCn2cc(C(N)=O)nc2-3)C1=O] | 9-fluoro-10-[2-[(3S)-3-hydroxy-1-methyl-2-oxo-pyrrolidin-3-yl]ethynyl]-5,6-dihydroimidazo[1,2-d][1,4]benzoxazepine-2-carboxamide |
| 266 | 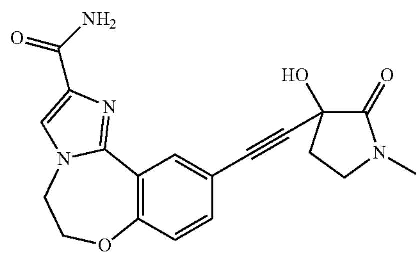 [SMILES: CN1CCC(O)(C#Cc2ccc3c(c2)-c2nc(C(N)=O)cn2CCO3)C1=O] | 10-[2-(3-hydroxy-1-methyl-2-oxo-pyrrolidin-3-yl)ethynyl]-5,6-dihydroimidazo[1,2-d][1,4]benzoxazepine-2-carboxamide |
| 267 | 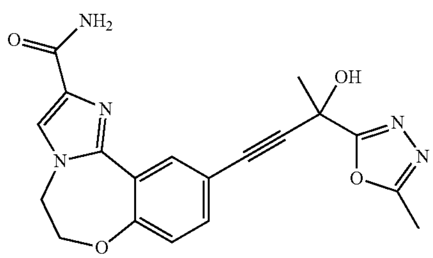 [SMILES: Cc1nnc(C(C)(O)C#Cc2ccc3c(c2)-c2nc(C(N)=O)cn2CCO3)o1] | 10-[3-hydroxy-3-(5-methyl-1,3,4-oxadiazol-2-yl)but-1-ynyl]-5,6-dihydroimidazo[1,2-d][1,4]benzoxazepine-2-carboxamide |
| 268 | 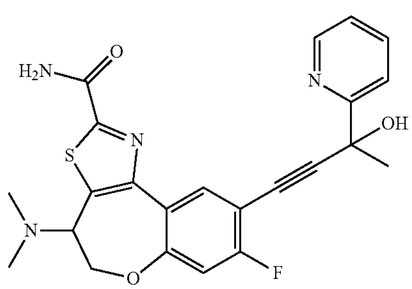 [SMILES: CN(C)C1COc2cc(F)c(C#CC(C)(O)c3ccccn3)cc2-c2nc(C(N)=O)sc21] | 4-(dimethylamino)-8-fluoro-9-[3-hydroxy-3-(2-pyridyl)but-1-ynyl]-4,5-dihydro-[1]benzoxepino[5,4-d]thiazole-2-carboxamide |
| 270 | 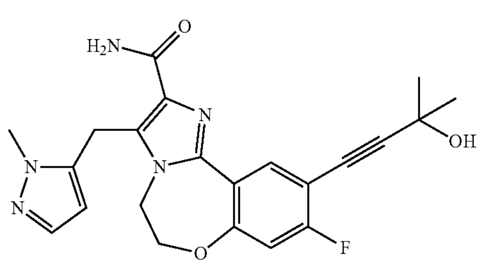 [SMILES: Cn1nccc1Cc1c(C(N)=O)nc2n1CCOc1cc(F)c(C#CC(C)(C)O)cc1-2] | 9-fluoro-10-(3-hydroxy-3-methyl-but-1-ynyl)-3-[(2-methylpyrazol-3-yl)methyl]-5,6-dihydroimidazo[1,2-d][1,4]benzoxazepine-2-carboxamide |

TABLE 1A-continued

| No. | Structure | Name |
|---|---|---|
| 275 | 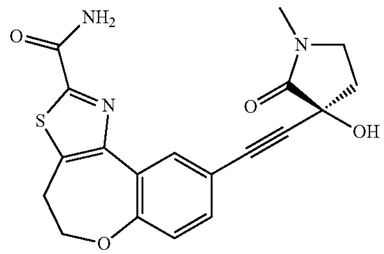 [SMILES: CN1CC[C@](O)(C#Cc2ccc3c(c2)-c2nc(C(N)=O)sc2CCO3)C1=O] | 9-[2-[(3S)-3-hydroxy-1-methyl-2-oxo-pyrrolidin-3-yl]ethynyl]-4,5-dihydro-[1]benzoxepino[5,4-d]thiazole-2-carboxamide |
| 276 | 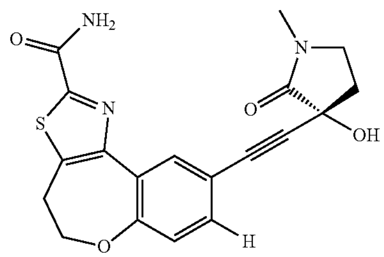 [SMILES: CN1CC[C@@](O)(C#Cc2ccc3c(c2)-c2nc(C(N)=O)sc2CCO3)C1=O] | 9-[2-[(3R)-3-hydroxy-1-methyl-2-oxo-pyrrolidin-3-yl]ethynyl]-4,5-dihydro-[1]benzoxepino[5,4-d]thiazole-2-carboxamide |
| 277 | 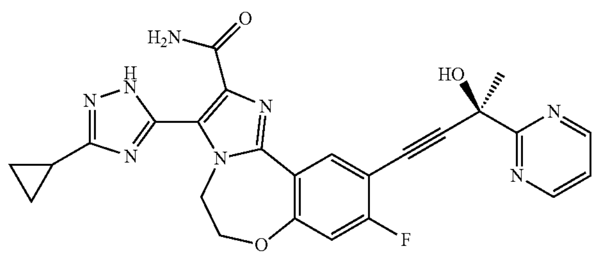 [SMILES: C[C@@](O)(C#Cc1cc2c(cc1F)OCCn1c-2nc(C(N)=O)c1-c1nc(C2CC2)n[nH]1)c1ncccn1] | 3-(3-cyclopropyl-1H-1,2,4-triazol-5-yl)-9-fluoro-10-[(3R)-3-hydroxy-3-pyrimidin-2-yl-but-1-ynyl]-5,6-dihydroimidazo[1,2-d][1,4]benzoxazepine-2-carboxamide |
| 279 | 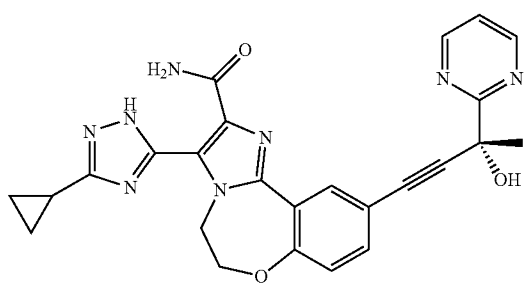 [SMILES: C[C@@](O)(C#Cc1ccc2c(c1)-c1nc(C(N)=O)c(-c3nc(C4CC4)n[nH]3)n1CCO2)c1ncccn1] | 3-(3-cyclopropyl-1H-1,2,4-triazol-5-yl)-10-[(3R)-3-hydroxy-3-pyrimidin-2-yl-but-1-ynyl]-5,6-dihydroimidazo[1,2-d][1,4]benzoxazepine-2-carboxamide |
| 285 | 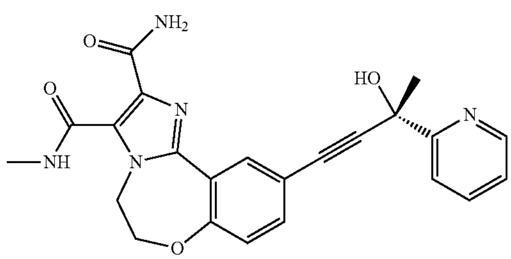 [SMILES: CNC(=O)c1c(C(N)=O)nc2n1CCOc1ccc(C#C[C@](C)(O)c3ccccn3)cc1-2] | 10-[(3S)-3-hydroxy-3-(2-pyridyl)but-1-ynyl]-N3-methyl-5,6-dihydroimidazo[1,2-d][1,4]benzoxazepine-2,3-dicarboxamide |
| 288 | 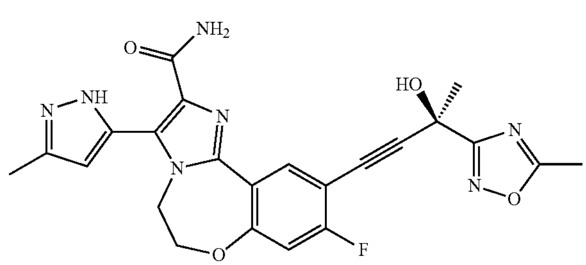 | 9-fluoro-10-[(3R)-3-hydroxy-3-(5-methyl-1,2,4-oxadiazol-3-yl)but-1-ynyl]-3-(3-methyl-1H-pyrazol-5-yl)-5,6-dihydroimidazo[1,2-d][1,4]benzoxazepine-2-carboxamide |

TABLE 1A-continued

| No. | Structure | Name |
|---|---|---|
| 291 | 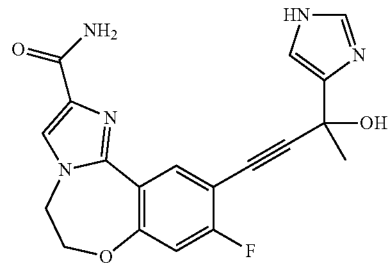 [SMILES: CC(O)(C#Cc1cc2c(cc1F)OCCn1cc(C(N)=O)nc1-2)c1c[nH]cn1] | 9-fluoro-10-[3-hydroxy-3-(1H-imidazol-4-yl)but-1-ynyl]-5,6-dihydroimidazo[1,2-d][1,4]benzoxazepine-2-carboxamide |
| 292 | 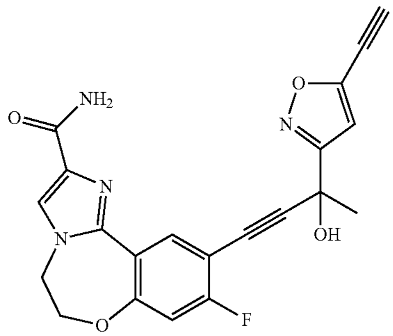 [SMILES: C#Cc1cc(C(C)(O)C#Cc2cc3c(cc2F)OCCn2cc(C(N)=O)nc2-3)no1] | 10-[3-(5-ethynylisoxazol-3-yl)-3-hydroxy-but-1-ynyl]-9-fluoro-5,6-dihydroimidazo[1,2-d][1,4]benzoxazepine-2-carboxamide |
| 293 | 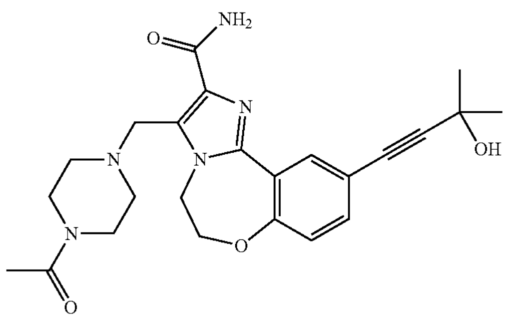 [SMILES: CC(=O)N1CCN(Cc2c(C(N)=O)nc3n2CCOc2ccc(C#CC(C)(C)O)cc2-3)CC1] | 3-[(4-acetylpiperazin-1-yl)methyl]-10-(3-hydroxy-3-methyl-but-1-ynyl)-5,6-dihydroimidazo[1,2-d][1,4]benzoxazepine-2-carboxamide |
| 294 | 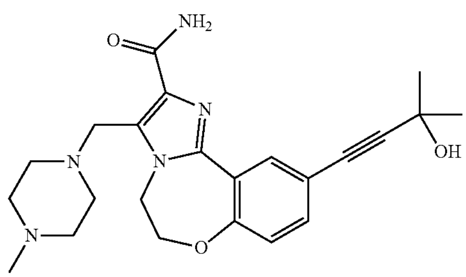 [SMILES: CN1CCN(Cc2c(C(N)=O)nc3n2CCOc2ccc(C#CC(C)(C)O)cc2-3)CC1] | 10-(3-hydroxy-3-methyl-but-1-ynyl)-3-[(4-methylpiperazin-1-yl)methyl]-5,6-dihydroimidazo[1,2-d][1,4]benzoxazepine-2-carboxamide |
| 301 | 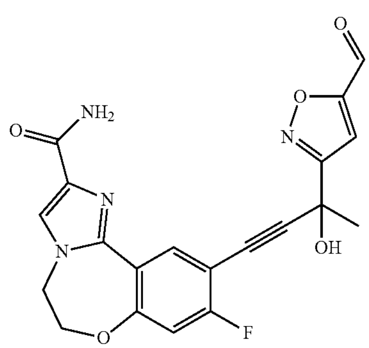 [SMILES: CC(O)(C#Cc1cc2c(cc1F)OCCn1cc(C(N)=O)nc1-2)c1cc(C=O)on1] | 9-fluoro-10-[3-(5-formylisoxazol-3-yl)-3-hydroxy-but-1-ynyl]-5,6-dihydroimidazo[1,2-d][1,4]benzoxazepine-2-carboxamide |

TABLE 1A-continued

| No. | Structure | Name |
|---|---|---|
| 311 | 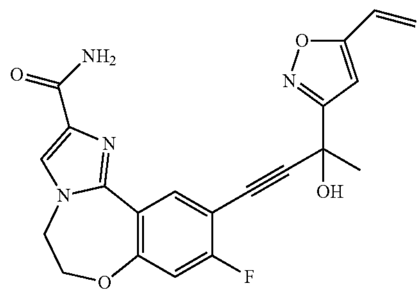 [SMILES: C=Cc1cc(C(C)(O)C#Cc2cc3c(cc2F)OCCn2cc(C(N)=O)nc2-3)no1] | 9-fluoro-10-[3-hydroxy-3-(5-vinylisoxazol-3-yl)but-1-ynyl]-5,6-dihydroimidazo[1,2-d][1,4]benzoxazepine-2-carboxamide |
| 341 | 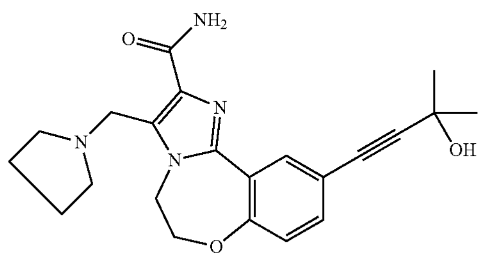 [SMILES: CC(C)(O)C#Cc1ccc2c(c1)-c1nc(C(N)=O)c(CN3CCCC3)n1CCO2] | 10-(3-hydroxy-3-methyl-but-1-ynyl)-3-(pyrrolidin-1-ylmethyl)-5,6-dihydroimidazo[1,2-d][1,4]benzoxazepine-2-carboxamide |
| 342 | 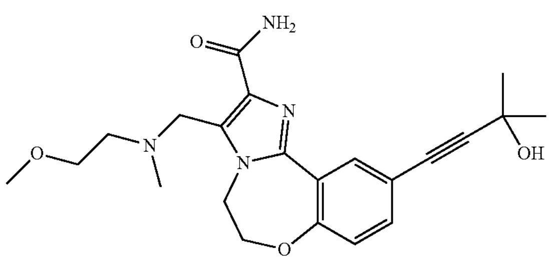 [SMILES: COCCN(C)Cc1c(C(N)=O)nc2n1CCOc1ccc(C#CC(C)(C)O)cc1-2] | 10-(3-hydroxy-3-methyl-but-1-ynyl)-3-[[2-methoxyethyl(methyl)amino]methyl]-5,6-dihydroimidazo[1,2-d][1,4]benzoxazepine-2-carboxamide |
| 343 | 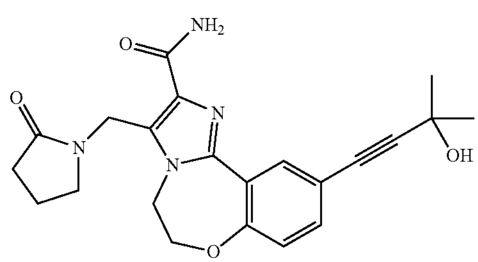 [SMILES: CC(C)(O)C#Cc1ccc2c(c1)-c1nc(C(N)=O)c(CN3CCCC3=O)n1CCO2] | 10-(3-hydroxy-3-methyl-but-1-ynyl)-3-[(2-oxopyrrolidin-1-yl)methyl]-5,6-dihydroimidazo[1,2-d][1,4]benzoxazepine-2-carboxamide |
| 351 | 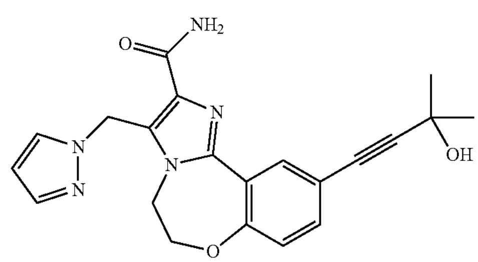 [SMILES: CC(C)(O)C#Cc1ccc2c(c1)-c1nc(C(N)=O)c(Cn3cccn3)n1CCO2] | 10-(3-hydroxy-3-methyl-but-1-ynyl)-3-(pyrazol-1-ylmethyl)-5,6-dihydroimidazo[1,2-d][1,4]benzoxazepine-2-carboxamide |
| 362 | 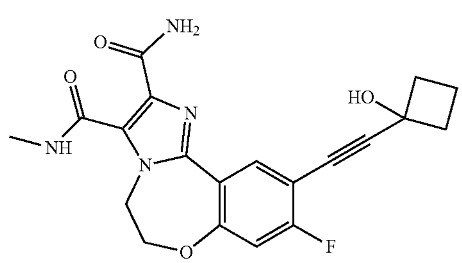 [SMILES: CNC(=O)c1c(C(N)=O)nc2n1CCOc1cc(F)c(C#CC3(O)CCC3)cc1-2] | 9-fluoro-10-[2-(1-hydroxycyclobutyl)ethynyl]-N3-methyl-5,6-dihydroimidazo[1,2-d][1,4]benzoxazepine-2,3-dicarboxamide |

TABLE 1A-continued

| No. | Structure | Name |
|---|---|---|
| 370 | 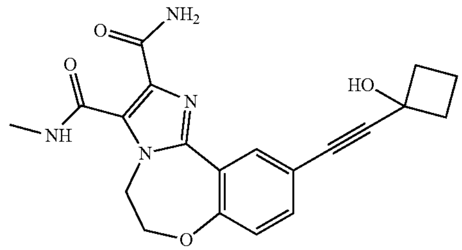 [SMILES: CNC(=O)c1c(C(N)=O)nc2n1CCOc1ccc(C#CC3(O)CCC3)cc1-2] | 10-[2-(1-hydroxycyclobutyl)ethynyl]-N3-methyl-5,6-dihydroimidazo[1,2-d][1,4]benzoxazepine-2,3-dicarboxamide |
| 372 | 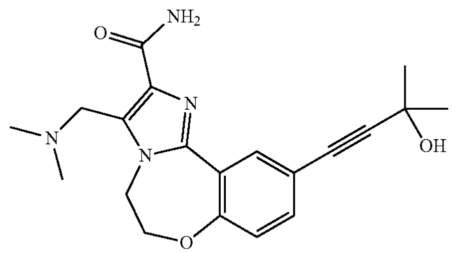 [SMILES: CN(C)Cc1c(C(N)=O)nc2n1CCOc1ccc(C#CC(C)(C)O)cc1-2] | 3-[(dimethylamino)methyl]-10-(3-hydroxy-3-methyl-but-1-ynyl)-5,6-dihydroimidazo[1,2-d][1,4]benzoxazepine-2-carboxamide |
| 373 | 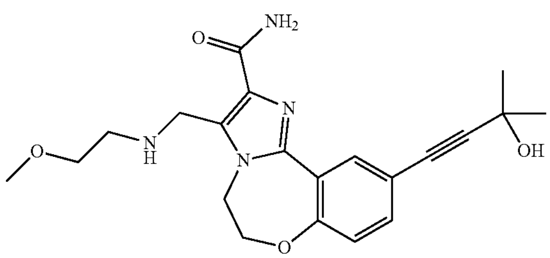 [SMILES: COCCNCc1c(C(N)=O)nc2n1CCOc1ccc(C#CC(C)(C)O)cc1-2] | 10-(3-hydroxy-3-methyl-but-1-ynyl)-3-[(2-methoxyethylamino)methyl]-5,6-dihydroimidazo[1,2-d][1,4]benzoxazepine-2-carboxamide |
| 374 | 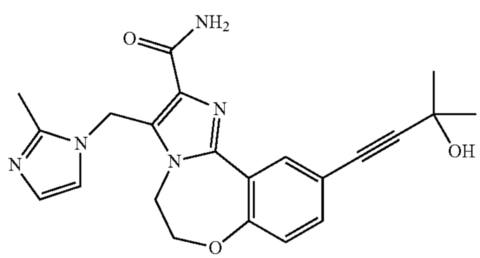 [SMILES: Cc1nccn1Cc1c(C(N)=O)nc2n1CCOc1ccc(C#CC(C)(C)O)cc1-2] | 10-(3-hydroxy-3-methyl-but-1-ynyl)-3-[(2-methylimidazol-1-yl)methyl]-5,6-dihydroimidazo[1,2-d][1,4]benzoxazepine-2-carboxamide |
| 375 | 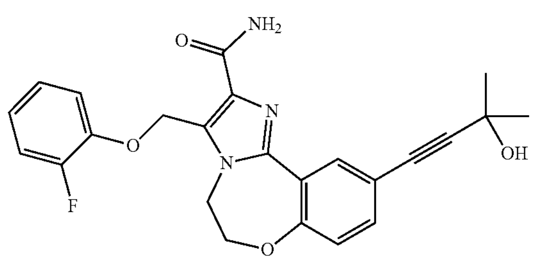 [SMILES: CC(C)(O)C#Cc1ccc2c(c1)-c1nc(C(N)=O)c(COc3ccccc3F)n1CCO2] | 3-[(2-fluorophenoxy)methyl]-10-(3-hydroxy-3-methyl-but-1-ynyl)-5,6-dihydroimidazo[1,2-d][1,4]benzoxazepine-2-carboxamide |
| 376 | 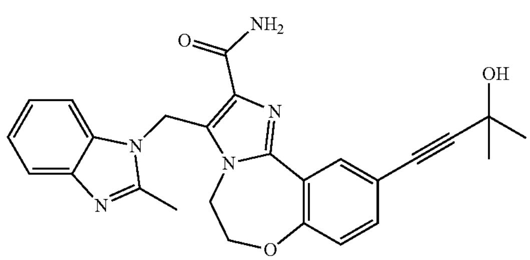 [SMILES: Cc1nc2ccccc2n1Cc1c(C(N)=O)nc2n1CCOc1ccc(C#CC(C)(C)O)cc1-2] | 10-(3-hydroxy-3-methyl-but-1-ynyl)-3-[(2-methylbenzimidazol-1-yl)methyl]-5,6-dihydroimidazo[1,2-d][1,4]benzoxazepine-2-carboxamide |

TABLE 1A-continued

| No. | Structure | Name |
|-----|-----------|------|
| 377 | 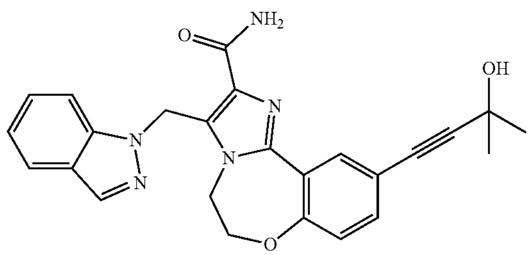 [SMILES: CC(C)(O)C#Cc1ccc2c(c1)-c1nc(C(N)=O)c(Cn3ncc4ccccc43)n1CCO2] | 10-(3-hydroxy-3-methyl-but-1-ynyl)-3-(indazol-1-ylmethyl)-5,6-dihydroimidazo[1,2-d][1,4]benzoxazepine-2-carboxamide |
| 384 | 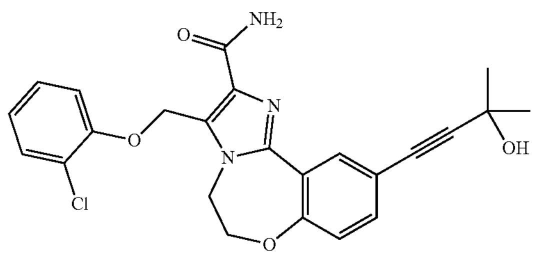 [SMILES: CC(C)(O)C#Cc1ccc2c(c1)-c1nc(C(N)=O)c(COc3ccccc3Cl)n1CCO2] | 3-[(2-chlorophenoxy)methyl]-10-(3-hydroxy-3-methyl-but-1-ynyl)-5,6-dihydroimidazo[1,2-d][1,4]benzoxazepine-2-carboxamide |
| 386 | 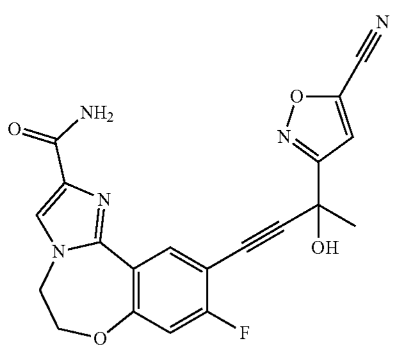 [SMILES: CC(O)(C#Cc1cc2c(cc1F)OCCn1cc(C(N)=O)nc1-2)c1cc(C#N)on1] | 10-[3-(5-cyanoisoxazol-3-yl)-3-hydroxy-but-1-ynyl]-9-fluoro-5,6-dihydroimidazo[1,2-d][1,4]benzoxazepine-2-carboxamide |
| 387 | 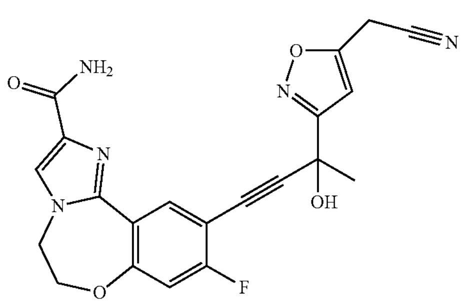 [SMILES: CC(O)(C#Cc1cc2c(cc1F)OCCn1cc(C(N)=O)nc1-2)c1cc(CC#N)on1] | 10-[3-[5-(cyanomethyl)isoxazol-3-yl]-3-hydroxy-but-1-ynyl]-9-fluoro-5,6-dihydroimidazo[1,2-d][1,4]benzoxazepine-2-carboxamide |
| 388 | 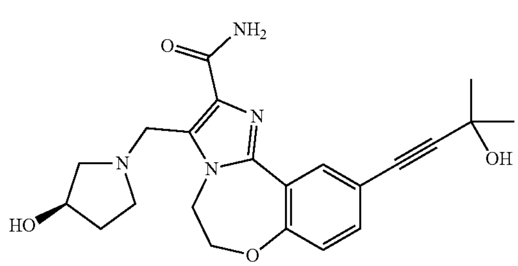 [SMILES: CC(C)(O)C#Cc1ccc2c(c1)-c1nc(C(N)=O)c(CN3CC[C@@H](O)C3)n1CCO2] | 10-(3-hydroxy-3-methyl-but-1-ynyl)-3-[[(3R)-3-hydroxypyrrolidin-1-yl]methyl]-5,6-dihydroimidazo[1,2-d][1,4]benzoxazepine-2-carboxamide |

TABLE 1A-continued

| No. | Structure | Name |
|---|---|---|
| 389 | 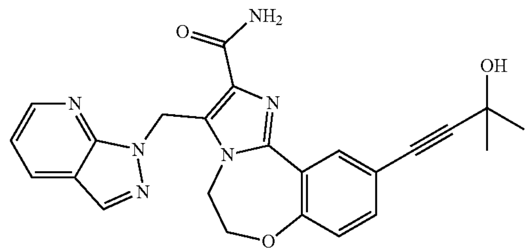 [SMILES: CC(C)(O)C#Cc1ccc2c(c1)-c1nc(C(N)=O)c(Cn3ncc4cccnc43)n1CCO2] | 10-(3-hydroxy-3-methyl-but-1-ynyl)-3-(pyrazolo[3,4-b]pyridin-1-ylmethyl)-5,6-dihydroimidazo[1,2-d][1,4]benzoxazepine-2-carboxamide |
| 394 | 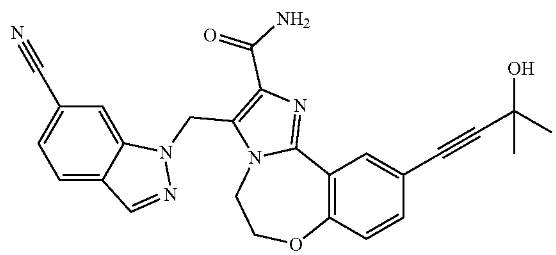 [SMILES: CC(C)(O)C#Cc1ccc2c(c1)-c1nc(C(N)=O)c(Cn3ncc4ccc(C#N)cc43)n1CCO2] | 3-[(6-cyanoindazol-1-yl)methyl]-10-(3-hydroxy-3-methyl-but-1-ynyl)-5,6-dihydroimidazo[1,2-d][1,4]benzoxazepine-2-carboxamide |
| 395 | 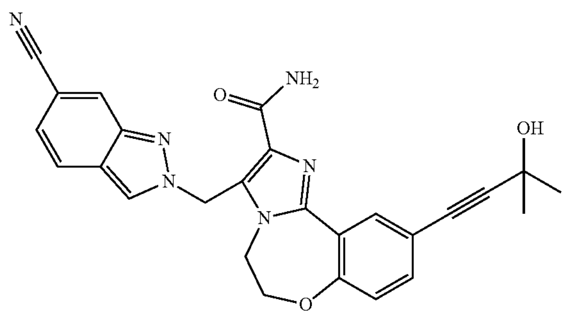 [SMILES: CC(C)(O)C#Cc1ccc2c(c1)-c1nc(C(N)=O)c(Cn3cc4ccc(C#N)cc4n3)n1CCO2] | 3-[(6-cyanoindazol-2-yl)methyl]-10-(3-hydroxy-3-methyl-but-1-ynyl)-5,6-dihydroimidazo[1,2-d][1,4]benzoxazepine-2-carboxamide |
| 396 | 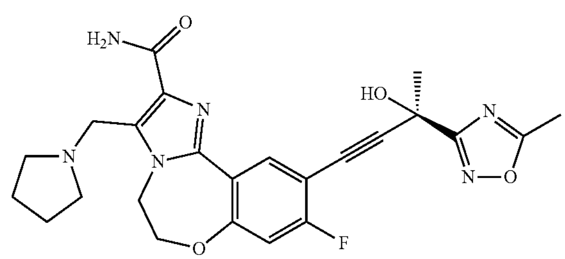 [SMILES: Cc1nc([C@](C)(O)C#Cc2cc3c(cc2F)OCCn2c-3nc(C(N)=O)c2CN2CCCC2)no1] | 9-fluoro-10-[(3R)-3-hydroxy-3-(5-methyl-1,2,4-oxadiazol-3-yl)but-1-ynyl]-3-(pyrrolidin-1-ylmethyl)-5,6-dihydroimidazo[1,2-d][1,4]benzoxazepine-2-carboxamide |
| 397 | 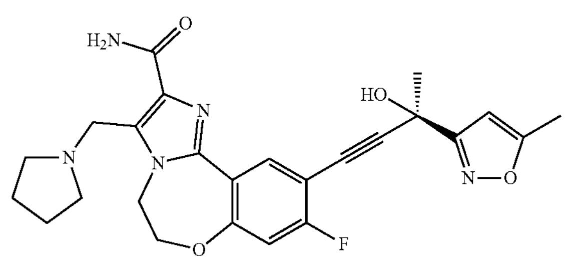 [SMILES: Cc1cc([C@](C)(O)C#Cc2cc3c(cc2F)OCCn2c-3nc(C(N)=O)c2CN2CCCC2)no1] | 9-fluoro-10-[(3R)-3-hydroxy-3-(5-methylisoxazol-3-yl)but-1-ynyl]-3-(pyrrolidin-1-ylmethyl)-5,6-dihydroimidazo[1,2-d][1,4]benzoxazepine-2-carboxamide |
| 398 | 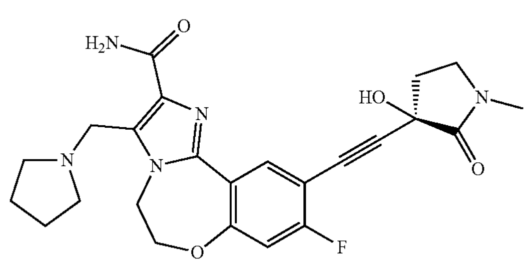 [SMILES: CN1CC[C@@](O)(C#Cc2cc3c(cc2F)OCCn2c-3nc(C(N)=O)c2CN2CCCC2)C1=O] | 9-fluoro-10-[2-[(3R)-3-hydroxy-1-methyl-2-oxo-pyrrolidin-3-yl]ethynyl]-3-(pyrrolidin-1-ylmethyl)-5,6-dihydroimidazo[1,2-d][1,4]benzoxazepine-2-carboxamide |

TABLE 1A-continued

| No. | Structure | Name |
|---|---|---|
| 400 | 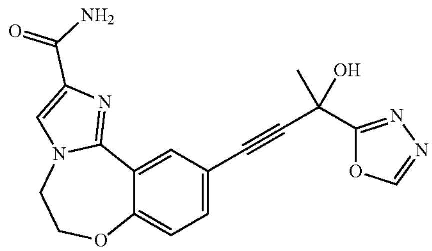 [SMILES: CC(O)(C#Cc1ccc2c(c1)-c1nc(C(N)=O)cn1CCO2)c1nnco1] | 10-[3-hydroxy-3-(1,3,4-oxadiazol-2-yl)but-1-ynyl]-5,6-dihydroimidazo[1,2-d][1,4]benzoxazepine-2-carboxamide |
| 401 | 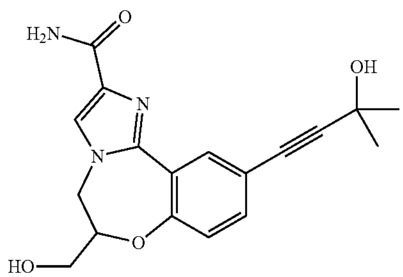 [SMILES: CC(C)(O)C#Cc1ccc2c(c1)-c1nc(C(N)=O)cn1CC(CO)O2] | 6-(hydroxymethyl)-10-(3-hydroxy-3-methyl-but-1-ynyl)-5,6-dihydroimidazo[1,2-d][1,4]benzoxazepine-2-carboxamide |
| 402 | 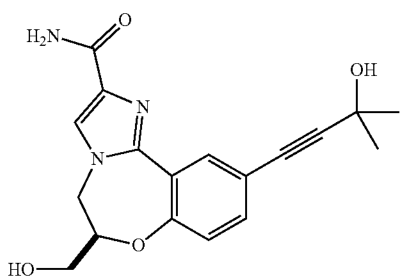 [SMILES: CC(C)(O)C#Cc1ccc2c(c1)-c1nc(C(N)=O)cn1C[C@H](CO)O2] | (R)-10-(3-hydroxy-3-methylbut-1-yn-1-yl)-6-(hydroxymethyl)-5,6-dihydrobenzo[f]imidazo[1,2-d][1,4]oxazepine-2-carboxamide |
| 403 | 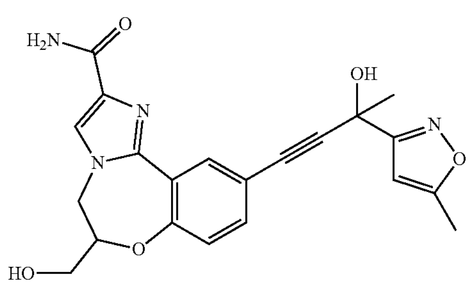 [SMILES: Cc1cc(C(C)(O)C#Cc2ccc3c(c2)-c2nc(C(N)=O)cn2CC(CO)O3)no1] | 6-(hydroxymethyl)-10-[3-hydroxy-3-(5-methylisoxazol-3-yl)but-1-ynyl]-5,6-dihydroimidazo[1,2-d][1,4]benzoxazepine-2-carboxamide |
| 404 | 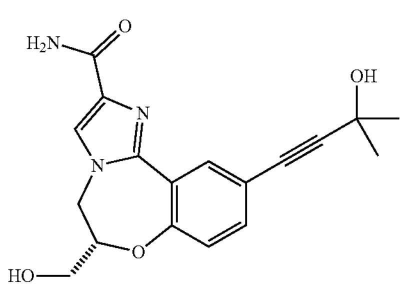 [SMILES: CC(C)(O)C#Cc1ccc2c(c1)-c1nc(C(N)=O)cn1C[C@@H](CO)O2] | (S)-10-(3-hydroxy-3-methylbut-1-yn-1-yl)-6-(hydroxymethyl)-5,6-dihydrobenzo[f]imidazo[1,2-d][1,4]oxazepine-2-carboxamide |

TABLE 1A-continued

| No. | Structure | Name |
|---|---|---|
| 406 | 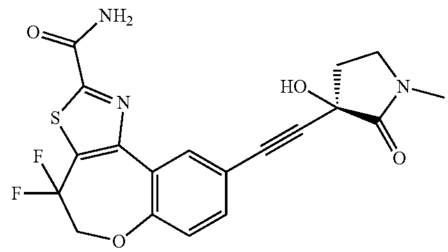 [SMILES: CN1CC[C@@](O)(C#Cc2ccc3c(c2)-c2nc(C(N)=O)sc2C(F)(F)CO3)C1=O] | 4,4-difluoro-9-[2-[(3R)-3-hydroxy-1-methyl-2-oxo-pyrrolidin-3-yl]ethynyl]-5H-[1]benzoxepino[5,4-d]thiazole-2-carboxamide |
| 407 | 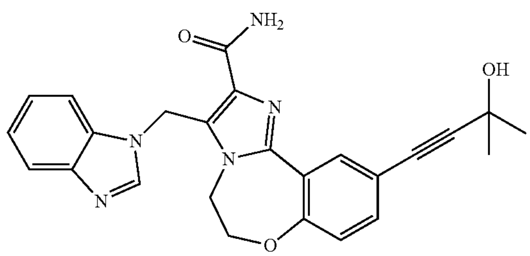 [SMILES: CC(C)(O)C#Cc1ccc2c(c1)-c1nc(C(N)=O)c(Cn3cnc4ccccc43)n1CCO2] | 3-(benzimidazol-1-ylmethyl)-10-(3-hydroxy-3-methyl-but-1-ynyl)-5,6-dihydroimidazo[1,2-d][1,4]benzoxazepine-2-carboxamide |
| 408 | 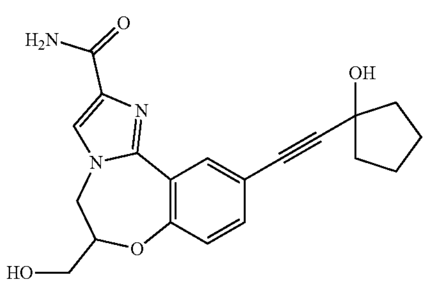 [SMILES: NC(=O)c1cn2c(n1)-c1cc(C#CC3(O)CCCC3)ccc1OC(CO)C2] | 10-[2-(1-hydroxycyclopentyl)ethynyl]-6-(hydroxymethyl)-5,6-dihydroimidazo[1,2-d][1,4]benzoxazepine-2-carboxamide |
| 409 | 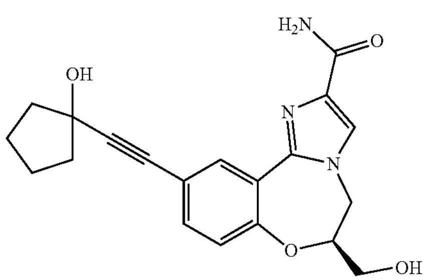 [SMILES: NC(=O)c1cn2c(n1)-c1cc(C#CC3(O)CCCC3)ccc1O[C@H](CO)C2] | (S)-10-((1-hydroxycyclopentyl)ethynyl)-6-(hydroxymethyl)-5,6-dihydrobenzo[f]imidazo[1,2-d][1,4]oxazepine-2-carboxamide |
| 410 | 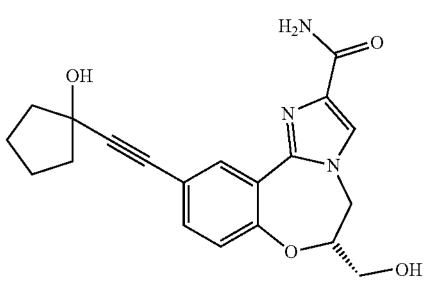 | (R)-10-((1-hydroxycyclopentyl)ethynyl)-6-(hydroxymethyl)-5,6-dihydrobenzo[f]imidazo[1,2-d][1,4]oxazepine-2-carboxamide |

| No. | Structure | Name |
|---|---|---|
| 412 | 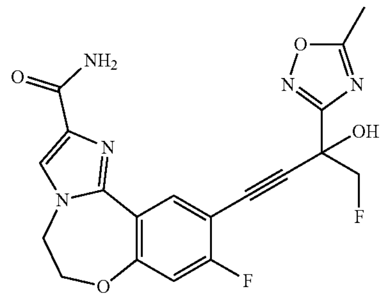 [SMILES: Cc1nc(C(O)(C#Cc2cc3c(cc2F)OCCn2cc(C(N)=O)nc2-3)CF)no1] | 9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |
| 413 | 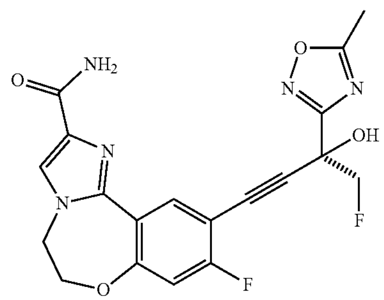 [SMILES: Cc1nc([C@@](O)(C#Cc2cc3c(cc2F)OCCn2cc(C(N)=O)nc2-3)CF)no1] | (S)-9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |
| 414 | 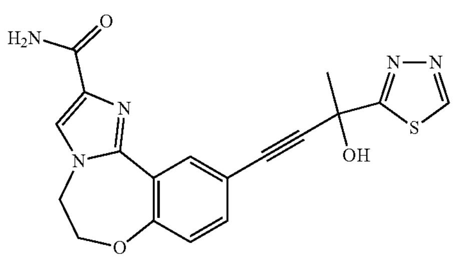 [SMILES: CC(O)(C#Cc1ccc2c(c1)-c1nc(C(N)=O)cn1CCO2)c1nncs1] | 10-[3-hydroxy-3-(1,3,4-thiadiazol-2-yl)but-1-ynyl]-5,6-dihydroimidazo[1,2-d][1,4]benzoxazepine-2-carboxamide |
| 415 | 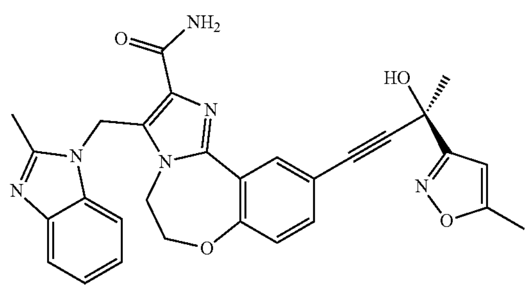 | 10-[(3R)-3-hydroxy-3-(5-methylisoxazol-3-yl)but-1-ynyl]-3-[(2-methylbenzimidazol-1-yl)methyl]-5,6-dihydroimidazo[1,2-d][1,4]benzoxazepine-2-carboxamide |
| 416 | 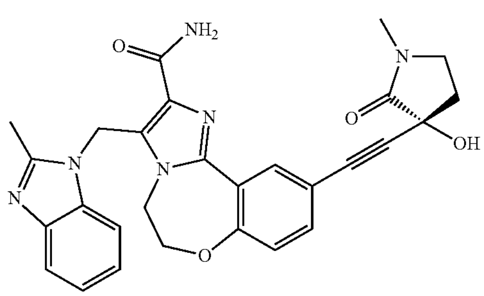 [SMILES: Cc1nc2ccccc2n1Cc1c(C(N)=O)nc2n1CCOc1ccc(C#C[C@]3(O)CCN(C)C3=O)cc1-2] | 10-[2-[(3R)-3-hydroxy-1-methyl-2-oxopyrrolidin-3-yl]ethynyl]-3-[(2-methylbenzimidazol-1-yl)methyl]-5,6-dihydroimidazo[1,2-d][1,4]benzoxazepine-2-carboxamide |

TABLE 1A-continued

| No. | Structure | Name |
|---|---|---|
| 417 | 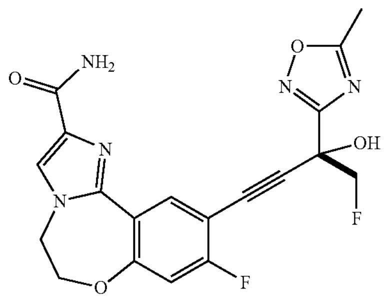 [SMILES: Cc1nc([C@](O)(C#Cc2cc3c(cc2F)OCCn2cc(C(N)=O)nc2-3)CF)no1] | (R)-9-fluoro-10-(4-fluoro-3-hydroxy-3-(5-methyl-1,2,4-oxadiazol-3-yl)but-1-ynyl)-5,6-dihydrobenzo[f]imidazo[1,2-d][1,4]oxazepine-2-carboxamide |
| 418 | 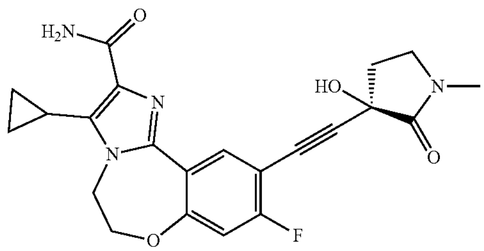 [SMILES: CN1CC[C@@](O)(C#Cc2cc3c(cc2F)OCCn2c-3nc(C(N)=O)c2C2CC2)C1=O] | 3-cyclopropyl-9-fluoro-10-[2-[(3R)-3-hydroxy-1-methyl-2-oxo-pyrrolidin-3-yl]ethynyl]-5,6-dihydroimidazo[1,2-d][1,4]benzoxazepine-2-carboxamide |
| 419 | 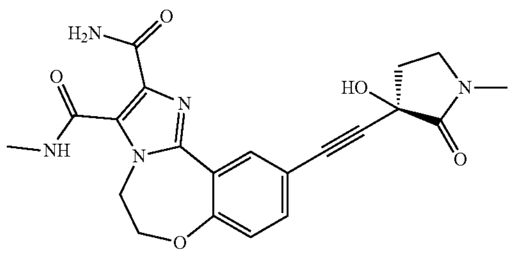 | 10-[2-[(3R)-3-hydroxy-1-methyl-2-oxo-pyrrolidin-3-yl]ethynyl]-N3-methyl-5,6-dihydroimidazo[1,2-d][1,4]benzoxazepine-2,3-dicarboxamide |
| 420 | 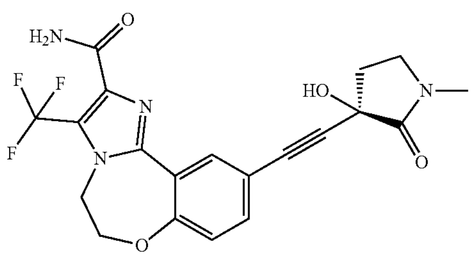 [SMILES: CN1CC[C@@](O)(C#Cc2ccc3c(c2)-c2nc(C(N)=O)c(C(F)(F)F)n2CCO3)C1=O] | 10-[2-[(3R)-3-hydroxy-1-methyl-2-oxo-pyrrolidin-3-yl]ethynyl]-3-(trifluoromethyl)-5,6-dihydroimidazo[1,2-d][1,4]benzoxazepine-2-carboxamide |
| 421 | 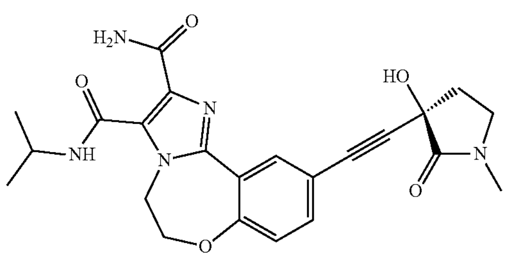 [SMILES: CC(C)NC(=O)c1c(C(N)=O)nc2n1CCOc1ccc(C#C[C@]3(O)CCN(C)C3=O)cc1-2] | 10-[2-[(3R)-3-hydroxy-1-methyl-2-oxo-pyrrolidin-3-yl]ethynyl]-N3-isopropyl-5,6-dihydroimidazo[1,2-d][1,4]benzoxazepine-2,3-dicarboxamide |
| 422 | 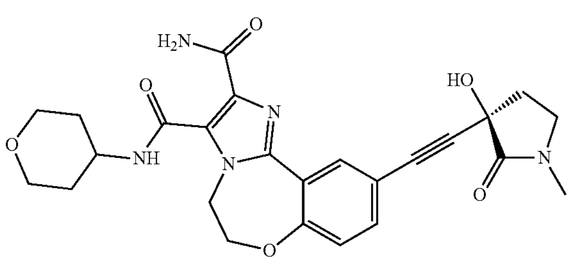 [SMILES: CN1CC[C@@](O)(C#Cc2ccc3c(c2)-c2nc(C(N)=O)c(C(=O)NC4CCOCC4)n2CCO3)C1=O] | 10-[2-[(3R)-3-hydroxy-1-methyl-2-oxo-pyrrolidin-3-yl]ethynyl]-N3-tetrahydropyran-4-yl-5,6-dihydroimidazo[1,2-d][1,4]benzoxazepine-2,3-dicarboxamide |

TABLE 1A-continued

| No. | Structure | Name |
|---|---|---|
| 428 | 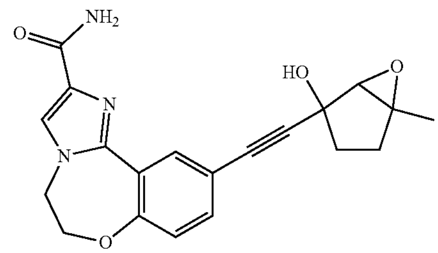 [SMILES: CC12CCC(O)(C#Cc3ccc4c(c3)-c3nc(C(N)=O)cn3CCO4)C1O2] | 10-[2-(2-hydroxy-5-methyl-6-oxabicyclo[3.1.0]hexan-2-yl)ethynyl]-5,6-dihydroimidazo[1,2-d][1,4]benzoxazepine-2-carboxamide |
| 429 | 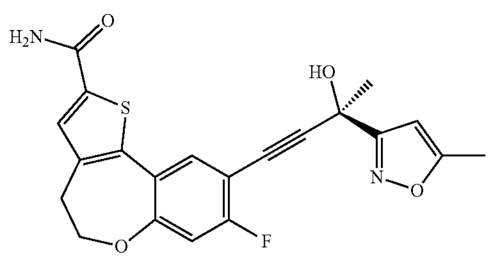 [SMILES: Cc1cc([C@](C)(O)C#Cc2cc3c(cc2F)OCCc2cc(C(N)=O)sc2-3)no1] | 8-fluoro-9-[(3R)-3-hydroxy-3-(5-methylisoxazol-3-yl)but-1-ynyl]-4,5-dihydrothieno[3,2-d][1]benzoxepine-2-carboxamide |
| 430 | 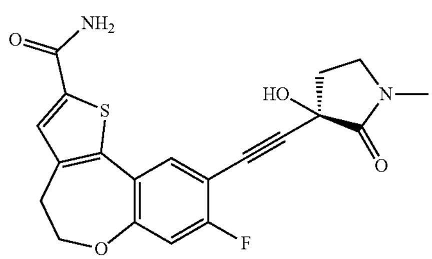 [SMILES: CN1CC[C@@](O)(C#Cc2cc3c(cc2F)OCCc2cc(C(N)=O)sc2-3)C1=O] | 8-fluoro-9-[2-[(3R)-3-hydroxy-1-methyl-2-oxo-pyrrolidin-3-yl]ethynyl]-4,5-dihydrothieno[3,2-d][1]benzoxepine-2-carboxamide |
| 431 | 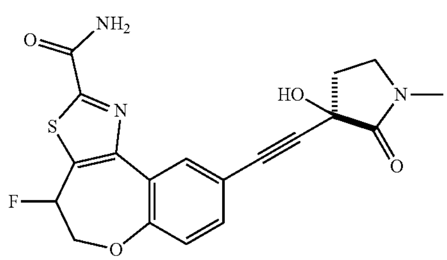 [SMILES: CN1CC[C@@](O)(C#Cc2ccc3c(c2)-c2nc(C(N)=O)sc2C(F)CO3)C1=O] | 4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 432 | 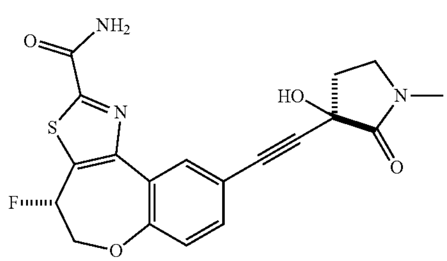 | (S)-4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 433 | 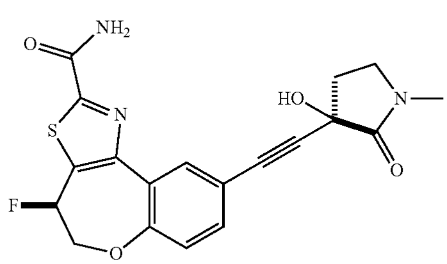 [SMILES: CN1CC[C@@](O)(C#Cc2ccc3c(c2)-c2nc(C(N)=O)sc2[C@H](F)CO3)C1=O] | (R)-4-fluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1A-continued

| No. | Structure | Name |
|---|---|---|
| 434 | 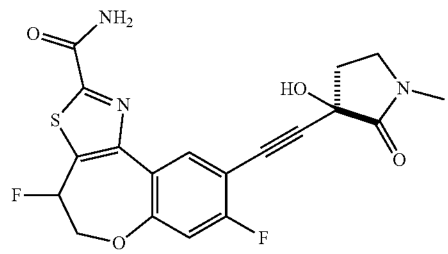 | 4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 435 | 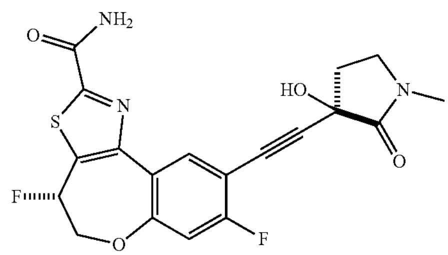 [SMILES: CN1CC[C@@](O)(C#Cc2cc3c(cc2F)OC[C@H](F)c2sc(C(N)=O)nc2-3)C1=O] | (S)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 436 | 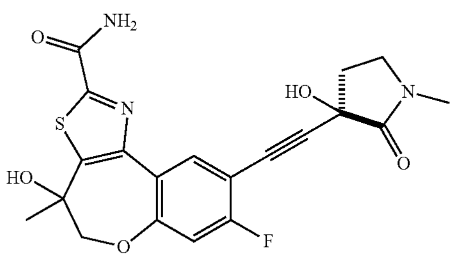 [SMILES: CN1CC[C@@](O)(C#Cc2cc3c(cc2F)OCC(C)(O)c2sc(C(N)=O)nc2-3)C1=O] | 8-fluoro-4-hydroxy-9-((3-(R)-hydroxy-1-methyl-2-oxopyrrolidin-3-yl)ethynyl)-4-methyl-4,5-dihydrobenzo[2,3]oxepino[4,5-d]thiazole-2-carboxamide |
| 437 | 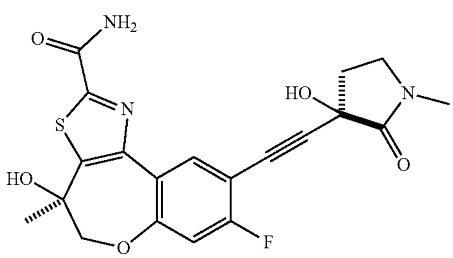 [SMILES: CN1CC[C@@](O)(C#Cc2cc3c(cc2F)OC[C@@](C)(O)c2sc(C(N)=O)nc2-3)C1=O] | (R)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 438 | 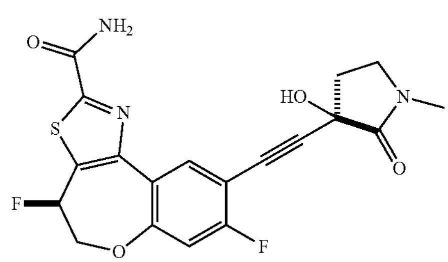 [SMILES: CN1CC[C@@](O)(C#Cc2cc3c(cc2F)OC[C@@H](F)c2sc(C(N)=O)nc2-3)C1=O] | (R)-4,8-difluoro-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 439 | 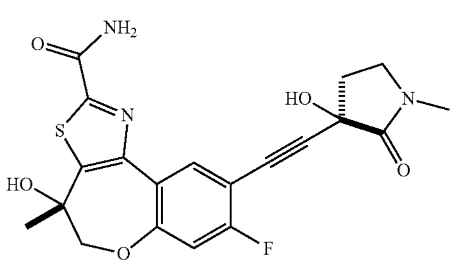 [SMILES: CN1CC[C@@](O)(C#Cc2cc3c(cc2F)OC[C@](C)(O)c2sc(C(N)=O)nc2-3)C1=O] | (S)-8-fluoro-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |

TABLE 1A-continued

| No. | Structure | Name |
|---|---|---|
| 440 | 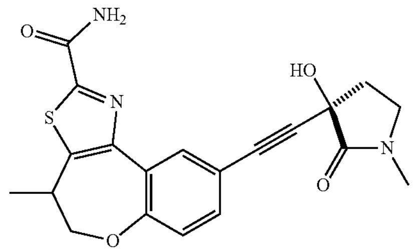 | 9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 441 | 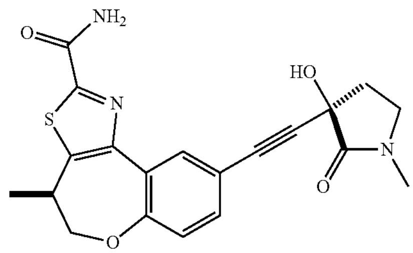 | (R)-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 442 | 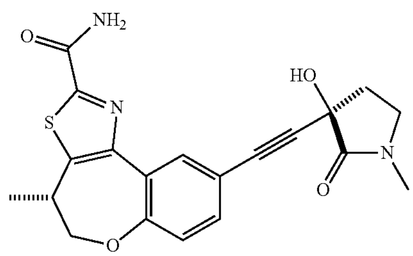 | (S)-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 443 | 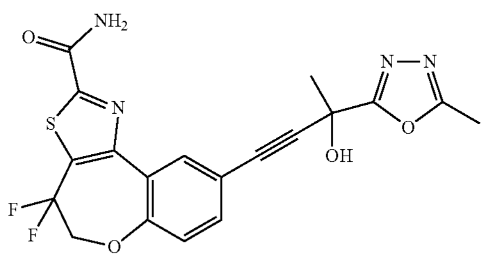 [SMILES: Cc1nnc(C(C)(O)C#Cc2ccc3c(c2)-c2nc(C(N)=O)sc2C(F)(F)CO3)o1] | 4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide |
| 444 | 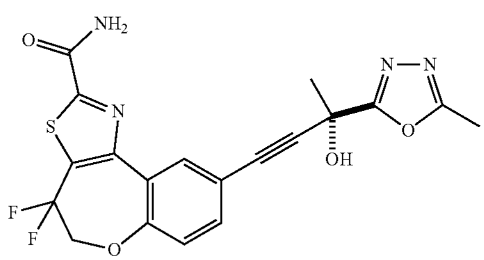 [SMILES: Cc1nnc([C@@](C)(O)C#Cc2ccc3c(c2)-c2nc(C(N)=O)sc2C(F)(F)CO3)o1] | (S)-4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide |
| 445 | 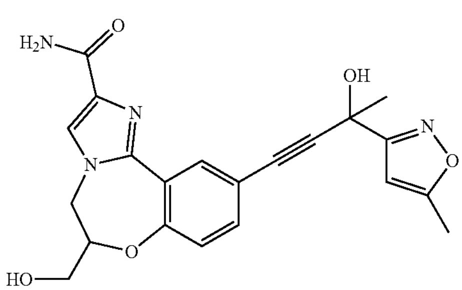 [SMILES: Cc1cc(C(C)(O)C#Cc2ccc3c(c2)-c2nc(C(N)=O)cn2CC(CO)O3)no1] | 6-(hydroxymethyl)-10-[3-hydroxy-3-(5-methylisoxazol-3-yl)but-1-ynyl]-5,6-dihydroimidazo[1,2-d][1,4]benzoxazepine-2-carboxamide |

TABLE 1A-continued

| No. | Structure | Name |
|---|---|---|
| 446 | 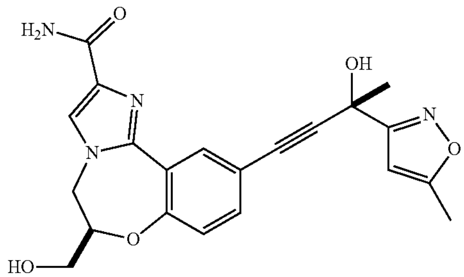 [SMILES: Cc1cc([C@@](C)(O)C#Cc2ccc3c(c2)-c2nc(C(N)=O)cn2C[C@H](CO)O3)no1] | 6-(R)-(hydroxymethyl)-10-[3-(S)-hydroxy-3-(5-methylisoxazol-3-yl)but-1-ynyl]-5,6-dihydroimidazo[1,2-d][1,4]benzoxazepine-2-carboxamide |
| 447 | 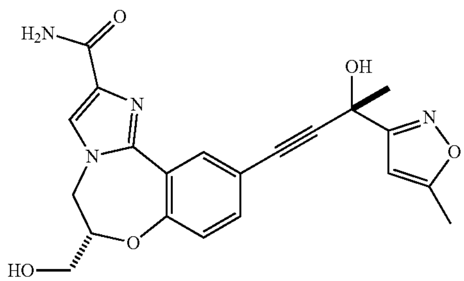 [SMILES: Cc1cc([C@@](C)(O)C#Cc2ccc3c(c2)-c2nc(C(N)=O)cn2C[C@@H](CO)O3)no1] | (S)-10-((S)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |
| 448 | 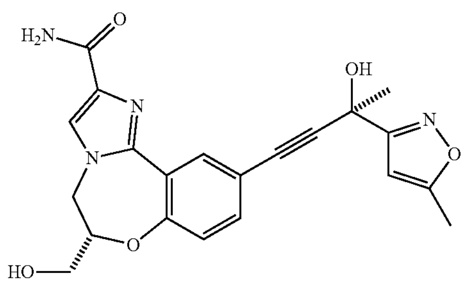 [SMILES: Cc1cc([C@](C)(O)C#Cc2ccc3c(c2)-c2nc(C(N)=O)cn2C[C@@H](CO)O3)no1] | (S)-10-((R)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |
| 449 | 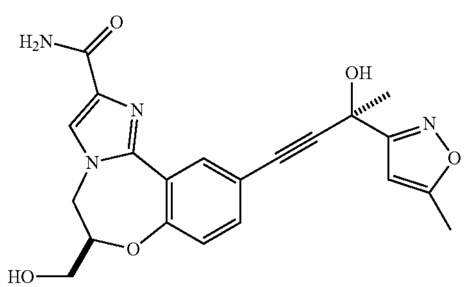 [SMILES: Cc1cc([C@](C)(O)C#Cc2ccc3c(c2)-c2nc(C(N)=O)cn2C[C@H](CO)O3)no1] | (R)-10-((R)-3-hydroxy-3-(5-methylisoxazol-3-yl)but-1-ynyl)-6-(hydroxymethyl)-5,6-dihydrobenzo[f]imidazo[1,2-d][1,4]oxazepine-2-carboxamide |
| 451 | 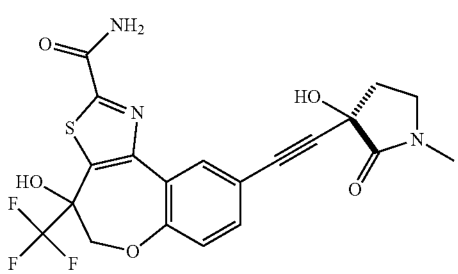 | 4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |

TABLE 1A-continued

| No. | Structure | Name |
|---|---|---|
| 452 | 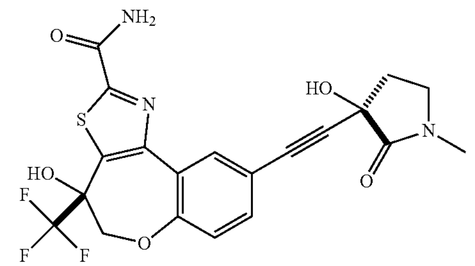 | (R)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |
| 453 | 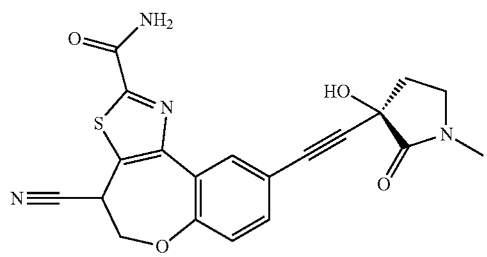 [SMILES: CN1CC[C@@](O)(C#Cc2ccc3c(c2)-c2nc(C(N)=O)sc2C(C#N)CO3)C1=O] | 4-cyano-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 454 | 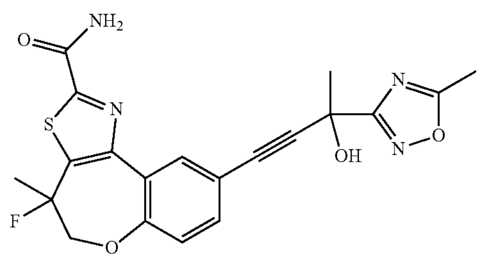 | 4-fluoro-9-[3-hydroxy-3-(5-methyl-1,2,4-oxadiazol-3-yl)but-1-ynyl]-4-methyl-5H-[1]benzoxepino[5,4-d]thiazole-2-carboxamide |
| 455 | 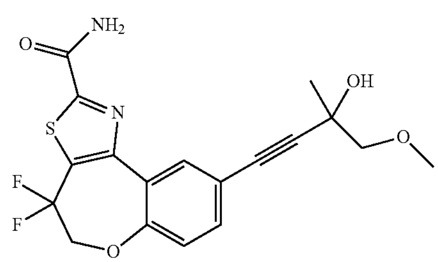 [SMILES: COCC(C)(O)C#Cc1ccc2c(c1)-c1nc(C(N)=O)sc1C(F)(F)CO2] | 4,4-difluoro-9-(3-hydroxy-4-methoxy-3-methylbut-1-yn-1-yl)-4,5-dihydrobenzo[2,3]oxepino[4,5-d]thiazole-2-carboxamide |
| 456 | 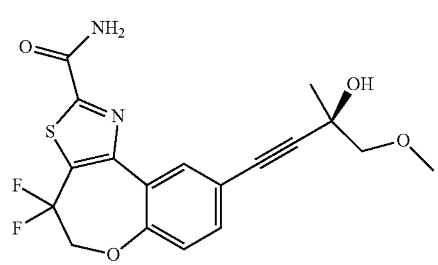 [SMILES: COC[C@](C)(O)C#Cc1ccc2c(c1)-c1nc(C(N)=O)sc1C(F)(F)CO2] | (R)-4,4-difluoro-9-(3-hydroxy-4-methoxy-3-methylbut-1-yn-1-yl)-4,5-dihydrobenzo[2,3]oxepino[4,5-d]thiazole-2-carboxamide |
| 457 | 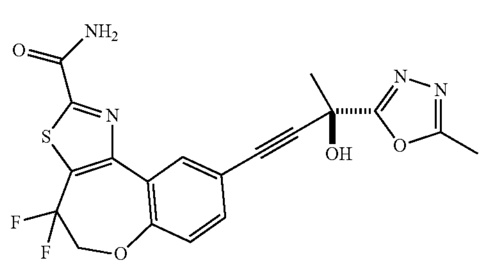 [SMILES: Cc1nnc([C@](C)(O)C#Cc2ccc3c(c2)-c2nc(C(N)=O)sc2C(F)(F)CO3)o1] | (R)-4,4-difluoro-9-(3-hydroxy-3-(5-methyl-1,3,4-oxadiazol-2-yl)but-1-yn-1-yl)-4,5-dihydrobenzo[2,3]oxepino[4,5-d]thiazole-2-carboxamide |

TABLE 1A-continued

| No. | Structure | Name |
|-----|-----------|------|
| 458 | 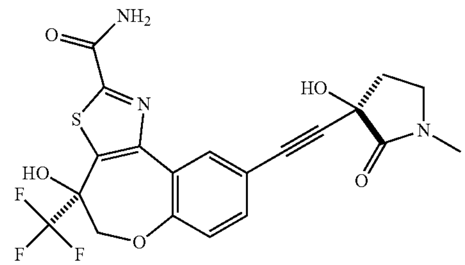 | (S)-4-hydroxy-9-(((R)-3-hydroxy-1-methyl-2-oxopyrrolidin-3-yl)ethynyl)-4-(trifluoromethyl)-4,5-dihydrobenzo[2,3]oxepino[4,5-d]thiazole-2-carboxamide |
| 459 | 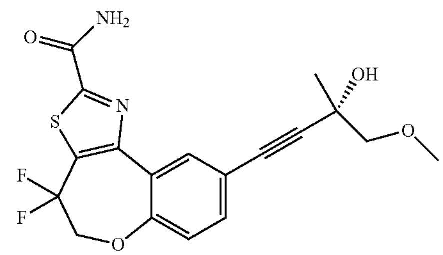 | (S)-4,4-difluoro-9-(3-hydroxy-4-methoxy-3-methylbut-1-yn-1-yl)-4,5-dihydrobenzo[2,3]oxepino[4,5-d]thiazole-2-carboxamide |
| 460 | 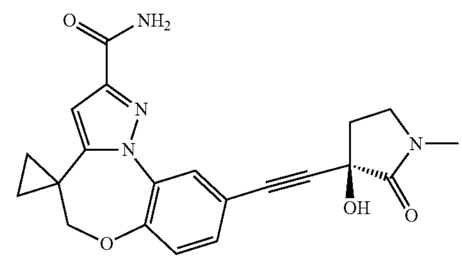 [SMILES: CN1CC[C@@](O)(C#Cc2ccc3c(c2)-n2nc(C(N)=O)cc2C2(CC2)CO3)C1=O] | 9-[2-[(3R)-3-hydroxy-1-methyl-2-oxo-pyrrolidin-3-yl]ethynyl]spiro[5H-pyrazolo[5,1-d][1,5]benzoxazepine-4,1'-cyclopropane]-2-carboxamide |
| 461 | 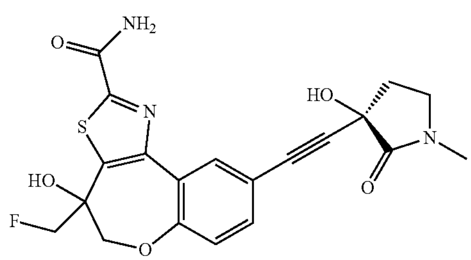 [SMILES: CN1CC[C@@](O)(C#Cc2ccc3c(c2)-c2nc(C(N)=O)sc2C(O)(CF)CO3)C1=O] | 4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 462 | 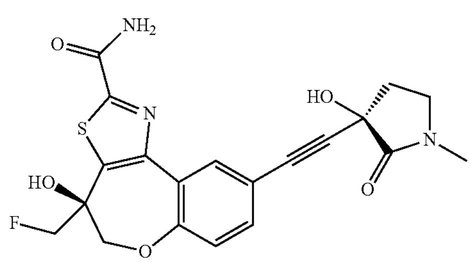 [SMILES: CN1CC[C@@](O)(C#Cc2ccc3c(c2)-c2nc(C(N)=O)sc2[C@@](O)(CF)CO3)C1=O] | (S)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 463 | 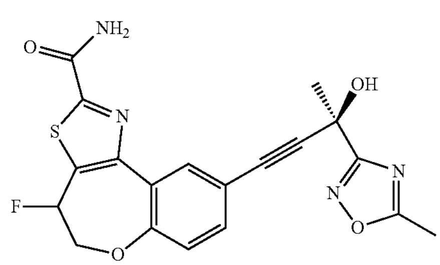 [SMILES: Cc1nc([C@](C)(O)C#Cc2ccc3c(c2)-c2nc(C(N)=O)sc2C(F)CO3)no1] | 4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |

TABLE 1A-continued

| No. | Structure | Name |
|---|---|---|
| 464 | 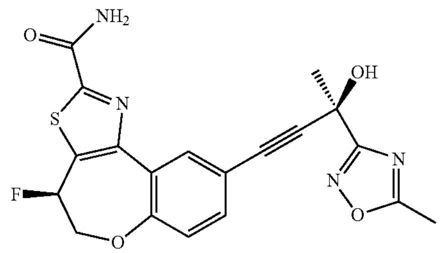 [SMILES: Cc1nc([C@](C)(O)C#Cc2ccc3c(c2)-c2nc(C(N)=O)sc2[C@H](F)CO3)no1] | (R)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 465 | 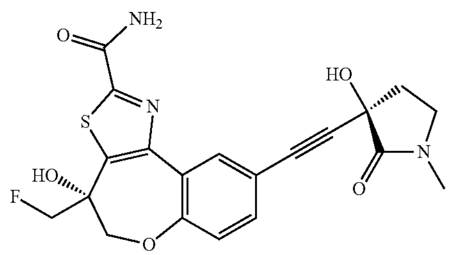 [SMILES: CN1CC[C@@](O)(C#Cc2ccc3c(c2)-c2nc(C(N)=O)sc2[C@](O)(CF)CO3)C1=O] | (R)-4-(fluoromethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 466 | 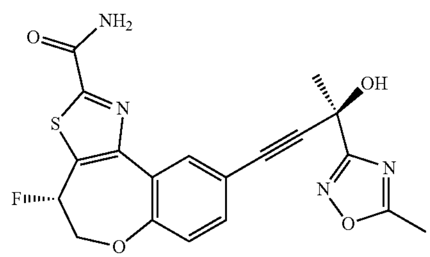 [SMILES: Cc1nc([C@](C)(O)C#Cc2ccc3c(c2)-c2nc(C(N)=O)sc2[C@@H](F)CO3)no1] | (S)-4-fluoro-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 467 | 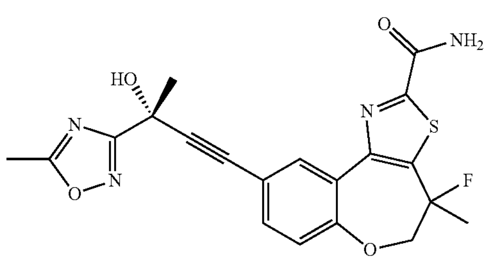 | 4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |
| 468 | 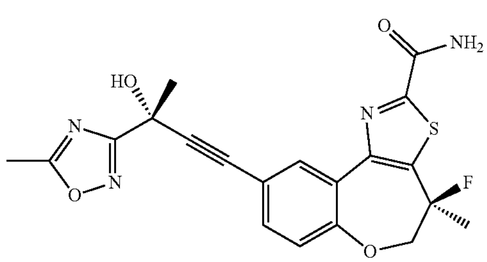 | (S)-4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |
| 469 | 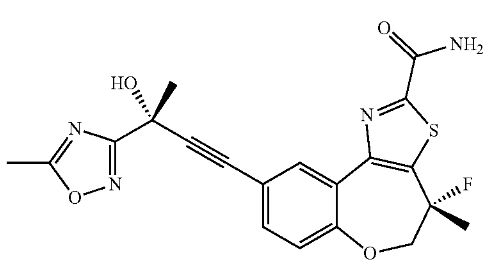 | (R)-4-fluoro-9-[3-hydroxy-3-((R)-5-methyl-1,2,4-oxadiazol-3-yl)but-1-ynyl]-4-methyl-5H-[1]benzoxepino[5,4-d]thiazole-2-carboxamide |

TABLE 1A-continued

| No. | Structure | Name |
|---|---|---|
| 470 | 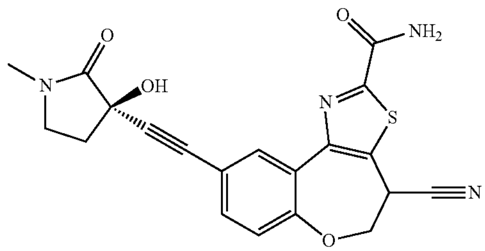 [SMILES: CN1CC[C@@](O)(C#Cc2ccc3c(c2)-c2nc(C(N)=O)sc2C(C#N)CO3)C1=O] | 4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |
| 471 | 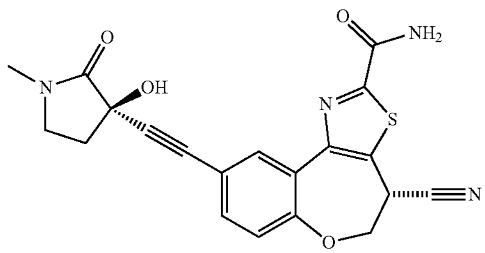 | (R)-4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |
| 472 | 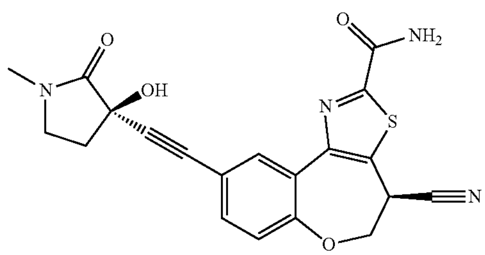 [SMILES: CN1CC[C@@](O)(C#Cc2ccc3c(c2)-c2nc(C(N)=O)sc2[C@@H](C#N)CO3)C1=O] | (S)-4-cyano-9-[2-((R)-3-hydroxy-1-methyl-2-oxo-pyrrolidin-3-yl)ethynyl]-4,5-dihydro-[1]benzoxepino[5,4-d]thiazole-2-carboxamide |
| 473 | 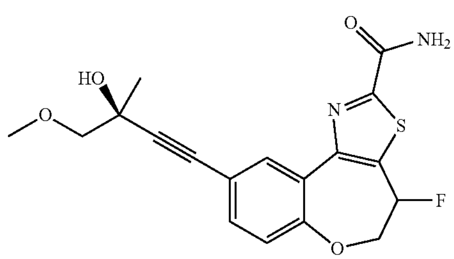 [SMILES: COC[C@@](C)(O)C#Cc1ccc2c(c1)-c1nc(C(N)=O)sc1C(F)CO2] | (S)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 474 | 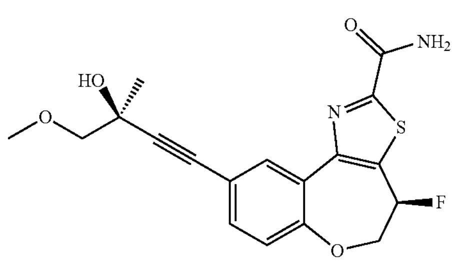 [SMILES: COC[C@@](C)(O)C#Cc1ccc2c(c1)-c1nc(C(N)=O)sc1[C@@H](F)CO2] | (S)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 475 | 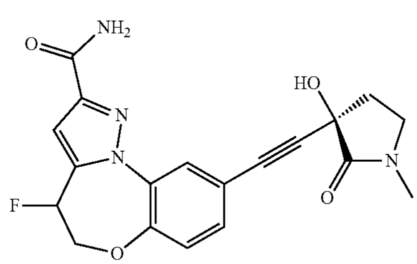 [SMILES: CN1CC[C@@](O)(C#Cc2ccc3c(c2)-n2nc(C(N)=O)cc2C(F)CO3)C1=O] | 4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1A-continued

| No. | Structure | Name |
|---|---|---|
| 476 | 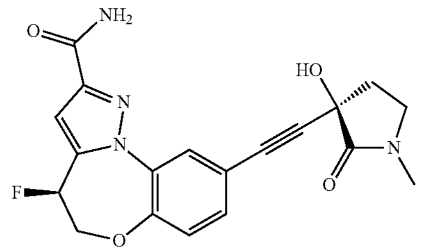 [SMILES: CN1CC[C@@](O)(C#Cc2ccc3c(c2)-n2nc(C(N)=O)cc2[C@H](F)CO3)C1=O] | (S)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 477 | 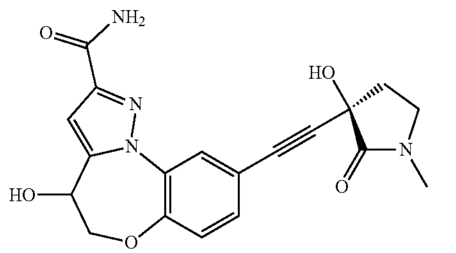 [SMILES: CN1CC[C@@](O)(C#Cc2ccc3c(c2)-n2nc(C(N)=O)cc2C(O)CO3)C1=O] | 4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 478 | 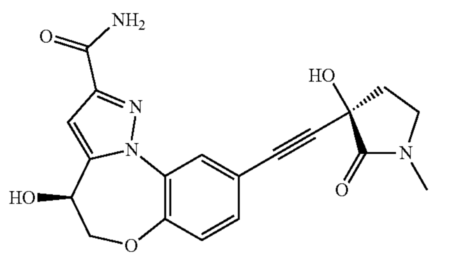 [SMILES: CN1CC[C@@](O)(C#Cc2ccc3c(c2)-n2nc(C(N)=O)cc2[C@H](O)CO3)C1=O] | (S)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 479 | 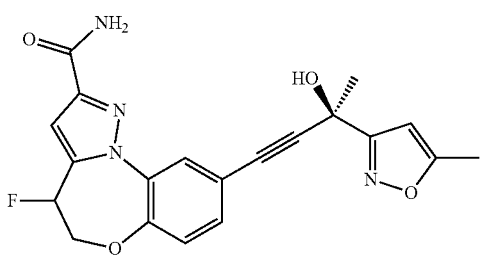 [SMILES: Cc1cc([C@](C)(O)C#Cc2ccc3c(c2)-n2nc(C(N)=O)cc2C(F)CO3)no1] | 4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 480 | 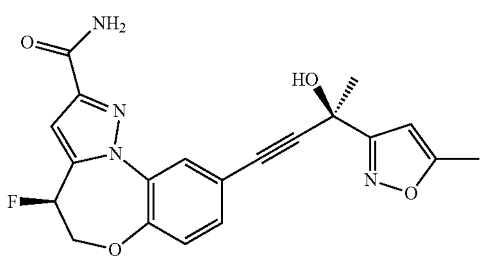 [SMILES: Cc1cc([C@](C)(O)C#Cc2ccc3c(c2)-n2nc(C(N)=O)cc2[C@H](F)CO3)no1] | (S)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 481 | 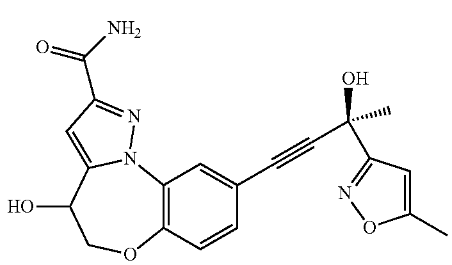 [SMILES: Cc1cc([C@](C)(O)C#Cc2ccc3c(c2)-n2nc(C(N)=O)cc2C(O)CO3)no1] | 4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |

TABLE 1A-continued

| No. | Structure | Name |
|---|---|---|
| 482 | 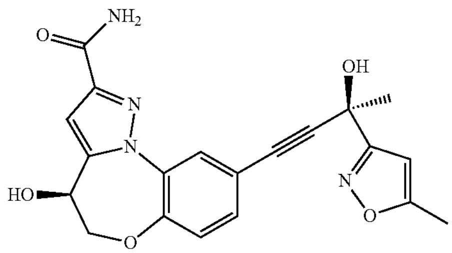 [SMILES: Cc1cc([C@](C)(O)C#Cc2ccc3c(c2)-n2nc(C(N)=O)cc2[C@H](O)CO3)no1] | (S)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 483 | 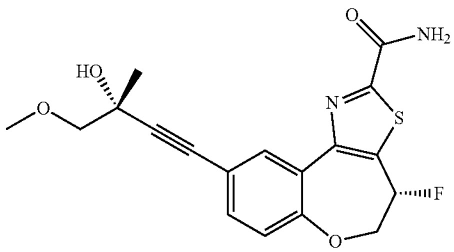 [SMILES: COC[C@](C)(O)C#Cc1ccc2c(c1)-c1nc(C(N)=O)sc1[C@H](F)CO2] | (R)-4-fluoro-9-((R)-3-hydroxy-4-methoxy-3-methylbut-1-yn-1-yl)-4,5-dihydrobenzo[2,3]oxepino[4,5-d]thiazole-2-carboxamide |
| 484 | 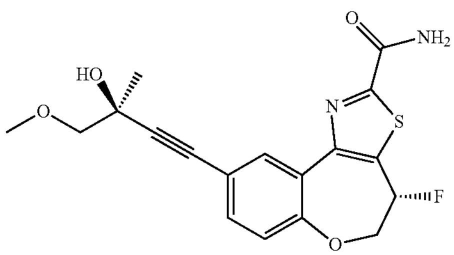 [SMILES: COC[C@@](C)(O)C#Cc1ccc2c(c1)-c1nc(C(N)=O)sc1[C@H](F)CO2] | (R)-4-fluoro-9-((S)-3-hydroxy-4-methoxy-3-methylbut-1-yn-1-yl)-4,5-dihydrobenzo[2,3]oxepino[4,5-d]thiazole-2-carboxamide |
| 485 | 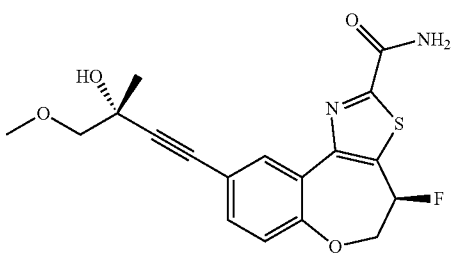 [SMILES: COC[C@](C)(O)C#Cc1ccc2c(c1)-c1nc(C(N)=O)sc1[C@@H](F)CO2] | (S)-4-fluoro-9-((R)-3-hydroxy-4-methoxy-3-methylbut-1-yn-1-yl)-4,5-dihydrobenzo[2,3]oxepino[4,5-d]thiazole-2-carboxamide |
| 486 | 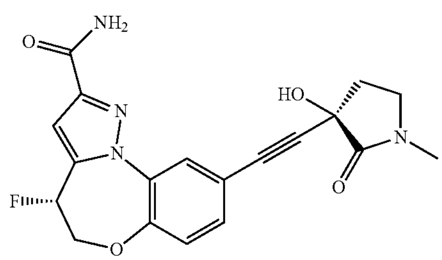 [SMILES: CN1CC[C@@](O)(C#Cc2ccc3c(c2)-n2nc(C(N)=O)cc2[C@@H](F)CO3)C1=O] | (R)-4-fluoro-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |
| 487 | 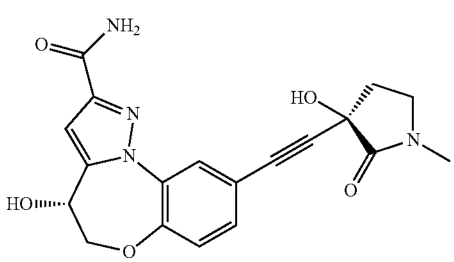 [SMILES: CN1CC[C@@](O)(C#Cc2ccc3c(c2)-n2nc(C(N)=O)cc2[C@@H](O)CO3)C1=O] | (R)-4-hydroxy-9-(((R)-3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1A-continued

| No. | Structure | Name |
|---|---|---|
| 488 | 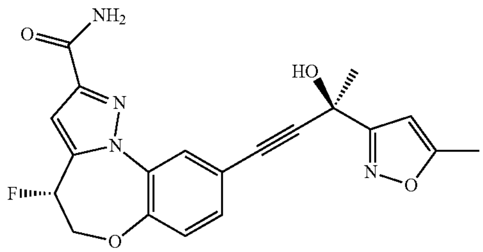 [SMILES: Cc1cc([C@](C)(O)C#Cc2ccc3c(c2)-n2nc(C(N)=O)cc2[C@@H](F)CO3)no1] | (R)-4-fluoro-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 489 | 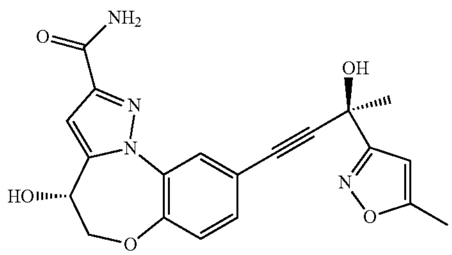 [SMILES: Cc1cc([C@](C)(O)C#Cc2ccc3c(c2)-n2nc(C(N)=O)cc2[C@@H](O)CO3)no1] | (R)-4-hydroxy-9-((R)-3-hydroxy-3-(5-methylisoxazol-3-yl)but-1-yn-1-yl)-4,5-dihydrobenzo[b]pyrazolo[1,5-d][1,4]oxazepine-2-carboxamide |
| 490 | 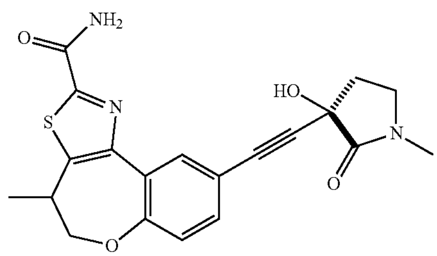 | 9-[2-((R)-3-hydroxy-1-methyl-2-oxo-pyrrolidin-3-yl)ethynyl]-4-methyl-4,5-dihydro-[1]benzoxepino[5,4-d]thiazole-2-carboxamide |
| 491 | 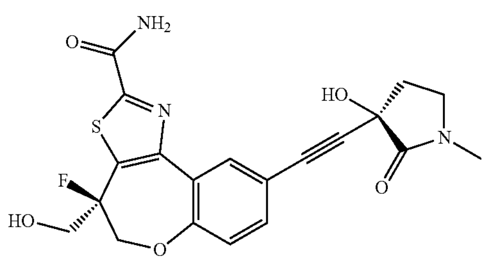 [SMILES: CN1CC[C@@](O)(C#Cc2ccc3c(c2)-c2nc(C(N)=O)sc2[C@@](F)(CO)CO3)C1=O] | (R)-4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 492 | 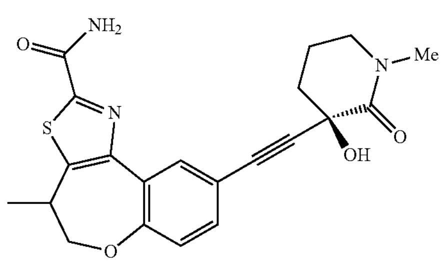 | 9-(((R)-3-hydroxy-1-methyl-2-oxopiperidin-3-yl)ethynyl)-4-methyl-4,5-dihydrobenzo[2,3]oxepino[4,5-d]thiazole-2-carboxamide |
| 493 | 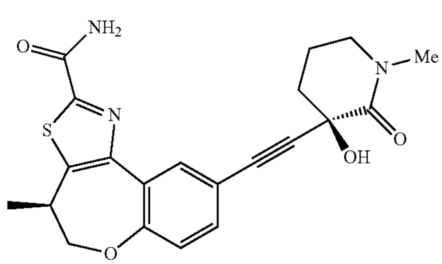 [SMILES: C[C@@H]1COc2ccc(C#C[C@]3(O)CCCN(C)C3=O)cc2-c2nc(C(N)=O)sc21] | (R)-9-(((R)-3-hydroxy-1-methyl-2-oxopiperidin-3-yl)ethynyl)-4-methyl-4,5-dihydrobenzo[2,3]oxepino[4,5-d]thiazole-2-carboxamide |

TABLE 1A-continued

| No. | Structure | Name |
|---|---|---|
| 494 | 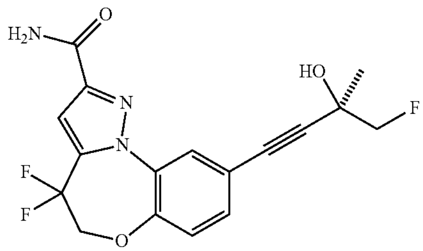 [SMILES: C[C@@](O)(C#Cc1ccc2c(c1)-n1nc(C(N)=O)cc1C(F)(F)CO2)CF] | 4,4-difluoro-9-(4-fluoro-(R)-3-hydroxy-3-methyl-but-1-ynyl)-5H-pyrazolo[5,1-d][1,5]benzoxazepine-2-carboxamide |
| 495 | 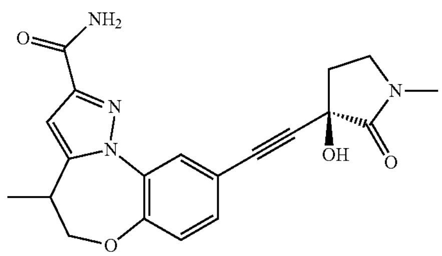 | 9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 496 | 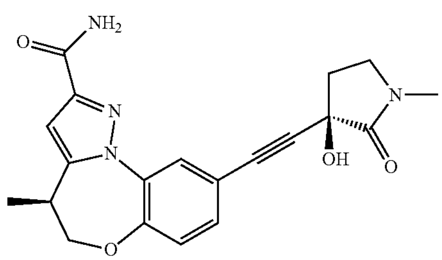 | (S)-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 497 | 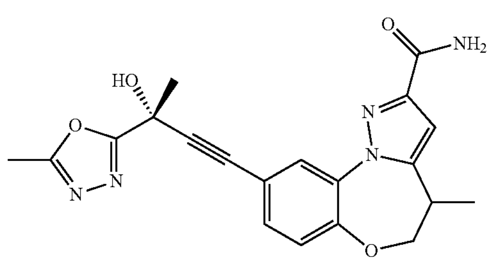 | 9-[3-(R)-hydroxy-3-(5-methyl-1,3,4-oxadiazol-2-yl)but-1-ynyl]-4-methyl-4,5-dihydropyrazolo[5,1-d][1,5]benzoxazepine-2-carboxamide |
| 498 | 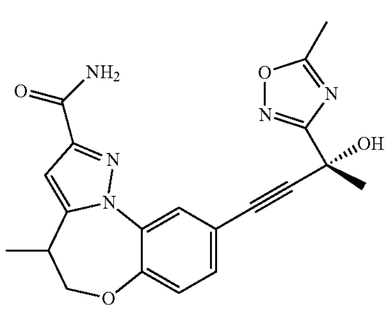 [SMILES: Cc1nc([C@](C)(O)C#Cc2ccc3c(c2)-n2nc(C(N)=O)cc2C(C)CO3)no1] | 9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |

TABLE 1A-continued

| No. | Structure | Name |
|---|---|---|
| 499 | 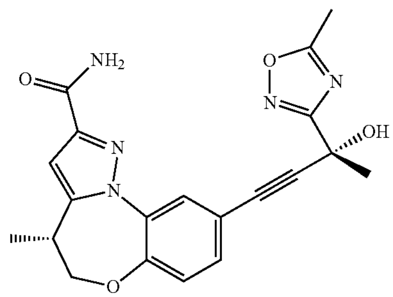 [SMILES: Cc1nc([C@](C)(O)C#Cc2ccc3c(c2)-n2nc(C(N)=O)cc2[C@@H](C)CO3)no1] | (R)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |
| 500 | 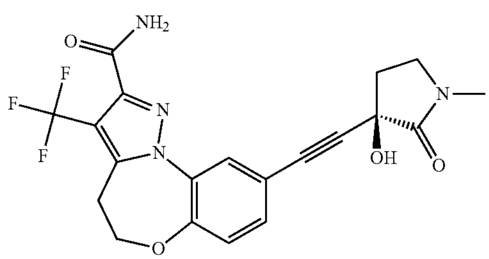 [SMILES: CN1CC[C@@](O)(C#Cc2ccc3c(c2)-n2nc(C(N)=O)c(C(F)(F)F)c2CCO3)C1=O] | 9-[2-[(3R)-3-hydroxy-1-methyl-2-oxo-pyrrolidin-3-yl]ethynyl]-3-(trifluoromethyl)-4,5-dihydropyrazolo[5,1-d][1,5]benzoxazepine-2-carboxamide |
| 501 | 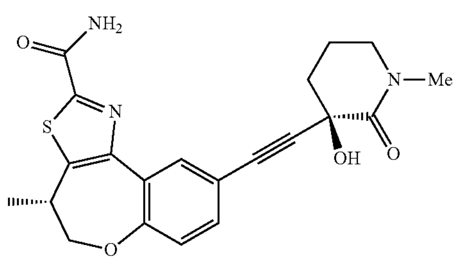 [SMILES: C[C@H]1COc2ccc(C#C[C@]3(O)CCCN(C)C3=O)cc2-c2nc(C(N)=O)sc21] | (S)-9-(((R)-3-hydroxy-1-methyl-2-oxopiperidin-3-yl)ethynyl)-4-methyl-4,5-dihydrobenzo[2,3]oxepino[4,5-d]thiazole-2-carboxamid |
| 502 | 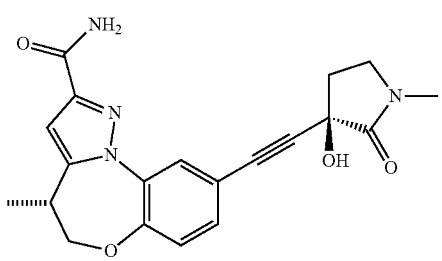 | (R)-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 503 | 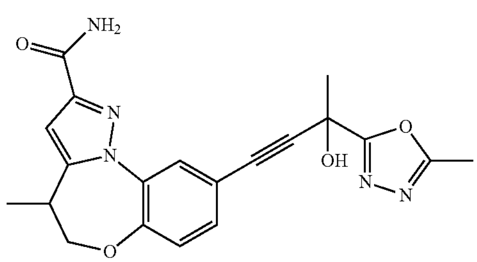 | 9-[3-hydroxy-3-(5-methyl-1,3,4-oxadiazol-2-yl)but-1-ynyl]-4-methyl-4,5-dihydropyrazolo[5,1-d][1,5]benzoxazepine-2-carboxamide |

TABLE 1A-continued

| No. | Structure | Name |
|---|---|---|
| 504 | 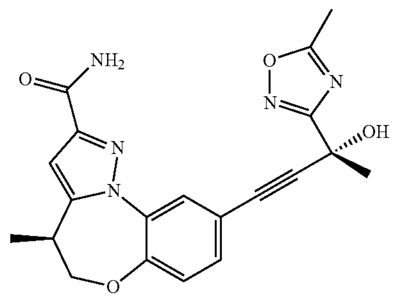 [SMILES: Cc1nc([C@](C)(O)C#Cc2ccc3c(c2)-n2nc(C(N)=O)cc2[C@H](C)CO3)no1] | (S)-9-((R)-3-hydroxy-3-(5-methyl-1,2,4-oxadiazol-3-yl)but-1-yn-1-yl)-4-methyl-4,5-dihydrobenzo[b]pyrazolo[1,5-d][1,4]oxazepine-2-carboxamide |
| 505 | 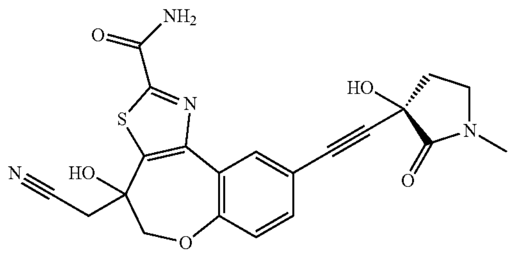 [SMILES: CN1CC[C@@](O)(C#Cc2ccc3c(c2)-c2nc(C(N)=O)sc2C(O)(CC#N)CO3)C1=O] | 4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 506 | 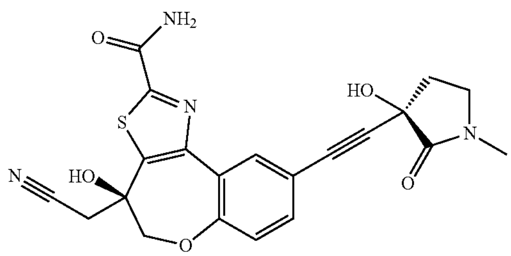 [SMILES: CN1CC[C@@](O)(C#Cc2ccc3c(c2)-c2nc(C(N)=O)sc2[C@@](O)(CC#N)CO3)C1=O] | (R)-4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 507 | 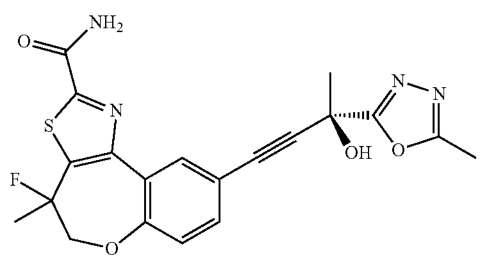 [SMILES: Cc1nnc([C@](C)(O)C#Cc2ccc3c(c2)-c2nc(C(N)=O)sc2C(C)(F)CO3)o1] | 4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide |
| 508 | 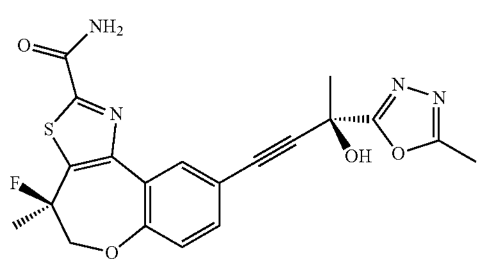 [SMILES: Cc1nnc([C@](C)(O)C#Cc2ccc3c(c2)-c2nc(C(N)=O)sc2[C@](C)(F)CO3)o1] | (R)-4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide |
| 509 | 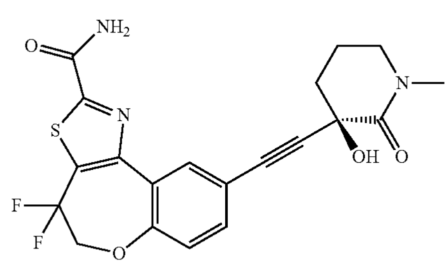 [SMILES: CN1CCC[C@@](O)(C#Cc2ccc3c(c2)-c2nc(C(N)=O)sc2C(F)(F)CO3)C1=O] | 4,4-difluoro-9-[2-[(3R)-3-hydroxy-1-methyl-2-oxo-3-piperidyl]ethynyl]-5H-[1]benzoxepino[5,4-d]thiazole-2-carboxamide |

TABLE 1A-continued

| No. | Structure | Name |
|---|---|---|
| 510 | 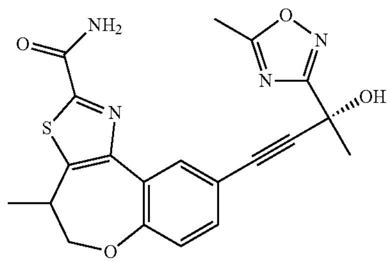 [SMILES: Cc1nc([C@](C)(O)C#Cc2ccc3c(c2)-c2nc(C(N)=O)sc2C(C)CO3)no1] | 9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 511 | 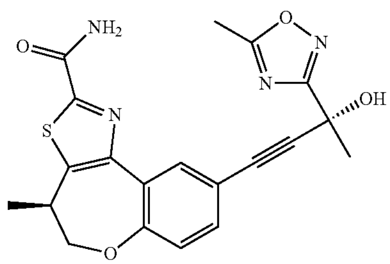 [SMILES: Cc1nc([C@](C)(O)C#Cc2ccc3c(c2)-c2nc(C(N)=O)sc2[C@H](C)CO3)no1] | (R)-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 512 | 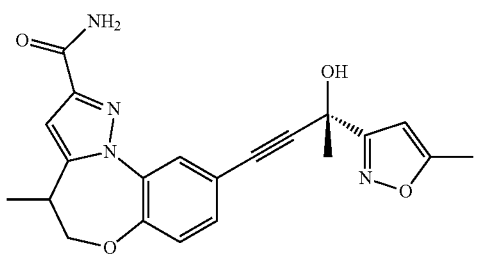 | 9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 513 | 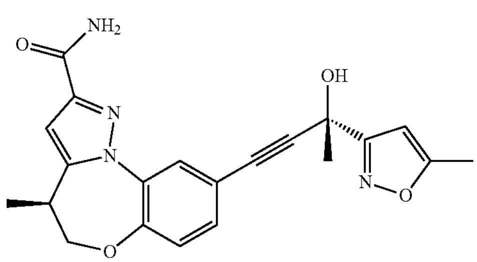 | (R)-9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 514 | 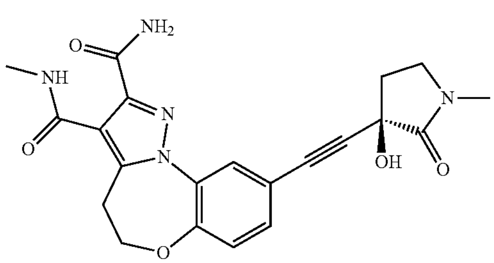 | 9-[2-[(3R)-3-hydroxy-1-methyl-2-oxo-pyrrolidin-3-yl]ethynyl]-N3-methyl-4,5-dihydropyrazolo[5,1-d][1,5]benzoxazepine-2,3-dicarboxamide |
| 515 | 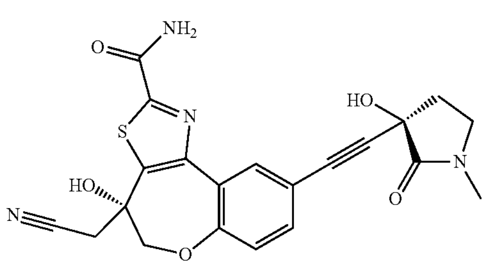 [SMILES: CN1CC[C@@](O)(C#Cc2ccc3c(c2)-c2nc(C(N)=O)sc2[C@](O)(CC#N)CO3)C1=O] | (S)-4-(cyanomethyl)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1A-continued

| No. | Structure | Name |
|---|---|---|
| 516 | 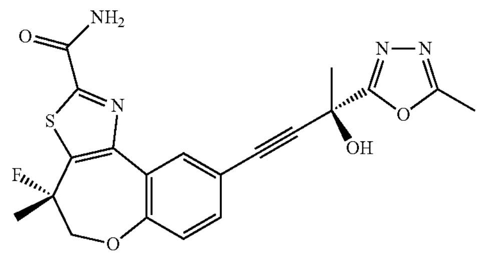 [SMILES: Cc1nnc([C@](C)(O)C#Cc2ccc3c(c2)-c2nc(C(N)=O)sc2[C@@](C)(F)CO3)o1] | (S)-4-fluoro-9-((R)-3-hydroxy-3-(5-methyl-1,3,4-oxadiazol-2-yl)but-1-yn-1-yl)-4-methyl-4,5-dihydrobenzo[2,3]oxepino[4,5-d]thiazole-2-carboxamide |
| 517 | 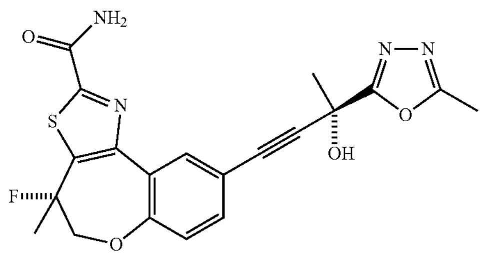 [SMILES: Cc1nnc([C@@](C)(O)C#Cc2ccc3c(c2)-c2nc(C(N)=O)sc2[C@@](C)(F)CO3)o1] | 4-(S)-fluoro-9-[3-(S)-hydroxy-3-(5-methyl-1,3,4-oxadiazol-2-yl)but-1-ynyl]-4-methyl-5H-[1]benzoxepino[5,4-d]thiazole-2-carboxamide |
| 518 | 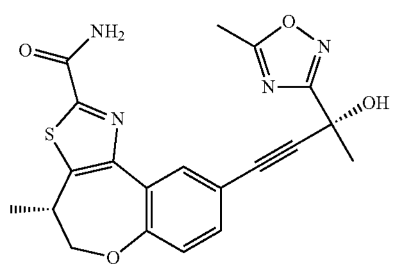 [SMILES: Cc1nc([C@](C)(O)C#Cc2ccc3c(c2)-c2nc(C(N)=O)sc2[C@@H](C)CO3)no1] | (S)-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 519 | 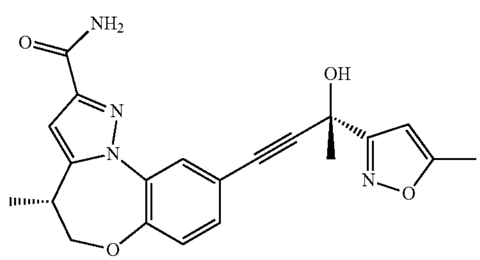 | (S)-9-((S)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 520 | 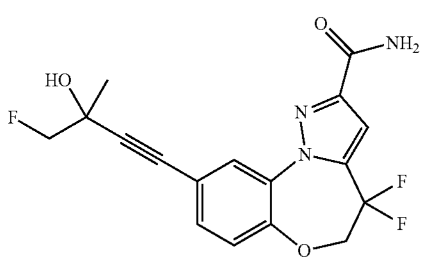 [SMILES: CC(O)(C#Cc1ccc2c(c1)-n1nc(C(N)=O)cc1C(F)(F)CO2)CF] | 4,4-difluoro-9-(4-fluoro-3-hydroxy-3-methyl-but-1-ynyl)-5H-pyrazolo[5,1-d][1,5]benzoxazepine-2-carboxamide |
| 521 | 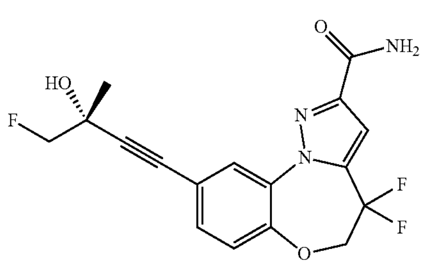 [SMILES: C[C@@](O)(C#Cc1ccc2c(c1)-n1nc(C(N)=O)cc1C(F)(F)CO2)CF] | 4,4-difluoro-9-(4-fluoro-(R)-3-hydroxy-3-methyl-but-1-ynyl)-5H-pyrazolo[5,1-d][1,5]benzoxazepine-2-carboxamide |

TABLE 1A-continued

| No. | Structure | Name |
|---|---|---|
| 522 | 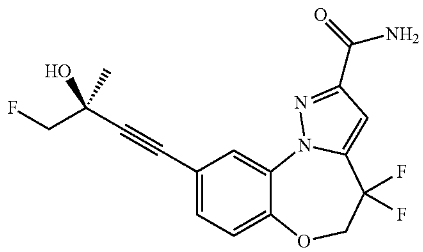 [SMILES: C[C@](O)(C#Cc1ccc2c(c1)-n1nc(C(N)=O)cc1C(F)(F)CO2)CF] | 4,4-difluoro-9-(4-fluoro-3-(S)-hydroxy-3-methyl-but-1-ynyl)-5H-pyrazolo[5,1-d][1,5]benzoxazepine-2-carboxamide |
| 523 | 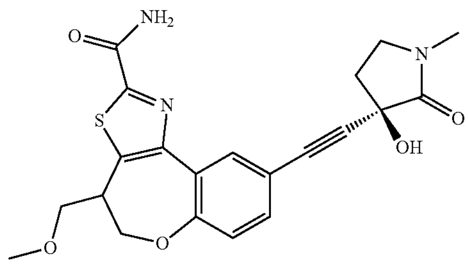 [SMILES: COCC1COc2ccc(C#C[C@]3(O)CCN(C)C3=O)cc2-c2nc(C(N)=O)sc21] | 9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide |
| 524 | 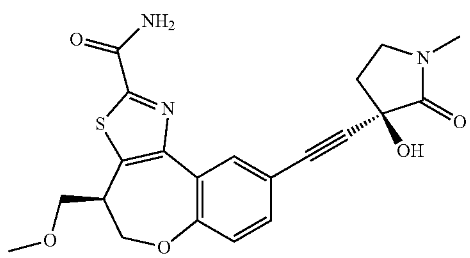 [SMILES: COC[C@@H]1COc2ccc(C#C[C@]3(O)CCN(C)C3=O)cc2-c2nc(C(N)=O)sc21] | (R)-9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide |
| 525 | 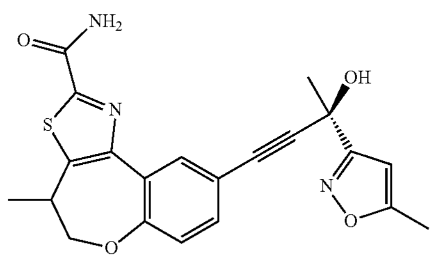 | 9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 526 | 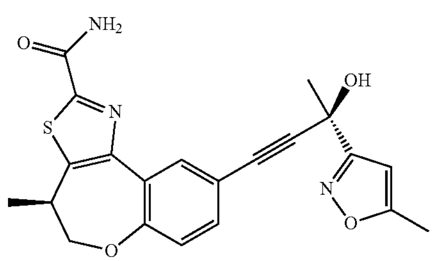 | (R)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 527 | 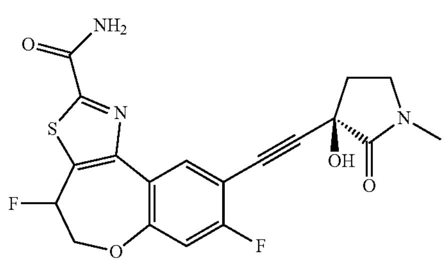 [SMILES: CN1CC[C@@](O)(C#Cc2cc3c(cc2F)OCC(F)c2sc(C(N)=O)nc2-3)C1=O] | 7,12-difluoro-13-[2-[(3R)-3-hydroxy-1-methyl-2-oxopyrrolidin-3-yl]ethynyl]-9-oxa-5-thia-3-azatricyclo[8.4.0.0[2,6]]tetradeca-1(10),2(6),3,11,13-pentaene-4-carboxamide |

TABLE 1A-continued

| No. | Structure | Name |
|---|---|---|
| 528 | 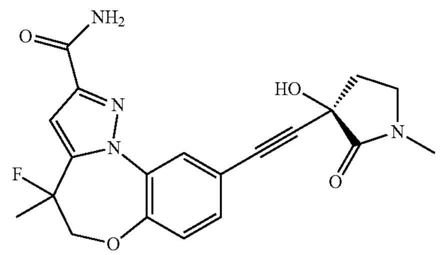 [SMILES: CN1CC[C@@](O)(C#Cc2ccc3c(c2)-n2nc(C(N)=O)cc2C(C)(F)CO3)C1=O] | 4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 529 | 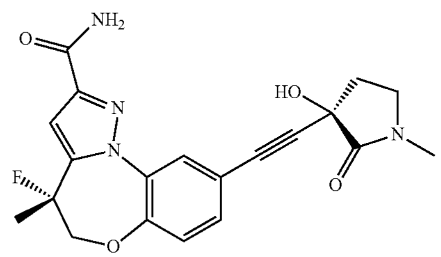 [SMILES: CN1CC[C@@](O)(C#Cc2ccc3c(c2)-n2nc(C(N)=O)cc2[C@@](C)(F)CO3)C1=O] | (R)-4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 530 | 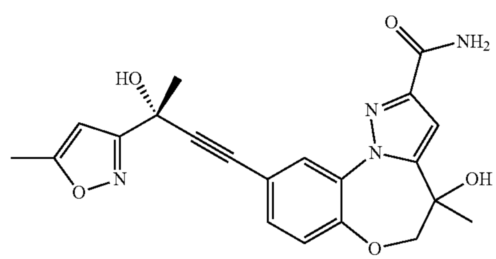 | 4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxamide |
| 531 | 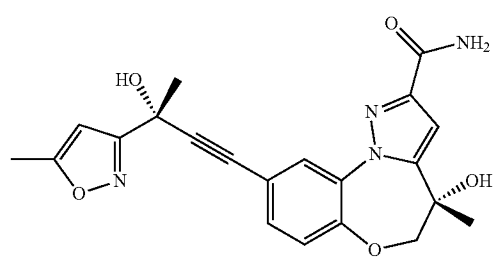 | (S)-4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxamide |
| 532 | 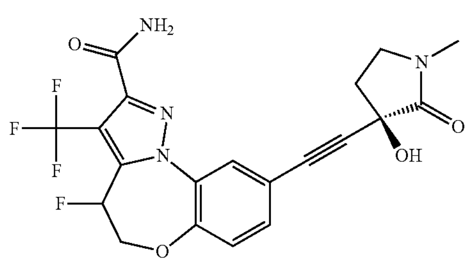 | 4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 533 | 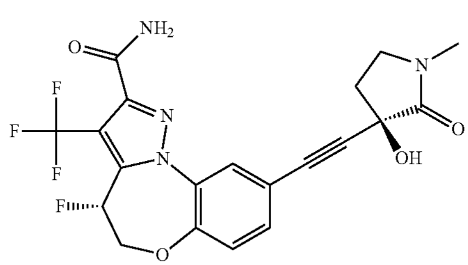 [SMILES: CN1CC[C@@](O)(C#Cc2ccc3c(c2)-n2nc(C(N)=O)c(C(F)(F)F)c2C(F)CO3)C1=O] | (R)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |

TABLE 1A-continued

| No. | Structure | Name |
|---|---|---|
| 534 | 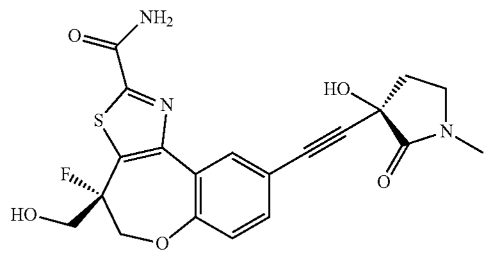 [SMILES: CN1CC[C@@](O)(C#Cc2ccc3c(c2)-c2nc(C(N)=O)sc2[C@](F)(CO)CO3)C1=O] | (S)-4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 535 | 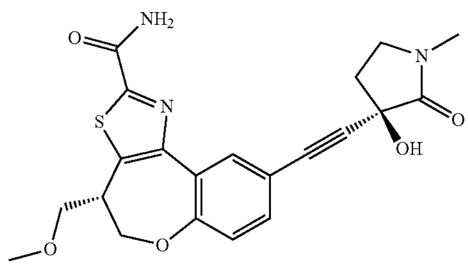 | (S)-9-(((R)-3-hydroxy-1-methyl-2-oxopyrrolidin-3-yl)ethynyl)-4-(methoxymethyl)-4,5-dihydrobenzo[2,3]oxepino[4,5-d]thiazole-2-carboxamide |
| 536 | 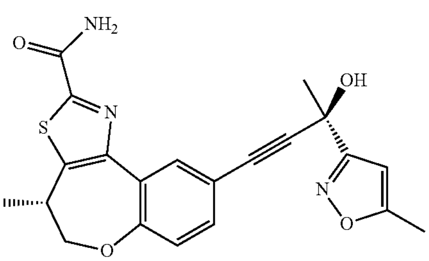 | (S)-9-((R)-3-hydroxy-3-(5-methylisoxazol-3-yl)but-1-yn-1-yl)-4-methyl-4,5-dihydrobenzo[2,3]oxepino[4,5-d]thiazole-2-carboxamide |
| 537 | 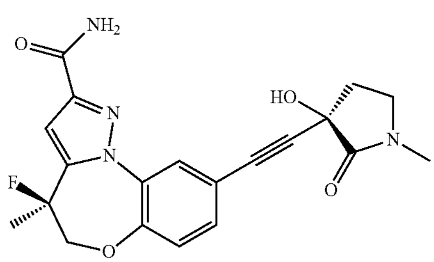 [SMILES: CN1CC[C@@](O)(C#Cc2ccc3c(c2)-n2nc(C(N)=O)cc2[C@](C)(F)CO3)C1=O] | (S)-4-fluoro-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 538 | 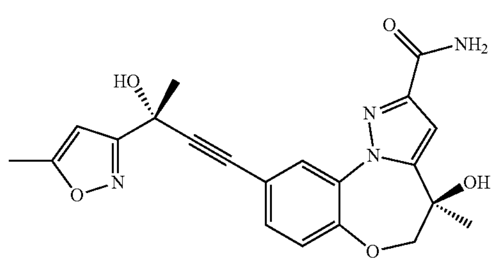 | (R)-4-hydroxy-9-[(R)-3-hydroxy-3-(5-methylisoxazol-3-yl)but-1-ynyl]-4-methyl-5H-pyrazolo[5,1-d][1,5]benzoxazepine-2-carboxamide |
| 539 | 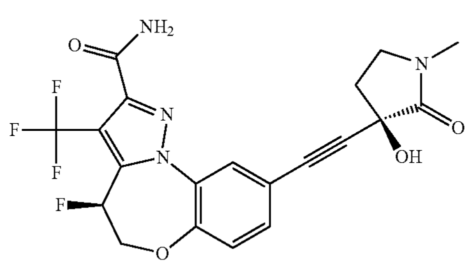 | (S)-4-fluoro-9-(((R)-3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |

TABLE 1A-continued

| No. | Structure | Name |
|---|---|---|
| 540 | 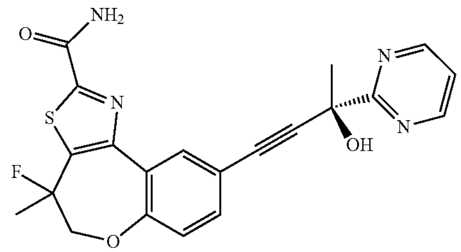 [SMILES: CC1(F)COc2ccc(C#C[C@@](C)(O)c3ncccn3)cc2-c2nc(C(N)=O)sc21] | 4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 541 | 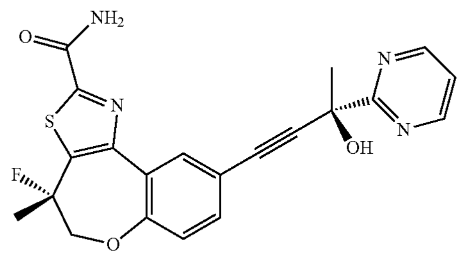 [SMILES: C[C@]1(F)COc2ccc(C#C[C@@](C)(O)c3ncccn3)cc2-c2nc(C(N)=O)sc21] | (S)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 542 | 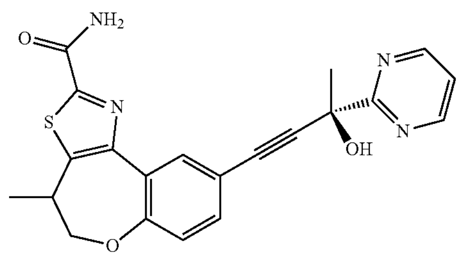 [SMILES: CC1COc2ccc(C#C[C@@](C)(O)c3ncccn3)cc2-c2nc(C(N)=O)sc21] | 9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 543 | 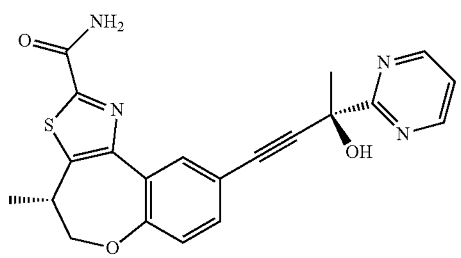 [SMILES: C[C@H]1COc2ccc(C#C[C@@](C)(O)c3ncccn3)cc2-c2nc(C(N)=O)sc21] | (S)-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 544 | 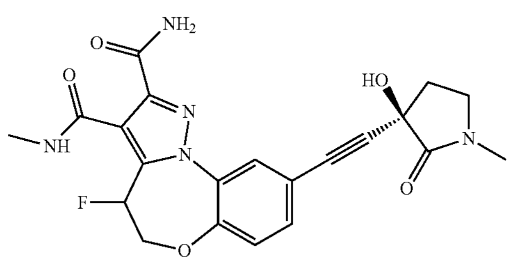 | 4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |
| 545 | 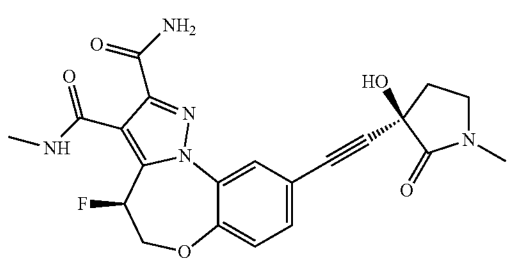 | (S)-4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |

TABLE 1A-continued

| No. | Structure | Name |
|---|---|---|
| 546 | 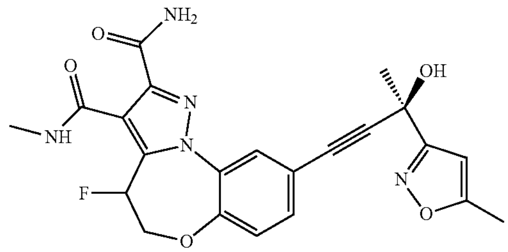 | 4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |
| 547 | 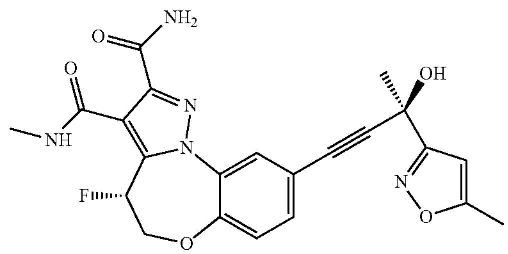 | (R)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |
| 548 | 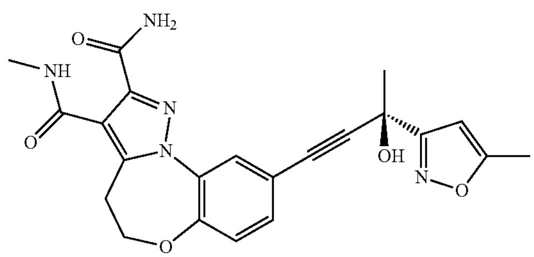 | 9-[(3R)-3-hydroxy-3-(5-methylisoxazol-3-yl)but-1-ynyl]-N3-methyl-4,5-dihydropyrazolo[5,1-d][1,5]benzoxazepine-2,3-dicarboxamide |
| 549 | 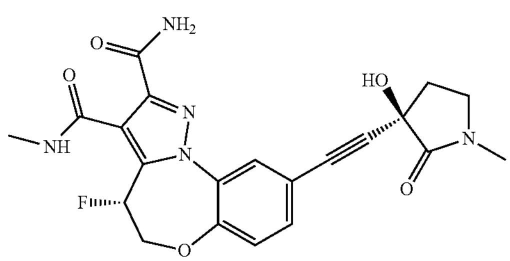 | (R)-4-fluoro-9-(((R)-3-hydroxy-1-methyl-2-oxopyrrolidin-3-yl)ethynyl)-N3-methyl-4,5-dihydrobenzo[b]pyrazolo[1,5-d][1,4]oxazepine-2,3-dicarboxamide |
| 550 | 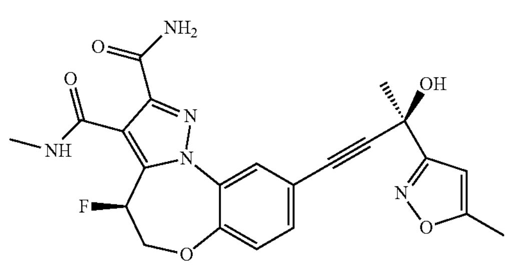 | (S)-4-fluoro-9-((R)-3-hydroxy-3-(5-methylisoxazol-3-yl)but-1-yn-1-yl)-N3-methyl-4,5-dihydrobenzo[b]pyrazolo[1,5-d][1,4]oxazepine-2,3-dicarboxamide |
| 551 | 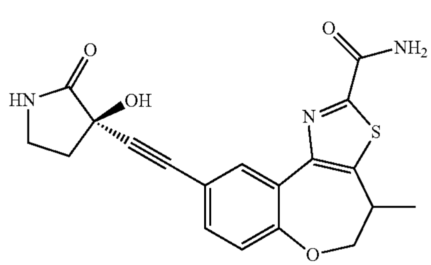 [SMILES: CC1COc2ccc(C#C[C@]3(O)CCNC3=O)cc2-c2nc(C(N)=O)sc21] | 9-[2-((R)-3-hydroxy-2-oxo-pyrrolidin-3-yl)ethynyl]-4-methyl-4,5-dihydro-[1]benzoxepino[5,4-d]thiazole-2-carboxamide |

TABLE 1A-continued

| No. | Structure | Name |
|---|---|---|
| 552 | 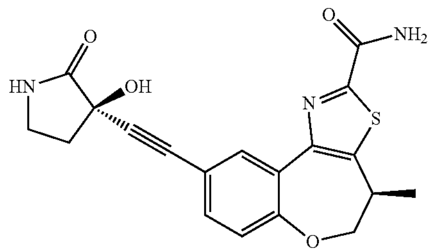 [SMILES: C[C@H]1COc2ccc(C#C[C@]3(O)CCNC3=O)cc2-c2nc(C(N)=O)sc21] | 9-[2-((R)-3-hydroxy-2-oxo-pyrrolidin-3-yl)ethynyl]-(S)-4-methyl-4,5-dihydro-[1]benzoxepino[5,4-d]thiazole-2-carboxamide |
| 553 | 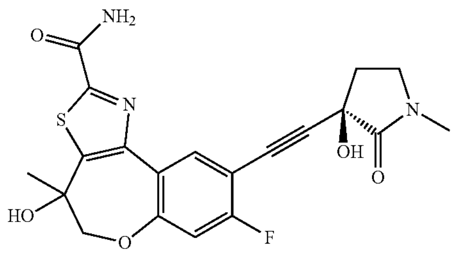 | 8-fluoro-4-hydroxy-9-[2-((R)-3-hydroxy-1-methyl-2-oxo-pyrrolidin-3-yl)ethynyl]-4-methyl-5H-[1]benzoxepino[5,4-d]thiazole-2-carboxamide |
| 554 | 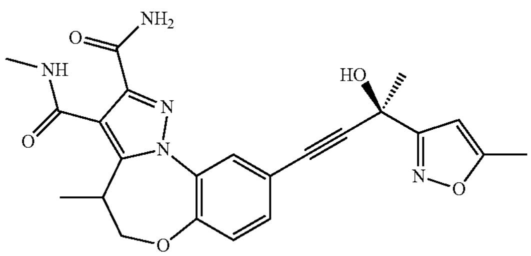 | 9-[(R)-3-hydroxy-3-(5-methylisoxazol-3-yl)but-1-ynyl]-N3,4-dimethyl-4,5-dihydropyrazolo[5,1-d][1,5]benzoxazepine-2,3-dicarboxamide |
| 555 | 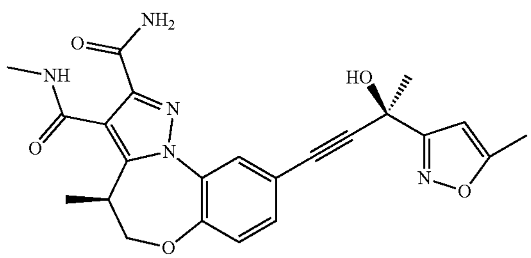 | 9-[(R)-3-hydroxy-3-(5-methylisoxazol-3-yl)but-1-ynyl]-N3,4-(S)-dimethyl-4,5-dihydropyrazolo[5,1-d][1,5]benzoxazepine-2,3-dicarboxamide |
| 556 | 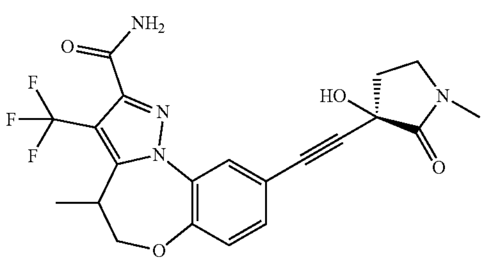 [SMILES: CC1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-methyl-3-(trifluoromethyl)-4,5-dihydropyrazolo[5,1-d][1,5]benzoxazepine-2-carboxamide |
| 557 | 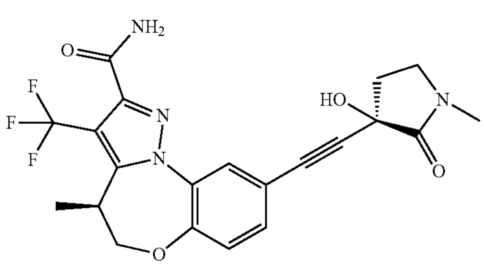 [SMILES: C[C@@H]1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-(S)-methyl-3-(trifluoromethyl)-4,5-dihydropyrazolo[5,1-d][1,5]benzoxazepine-2-carboxamide |

TABLE 1A-continued

| No. | Structure | Name |
|---|---|---|
| 558 | 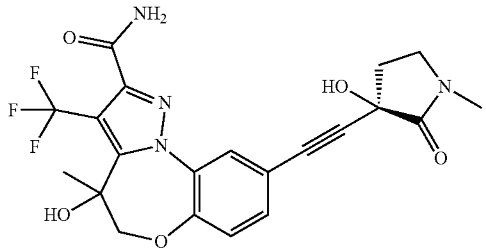 [SMILES: CN1CC[C@@](O)(C#Cc2ccc3c(c2)-n2nc(C(N)=O)c(C(F)(F)F)c2C(C)(O)CO3)C1=O] | 4-hydroxy-9-[2-((R)-3-hydroxy-1-methyl-2-oxo-pyrrolidin-3-yl)ethynyl]-4-methyl-3-(trifluoromethyl)-5H-pyrazolo[5,1-d][1,5]benzoxazepine-2-carboxamide |
| 559 | 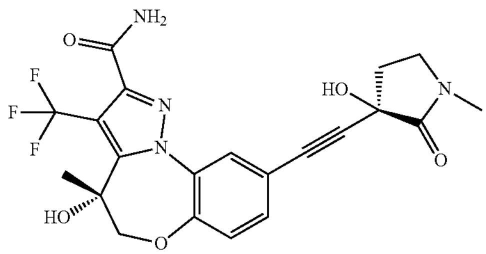 [SMILES: CN1CC[C@@](O)(C#Cc2ccc3c(c2)-n2nc(C(N)=O)c(C(F)(F)F)c2[C@@](C)(O)CO3)C1=O] | (R)-4-hydroxy-9-[2-((R)-3-hydroxy-1-methyl-2-oxo-pyrrolidin-3-yl)ethynyl]-4-methyl-3-(trifluoromethyl)-5H-pyrazolo[5,1-d][1,5]benzoxazepine-2-carboxamide |
| 560 | 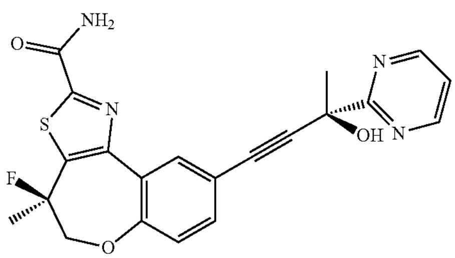 [SMILES: C[C@@](O)(C#Cc1ccc2c(c1)-c1nc(C(N)=O)sc1[C@](C)(F)CO2)c1ncccn1] | (R)-4-fluoro-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 561 | 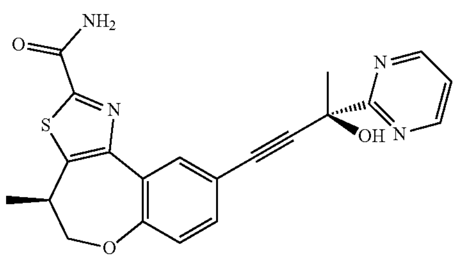 [SMILES: C[C@@H]1COc2ccc(C#C[C@@](C)(O)c3ncccn3)cc2-c2nc(C(N)=O)sc21] | (R)-9-((R)-3-hydroxy-3-(pyrimidin-2-yl)but-1-yn-1-yl)-4-methyl-4,5-dihydrobenzo[2,3]oxepino[4,5-d]thiazole-2-carboxamide |
| 562 | 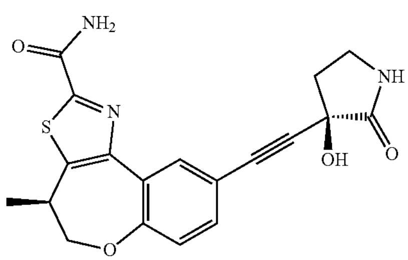 [SMILES: C[C@@H]1COc2ccc(C#C[C@]3(O)CCNC3=O)cc2-c2nc(C(N)=O)sc21] | 9-[2-((R)-3-hydroxy-2-oxo-pyrrolidin-3-yl)ethynyl]-(R)-4-methyl-4,5-dihydro-[1]benzoxepino[5,4-d]thiazole-2-carboxamide |
| 563 | 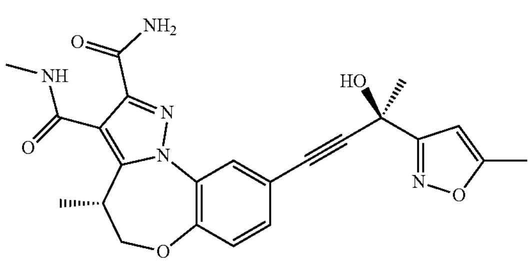 | 9-[(R)-3-hydroxy-3-(5-methylisoxazol-3-yl)but-1-ynyl]-N3,4-(R)-dimethyl-4,5-dihydropyrazolo[5,1-d][1,5]benzoxazepine-2,3-dicarboxamide |

TABLE 1A-continued

| No. | Structure | Name |
|---|---|---|
| 564 | 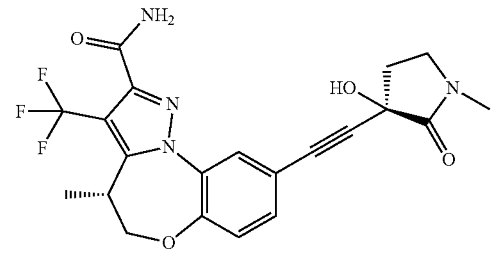 [SMILES: C[C@H]1COc2ccc(C#C[C@]3(O)CCN(C)C3=O)cc2-n2nc(C(N)=O)c(C(F)(F)F)c21] | 9-[2-((R)-3-hydroxy-1-methyl-2-oxo-pyrrolidin-3-yl)ethynyl]-4-(R)-methyl-3-(trifluoromethyl)-4,5-dihydropyrazolo[5,1-d][1,5]benzoxazepine-2-carboxamide |
| 565 | 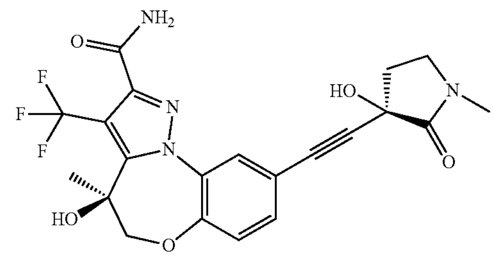 [SMILES: CN1CC[C@@](O)(C#Cc2ccc3c(c2)-n2nc(C(N)=O)c(C(F)(F)F)c2[C@](C)(O)CO3)C1=O] | (S)-4-hydroxy-9-[2-((R)-3-hydroxy-1-methyl-2-oxo-pyrrolidin-3-yl)ethynyl]-4-methyl-3-(trifluoromethyl)-5H-pyrazolo[5,1-d][1,5]benzoxazepine-2-carboxamide |
| 566 | 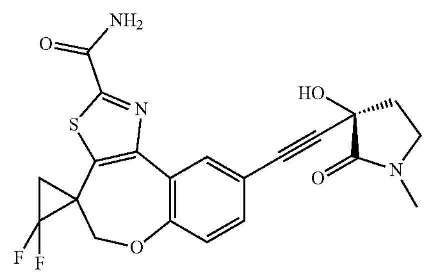 [SMILES: CN1CC[C@@](O)(C#Cc2ccc3c(c2)-c2nc(C(N)=O)sc2C2(CO3)CC2(F)F)C1=O] | 1',1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 567 | 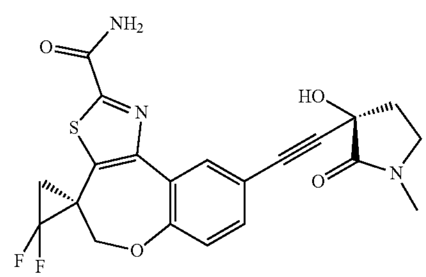 [SMILES: CN1CC[C@@](O)(C#Cc2ccc3c(c2)-c2nc(C(N)=O)sc2[C@]2(CO3)CC2(F)F)C1=O] | (S)-1',1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 568 | 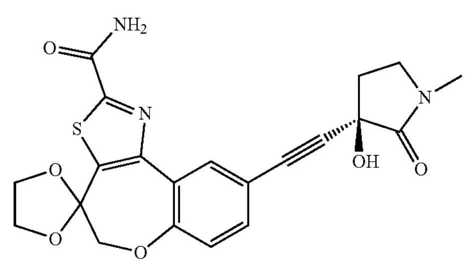 [SMILES: CN1CC[C@@](O)(C#Cc2ccc3c(c2)-c2nc(C(N)=O)sc2C2(CO3)OCCO2)C1=O] | 9'-[2-[(3R)-3-hydroxy-1-methyl-2-oxo-pyrrolidin-3-yl]ethynyl]spiro[1,3-dioxolane-2,4'-5H-[1]benzoxepino[5,4-d]thiazole]-2'-carboxamide |
| 569 | 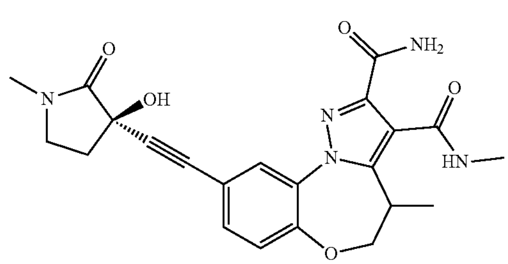 | 9-[2-((R)-3-hydroxy-1-methyl-2-oxo-pyrrolidin-3-yl)ethynyl]-N3,4-dimethyl-4,5-dihydropyrazolo[5,1-d][1,5]benzoxazepine-2,3-dicarboxamide |

TABLE 1A-continued

| No. | Structure | Name |
|---|---|---|
| 570 | 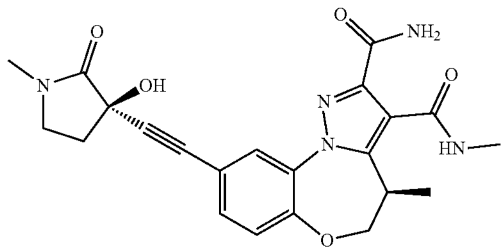 | 9-[2-((R)-3-hydroxy-1-methyl-2-oxo-pyrrolidin-3-yl)ethynyl]-N3,4-(R)-dimethyl-4,5-dihydropyrazolo[5,1-d][1,5]benzoxazepine-2,3-dicarboxamide |
| 571 | 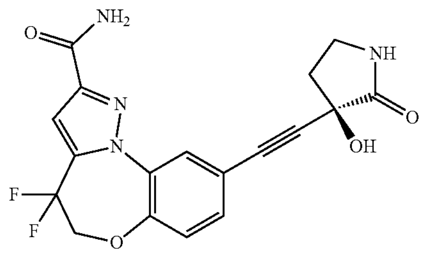 [SMILES: NC(=O)c1cc2n(n1)-c1cc(C#C[C@]3(O)CCNC3=O)ccc1OCC2(F)F] | 4,4-difluoro-9-[2-[(3R)-3-hydroxy-2-oxo-pyrrolidin-3-yl]ethynyl]-5H-pyrazolo[5,1-d][1,5]benzoxazepine-2-carboxamide |
| 572 | 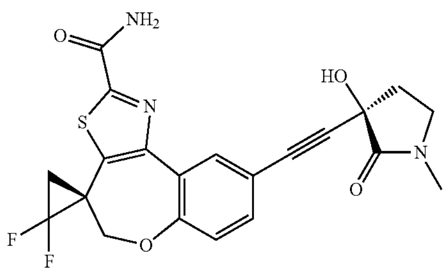 [SMILES: CN1CC[C@@](O)(C#Cc2ccc3c(c2)-c2nc(C(N)=O)sc2[C@@]2(CO3)CC2(F)F)C1=O] | (R)-1',1'-difluoro-9-[2-((R)-3-hydroxy-1-methyl-2-oxo-pyrrolidin-3-yl)ethynyl]spiro[5H-[1]benzoxepino[5,4-d]thiazole-4,2'-cyclopropane]-2-carboxamide |
| 573 | 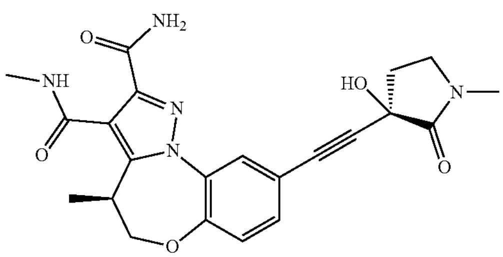 | 9-[2-((R)-3-hydroxy-1-methyl-2-oxo-pyrrolidin-3-yl)ethynyl]-N3,4-(S)-dimethyl-4,5-dihydropyrazolo[5,1-d][1,5]benzoxazepine-2,3-dicarboxamide |
| 574 | 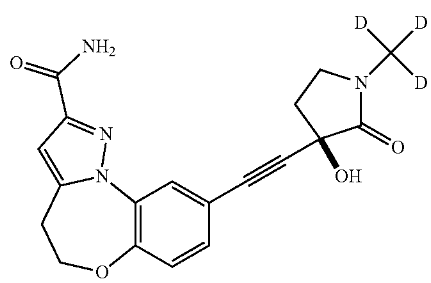 [SMILES: [2H]C([2H])([2H])N1CC[C@@](O)(C#Cc2ccc3c(c2)-n2nc(C(N)=O)cc2CCO3)C1=O] | 9-[2-[3-(R)-hydroxy-2-oxo-1-(trideuteriomethyl)pyrrolidin-3-yl]ethynyl]-4,5-dihydropyrazolo[5,1-d][1,5]benzoxazepine-2-carboxamide |
| 575 | 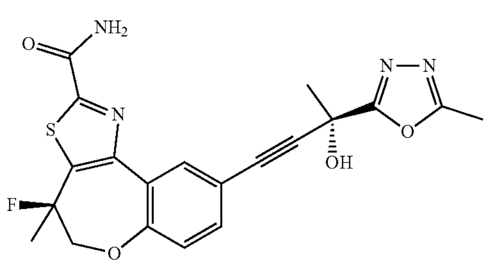 [SMILES: Cc1nnc([C@@](C)(O)C#Cc2ccc3c(c2)-c2nc(C(N)=O)sc2[C@](C)(F)CO3)o1] | 4-(R)-fluoro-9-[3-(S)-hydroxy-3-(5-methyl-1,3,4-oxadiazol-2-yl)but-1-ynyl]-4-methyl-5H-[1]benzoxepino[5,4-d]thiazole-2-carboxamide |

TABLE 1A-continued

| No. | Structure | Name |
|---|---|---|
| 576 | 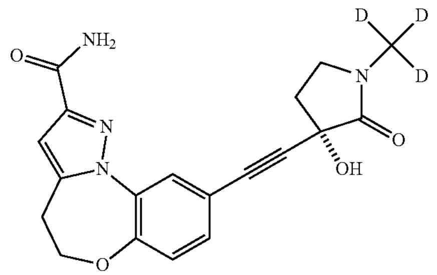 [SMILES: [2H]C([2H])([2H])N1CC[C@](O)(C#Cc2ccc3c(c2)-n2nc(C(N)=O)cc2CCO3)C1=O] | 9-[2-[3-(S)-hydroxy-2-oxo-1-(trideuteriomethyl)pyrrolidin-3-yl]ethynyl]-4,5-dihydropyrazolo[5,1-d][1,5]benzoxazepine-2-carboxamide |
| 577 | 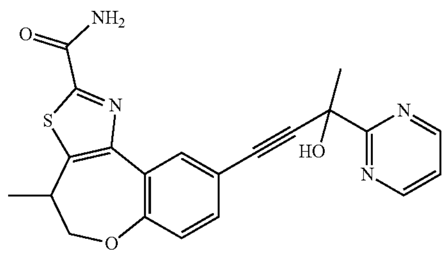 [SMILES: CC1COc2ccc(C#CC(C)(O)c3ncccn3)cc2-c2nc(C(N)=O)sc21] | 9-(3-hydroxy-3-pyrimidin-2-yl-but-1-ynyl)-4-methyl-4,5-dihydro-[1]benzoxepino[5,4-d]thiazole-2-carboxamide |
| 578 | 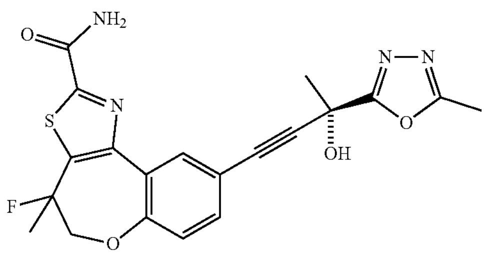 [SMILES: Cc1nnc([C@@](C)(O)C#Cc2ccc3c(c2)-c2nc(C(N)=O)sc2C(C)(F)CO3)o1] | 4-fluoro-9-[3-(S)-hydroxy-3-(5-methyl-1,3,4-oxadiazol-2-yl)but-1-ynyl]-4-methyl-5H-[1]benzoxepino[5,4-d]thiazole-2-carboxamide |
| 579 | 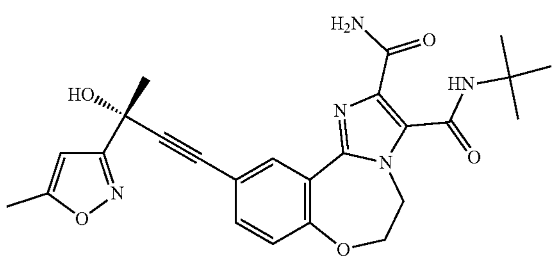 [SMILES: Cc1cc([C@](C)(O)C#Cc2ccc3c(c2)-c2nc(C(N)=O)c(C(=O)NC(C)(C)C)n2CCO3)no1] | (R)-N3-(tert-butyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 580 | 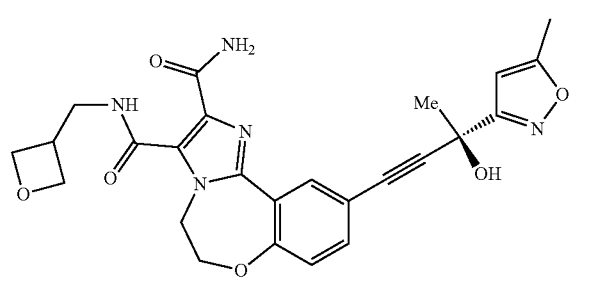 [SMILES: Cc1cc([C@](C)(O)C#Cc2ccc3c(c2)-c2nc(C(N)=O)c(C(=O)NCC4COC4)n2CCO3)no1] | (R)-10-(3-hydroxy-3-(5-methylisoxazol-3-yl)but-1-yn-1-yl)-N3-(oxetan-3-ylmethyl)-5,6-dihydrobenzo[f]imidazo[1,2-d][1,4]oxazepine-2,3-dicarboxamide |
| 581 | 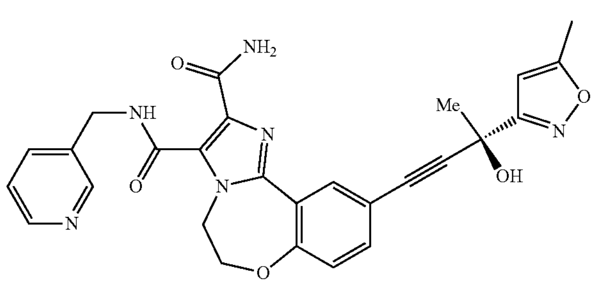 [SMILES: Cc1cc([C@](C)(O)C#Cc2ccc3c(c2)-c2nc(C(N)=O)c(C(=O)NCc4cccnc4)n2CCO3)no1] | (R)-10-(3-hydroxy-3-(5-methylisoxazol-3-yl)but-1-yn-1-yl)-N3-(pyridin-3-ylmethyl)-5,6-dihydrobenzo[f]imidazo[1,2-d][1,4]oxazepine-2,3-dicarboxamide |

TABLE 1A-continued

| No. | Structure | Name |
|---|---|---|
| 582 | 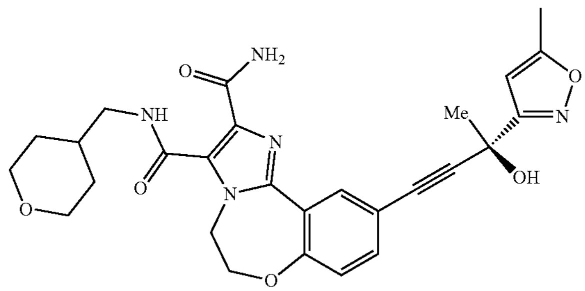 [SMILES: Cc1cc([C@](C)(O)C#Cc2ccc3c(c2)-c2nc(C(N)=O)c(C(=O)NCC4CCOCC4)n2CCO3)no1] | (R)-10-(3-hydroxy-3-(5-methylisoxazol-3-yl)but-1-yn-1-yl)-N3-((tetrahydro-2H-pyran-4-yl)methyl)-5,6-dihydrobenzo[f]imidazo[1,2-d][1,4]oxazepine-2,3-dicarboxamide |
| 583 | 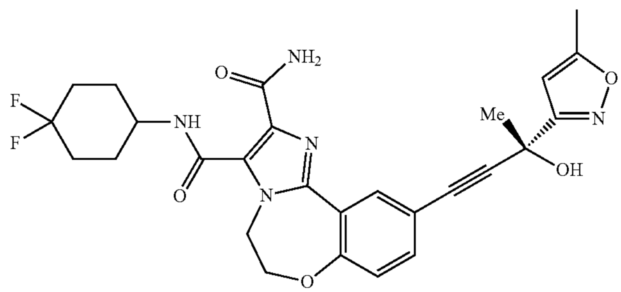 | (R)-N3-(4,4-difluorocyclohexyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 584 | 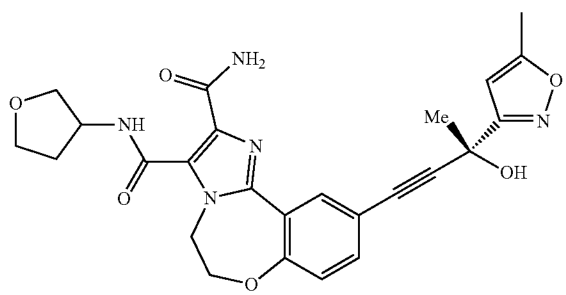 [SMILES: Cc1cc([C@](C)(O)C#Cc2ccc3c(c2)-c2nc(C(N)=O)c(C(=O)NC4CCOC4)n2CCO3)no1] | 10-((R)-3-hydroxy-3-(5-methylisoxazol-3-yl)but-1-yn-1-yl)-N3-(tetrahydrofuran-3-yl)-5,6-dihydrobenzo[f]imidazo[1,2-d][1,4]oxazepine-2,3-dicarboxamide |
| 585 | 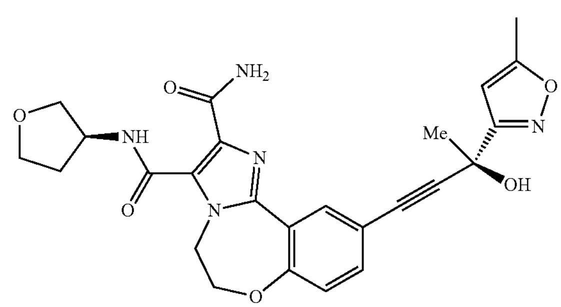 [SMILES: Cc1cc([C@](C)(O)C#Cc2ccc3c(c2)-c2nc(C(N)=O)c(C(=O)N[C@H]4CCOC4)n2CCO3)no1] | 10-((R)-3-hydroxy-3-(5-methylisoxazol-3-yl)but-1-yn-1-yl)-N3-((S)-tetrahydrofuran-3-yl)-5,6-dihydrobenzo[f]imidazo[1,2-d][1,4]oxazepine-2,3-dicarboxamide |
| 586 | 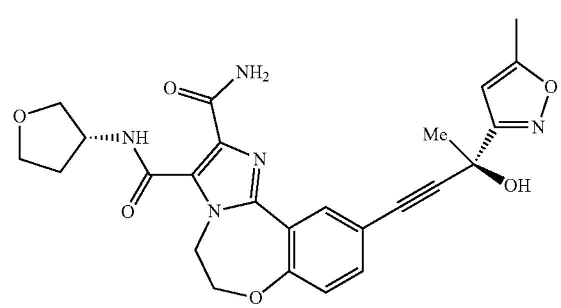 [SMILES: Cc1cc([C@](C)(O)C#Cc2ccc3c(c2)-c2nc(C(N)=O)c(C(=O)N[C@@H]4CCOC4)n2CCO3)no1] | 10-((R)-3-hydroxy-3-(5-methylisoxazol-3-yl)but-1-yn-1-yl)-N3-((R)-tetrahydrofuran-3-yl)-5,6-dihydrobenzo[f]imidazo[1,2-d][1,4]oxazepine-2,3-dicarboxamide |

TABLE 1A-continued

| No. | Structure | Name |
|---|---|---|
| 587 | 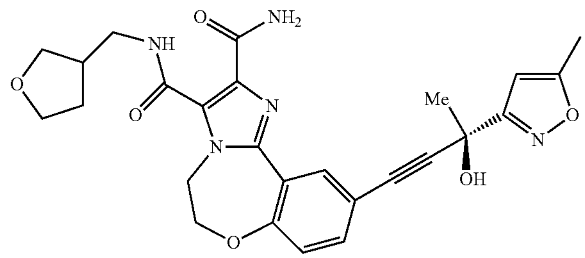 [SMILES: Cc1cc([C@](C)(O)C#Cc2ccc3c(c2)-c2nc(C(N)=O)c(C(=O)NCC4CCOC4)n2CCO3)no1] | 10-((R)-3-hydroxy-3-(5-methylisoxazol-3-yl)but-1-yn-1-yl)-N3-((tetrahydrofuran-3-yl)methyl)-5,6-dihydrobenzo[f]imidazo[1,2-d][1,4]oxazepine-2,3-dicarboxamide |
| 588 | 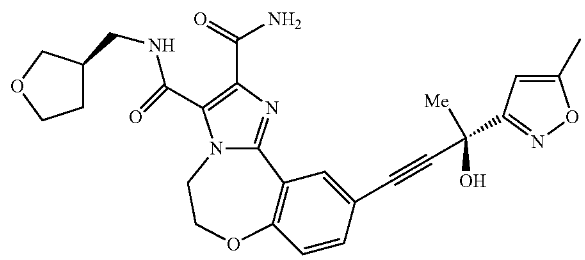 [SMILES: Cc1cc([C@](C)(O)C#Cc2ccc3c(c2)-c2nc(C(N)=O)c(C(=O)NC[C@H]4CCOC4)n2CCO3)no1] | 10-((R)-3-hydroxy-3-(5-methylisoxazol-3-yl)but-1-yn-1-yl)-N3-(((R)-tetrahydrofuran-3-yl)methyl)-5,6-dihydrobenzo[f]imidazo[1,2-d][1,4]oxazepine-2,3-dicarboxamide |
| 589 | 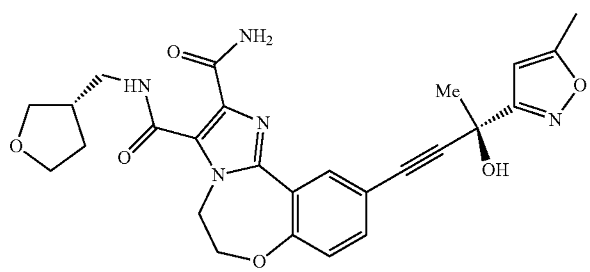 [SMILES: Cc1cc([C@](C)(O)C#Cc2ccc3c(c2)-c2nc(C(N)=O)c(C(=O)NC[C@@H]4CCOC4)n2CCO3)no1] | 10-((R)-3-hydroxy-3-(5-methylisoxazol-3-yl)but-1-yn-1-yl)-N3-(((S)-tetrahydrofuran-3-yl)methyl)-5,6-dihydrobenzo[f]imidazo[1,2-d][1,4]oxazepine-2,3-dicarboxamide |
| 590 | 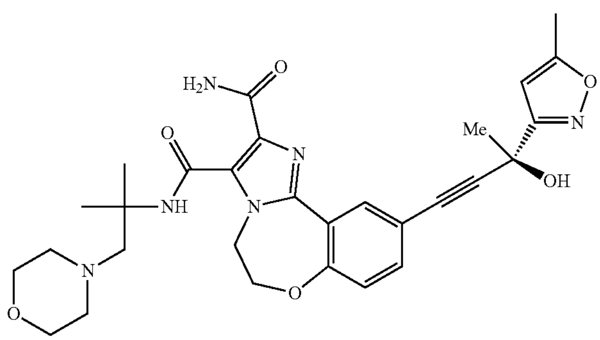 [SMILES: Cc1cc([C@](C)(O)C#Cc2ccc3c(c2)-c2nc(C(N)=O)c(C(=O)NC(C)(C)CN4CCOCC4)n2CCO3)no1] | (R)-10-(3-hydroxy-3-(5-methylisoxazol-3-yl)but-1-yn-1-yl)-N3-(2-methyl-1-morpholinopropan-2-yl)-5,6-dihydrobenzo[f]imidazo[1,2-d][1,4]oxazepine-2,3-dicarboxamide |
| 591 | 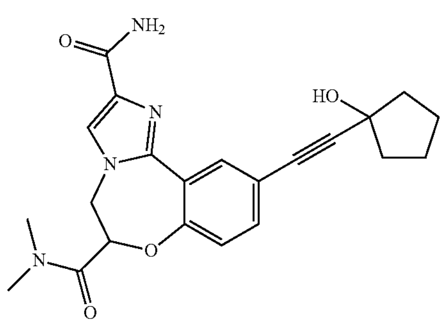 [SMILES: CN(C)C(=O)C1Cn2cc(C(N)=O)nc2-c2cc(C#CC3(O)CCCC3)ccc2O1] | 10-((1-hydroxycyclopentyl)ethynyl)-N6,N6-dimethyl-5,6-dihydrobenzo[f]imidazo[1,2-d][1,4]oxazepine-2,6-dicarboxamide |

TABLE 1A-continued

| No. | Structure | Name |
|---|---|---|
| 592 | 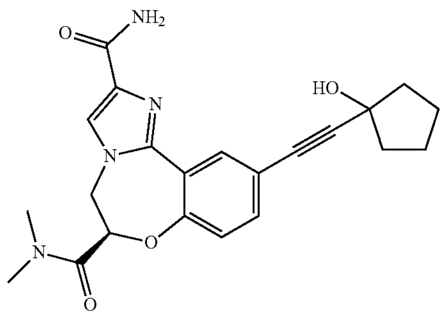 [SMILES: CN(C)C(=O)[C@H]1Cn2cc(C(N)=O)nc2-c2cc(C#CC3(O)CCCC3)ccc2O1] | (R)-10-((1-hydroxycyclopentyl)ethynyl)-N6,N6-dimethyl-5,6-dihydrobenzo[f]imidazo[1,2-d][1,4]oxazepine-2,6-dicarboxamide |
| 593 | 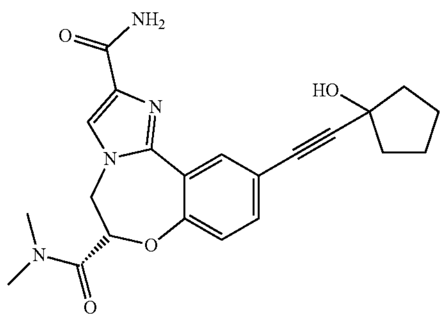 | (S)-10-((1-hydroxycyclopentyl)ethynyl)-N6,N6-dimethyl-5,6-dihydrobenzo[f]imidazo[1,2-d][1,4]oxazepine-2,6-dicarboxamide |
| 594 | 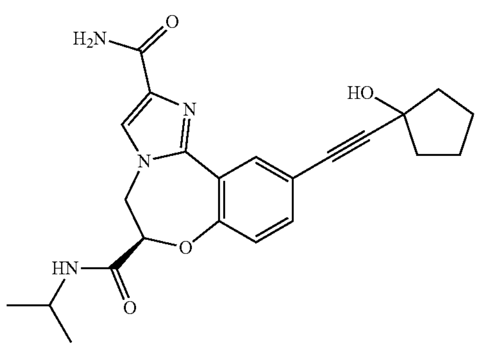 [SMILES: CC(C)NC(=O)[C@H]1Cn2cc(C(N)=O)nc2-c2cc(C#CC3(O)CCCC3)ccc2O1] | 10-((1-hydroxycyclopentyl)ethynyl)-N6-isopropyl-5,6-dihydrobenzo[f]imidazo[1,2-d][1,4]oxazepine-2,6-dicarboxamide |
| 595 | 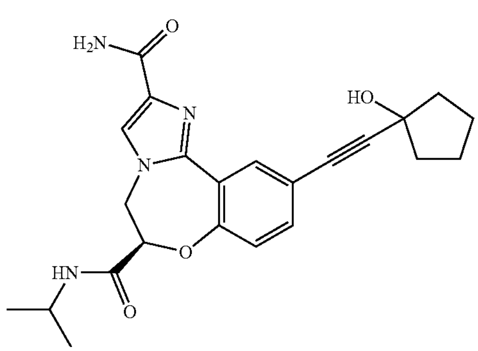 [SMILES: CC(C)NC(=O)[C@H]1Cn2cc(C(N)=O)nc2-c2cc(C#CC3(O)CCCC3)ccc2O1] | (R)-10-((1-hydroxycyclopentyl)ethynyl)-N6-isopropyl-5,6-dihydrobenzo[f]imidazo[1,2-d][1,4]oxazepine-2,6-dicarboxamide |

TABLE 1A-continued

| No. | Structure | Name |
|---|---|---|
| 596 | 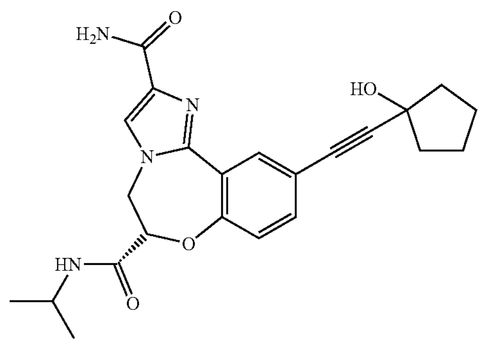 | (S)-10-((1-hydroxycyclopentyl)ethynyl)-N6-isopropyl-5,6-dihydrobenzo[f]imidazo[1,2-d][1,4]oxazepine-2,6-dicarboxamide |
| 597 | 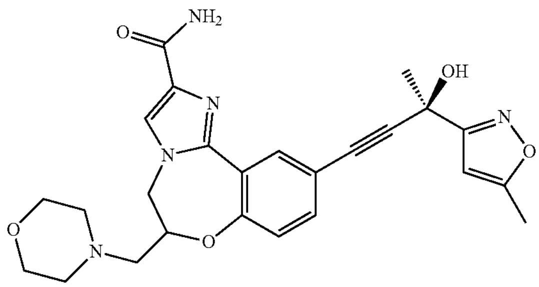 [SMILES: Cc1cc([C@](C)(O)C#Cc2ccc3c(c2)-c2nc(C(N)=O)cn2CC(CN2CCOCC2)O3)no1] | 10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide |
| 598 | 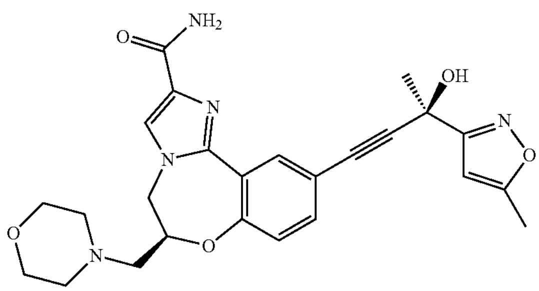 [SMILES: Cc1cc([C@](C)(O)C#Cc2ccc3c(c2)-c2nc(C(N)=O)cn2C[C@H](CN2CCOCC2)O3)no1] | (S)-10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide |
| 599 | 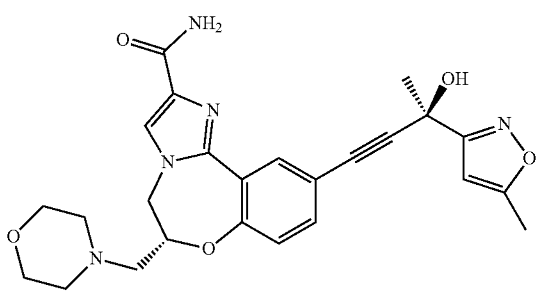 [SMILES: Cc1cc([C@](C)(O)C#Cc2ccc3c(c2)-c2nc(C(N)=O)cn2C[C@@H](CN2CCOCC2)O3)no1] | (R)-10-((R)-3-hydroxy-3-(5-methylisoxazol-3-yl)but-1-yn-1-yl)-6-(morpholinomethyl)-5,6-dihydrobenzo[f]imidazo[1,2-d][1,4]oxazepine-2-carboxamide |
| 600 | 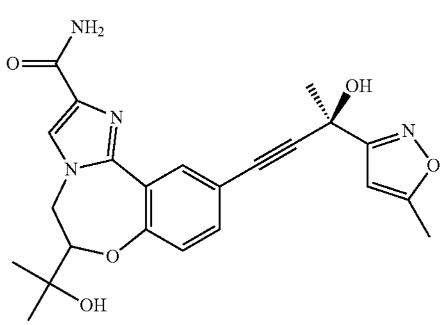 [SMILES: Cc1cc([C@](C)(O)C#Cc2ccc3c(c2)-c2nc(C(N)=O)cn2CC(C(C)(C)O)O3)no1] | 10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide |

TABLE 1A-continued

| No. | Structure | Name |
|---|---|---|
| 601 | 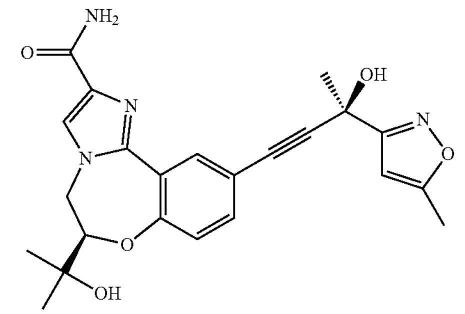 [SMILES: Cc1cc([C@](C)(O)C#Cc2ccc3c(c2)-c2nc(C(N)=O)cn2C[C@H](C(C)(C)O)O3)no1] | (R)-10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide |
| 602 | 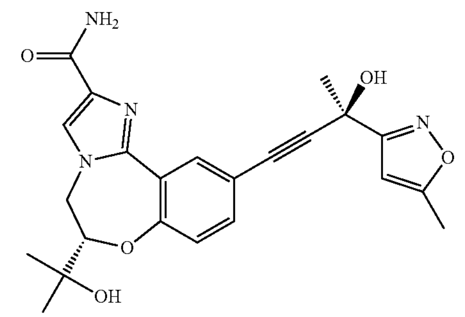 [SMILES: Cc1cc([C@](C)(O)C#Cc2ccc3c(c2)-c2nc(C(N)=O)cn2C[C@@H](C(C)(C)O)O3)no1] | (S)-10-((R)-3-hydroxy-3-(5-methylisoxazol-3-yl)but-1-yn-1-yl)-6-(2-hydroxypropan-2-yl)-5,6-dihydrobenzo[f]imidazo[1,2-d][1,4]oxazepine-2-carboxamide |
| 603 | 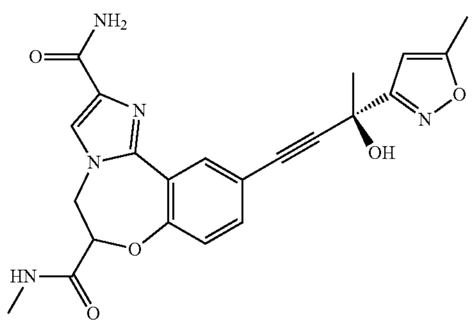 | 10-((R)-3-hydroxy-3-(5-methylisoxazol-3-yl)but-1-yn-1-yl)-N6-methyl-5,6-dihydrobenzo[f]imidazo[1,2-d][1,4]oxazepine-2,6-dicarboxamide |
| 604 | 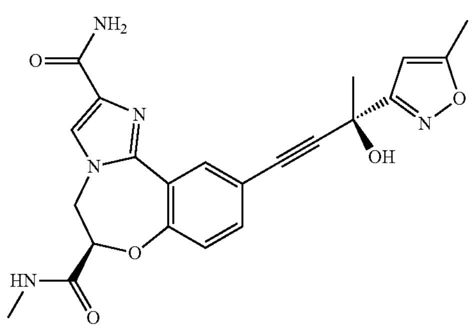 | (R)-10-((R)-3-hydroxy-3-(5-methylisoxazol-3-yl)but-1-yn-1-yl)-N6-methyl-5,6-dihydrobenzo[f]imidazo[1,2-d][1,4]oxazepine-2,6-dicarboxamide |
| 605 | 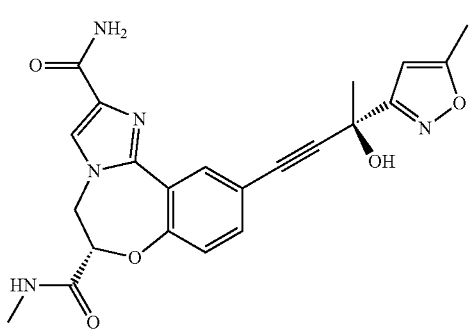 | (R)-10-((R)-3-hydroxy-3-(5-methylisoxazol-3-yl)but-1-yn-1-yl)-N6-methyl-5,6-dihydrobenzo[f]imidazo[1,2-d][1,4]oxazepine-2,6-dicarboxamide |

| No. | Structure | Name |
|---|---|---|
| 606 | 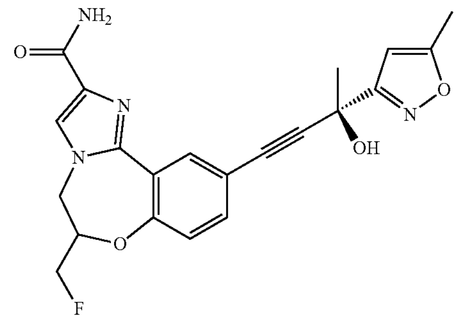 [SMILES: Cc1cc([C@](C)(O)C#Cc2ccc3c(c2)-c2nc(C(N)=O)cn2CC(CF)O3)no1] | 6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide and (S)-6-(fluoromethyl)-10-(R)-3-hydroxy-3-(5-methylisoxazol-3-yl)but-1-yn-1-yl)-5,6-dihydrobenzo[f]imidazo[1,2-d][1,4]oxazepine-2-carboxamide |
| 607 | 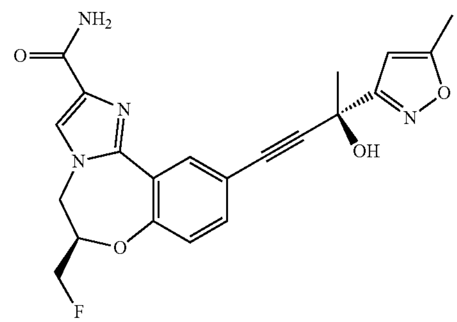 [SMILES: Cc1cc([C@](C)(O)C#Cc2ccc3c(c2)-c2nc(C(N)=O)cn2C[C@H](CF)O3)no1] | (R)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide |
| 608 | 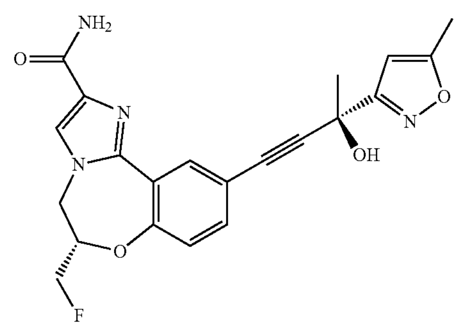 [SMILES: Cc1cc([C@](C)(O)C#Cc2ccc3c(c2)-c2nc(C(N)=O)cn2C[C@@H](CF)O3)no1] | (S)-6-(fluoromethyl)-10-((R)-3-hydroxy-3-(5-methylisoxazol-3-yl)but-1-yn-1-yl)-5,6-dihydrobenzo[f]imidazo[1,2-d][1,4]oxazepine-2-carboxamide |
| 611 | 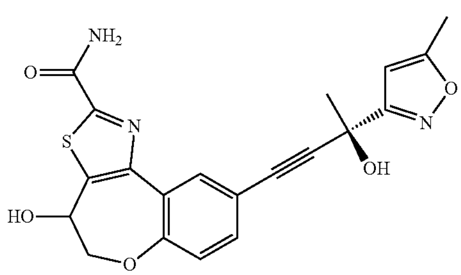 [SMILES: Cc1cc([C@](C)(O)C#Cc2ccc3c(c2)-c2nc(C(N)=O)sc2C(O)CO3)no1] | 4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 612 | 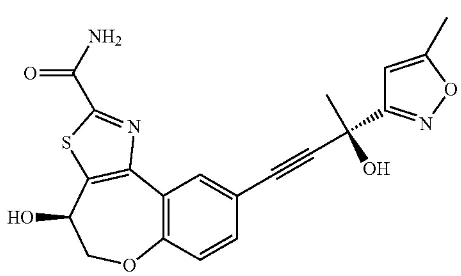 [SMILES: Cc1cc([C@](C)(O)C#Cc2ccc3c(c2)-c2nc(C(N)=O)sc2[C@H](O)CO3)no1] | (R)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |

TABLE 1A-continued

| No. | Structure | Name |
|---|---|---|
| 613 | 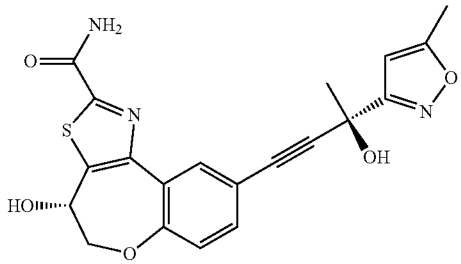 [SMILES: Cc1cc([C@](C)(O)C#Cc2ccc3c(c2)-c2nc(C(N)=O)sc2[C@@H](O)CO3)no1] | and (S)-4-hydroxy-9-((R)-3-hydroxy-3-(5-methylisoxazol-3-yl)but-1-yn-1-yl)-4,5-dihydrobenzo[2,3]oxepino[4,5-d]thiazole-2-carboxamide |
| 614 | 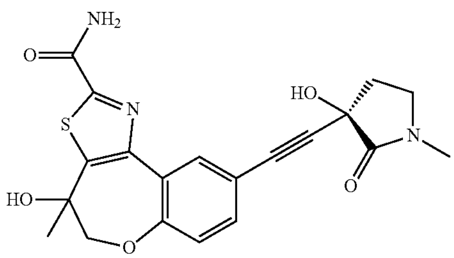 [SMILES: CN1CC[C@@](O)(C#Cc2ccc3c(c2)-c2nc(C(N)=O)sc2C(C)(O)CO3)C1=O] | 4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 615 | 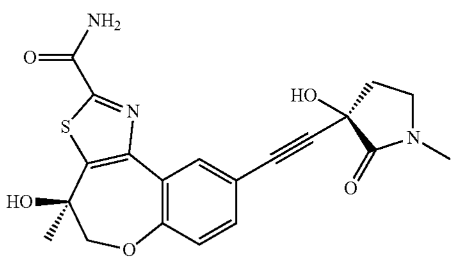 [SMILES: CN1CC[C@@](O)(C#Cc2ccc3c(c2)-c2nc(C(N)=O)sc2[C@](C)(O)CO3)C1=O] | (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 616 | 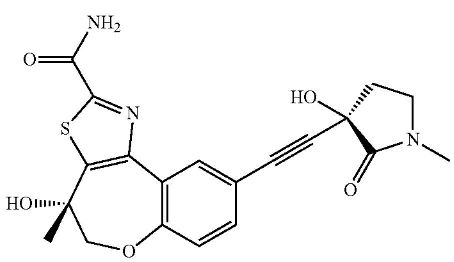 [SMILES: CN1CC[C@@](O)(C#Cc2ccc3c(c2)-c2nc(C(N)=O)sc2[C@@](C)(O)CO3)C1=O] | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 617 | 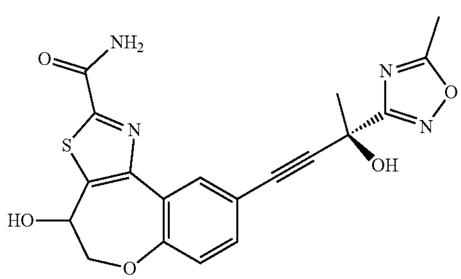 | 4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 618 | 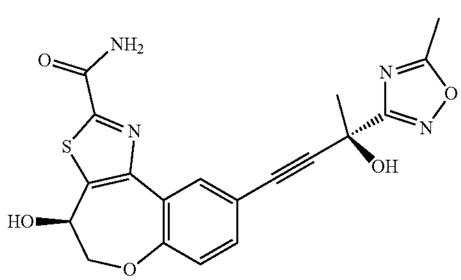 [SMILES: Cc1nc([C@](C)(O)C#Cc2ccc3c(c2)-c2nc(C(N)=O)sc2[C@H](O)CO3)no1] | (R)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |

| No. | Structure | Name |
|---|---|---|
| 619 | 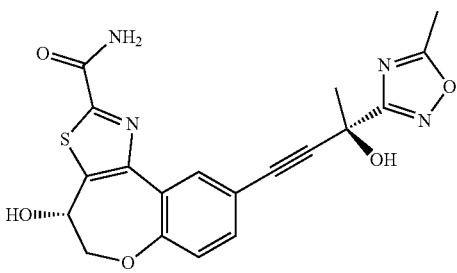 [SMILES: Cc1nc([C@](C)(O)C#Cc2ccc3c(c2)-c2nc(C(N)=O)sc2[C@@H](O)CO3)no1] | (S)-4-hydroxy-9-((R)-3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 620 | 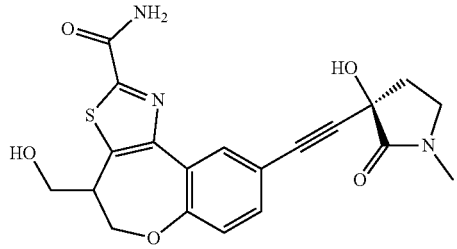 [SMILES: CN1CC[C@@](O)(C#Cc2ccc3c(c2)-c2nc(C(N)=O)sc2C(CO)CO3)C1=O] | 9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 621 | 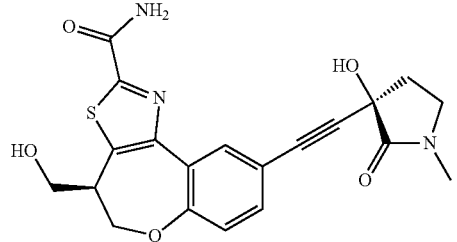 [SMILES: CN1CC[C@@](O)(C#Cc2ccc3c(c2)-c2nc(C(N)=O)sc2[C@H](CO)CO3)C1=O] | (R)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 622 | 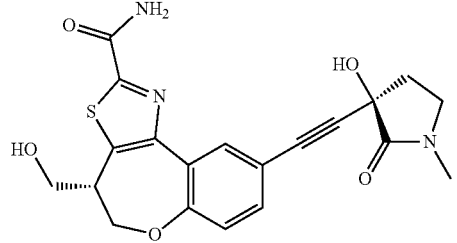 [SMILES: CN1CC[C@@](O)(C#Cc2ccc3c(c2)-c2nc(C(N)=O)sc2[C@@H](CO)CO3)C1=O] | (S)-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 623 | 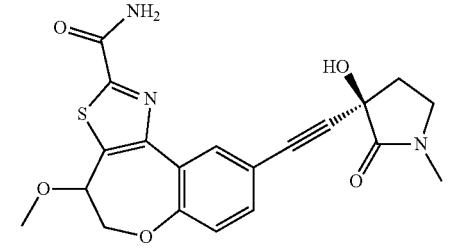 | 9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide |
| 624 | 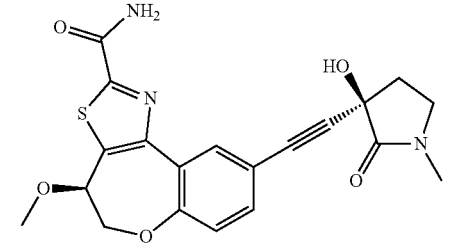 | (R)-9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide |

TABLE 1A-continued

| No. | Structure | Name |
|---|---|---|
| 625 | 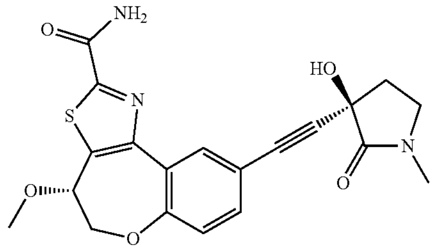 | (S)-9-(((R)-3-hydroxy-1-methyl-2-oxopyrrolidin-3-yl)ethynyl)-4-methoxy-4,5-dihydrobenzo[2,3]oxepino[4,5-d]thiazole-2-carboxamide |
| 626 | 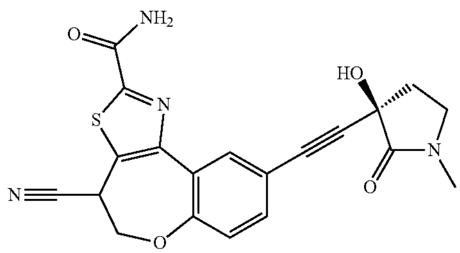 [SMILES: CN1CC[C@@](O)(C#Cc2ccc3c(c2)-c2nc(C(N)=O)sc2C(C#N)CO3)C1=O] | 4-cyano-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 627 | 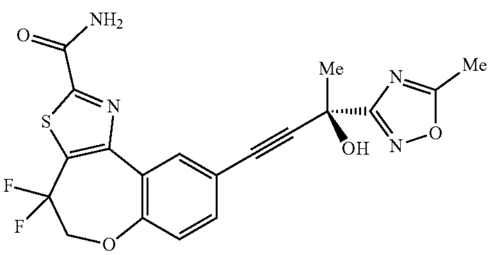 [SMILES: Cc1nc([C@](C)(O)C#Cc2ccc3c(c2)-c2nc(C(N)=O)sc2C(F)(F)CO3)no1] | (R)-4,4-difluoro-9-(3-hydroxy-3-(5-methyl-1,2,4-oxadiazol-3-yl)but-1-yn-1-yl)-4,5-dihydrobenzo[2,3]oxepino[4,5-d]thiazole-2-carboxamide |
| 628 | 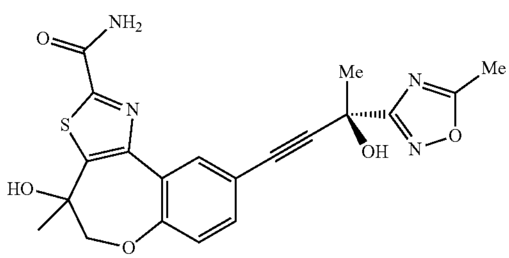 [SMILES: Cc1nc([C@](C)(O)C#Cc2ccc3c(c2)-c2nc(C(N)=O)sc2C(C)(O)CO3)no1] | 4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 629 | 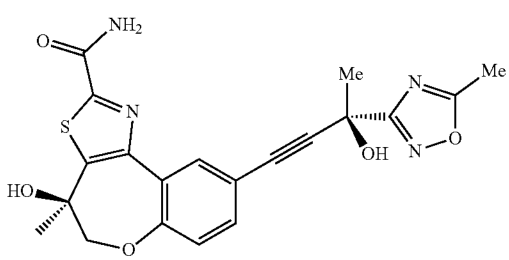 [SMILES: Cc1nc([C@](C)(O)C#Cc2ccc3c(c2)-c2nc(C(N)=O)sc2[C@](C)(O)CO3)no1] | (R)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |
| 630 | 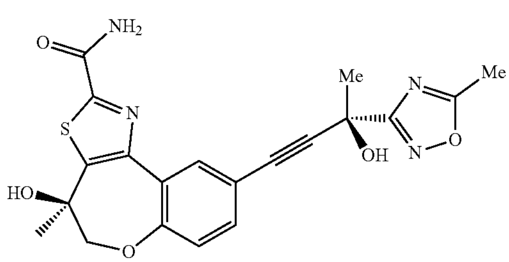 [SMILES: Cc1nc([C@](C)(O)C#Cc2ccc3c(c2)-c2nc(C(N)=O)sc2[C@](C)(O)CO3)no1] | (S)-4-hydroxy-9-((R)-3-hydroxy-3-(5-methyl-1,2,4-oxadiazol-3-yl)but-1-yn-1-yl)-4-methyl-4,5-dihydrobenzo[2,3]oxepino[4,5-d]thiazole-2-carboxamide |

TABLE 1A-continued

| No. | Structure | Name |
|---|---|---|
| 631 | 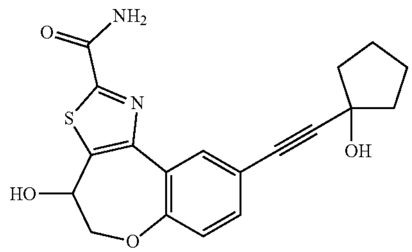 [SMILES: NC(=O)c1nc2c(s1)C(O)COc1ccc(C#CC3(O)CCCC3)cc1-2] | 4-hydroxy-9-((1-hydroxycyclopentyl)ethynyl)-4,5-dihydrobenzo[2,3]oxepino[4,5-d]thiazole-2-carboxamide |
| 632 | 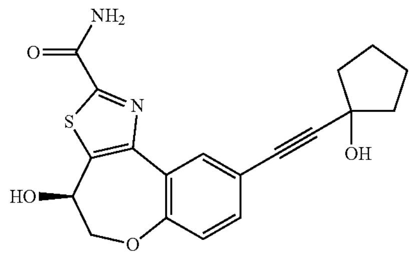 [SMILES: NC(=O)c1nc2c(s1)[C@H](O)COc1ccc(C#CC3(O)CCCC3)cc1-2] | (R)-4-hydroxy-9-((1-hydroxycyclopentyl)ethynyl)-4,5-dihydrobenzo[2,3]oxepino[4,5-d]thiazole-2-carboxamide |
| 633 | 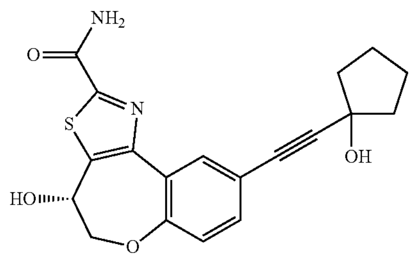 [SMILES: NC(=O)c1nc2c(s1)[C@@H](O)COc1ccc(C#CC3(O)CCCC3)cc1-2] | (S)-4-hydroxy-9-((1-hydroxycyclopentyl)ethynyl)-4,5-dihydrobenzo[2,3]oxepino[4,5-d]thiazole-2-carboxamide |
| 634 | 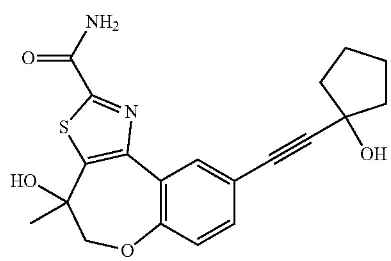 [SMILES: CC1(O)COc2ccc(C#CC3(O)CCCC3)cc2-c2nc(C(N)=O)sc21] | 4-hydroxy-9-((1-hydroxycyclopentyl)ethynyl)-4-methyl-4,5-dihydrobenzo[2,3]oxepino[4,5-d]thiazole-2-carboxamide |
| 635 | 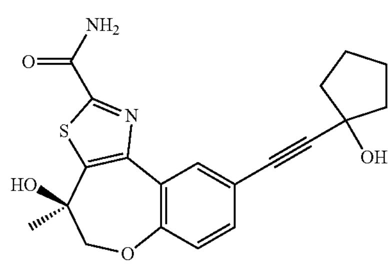 [SMILES: C[C@@]1(O)COc2ccc(C#CC3(O)CCCC3)cc2-c2nc(C(N)=O)sc21] | (R)-4-hydroxy-9-((1-hydroxycyclopentyl)ethynyl)-4-methyl-4,5-dihydrobenzo[2,3]oxepino[4,5-d]thiazole-2-carboxamide |
| 636 | 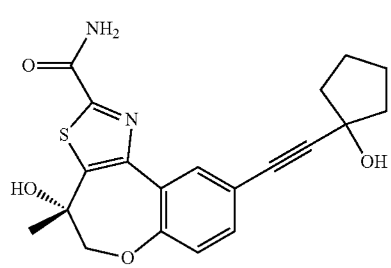 [SMILES: C[C@]1(O)COc2ccc(C#CC3(O)CCCC3)cc2-c2nc(C(N)=O)sc21] | (S)-4-hydroxy-9-((1-hydroxycyclopentyl)ethynyl)-4-methyl-4,5-dihydrobenzo[2,3]oxepino[4,5-d]thiazole-2-carboxamide |

TABLE 1A-continued

| No. | Structure | Name |
|---|---|---|
| 637 | 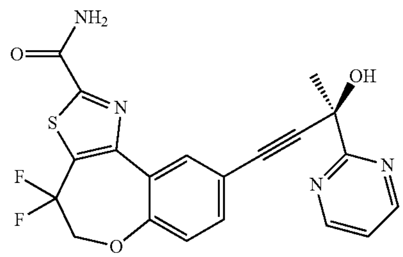 [SMILES: C[C@@](O)(C#Cc1ccc2c(c1)-c1nc(C(N)=O)sc1C(F)(F)CO2)c1ncccn1] | (R)-4,4-difluoro-9-(3-hydroxy-3-(pyrimidin-2-yl)but-1-yn-1-yl)-4,5-dihydrobenzo[2,3]oxepino[4,5-d]thiazole-2-carboxamide |
| 638 | 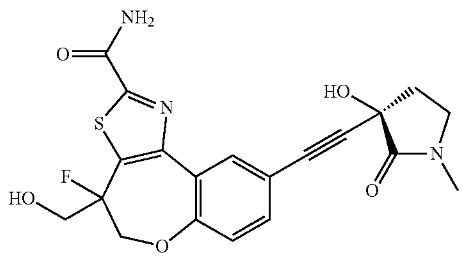 [SMILES: CN1CC[C@@](O)(C#Cc2ccc3c(c2)-c2nc(C(N)=O)sc2C(F)(CO)CO3)C1=O] | 4-fluoro-9-(((R)-3-hydroxy-1-methyl-2-oxopyrrolidin-3-yl)ethynyl)-4-(hydroxymethyl)-4,5-dihydrobenzo[2,3]oxepino[4,5-d]thiazole-2-carboxamide |
| 639 | 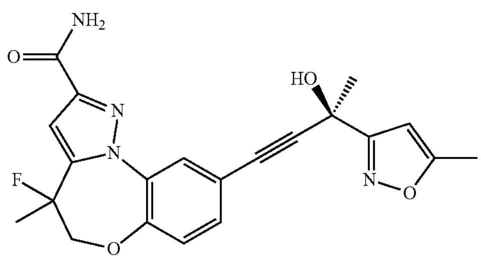 [SMILES: Cc1cc([C@](C)(O)C#Cc2ccc3c(c2)-n2nc(C(N)=O)cc2C(C)(F)CO3)no1] | 4-fluoro-9-((R)-3-hydroxy-3-(5-methylisoxazol-3-yl)but-1-yn-1-yl)-4-methyl-4,5-dihydrobenzo[b]pyrazolo[1,5-d][1,4]oxazepine-2-carboxamide |
| 640 | 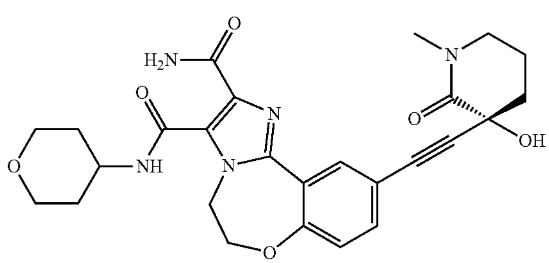 [SMILES: CN1CCC[C@@](O)(C#Cc2ccc3c(c2)-c2nc(C(N)=O)c(C(=O)NC4CCOCC4)n2CCO3)C1=O] | 10-[2-[(3R)-3-hydroxy-1-methyl-2-oxo-3-piperidyl]ethynyl]-N3-tetrahydropyran-4-yl-5,6-dihydroimidazo[1,2-d][1,4]benzoxazepine-2,3-dicarboxamide |
| 641 | 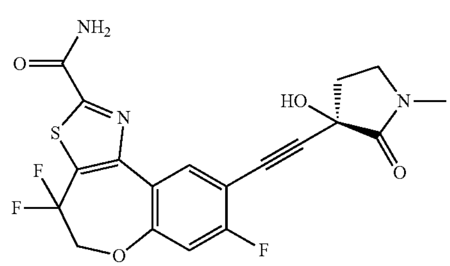 [SMILES: CN1CC[C@@](O)(C#Cc2cc3c(cc2F)OCC(F)(F)c2sc(C(N)=O)nc2-3)C1=O] | 4,4,8-trifluoro-9-[2-[(3R)-3-hydroxy-1-methyl-2-oxo-pyrrolidin-3-yl]ethynyl]-5H-[1]benzoxepino[5,4-d]thiazole-2-carboxamide |
| 642 | 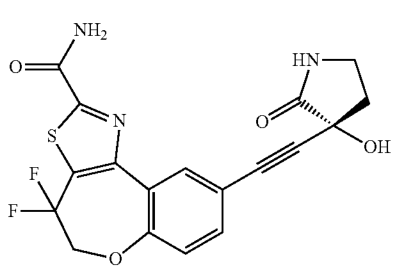 [SMILES: NC(=O)c1nc2c(s1)C(F)(F)COc1ccc(C#C[C@]3(O)CCNC3=O)cc1-2] | (R)-4,4-difluoro-9-((3-hydroxy-2-oxopyrrolidin-3-yl)ethynyl)-4,5-dihydrobenzo[2,3]oxepino[4,5-d]thiazole-2-carboxamide |

TABLE 1A-continued

| No. | Structure | Name |
|---|---|---|
| 643 | 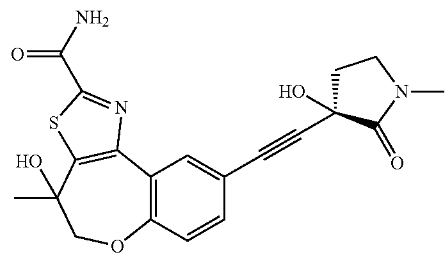 | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide and (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 644 | 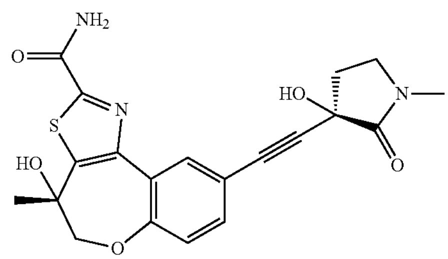 | (S)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 645 | 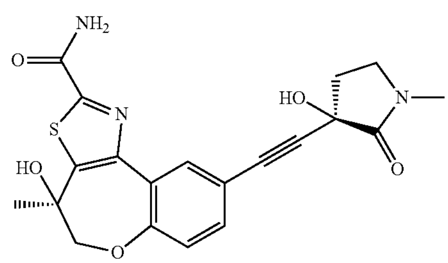 | (R)-4-hydroxy-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 646 | 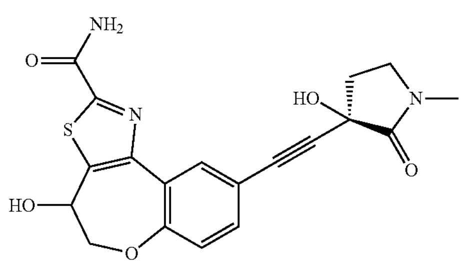 [SMILES: CN1CC[C@@](O)(C#Cc2ccc3c(c2)-c2nc(C(N)=O)sc2C(O)CO3)C1=O] | 4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 647 | 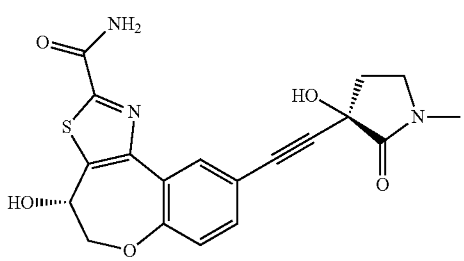 [SMILES: CN1CC[C@@](O)(C#Cc2ccc3c(c2)-c2nc(C(N)=O)sc2[C@@H](O)CO3)C1=O] | (S)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 648 | 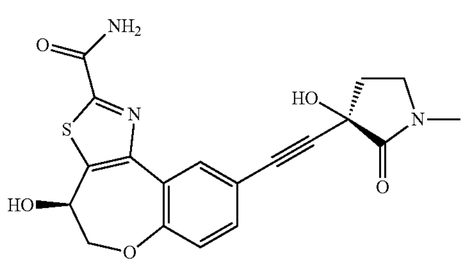 [SMILES: CN1CC[C@@](O)(C#Cc2ccc3c(c2)-c2nc(C(N)=O)sc2[C@H](O)CO3)C1=O] | (R)-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1A-continued

| No. | Structure | Name |
|---|---|---|
| 649 | 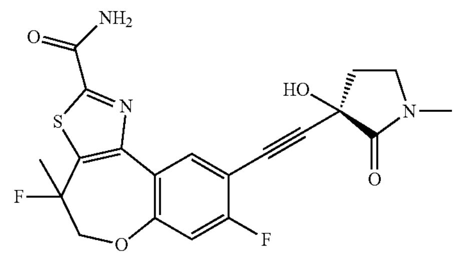 | 4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 650 | 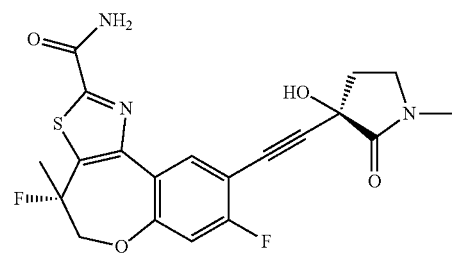 [SMILES: CN1CC[C@@](O)(C#Cc2cc3c(cc2F)OC[C@](C)(F)c2sc(C(N)=O)nc2-3)C1=O] | (S)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 651 | 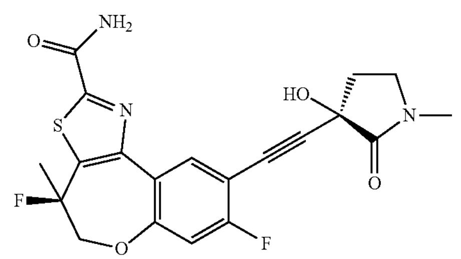 [SMILES: CN1CC[C@@](O)(C#Cc2cc3c(cc2F)OC[C@@](C)(F)c2sc(C(N)=O)nc2-3)C1=O] | (R)-4,8-difluoro-9-(((R)-3-hydroxy-1-methyl-2-oxopyrrolidin-3-yl)ethynyl)-4-methyl-4,5-dihydrobenzo[2,3]oxepino[4,5-d]thiazole-2-carboxamide |
| 655 | 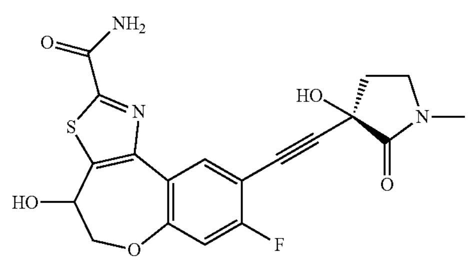 | 8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 656 | 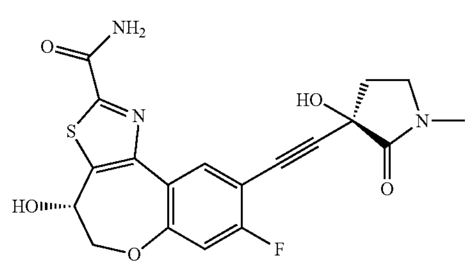 [SMILES: CN1CC[C@@](O)(C#Cc2cc3c(cc2F)OCC(O)c2sc(C(N)=O)nc2-3)C1=O] | (S)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 657 | 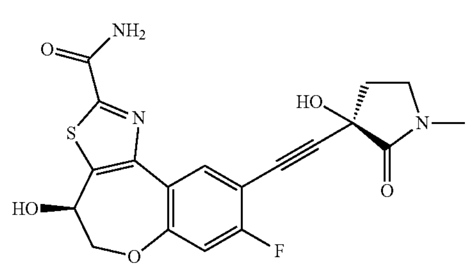 | (R)-8-fluoro-4-hydroxy-9-(((R)-3-hydroxy-1-methyl-2-oxopyrrolidin-3-yl)ethynyl)-4,5-dihydrobenzo[2,3]oxepino[4,5-d]thiazole-2-carboxamide |

TABLE 1A-continued

| No. | Structure | Name |
|---|---|---|
| 661 | 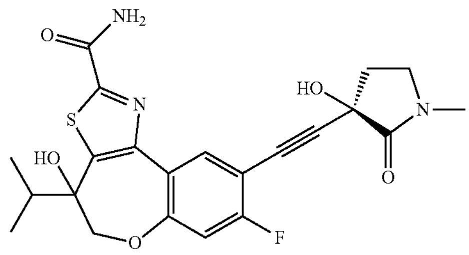 [SMILES: CC(C)C1(O)COc2cc(F)c(C#C[C@]3(O)CCN(C)C3=O)cc2-c2nc(C(N)=O)sc21] | 8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 662 | 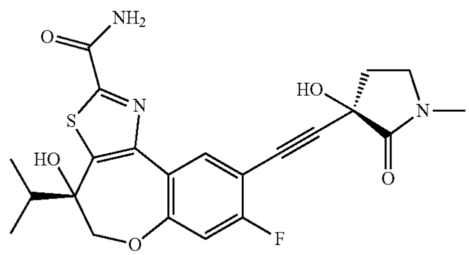 [SMILES: CC(C)[C@]1(O)COc2cc(F)c(C#C[C@]3(O)CCN(C)C3=O)cc2-c2nc(C(N)=O)sc21] | (S)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 663 | 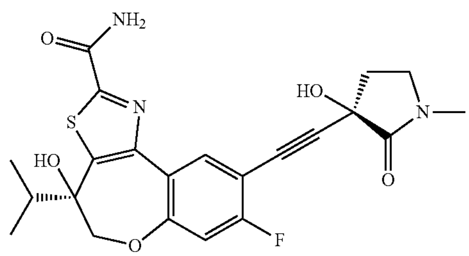 [SMILES: CC(C)[C@@]1(O)COc2cc(F)c(C#C[C@]3(O)CCN(C)C3=O)cc2-c2nc(C(N)=O)sc21] | (R)-8-fluoro-4-hydroxy-9-(((R)-3-hydroxy-1-methyl-2-oxopyrrolidin-3-yl)ethynyl)-4-isopropyl-4,5-dihydrobenzo[2,3]oxepino[4,5-d]thiazole-2-carboxamide |
| 672 | 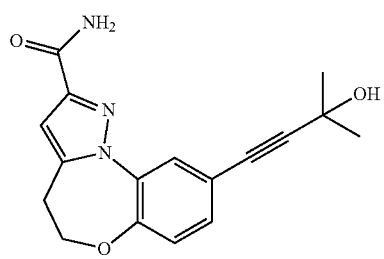 [SMILES: CC(C)(O)C#Cc1ccc2c(c1)-n1nc(C(N)=O)cc1CCO2] | 9-(3-hydroxy-3-methylbut-1-yn-1-yl)-4,5-dihydrobenzo[b]pyrazolo[1,5-[1,4]oxazepine-2-carboxamide |
| 673 | 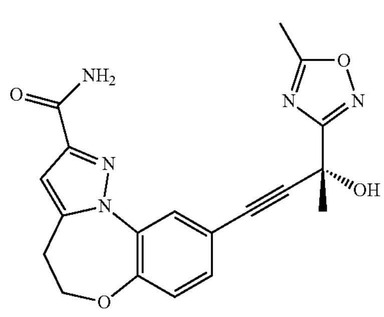 [SMILES: Cc1nc([C@](C)(O)C#Cc2ccc3c(c2)-n2nc(C(N)=O)cc2CCO3)no1] | (R)-9-(3-hydroxy-3-(5-methyl-1,2,4-oxadiazol-3-yl)but-1-yn-1-yl)-4,5-dihydrobenzo[b]pyrazolo[1,5-d][1,4]oxazepine-2-carboxamide |

TABLE 1A-continued

| No. | Structure | Name |
|---|---|---|
| 674 | 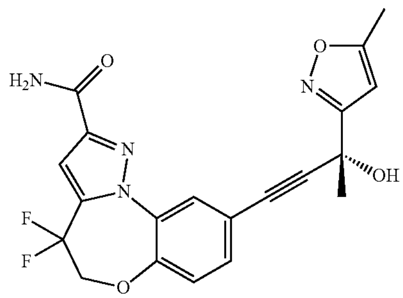 [SMILES: Cc1cc([C@](C)(O)C#Cc2ccc3c(c2)-n2nc(C(N)=O)cc2C(F)(F)CO3)no1] | (R)-4,4-difluoro-9-(3-hydroxy-3-(5-methylisoxazol-3-yl)but-1-yn-1-yl)-4,5-dihydrobenzo[b]pyrazolo[1,5-d][1,4]oxazepine-2-carboxamide |
| 675 | 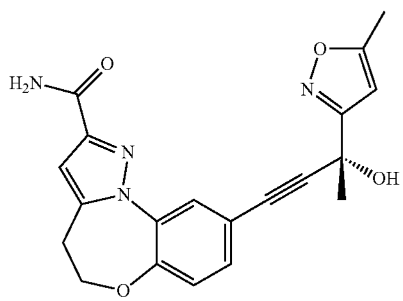 [SMILES: Cc1cc([C@](C)(O)C#Cc2ccc3c(c2)-n2nc(C(N)=O)cc2CCO3)no1] | (R)-9-(3-hydroxy-3-(5-methylisoxazol-3-yl)but-1-yn-1-yl)-4,5-dihydrobenzo[b]pyrazolo[1,5-d][1,4]oxazepine-2-carboxamide |
| 676 | 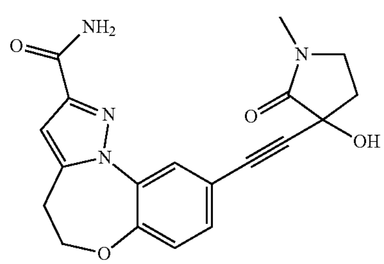 [SMILES: CN1CCC(O)(C#Cc2ccc3c(c2)-n2nc(C(N)=O)cc2CCO3)C1=O] | 9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 677 | 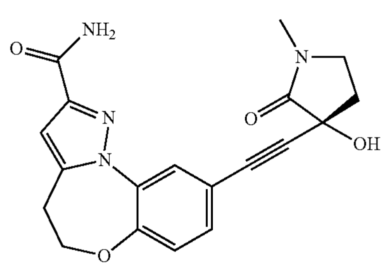 [SMILES: CN1CC[C@@](O)(C#Cc2ccc3c(c2)-n2nc(C(N)=O)cc2CCO3)C1=O] | (R)-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 678 | 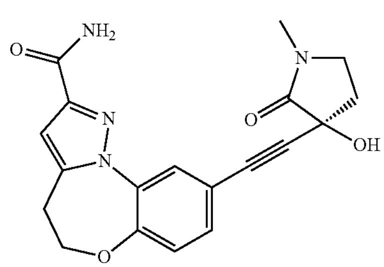 | (S)-9-((3-hydroxy-1-methyl-2-oxopyrrolidin-3-yl)ethynyl)-4,5-dihydrobenzo[b]pyrazolo[1,5-d][1,4]oxazepine-2-carboxamide |

TABLE 1A-continued

| No. | Structure | Name |
|-----|-----------|------|
| 679 | 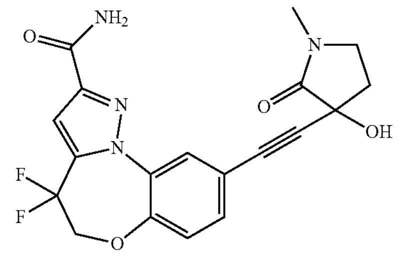 | 4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 680 | 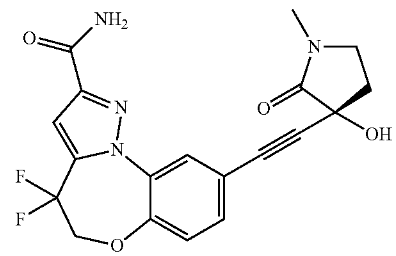 [SMILES: CN1CC[C@@](O)(C#Cc2ccc3c(c2)-n2nc(C(N)=O)cc2C(F)(F)CO3)C1=O] | (R)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 681 | 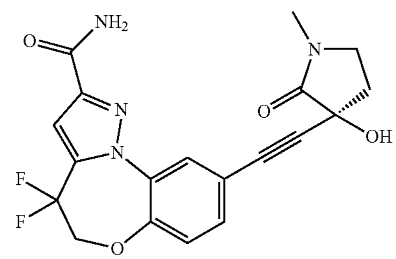 | (S)-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 682 | 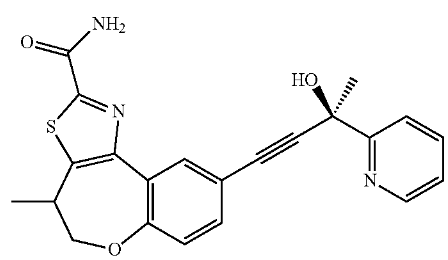 [SMILES: CC1COc2ccc(C#C[C@@](C)(O)c3ccccn3)cc2-c2nc(C(N)=O)sc21] | 9-((R)-3-hydroxy-3-(pyridin-2-yl)but-1-yn-1-yl)-4-methyl-4,5-dihydrobenzo[2,3]oxepino[4,5-d]thiazole-2-carboxamide |
| 683 | 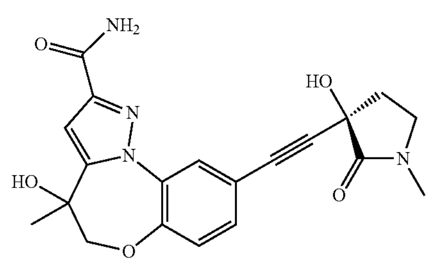 [SMILES: CN1CC[C@@](O)(C#Cc2ccc3c(c2)-n2nc(C(N)=O)cc2C(C)(O)CO3)C1=O] | 4-hydroxy-9-(((R)-3-hydroxy-1-methyl-2-oxopyrrolidin-3-yl)ethynyl)-4-methyl-4,5-dihydrobenzo[b]pyrazolo[1,5-d][1,4]oxazepine-2-carboxamide |
| 684 | 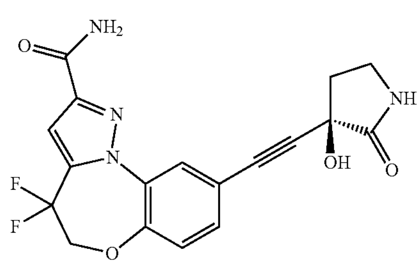 [SMILES: NC(=O)c1cc2n(n1)-c1cc(C#C[C@]3(O)CCNC3=O)ccc1OCC2(F)F] | (R)-4,4-difluoro-9-((3-hydroxy-2-oxopyrrolidin-3-yl)ethynyl)-4,5-dihydrobenzo[b]pyrazolo[1,5-d][1,4]oxazepine-2-carboxamide |

TABLE 1A-continued

| No. | Structure | Name |
|---|---|---|
| 685 | 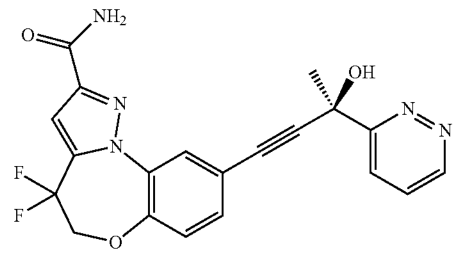 [SMILES: C[C@@](O)(C#Cc1ccc2c(c1)-n1nc(C(N)=O)cc1C(F)(F)CO2)c1cccnn1] | (R)-4,4-difluoro-9-(3-hydroxy-3-(pyridazin-3-yl)but-1-yn-1-yl)-4,5-dihydrobenzo[b]pyrazolo[1,5-d][1,4]oxazepine-2-carboxamide |
| 686 | 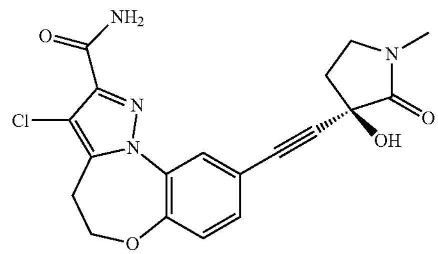 [SMILES: CN1CC[C@@](O)(C#Cc2ccc3c(c2)-n2nc(C(N)=O)c(Cl)c2CCO3)C1=O] | (R)-3-chloro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 687 | 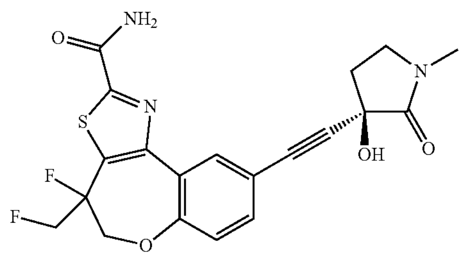 [SMILES: CN1CC[C@@](O)(C#Cc2ccc3c(c2)-c2nc(C(N)=O)sc2C(F)(CF)CO3)C1=O] | 4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 688 | 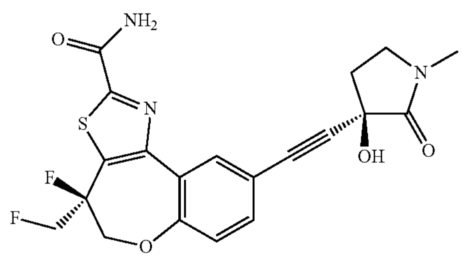 [SMILES: CN1CC[C@@](O)(C#Cc2ccc3c(c2)-c2nc(C(N)=O)sc2[C@@](F)(CF)CO3)C1=O] | (S)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 689 | 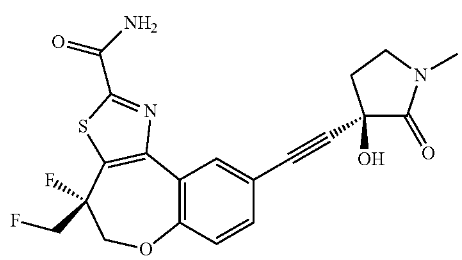 [SMILES: CN1CC[C@@](O)(C#Cc2ccc3c(c2)-c2nc(C(N)=O)sc2[C@](F)(CF)CO3)C1=O] | (R)-4-fluoro-4-(fluoromethyl)-9-(((R)-3-hydroxy-1-methyl-2-oxopyrrolidin-3-yl)ethynyl)-4,5-dihydrobenzo[2,3]oxepino[4,5-d]thiazole-2-carboxamide |
| 690 | 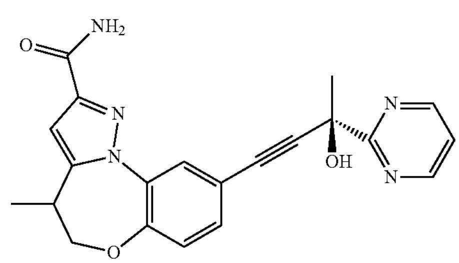 | 9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |

| No. | Structure | Name |
| --- | --- | --- |
| 691 | 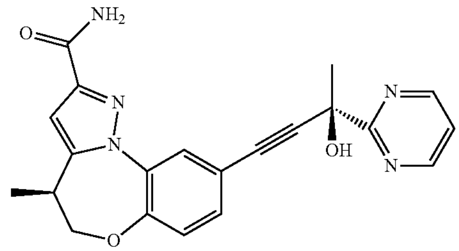 [SMILES: C[C@@H]1COc2ccc(C#C[C@@](C)(O)c3ncccn3)cc2-n2nc(C(N)=O)cc21] | (S)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |
| 692 | 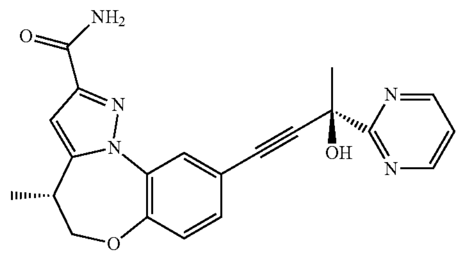 [SMILES: C[C@H]1COc2ccc(C#C[C@@](C)(O)c3ncccn3)cc2-n2nc(C(N)=O)cc21] | (R)-9-((R)-3-hydroxy-3-(pyrimidin-2-yl)but-1-yn-1-yl)-4-methyl-4,5-dihydrobenzo[b]pyrazolo[1,5-d][1,4]oxazepine-2-carboxamide |
| 693 | 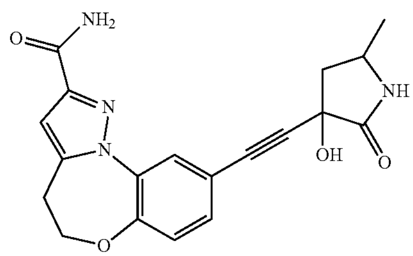 [SMILES: CC1CC(O)(C#Cc2ccc3c(c2)-n2nc(C(N)=O)cc2CCO3)C(=O)N1] | 9-((3-hydroxy-5-methyl-2-oxopyrrolidin-3-yl)ethynyl)-4,5-dihydrobenzo[b]pyrazolo[1,5-d][1,4]oxazepine-2-carboxamide |
| 694 | 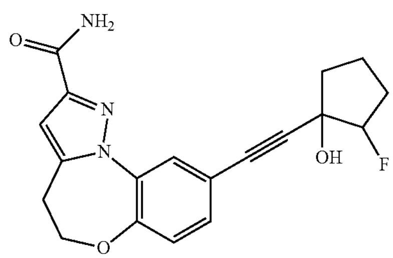 [SMILES: NC(=O)c1cc2n(n1)-c1cc(C#CC3(O)CCCC3F)ccc1OCC2] | 9-((2-fluoro-1-hydroxycyclopentyl)ethynyl)-4,5-dihydrobenzo[b]pyrazolo[1,5-d][1,4]oxazepine-2-carboxamide |
| 695 | 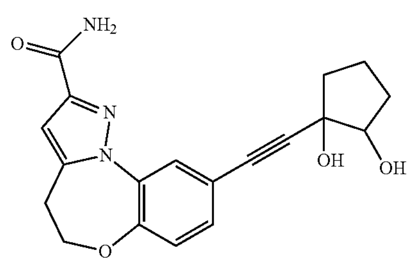 [SMILES: NC(=O)c1cc2n(n1)-c1cc(C#CC3(O)CCCC3O)ccc1OCC2] | 9-((1,2-dihydroxycyclopentyl)ethynyl)-4,5-dihydrobenzo[b]pyrazolo[1,5-d][1,4]oxazepine-2-carboxamide |
| 696 | 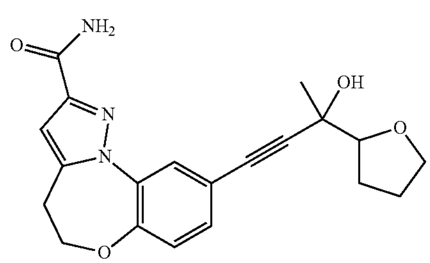 [SMILES: CC(O)(C#Cc1ccc2c(c1)-n1nc(C(N)=O)cc1CCO2)C1CCCO1] | 9-(3-hydroxy-3-(tetrahydrofuran-2-yl)but-1-yn-1-yl)-4,5-dihydrobenzo[b]pyrazolo[1,5-d][1,4]oxazepine-2-carboxamide |

TABLE 1A-continued

| No. | Structure | Name |
|---|---|---|
| 697 | 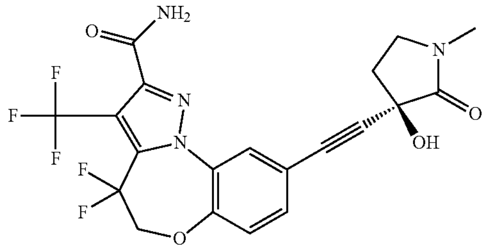 [SMILES: CN1CC[C@@](O)(C#Cc2ccc3c(c2)-n2nc(C(N)=O)c(C(F)(F)F)c2C(F)(F)CO3)C1=O] | (R)-4,4-difluoro-9-((3-hydroxy-1-methyl-2-oxopyrrolidin-3-yl)ethynyl)-3-(trifluoromethyl)-4,5-dihydrobenzo[b]pyrazolo[1,5-d][1,4]oxazepine-2-carboxamide |
| 698 | 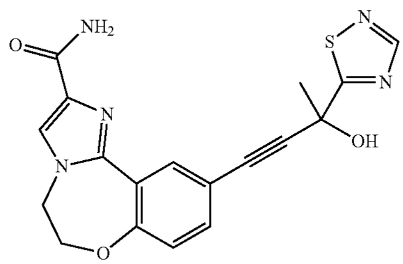 [SMILES: CC(O)(C#Cc1ccc2c(c1)-c1nc(C(N)=O)cn1CCO2)c1ncns1] | 10-(3-hydroxy-3-(1,2,4-thiadiazol-5-yl)but-1-yn-1-yl)-5,6-dihydrobenzo[f]imidazo[1,2-d][1,4]oxazepine-2-carboxamide |
| 699 | 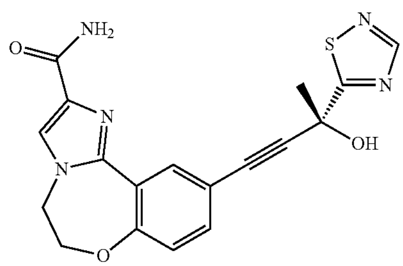 [SMILES: C[C@@](O)(C#Cc1ccc2c(c1)-c1nc(C(N)=O)cn1CCO2)c1ncns1] | (R)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide |
| 700 | 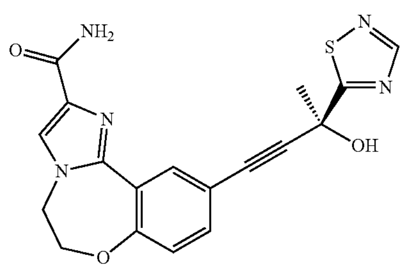 [SMILES: C[C@](O)(C#Cc1ccc2c(c1)-c1nc(C(N)=O)cn1CCO2)c1ncns1] | S)-10-(3-hydroxy-3-(1,2,4-thiadiazol-5-yl)but-1-yn-1-yl)-5,6-dihydrobenzo[f]imidazo[1,2-d][1,4]oxazepine-2-carboxamide |
| 701 | 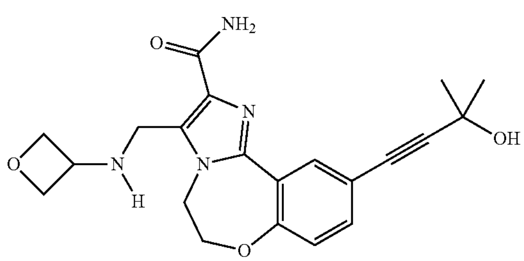 [SMILES: CC(C)(O)C#Cc1ccc2c(c1)-c1nc(C(N)=O)c(CNC3COC3)n1CCO2] | 10-(3-hydroxy-3-methylbut-1-yn-1-yl)-3-((oxetan-3-ylamino)methyl)-5,6-dihydrobenzo[f]imidazo[1,2-d][1,4]oxazepine-2-carboxamide |
| 702 | 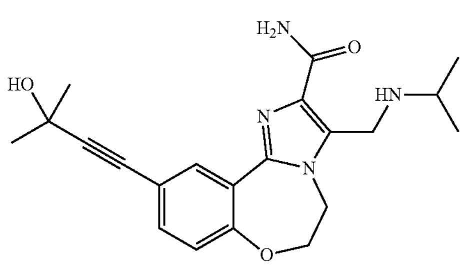 [SMILES: CC(C)NCc1c(C(N)=O)nc2n1CCOc1ccc(C#CC(C)(C)O)cc1-2] | 10-(3-hydroxy-3-methylbut-1-yn-1-yl)-3-((isopropylamino)methyl)-5,6-dihydrobenzo[f]imidazo[1,2-d][1,4]oxazepine-2-carboxamide |

TABLE 1A-continued

| No. | Structure | Name |
|---|---|---|
| 703 | 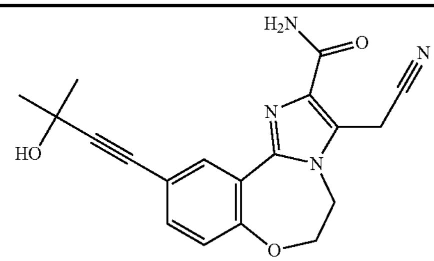 | 3-(cyanomethyl)-10-(3-hydroxy-3-methylbut-1-yn-1-yl)-5,6-dihydrobenzo[f]imidazo[1,2-d][1,4]oxazepine-2-carboxamide |
| 704 | 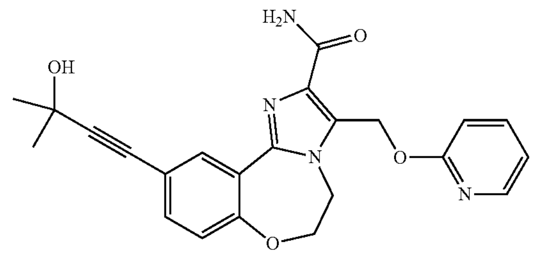 [SMILES: CC(C)(O)C#Cc1ccc2c(c1)-c1nc(C(N)=O)c(COc3ccccn3)n1CCO2] | 10-(3-hydroxy-3-methylbut-1-yn-1-yl)-3-((pyridin-2-yloxy)methyl)-5,6-dihydrobenzo[f]imidazo[1,2-d][1,4]oxazepine-2-carboxamide |
| 705 | 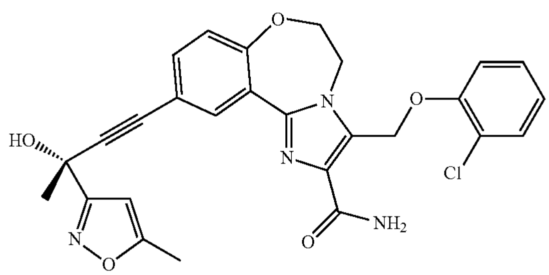 [SMILES: Cc1cc([C@](C)(O)C#Cc2ccc3c(c2)-c2nc(C(N)=O)c(COc4ccccc4Cl)n2CCO3)no1] | (R)-3-((2-chlorophenoxy)methyl)-10-(3-hydroxy-3-(5-methylisoxazol-3-yl)but-1-yn-1-yl)-5,6-dihydrobenzo[f]imidazo[1,2-d][1,4]oxazepine-2-carboxamide |
| 706 | 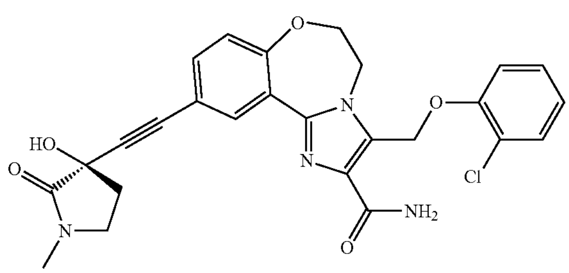 [SMILES: CN1CC[C@@](O)(C#Cc2ccc3c(c2)-c2nc(C(N)=O)c(COc4ccccc4Cl)n2CCO3)C1=O] | (R)-3-((2-chlorophenoxy)methyl)-10-((3-hydroxy-1-methyl-2-oxopyrrolidin-3-yl)ethynyl)-5,6-dihydrobenzo[f]imidazo[1,2-d][1,4]oxazepine-2-carboxamide |
| 707 | 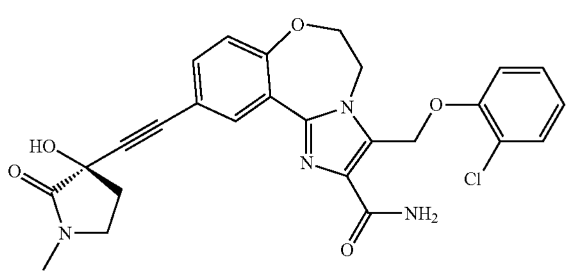 [SMILES: CN1CC[C@@](O)(C#Cc2ccc3c(c2)-c2nc(C(N)=O)c(COc4ccccc4Cl)n2CCO3)C1=O] | (R)-3-((2-chlorophenoxy)methyl)-10-((3-hydroxy-1-methyl-2-oxopyrrolidin-3-yl)ethynyl)-5,6-dihydrobenzo[f]imidazo[1,2-d][1,4]oxazepine-2-carboxamide |
| 708 | 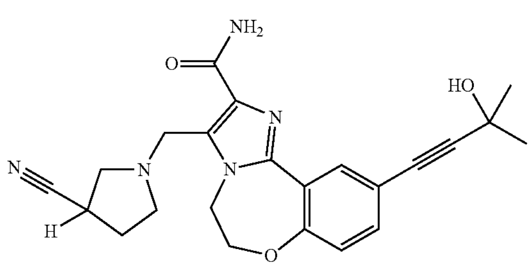 [SMILES: CC(C)(O)C#Cc1ccc2c(c1)-c1nc(C(N)=O)c(CN3CCC(C#N)C3)n1CCO2] | 3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |

TABLE 1A-continued

| No. | Structure | Name |
|---|---|---|
| 709 | 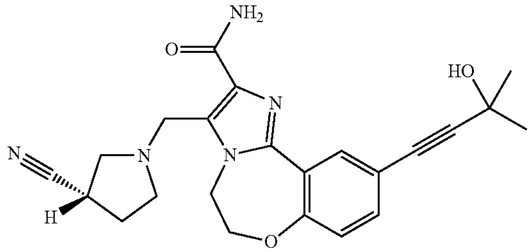 [SMILES: CC(C)(O)C#Cc1ccc2c(c1)-c1nc(C(N)=O)c(CN3CC[C@H](C#N)C3)n1CCO2] | (S)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |
| 710 | 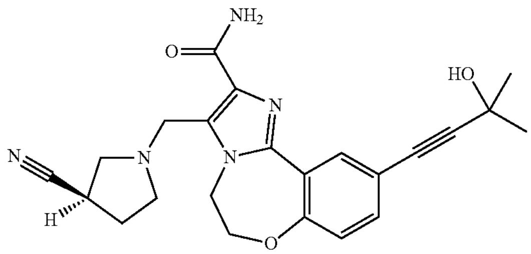 [SMILES: CC(C)(O)C#Cc1ccc2c(c1)-c1nc(C(N)=O)c(CN3CC[C@@H](C#N)C3)n1CCO2] | (R)-3-((3-cyanopyrrolidin-1-yl)methyl)-10-(3-hydroxy-3-methylbut-1-yn-1-yl)-5,6-dihydrobenzo[f]imidazo[1,2-d][1,4]oxazepine-2-carboxamide |
| 711 | 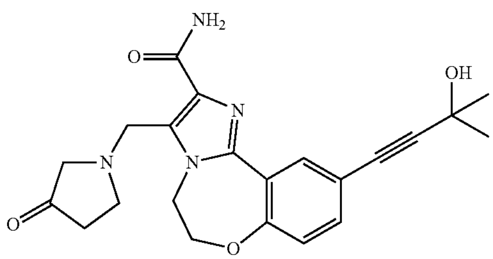 [SMILES: CC(C)(O)C#Cc1ccc2c(c1)-c1nc(C(N)=O)c(CN3CCC(=O)C3)n1CCO2] | 10-(3-hydroxy-3-methylbut-1-yn-1-yl)-3-((3-oxopyrrolidin-1-yl)methyl)-5,6-dihydrobenzo[f]imidazo[1,2-d][1,4]oxazepine-2-carboxamide |
| 712 | 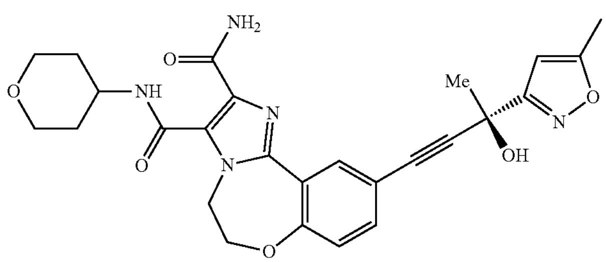 [SMILES: Cc1cc([C@](C)(O)C#Cc2ccc3c(c2)-c2nc(C(N)=O)c(C(=O)NC4CCOCC4)n2CCO3)no1] | (R)-10-(3-hydroxy-3-(5-methylisoxazol-3-yl)but-1-yn-1-yl)-N3-(tetrahydro-2H-pyran-4-yl)-5,6-dihydrobenzo[f]imidazo[1,2-d][1,4]oxazepine-2,3-dicarboxamide |
| 713 | 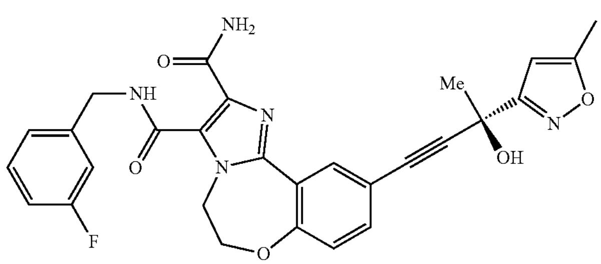 [SMILES: Cc1cc([C@](C)(O)C#Cc2ccc3c(c2)-c2nc(C(N)=O)c(C(=O)NCc4cccc(F)c4)n2CCO3)no1] | (R)-N3-(3-fluorobenzyl)-10-(3-hydroxy-3-(5-methylisoxazol-3-yl)but-1-yn-1-yl)-5,6-dihydrobenzo[f]imidazo[1,2-d][1,4]oxazepine-2,3-dicarboxamide |
| 714 | 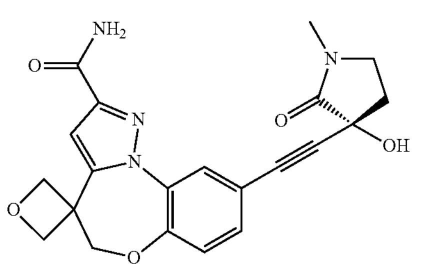 [SMILES: CN1CC[C@@](O)(C#Cc2ccc3c(c2)-n2nc(C(N)=O)cc2C2(COC2)CO3)C1=O] | (R)-9-((3-hydroxy-1-methyl-2-oxopyrrolidin-3-yl)ethynyl)-5H-spiro[benzo[b]pyrazolo[1,5-d][1,4]oxazepine-4,3'-oxetane]-2-carboxamid |

TABLE 1A-continued

| No. | Structure | Name |
|---|---|---|
| 715 | 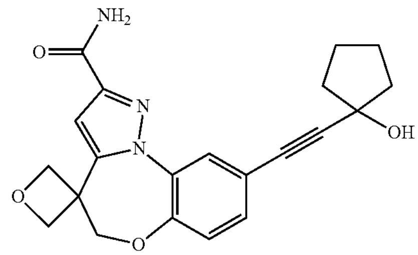 [SMILES: NC(=O)c1cc2n(n1)-c1cc(C#CC3(O)CCCC3)ccc1OCC21COC1] | 9-((1-hydroxycyclopentyl)ethynyl)-5H-spiro[benzo[b]pyrazolo[1,5-d][1,4]oxazepine-4,3'-oxetane]-2-carboxamide |
| 716 | 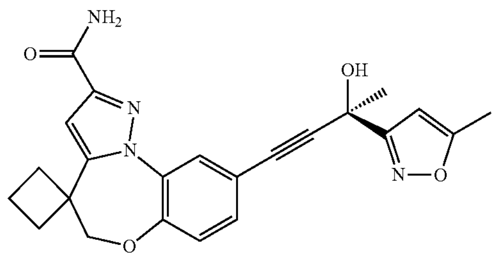 [SMILES: Cc1cc([C@](C)(O)C#Cc2ccc3c(c2)-n2nc(C(N)=O)cc2C2(CCC2)CO3)no1] | (R)-9-(3-hydroxy-3-(5-methylisoxazol-3-yl)but-1-yn-1-yl)-5H-spiro[benzo[b]pyrazolo[1,5-d][1,4]oxazepine-4,1'-cyclobutane]-2-carboxamide |
| 717 | 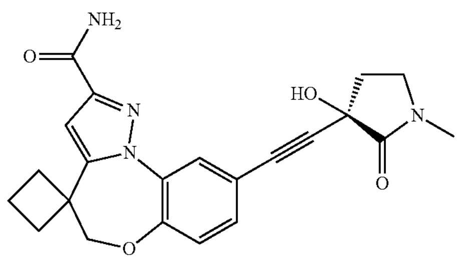 [SMILES: CN1CC[C@@](O)(C#Cc2ccc3c(c2)-n2nc(C(N)=O)cc2C2(CCC2)CO3)C1=O] | (R)-9-((3-hydroxy-1-methyl-2-oxopyrrolidin-3-yl)ethynyl)-5H-spiro[benzo[b]pyrazolo[1,5-d][1,4]oxazepine-4,1'-cyclobutane]-2-carboxamide |
| 718 | 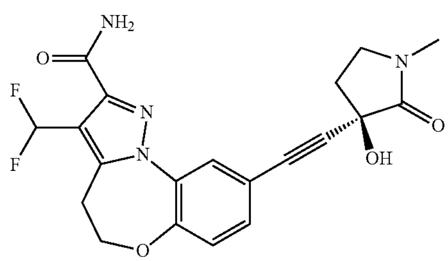 [SMILES: CN1CC[C@@](O)(C#Cc2ccc3c(c2)-n2nc(C(N)=O)c(C(F)F)c2CCO3)C1=O] | (R)-3-(difluoromethyl)-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 719 | 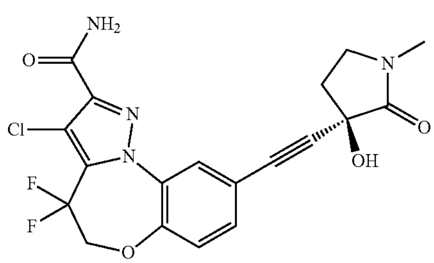 [SMILES: CN1CC[C@@](O)(C#Cc2ccc3c(c2)-n2nc(C(N)=O)c(Cl)c2C(F)(F)CO3)C1=O] | (R)-3-chloro-4,4-difluoro-9-((3-hydroxy-1-methyl-2-oxopyrrolidin-3-yl)ethynyl)-4,5-dihydrobenzo[b]pyrazolo[1,5-d][1,4]oxazepine-2-carboxamide |
| 720 | 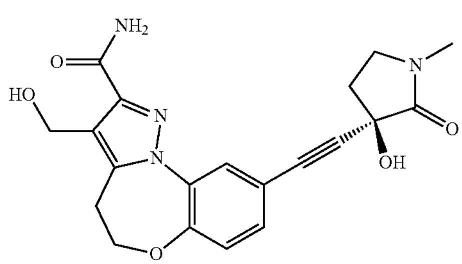 [SMILES: CN1CC[C@@](O)(C#Cc2ccc3c(c2)-n2nc(C(N)=O)c(CO)c2CCO3)C1=O] | (R)-9-((3-hydroxy-1-methyl-2-oxopyrrolidin-3-yl)ethynyl)-3-(hydroxymethyl)-4,5-dihydrobenzo[b]pyrazolo[1,5-d][1,4]oxazepine-2-carboxamide. |

\* \* \* \* \*